(12) United States Patent
Nakano et al.

(10) Patent No.: US 12,284,915 B2
(45) Date of Patent: Apr. 22, 2025

(54) ORGANIC ELECTROLUMINESCENCE DEVICE AND ELECTRONIC APPARATUS PROVIDED WITH THE SAME

(71) Applicant: IDEMITSU KOSAN CO., LTD., Tokyo (JP)

(72) Inventors: Yuki Nakano, Sodegaura (JP); Taro Yamaki, Sodegaura (JP); Satomi Tasaki, Sodegaura (JP); Tomoki Kato, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 866 days.

(21) Appl. No.: 17/282,971

(22) PCT Filed: Oct. 9, 2019

(86) PCT No.: PCT/JP2019/039870
§ 371 (c)(1),
(2) Date: Apr. 5, 2021

(87) PCT Pub. No.: WO2020/075769
PCT Pub. Date: Apr. 16, 2020

(65) Prior Publication Data
US 2023/0011996 A1 Jan. 12, 2023

Related U.S. Application Data

(63) Continuation-in-part of application No. 16/557,675, filed on Aug. 30, 2019, now Pat. No. 10,763,444, and
(Continued)

(30) Foreign Application Priority Data

Oct. 9, 2018 (JP) .................................. 2018-190838
Oct. 9, 2018 (JP) .................................. 2018-191224
(Continued)

(51) Int. Cl.
*H10K 85/60* (2023.01)
*C07D 307/91* (2006.01)
(Continued)

(52) U.S. Cl.
CPC ....... *H10K 85/6574* (2023.02); *C07D 307/91* (2013.01); *C07D 487/22* (2013.01);
(Continued)

(58) Field of Classification Search
None
See application file for complete search history.

(56) References Cited

U.S. PATENT DOCUMENTS 10,763,444 B2  9/2020 Nakano et al.
10,804,474 B2  10/2020 Nakano et al.
(Continued)

FOREIGN PATENT DOCUMENTS

CN  110317186 A  10/2019
CN  111937173 A  11/2020
(Continued)

OTHER PUBLICATIONS

International Search Report dated Dec. 24, 2019 for corresponding Application No. PCT/JP2019/039870.
(Continued)

*Primary Examiner* — Jeffrey D Washville
(74) *Attorney, Agent, or Firm* — Foley & Lardner LLP

(57) ABSTRACT

An organic electroluminescence device including a cathode, an anode, and an emitting layer disposed between the cathode and the anode, wherein the emitting layer includes a compound represented by the following formula (1) and one or more compounds selected from the group consisting of compounds represented by each of formulas (11), (21),
(Continued)

(31), (41), (51), (61), (71) and (81). In the formula (1), at least one of $R_1$ to $R_8$ is a deuterium atom.

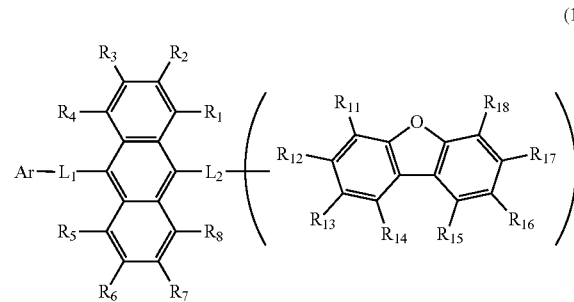

28 Claims, 1 Drawing Sheet

Related U.S. Application Data a continuation-in-part of application No. 16/593,743, filed on Oct. 4, 2019, now Pat. No. 10,804,474.

(30) Foreign Application Priority Data

May 30, 2019 (JP) .................................. 2019-101578
May 30, 2019 (JP) .................................. 2019-101675

(51) Int. Cl.
| | | |
|---|---|---|
| *C07D 487/22* | (2006.01) | |
| *C07D 493/04* | (2006.01) | |
| *C07D 493/10* | (2006.01) | |
| *C07F 5/02* | (2006.01) | |
| *C09K 11/06* | (2006.01) | |
| *H10K 50/11* | (2023.01) | |
| *H10K 50/15* | (2023.01) | |
| *H10K 50/16* | (2023.01) | |
| *H10K 85/30* | (2023.01) | |
| *H10K 101/10* | (2023.01) | |

(52) U.S. Cl.
CPC ......... *C07D 493/04* (2013.01); *C07D 493/10* (2013.01); *C07F 5/027* (2013.01); *C09K 11/06* (2013.01); *H10K 85/30* (2023.02); *H10K 85/615* (2023.02); *H10K 85/626* (2023.02); *H10K 85/633* (2023.02); *H10K 85/636* (2023.02); *H10K 85/6572* (2023.02); *C07B 2200/05* (2013.01); *C09K 2211/1018* (2013.01); *H10K 50/11* (2023.02); *H10K 50/15* (2023.02); *H10K 50/16* (2023.02); *H10K 85/622* (2023.02); *H10K 85/624* (2023.02); *H10K 2101/10* (2023.02)

(56) References Cited

U.S. PATENT DOCUMENTS

| | | |
|---|---|---|
| 11,482,675 B1 | 10/2022 | Tasaki et al. |
| 2014/0001459 A1 | 1/2014 | Gao |
| 2015/0236274 A1 | 8/2015 | Hatakeyama et al. |
| 2016/0079542 A1 | 3/2016 | Itoi |
| 2016/0204355 A1 | 7/2016 | Kim et al. |
| 2016/0351817 A1 | 12/2016 | Kim et al. |
| 2016/0351818 A1 | 12/2016 | Kim et al. |
| 2017/0018723 A1 | 1/2017 | Cha et al. |
| 2017/0025608 A1 | 1/2017 | Herron et al. |
| 2017/0125686 A1 | 5/2017 | Heil et al. |
| 2017/0324045 A1 | 11/2017 | Takahashi et al. |
| 2018/0009776 A1 | 1/2018 | Cha et al. |
| 2018/0019430 A1 | 1/2018 | Cha et al. |
| 2018/0123055 A1 | 5/2018 | Park et al. |
| 2018/0198076 A1 | 7/2018 | Takahashi et al. |
| 2018/0233669 A1 | 8/2018 | Lee et al. |
| 2018/0277771 A1 | 9/2018 | Park et al. |
| 2018/0301629 A1 | 10/2018 | Hatakeyama et al. |
| 2019/0058124 A1 | 2/2019 | Hatakeyama et al. |
| 2019/0097142 A1 | 3/2019 | Takahashi et al. |
| 2019/0207112 A1 | 7/2019 | Hatakeyama et al. |
| 2019/0305227 A1 | 10/2019 | Yoon et al. |
| 2019/0341556 A1 | 11/2019 | Takahashi et al. |
| 2019/0393420 A1 | 12/2019 | Takeda et al. |
| 2019/0393429 A1 | 12/2019 | Takahashi et al. |
| 2021/0053998 A1* | 2/2021 | Kim .................. H10K 85/6572 |
| 2022/0246864 A1 | 8/2022 | Yoon et al. |

FOREIGN PATENT DOCUMENTS

| | | |
|---|---|---|
| CN | 112005392 A | 11/2020 |
| EP | 3 524 660 A1 | 8/2019 |
| JP | 2006-151844 A | 6/2006 |
| JP | 2015-153911 A | 8/2015 |
| JP | 2017-514807 A | 6/2017 |
| JP | 2018-157209 A | 10/2018 |
| KR | 20090086015 A | 8/2009 |
| KR | 20130022071 A | 3/2013 |
| KR | 20140058290 A | 5/2014 |
| KR | 10-2016-0102881 A | 8/2016 |
| KR | 20170039020 | 4/2017 |
| KR | 20190056338 A | 5/2019 |
| KR | 20190113498 A | 10/2019 |
| KR | 1020190139794 A | 12/2019 |
| KR | 20200019272 A | 2/2020 |
| KR | 20200030003 A | 12/2020 |
| WO | WO-2010/066830 A1 | 6/2010 |
| WO | WO-2010/071362 A2 | 6/2010 |
| WO | WO-2010/099534 A2 | 9/2010 |
| WO | WO-2010/135395 A1 | 11/2010 |
| WO | WO-2013/106041 A1 | 7/2013 |
| WO | WO-2015/102118 A1 | 7/2015 |
| WO | WO-2015/181667 A1 | 12/2015 |
| WO | WO-2016/117848 A1 | 7/2016 |
| WO | WO-2016/152544 A1 | 9/2016 |
| WO | WO-2017/023021 A1 | 2/2017 |
| WO | WO-2017/188111 A1 | 11/2017 |
| WO | WO-2018/151065 A1 | 8/2018 |
| WO | WO-2020/022751 A1 | 1/2020 |

OTHER PUBLICATIONS

Written Opinion of the International Searching Authority issued in Application No. PCT/JP2019/039870.
Office Action issued in corresponding Chinese Patent Application No. 201980066851.7 dated Dec. 5, 2023 (10 pages).
Third Party Submission issued in corresponding Korean Patent Application No. 10-2021-7010371, dated Dec. 19, 2022.
International Preliminary Report on Patentability (including the Written Opinion), dated Apr. 22, 2021, issued in corresponding PCT Application No. PCT/JP2019/039846 (9 pages).
Tsuji et al., "The hydrogen/deuterium isotope effect of the host material on the lifetime of organic light-emitting diodes." Chemical Communications, vol. 50, Sep. 15, 2014, pp. 14870-14872.
Yao et al. "Lifetime Enhancement and Degradation Study of Blue OLEDs Using Deuterated Materials" ACS Applied Materials & Interfaces, vol. 15, Jan. 26, 2023, pp. 7255-7262.
Wu, C.L. et al., 2014. High efficiency non-dopant blue organic light-emitting diodes based on anthracene-based fluorophores with molecular design of charge transport and red-shifted emission proof. Journal of Materials Chemistry C, 2(35), pp. 7188-7200. (2014).
Lee et al., Journal of Nanoscience and Nanotechnology, vol. 16, (2016), pp. 8460-8464.
Third-Party Submission issued in corresponding Korean Patent Application No. 10-2021-7010371, dated Nov. 16, 2022 (42 pages).

(56) References Cited

OTHER PUBLICATIONS

Kr 10-2018-0036167-A: Priority Application for US 2019/0305227-A1.

* cited by examiner

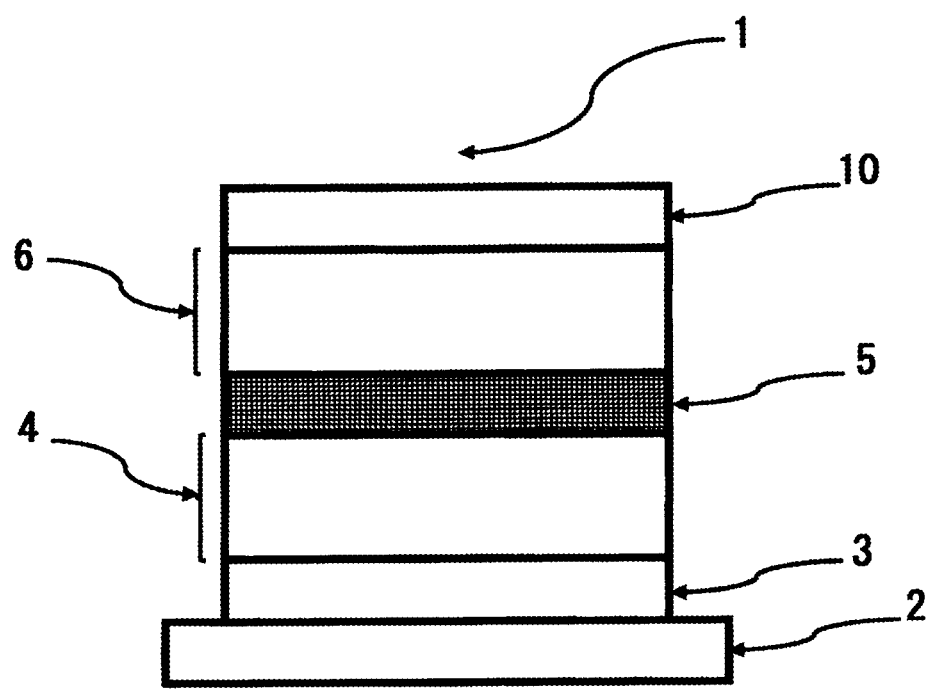

ORGANIC ELECTROLUMINESCENCE DEVICE AND ELECTRONIC APPARATUS PROVIDED WITH THE SAME

CROSS-REFERENCE TO RELATED APPLICATIONS

The present application claims priority under 35 U.S.C. § 371 to International Patent Application No. PCT/JP2019/039870, filed Oct. 9, 2021, which claims priority to and the benefit of U.S. application Ser. No. 16/557,675, filed Aug. 30, 2019, and U.S. Application No. Oct. 4, 2019, and Japanese Application No. 2018-191224, filed Oct. 9, 2018, and Japanese Application No. 2018-190838, filed Oct. 9, 2018, and Japanese Application No. 2019-101578, filed May 30, 2019, and Japanese Application No. 2019-101675, filed May 30, 2019. The contents of these applications are hereby incorporated by reference in their entireties.

TECHNICAL FIELD

The invention relates to an organic electroluminescence device and an electronic apparatus provided with the organic electroluminescence device.

BACKGROUND ART

When a voltage is applied to an organic electroluminescence device (hereinafter may be referred to as an organic EL device), holes are injected to an emitting layer from an anode and electrons are injected to an emitting layer from a cathode. In the emitting layer, injected holes and electrons are re-combined and excitons are formed.

Although materials for an organic EL device are being improved gradually to increase the performances of the organic EL device (for example, Patent Documents 1 to 6), high performances are further offered. In particular, improvement in lifetime of an organic EL device is an important task relating to a lifetime of commercial products provided with the organic EL device, and thus a material enabling to realize a long-lifetime organic EL device is required.

RELATED ART DOCUMENTS

Patent Documents

Patent Document 1: WO2017/188111
Patent Document 2: Publication of US Patent Application No. 2017/324045
Patent Document 3: WO2010/099534
Patent Document 4: WO2010/135395
Patent Document 5: WO2010/071362
Patent Document 6: WO2018/066830

SUMMARY OF THE INVENTION

An object of the invention is to provide an organic EL device having a long lifetime, and to provide an electronic apparatus provided with the organic EL device.

As a result of extensive studies, the inventors have found that an organic EL device having a long lifetime can be obtained by using compounds having a specific structure in an emitting layer of the organic EL device in combination, and they have achieved the invention.

According to the invention, the following organic EL device and electric apparatus can be provided.

1. An organic electroluminescence device comprising:
   a cathode,
   an anode, and
   an emitting layer disposed between the cathode and the anode, wherein
   the emitting layer comprises a compound represented by the following formula (1) and one or more compounds selected from the group consisting of compounds represented by each of formulas (11), (21), (31), (41), (51), (61), (71) and (81):

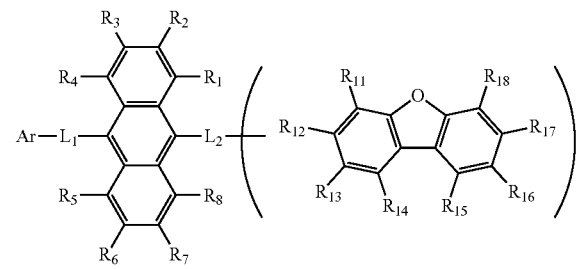

(1)

wherein in the formula (1),
$R_1$ to $R_8$ are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;
$R_{901}$ to $R_{907}$ are independently
a hydrogen atom,
a substituted or unsubstituted alkyl group having 1 to 50 carbon atoms,
a substituted or unsubstituted cycloalkyl group having 3 to 50 ring carbon atoms,
a substituted or unsubstituted aryl group having 6 to 50 ring carbon atoms, or
a substituted or unsubstituted monovalent heterocyclic group having 5 to 50 ring atoms;
when two or more of $R_{901}$ to $R_{907}$ exist, two or more of $R_{901}$ to $R_{907}$ may be the same with or different from each other;
at least one of $R_1$ to $R_8$ is a deuterium atom;
two or more adjacent groups of $R_1$ to $R_4$ and two or more adjacent groups of $R_5$ to $R_8$ do not form a ring;
$L_1$ and $L_2$ are independently
a single bond,
a substituted or unsubstituted arylene group having 6 to 30 ring carbon atoms, or a substituted or unsubstituted divalent heterocyclic group having 5 to 30 ring atoms;
Ar is
a substituted or unsubstituted aryl group having 6 to 50 ring carbon atoms, or
a substituted or unsubstituted monovalent heterocyclic group having 5 to 50 ring atoms;
one of $R_{11}$ to $R_{18}$ is a single bond bonding to $L_2$;
$R_{11}$ to $R_{18}$ which are not single bonds bonding to $L_2$ are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;
$R_{901}$ to $R_{907}$ are as defined in $R_1$ to $R_8$; and
two or more adjacent groups of $R_{11}$ to $R_{18}$ do not form a ring;

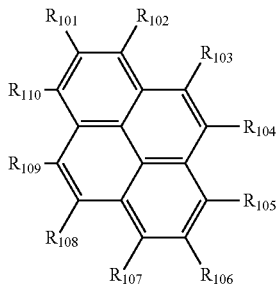
(11)

wherein, in the formula (11),
one or more pairs of two or more adjacent groups of $R_{101}$ to $R_{110}$ are bonded with each other to form a substituted or unsubstituted, saturated or unsaturated ring, or do not form a substituted or unsubstituted, saturated or unsaturated ring;
at least one of $R_{101}$ to $R_{110}$ is a monovalent group represented by the formula (12);
$R_{101}$ to $R_{110}$ that do not form the substituted or unsubstituted, saturated or unsaturated ring and that are not a monovalent group represented by the following formula (12) are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms, —Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;
$R_{901}$ to $R_{907}$ are as defined in the formula (1);

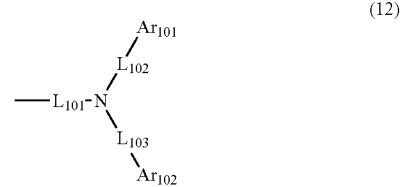
(12)

wherein, in the formula (12), $Ar_{101}$ and $Ar_{102}$ are independently
a substituted or unsubstituted aryl group having 6 to 50 ring carbon atoms, or
a substituted or unsubstituted monovalent heterocyclic group having 5 to 50 ring atoms;
$L_{101}$ to $L_{103}$ are independently
a single bonded,
a substituted or unsubstituted arylene group having 6 to 30 ring carbon atoms, or
a substituted or unsubstituted divalent heterocyclic group having 5 to 30 ring atoms;

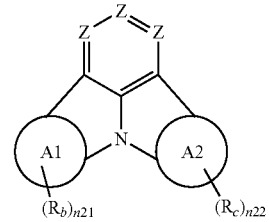
(21)

wherein, in the formula (21),
Zs are independently $CR_a$ or N;
A1 ring and A2 ring are independently a substituted or unsubstituted aromatic hydrocarbon ring having 6 to 50 ring carbon atoms, or a substituted or unsubstituted heterocyclic ring having 5 to 50 ring atoms;
when a plurality of $R_a$s exist, one or more pairs of two or more adjacent groups of $R_a$ are bonded with each other to form a substituted or unsubstituted, saturated or unsaturated ring, or do not form a substituted or unsubstituted, saturated or unsaturated ring;
when a plurality of $R_b$s exist, one or more pairs of two or more adjacent groups of $R_b$ are bonded with each other to form a substituted or unsubstituted, saturated or unsaturated ring, or do not form a substituted or unsubstituted, saturated or unsaturated ring;
when a plurality of $R_c$s exist, one or more pairs of two or more adjacent groups of $R_c$ are bonded with each other to form a substituted or unsubstituted, saturated or unsaturated ring, or do not form a substituted or unsubstituted, saturated or unsaturated ring;
n21 and n22 are independently an integer of 0 to 4;
$R_a$ to $R_c$ that do not form the substituted or unsubstituted, saturated or unsaturated ring are independently a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;
$R_{901}$ to $R_{907}$ are as defined in the formula (1);

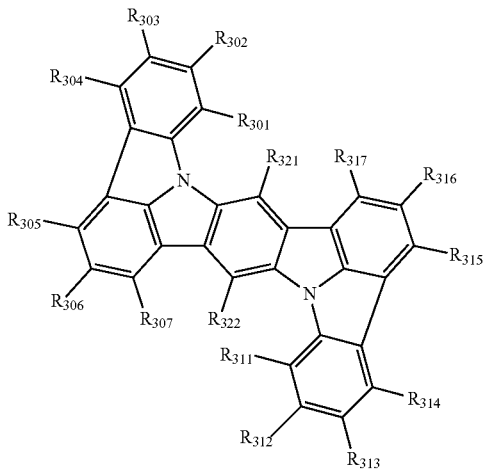

(31)

wherein, in the formula (31),
one or more pairs of two or more adjacent groups of $R_{301}$ to $R_{307}$ and $R_{311}$ to $R_{317}$ form a substituted or unsubstituted, saturated or unsaturated ring, or do not form a substituted or unsubstituted saturated or unsaturated ring;
$R_{301}$ to $R_{307}$ and $R_{311}$ to $R_{317}$ that do not form the substituted or unsubstituted, saturated or unsaturated ring are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;
$R_{321}$ and $R_{322}$ are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;
$R_{901}$ to $R_{907}$ are as defined in the formula (1);

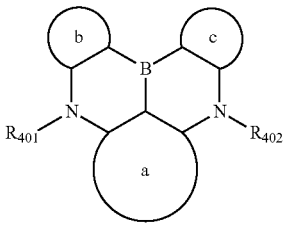

(41)

wherein, in the formula (41),
a ring, b ring and c ring are independently
a substituted or unsubstituted aromatic hydrocarbon ring having 6 to 50 ring carbon atoms, or
a substituted or unsubstituted heterocyclic ring having 5 to 50 ring atoms;
$R_{401}$ and $R_{402}$ are independently bonded to the a ring, the b ring or the c ring to form a substituted or unsubstituted heterocyclic ring or do not form a substituted or unsubstituted heterocyclic ring;
$R_{401}$ and $R_{402}$ that do not form the substituted or unsubstituted heterocyclic ring are independently
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
a substituted or unsubstituted aryl group having 6 to 50 ring carbon atoms, or
a substituted or unsubstituted monovalent heterocyclic group having 5 to 50 ring atoms;

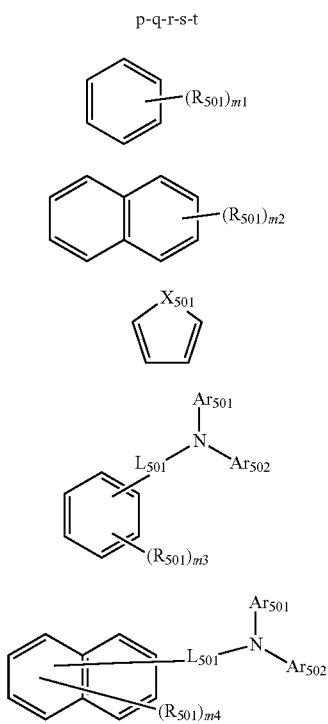

(51) p-q-r-s-t

(52) (R$_{501}$)$_{m1}$ [benzene ring]

(53) (R$_{501}$)$_{m2}$ [naphthalene ring]

(54) X$_{501}$ [five-membered ring]

(55) [benzene with Ar$_{501}$, Ar$_{502}$, L$_{501}$, (R$_{501}$)$_{m3}$]

(56) [naphthalene with Ar$_{501}$, Ar$_{502}$, L$_{501}$, (R$_{501}$)$_{m4}$]

wherein, in the formula (51),
r ring is a ring represented by the formula (52) or formula (53) which is fused to an adjacent ring at an arbitrary position;
q ring and s ring are independently a ring represented by the formula (54) which is fused to an adjacent ring at an arbitrary position;
p ring and t ring are independently a ring represented by the formula (55) or the formula (56) which is fused to an adjacent ring at an arbitrary position;
when a plurality of R$_{501}$s exist, adjacent R$_{501}$s are bonded with each other to form a substituted or unsubstituted, saturated or unsaturated ring, or do not form a substituted or unsubstituted, saturated or unsaturated ring;
X$_{501}$ is an oxygen atom, a sulfur atom, or NR$_{502}$;
R$_{501}$ and R$_{502}$ that do not form the substituted or unsubstituted saturated or unsaturated ring are
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si(R$_{901}$)(R$_{902}$)(R$_{903}$),
—O—(R$_{904}$),
—S—(R$_{905}$),
—N(R$_{906}$)(R$_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;
R$_{901}$ to R$_{907}$ are as defined in the formula (1);
Ar$_{501}$ and Ar$_{502}$ are independently
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
a substituted or unsubstituted aryl group having 6 to 50 ring carbon atoms, or
a substituted or unsubstituted monovalent heterocyclic group having 5 to 50 ring atoms;
L$_{501}$ is
a substituted or unsubstituted alkylene group having 1 to 50 carbon atoms,
a substituted or unsubstituted alkenylene group having 2 to 50 carbon atoms,
a substituted or unsubstituted alkynylene group having 2 to 50 carbon atoms,
a substituted or unsubstituted cycloalkylene group having 3 to 50 ring carbon atoms,
a substituted or unsubstituted arylene group having 6 to 50 ring carbon atoms, or
a substituted or unsubstituted divalent heterocyclic group having 5 to 50 ring atoms;
m1 is an integer of 0 to 2, m2 is an integer of 0 to 4, m3s are independently an integer of 0 to 3, and m4s are independently an integer of 0 to 5; when a plurality of R$_{501}$s exist, the R$_{501}$s may be the same or different;

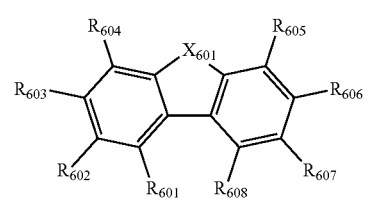

(61)

wherein, in the formula (61),
at least one pair of R$_{601}$ and R$_{602}$, R$_{602}$ and R$_{603}$, and R$_{603}$ and R$_{604}$ are bonded with each other to form a divalent group represented by the formula (62);
at least one pair of R$_{605}$ and R$_{606}$, R$_{606}$ and R$_{607}$, and R$_{607}$ and R$_{608}$ are bonded with each other to form a divalent group represented by formula (63);

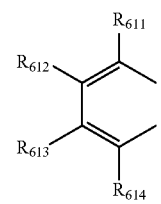

(62)

-continued (63)

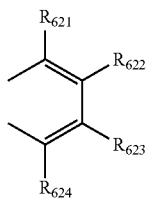

at least one of $R_{601}$ to $R_{604}$ that does not form the divalent group represented by the formula (62), and $R_{611}$ to $R_{614}$ is a monovalent group represented by the following formula (64);

at least one of $R_{605}$ to $R_{608}$ that do not form the divalent group represented by the formula (63), and $R_{621}$ to $R_{624}$ is a monovalent group represented by the following formula (64);

$X_{601}$ is an oxygen atom, a sulfur atom, or $NR_{609}$;

$R_{601}$ to $R_{608}$ that do not form the divalent group represented by the formulas (62) and (63) and that is not the monovalent group represented by the formula (64), $R_{611}$ to $R_{614}$ and $R_{621}$ to $R_{624}$ that are not the monovalent group represented by the formula (64), and $R_{609}$ are independently a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;

$R_{901}$ to $R_{907}$ are as defined in the formula (1);

(64)

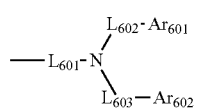

wherein, in the formula (64), $Ar_{601}$ and $Ar_{602}$ are independently
a substituted or unsubstituted aryl group having 6 to 50 ring carbon atoms, or
a substituted or unsubstituted monovalent heterocyclic group having 5 to 50 ring atoms;

$L_{601}$ to $L_{603}$ are independently
a single bonded,
a substituted or unsubstituted arylene group having 6 to 30 ring carbon atoms,
a substituted or unsubstituted divalent heterocyclic group having 5 to 30 ring atoms, or
a divalent linking group formed by bonding 2 to 4 above mentioned groups;

(71)

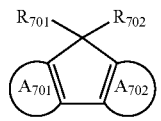

wherein, in the formula (71),
$A_{701}$ ring and $A_{702}$ ring are independently
a substituted or unsubstituted aromatic hydrocarbon ring having 6 to 50 ring carbon atoms, or
a substituted or unsubstituted heterocyclic ring having 5 to 50 ring atoms;
One or more rings selected from the group consisting of $A_{701}$ ring and $A_{702}$ ring are bonded to the bond * of the structure represented by the following formula (72);

(72)

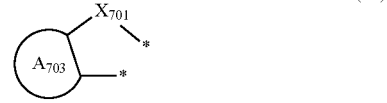

wherein, in the formula (72),
$A_{703}$ rings are independently
a substituted or unsubstituted aromatic hydrocarbon ring having 6 to 50 ring carbon atoms, or
a substituted or unsubstituted heterocyclic ring having 5 to 50 ring atoms;

$X_{701}$ is $NR_{703}$, $C(R_{704})(R_{705})$, $Si(R_{706})(R_{707})$, $Ge(R_{708})(R_{709})$, O, S or Se;

$R_{701}$ and $R_{702}$ are bonded with each other to form a substituted or unsubstituted, saturated or unsaturated ring or do not form a substituted or unsubstituted saturated or unsaturated ring;

$R_{701}$ and $R_{702}$ that do not form the substituted or unsubstituted, saturated or unsaturated ring, and $R_{703}$ to $R_{709}$ are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;

$R_{901}$ to $R_{907}$ are as defined in the formula (1);

(81)

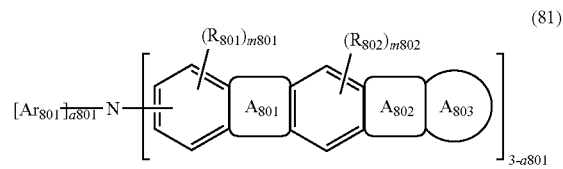

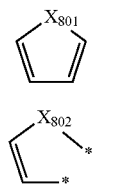

wherein, in the formula (81),
$A_{801}$ ring is a ring represented by the formula (82) which is fused to an adjacent ring at an arbitrary position;
$A_{802}$ ring is a ring represented by the formula (83) which is fused to an adjacent ring at an arbitrary position;
two bonds * bond to $A_{803}$ ring at an arbitrary position;
$X_{801}$ and $X_{802}$ are independently $C(R_{803})(R_{804})$, $Si(R_{805})(R_{806})$, an oxygen atom, or a sulfur atom;
$A_{803}$ ring is a substituted or unsubstituted aromatic hydrocarbon ring having 6 to 50 ring carbon atoms, or a substituted or unsubstituted heterocyclic ring having 5 to 50 ring atoms;
$Ar_{801}$ is a substituted or unsubstituted aryl group having 6 to 50 ring carbon atoms, or a substituted or unsubstituted monovalent heterocyclic group having 5 to 50 ring atoms;
$R_{801}$ to $R_{806}$ are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—$Si(R_{901})(R_{902})(R_{903})$,
—O—$(R_{904})$,
—S—$(R_{905})$,
—$N(R_{906})(R_{907})$,
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;
  $R_{901}$ to $R_{907}$ are as defined in the formula (1);
  m801 and m802 are independently an integer of 0 to 2; when these are 2, a plurality of $R_{801}$s or $R_{802}$s may be the same or different;
  a801 is an integer of 0 to 2; when a801 is 0 or 1, the structure in the parentheses indicated by "3-a801" may be the same as or different from each other; when a801 is 2, $Ar_{801}$s may be the same or different from each other.

2. An electronic apparatus provided with the organic electroluminescence device according to the above 1.

According to the invention, an organic EL device having a long lifetime, and an electronic apparatus provided with the organic EL device can be provided.

BRIEF DESCRIPTION OF THE DRAWINGS

The FIGURE is a view showing a schematic configuration of one embodiment of the organic EL device of the invention.

MODE FOR CARRYING OUT THE INVENTION

Definition

In the present specification, a hydrogen atom means an atom including isotopes different in the number of neutrons, namely, a protium, a deuterium and a tritium.

In the present specification, to a bondable position in which a symbol such as "R", or "D" representing a deuterium atom is not specified in a chemical formula, a hydrogen atom, that is, a light hydrogen atom, a deuterium atom, or a tritium atom is bonded thereto.

In the present specification, a term "ring carbon atoms" represents the number of carbon atoms among atoms forming a subject ring itself of a compound having a structure in which atoms are bonded in a ring form (for example, a monocyclic compound, a fused ring compound, a cross-linked compound, a carbocyclic compound or a heterocyclic compound). When the subject ring is substituted by a substituent, the carbon contained in the substituent is not included in the number of ring carbon atoms. The same shall apply to the "ring carbon atoms" described below, unless otherwise noted. For example, a benzene ring has 6 ring carbon atoms, a naphthalene ring has 10 ring carbon atoms, a pyridine ring has 5 ring carbon atoms, and a furan ring has 4 ring carbon atoms. Further, for example, a 9,9-diphenylfluorenyl group has 13 ring carbon atoms, and a 9,9'-spirobifluorenyl group has 25 ring carbon atoms.

Further, when the benzene ring or the naphthalene ring is substituted by an alkyl group as a substituent, for example, the number of carbon atoms of the alkyl group is not included in the ring carbon atoms.

In the present specification, a term "ring atoms" represents the number of atoms forming a subject ring itself of a compound having a structure in which atoms are bonded in a ring form (for example, a monocycle, a fused ring and a ring assembly) (for example, a monocyclic compound, a fused ring compound, a cross-linked compound, a carbocyclic compound or a heterocyclic compound). The term "ring atoms" does not include atoms which do not form the ring (for example, a hydrogen atom which terminates a bond of the atoms forming the ring) or atoms contained in a substituent when the ring is substituted by the substituent. The same shall apply to the "ring atoms" described below, unless otherwise noted. For example, a pyridine ring has 6 ring atoms, a quinazoline ring has 10 ring atoms, and a furan ring has 5 ring atoms. A hydrogen atom bonded with a carbon atom of the pyridine ring or the quinazoline ring or an atom forming the substituent is not included in the number of the ring atoms.

In the present specification, a term "XX to YY carbon atoms" in an expression of "substituted or unsubstituted ZZ group having XX to YY carbon atoms" represents the number of carbon atoms when the ZZ group is unsubstituted. The number of carbon atoms of a substituent when the ZZ group is substituted is not included. Here, "YY" is larger than "XX", and "XX" and "YY" each mean an integer of 1 or more.

In the present specification, a term "XX to YY atoms" in an expression of "substituted or unsubstituted ZZ group having XX to YY atoms" represents the number of atoms when the ZZ group is unsubstituted. The number of atoms of a substituent when the group is substituted is not included. Here, "YY" is larger than "XX", and "XX" and "YY" each mean an integer of 1 or more.

A term "unsubstituted" in the case of "substituted or unsubstituted ZZ group" means that the ZZ group is not substituted by a substituent, and a hydrogen atom is bonded therewith. Alternatively, a term "substituted" in the case of "substituted or unsubstituted ZZ group" means that one or more hydrogen atoms in the ZZ group are substituted by a substituent. Similarly, a term "substituted" in the case of "BB group substituted by an AA group" means that one or more hydrogen atoms in the BB group are substituted by the AA group.

Hereinafter, the substituent described herein will be described.

The number of the ring carbon atoms of the "unsubstituted aryl group" described herein is 6 to 50, preferably 6 to 30, and more preferably 6 to 18, unless otherwise specified.

The number of the ring carbon atoms of the "unsubstituted heterocyclic group" described herein is 5 to 50, preferably 5 to 30, and more preferably 5 to 18, unless otherwise specified.

The number of the carbon atoms of the "unsubstituted alkyl group" described herein is 1 to 50, preferably 1 to 20, and more preferably 1 to 6, unless otherwise specified.

The number of the carbon atoms of the "unsubstituted alkenyl group" described herein is 2 to 50, preferably 2 to 20, and more preferably 2 to 6, unless otherwise specified.

The number of the carbon atoms of the "unsubstituted alkynyl group" described herein is 2 to 50, preferably 2 to 20, and more preferably 2 to 6, unless otherwise specified.

The number of the ring carbon atoms of the "unsubstituted cycloalkyl group" described herein is 3 to 50, preferably 3 to 20, and more preferably 3 to 6, unless otherwise specified.

The number of the ring carbon atoms of the "unsubstituted arylene group" described herein is 6 to 50, preferably 6 to 30, and more preferably 6 to 18, unless otherwise specified.

The number of the ring atoms of the "unsubstituted divalent heterocyclic group" described herein is 5 to 50, preferably 5 to 30, and more preferably 5 to 18, unless otherwise specified.

The number of the carbon atoms of the "unsubstituted alkylene group" described herein is 1 to 50, preferably 1 to 20, and more preferably 1 to 6, unless otherwise specified.

Specific examples (specific example group G1) of the "substituted or unsubstituted aryl group" described herein include an unsubstituted aryl group and a substituted aryl group described below. (Here, a term "unsubstituted aryl group" refers to a case where the "substituted or unsubstituted aryl group" is the "unsubstituted aryl group," and a term "substituted aryl group" refers to a case where the "substituted or unsubstituted aryl group" is the "substituted aryl group". Hereinafter, a case of merely "aryl group" includes both the "unsubstituted aryl group" and the "substituted aryl group".

The "substituted aryl group" refers to a case where the "unsubstituted aryl group" has a substituent, and specific examples thereof include a group in which the "unsubstituted aryl group" has the substituent, and a substituted aryl group described below. It should be noted that examples of the "unsubstituted aryl group" and examples of the "substituted aryl group" listed herein are only one example, and the "substituted aryl group" described herein also includes a group in which a group in which "unsubstituted aryl group" has a substituent further has a substituent, and a group in which "substituted aryl group" further has a substituent, and the like.

An unsubstituted aryl group:
a phenyl group,
a p-biphenyl group,
a m-biphenyl group,
an o-biphenyl group,
a p-terphenyl-4-yl group,
a p-terphenyl-3-yl group,
a p-terphenyl-2-yl group,
a m-terphenyl-4-yl group,
a m-terphenyl-3-yl group,
a m-terphenyl-2-yl group,
an o-terphenyl-4-yl group,
an o-terphenyl-3-yl group,
an o-terphenyl-2-yl group,
a 1-naphthyl group,
a 2-naphthyl group,
an anthryl group,
a benzanthryl group,
a phenanthryl group,
a benzophenanthryl group,
a phenalenyl group,
a pyrenyl group,
a chrysenyl group,
a benzochrysenyl group,
a triphenylenyl group,
a benzotriphenylenyl group,
a tetracenyl group,
a pentacenyl group,
a fluorenyl group,
a 9,9'-spirobifluorenyl group,
a benzofluorenyl group,
a dibenzofluorenyl group,
a fluoranethenyl group,
a benzofluoranthenyl group, and
a perylenyl group.
A substituted aryl group:
an o-tolyl group,
a m-tolyl group,
a p-tolyl group,
a p-xylyl group,
a m-xylyl group,
an o-xylyl group,
a p-isopropyl phenyl group,
a m-isopropyl phenyl group,
an o-isopropyl phenyl group,
a p-t-butylphenyl group,
a m-t-butylphenyl group,
an o-t-butylphenyl group,
a 3,4,5-trimethylphenyl group,
a 9,9-dimethylfluorenyl group,
a 9,9-diphenylfluorenyl group
a 9,9-di(4-methylphenyl)fluorenyl group,
a 9,9-di(4-isopropylphenyl)fluorenyl group,
a 9,9-di(4-t-butylphenyl)fluorenyl group,
a cyanophenyl group,
a triphenylsilylphenyl group,
a trimethylsilylphenyl group,
a phenylnaphthyl group, and
a naphthylphenyl group.

The "heterocyclic group" described herein is a ring group having at least one hetero atom in the ring atom. Specific examples of the hetero atom include a nitrogen atom, an oxygen atom, a sulfur atom, a silicon atom, a phosphorus atom and a boron atom.

The "heterocyclic group" described herein may be a monocyclic group, or a fused ring group.

The "heterocyclic group" described herein may be an aromatic heterocyclic group, or an aliphatic heterocyclic group.

Specific examples (specific example group G2) of the "substituted or unsubstituted heterocyclic group" include an unsubstituted heterocyclic group and a substituted heterocyclic group described below. (Here, the unsubstituted heterocyclic group refers to a case where the "substituted or unsubstituted heterocyclic group" is the "unsubstituted heterocyclic group," and the substituted heterocyclic group refers to a case where the "substituted or unsubstituted heterocyclic group" is the "substituted heterocyclic group". Hereinafter, the case of merely "heterocyclic group" includes both the "unsubstituted heterocyclic group" and the "substituted heterocyclic group".

The "substituted heterocyclic group" refers to a case where the "unsubstituted heterocyclic group" has a substituent, and specific examples thereof include a group in which the "unsubstituted heterocyclic group" has a substituent, and a substituted heterocyclic group described below. It should be noted that examples of the "unsubstituted heterocyclic group" and examples of the "substituted heterocyclic group" listed herein are merely one example, and the "substituted heterocyclic group" described herein also includes a group in which "unsubstituted heterocyclic group" which has a substituent further has a substituent, and a group in which "substituted heterocyclic group" further has a substituent, and the like.

An unsubstituted heterocyclic group having a nitrogen atom:
  a pyrrolyl group,
  an imidazolyl group,
  a pyrazolyl group,
  a triazolyl group,
  a tetrazolyl group,
  an oxazolyl group,
  an isoxazolyl group,
  an oxadiazolyl group,
  a thiazolyl group,
  an isothiazolyl group,
  a thiadiazolyl group,
  a pyridyl group,
  a pyridazinyl group,
  a pyrimidinyl group,
  a pyrazinyl group,
  a triazinyl group,
  an indolyl group,
  an isoindolyl group,
  an indolizinyl group,
  a quinolizinyl group,
  a quinolyl group,
  an isoquinolyl group,
  a cinnolyl group,
  a phthalazinyl group,
  a quinazolinyl group,
  a quinoxalinyl group,
  a benzimidazolyl group,
  an indazolyl group,
  a phenanthrolinyl group,
  a phenanthridinyl group
  an acridinyl group,
  a phenazinyl group,
  a carbazolyl group,
  a benzocarbazolyl group,
  a morpholino group,
  a phenoxazinyl group,
  a phenothiazinyl group,
  an azacarbazolyl group, and
  a diazacarbazolyl group.

An unsubstituted heterocyclic group having an oxygen atom:
  a furyl group,
  an oxazolyl group,
  an isoxazolyl group,
  an oxadiazolyl group,
  a xanthenyl group,
  a benzofuranyl group,
  an isobenzofuranyl group,
  a dibenzofuranyl group,
  a naphthobenzofuranyl group,
  a benzooxazolyl group,
  a benzisoxazolyl group,
  a phenoxazinyl group,
  a morpholino group,
  a dinaphthofuranyl group,
  an azadibenzofuranyl group,
  a diazadibenzofuranyl group,
  an azanaphthobenzofuranyl group, and
  a diazanaphthobenzofuranyl group.

An unsubstituted heterocyclic group having a sulfur atom:
  a thienyl group,
  a thiazolyl group,
  an isothiazolyl group,
  a thiadiazolyl group,
  a benzothiophenyl group,
  an isobenzothiophenyl group,
  a dibenzothiophenyl group,
  a naphthobenzothiophenyl group,
  a benzothiazolyl group,
  a benzisothiazolyl group,
  a phenothiazinyl group,
  a dinaphthothiophenyl group,
  an azadibenzothiophenyl group,
  a diazadibenzothiophenyl group,
  an azanaphthobenzothiophenyl group, and
  a diazanaphthobenzothiophenyl group.

A substituted heterocyclic group having a nitrogen atom:
  a (9-phenyl)carbazolyl group,
  a (9-biphenylyl)carbazolyl group,
  a (9-phenyl)phenylcarbazolyl group,
  a (9-naphthyl)carbazolyl group,
  a diphenylcarbazol-9-yl group,
  a phenylcarbazol-9-yl group,
  a methylbenzimidazolyl group,
  an ethylbenzimidazolyl group,
  a phenyltriazinyl group,
  a biphenylyltriazinyl group,
  a diphenyltriazinyl group,
  a phenylquinazolinyl group, and
  a biphenylylquinazolinyl group.

A substituted heterocyclic group having an oxygen atom:
  a phenyldibenzofuranyl group,
  a methyldibenzofuranyl group,
  a t-butyldibenzofuranyl group, and
  a monovalent residue of spiro[9H-xanthene-9,9'-[9H]fluorene].

A substituted heterocyclic group having a sulfur atom:
  a phenyldibenzothiophenyl group,
  a methyldibenzothiophenyl group,
  a t-butyldibenzothiophenyl group, and
  a monovalent residue of spiro[9H-thioxanthene-9,9'-[9H]fluorene].

A monovalent group derived from the following unsubstituted heterocyclic ring containing at least one of a nitrogen atom, an oxygen atom and a sulfur atom by removal of one hydrogen atom bonded to the ring atoms thereof, and a monovalent group in which a monovalent group derived from the following unsubstituted heterocyclic ring has a substituent by removal of one hydrogen atom bonded to the ring atoms thereof:
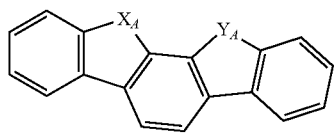
(XY-1)
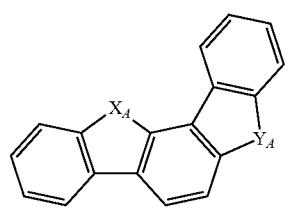
(XY-2)
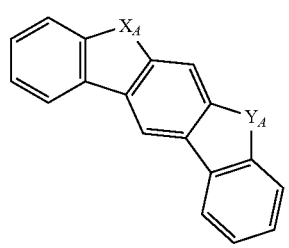
(XY-3)
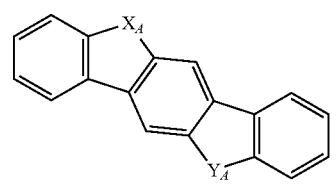
(XY-4)
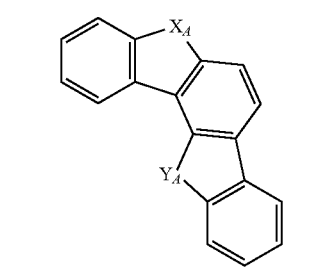
(XY-5)
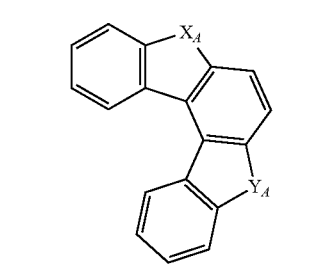
(XY-6)
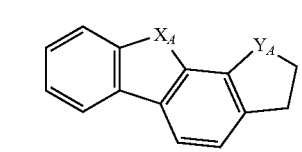
(XY-7)
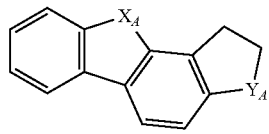
(XY-8)
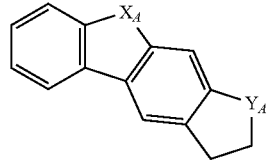
(XY-9)
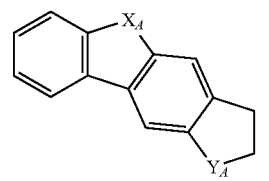
(XY-10)
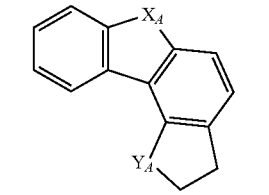
(XY-11)
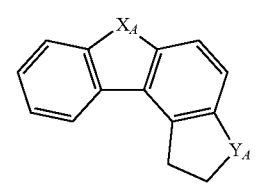
(XY-12)
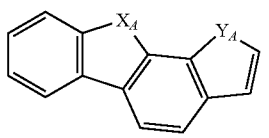
(XY-13)
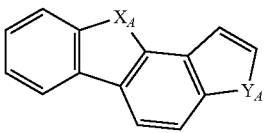
(XY-14)
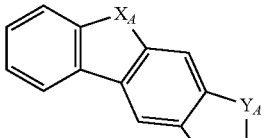
(XY-15)
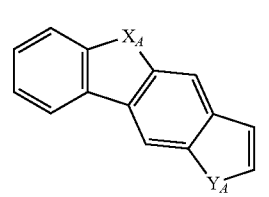
(XY-16)

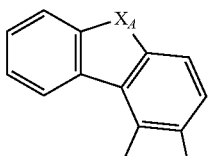
(XY-17)

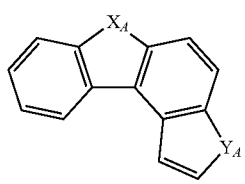
(XY-18)

In the formulas (XY-1) to (XY-18), $X_A$ and $Y_A$ are independently an oxygen atom, a sulfur atom, NH or $CH_2$. However, at least one of $X_A$ and $Y_A$ is an oxygen atom, a sulfur atom or NH.

The heterocyclic ring represented by the formulas (XY-1) to (XY-18) becomes a monovalent heterocyclic group having a bond at an arbitrary position.

An expression "the monovalent group derived from the unsubstituted heterocyclic ring represented by the formulas (XY-1) to (XY-18) has a substituent" refers to a case where the hydrogen atom bonded with the carbon atom which constitutes a skeleton of the formulas is substituted by a substituent, or a state in which $X_A$ or $Y_A$ is NH or $CH_2$, and the hydrogen atom in the NH or $CH_2$ is replaced with a substituent.

Specific examples (specific example group G3) of the "substituted or unsubstituted alkyl group" include an unsubstituted alkyl group and a substituted alkyl group described below. (Here, the unsubstituted alkyl group refers to a case where the "substituted or unsubstituted alkyl group" is the "unsubstituted alkyl group," and the substituted alkyl group refers to a case where the "substituted or unsubstituted alkyl group" is the "substituted alkyl group"). Hereinafter, the case of merely "alkyl group" includes both the "unsubstituted alkyl group" and the "substituted alkyl group".

The "substituted alkyl group" refers to a case where the "unsubstituted alkyl group" has a substituent, and specific examples thereof include a group in which the "unsubstituted alkyl group" has a substituent, and a substituted alkyl group described below. It should be noted that examples of the "unsubstituted alkyl group" and examples of the "substituted alkyl group" listed herein are merely one example, and the "substituted alkyl group" described herein also includes a group in which "unsubstituted alkyl group" has a substituent further has a substituent, a group in which "substituted alkyl group" further has a substituent, and the like.

An unsubstituted alkyl group:
a methyl group,
an ethyl group,
a n-propyl group,
an isopropyl group,
a n-butyl group,
an isobutyl group,
a s-butyl group, and
a t-butyl group.
A substituted alkyl group:
a heptafluoropropyl group (including an isomer),
a pentafluoroethyl group,
a 2,2,2-trifluoroethyl group, and
a trifluoromethyl group.

Specific examples (specific example group G4) of the "substituted or unsubstituted alkenyl group" include an unsubstituted alkenyl group and a substituted alkenyl group described below. (Here, the unsubstituted alkenyl group refers to a case where the "substituted or unsubstituted alkenyl group" is the "unsubstituted alkenyl group," and the substituted alkenyl group refers to a case where the "substituted or unsubstituted alkenyl group" is the "substituted alkenyl group"). Hereinafter, the case of merely "alkenyl group" includes both the "unsubstituted alkenyl group" and the "substituted alkenyl group".

The "substituted alkenyl group" refers to a case where the "unsubstituted alkenyl group" has a substituent, and specific examples thereof include a group in which the "unsubstituted alkenyl group" has a substituent, and a substituted alkenyl group described below. It should be noted that examples of the "unsubstituted alkenyl group" and examples of the "substituted alkenyl group" listed herein are merely one example, and the "substituted alkenyl group" described herein also includes a group in which "unsubstituted alkenyl group" has a substituent further has a substituent, a group in which "substituted alkenyl group" further has a substituent, and the like.

An unsubstituted alkenyl group and a substituted alkenyl group:
a vinyl group,
an allyl group,
a 1-butenyl group,
a 2-butenyl group,
a 3-butenyl group,
a 1,3-butanedienyl group,
a 1-methylvinyl group,
a 1-methylallyl group,
a 1,1-dimethylallyl group,
a 2-methylallyl group, and
a 1,2-dimethylallyl group.

Specific examples (specific example group G5) of the "substituted or unsubstituted alkynyl group" include an unsubstituted alkynyl group described below. (Here, the unsubstituted alkynyl group refers to a case where the "substituted or unsubstituted alkynyl group" is the "unsubstituted alkynyl group"). Hereinafter, a case of merely "alkynyl group" includes both the "unsubstituted alkynyl group" and the "substituted alkynyl group".

The "substituted alkynyl group" refers to a case where the "unsubstituted alkynyl group" has a substituent, and specific examples thereof include a group in which the "unsubstituted alkynyl group" described below has a substituent.

An unsubstituted alkynyl group:
an ethynyl group.

Specific examples (specific example group G6) of the "substituted or unsubstituted cycloalkyl group" described herein include an unsubstituted cycloalkyl group and a substituted cycloalkyl group described below. (Here, the unsubstituted cycloalkyl group refers to a case where the "substituted or unsubstituted cycloalkyl group" is the "unsubstituted cycloalkyl group," and the substituted cycloalkyl group refers to a case where the "substituted or unsubstituted cycloalkyl group" is the "substituted cycloalkyl group"). Hereinafter, a case of merely "cycloalkyl group" includes both the "unsubstituted cycloalkyl group" and the "substituted cycloalkyl group".

The "substituted cycloalkyl group" refers to a case where the "unsubstituted cycloalkyl group" a the substituent, and specific examples thereof include a group in which the "unsubstituted cycloalkyl group" has a substituent, and a substituted cycloalkyl group described below. It should be noted that examples of the "unsubstituted cycloalkyl group" and examples of the "substituted cycloalkyl group" listed herein are merely one example, and the "substituted cycloalkyl group" described herein also includes a group in which "unsubstituted cycloalkyl group" has a substituent further has a substituent, a group in which "substituted cycloalkyl group" further has a substituent, and the like.

An unsubstituted aliphatic ring group:
a cyclopropyl group,
a cyclobutyl group,
a cyclopentyl group,
a cyclohexyl group,
a 1-adamantyl group,
a 2-adamantyl group,
a 1-norbornyl group, and
a 2-norbornyl group.

A substituted cycloalkyl group:
a 4-methylcyclohexyl group.

Specific examples (specific example group G7) of the group represented by —Si($R_{901}$)($R_{902}$)($R_{903}$) described herein include
—Si(G1)(G1)(G1),
—Si(G1)(G2)(G2),
—Si(G1)(G1)(G2),
—Si(G2)(G2)(G2),
—Si(G3)(G3)(G3),
—Si(G5)(G5)(G5) and
—Si(G6)(G6)(G6).

In which,
G1 is the "aryl group" described in the specific example group G1.
G2 is the "heterocyclic group" described in the specific example group G2.
G3 is the "alkyl group" described in the specific example group G3.
G5 is the "alkynyl group" described in the specific example group G5.
G6 is the "cycloalkyl group" described in the specific example group G6.

Specific examples (specific example group G8) of the group represented by —O—($R_{904}$) described herein include
—O(G1),
—O(G2),
—O(G3) and
—O(G6).

In which,
G1 is the "aryl group" described in the specific example group G1.
G2 is the "heterocyclic group" described in the specific example group G2.
G3 is the "alkyl group" described in the specific example group G3.
G6 is the "cycloalkyl group" described in the specific example group G6.

Specific examples (specific example group G9) of the group represented by —S—($R_{905}$) described herein include
—S(G1),
—S(G2),
—S(G3) and
—S(G6).

In which,
G1 is the "aryl group" described in the specific example group G1.
G2 is the "heterocycle group" described in the specific example group G2.
G3 is the "alkyl group" described in the specific example group G3.
G6 is the "cycloalkyl group" described in the specific example group G6.

Specific examples (specific example group G10) of the group represented by —N($R_{906}$)($R_{907}$) described herein include
—N(G1)(G1),
—N(G2)(G2),
—N(G1)(G2),
—N(G3)(G3) and
—N(G6) (G6).

In which,
G1 is the "aryl group" described in the specific example group G1.
G2 is the "heterocycle group" described in the specific example group G2.
G3 is the "alkyl group" described in the specific example group G3.
G6 is the "cycloalkyl group" described in the specific example group G6.

Specific examples (specific example group G11) of the "halogen atom" described herein include a fluorine atom, a chlorine atom, a bromine atom and an iodine atom.

Specific examples of the "alkoxy group" described herein include a group represented by —O(G3), where G3 is the "alkyl group" described in the specific example group G3. The number of carbon atoms of the "unsubstituted alkoxy group" are 1 to 50, preferably 1 to 30, and more preferably 1 to 18, unless otherwise specified.

Specific examples of the "alkylthio group" described herein include a group represented by —S(G3), where G3 is the "alkyl group" described in the specific example group G3. The number of carbon atoms of the "unsubstituted alkylthio group" are 1 to 50, preferably 1 to 30, and more preferably 1 to 18, unless otherwise specified.

Specific examples of the "aryloxy group" described herein include a group represented by —O(G1), where G1 is the "aryl group" described in the specific example group G1. The number of ring carbon atoms of the "unsubstituted aryloxy group" are 6 to 50, preferably 6 to 30, and more preferably 6 to 18, unless otherwise specified.

Specific examples of the "arylthio group" described herein include a group represented by —S(G1), where G1 is the "aryl group" described in the specific example group G1. The number of ring carbon atoms of the "unsubstituted arylthio group" are 6 to 50, preferably 6 to 30, and more preferably 6 to 18, unless otherwise specified.

Specific examples of the "aralkyl group" described herein include a group represented by -(G3)-(G1), where G3 is the "alkyl group" described in the specific example group G3, and G1 is the "aryl group" described in the specific example group G1. Accordingly, the "aralkyl group" is one embodiment of the "substituted alkyl group" substituted by the "aryl group". The number of carbon atoms of the "unsubstituted aralkyl group," which is the "unsubstituted alkyl group" substituted by the "unsubstituted aryl group," are 7 to 50, preferably 7 to 30, and more preferably 7 to 18, unless otherwise specified.

Specific example of the "aralkyl group" include a benzyl group, a 1-phenylethyl group, a 2-phenylethyl group, a 1-phenylisopropyl group, a 2-phenylisopropyl group, a phenyl-t-butyl group, an α-naphthylmethyl group, a 1-α-naphthylethyl group, a 2-α-naphthylethyl group, a 1-α-naphthylisopropyl group, a 2-α-naphthylisopropyl group, a β-naphthylmethyl group, a 1-β-naphthylethyl group, a 2-β-naphthylethyl group, a 1-β-naphthylisopropyl group, and a 2-β-naphthylisopropyl group.

The substituted or unsubstituted aryl group described herein is, unless otherwise specified, preferably a phenyl group, a p-biphenyl group, a m-biphenyl group, an o-biphenyl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group, an o-terphenyl-4-yl group, an o-terphenyl-3-yl group, an o-terphenyl-2-yl group, a 1-naphthyl group, a 2-naphthyl group, an anthryl group, a phenanthryl group, a pyrenyl group, a chrysenyl group, a triphenylenyl group, a fluorenyl group, a 9,9'-spirobifluorenyl group, a 9,9-diphenylfluorenyl group, or the like.

The substituted or unsubstituted heterocyclic group described herein is, unless otherwise specified, preferably a pyridyl group, a pyrimidinyl group, a triazinyl group, a quinolyl group, an isoquinolyl group, a quinazolinyl group, a benzimidazolyl group, a phenanthrolinyl group, a carbazolyl group (a 1-carbazolyl group, a 2-carbazolyl group, a 3-carbazolyl group, a 4-carbazolyl group, or a 9-carbazolyl group), a benzocarbazolyl group, an azacarbazolyl group, a diazacarbazolyl group, a dibenzofuranyl group, a naphthobenzofuranyl group, an azadibenzofuranyl group, a diazadibenzofuranyl group, a dibenzothiophenyl group, a naphthobenzothiophenyl group, an azadibenzothiophenyl group, a diazadibenzothiophenyl group, a (9-phenyl)carbazolyl group (a (9-phenyl)carbazol-1-yl group, a (9-phenyl)carbazol-2-yl group, a (9-phenyl)carbazol-3-yl group, or a (9-phenyl)carbazol-4-yl group), a (9-biphenylyl)carbazolyl group, a (9-phenyl)phenylcarbazolyl group, a diphenylcarbazole-9-yl group, a phenylcarbazol-9-yl group, a phenyltriazinyl group, a biphenylyltriazinyl group, diphenyltriazinyl group, a phenyldibenzofuranyl group, a phenyldibenzothiophenyl group, an indrocarbazolyl group, a pyrazinyl group, a pyridazinyl group, a quinazolinyl group, a cinnolinyl group, a phthalazinyl group, a quinoxalinyl group, a pyrrolyl group, an indolyl group, a pyrrolo[3,2,1-jk]carbazolyl group, a furanyl group, a benzofuranyl group, a thiophenyl group, a benzothiophenyl group, a pyrazolyl group, an imidazolyl group, a benzimidazolyl group, a triazolyl group, an oxazolyl group, a benzoxazolyl group, a thiazolyl group, a benzothiazolyl group, an isothiazolyl group, a benzisothiazolyl group, a thiadiazolyl group, an isoxazolyl group, a benzisoxazolyl group, a pyrrolidinyl group, a piperidinyl group, a piperazinyl group, an imidazolidinyl group, an indro[3,2,1-jk]carbazolyl group, a dibenzothiophenyl group, or the like.

The dibenzofuranyl group and the dibenzothiophenyl group as described above are specifically any group described below, unless otherwise specified.

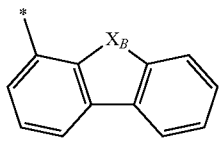
(XY-76)

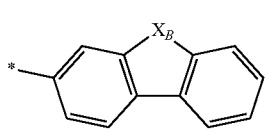
(XY-77)

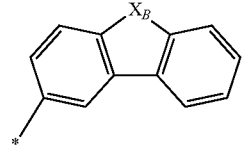
(XY-78)

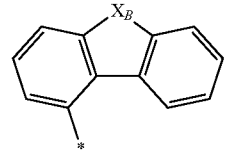
(XY-79)

In the formulas (XY-76) to (XY-79), $X_B$ is an oxygen atom or a sulfur atom.

The substituted or unsubstituted alkyl group described herein is, unless otherwise specified, preferably a methyl group, an ethyl group, a propyl group, an isopropyl group, a n-butyl group, an isobutyl group, a t-butyl group, or the like.

The "substituted or unsubstituted arylene group" descried herein refers to a group in which the above-described "aryl group" is converted into divalence, unless otherwise specified. Specific examples (specific example group G12) of the "substituted or unsubstituted arylene group" include a group in which the "aryl group" described in the specific example group G1 is converted into divalence. Namely, specific examples (specific example group G12) of the "substituted or unsubstituted arylene group" refer to a group derived from the "aryl group" described in specific example group G1 by removal of one hydrogen atom bonded to the ring carbon atoms thereof.

Specific examples (specific example group G13) of the "substituted or unsubstituted divalent heterocyclic group" include a group in which the "heterocyclic group" described in the specific example group G2 is converted into divalence. Namely, specific examples (specific example group G13) of the "substituted or unsubstituted divalent heterocyclic group" refer to a group derived from the "heterocyclic group" described in specific example group G2 by removal of one hydrogen atom bonded to the ring atoms thereof.

Specific examples (specific example group G14) of the "substituted or unsubstituted alkylene group" include a group in which the "alkyl group" described in the specific example group G3 is converted into divalence. Namely, specific examples (specific example group G14) of the "substituted or unsubstituted alkylene group" refer to a group derived from the "alkyl group" described in specific example group G3 by removal of one hydrogen atom bonded to the carbon atoms constituting the alkane structure thereof.

The substituted or unsubstituted arylene group described herein is any group described below, unless otherwise specified.

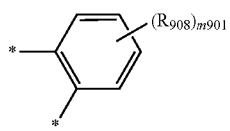
(XY-20)

(XY-21) 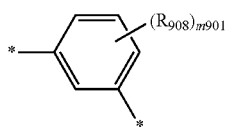
(XY-22) 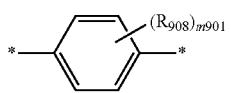
(XY-23) 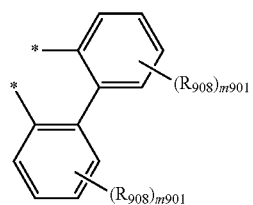
(XY-24) 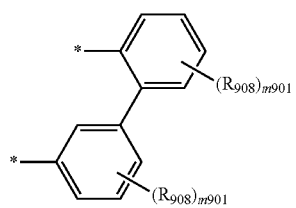
(XY-25) 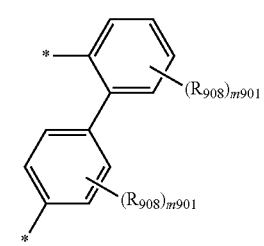
(XY-26) 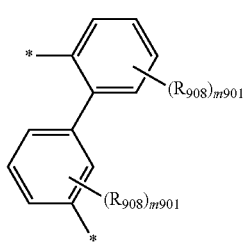
(XY-27) 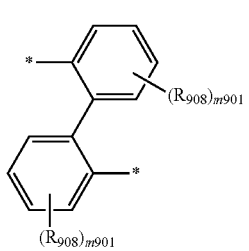
(XY-28) 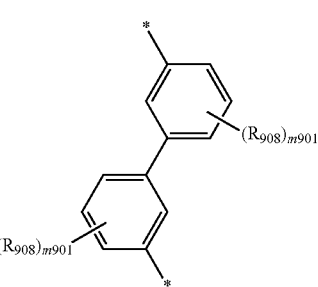
(XY-29) 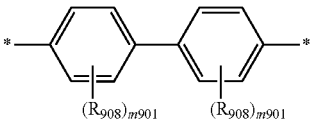
(XY-83) 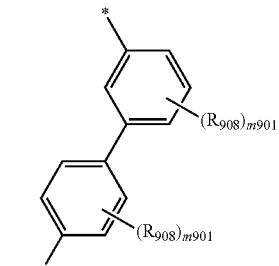
(XY-84) 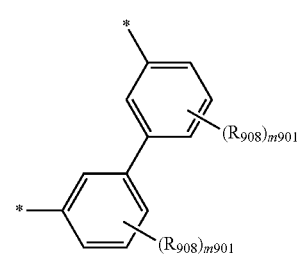
In the formulas (XY-20) to (XY-29), (XY-83) and (XY-84), $R_{908}$ is a substituent.
Then, m901 is an integer of 0 to 4, and when m901 is 2 or more, a plurality of $R_{908}$ may be the same with or different from each other.
(XY-30) 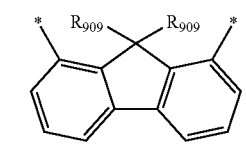
(XY-31) 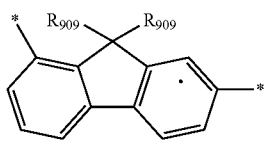
(XY-32) 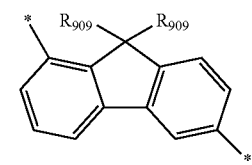

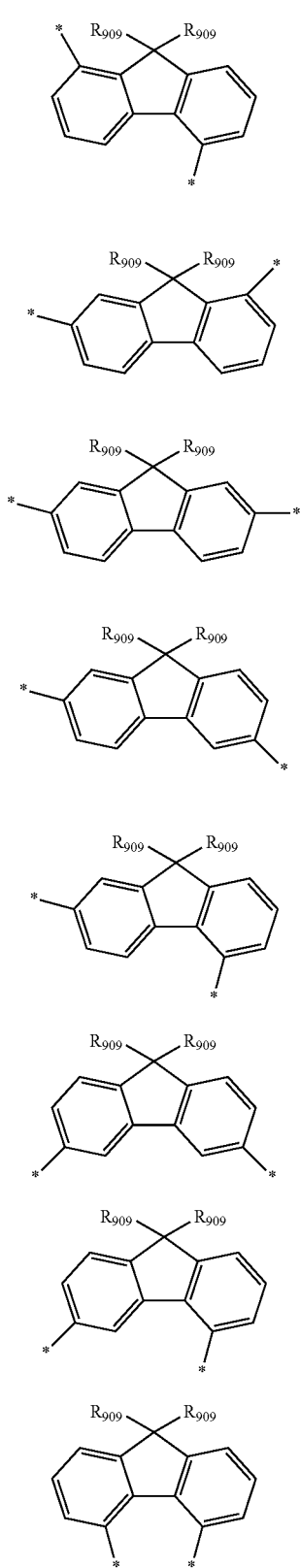

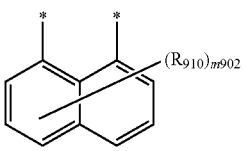

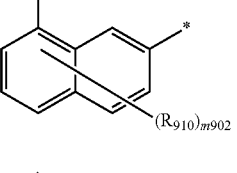

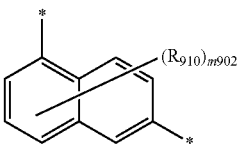

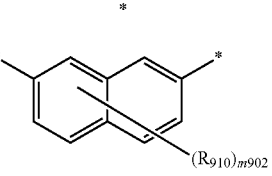

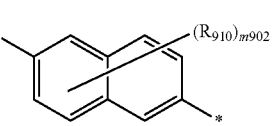

In the formulas (XY-41) to (XY-46), $R_{910}$ is a substituent. Then, m902 is an integer of 0 to 6. When m902 is 2 or more, a plurality of $R_{910}$ may be the same with or different from each other.

The substituted or unsubstituted divalent heterocyclic group described herein is preferably any group described below, unless otherwise specified.

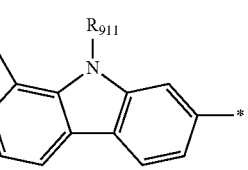

In the formulas (XY-30) to (XY-40), $R_{909}$ is independently a hydrogen atom or a substituent. Two of $R_{909}$ may be bonded with each other through a single bond to form a ring.

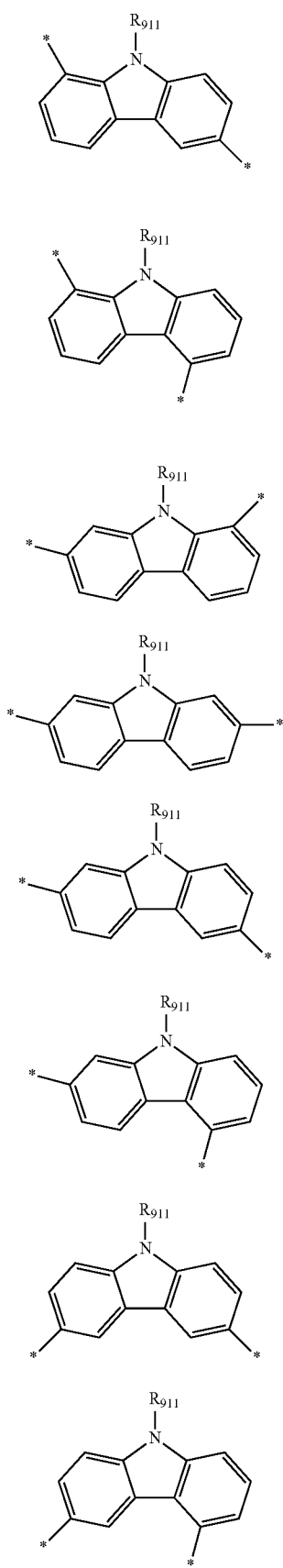
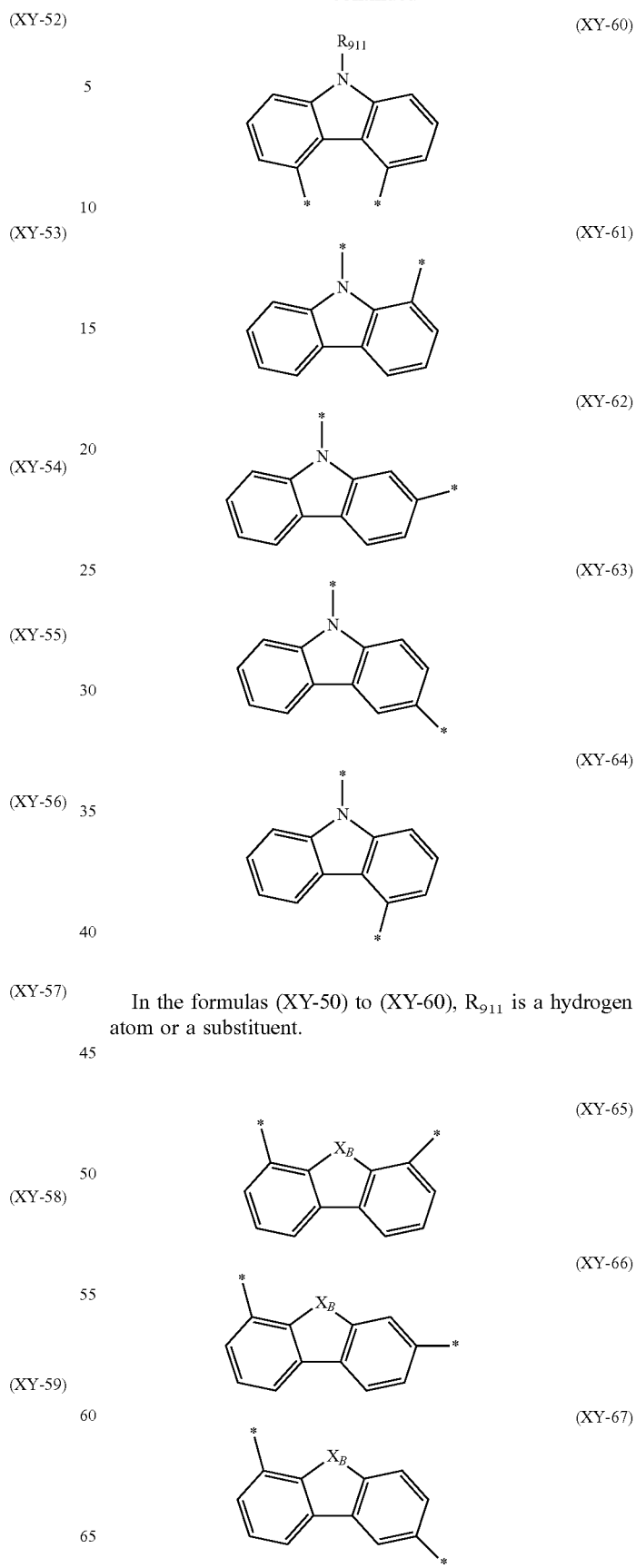
In the formulas (XY-50) to (XY-60), R₉₁₁ is a hydrogen atom or a substituent.

-continued (XY-68)
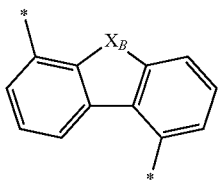

(XY-69)
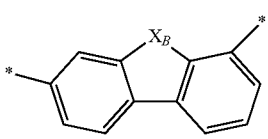

(XY-70)
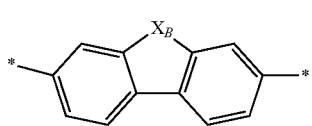

(XY-71)
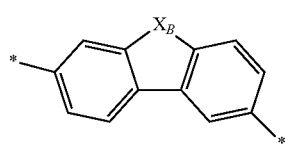

(XY-72)
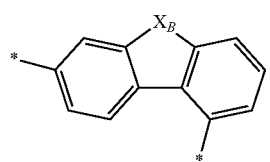

(XY-73)
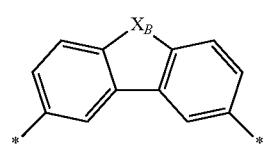

(XY-74)

(XY-75)
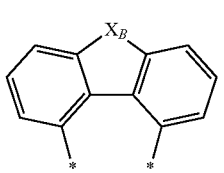

In the formulas (XY-65) to (XY-75), $X_B$ is an oxygen atom or a sulfur atom.

Herein, a case where "one or more sets of two or more groups adjacent to each other are bonded with each other to form a substituted or unsubstituted and saturated or unsaturated ring" will be described by taking, as an example, a case of an anthracene compound represented by the following formula (XY-80) in which a mother skeleton is an anthracene ring.

(XY-80)
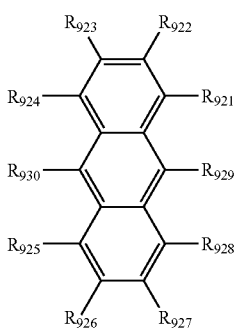

For example, two adjacent to each other into one set when "one or more sets of two or more groups adjacent to each other are bonded with each other to form the ring" among $R_{921}$ to $R_{930}$ include $R_{921}$ and $R_{922}$, $R_{922}$ and $R_{923}$, $R_{923}$ and $R_{924}$, $R_{924}$ and $R_{930}$, $R_{930}$ and $R_{925}$, $R_{925}$ and $R_{926}$, $R_{926}$ and $R_{927}$, $R_{927}$ and $R_{928}$, $R_{928}$ and $R_{929}$, and $R_{929}$ and $R_{921}$.

The above-described "one or more sets" means that two or more sets of two groups adjacent to each other may simultaneously form the ring. For example, a case where $R_{921}$ and $R_{922}$ are bonded with each other to form a ring A, and simultaneously $R_{925}$ and $R_{926}$ are bonded with each other to form a ring B is represented by the following formula (XY-81).

(XY-81)
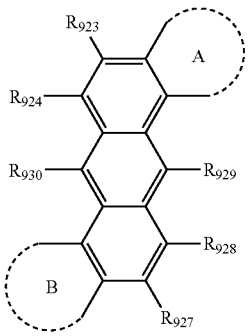

A case where "two or more groups adjacent to each other" form a ring means that, for example, $R_{921}$ and $R_{922}$ are bonded with each other to form a ring A, and $R_{922}$ and $R_{923}$ are bonded with each other to form a ring C. A case where the ring A and ring C sharing $R_{922}$ are formed, in which the ring A and the ring C are fused to the anthracene mother skeleton by three of $R_{921}$ to $R_{923}$ adjacent to each other, is represented by the following (XY-82).

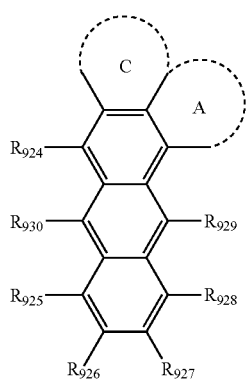

(XY-82)

The rings A to C formed in the formulas (XY-81) and (XY-82) are a saturated or unsaturated ring.

A term "unsaturated ring" means an aromatic hydrocarbon ring or an aromatic heterocyclic ring. A term "saturated ring" means an aliphatic hydrocarbon ring or an aliphatic heterocyclic ring.

For example, the ring A formed by $R_{921}$ and $R_{922}$ being bonded with each other, represented by the formula (XY-81), means a ring formed by a carbon atom of the anthracene skeleton bonded with $R_{921}$, a carbon atom of the anthracene skeleton bonded with $R_{922}$, and one or more arbitrary elements. Specific examples include, when the ring A is formed by $R_{921}$ and $R_{922}$, a case where an unsaturated ring is formed of a carbon atom of an anthracene skeleton bonded with $R_{921}$, a carbon atom of the anthracene skeleton bonded with $R_{922}$, and four carbon atoms, in which a ring formed by $R_{921}$ and $R_{922}$ is formed into a benzene ring. Further, when a saturated ring is formed, the ring is formed into a cyclohexane ring.

Here, "arbitrary elements" are preferably a C element, a N element, an O element and a S element. In the arbitrary elements (for example, a case of the C element or the N element), the bond(s) that is(are) not involved in the formation of the ring may be terminated by a hydrogen atom, or may be substituted by an arbitrary substituent. When the ring contains the arbitrary elements other than the C element, the ring to be formed is a heterocyclic ring.

The number of "one or more arbitrary elements" forming the saturated or unsaturated ring is preferably 2 or more and 15 or less, more preferably 3 or more and 12 or less, and further preferably 3 or more and 5 or less.

As specific examples of the aromatic hydrocarbon ring, a structure in which the aryl group described in specific example group G1 is terminated with a hydrogen atom may be mentioned.

As specific examples of the aromatic heterocyclic ring, a structure in which the aromatic heterocyclic group described in specific example group G2 is terminated with a hydrogen atom may be mentioned.

As specific examples of the aliphatic hydrocarbon ring, a structure in which the cycloalkyl group described in specific example group G6 is terminated with a hydrogen atom may be mentioned.

When the above-described "saturated or unsaturated ring" has a substituent, the substituent is an "arbitrary substituent" as described below, for example. When the above-mentioned "saturated or unsaturated ring" has a substituent, specific examples of the substituent refer to the substituents described in above-mentioned "the substituent described herein".

In one embodiment of the present specification, the substituent (hereinafter, referred to as an "arbitrary substituent" in several cases) in the case of the "substituted or unsubstituted" is a group selected from the group consisting of
an unsubstituted alkyl group having 1 to 50 carbon atoms,
an unsubstituted alkenyl group having 2 to 50 carbon atoms,
an unsubstituted alkynyl group having 2 to 50 carbon atoms,
an unsubstituted cycloalkyl group having 3 to 50 ring carbon atoms,
—Si($R_{901}$)($R_{902}$)($R_{903}$),
—O—($R_{904}$),
—S—($R_{905}$)
—N($R_{906}$)($R_{907}$)
wherein,
$R_{901}$ to $R_{907}$ are independently
a hydrogen atom,
a substituted or unsubstituted alkyl group having 1 to 50 carbon atoms,
a substituted or unsubstituted cycloalkyl group having 3 to 50 ring carbon atoms,
a substituted or unsubstituted aryl group having 6 to 50 ring carbon atoms, or
a substituted or unsubstituted monovalent heterocyclic group having 5 to 50 ring atoms; and when two or more of $R_{901}$ to $R_{907}$ exist, two or more of $R_{901}$ to $R_{907}$ may be the same with or different from each other,
a halogen atom, a cyano group, a nitro group,
an unsubstituted aryl group having 6 to 50 ring carbon atoms, and
an unsubstituted monovalent heterocyclic group having 5 to 50 ring atoms.

In one embodiment, the substituent in the case of "substituted or unsubstituted" is a group selected from the group consisting of
an alkyl group having 1 to 50 carbon atoms,
an aryl group having 6 to 50 ring carbon atoms, and
a monovalent heterocyclic group having 5 to 50 ring atoms.

In one embodiment, the substituent in the case of "substituted or unsubstituted" is a group selected from the group consisting of
an alkyl group having 1 to 18 carbon atoms,
an aryl group having 6 to 18 ring carbon atoms, and
a monovalent heterocyclic group having 5 to 18 ring atoms.

Specific examples of each group of the arbitrary substituent described above are as described above.

Herein, unless otherwise specified, the saturated or unsaturated ring (preferably substituted or unsubstituted and saturated or unsaturated five-membered or six-membered ring, more preferably a benzene ring) may be formed by the arbitrary substituents adjacent to each other.

Herein, unless otherwise specified, the arbitrary substituent may further have the substituent. Specific examples of the substituent that the arbitrary substituent further has include to the ones same as the arbitrary substituent described above.

[Organic EL Device]

The organic EL device according to one aspect of the invention comprises a cathode, an anode and an emitting layer disposed between the cathode and the anode, and it is characterized in that the emitting layer comprises a compound represented by the following formula (1) and one or more compounds selected from the group consisting of compounds represented by each of formulas (11), (21), (31), (41), (51), (61), (71) and (81).

Each compound is described later.

The organic EL device according to one aspect of the invention exhibits high device performance by possessing the above-mentioned constitution. Specifically, it is possible to provide an organic EL device with longer life.

According to one aspect of the present invention, a method for improving a performance of an organic EL device can also be provided. the method is characterized in that the compound represented by the formula (1) and one or more compounds selected from the group consisting of the formulas (11) to (81) are used in combination in the emitting layer of the organic EL device. Specifically, the method can improve an organic EL device performance as compared with the case where a compound having the same structure as formula (1) except that only protium atoms are contained as hydrogen atoms (hereinafter also referred to as "protium compound") is used as a host material. The case where the protium compound is used means that a host material in an emitting layer consists essentially of the protium compound (the ratio of the protium compound to the sum of the protium compound and the compound represented by formula (1) is 90 mol % or more, 95 mol % or more, or 99 mol % or more).

That is, it is possible to increase a performance of an organic EL device by, instead of a protium compound or in addition to a protium compound, using a compound obtained by replacing at least one protium atoms on an anthracene skeleton of the protium compound with a deuterium atom (a compound represented by formula (1)) as a host material.

A schematic outline of the organic EL device of one aspect of the invention is explained by reference to the FIGURE.

The organic EL device 1 according to one aspect of the invention comprises substrate 2, anode 3, emitting layer 5, cathode 10, organic layer 4 disposed between the anode 3 and the emitting layer 5, and organic layer 6 disposed between the emitting layer 5 and the cathode 10.

The compound represented by the formula (1) and one or more compounds selected from a group consisting of compounds represented by each of formula (11), (21), (31), (41), (51), (61), (71) and (81) are contained in emitting layer 5 disposed between the anode 3 and the cathode 10. Each compound contained in the emitting layer 5 may be used singly or in combination of two or more.

(Compound Represented by Formula (1))

The compound represented by the formula (1) is explained below.

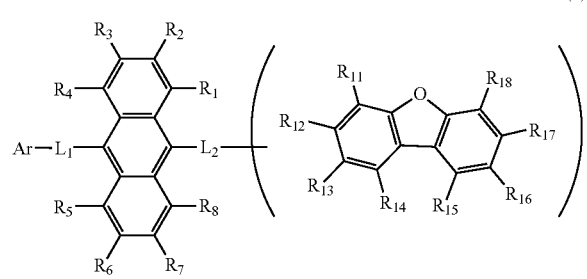

(1)

In the formula (1),
$R_1$ to $R_8$ are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;
$R_{901}$ to $R_{907}$ are independently
a hydrogen atom,
a substituted or unsubstituted alkyl group having 1 to 50 carbon atoms,
a substituted or unsubstituted cycloalkyl group having 3 to 50 ring carbon atoms,
a substituted or unsubstituted aryl group having 6 to 50 ring carbon atoms, or
a substituted or unsubstituted monovalent heterocyclic group having 5 to 50 ring atoms;
when two or more of $R_{901}$ to $R_{907}$ exist, two or more of $R_{901}$ to $R_{907}$ may be the same with or different from each other;
at least one of $R_1$ to $R_8$ is a deuterium atom;
two or more adjacent groups of $R_1$ to $R_4$ and two or more adjacent groups of $R_5$ to $R_8$ do not form a ring;
$L_1$ and $L_2$ are independently
a single bond,
a substituted or unsubstituted arylene group having 6 to 30 ring carbon atoms, or
a substituted or unsubstituted divalent heterocyclic group having 5 to 30 ring atoms;
Ar is
a substituted or unsubstituted aryl group having 6 to 50 ring carbon atoms, or
a substituted or unsubstituted monovalent heterocyclic group having 5 to 50 ring atoms;
one of $R_{11}$ to $R_{18}$ is a single bond bonding to $L_2$;
$R_{11}$ to $R_{18}$ which are not single bonds bonding to $L_2$ are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or a substituted or unsubstituted monovalent heterocyclic group having 5 to 50 ring atoms;

$R_{901}$ to $R_{907}$ are as defined in $R_1$ to $R_8$; and two or more adjacent groups of $R_{11}$ to $R_{18}$ do not form a ring.)

All of $R_1$ to $R_8$ may be deuterium atoms or a part of them (e.g., one or two of $R_1$ to $R_8$) may be deuterium atoms.

$R_1$ to $R_8$ that are not deuterium atoms are preferably hydrogen atoms (protium atoms).

In one embodiment, at least one hydrogen atom contained in one or more groups selected from a group consisting of $L_1$ and $L_2$ is a deuterium atom. In more detail, in one embodiment, one or more groups selected from the group consisting of $L_1$ and $L_2$ are an unsubstituted arylene group having 6 to 30 ring carbon atoms in which at least one hydrogen atom is a deuterium atom, or an unsubstituted divalent heterocyclic group having 5 to 30 ring atoms in which at least one hydrogen atom is a deuterium atom.

In one embodiment, $L_1$ and $L_2$ are independently a single bond, or a substituted or unsubstituted arylene group having 6 to 14 ring carbon atoms. It is preferable that at least one of $L_1$ and $L_2$ is a single bond.

In one embodiment, among $R_{11}$ to $R_{18}$, those which are not single bonds bonded to $L_2$ are hydrogen atoms.

In one embodiment, at least one of $R_{11}$ to $R_{18}$ which is not a single bond bonding to $L_2$ is a deuterium atom.

In one embodiment, at least one hydrogen atom contained in one or more Ar is a deuterium atom. In more detail, in one embodiment, Ar is an unsubstituted aryl group having 6 to 50 ring carbon atoms in which at least one hydrogen atom is a deuterium atom, or an unsubstituted monovalent heterocyclic group having 5 to 50 ring atoms in which at least one hydrogen atom is a deuterium atom.

Existence of a deuterium atom in the compound is confirmed by Mass Spectrometry or $^1$H-NMR Spectrometry. The bonding position of a deuterium atom in the compound is identified by $^1$H-NMR Spectrometry. In concrete terms, it is confirmed as follows.

If it is identified that, by Mass Spectrometry, a molecular weight of a target compound is greater by "one" than a molecular weight of a corresponding compound in which all hydrogen atoms are protium atoms, it is confirmed that one deuterium atom exists in the target compound. Further, the number of deuterium atoms in a molecule can be confirmed by an integration value obtained by $^1$H-NMR analysis on the target compound, since no signal is observed by performing $^1$H-NMR analysis on a deuterium atom. The bonding position of a deuterium can be identified by performing $^1$H-NMR analysis on the target compound and assigning signals.

In the organic EL device according to one aspect of the invention, the content ratio of the protium compound to the total of the compound represented by formula (1) and the protium compound in the emitting layer is preferably 99 mol % or less. The content ratio of the protium compound is confirmed by Mass Spectrometry.

In one embodiment, the emitting layer of the organic EL device according to one aspect of the invention includes the compound represented by the formula (1) and a protium compound, and the content ratio of the former to the total thereof is 30 mol % or more, 50 mol % or more, 70 mol % or more, 90 mol % or more, 95 mol % or more, 99 mol % or more, or 100 mol %.

Ar is preferably a substituted or unsubstituted aryl group having 6 to 50 ring carbon atoms, more preferably selected from groups represented by the following formulas (a1) to (a4).

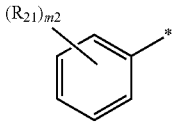

(a1)

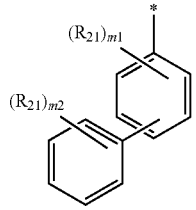

(a2)

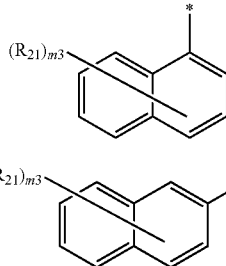

(a3)

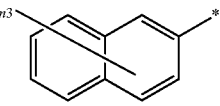

(a4)

wherein in the formulas (a1) to (a4),

* is a single bond bonding to $L_1$;

$R_{21}$ is a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms;

$R_{901}$ to $R_{907}$ are as defined in the formula (1);

m1 is an integer of 0 to 4;

m2 is an integer of 0 to 5;

m3 is an integer of 0 to 7;

when each of m1 to m3 is 2 or more, a plurality of $R_{21}$s may be the same or different; and when each of m1 to m3 is 2 or more, adjacent $R_{21}$s are bonded with each other to form a substituted or unsubstituted, saturated or unsaturated ring, or do not form a substituted or unsubstituted, saturated or unsaturated ring.

Preferably, $L_1$ and $L_2$ are independently a single bond, or a substituted or unsubstituted arylene group having 6 to 14 ring carbon atoms. It is preferable that at least one of $L_1$ and $L_2$ is a single bond.

In one embodiment, the compound represented by the formula (1) is a compound represented by following formula (2).

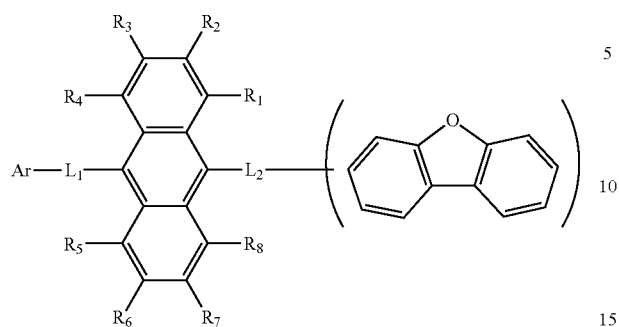

(2)

wherein in the formula (2), $R_1$ to $R_8$, Ar, $L_1$ and $L_2$ are as defined in the formula (1).

In one embodiment, the compound represented by the formula (1) is a compound represented by following formula (3).


(3)

wherein in the formula (3), Ar, $L_1$ and $L_2$ are as defined in the formula (1).

In one embodiment, the compound represented by the formula (1) is a compound represented by following formula (1A) or (1B).

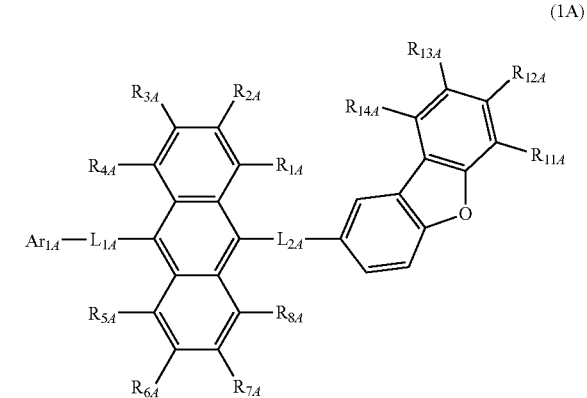

(1A)

(1B)

wherein in the formula (1A) and (1B), $R_{1A}$ to $R_{8A}$ are independently a hydrogen atom, and at least one of $R_{1A}$ to $R_{8A}$ is a deuterium atom;

$L_{1A}$ and $L_{2A}$ are independently a single bond, an unsubstituted phenylene group, or an unsubstituted naphthylene group;

$Ar_{1A}$ is a substituted or unsubstituted phenyl group or a substituted or unsubstituted naphthyl group, and the substituent for $Ar_{1A}$ is a phenyl group;

$R_{11A}$ to $R_{14A}$ are independently a hydrogen atom, or an unsubstituted aryl group including 6 to 50 ring carbon atoms; and two or more adjacent groups of $R_{11A}$ to $R_{14A}$ do not form a ring.

In one embodiment, in the formula (1A) or (1B), at least two of $R_{1A}$ to $R_{8A}$ are deuterium atoms.

In one embodiment, in the formula (1A) or (1B), $R_{1A}$ to $R_{8A}$ are all deuterium atoms.

In one embodiment, in the formula (1A) or (1B), at least one hydrogen atom contained in $Ar_{1A}$ is a deuterium atom.

In one embodiment, in the formula (1A) or (1B), $R_{11A}$ to $R_{14A}$ are hydrogen atoms.

In one embodiment, in the formula (1A) or (1B), $R_{11A}$ to $R_{14A}$ are deuterium atoms.

The compound represented by the formula (1) can be synthesized in accordance with the synthesis process described in Examples by using publicly known alternative reactions or materials corresponding to a target compound.

Examples of the compound represented by formula (1) include the following compounds.

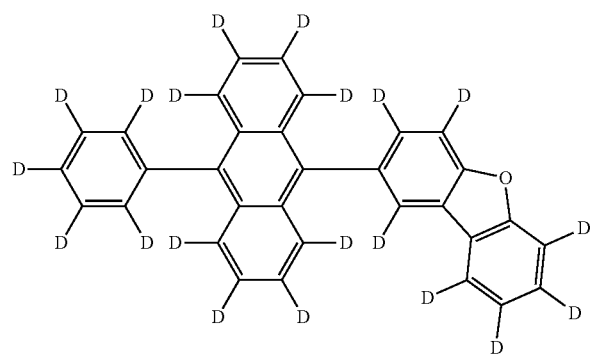
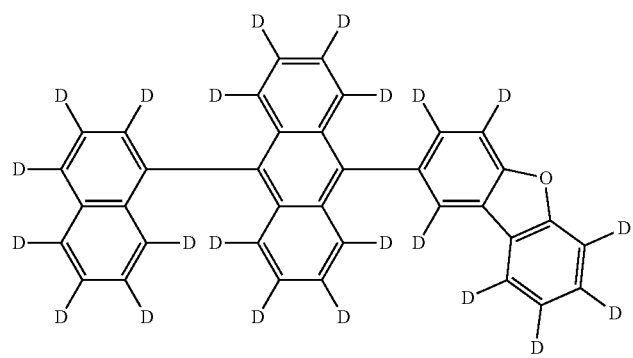
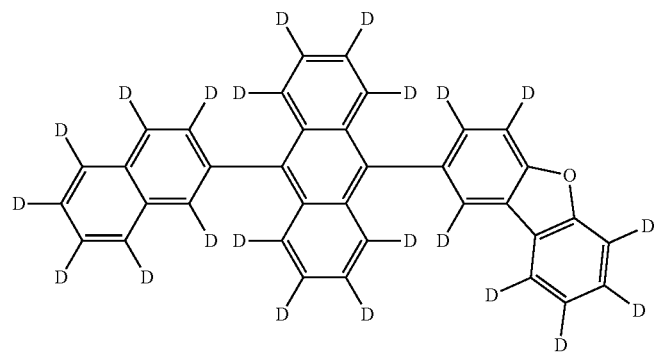
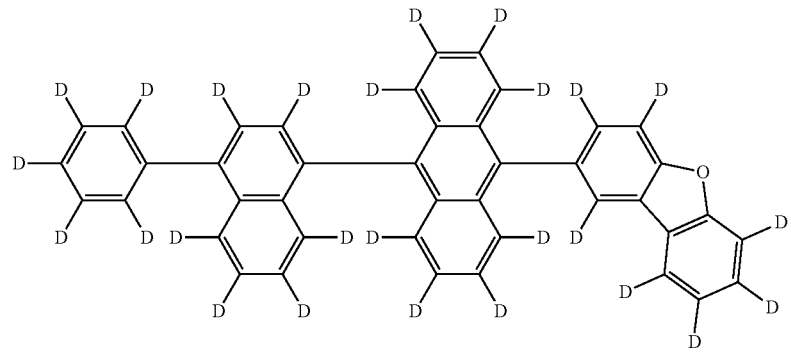

-continued
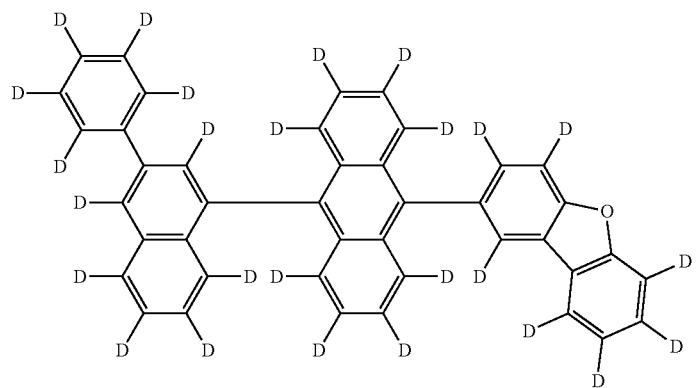
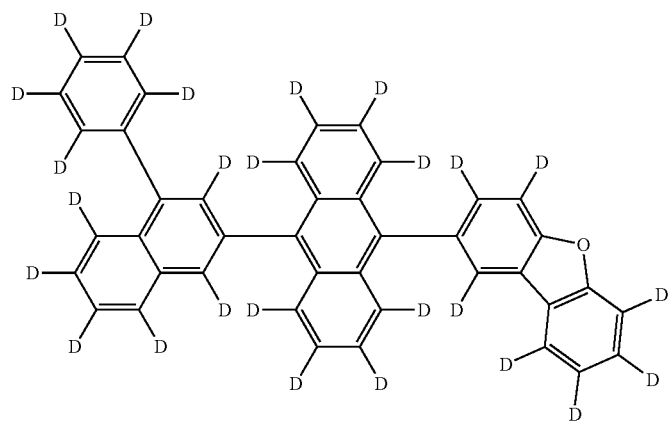
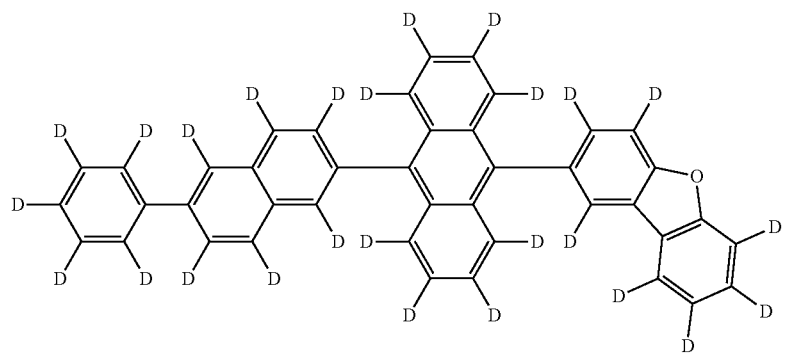
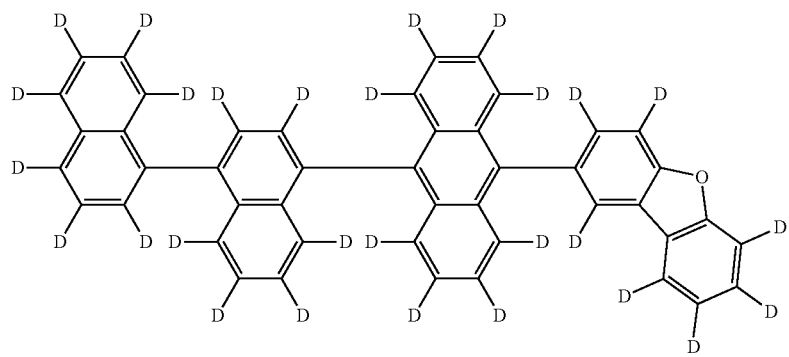

-continued
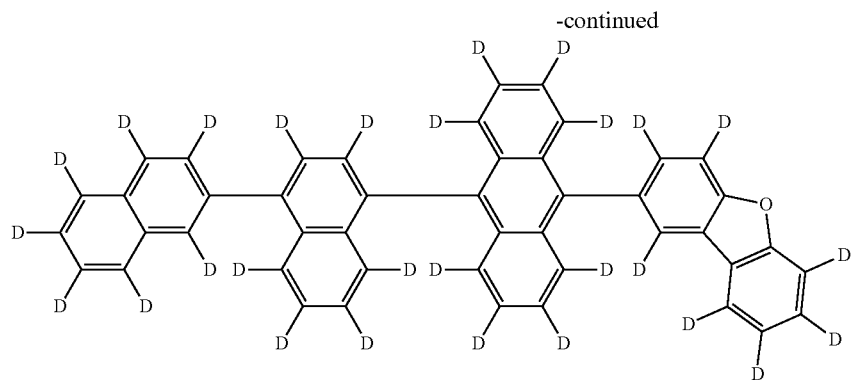
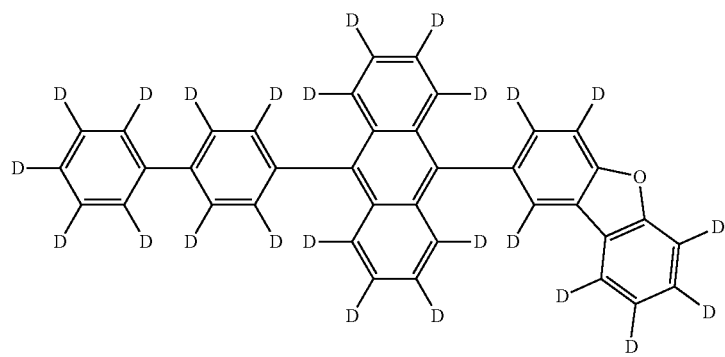
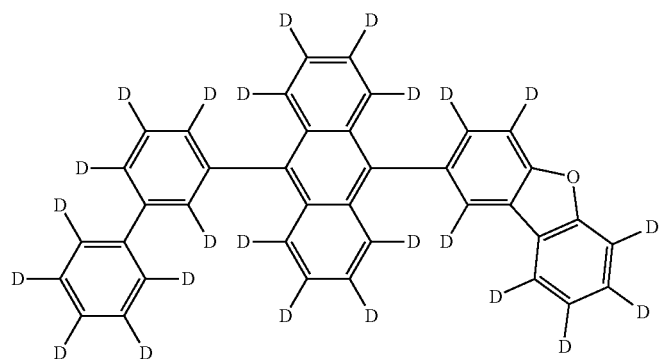
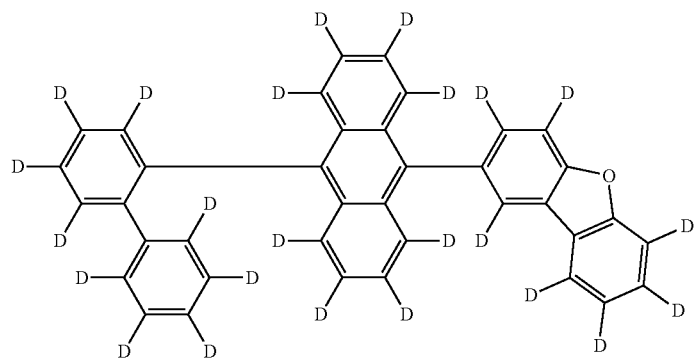

-continued
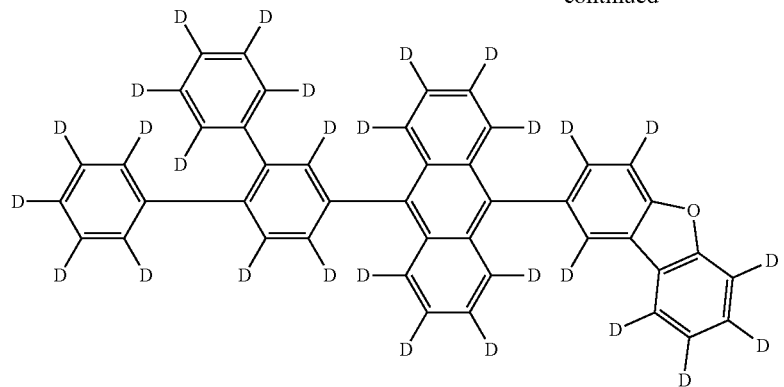
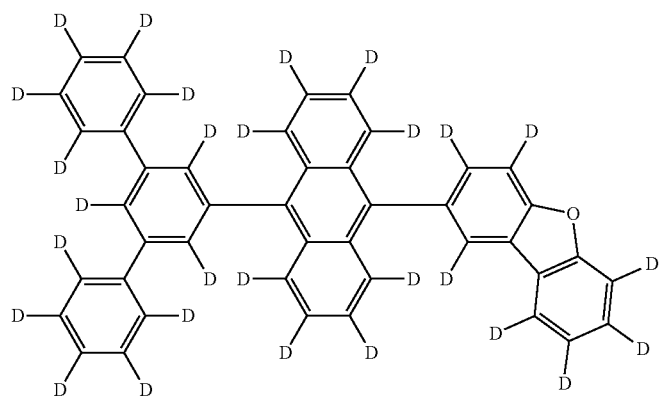
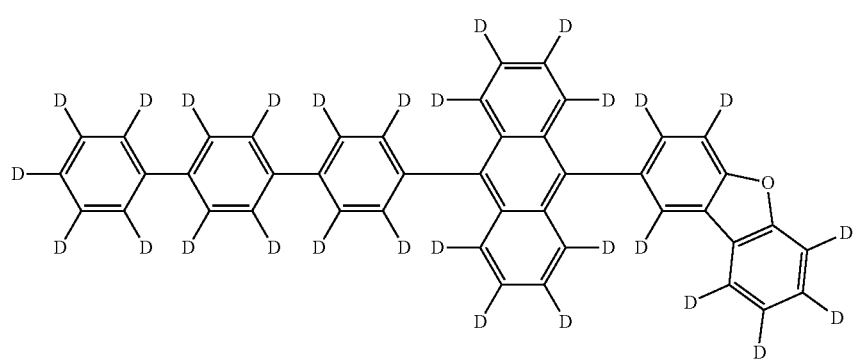
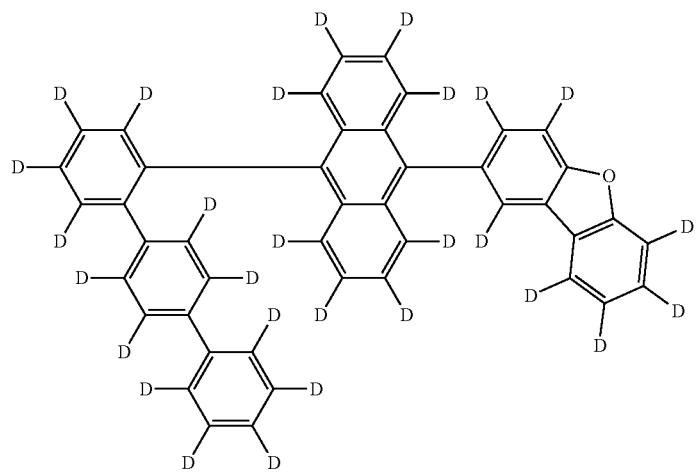

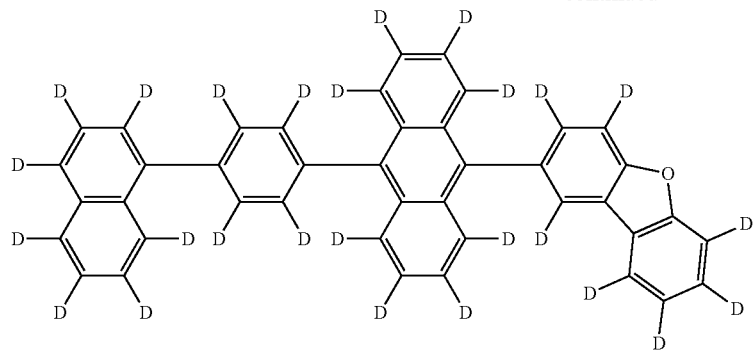
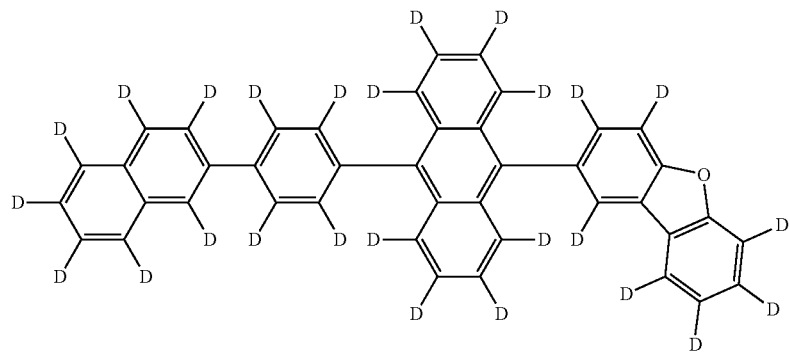
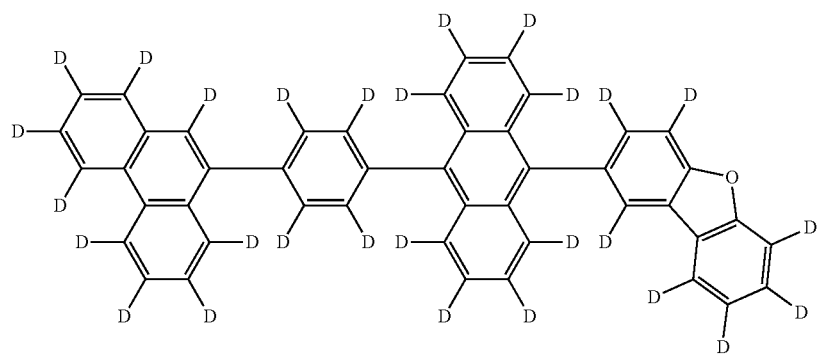
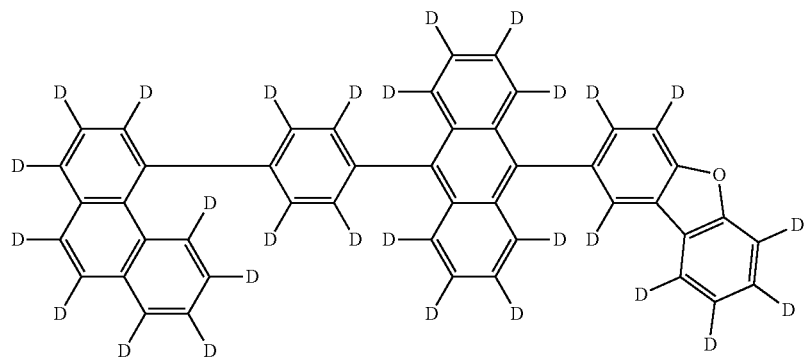

-continued
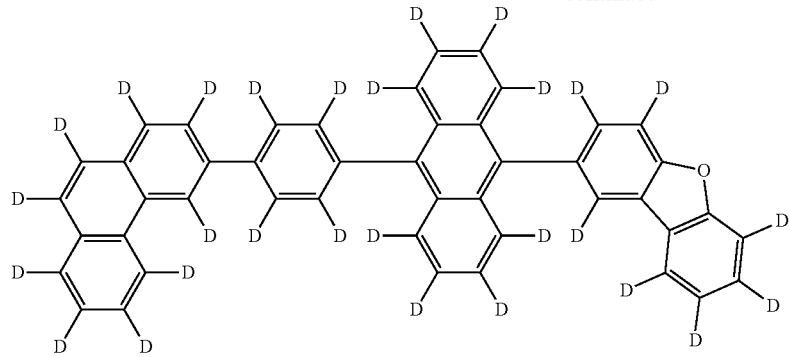
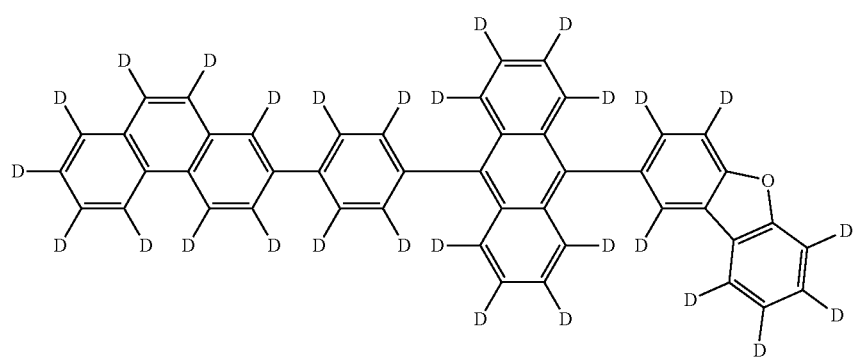
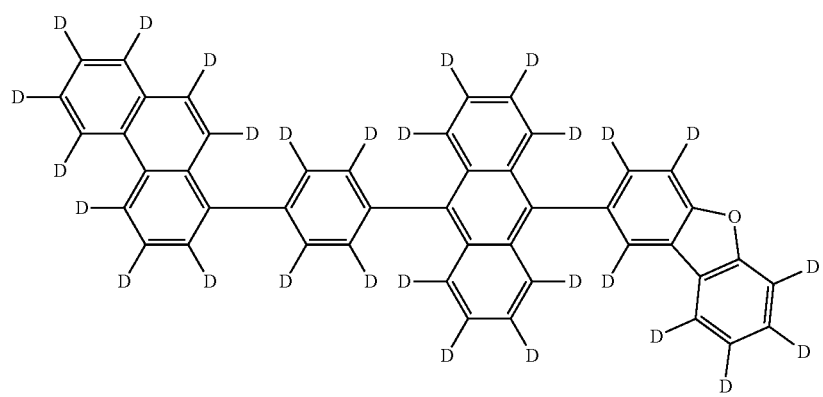
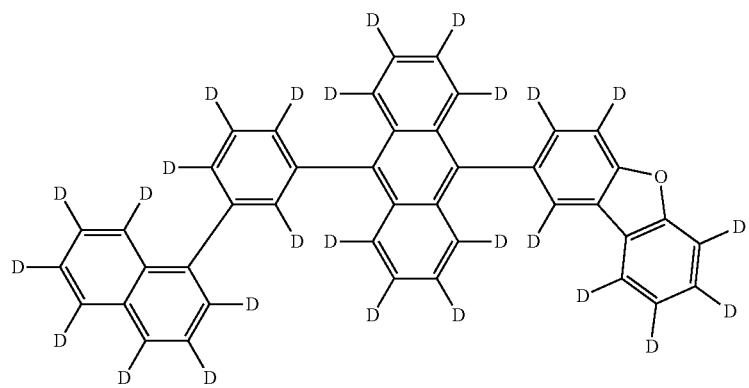

-continued
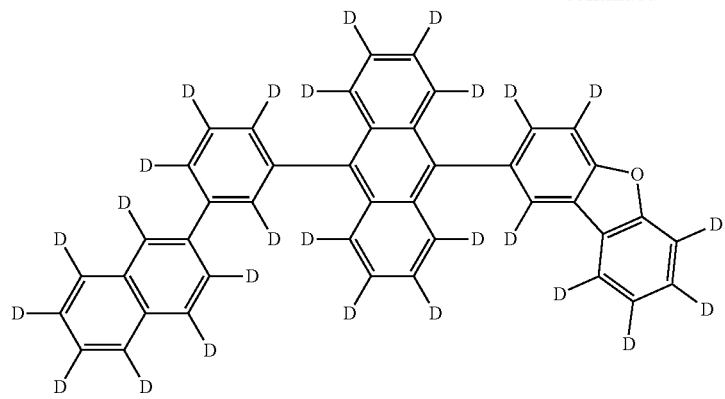
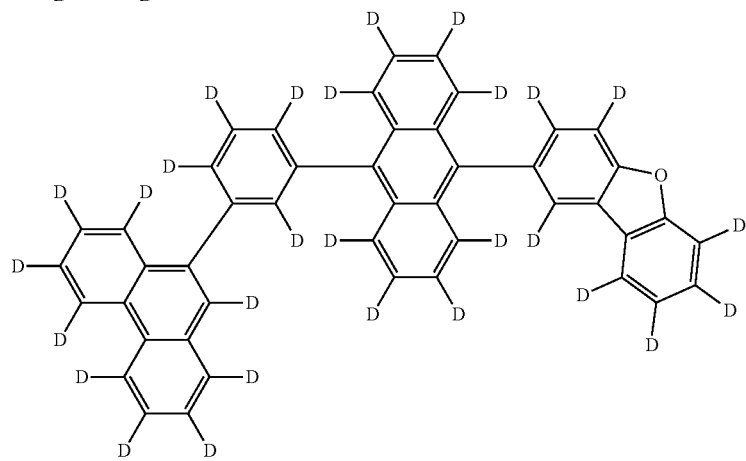
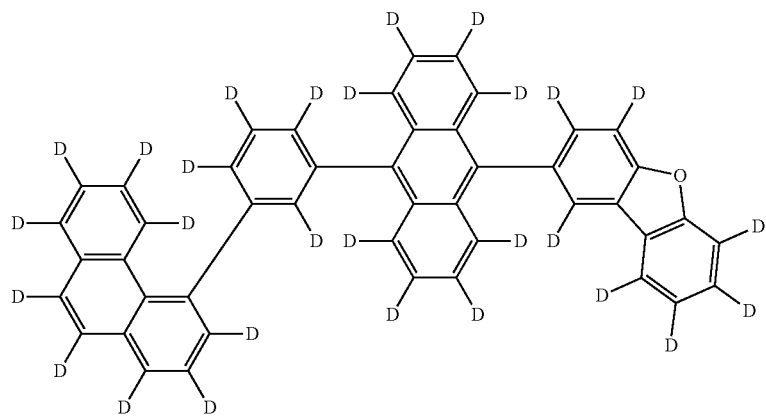
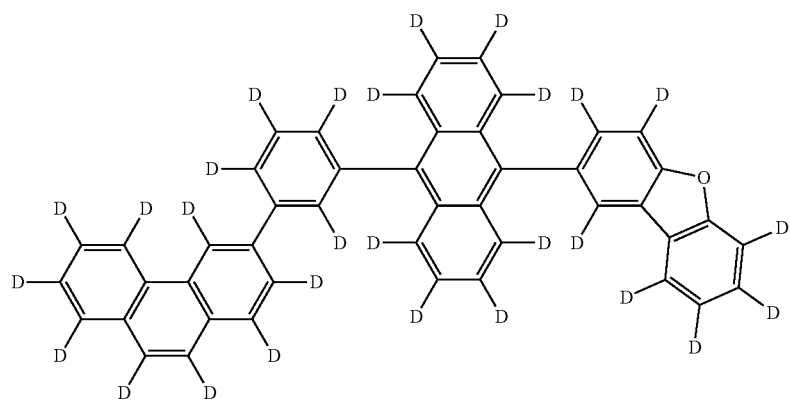

-continued
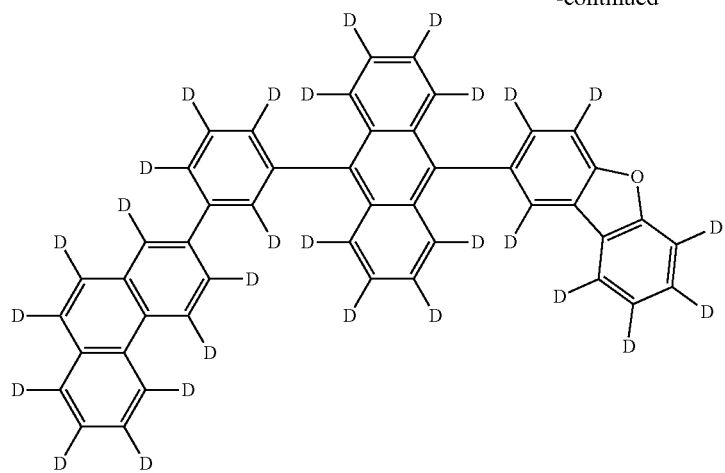
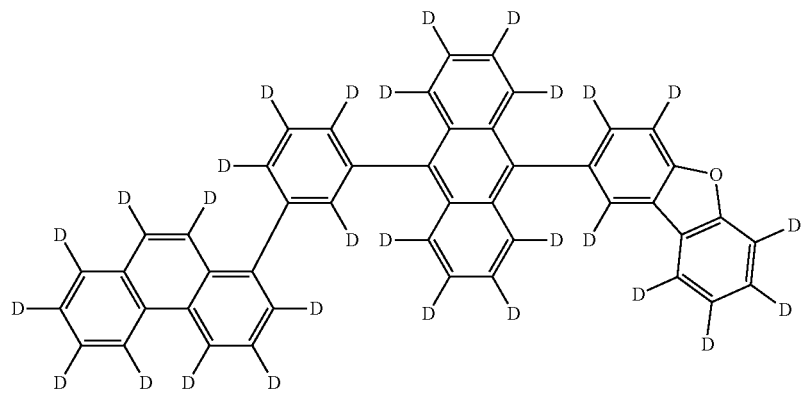
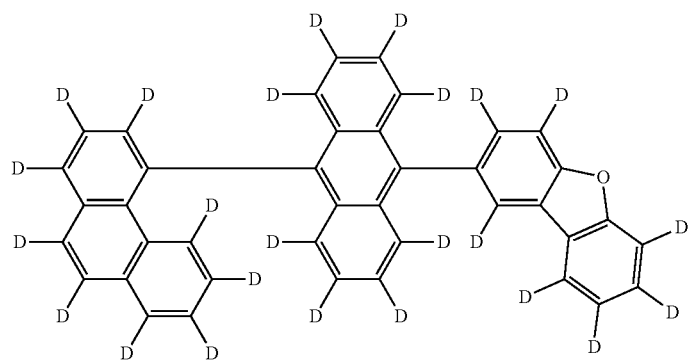
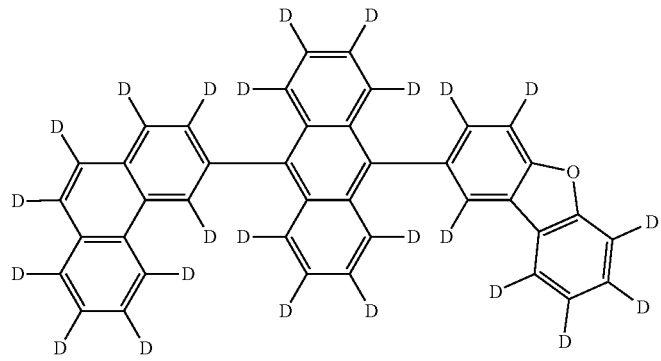

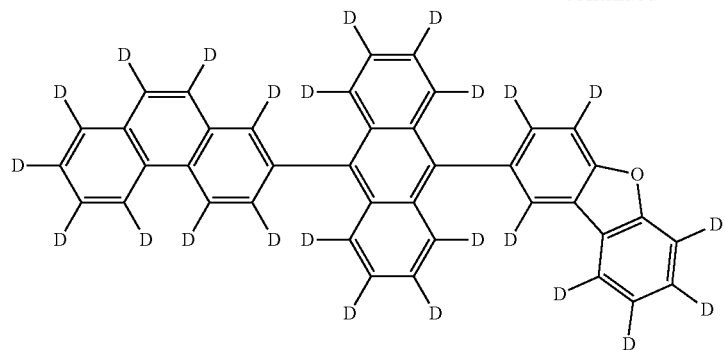
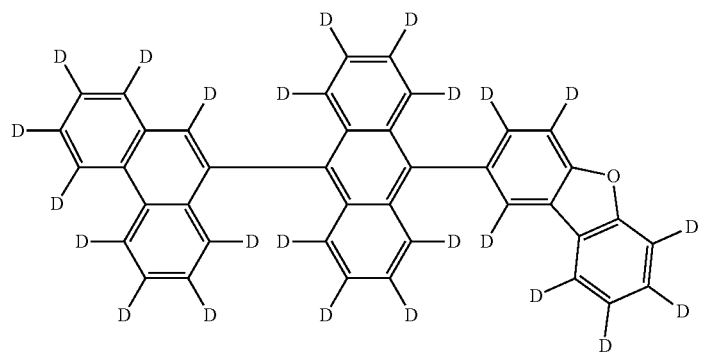
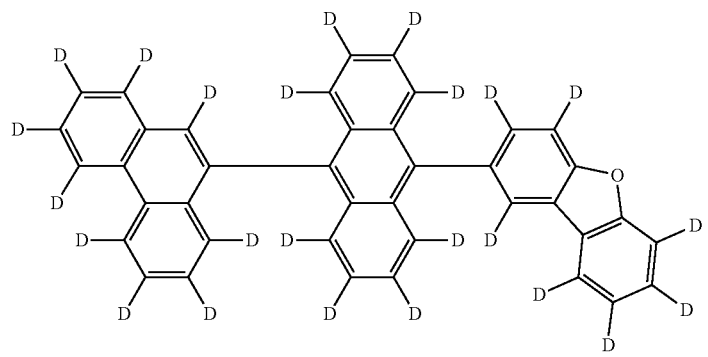
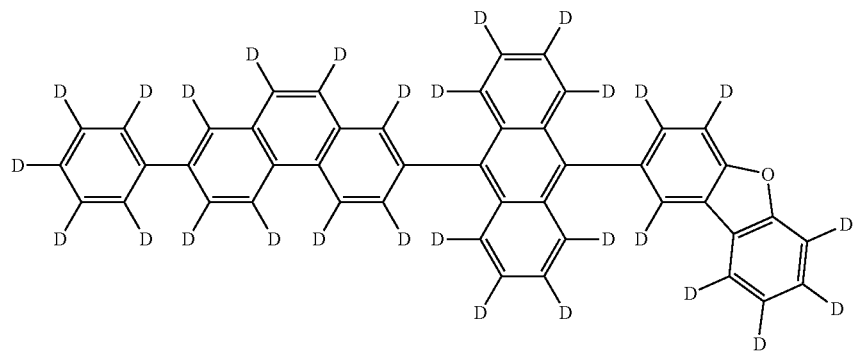

-continued
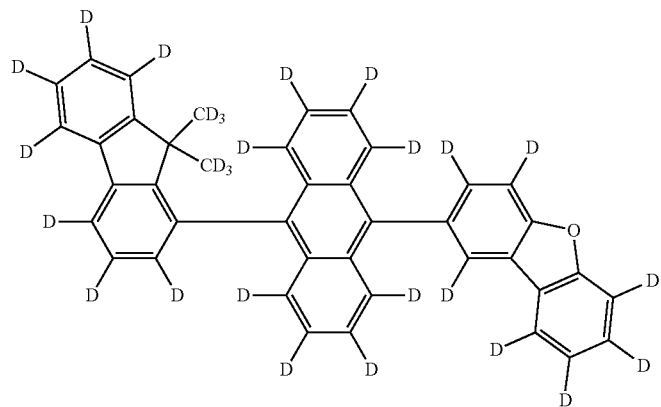
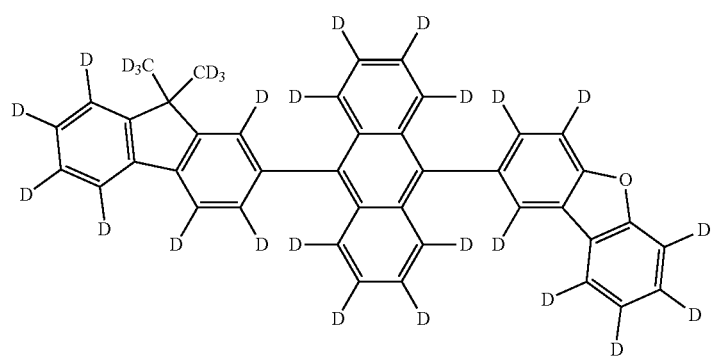
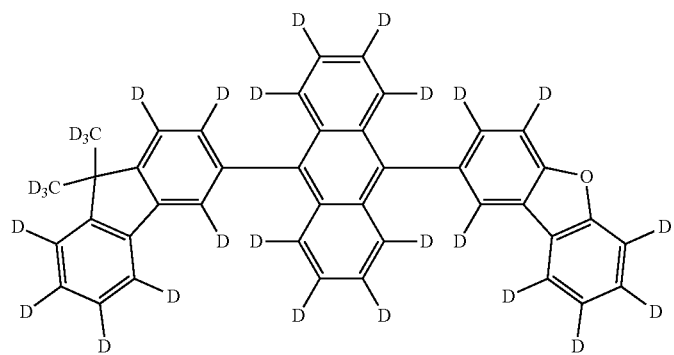
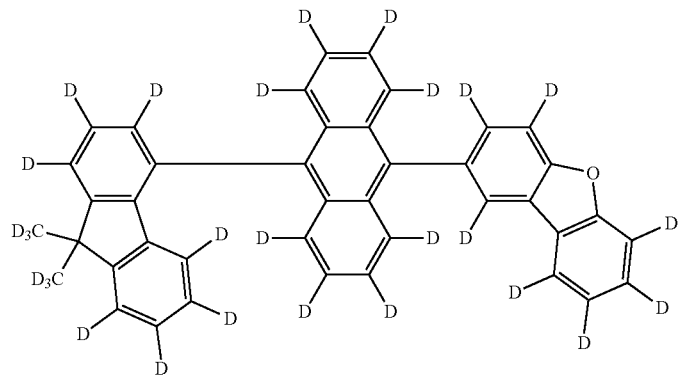

-continued
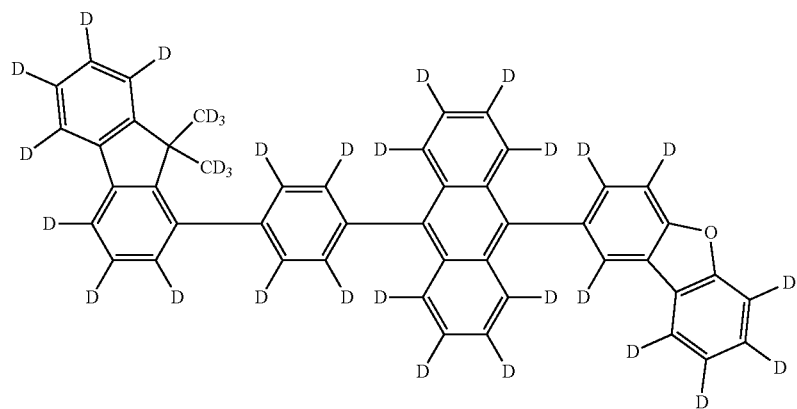
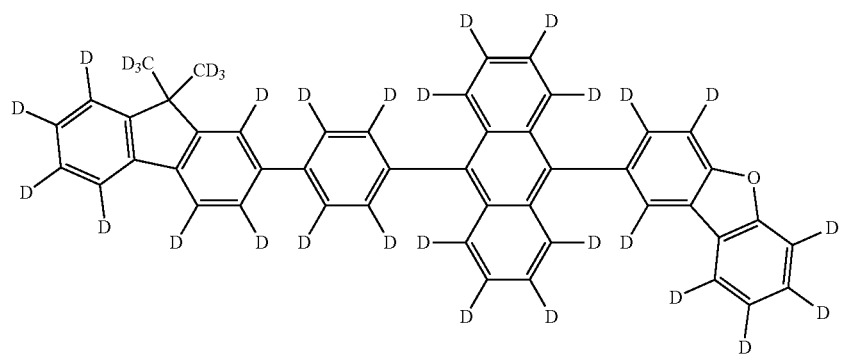
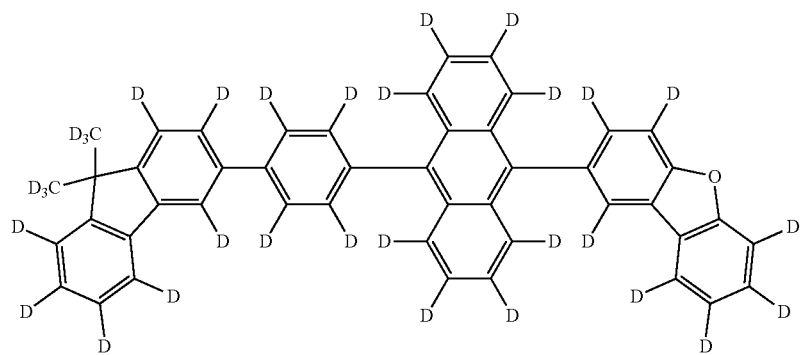
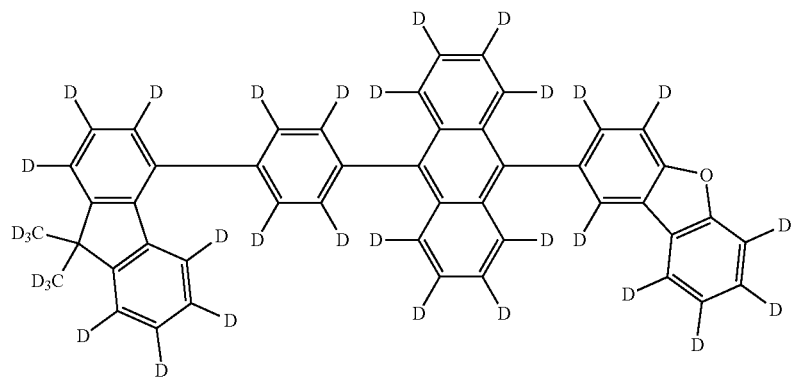

-continued
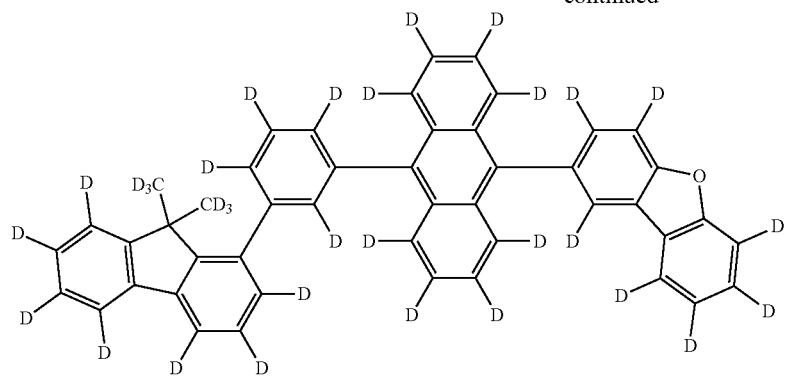
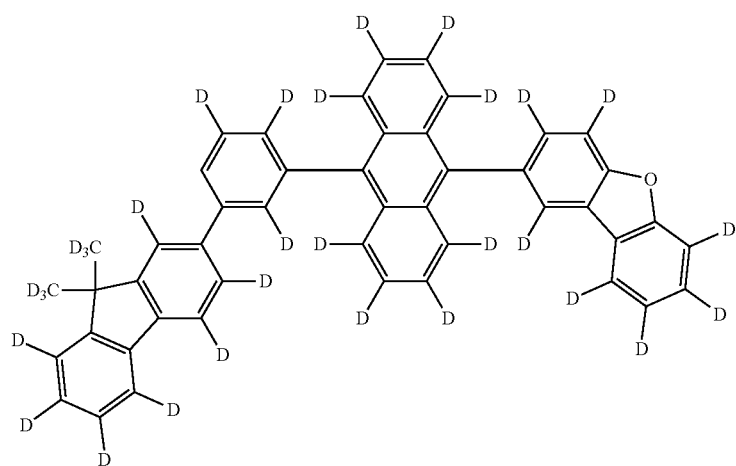
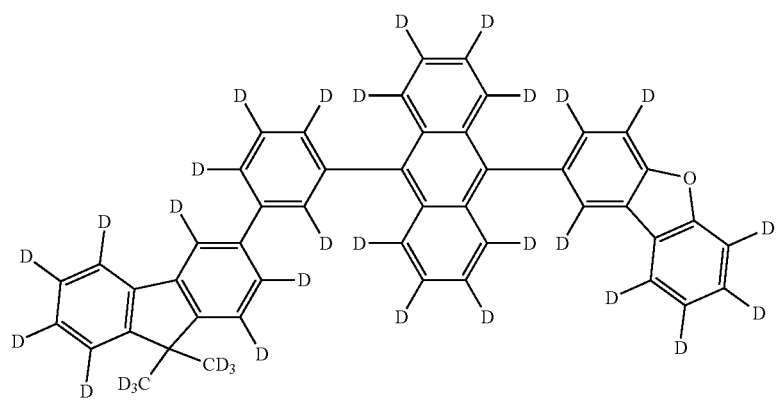
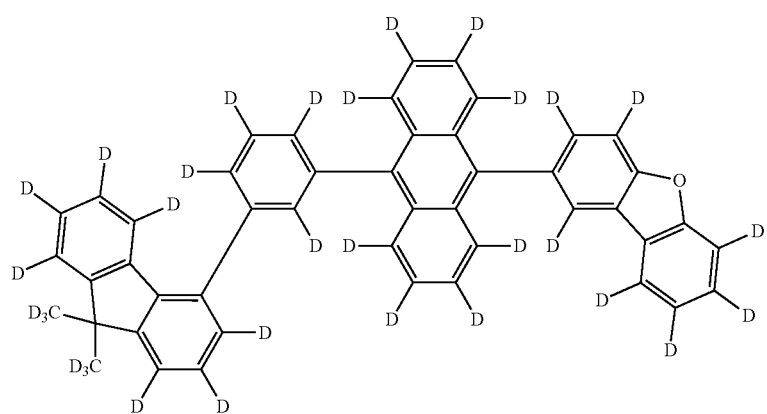

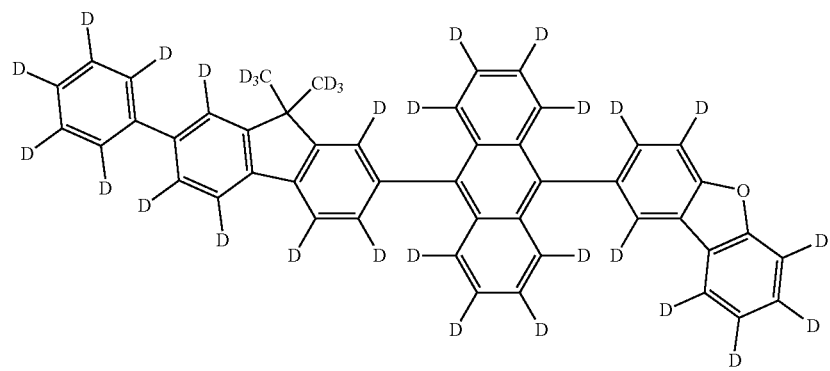
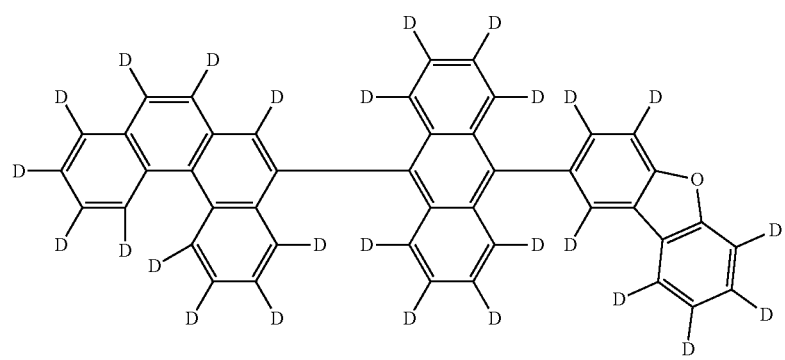
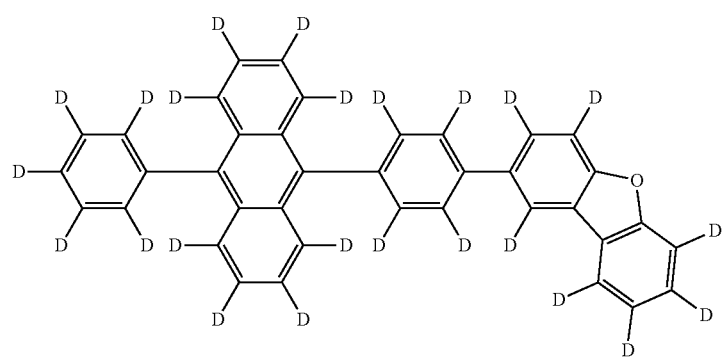
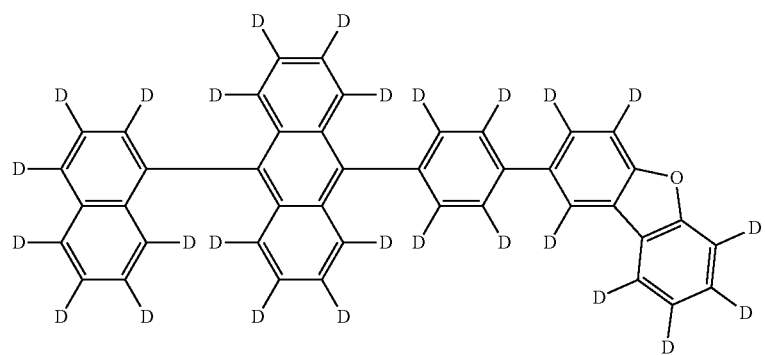

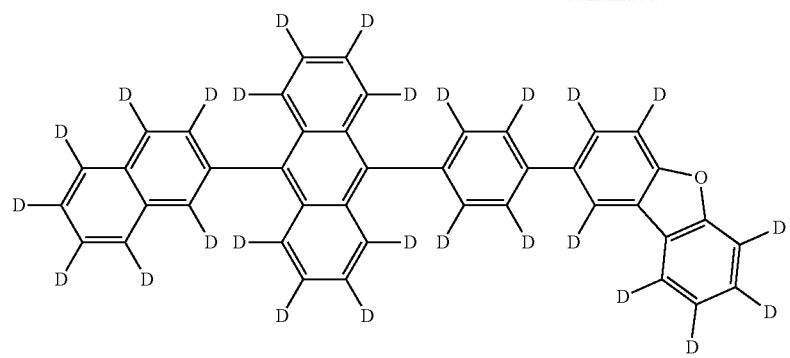
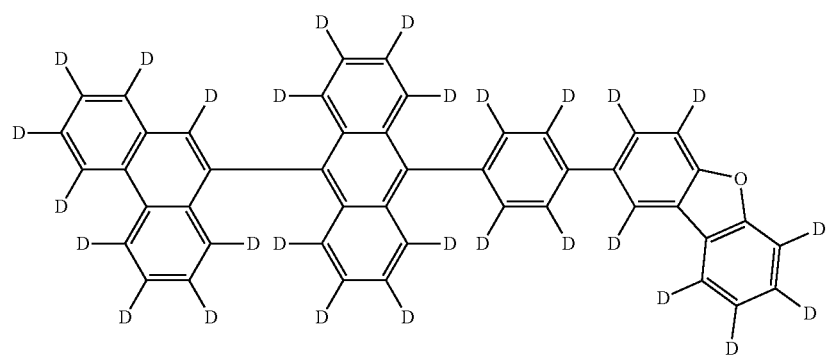
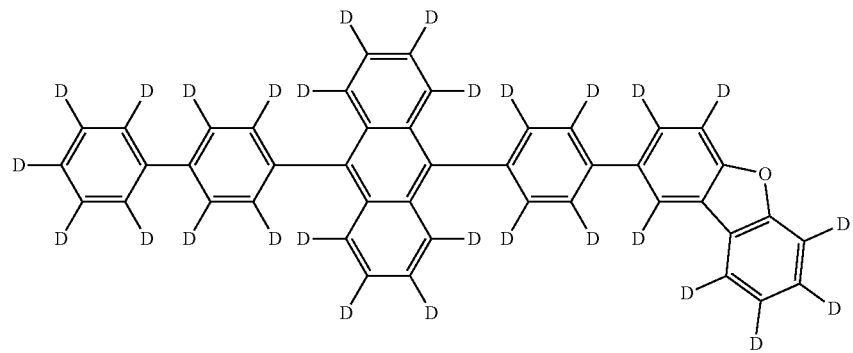
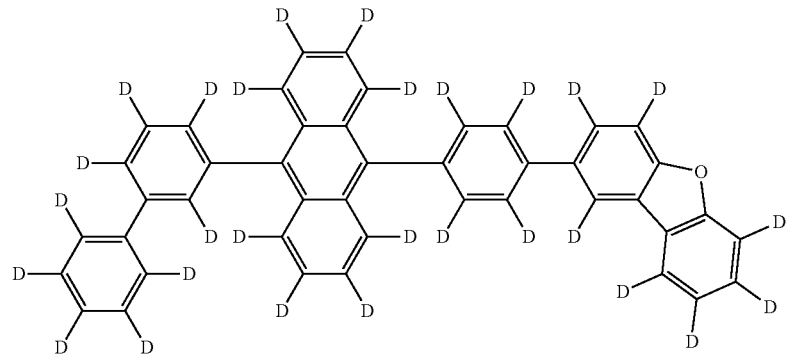

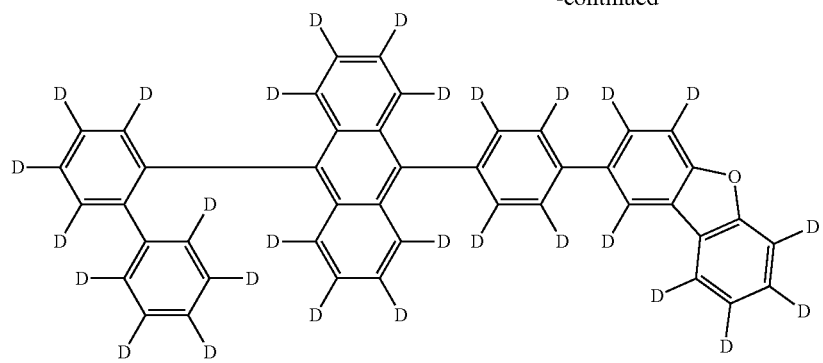
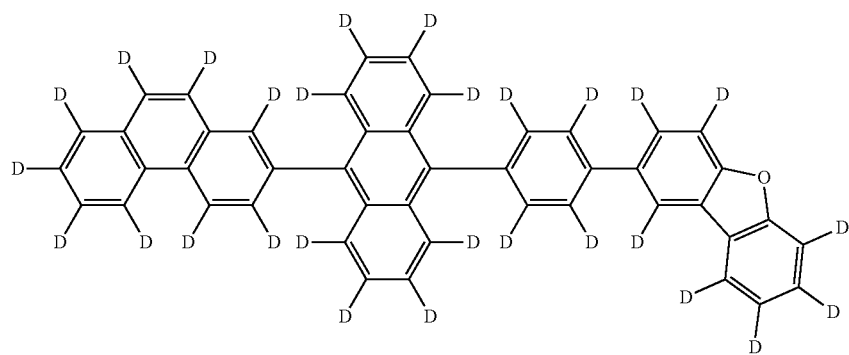
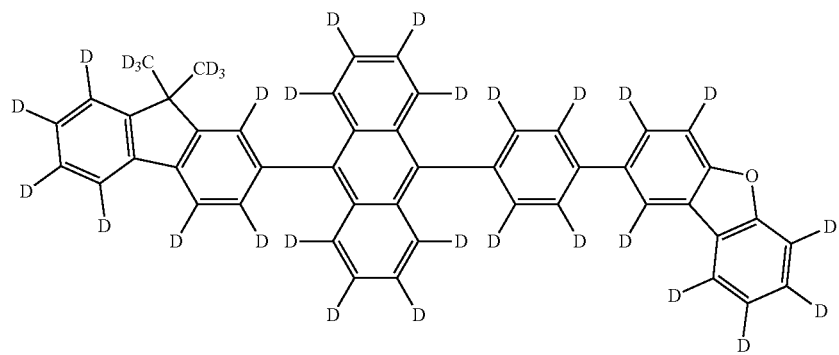
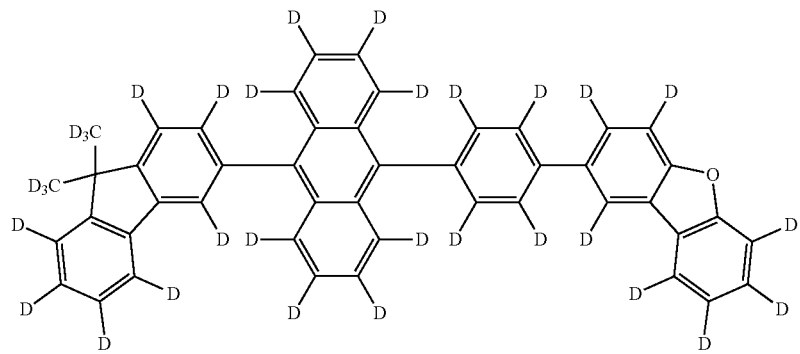

-continued
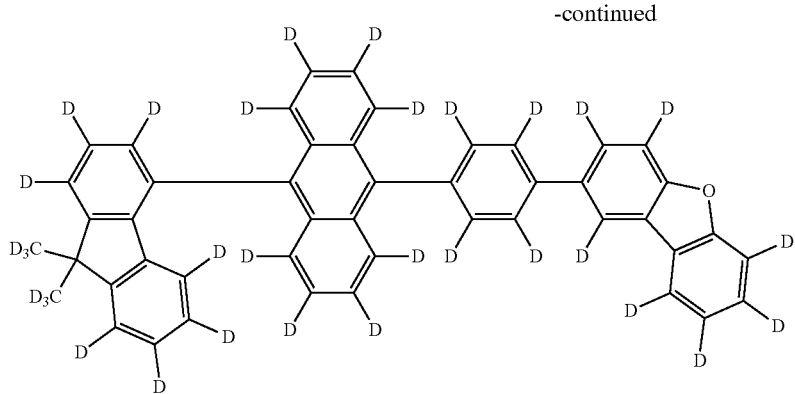
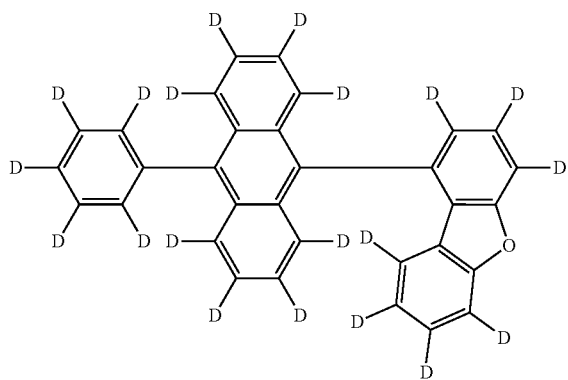
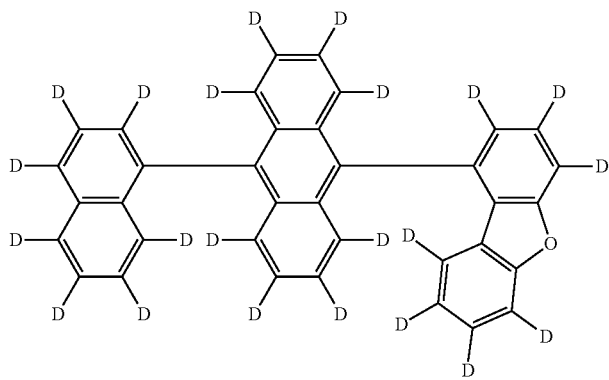
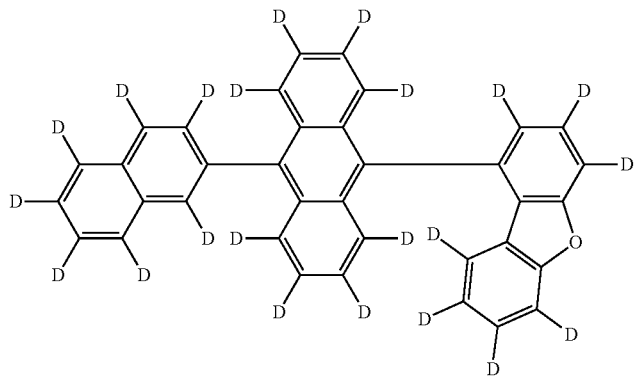

-continued
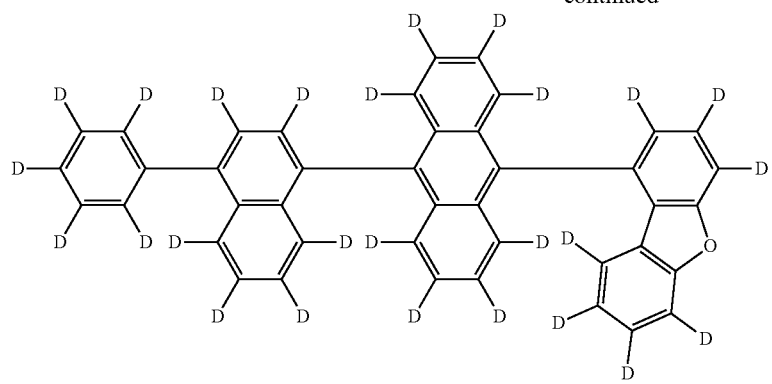
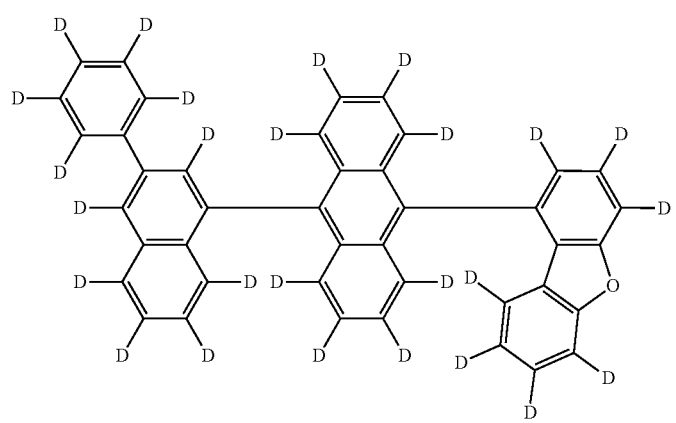
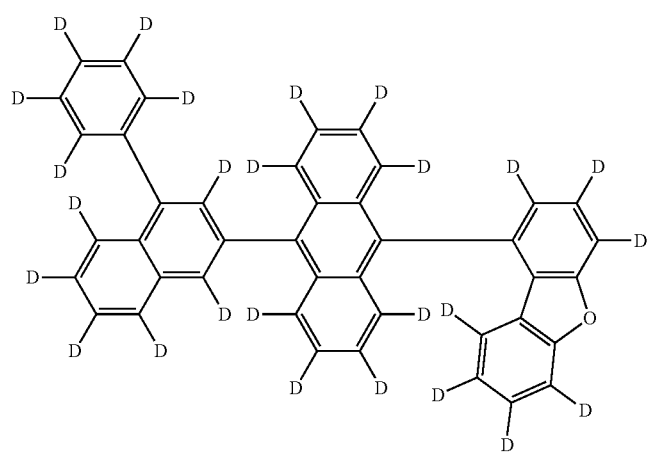
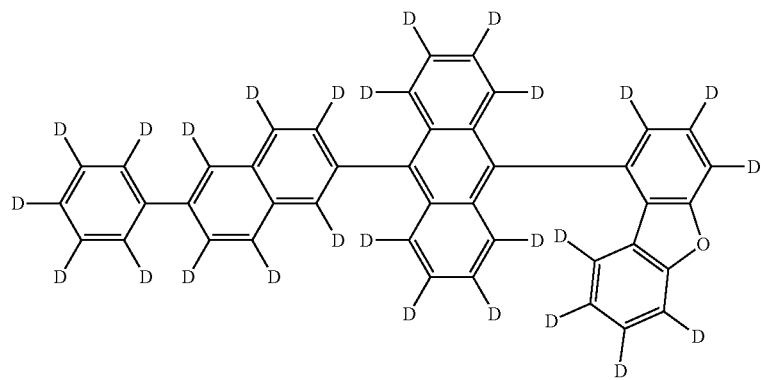

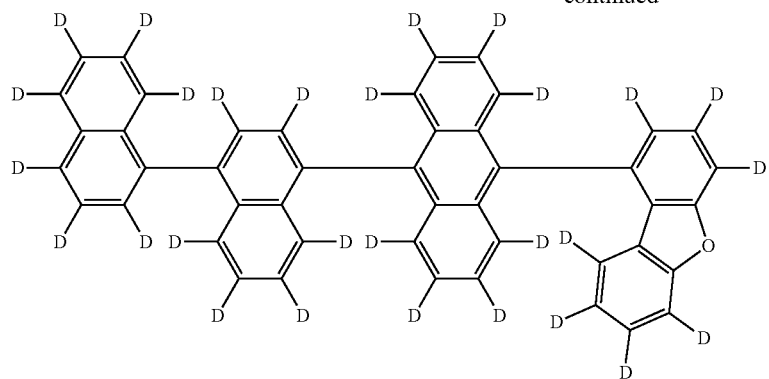
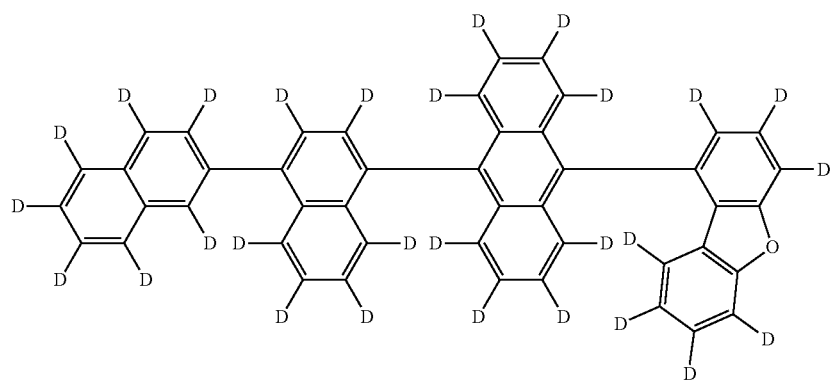
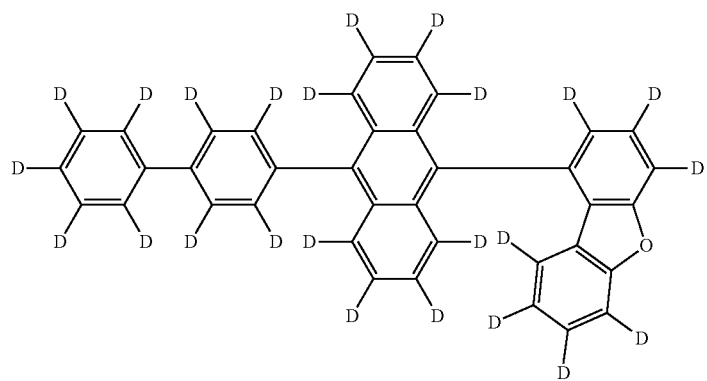
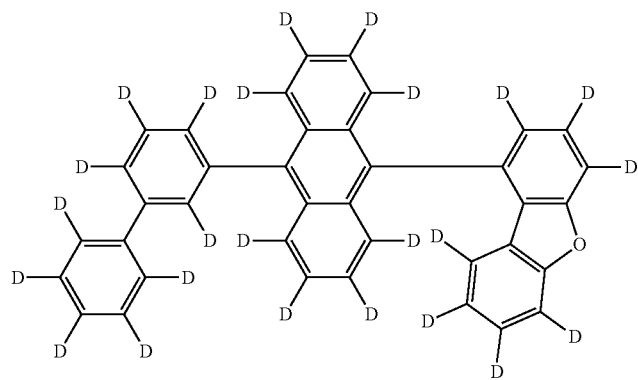

-continued
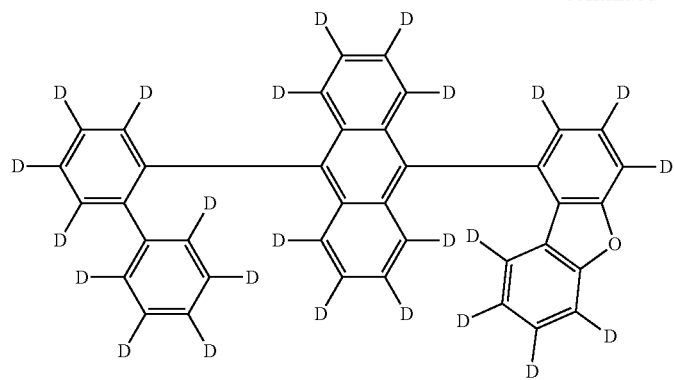
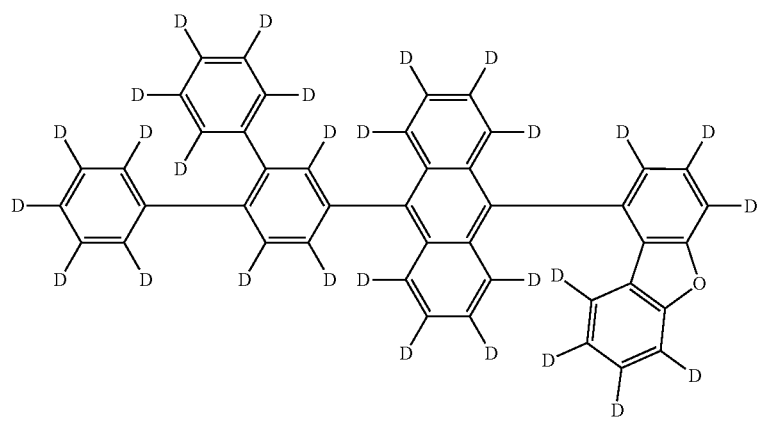
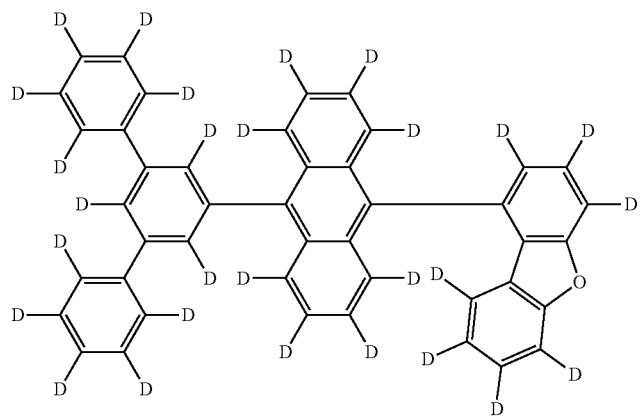
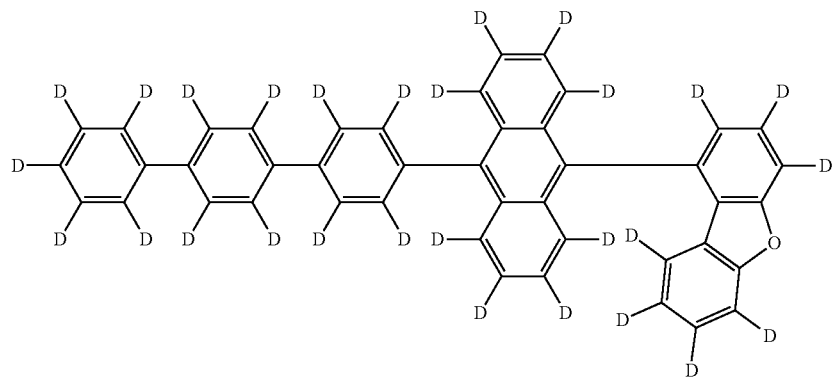

-continued
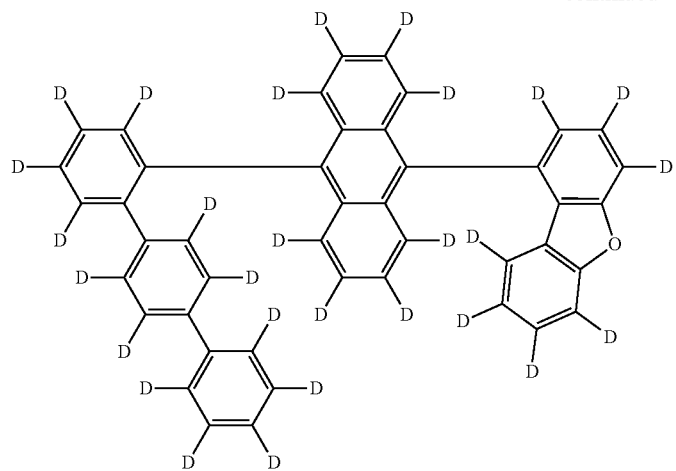
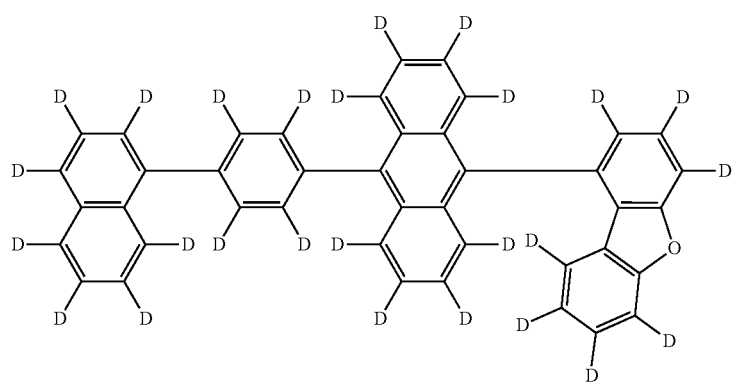
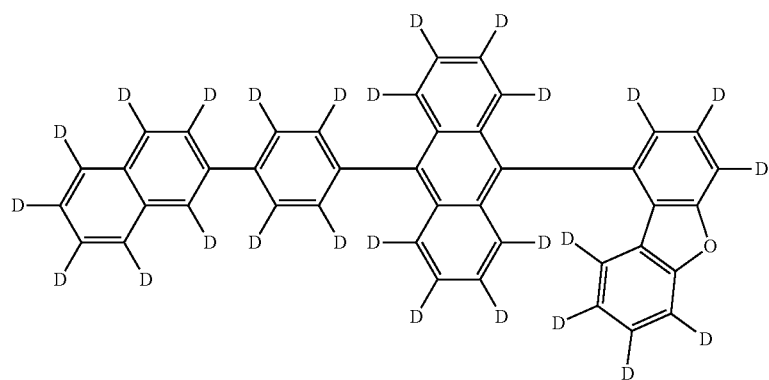
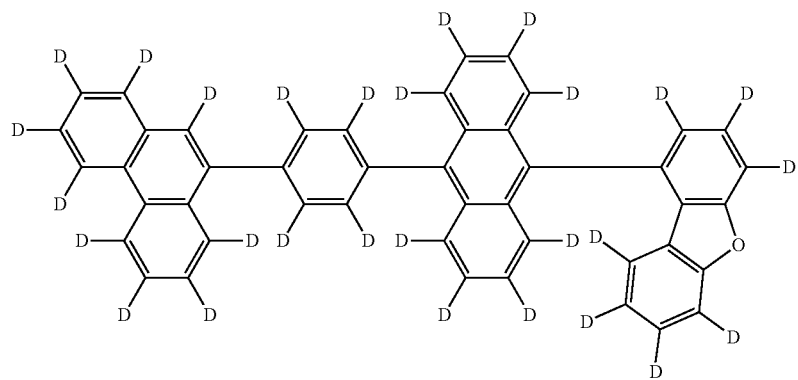

-continued
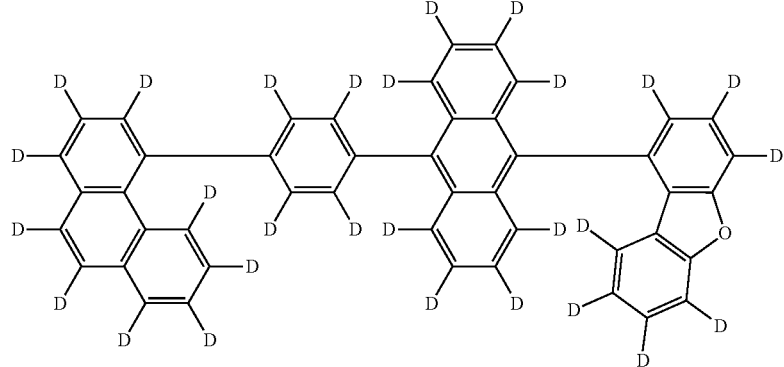
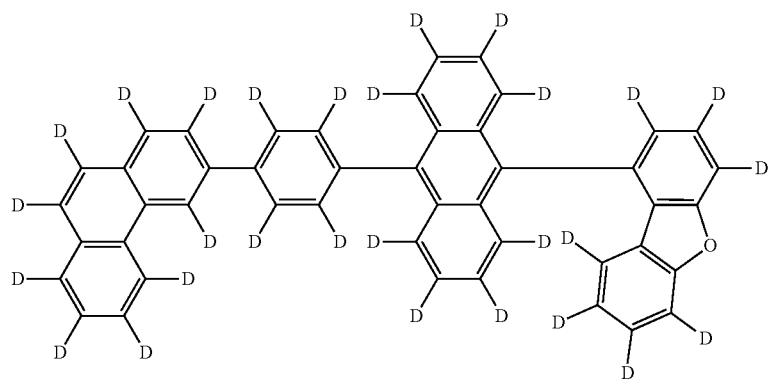
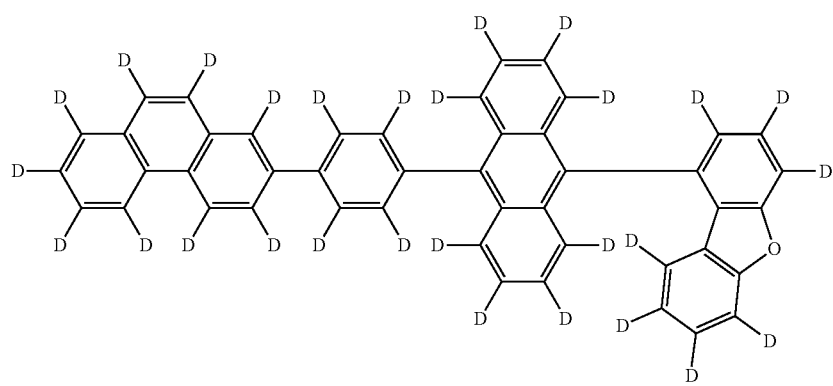
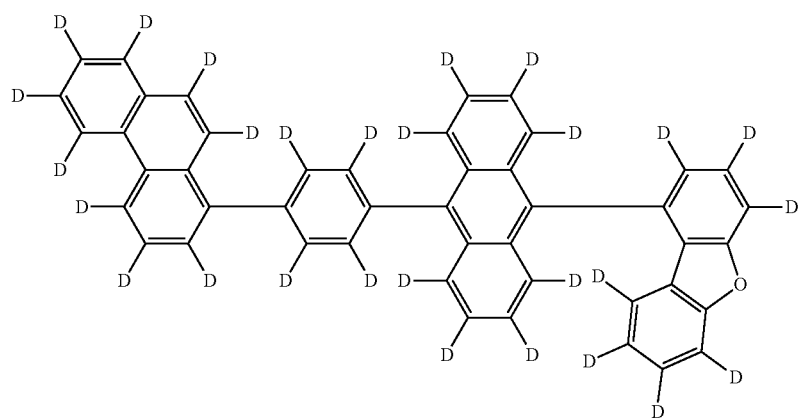

-continued
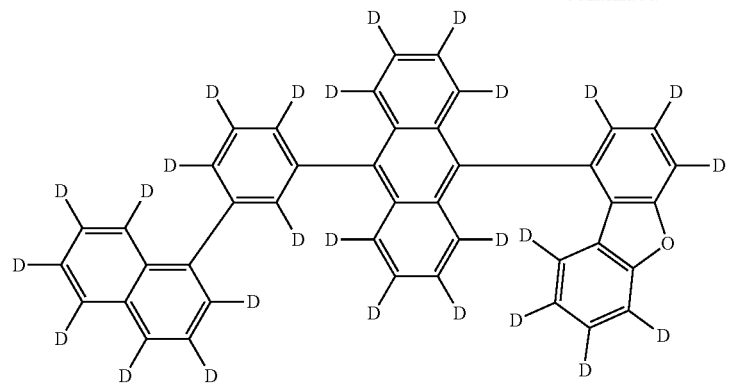
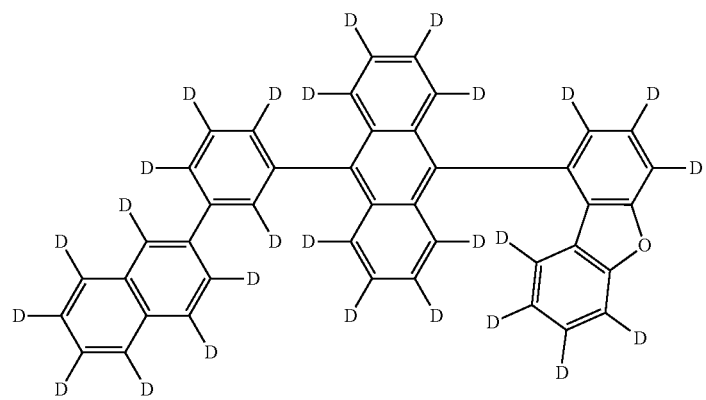
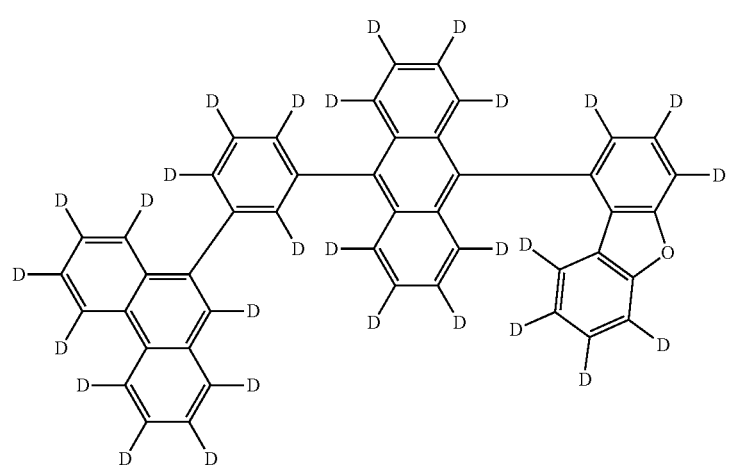
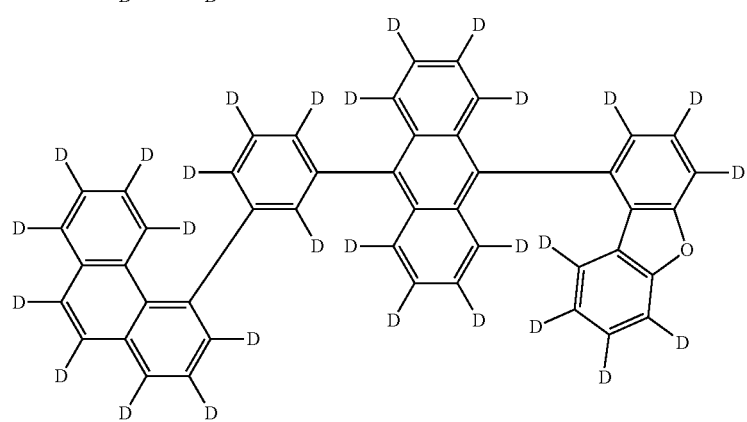

-continued
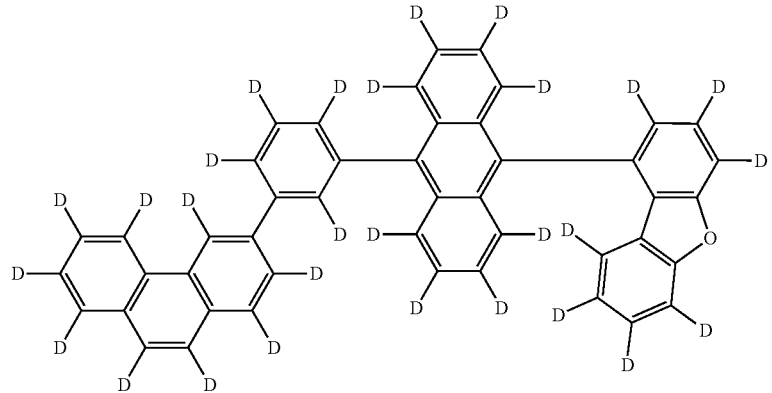
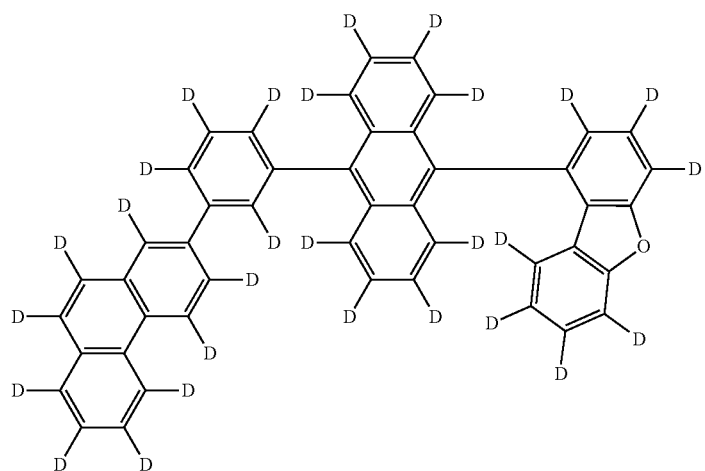
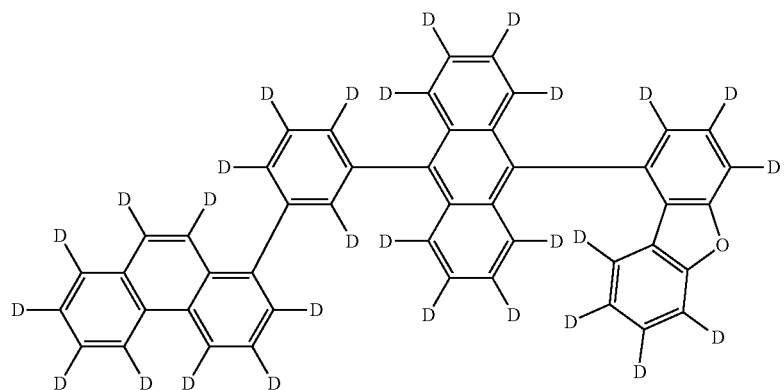
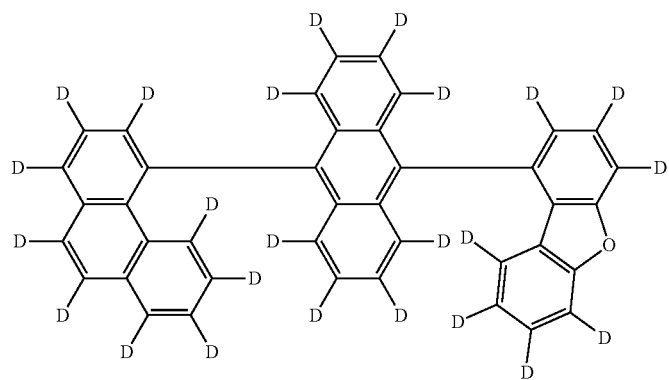

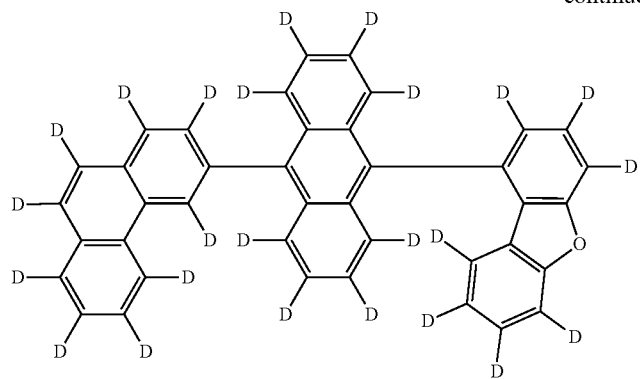
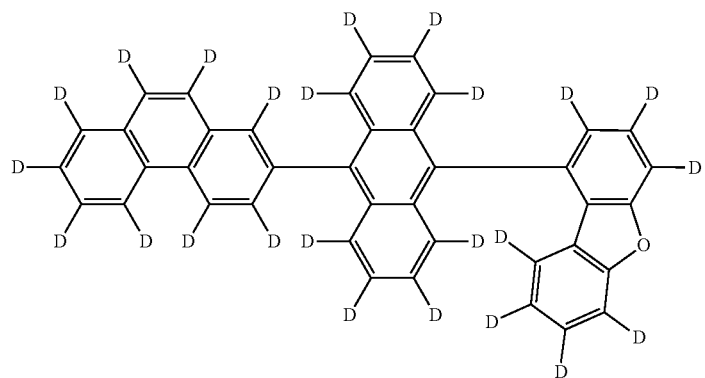
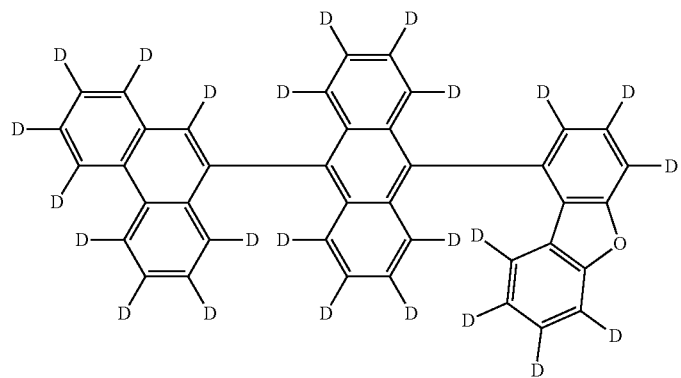
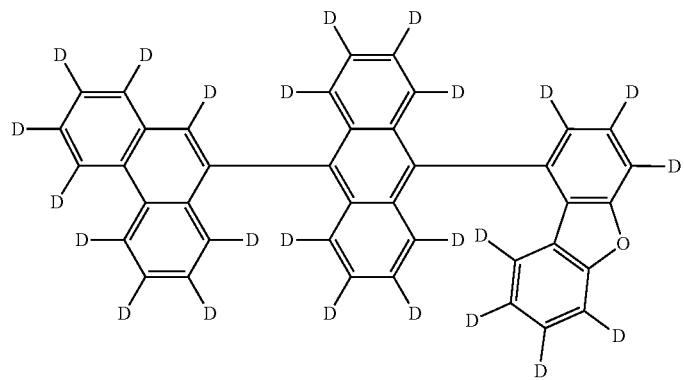

-continued
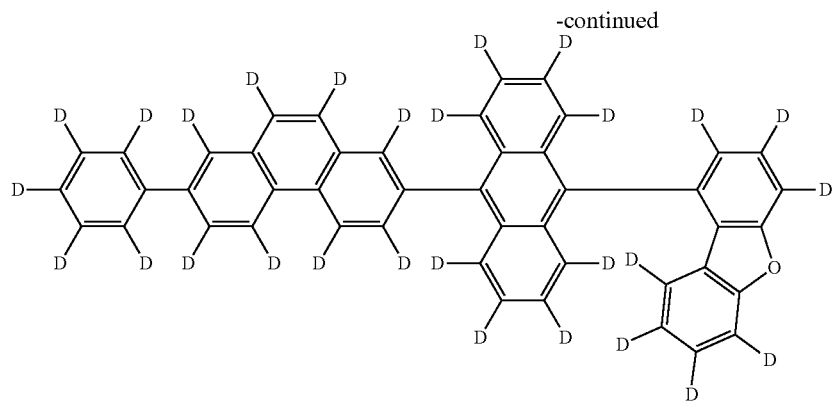
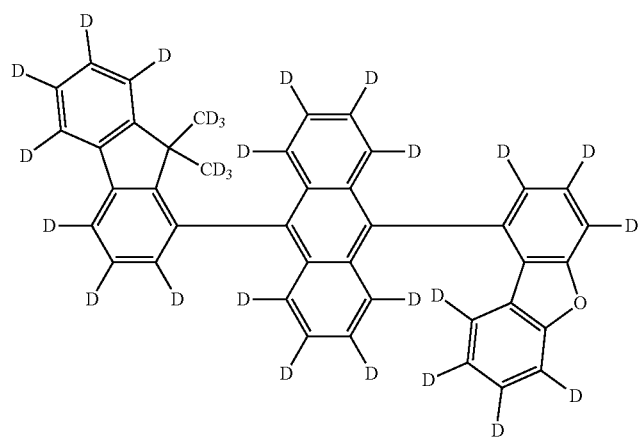
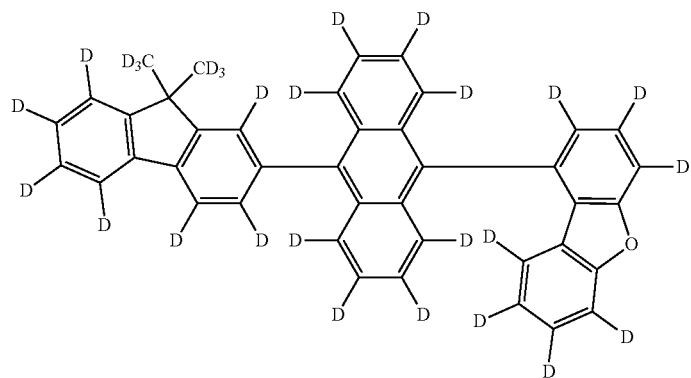
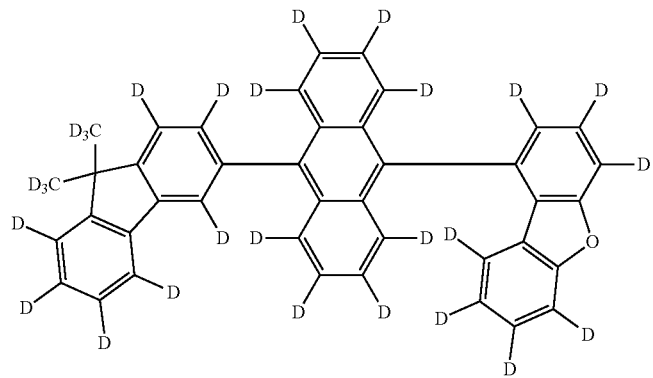

-continued
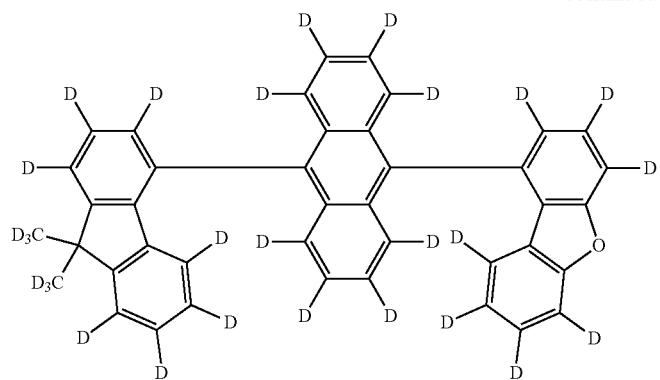
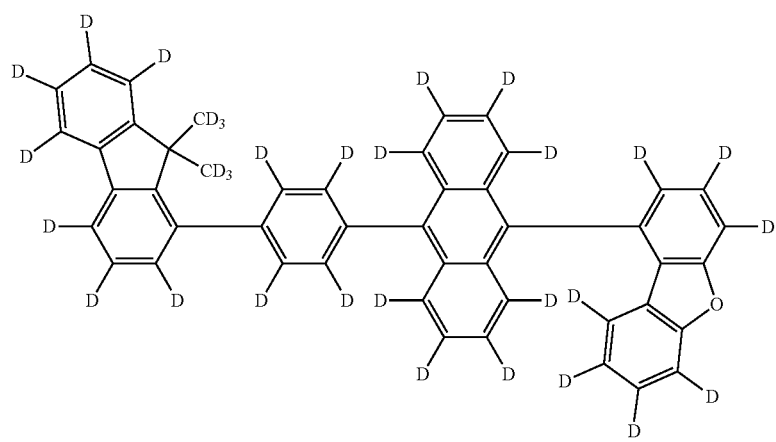
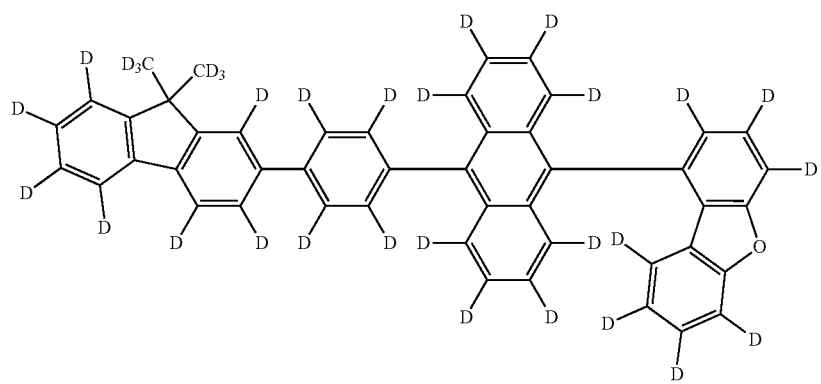
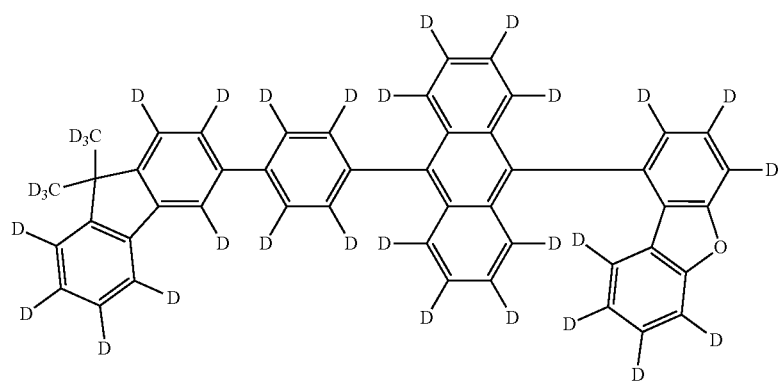

-continued
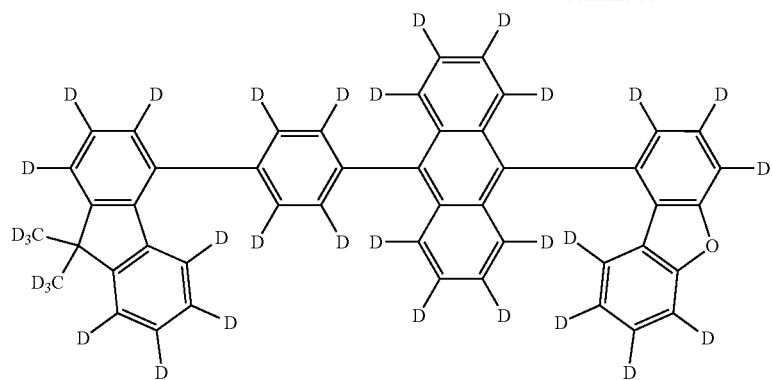
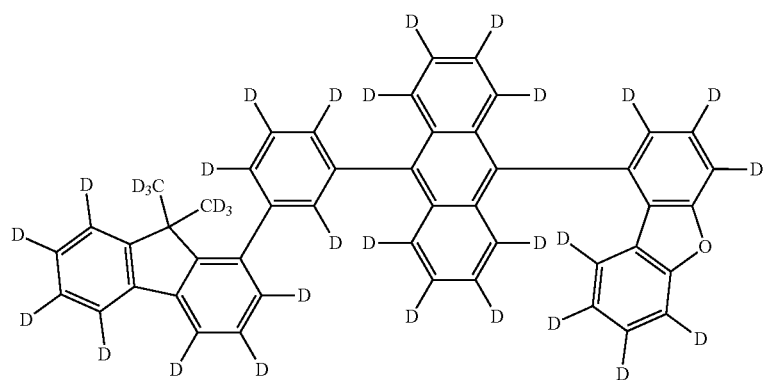
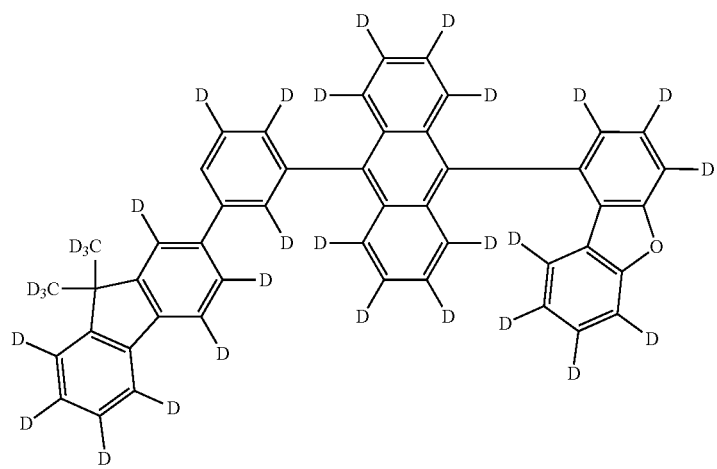
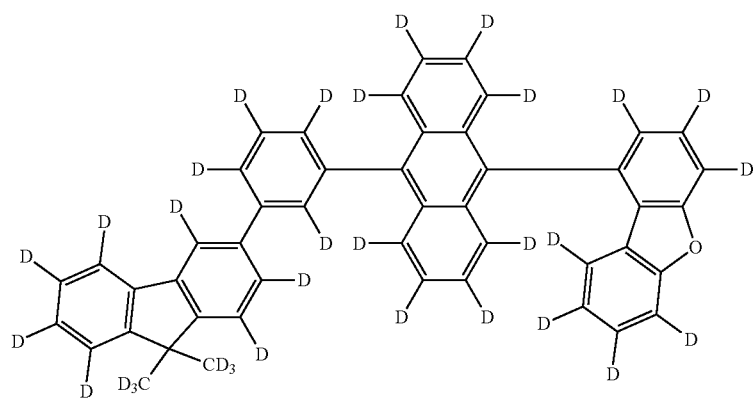

-continued
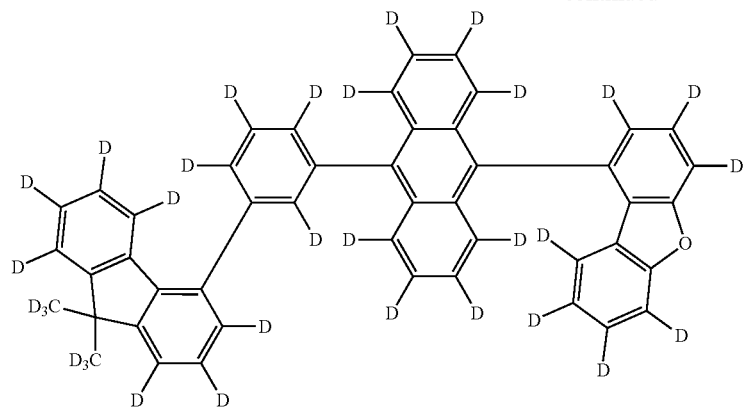
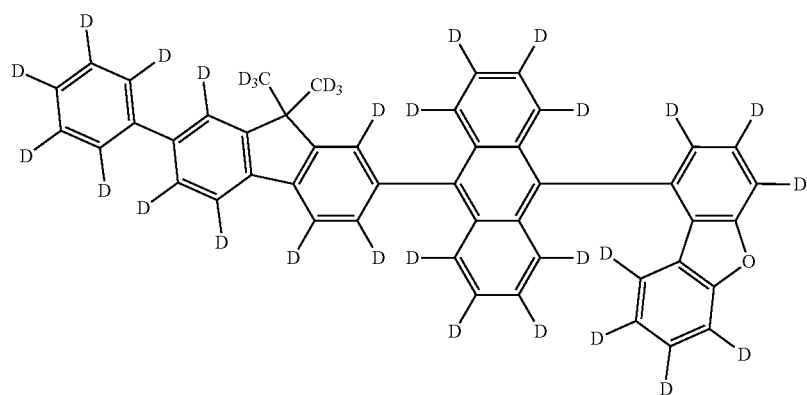
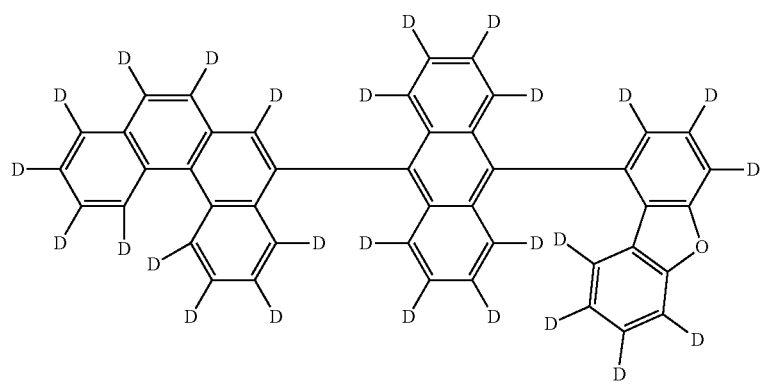
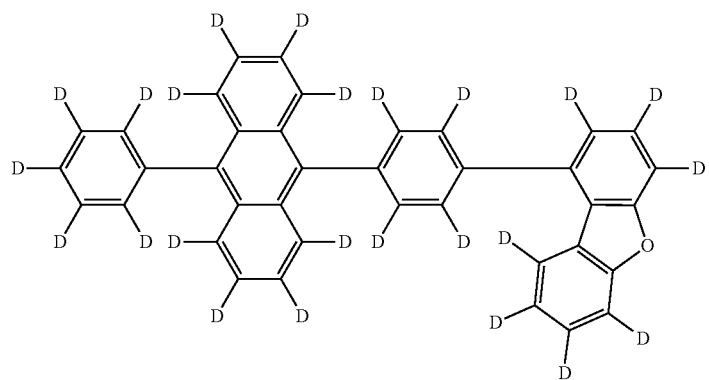

-continued
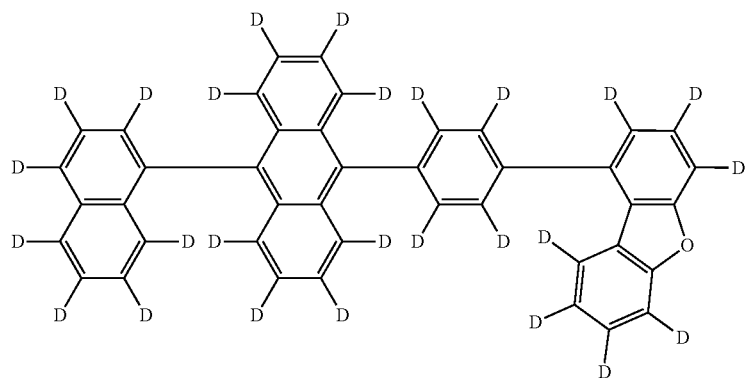
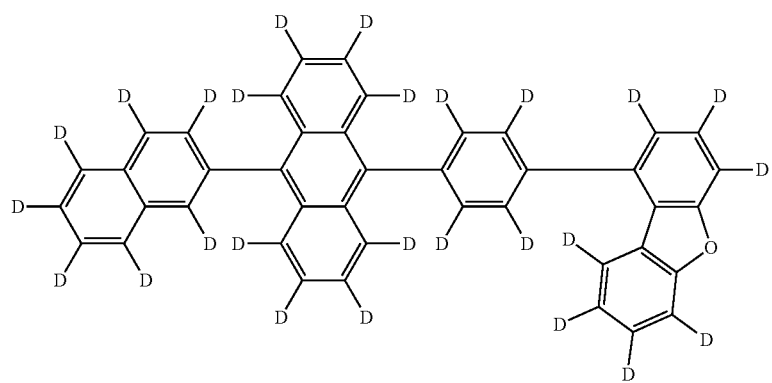
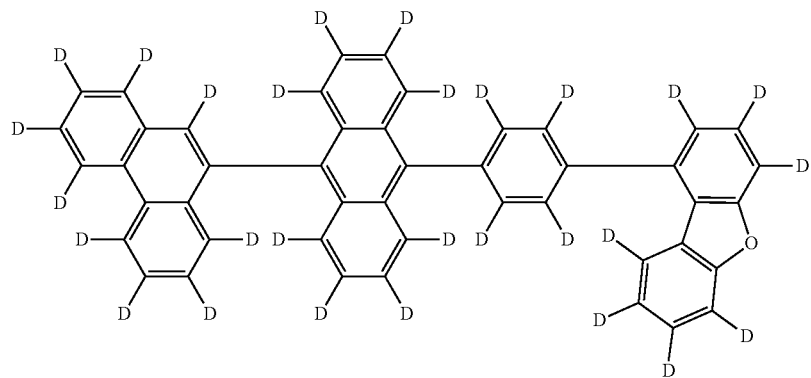
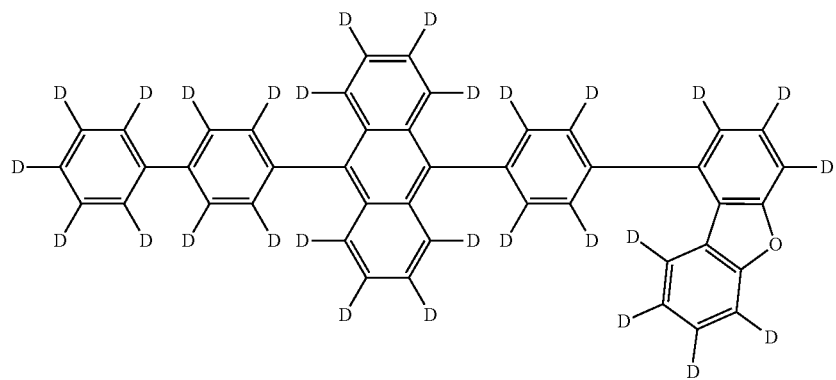

-continued
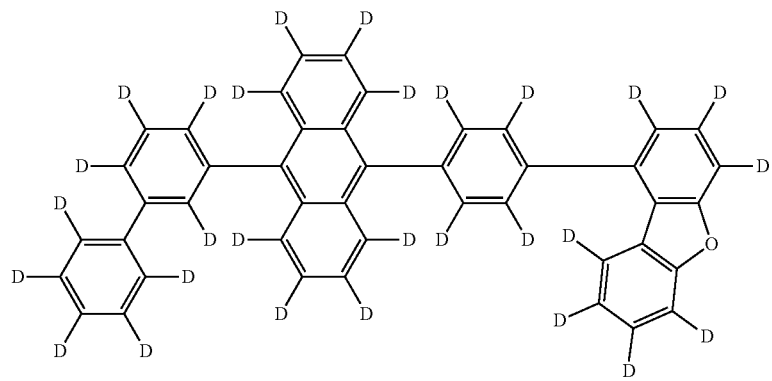
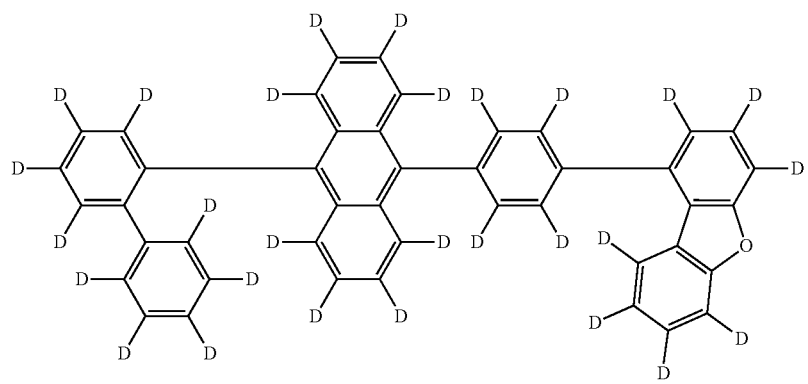
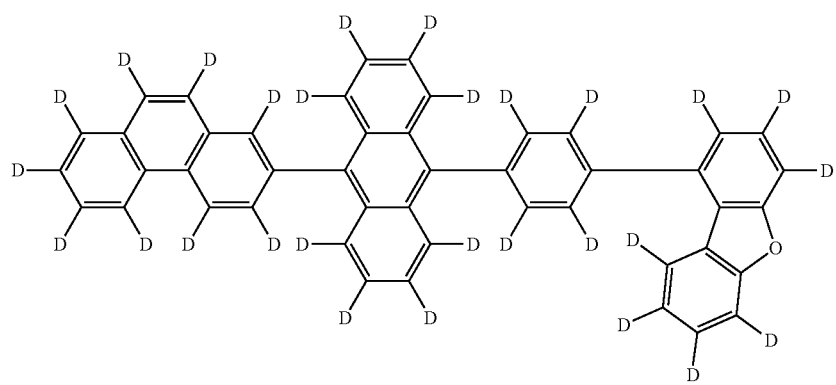
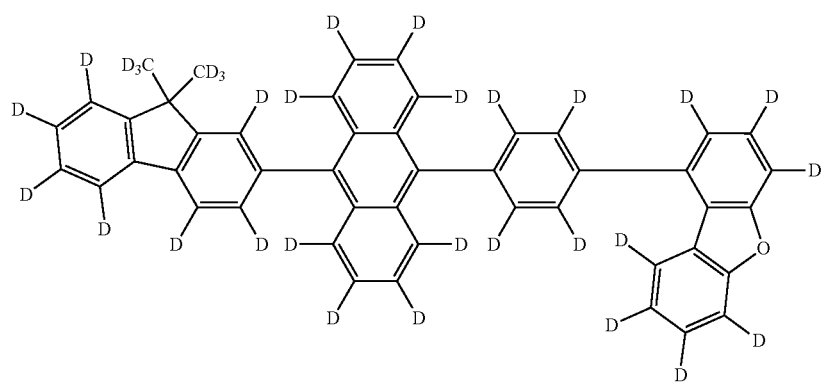

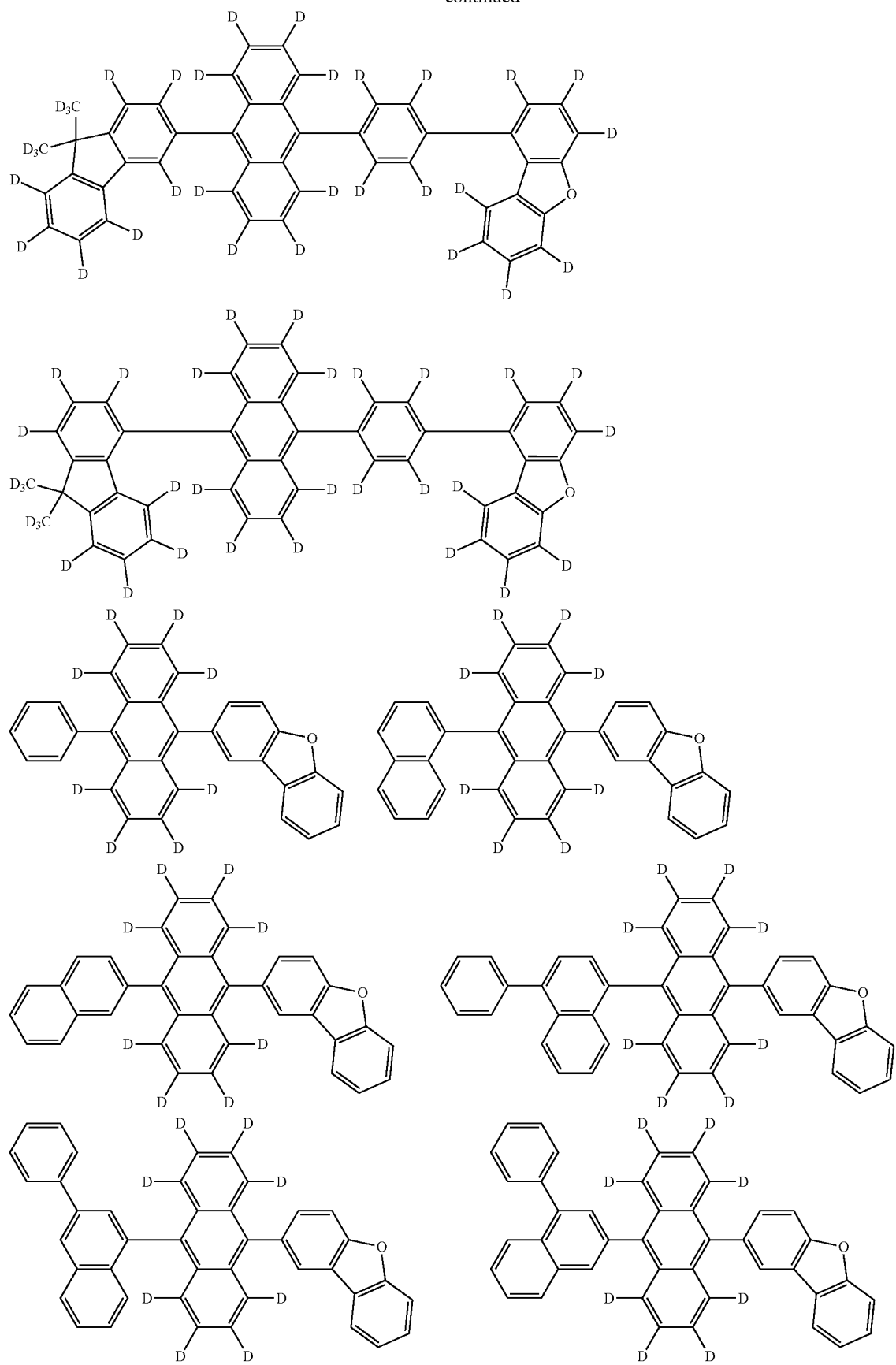

-continued
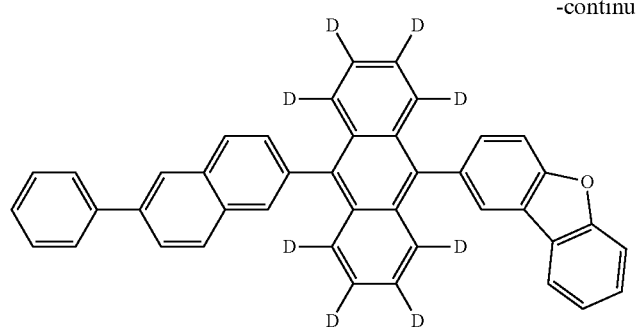
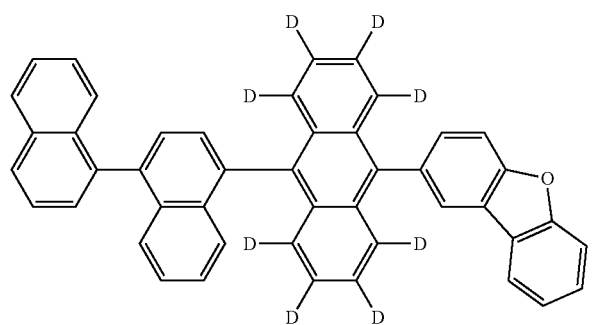
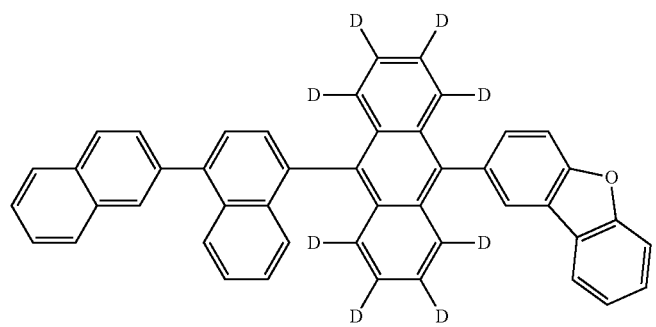
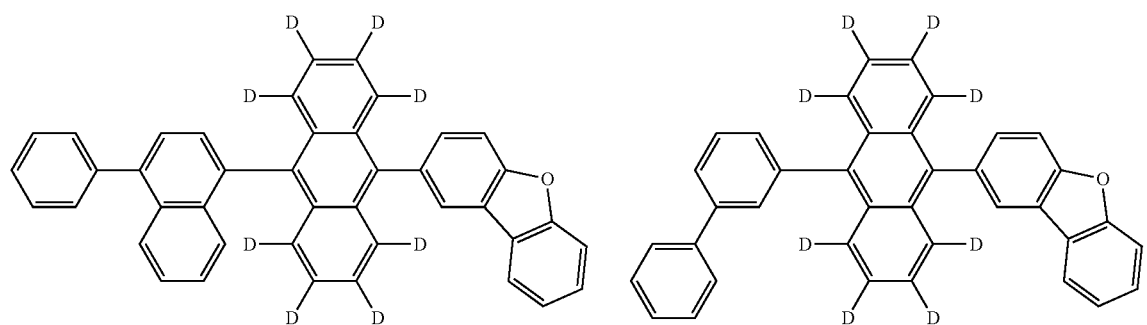
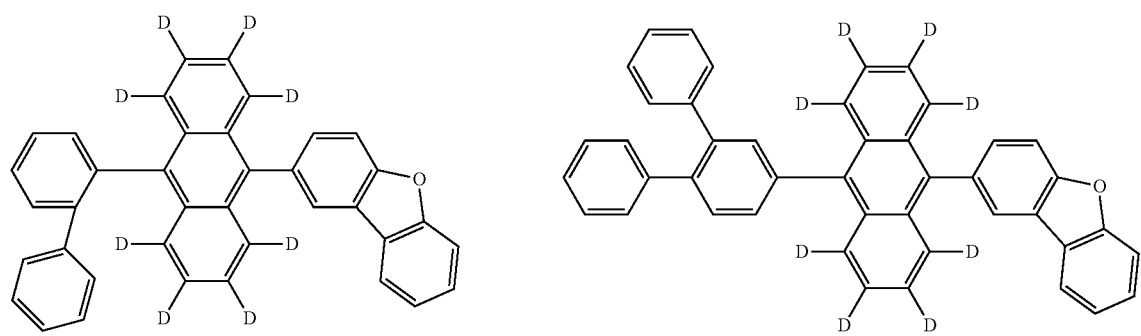

-continued
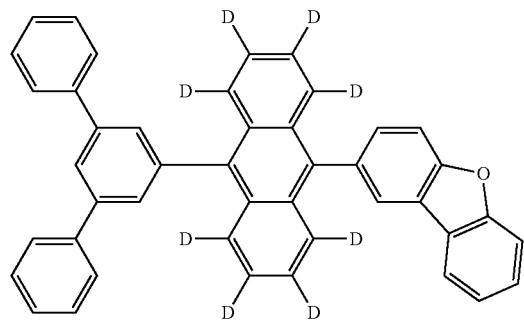
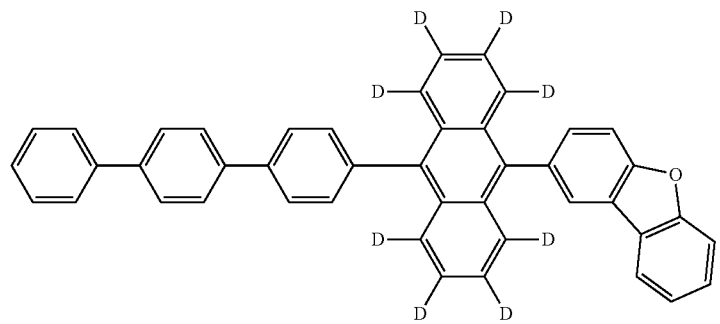
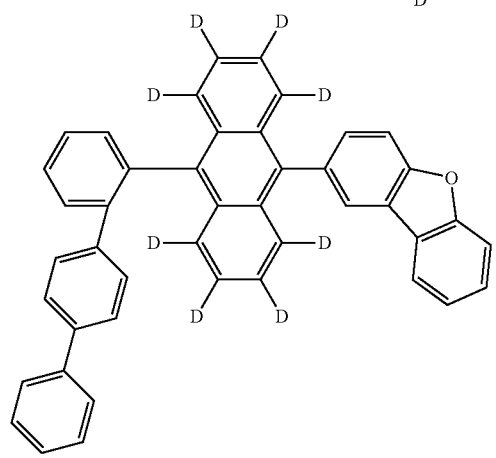
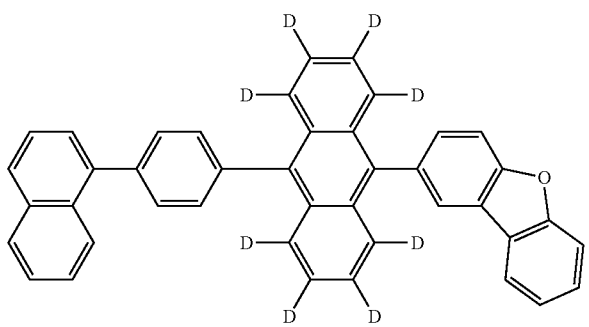
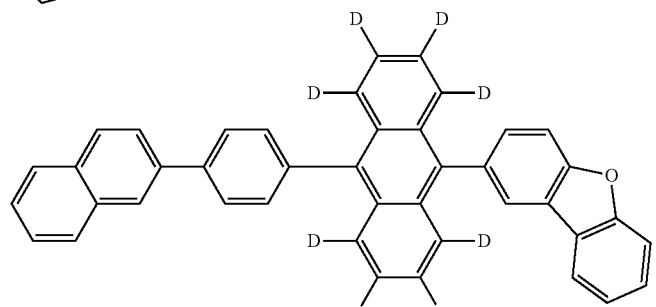
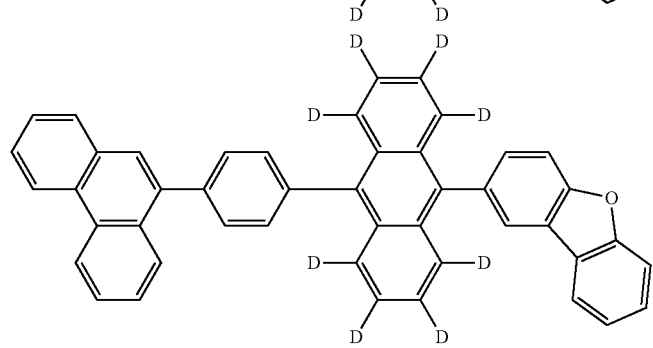

-continued
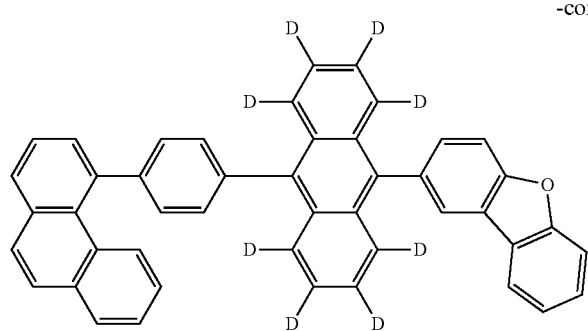
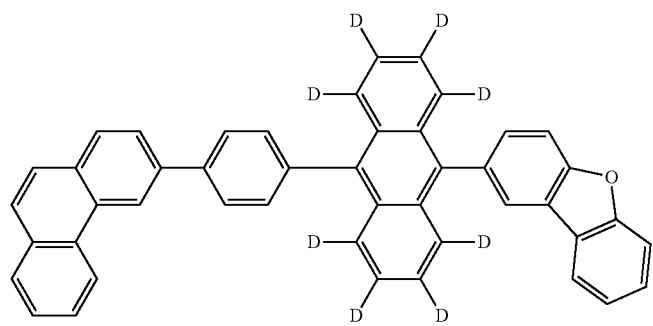
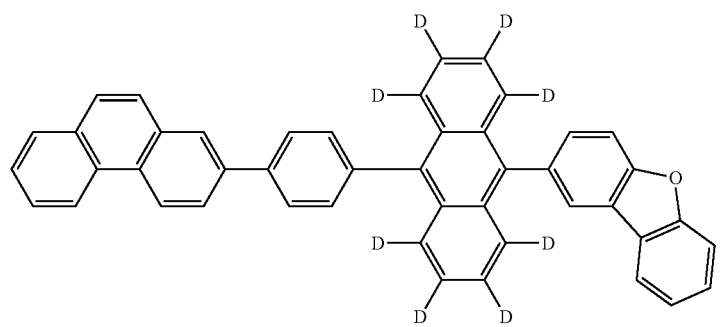
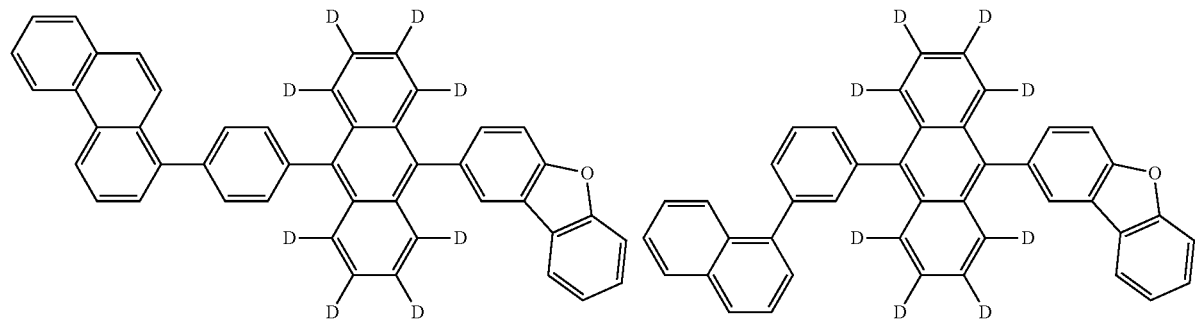
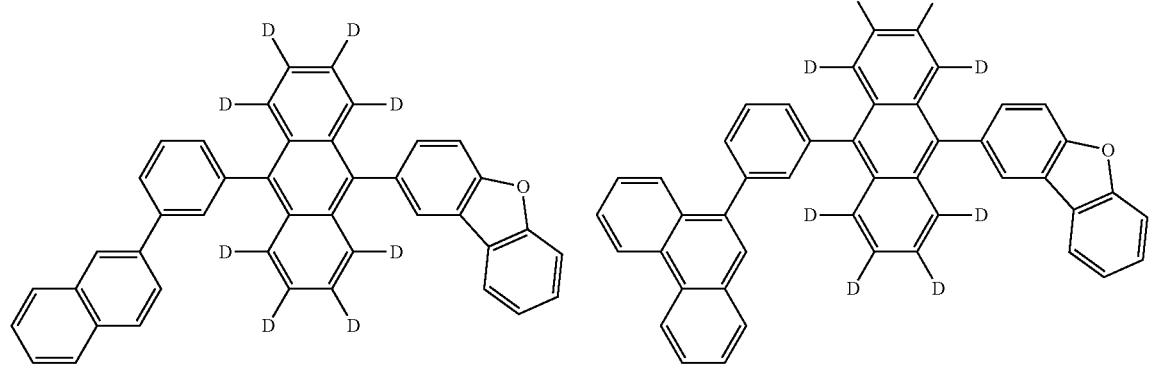

109 110
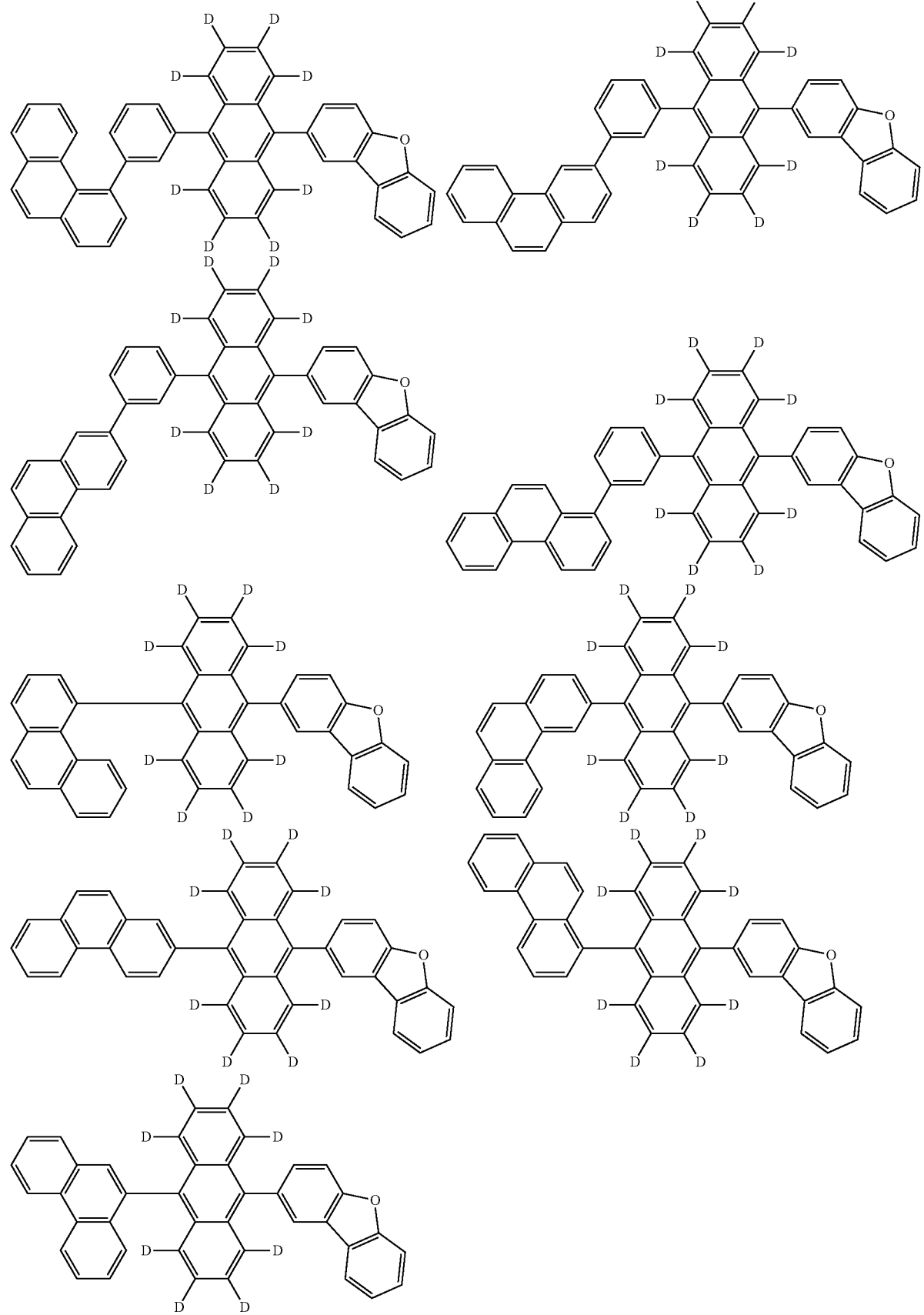
-continued

-continued
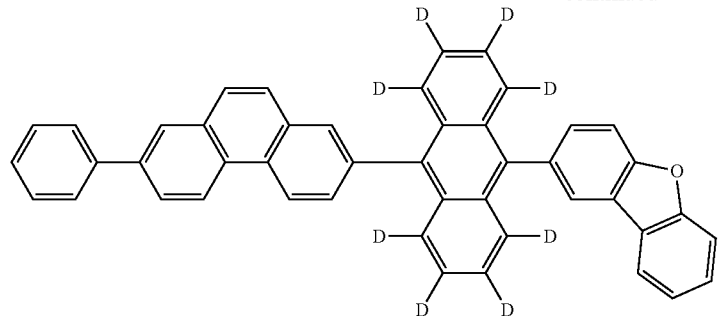
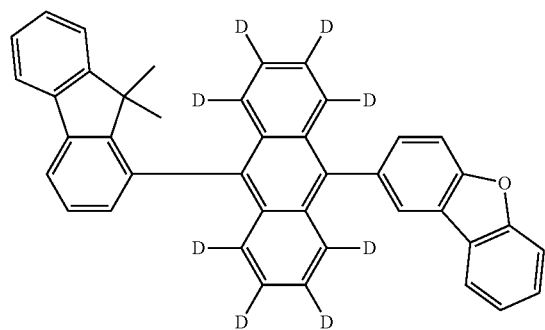
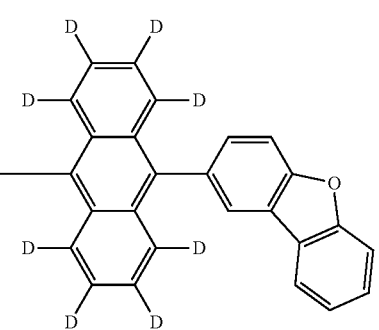
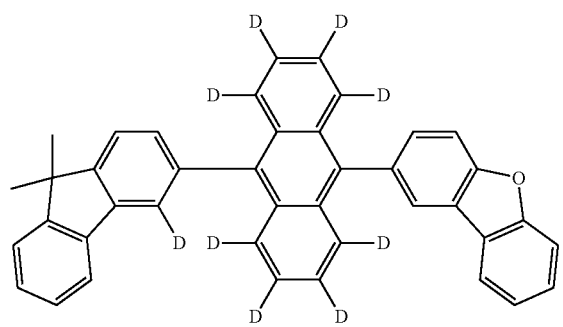
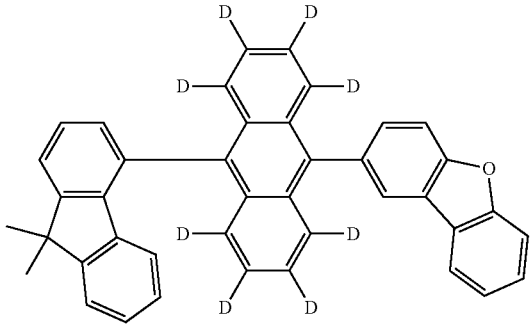
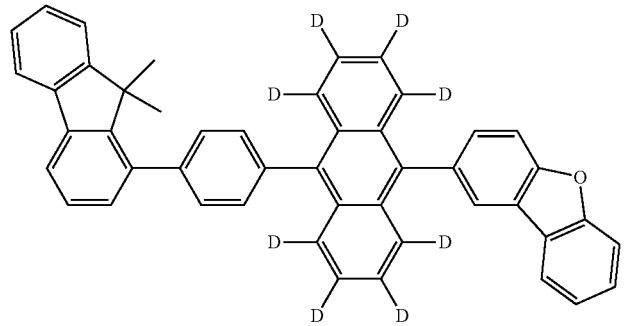
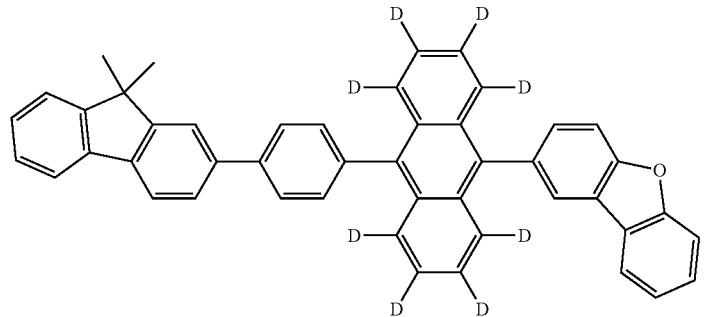

-continued
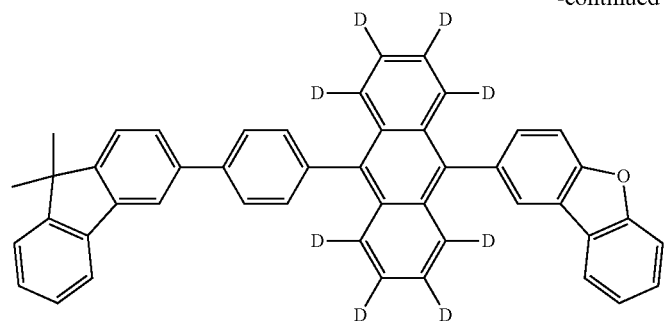
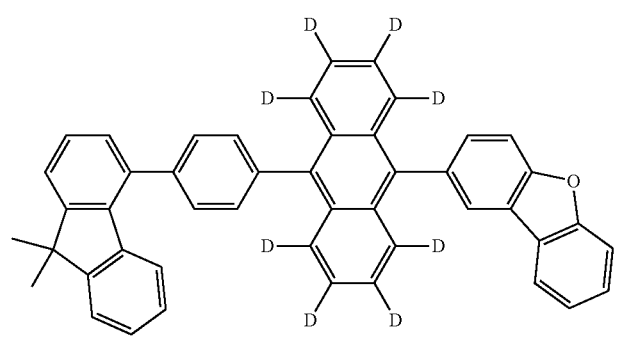
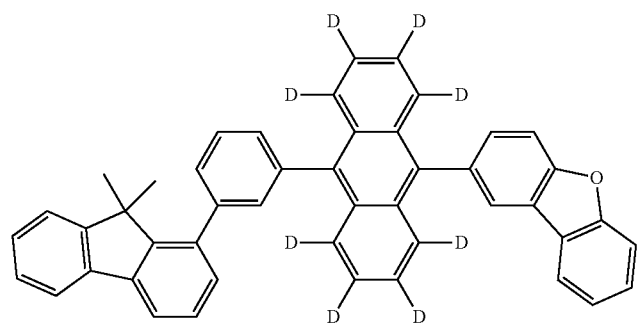
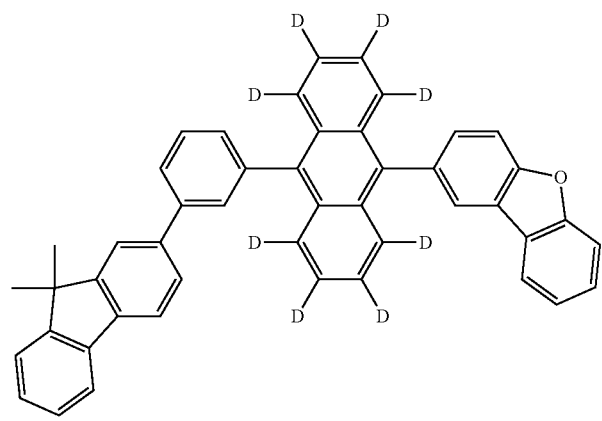

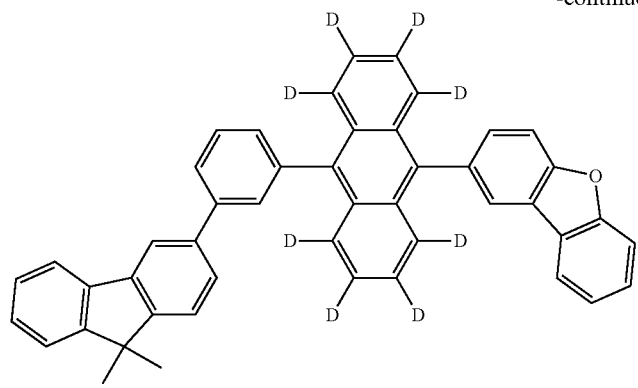
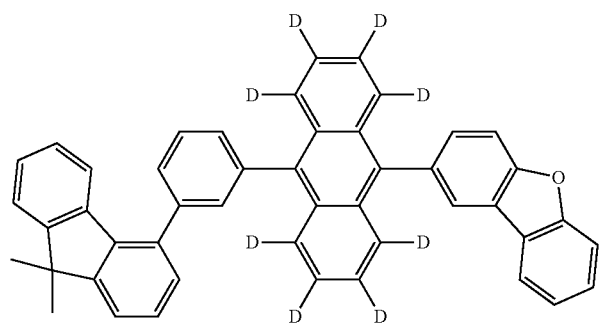
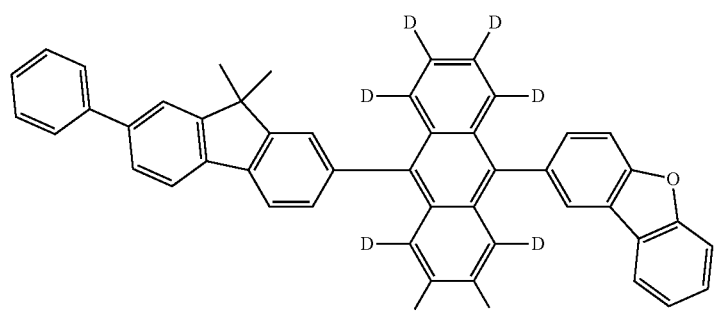
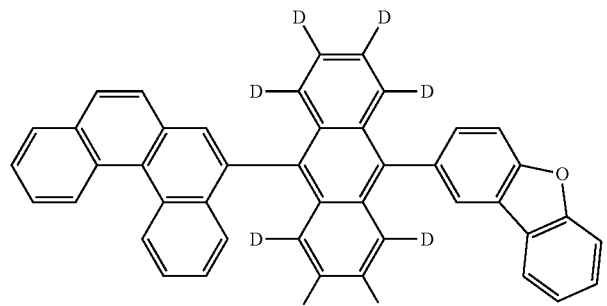
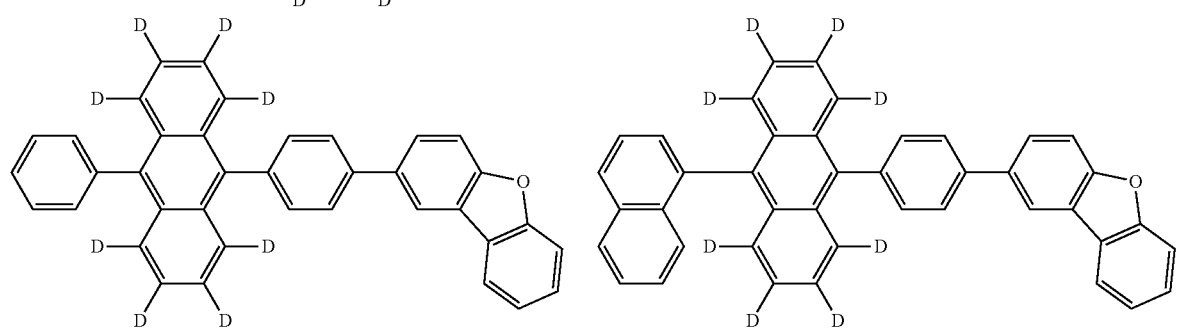

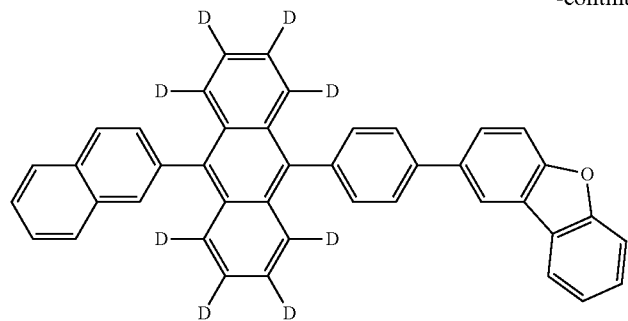
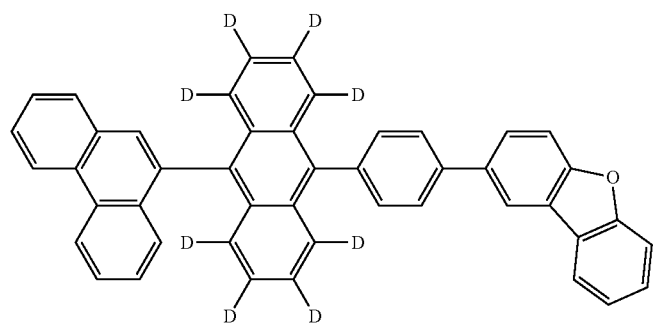
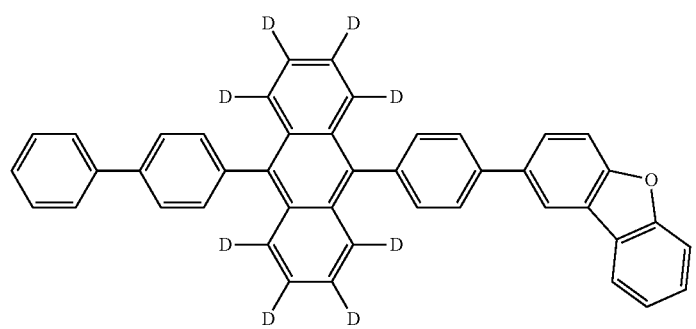
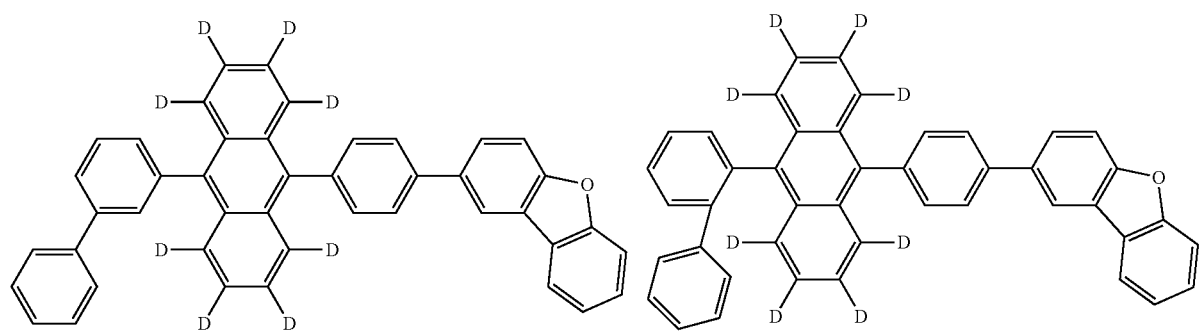
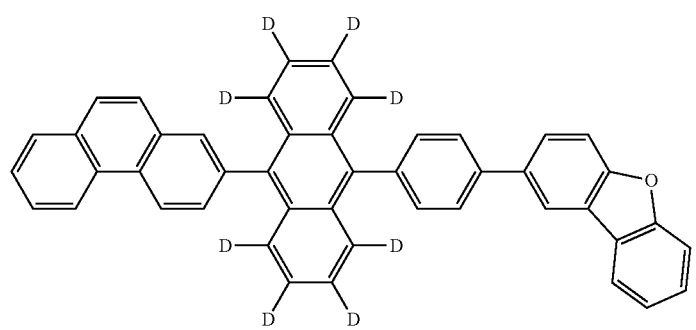

-continued
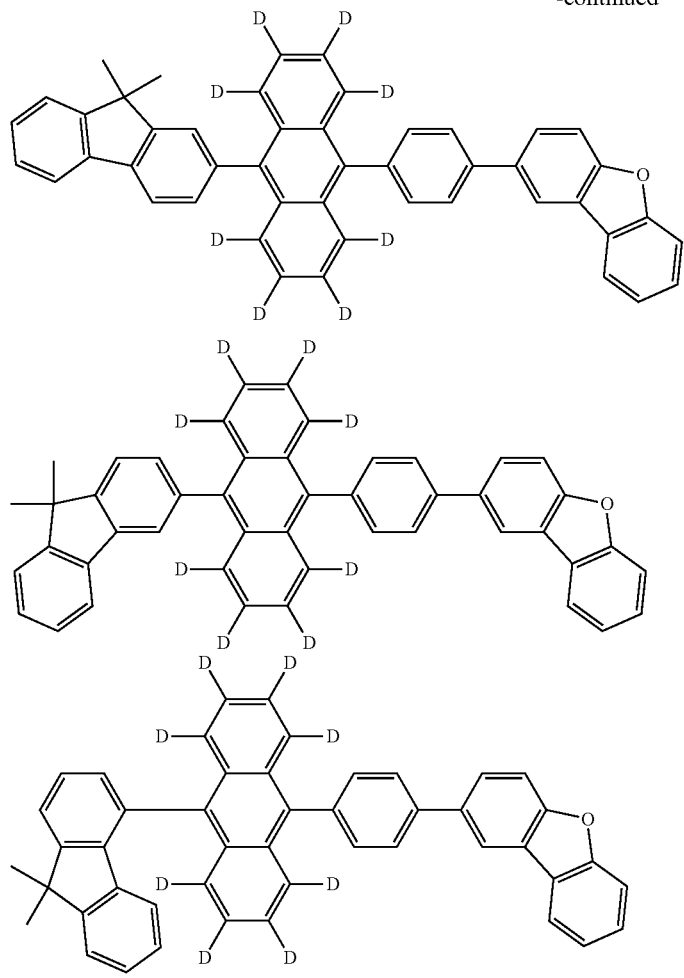
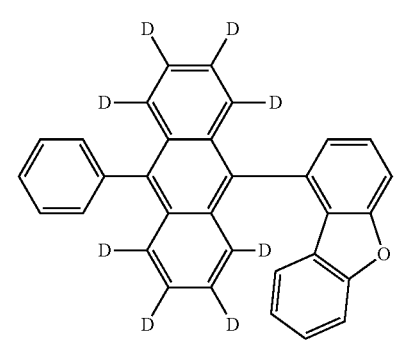
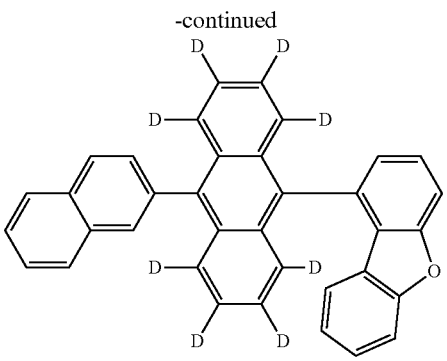
-continued
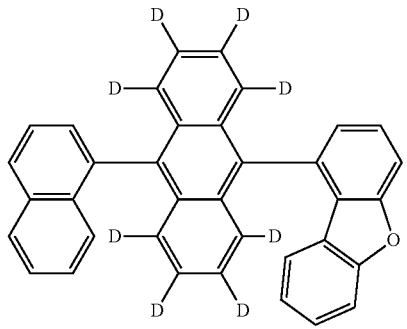
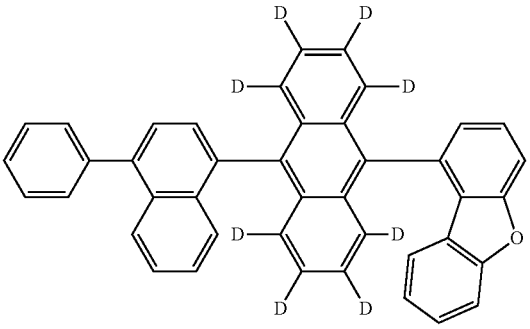

121
-continued
122
-continued
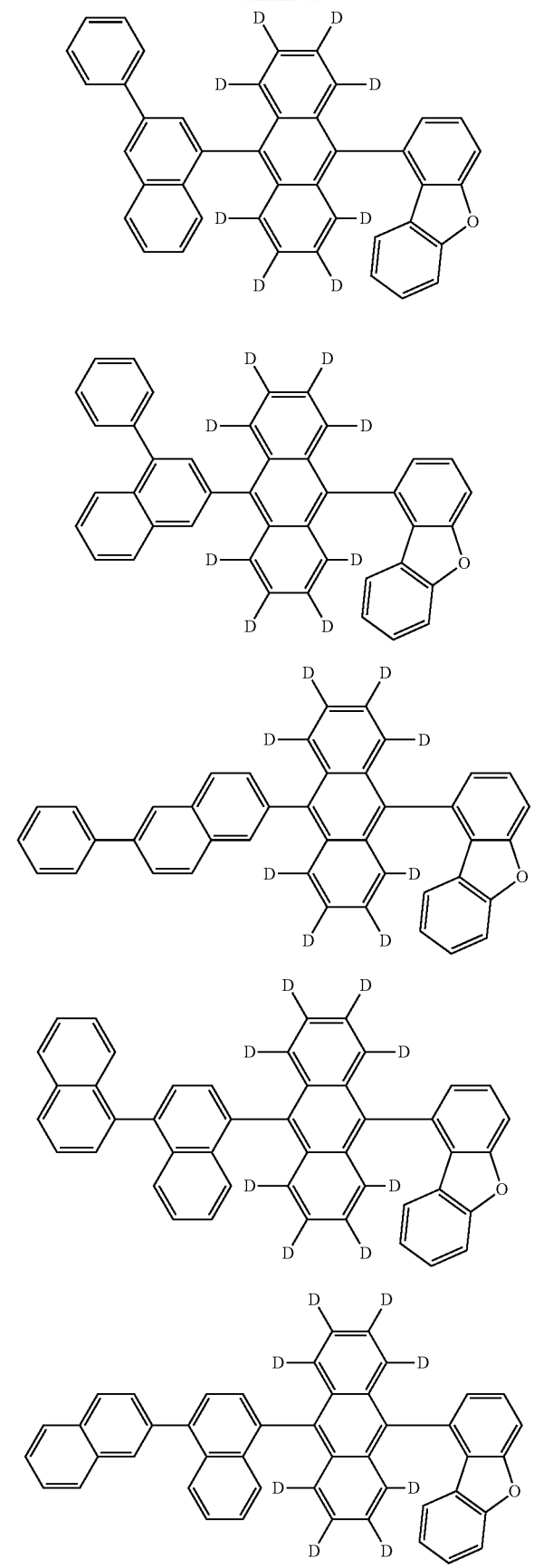
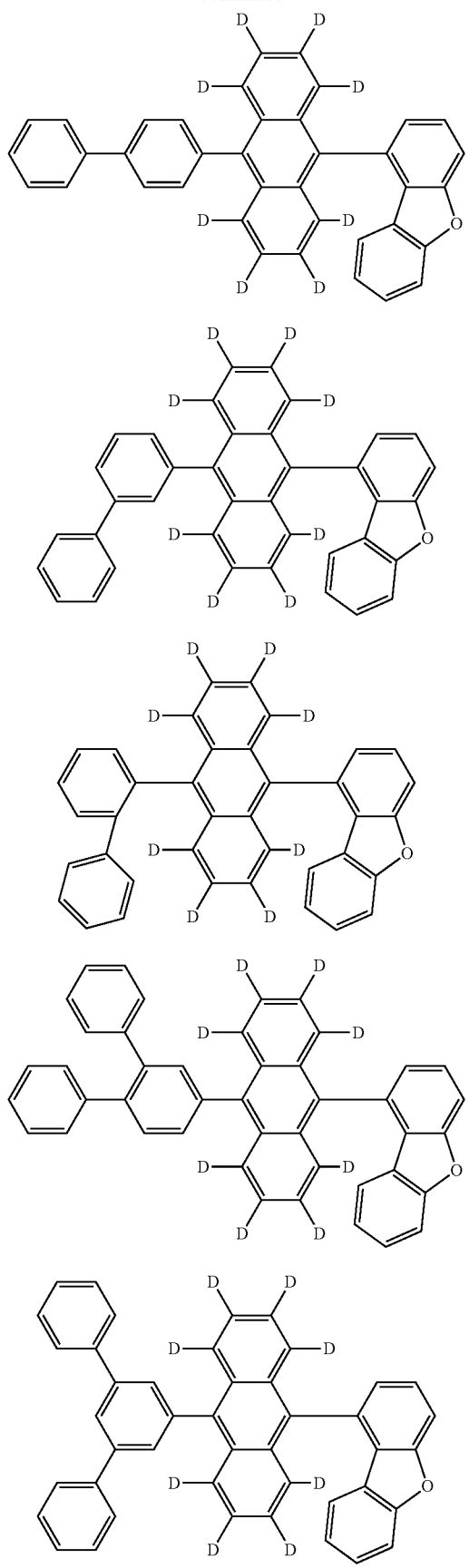

123
-continued
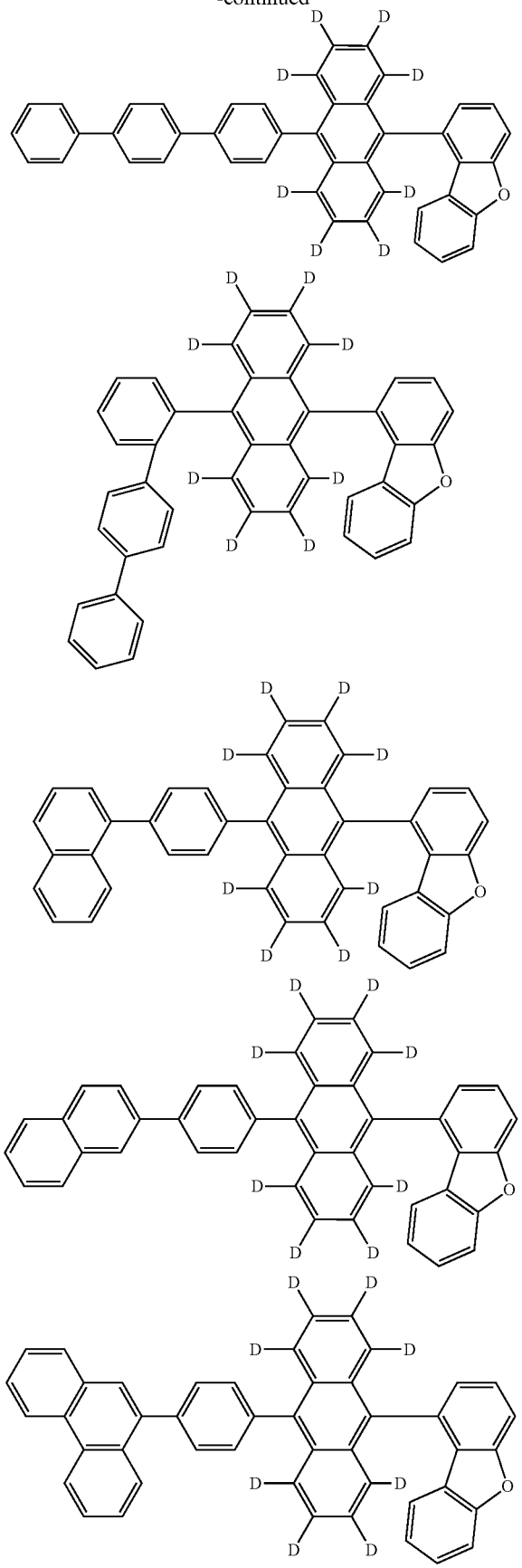
124
-continued
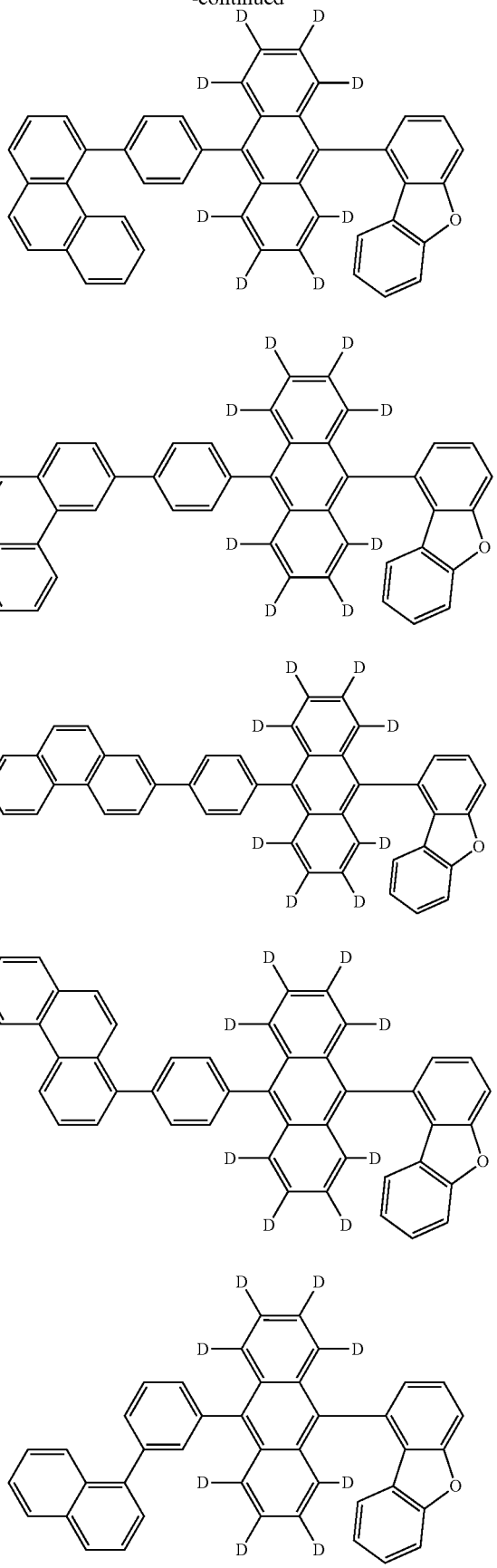

125
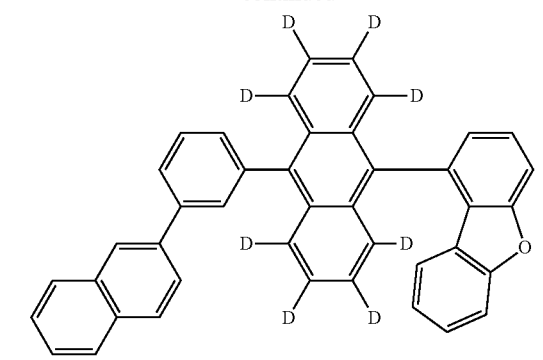
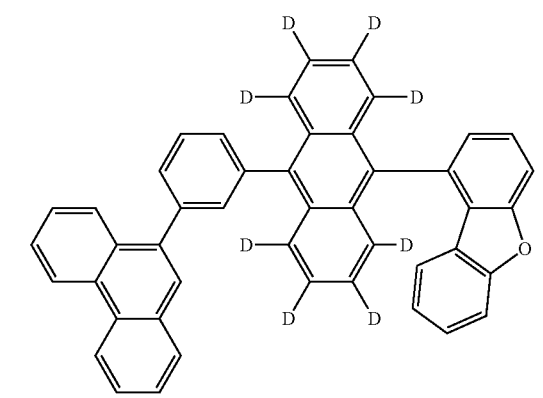
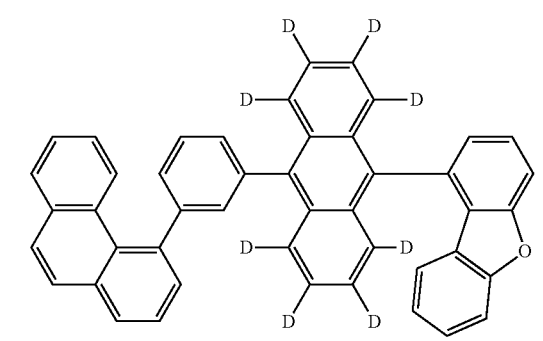
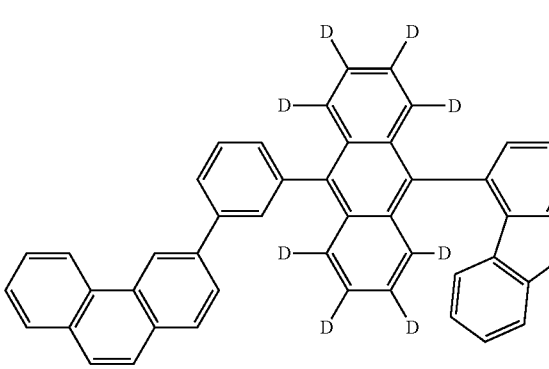
126
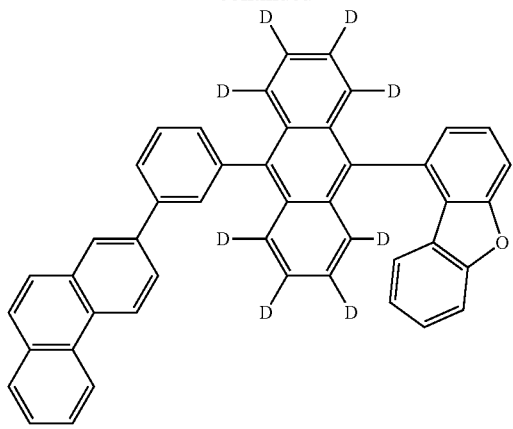
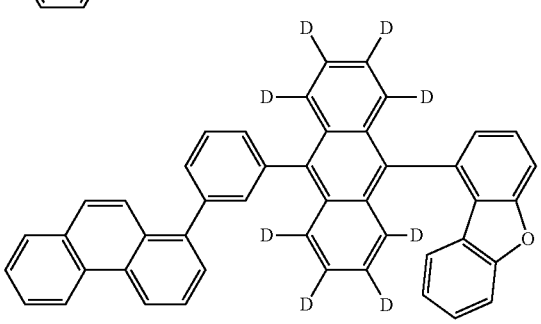
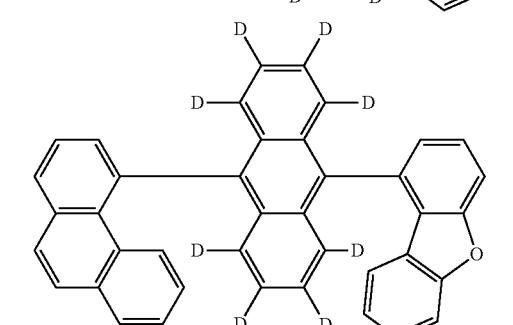
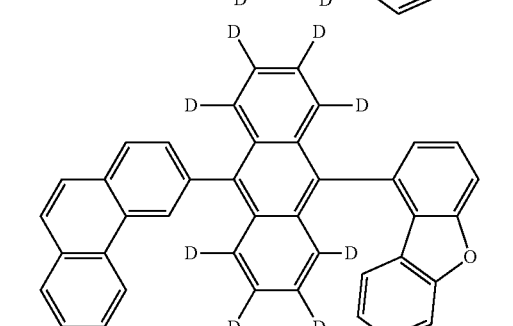
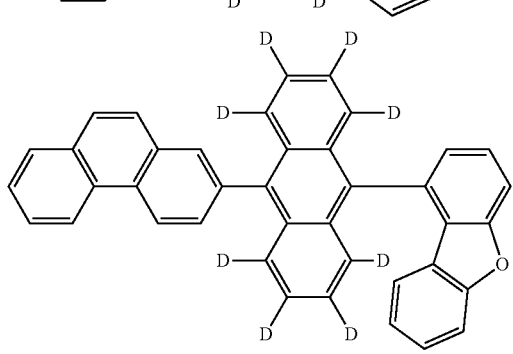

127
-continued
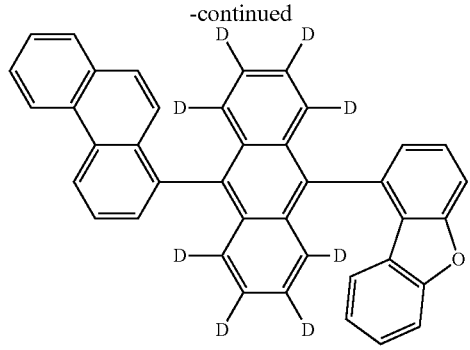
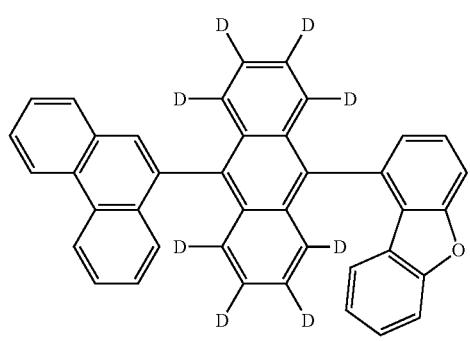
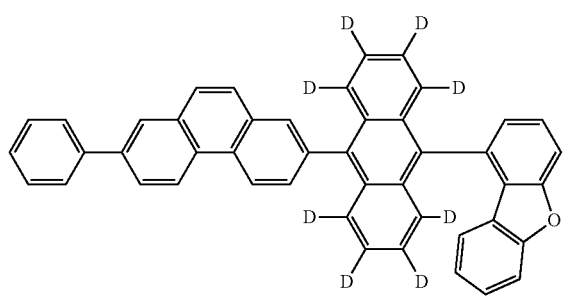
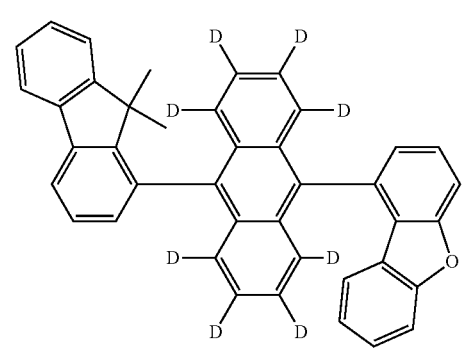
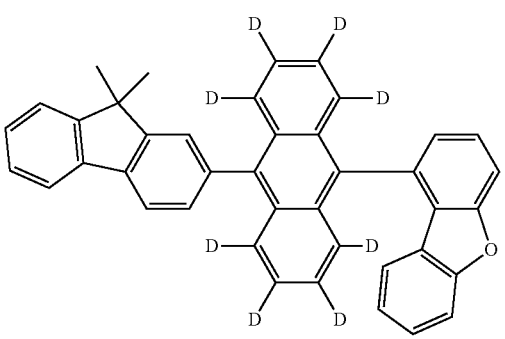
128
-continued
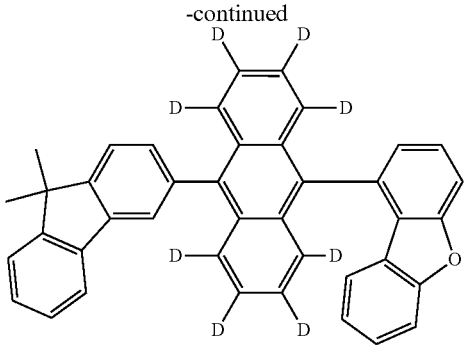
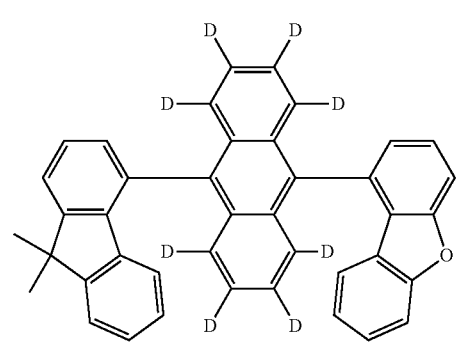
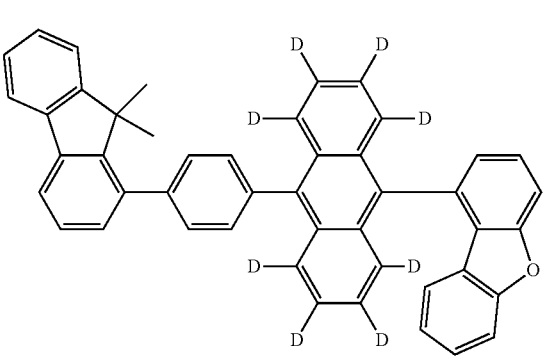
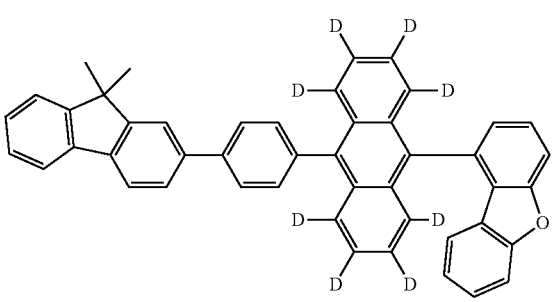
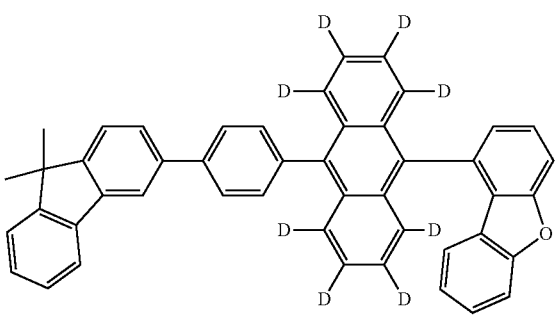

129
-continued
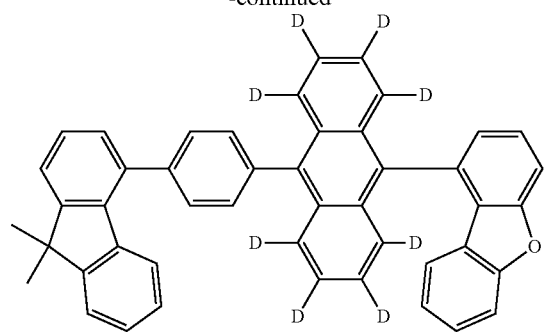
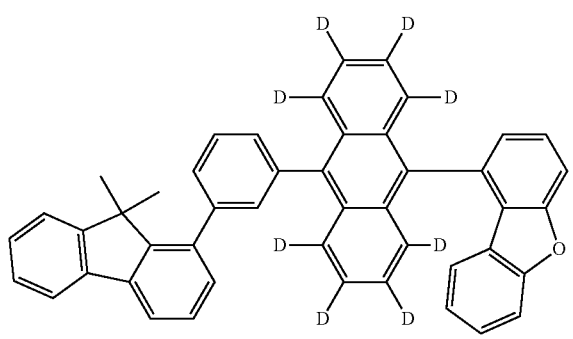
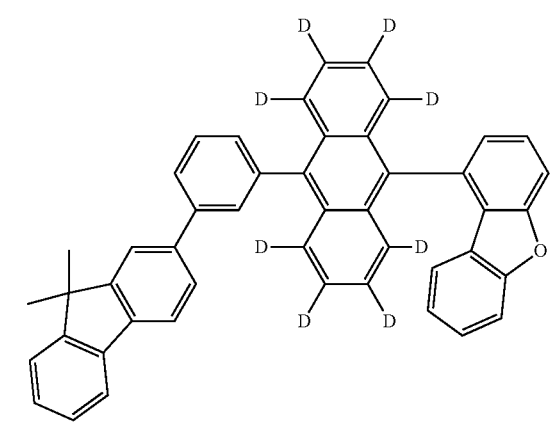
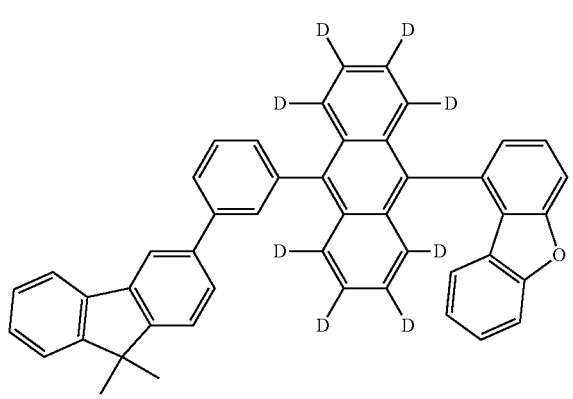
130
-continued
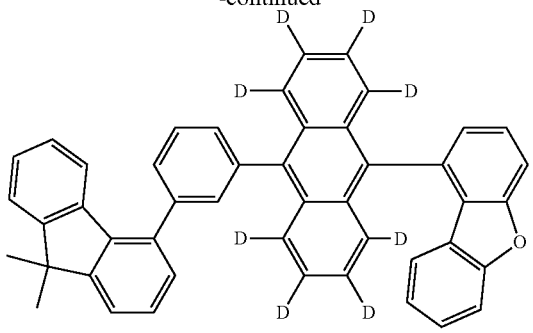
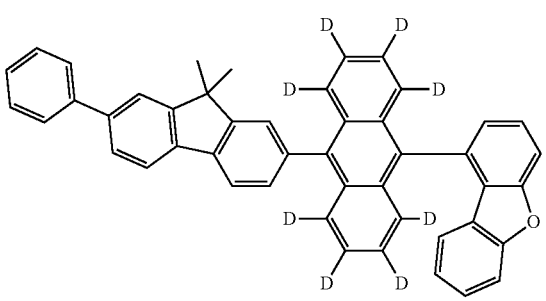
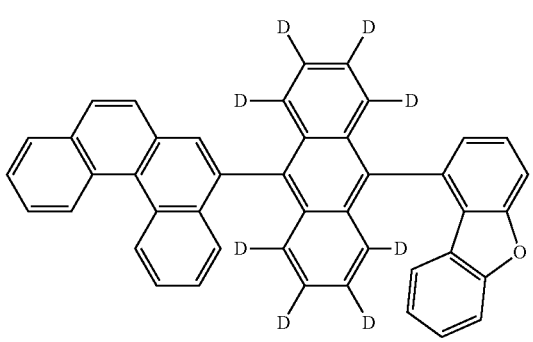
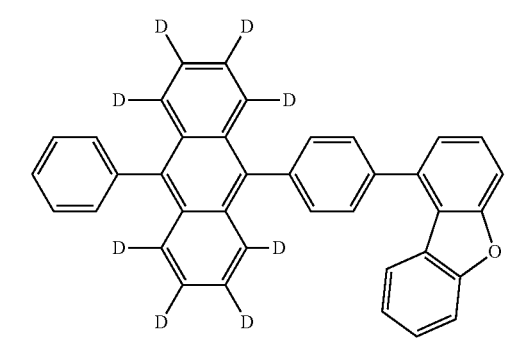
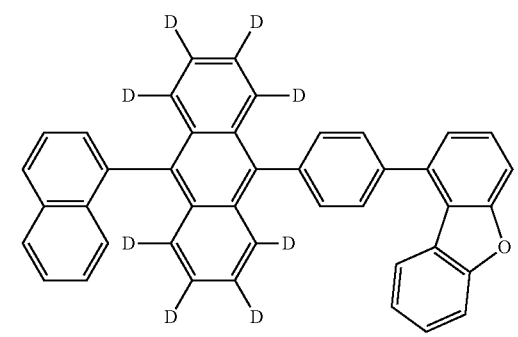

-continued
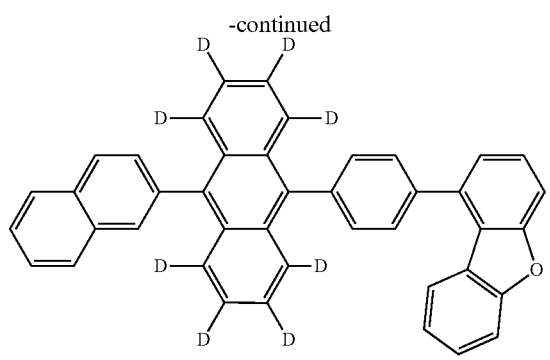
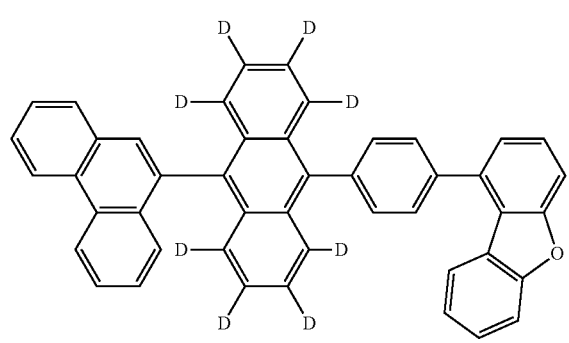
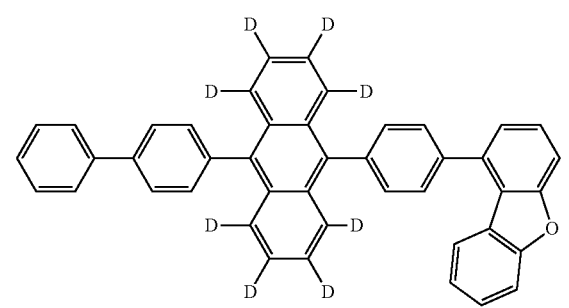
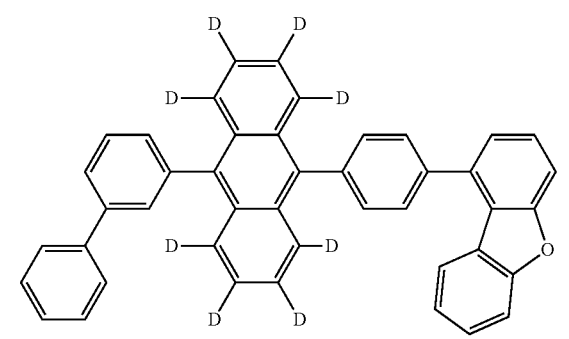
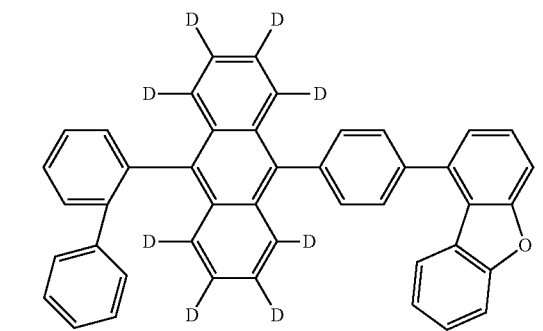
-continued
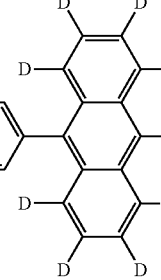
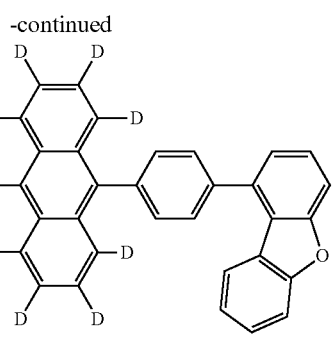
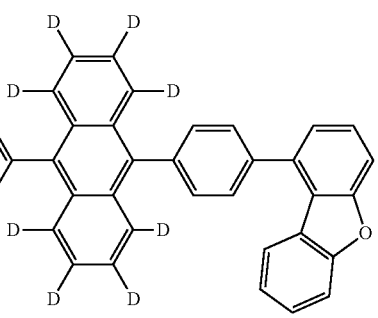
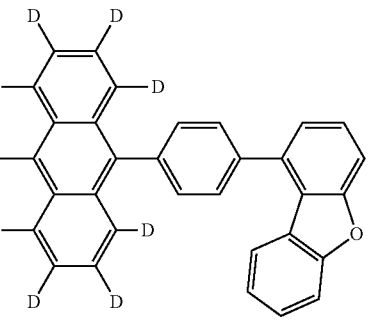
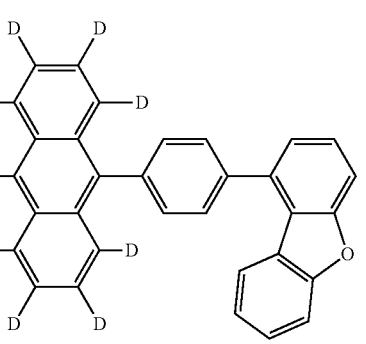
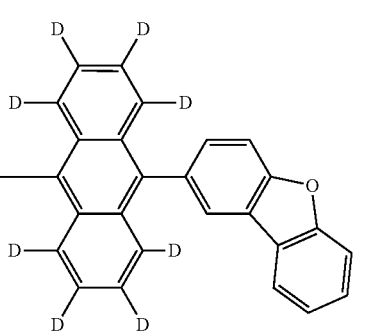

133
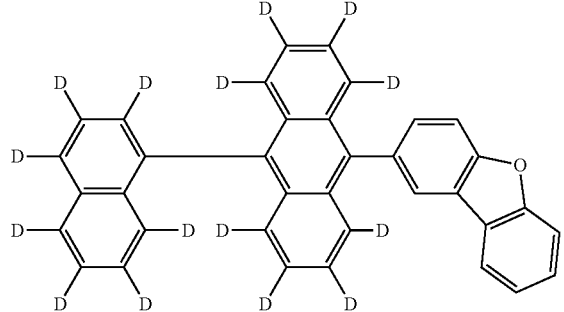
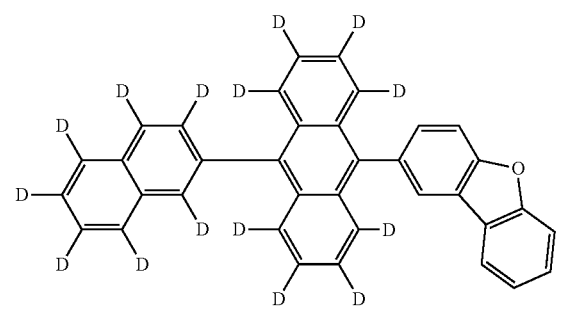
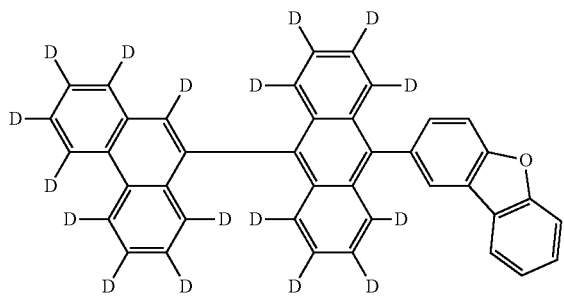
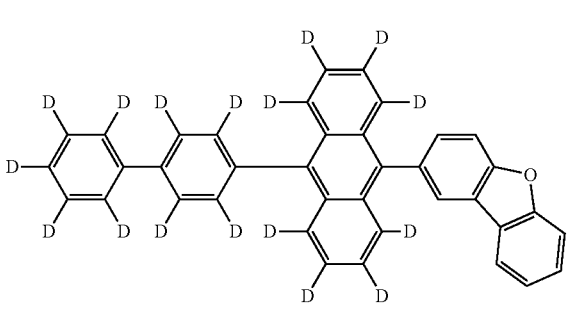
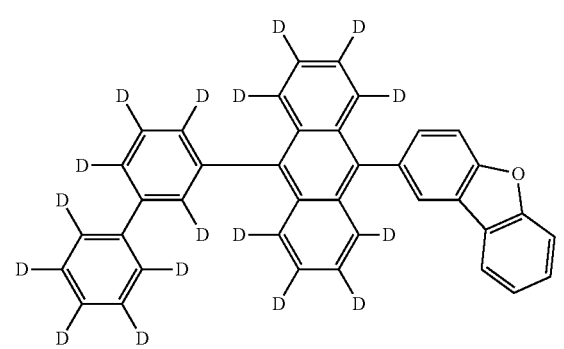
134
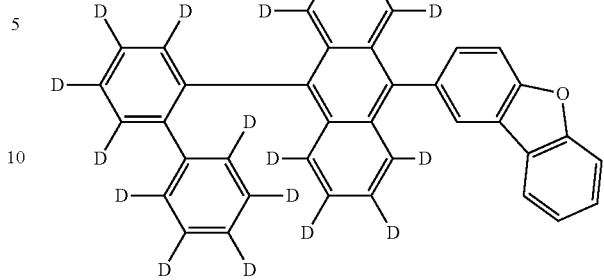
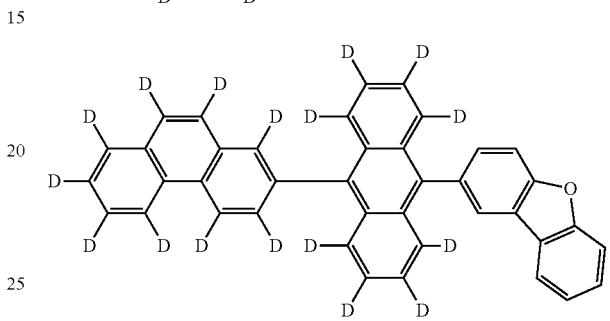
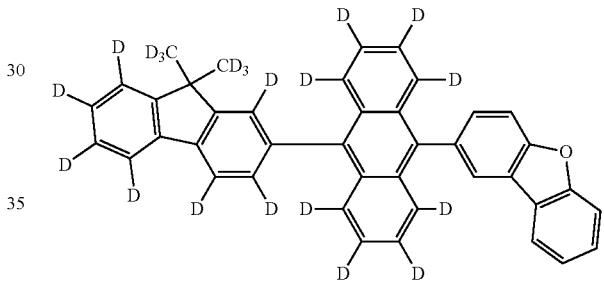
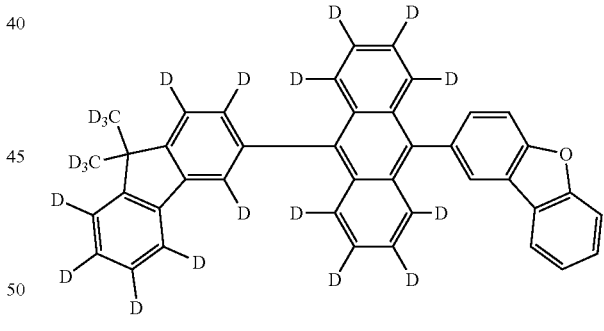
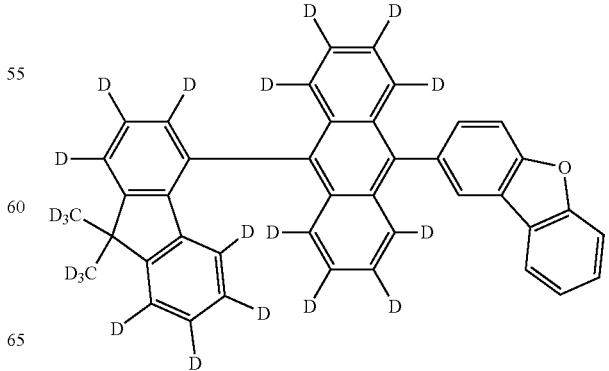

-continued
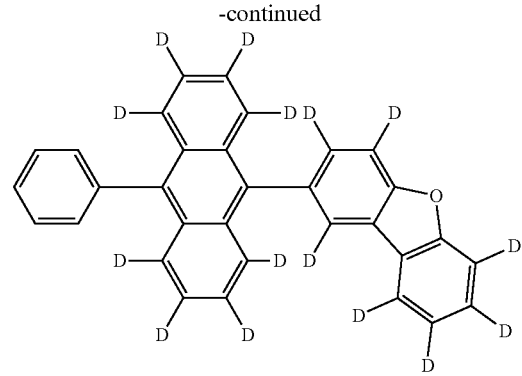
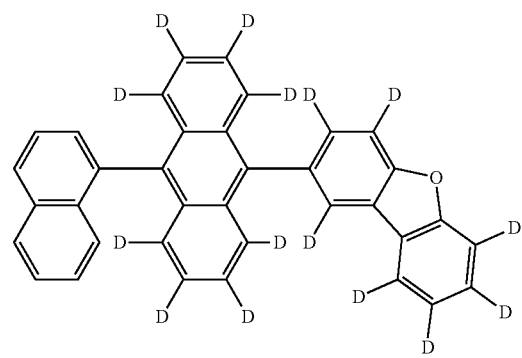
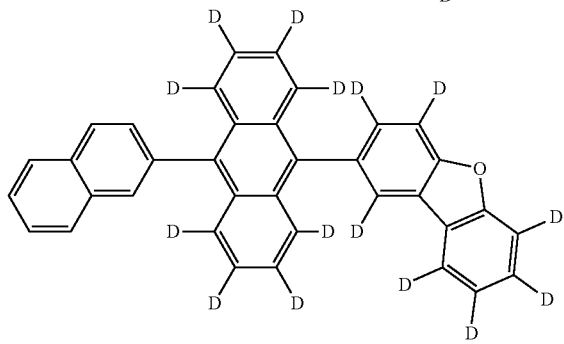
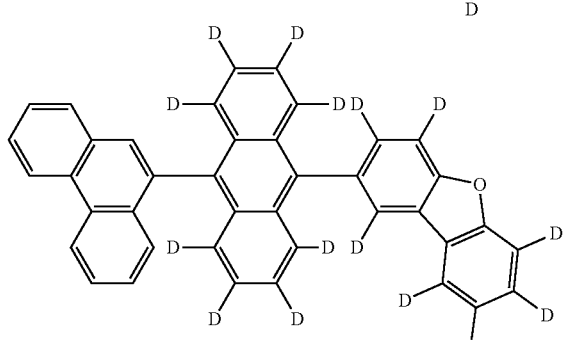
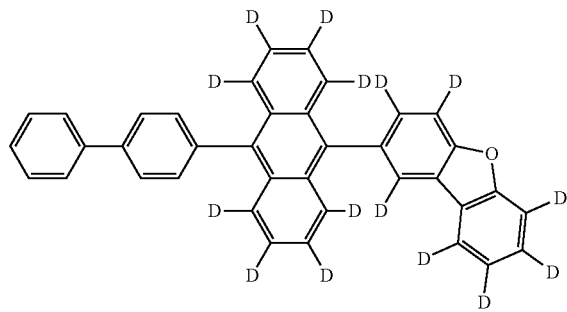
-continued
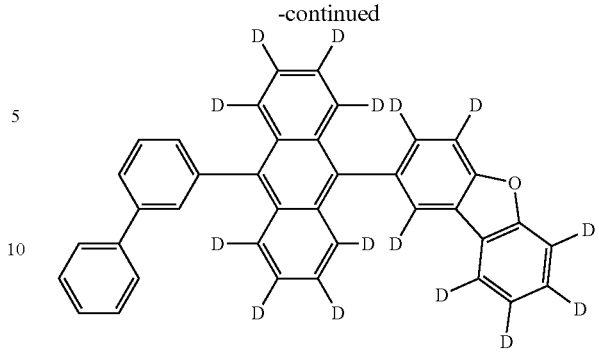
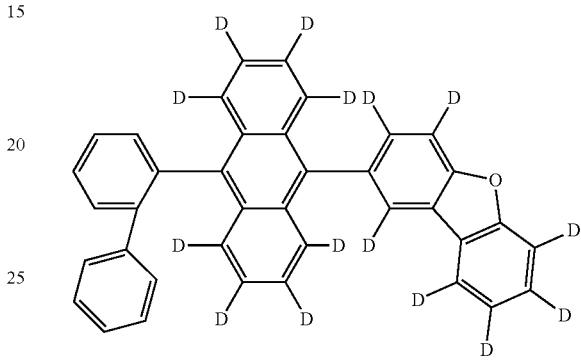
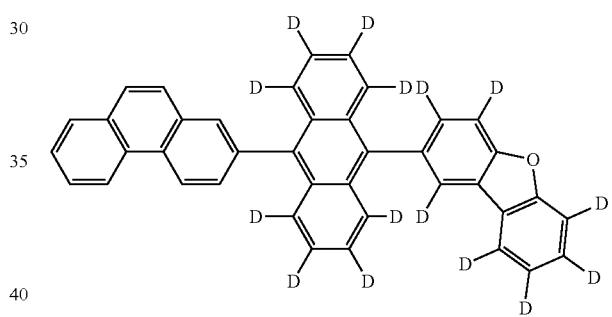
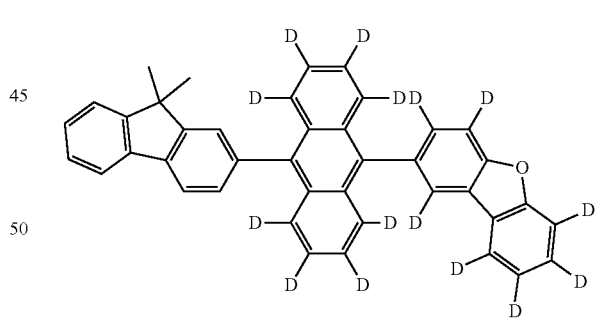
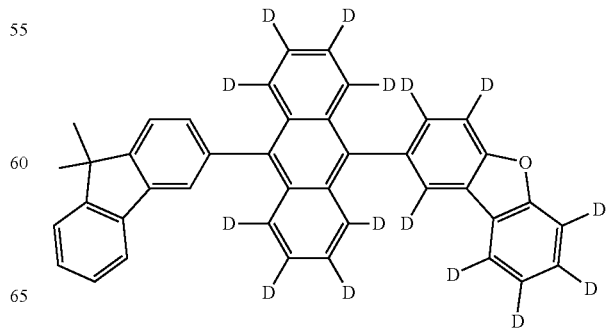

-continued
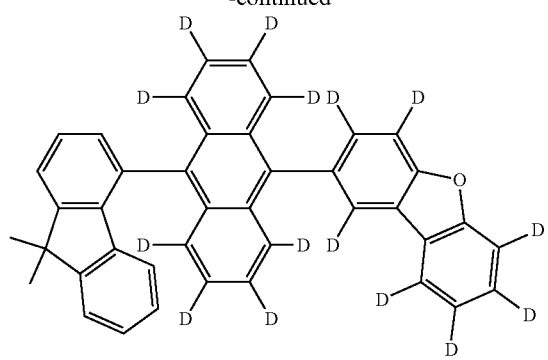
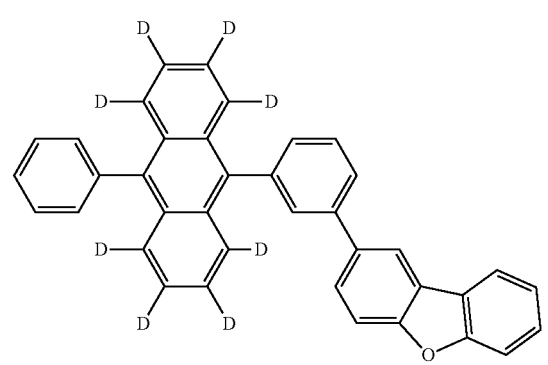
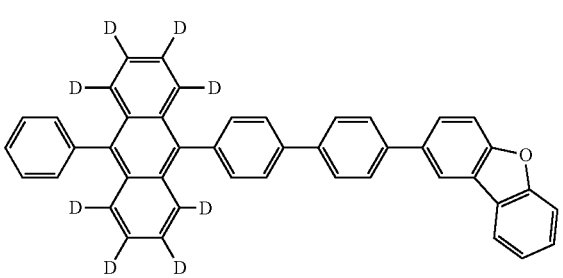
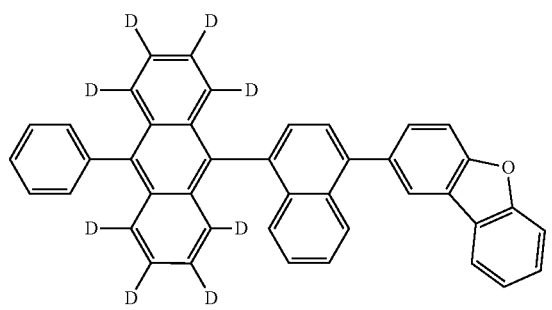
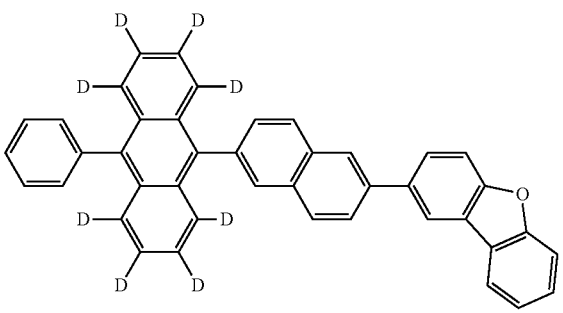
-continued
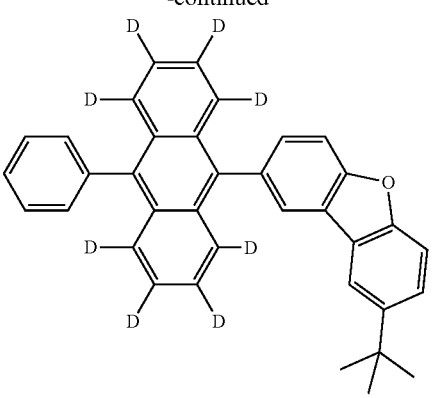
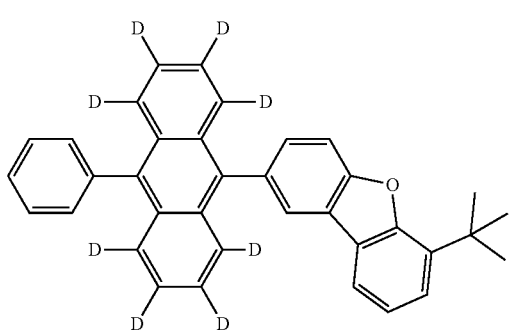
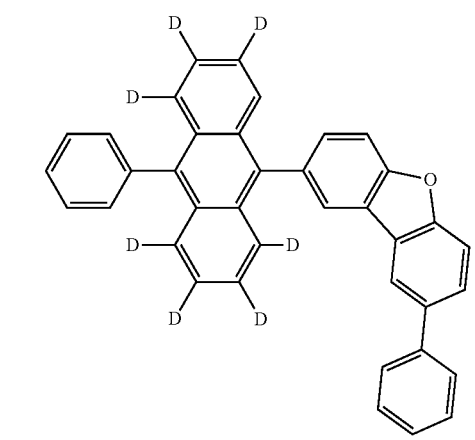
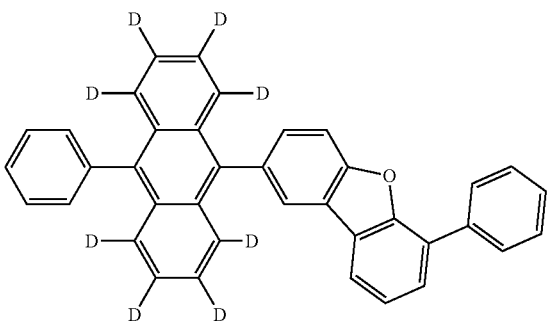

-continued
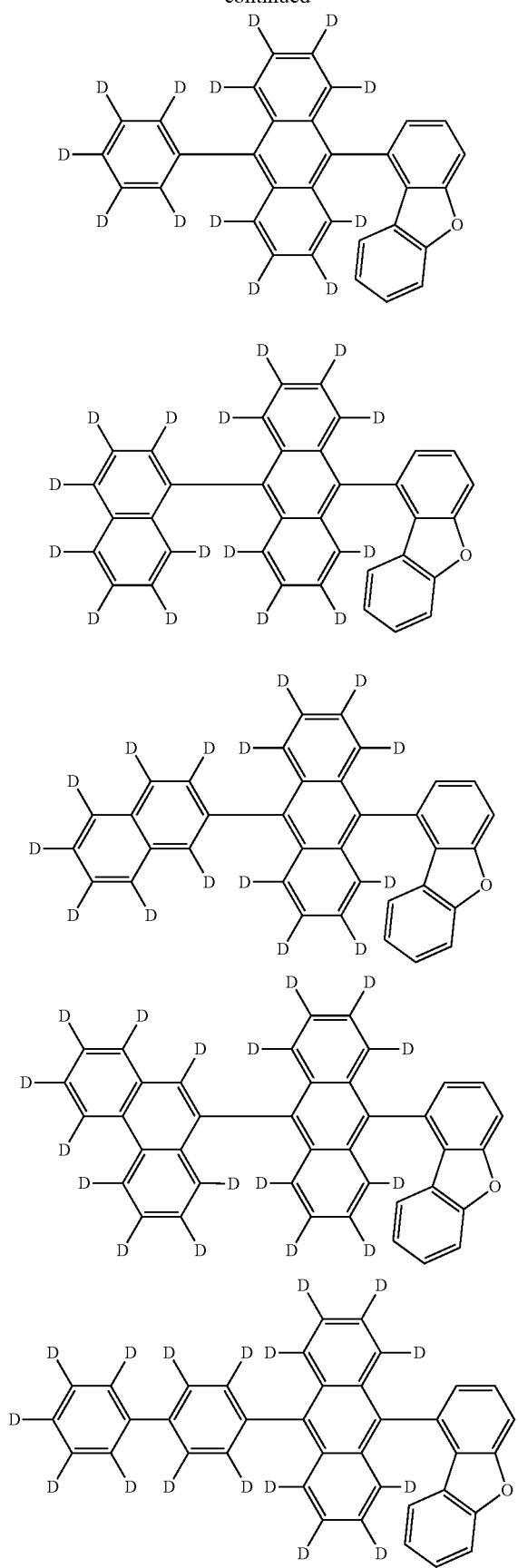
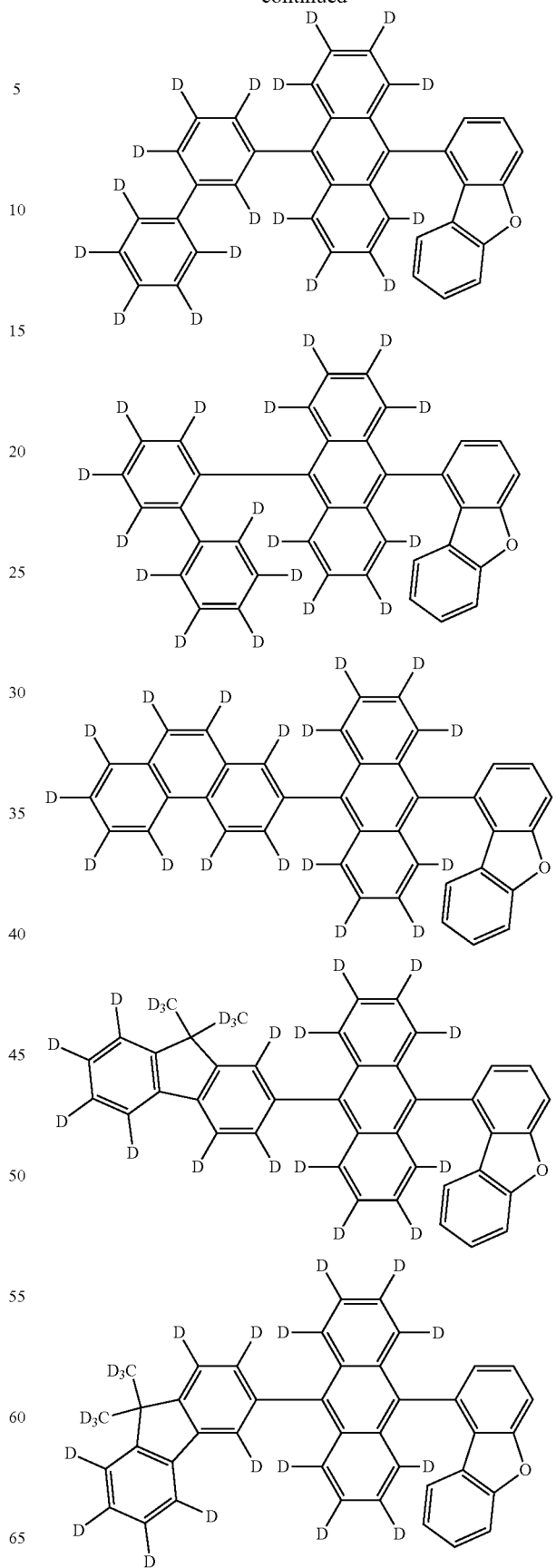

141
-continued
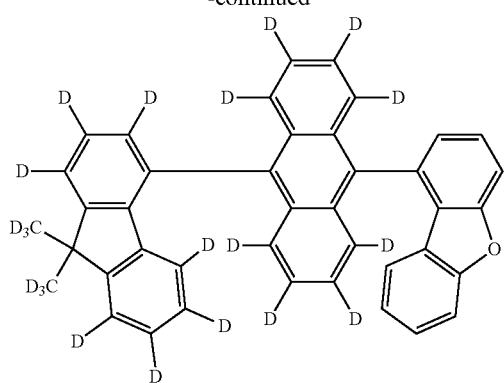
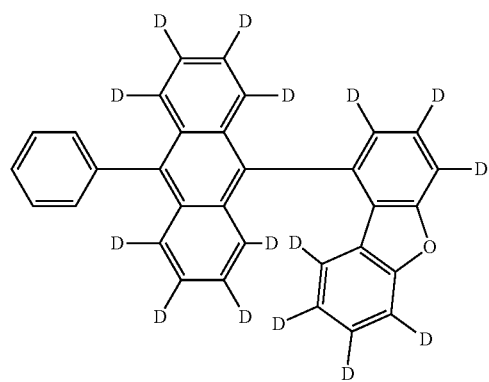
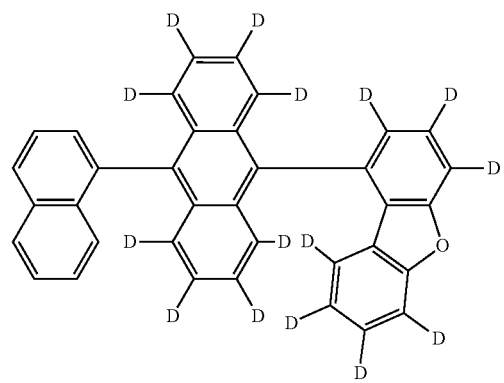
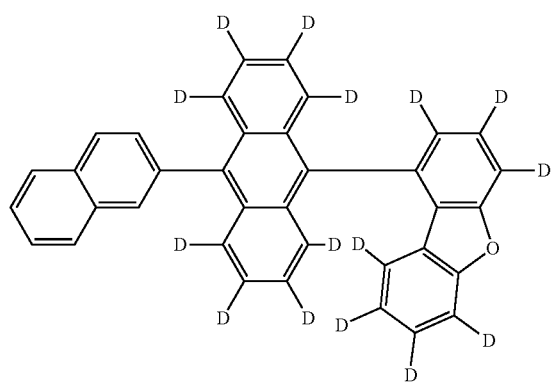
142
-continued
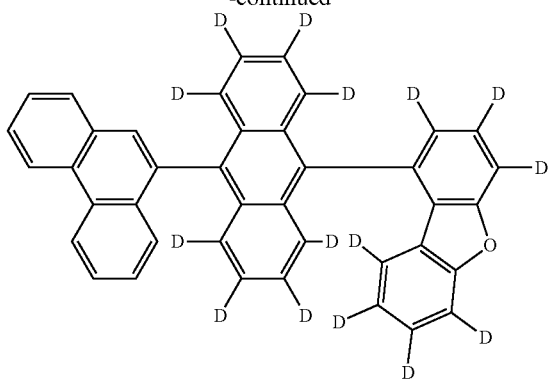
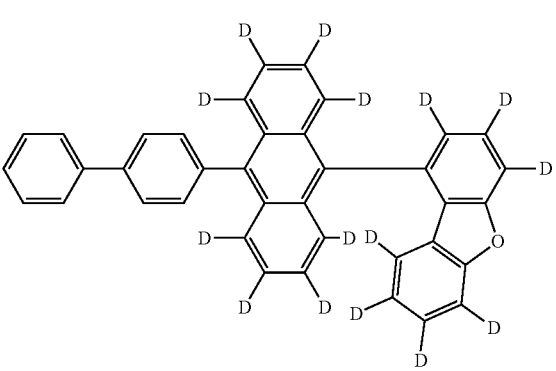
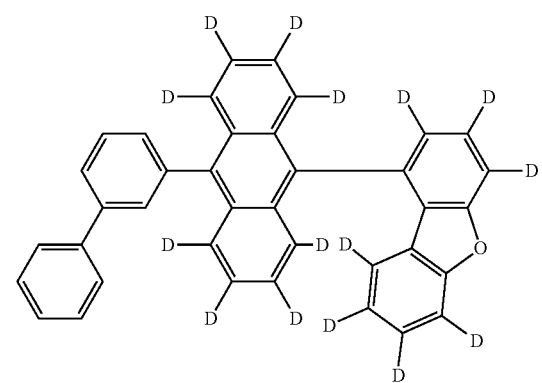
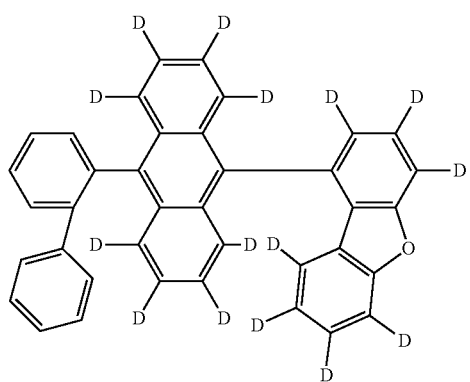

143 -continued
144 -continued
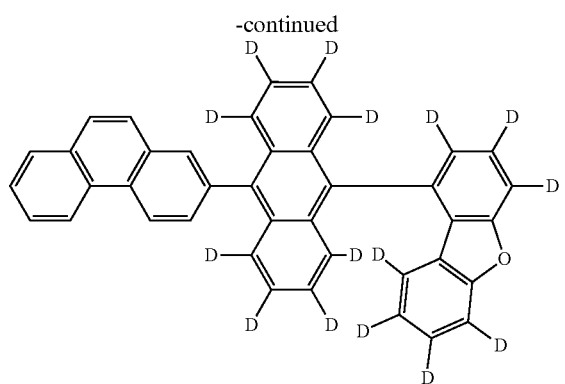
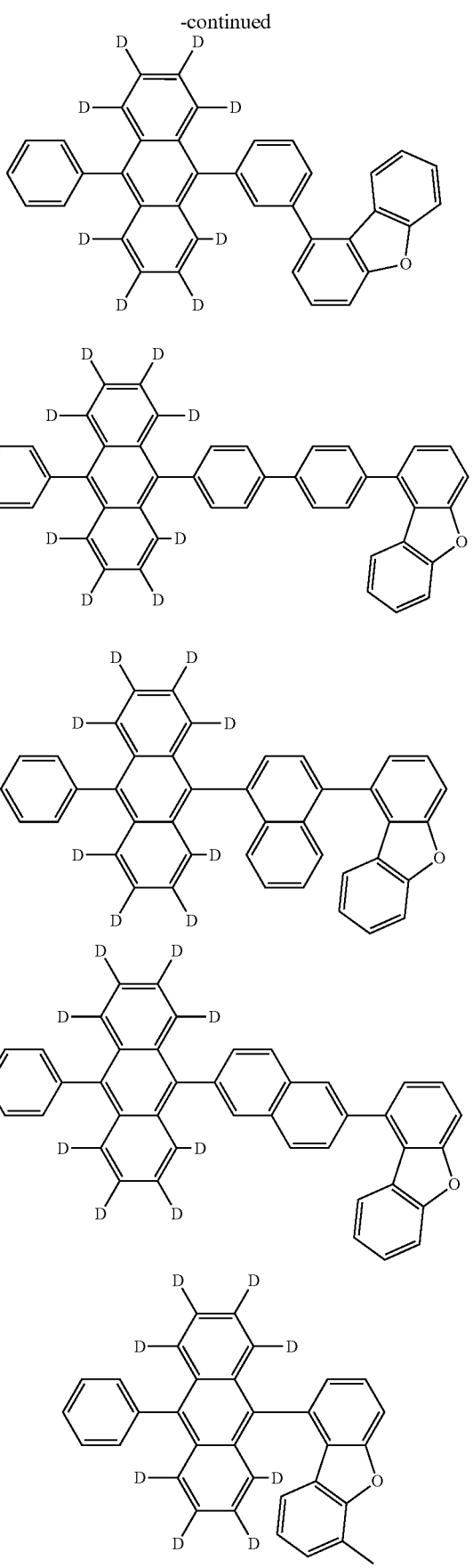

-continued

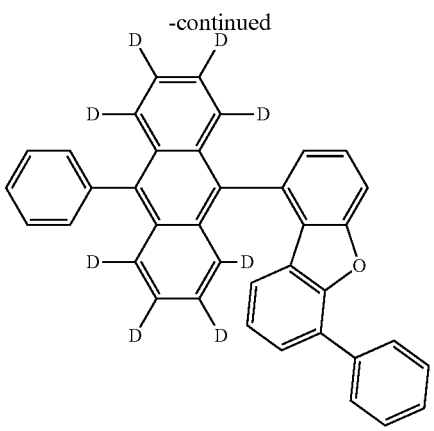

(Compound Represented by Formula (11))

The compound represented by the formula (11) is explained below.

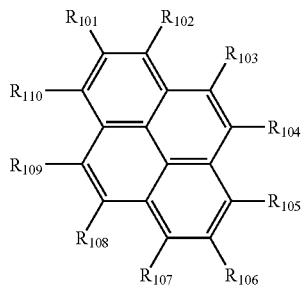

In the formula (11),
one or more pairs of two or more adjacent groups of $R_{101}$ to $R_{110}$ are bonded with each other to form a substituted or unsubstituted, saturated or unsaturated ring, or do not form a substituted or unsubstituted, saturated or unsaturated ring;
at least one of $R_{101}$ to $R_{110}$ is a monovalent group represented by the formula (12);
$R_{101}$ to $R_{110}$ that do not form the substituted or unsubstituted, saturated or unsaturated ring and that are not a monovalent group represented by the following formula (12) are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;
$R_{901}$ to $R_{907}$ are as defined in the formula (1);

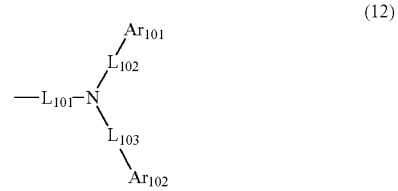

wherein, in the formula (12), $Ar_{101}$ and $Ar_{102}$ are independently
a substituted or unsubstituted aryl group having 6 to 50 ring carbon atoms, or
a substituted or unsubstituted monovalent heterocyclic group having 5 to 50 ring atoms;
$L_{101}$ to $L_{103}$ are independently
a single bonded,
a substituted or unsubstituted arylene group having 6 to 30 ring carbon atoms, or
a substituted or unsubstituted divalent heterocyclic group having 5 to 30 ring atoms;
In the formula (11), it is preferable that two of $R_{101}$ to $R_{110}$ are the group represented by the formula (12).
In one embodiment, the compound represented by the formula (11) is represented by the following formula (13):

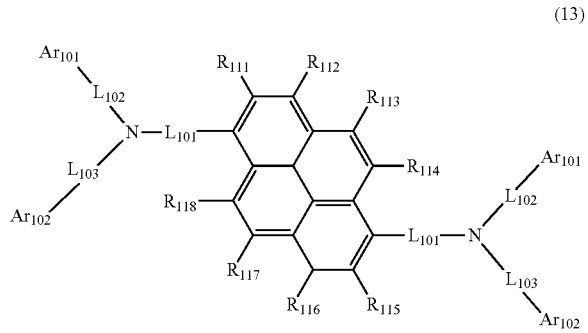

wherein in the formula (13), $R_{111}$ to $R_{118}$ are the same as $R_{101}$ to $R_{110}$ that is not a monovalent group represented by the formula (12) in the formula (11). $Ar_{101}$, $Ar_{102}$, $L_{101}$, $L_{102}$ and $L_{103}$ are as defined in the formula (12).
In the formula (11), $L_{101}$ is preferably a single bond and $L_{102}$ and $L_{103}$ are preferably a single bond.
In one embodiment, the compound represented by the formula (11) is represented by the formula (14) or (15).

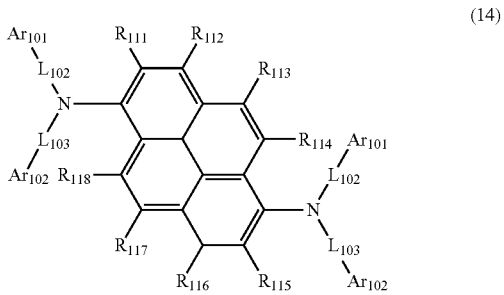

wherein in the formula (14), $R_{111}$ to $R_{118}$ are as defined in the formula (13). $Ar_{101}$, $Ar_{102}$, $L_{102}$ and $L_{103}$ are as defined in the formula (12).

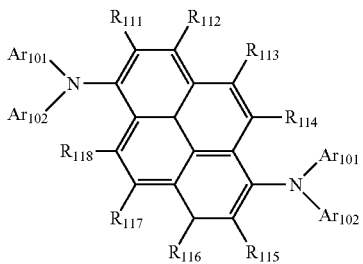

wherein in the formula (15), $R_{111}$ to $R_{118}$ are as defined in the formula (13). $Ar_{101}$ and $Ar_{102}$ are as defined in the formula (12).

In the formula (11) and formula (12), it is preferable that at least one of $Ar_{101}$ and $Ar_{102}$ is the group represented by the following formula (16).

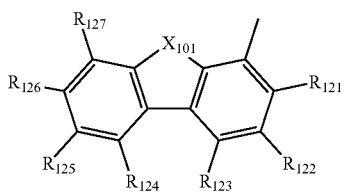

wherein in the formula (16), $X_{101}$ is an oxygen atom or a sulfur atom;

One or more pairs of two or more adjacent groups of $R_{121}$ to $R_{127}$ are bonded with each other to form a substituted or unsubstituted, saturated or unsaturated ring, or do not form a substituted or unsubstituted, saturated or unsaturated ring:

$R_{121}$ to $R_{127}$ that do not form the substituted or unsubstituted, saturated or unsaturated ring are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms; and $R_{901}$ to $R_{907}$ are as defined in the formula (1).

It is preferable that $X_{101}$ is an oxygen atom.

It is preferable that at least one of $R_{121}$ to $R_{127}$ is a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted monovalent heterocyclic group having 5 to 50 ring atoms.

It is preferable that in the formula (11) and formula (12), $Ar_{101}$ is a group represented by the formula (16) and $Ar_{102}$ is a substituted or unsubstituted aryl group having 6 to 50 ring carbon atoms.

In one embodiment, the compound represented by the formula (11) is represented by the following formula (17).

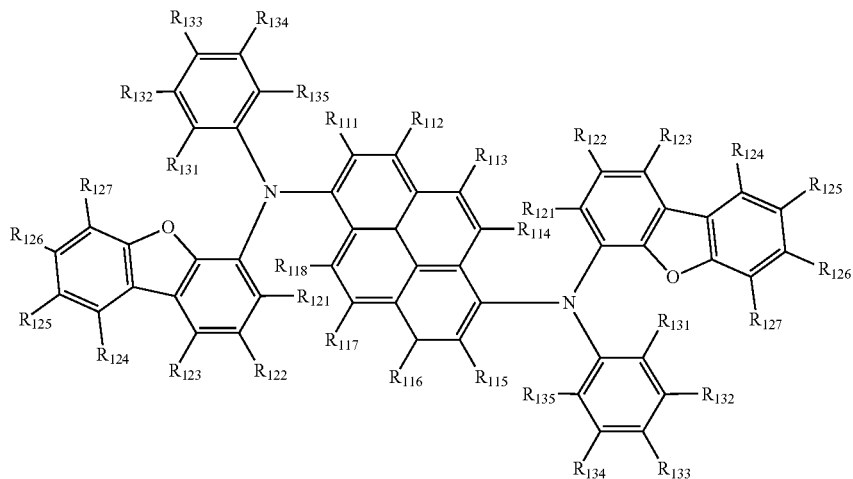

wherein in the formula (17), $R_{111}$ to $R_{118}$ are as defined in the formula (13), and $R_{121}$ to $R_{127}$ are as defined in the formula (16);

$R_{131}$ to $R_{135}$ are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms; and $R_{901}$ to $R_{907}$ are as defined in the formula (1).

As the compound represented by the formula (11), the following compounds can be given as specific examples, for example. In the following example compounds, Me represents a methyl group.

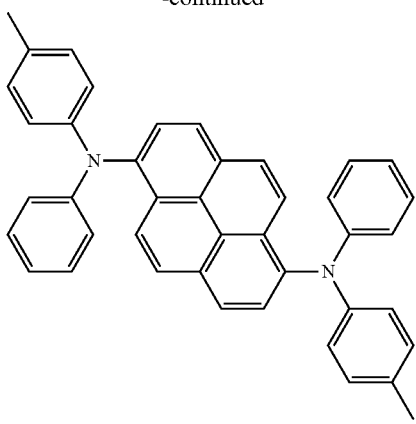

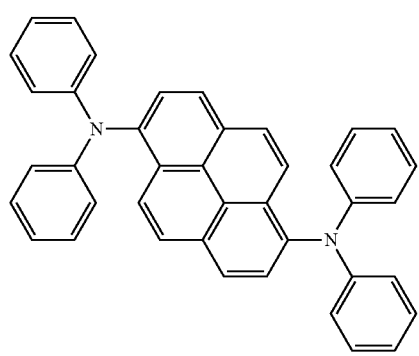

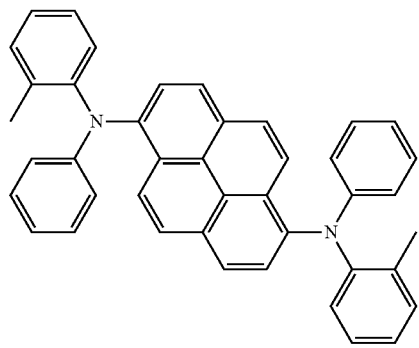

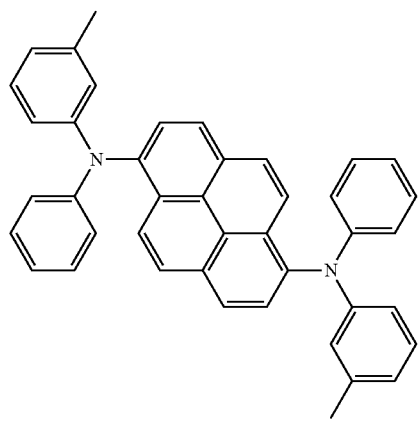

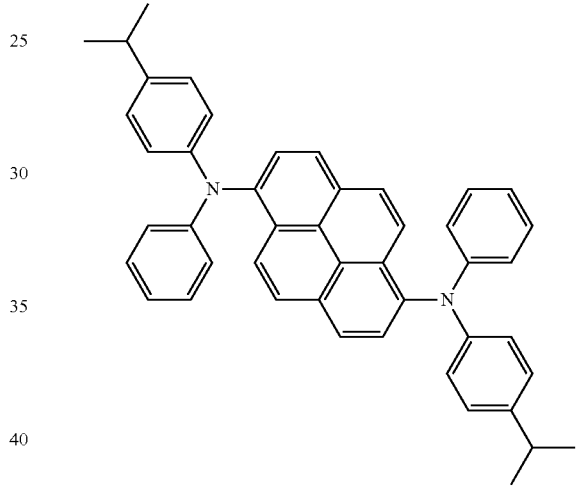

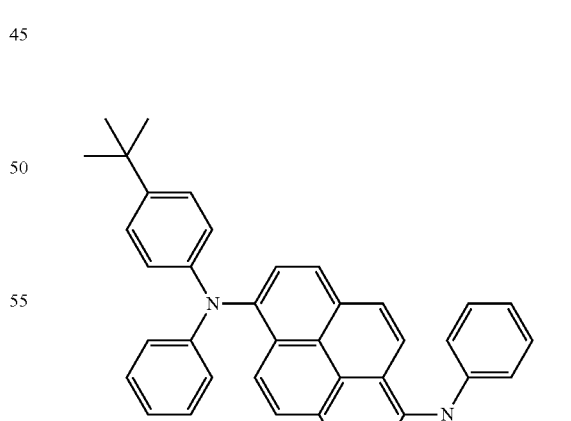

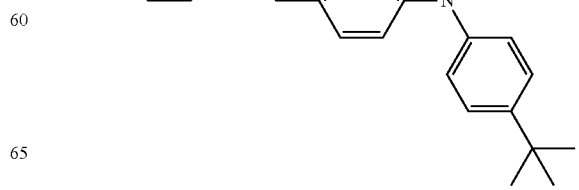

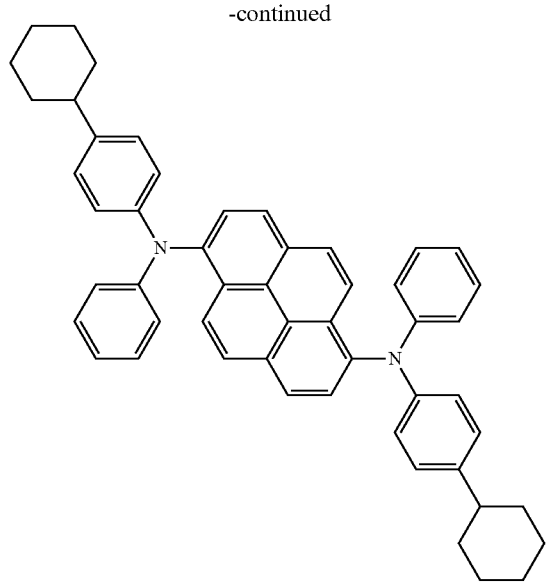
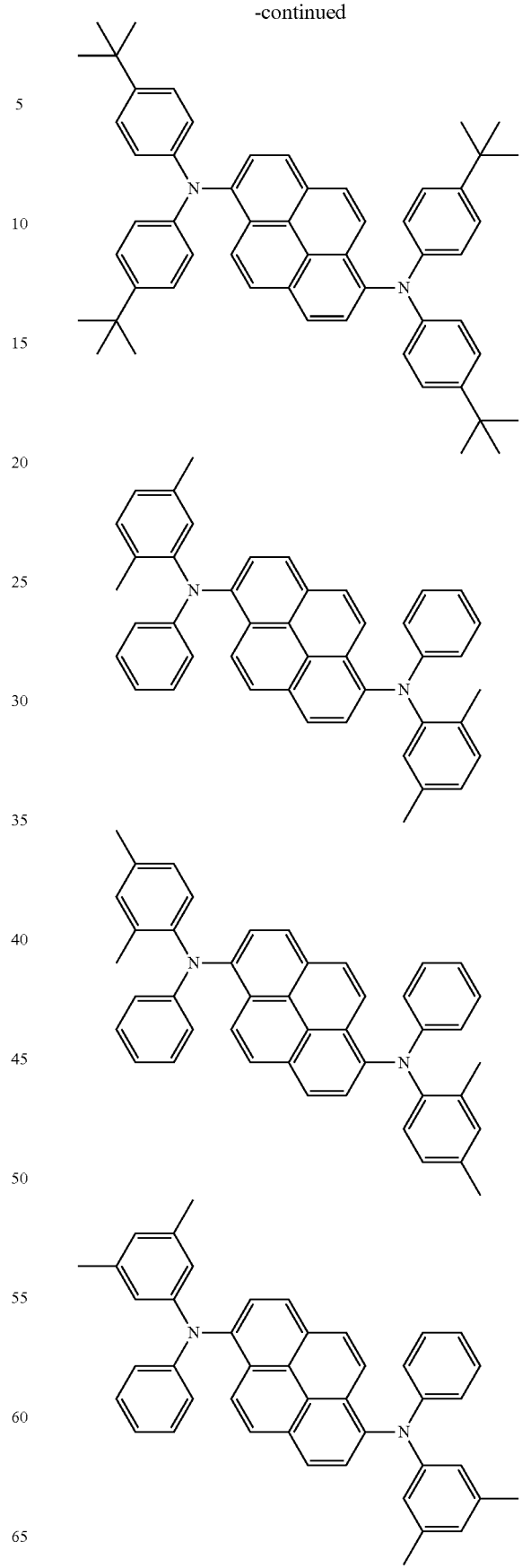

153
-continued
154
-continued
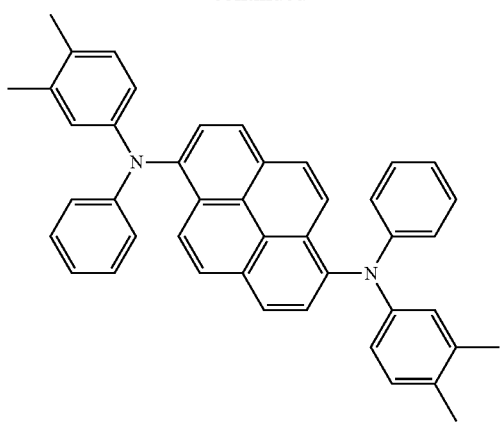
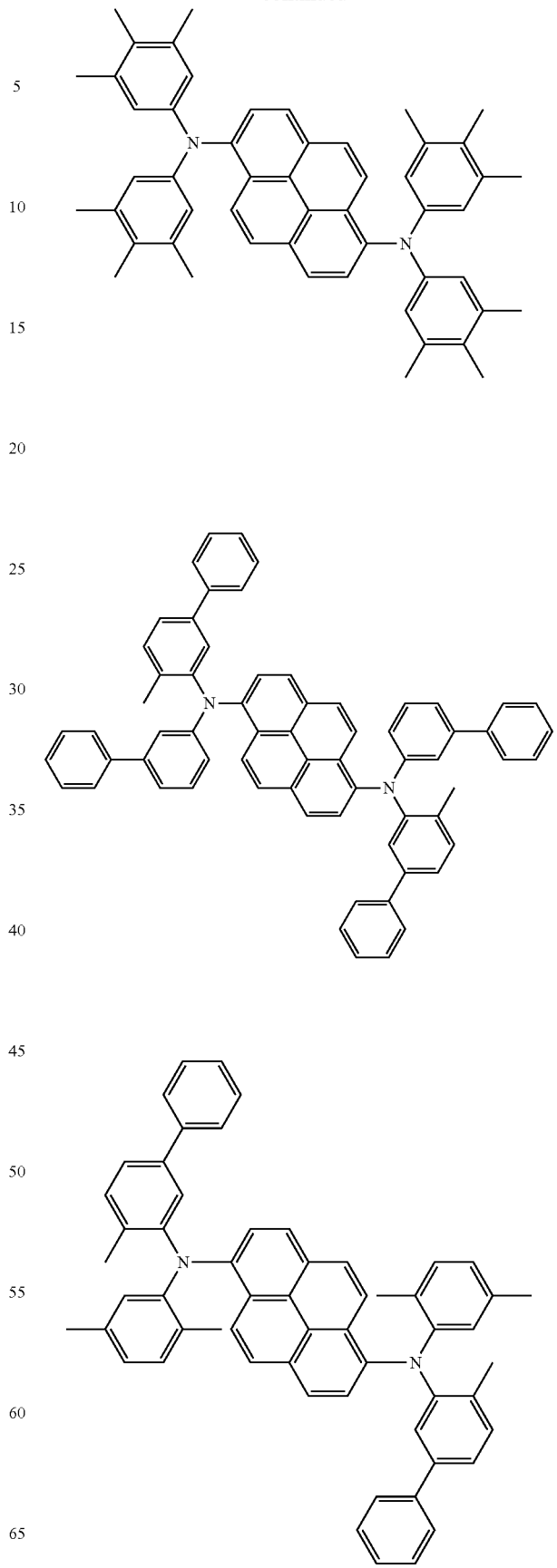

155
-continued
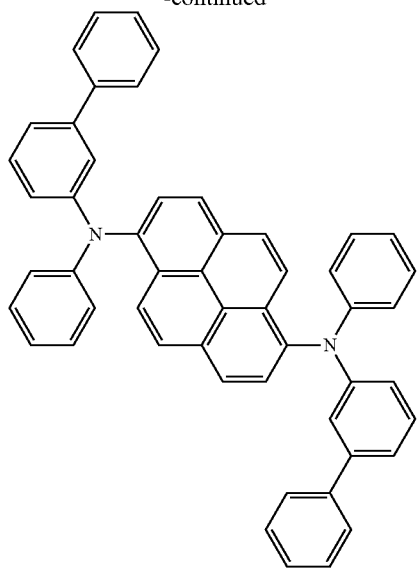
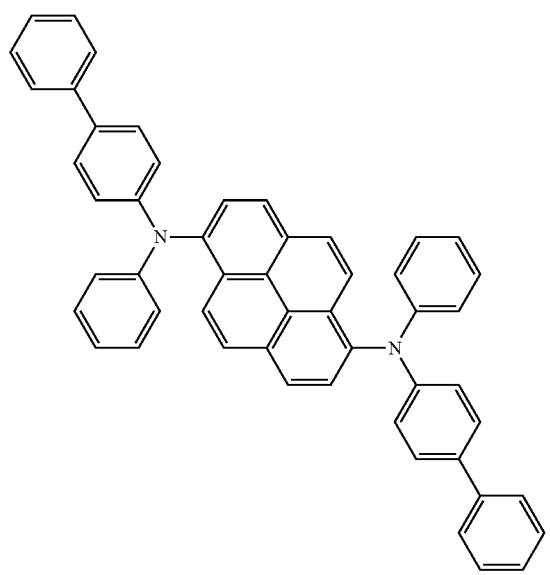
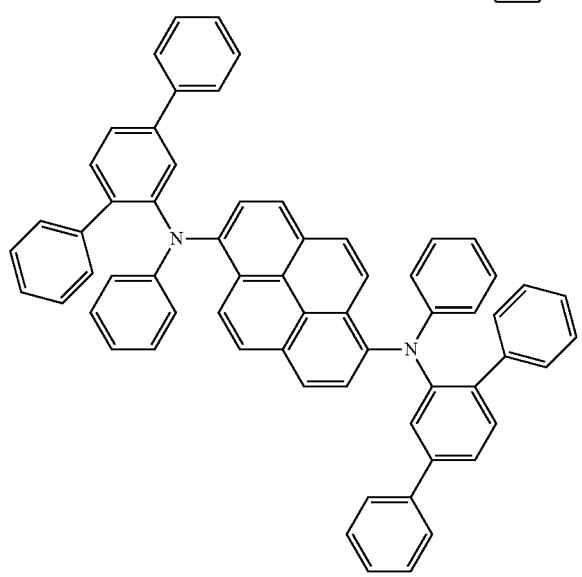
156
-continued
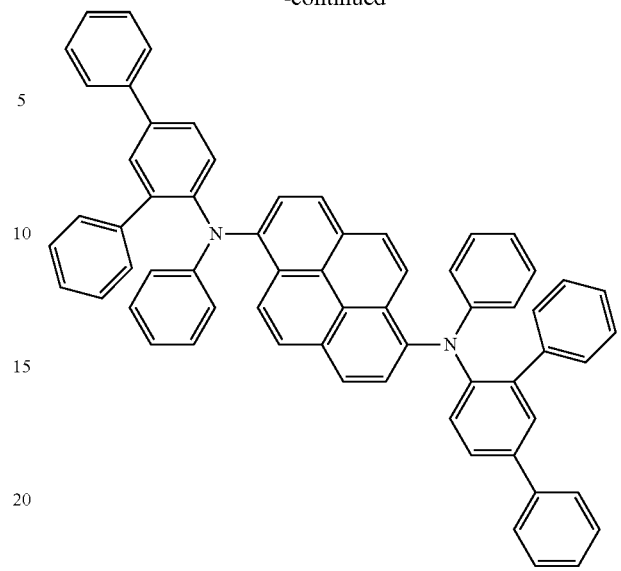
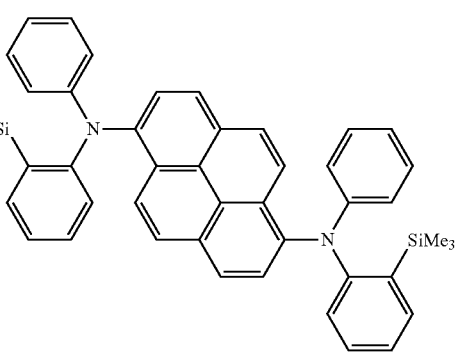
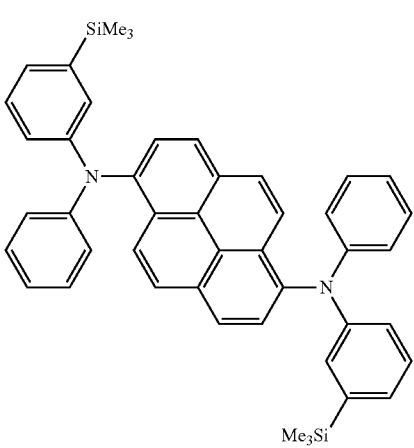

-continued
| 157 | 158 |
|---|---|
| 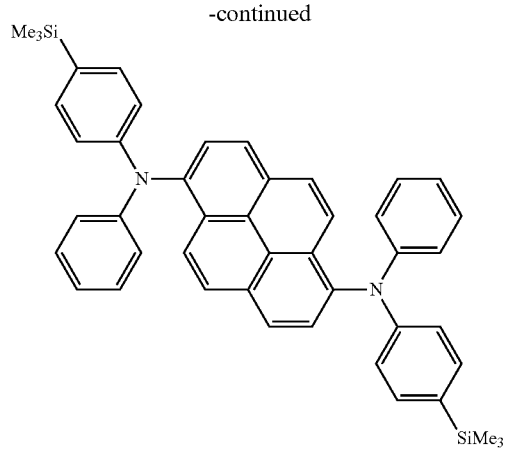 | 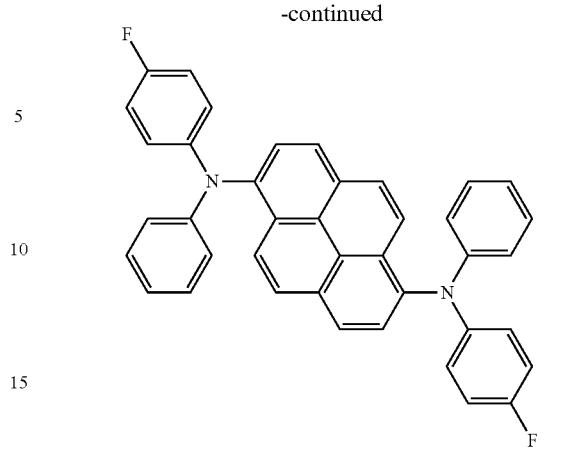 |
| 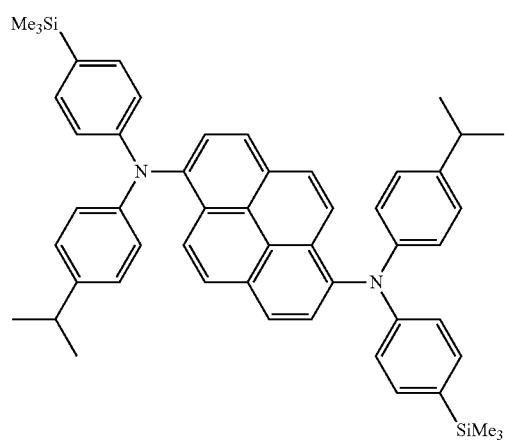 | 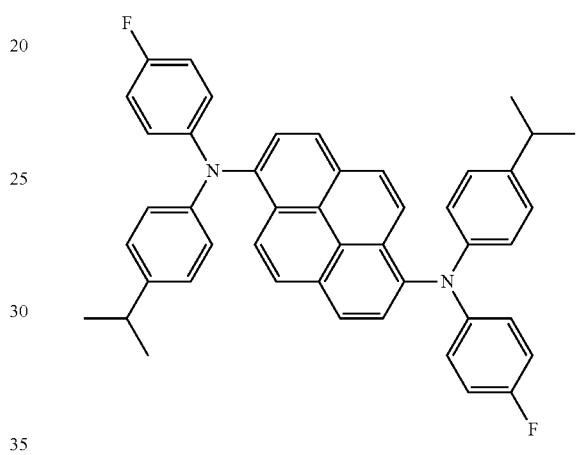 |
| 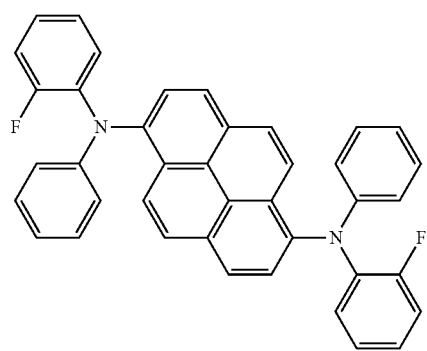 | 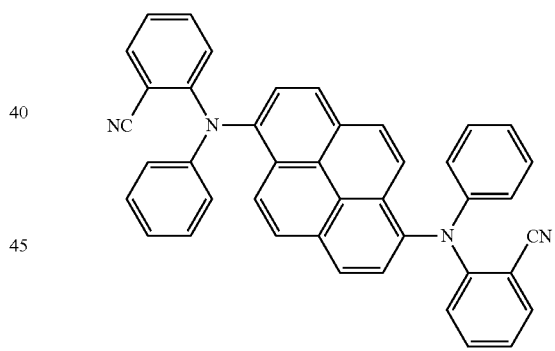 |
| 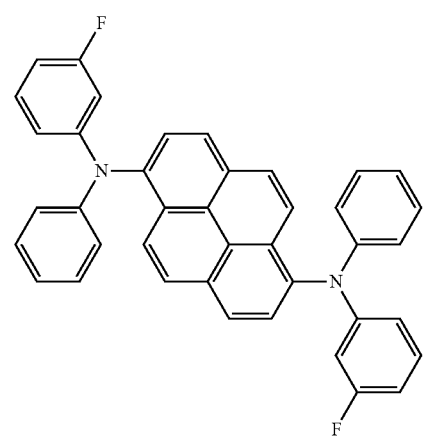 | 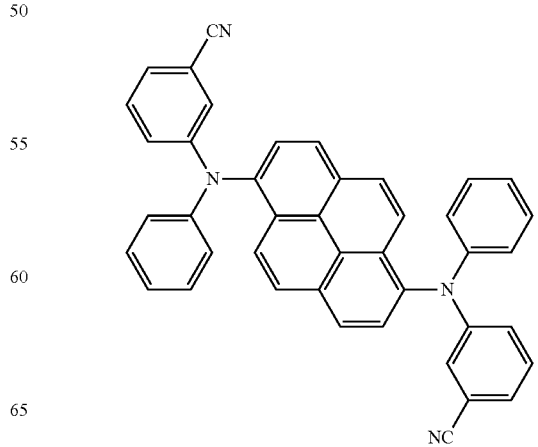 |

159
-continued
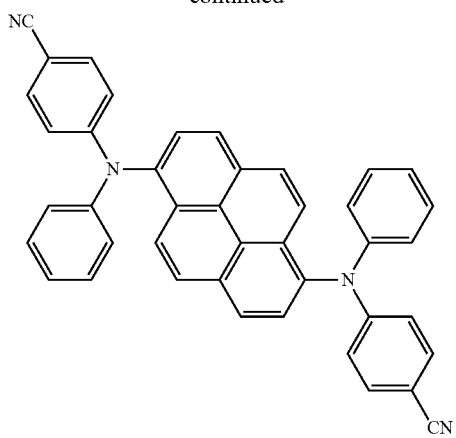
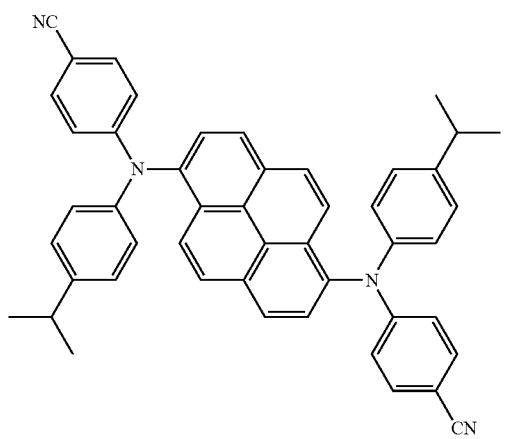
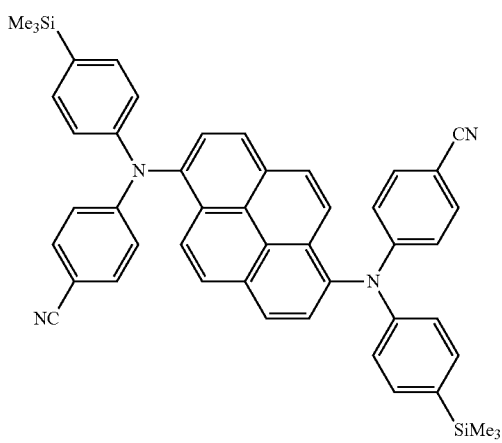
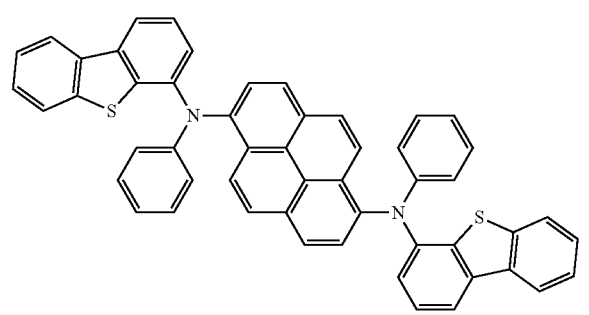
160
-continued
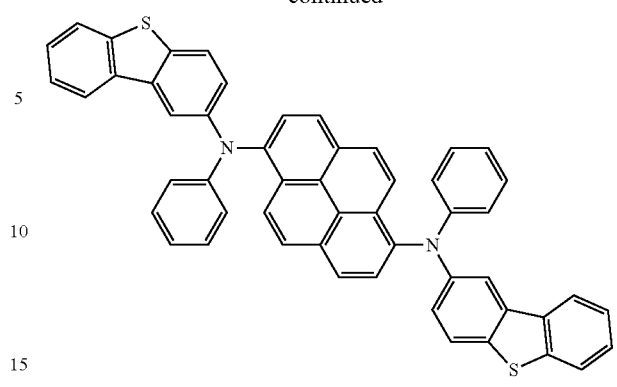
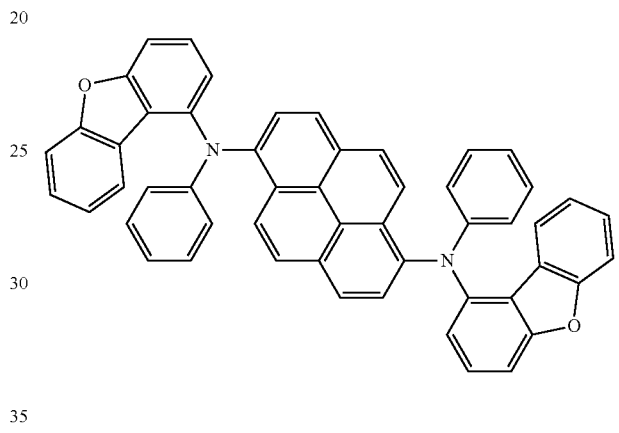
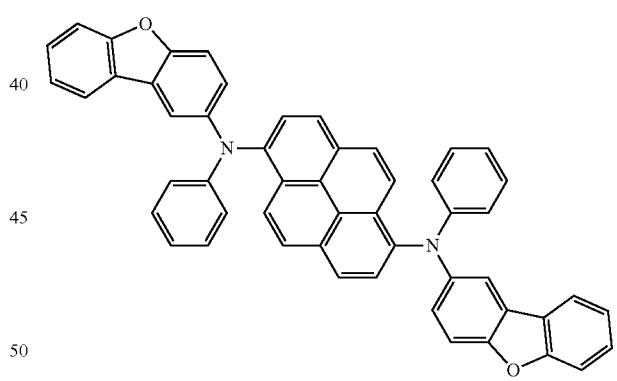
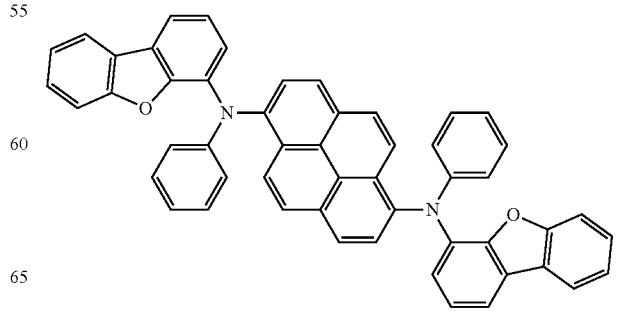

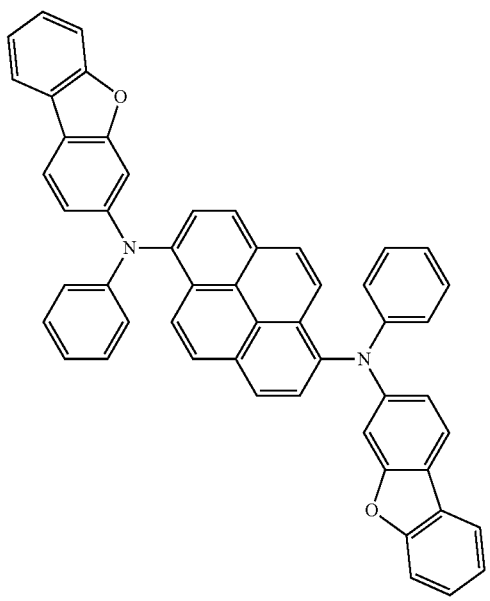
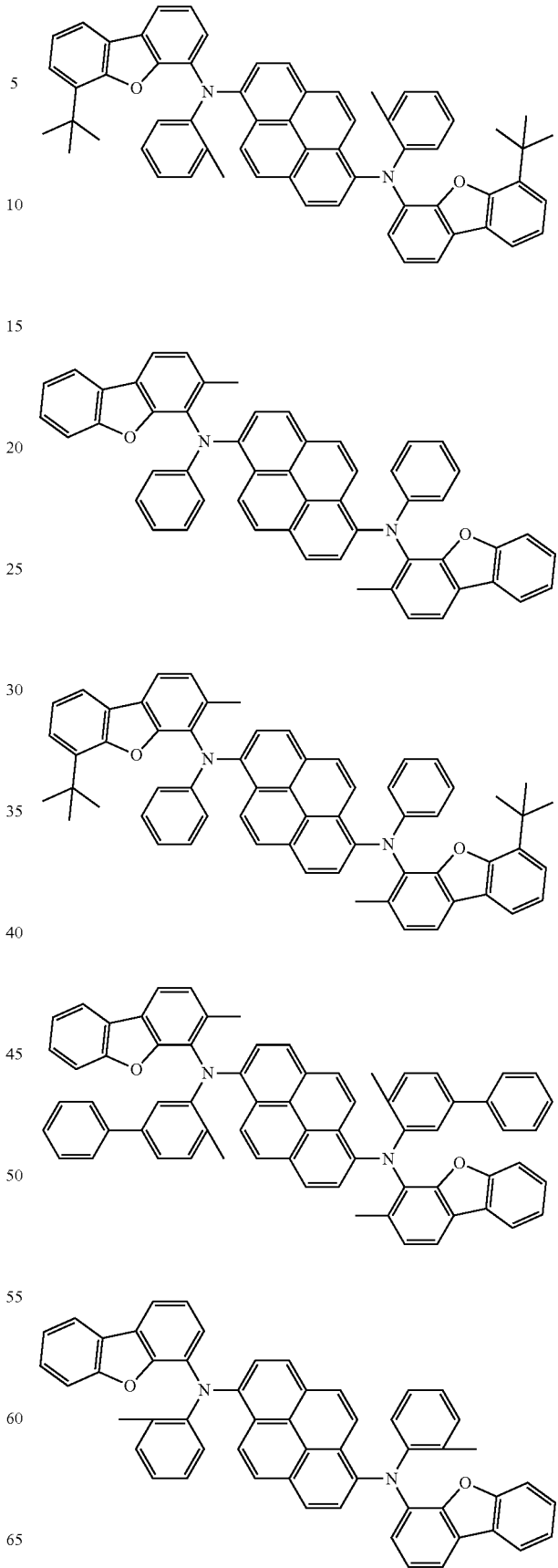

163
-continued
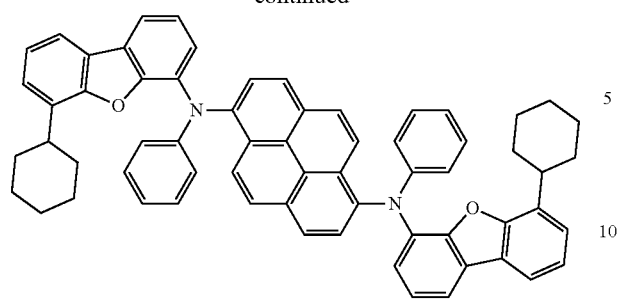
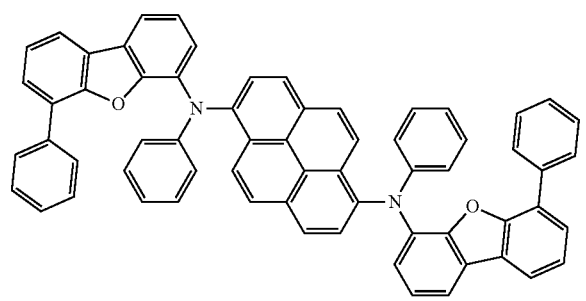
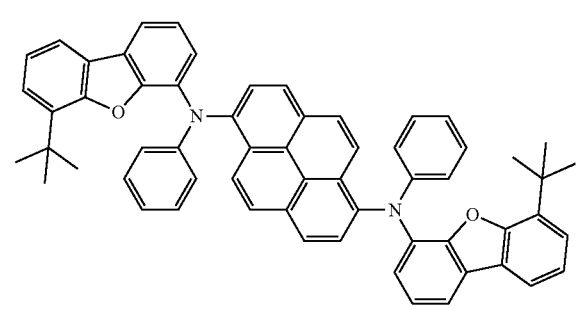
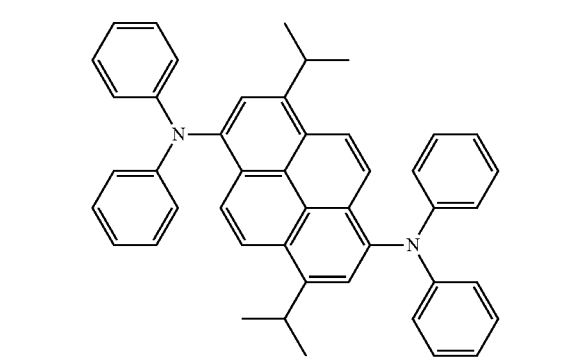
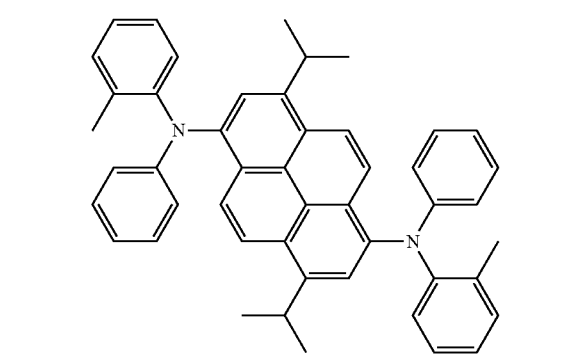
164
-continued
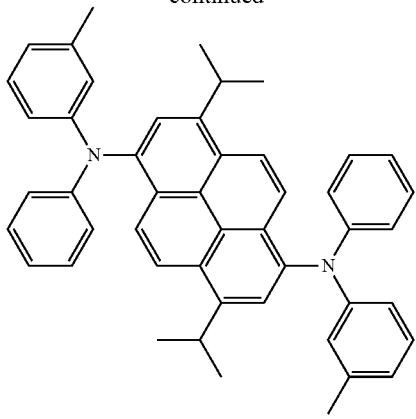
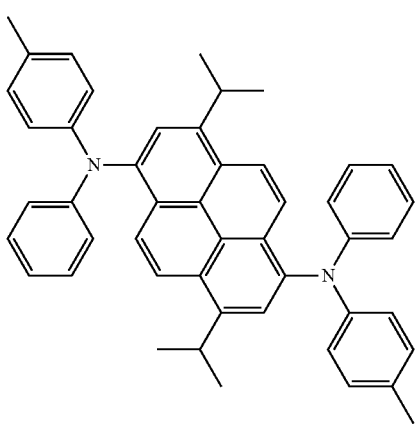
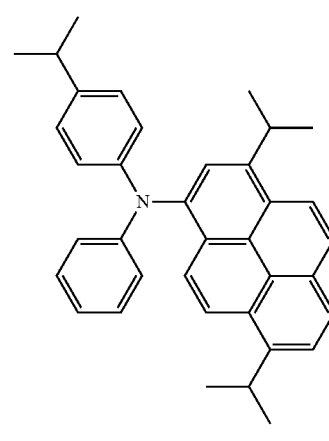

165
-continued
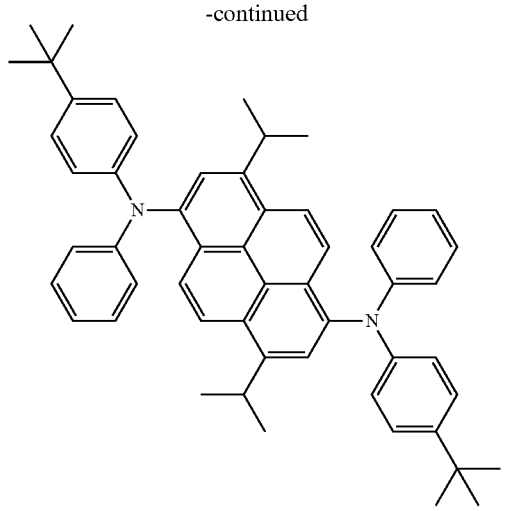
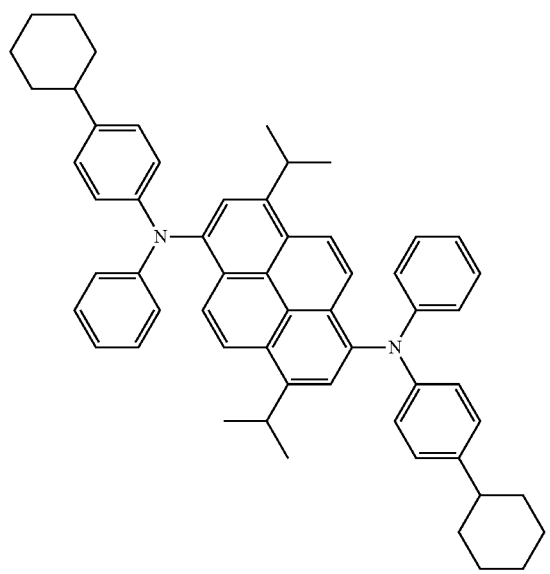
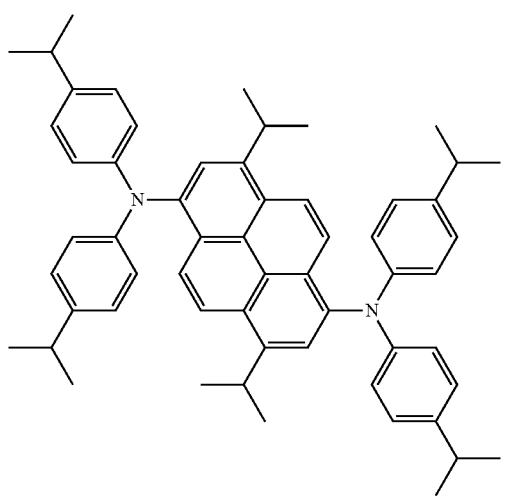
166
-continued
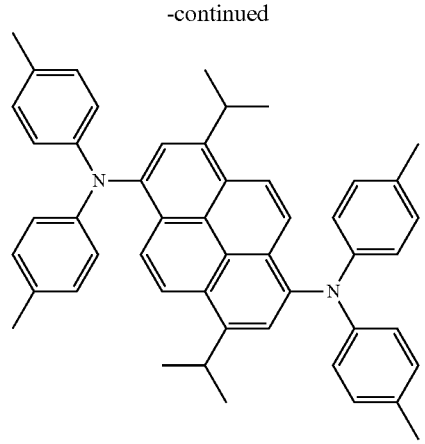
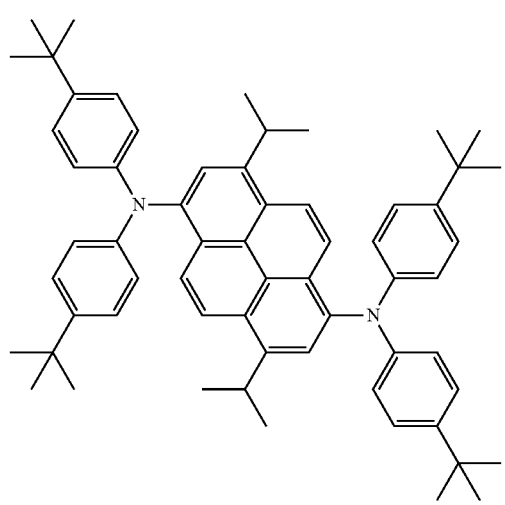
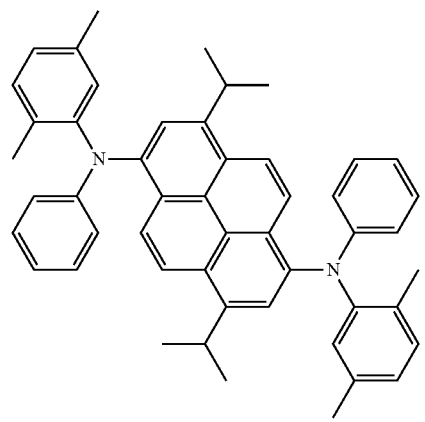

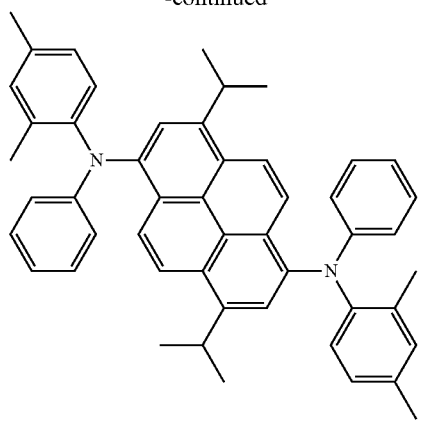
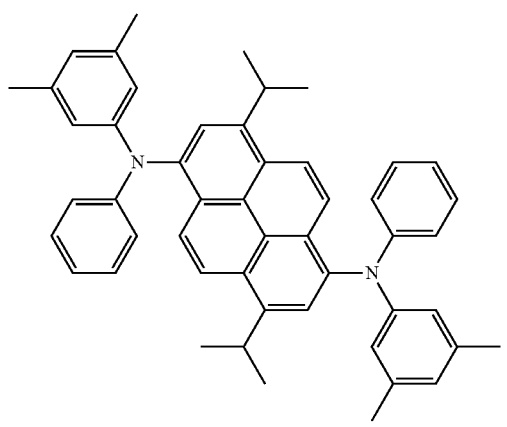
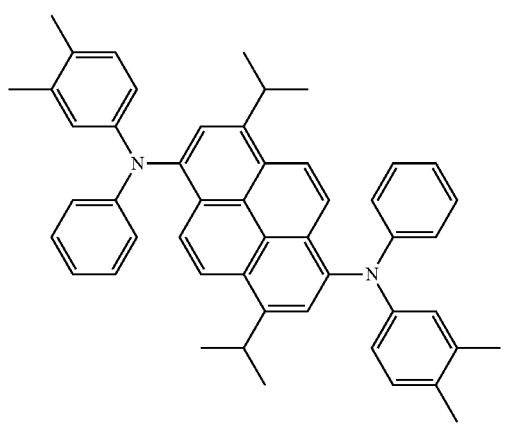
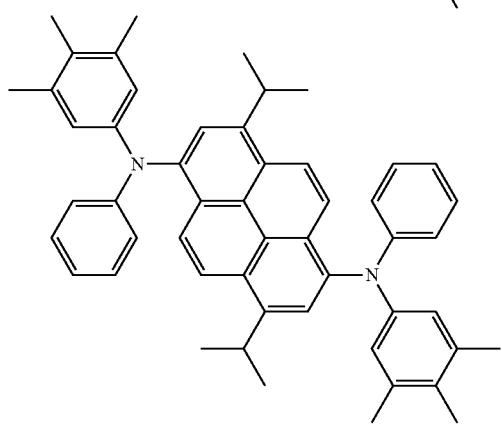
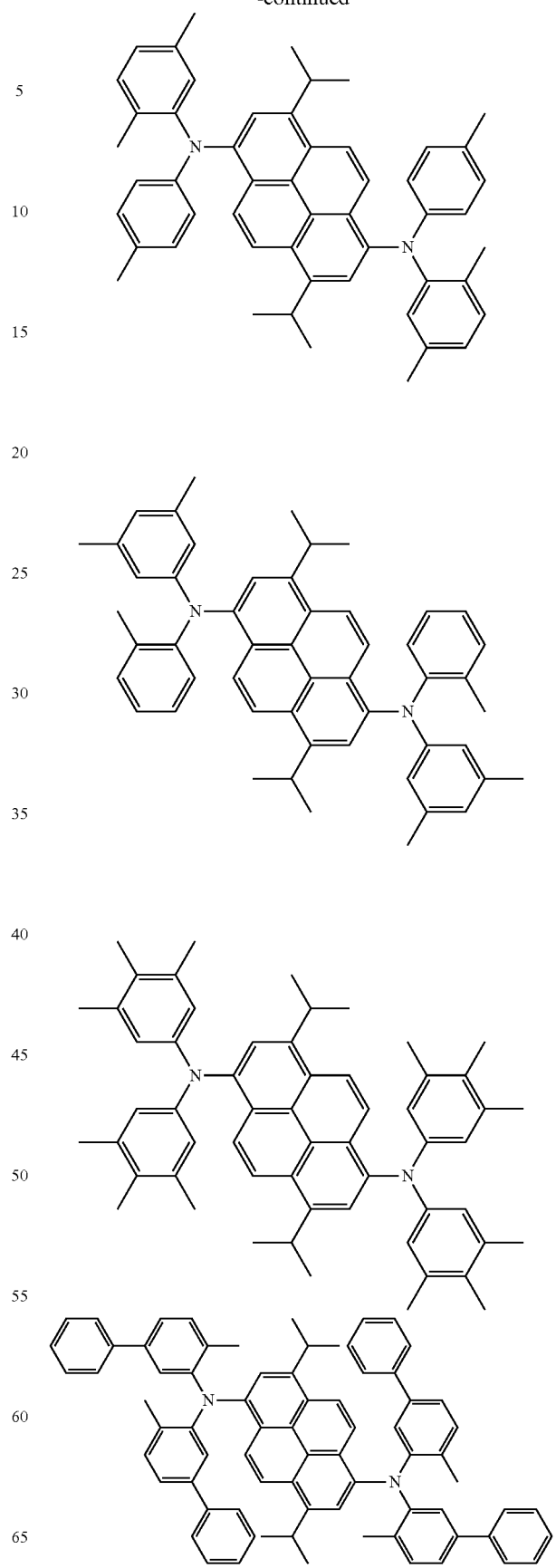

169
-continued
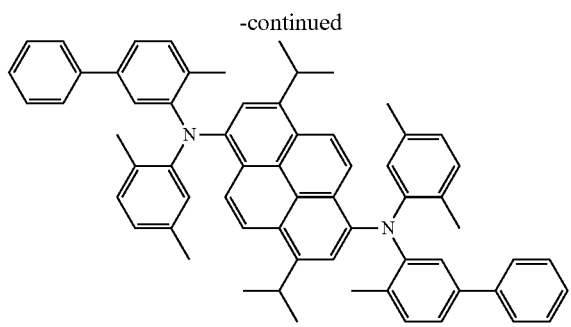
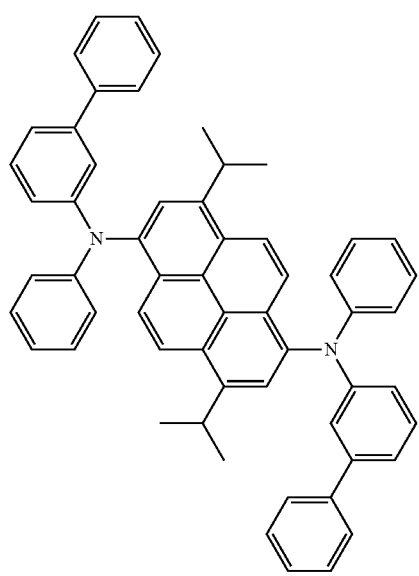
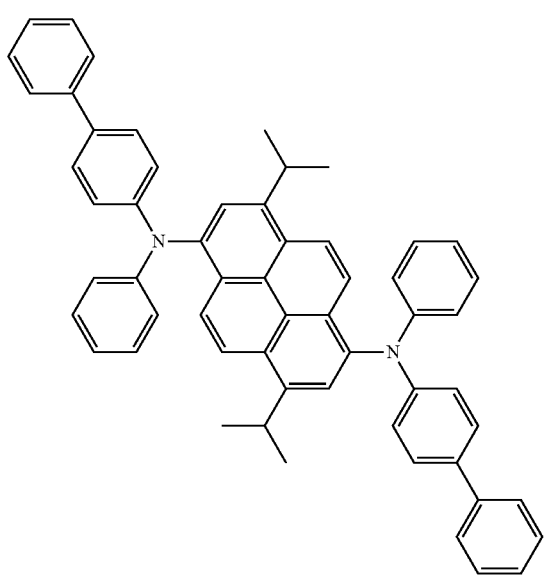
170
-continued
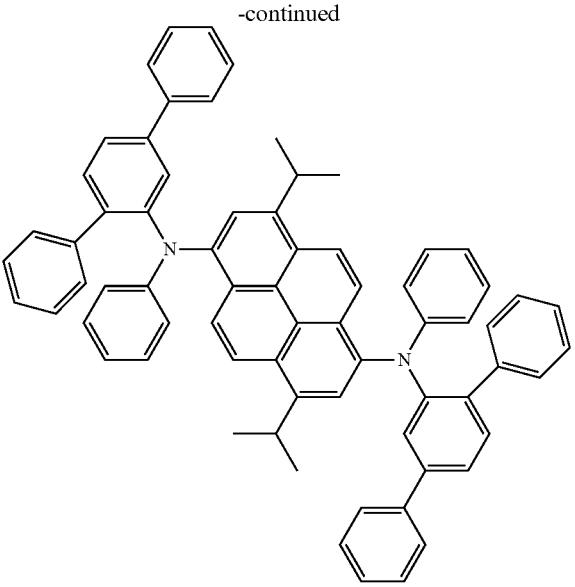
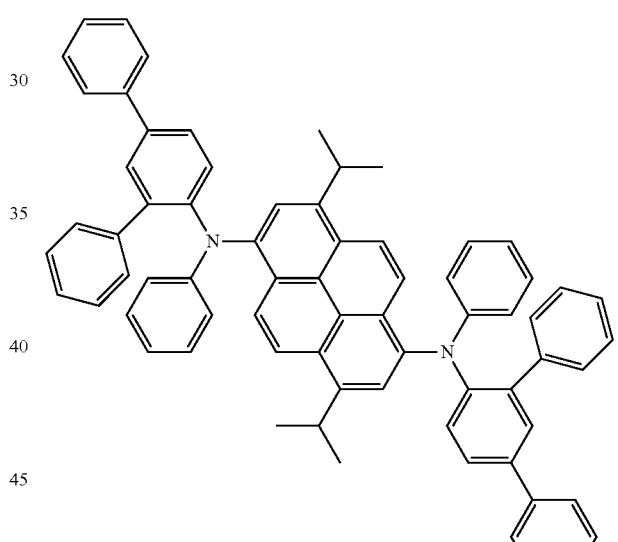
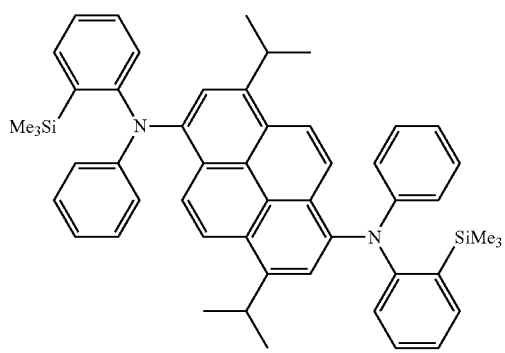

171
-continued
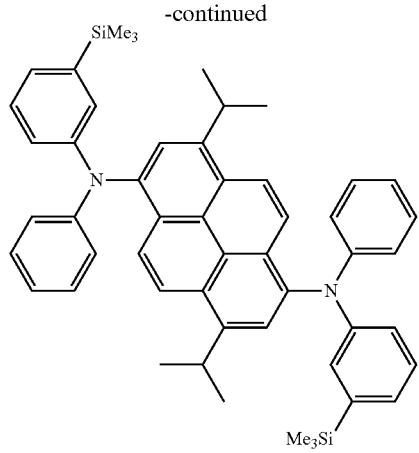
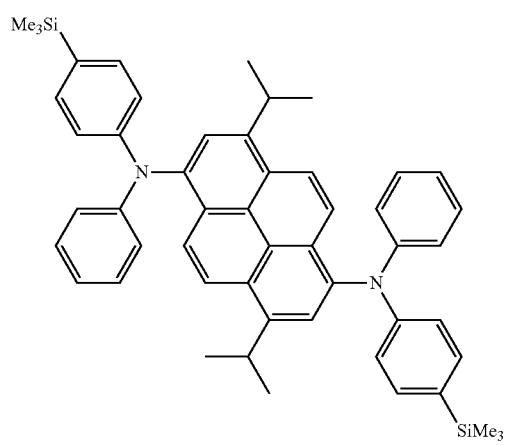
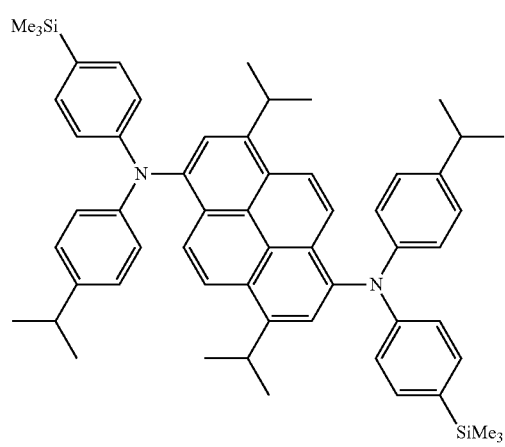
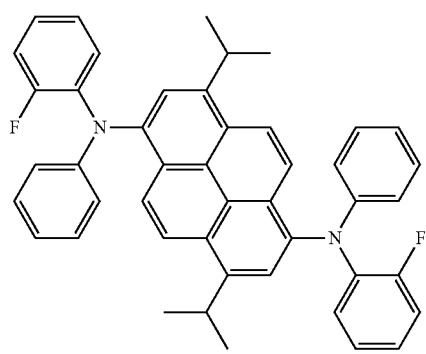
172
-continued
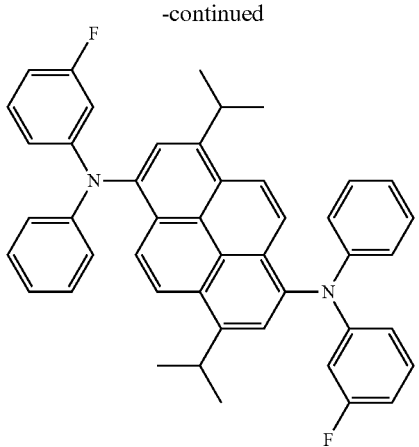
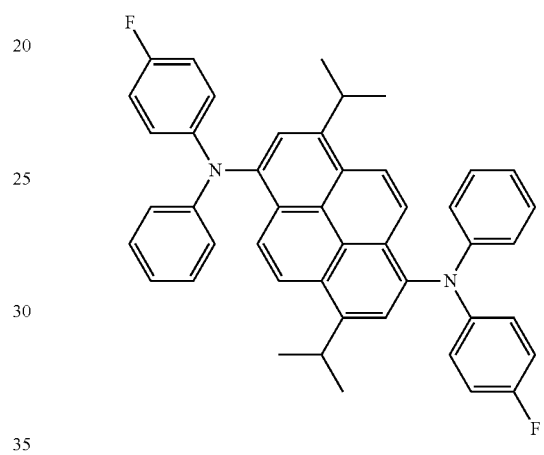
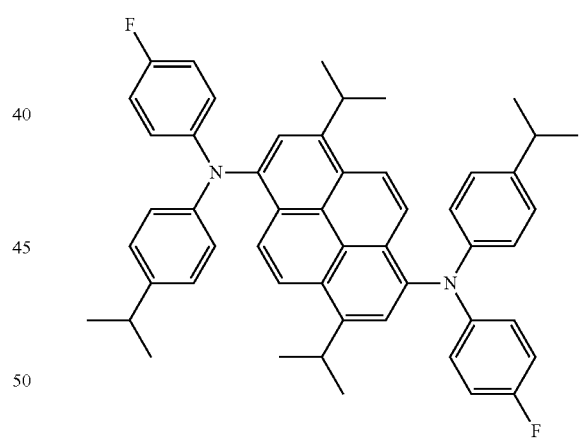
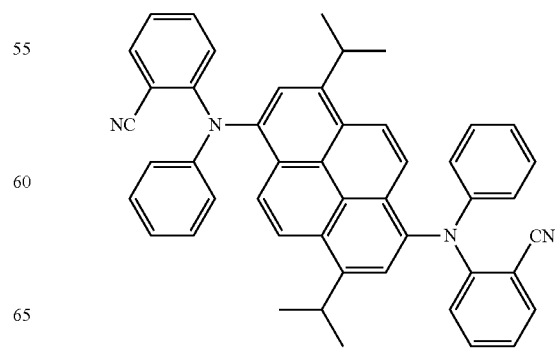

173
-continued
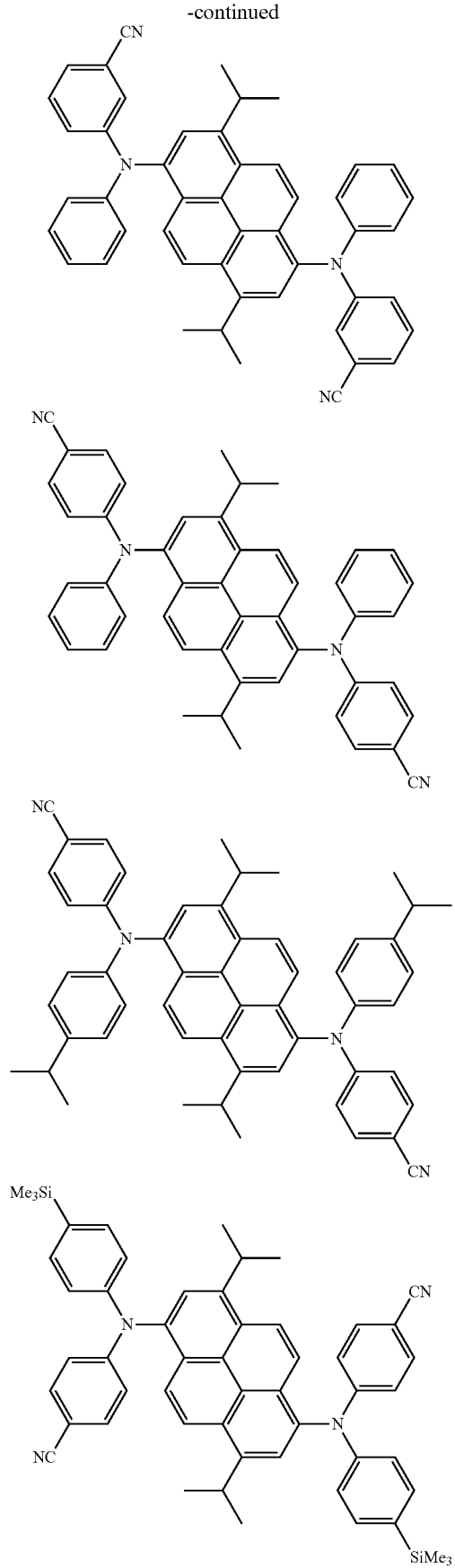
174
-continued
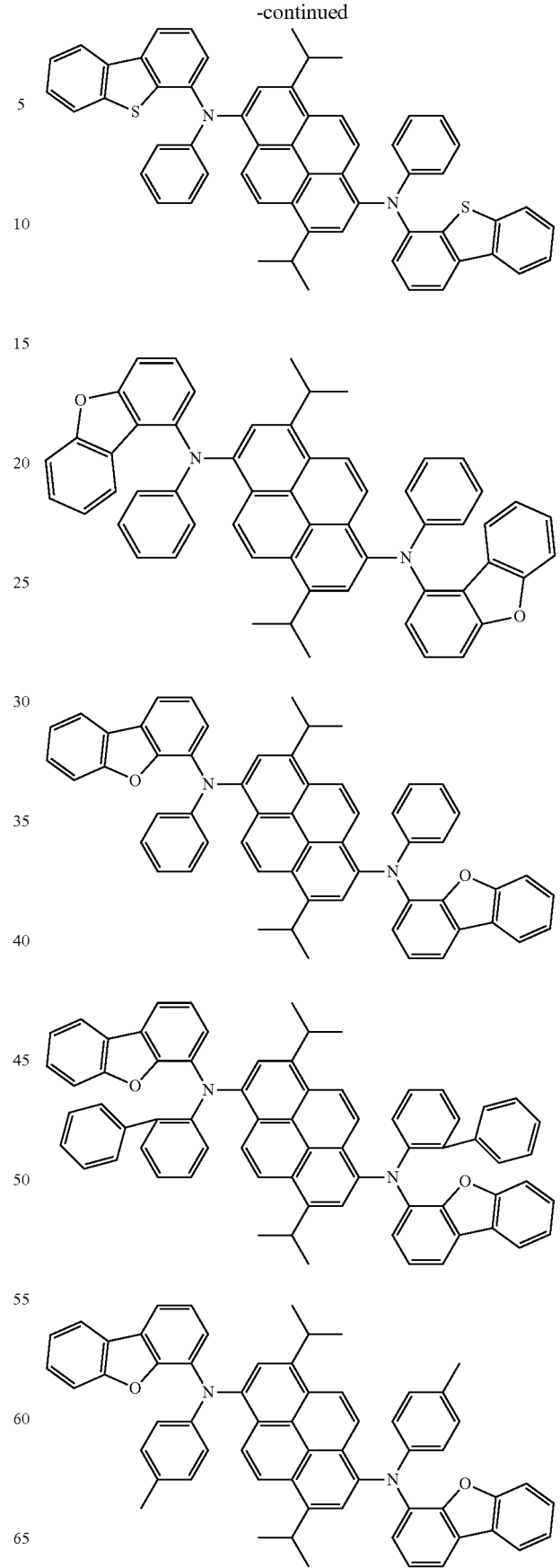

175
-continued
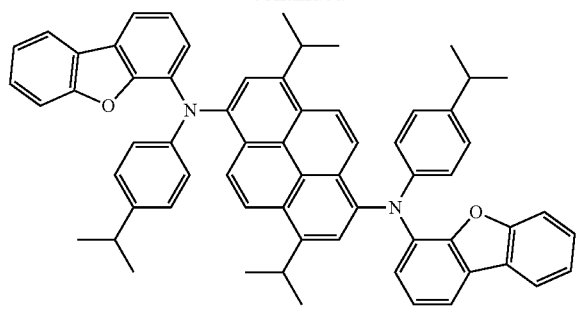
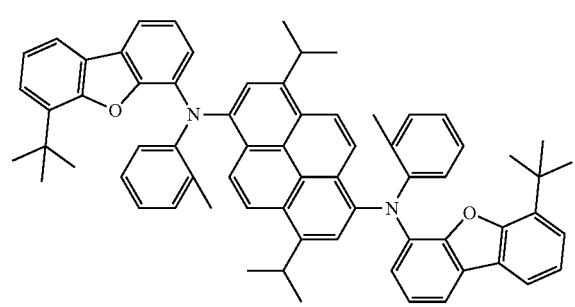
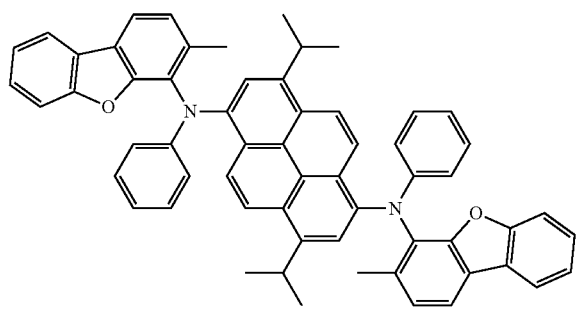
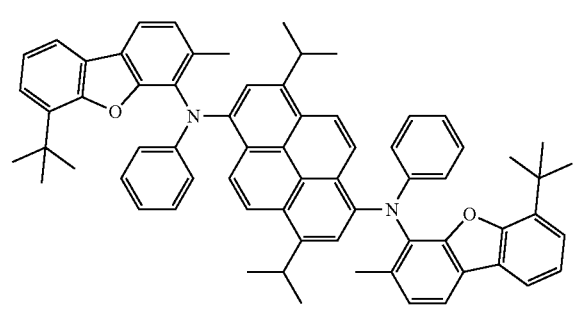
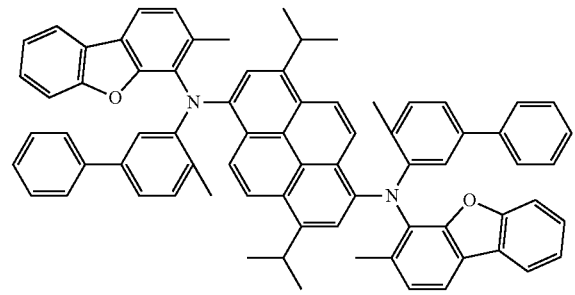
176
-continued
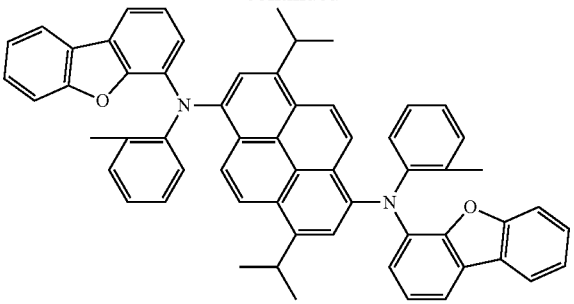
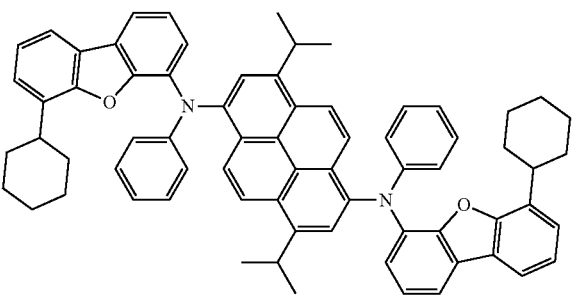
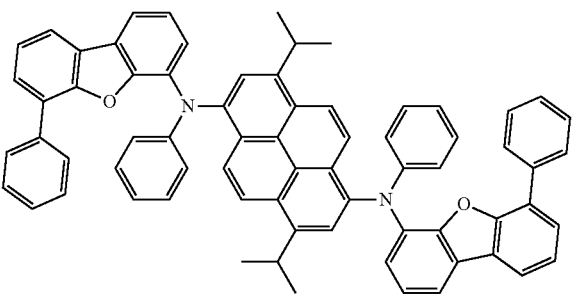
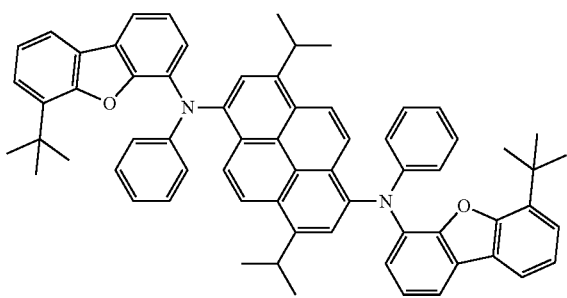
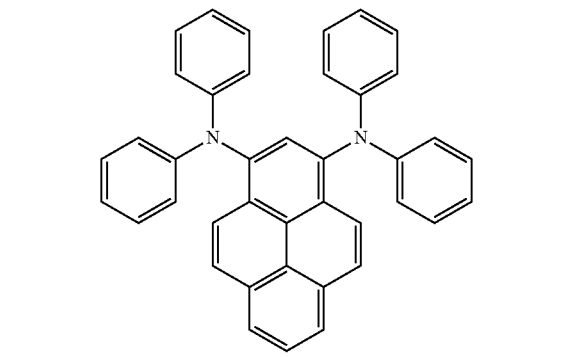

177
-continued
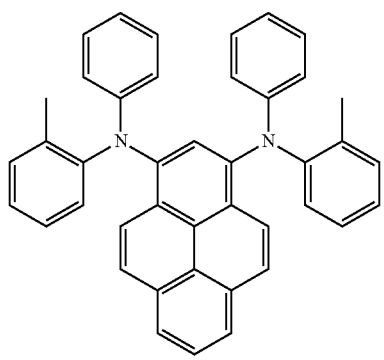
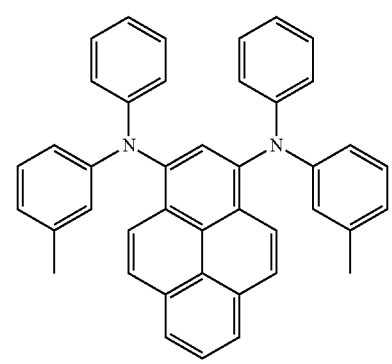
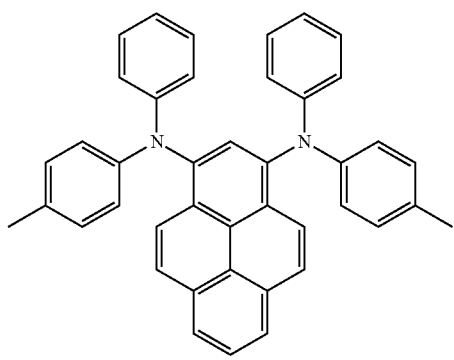
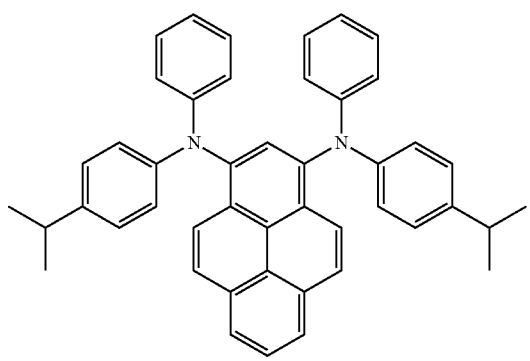
178
-continued
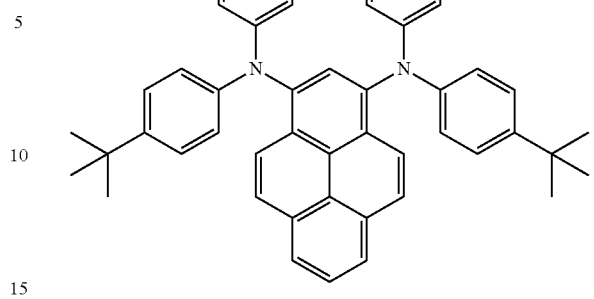
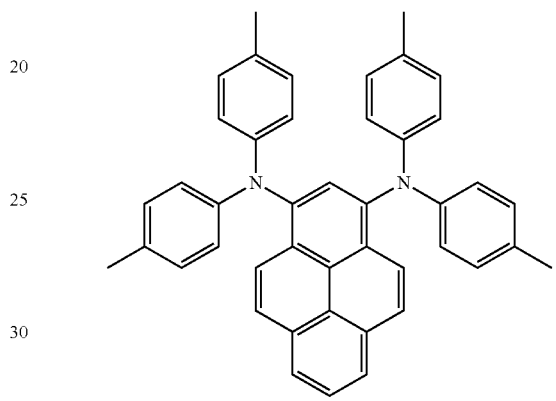
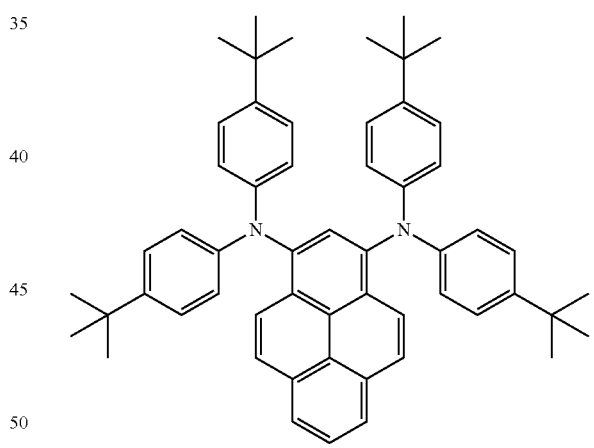
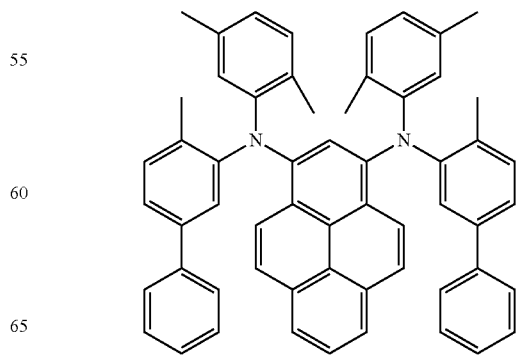

179
-continued
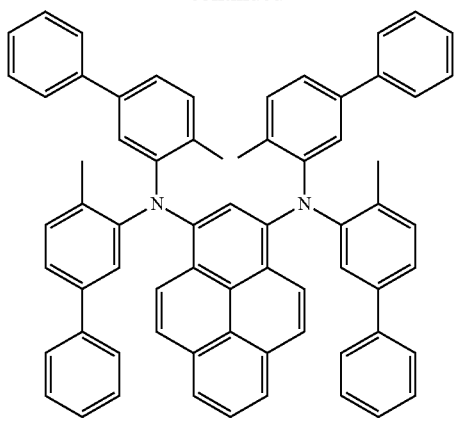
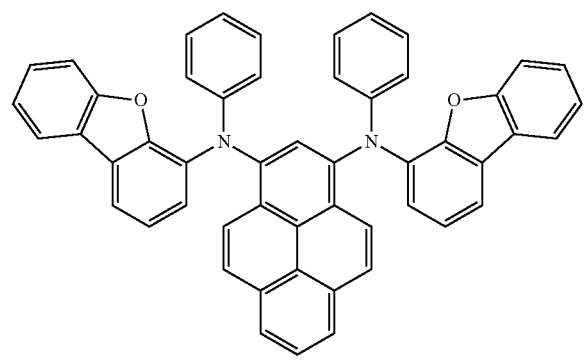
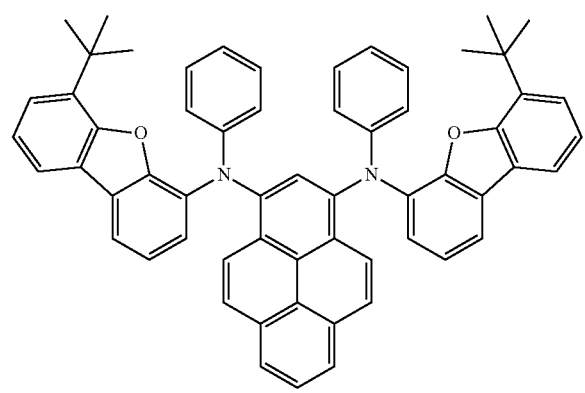
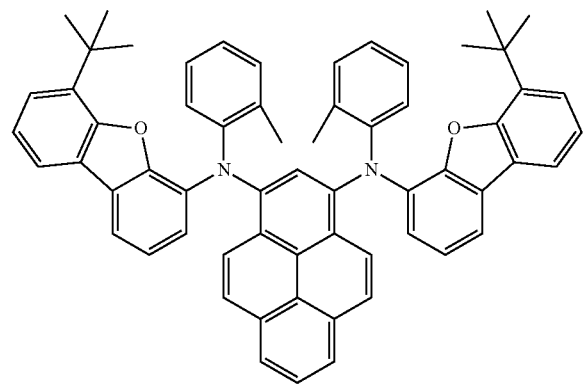
180
-continued
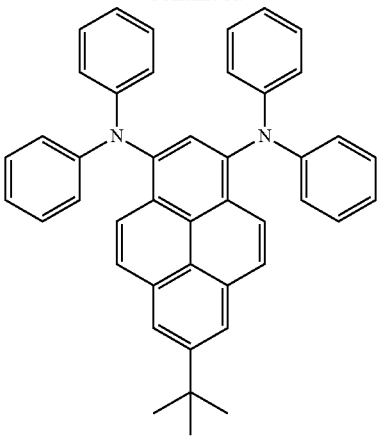
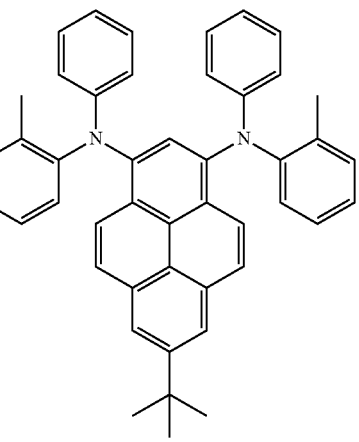
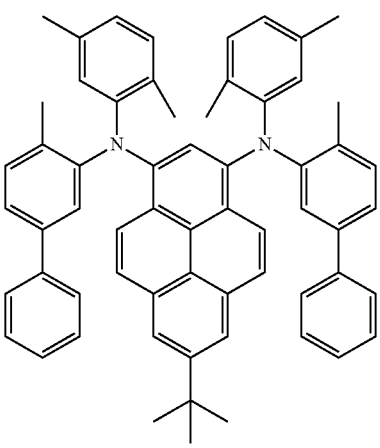

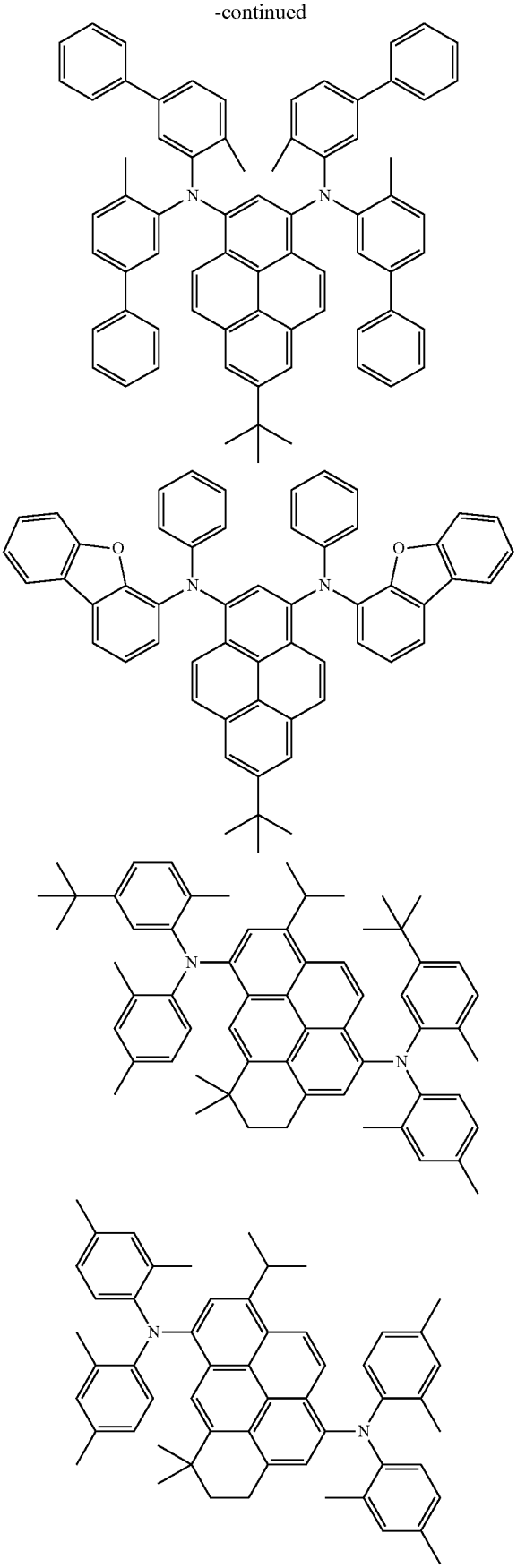
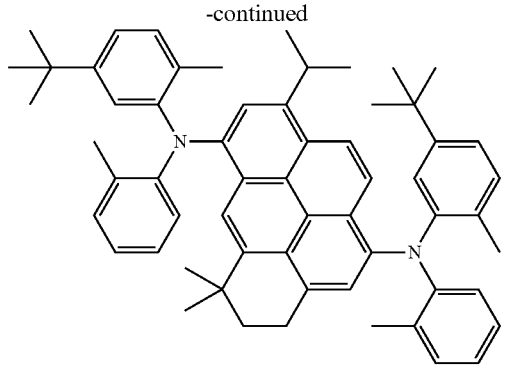
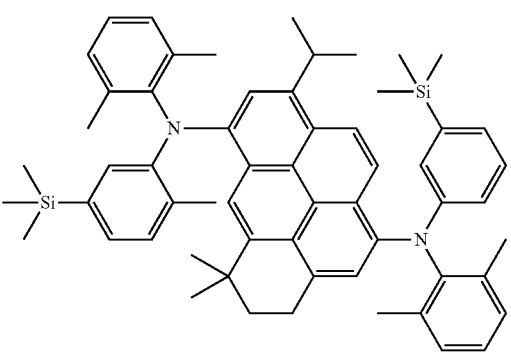
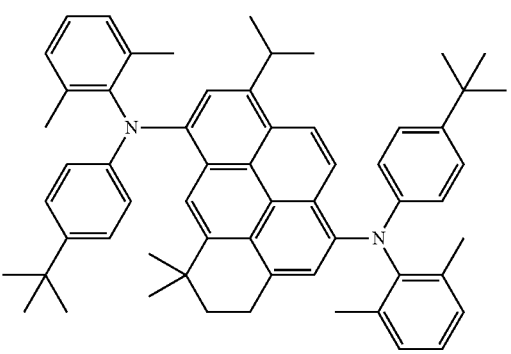
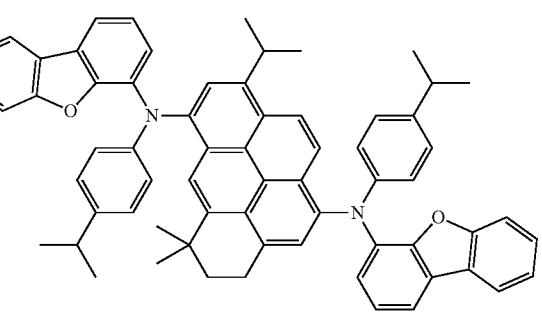

183
-continued
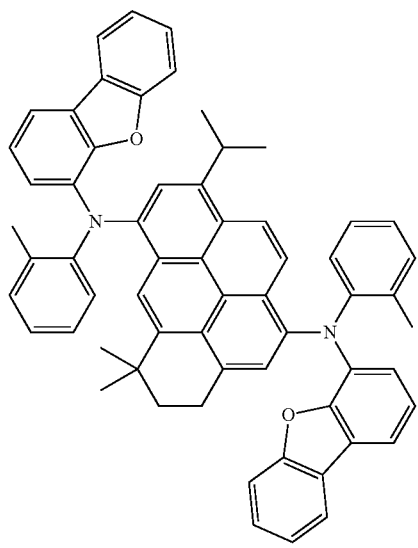
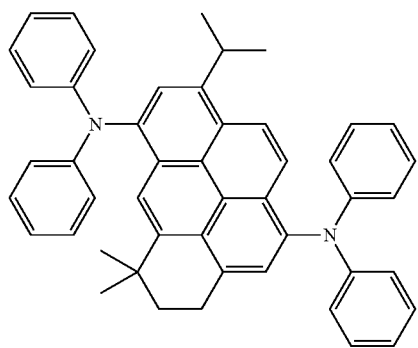
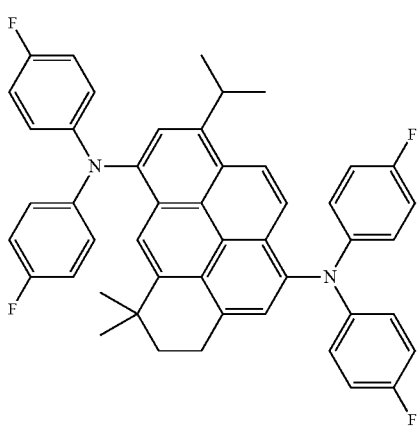
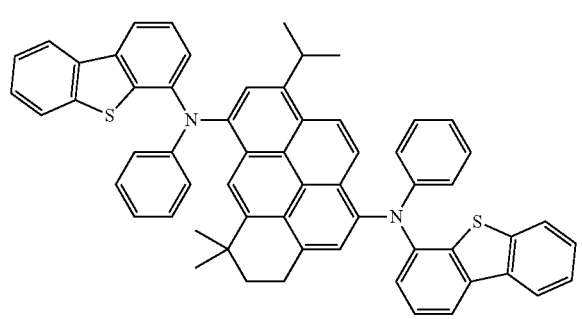
184
-continued
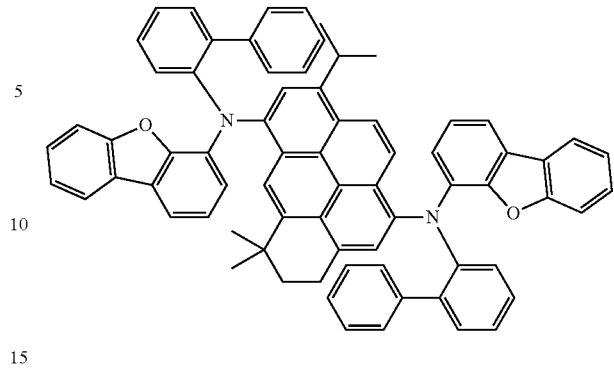
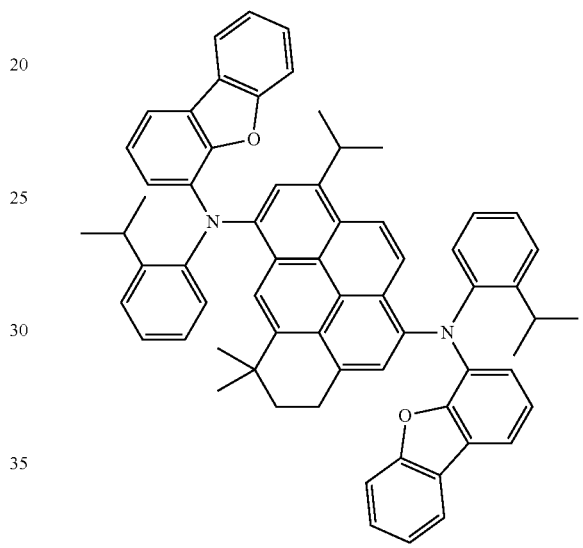
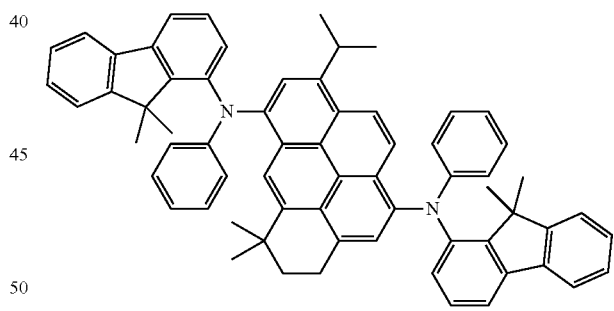
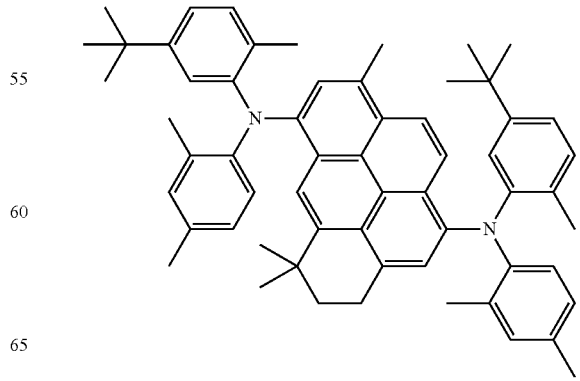

-continued

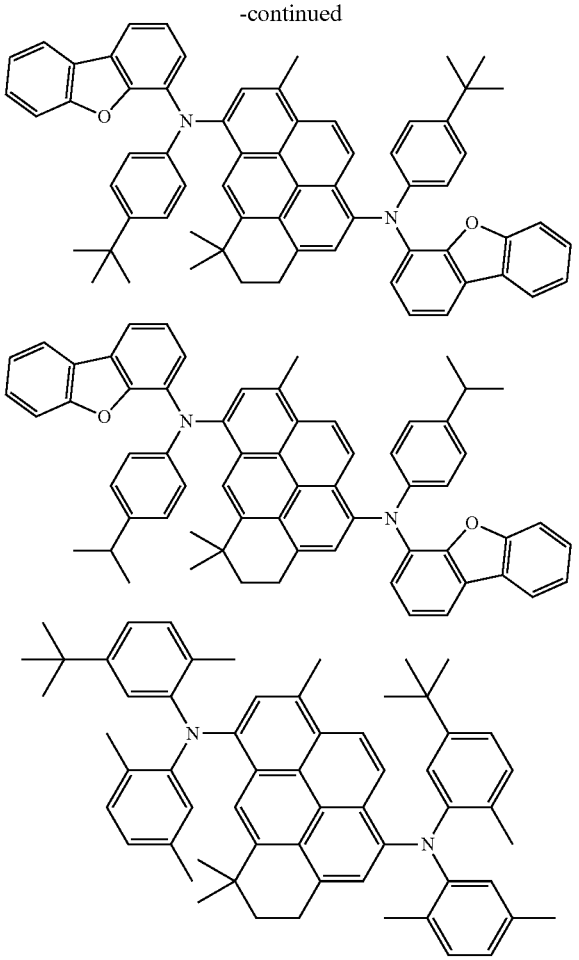

(Compound Represented by Formula (21))

The compound represented by the formula (21) is explained below.

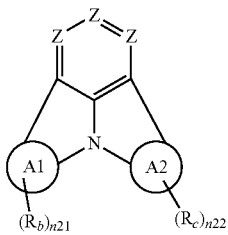

(21)

wherein, in the formula (21),
Zs are independently $CR_a$ or N;
A1 ring and A2 ring are independently a substituted or unsubstituted aromatic hydrocarbon ring having 6 to 50 ring carbon atoms, or a substituted or unsubstituted heterocyclic ring having 5 to 50 ring atoms;
when a plurality of $R_a$s exist, one or more pairs of two or more adjacent groups of $R_a$ are bonded with each other to form a substituted or unsubstituted, saturated or unsaturated ring, or do not form a substituted or unsubstituted, saturated or unsaturated ring;
when a plurality of $R_b$s exist, one or more pairs of two or more adjacent groups of $R_b$ are bonded with each other to form a substituted or unsubstituted, saturated or unsaturated ring, or do not form a substituted or unsubstituted, saturated or unsaturated ring;
when a plurality of $R_c$s exist, one or more pairs of two or more adjacent groups of $R_c$ are bonded with each other to form a substituted or unsubstituted, saturated or unsaturated ring, or do not form a substituted or unsubstituted, saturated or unsaturated ring;
n21 and n22 are independently an integer of 0 to 4;
$R_a$ to $R_c$ that do not form the substituted or unsubstituted, saturated or unsaturated ring are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;
$R_{901}$ to $R_{907}$ are as defined in the formula (1);
The "aromatic hydrocarbon ring" of A1 ring and A2 ring has the same structure as the compound obtained by introducing a hydrogen atom into the "aryl group" described above.
The "aromatic hydrocarbon ring" of the A1 ring and the A2 ring contains two carbon atoms in the fused bicyclic structure at the center of the formula (21) as ring atoms. Examples of "substituted or unsubstituted aromatic hydrocarbon ring having 6 to 50 ring carbon atoms" include compounds in which a hydrogen atom is introduced into the "aryl group" described in the example group G1.
The "heterocyclic ring" of A1 ring and A2 ring has the same structure as the compound obtained by introducing a hydrogen atom into the "heterocyclic group" described above. The "heterocyclic ring" of the A1 ring and the A2 ring contains two carbon atoms in the fused bicyclic structure at the center of the formula (21) as ring atoms. Examples of "substituted or unsubstituted heterocyclic ring having 5 to 50 ring atoms" include compounds in which a hydrogen atom is introduced into the "heterocyclic group" described in the example group G2.
$R_b$ is bonded to one of carbon atoms which form the aromatic hydrocarbon ring of A1 ring, or one of atoms which form the heterocycle of A1 ring.
$R_c$ is bonded to one of carbon atoms which form the aromatic hydrocarbon ring of A2 ring, or one of atoms which form the heterocycle of A2 ring.
It is preferable that at least one (preferably two) of $R_a$ to $R_c$ is a group represented by the following formula (21a).

-$L_{201}$-$Ar_{201}$ (21a)

wherein in the formula (21a),
$L_{201}$ is
a single bond,
a substituted or unsubstituted arylene group having 6 to 30 ring carbon atoms, or a substituted or unsubstituted bivalent heterocyclic group having 5 to 30 ring atoms;

$Ar_{201}$ is
a substituted or unsubstituted arylene group having 6 to 50 ring carbon atoms,
a substituted or unsubstituted monovalent heterocyclic group having 5 to 50 ring atoms, or
a group represented by the following formula (21b):

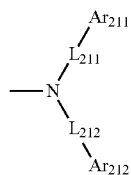
(21b)

wherein in the formula (21b),
$L_{211}$ and $L_{212}$ are independently
a single bond,
a substituted or unsubstituted arylene group having 6 to 30 ring carbon atoms, or
a substituted or unsubstituted divalent heterocyclic group having 5 to 30 ring atoms;

$Ar_{211}$ and $Ar_{212}$ are bonded with each other to form a substituted or unsubstituted, saturated or unsaturated ring, or do not form a substituted or unsubstituted, saturated or unsaturated ring; and $Ar_{211}$ and $Ar_{212}$ that do not form a substituted or unsubstituted, saturated or unsaturated ring are independently
a substituted or unsubstituted aryl group having 6 to 50 ring carbon atoms or
a substituted or unsubstituted monovalent heterocyclic group having 5 to 50 ring atoms.

In one embodiment, the compound represented by the formula (21) is represented by the following formula (22).

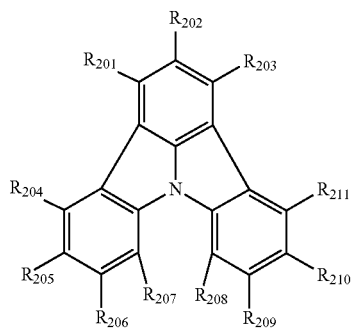
(22)

wherein in the formula (22),
one or more pairs of two or more adjacent groups of $R_{201}$ to $R_{211}$ are bonded with each other to form a substituted or unsubstituted, saturated or unsaturated ring, or do not form a substituted or unsubstituted saturated or unsaturated ring;

$R_{201}$ to $R_{211}$ that do not form the substituted or unsubstituted, saturated or unsaturated ring are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms; and
$R_{901}$ to $R_{907}$ are as defined in the formula (1))

It is preferable that at least one (preferably two) of $R_{201}$ to $R_{211}$ is the group represented by the formula (21a). It is preferable that $R_{204}$ and $R_{211}$ are the group represented by the formula (21a).

In one embodiment, the compound represented by the formula (21) is a compound obtained by bonding the structure represented by the following formula (21-1) or (21-2) to A1 ring. In one embodiment, the compound represented by the formula (22) is a compound obtained by bonding the structure represented by the following formula (21-1) or (21-2) to the ring to which $R_{204}$ to $R_{207}$ bonds to.

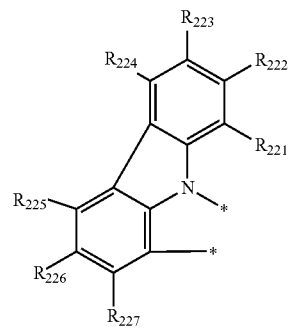
(21-1)

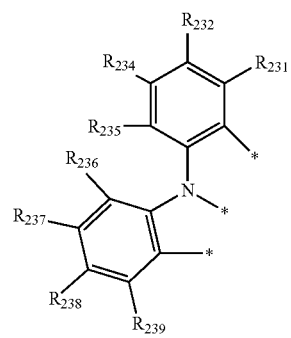
(21-2)

wherein in the formula (21-1), two bonds shown by * independently bond to a ring carbon atom in the aromatic hydrocarbon ring or a ring atom in the heterocyclic group in A1 ring in the formula (21), or bond to one of $R_{204}$ to $R_{207}$ in the formula (22);

wherein in the formula (21-2), three bonds shown by * independently bond to a ring carbon atom in the aromatic hydrocarbon ring or a ring atom in the heterocyclic group in A1 ring in the formula (21), or bond to one of $R_{204}$ to $R_{207}$ in the formula (22);

One or more pairs of two or more adjacent groups of $R_{221}$ to $R_{227}$ and $R_{221}$ to $R_{239}$ are bonded with each other to form a substituted or unsubstituted, saturated or unsaturated ring, or do not form a substituted or unsubstituted, saturated or unsaturated ring;

$R_{221}$ to $R_{227}$ and $R_{231}$ to $R_{239}$ that do not form the substituted or unsubstituted, saturated or unsaturated ring are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si$(R_{901})(R_{902})(R_{903})$,

—O—$(R_{904})$,

—S—$(R_{905})$,

—N$(R_{906})(R_{907})$, a halogen atom, a cyano group, a nitro group, a substituted or unsubstituted aryl group having 6 to 50 ring carbon atoms, or a substituted or unsubstituted monovalent heterocyclic group having 5 to 50 ring atoms; and $R_{901}$ to $R_{907}$ are as defined in the formula (1)

In one embodiment, the compound represented by the formula (21) is a compound represented by the following formula (21-3), (21-4), or (21-5).

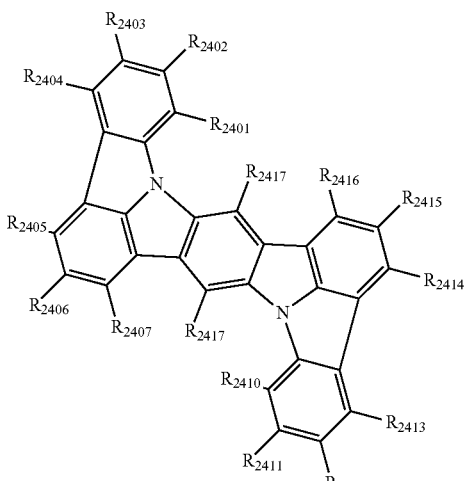

(21-3)

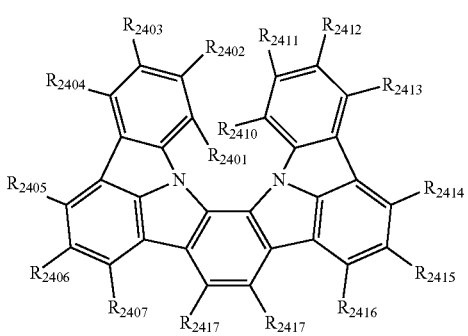

(21-4)

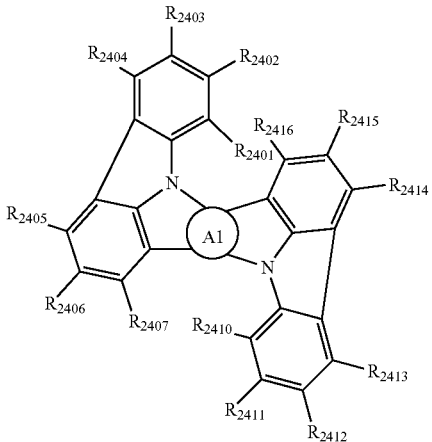

(21-5)

wherein in the formulas (21-3), (21-4) and (21-5),

A1 ring is as defined in the formula (21);

$R_{2401}$ to $R_{2407}$ are the same as $R_{221}$ to $R_{227}$ in the formulas (21-1) and (21-2);

$R_{2410}$ to $R_{2417}$ are the same as $R_{201}$ to $R_{211}$ in the formula (22); and the two $R_{2417}$s may be the same or different.

In one embodiment, the substituted or unsubstituted aromatic hydrocarbon ring having 6 to 50 ring carbon atoms of A1 ring in the formula (21-5) is a substituted or unsubstituted napthalene ring, or a substituted or unsubstituted fluorene ring.

In one embodiment, the substituted or unsubstituted heterocycle having 5 to 50 ring atoms of A1 ring in the formula (21-5) is a substituted or unsubstituted dibenzofuran ring, a substituted or unsubstituted carbazole ring, or a substituted or unsubstituted dibenzothiophene ring.

In one embodiment, the compound represented by the formula (21) or (22) is selected from the group consisting of the compounds represented by the following formulas (21-6-1) to (21-6-7).

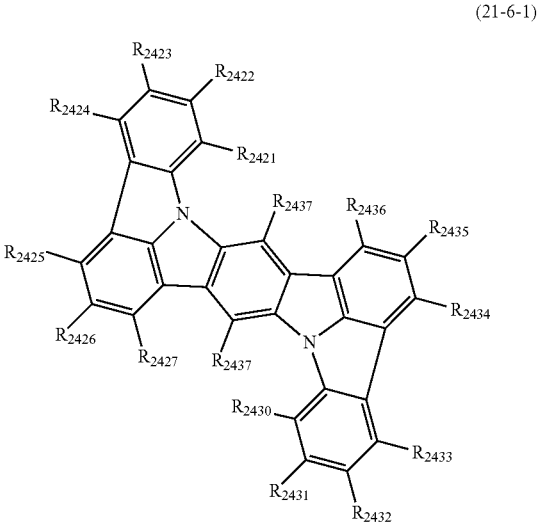

(21-6-1)

-continued

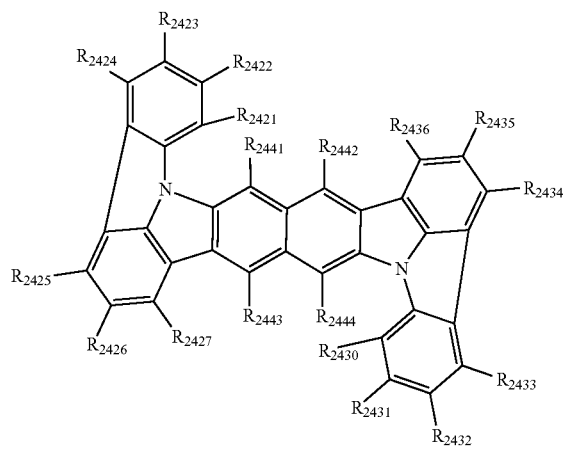
(21-6-2)

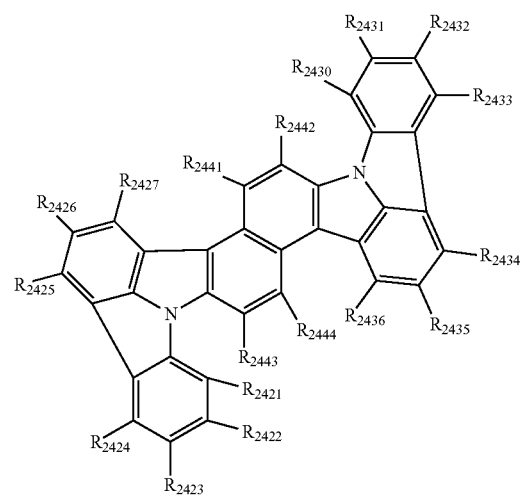
(21-6-3)

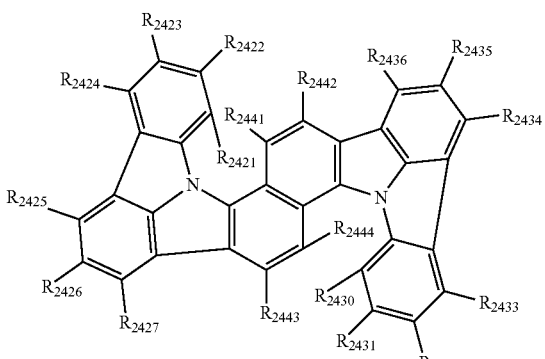
(21-6-4)

-continued

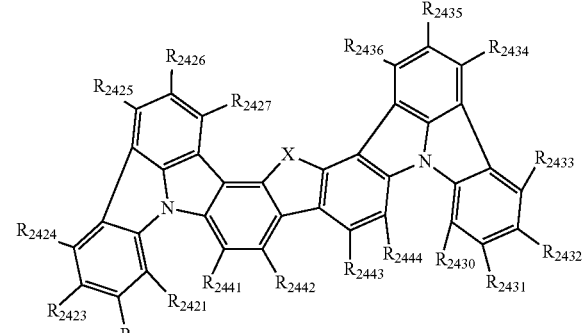
(21-6-5)

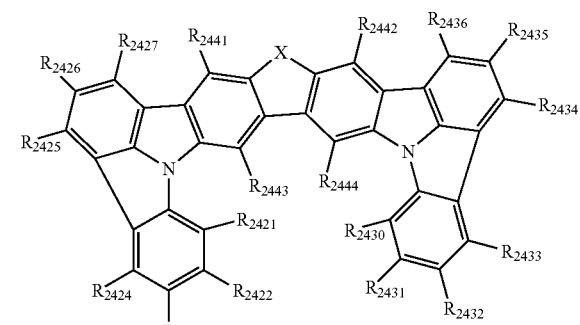
(21-6-6)

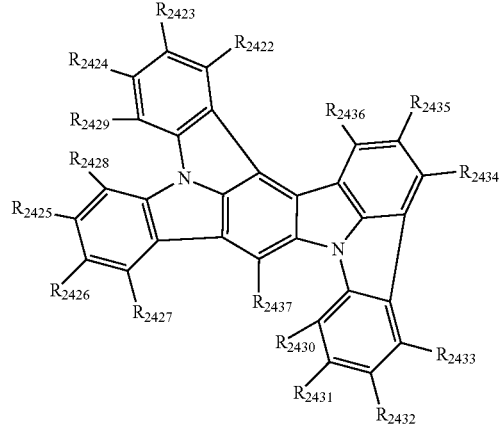
(21-6-7)

wherein in the formulas (21-6-1) to (21-6-7), $R_{2421}$ to $R_{2427}$ are the same as $R_{221}$ to $R_{227}$ in the formulas (21-1) and (21-2);

$R_{2430}$ to $R_{2437}$ and $R_{2441}$ to $R_{2444}$ are the same as $R_{201}$ to $R_{211}$ in the formula (22);

X is O, $NR_{901}$, or $C(R_{902})(R_{903})$; and $R_{901}$ to $R_{903}$ are as defined in the formula (1).

In one embodiment, in the compound represented by the formula (22), one or more pairs of two or more adjacent groups of $R_{201}$ to $R_{211}$ are bonded with each other to form a substituted or unsubstituted, saturated or unsaturated ring. This embodiment is described in the following formula (25).

(Compound Represented by Formula (25))

The compound represented by the formula (25) is explained below.

(25)

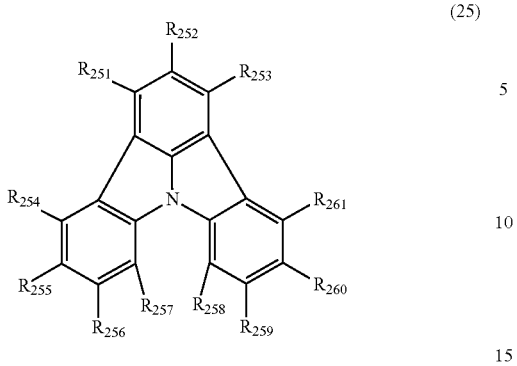

wherein in the formula (25), two or more pairs selected from a group consisting of $R_{251}$ and $R_{252}$, $R_{252}$ and $R_{253}$, $R_{254}$ and $R_{256}$, $R_{255}$ and $R_{256}$, $R_{256}$ and $R_{257}$, $R_{258}$ and $R_{259}$, $R_{259}$ and $R_{260}$, and $R_{260}$ and $R_{261}$ bond with each other to form a substituted or unsubstituted, saturated or unsaturated ring;

Provided that the pair of $R_{251}$ and $R_{252}$ and the pair of $R_{252}$ and $R_{253}$ do not form a ring simultaneously; the pair of $R_{254}$ and $R_{255}$ and the pair of $R_{255}$ and $R_{256}$ do not form a ring simultaneously; the pair of $R_{255}$ and $R_{256}$ and the pair of $R_{256}$ and $R_{257}$ do not form a ring simultaneously; the pair of $R_{258}$ and $R_{259}$ and the pair of $R_{259}$ and $R_{260}$ do not form a ring simultaneously; and the pair of $R_{259}$ and $R_{260}$ and the pair of $R_{260}$ and $R_{261}$ do not form a ring simultaneously;

When two or more rings are formed by $R_{251}$ to $R_{261}$, the rings may be the same or different;

$R_{251}$ to $R_{261}$ that do not form the substituted or unsubstituted, saturated or unsaturated ring are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, or —Si($R_{901}$)($R_{902}$)($R_{903}$),
—O—($R_{904}$),
—S—($R_{905}$),
—N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms; and $R_{901}$ to $R_{907}$ are as defined in the formula (1).

In the formula (25), $R_n$ and $R_{n+1}$ (n is an integer selected from 251, 252, 254 to 256 and 258 to 260) bond with each other to form a substituted or unsubstituted, saturated or unsaturated ring together with two ring carbon atoms to which $R_n$ and $R_{n+1}$ bond with. The ring is preferably configured with atoms selected from C atom, O atom, S atom and N atom, and the number of atoms is preferably 3 to 7, more preferably 5 or 6.

The number of the above-described ring structures in the compound represented by the formula (25) is, for example, 2, 3 or 4. Two or more ring structures may exist in the same benzene ring of the main skeleton in the formula (25), or may exist in different benzene rings. For example, the compound has three ring structures, one ring structure may exist in each of the three benzene rings in the formula (25).

As the above-mentioned ring structure in the compound represented by the formula (25), structures represented by the following formulas (251) to (260) can be given, for example.

(251)

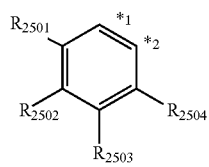

(252)

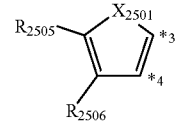

(253)

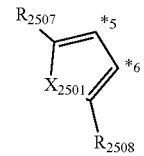

(254)

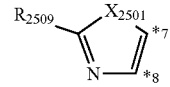

(255)

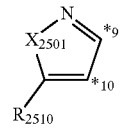

(256)

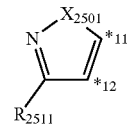

(257)

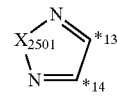

wherein in the formulas (251) to (257), each of *1 and *2, *3 and *4, *5 and *6, *7 and *8, *9 and *10, *11 and *12, and *13 and *14 represents two ring carbon atoms to which $R_n$ and $R_{n+1}$ bond, and $R_n$ may bond to either one of the two ring carbon atoms of *1 and *2, *3 and *4, *5 and *6, *7 and *8, *9 and *10, *11 and *12, and *13 and *14;

$X_{2501}$ is C($R_{2512}$)($R_{2513}$), $NR_{2514}$, O or S;

one or more pairs of two or more adjacent groups of $R_{2501}$ to $R_{2506}$ and $R_{2512}$ to $R_{2513}$ are bonded with each other to form a substituted or unsubstituted, saturated or unsaturated ring, or do not form a substituted or unsubstituted saturated or unsaturated ring; and $R_{2501}$ to $R_{2514}$ that do not form a substituted or unsubstituted saturated or unsaturated ring are the same as $R_{251}$ to $R_{261}$.

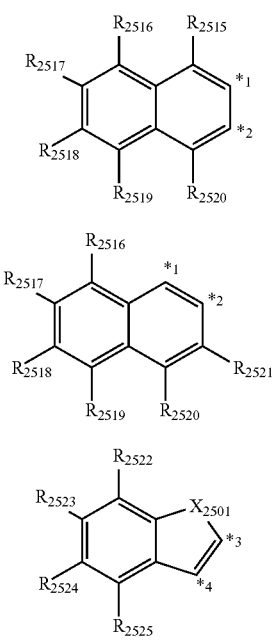

(258)

(259)

(260)

wherein in the formulas (258) to (260), each of *1 and *2, and *3 and *4 represents two ring carbon atoms to which $R_n$ and $R_{n+1}$ bond, and $R_n$ may bond to either one of the two ring carbon atoms of *1 and *2, or *3 and *4;

$X_{2501}$ is $C(R_{2512})(R_{2513})$, $NR_{2514}$, O or S;

one or more pairs of two or more adjacent groups of $R_{2515}$ to $R_{2525}$ bond to each other to form a substituted or unsubstituted, saturated or unsaturated ring, or do not form a substituted or unsubstituted saturated or unsaturated ring; and $R_{2515}$ to $R_{2521}$ and $R_{2522}$ to $R_{2525}$ that do not form a substituted or unsubstituted saturated or unsaturated ring are the same as $R_{251}$ to $R_{261}$.

In the formula (25), it is preferable that at least one of $R_{252}$, $R_{254}$, $R_{255}$, $R_{260}$ and $R_{261}$ (preferably at least one of $R_{252}$, $R_{255}$, and $R_{260}$, more preferably $R_{252}$) is a group which does not form a ring.

(i) Substituent in the case where the ring structure formed by $R_n$ and $R_{n+1}$ has a substituent in the formula (25), (ii) $R_{251}$ to $R_{261}$ that do not form a ring structure in the formula (25), and (iii) $R_{2501}$ to $R_{2514}$ and $R_{2515}$ to $R_{2525}$ in the formulas (251) to (260)

are preferably independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms,

—$N(R_{906})(R_{907})$, a substituted or unsubstituted aryl group having 6 to 50 ring carbon atoms, a substituted or unsubstituted monovalent heterocyclic group having 5 to 50 ring atoms, or a group selected from the following groups.

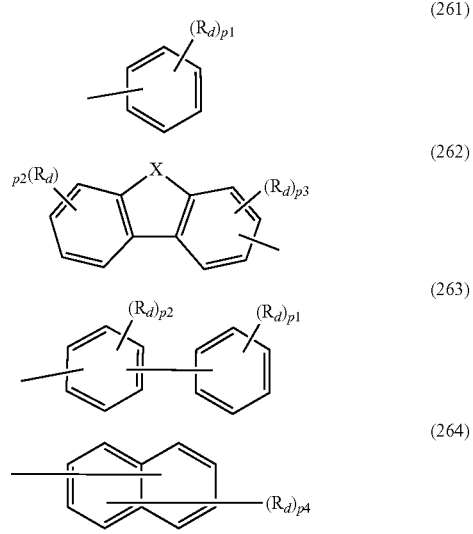

(261)

(262)

(263)

(264)

wherein in the formulas (261) to (264), $R_d$s are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —$Si(R_{901})(R_{902})(R_{903})$,

—O—$(R_{904})$,

—S—$(R_{905})$,

—$N(R_{906})(R_{907})$, a halogen atom, a cyano group, a nitro group, a substituted or unsubstituted aryl group having 6 to 50 ring carbon atoms, or a substituted or unsubstituted monovalent heterocyclic group having 5 to 50 ring atoms;

X is $C(R_{901})(R_{902})$, $NR_{903}$, O, or S;

$R_{901}$ to $R_{907}$ are as defined in the formula (1); and p1 is independently an integer of 0 to 5, p2 is independently an integer of 0 to 4, p3 is an integer of 0 to 3, and p4 is an integer of 0 to 7.

In one embodiment, the compound represented by the formula (25) is represented by the following formulas (25-1) to (25-6).

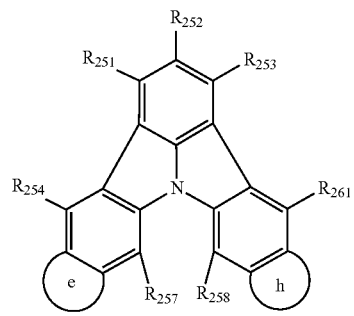

(25-1)

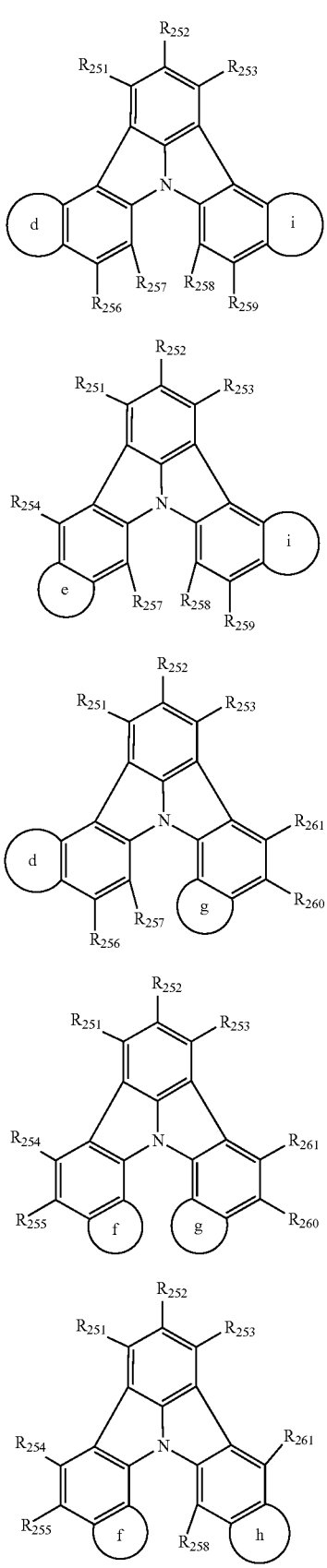
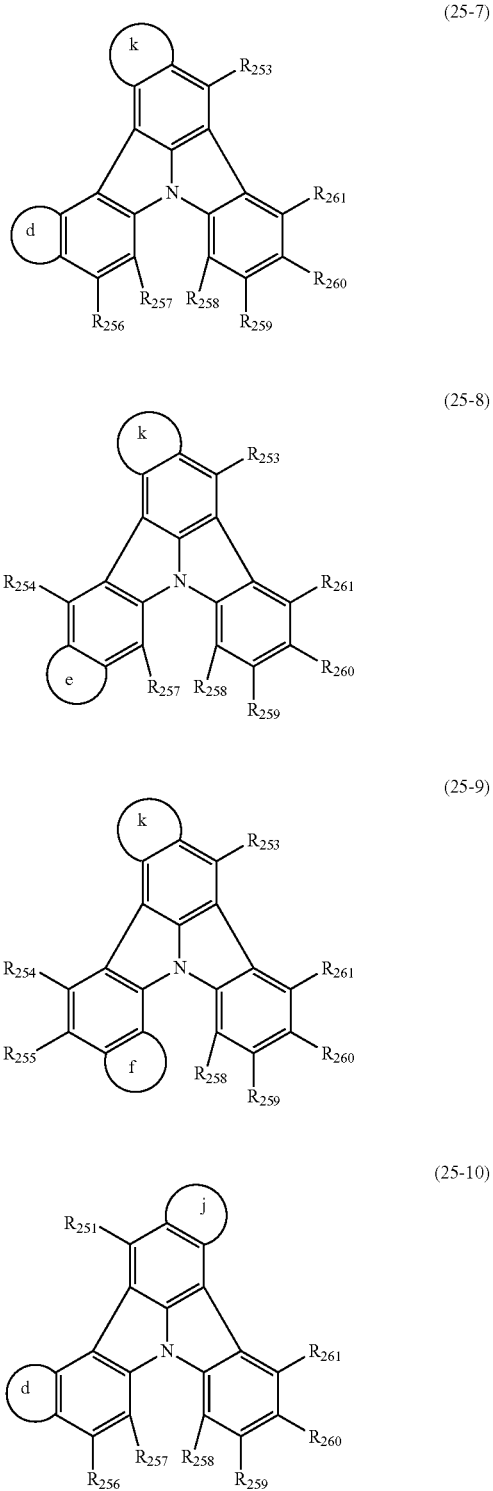
wherein in the formulas (25-1) to (25-6), ring d to ring i are independently a substituted or unsubstituted, saturated or unsaturated ring; and $R_{251}$ to $R_{261}$ are the same as defined in the formula (25).
In one embodiment, the compound represented by the formula (25) is represented by the following formulas (25-7) to (25-12).

(25-11)
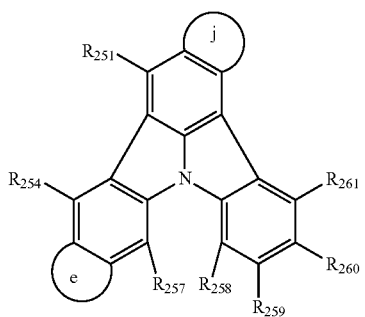
(25-12)
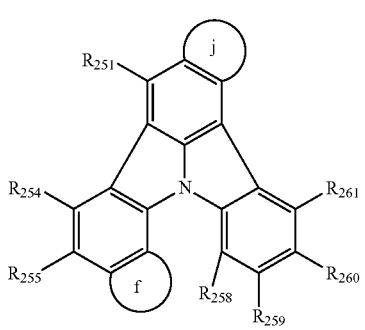
wherein in the formulas (25-7) to (25-12), ring d to ring f, ring k, and ring j are independently a substituted or unsubstituted, saturated or unsaturated ring; and $R_{251}$ to $R_{261}$ are the same as defined in the formula (25).
In one embodiment, the compound represented by the formula (25) is represented by the following formulas (25-13) to (25-21).
(25-13)
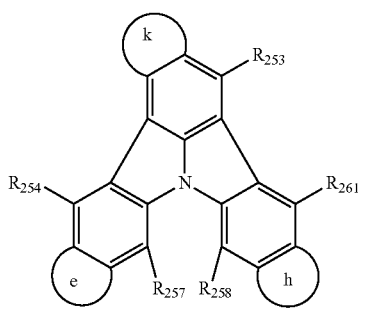
(25-14)
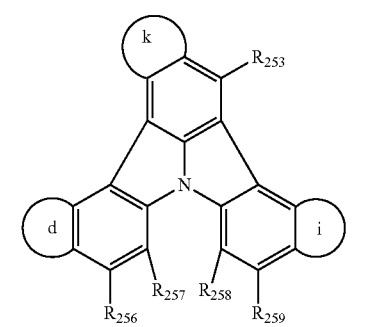
(25-15)
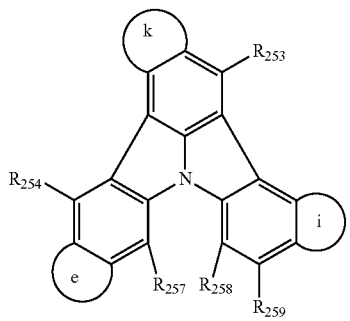
(25-16)
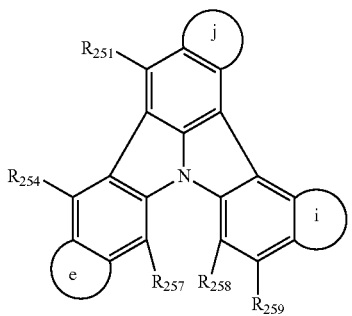
(25-17)
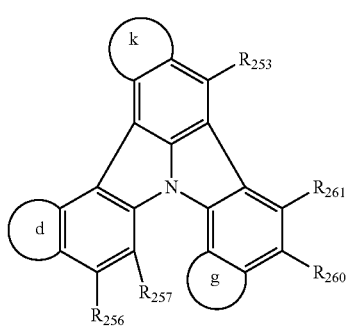
(25-18)
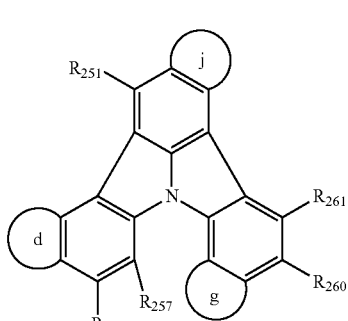
(25-19)
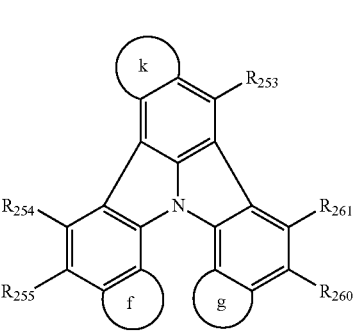

(25-20)
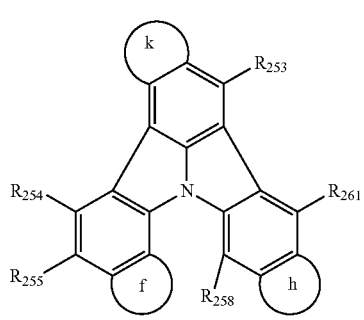

(25-21)
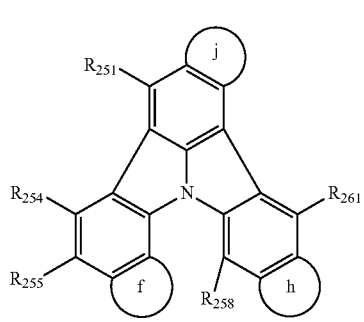

wherein in the formulas (25-13) to (25-21), ring d to ring k are independently a substituted or unsubstituted, saturated or unsaturated ring; and $R_{251}$ to $R_{261}$ are the same as defined in the formula (25).

As a substituent in the case where the ring g or ring h further has a substituent, a substituted or unsubstituted alkyl group having 1 to 50 carbon atoms, a substituted or unsubstituted aryl group having 6 to 50 ring carbon atoms, or a group represented by the formula (261), (263) or (264) can be given for example.

In one embodiment, the compound represented by the formula (25) is represented by one of the following formulas (25-22) to (25-25).

(25-22)
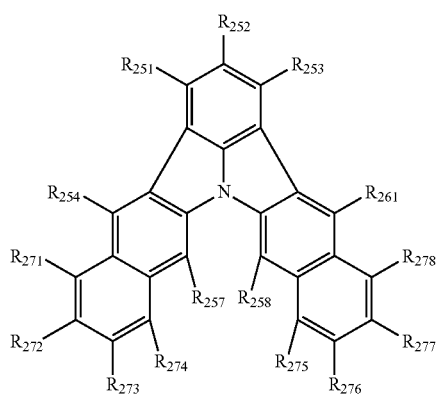

(25-23)
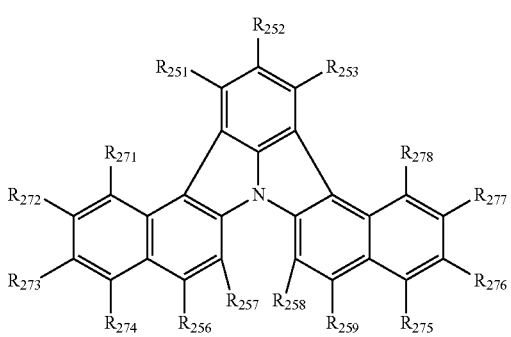

(25-24)
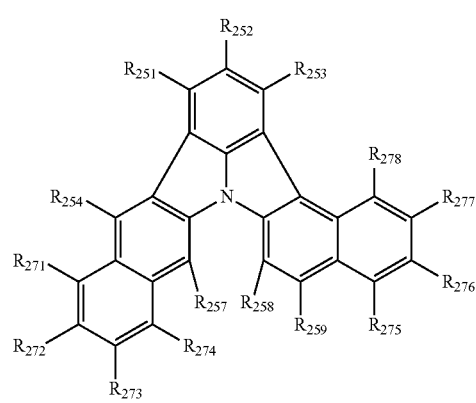

(25-25)
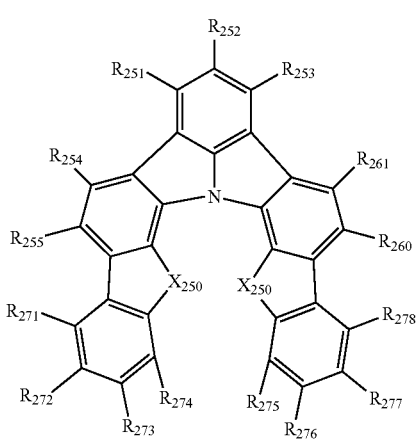

wherein in the formulas (25-22) to (25-25), $X_{250}$ is independently $C(R_{901})(R_{902})$, $NR_{903}$, O or S;

$R_{251}$ to $R_{261}$, and $R_{271}$ to $R_{278}$ are the same as $R_{251}$ to $R_{261}$ in the formula (25); and $R_{901}$ to $R_{903}$ are as defined in the formula (1).

In one embodiment, the compound represented by the formula (25) is represented by the following formula (25-26).

(25-26)
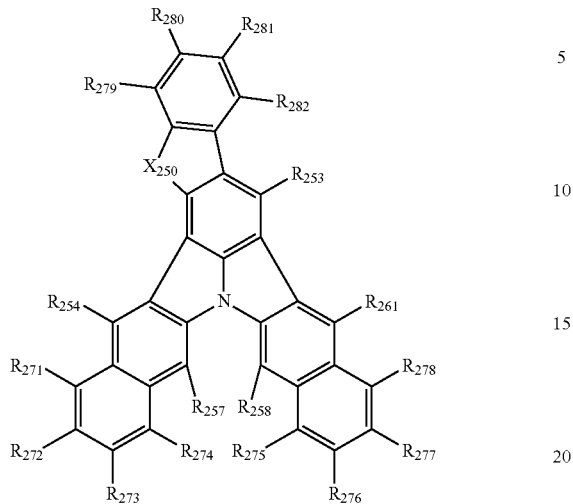
wherein in the formula (25-26), $X_{250}$ is $C(R_{901})(R_{902})$, $NR_{903}$, O or S; $R_{253}$, $R_{254}$, $R_{257}$, $R_{258}$, $R_{261}$, and $R_{271}$ to $R_{282}$ are the same as $R_{251}$ to $R_{261}$ in the formula (25); and $R_{901}$ to $R_{903}$ are as defined in the formula (1).
As the compound represented by the formula (21), the following compounds can be shown for example. In the following example compounds, Me represents methyl group.
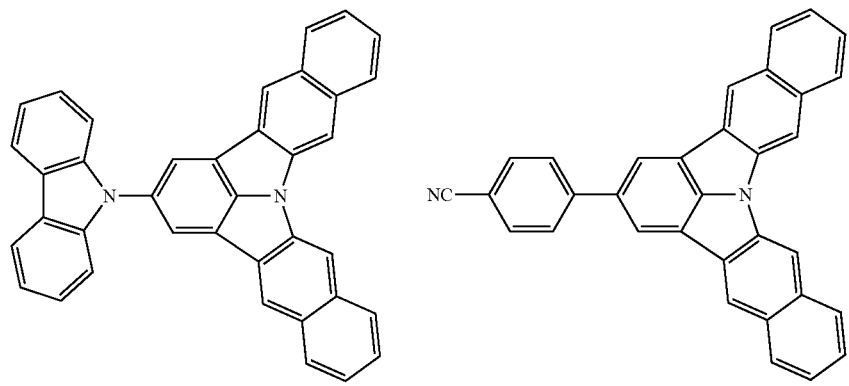
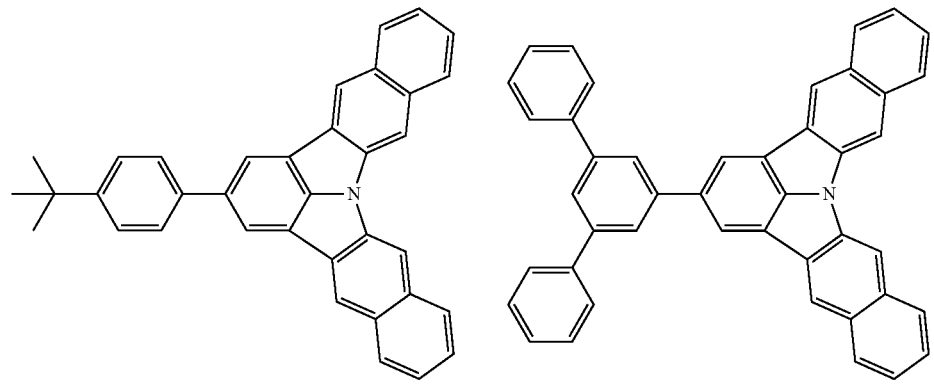

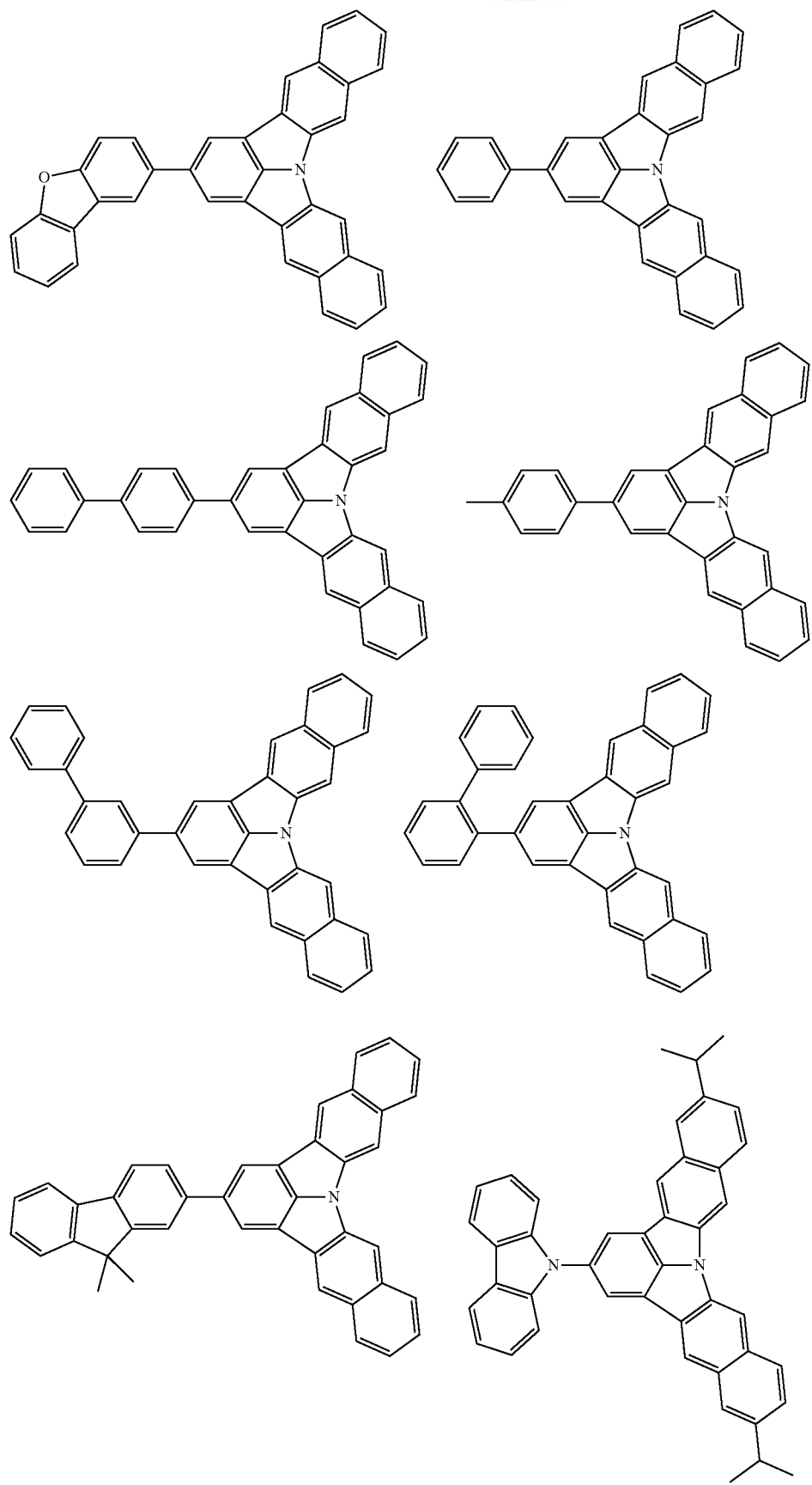

-continued
| 207 | 208 |
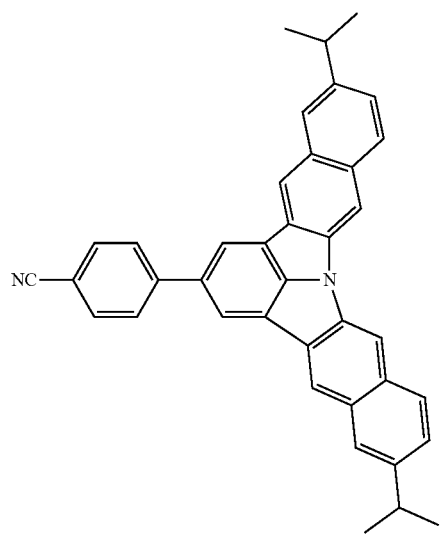
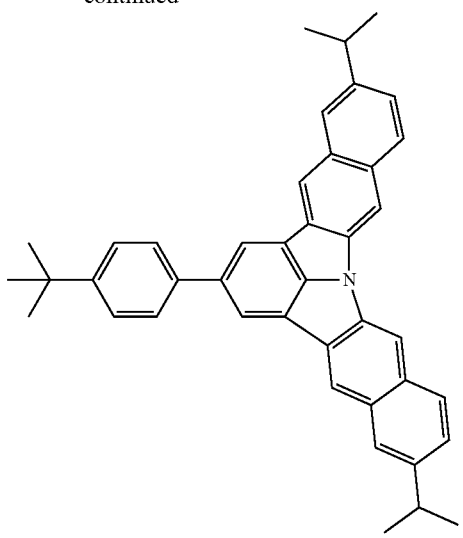
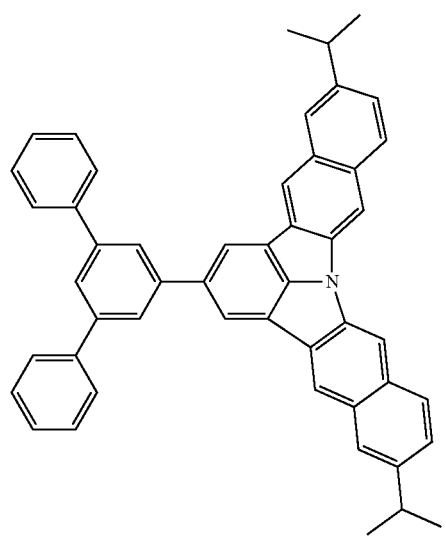
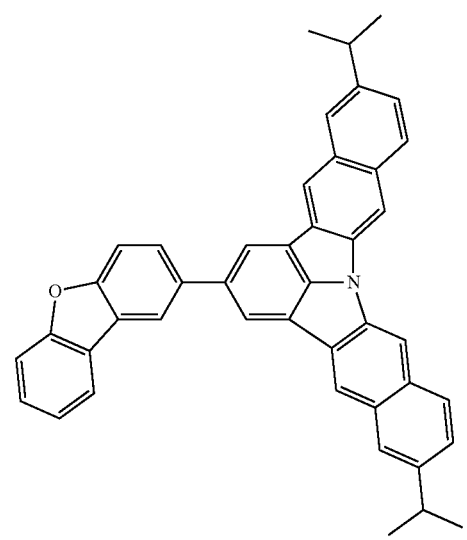
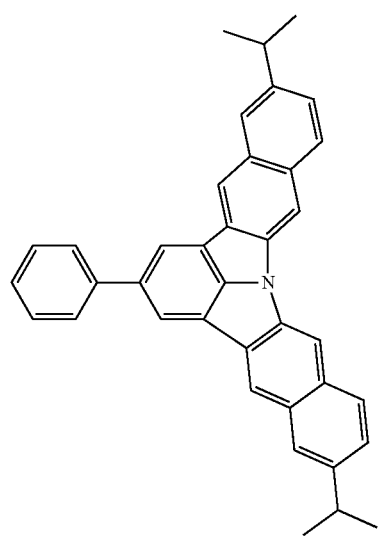
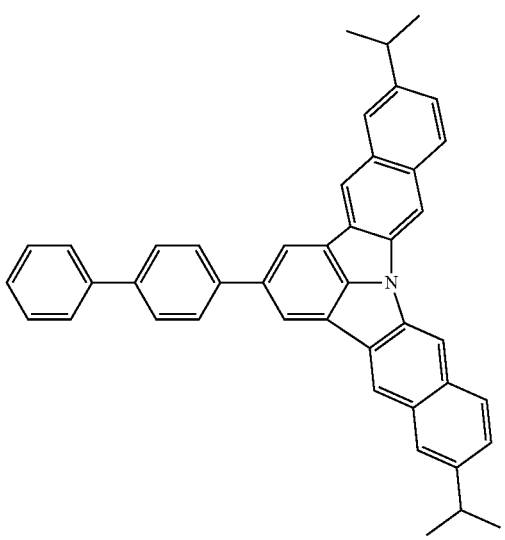

-continued
209
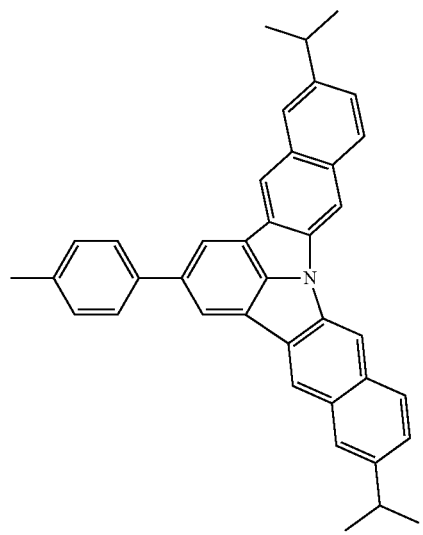
210
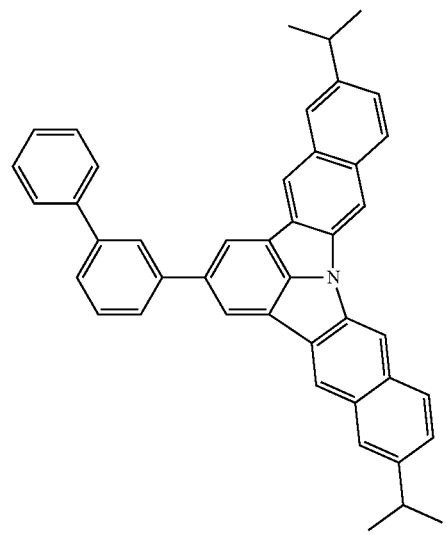
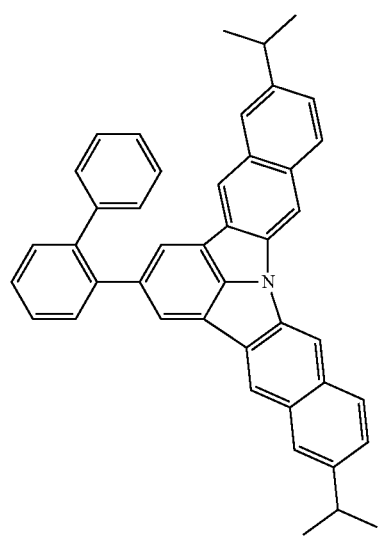
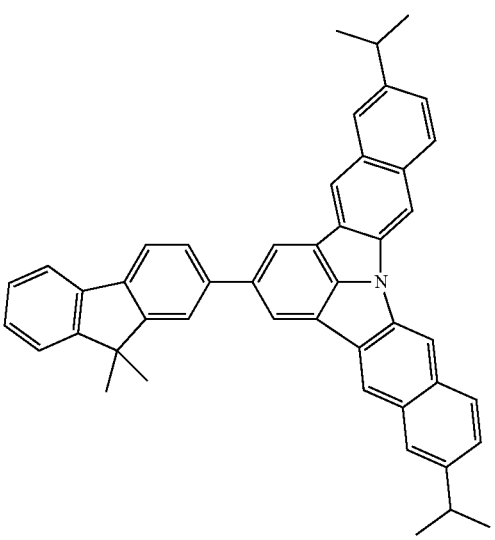
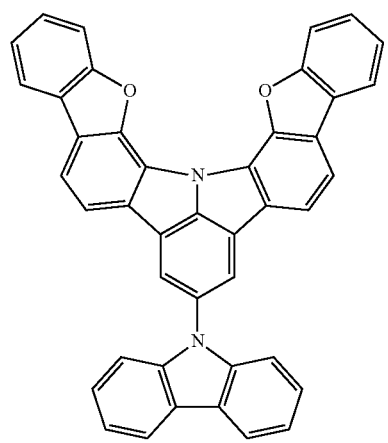
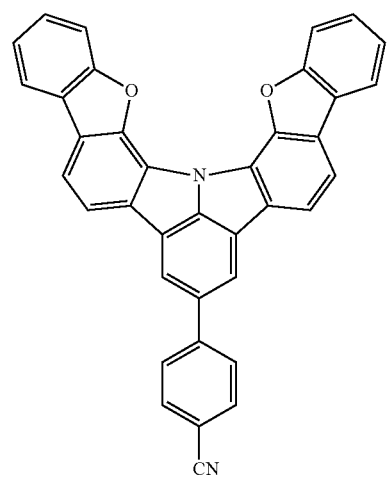
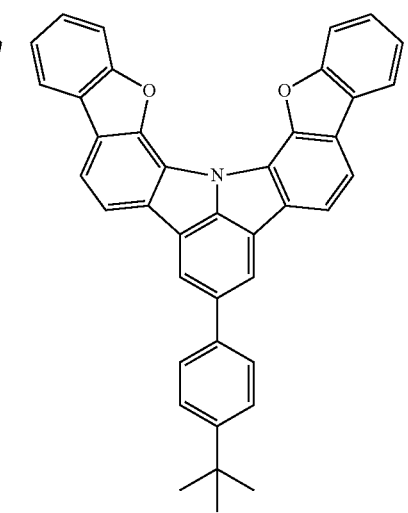

-continued
| 211 | | 212 |
|---|---|---|
| 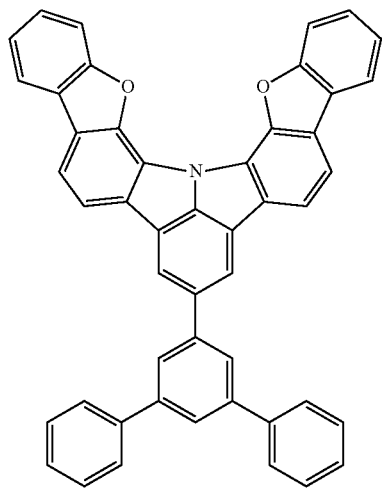 | 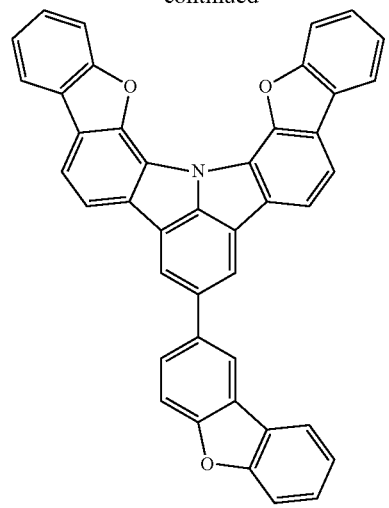 | 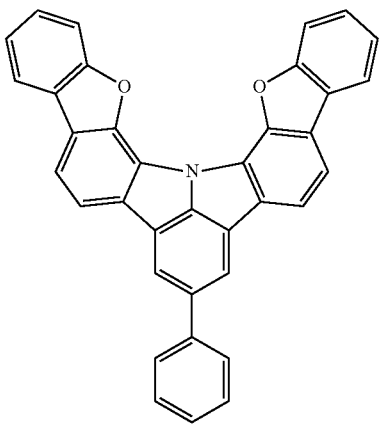 |
| 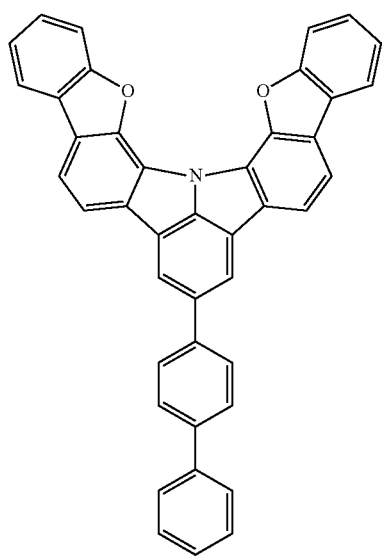 | 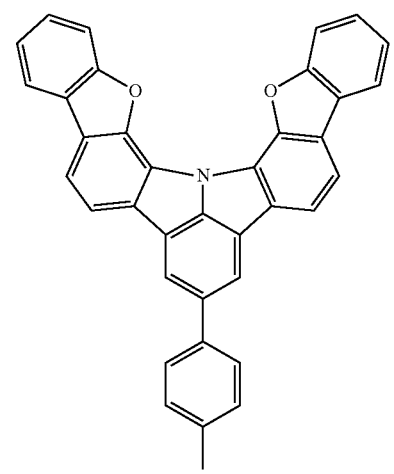 | 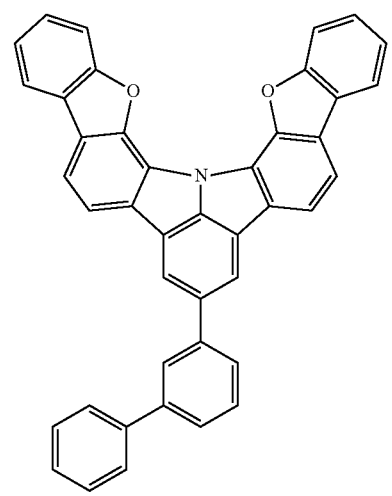 |
| 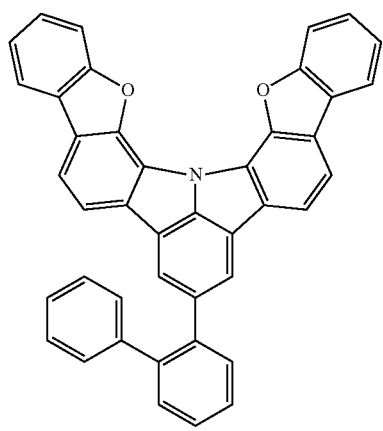 | 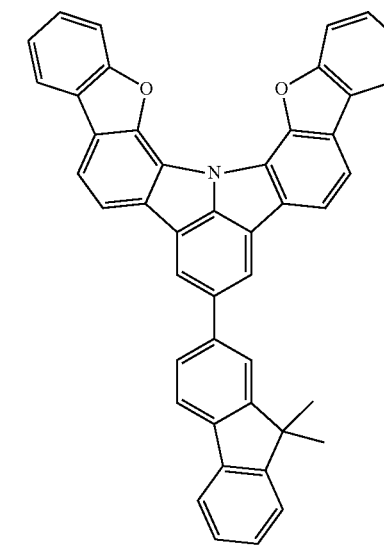 | |

213 214
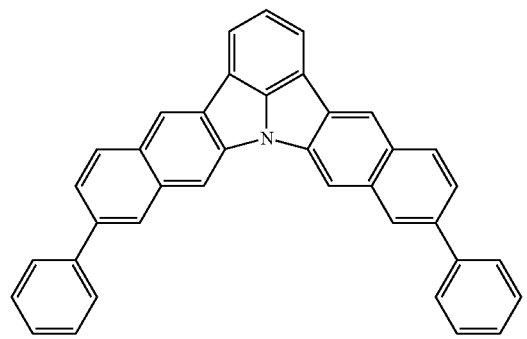
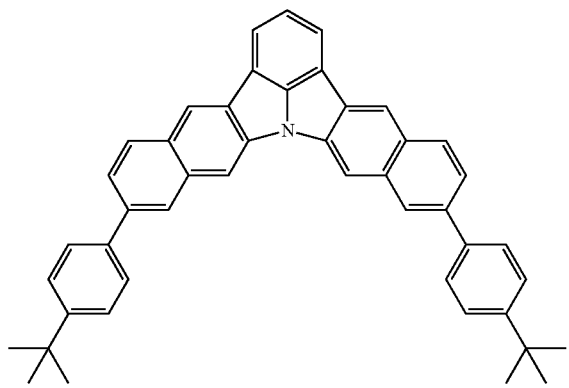
-continued
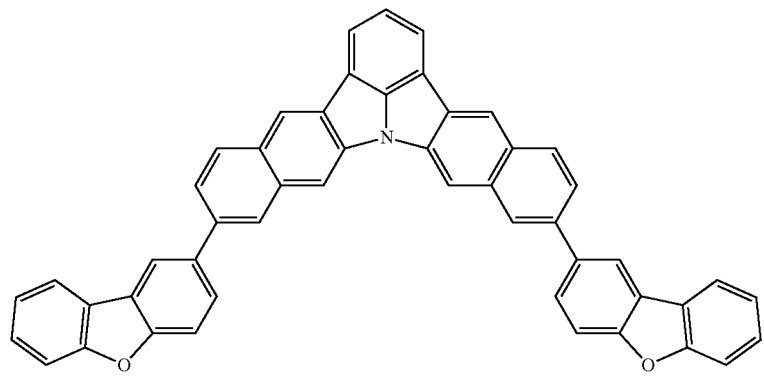
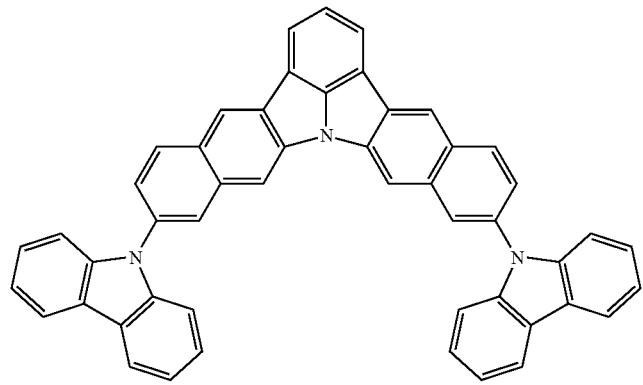
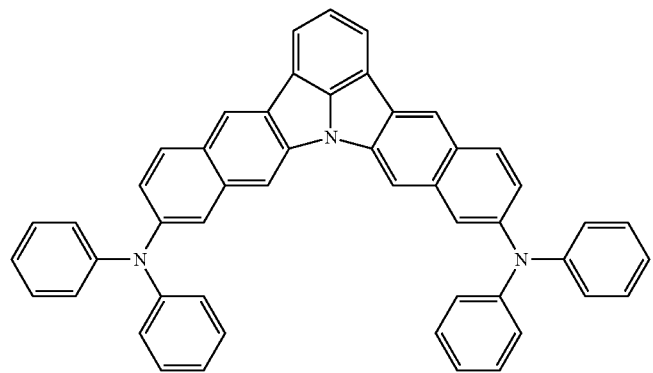

215 216
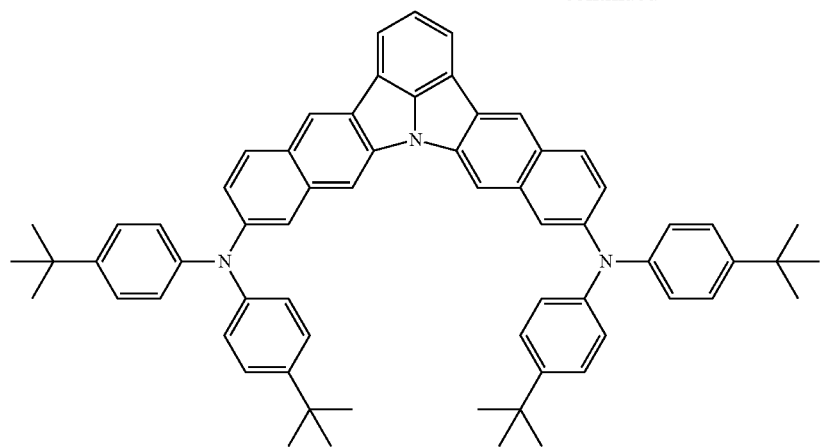
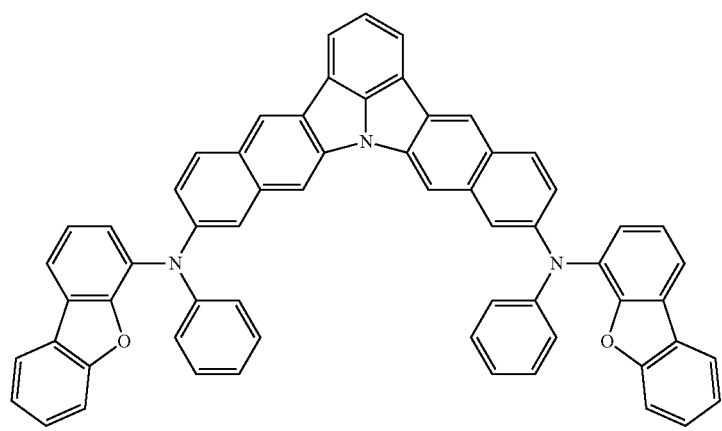
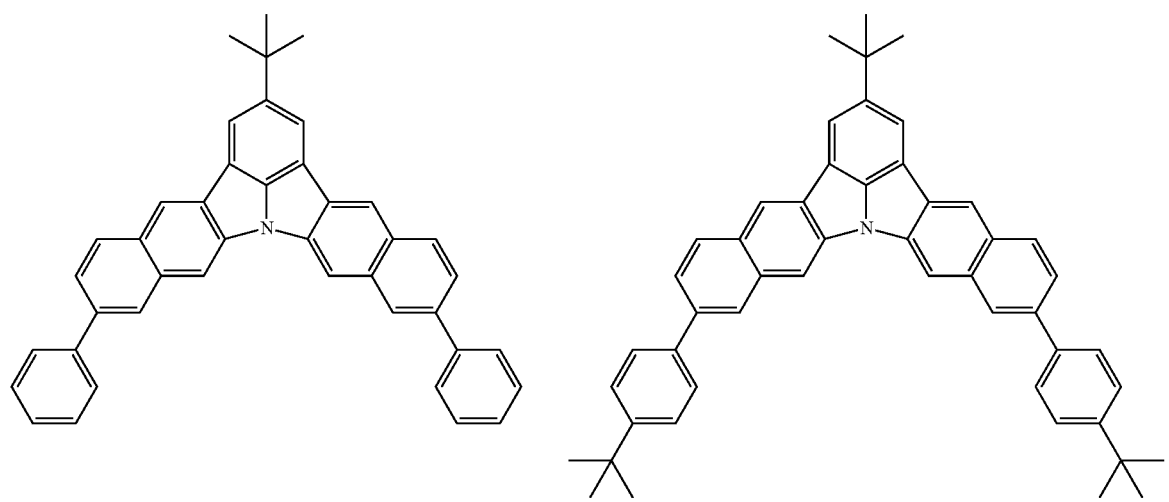

-continued
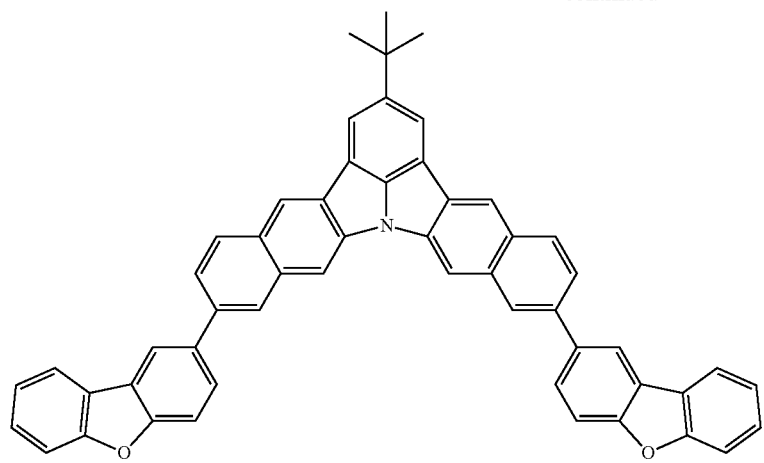
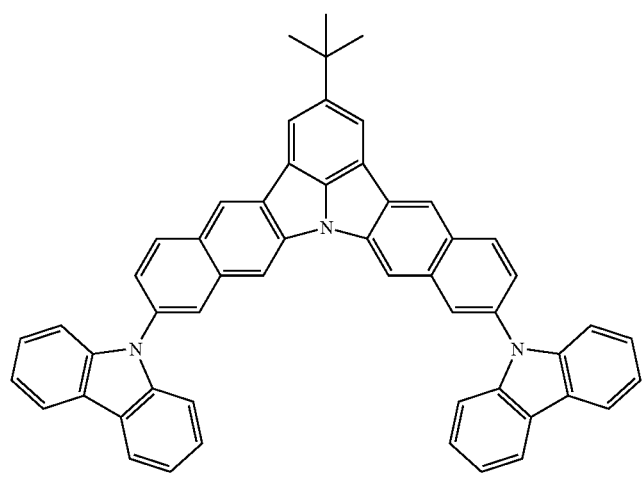
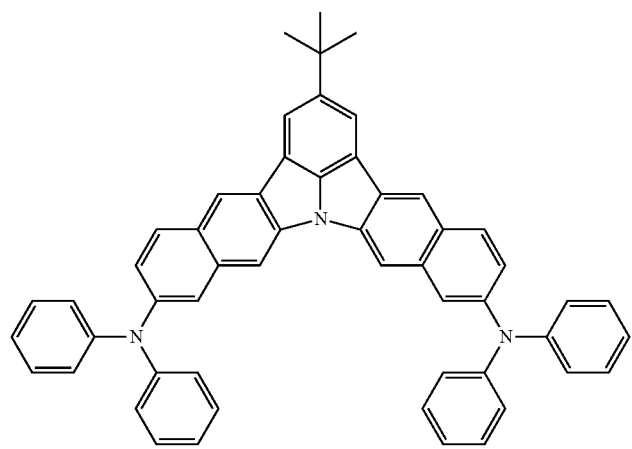

219 220
-continued
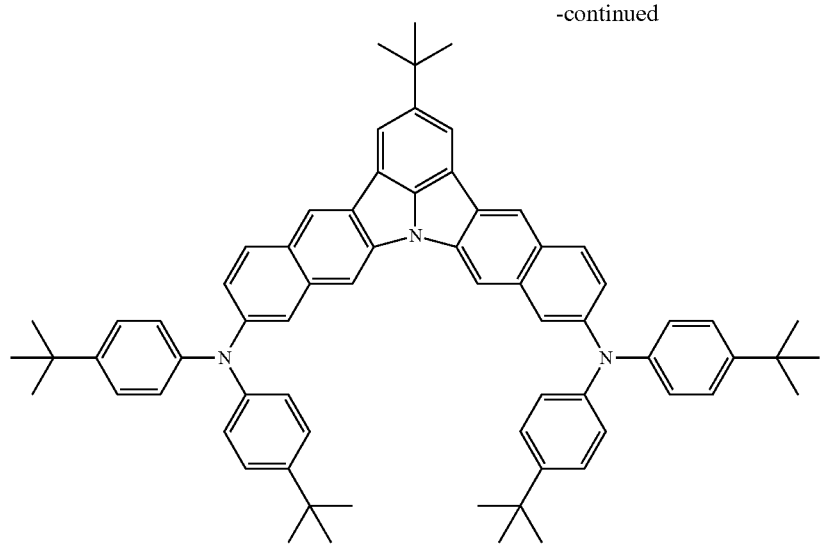
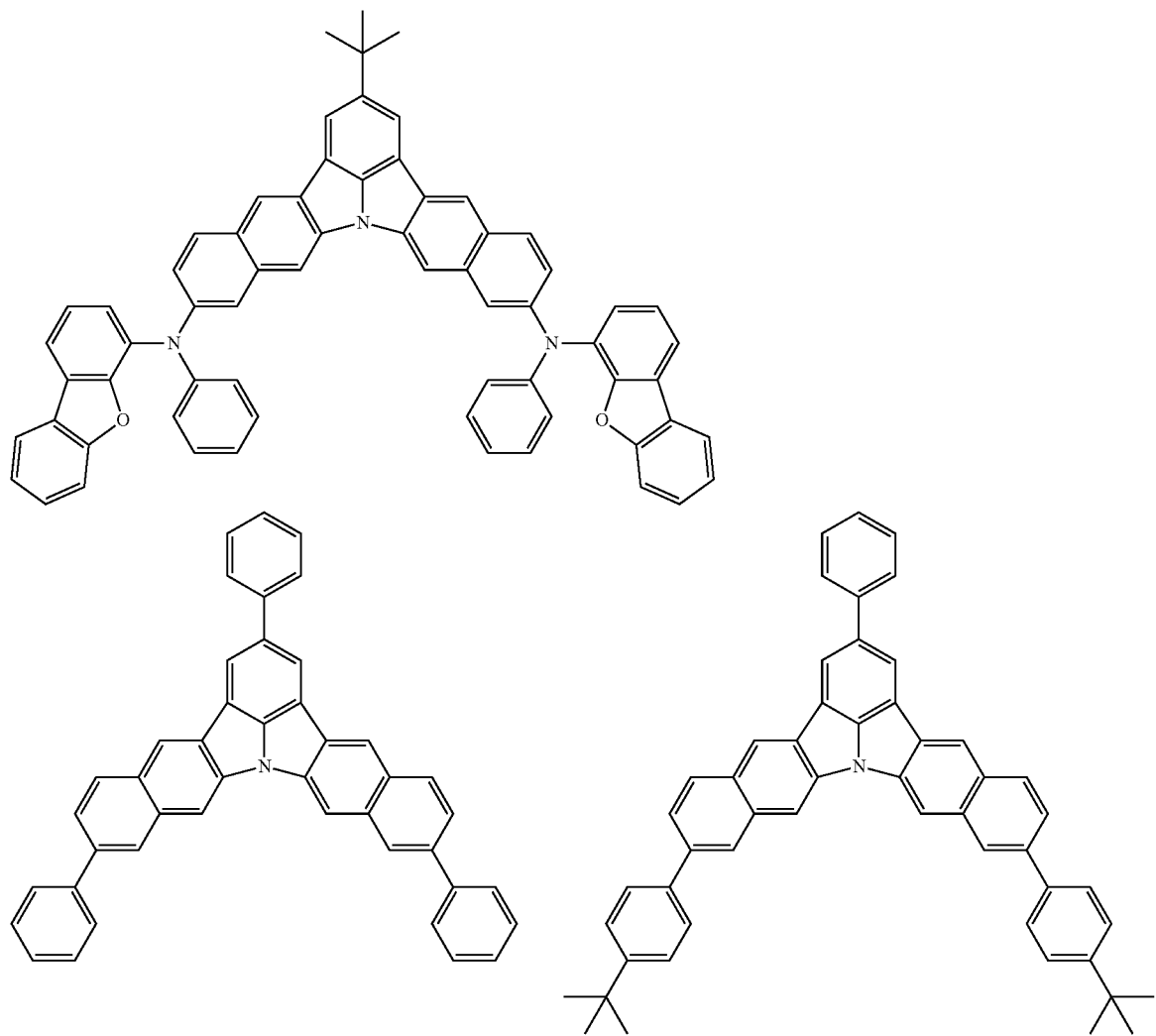

221
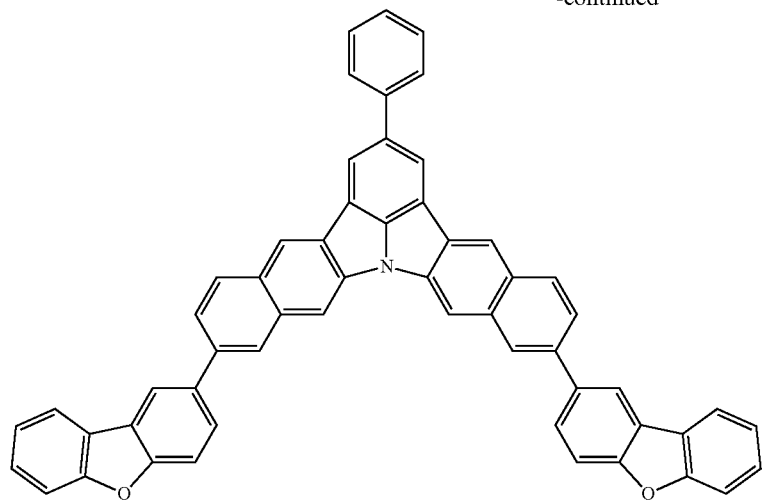
222
-continued
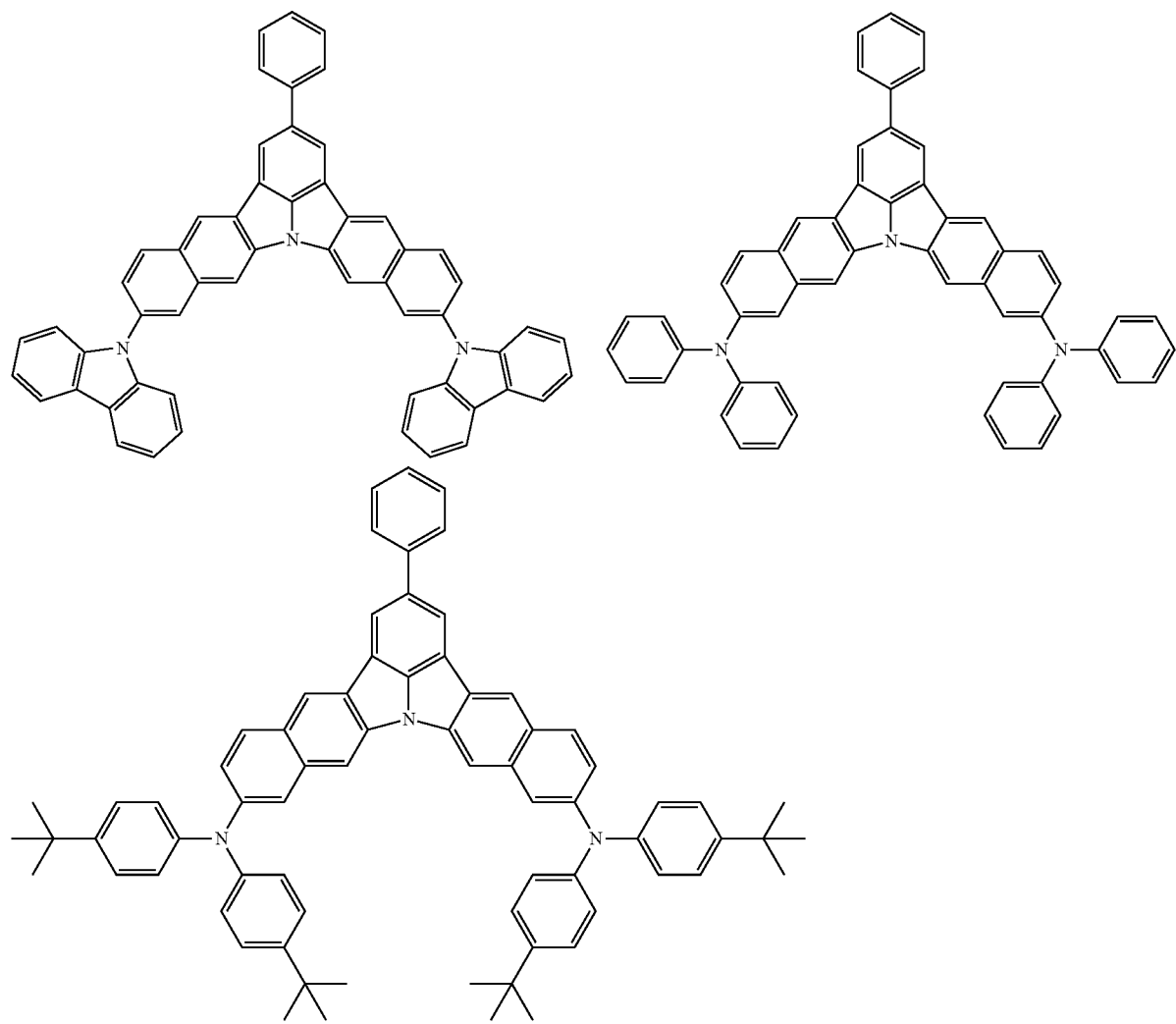

223
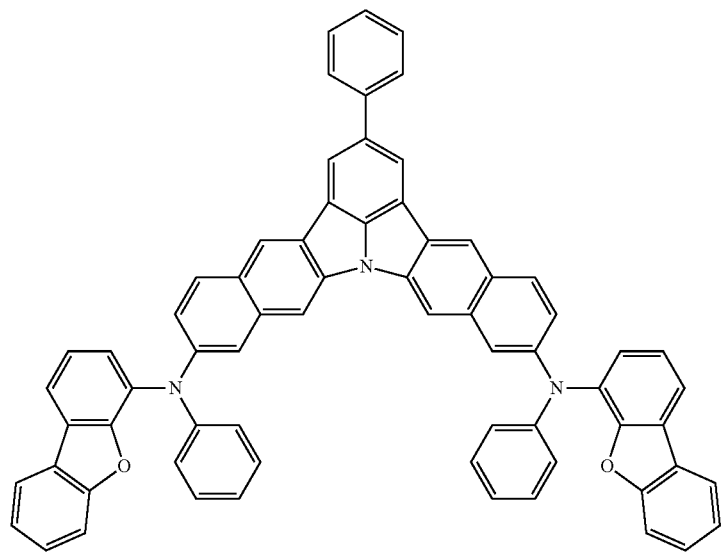
224
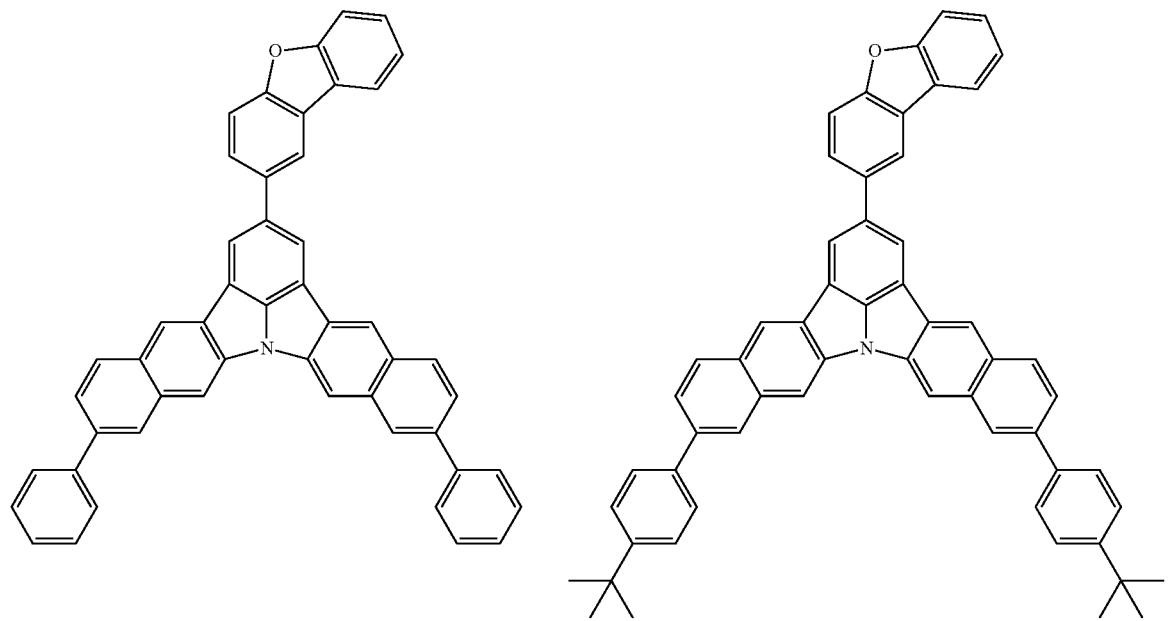

225
-continued
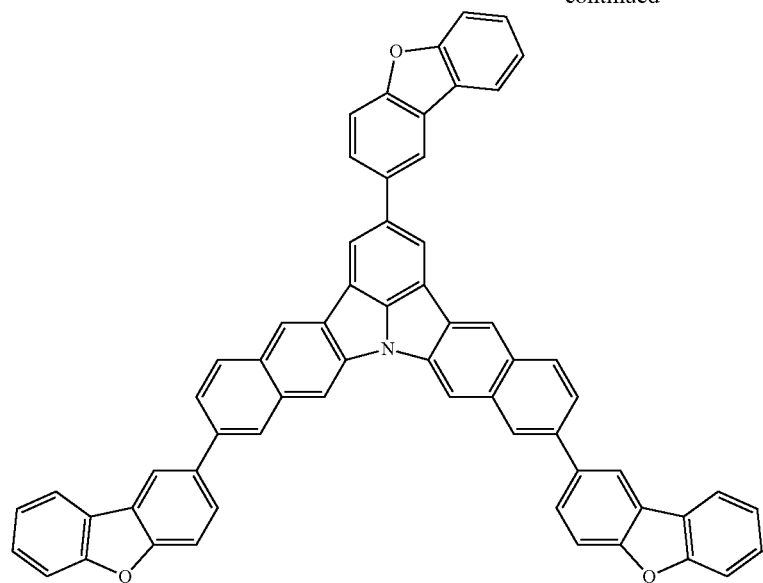
226
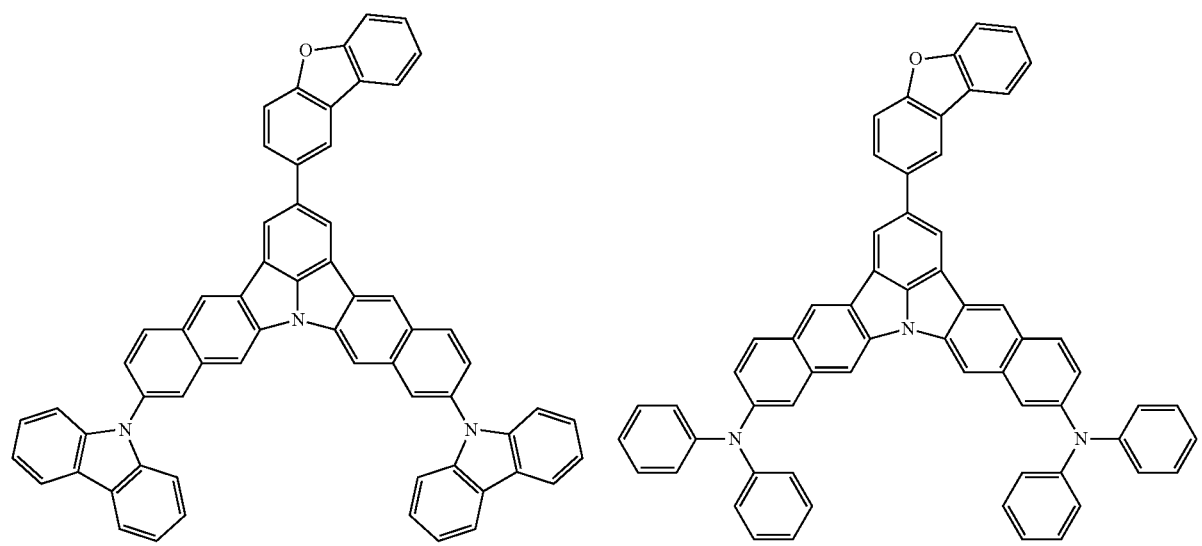

-continued
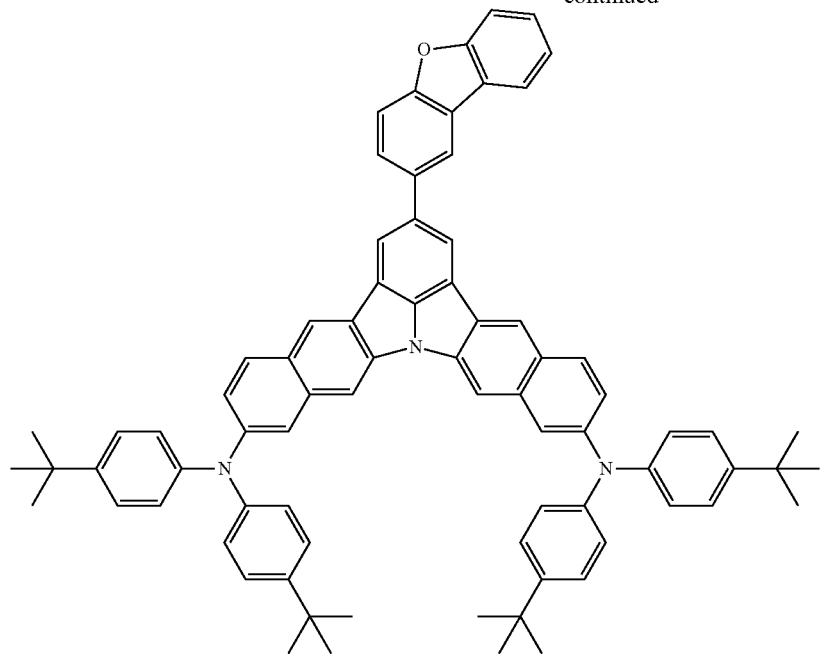
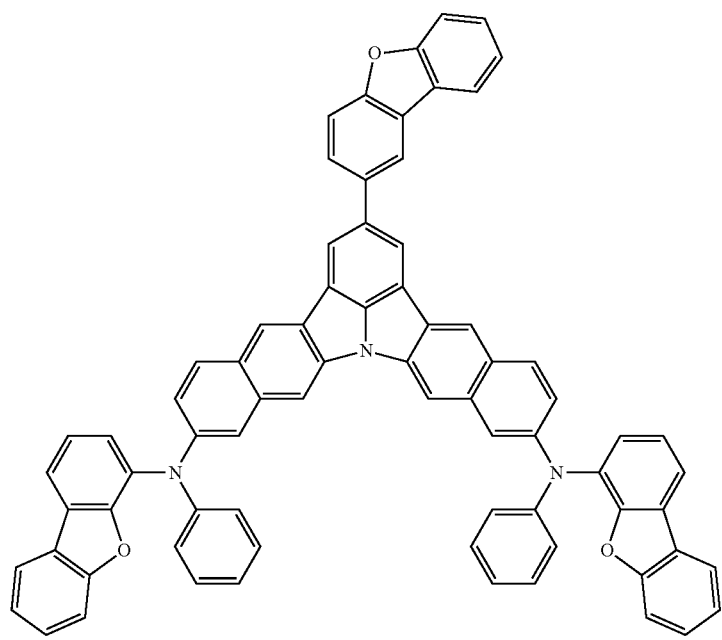

-continued
| 229 | 230 |
|---|---|
| 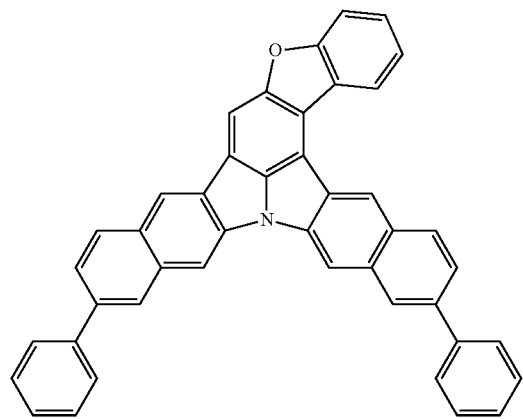 | 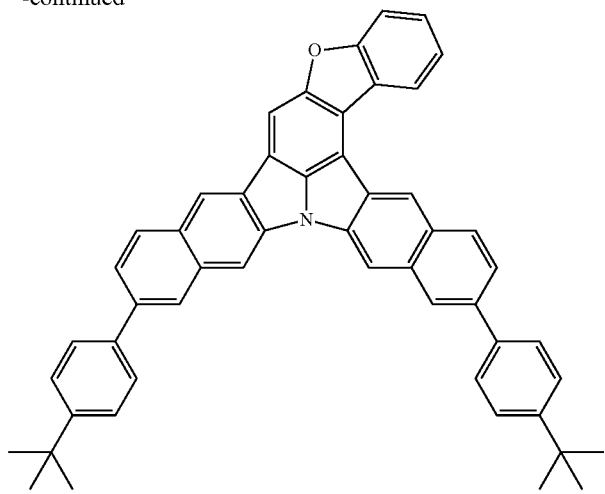 |
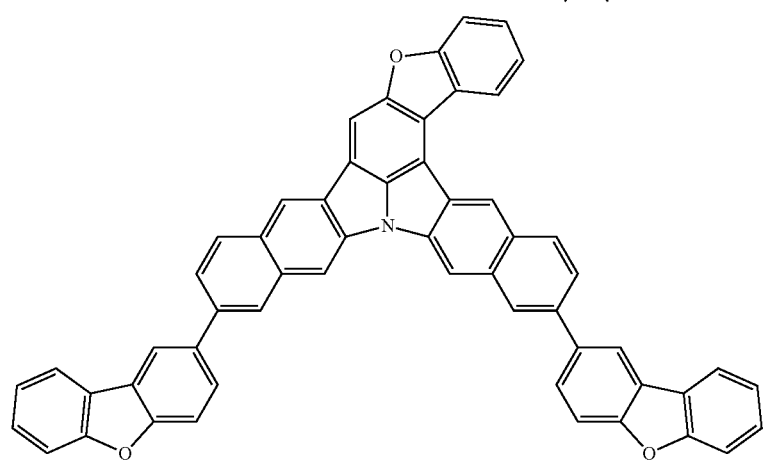
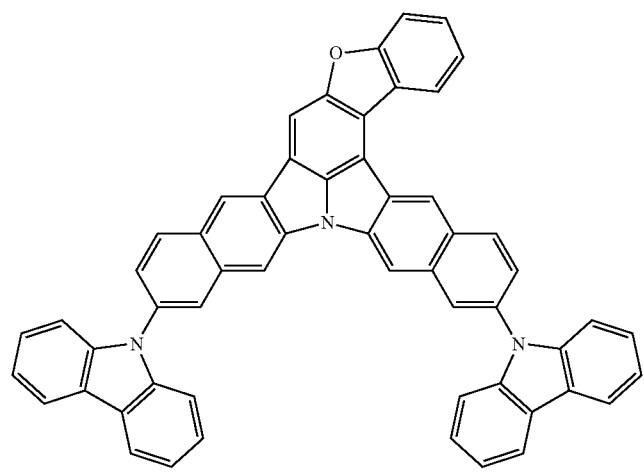

-continued
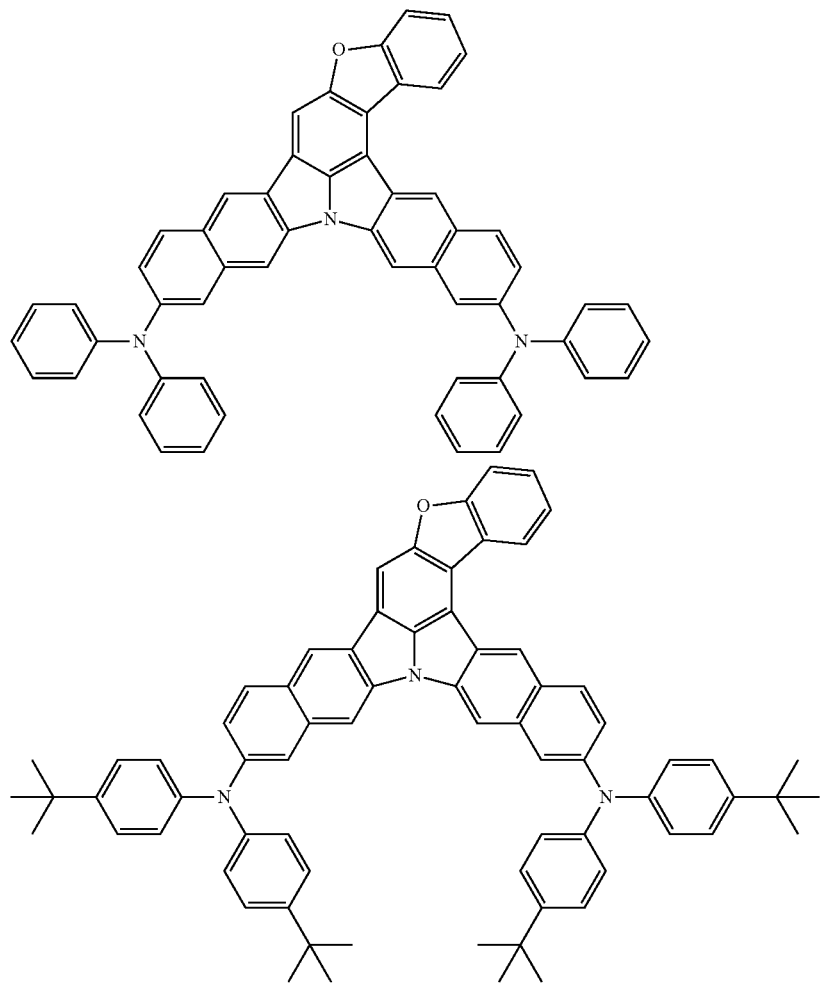
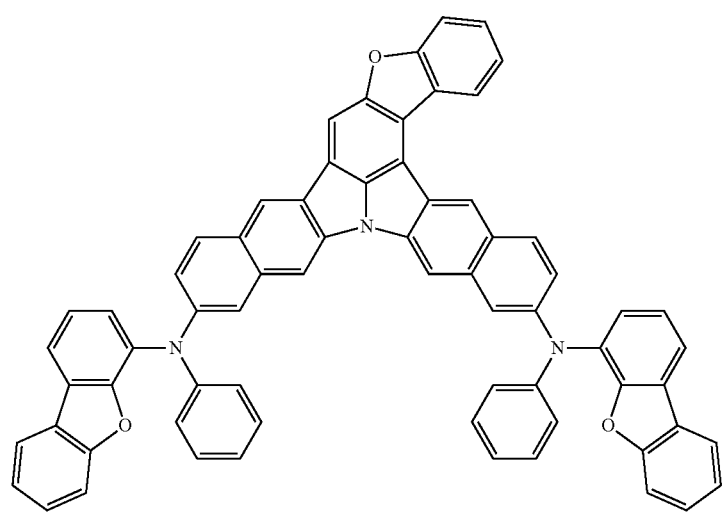

-continued
233 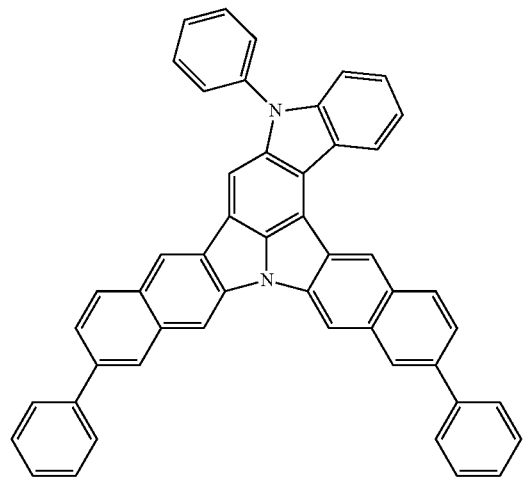 234 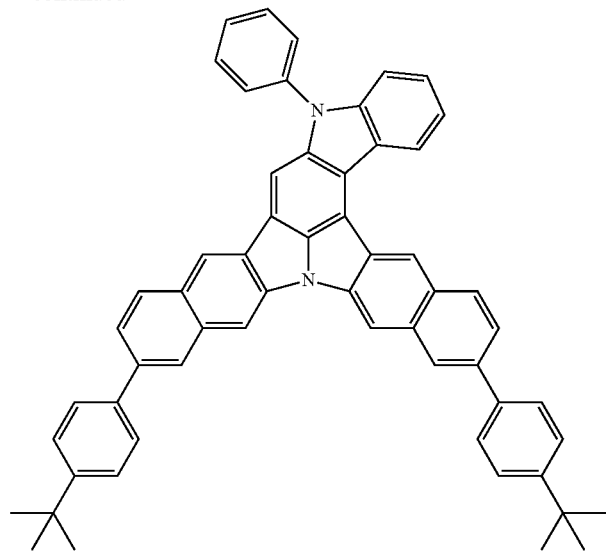
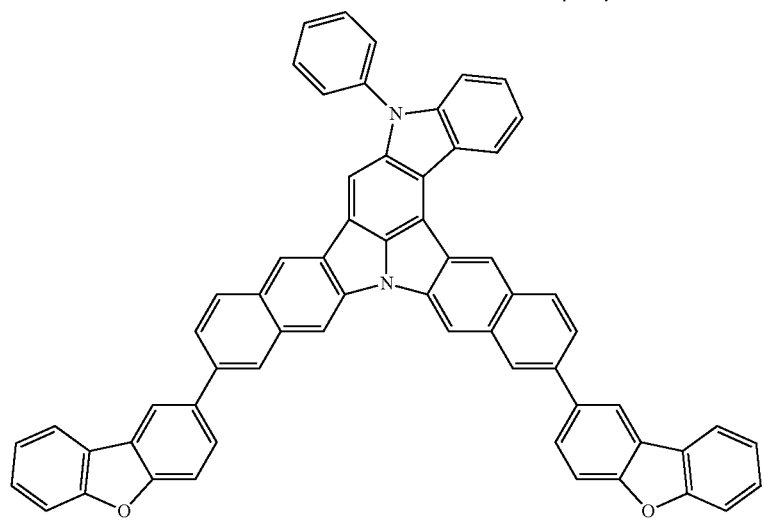
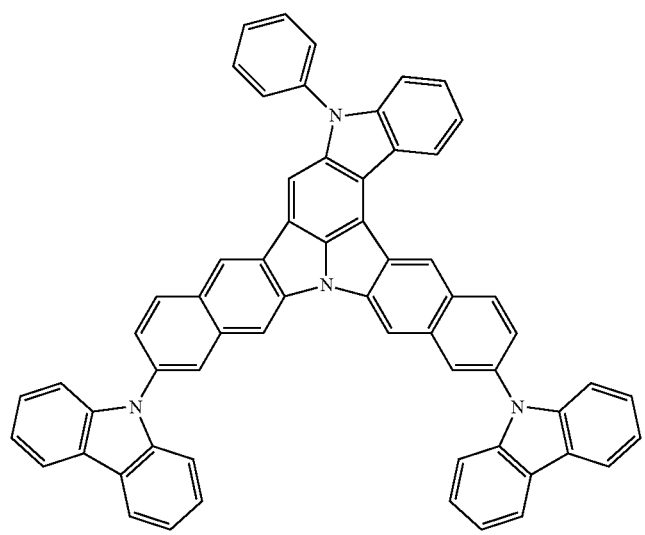

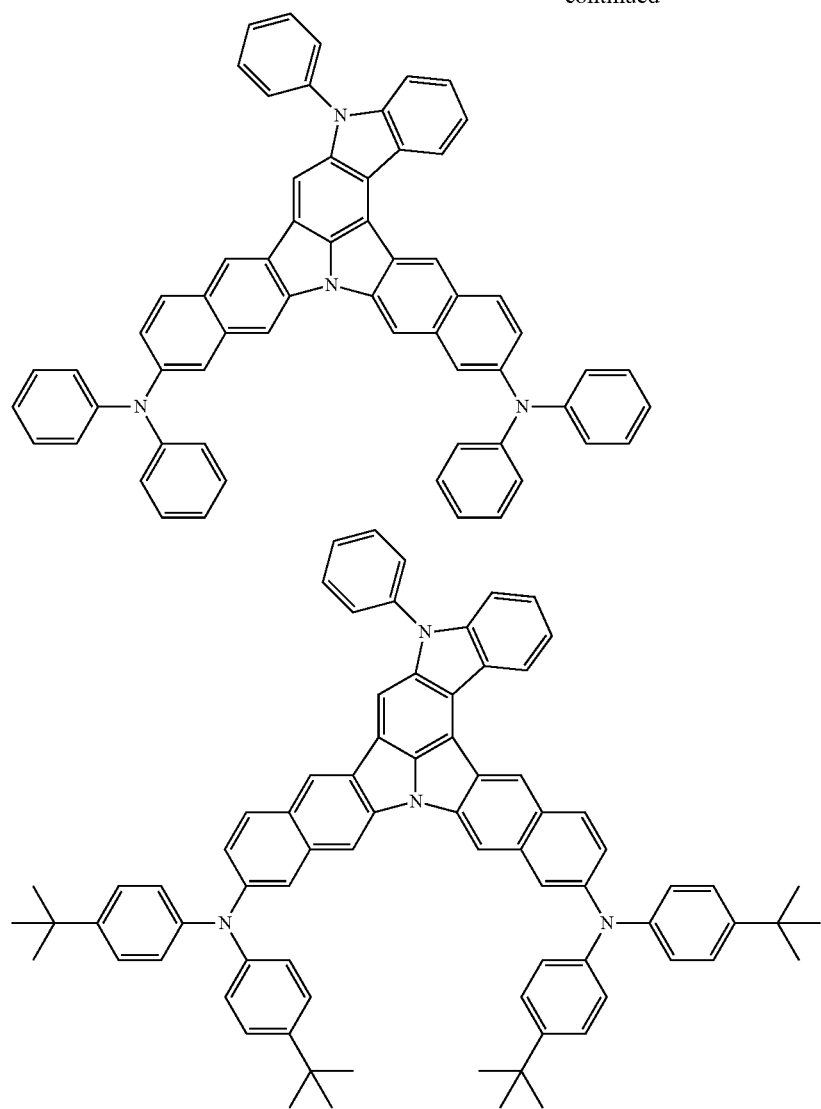
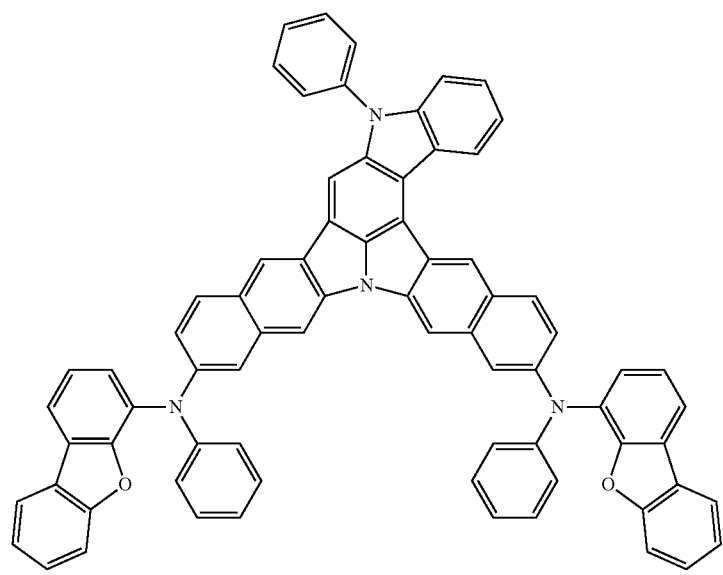

237 238
-continued
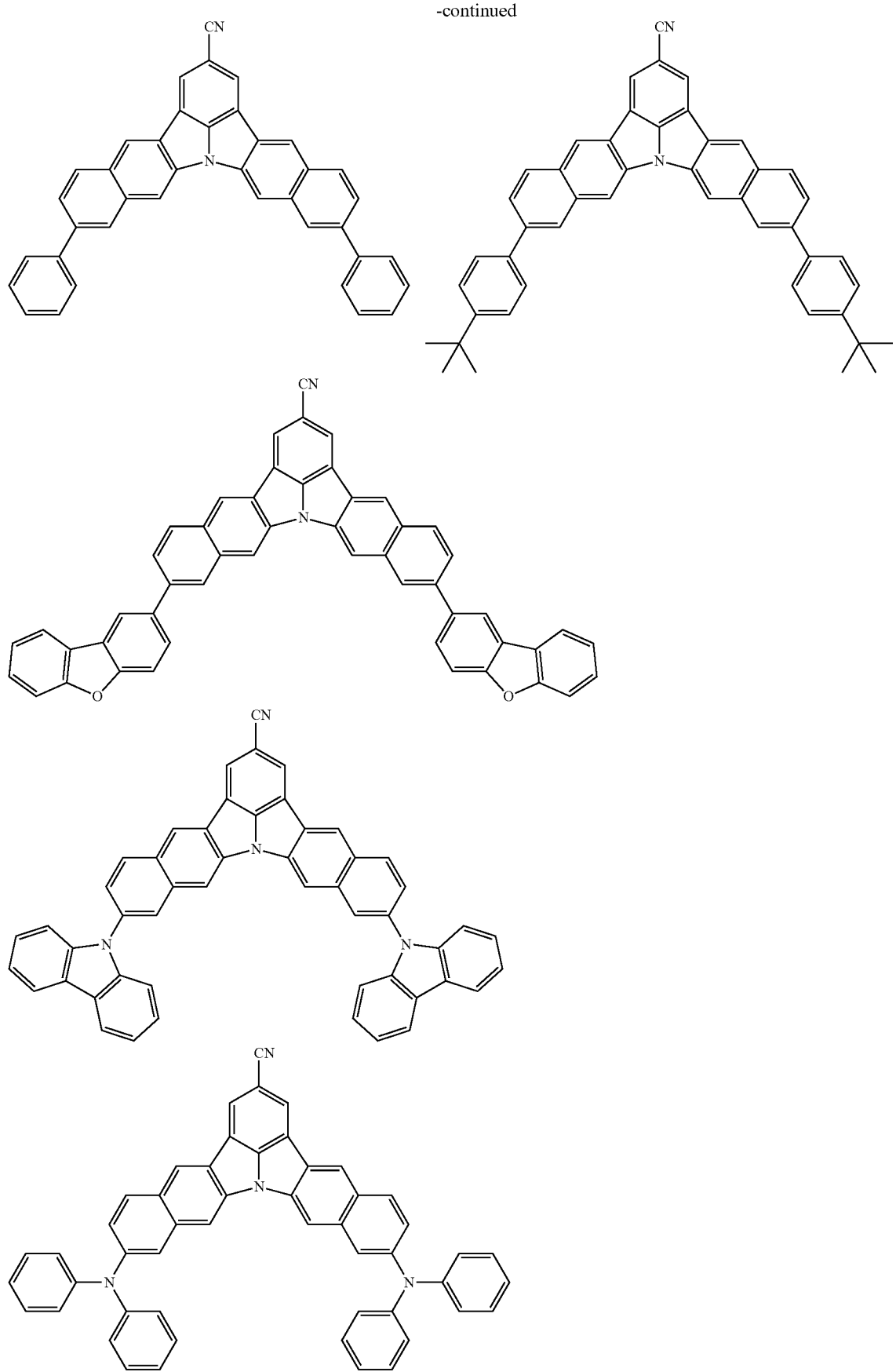

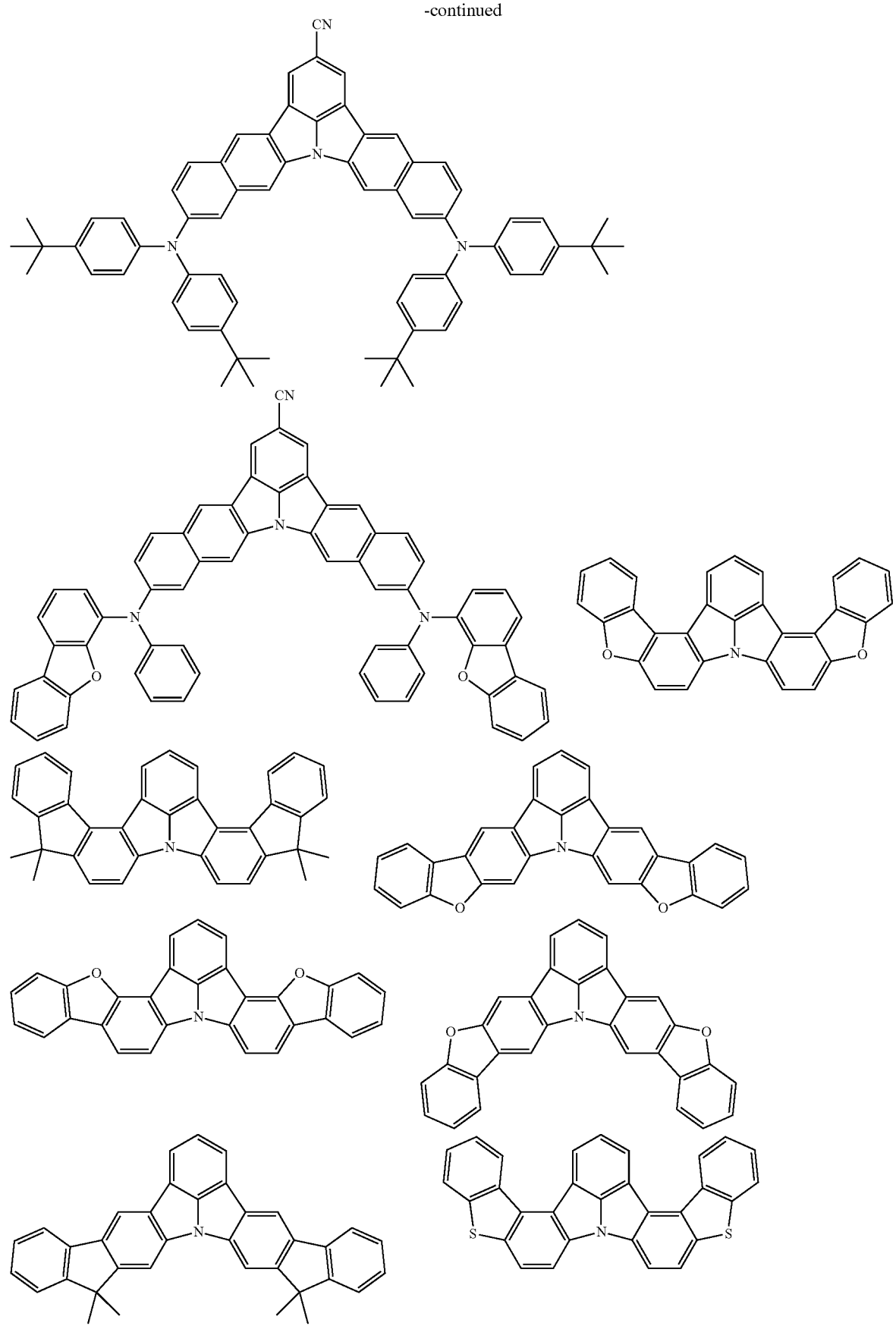

-continued
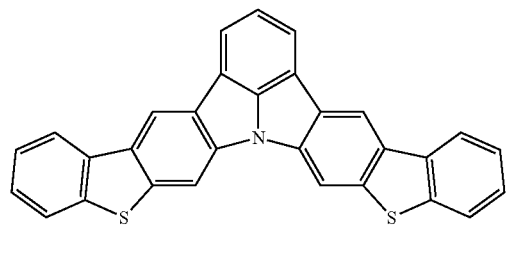
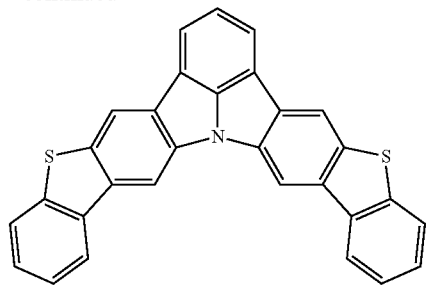
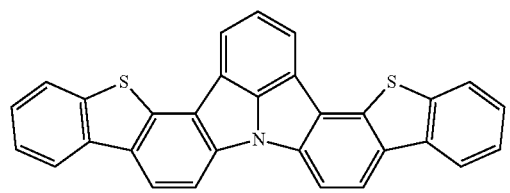
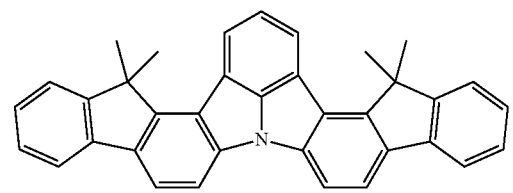
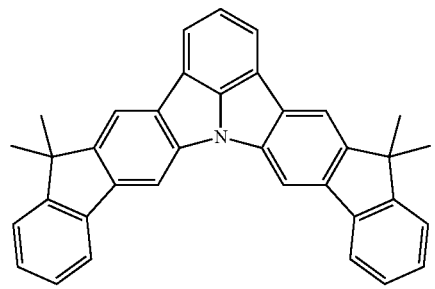
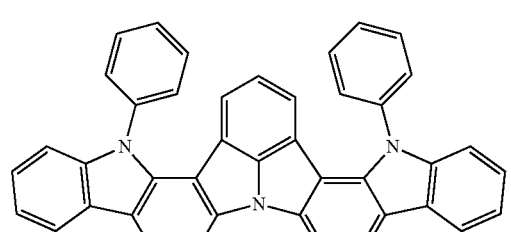
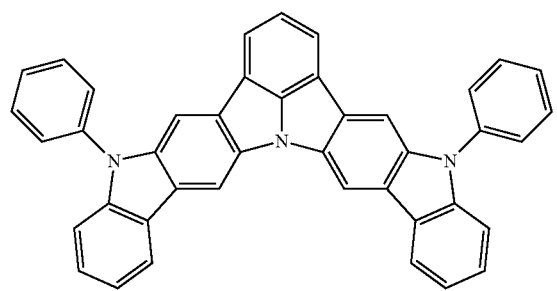
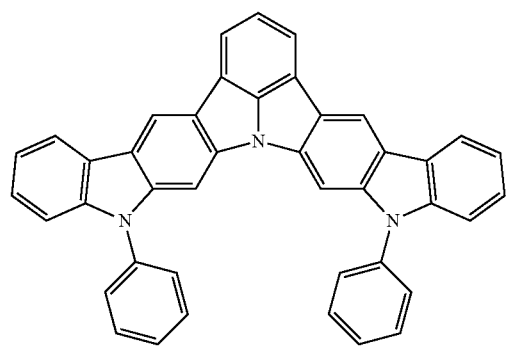
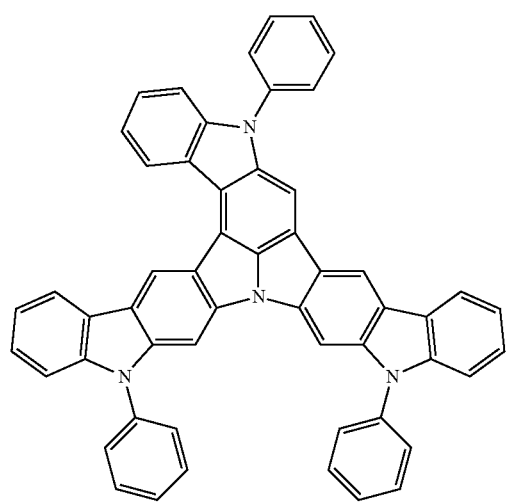
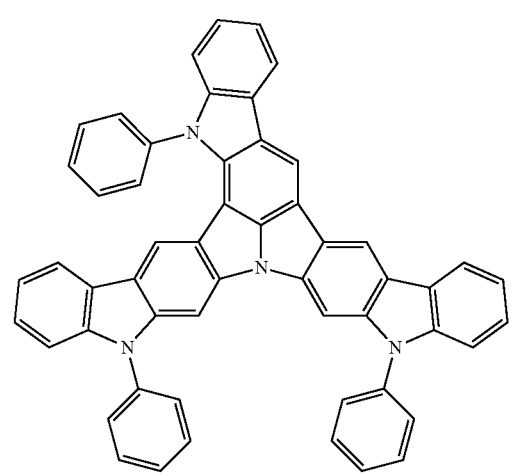

243
244
-continued
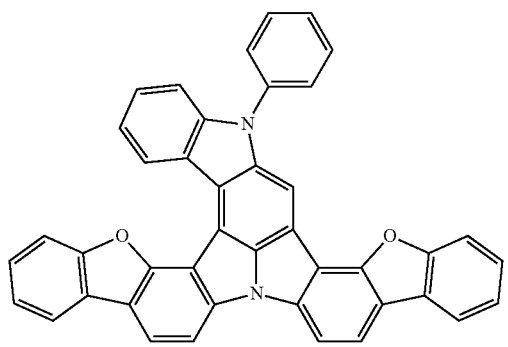
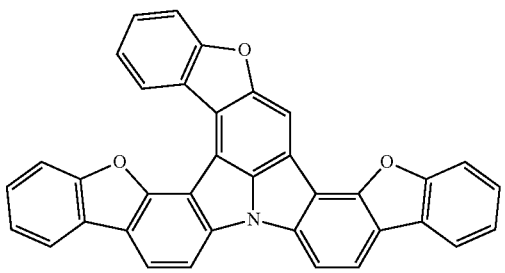
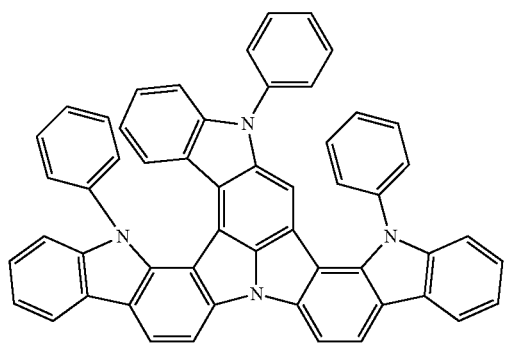
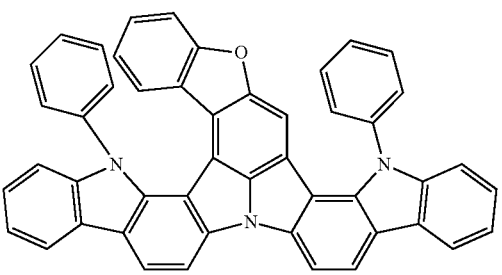
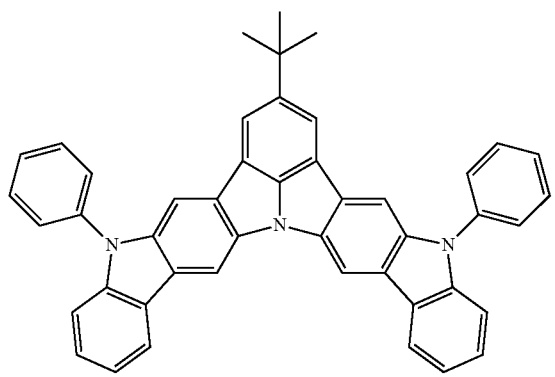
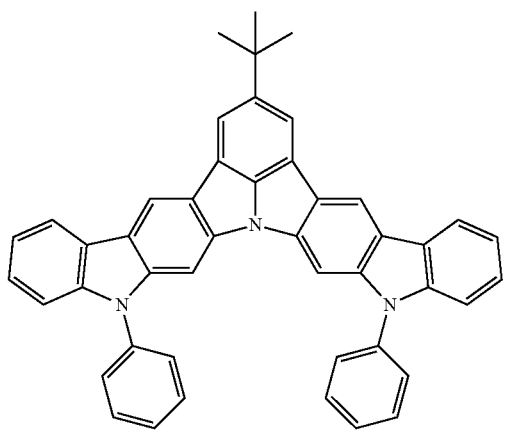
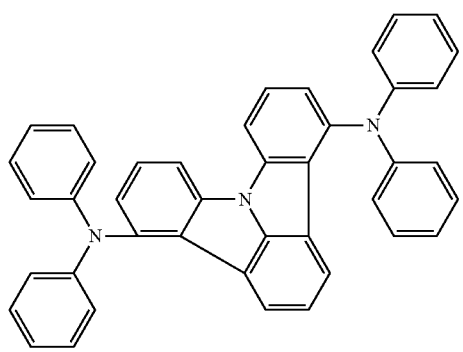
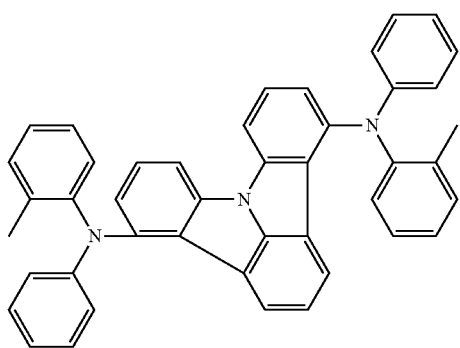

-continued
245
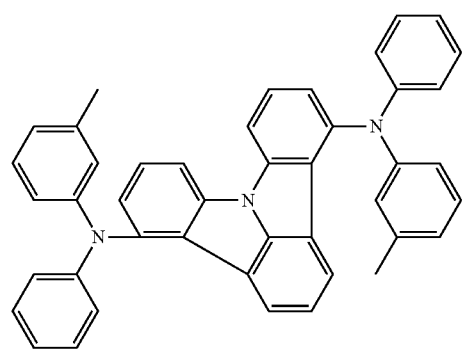
246
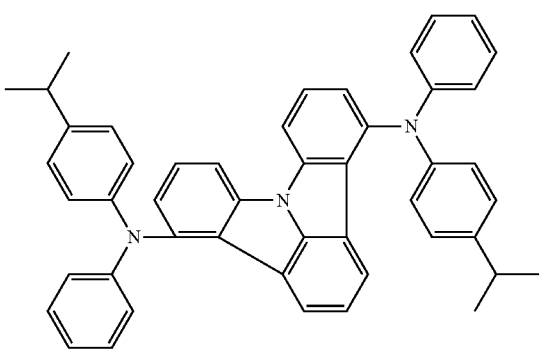
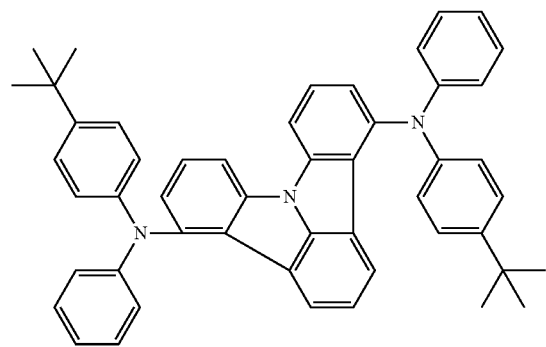
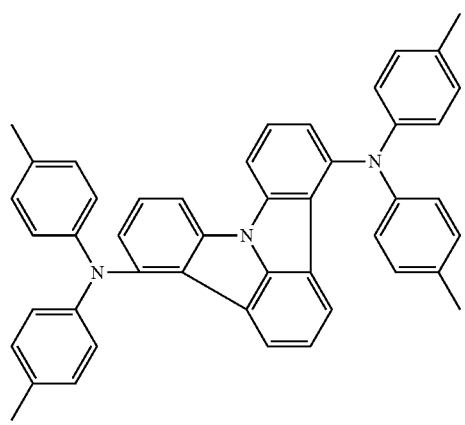
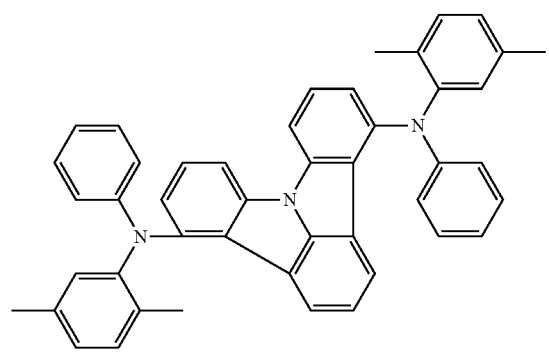
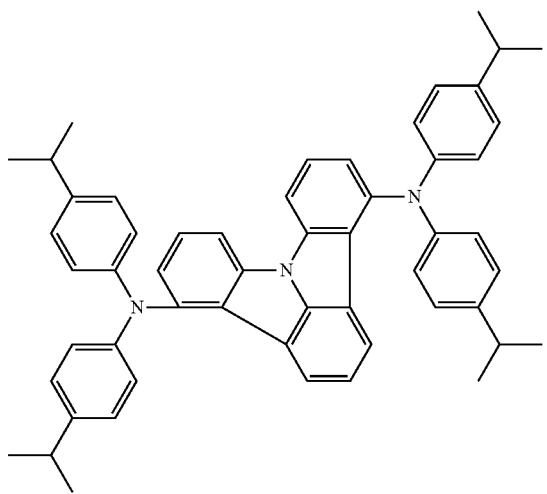

-continued
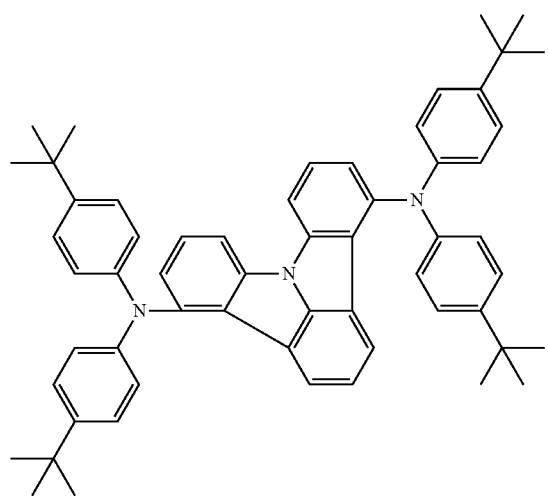
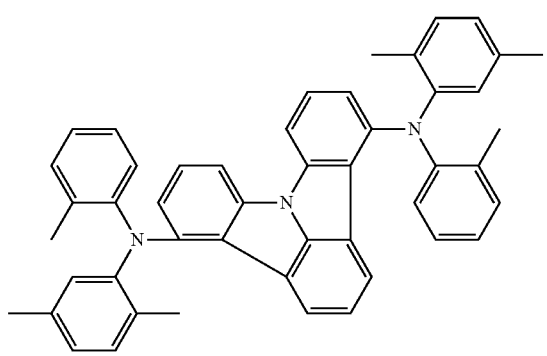
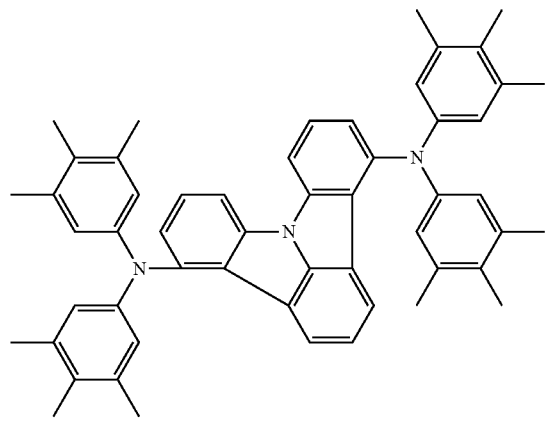
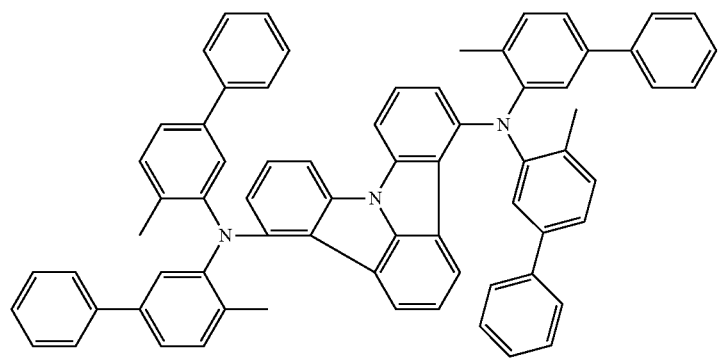
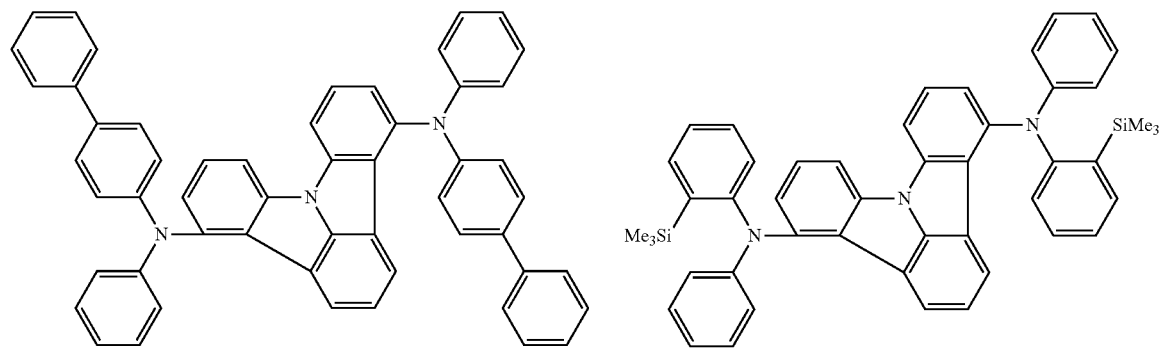

-continued
| 249 | 250 |
|---|---|
| 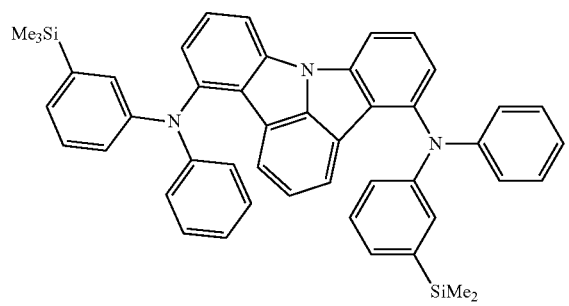 | 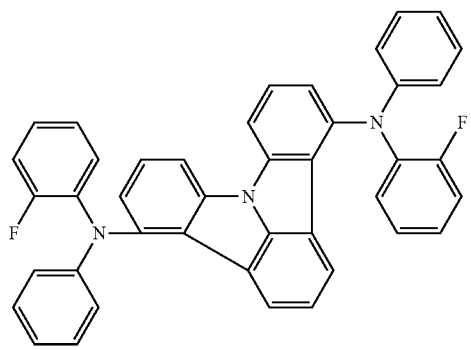 |
| 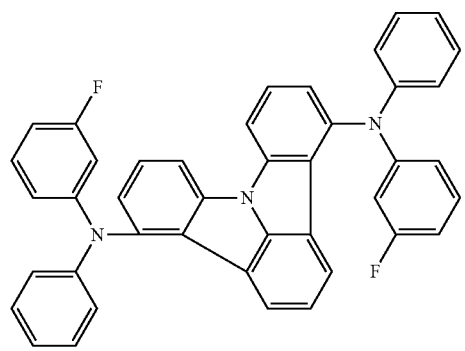 | 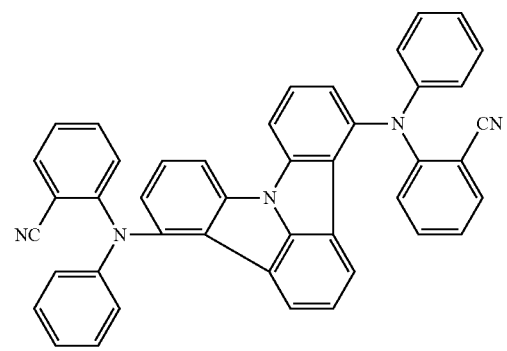 |
| 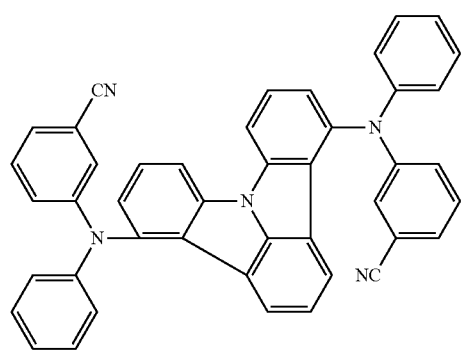 | 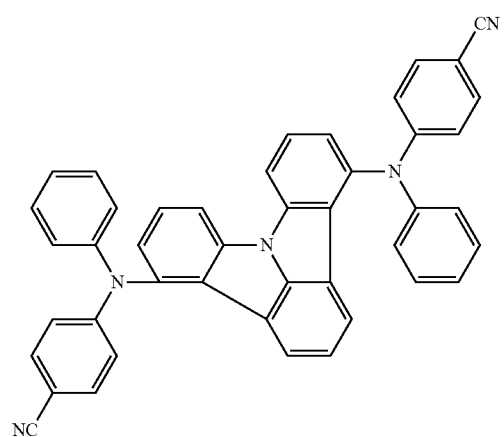 |
| 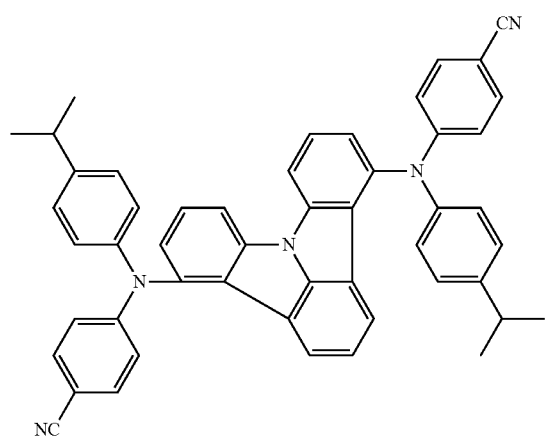 | 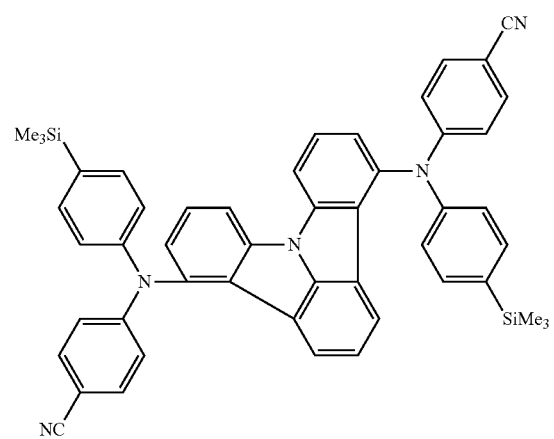 |

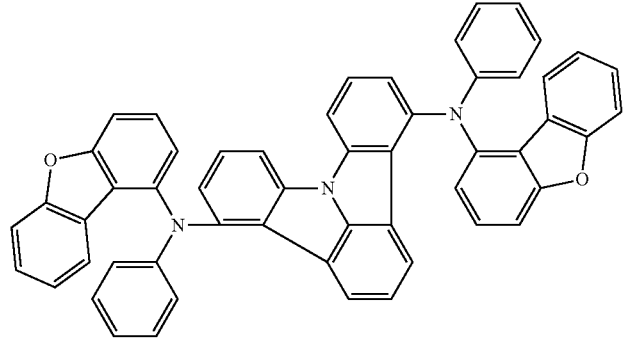
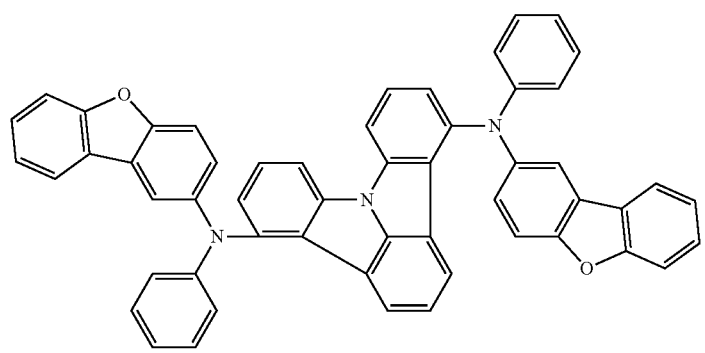
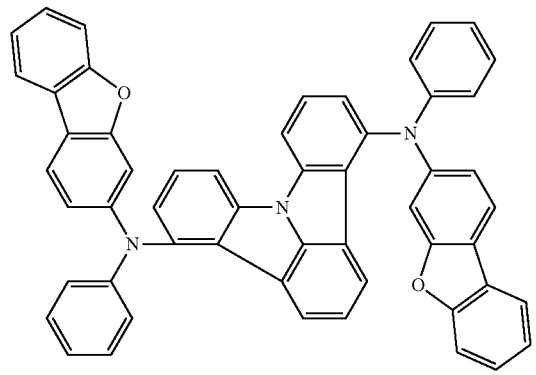
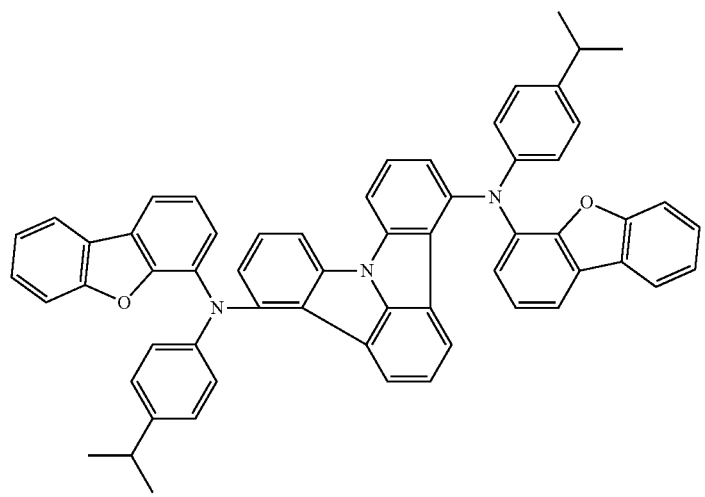

253 254
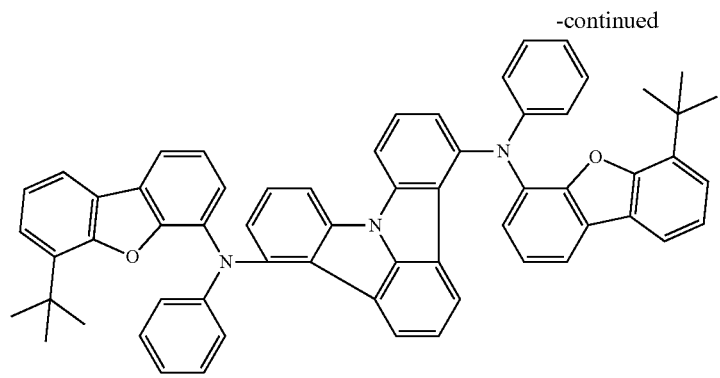
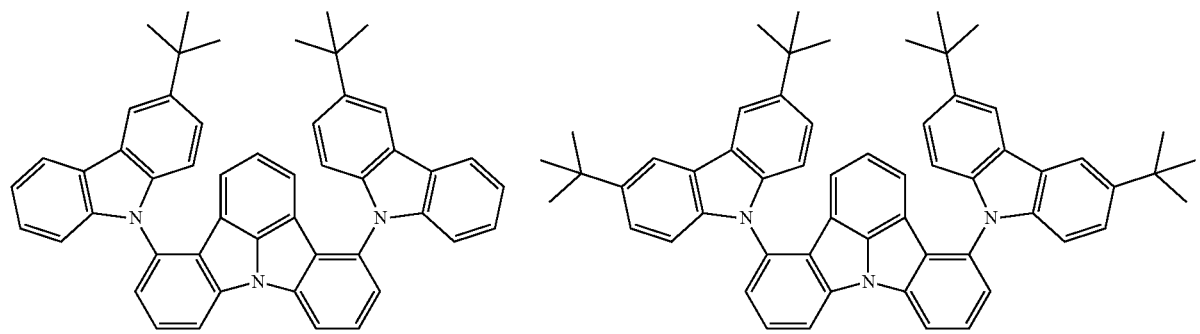
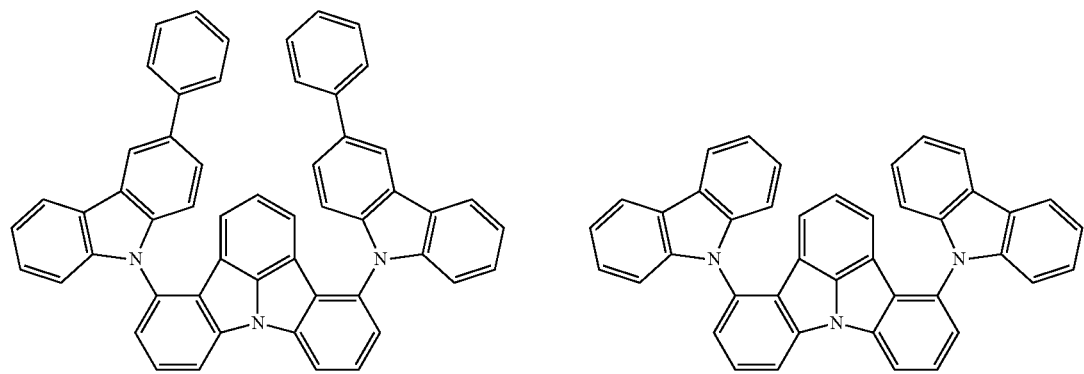
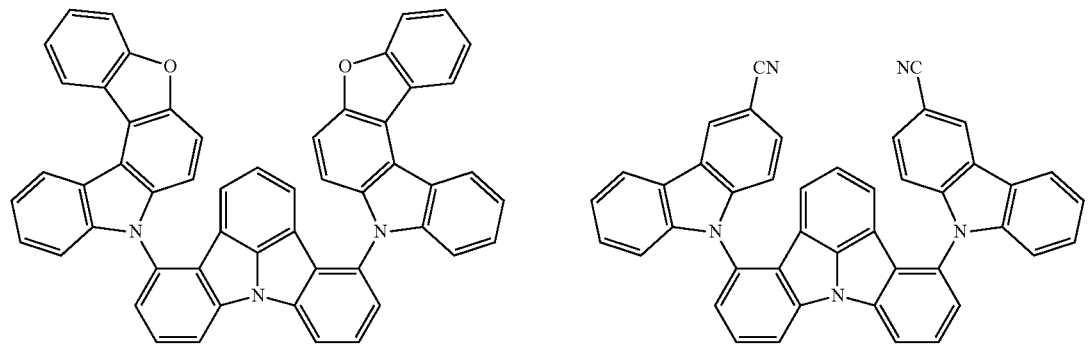

255 256
-continued
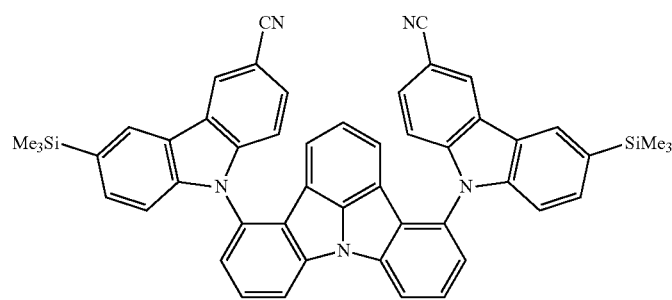 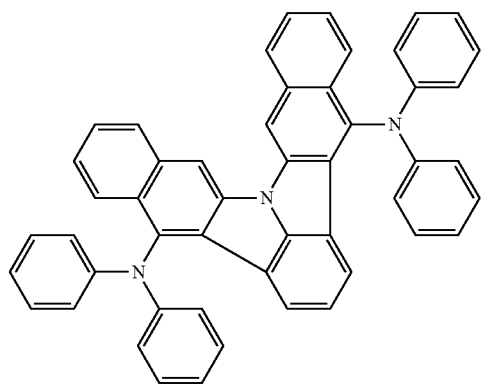
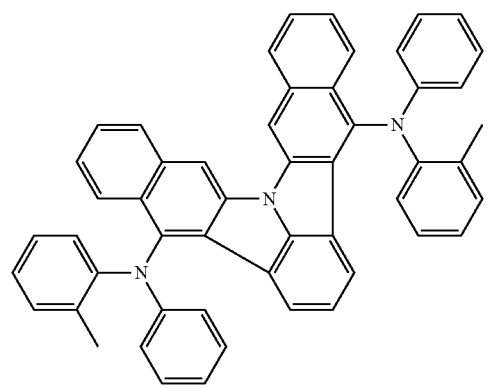 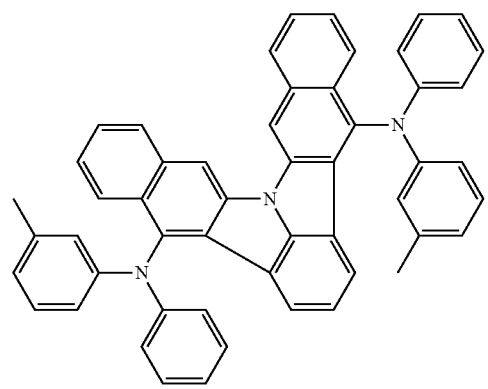
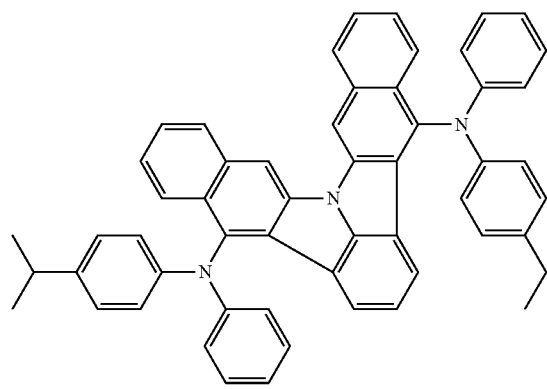 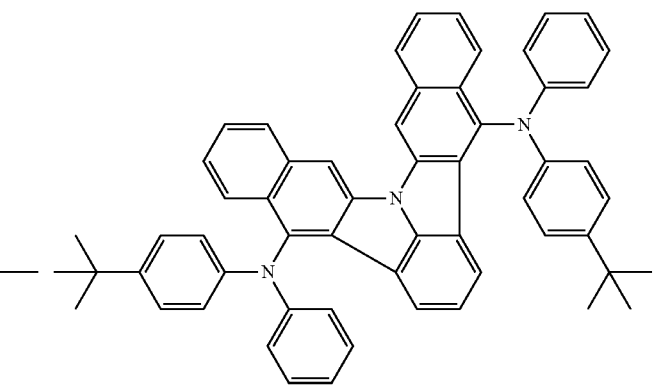
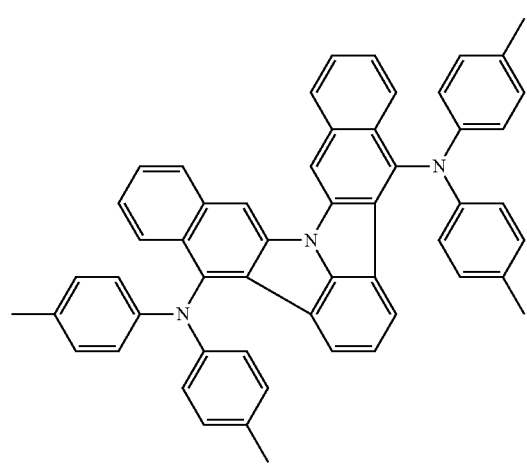 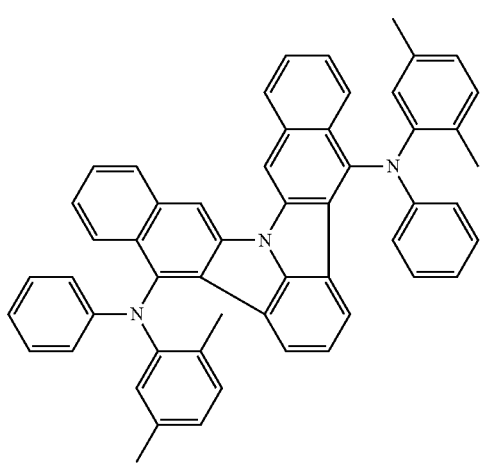

-continued
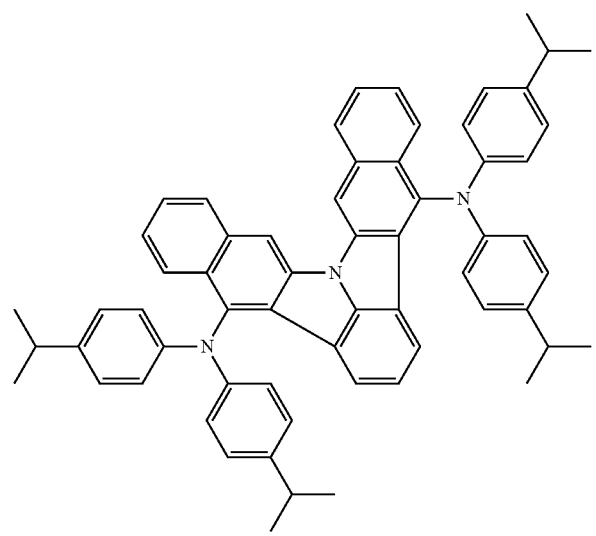
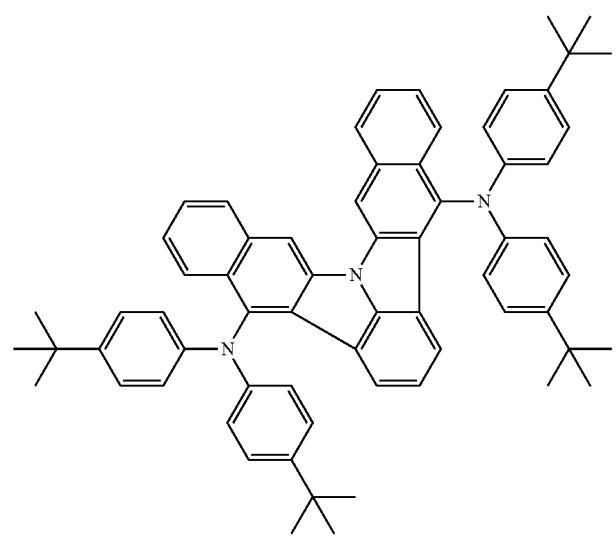
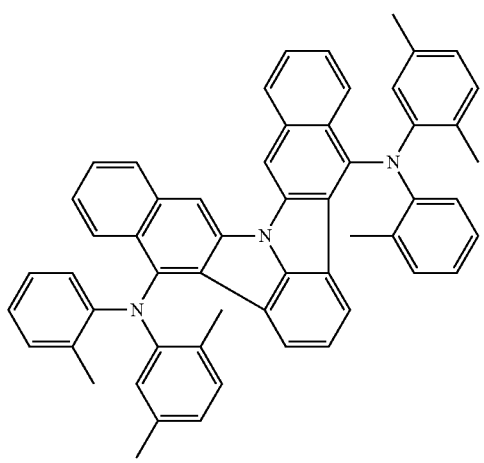
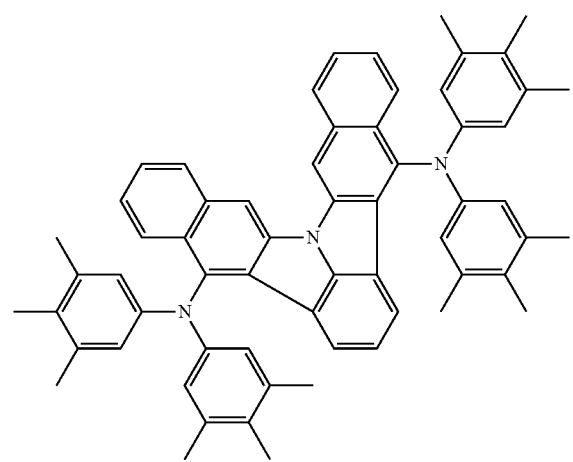

-continued
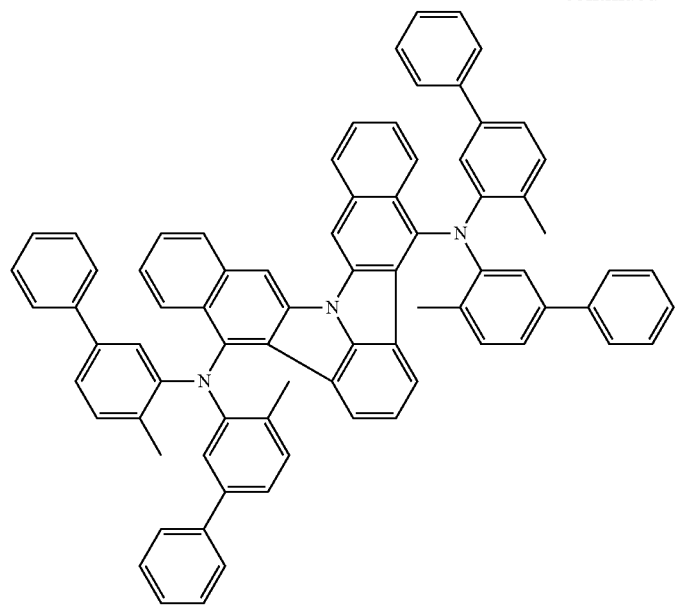
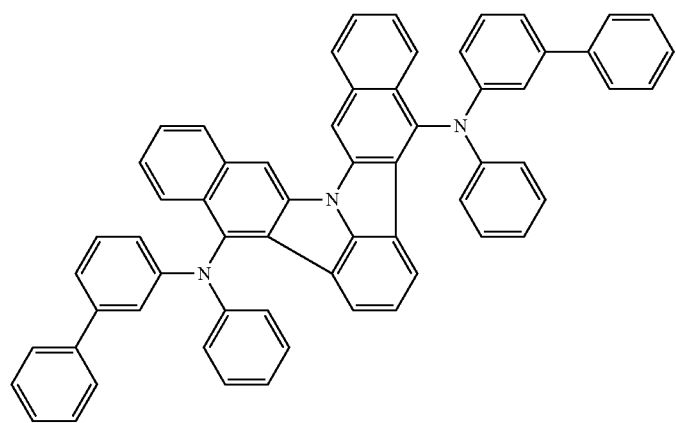
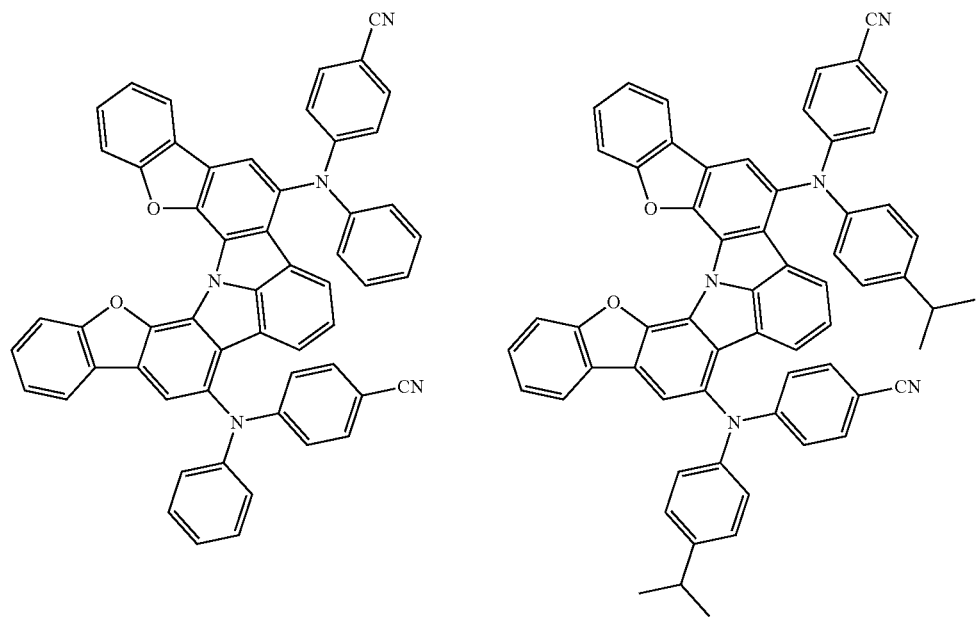

261
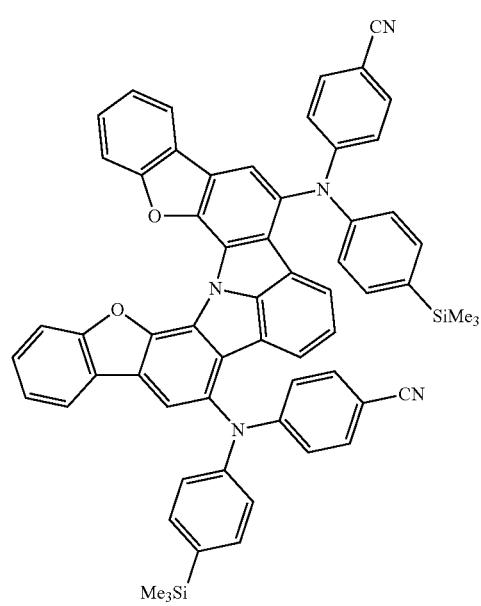
262
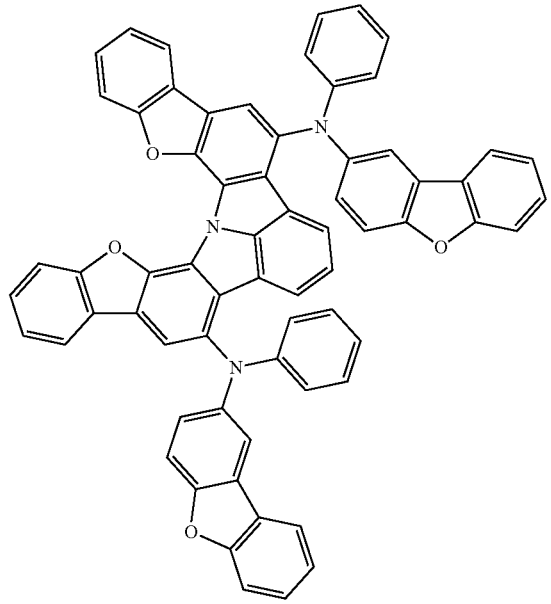
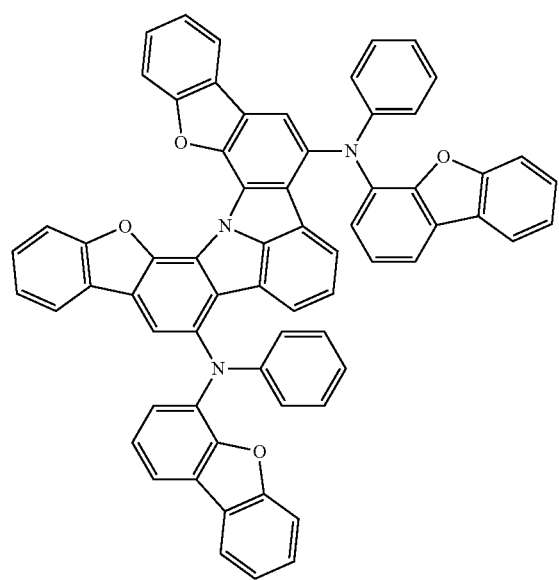
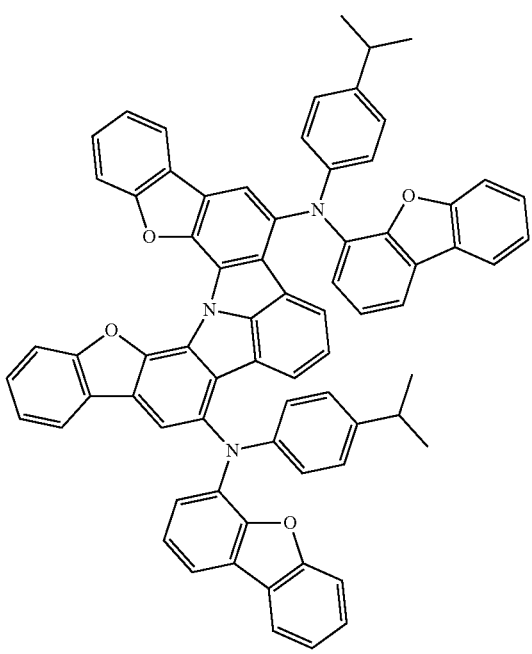

-continued
263
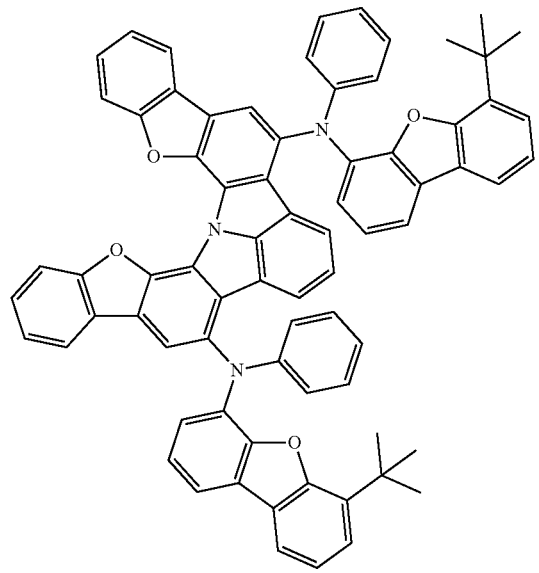
264
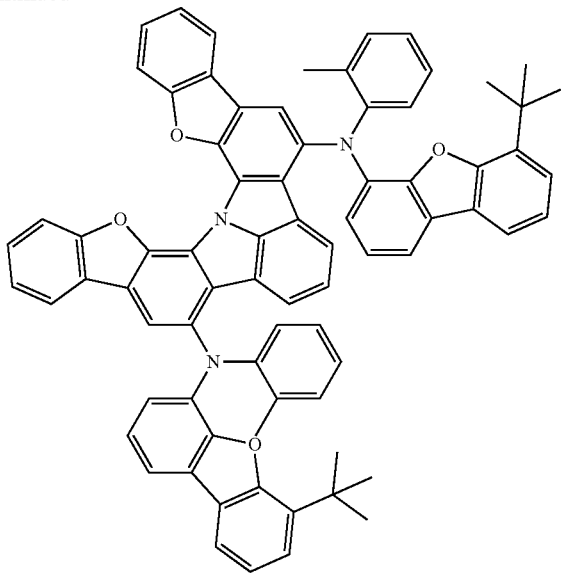
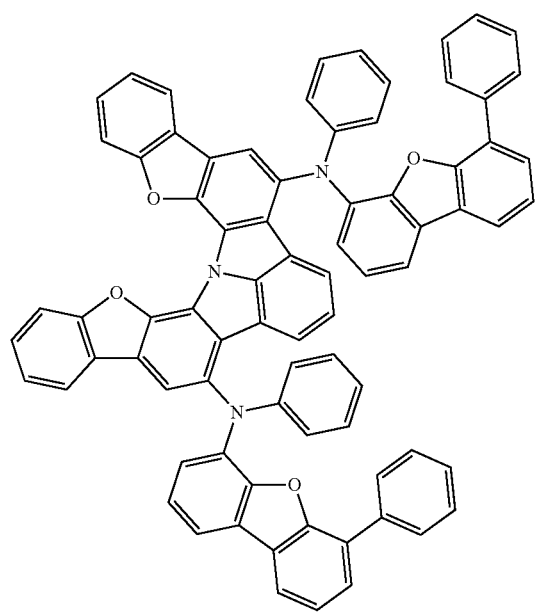
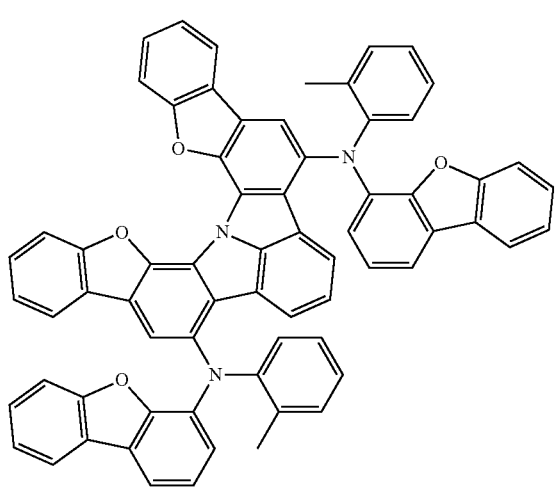
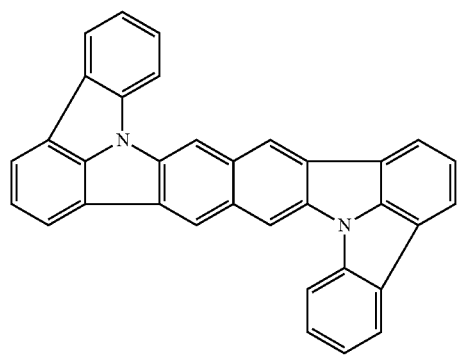
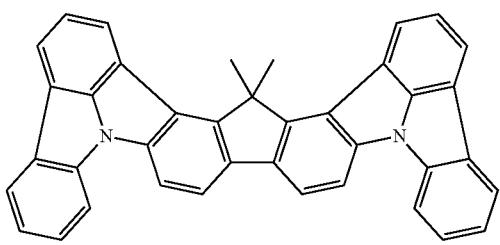

-continued
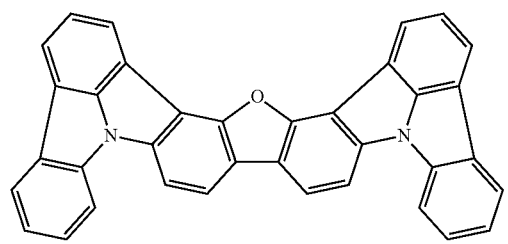 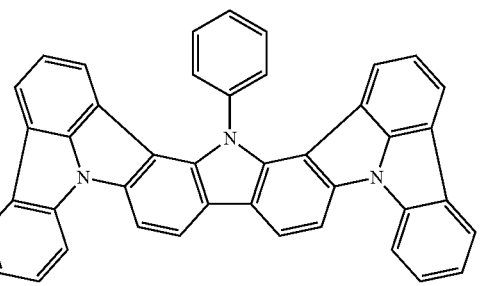
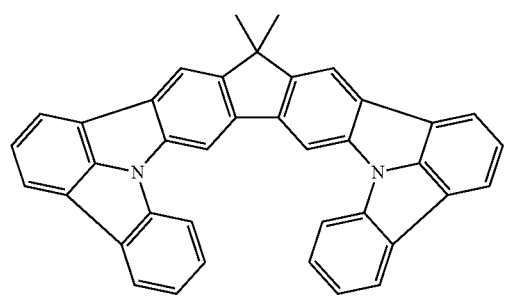 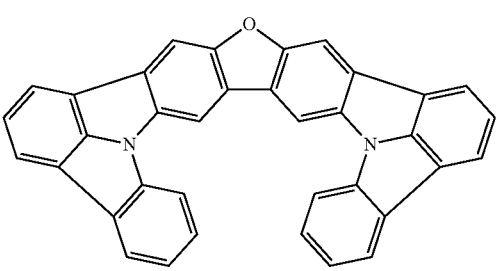
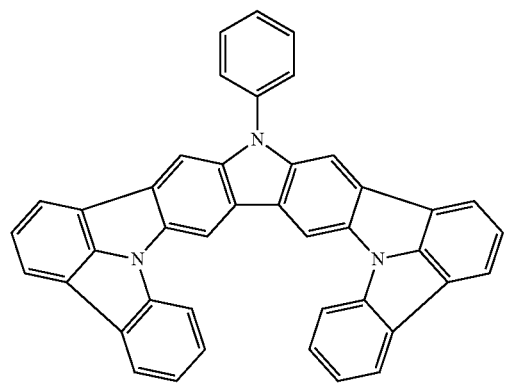 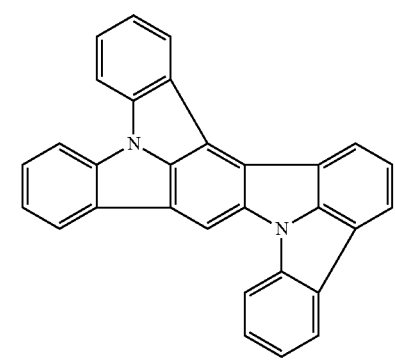
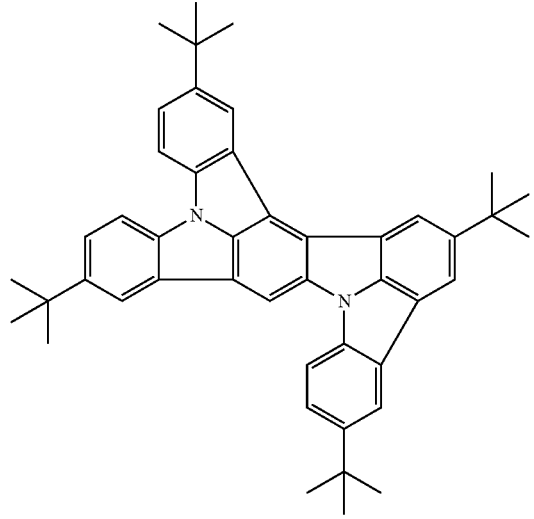 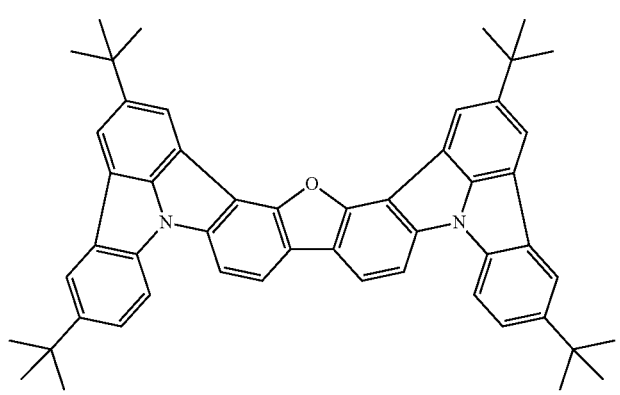

(Compound Represented by Formula (31))

The compound represented by the formula (31) is explained below.

The compound represented by formula (31) is a compound corresponding to the compound represented by the formula (21-3).

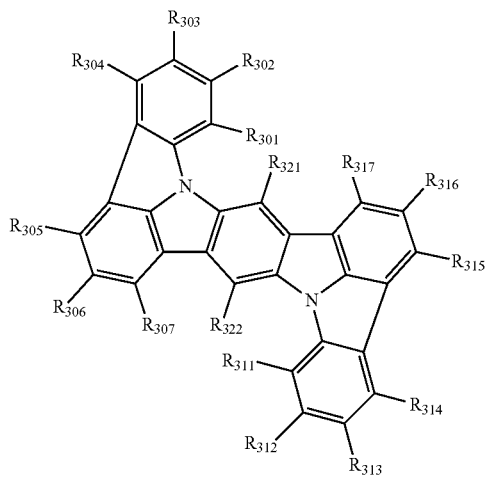

(31)

wherein in the formula (31),
one or more pairs of two or more adjacent groups of $R_{301}$ to $R_{307}$ and $R_{311}$ to $R_{317}$ form a substituted or unsubstituted, saturated or unsaturated ring, or do not form a substituted or unsubstituted, saturated or unsaturated ring;

$R_{301}$ to $R_{307}$ and $R_{311}$ to $R_{317}$ that do not form the substituted or unsubstituted, saturated or unsaturated ring are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;

$R_{321}$ and $R_{322}$ are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms; and $R_{901}$ to $R_{907}$ are as defined in the formula (1).

Example of "One pair of two or more adjacent groups of $R_{301}$ to $R_{307}$ and $R_{311}$ to $R_{317}$" is pairs of $R_{301}$ and $R_{302}$, $R_{302}$ and $R_{303}$, $R_{303}$ and $R_{304}$, $R_{305}$ and $R_{306}$, $R_{306}$ and $R_{307}$, and $R_{301}$, $R_{302}$ and $R_{303}$, and the like.

In one embodiment, at least one of $R_{301}$ to $R_{307}$ and $R_{311}$ to $R_{317}$, preferably two of $R_{301}$ to $R_{307}$ and $R_{311}$ to $R_{317}$ is a group represented by —N($R_{906}$)($R_{907}$).

In one embodiment, $R_{301}$ to $R_{307}$ and $R_{311}$ to $R_{317}$ are independently a hydrogen atom, a substituted or unsubstituted aryl group having 6 to 50 ring carbon atoms, or a substituted or unsubstituted monovalent heterocyclic group having 5 to 50 ring atoms.

In one embodiment, the compound represented by the formula (31) is a compound represented by the following formula (32).

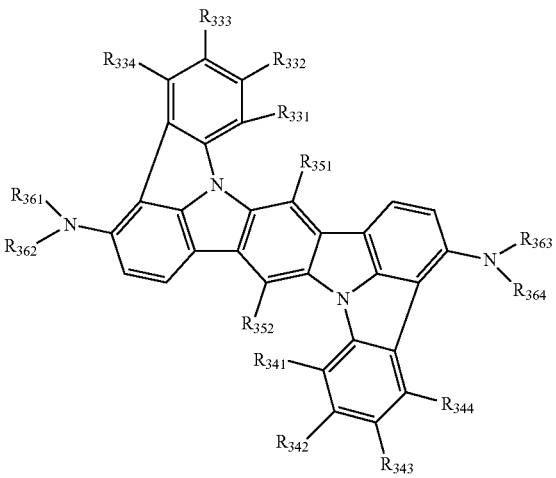

(32)

wherein in the formula (32),
one or more pairs of two or more adjacent groups of $R_{331}$ to $R_{334}$ and $R_{341}$ to $R_{344}$ form a substituted or unsubstituted, saturated or unsaturated ring, or do not form a substituted or unsubstituted saturated or unsaturated ring;

$R_{331}$ to $R_{334}$ and $R_{341}$ to $R_{344}$ that do not form the substituted or unsubstituted, saturated or unsaturated ring and $R_{351}$ and $R_{352}$ are independently
a hydrogen atom,
a substituted or unsubstituted aryl group having 6 to 50 ring carbon atoms, or
a substituted or unsubstituted monovalent heterocyclic group having 5 to 50 ring atoms; and $R_{361}$ to $R_{364}$ are independently
a substituted or unsubstituted aryl group having 6 to 50 ring carbon atoms, or
a substituted or unsubstituted monovalent heterocyclic group having 5 to 50 ring atoms.

In one embodiment, the compound represented by the formula (31) is a compound represented by the formula (33).

(33)

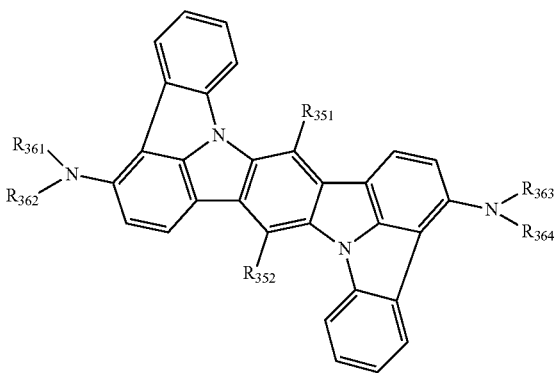

wherein in the formula (33), $R_{351}$, $R_{352}$, and $R_{361}$ to $R_{364}$ are as defined in the formula (32).

In one embodiment, the compound represented by the formula (31) is a compound represented by the formula (34) or (35).

(34)

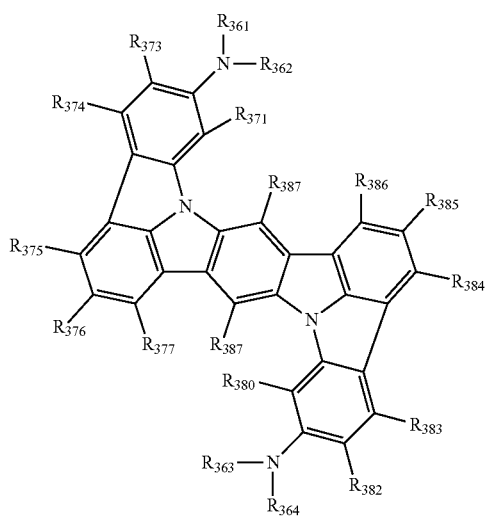

(35)

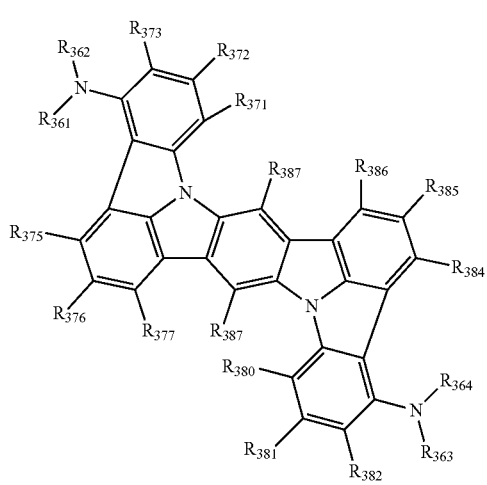

wherein in the formulas (34) and (35), $R_{361}$ to $R_{364}$ are as defined in the formula (32);

one or more pairs of two or more adjacent groups of $R_{371}$ to $R_{377}$ and $R_{380}$ to $R_{386}$ form a substituted or unsubstituted, saturated or unsaturated ring, or do not form a substituted or unsubstituted saturated or unsaturated ring; and $R_{371}$ to $R_{377}$ and $R_{380}$ to $R_{386}$ that do not form the substituted or unsubstituted, saturated or unsaturated ring and $R_{387}$ are independently a hydrogen atom, a substituted or unsubstituted aryl group having 6 to 50 ring carbon atoms, or a substituted or unsubstituted monovalent heterocyclic group having 5 to 50 ring atoms, and two $R_{387}$s may be the same with or different from each other.

In one embodiment, the compound represented by the formula (31) is a compound represented by the formula (34-2) or (35-2).

(34-2)

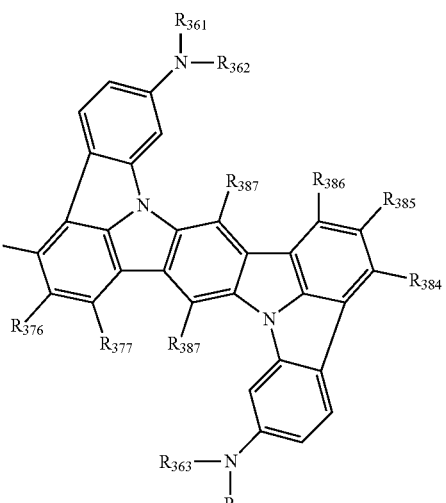

(35-2)

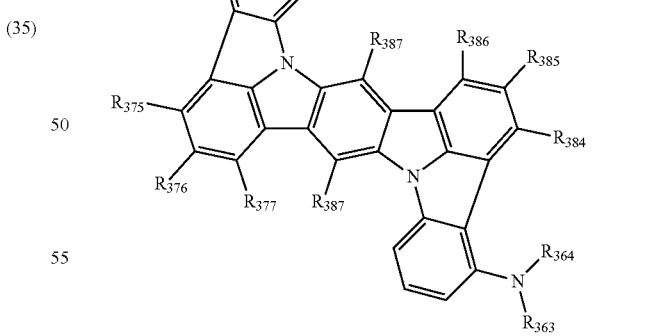

wherein in the formulas (34-2) and (35-2), $R_{361}$ to $R_{364}$, $R_{375}$ to $R_{377}$ and $R_{384}$ to $R_{387}$ are as defined in the formulas (34) and (35).

In one embodiment, $R_{361}$ to $R_{364}$ in the formulas (32), (33), (34), (35), (34-2) and (35-2) are independently a substituted or unsubstituted aryl group having 6 to 50 ring carbon atoms (preferably a substituted or unsubstituted phenyl group).

In one embodiment, $R_{321}$ and R322 in the formula (31) and $R_{351}$, R352 and $R_{387}$ in the formulas (32), (33), (34), (35), (34-2) and (35-2) are independently a hydrogen atom or a substituted or unsubstituted aryl group having 6 to 50 ring carbon atoms (preferably a substituted or unsubstituted phenyl group).

In one embodiment, the compound represented by the formula (31) is one or more compounds selected from the group consisting of the following formulas (32-11), (34-11) and (35-11).

(32-11)

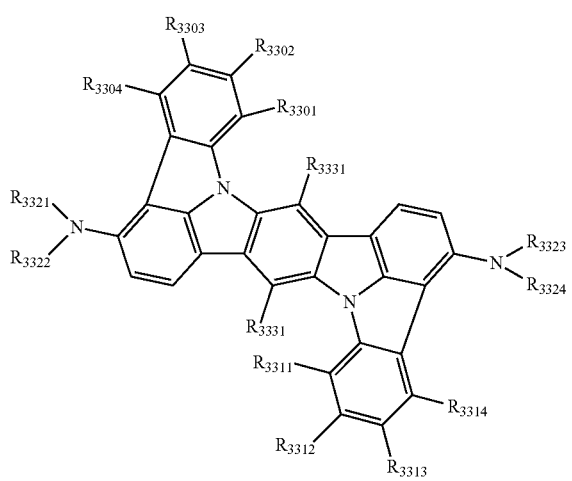

(34-11)

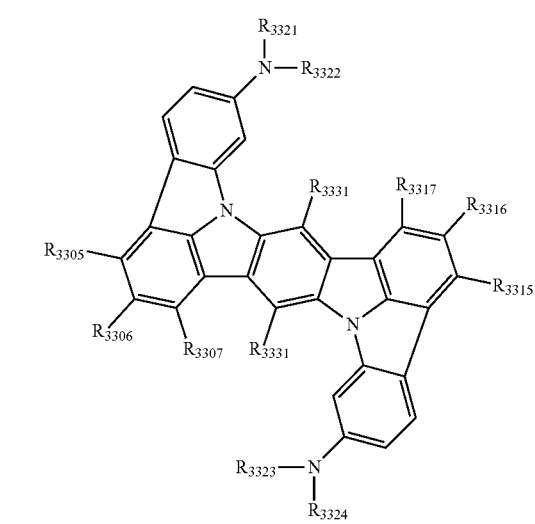

(35-11)

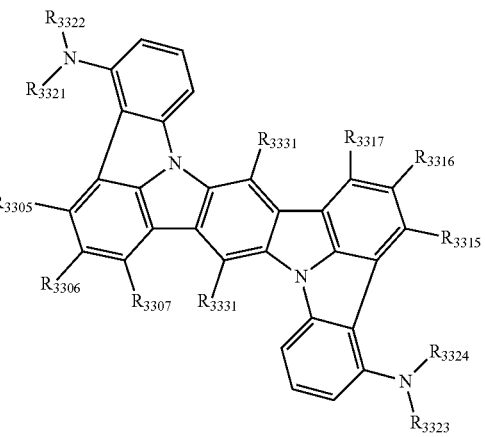

wherein in the formulas (32-11), (34-11) and (35-11), one or more pairs of two or more adjacent groups of $R_{3301}$ to $R_{3307}$ and $R_{3311}$ to $R_{3317}$ form a substituted or unsubstituted, saturated or unsaturated ring, or do not form a substituted or unsubstituted, saturated or unsaturated ring;

$R_{3301}$ to $R_{3307}$ and $R_{3311}$ to $R_{3317}$ that do not form the substituted or unsubstituted, saturated or unsaturated ring, and $R_{3331}$ are independently a hydrogen atom, a substituted or unsubstituted aryl group having 6 to 20 ring carbon atoms, or a substituted or unsubstituted monovalent heterocyclic group having 5 to 20 ring atoms;

two $R_{3331}$s may be the same with or different from each other; and $R_{3321}$ to $R_{3324}$ are independently a substituted or unsubstituted aryl group having 6 to 20 ring carbon atoms, or a substituted or unsubstituted monovalent heterocyclic group having 5 to 20 ring atoms.

In one embodiment, the one or more compounds selected from the group consisting of the formulas (32-11), (34-11) and (35-11) is one or more compounds selected from a group consisting of the following formulas (32-12), (34-12) and (35-12).

(32-12)

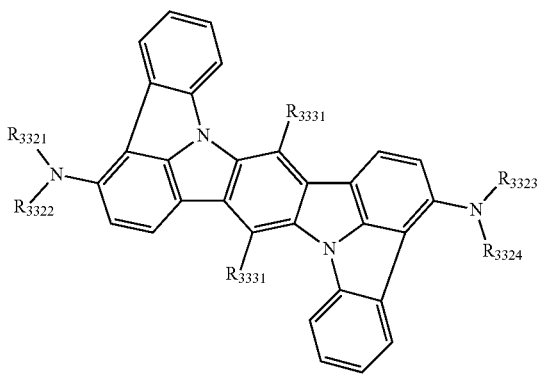

(34-12)

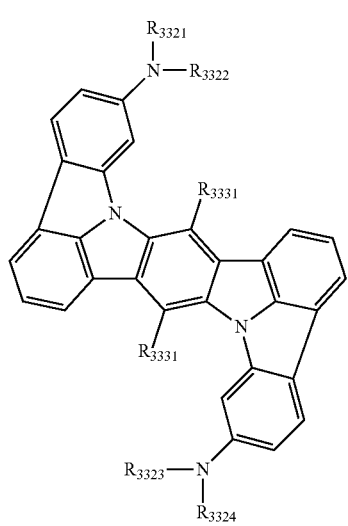

(35-12)

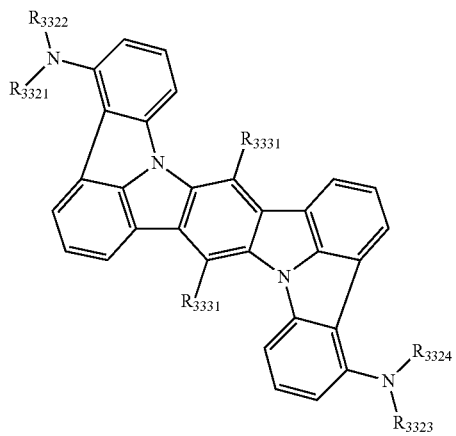

wherein in the formulas (32-12), (34-12) and (35-12), $R_{3321}$ to $R_{3324}$ and $R_{3331}$ are as defined in the formulas (32-11), (34-11) and (35-11).

in one embodiment, in the formulas (32-11), (34-11), (35-11), (32-12), (34-12) and (35-12), $R_{3321}$ to $R_{3324}$ are independently a substituted or unsubstituted phenyl group.

In one embodiment, in the formulas (32-11), (34-11), (35-11), (32-12), (34-12) and (35-12), two $R_{3331}$s are independently a hydrogen atom.

In one embodiment, in the formulas (32-11), (34-11), (35-11), (32-12), (34-12) and (35-12), the substituent in the case of "substituted or unsubstituted" is selected from the group consisting of an alkyl group having 1 to 20 carbon atoms, an aryl group having 6 to 20 ring carbon atoms, and a monovalent heterocyclic group having 5 to 20 ring atoms.

In one embodiment, in the formulas (32-11), (34-11), (35-11), (32-12), (34-12) and (35-12), the substituent in the case of "substituted or unsubstituted" is an alkyl group having 1 to 5 carbon atoms.

In one embodiment, in the formulas (32-11), (34-11), (35-11), (32-12), (34-12) and (35-12), $R_{3321}$ to $R_{3324}$ are independently a substituted or unsubstituted phenyl group, and two $R_{3331}$s are independently a hydrogen atom.

In one embodiment, in the formulas (32-11), (34-11), (35-11), (32-12), (34-12) and (35-12), $R_{3321}$ to $R_{3324}$ are independently a substituted or unsubstituted phenyl group, two $R_{3331}$s are independently a hydrogen atom, and the substituent in the case of "substituted or unsubstituted" is selected from the group consisting of an alkyl group having 1 to 20 carbon atoms, an aryl group having 6 to 20 ring carbon atoms, and a monovalent heterocyclic group having 5 to 20 ring atoms.

In one embodiment, in the formulas (32-11), (34-11), (35-11), (32-12), (34-12) and (35-12), $R_{3321}$ to $R_{3324}$ are independently a substituted or unsubstituted phenyl group, two $R_{3331}$s are independently a hydrogen atom, and the substituent in the case of "substituted or unsubstituted" is an alkyl group having 1 to 5 carbon atoms.

In one embodiment, in the compound represented by the formula (31), one or more pairs of two or more adjacent groups of $R_{301}$ to $R_{307}$ and $R_{311}$ to $R_{317}$ form a substituted or unsubstituted, saturated or unsaturated ring.

In one embodiment, the compound represented by the formula (31) is one or more compounds selected from the group consisting of the following formulas (36-1) to (36-6).

(36-1)

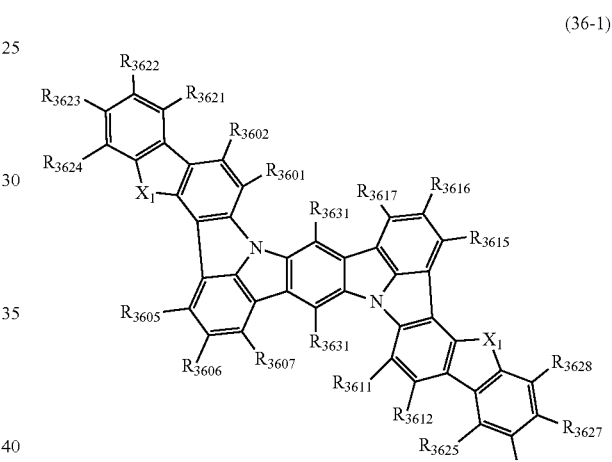

(36-2)

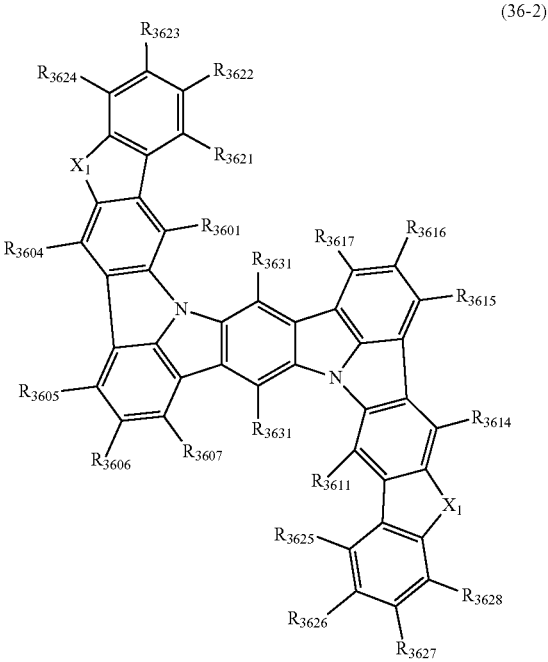

-continued (36-3)

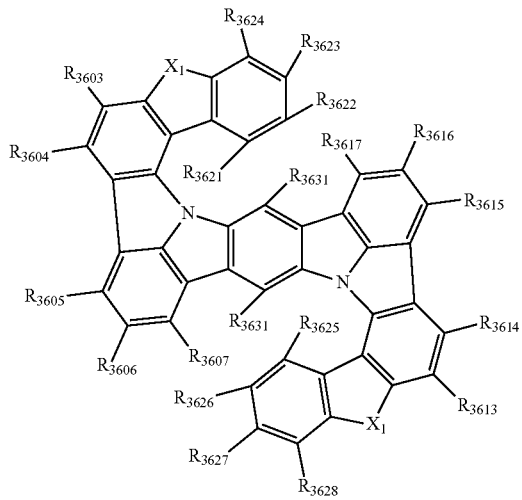

(36-4)

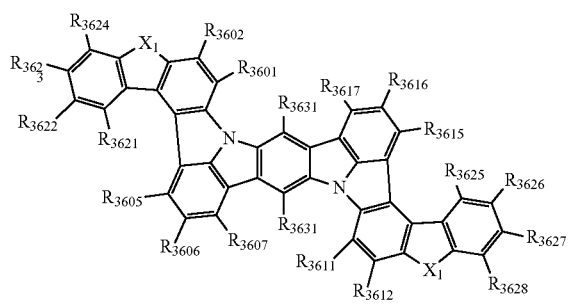

(36-5)

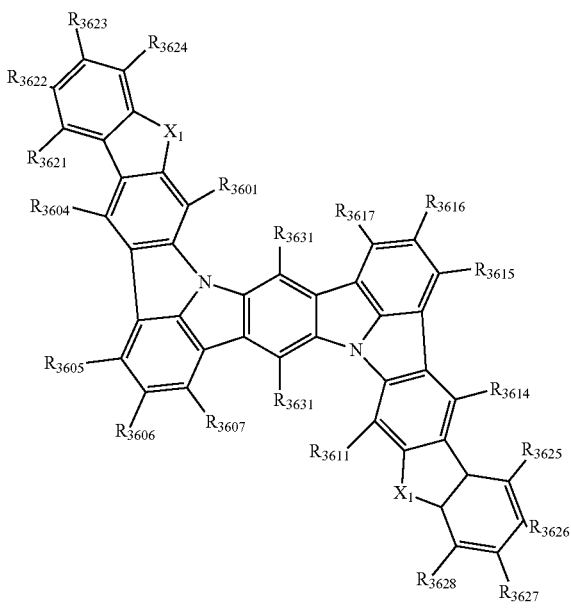

-continued (36-6)

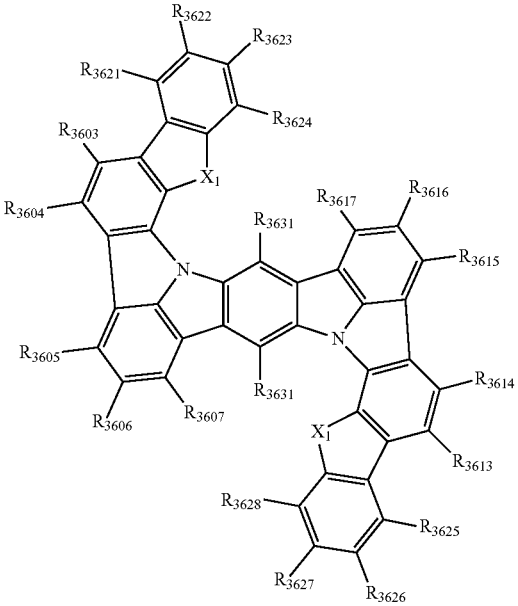

wherein in the formulas (36-1) to (36-6),
one or more pairs of two or more adjacent groups of $R_{3605}$ to $R_{3607}$, $R_{3615}$ to $R_{3617}$ and $R_{3631}$ bond with each other to form a substituted or unsubstituted, saturated or unsaturated ring or do not form the ring;
one or more pairs of two or more adjacent groups of $R_{3601}$ to $R_{3604}$, $R_{3611}$ to $R_{3614}$ and $R_{3621}$ to $R_{3628}$ bond with each other to form a substituted or unsubstituted, saturated or unsaturated ring or do not form the ring;
$R_{3601}$ to $R_{3607}$, $R_{3611}$ to $R_{3617}$, $R_{3621}$ to $R_{3629}$ and $R_{3631}$ that do not form the ring are independently
a hydrogen atom, a halogen atom, a cyano group, a nitro group,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a substituted or unsubstituted aryl group having 6 to 50 ring carbon atoms, or
a substituted or unsubstituted monovalent heterocyclic group having 5 to 50 ring atoms;
$R_{901}$ to $R_{907}$ are independently
a hydrogen atom,
a substituted or unsubstituted alkyl group having 1 to 50 carbon atoms,
a substituted or unsubstituted cycloalkyl group having 3 to 50 ring carbon atoms,
a substituted or unsubstituted aryl group having 6 to 50 ring carbon atoms, or
a substituted or unsubstituted monovalent heterocyclic group having 5 to 50 ring atoms;

when two or more of $R_{901}$ to $R_{907}$ exist, two or more of $R_{901}$ to $R_{907}$ may be the same with or different from each other;

$X_1$ is selected from O, S and $N(R_{3641})$, and two $X_1$s may be the same with or different from each other;

$R_{3641}$ and one or more groups selected from $R_{3601}$ to $R_{3604}$, $R_{3611}$ to $R_{3614}$, $R_{3624}$ and $R_{3628}$ bond with each other to form a substituted or unsubstituted, saturated or unsaturated ring or do not form the ring; and $R_{3641}$ that do not form the ring is a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted monovalent heterocyclic group having 5 to 50 ring atoms.

In one embodiment, the compound represented by the formula (31) is a compound represented by the formula (36-1) or (36-2), In one embodiment, the compound represented by the formula (31) is a compound represented by the formula (36-1).

In one embodiment, in the compound represented by the formulas (36-1) to (36-6), two $R_{3631}$s are phenyl groups.

In one embodiment, in the compound represented by the formulas (36-1) to (36-6), $X_1$ is $N(R_{3641})$.

In one embodiment, in the compound represented by the formulas (36-1) to (36-6), $R_{3641}$ is a substituted or unsubstituted aryl group having 6 to 50 ring carbon atoms.

In one embodiment, the compound represented by the formula (31) is a compound represented by the following formula (36-1-1).

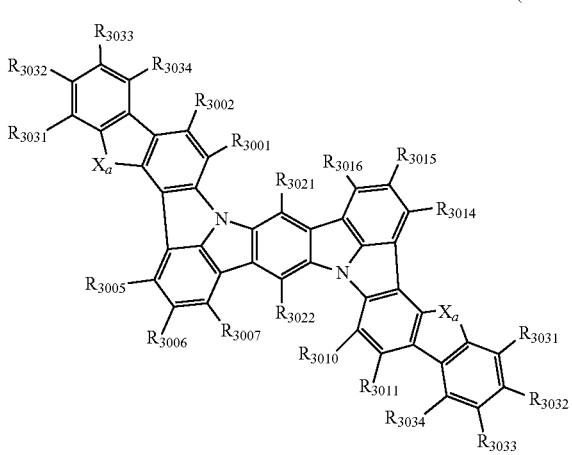

(36-1-1)

wherein in the formula (36-1-1), one or more pairs of two or more adjacent groups of $R_{3001}$, $R_{3002}$, $R_{3005}$ to $R_{3007}$, $R_{3010}$, $R_{3011}$, $R_{3014}$ to $R_{3016}$ and $R_{3031}$ to $R_{3034}$ bond with each other to form a substituted or unsubstituted, saturated or unsaturated ring or do not form the ring;

$X_a$s are independently selected from O, S and $N(R_{3035})$;

$R_{3035}$ and $R_{3031}$ bond with each other to form a substituted or unsubstituted, saturated or unsaturated ring or do not form the ring; and $R_{3001}$, $R_{3002}$, $R_{3005}$ to $R_{3007}$, $R_{3010}$, $R_{3011}$, $R_{3014}$ to $R_{3016}$ and $R_{3031}$ to $R_{3035}$ that do not form the ring and $R_{3021}$ and $R_{3022}$ are independently a hydrogen atom, a substituted or unsubstituted aryl group having 6 to 50 ring carbon atoms, or a substituted or unsubstituted monovalent heterocyclic group having 5 to 50 ring atoms.

In one embodiment, a substituent in the case of "substituted or unsubstituted" in the formulas (31) to (35), (34-2), (35-2), (32-11), (34-11), (35-11), (32-12), (34-12), (35-12), (36-1) to (36-6) and (36-1-1) is a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted monovalent heterocyclic group having 5 to 50 ring atoms.

As the compound represented by the formula (31), the following compounds can be given for example. In the following example compounds, Me represents methyl group.

279 280
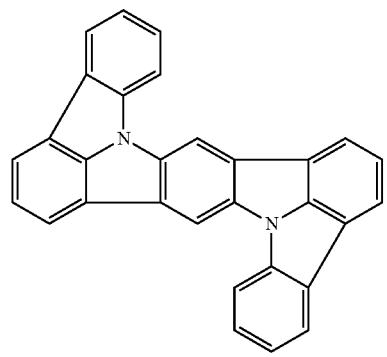
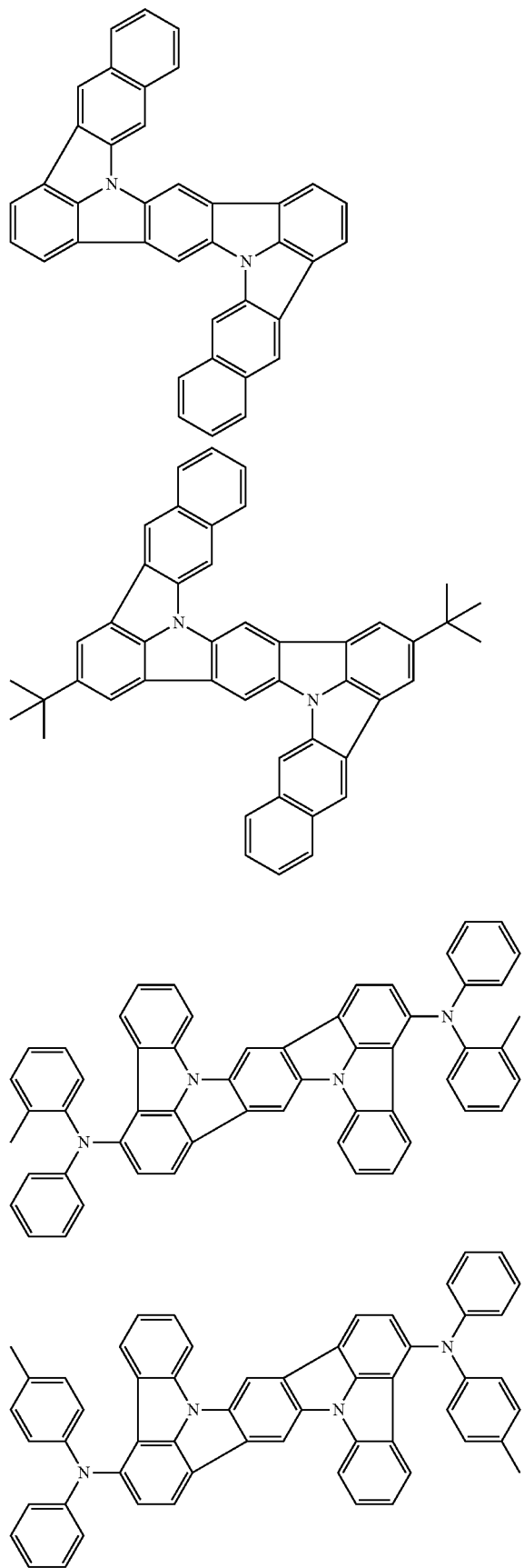

281 282
-continued
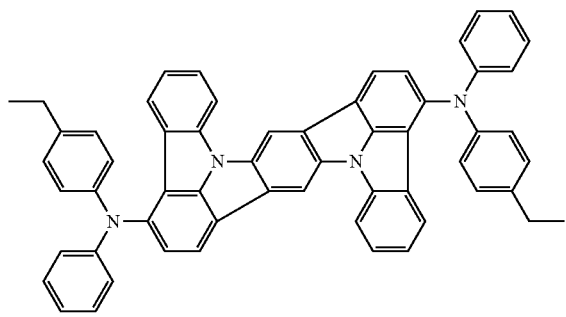
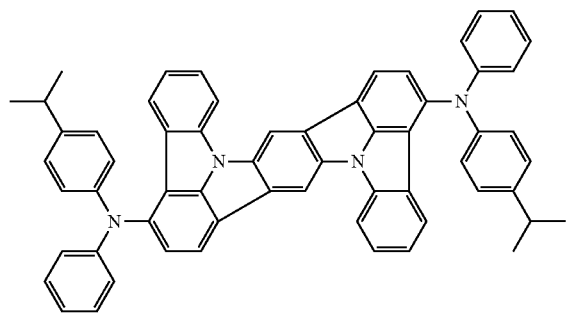
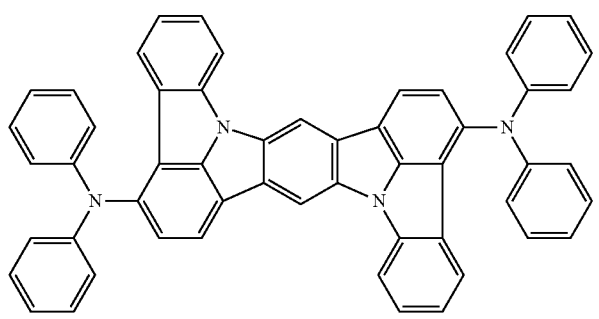
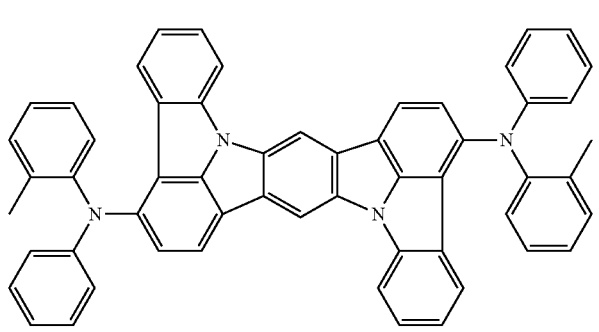
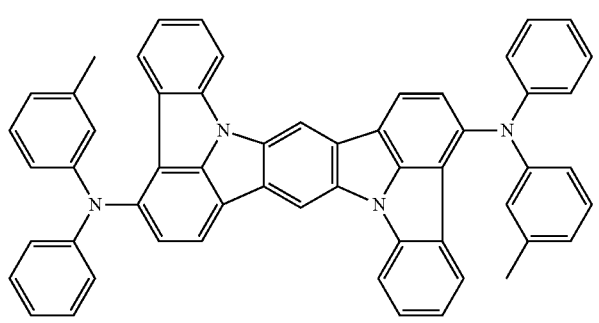
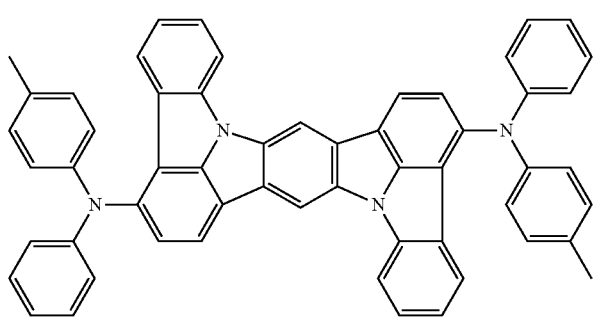
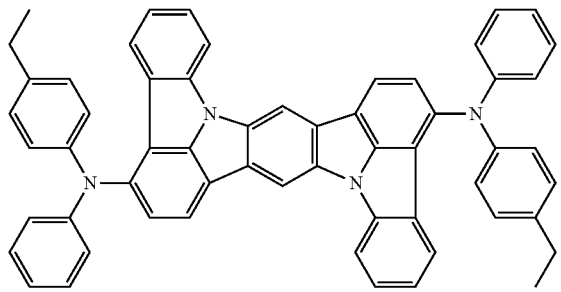
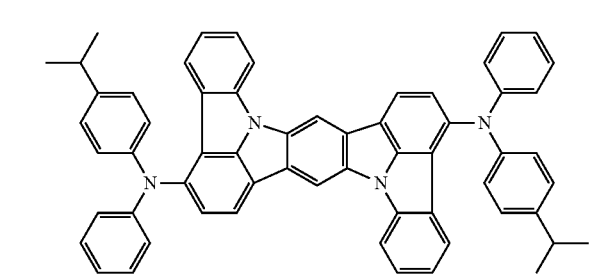
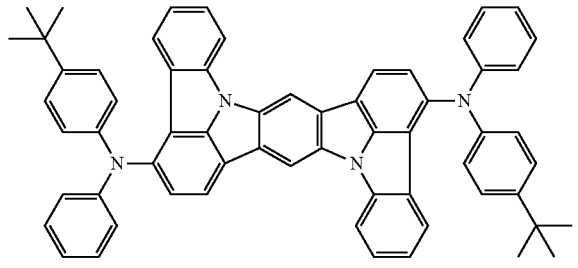
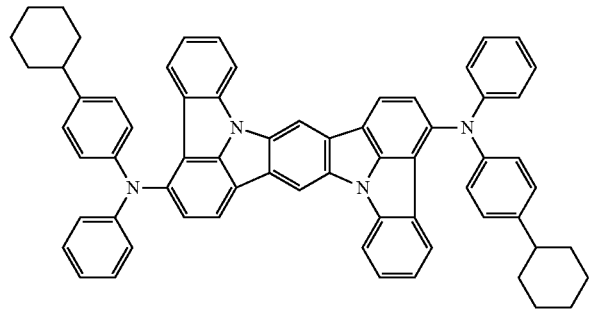

-continued
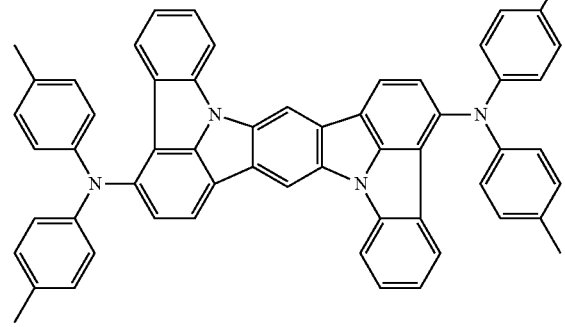
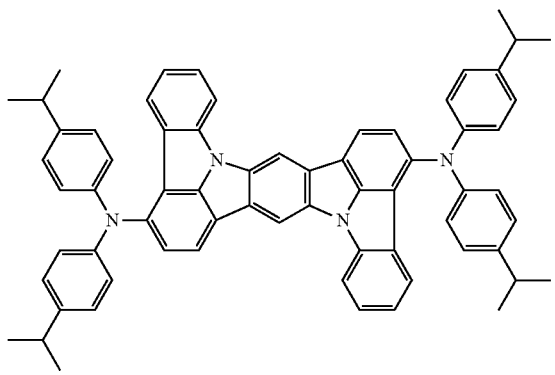
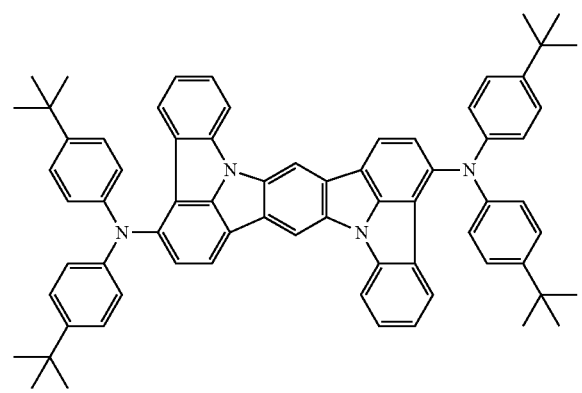
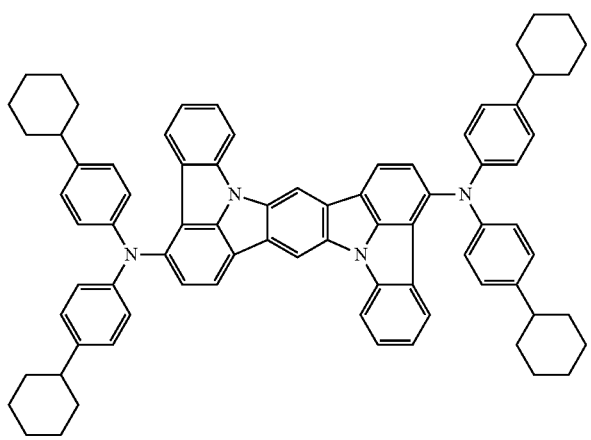
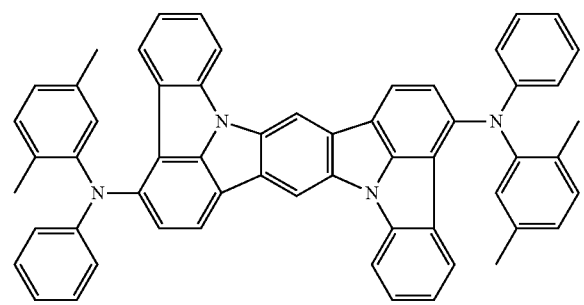
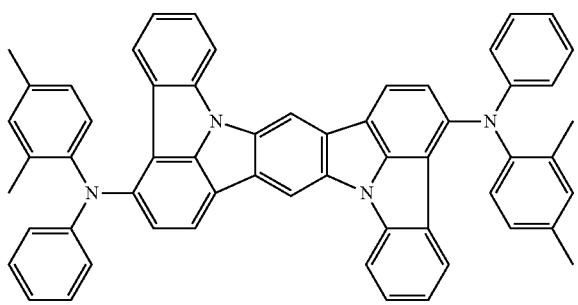
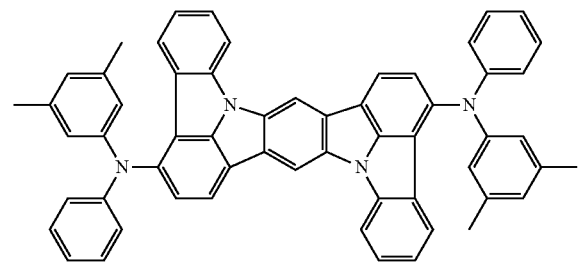
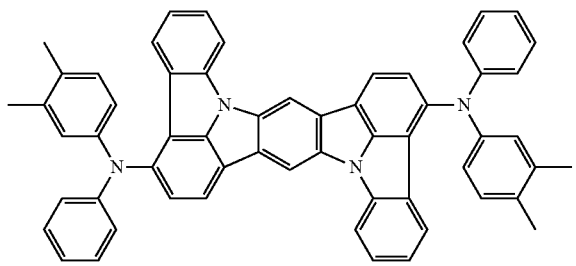
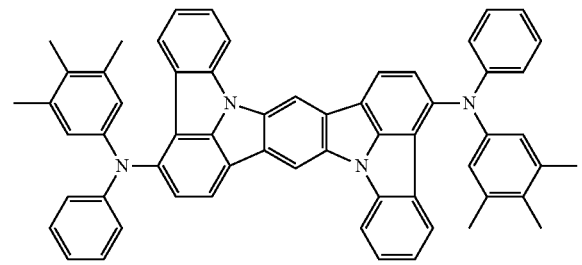
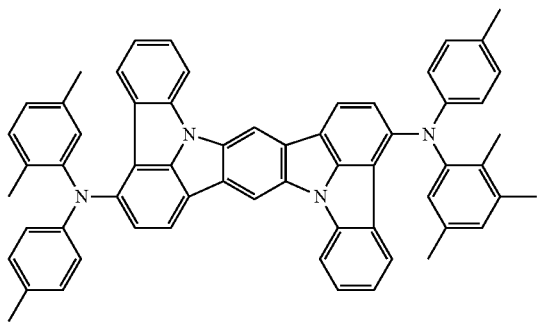

285 286
-continued
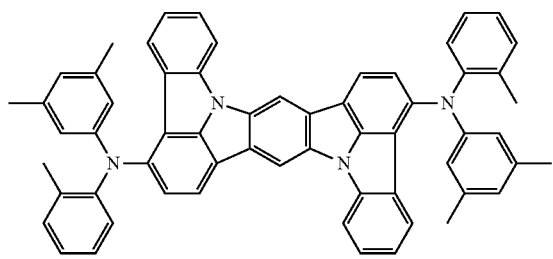
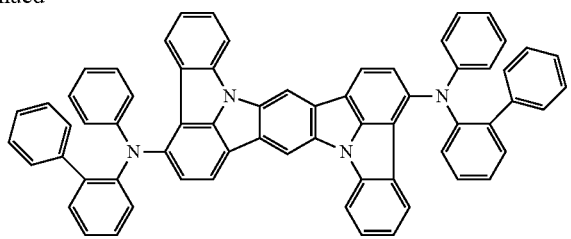
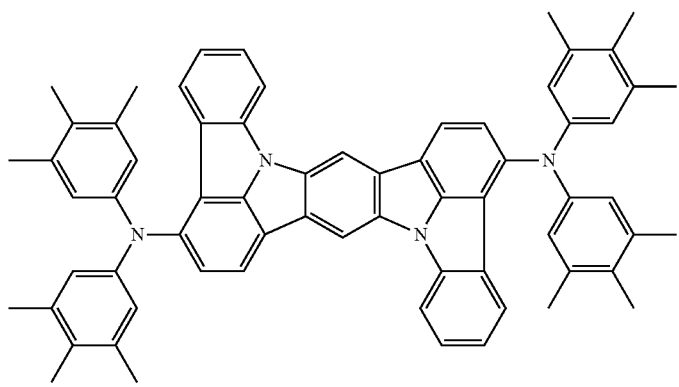
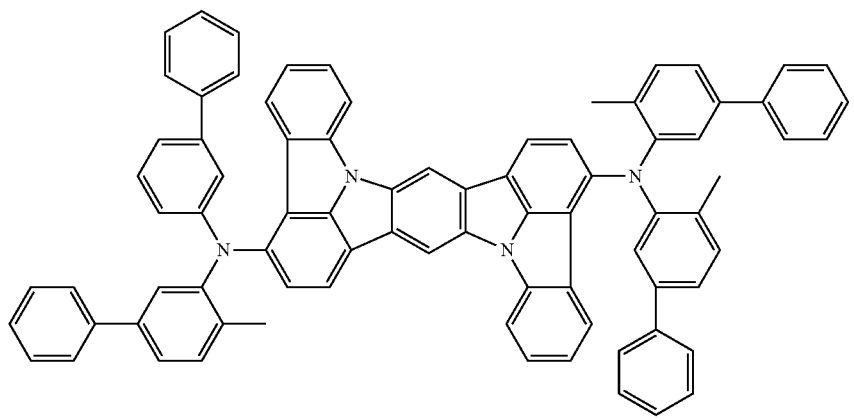
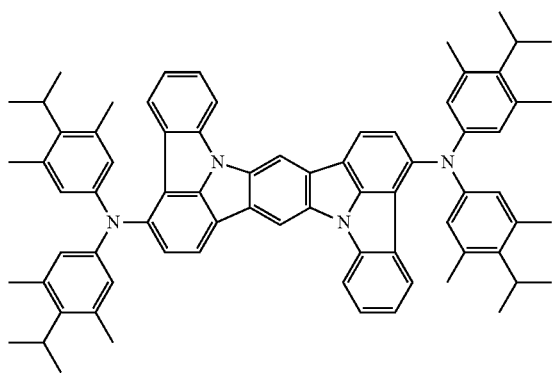
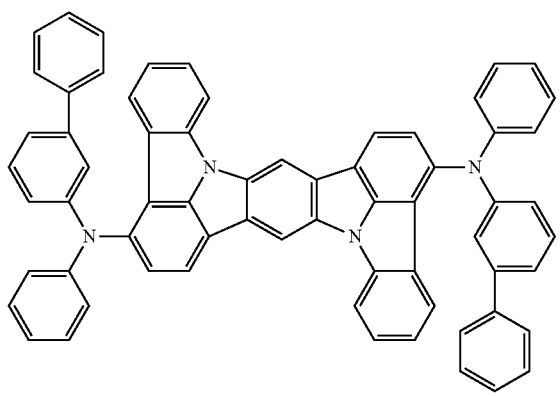

-continued
287 288
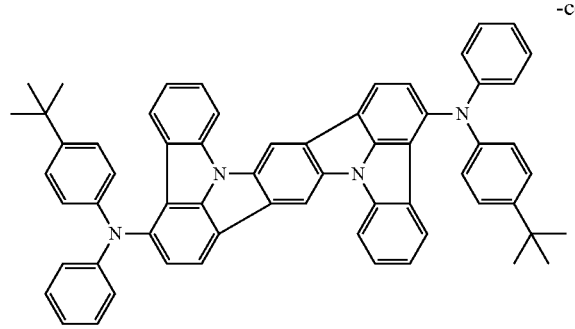
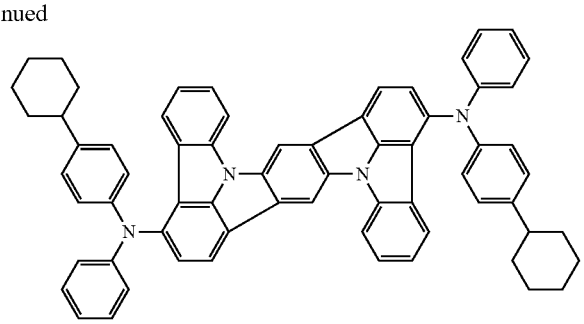
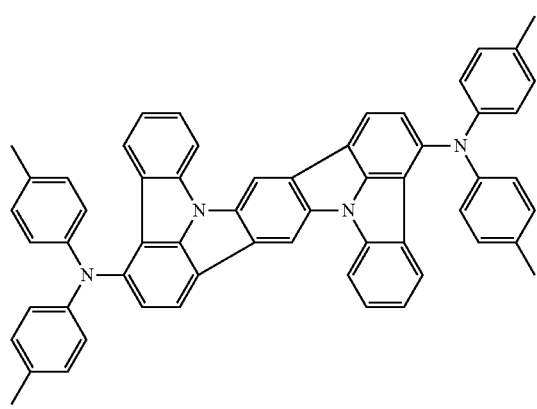
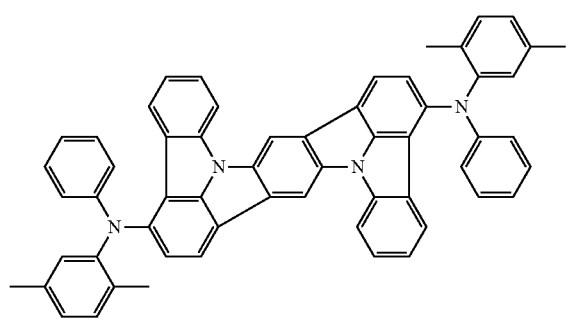
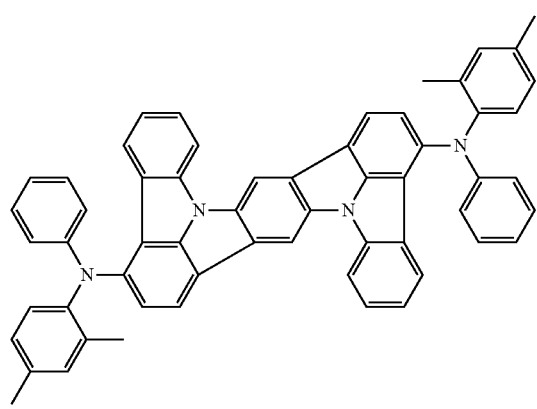
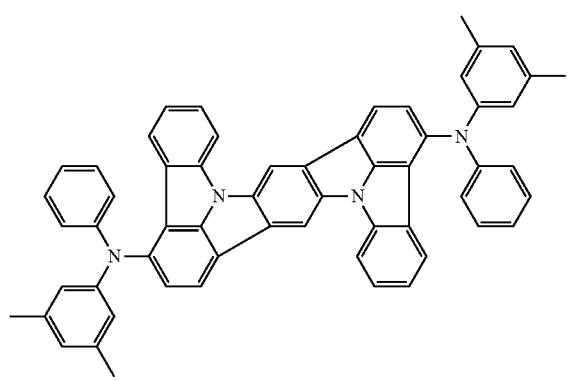
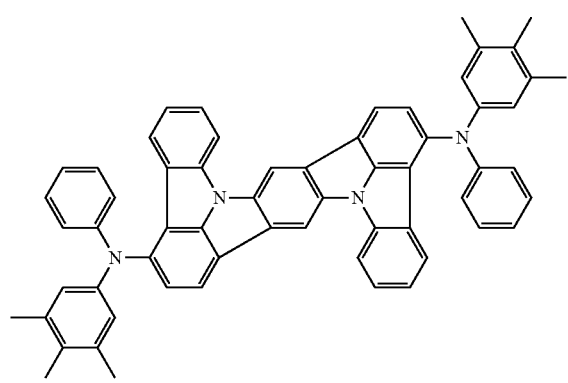
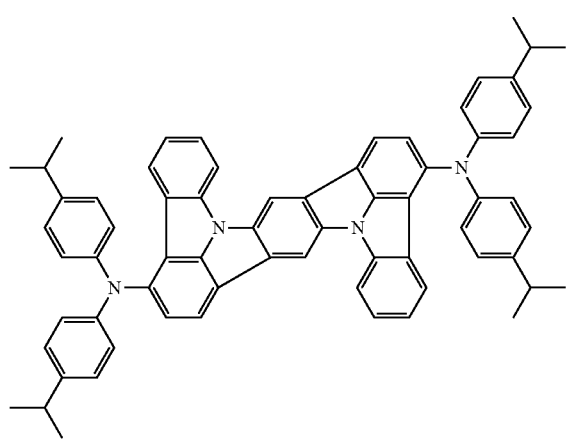

-continued
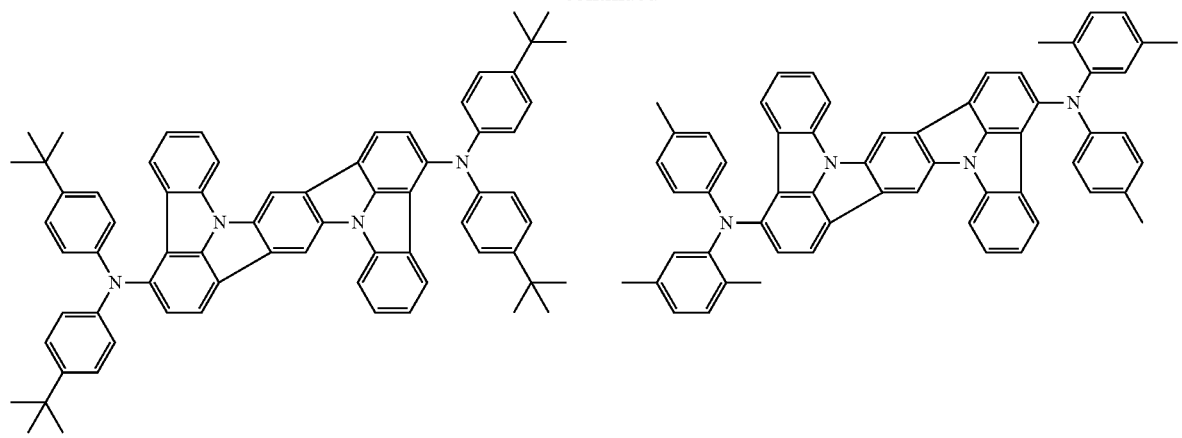
289 290
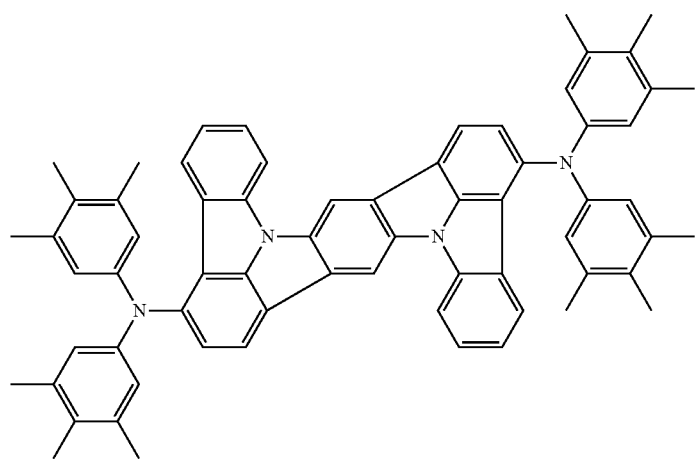
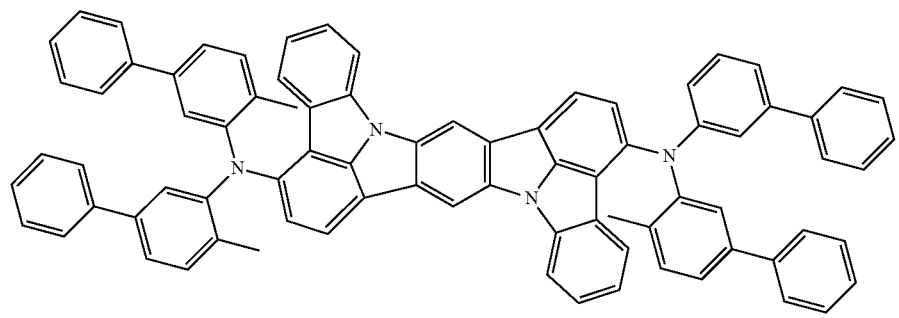
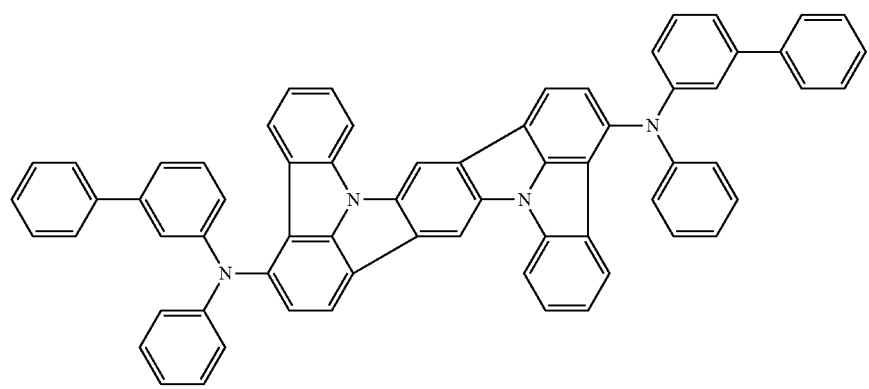

291 292
-continued
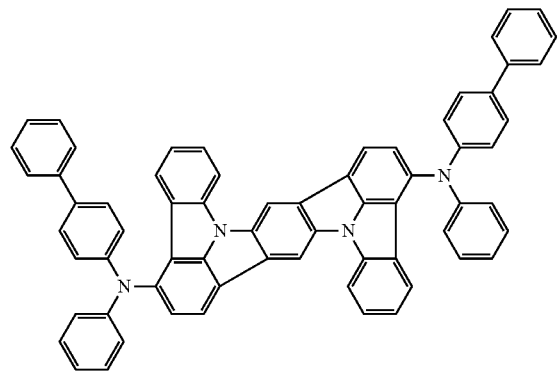
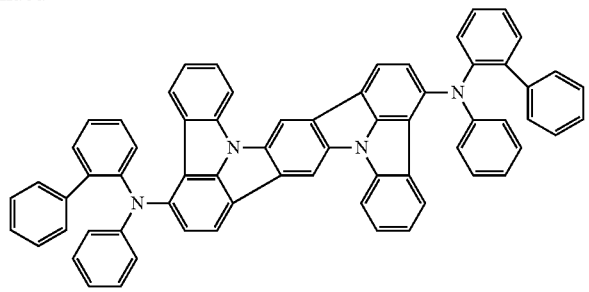
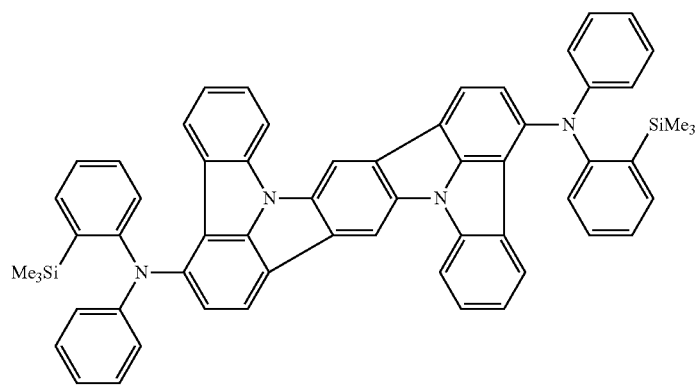
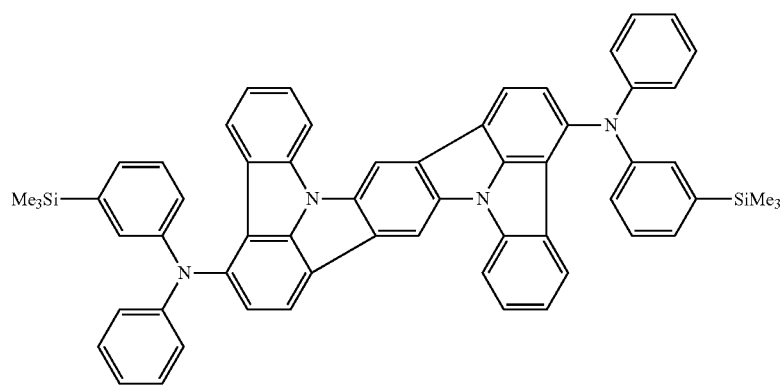
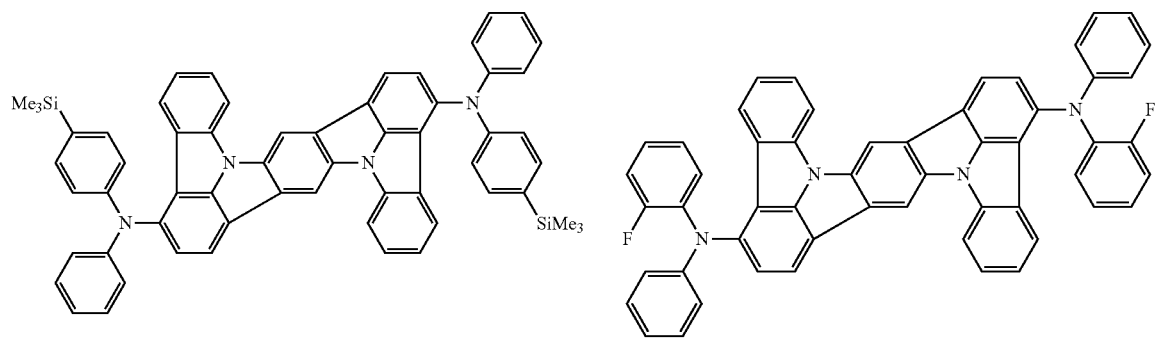

293
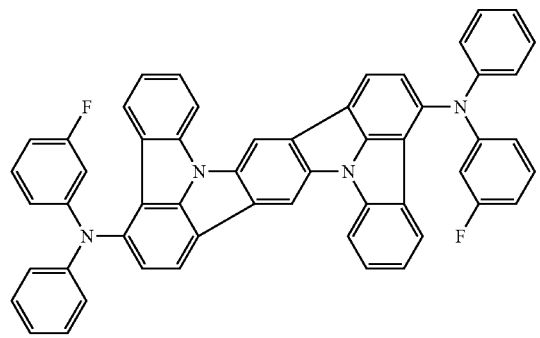
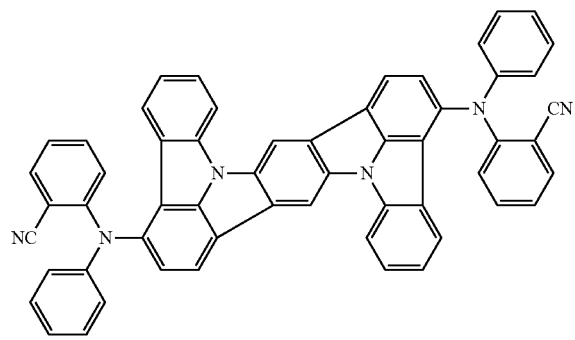
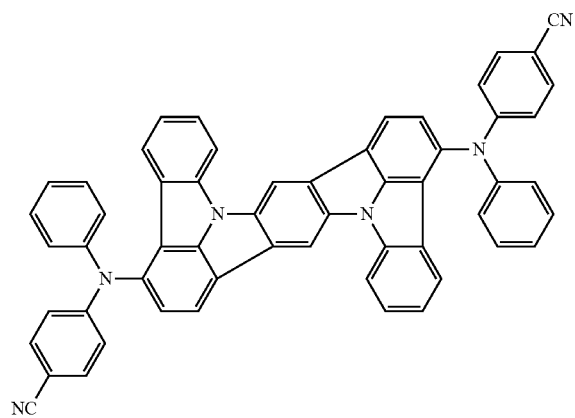
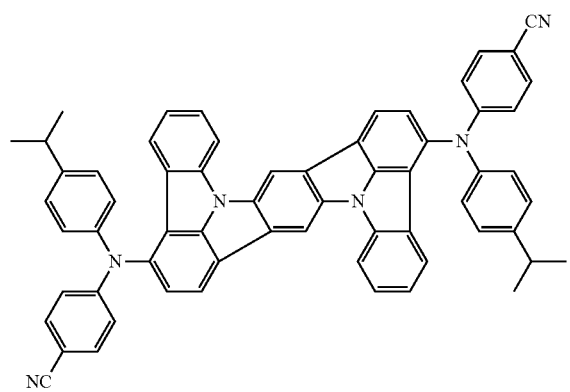
294
-continued
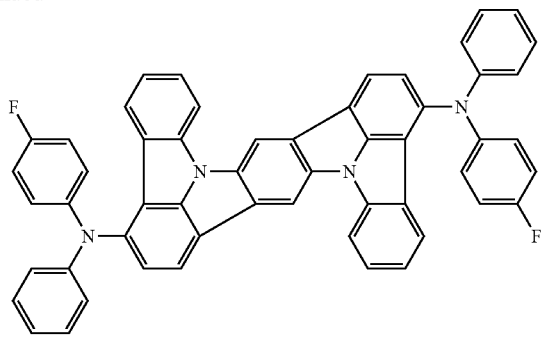
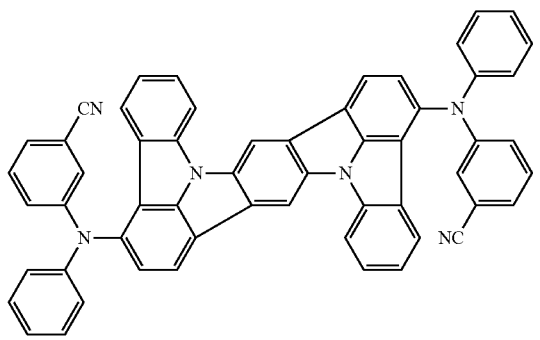
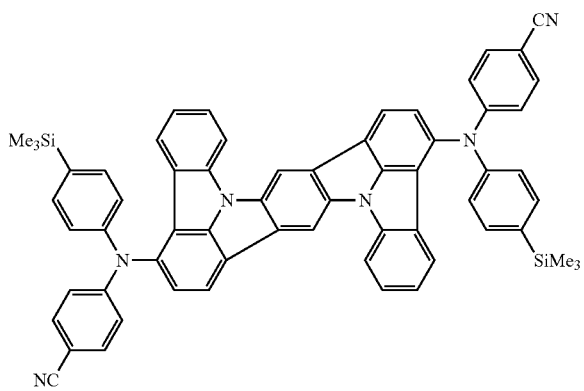
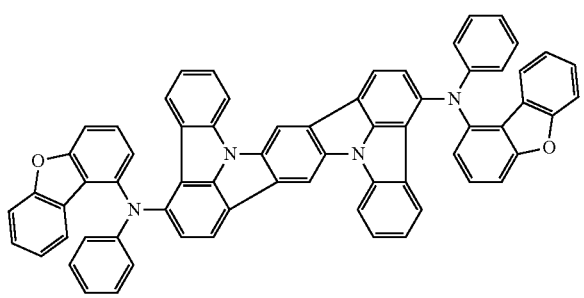

-continued
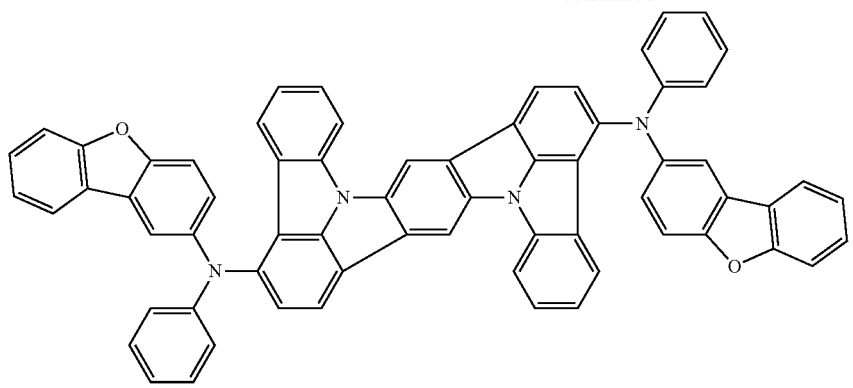
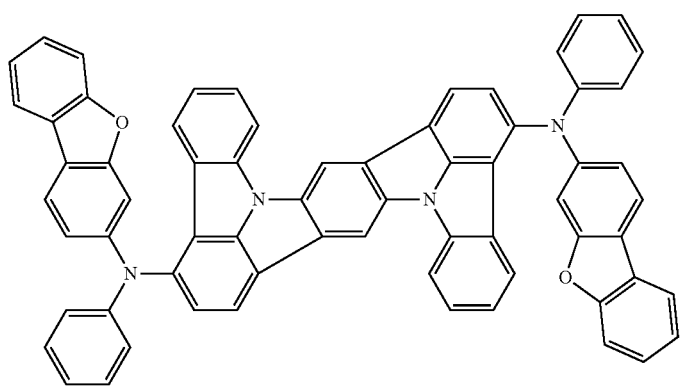
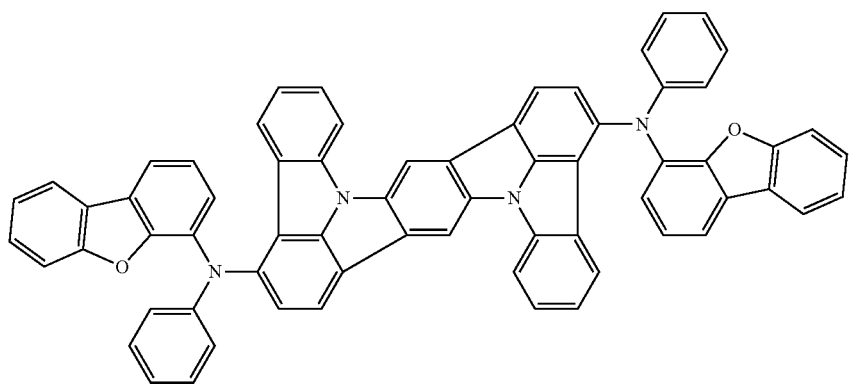
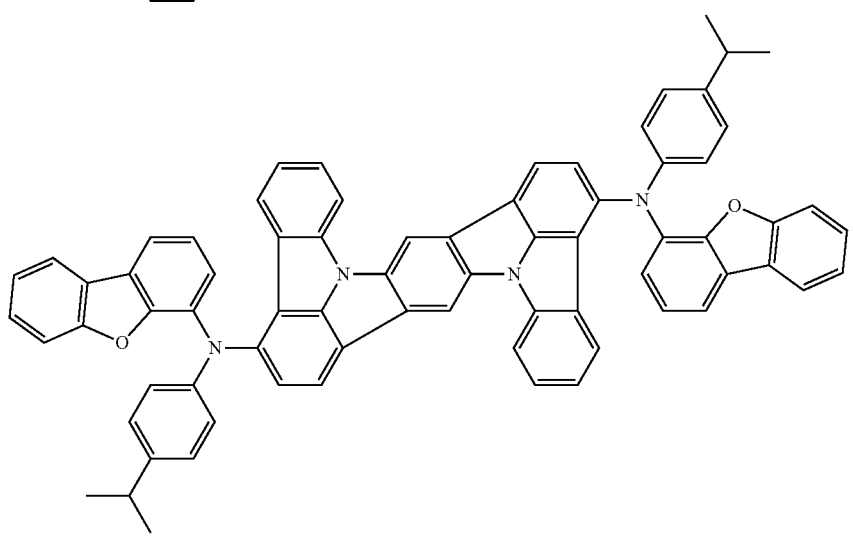

-continued
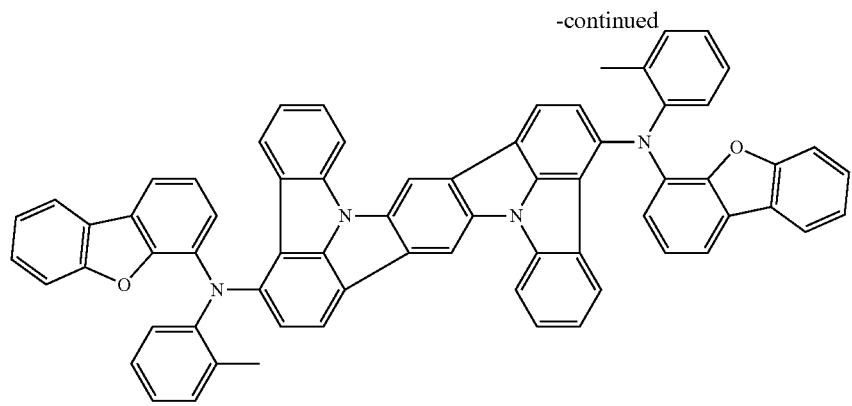
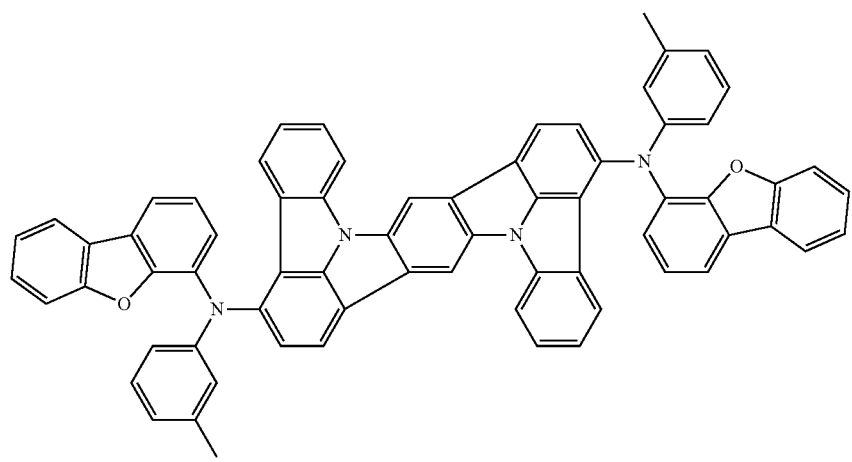
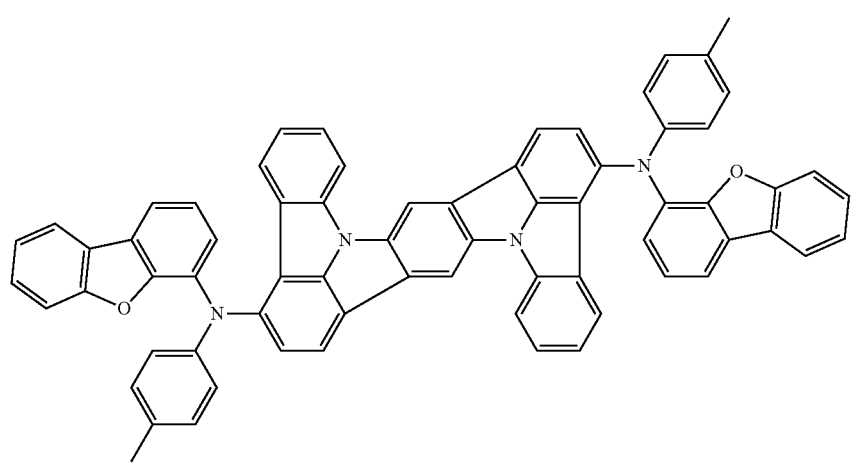

-continued
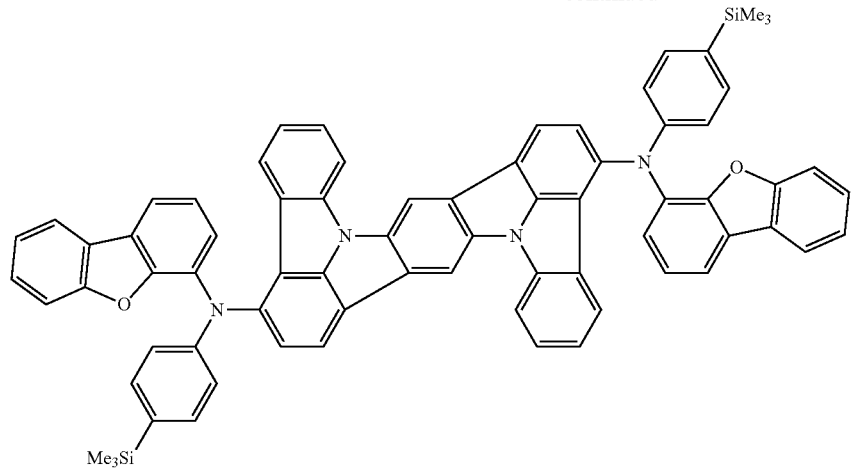
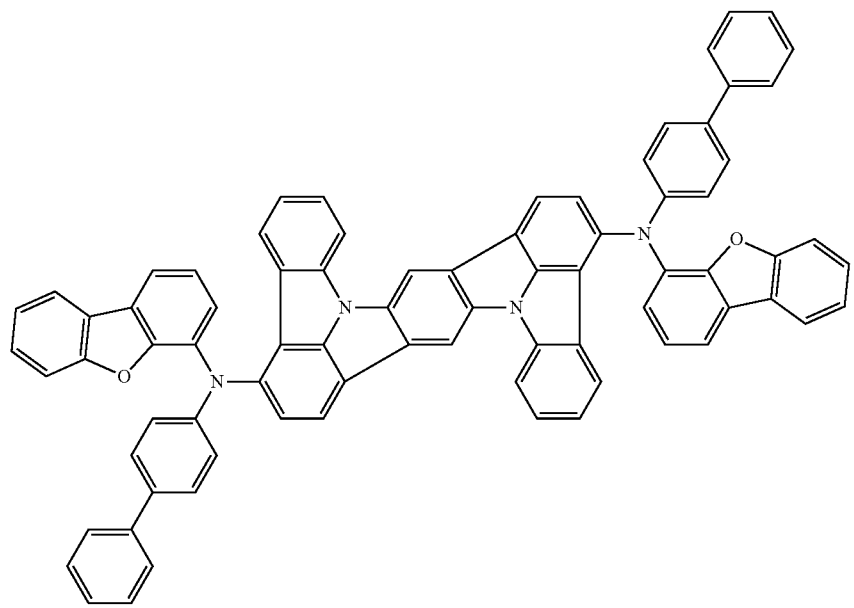
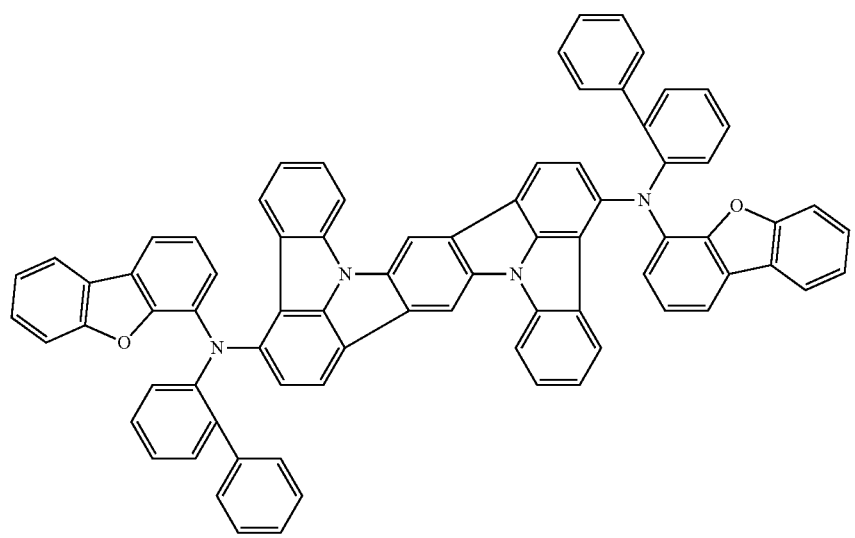

-continued
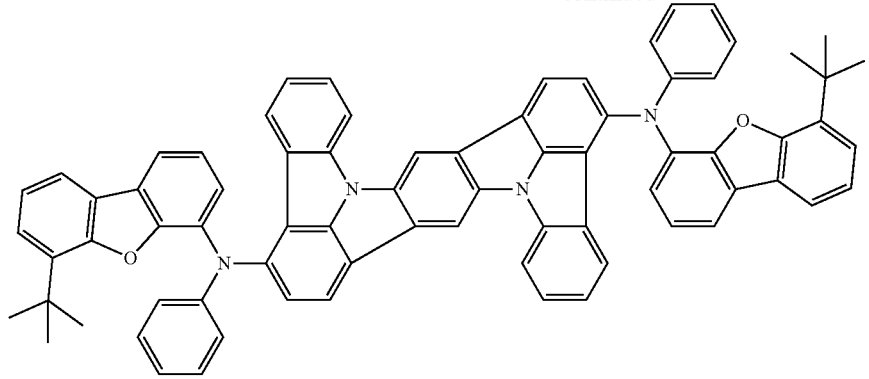
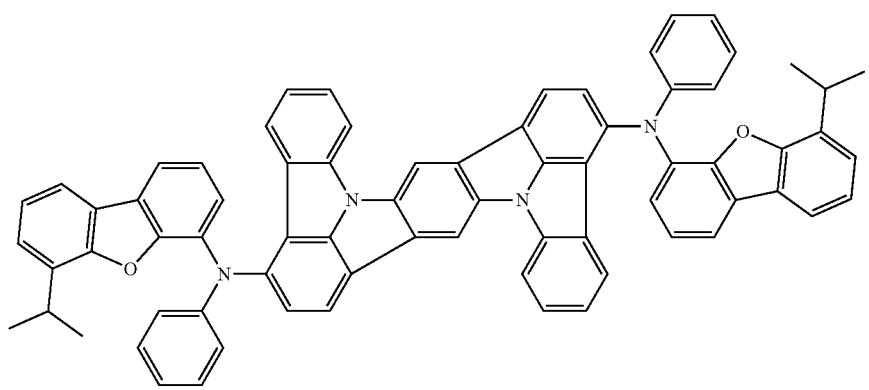
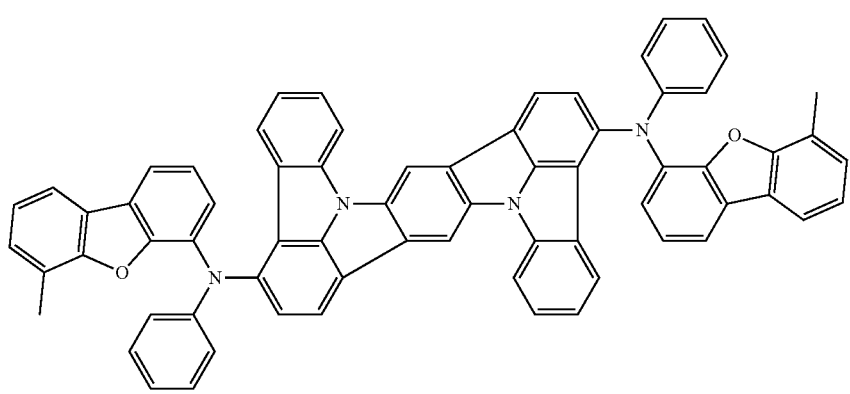
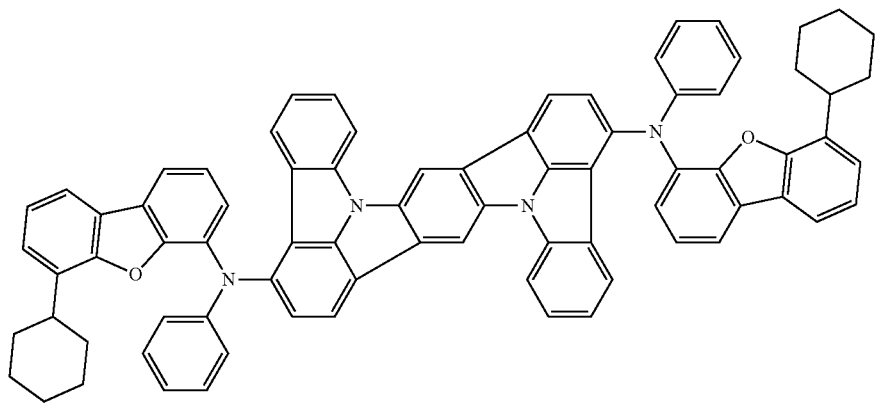

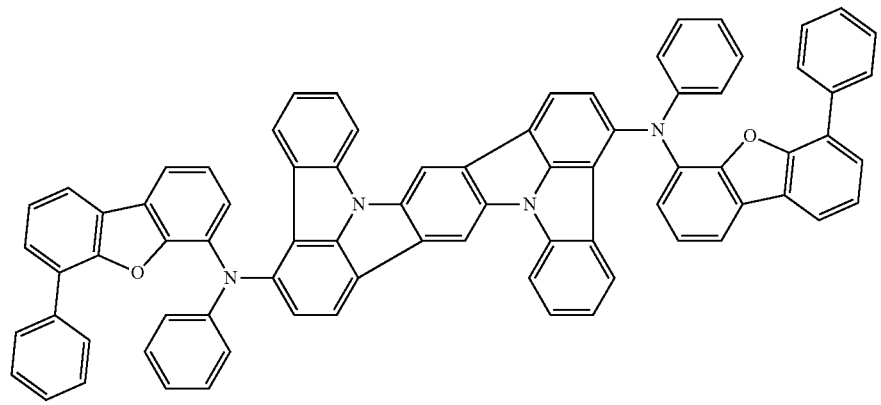
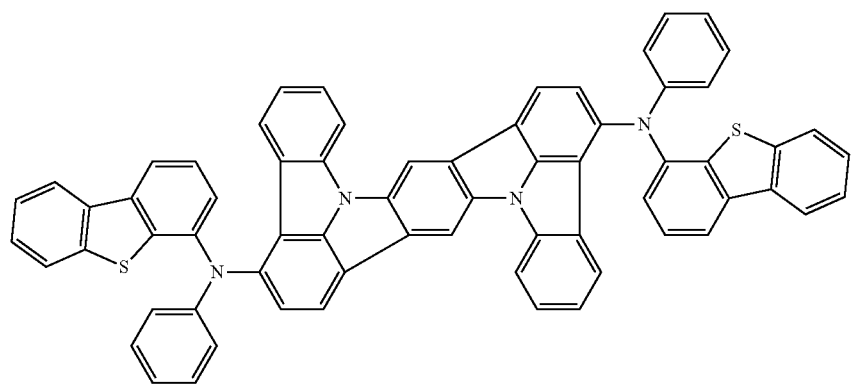
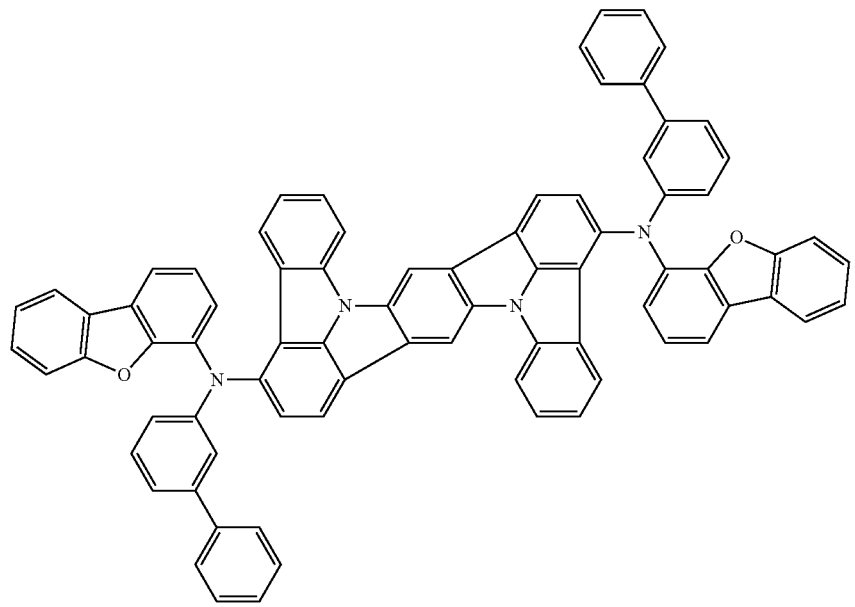
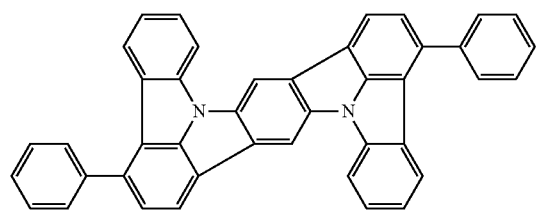
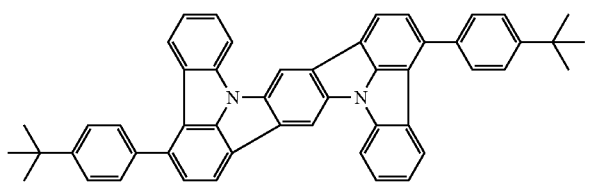

-continued
305
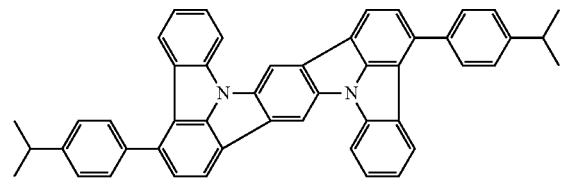
306
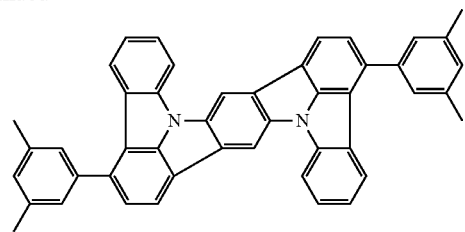
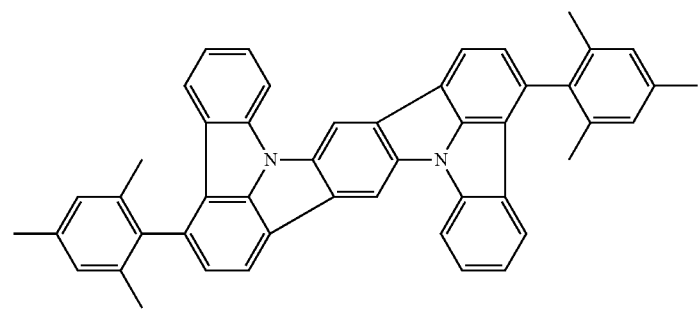
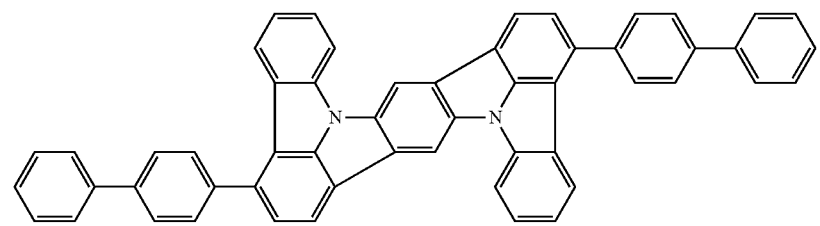
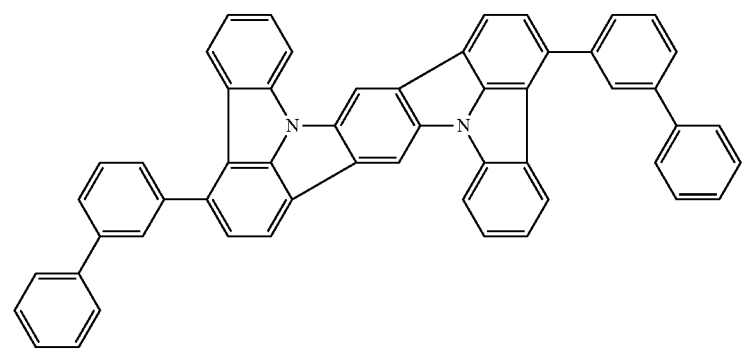
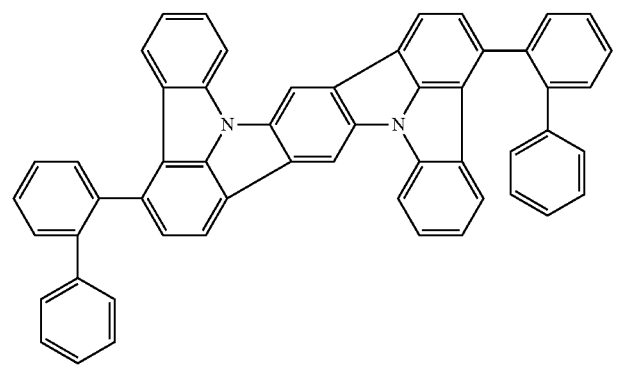

-continued
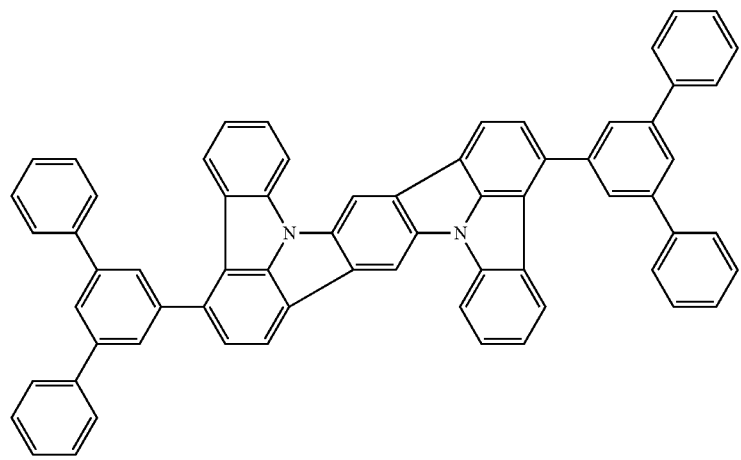
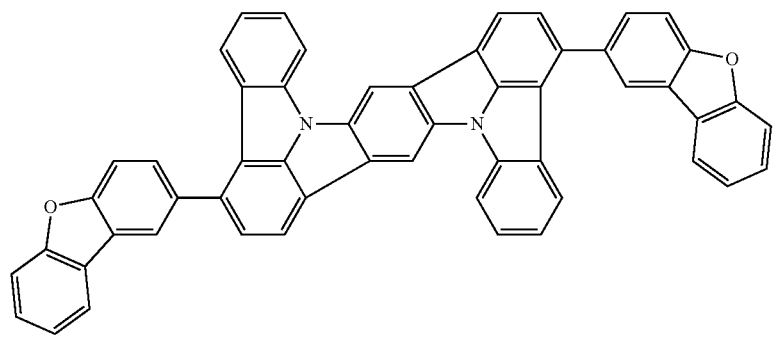
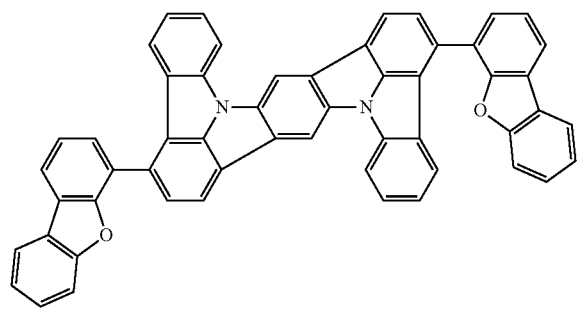
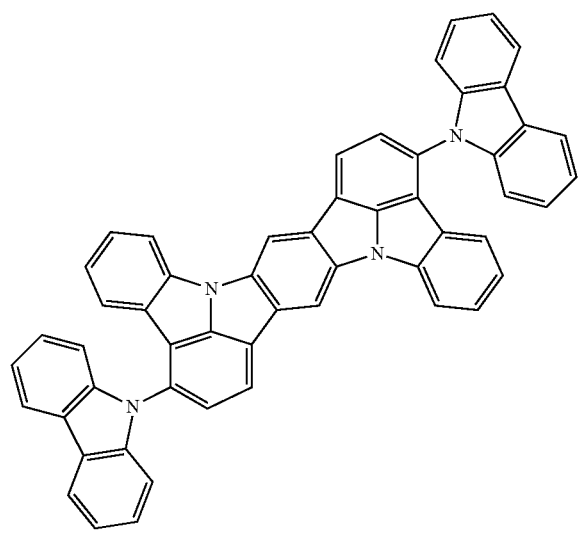
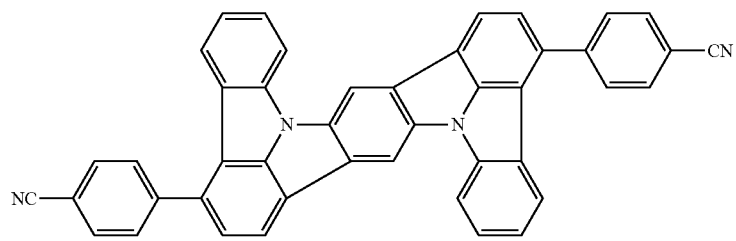

309
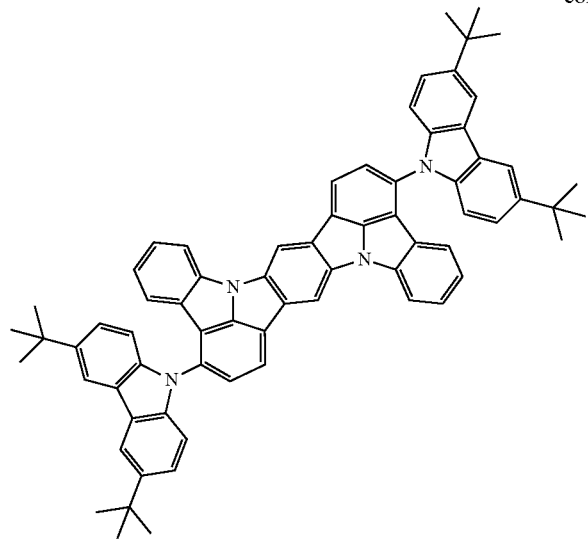
310
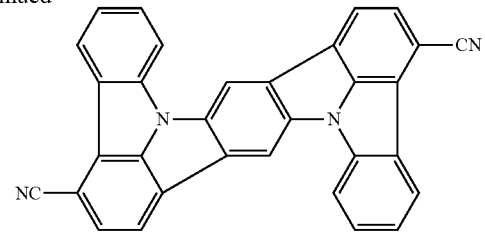
-continued
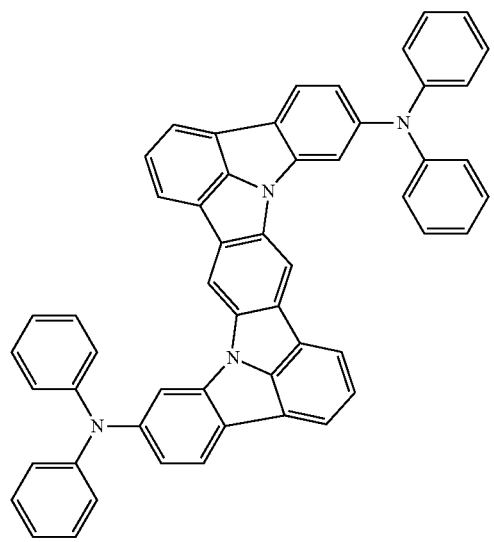
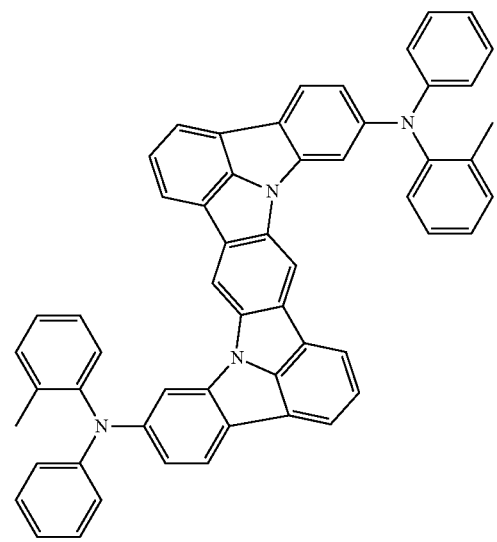
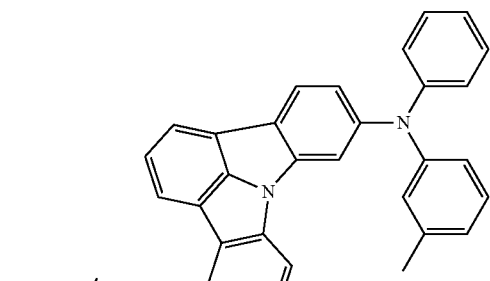
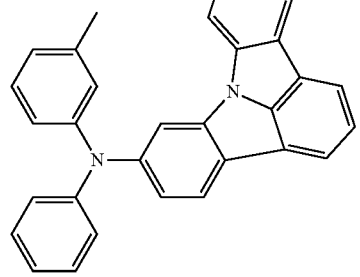
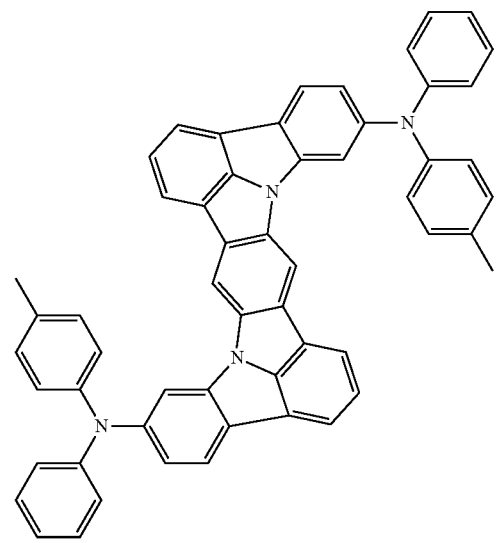

-continued
311
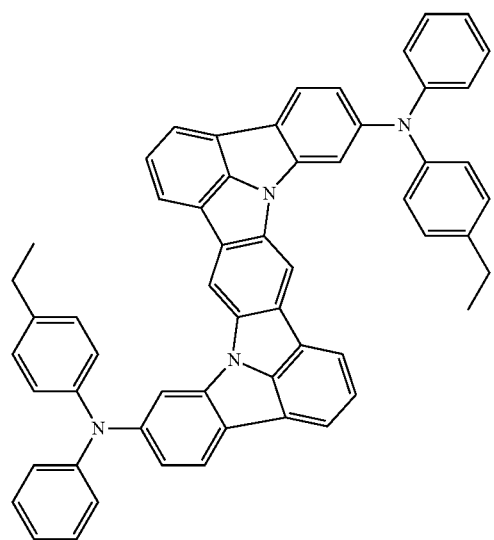
312
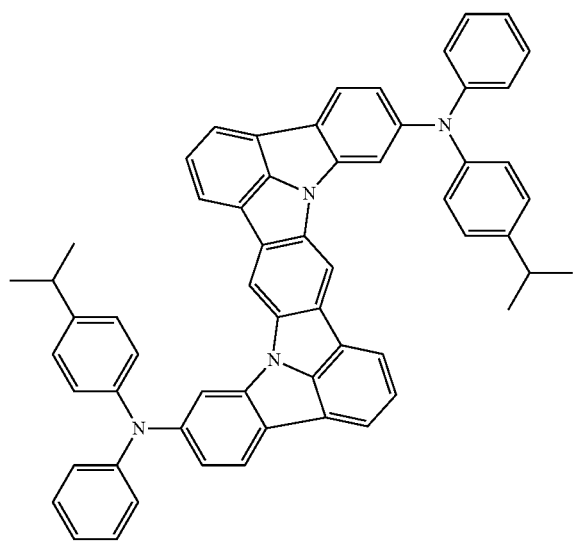
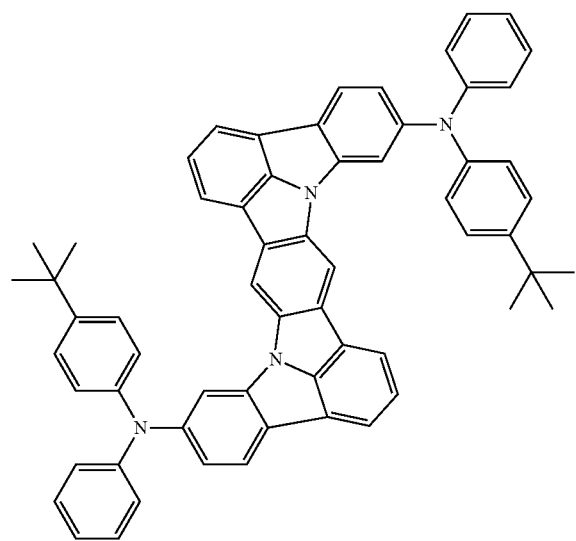
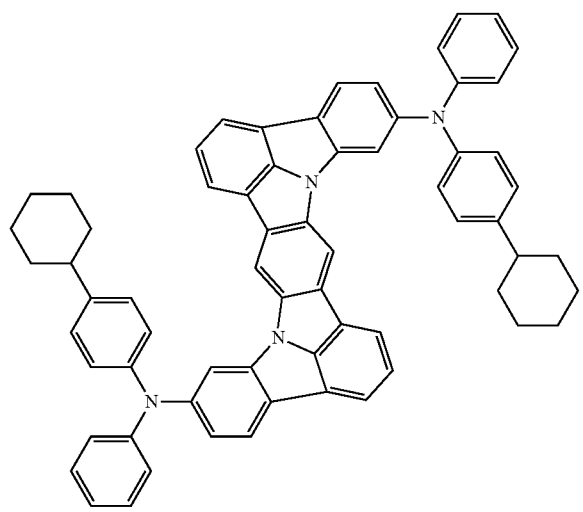

-continued
313
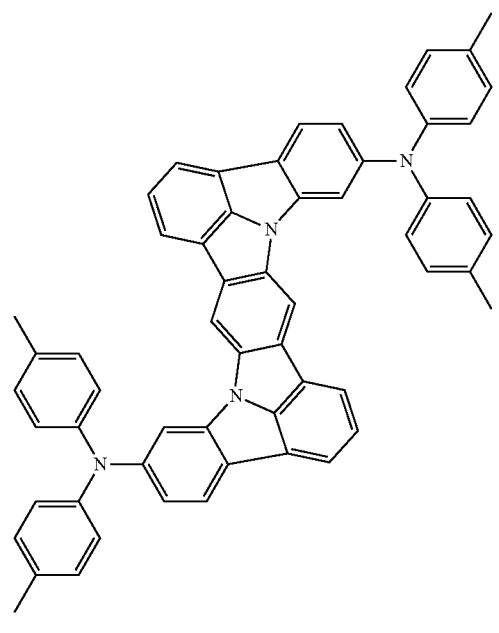
314
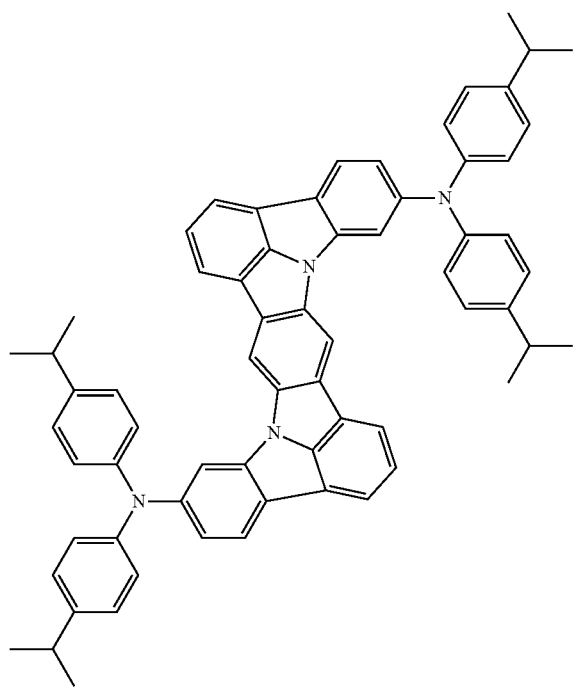
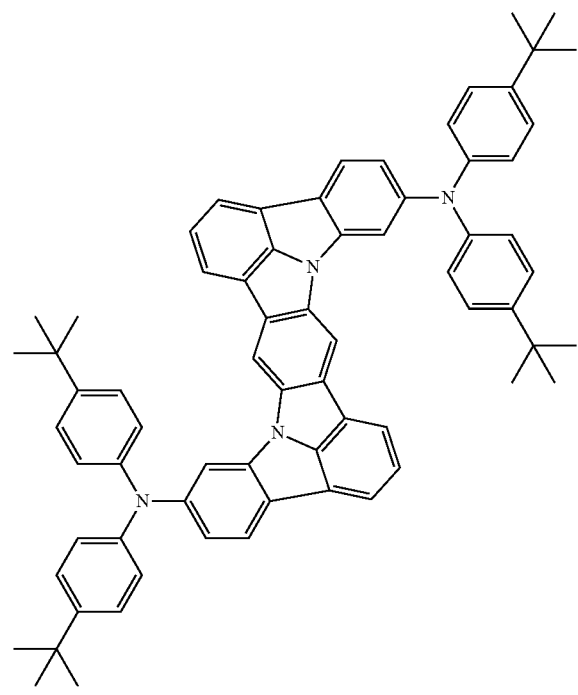
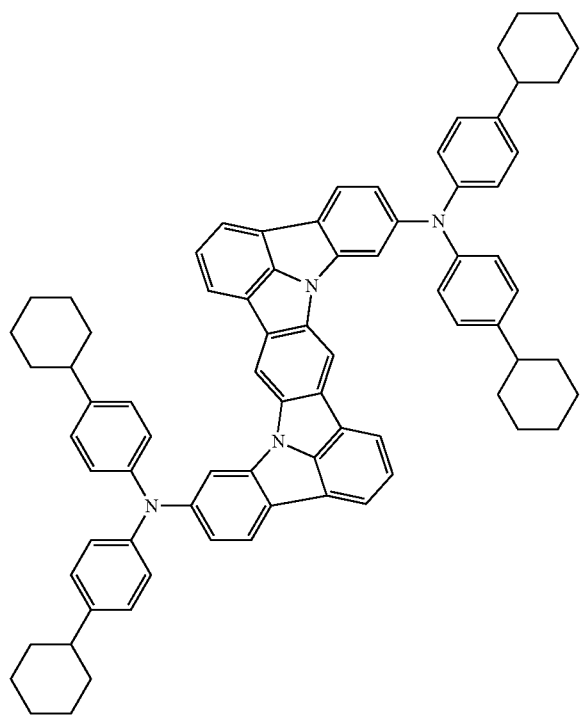

315 316
-continued
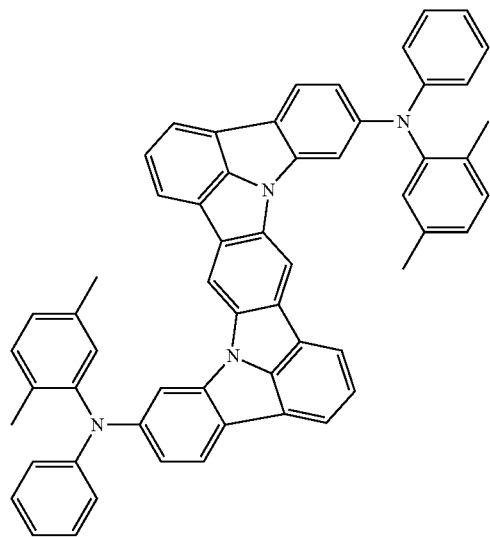 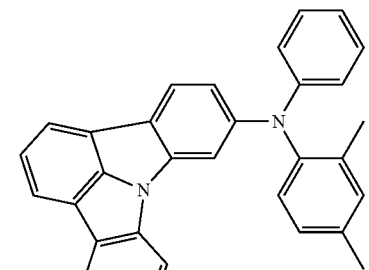
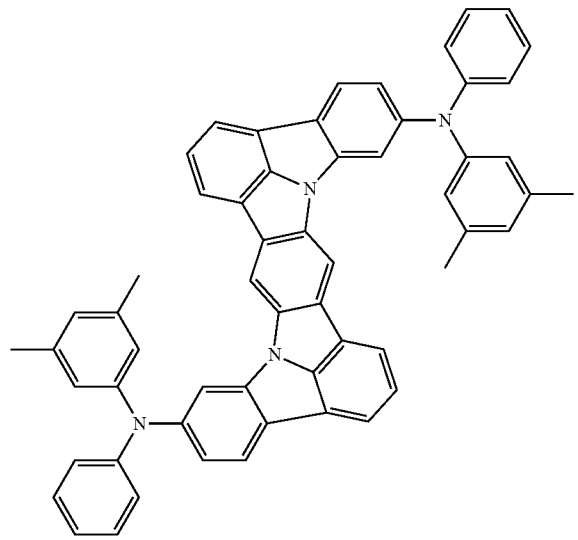 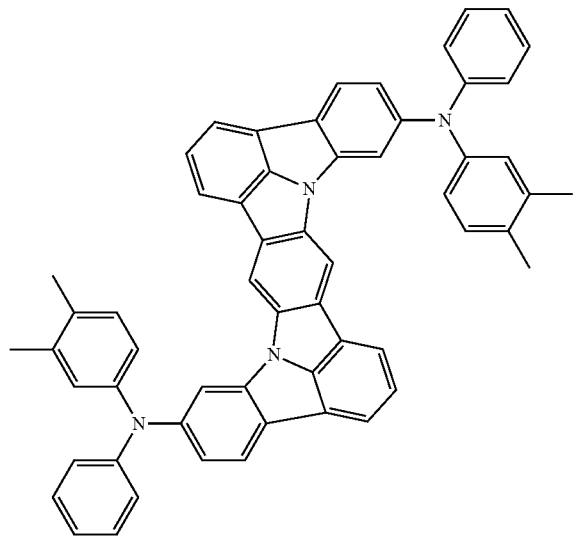
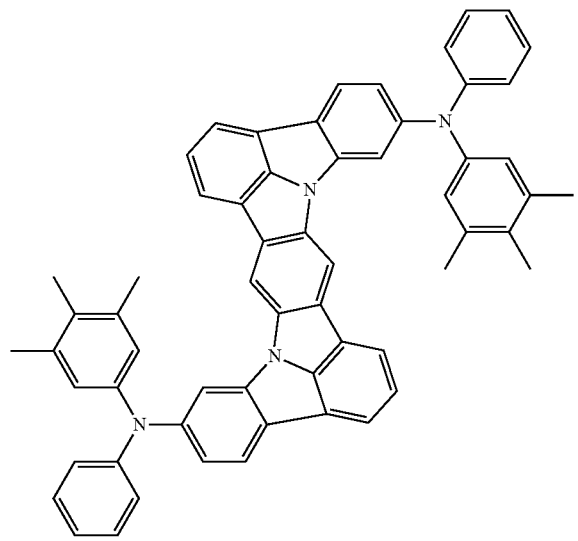 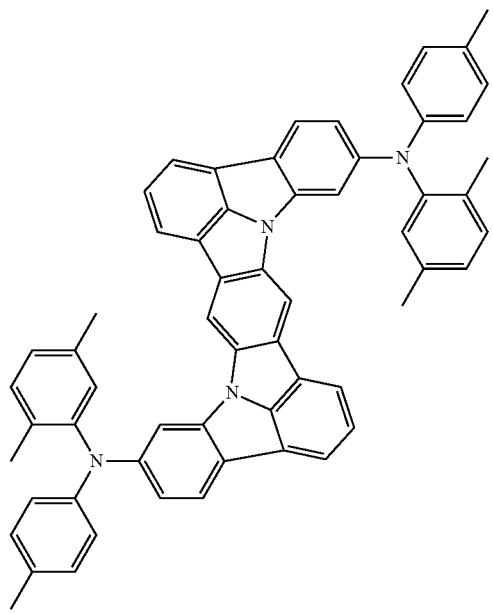

-continued
317
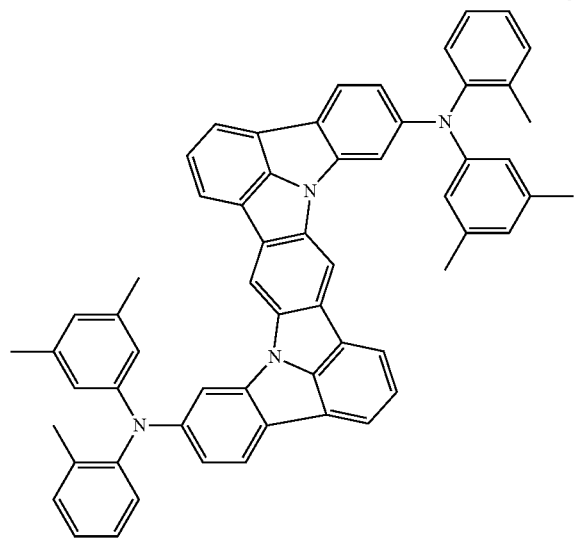
318
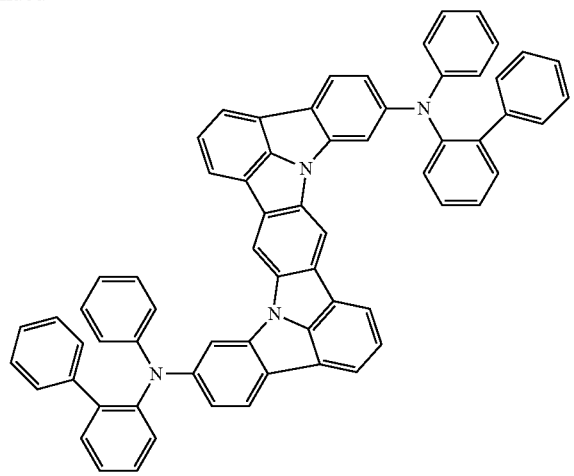
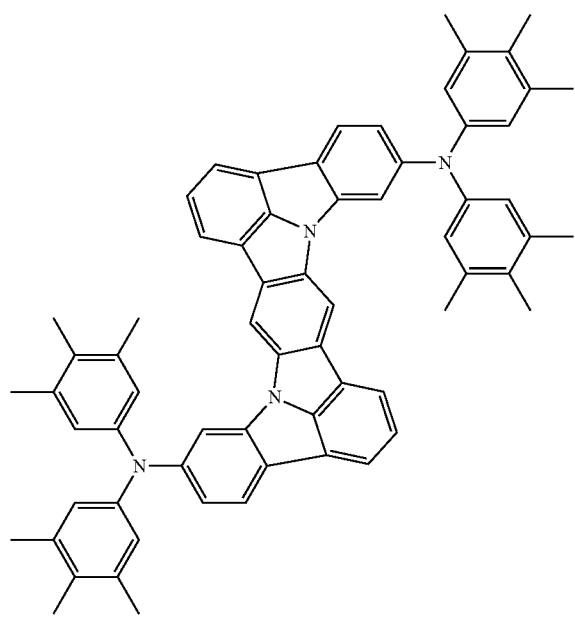
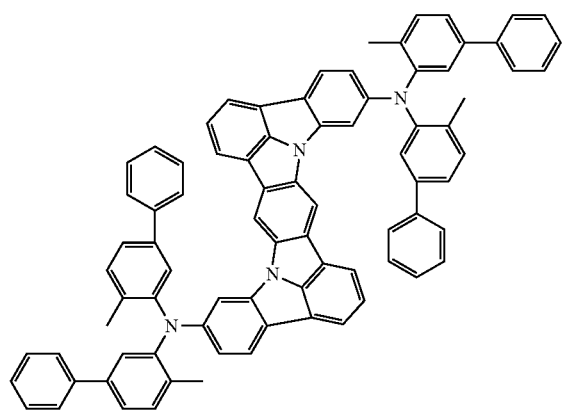

319 320
-continued
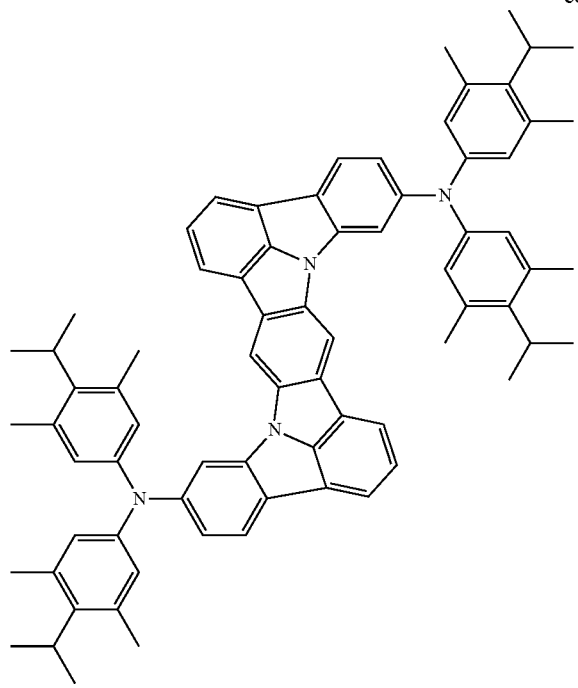
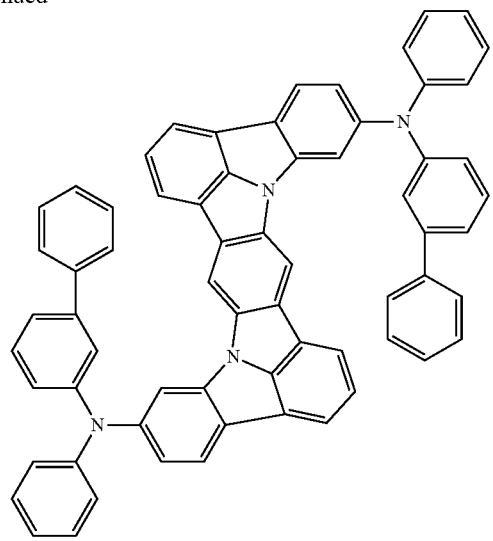
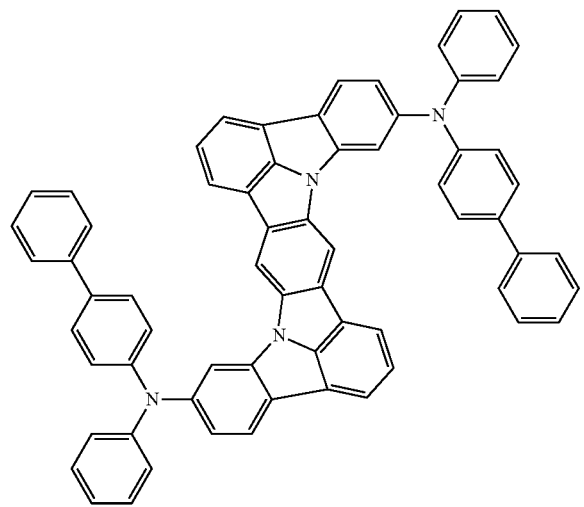
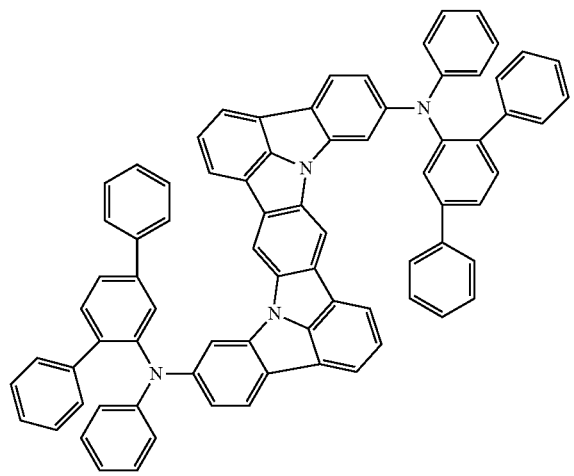
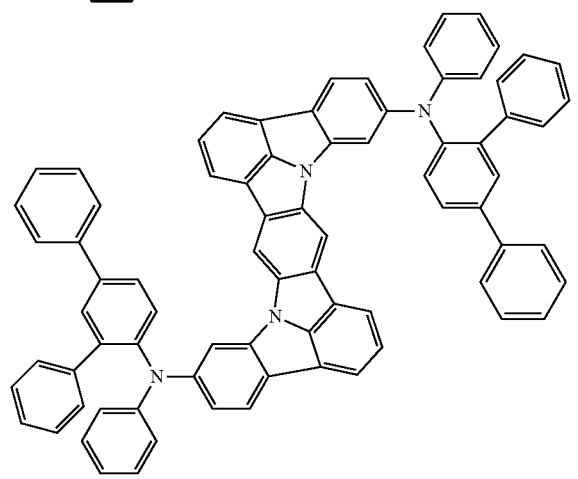
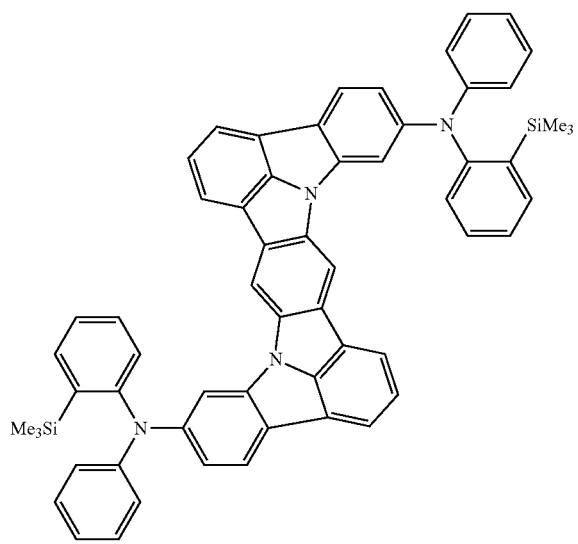

-continued
321
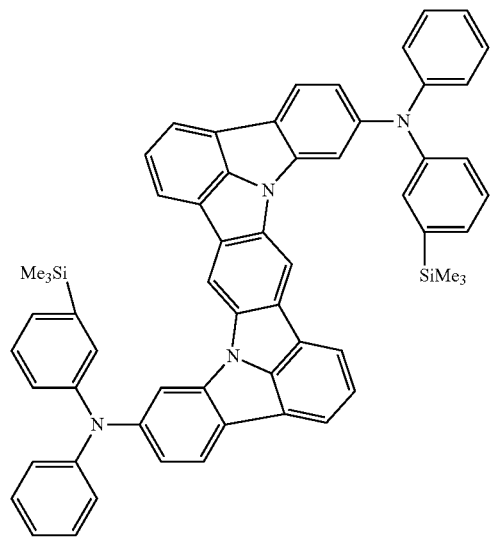
322
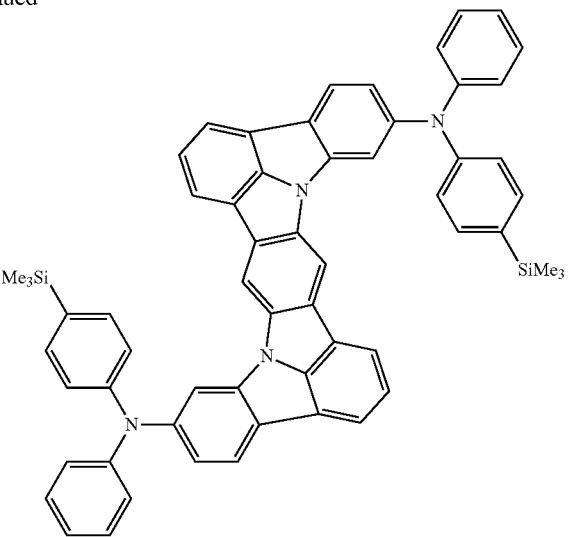
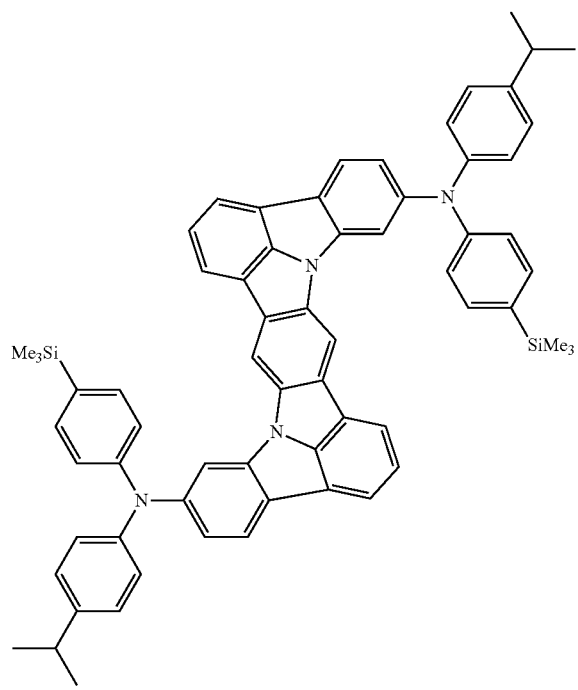
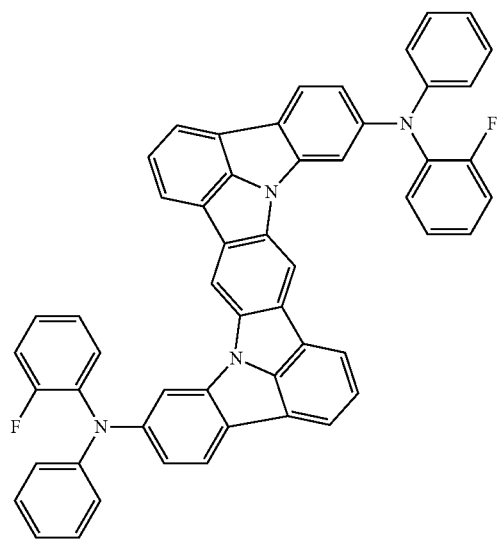

323 324
-continued
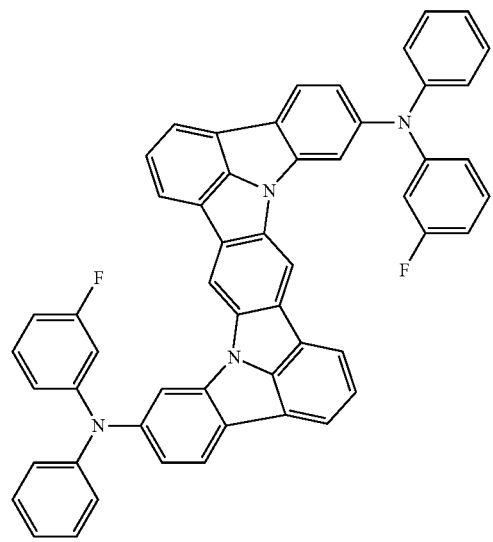
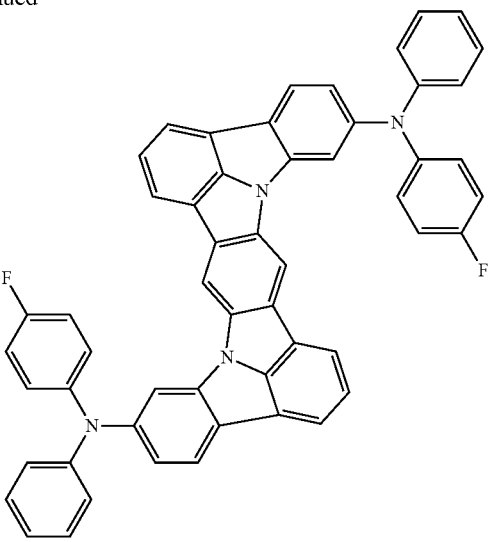
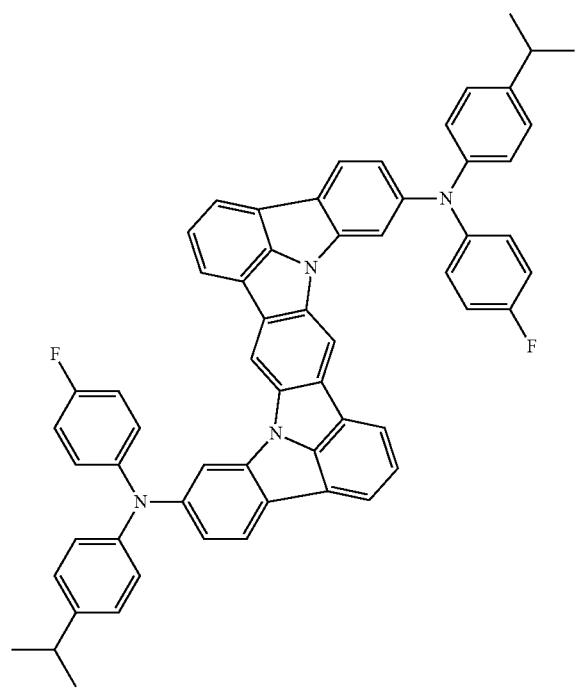 [SMILES: CC(C)c1ccc(N(c2ccc(C#N)cc2)c2ccc3c4cccc5c6cc7c(cc6n(c3c2)c45)c2cccc3c4ccc(N(c5ccc(C#N)cc5)c5ccc(C(C)C)cc5)cc4n7c32)cc1]
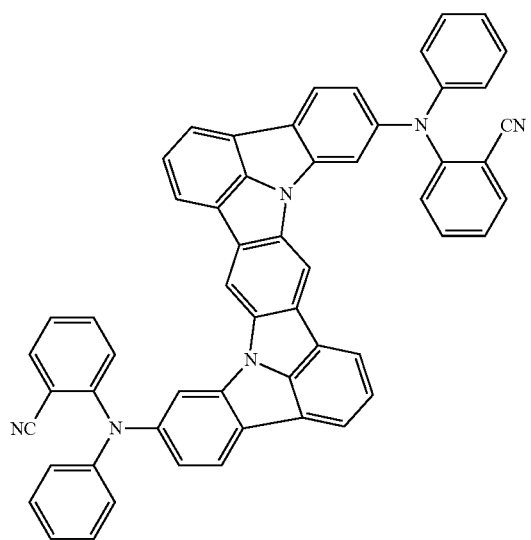

325 326
-continued
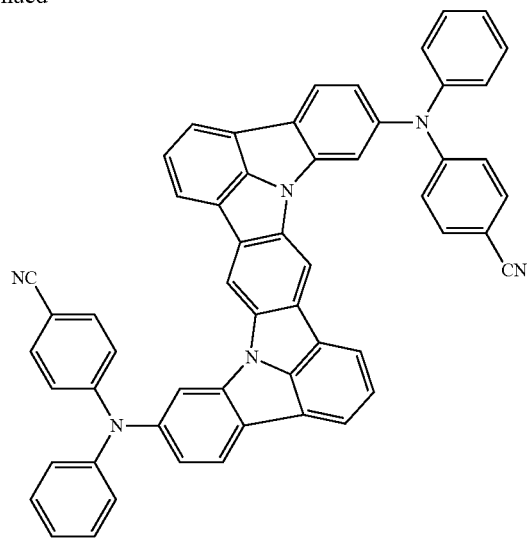
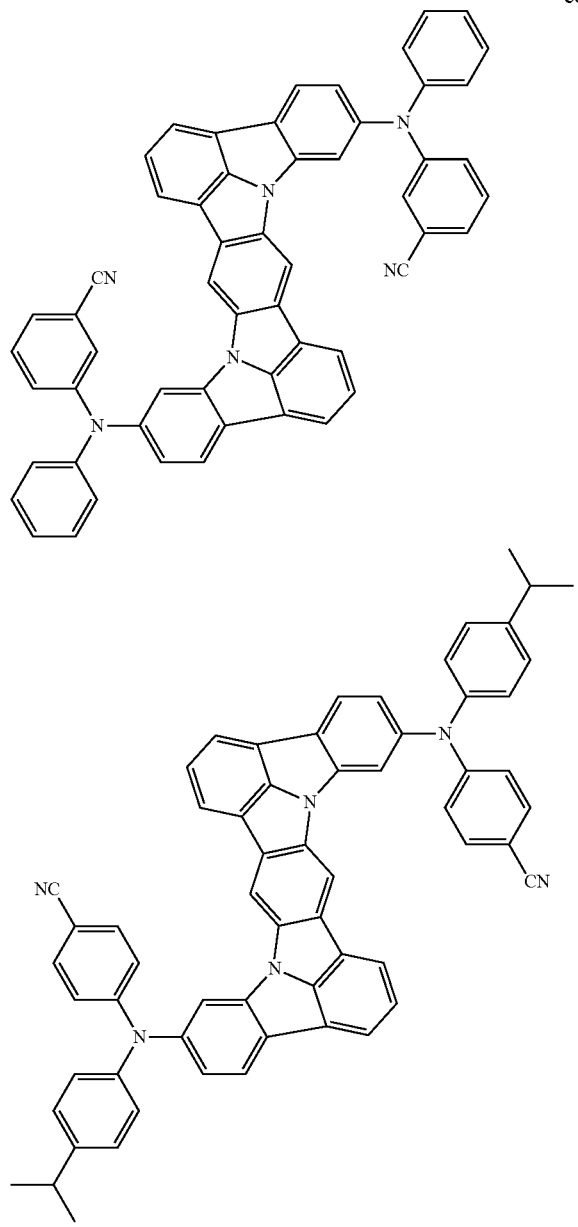
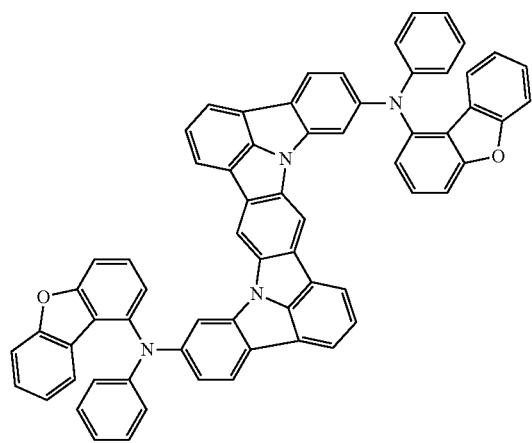
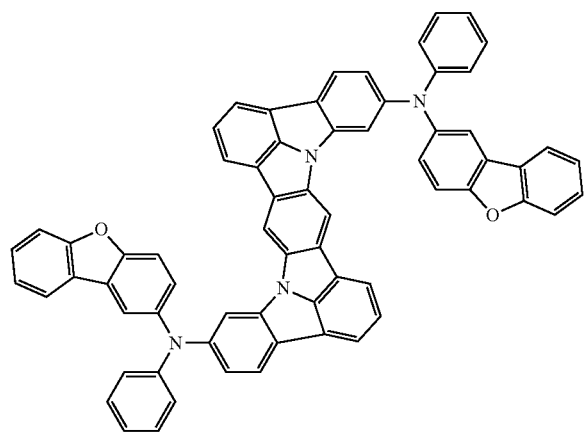

-continued
327
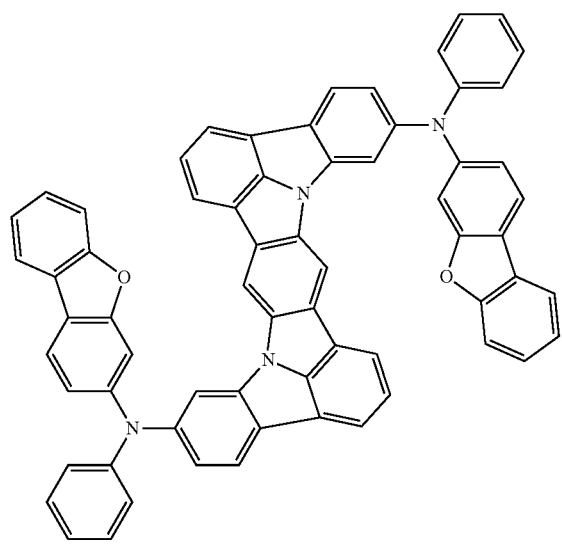
328
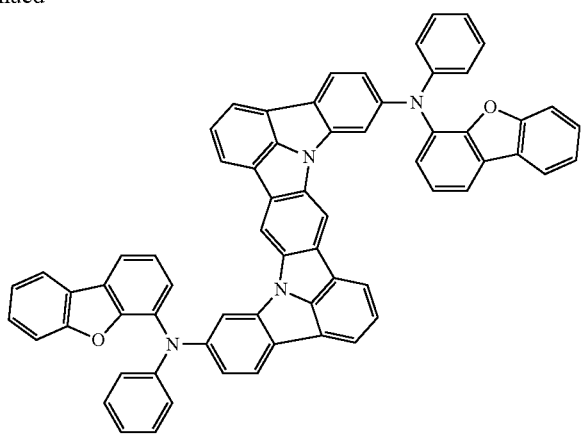
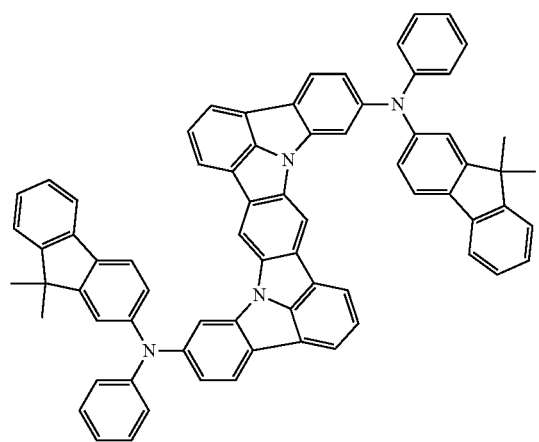
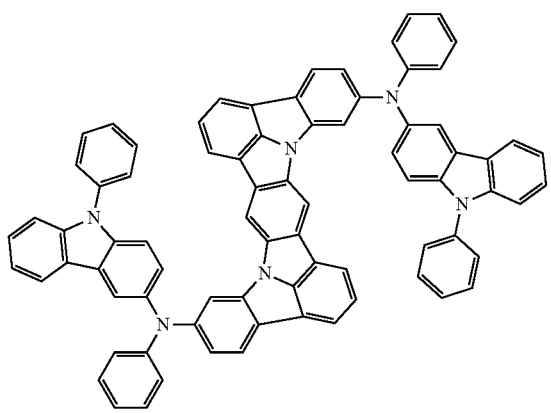
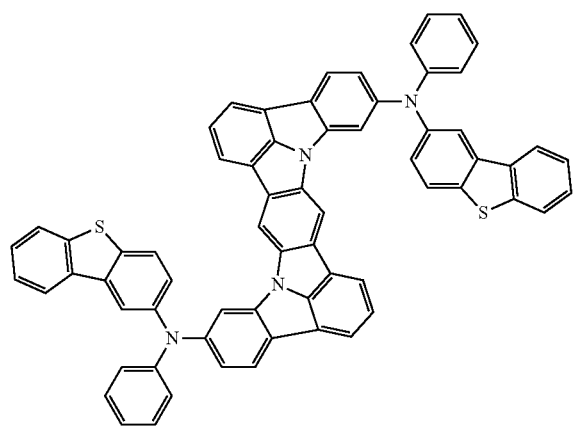
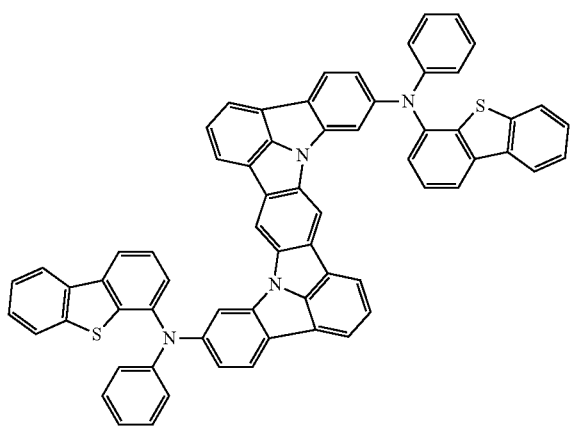

329
-continued
330
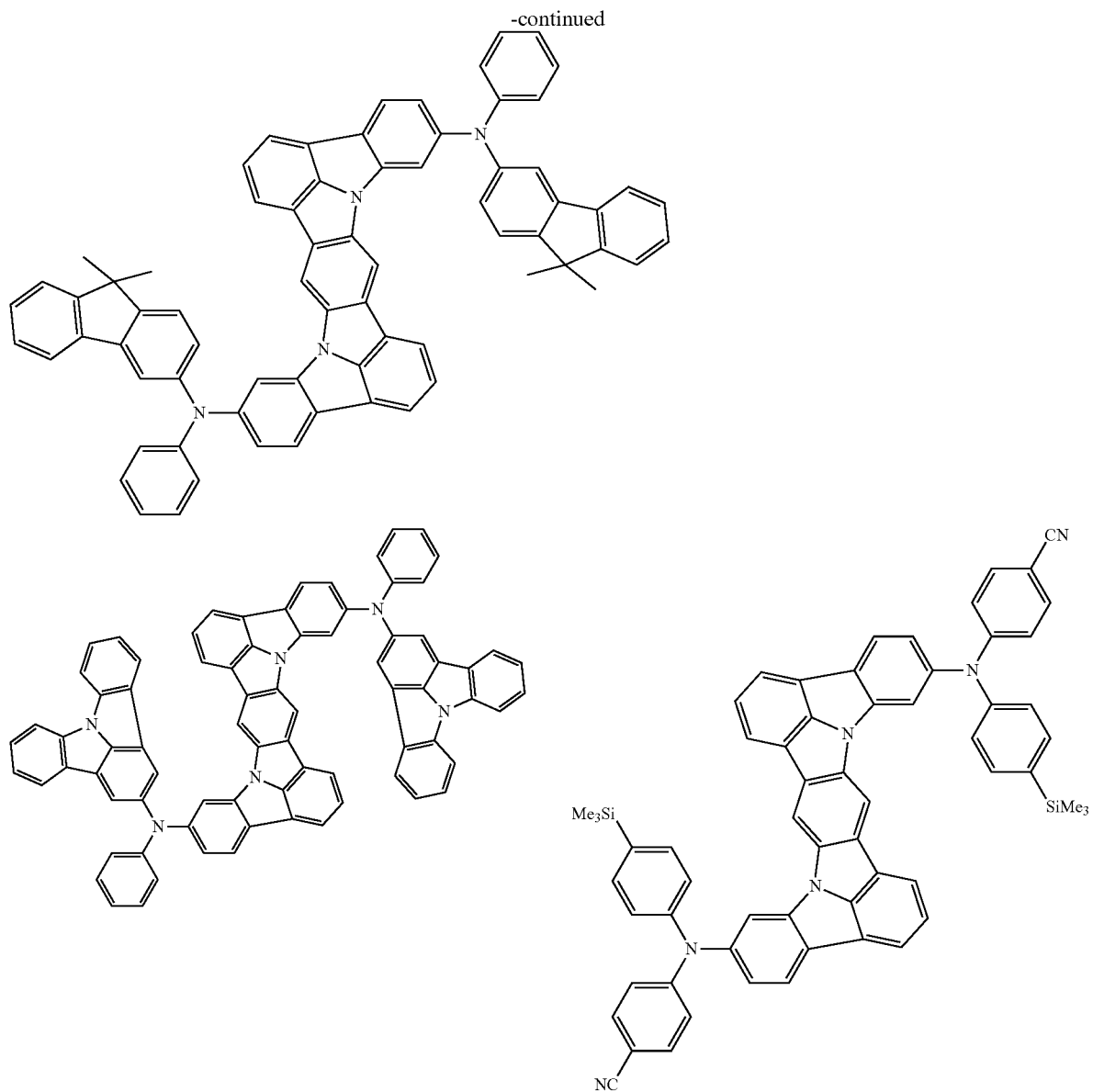
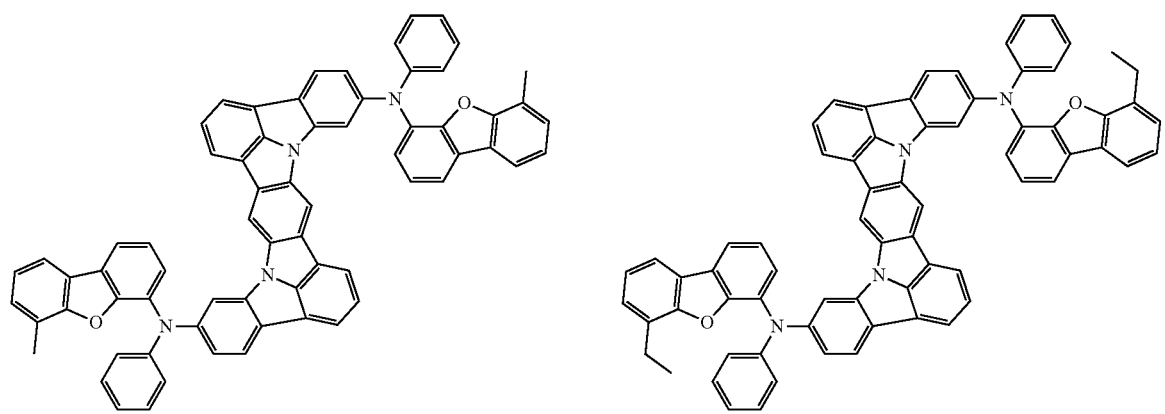

-continued
331
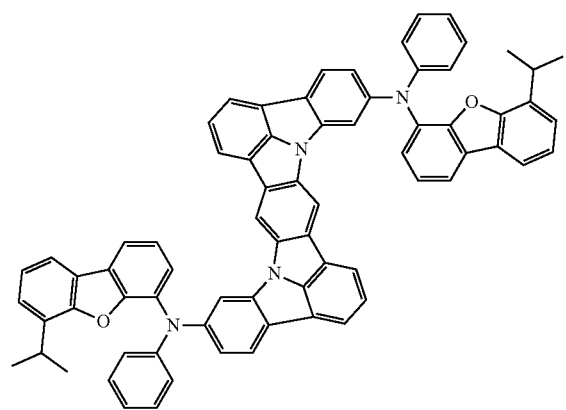
332
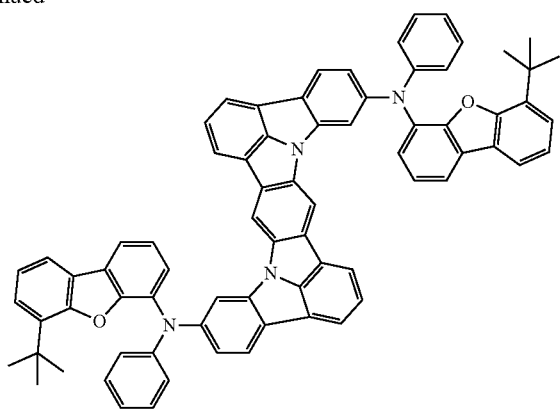
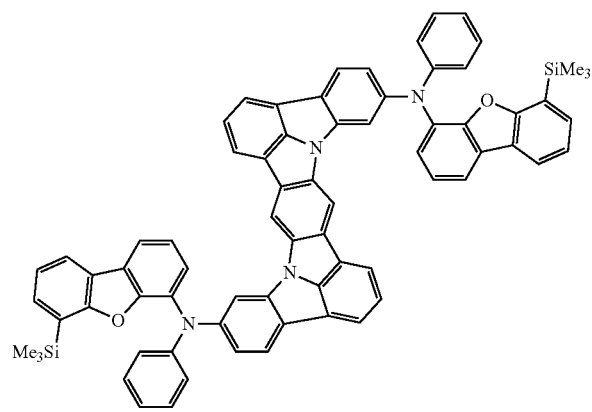
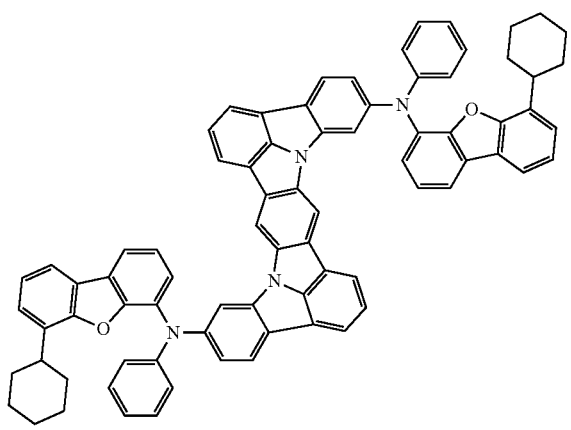
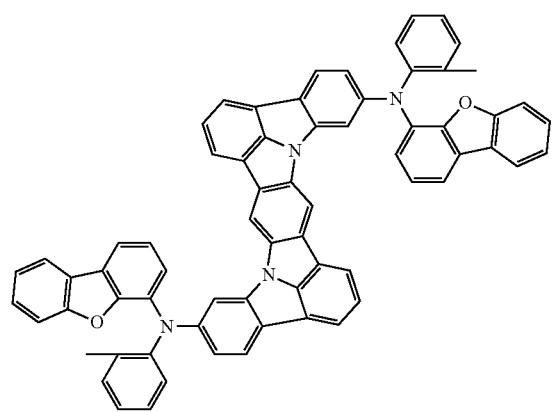
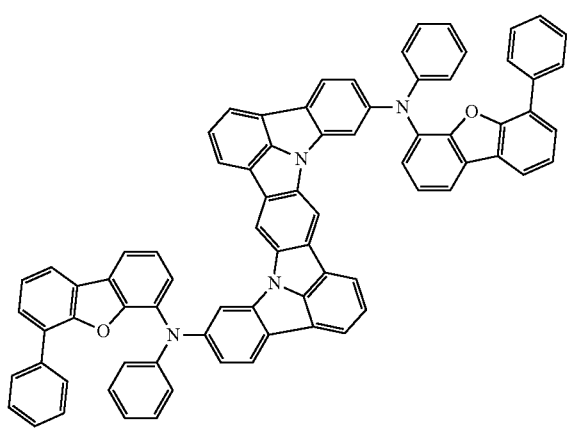

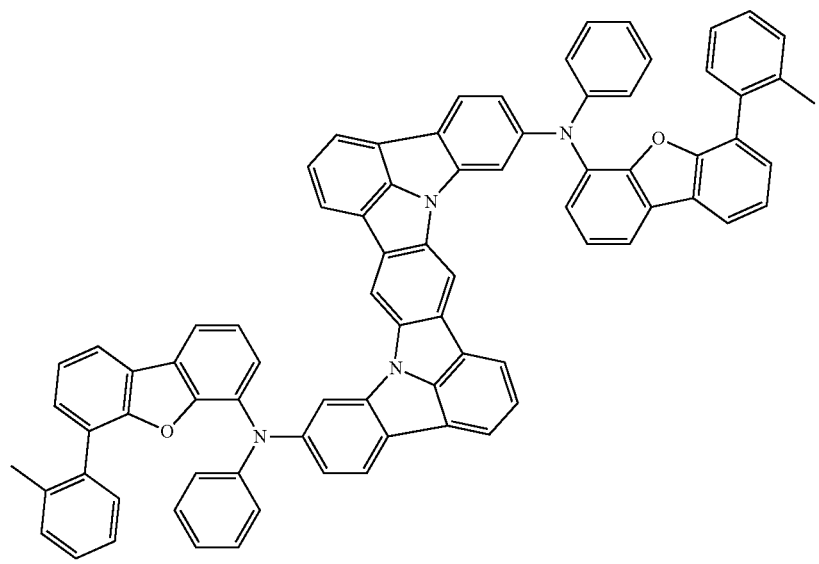
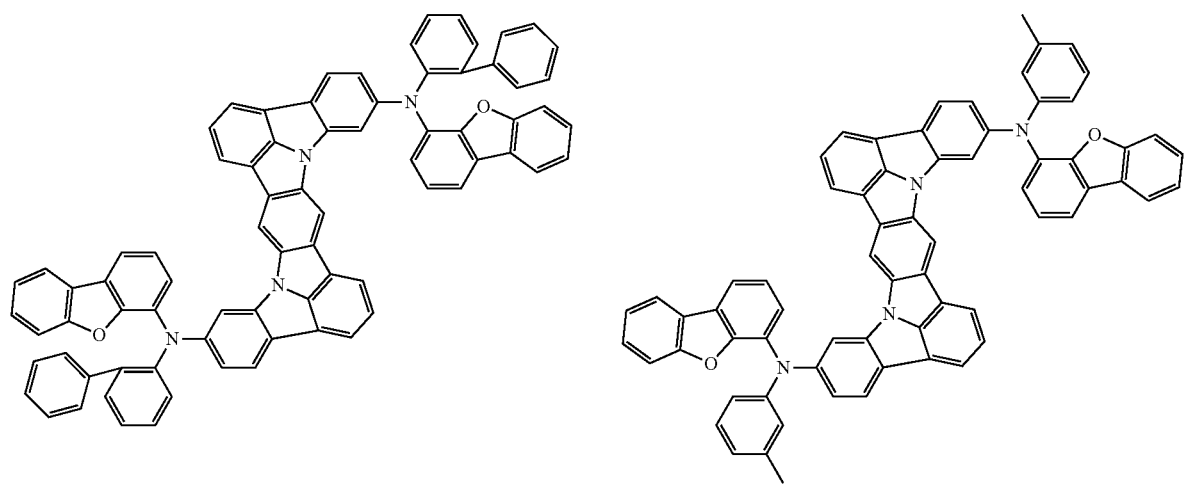
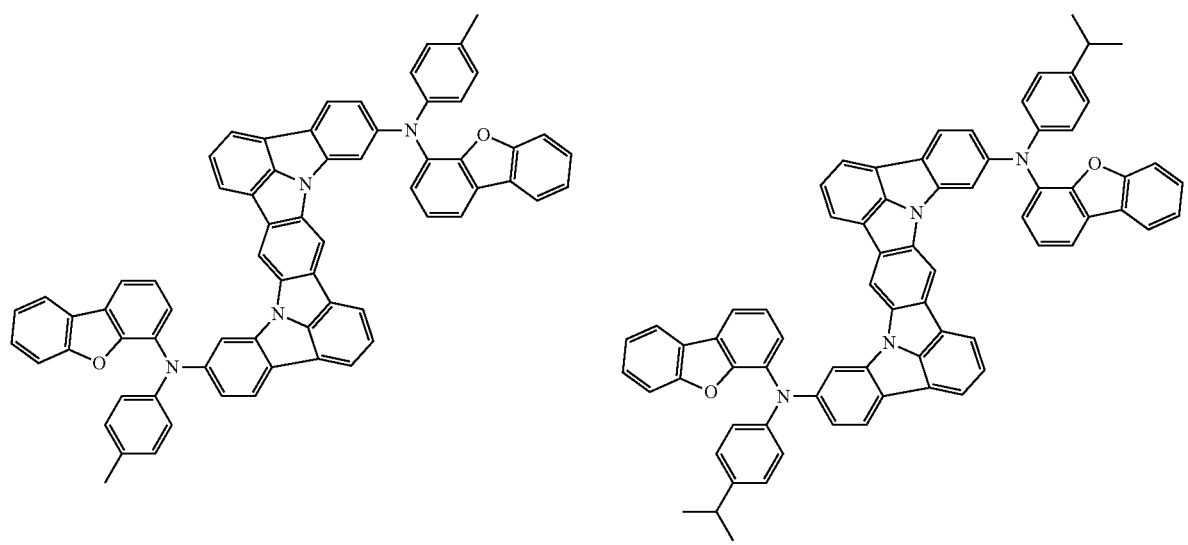

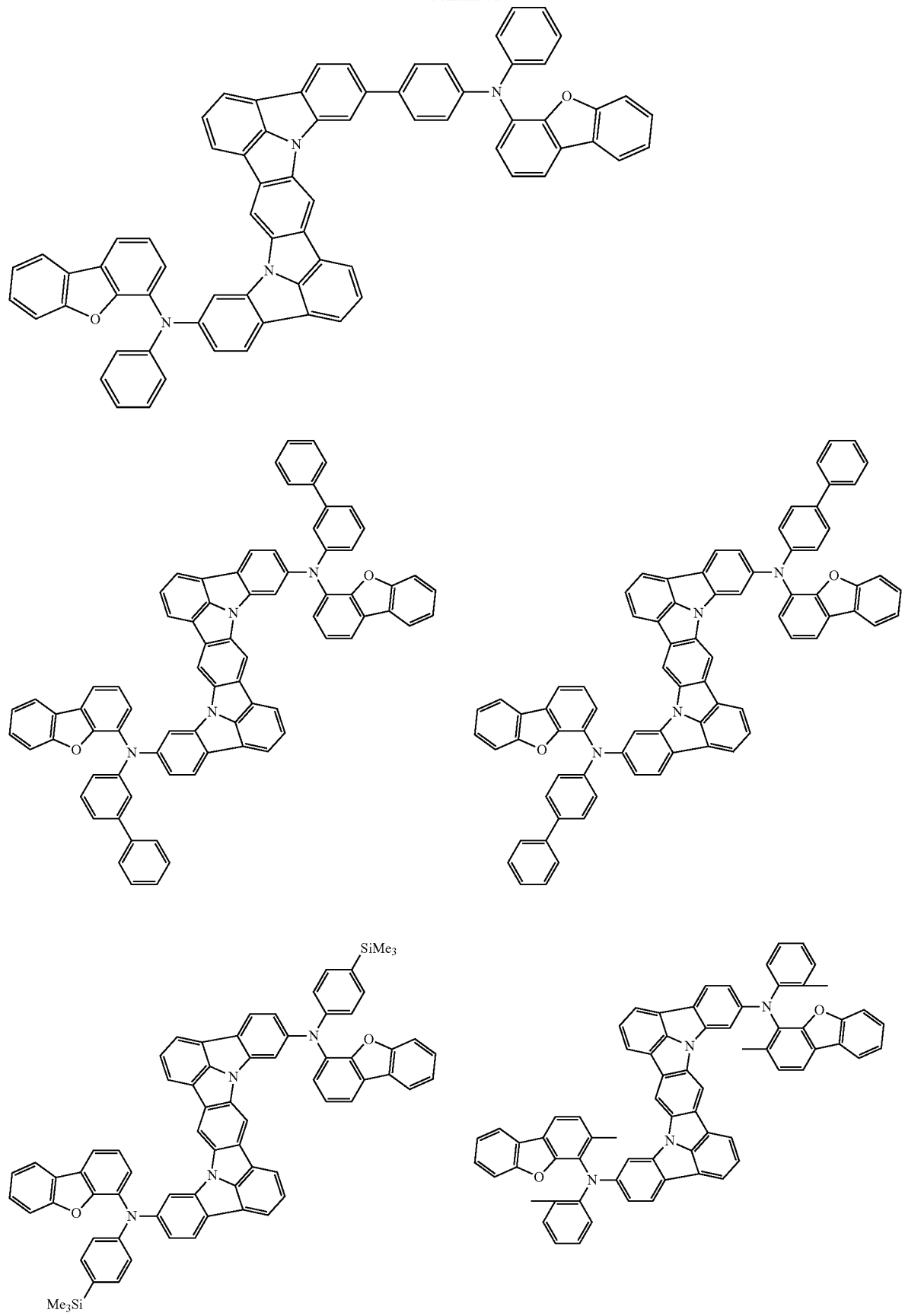

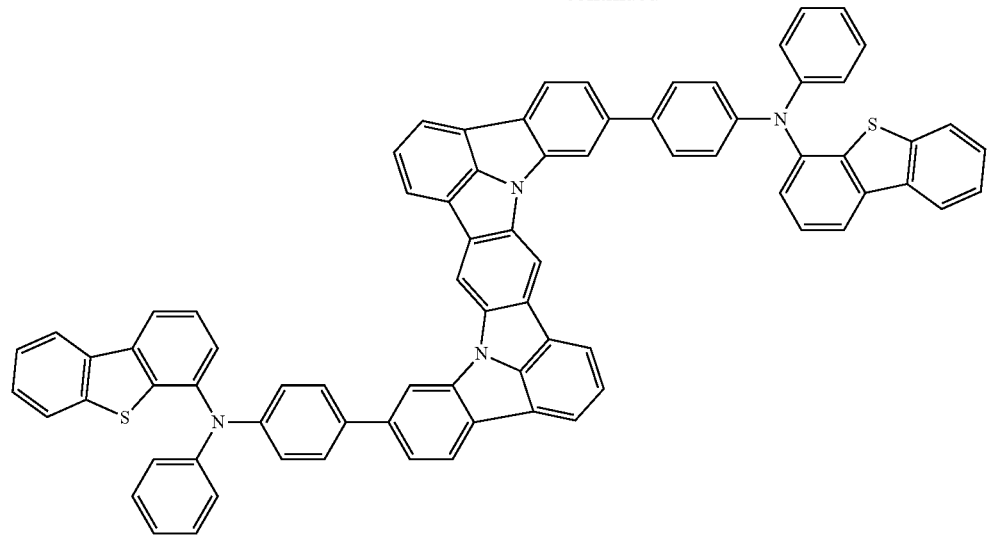
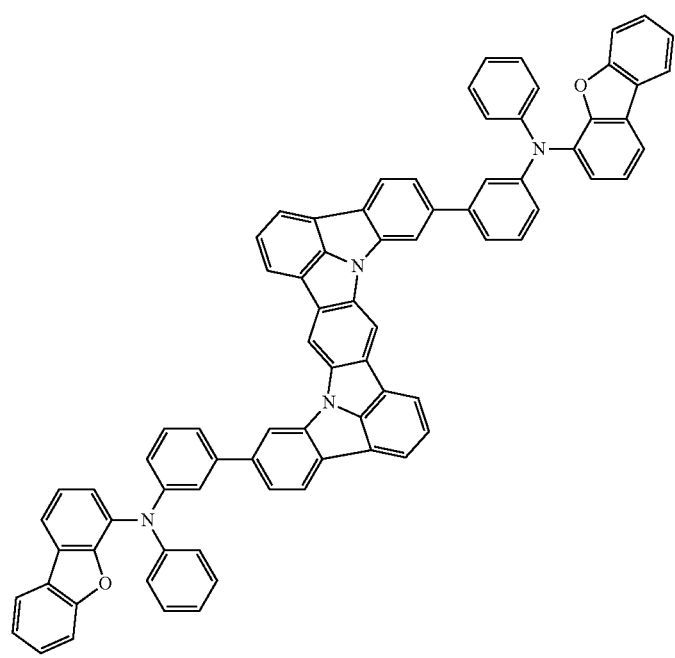

-continued
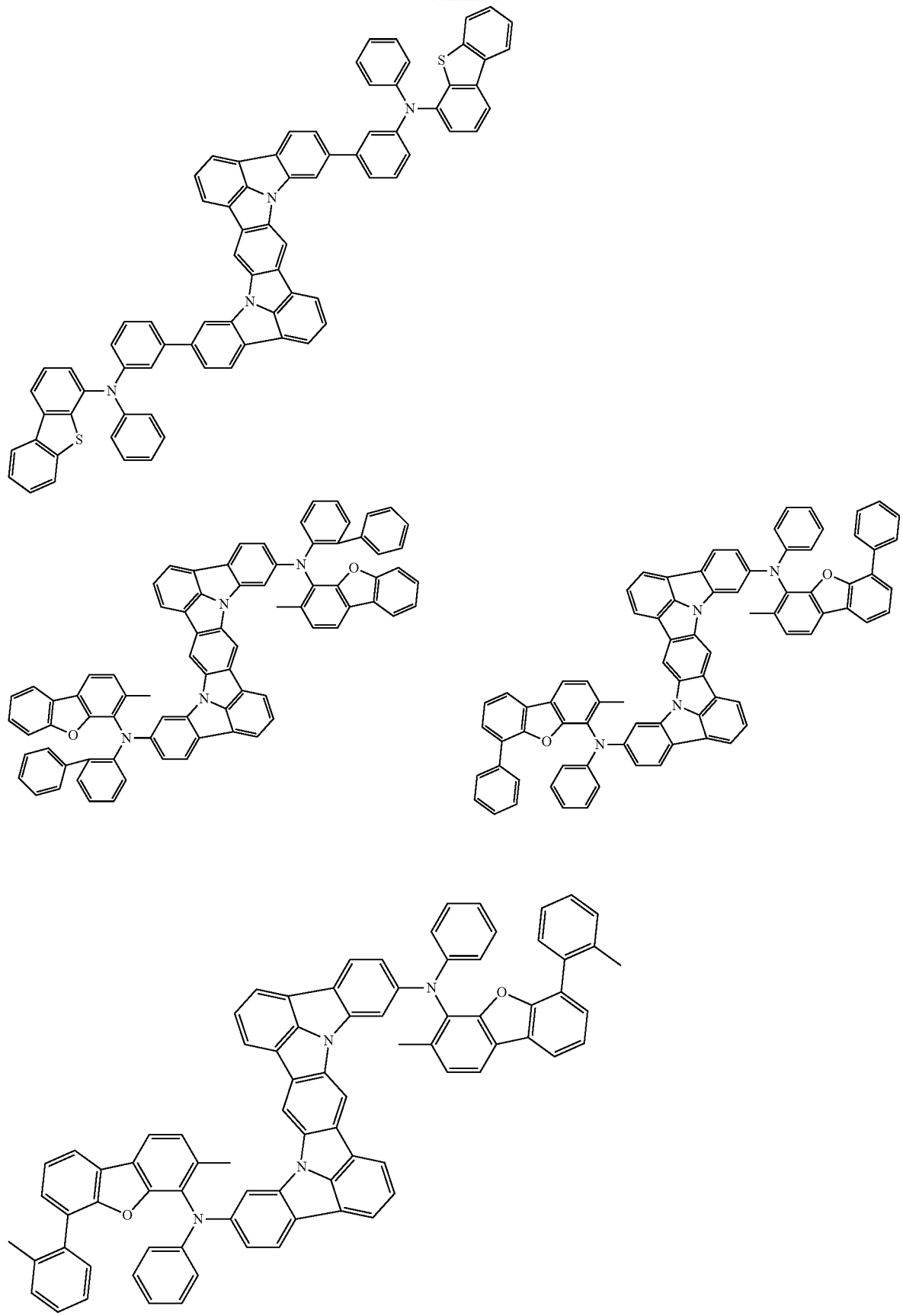

-continued
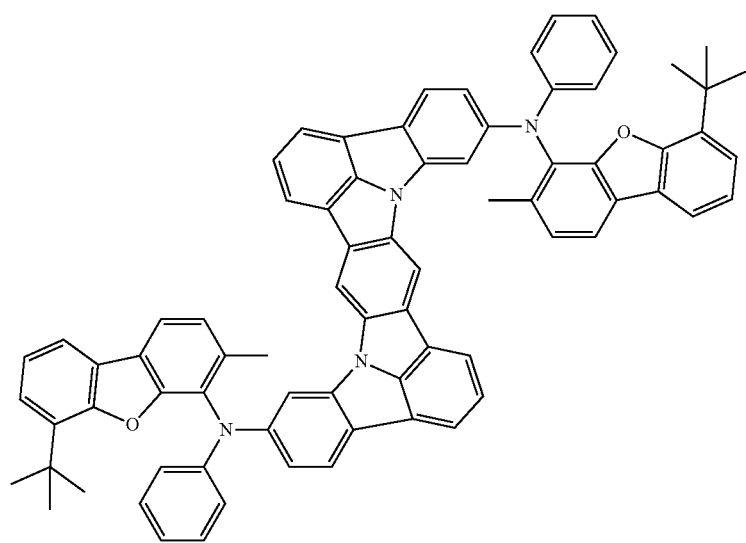
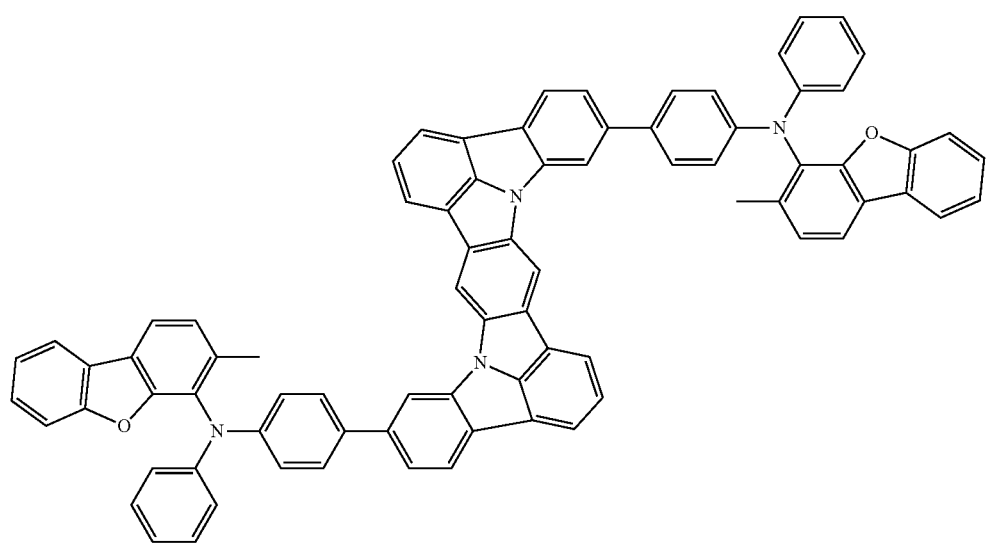

-continued
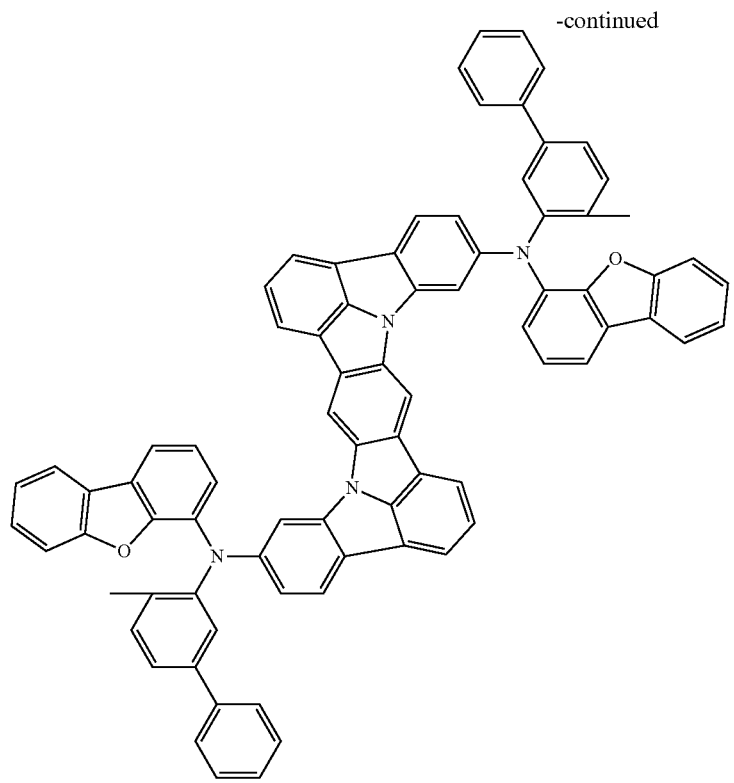
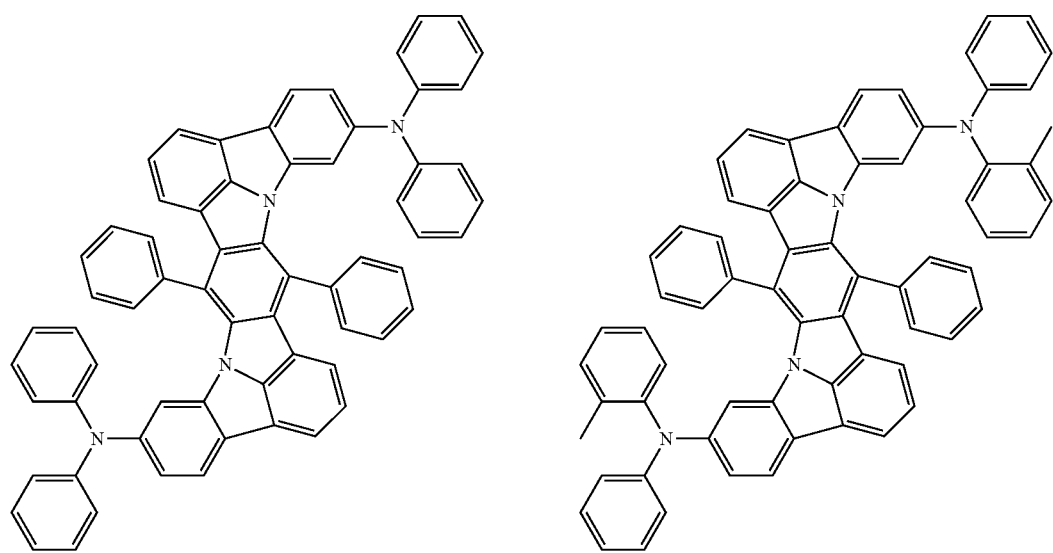

345
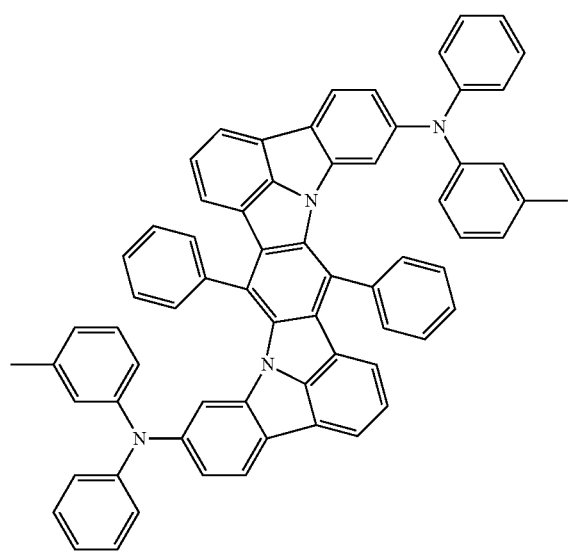
346
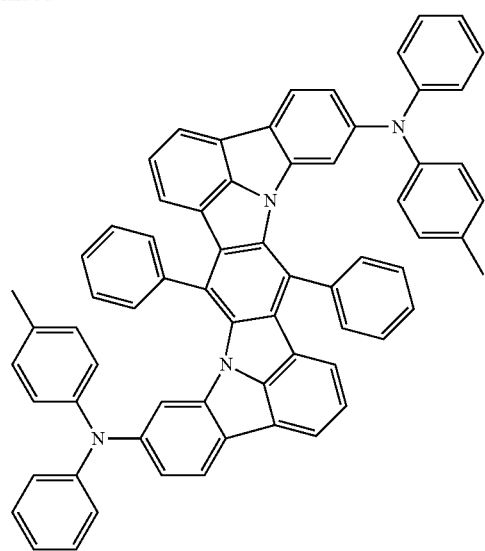
-continued
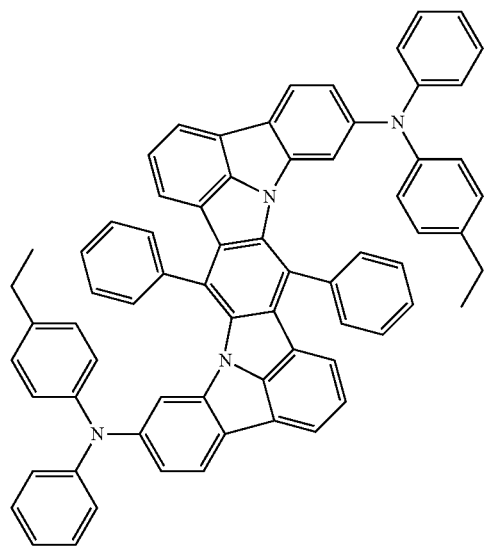
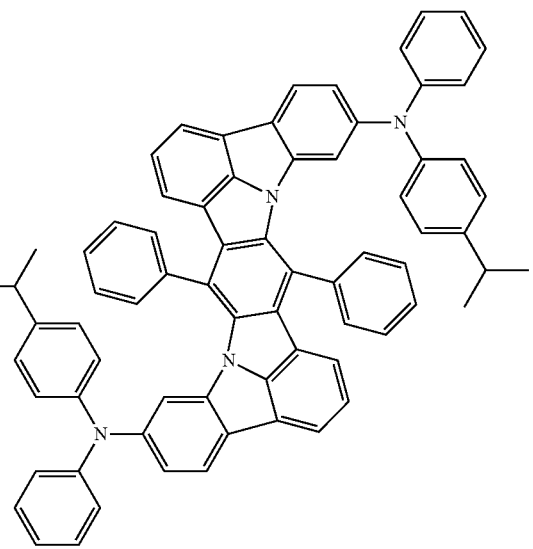
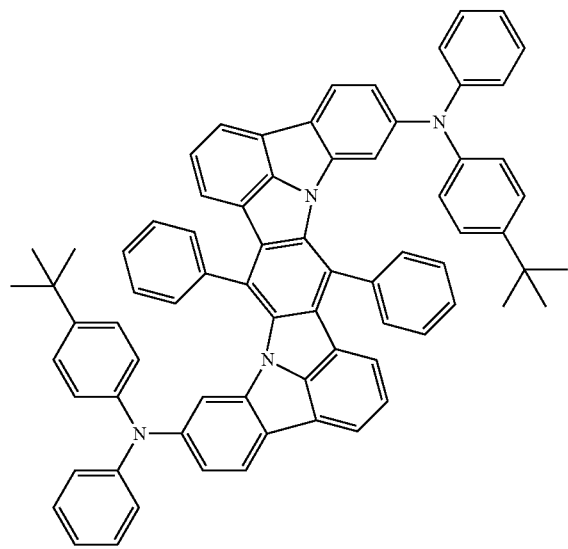
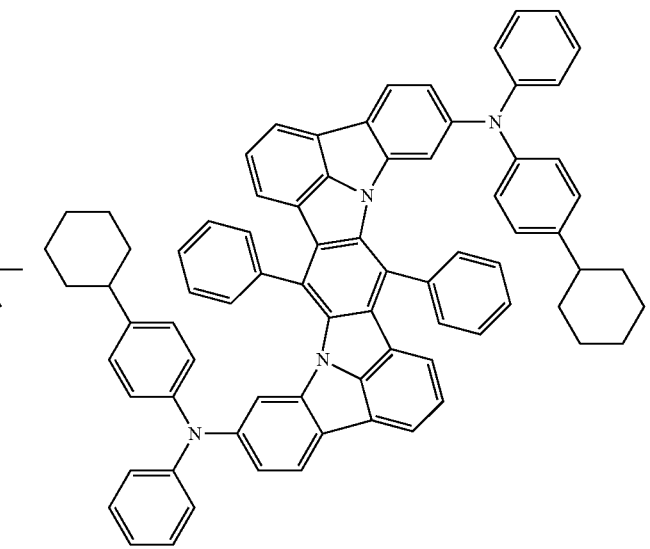

347
348
-continued
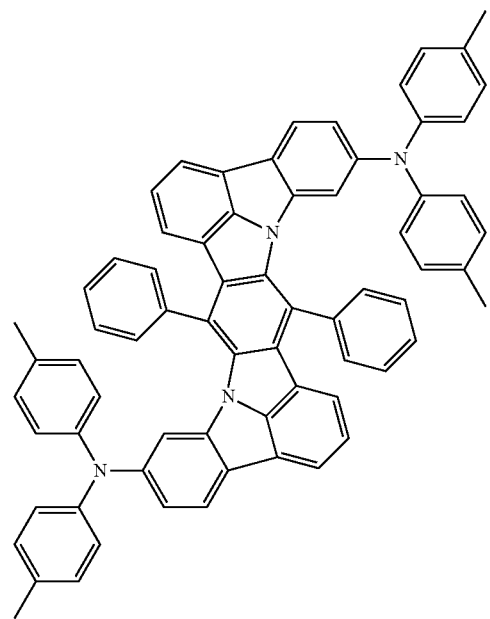
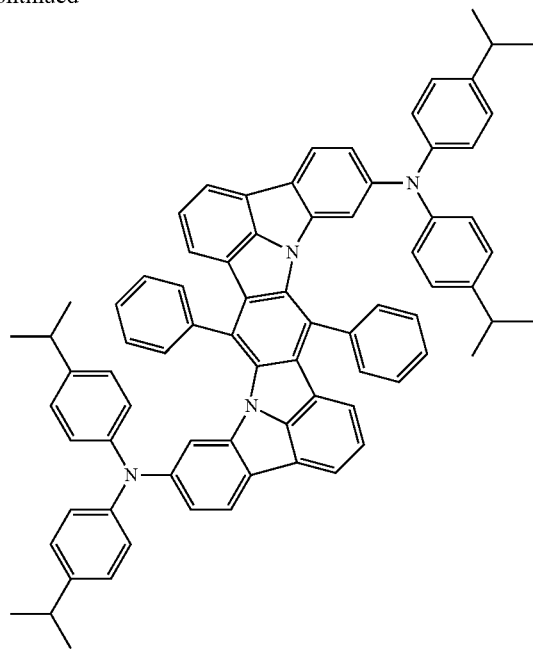
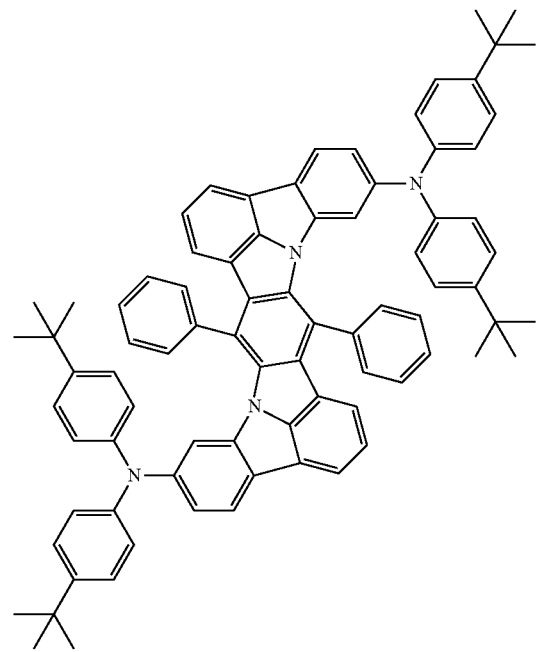
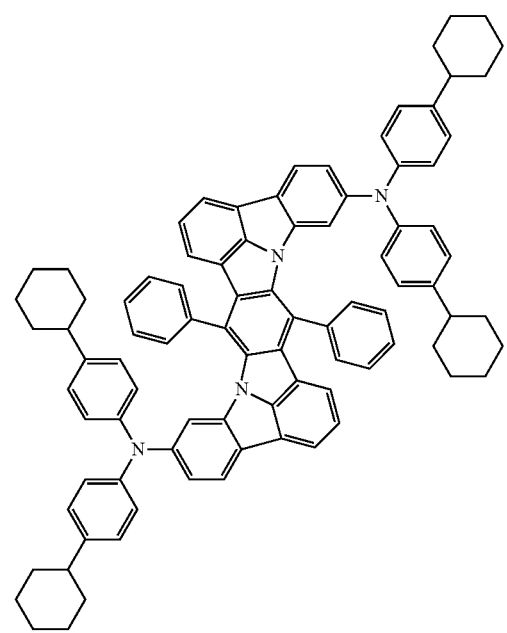

-continued
| 349 | 350 |
|---|---|
| 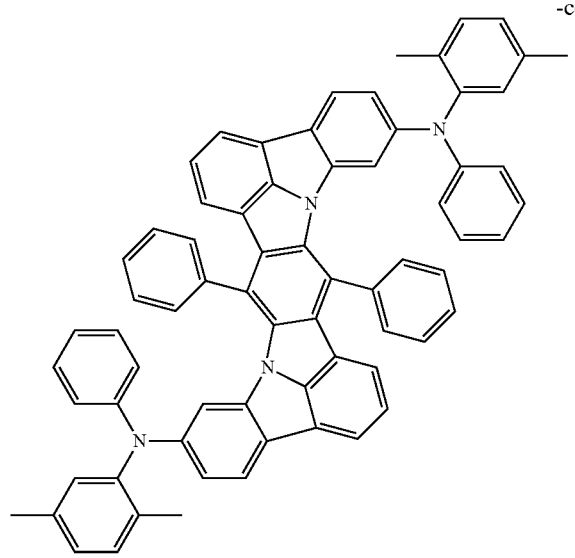 | 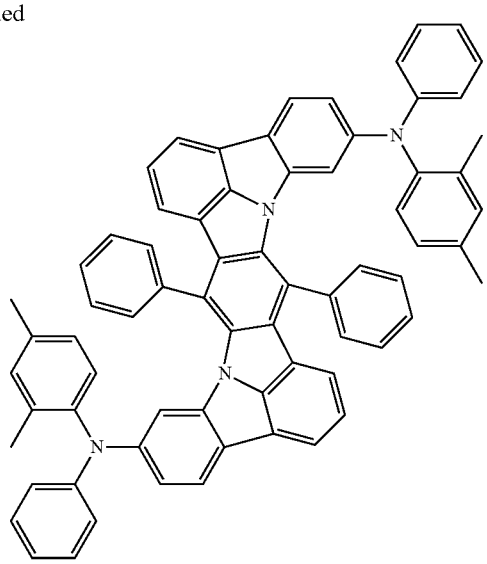 |
| 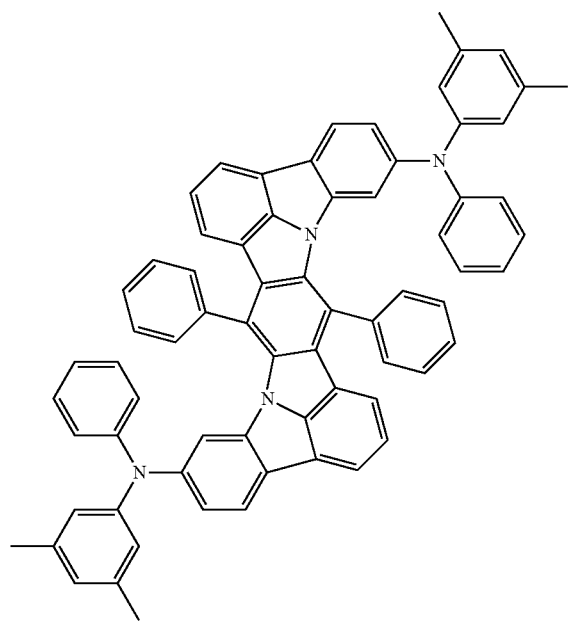 | 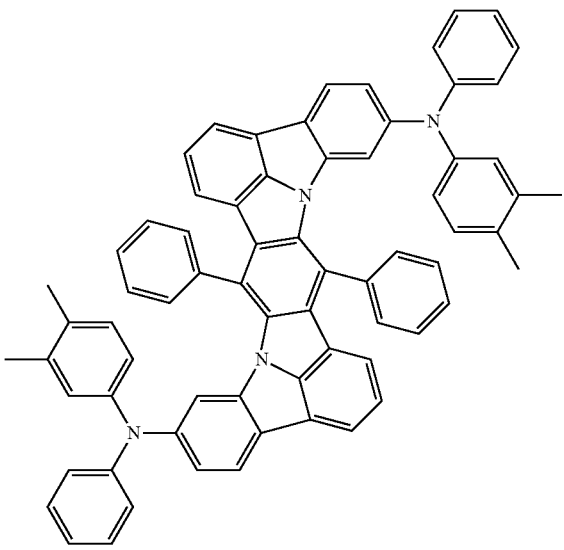 |

-continued
351
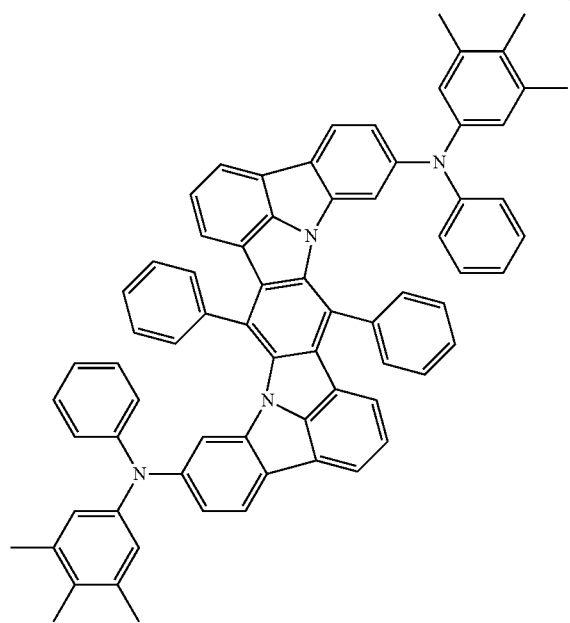
352
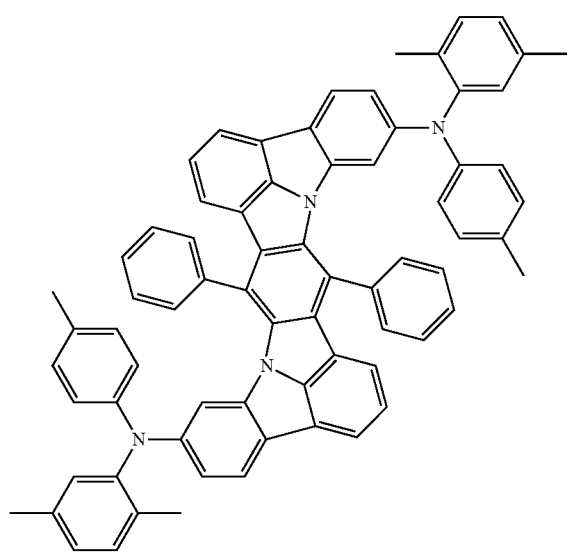
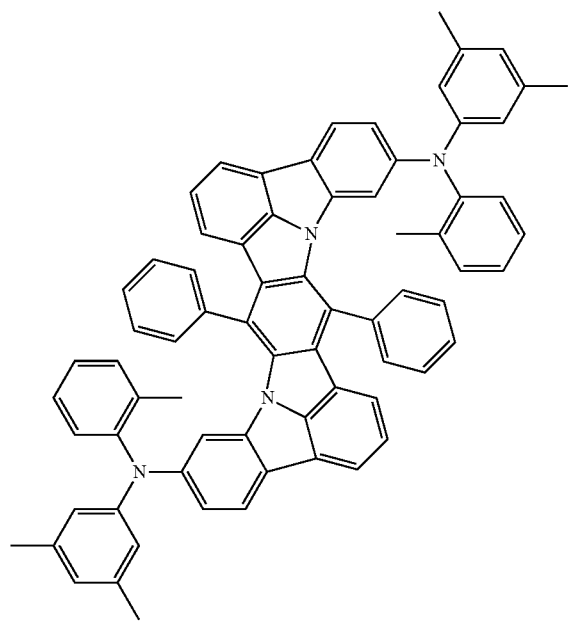

-continued
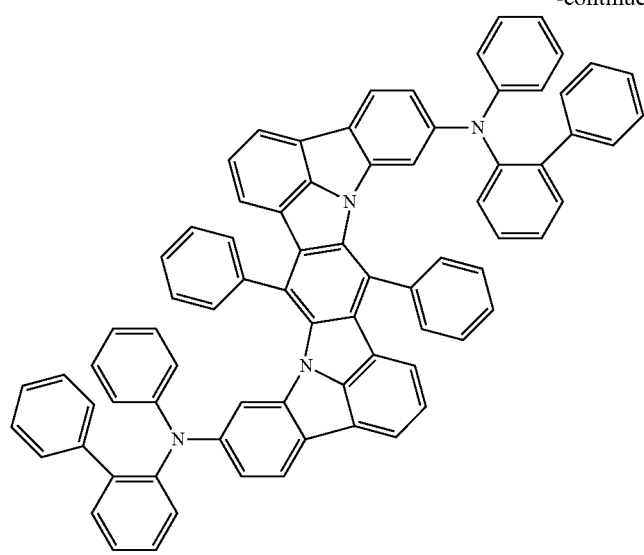
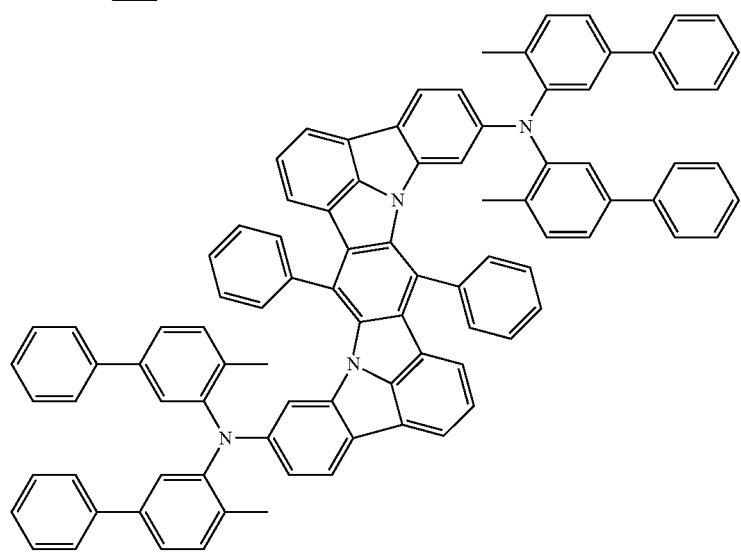
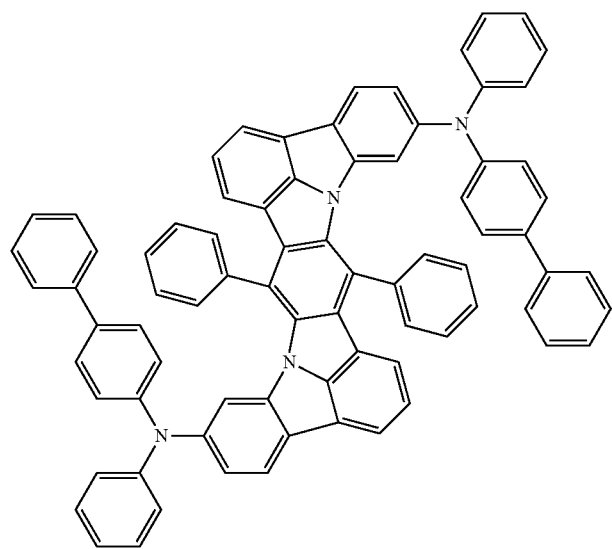

-continued
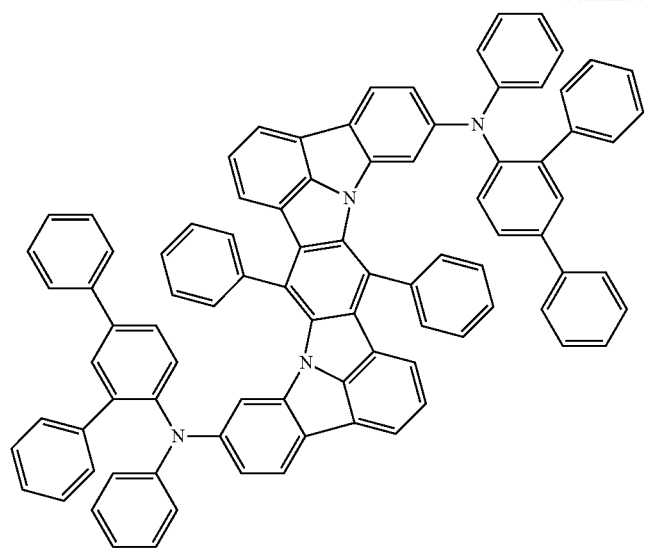
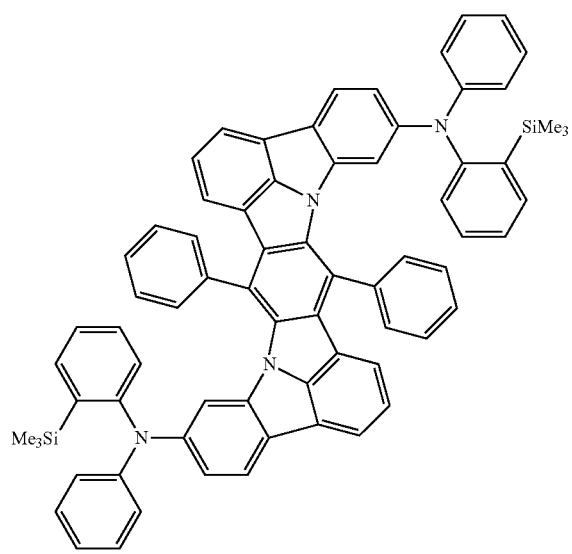
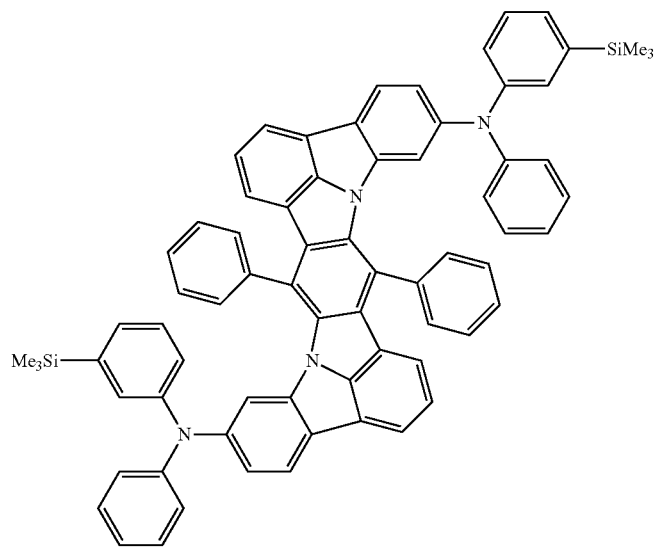

357
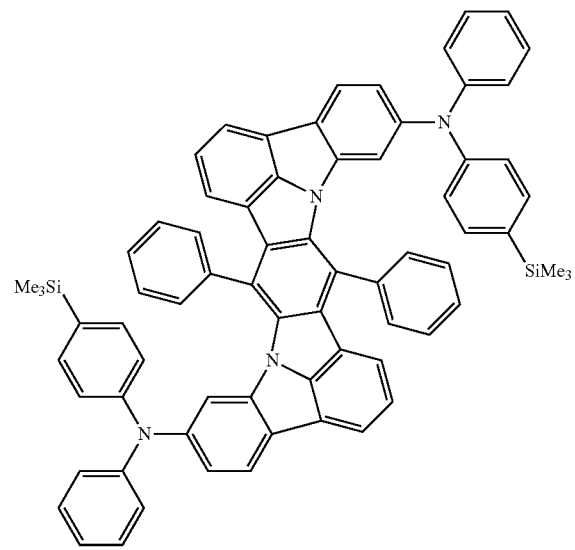
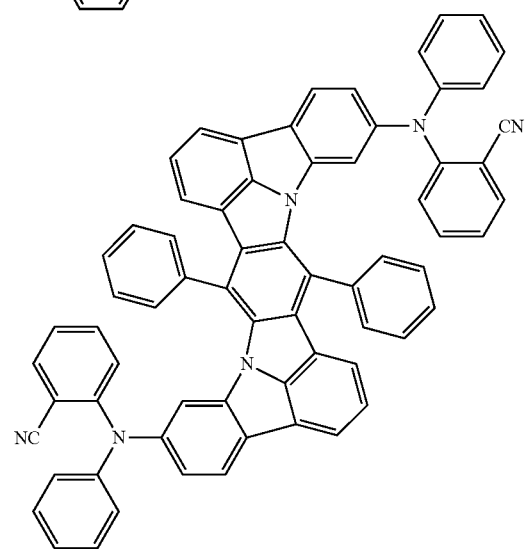
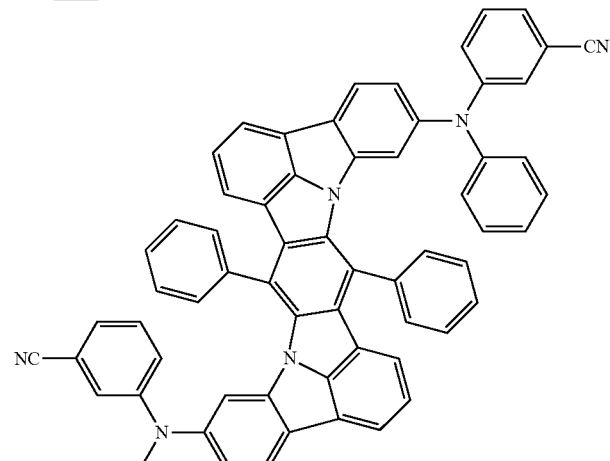
358
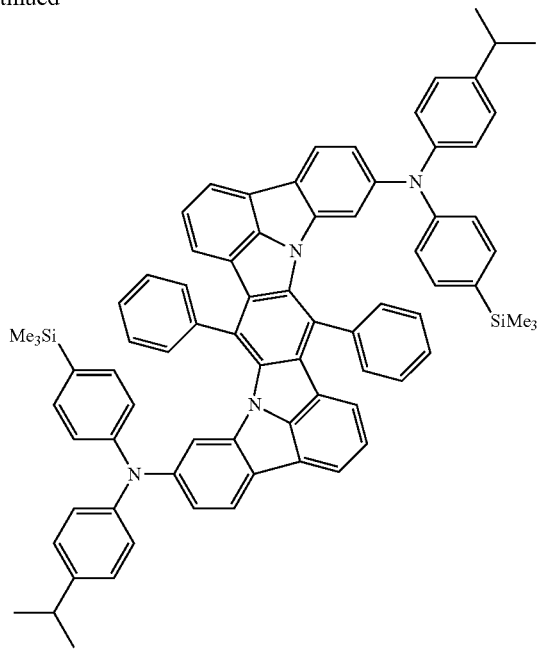
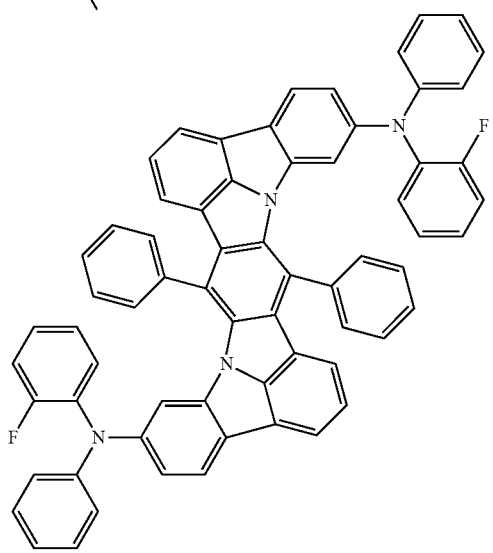
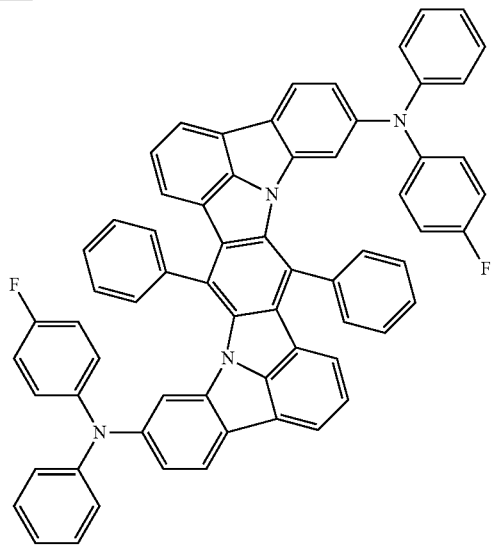

359            360
-continued
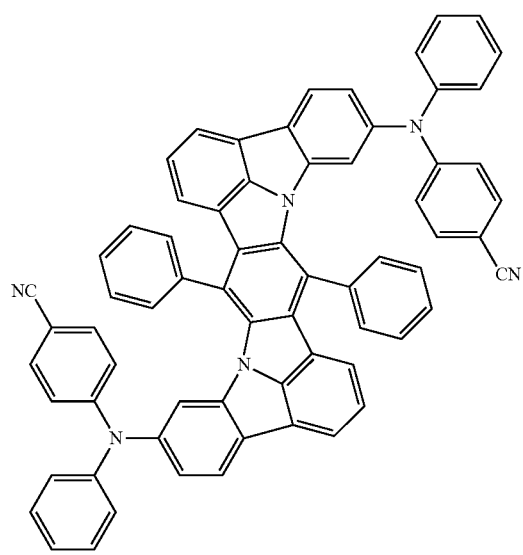
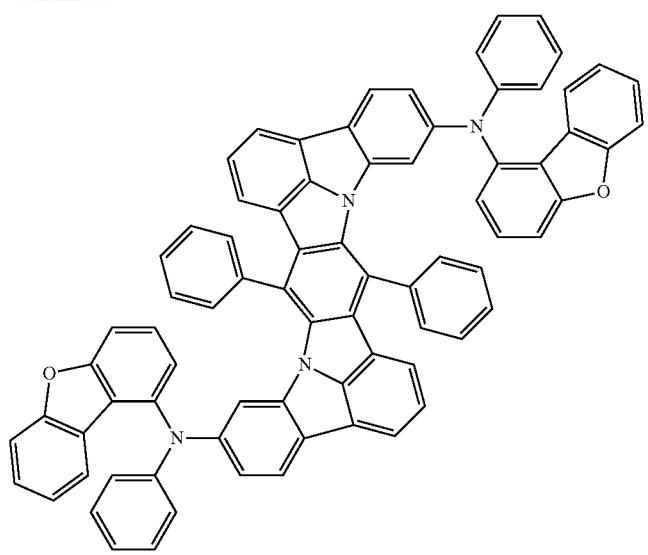
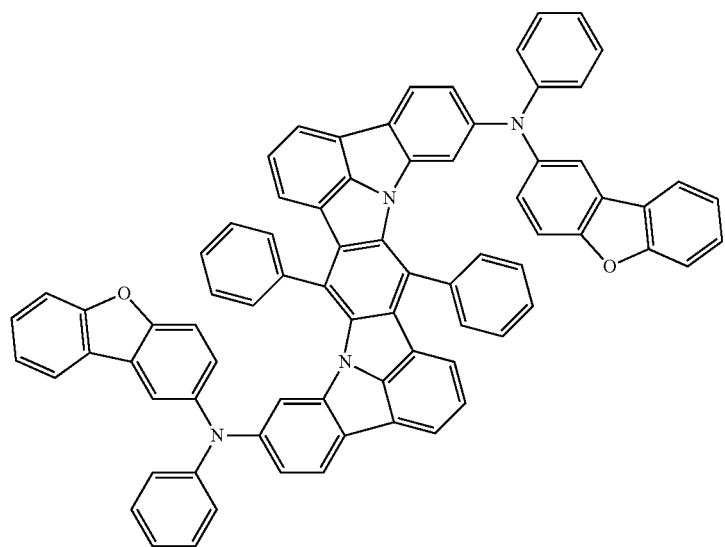
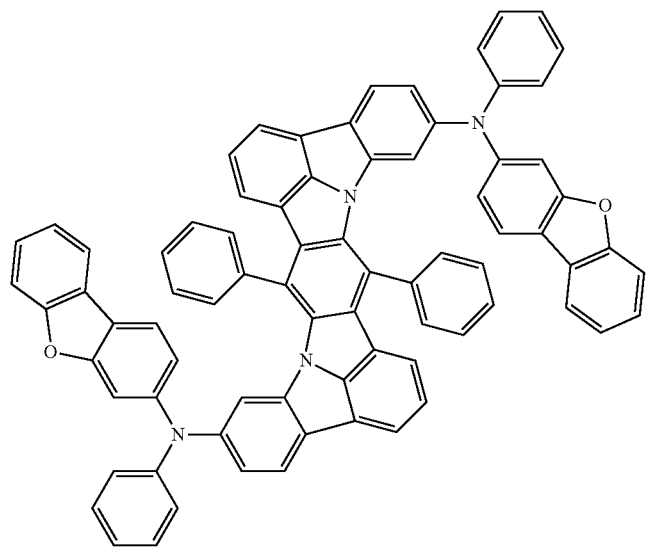

-continued
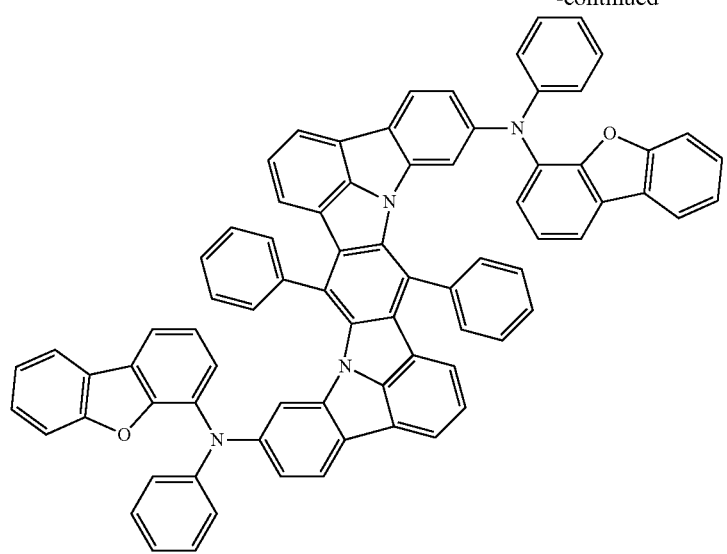
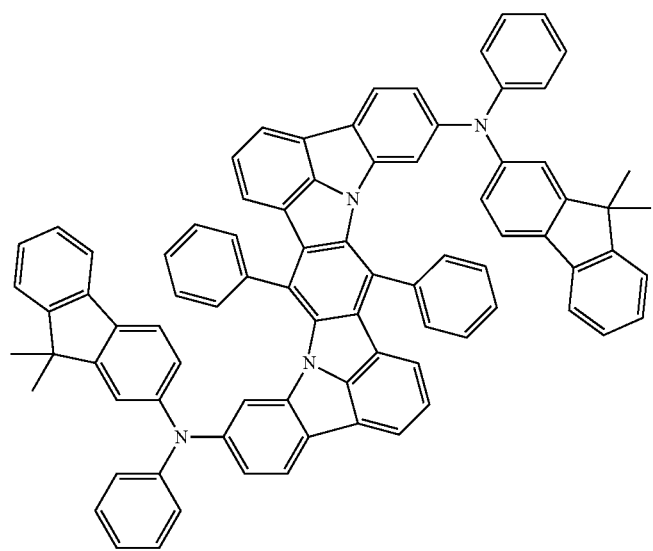
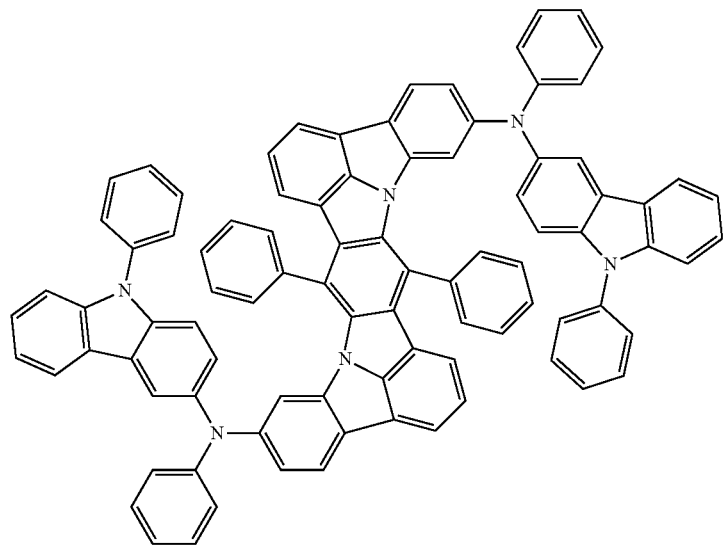

-continued
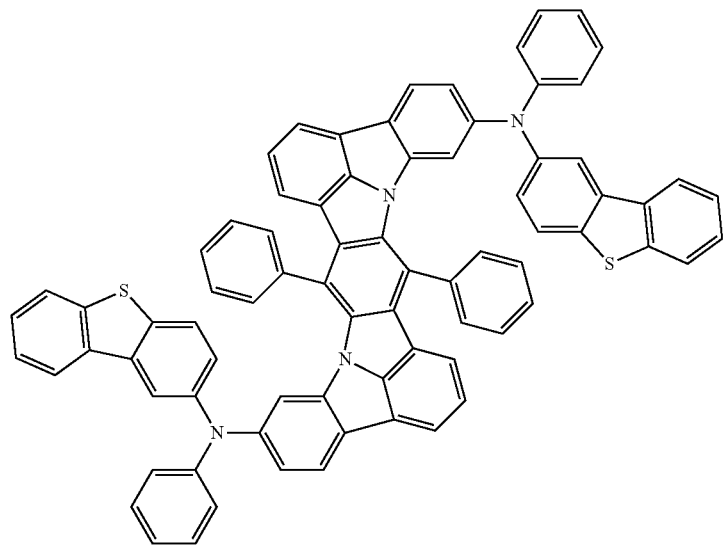
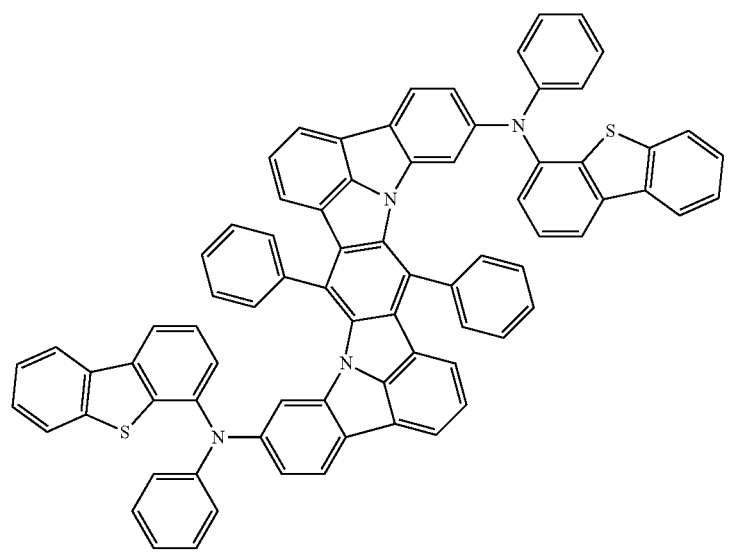
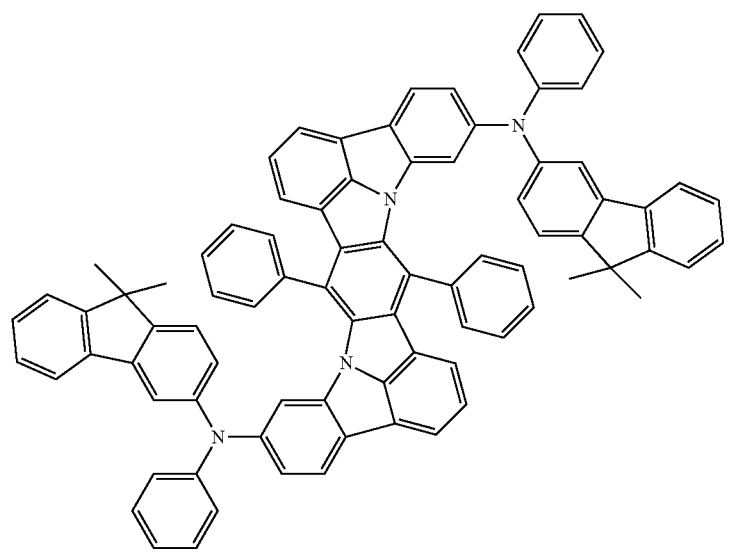

-continued
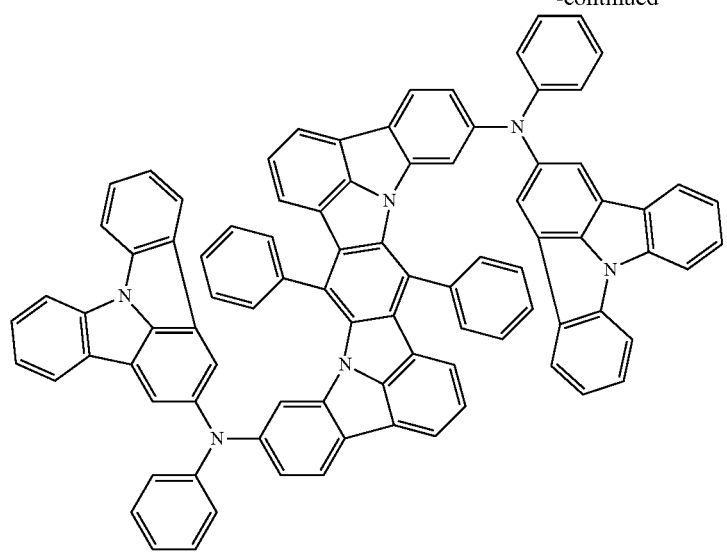
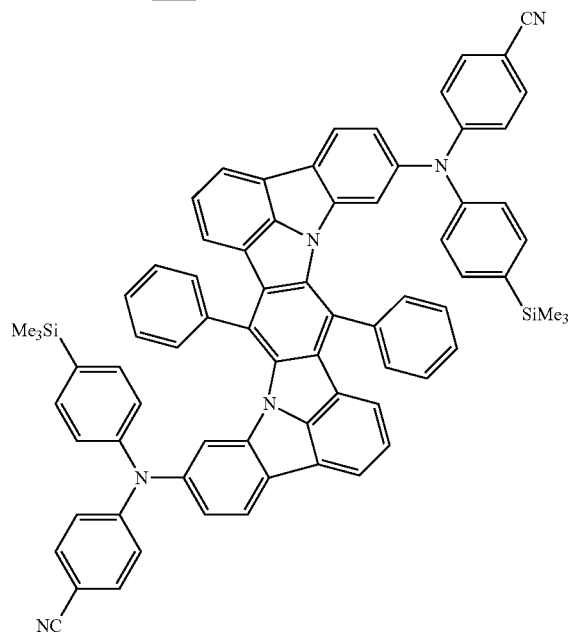
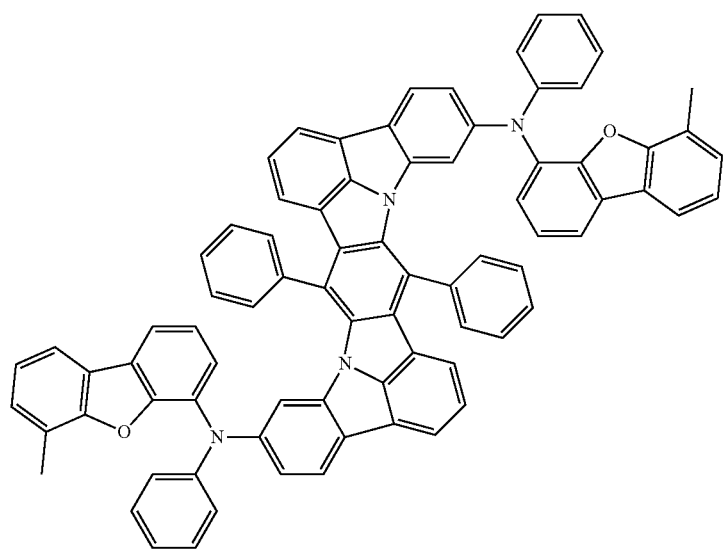

-continued
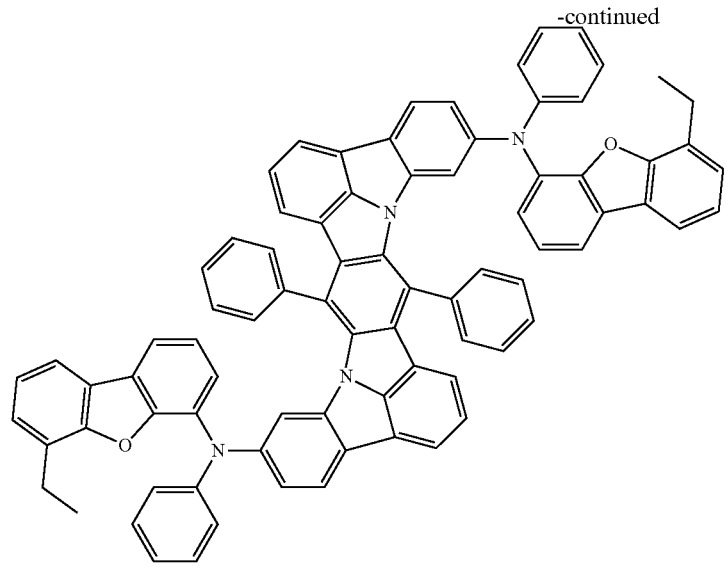
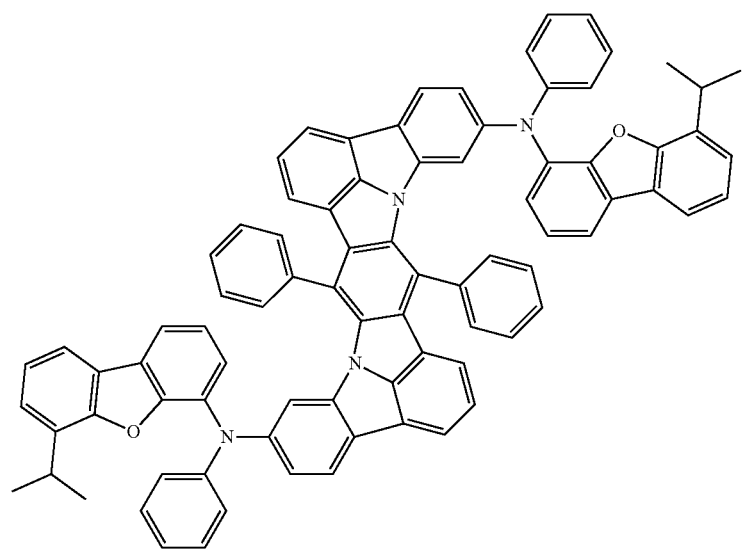
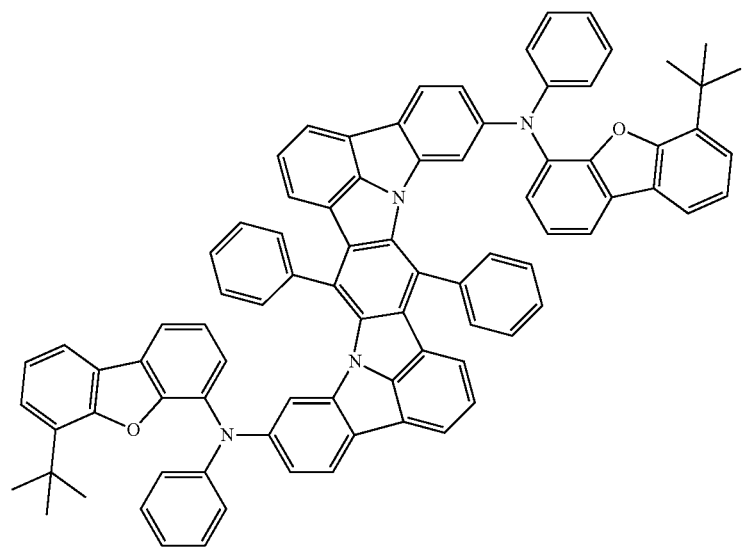

-continued
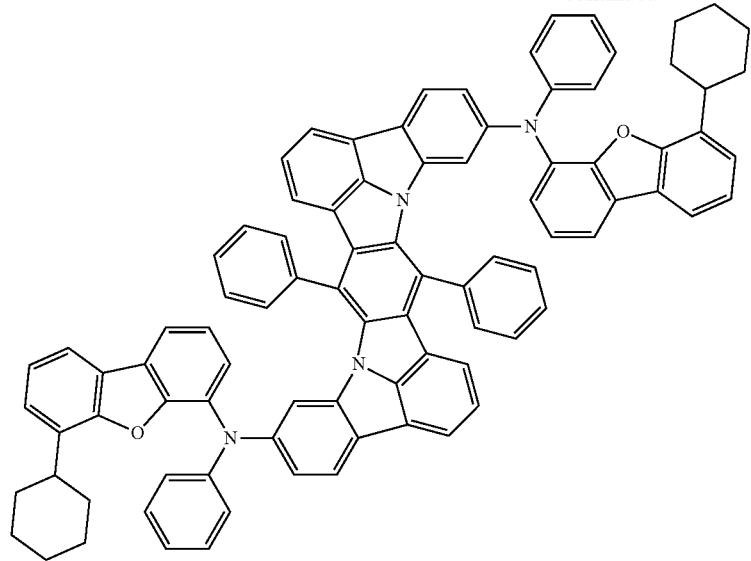
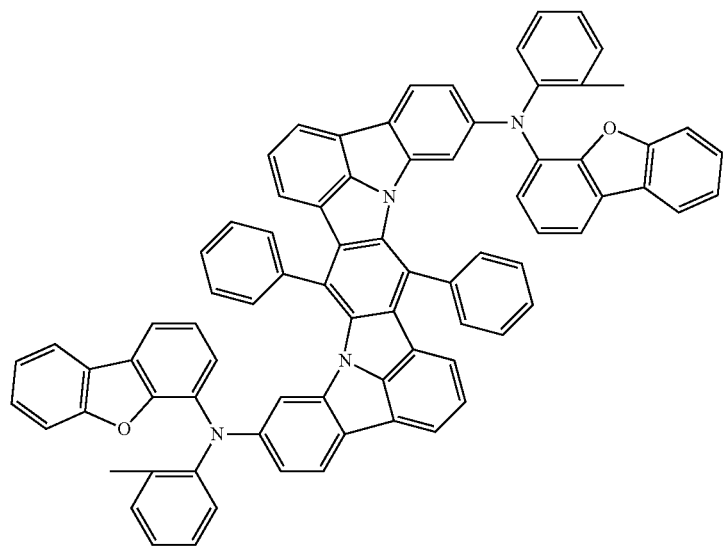
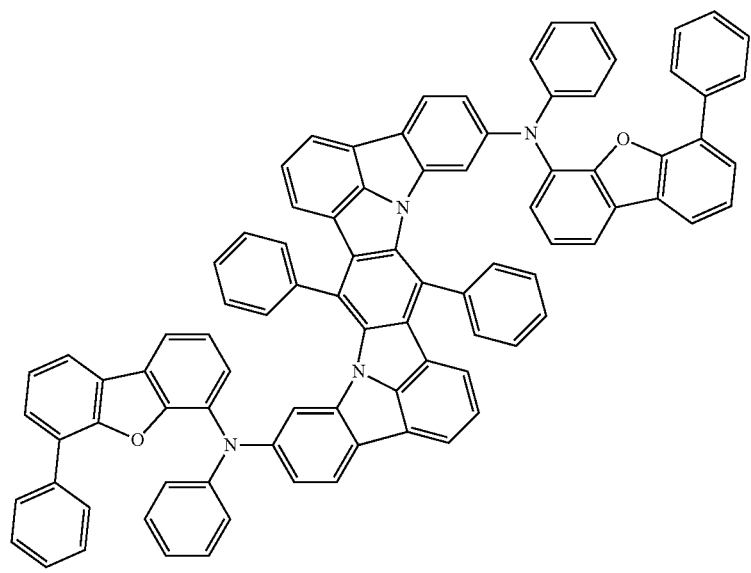

-continued
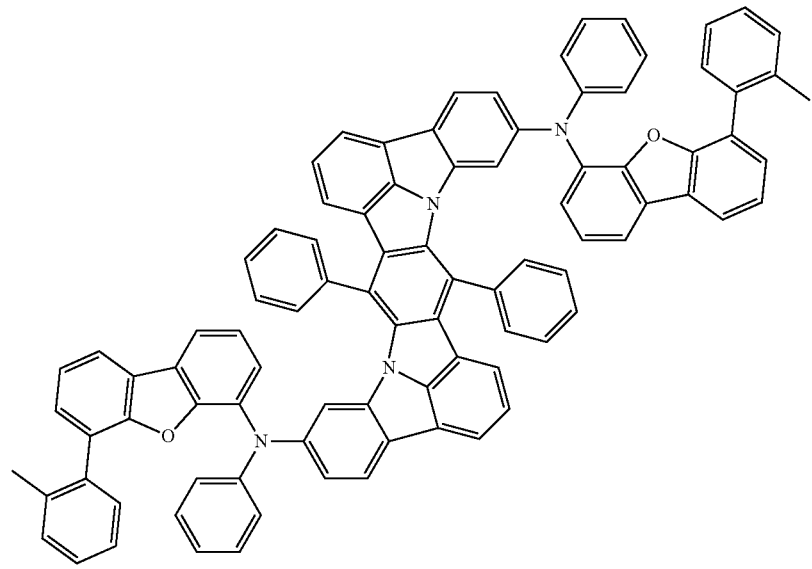
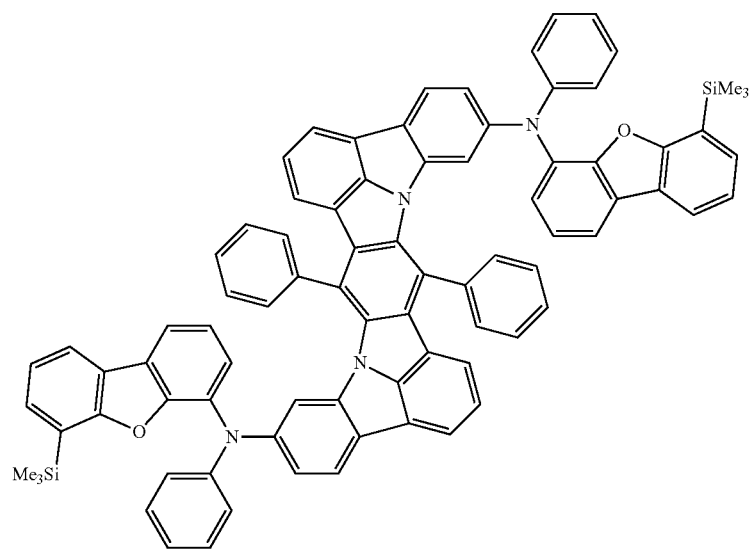
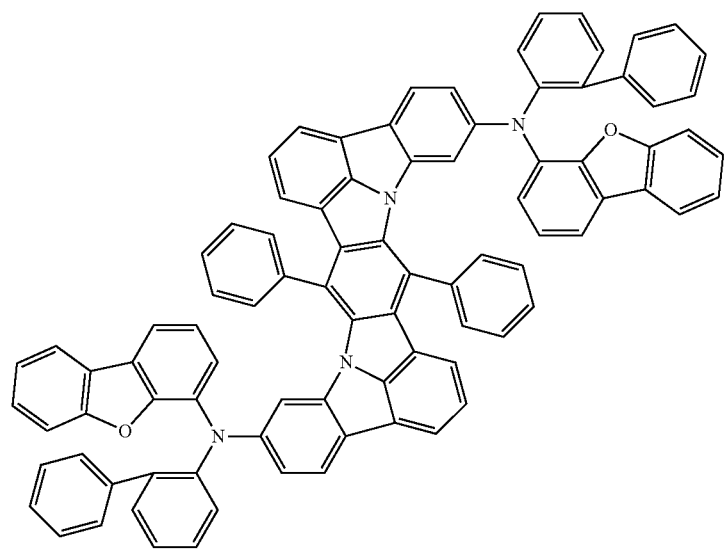

-continued
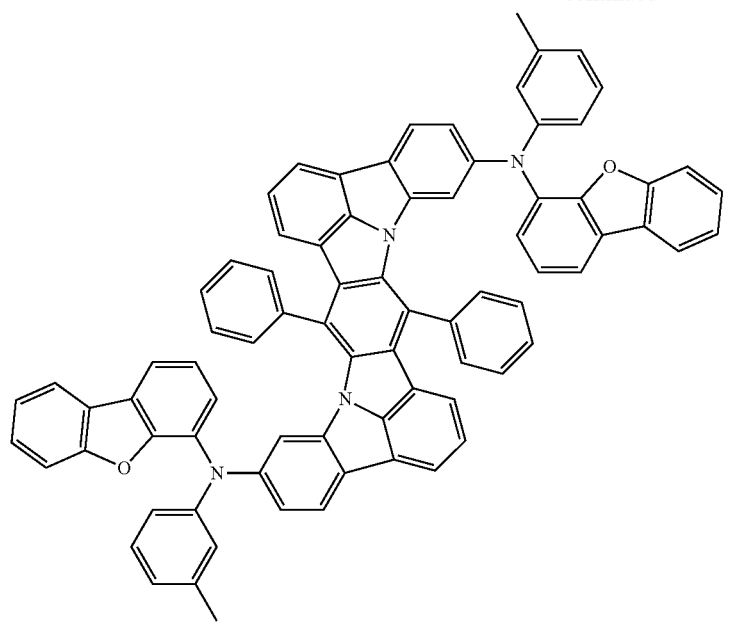
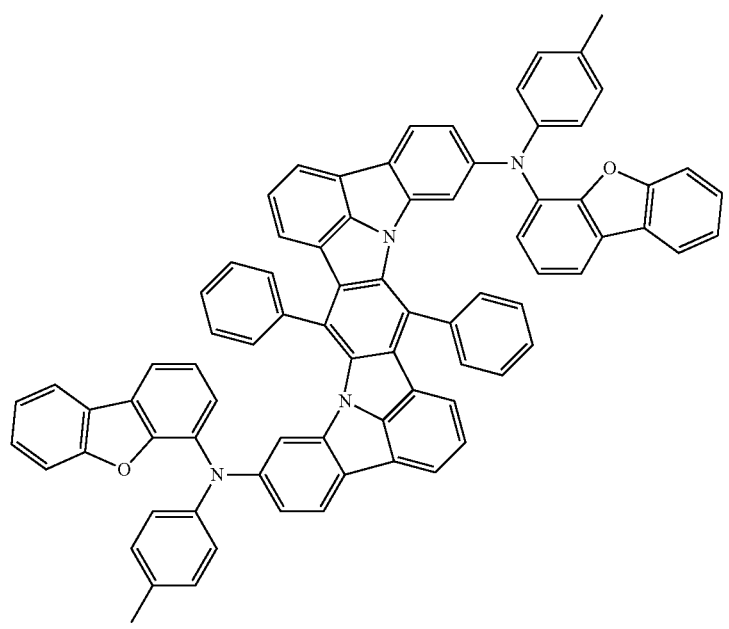

-continued
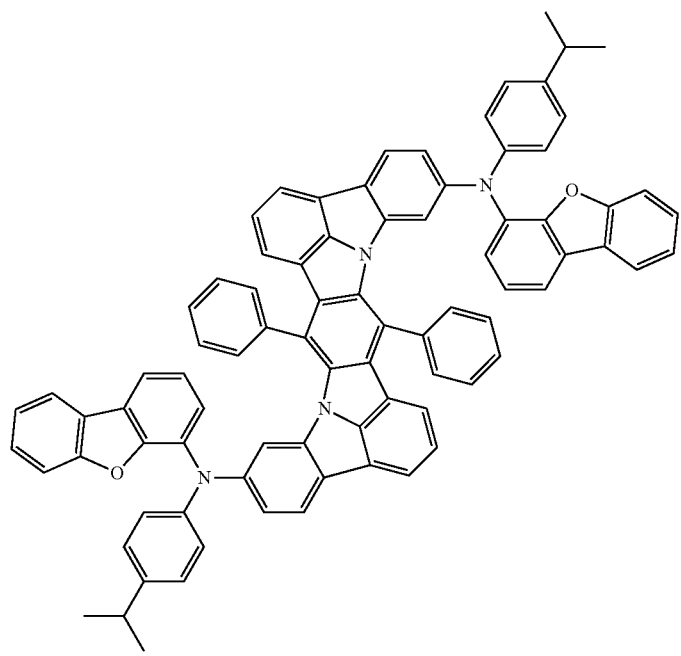
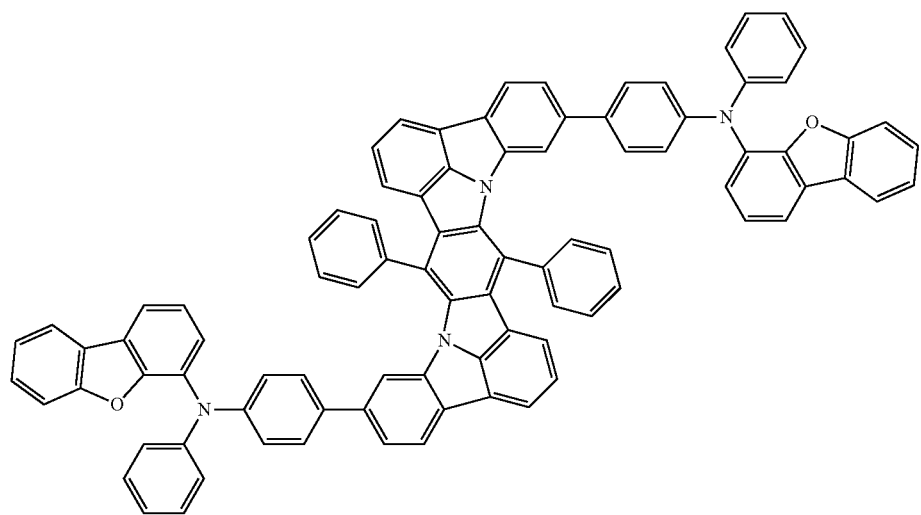

377 378
-continued
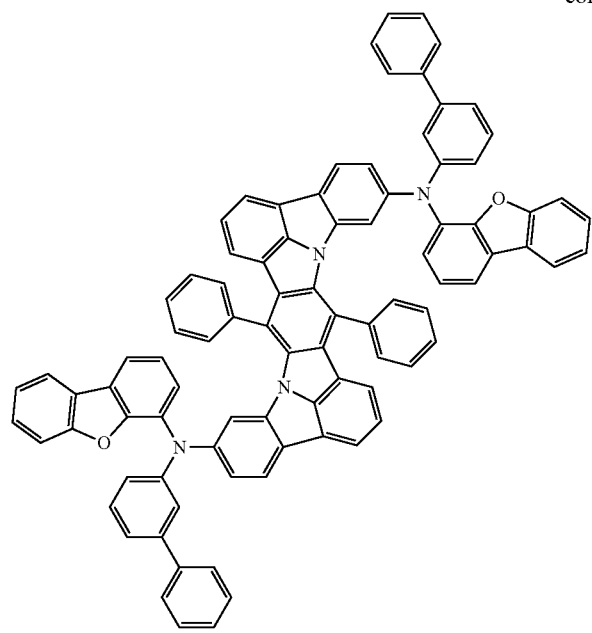
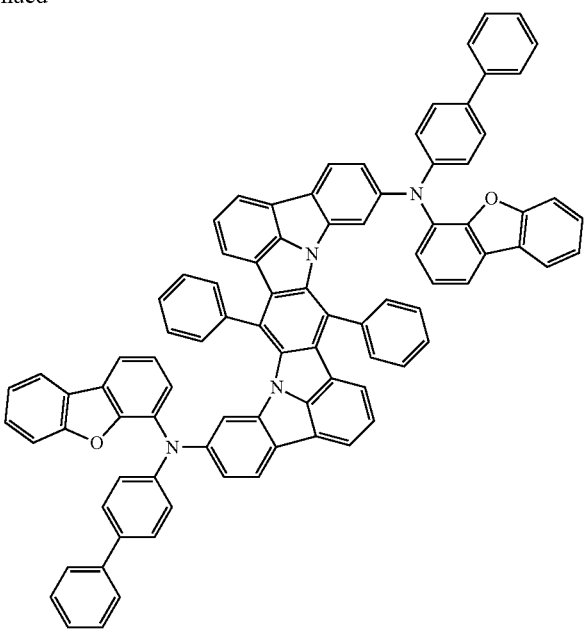
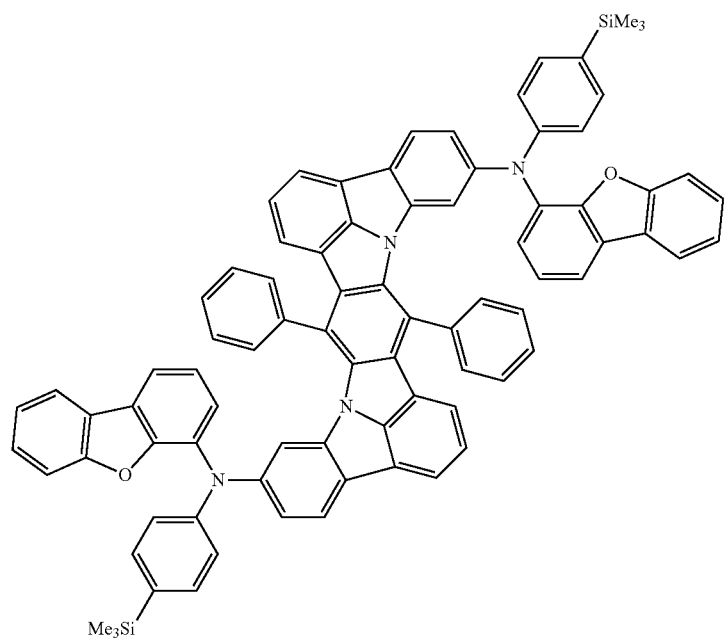

-continued
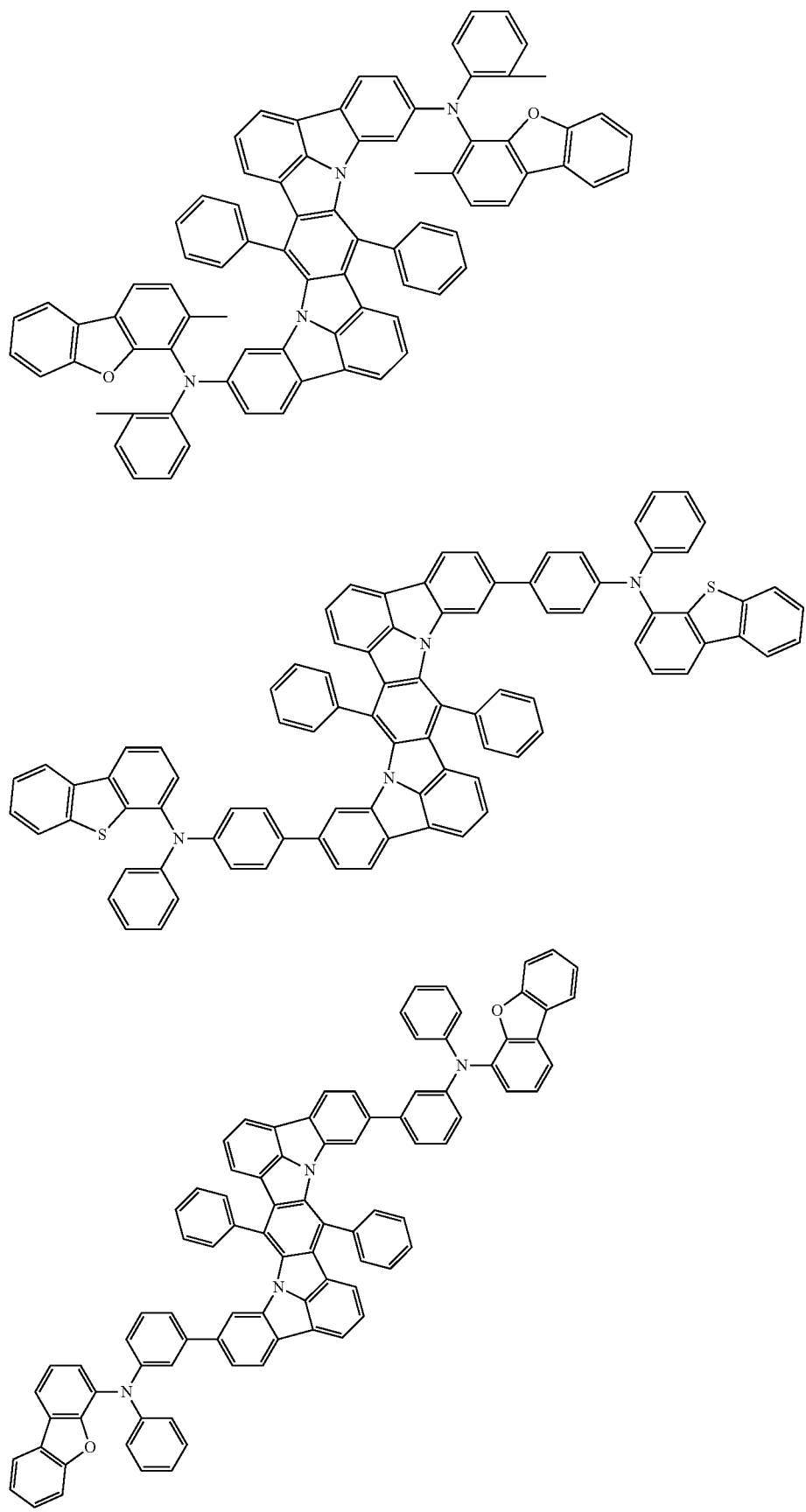

-continued
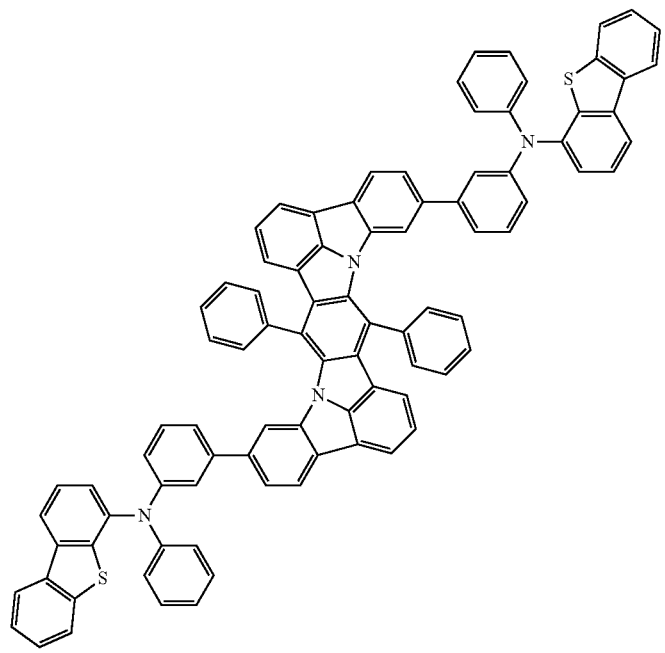
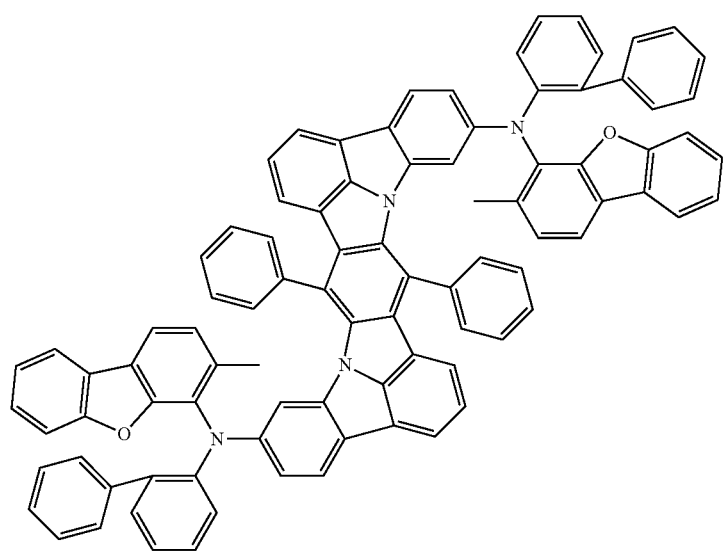

-continued
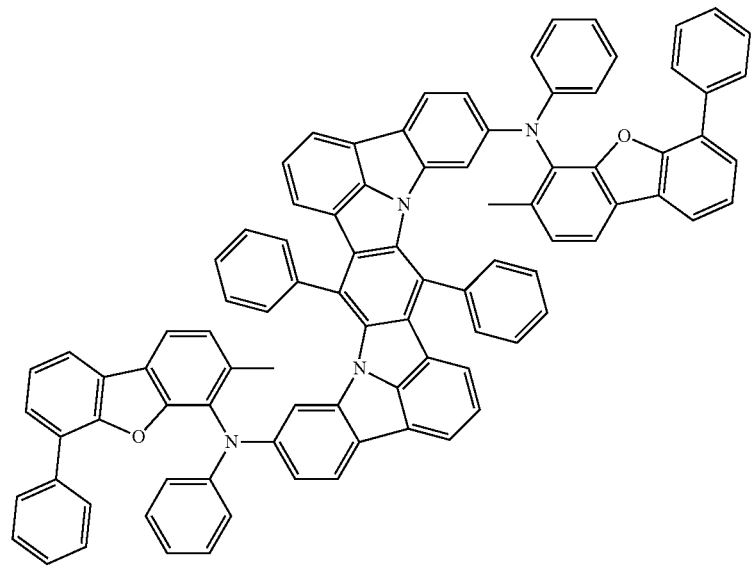
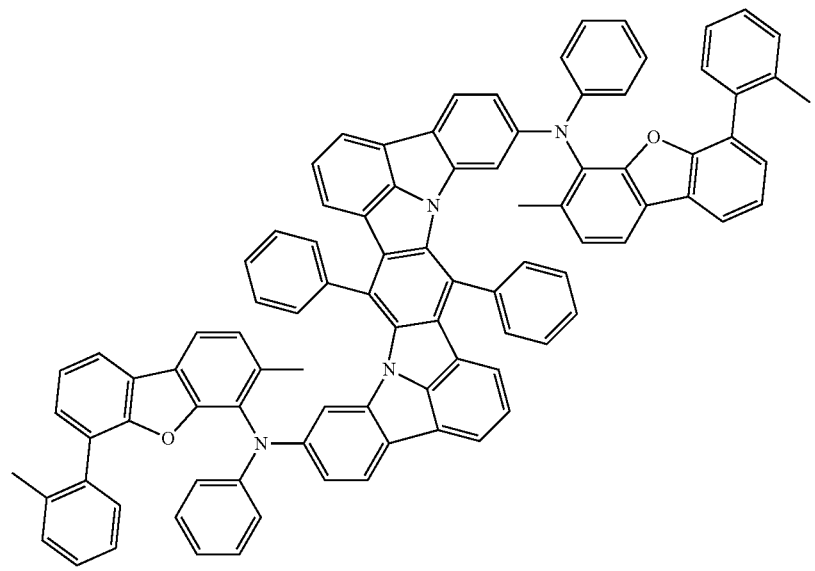
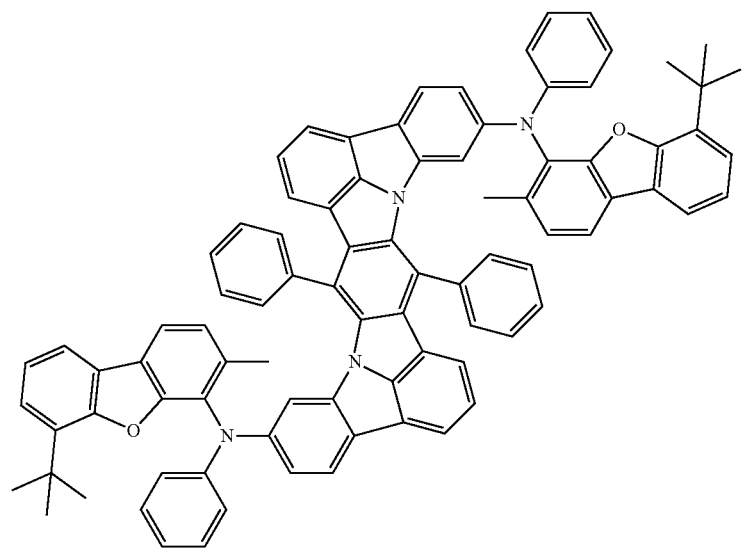

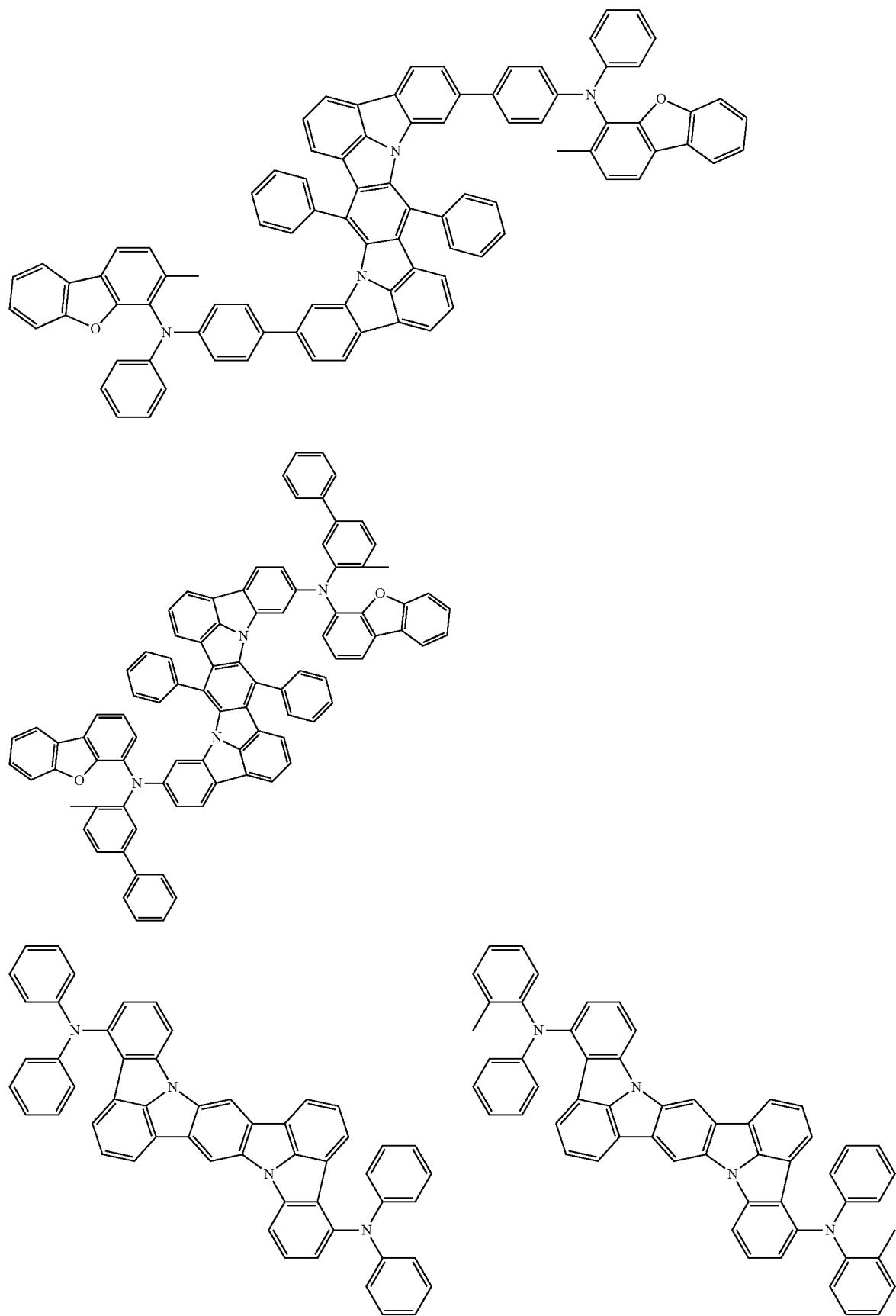

387
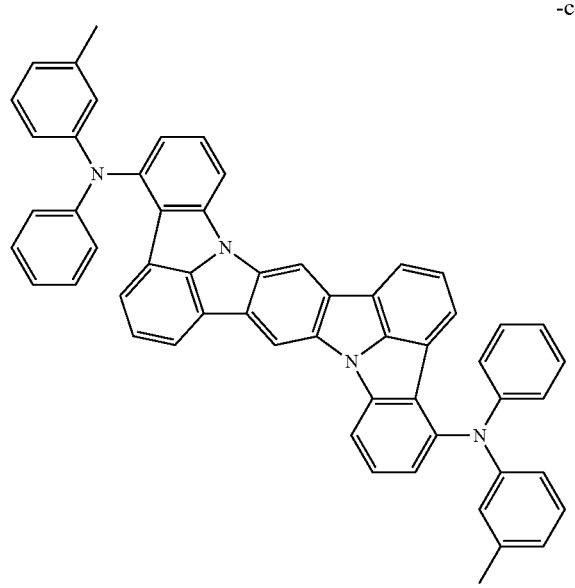
388
-continued
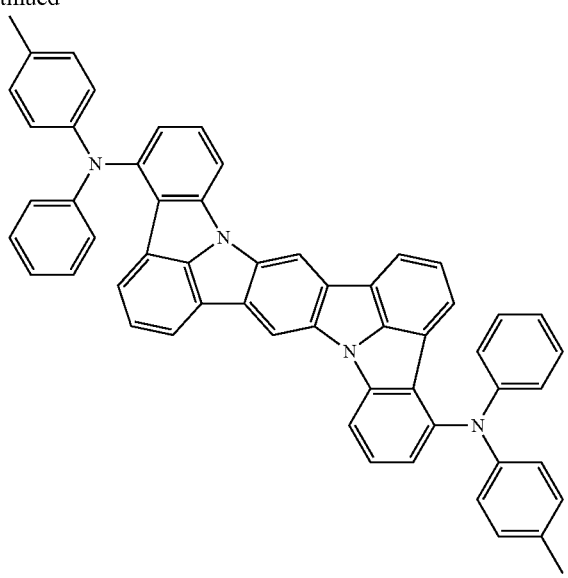
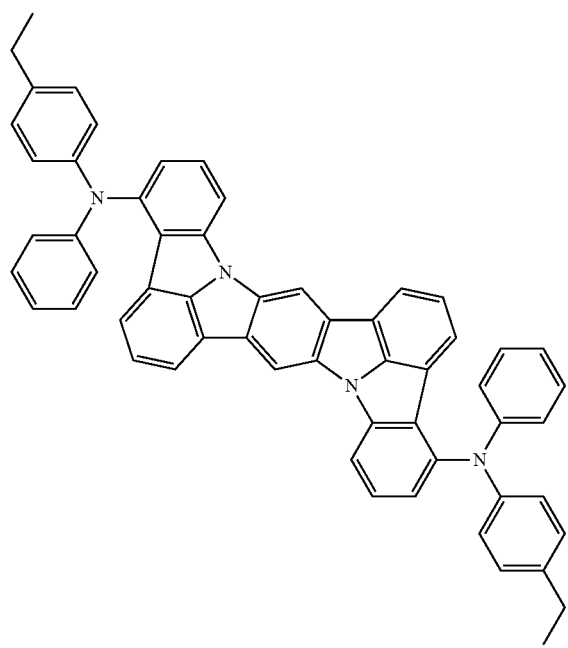

-continued
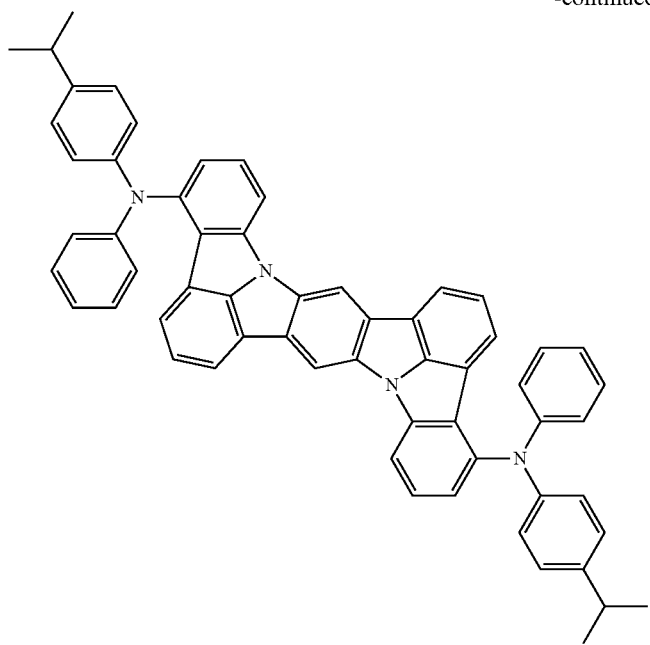
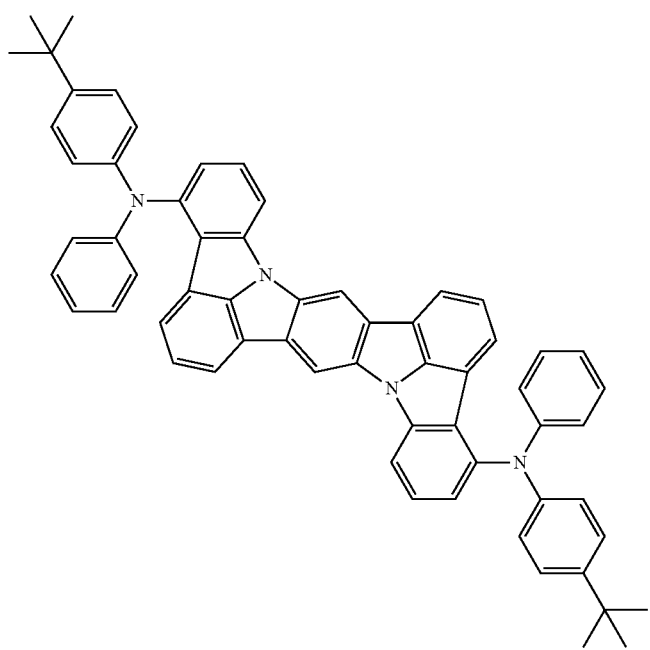

-continued
391
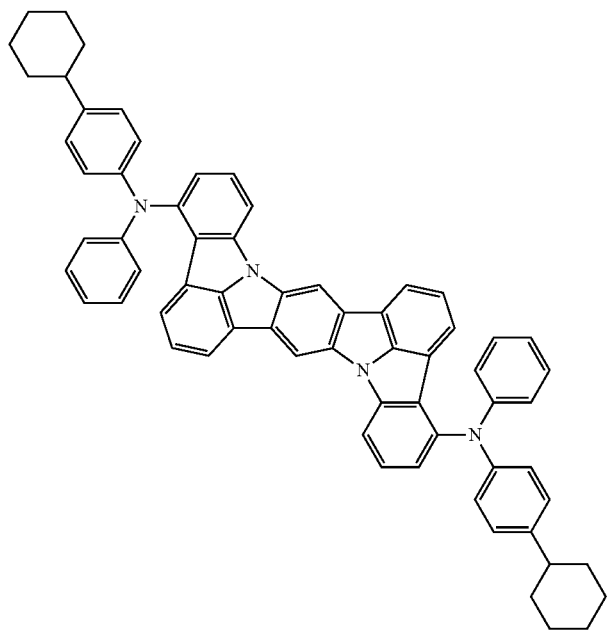
392
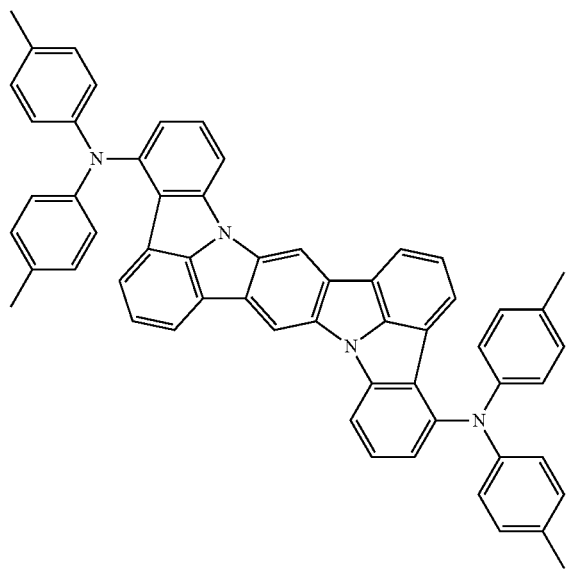
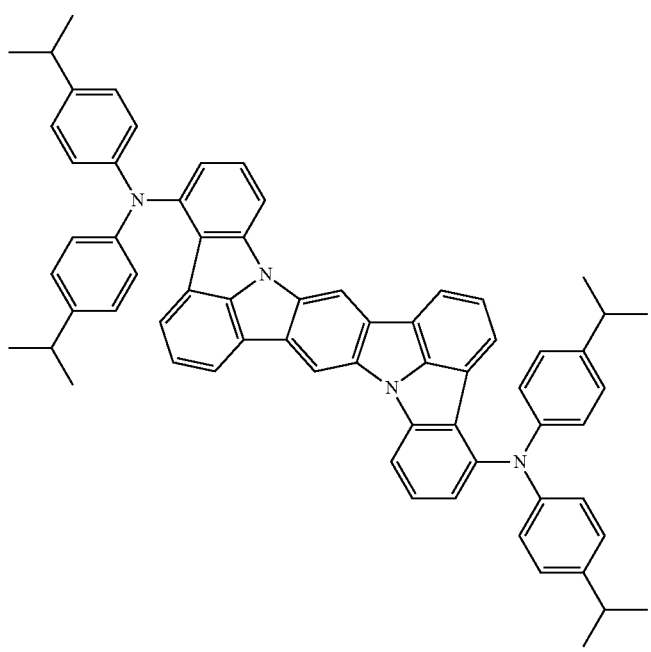

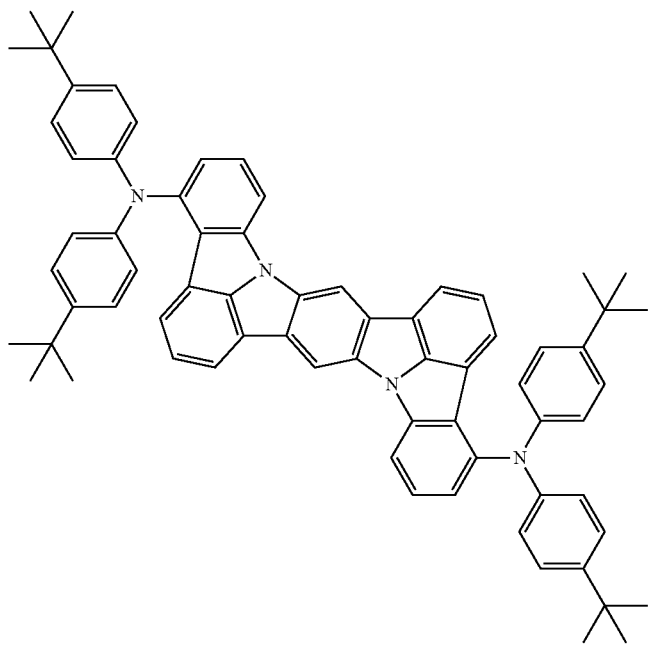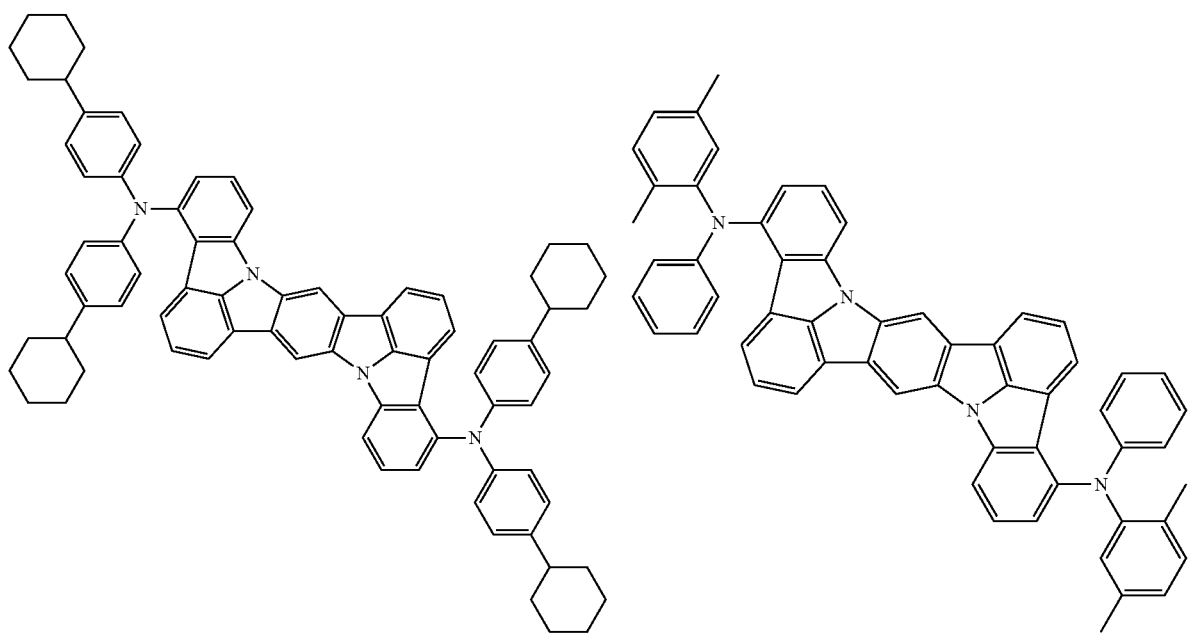

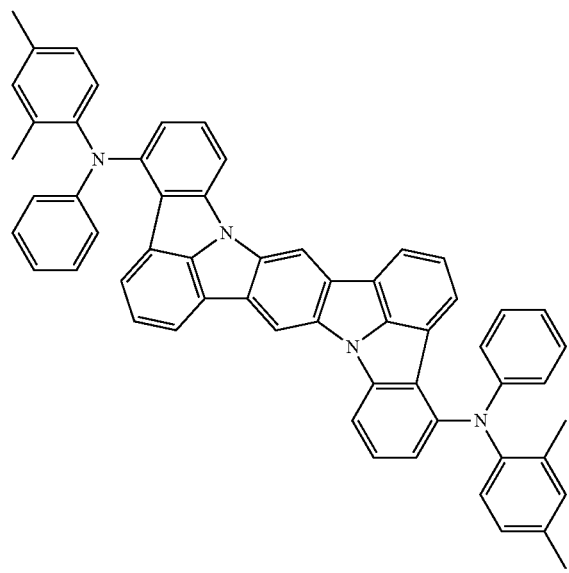
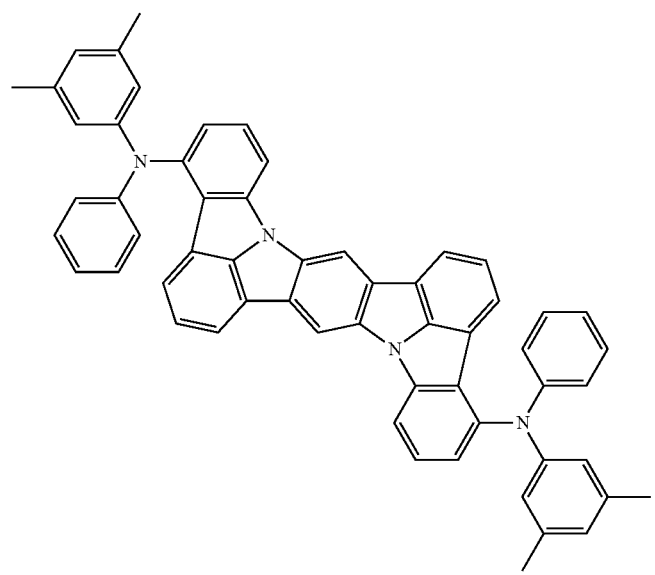
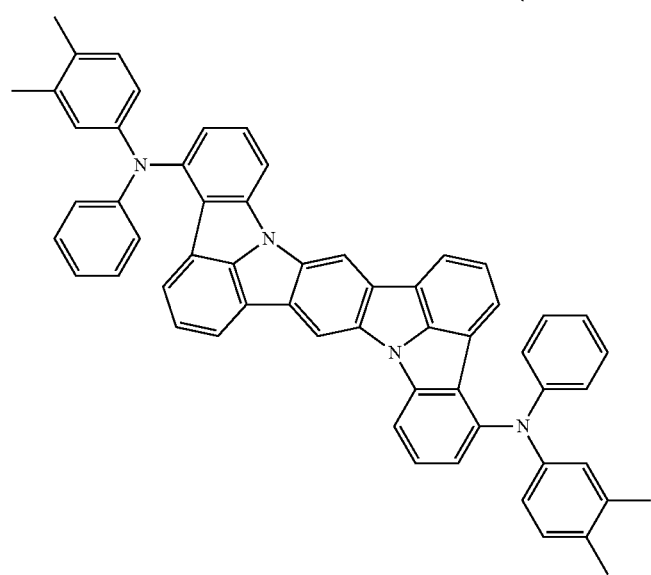

-continued
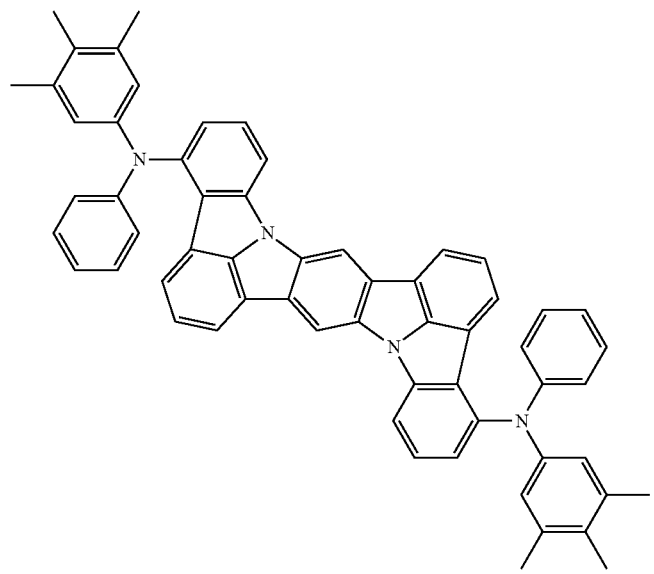
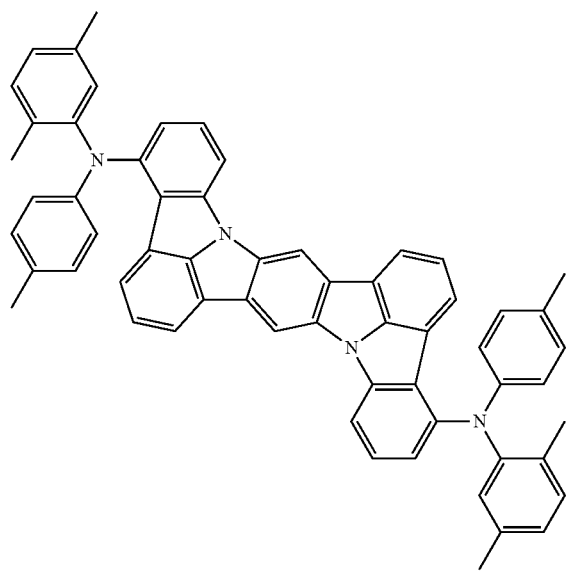
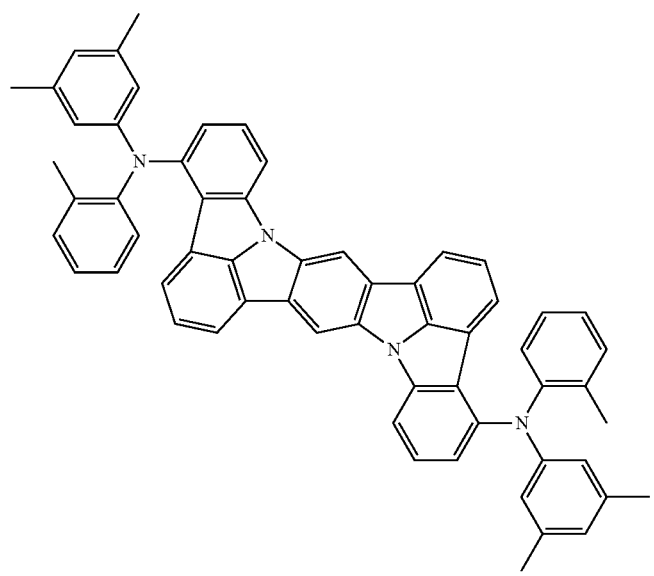

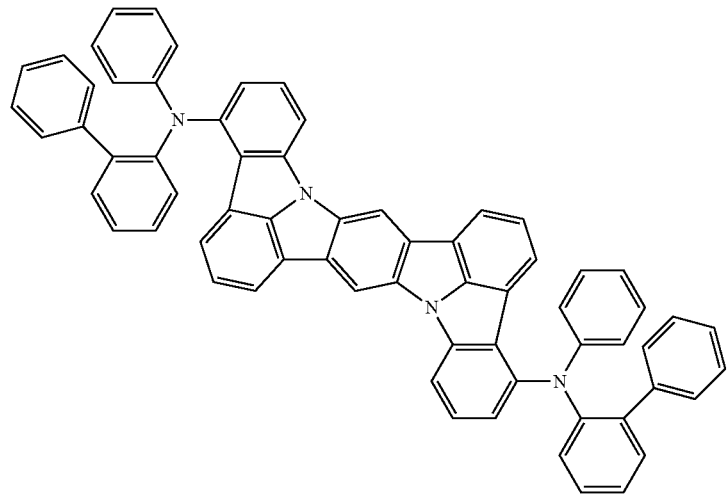
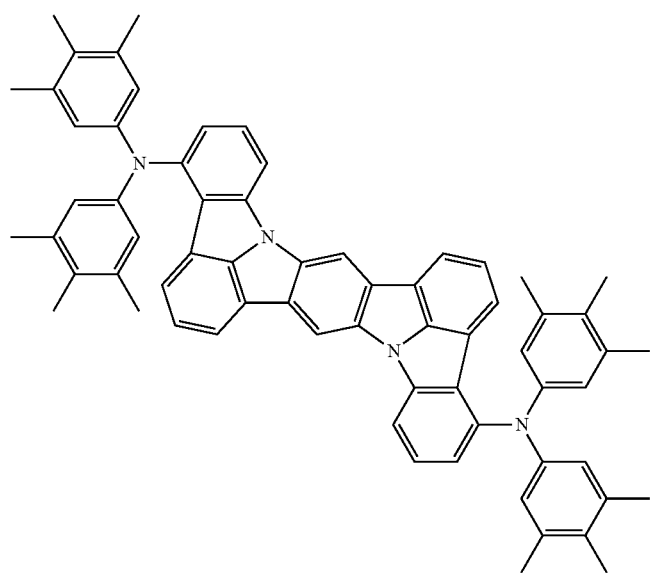
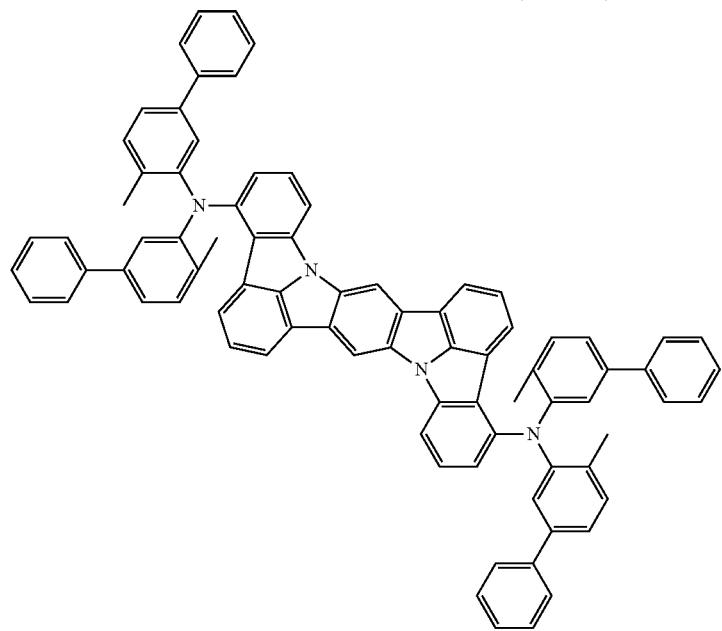

-continued
| 401 | 402 |
|---|---|
| 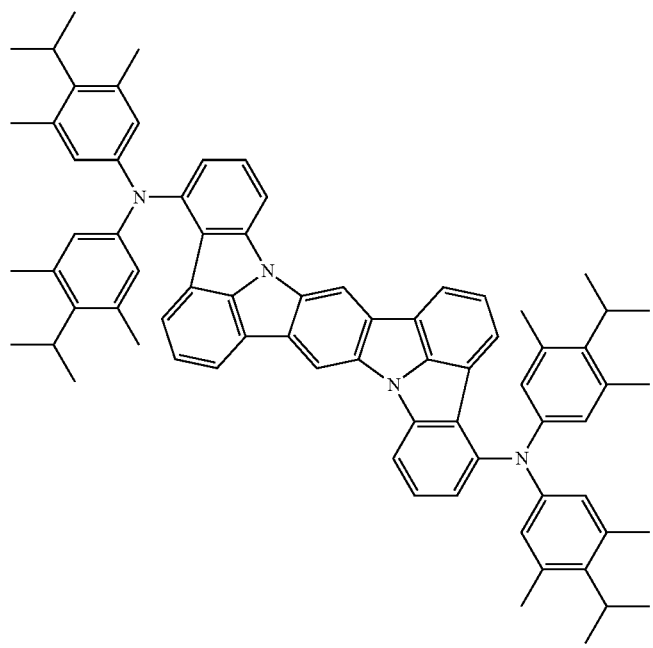 | 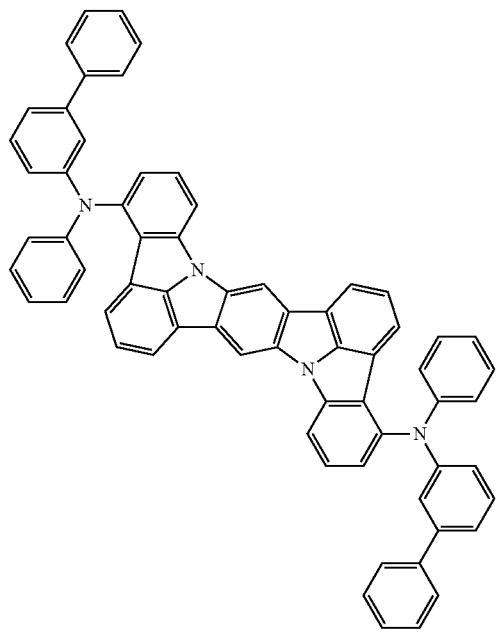 |
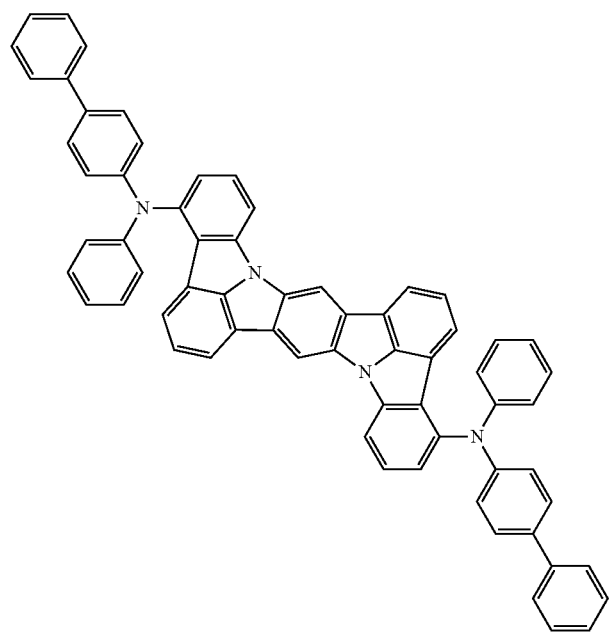

-continued
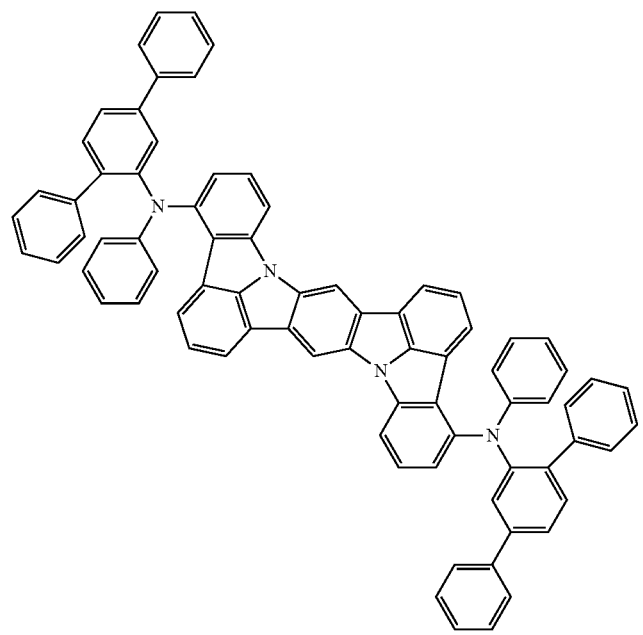
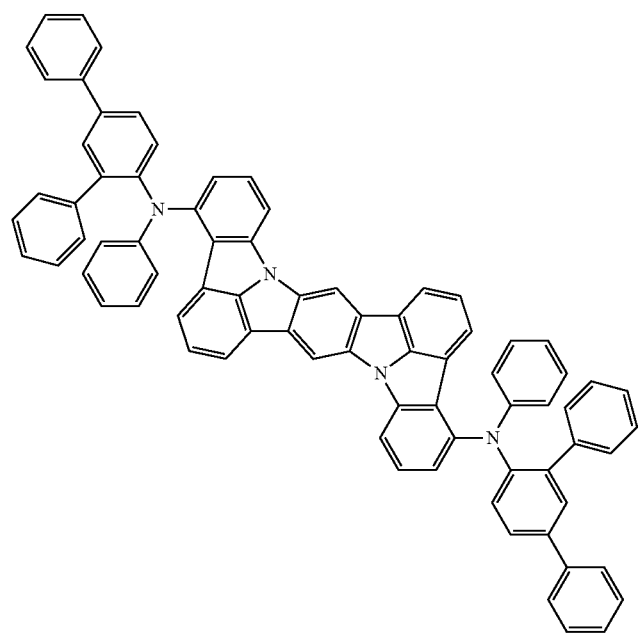

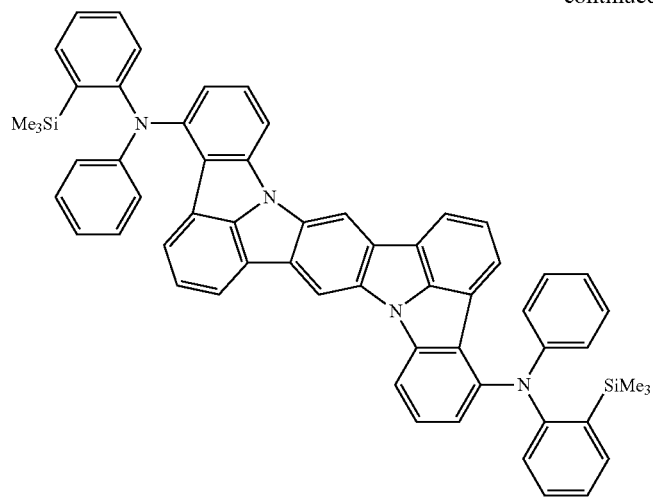
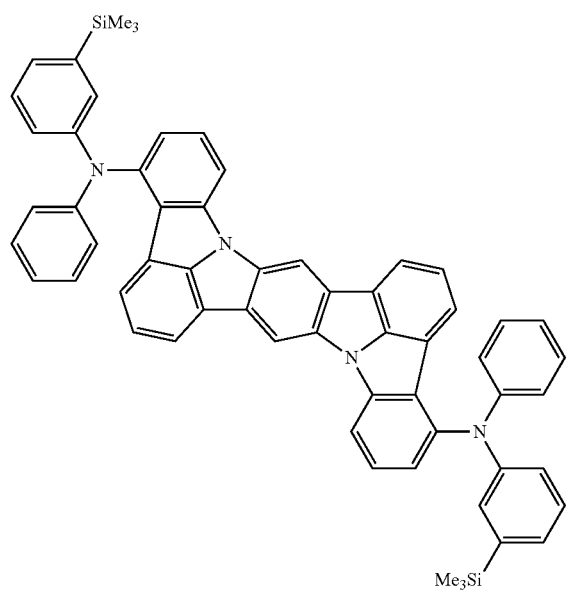
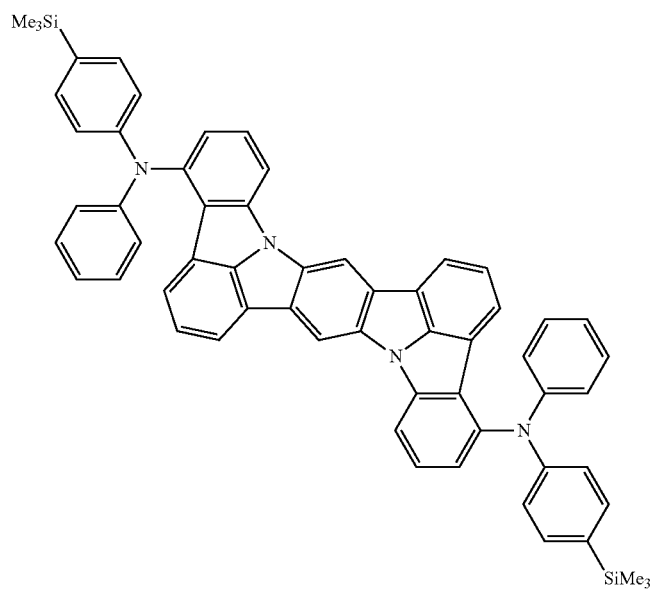

-continued
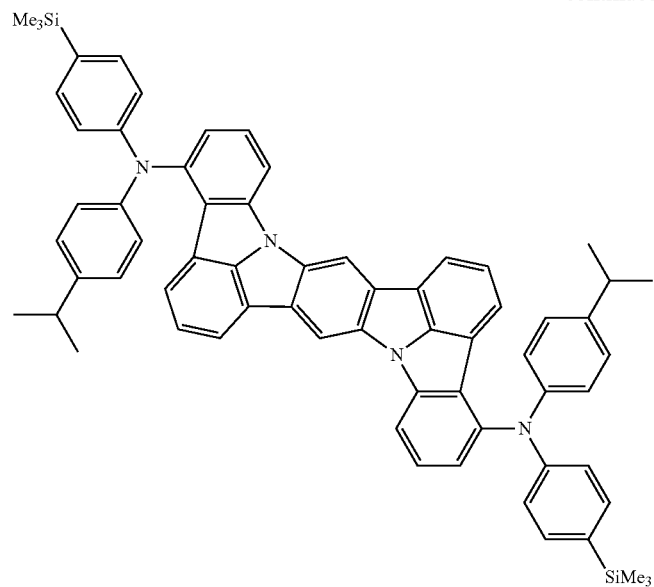
407
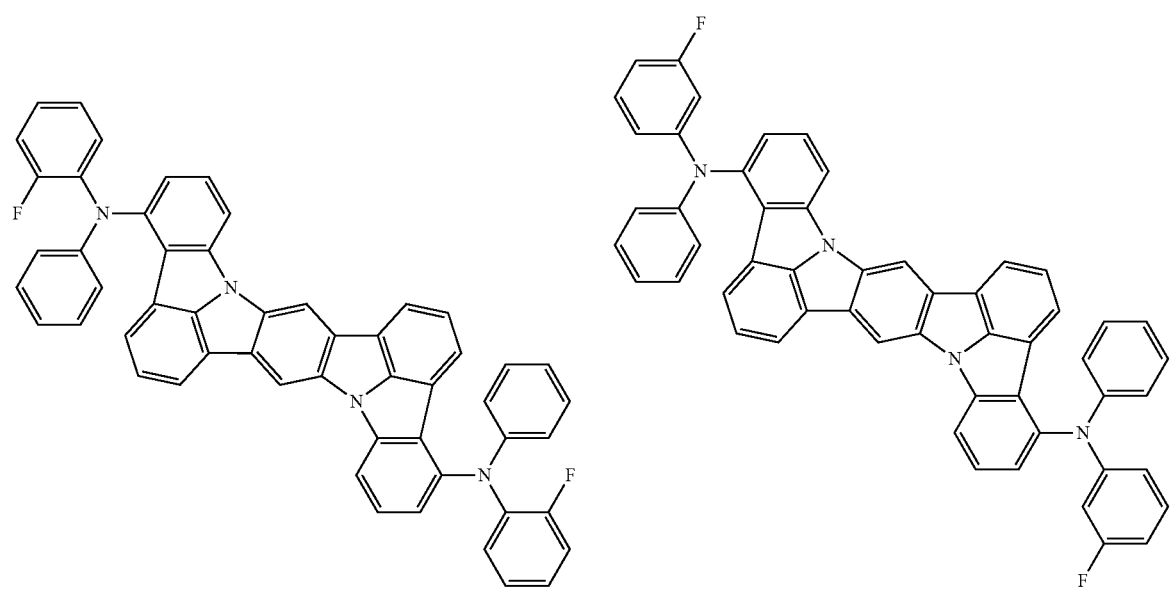
408

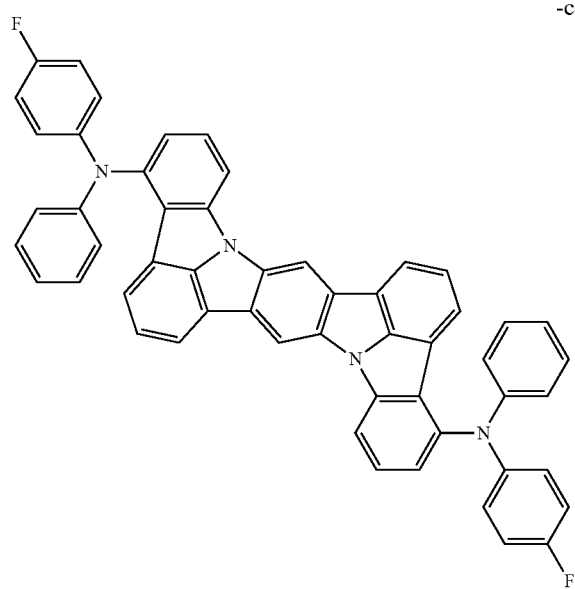
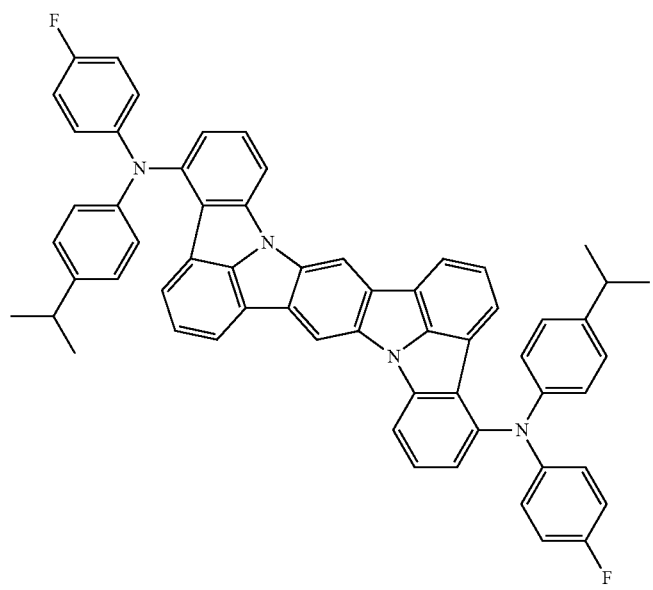

411
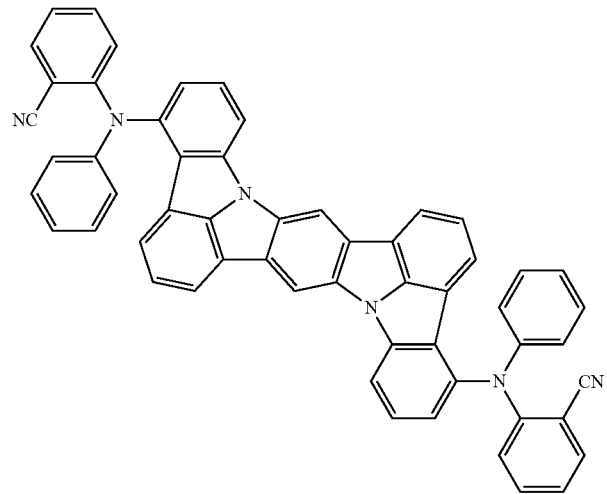
412
-continued
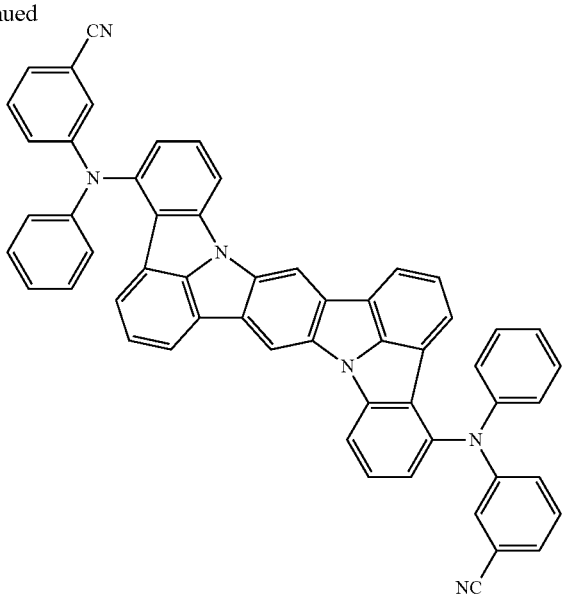
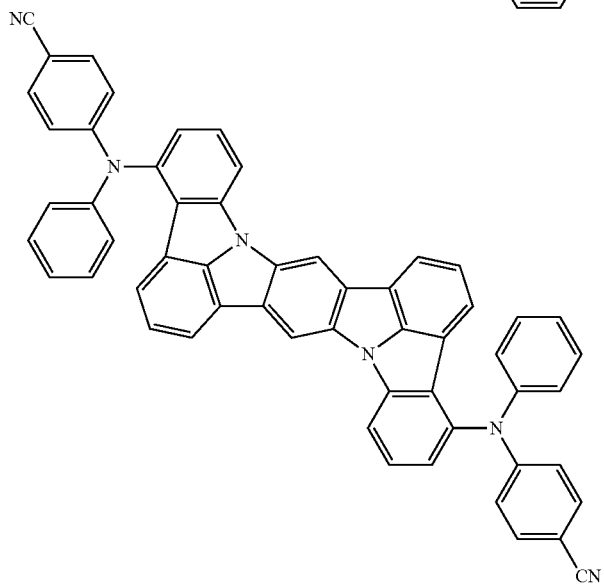
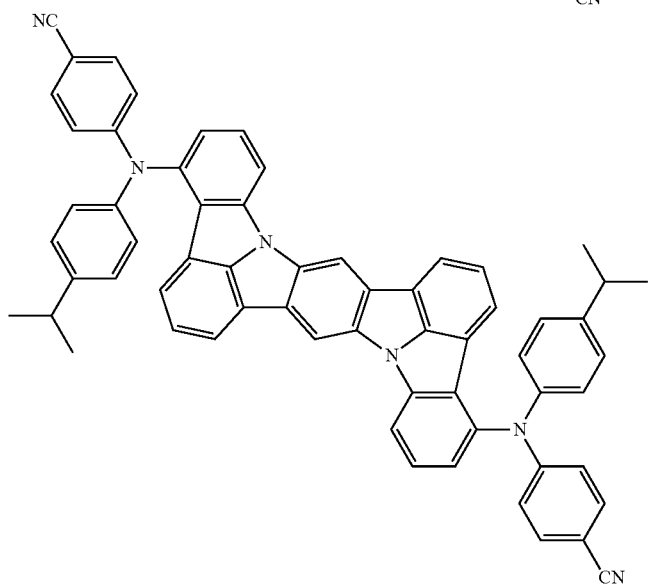

-continued
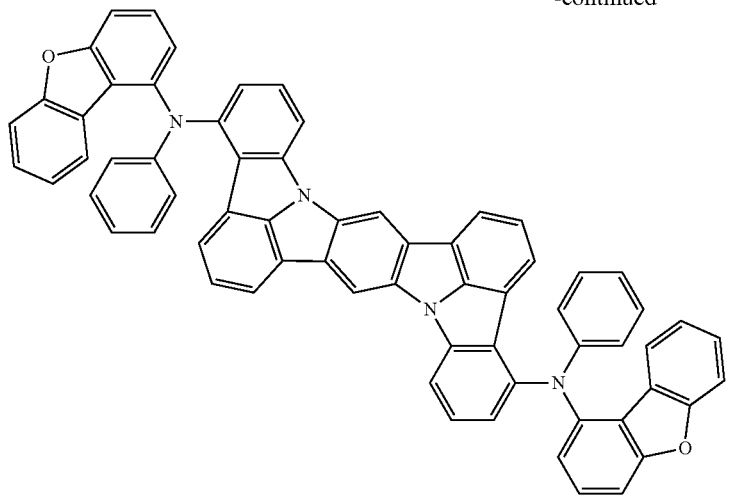
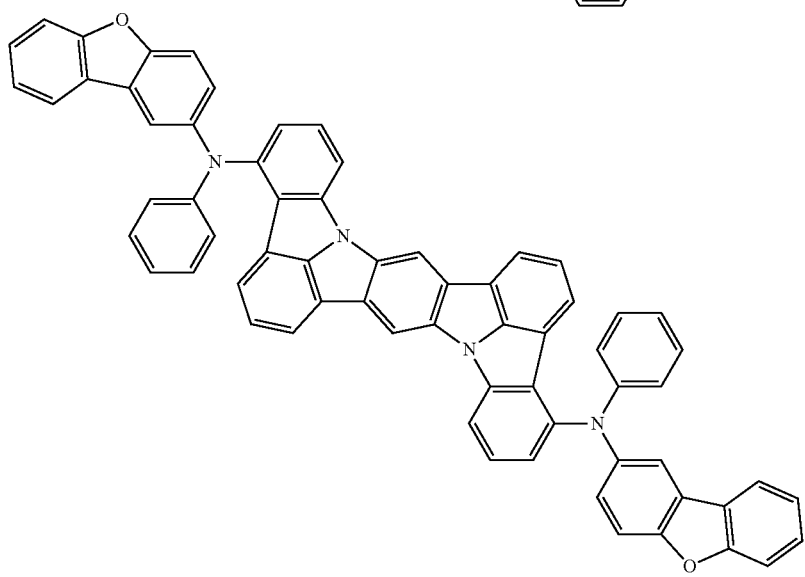
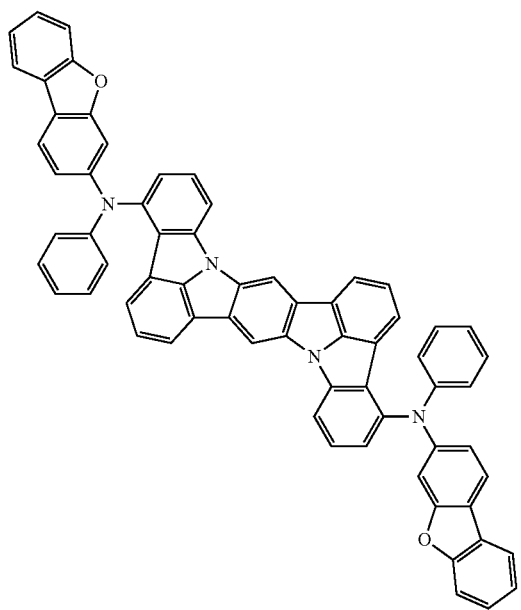

-continued
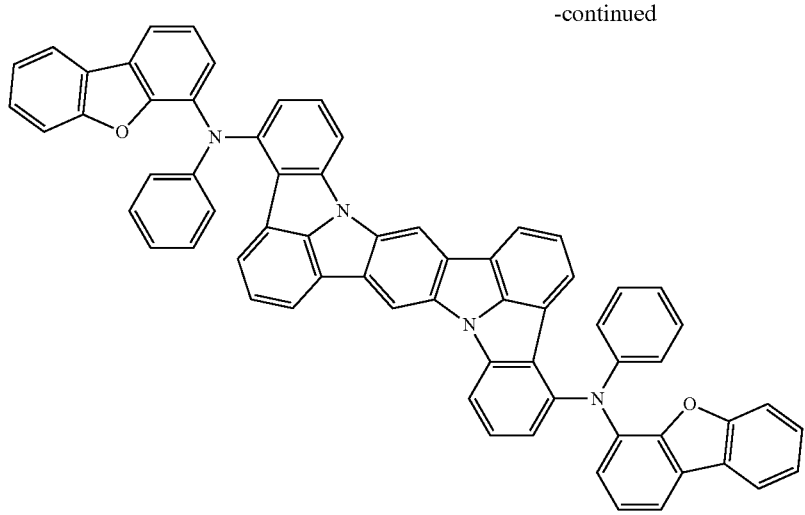
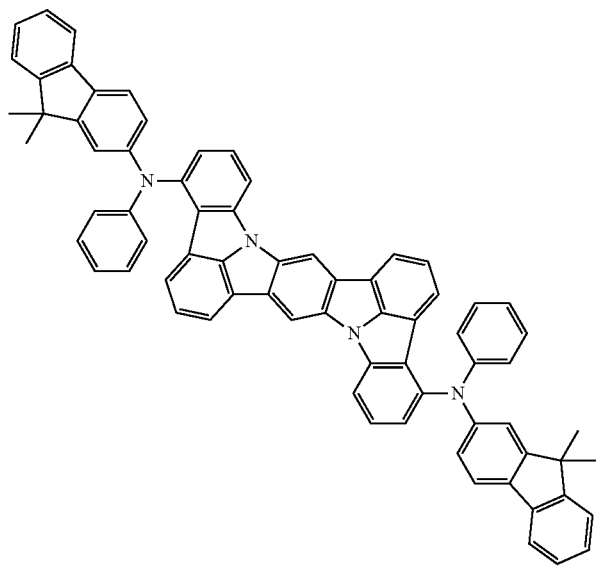
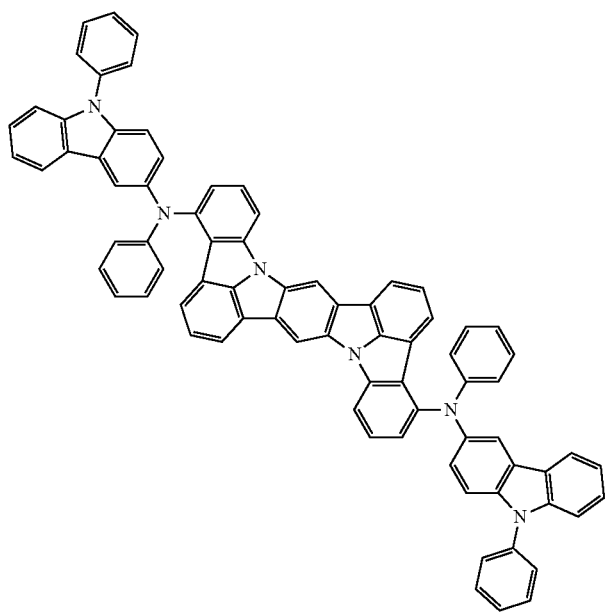

-continued
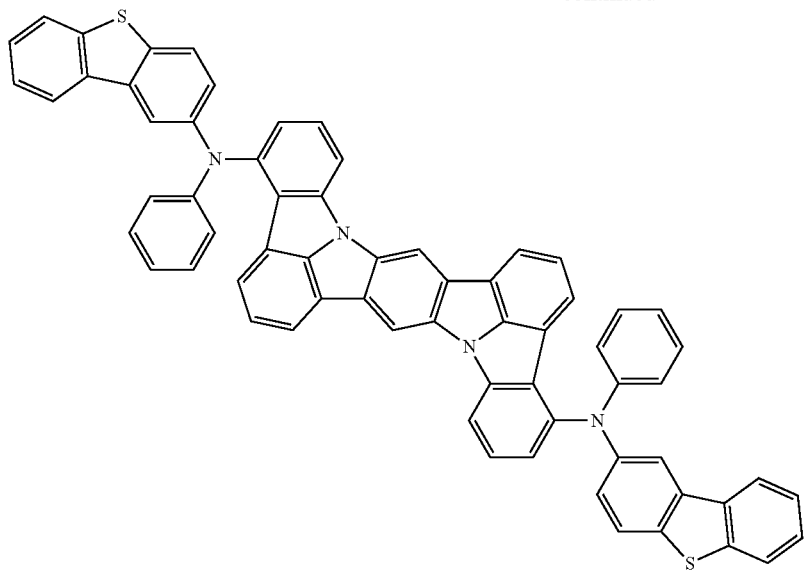
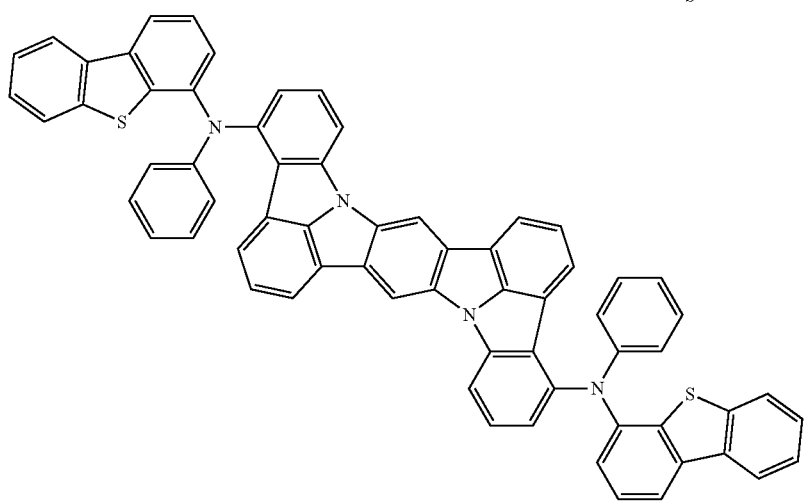
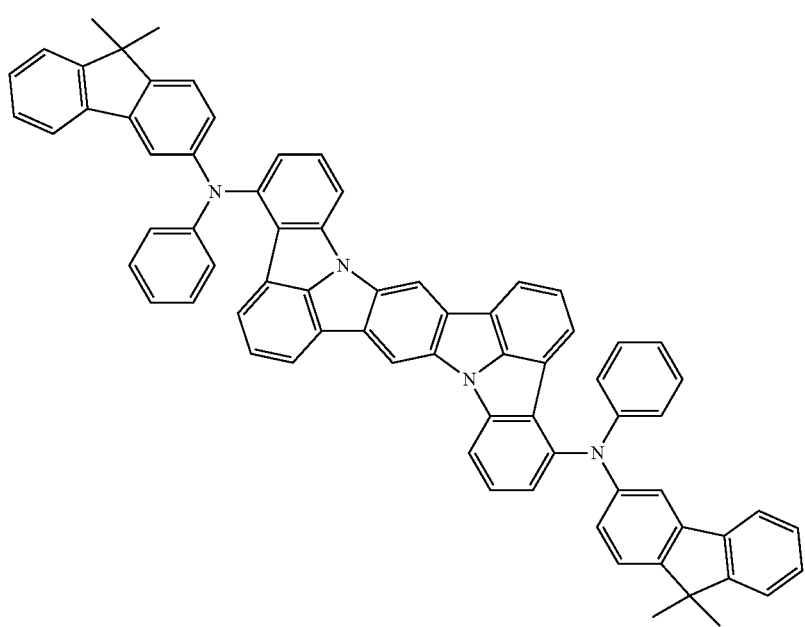

-continued
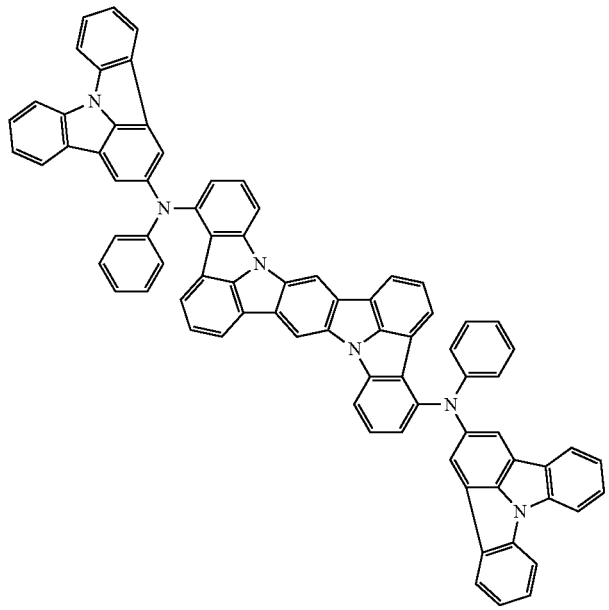
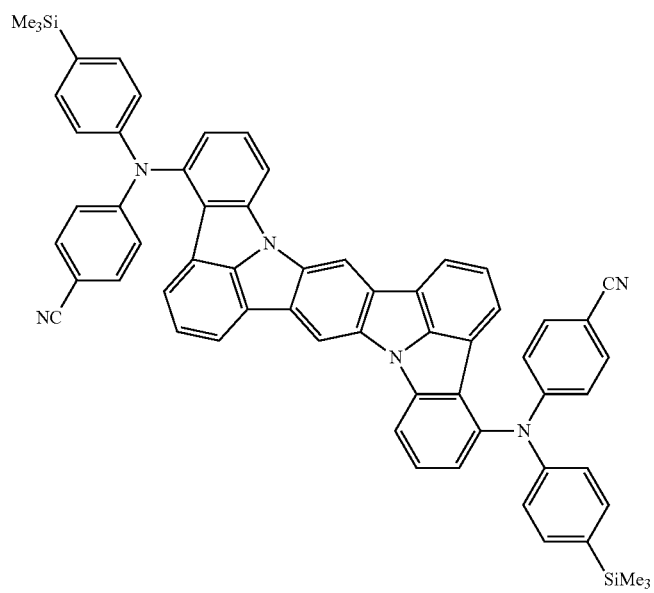
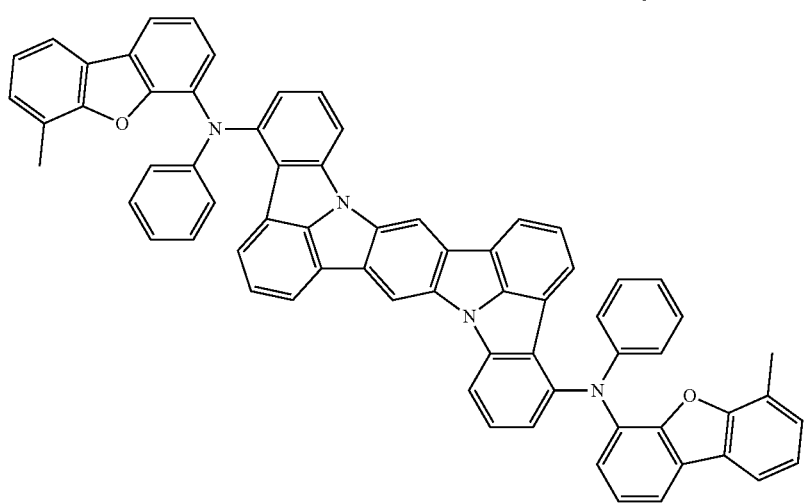

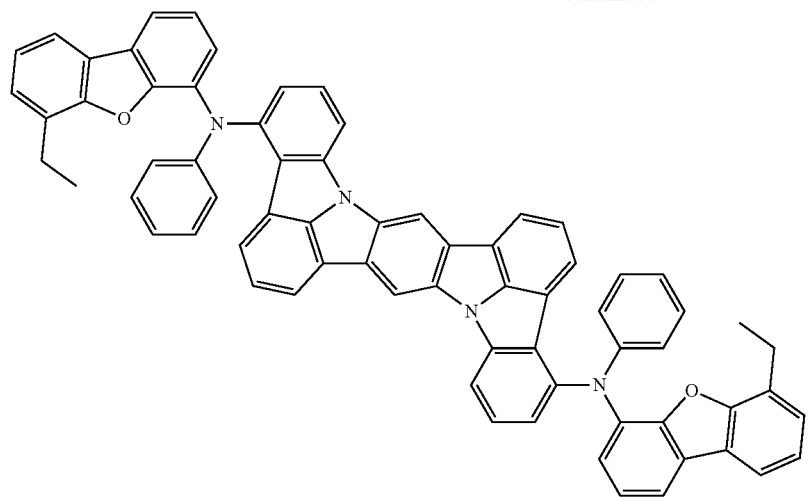
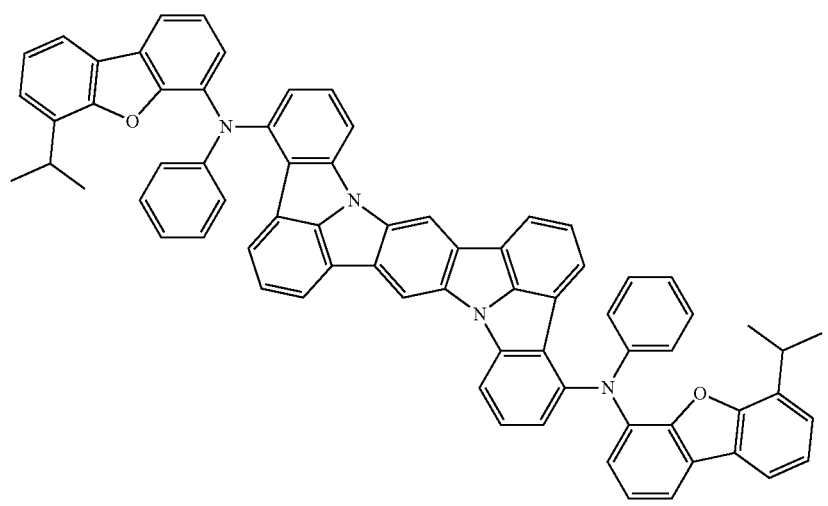
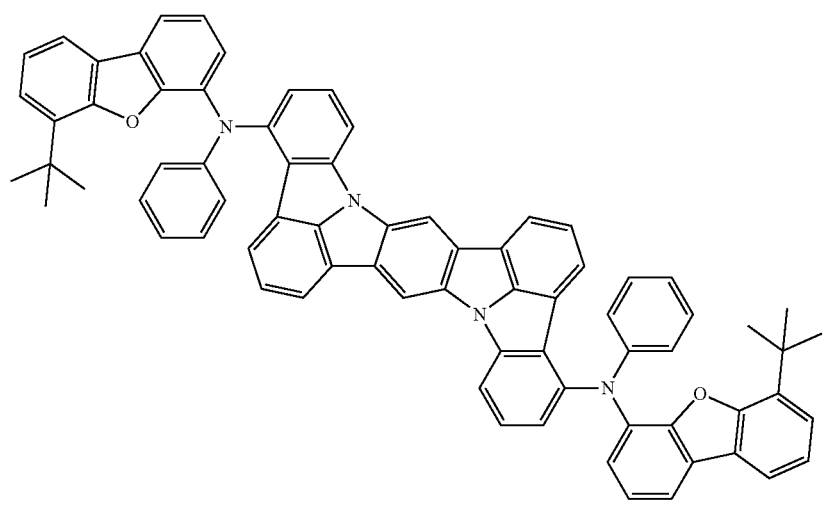

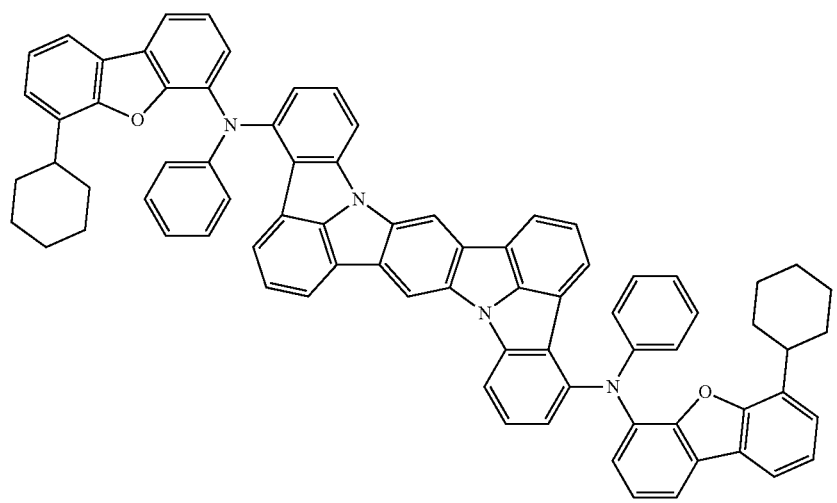
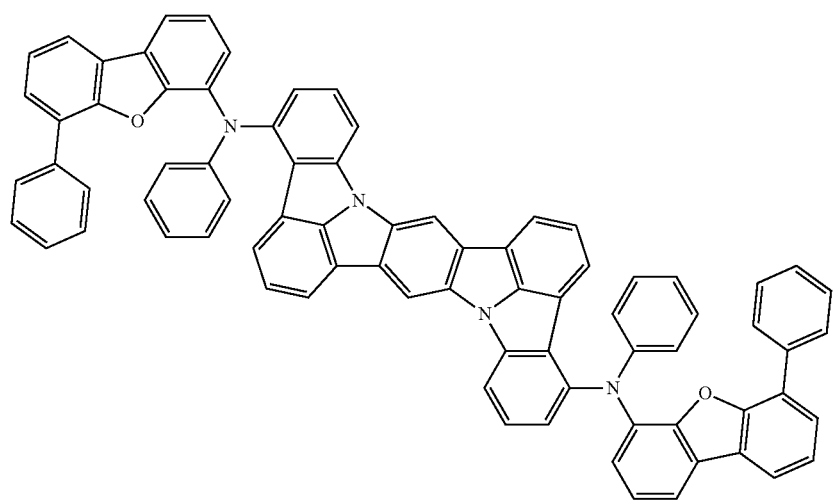
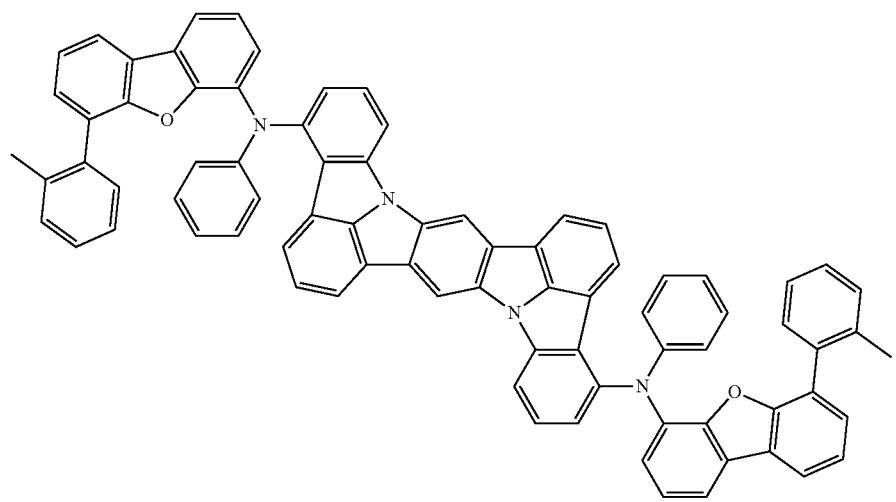

-continued
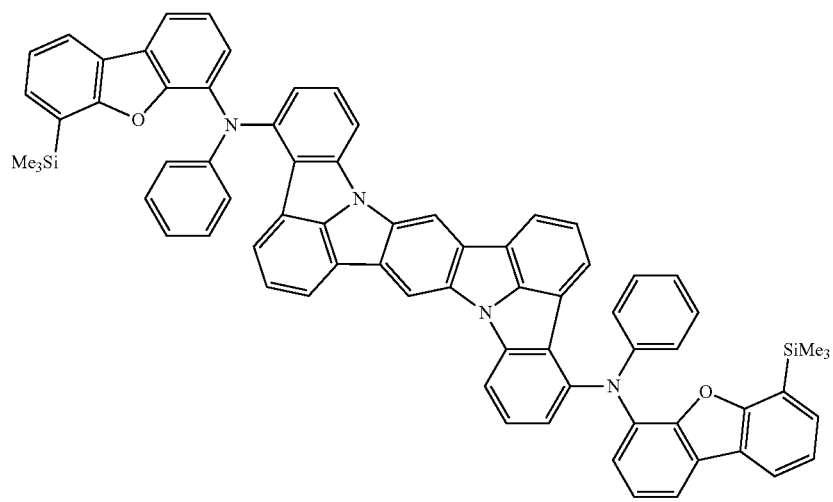
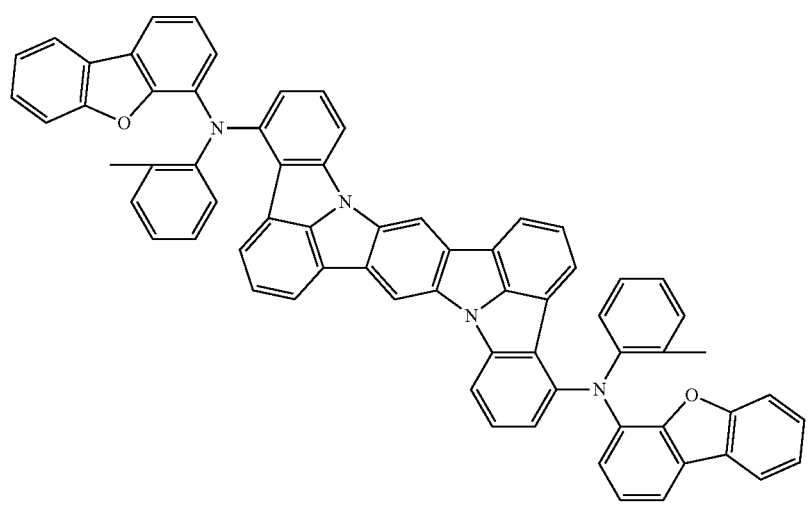
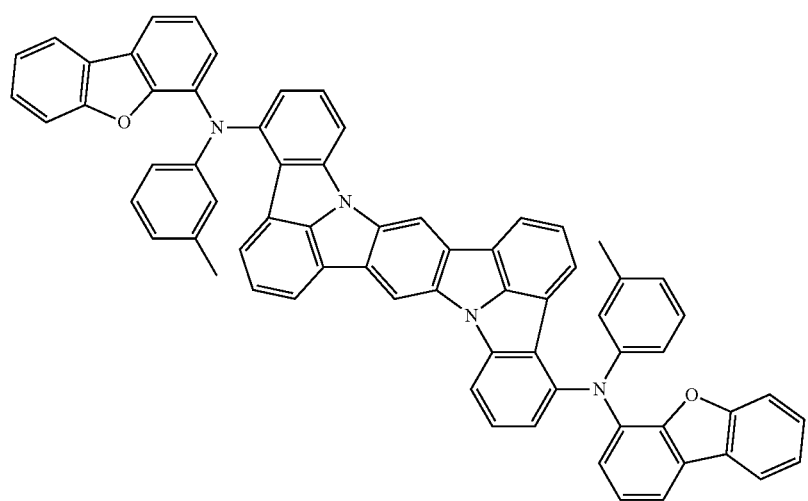

-continued
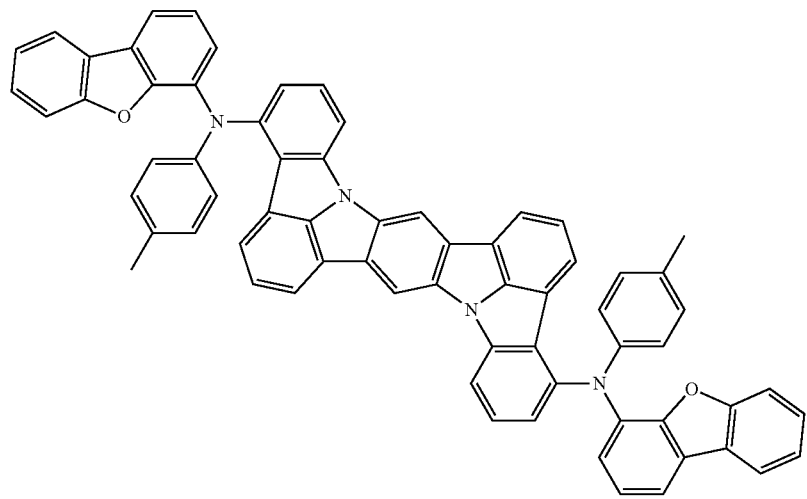
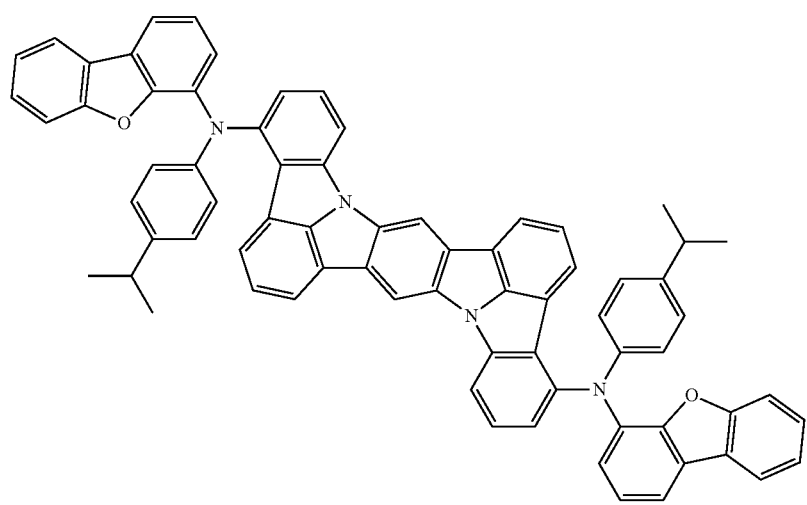
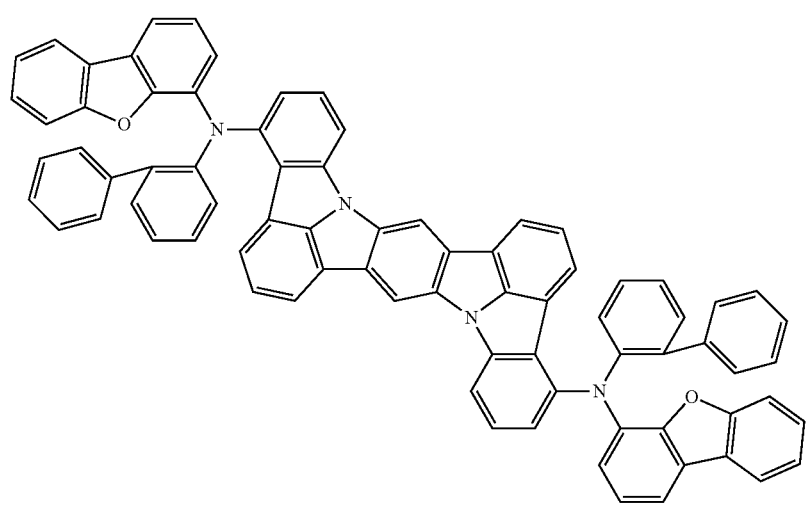

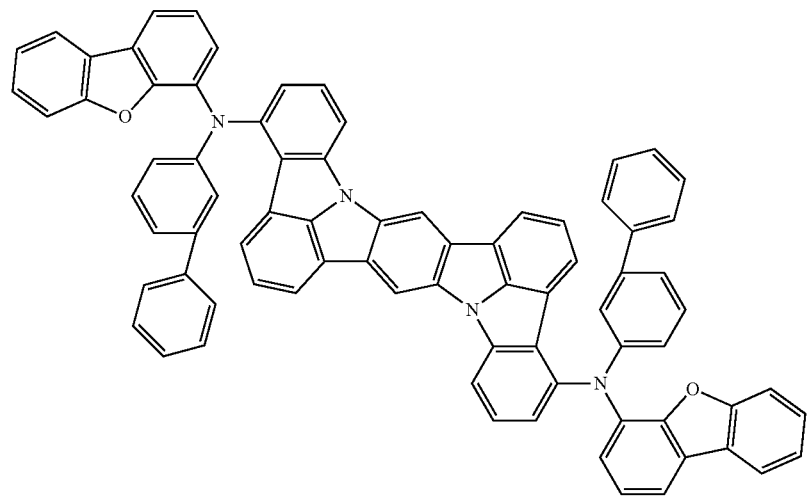
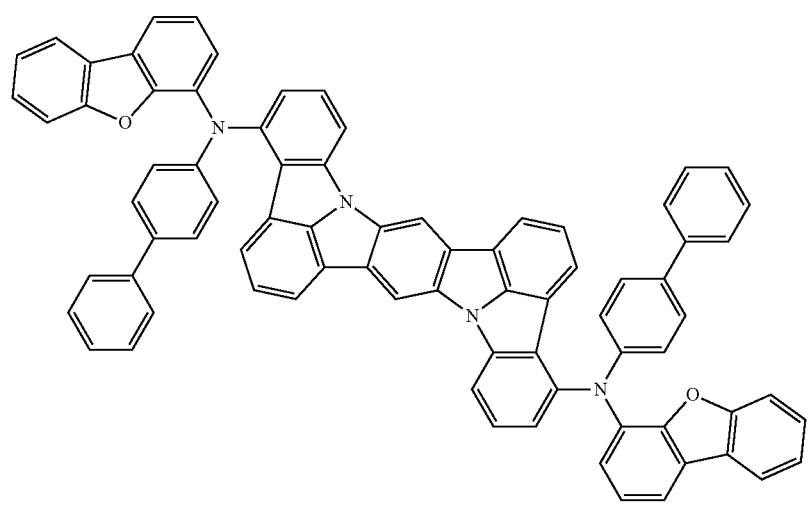
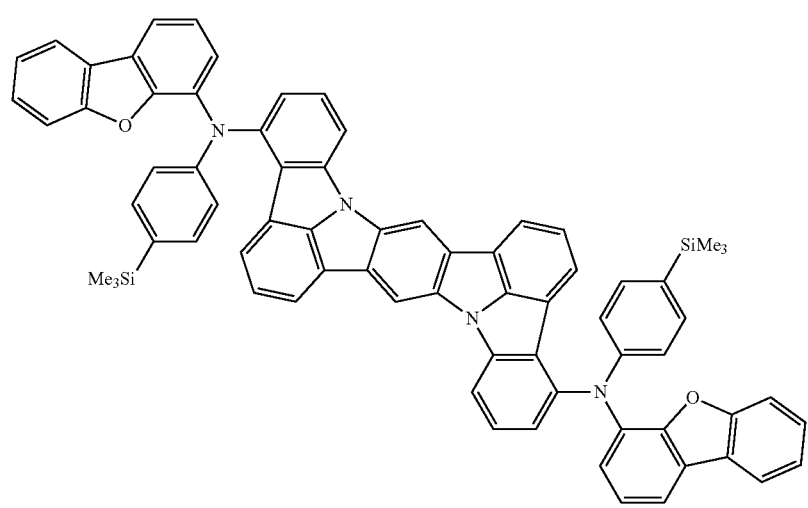

-continued
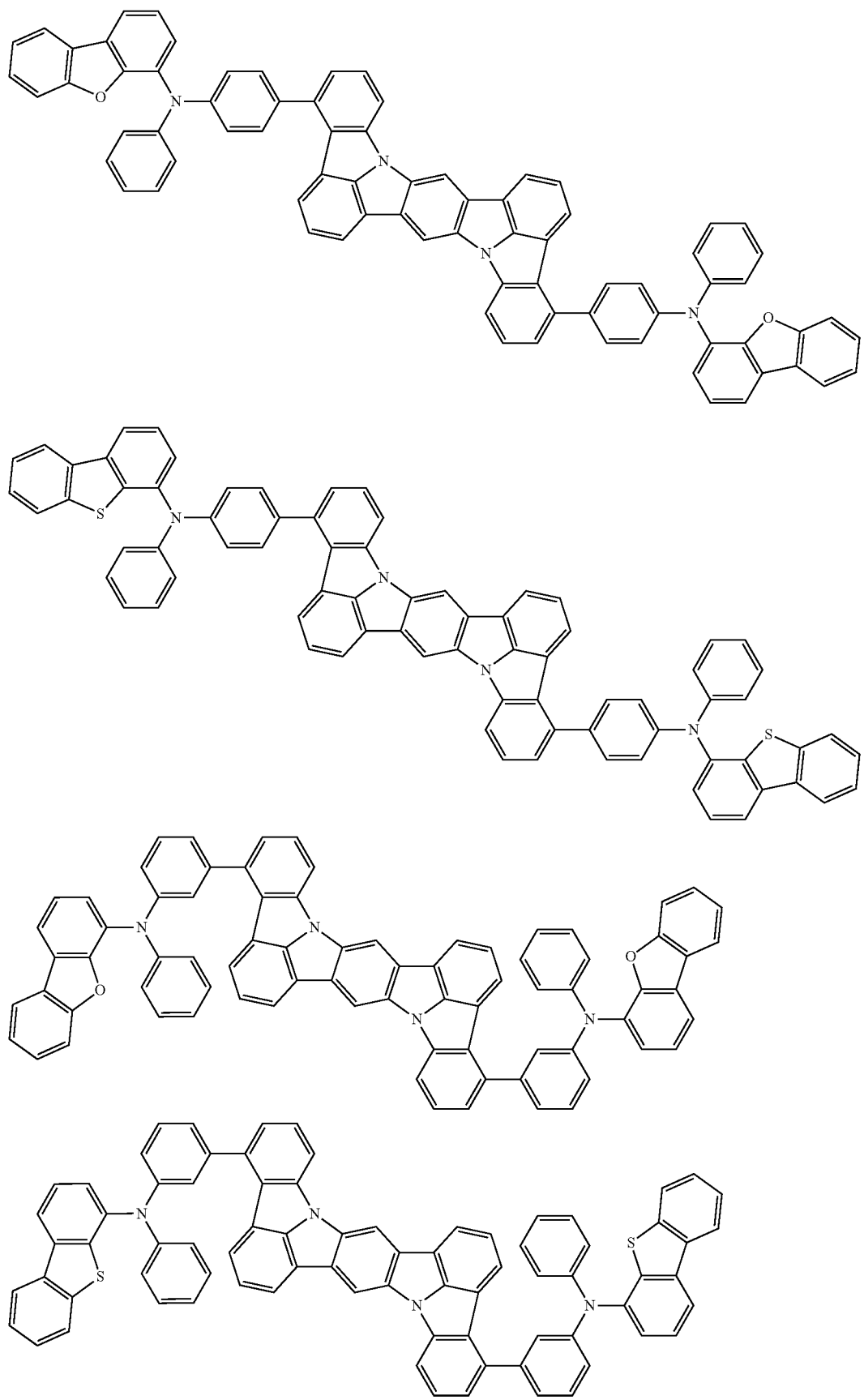

-continued
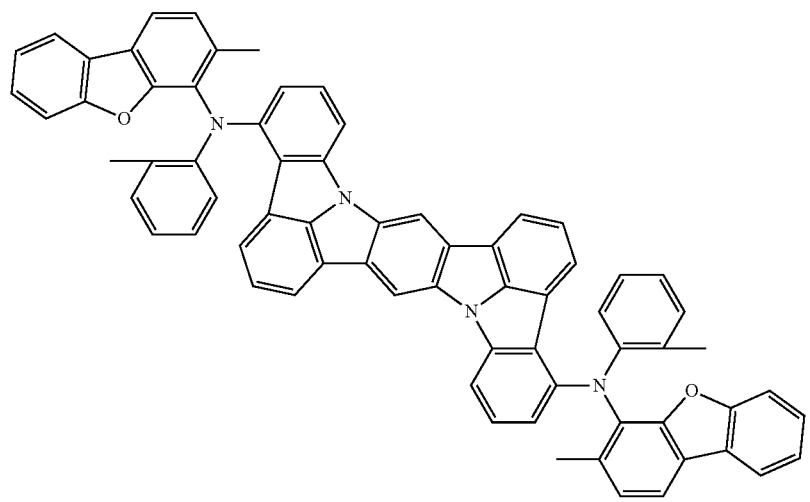
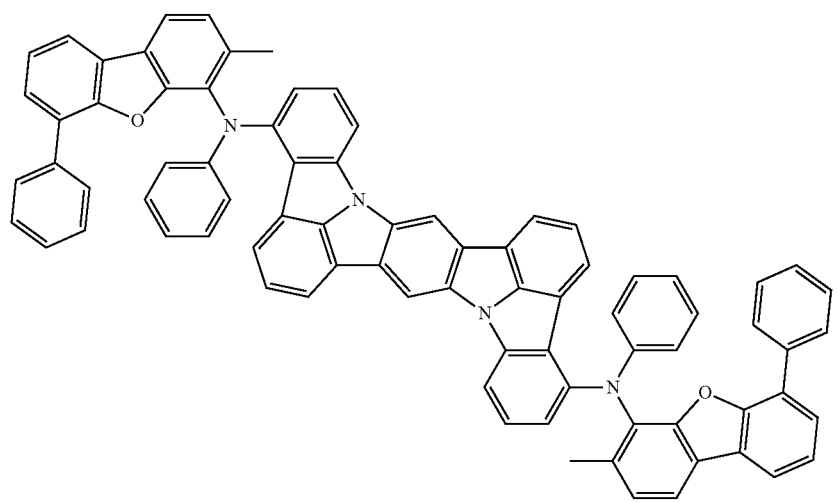
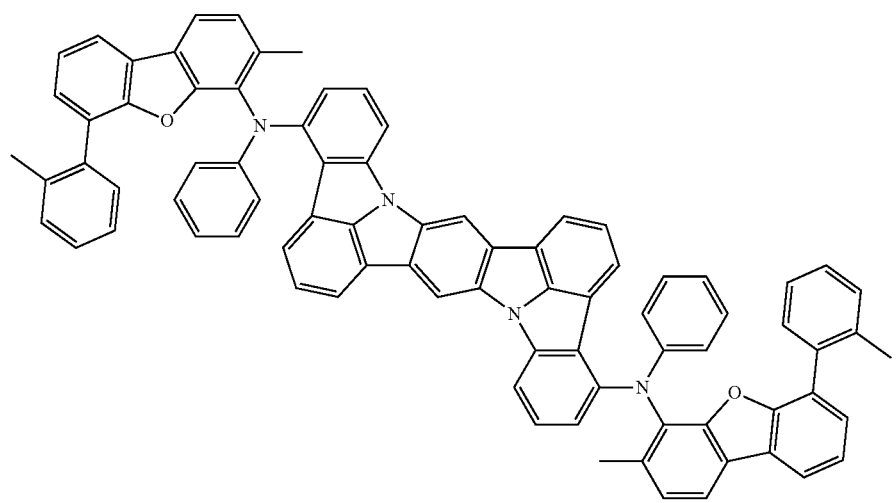

-continued
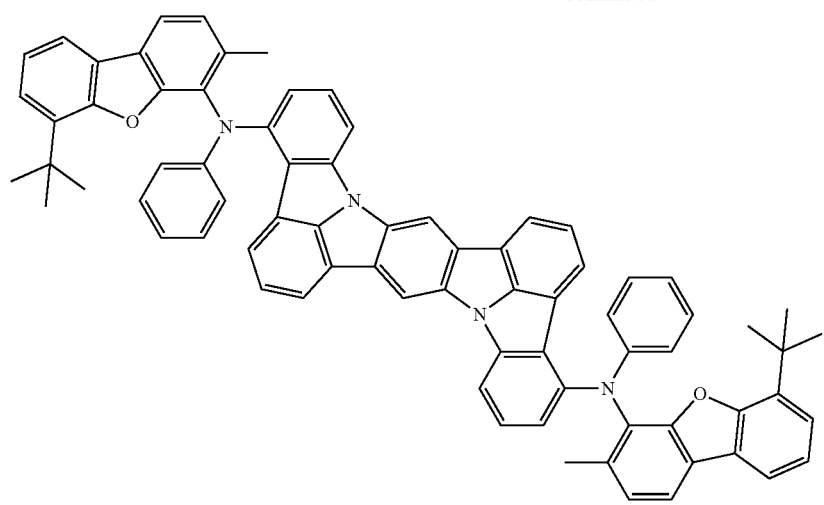
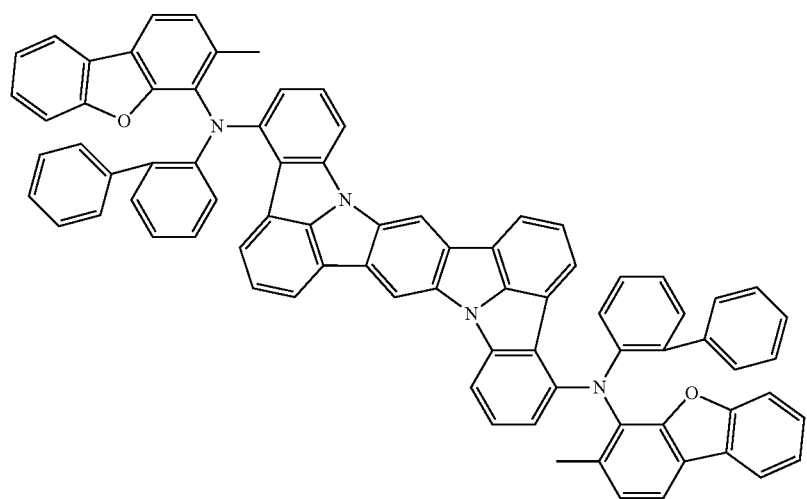
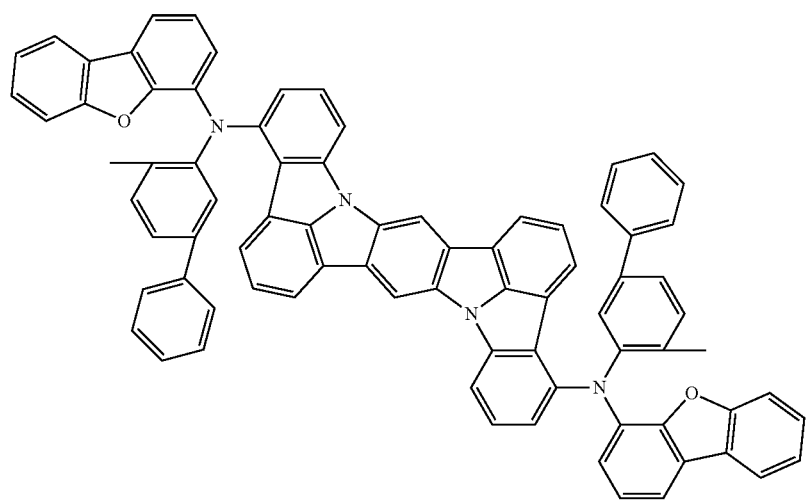

437 438
-continued
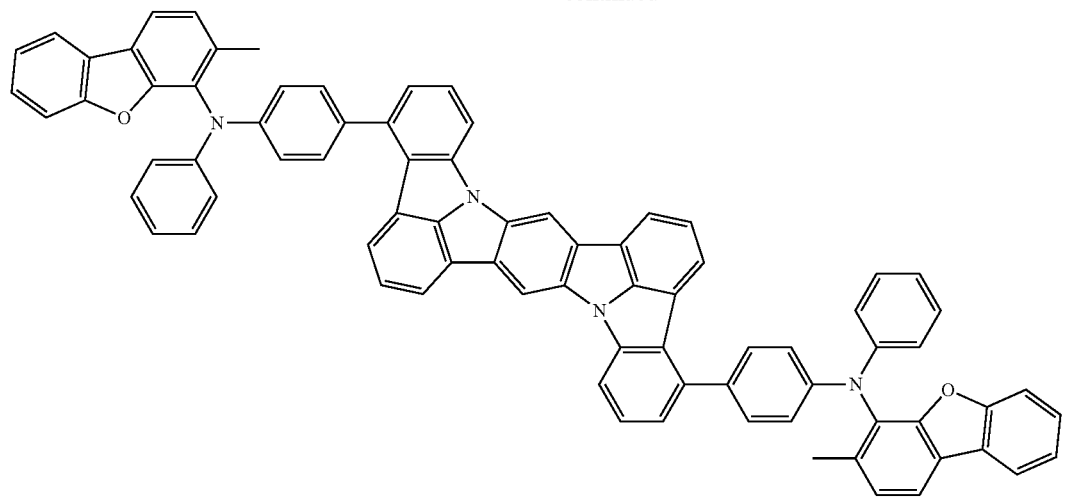
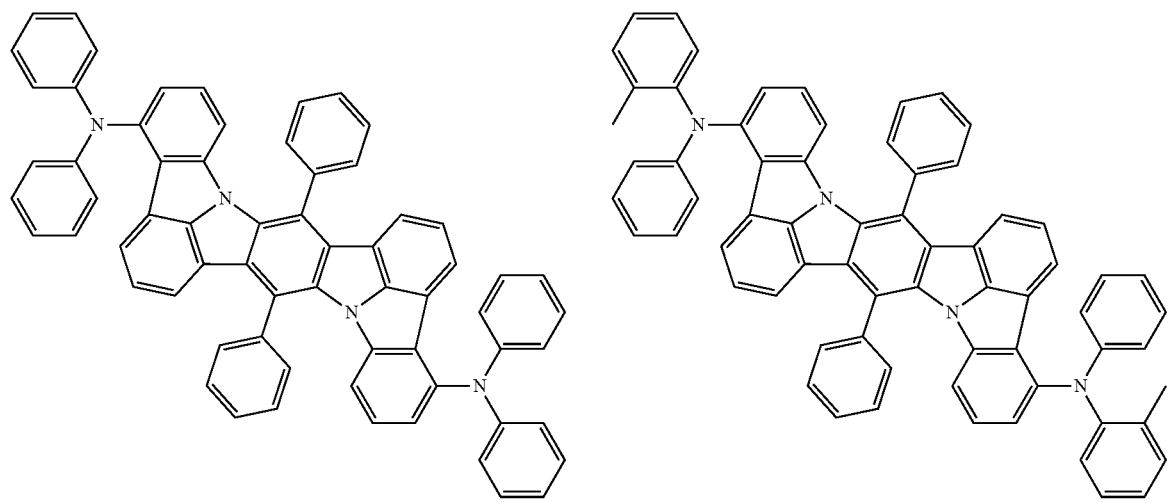
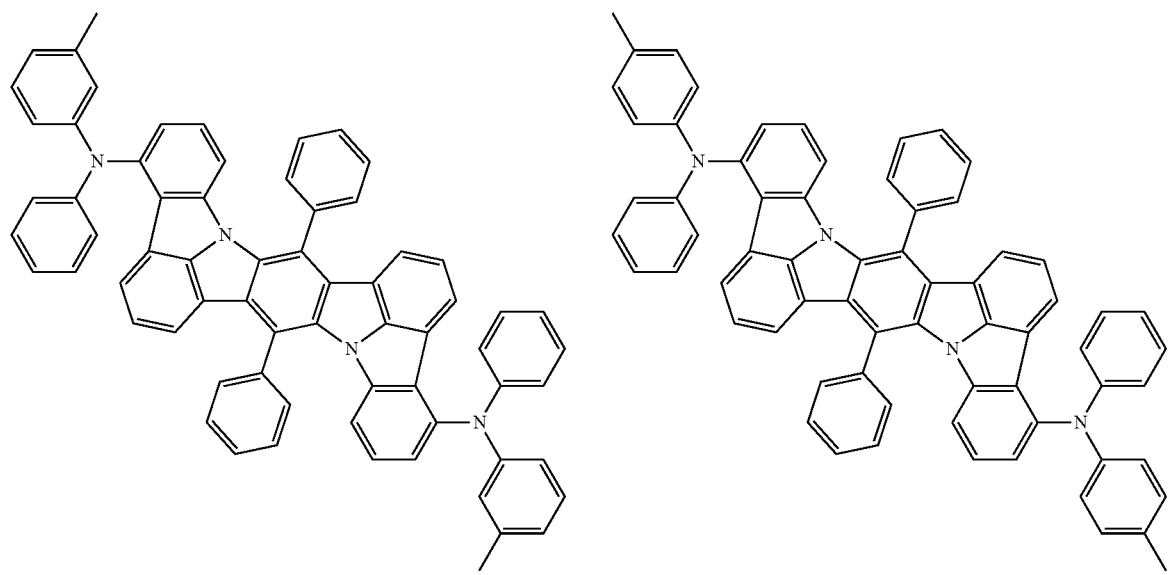

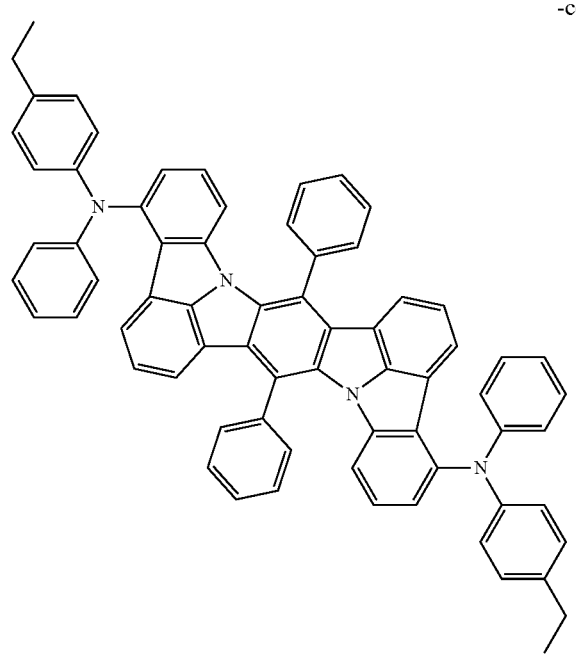
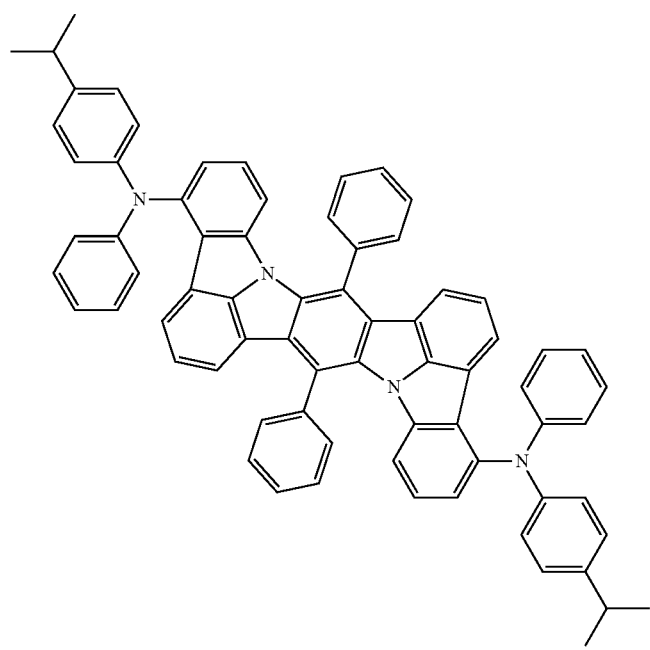

441 442
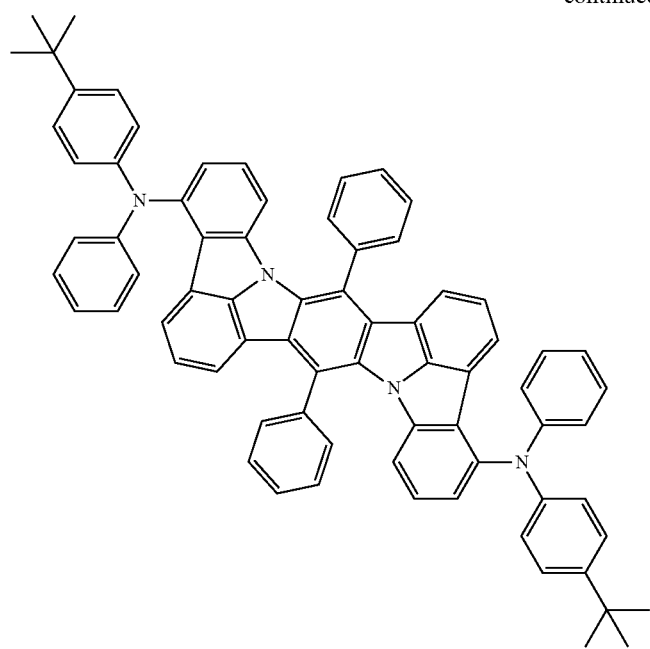
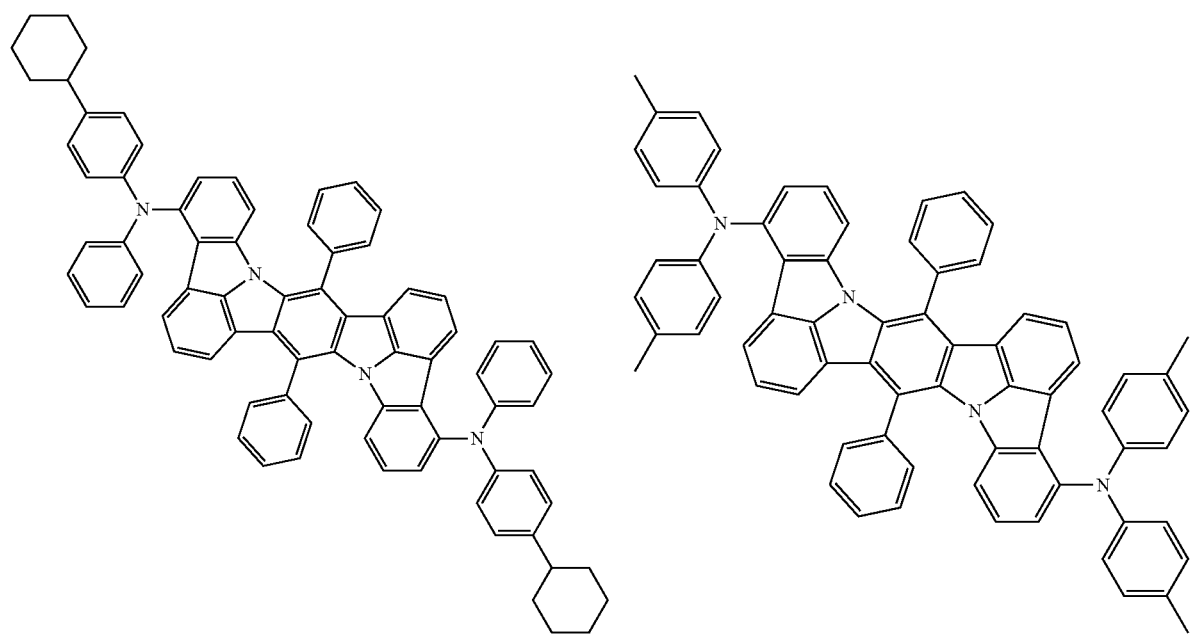

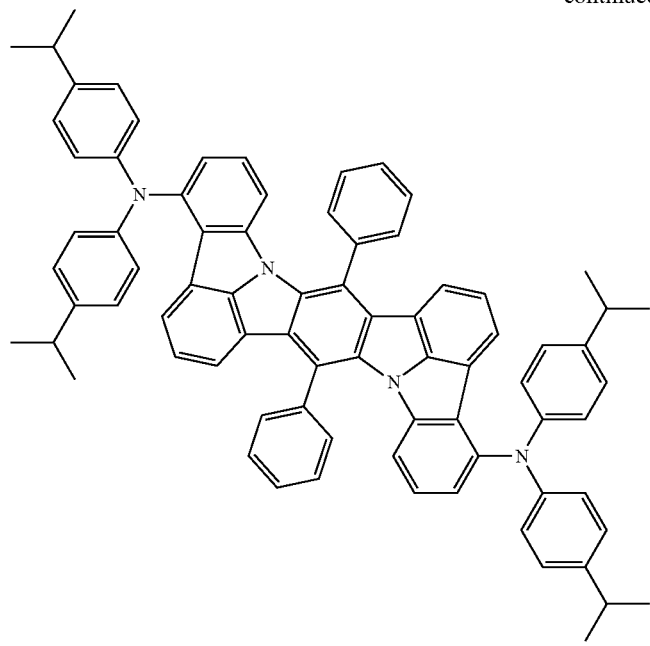
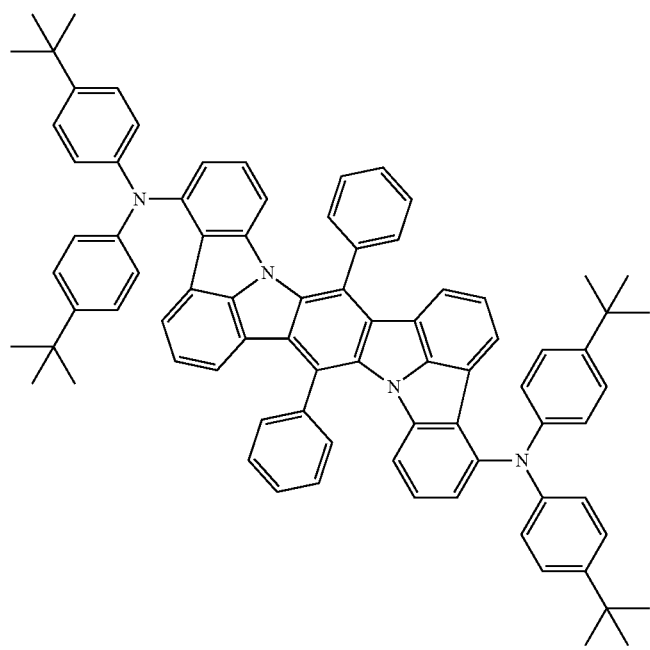

445 446
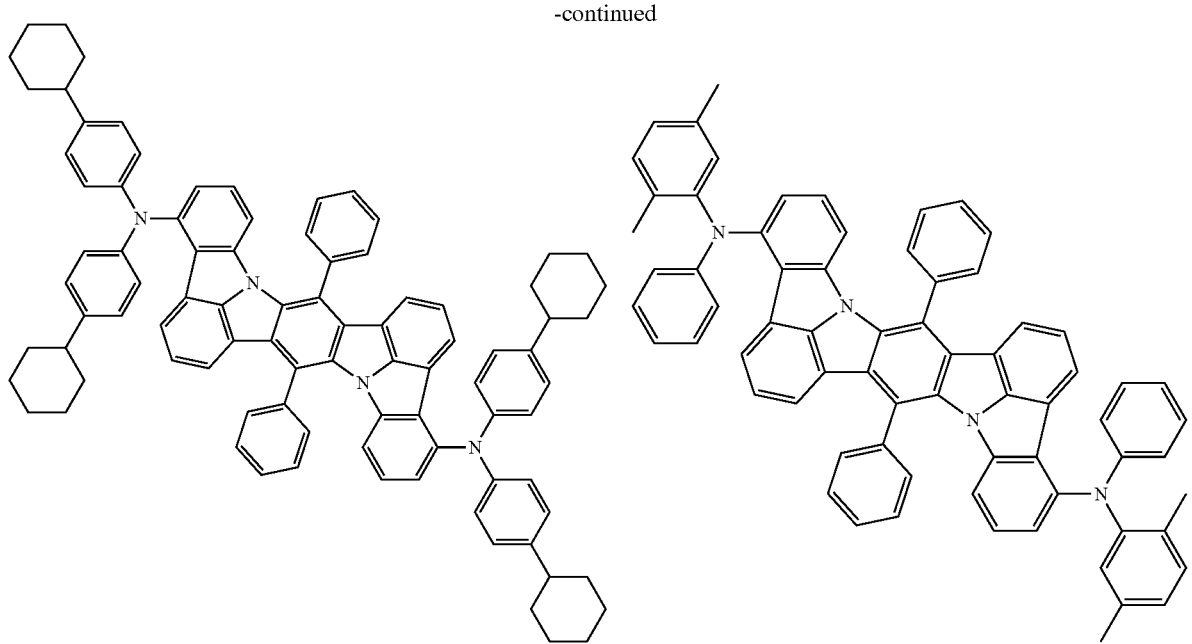
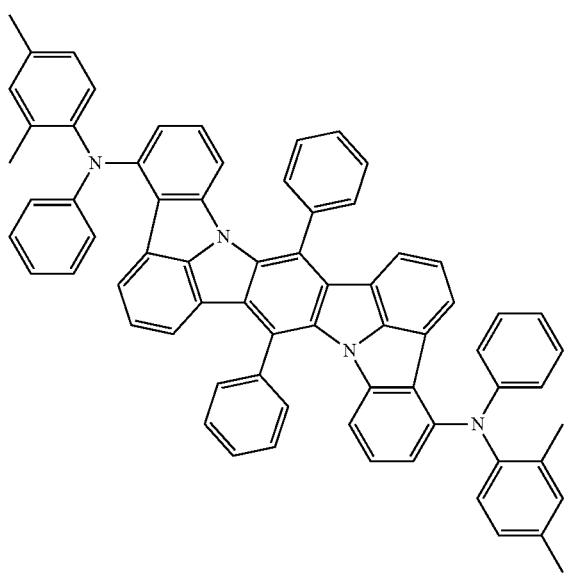

-continued
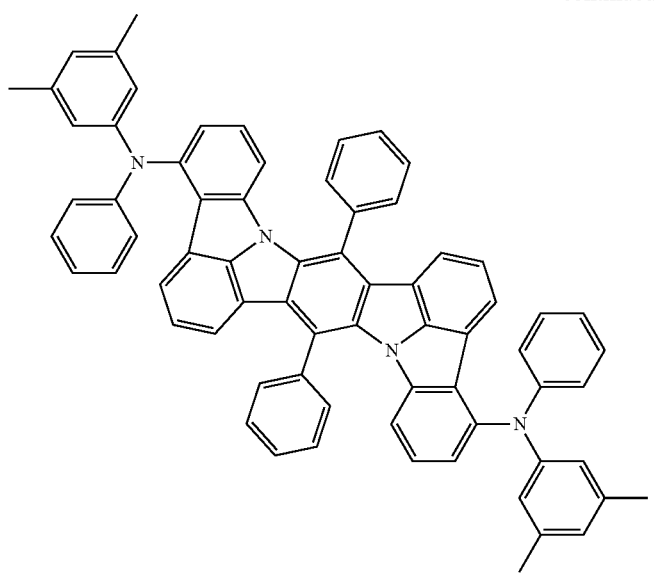
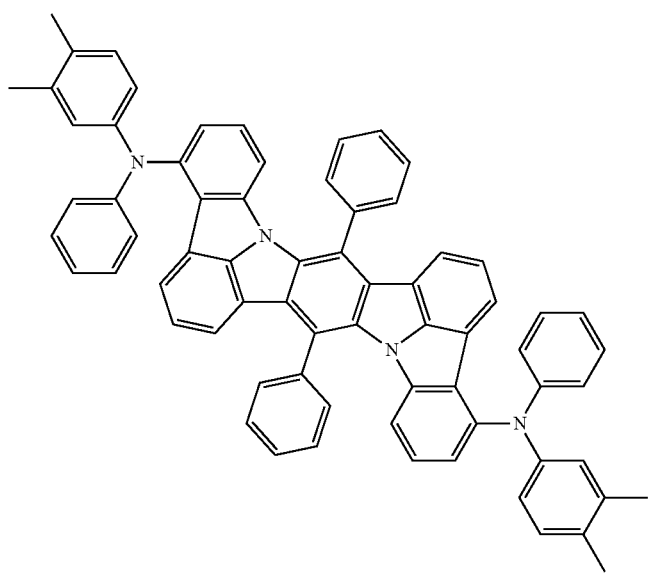
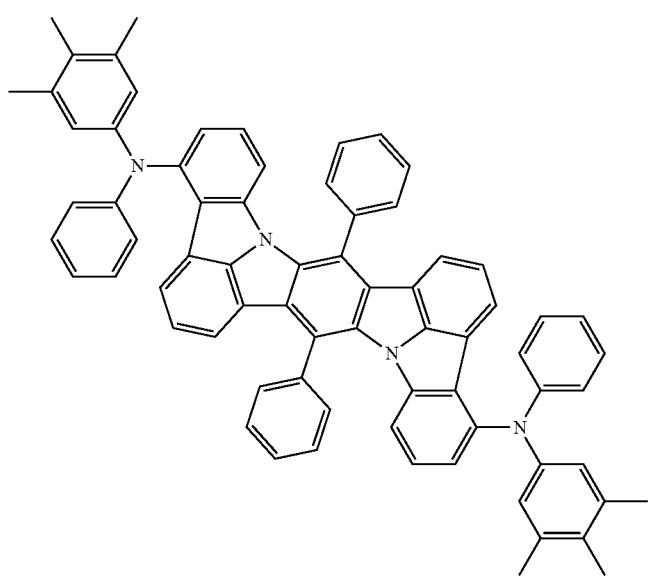

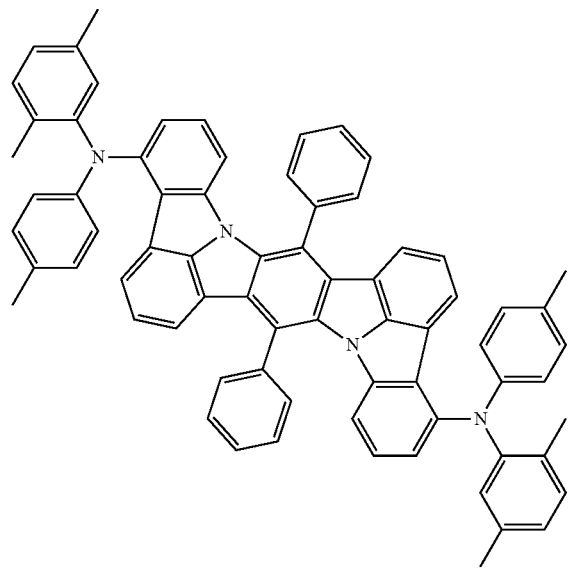
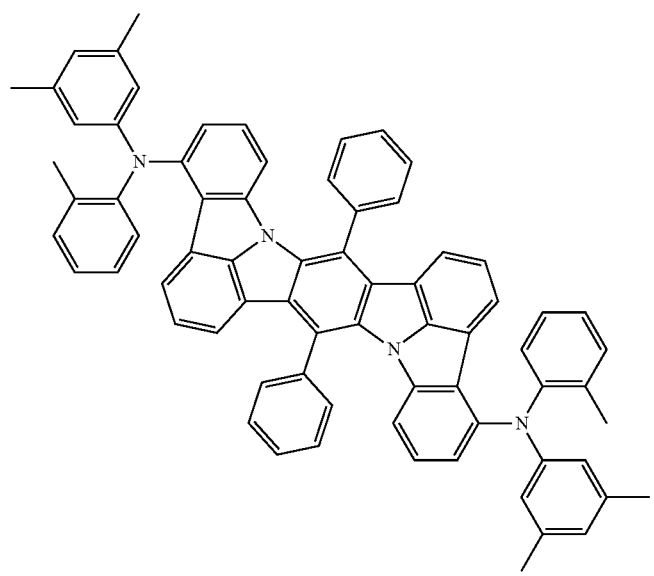
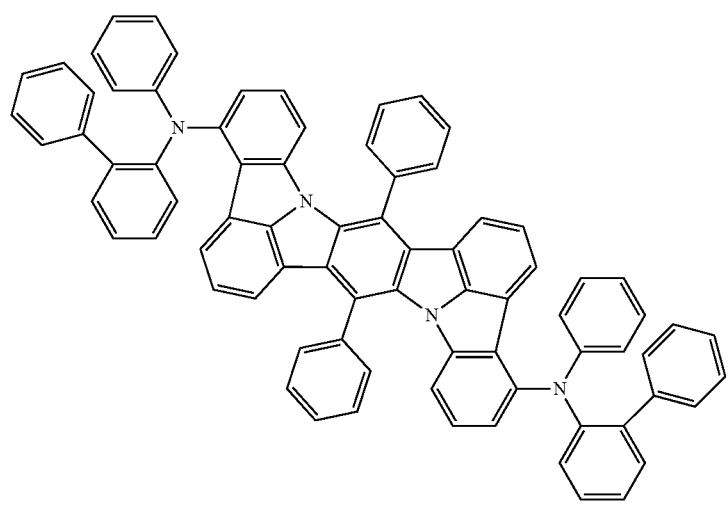

-continued
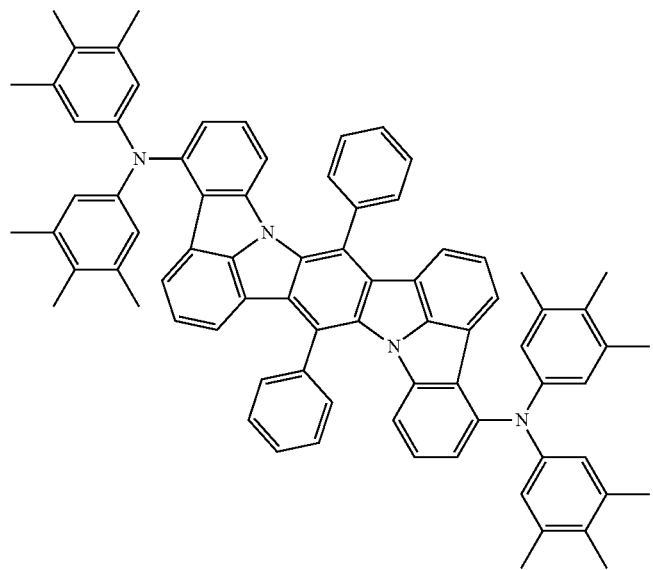
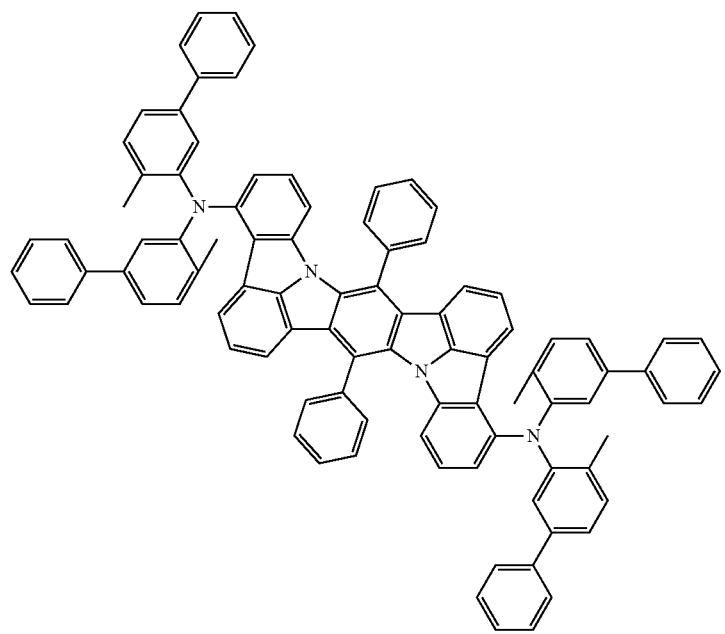

-continued
453
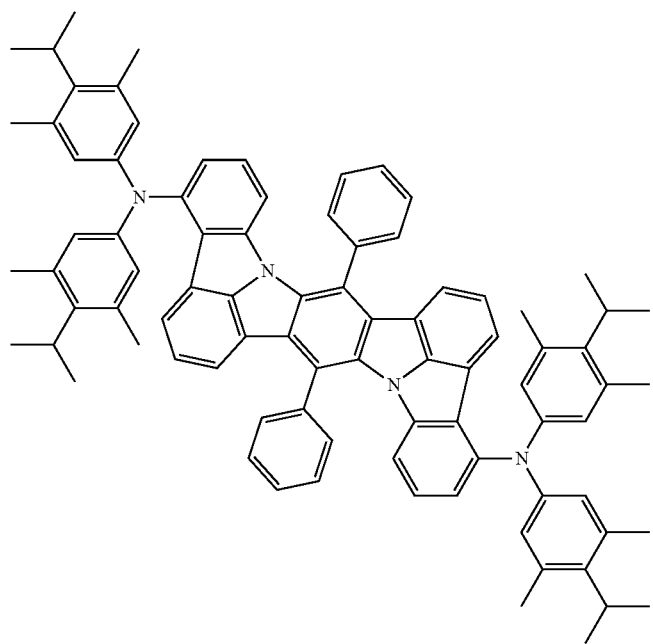
454
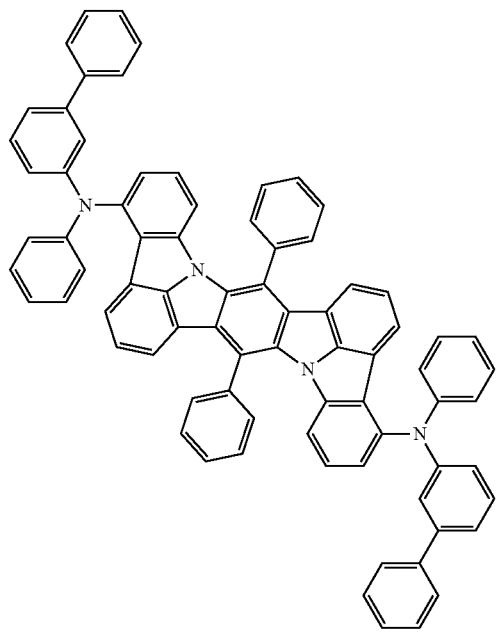
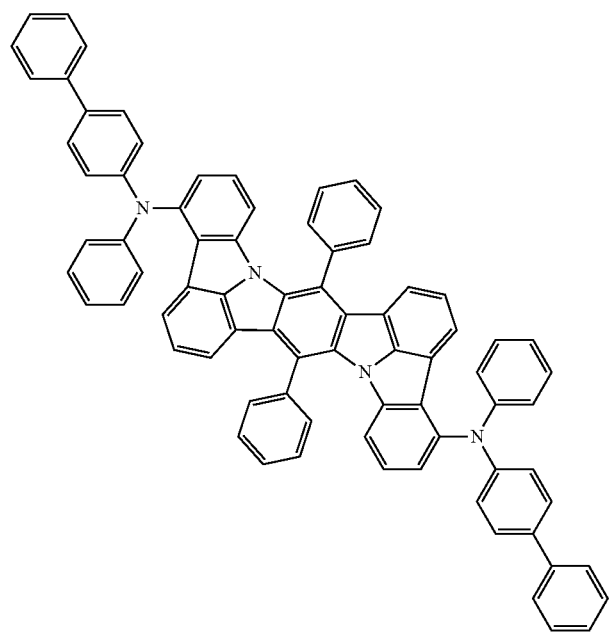

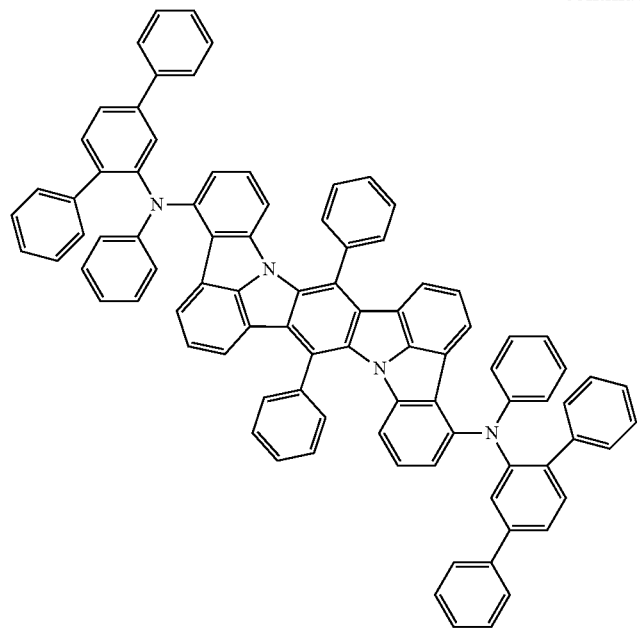
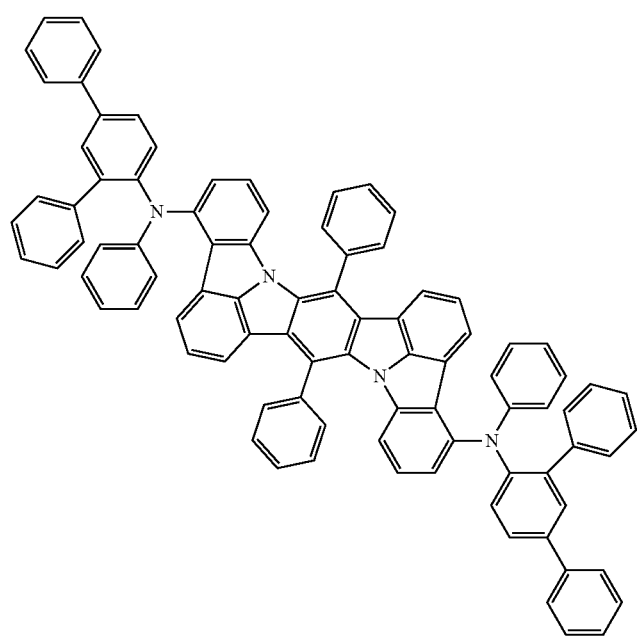

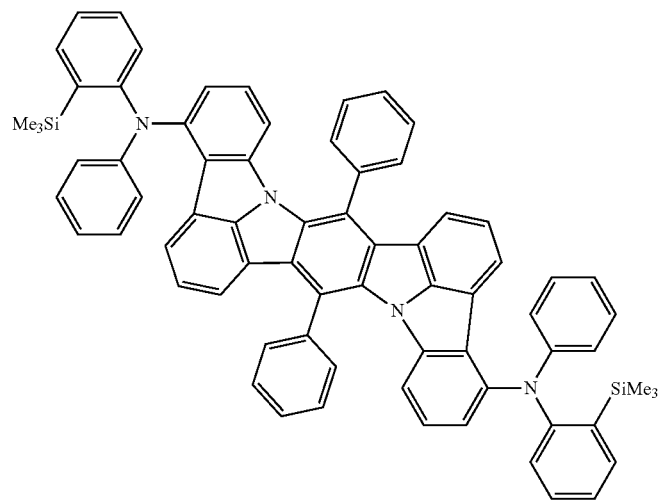
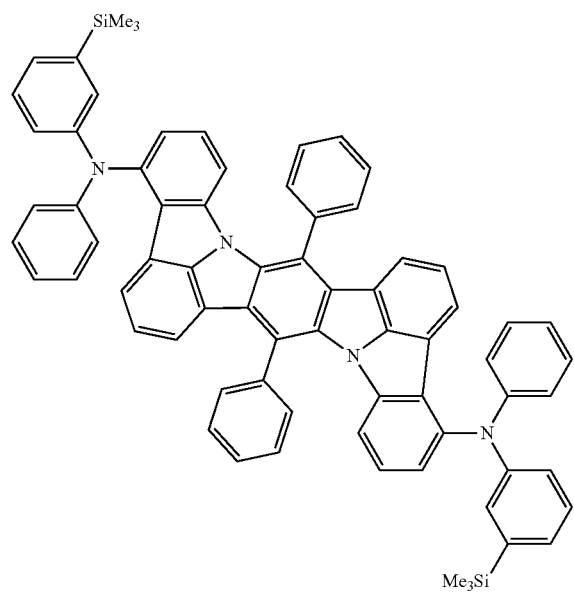
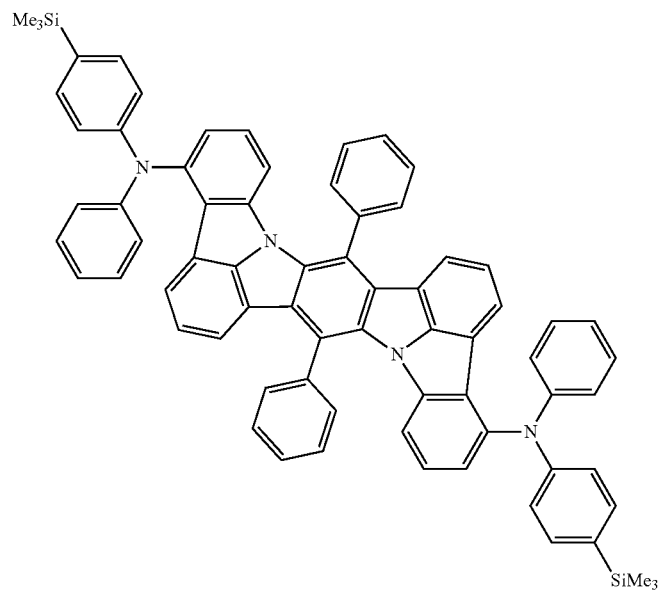

-continued
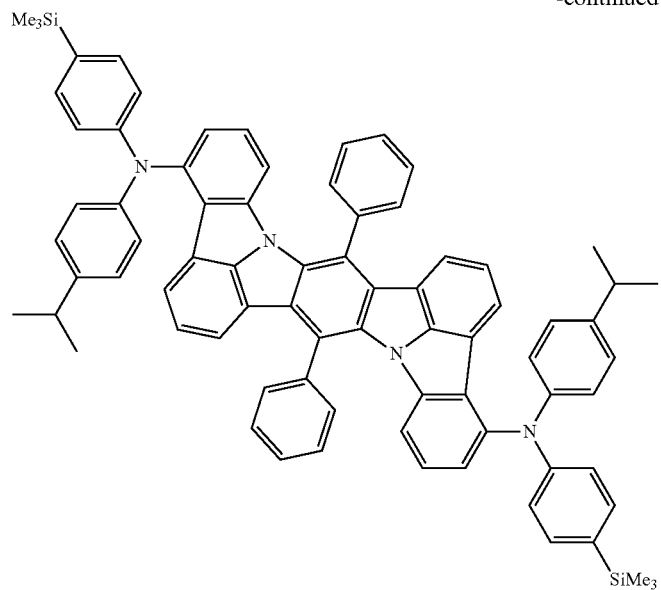
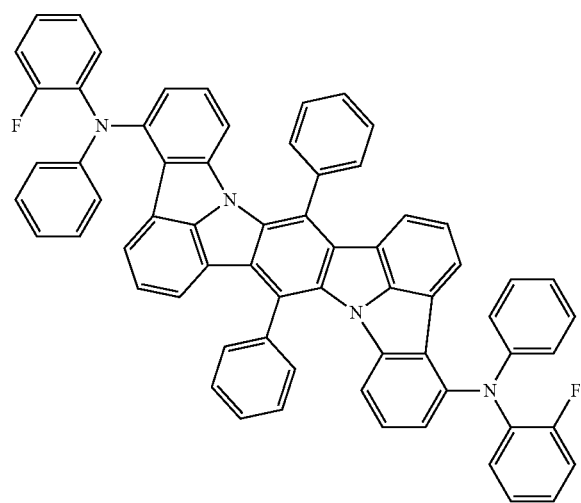
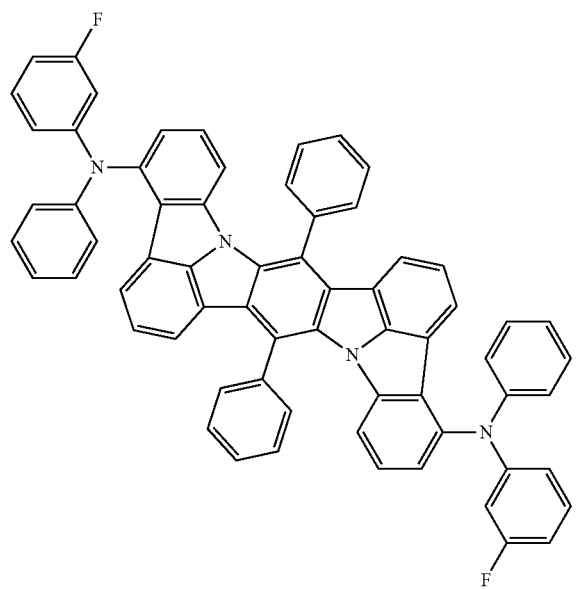

-continued
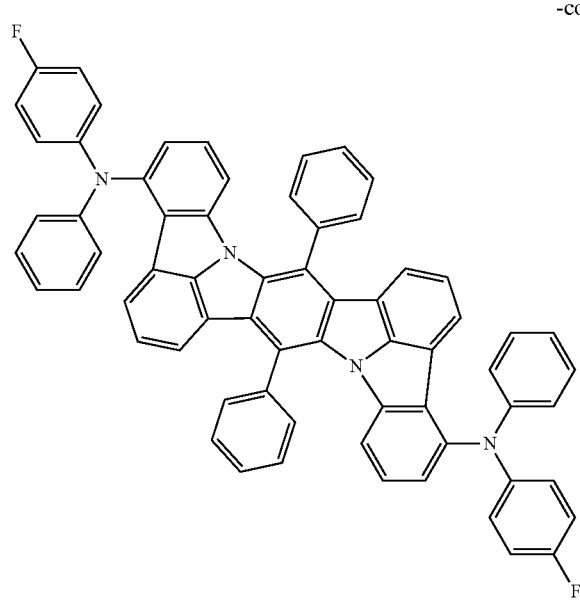
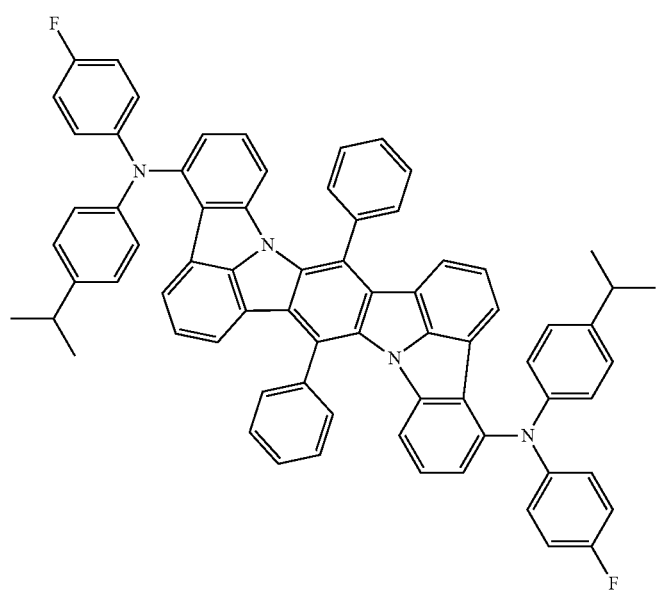
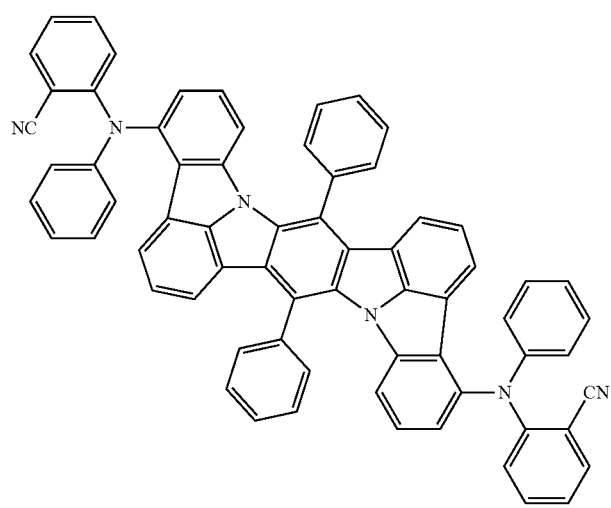

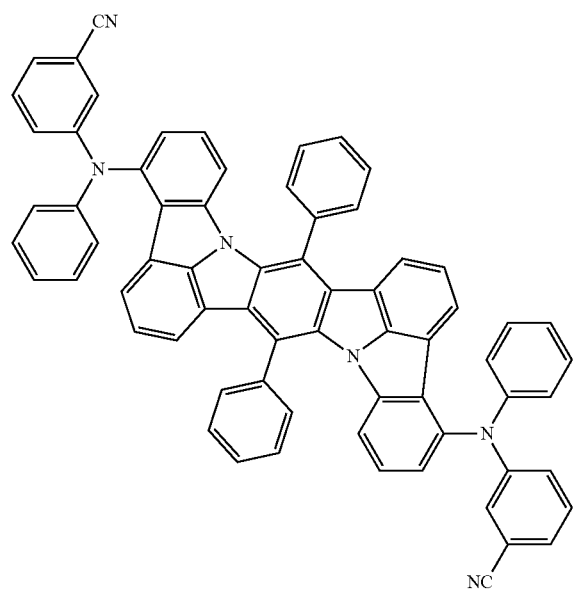
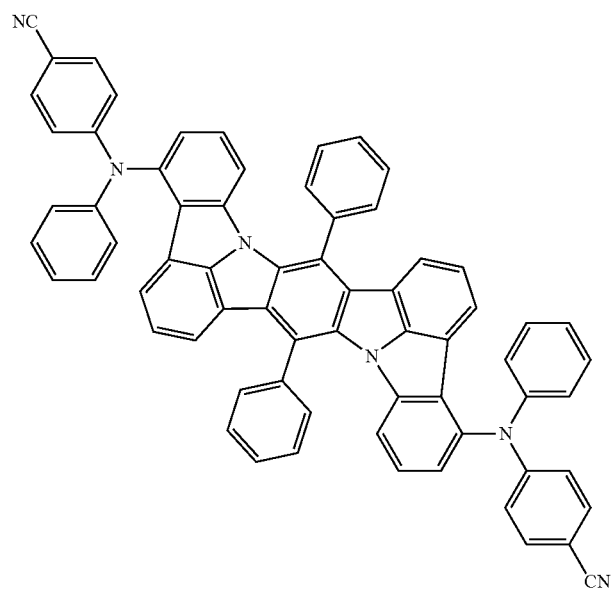

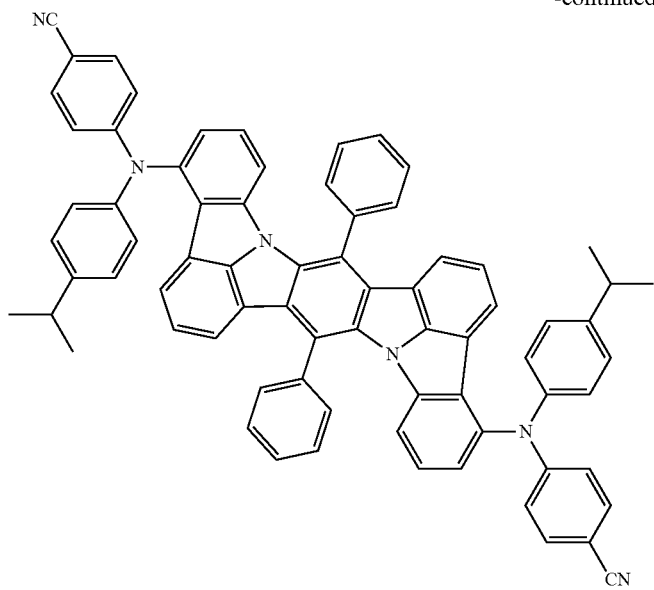
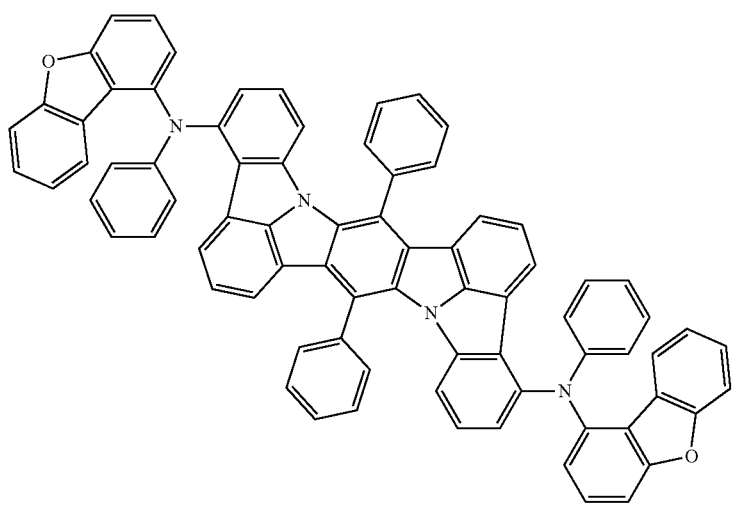
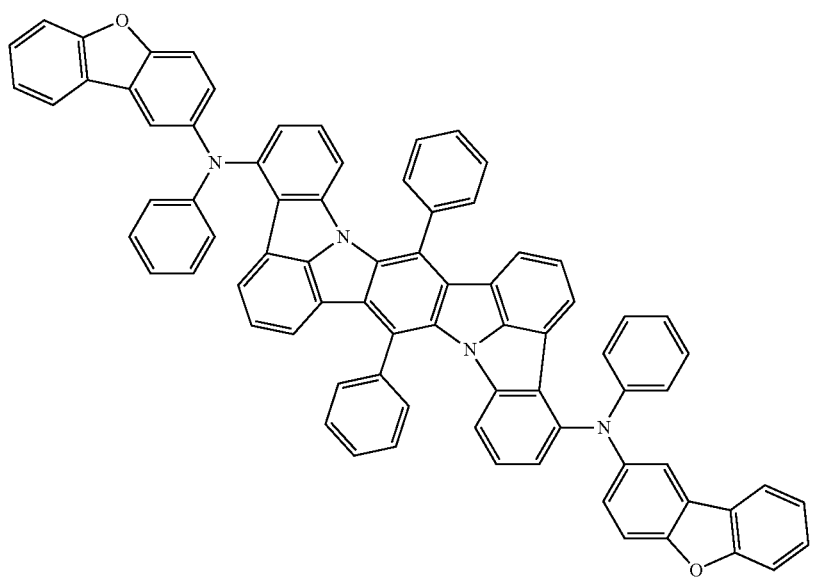

-continued
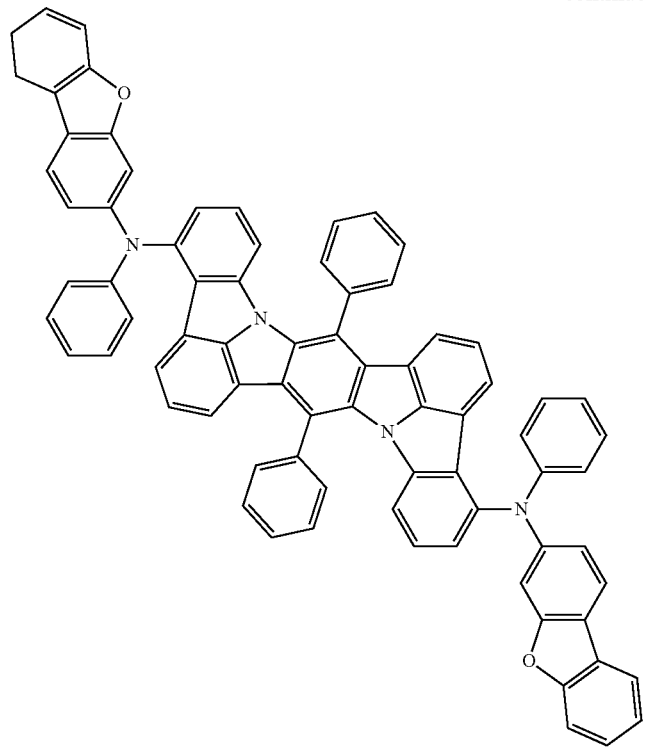
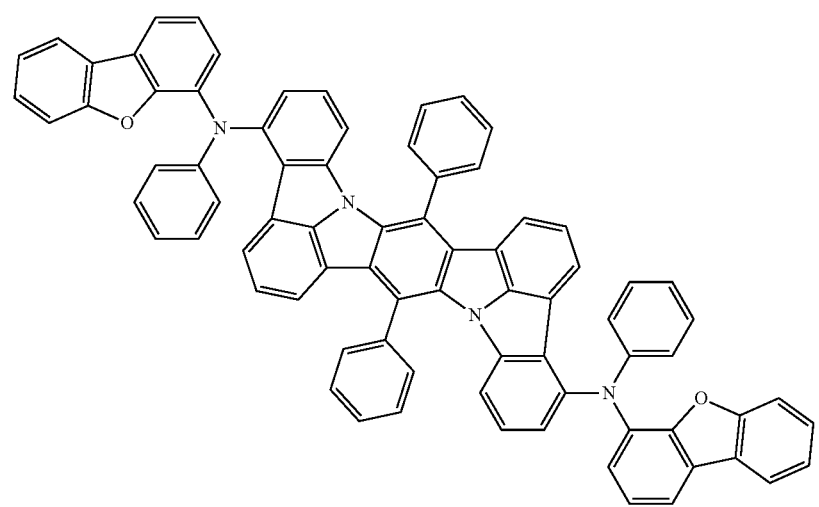

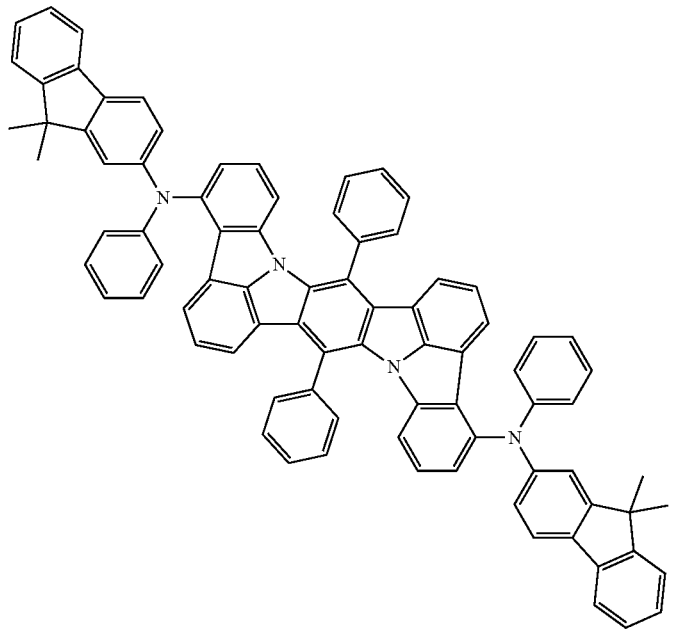
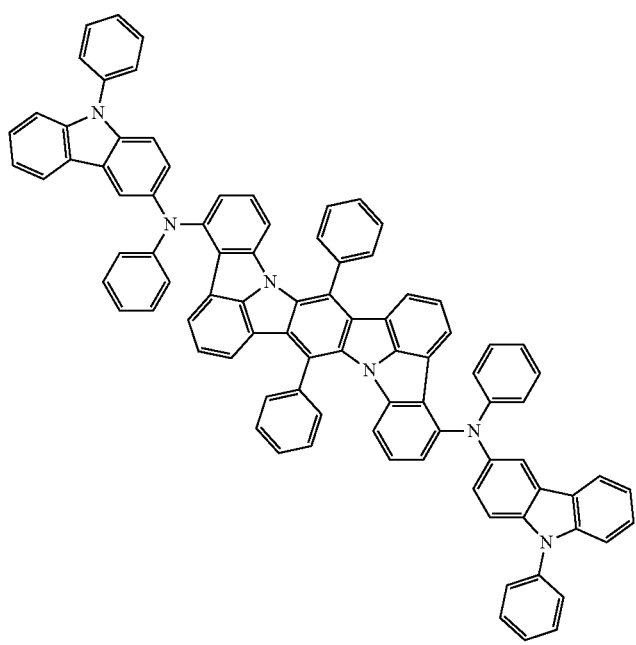

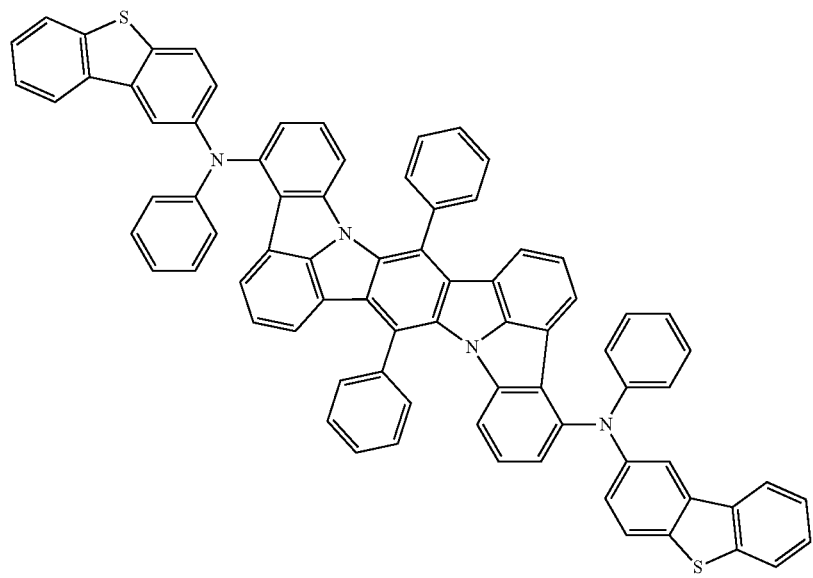
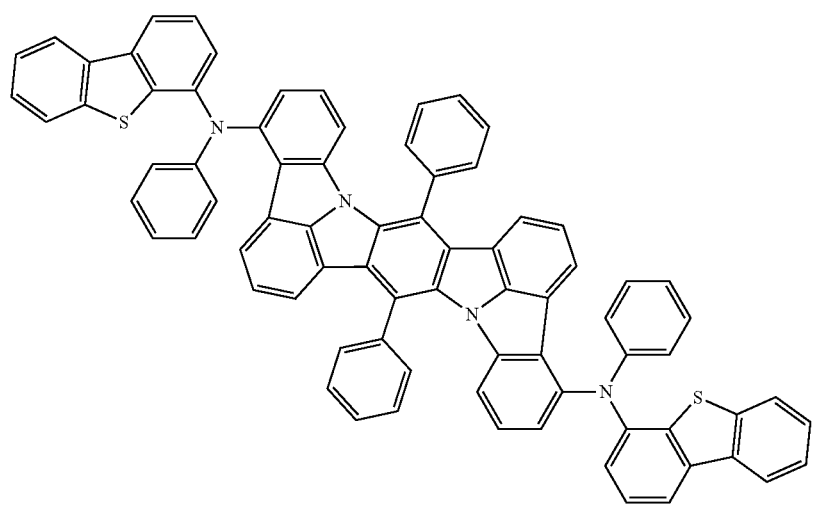
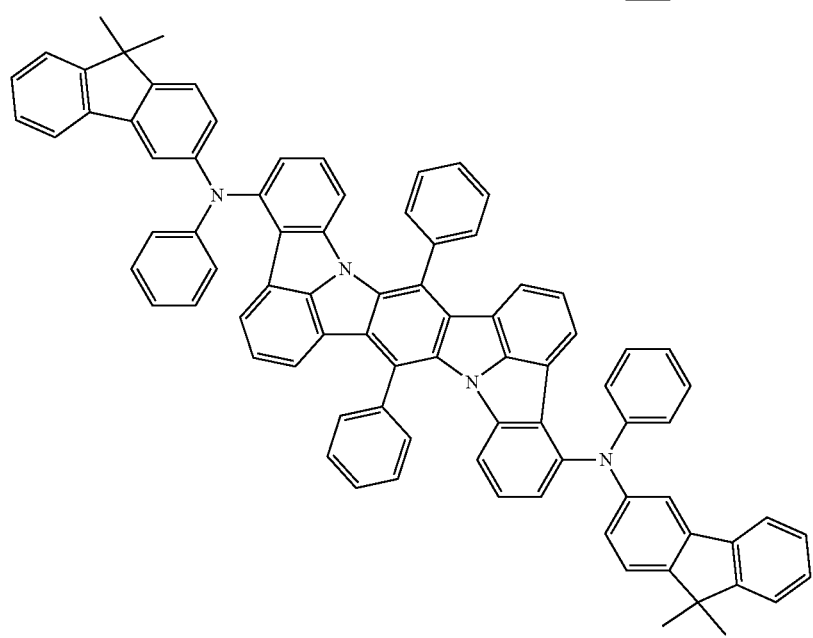

-continued
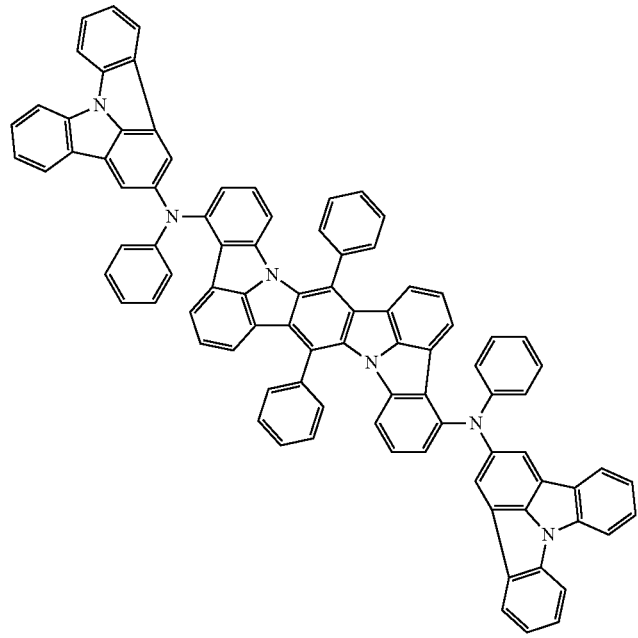
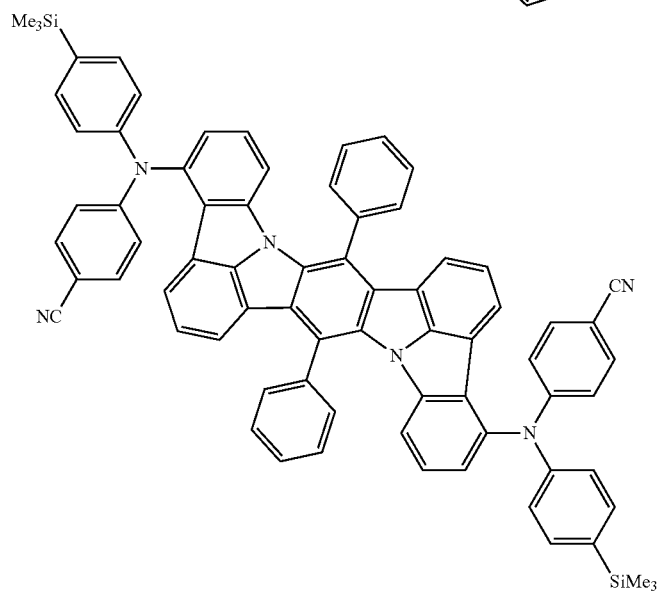
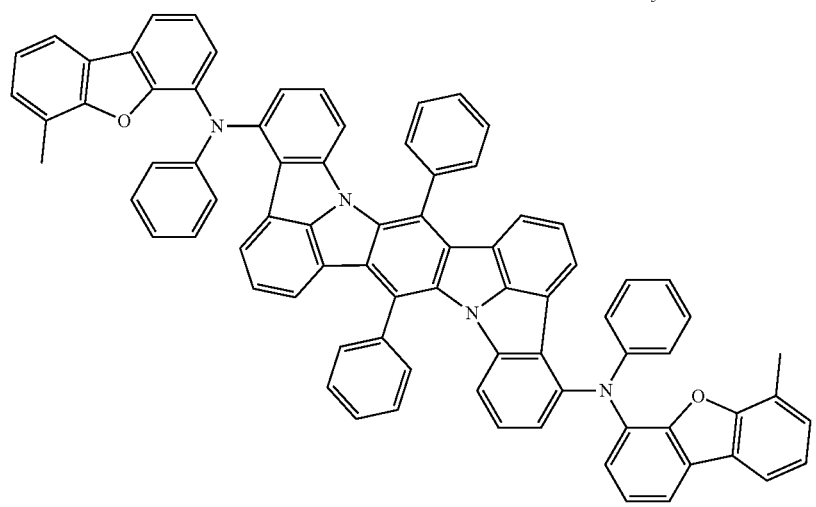

-continued
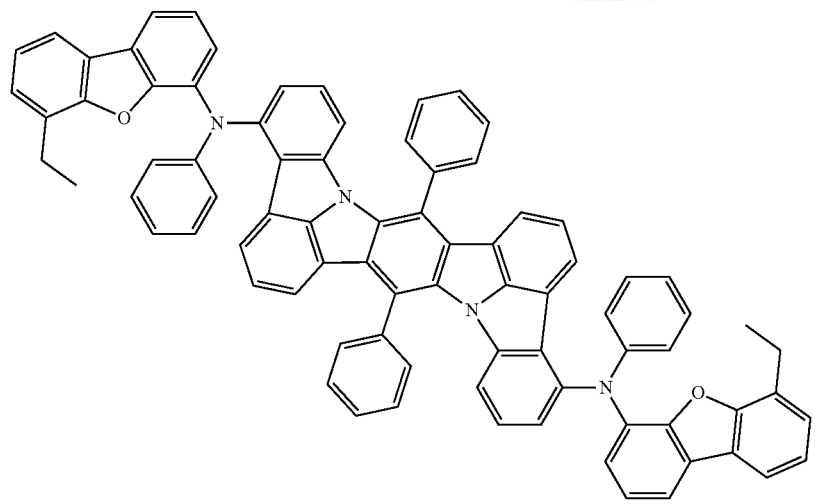
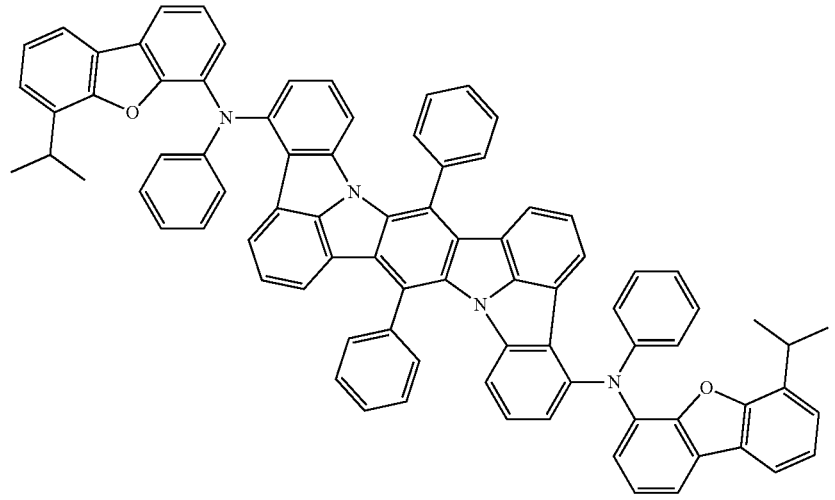
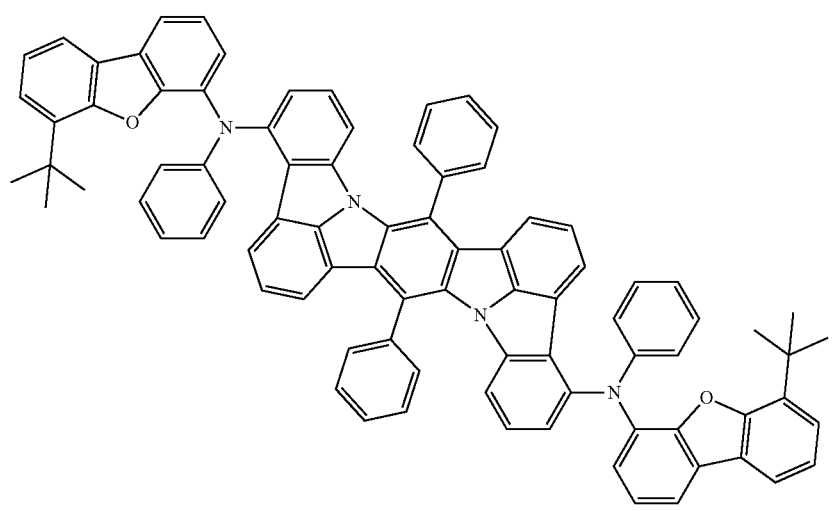

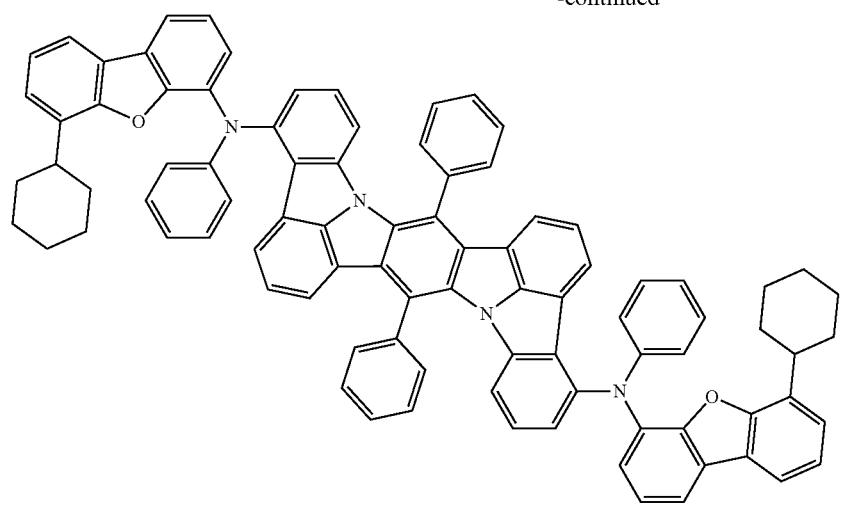

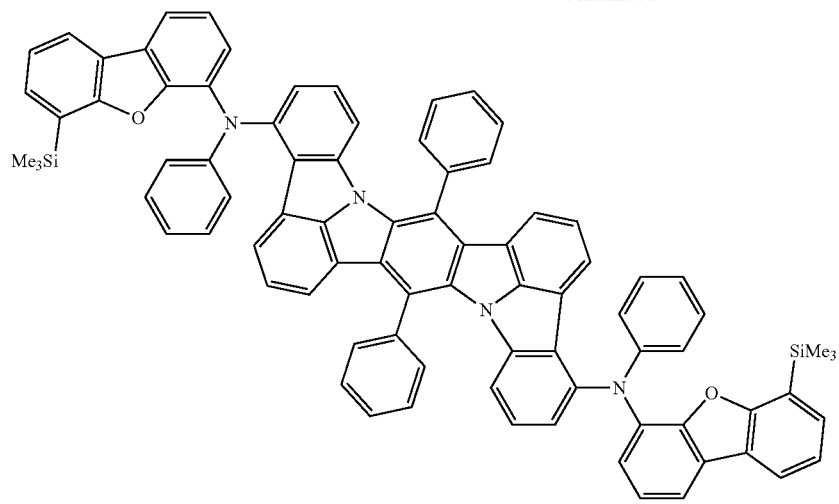

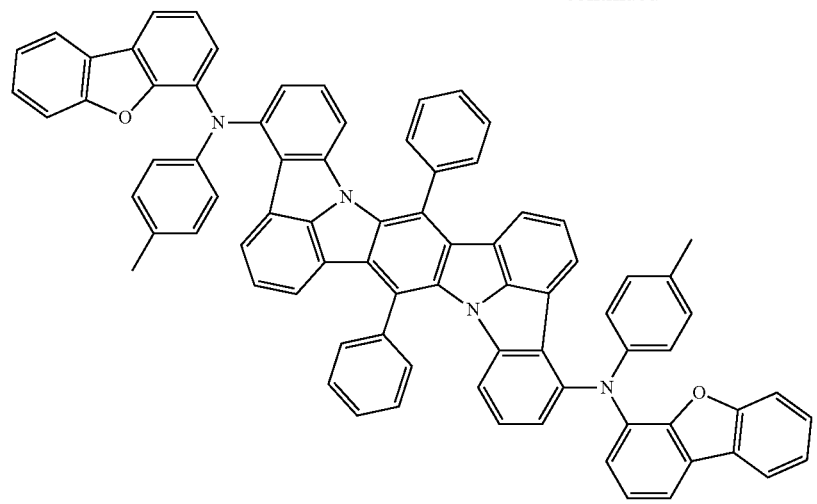
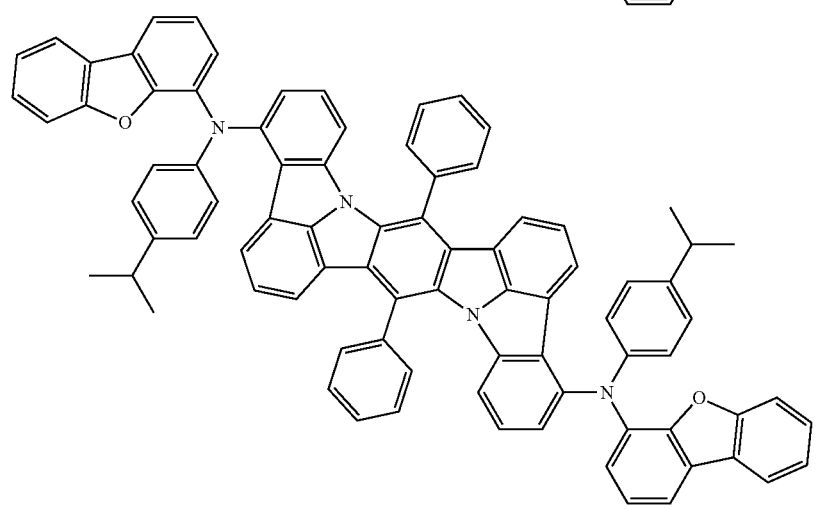
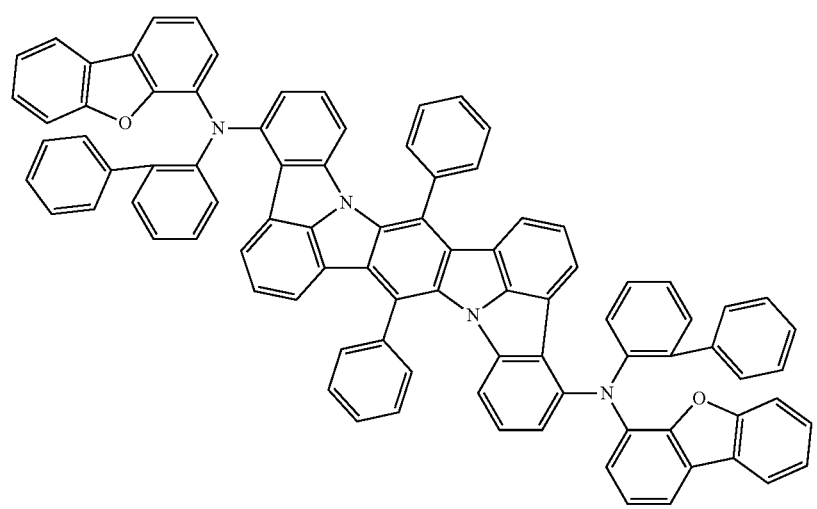

-continued
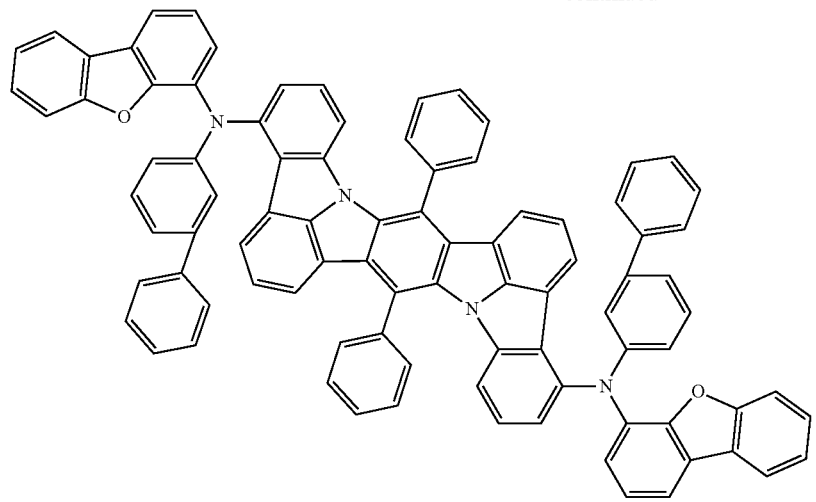
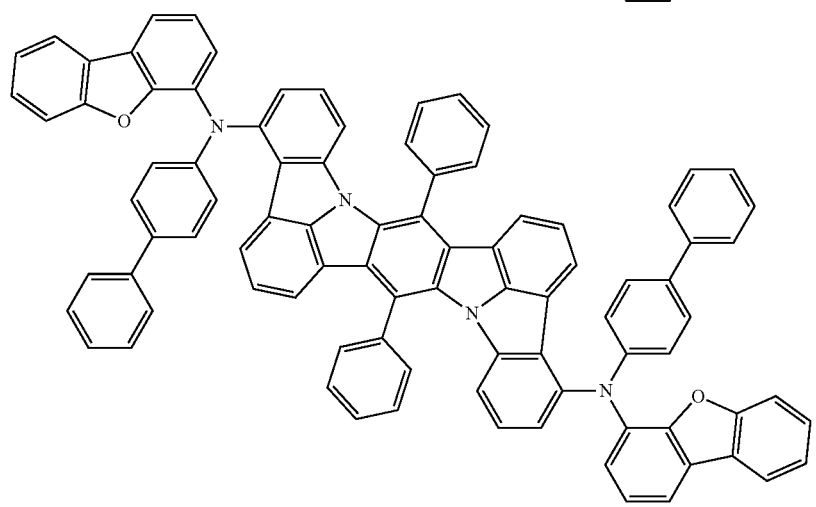
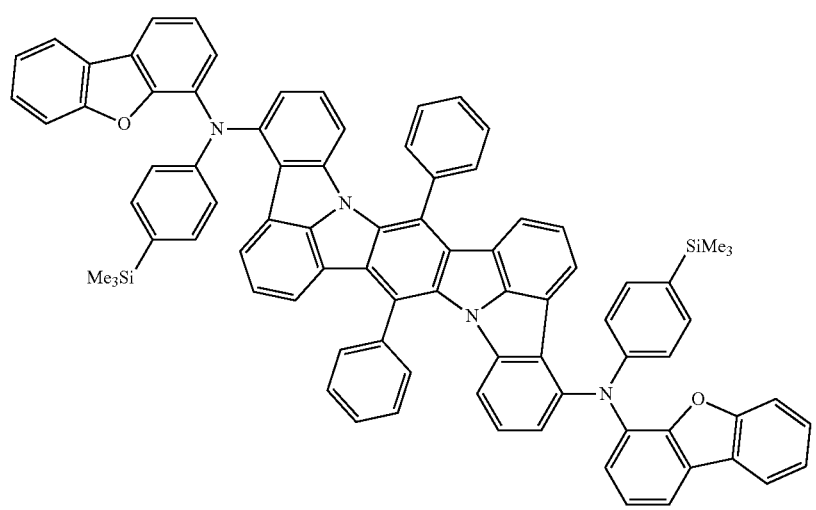

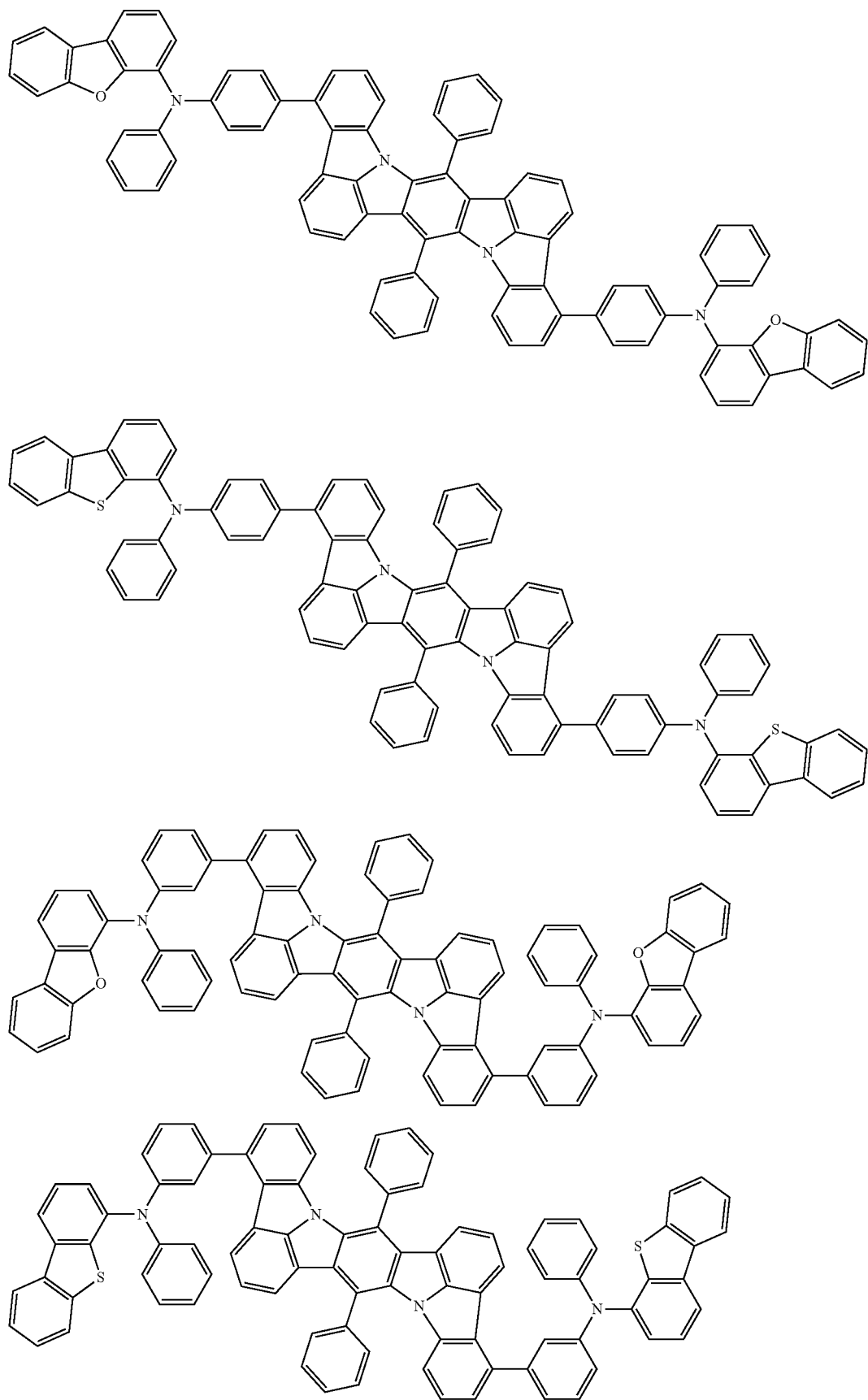

-continued
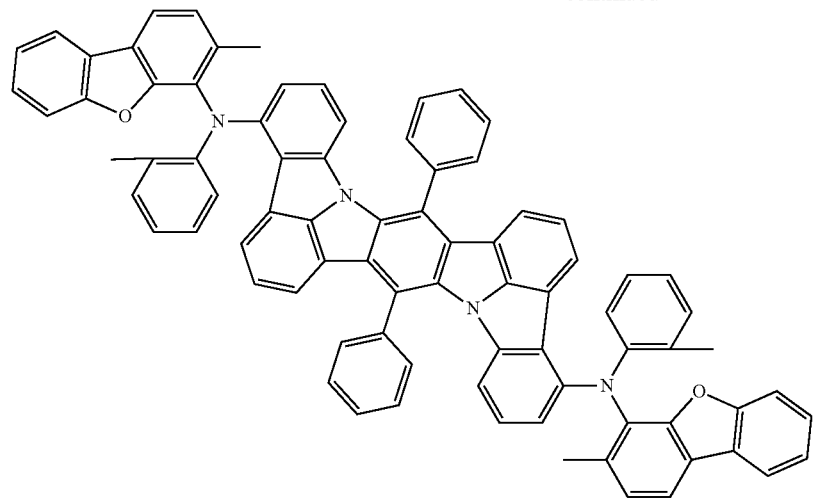
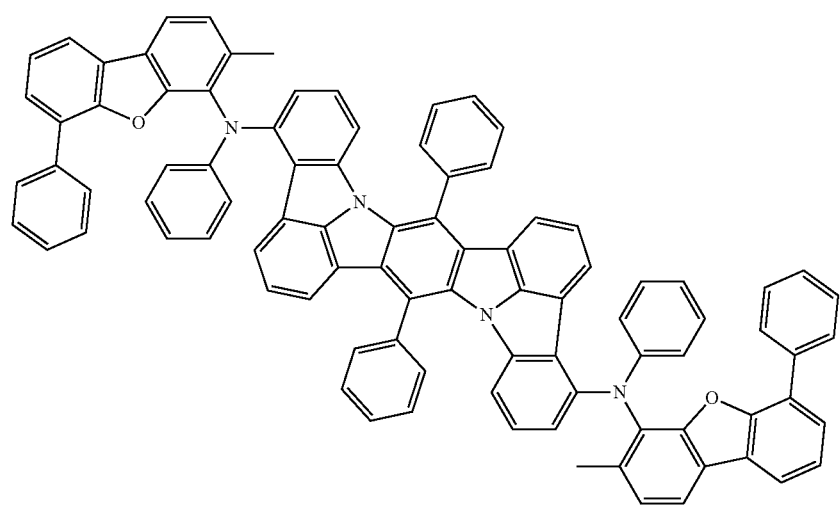
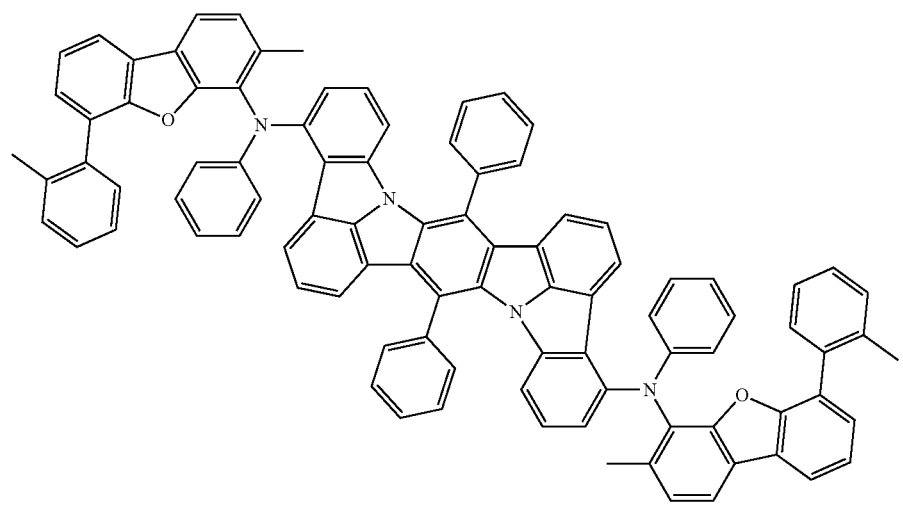

-continued
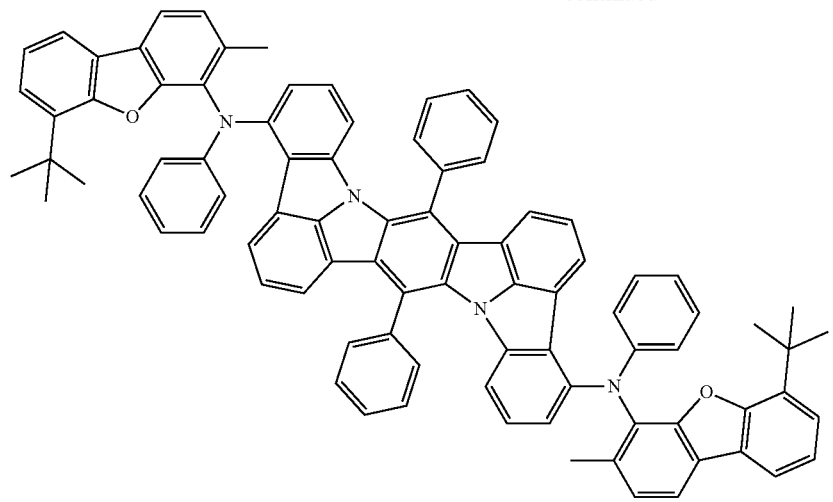
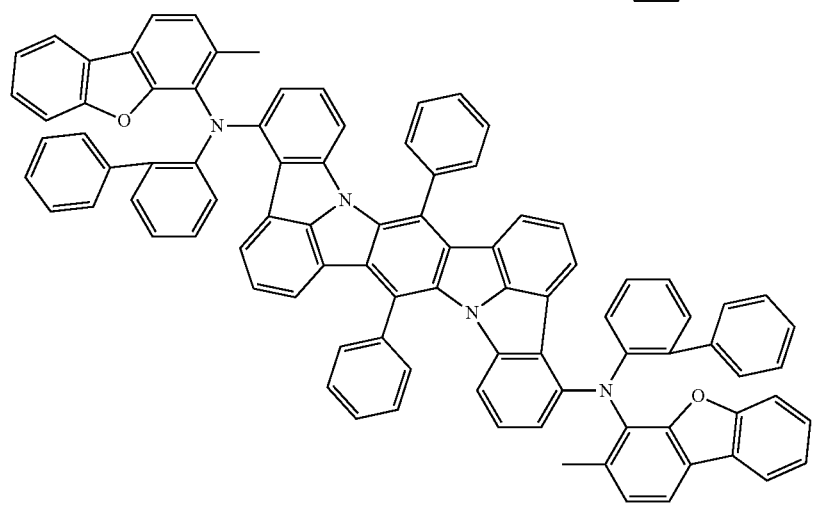
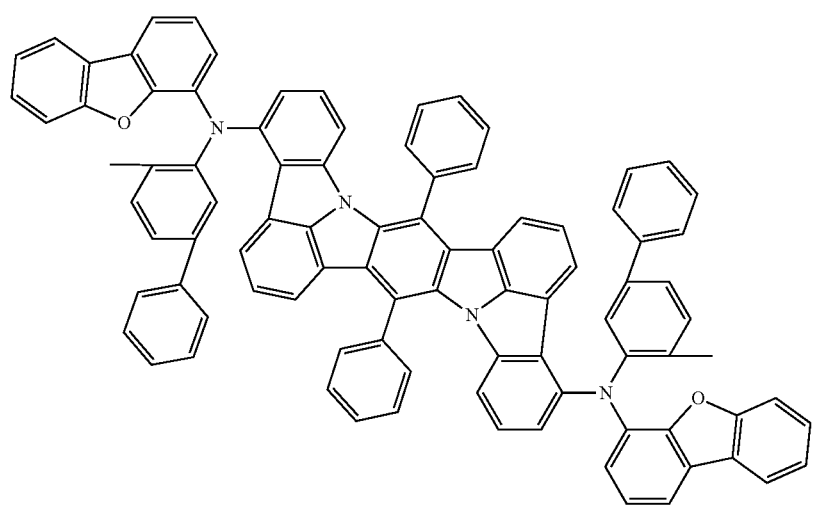

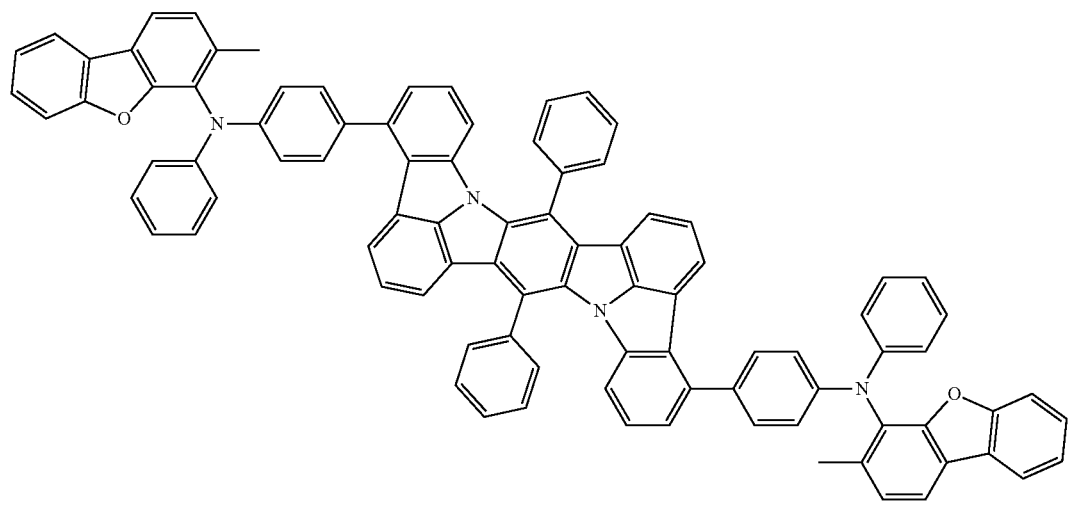
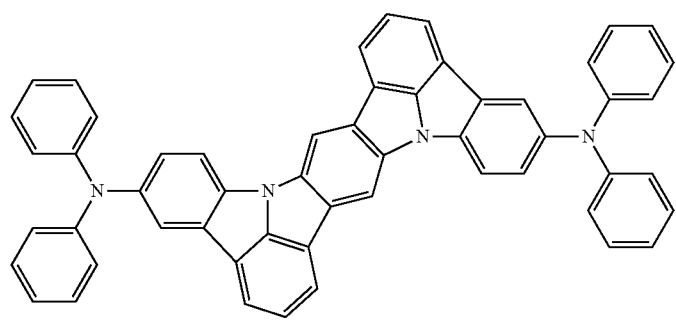
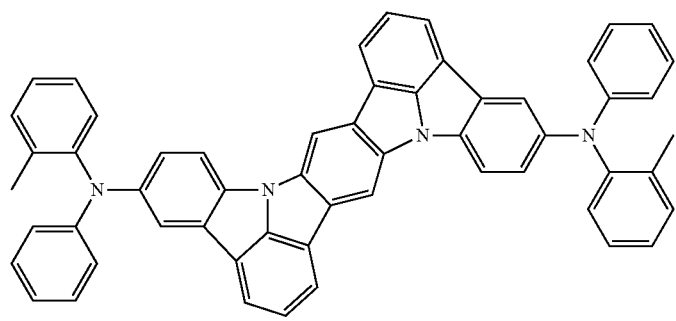
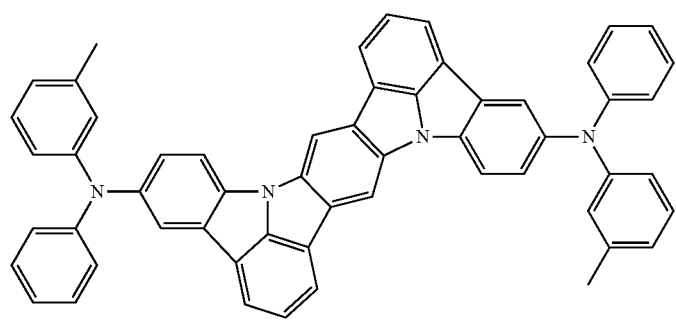

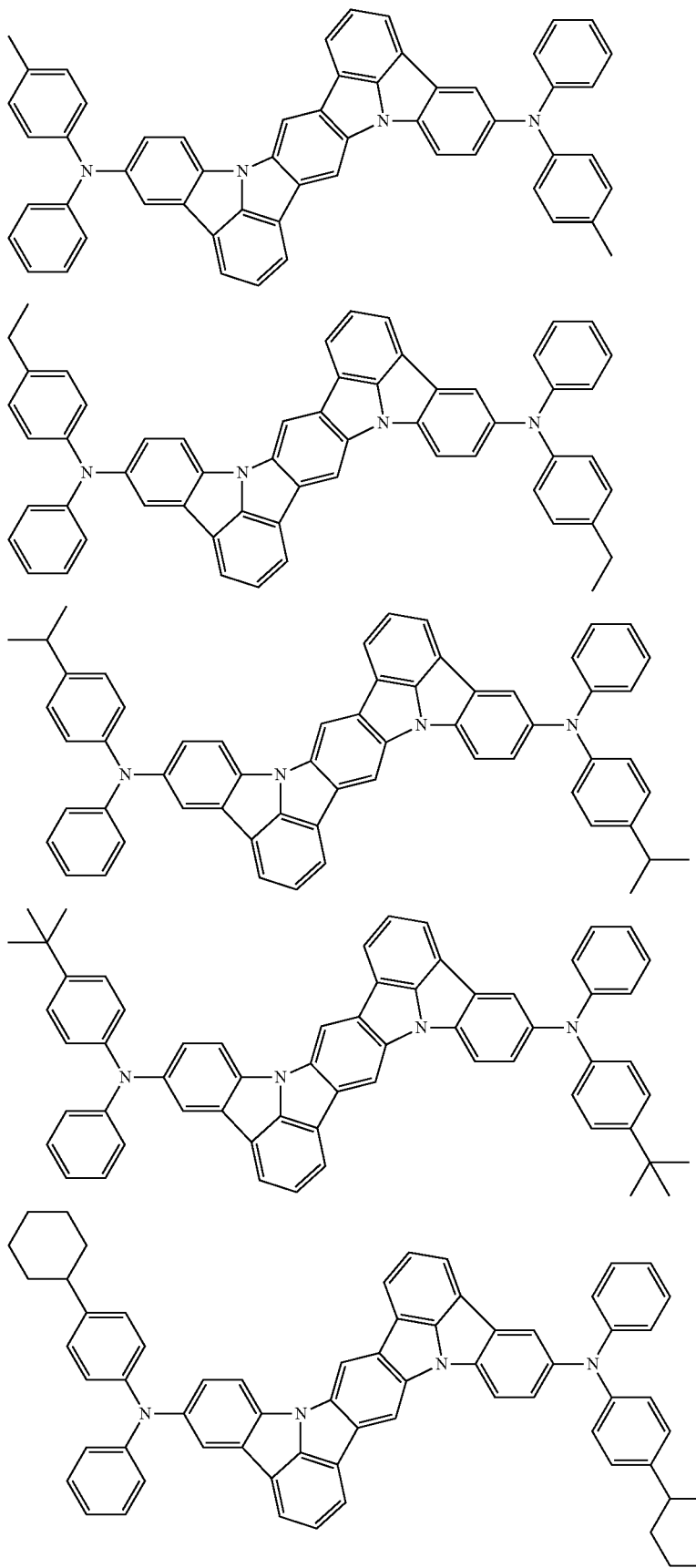

-continued
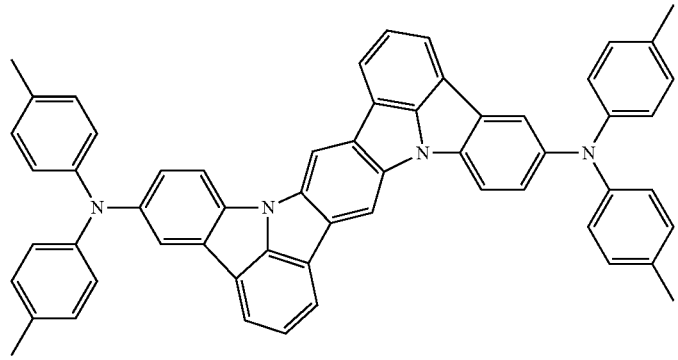
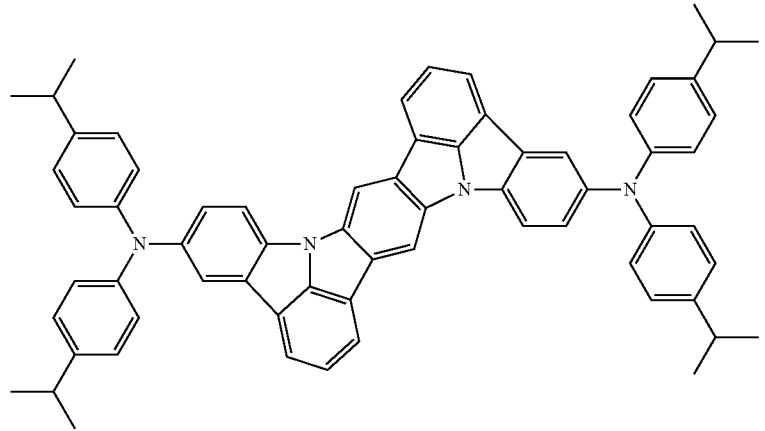
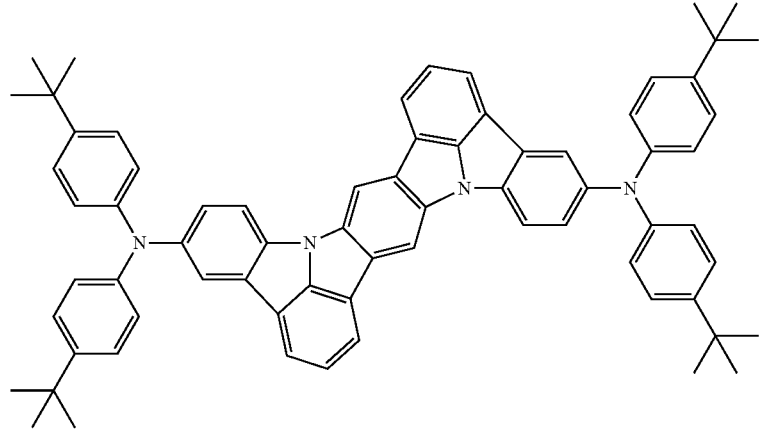
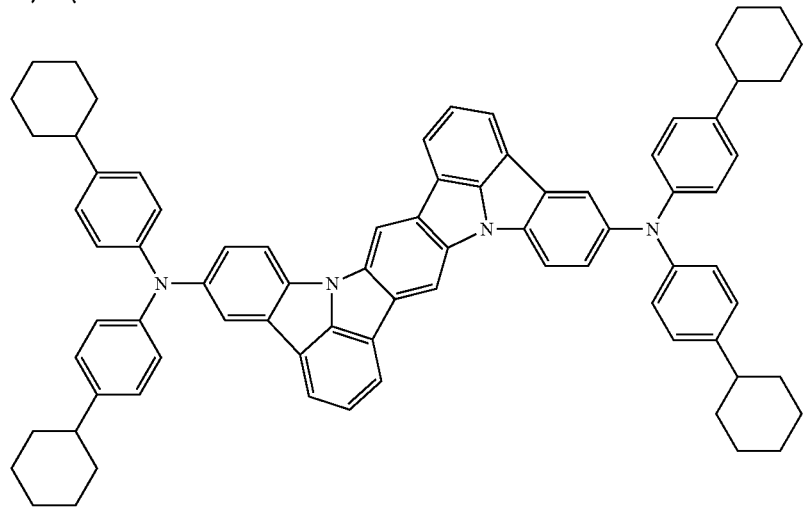

-continued
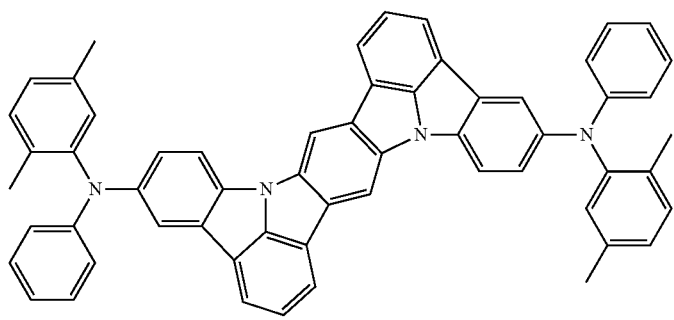
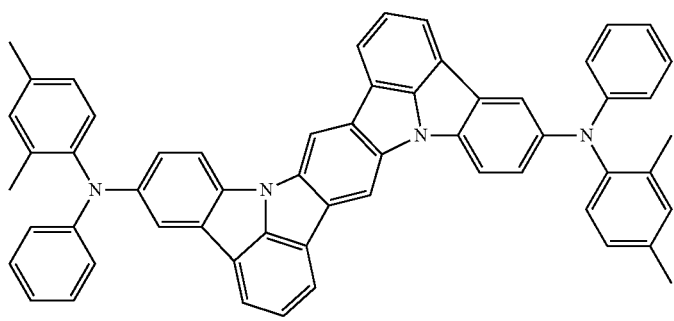
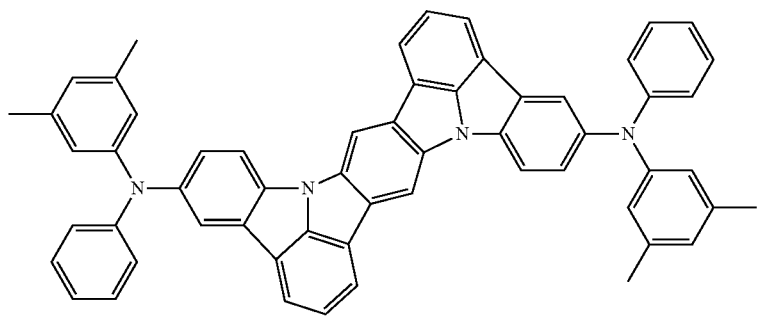
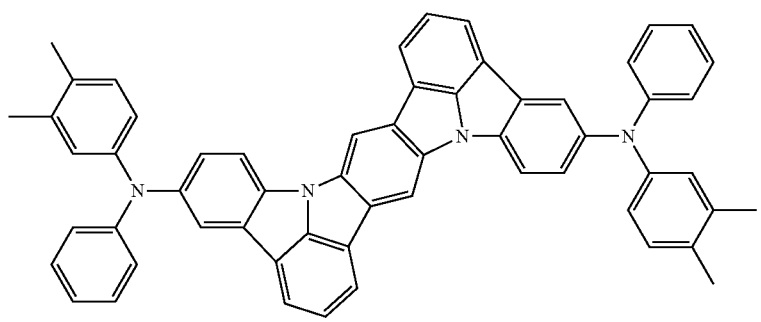
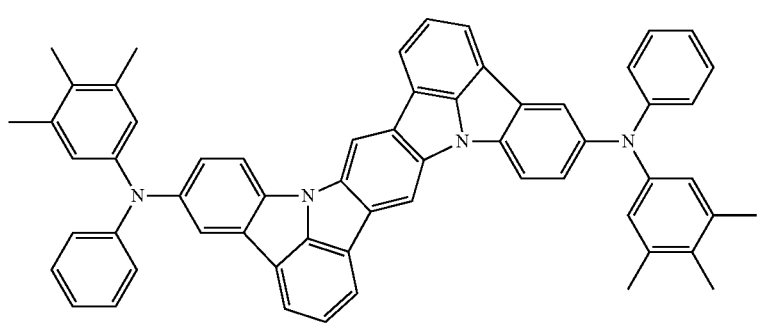

-continued
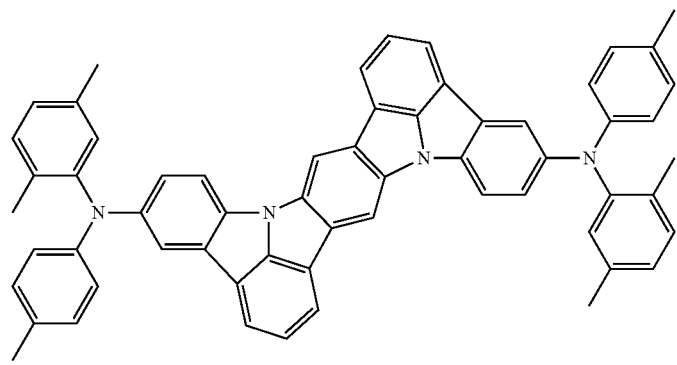
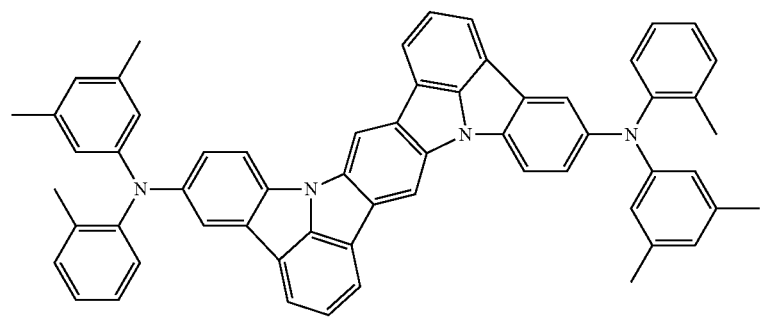
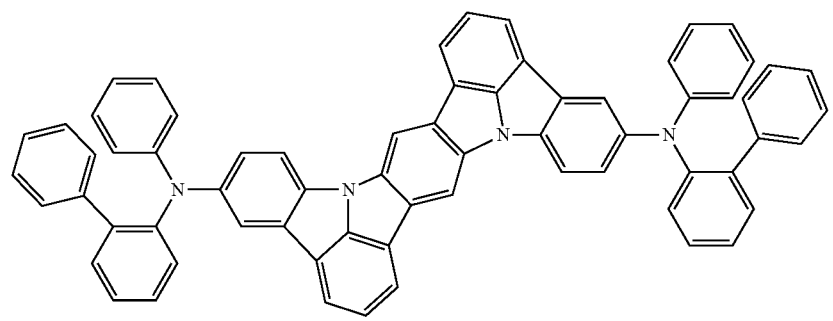
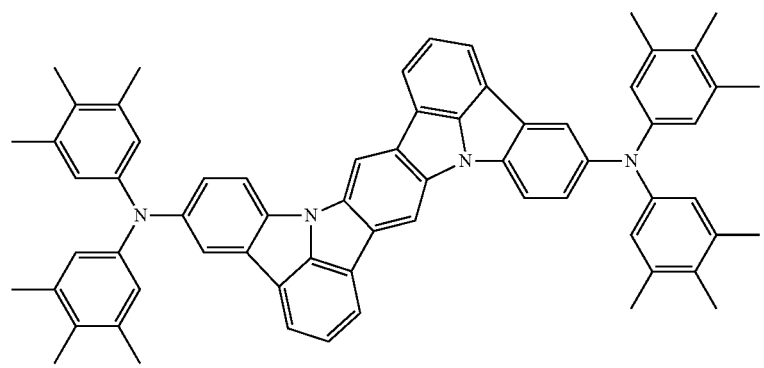

-continued
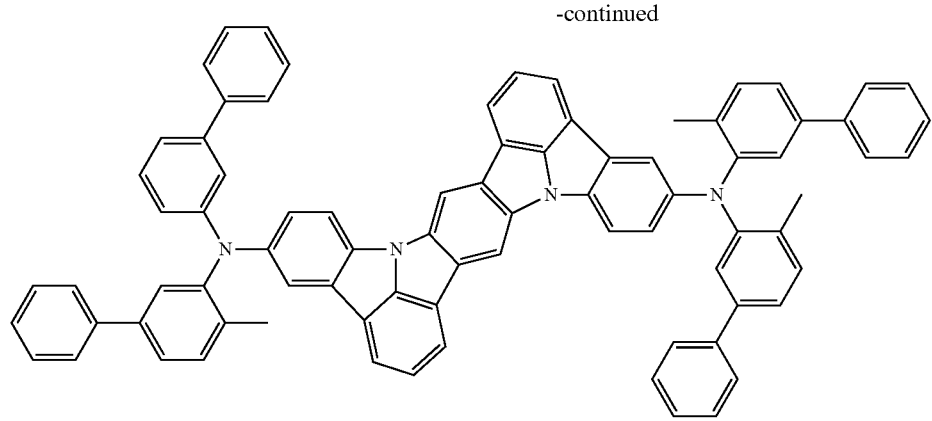
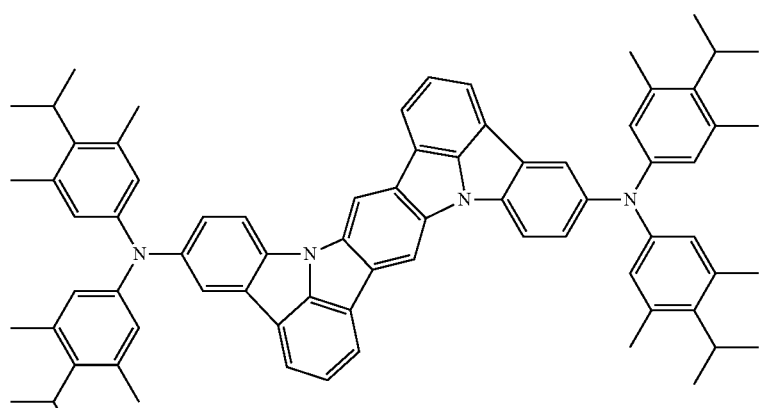
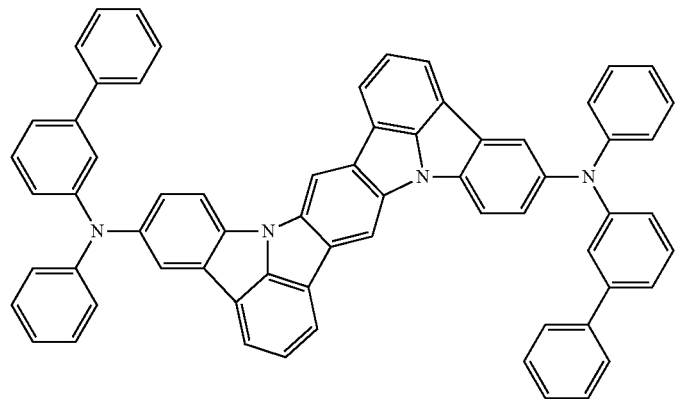
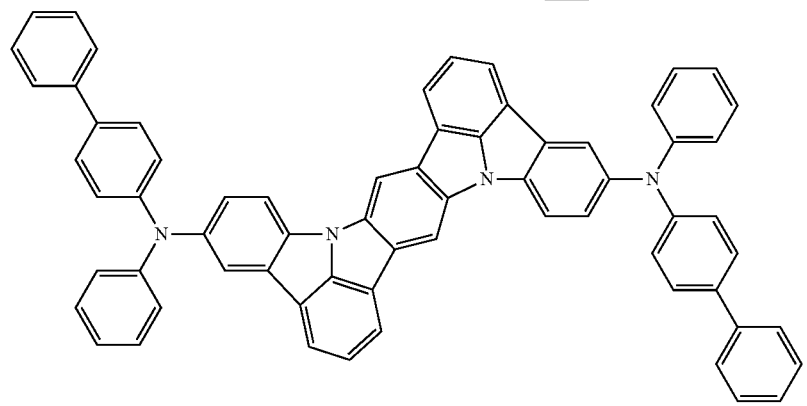

-continued
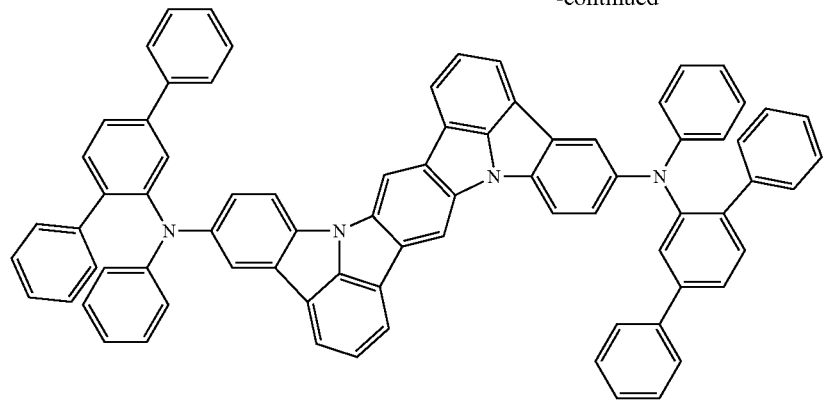
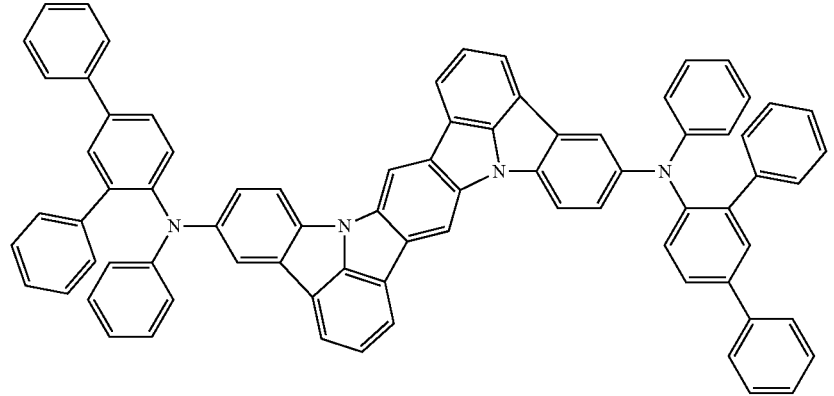
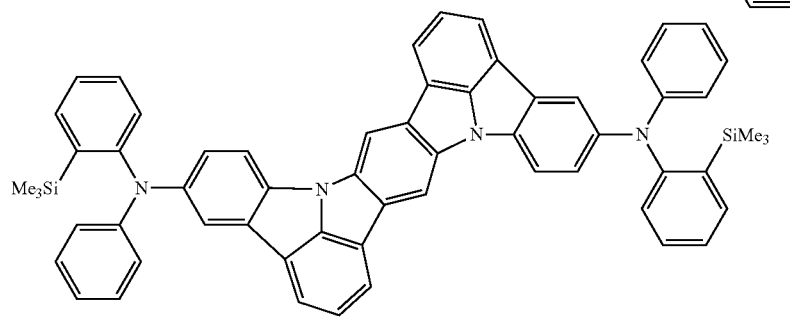
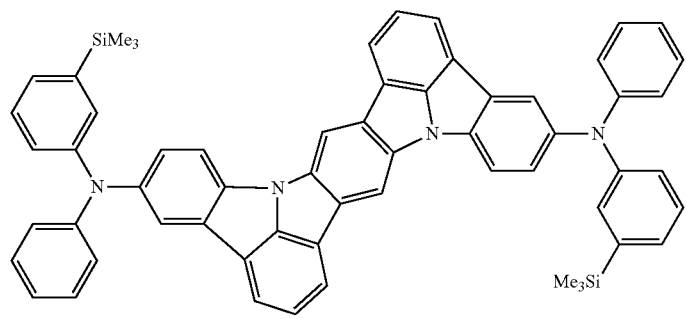
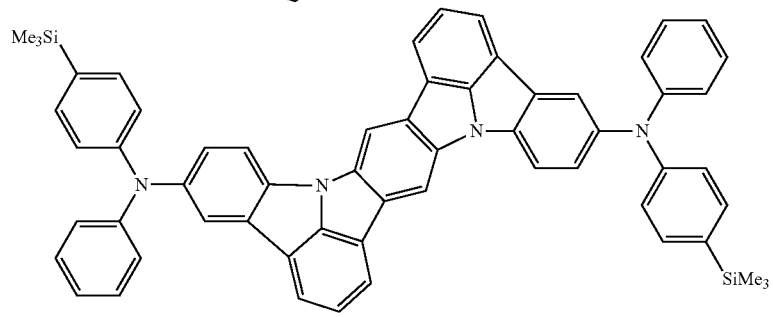

-continued
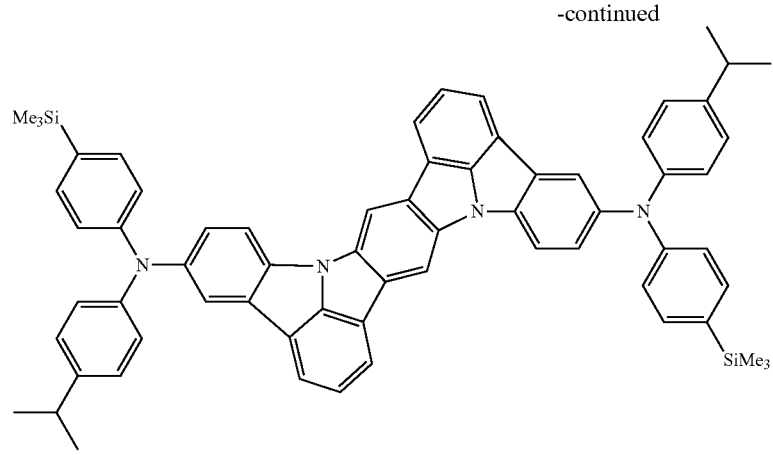
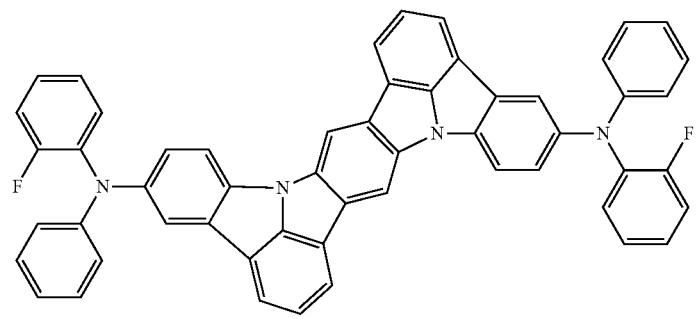
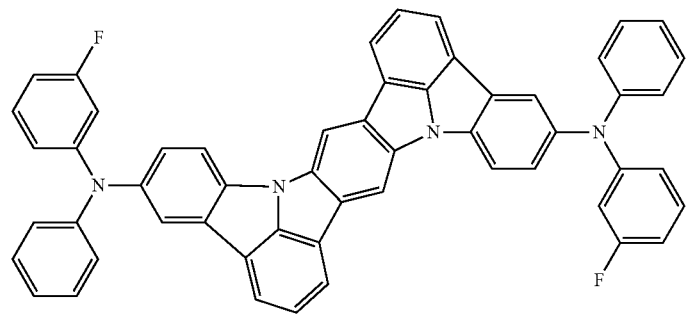
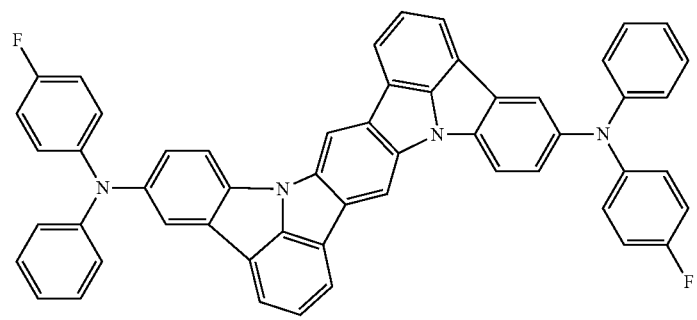

-continued
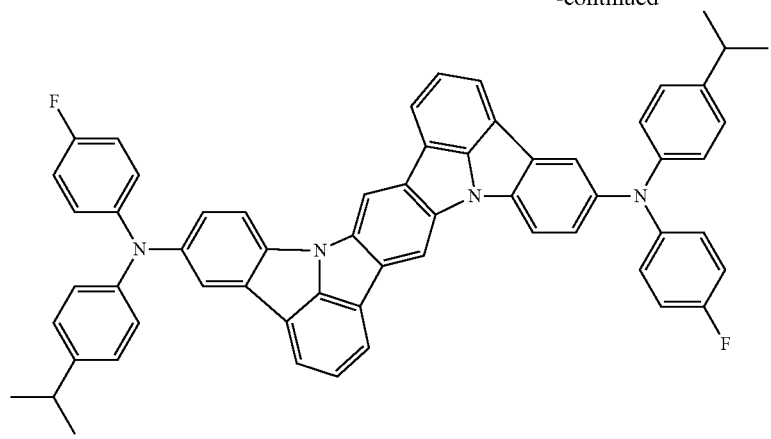
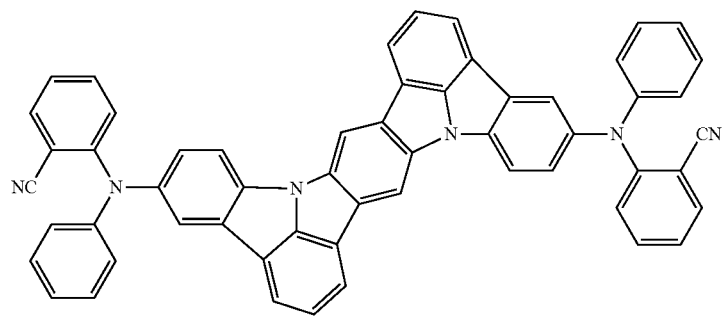
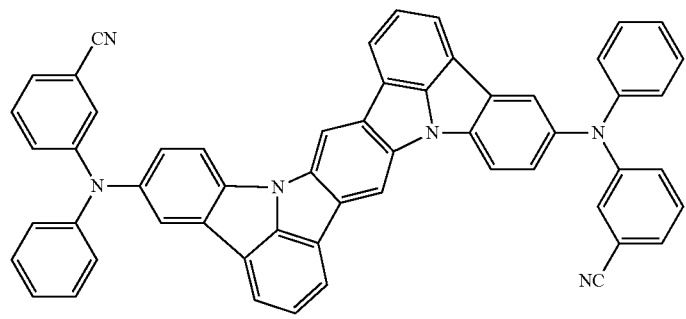
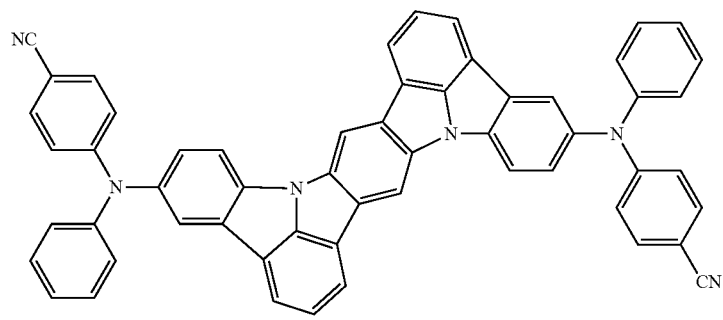

-continued
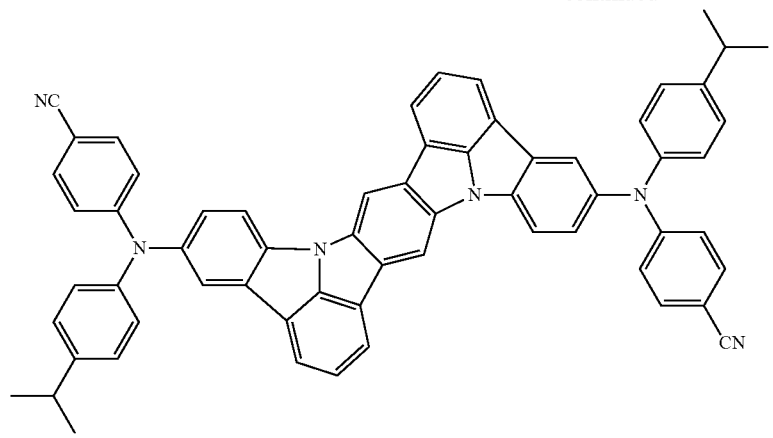
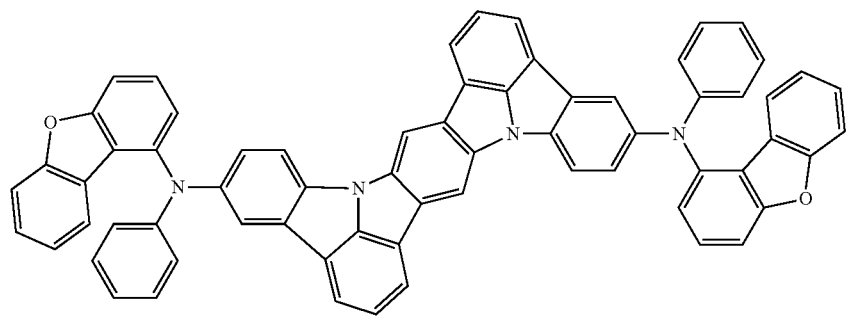
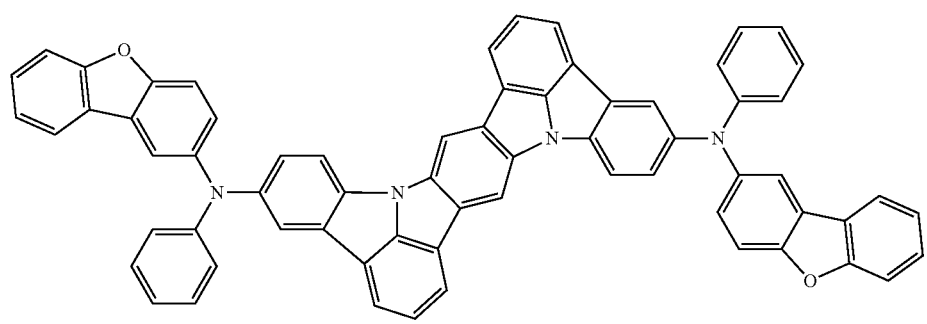
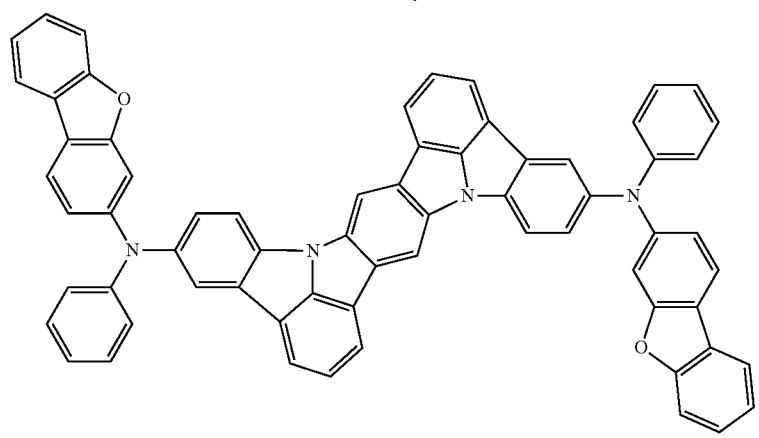

-continued
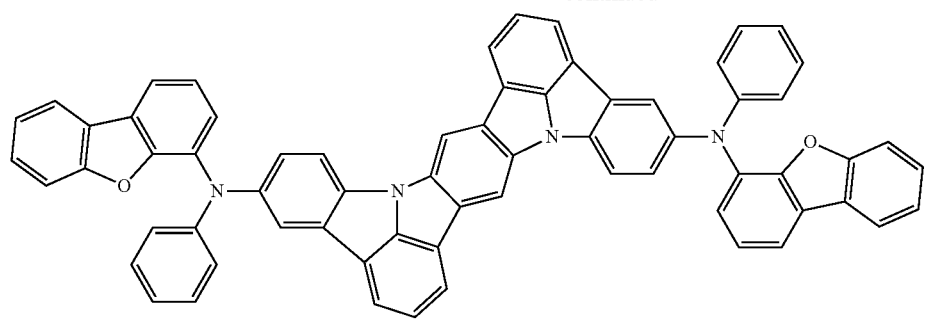
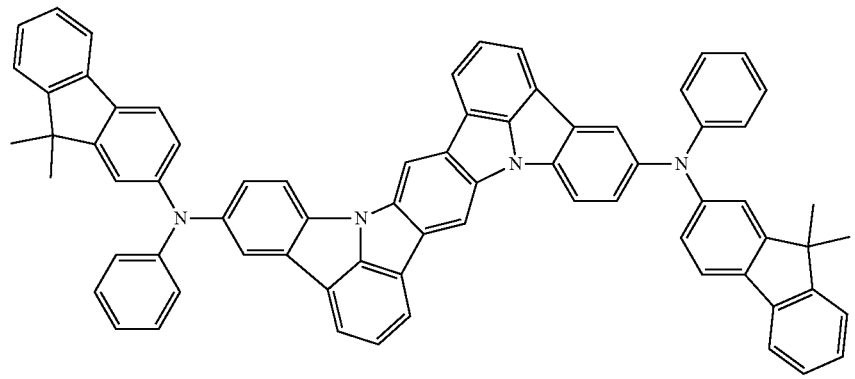
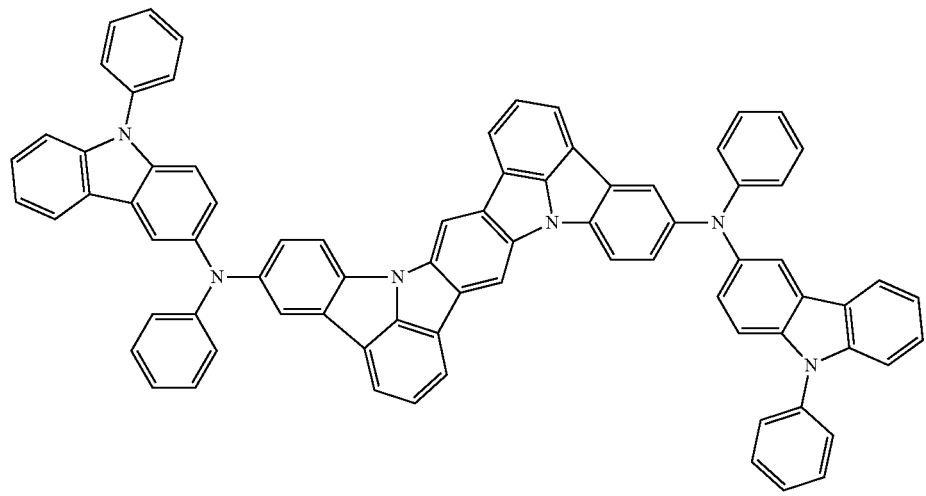
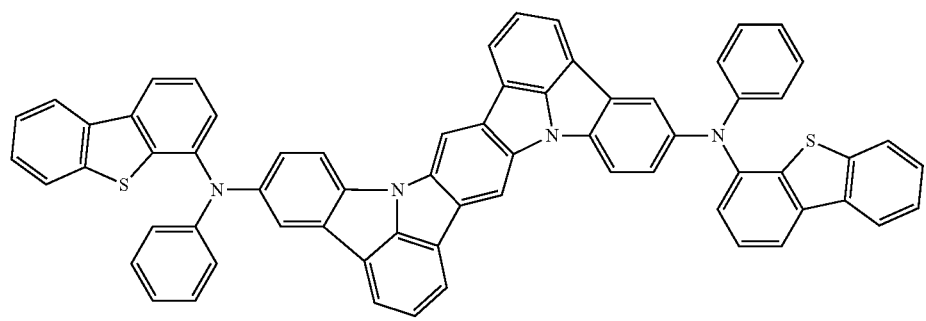

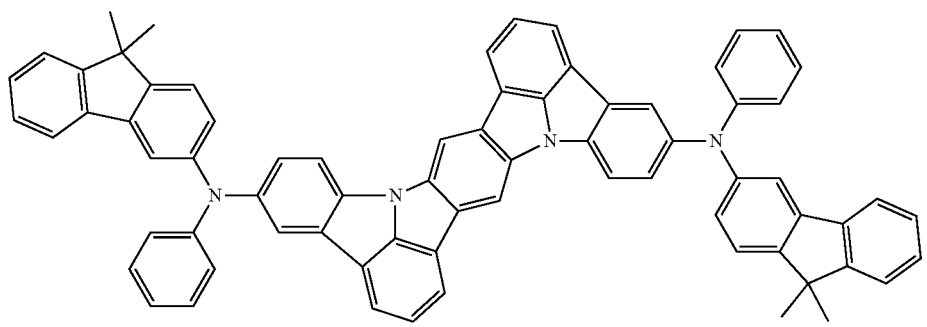
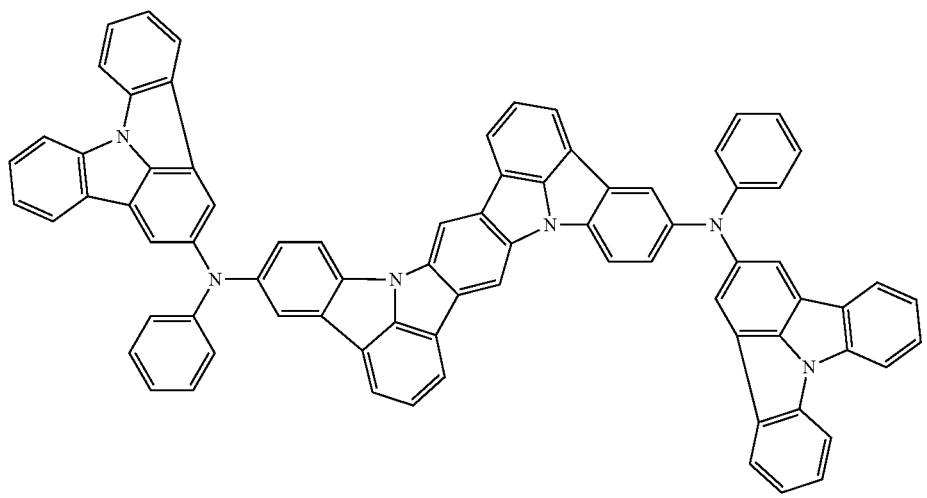
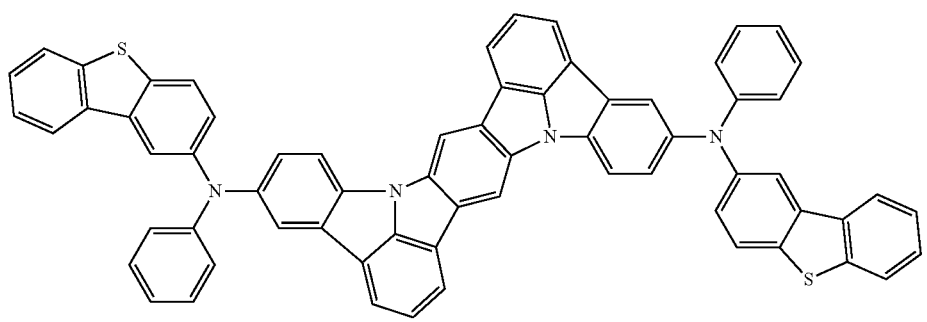
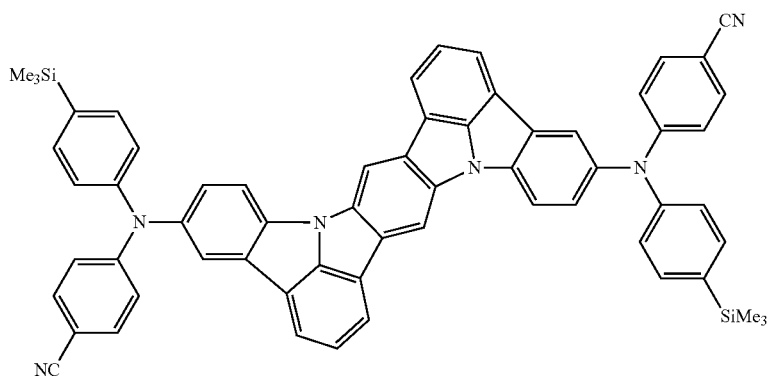

-continued
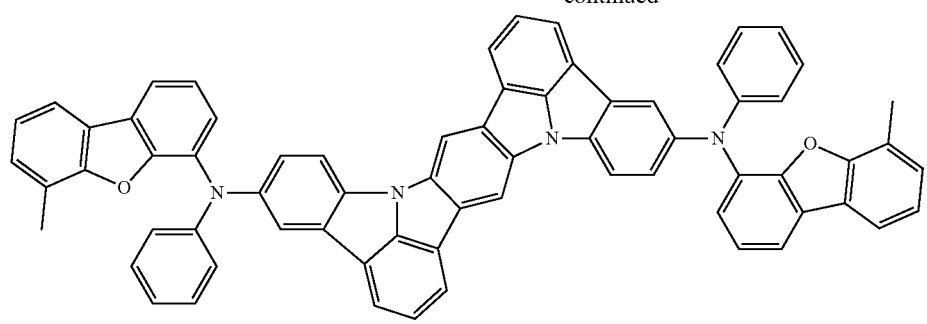
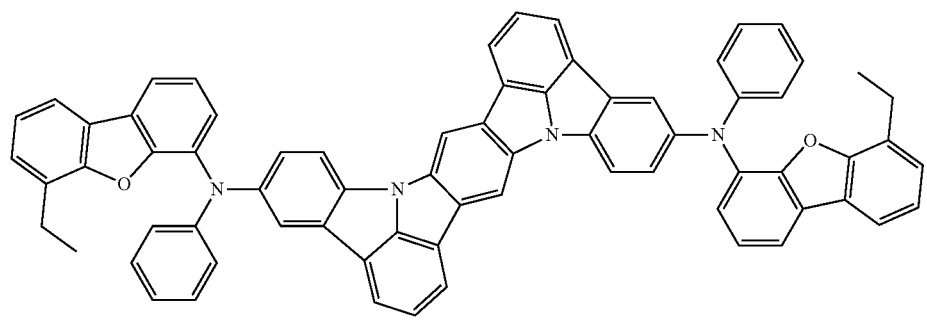
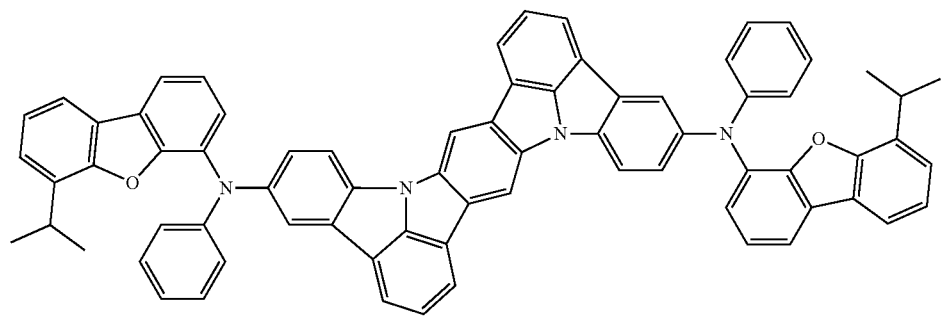
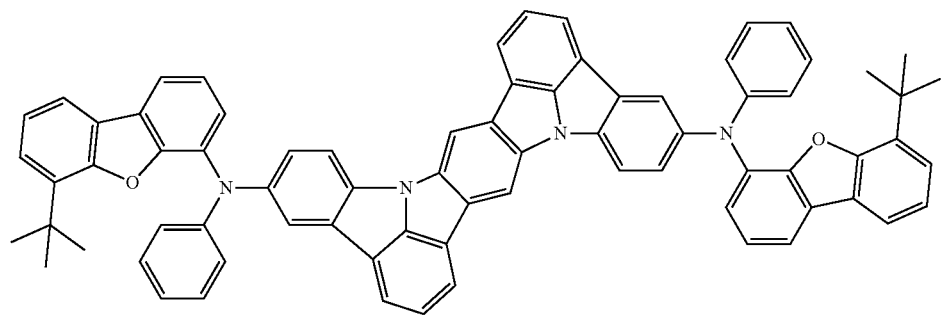
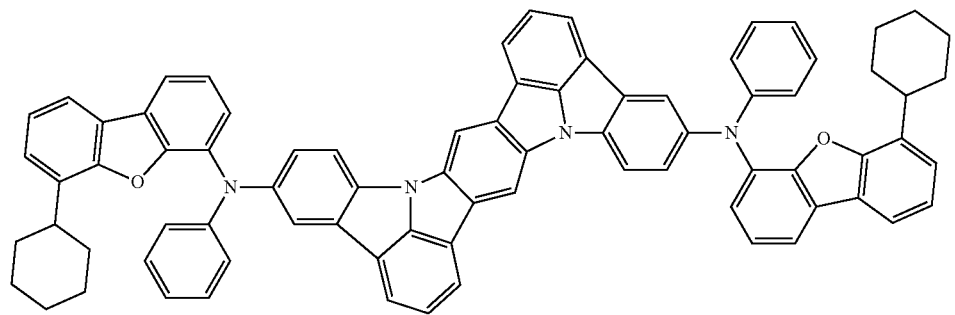

-continued
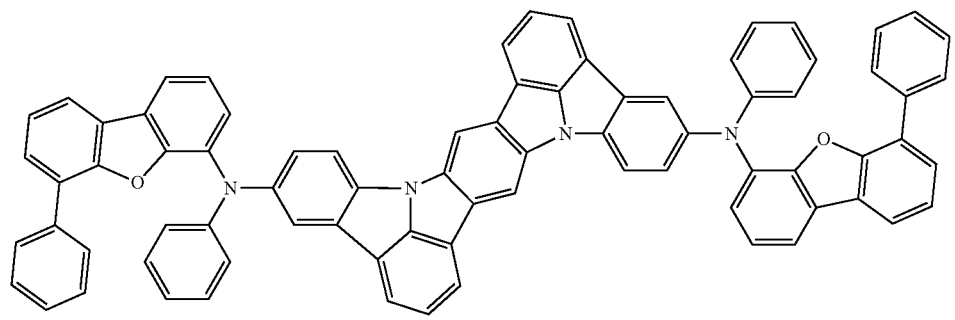
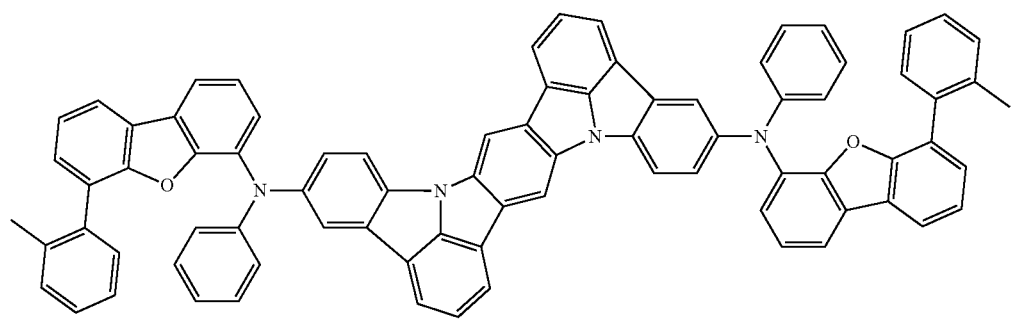
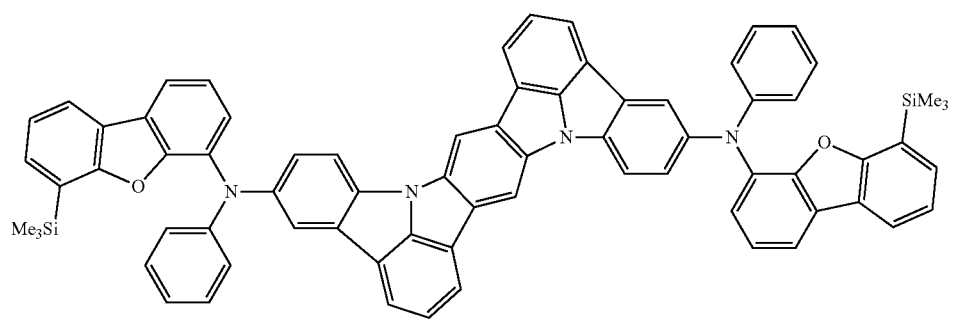
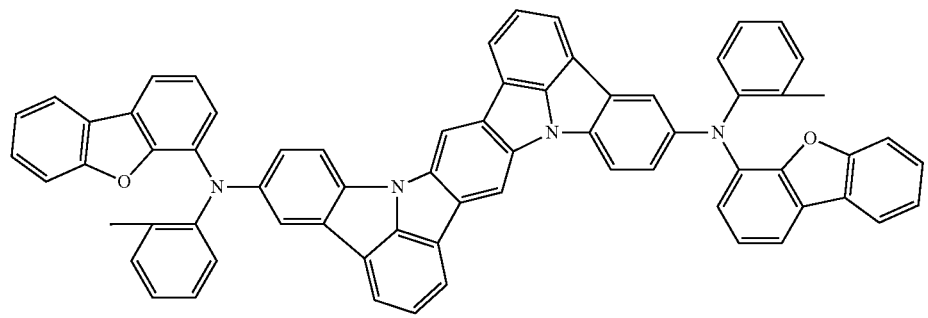
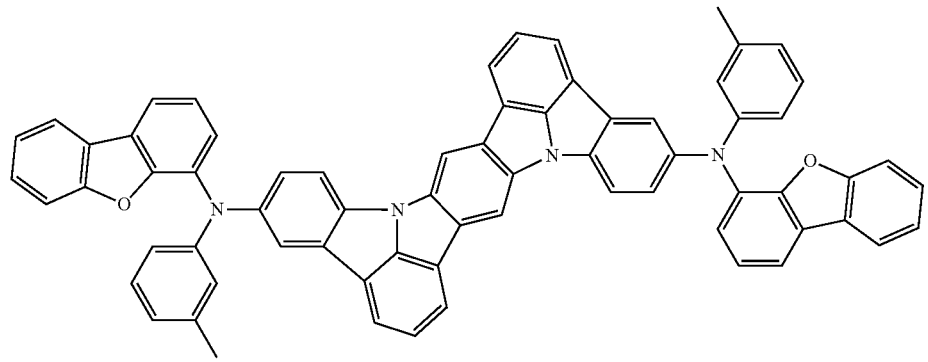

-continued
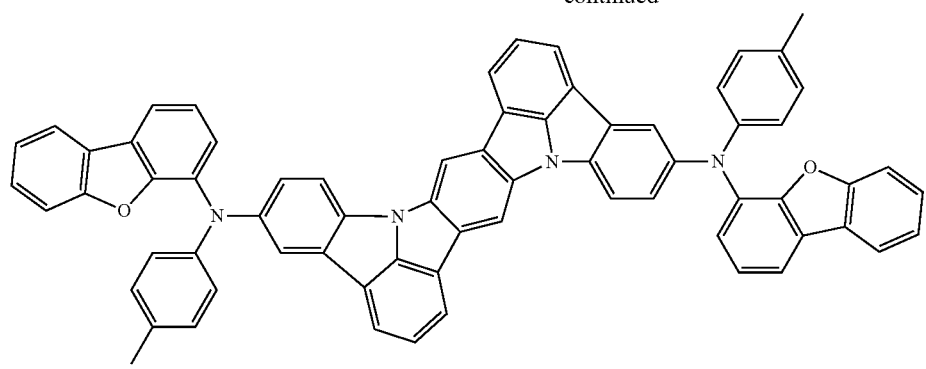
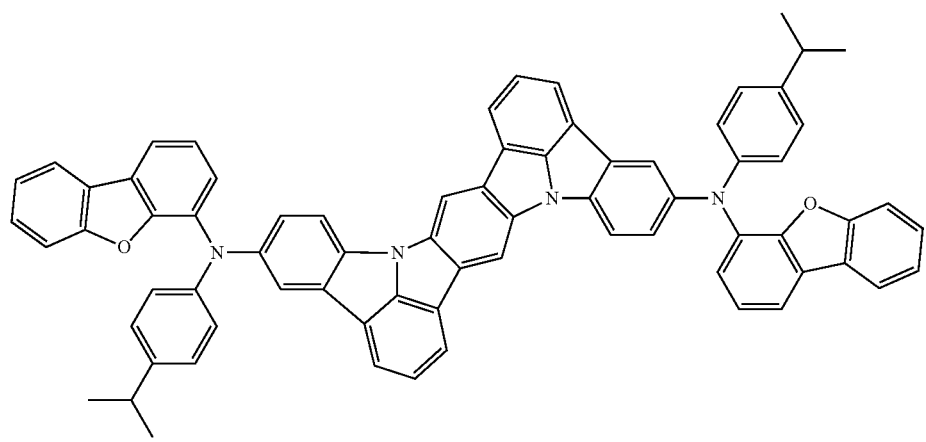
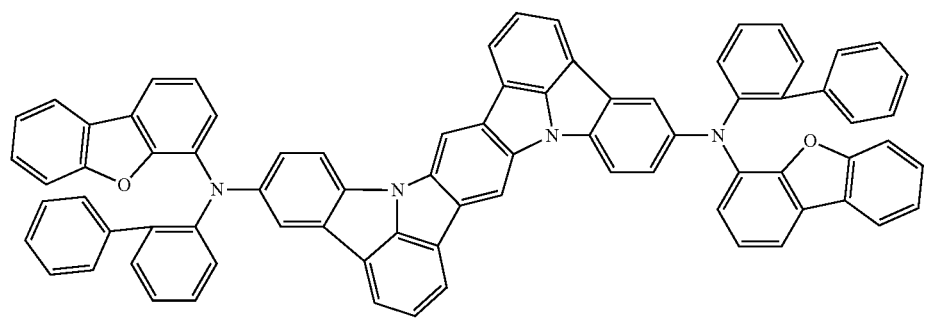
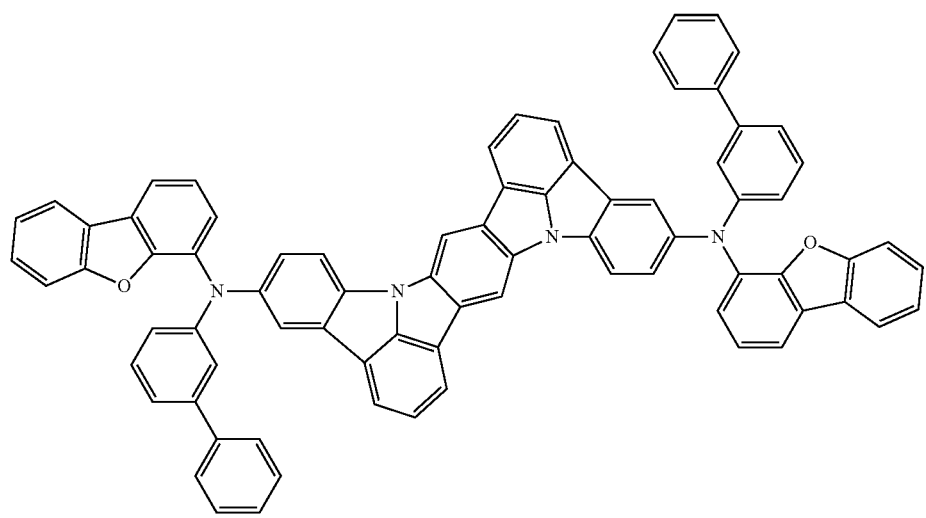

-continued
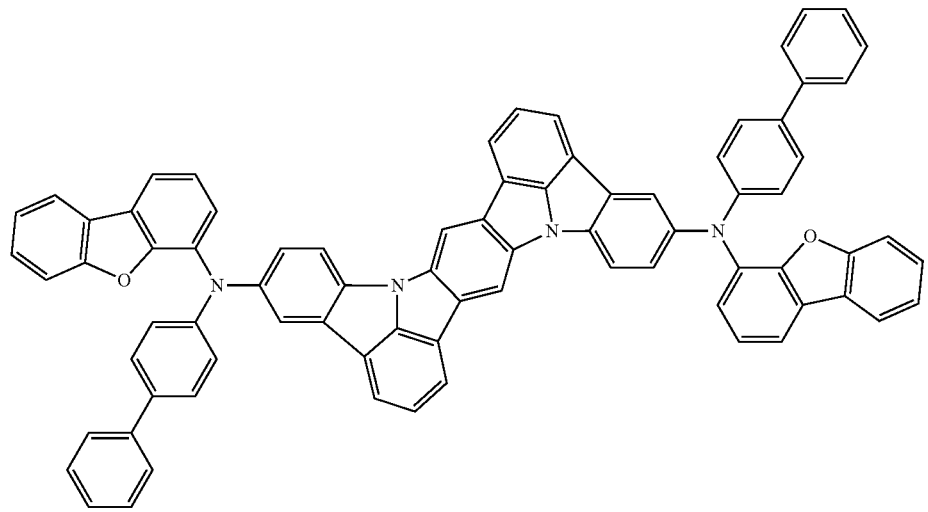
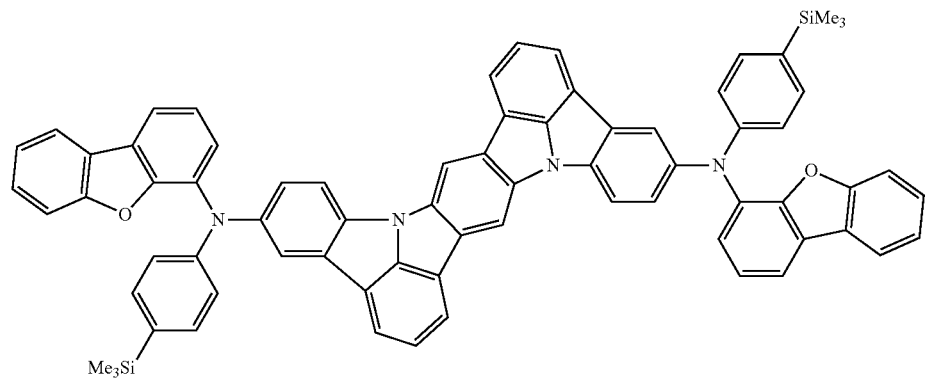
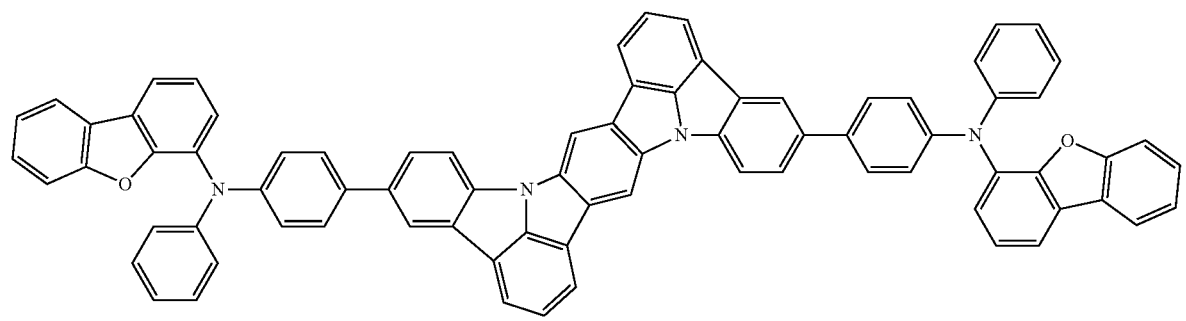
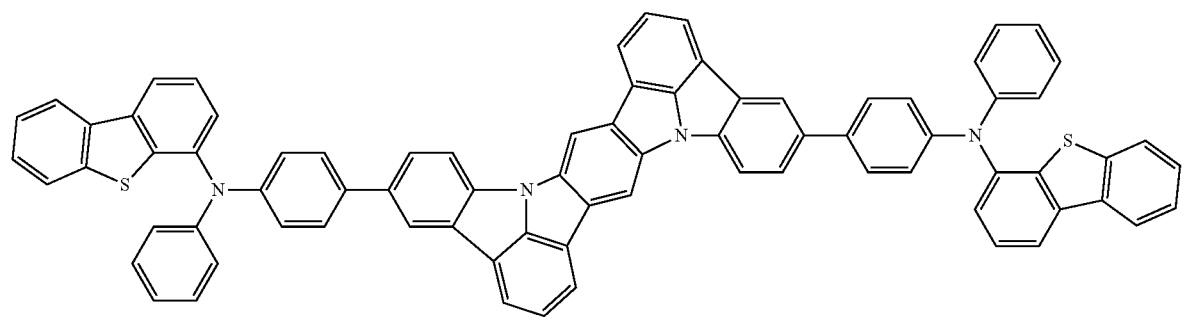

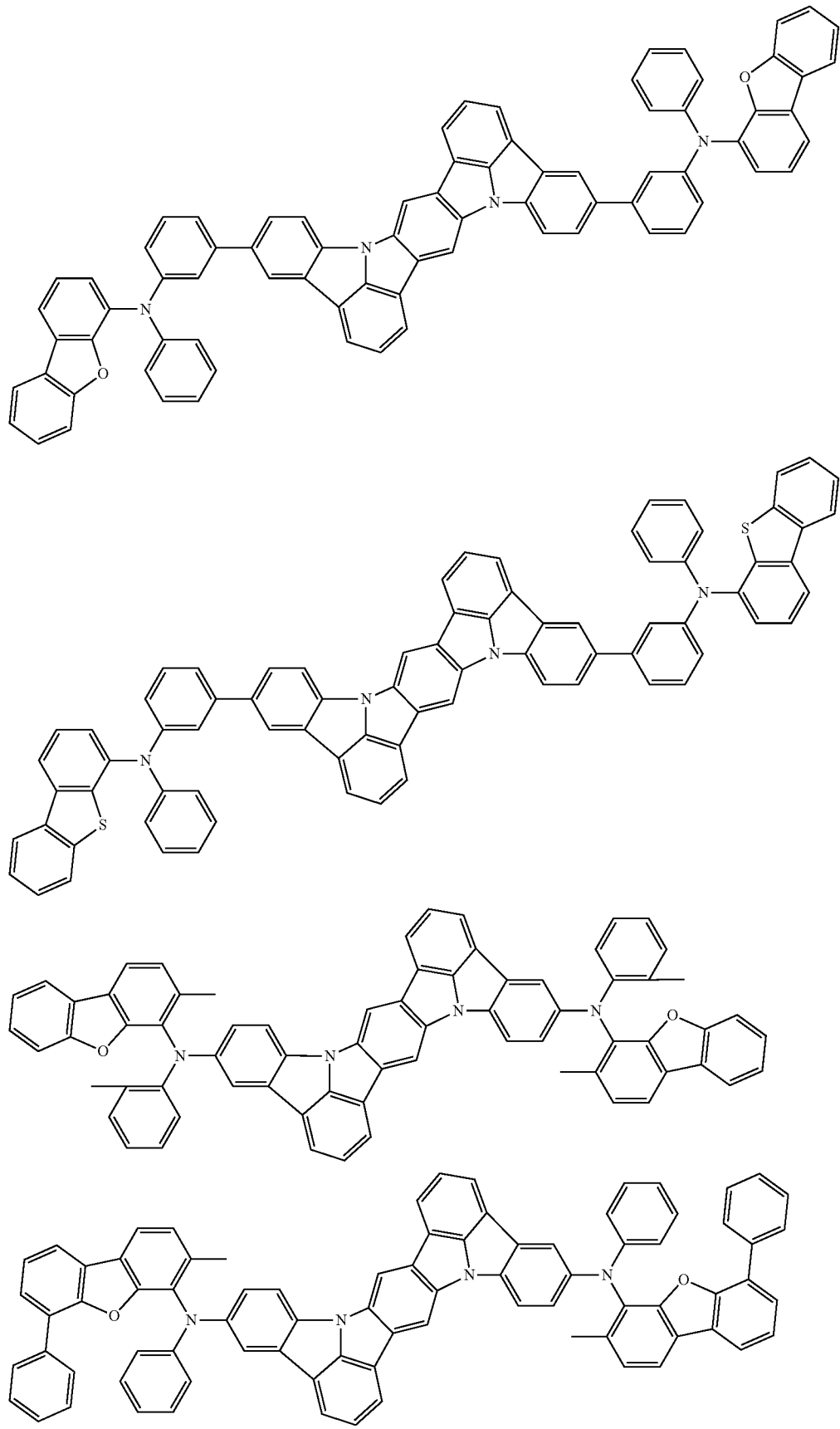

-continued
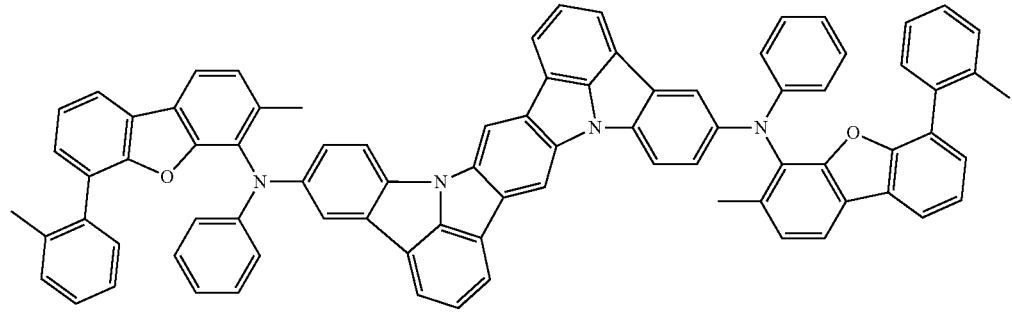
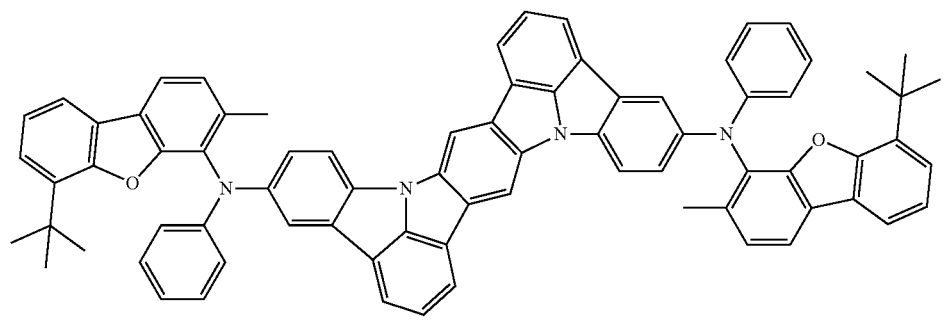
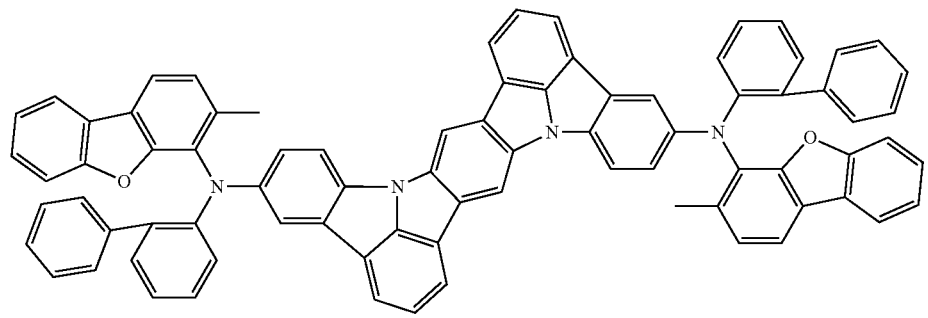
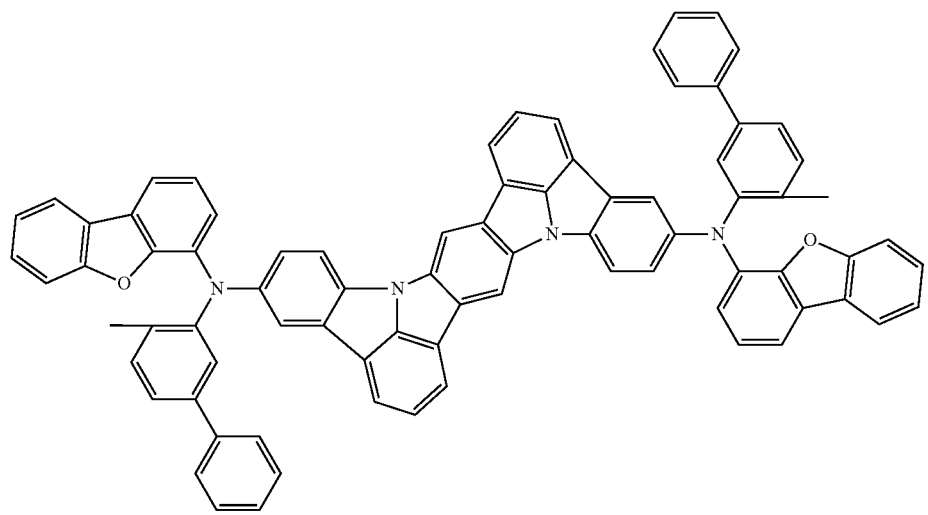

-continued
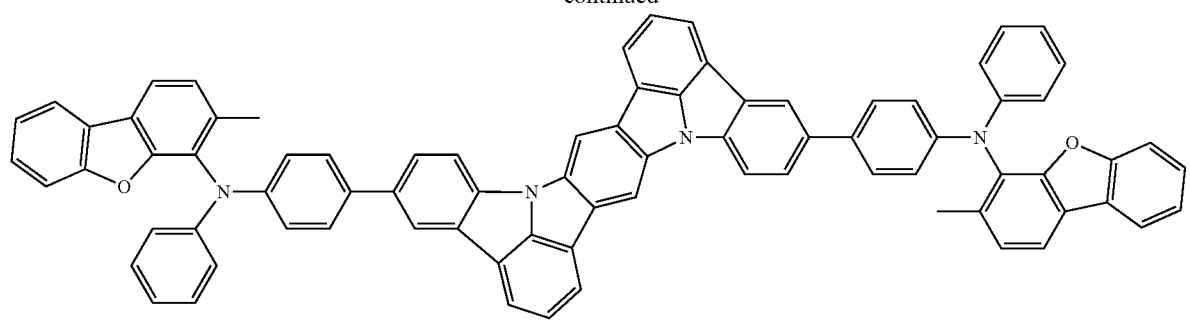
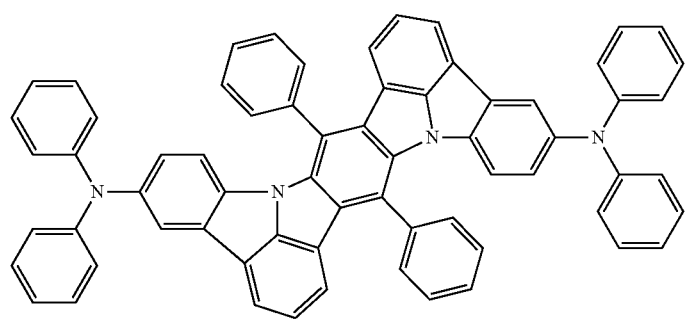
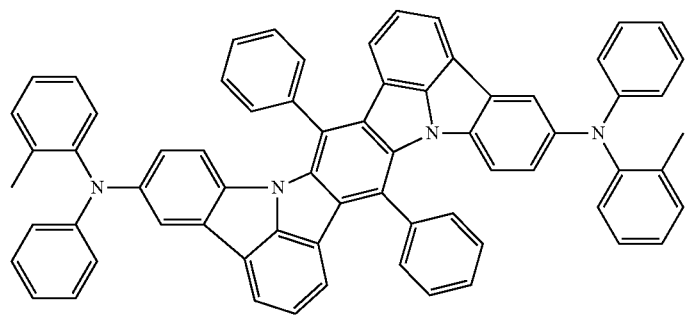
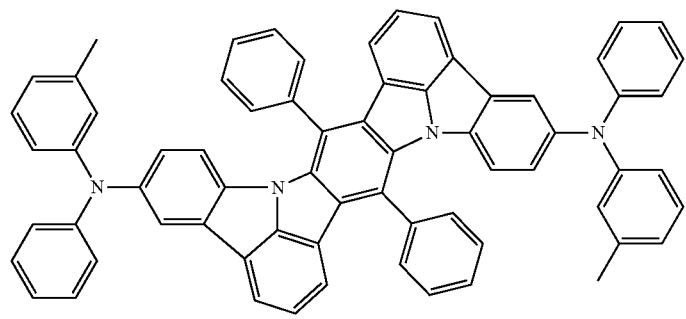
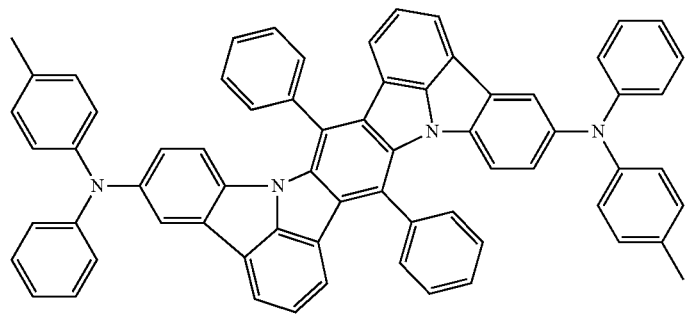

-continued
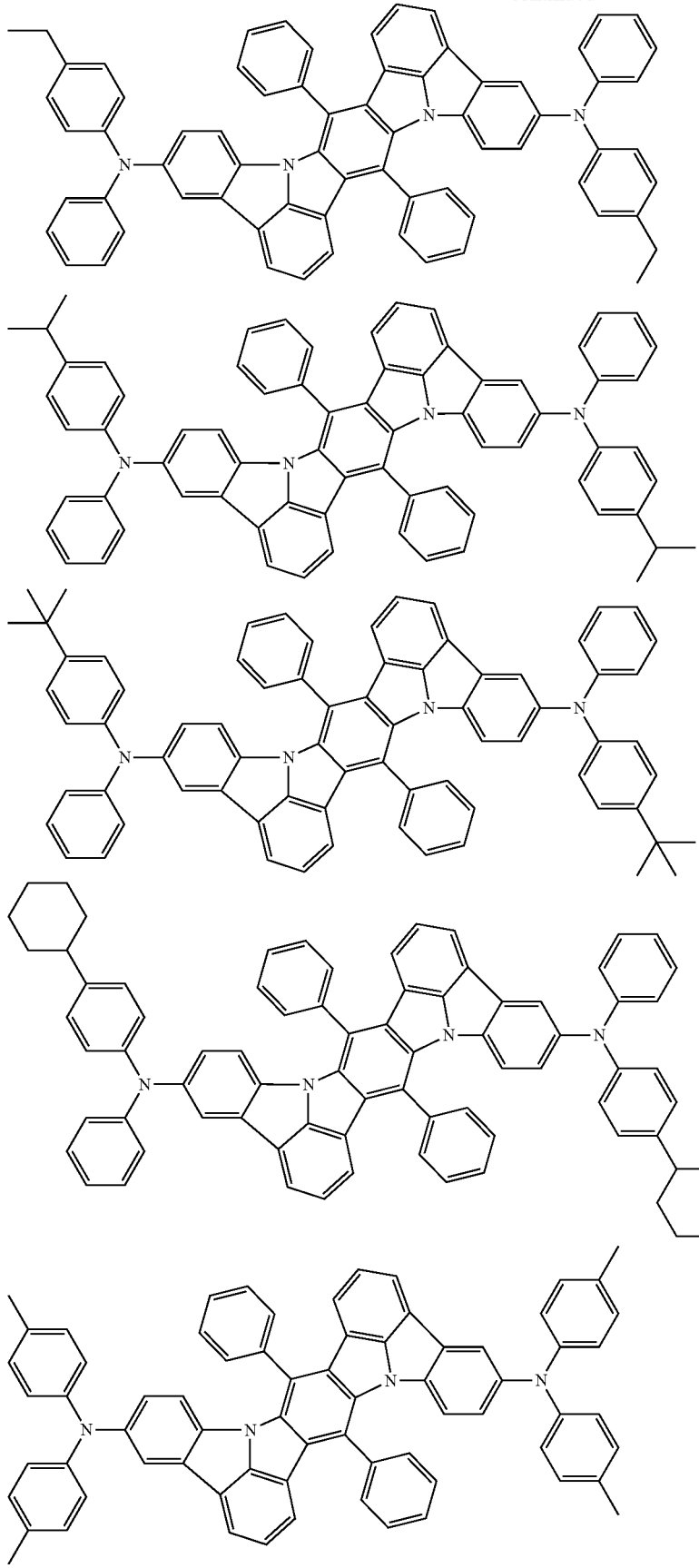

-continued
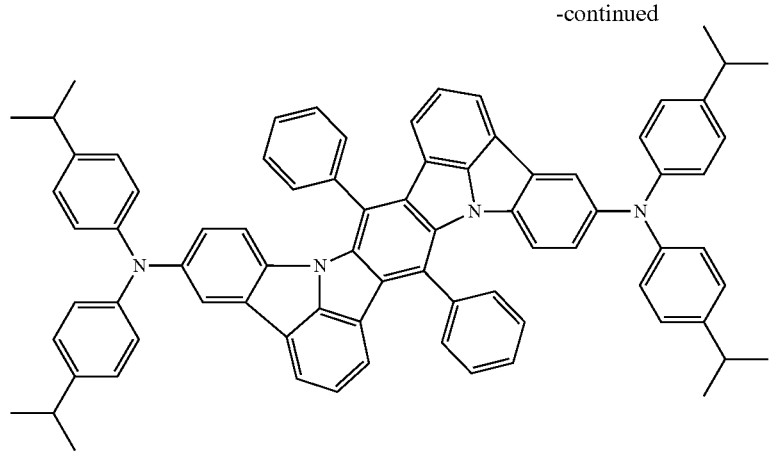
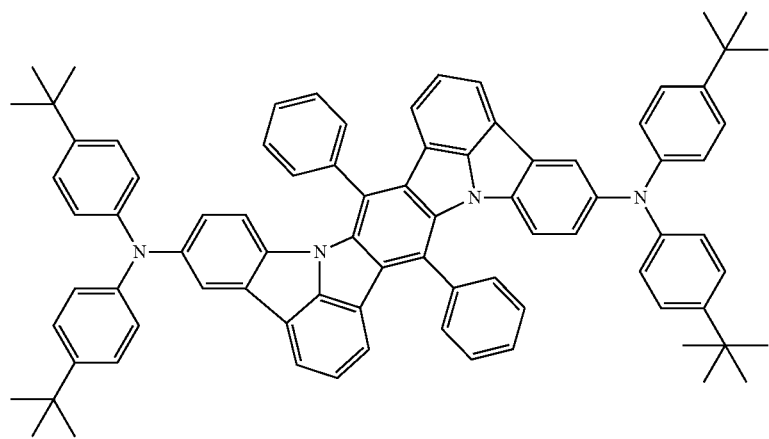
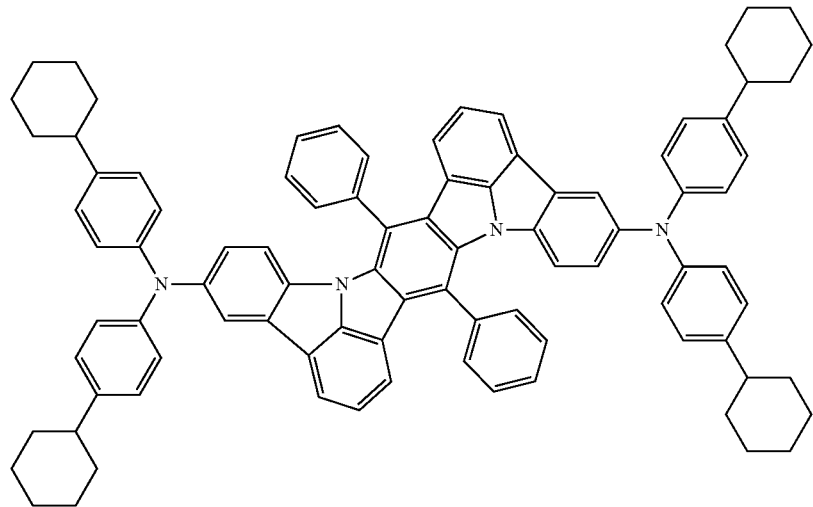
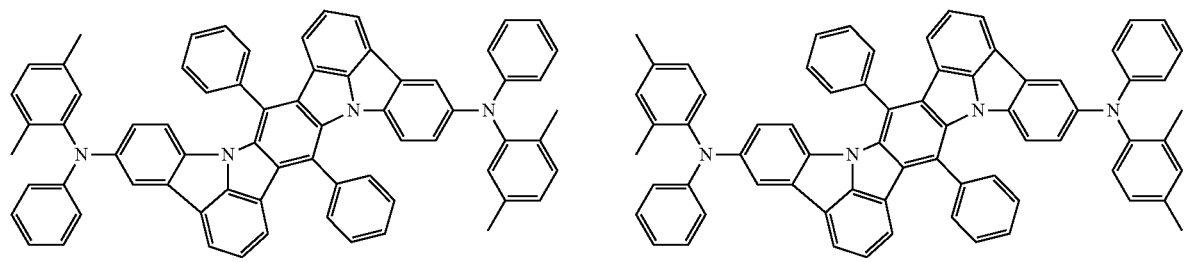

-continued
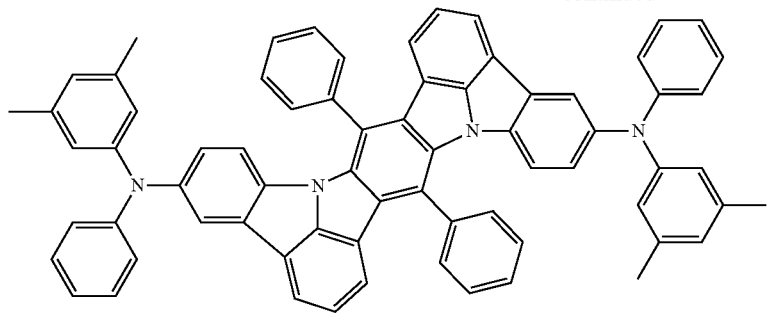
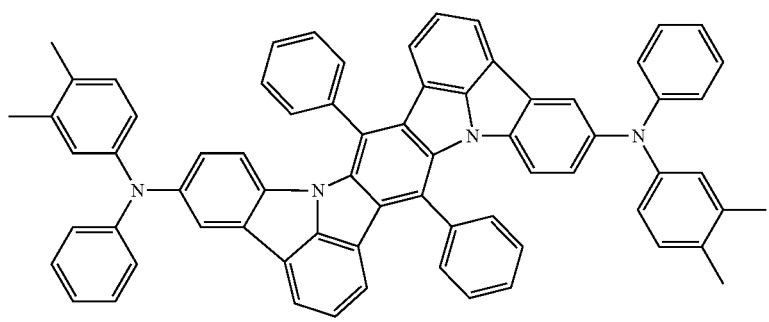
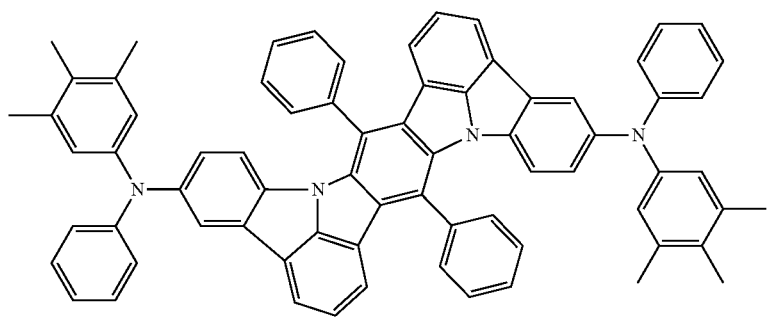
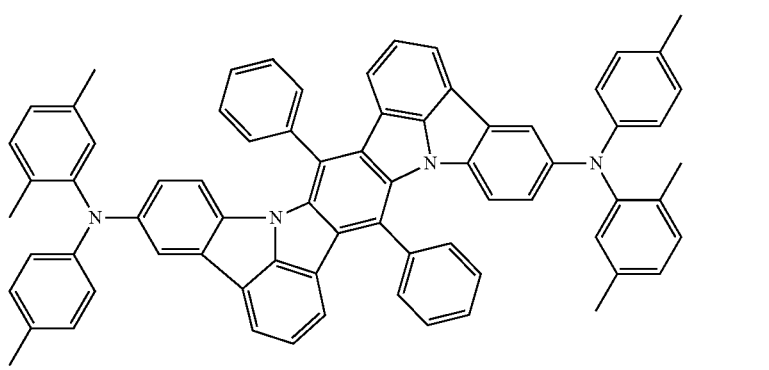
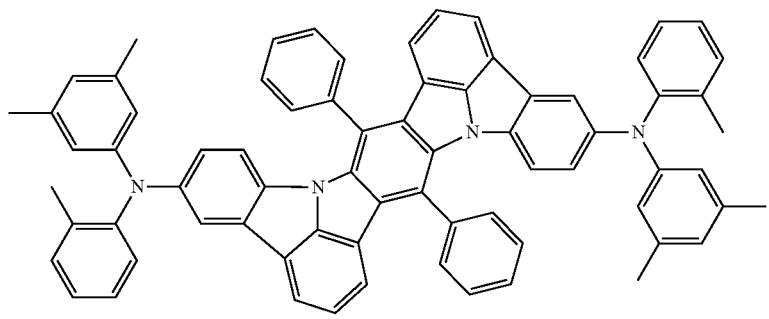

-continued
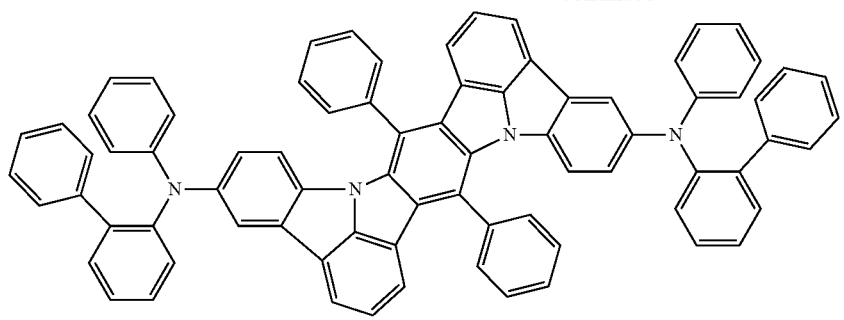
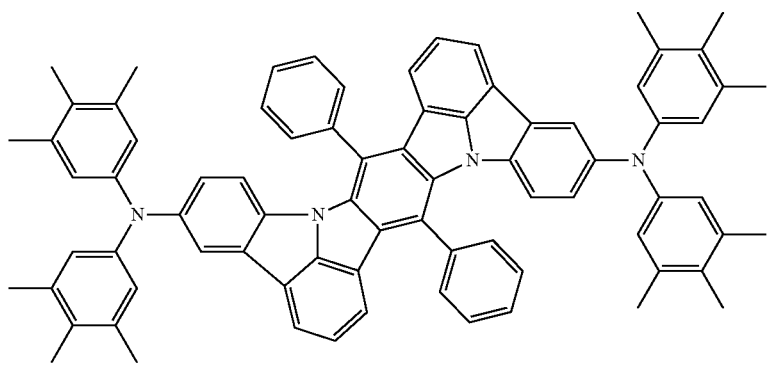
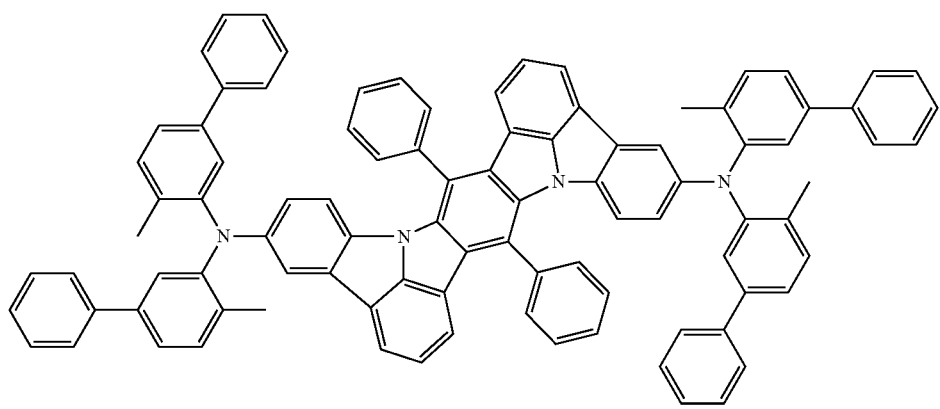
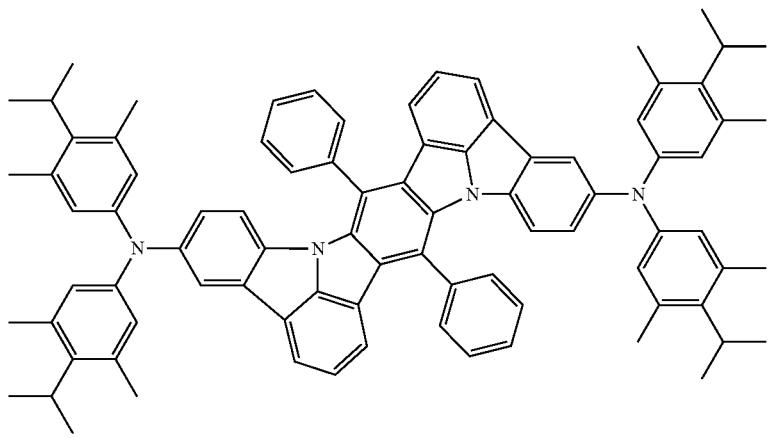

-continued
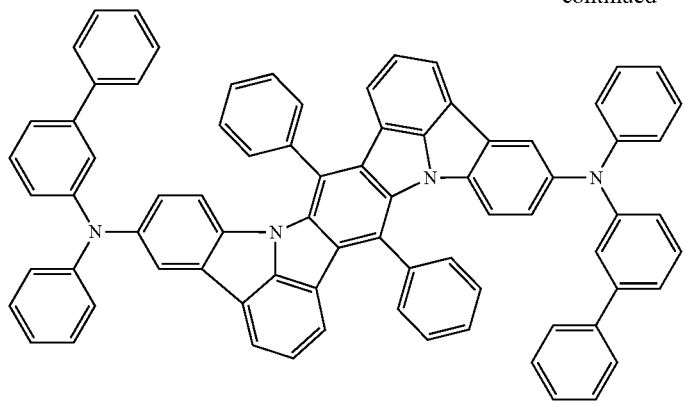
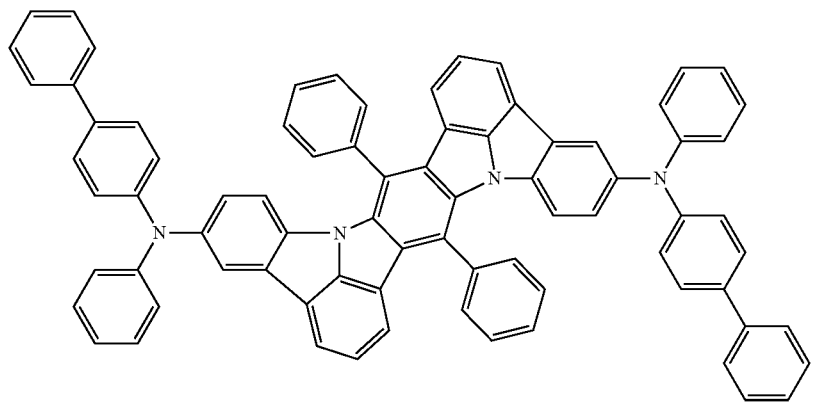
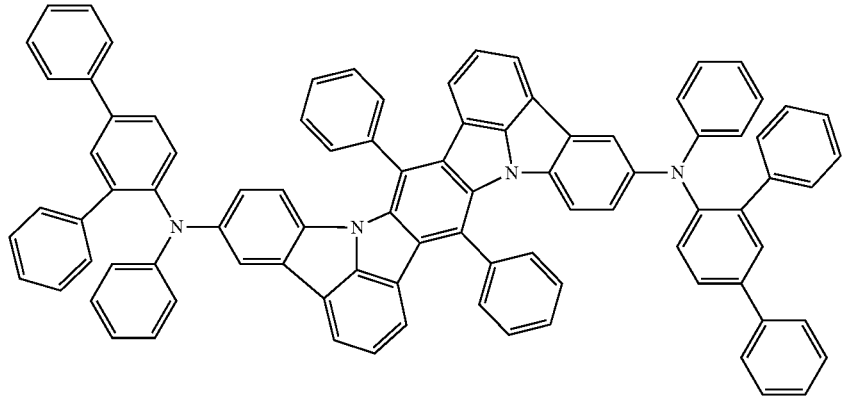

-continued
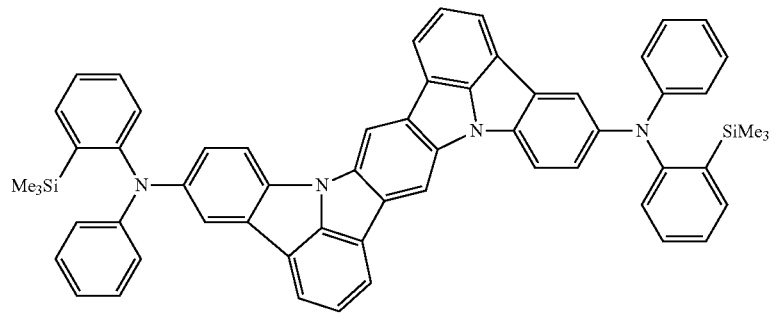
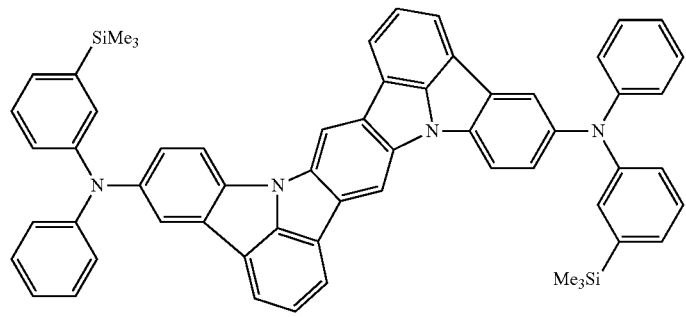
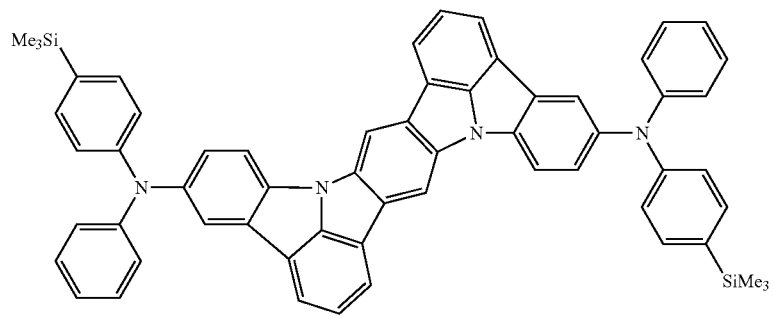
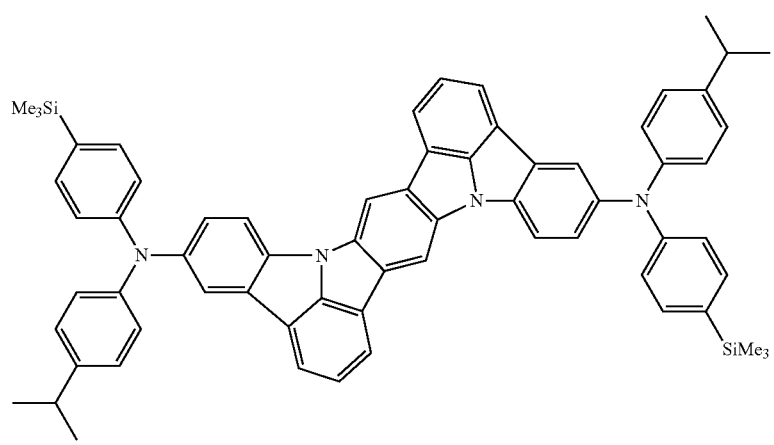
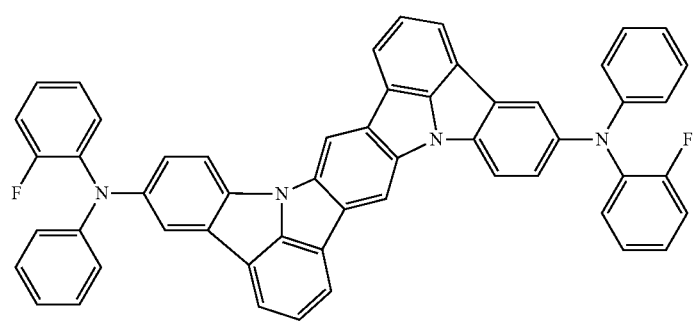

-continued
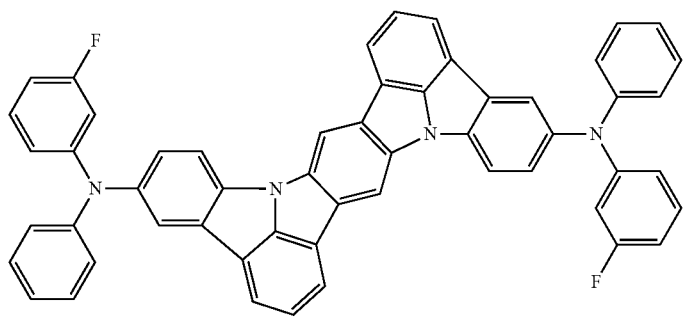
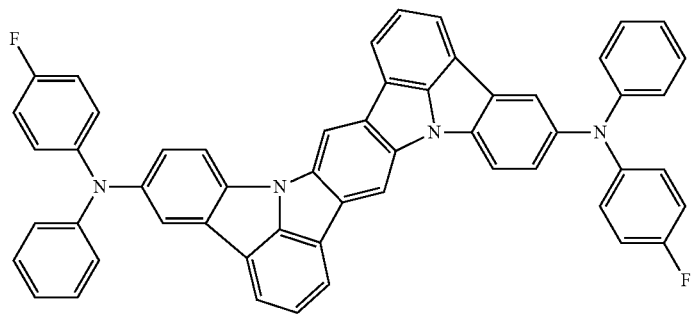
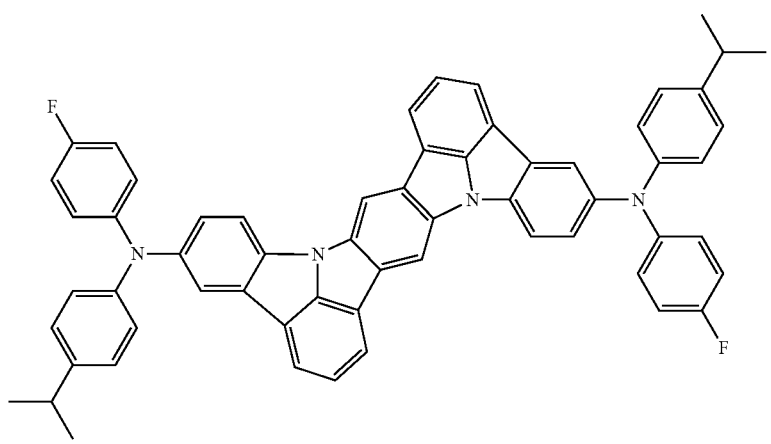
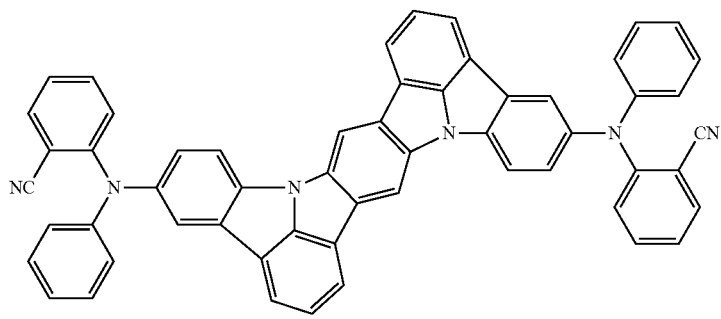
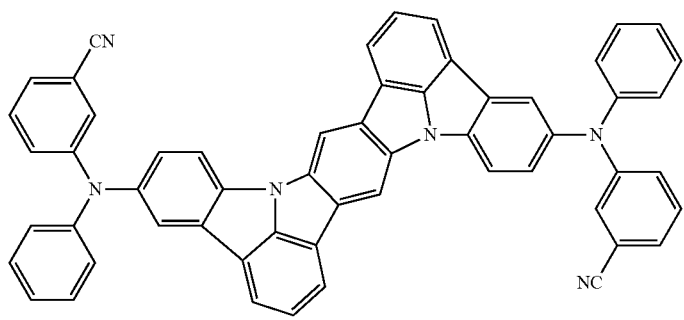

-continued
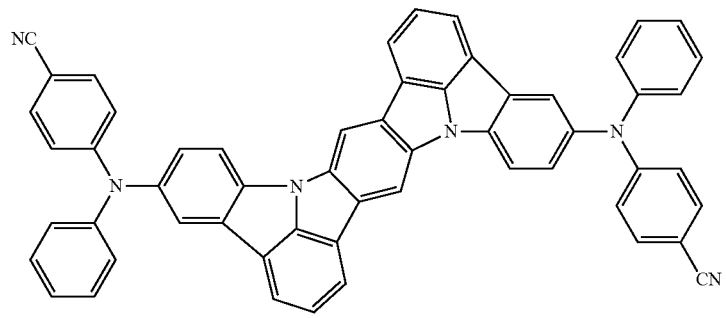
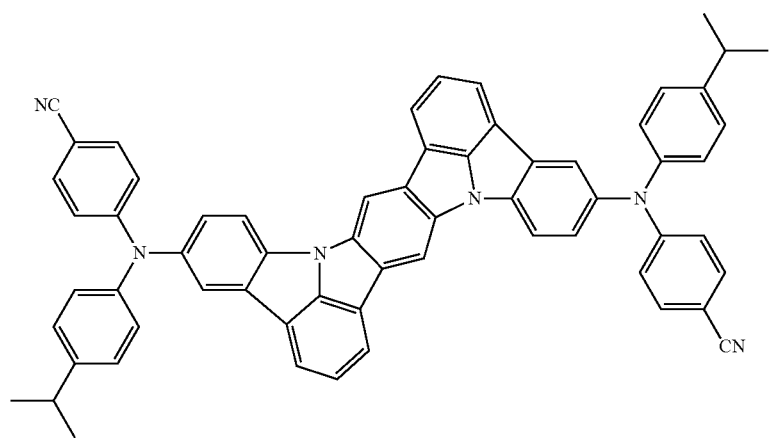
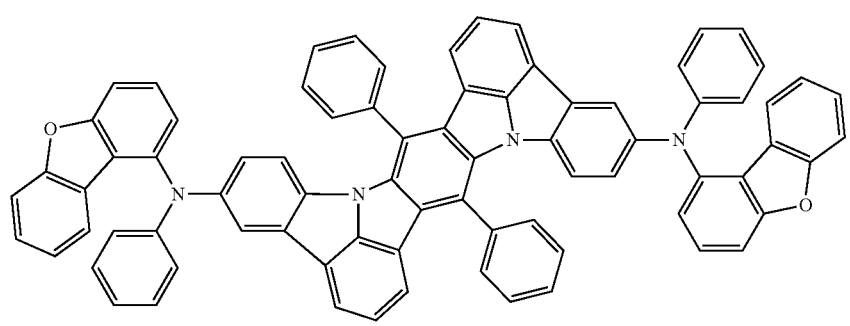
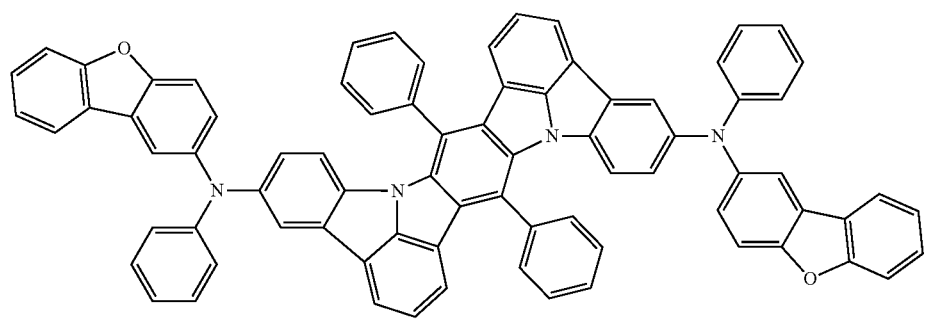

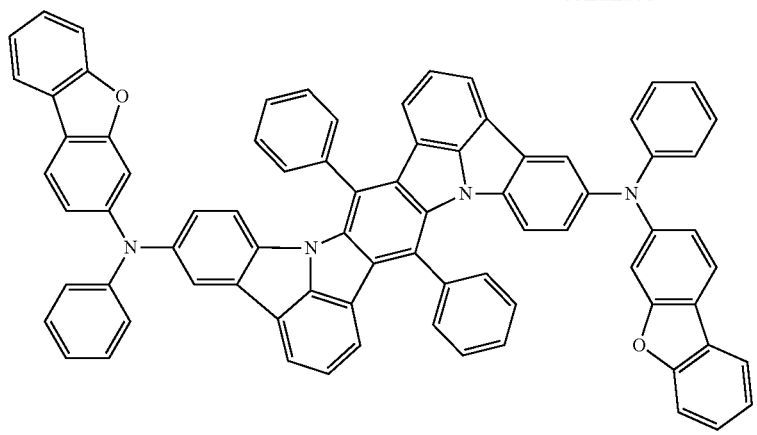
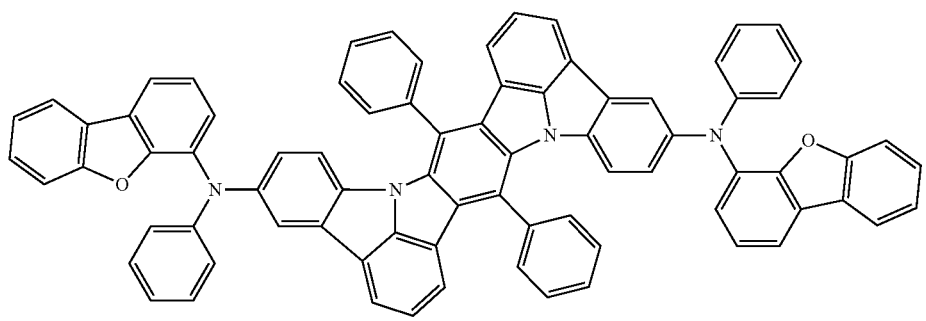
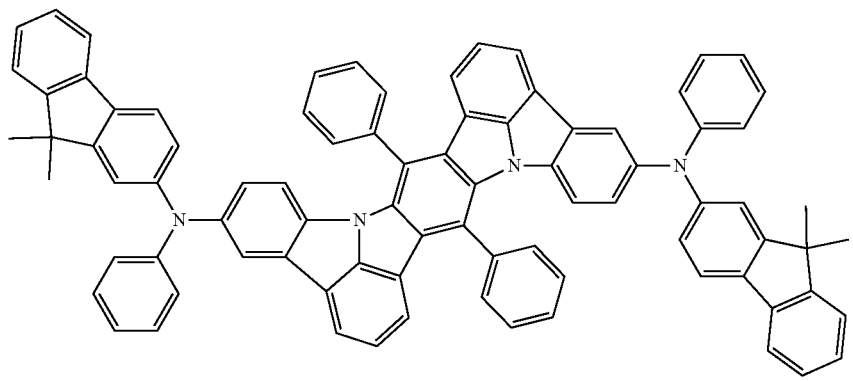
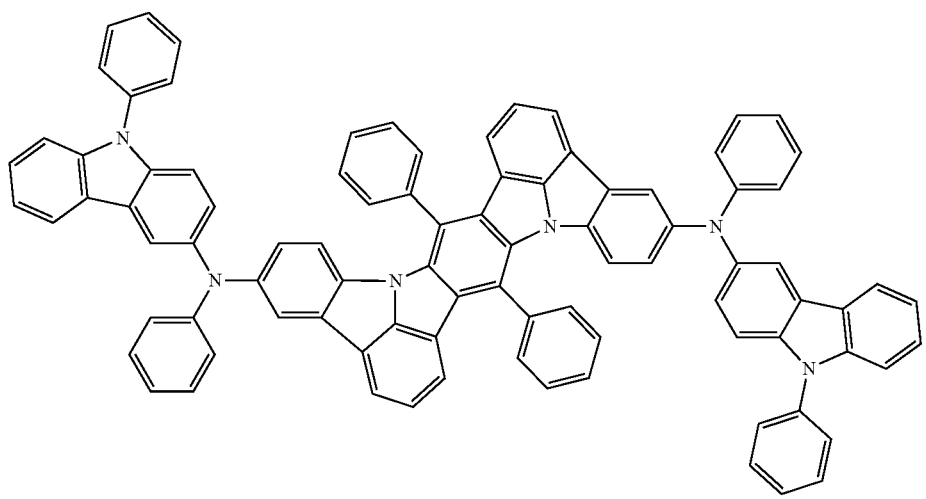

-continued
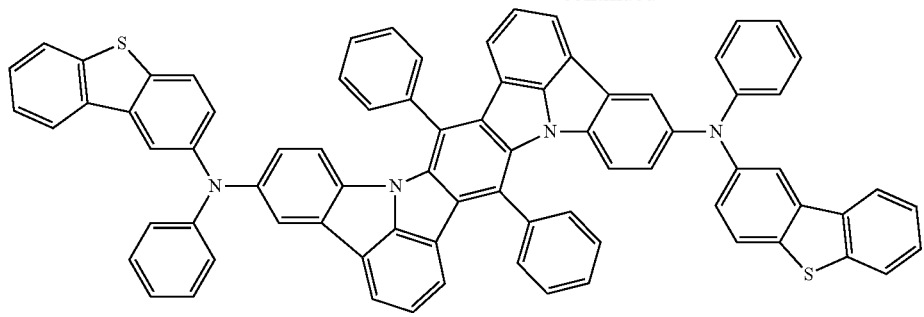
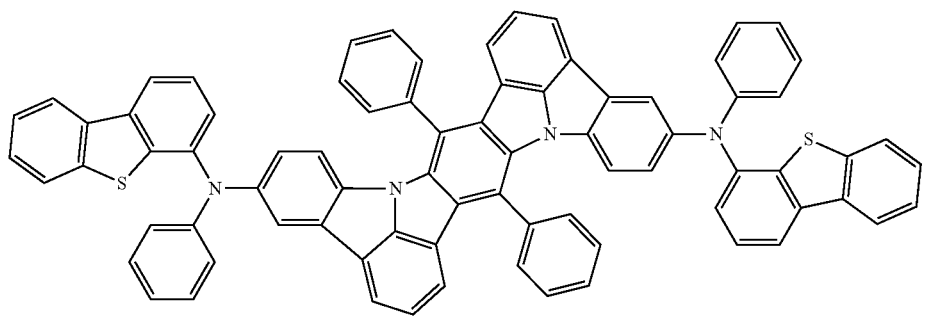
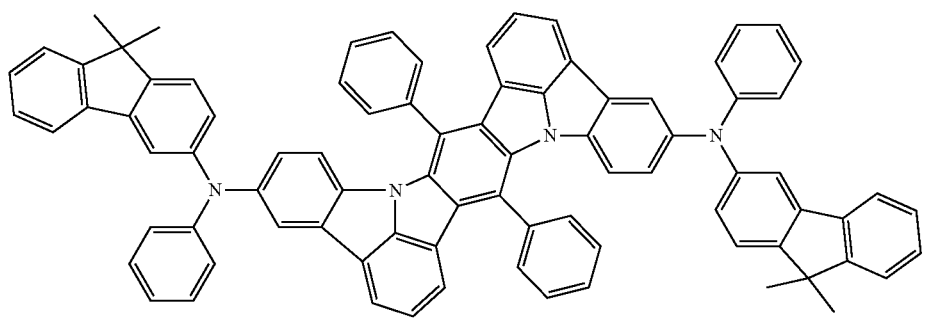
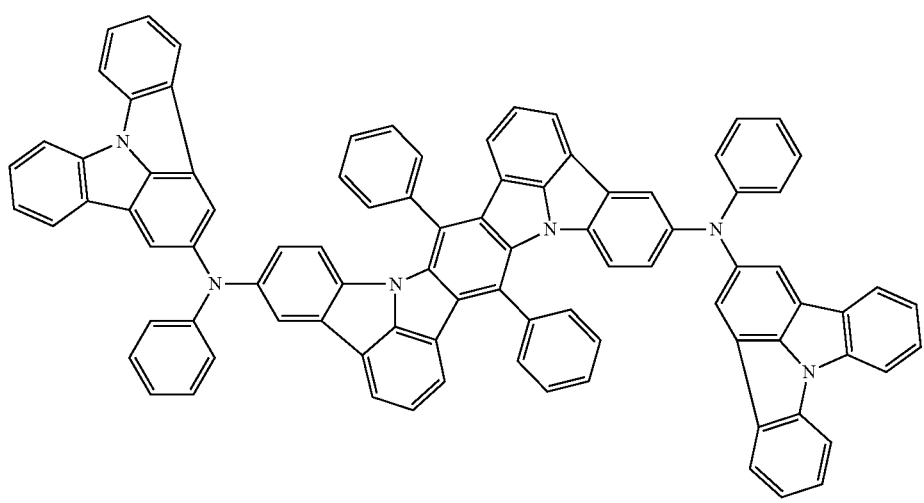

-continued
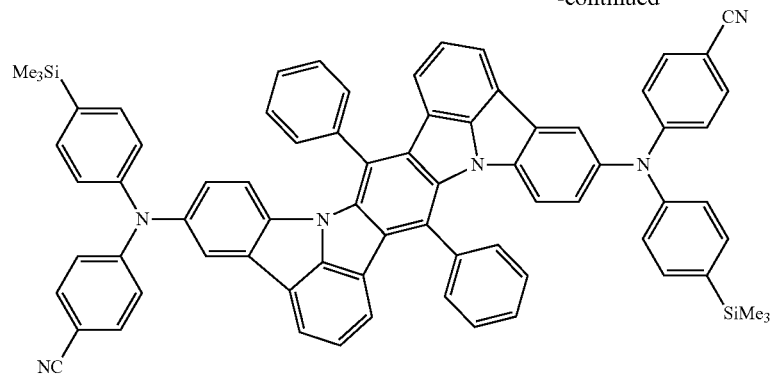
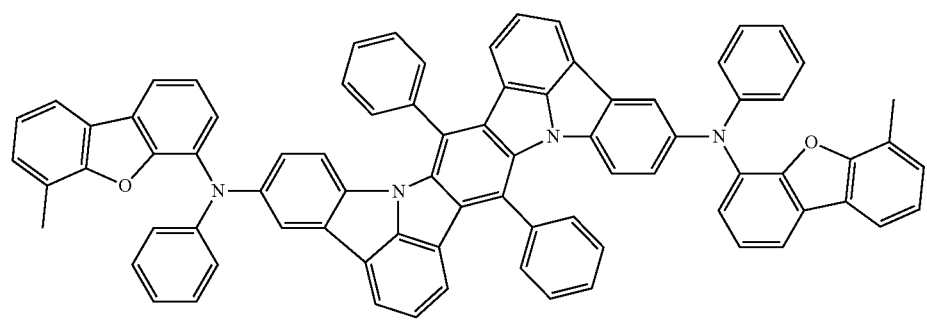
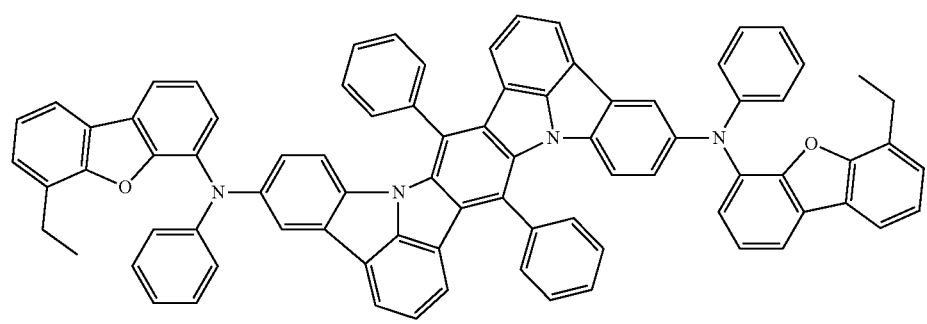
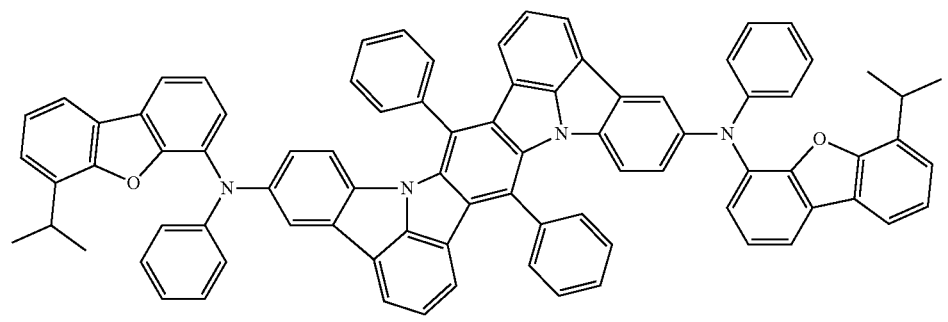

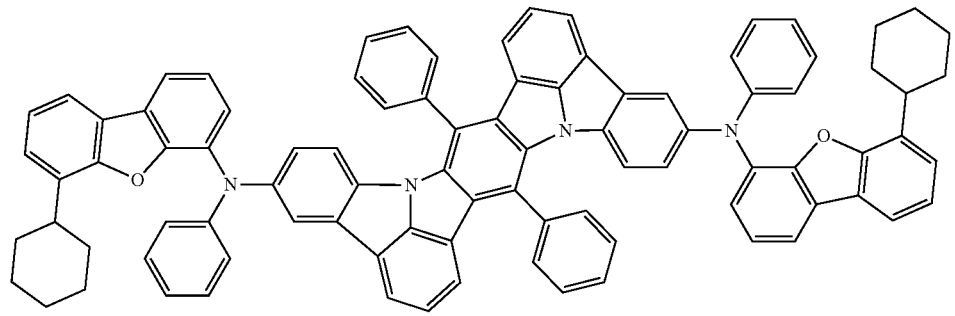
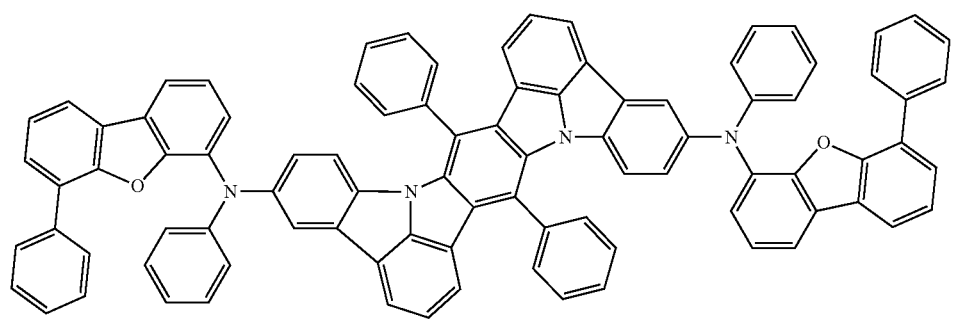
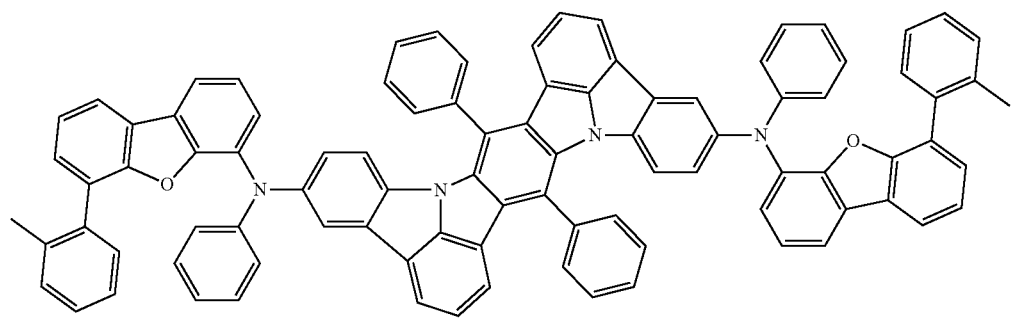
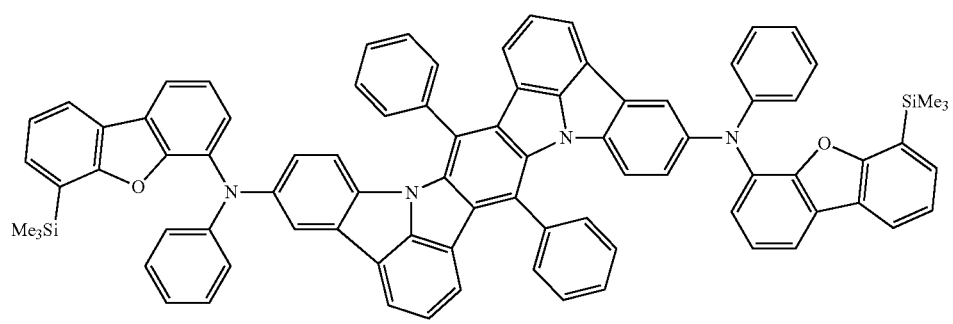
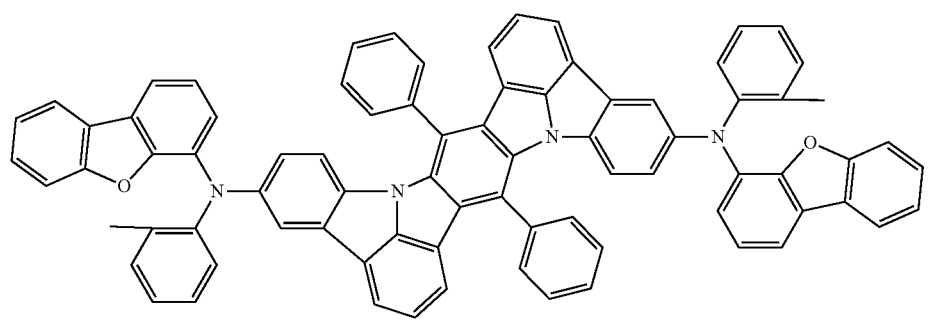

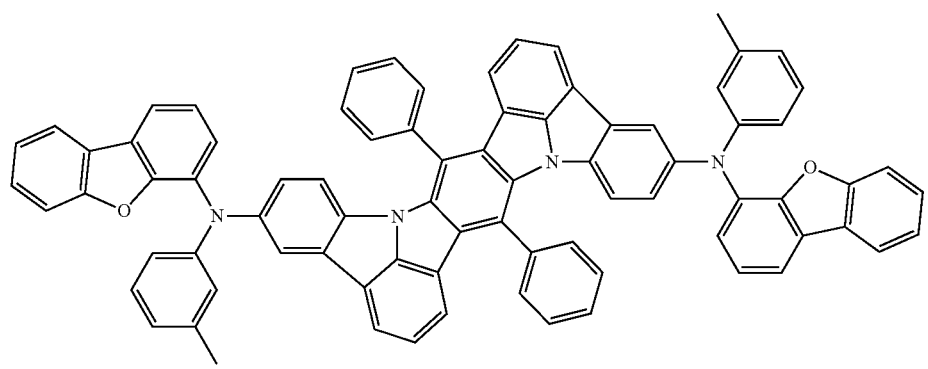
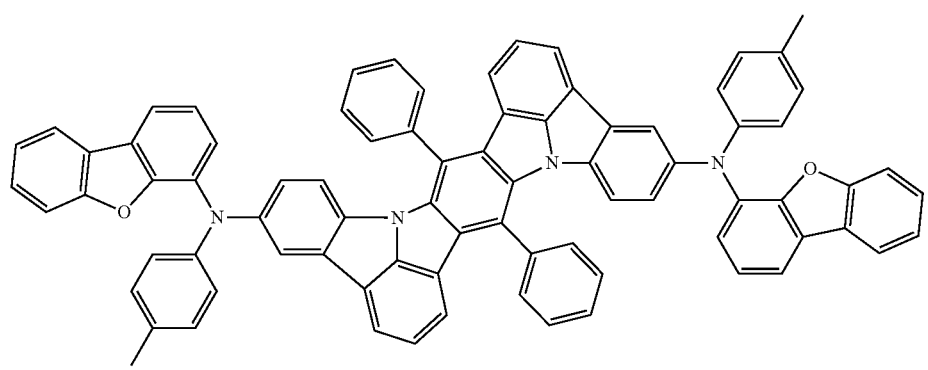
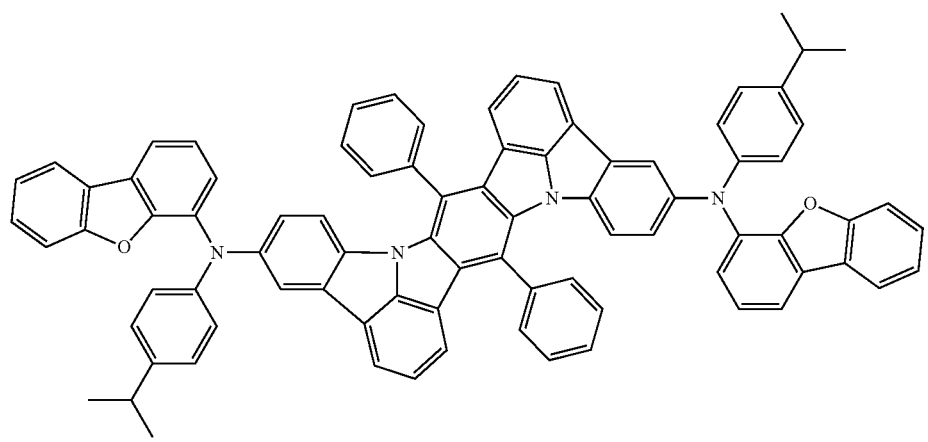
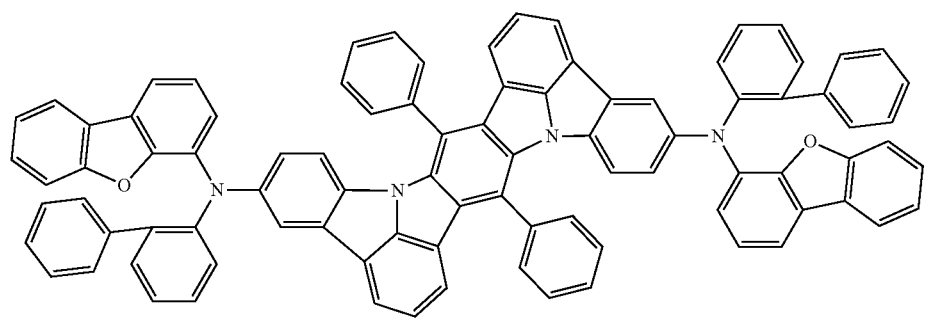

-continued
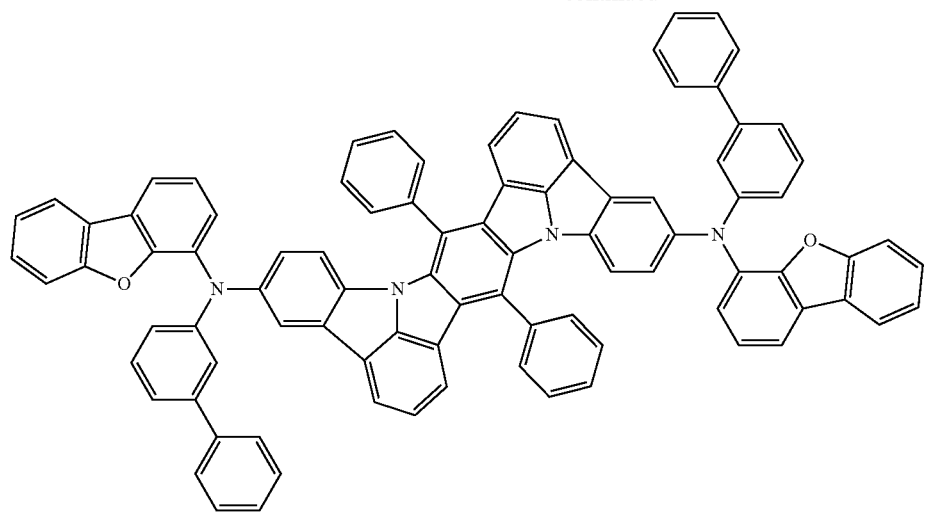
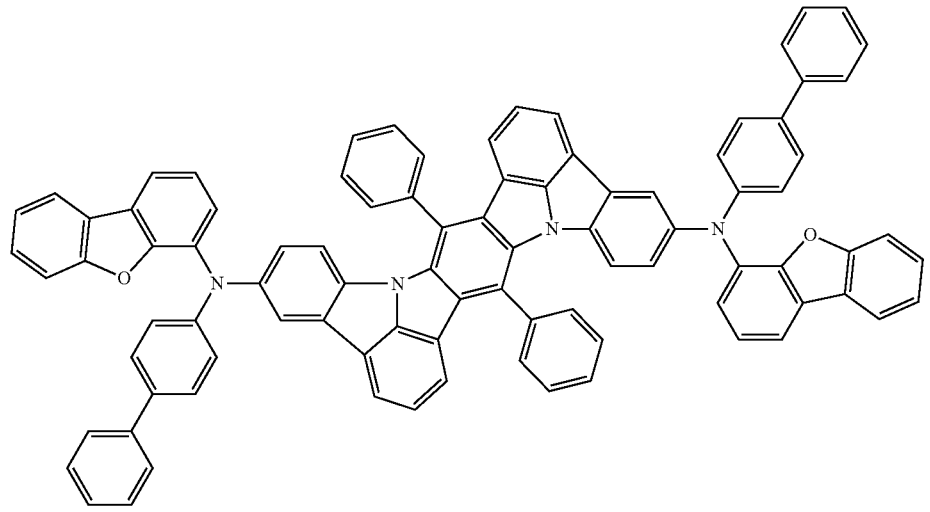
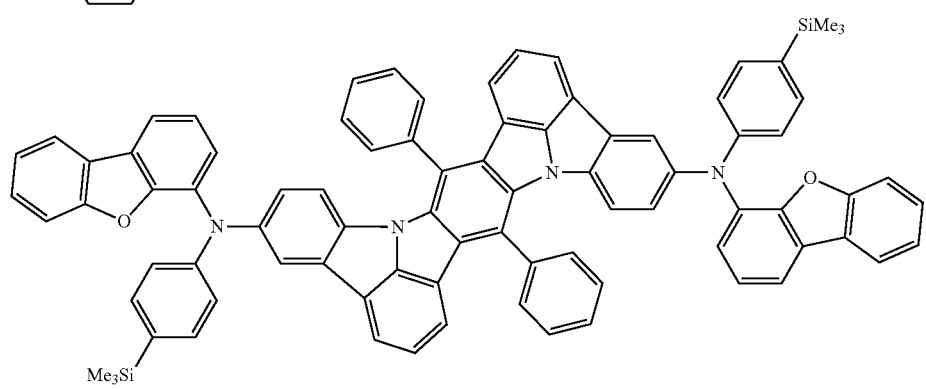
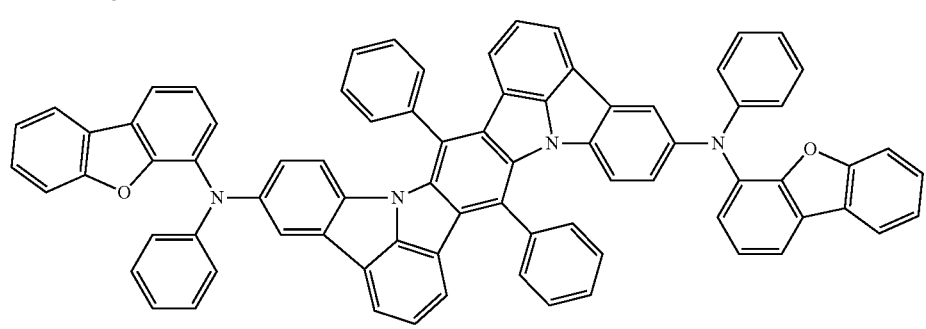

-continued
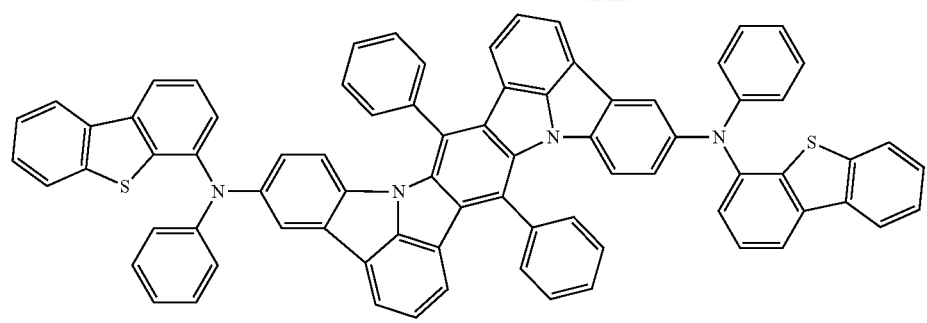
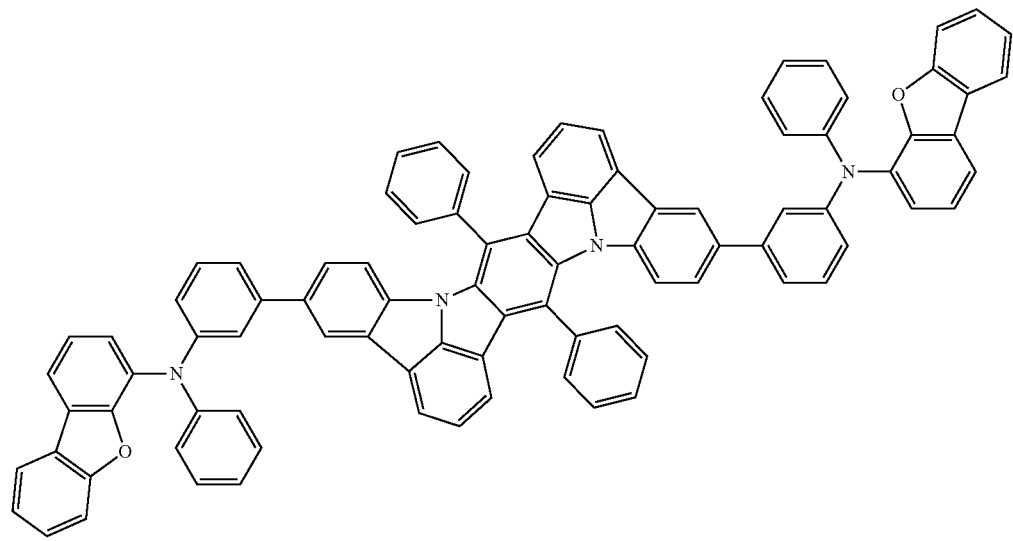
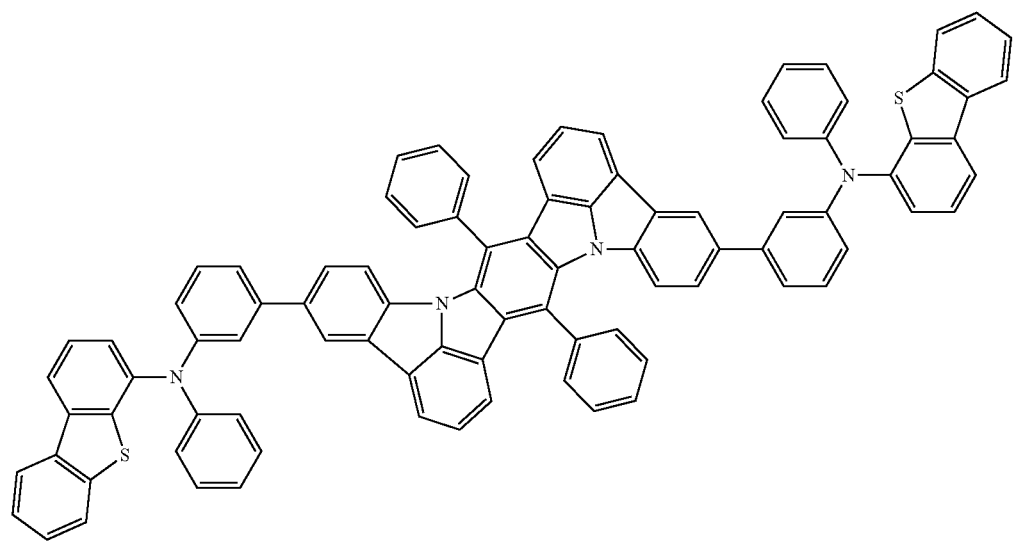
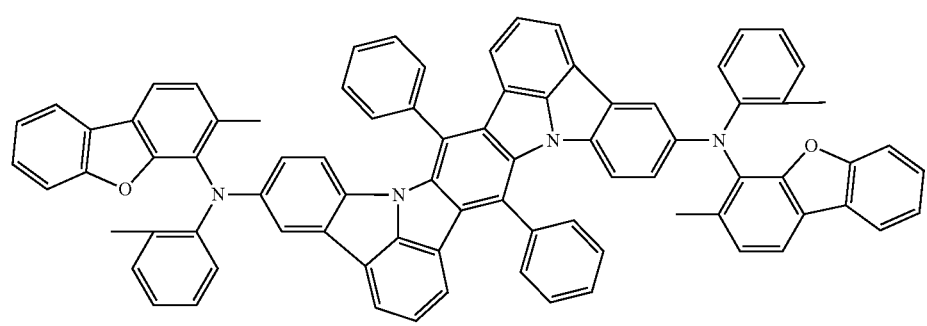

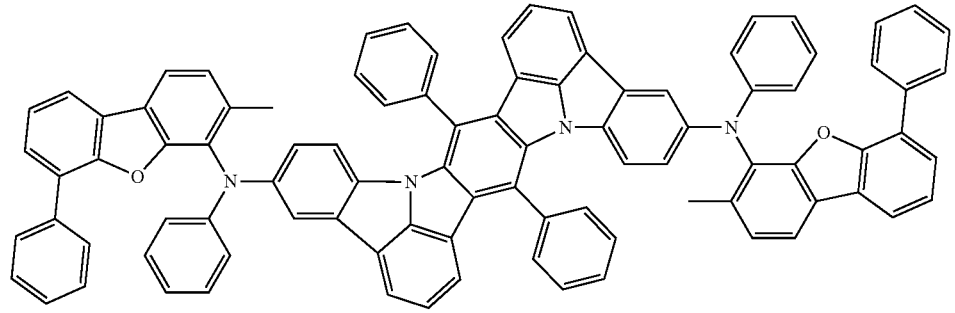
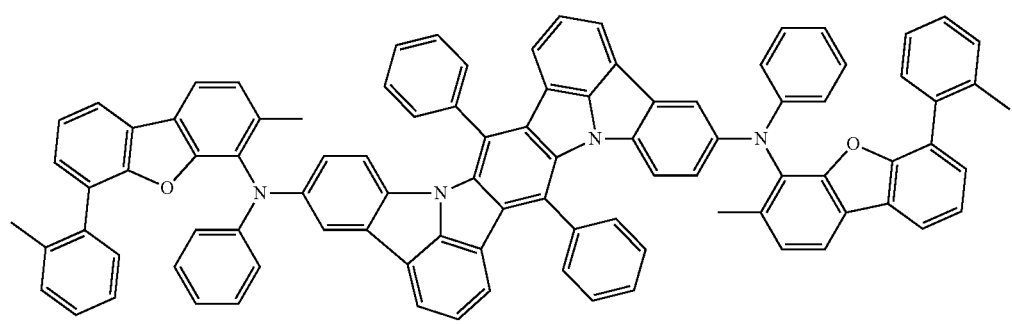
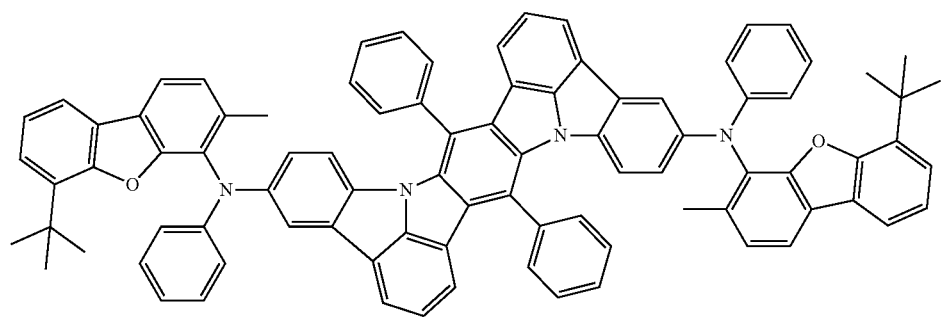
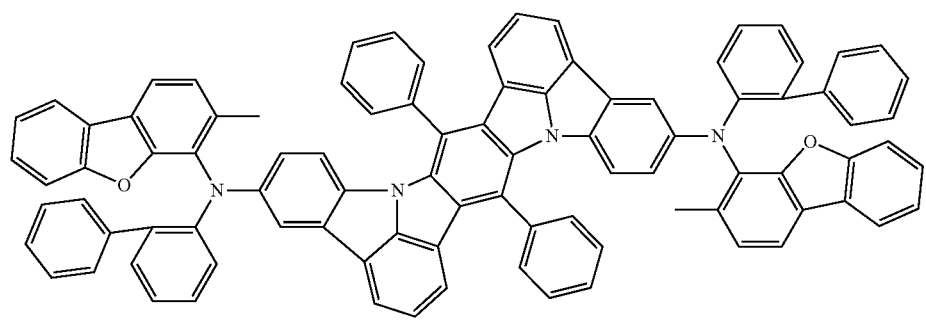

-continued
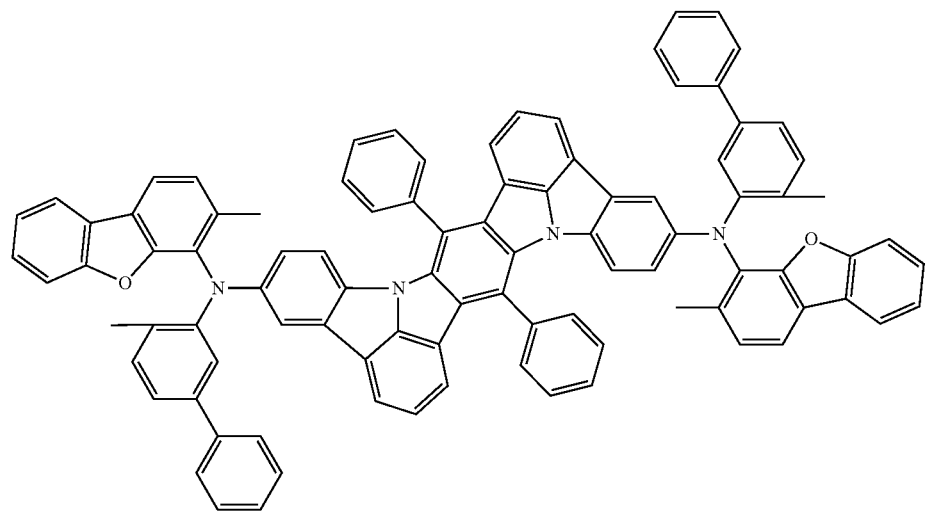
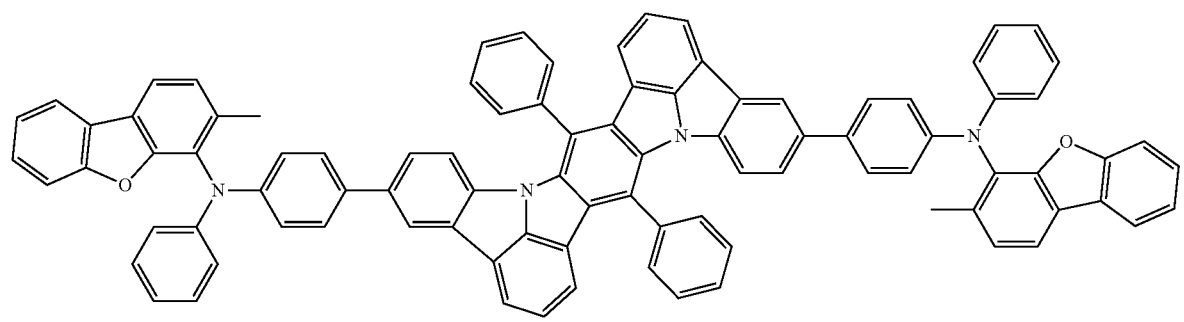

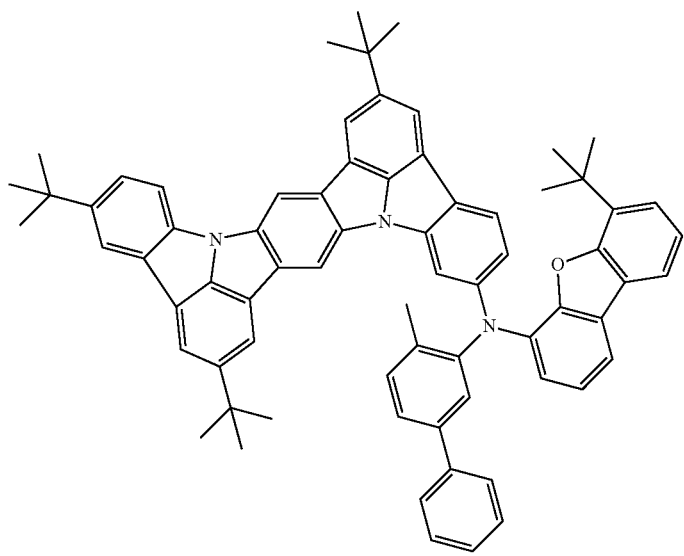
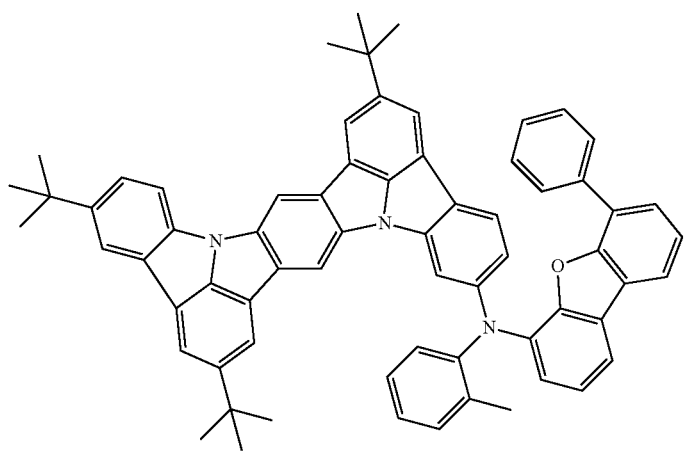
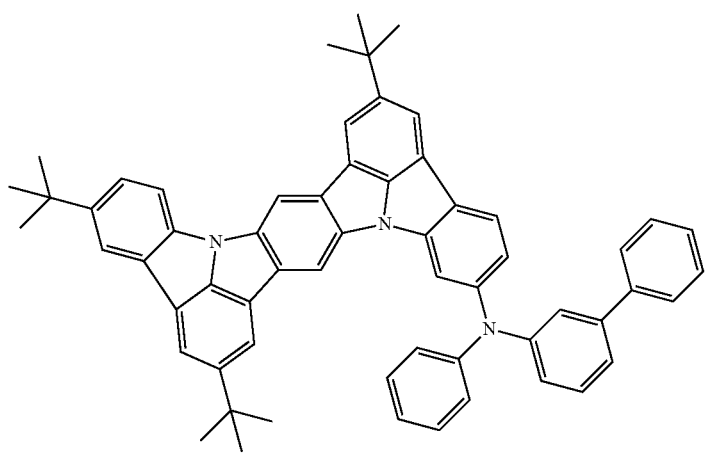

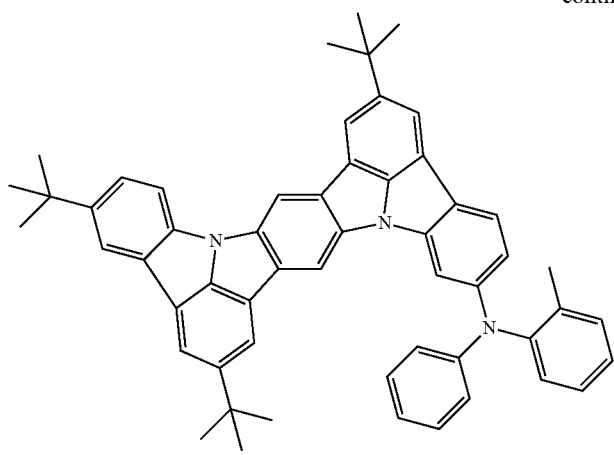
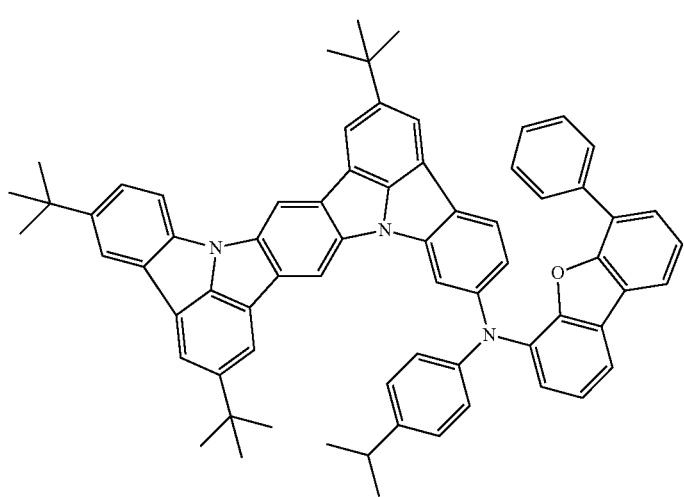
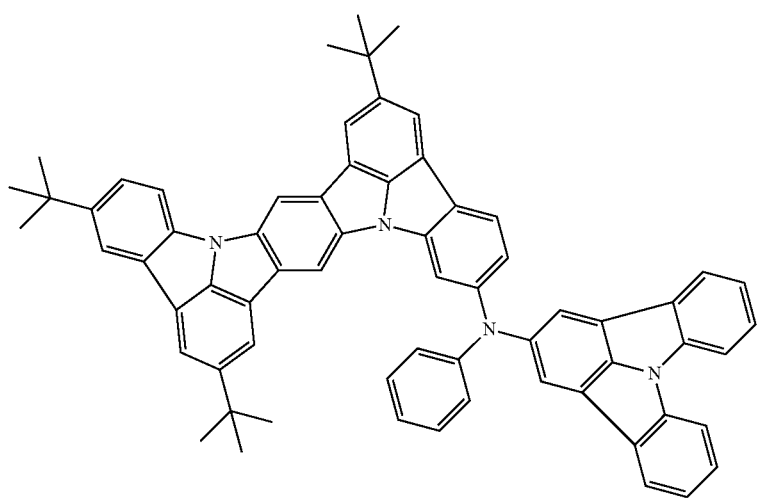

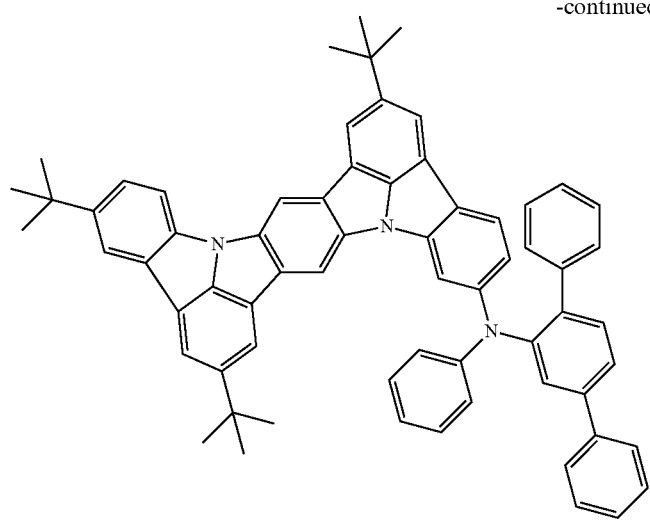
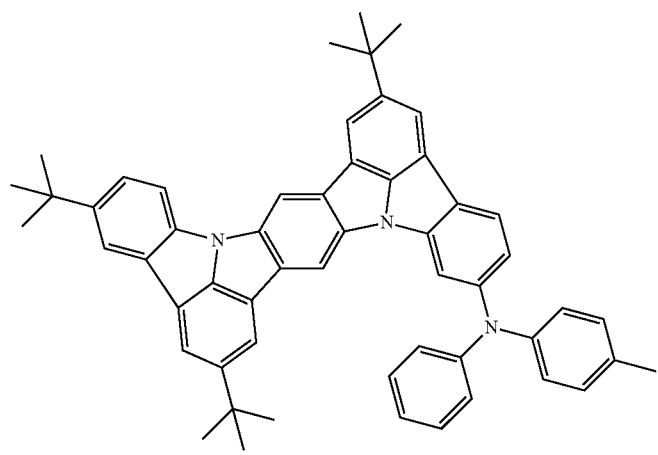
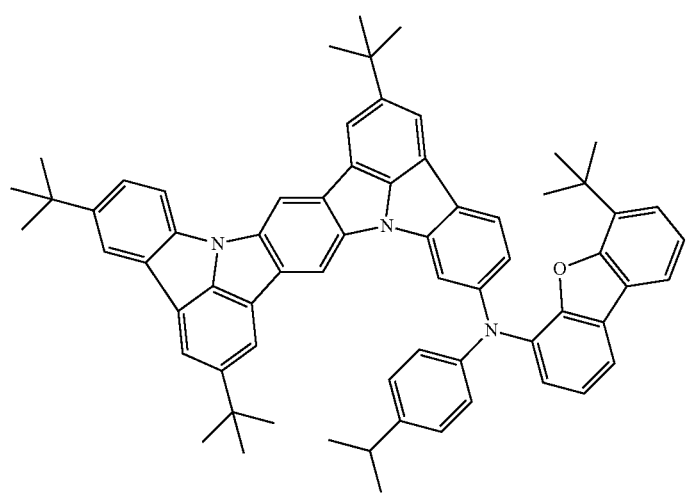

-continued
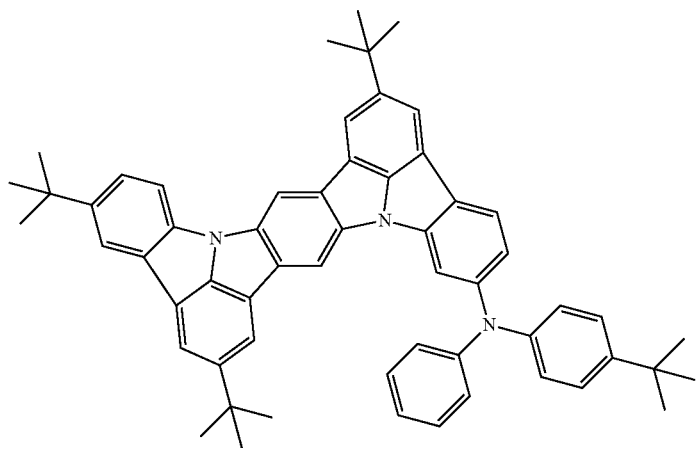
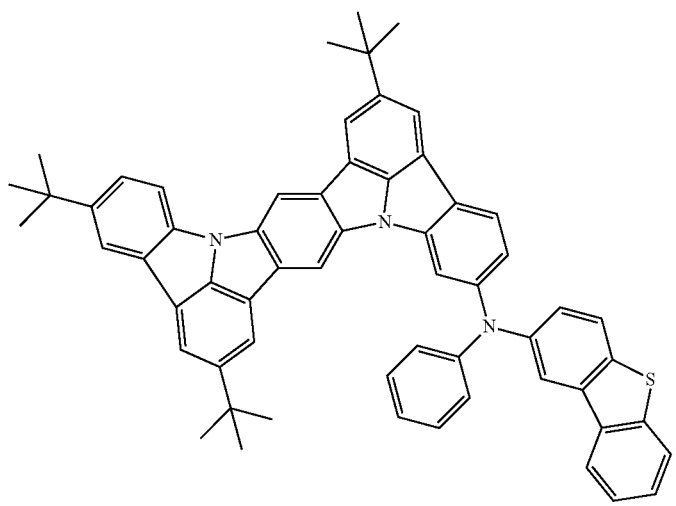
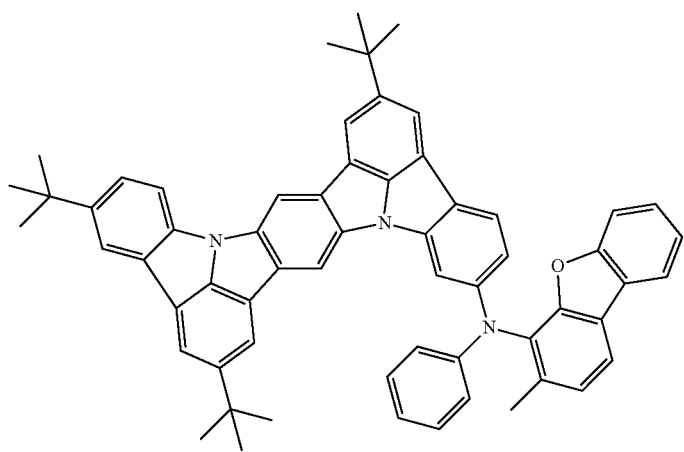

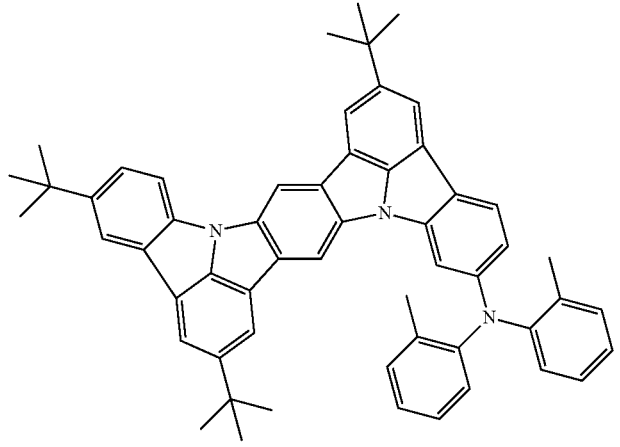
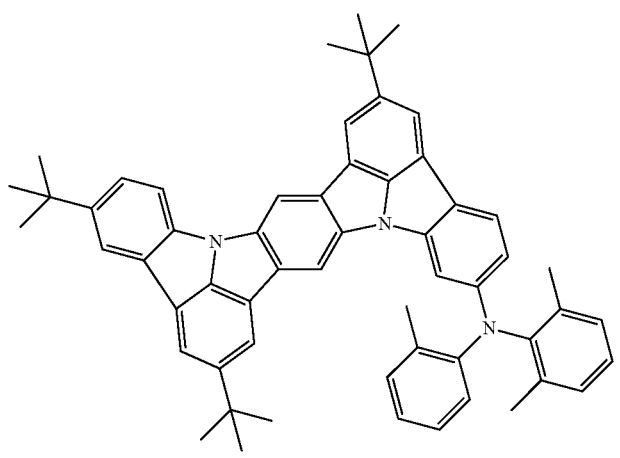
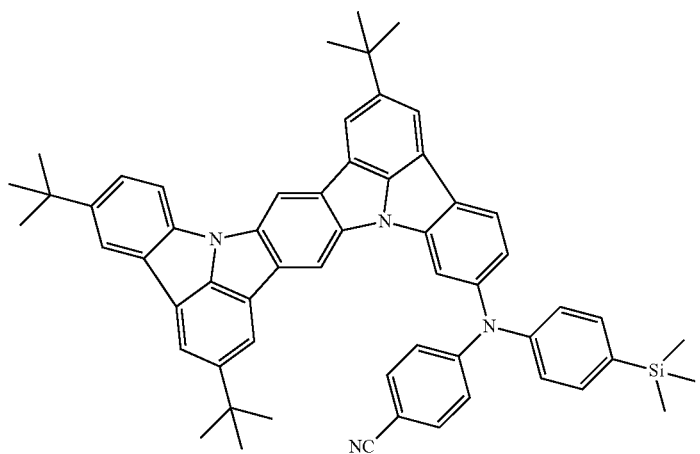

-continued
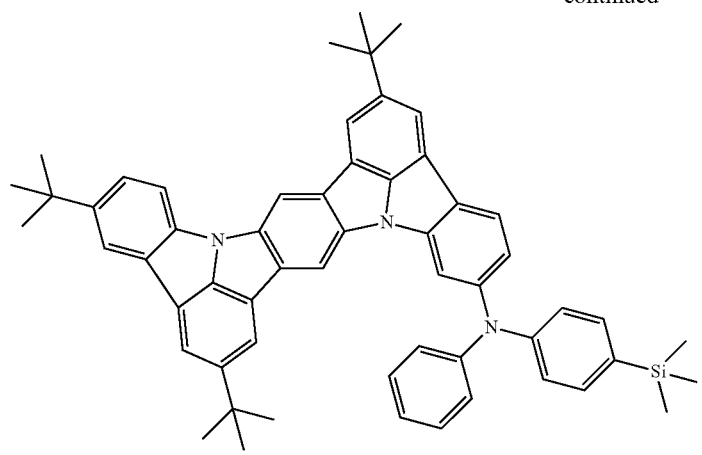
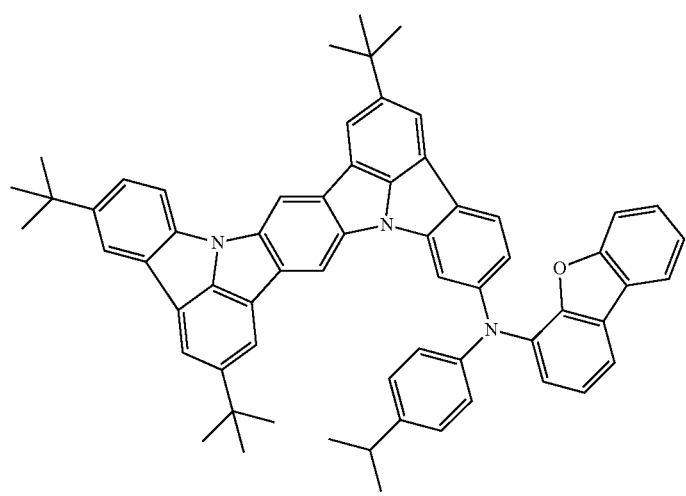
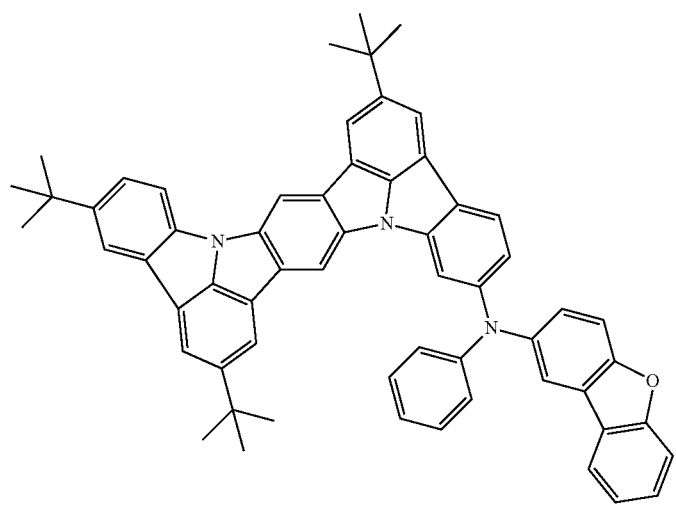

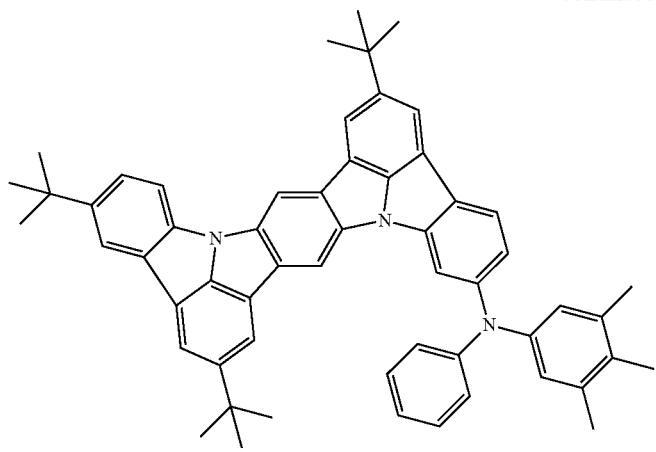
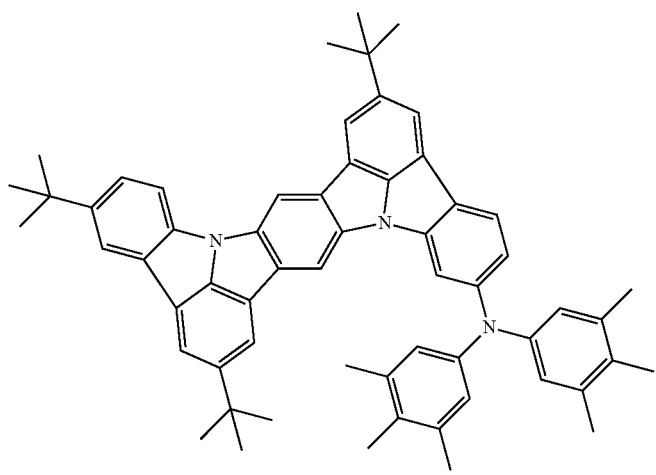
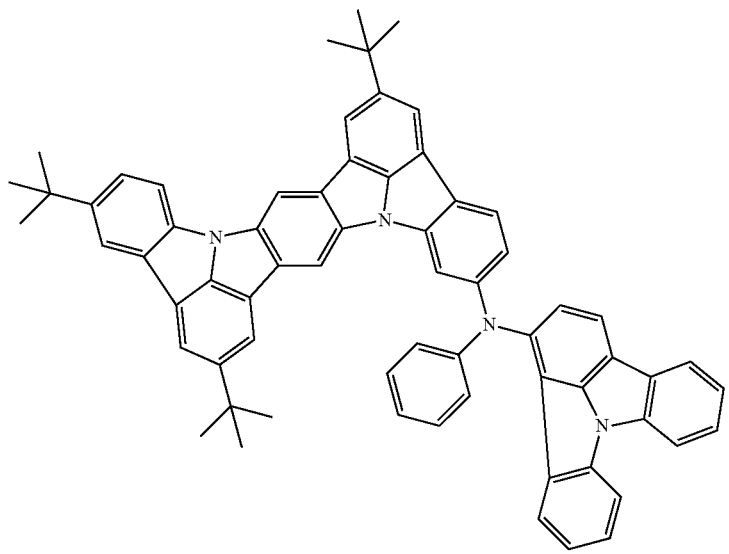

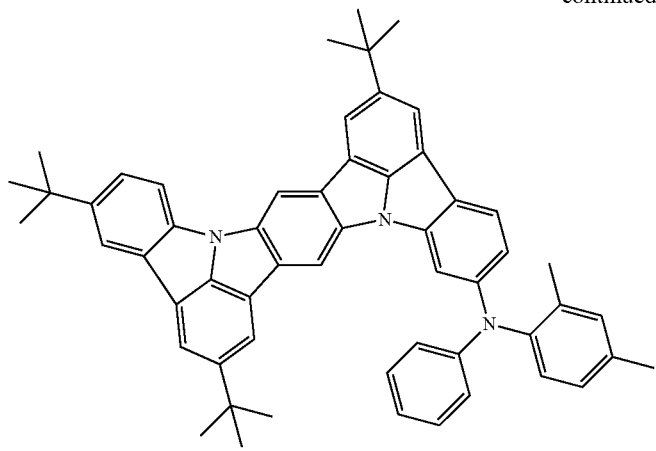
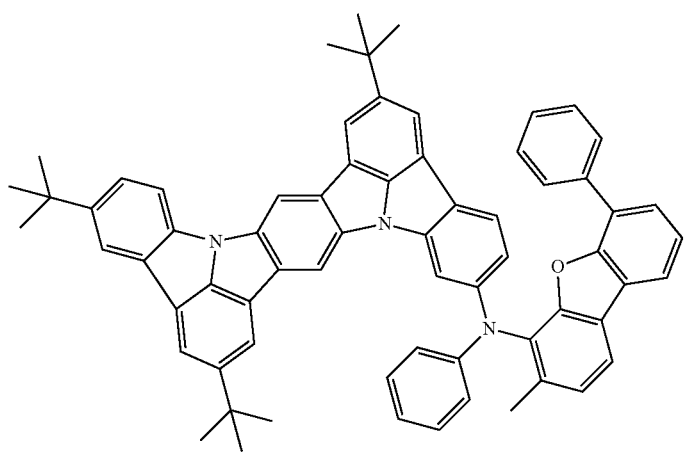
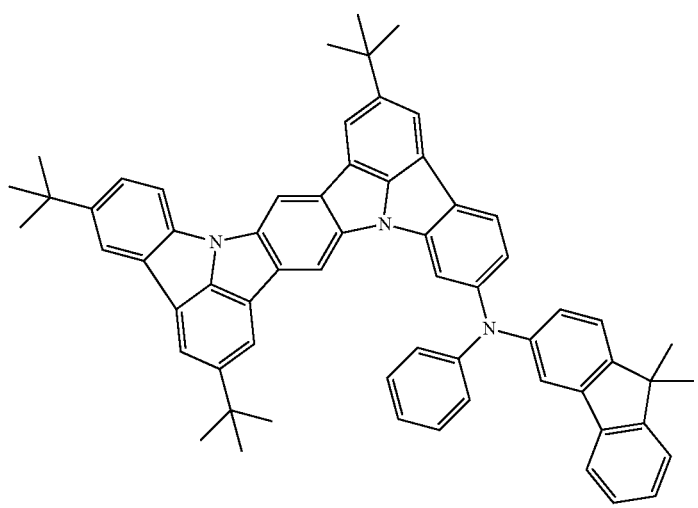

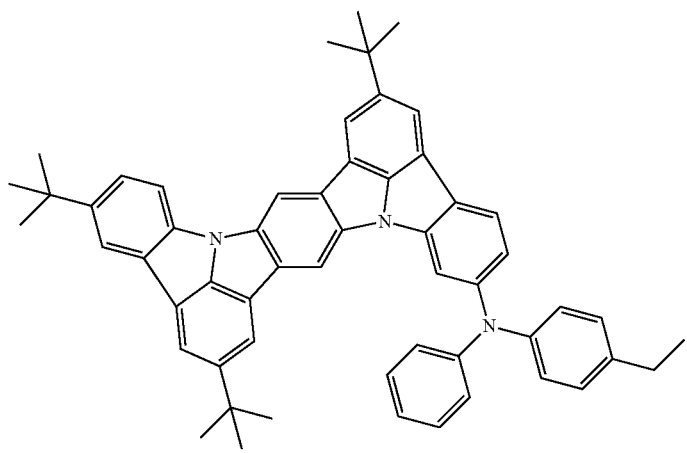
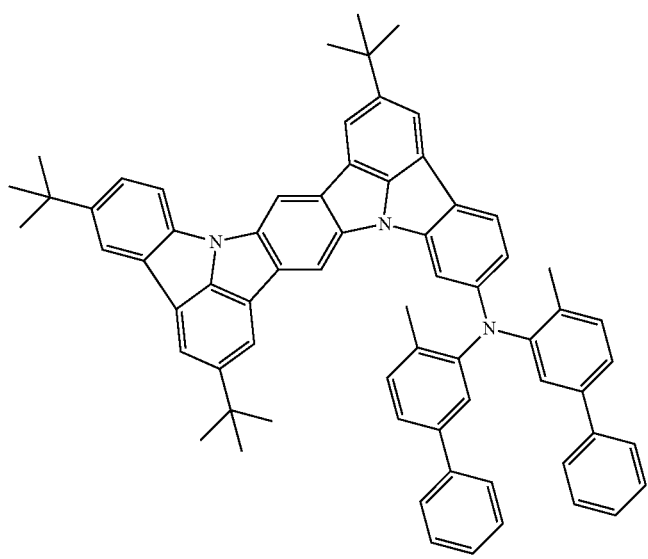
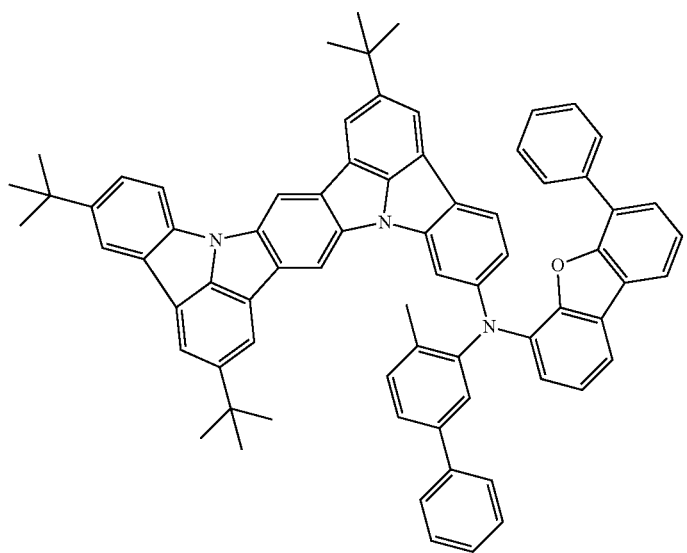

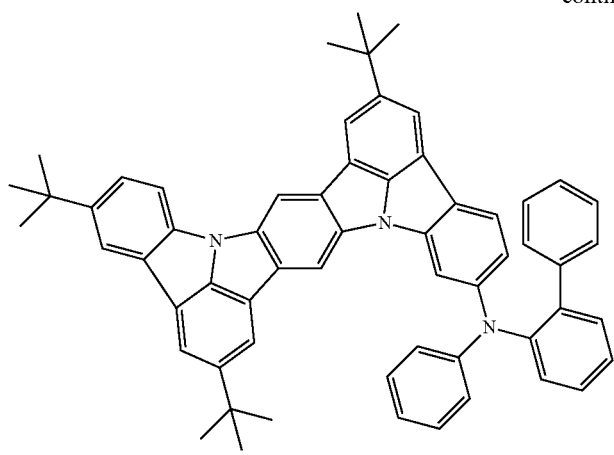
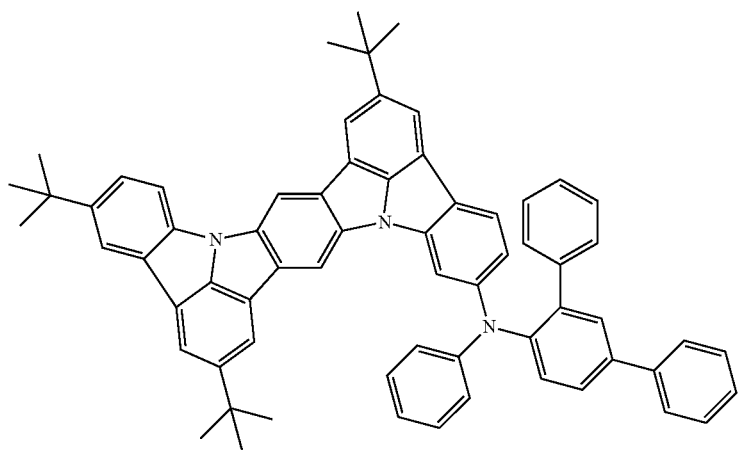
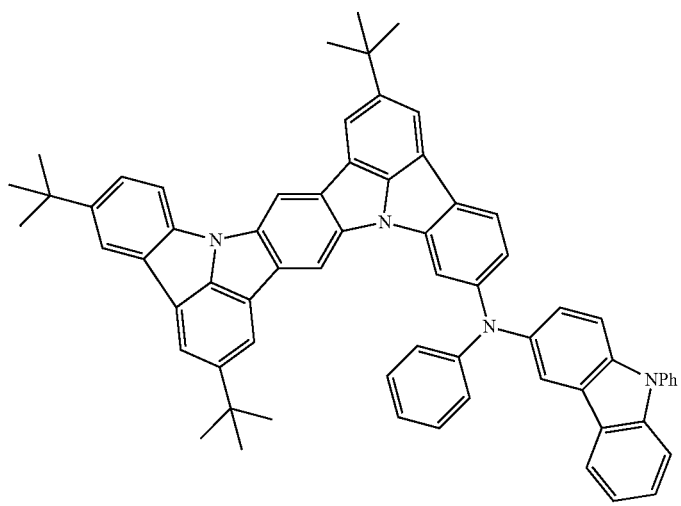

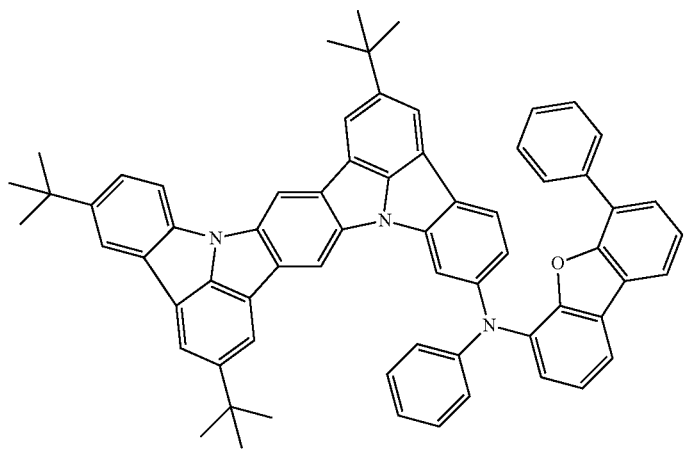
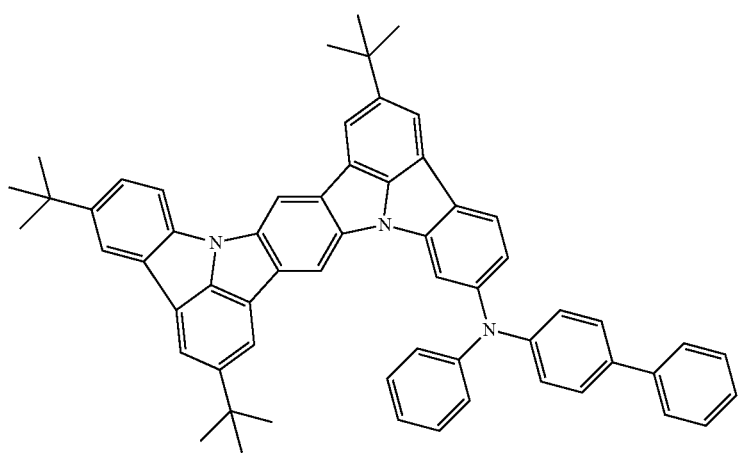
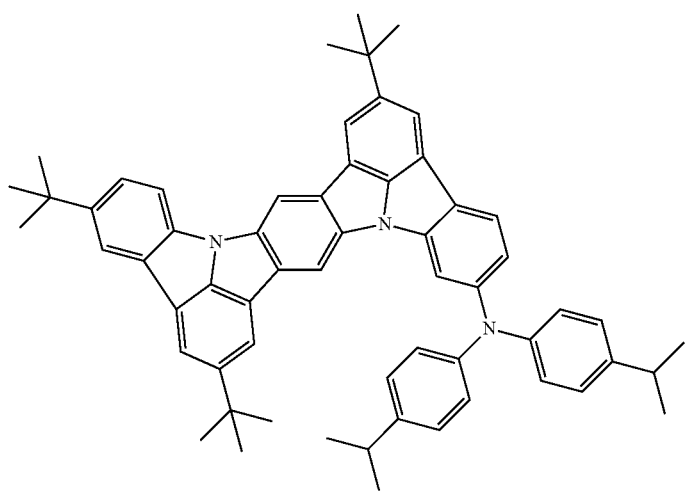

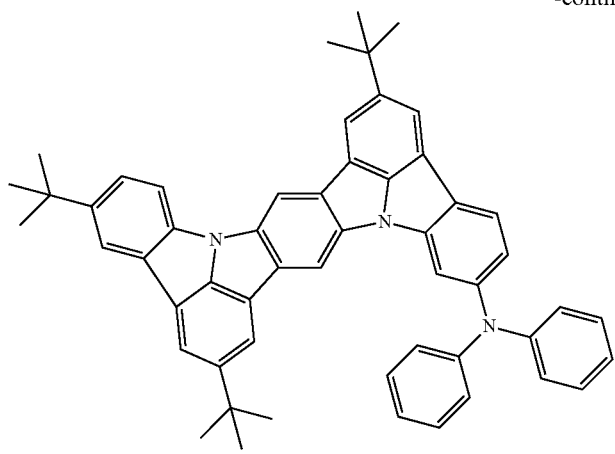
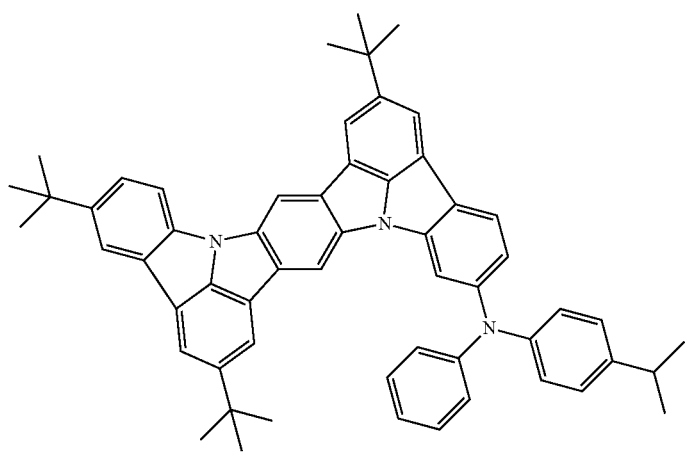
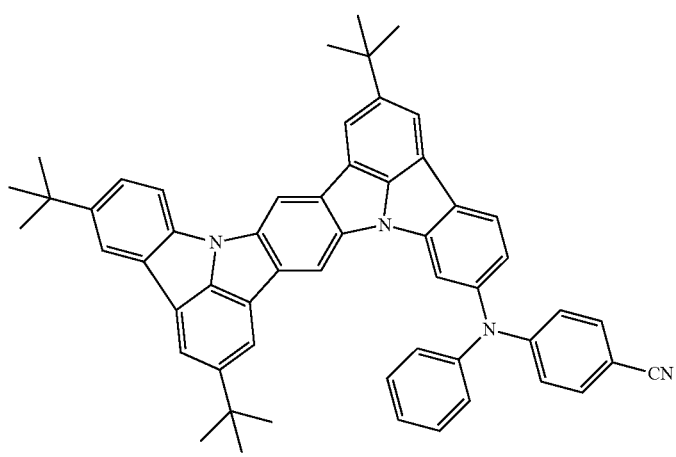

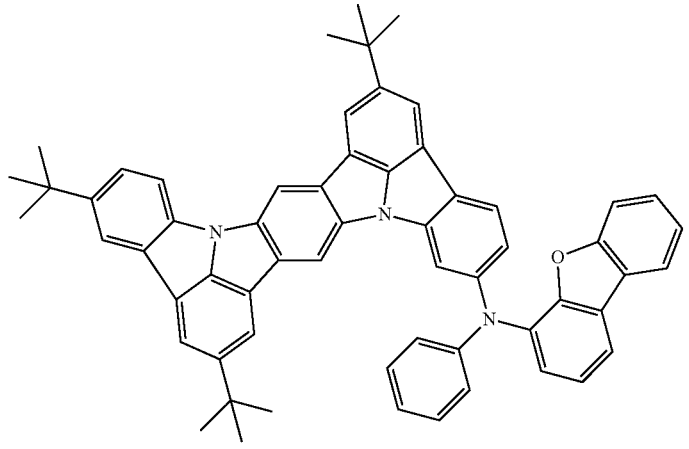
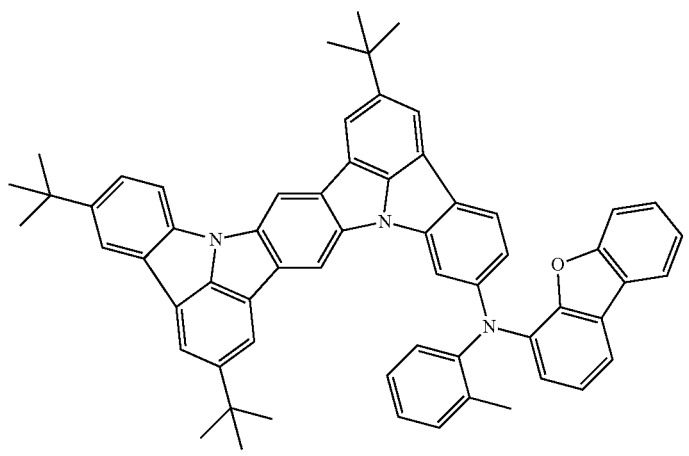
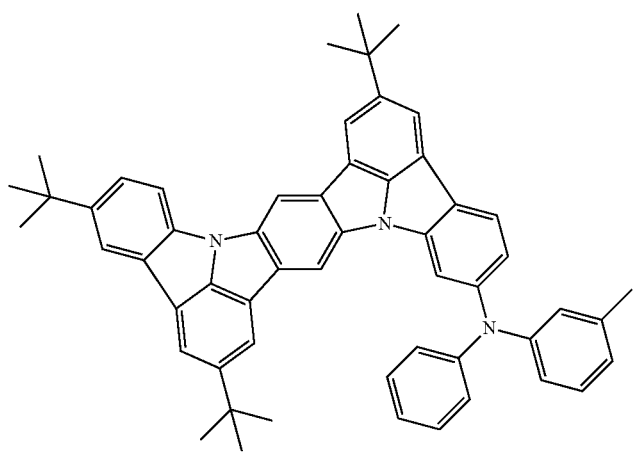

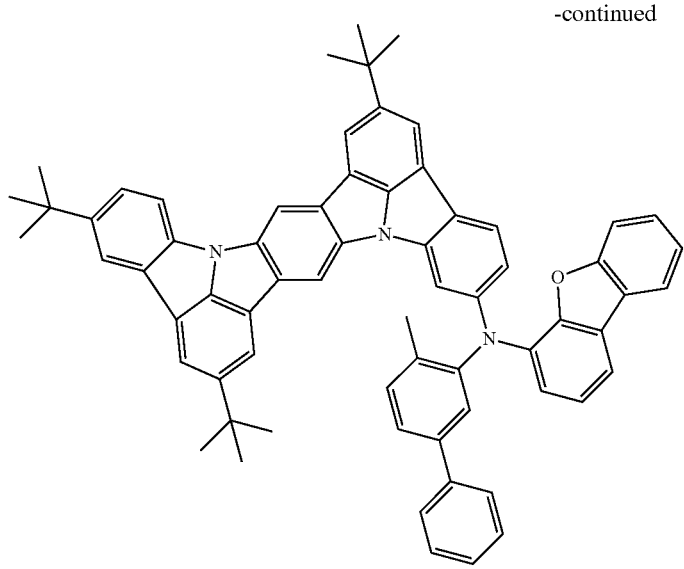
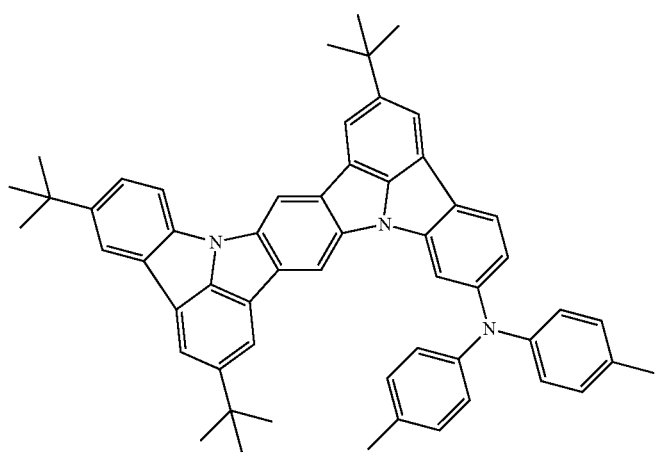
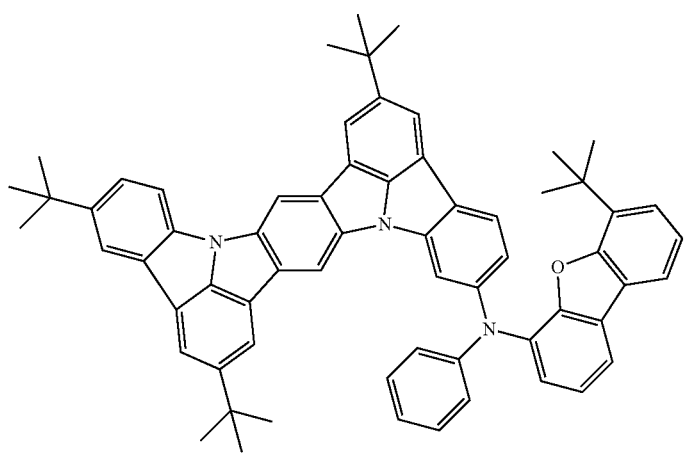

-continued
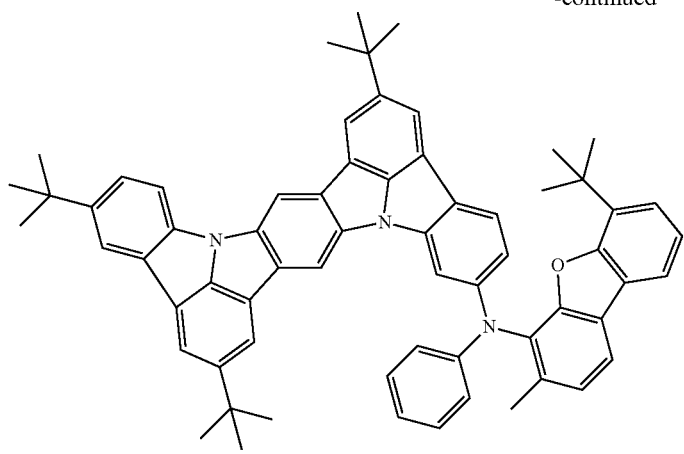
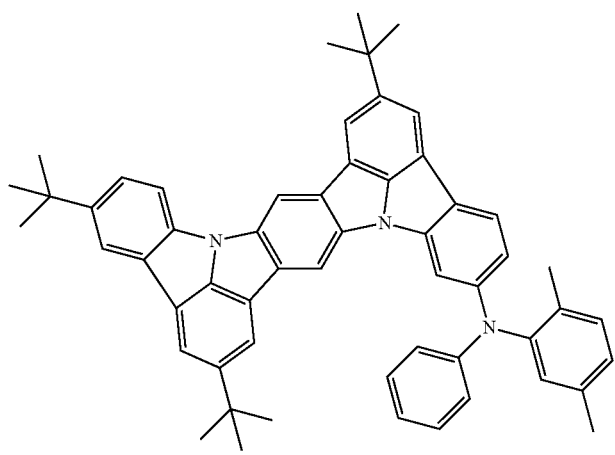
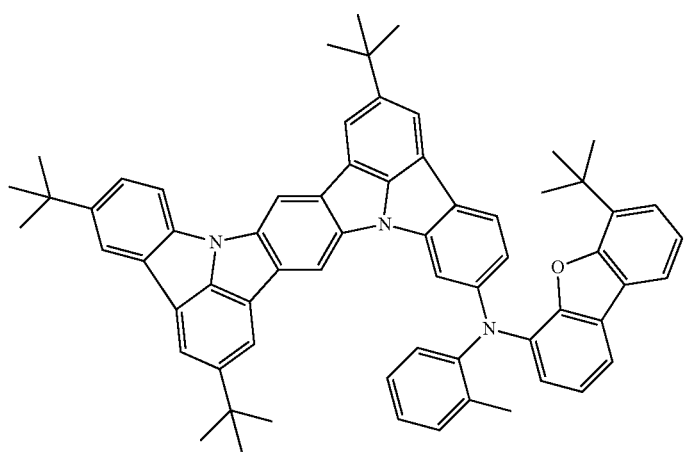

593
594
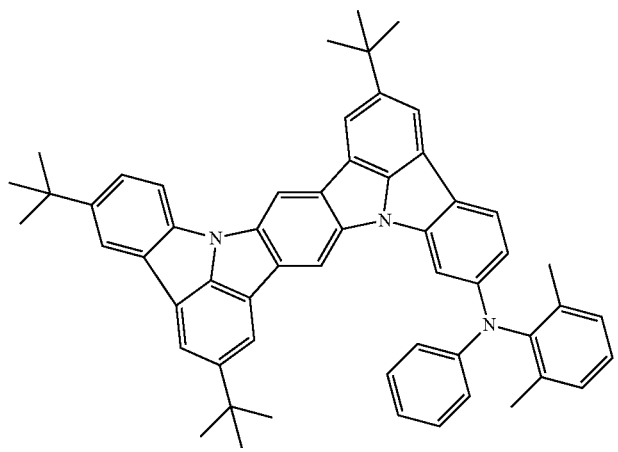
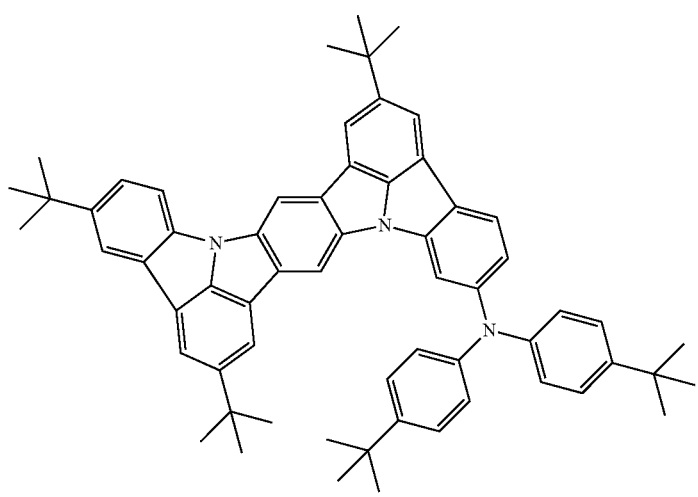
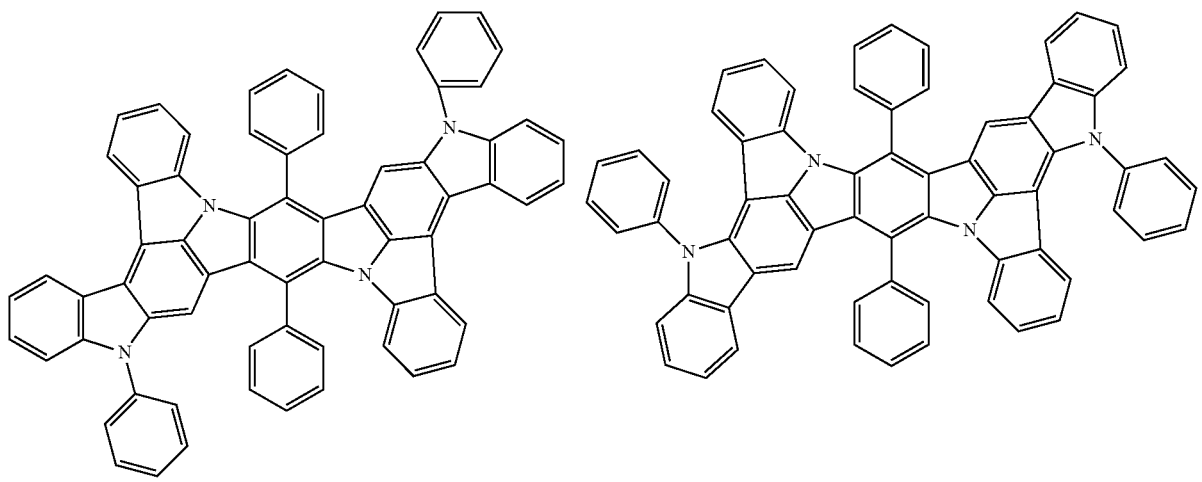

-continued
595 596
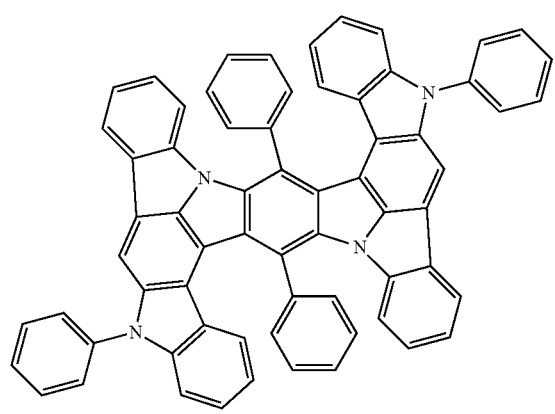
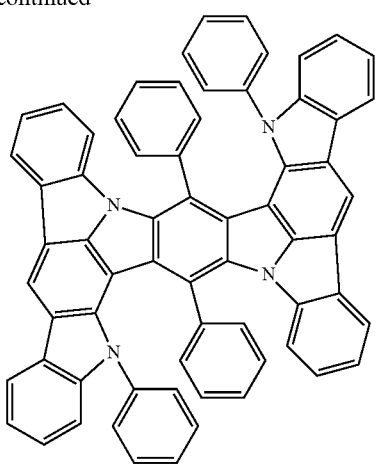
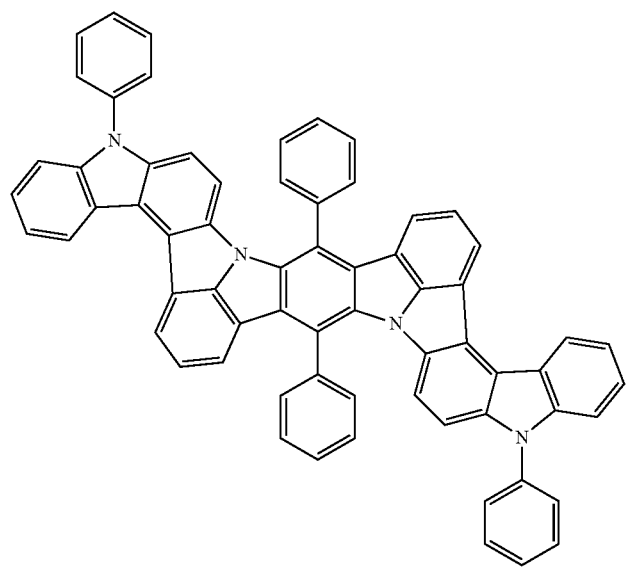
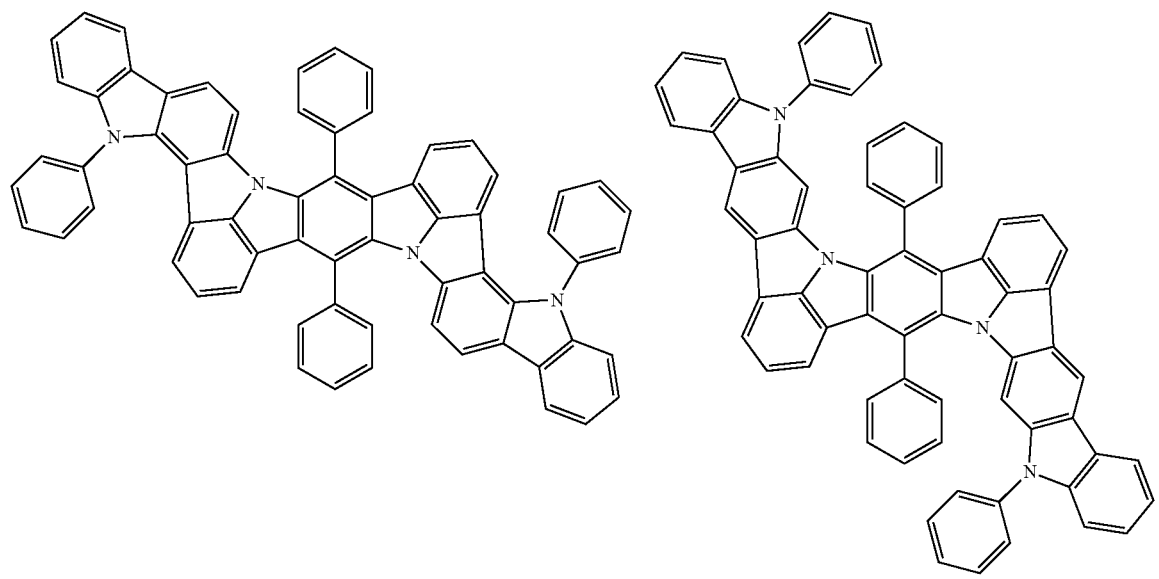

-continued
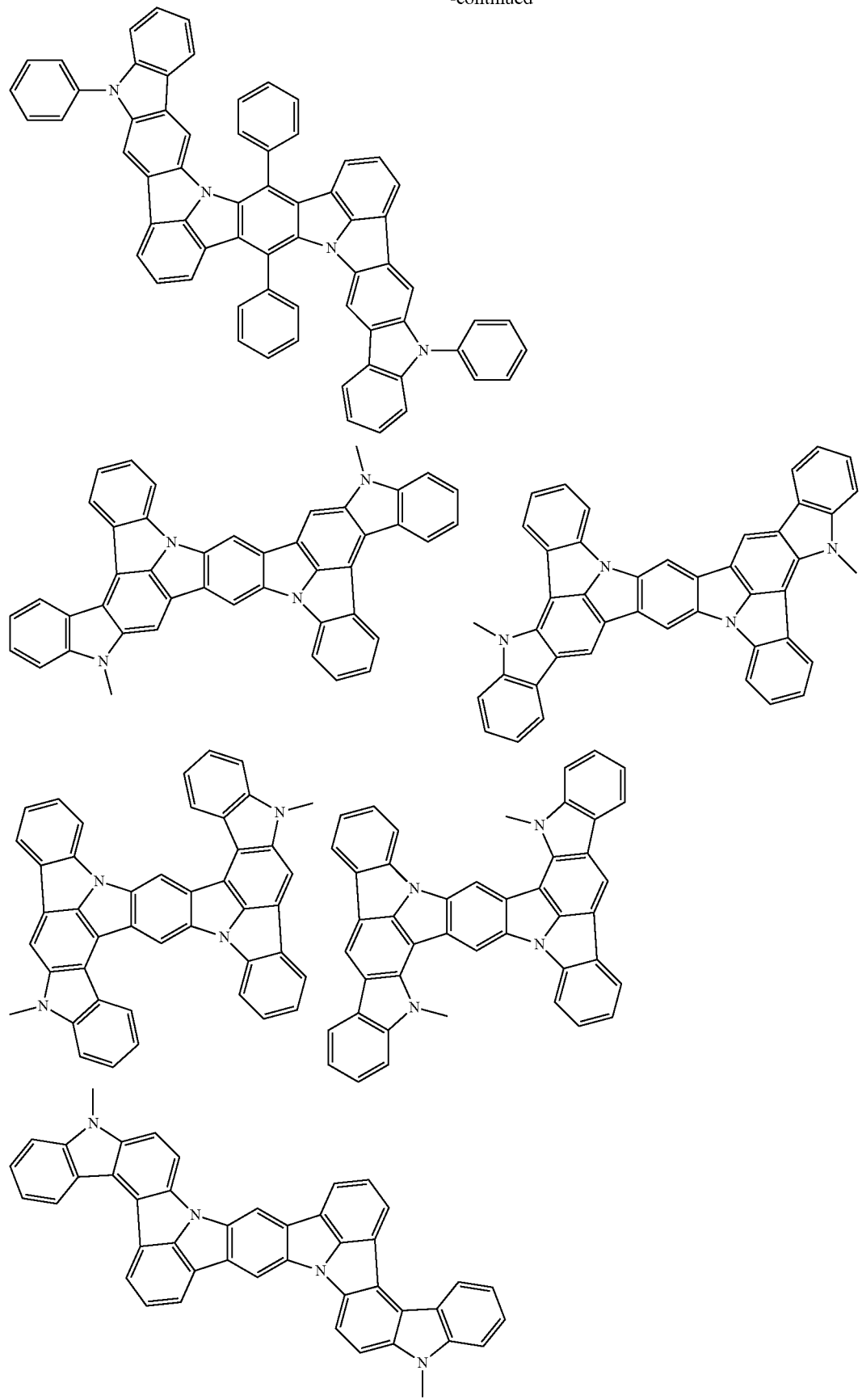

-continued
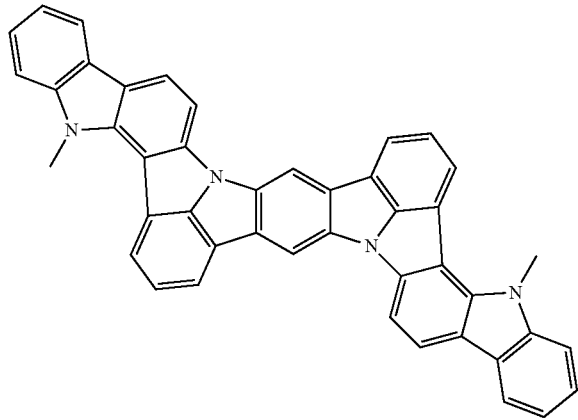
599
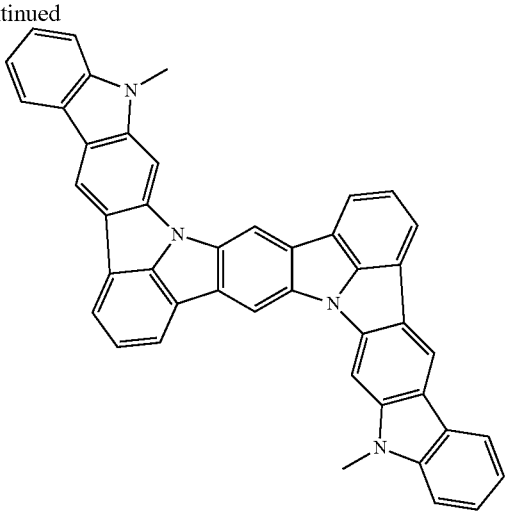
600
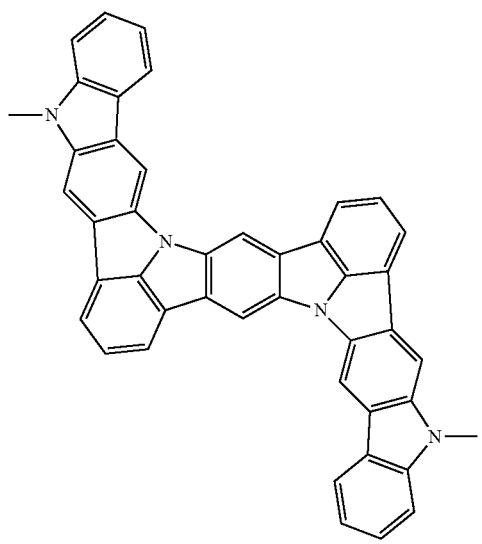
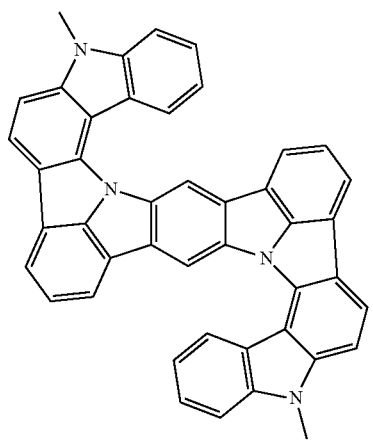
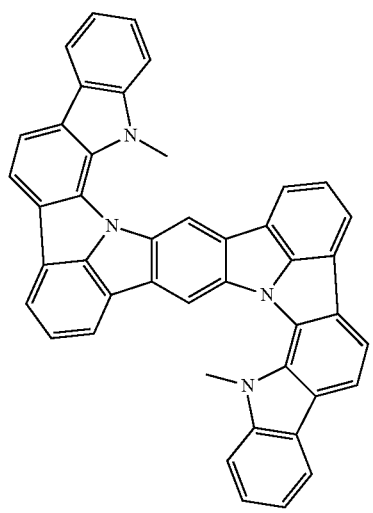
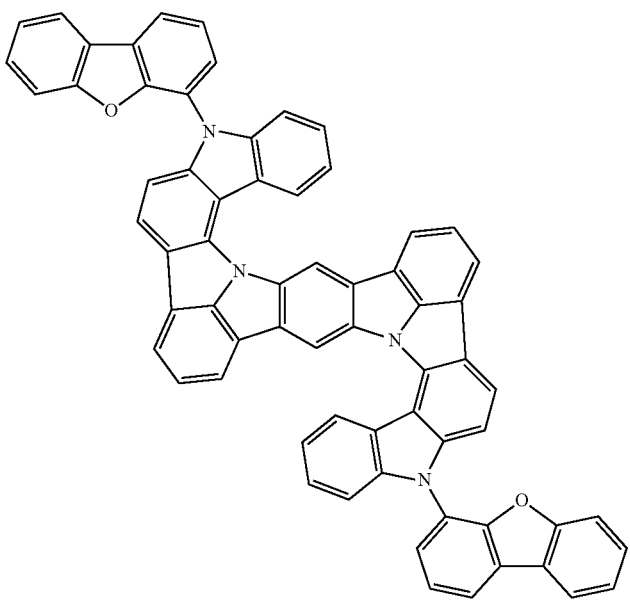

-continued
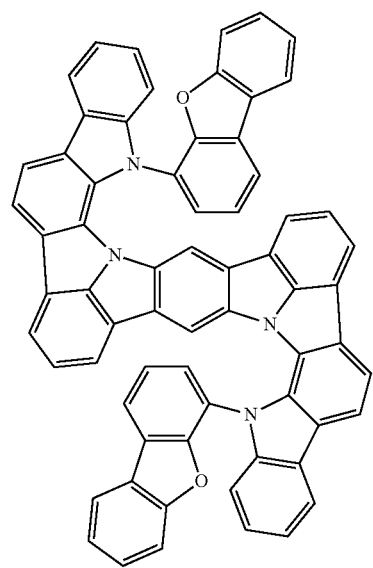
601
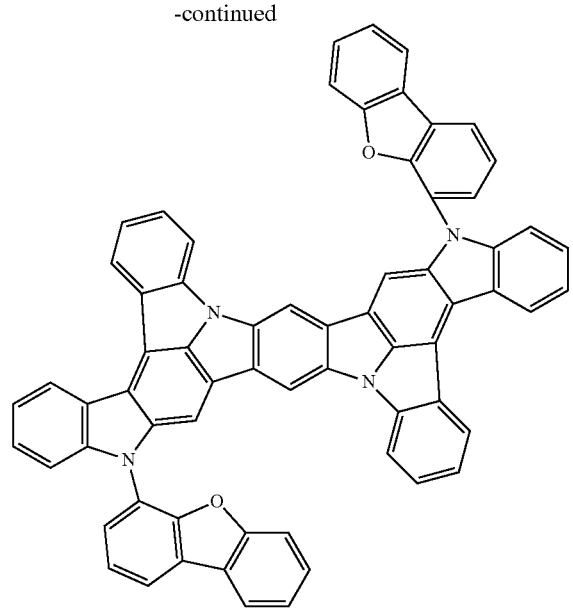
602
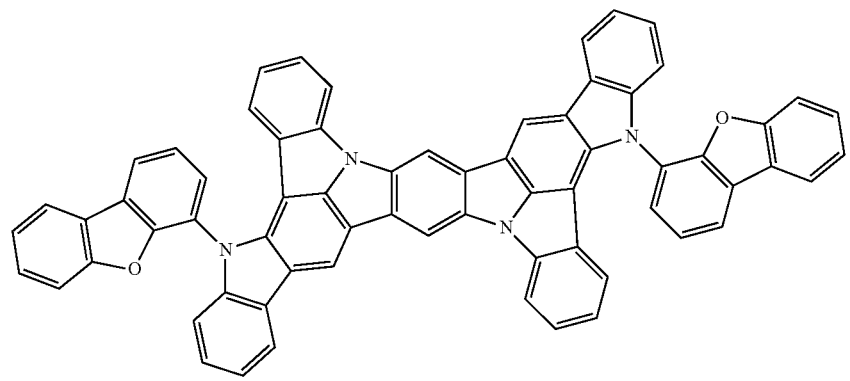
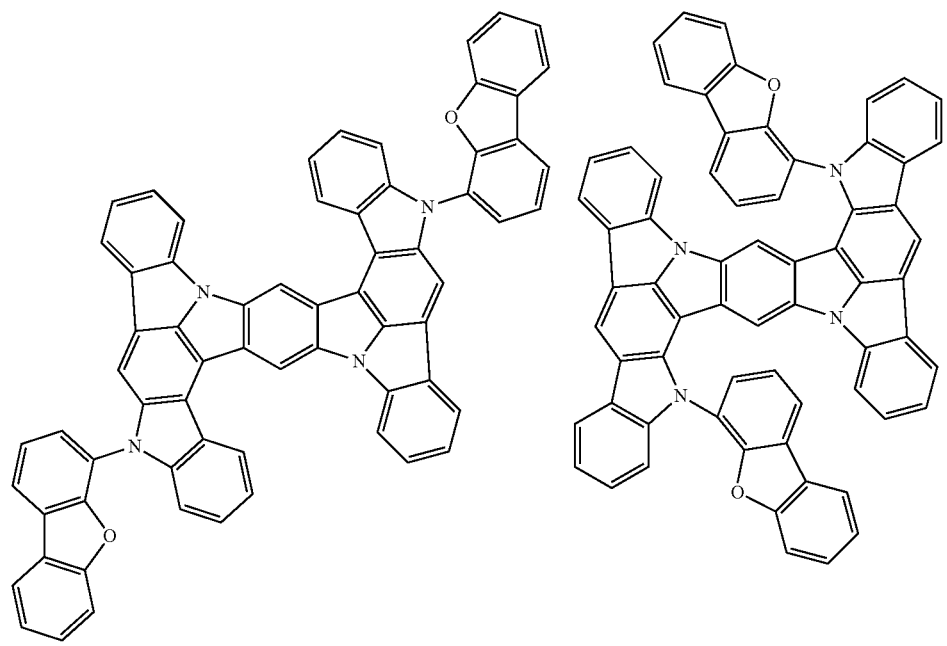

-continued
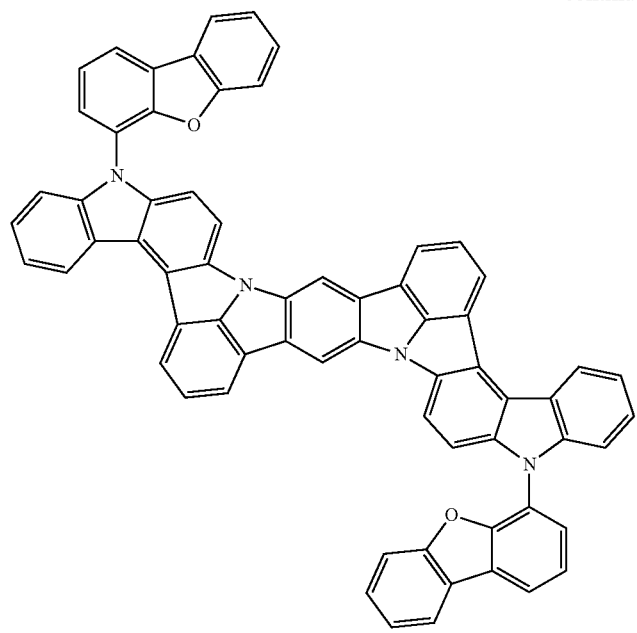
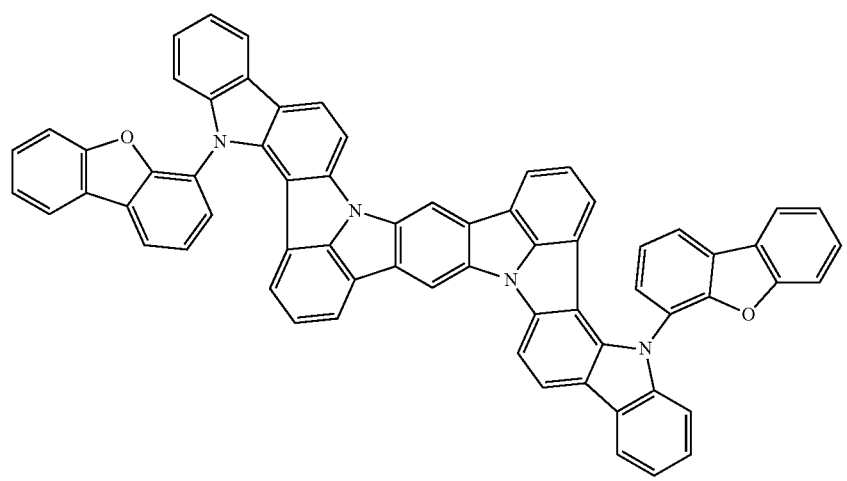
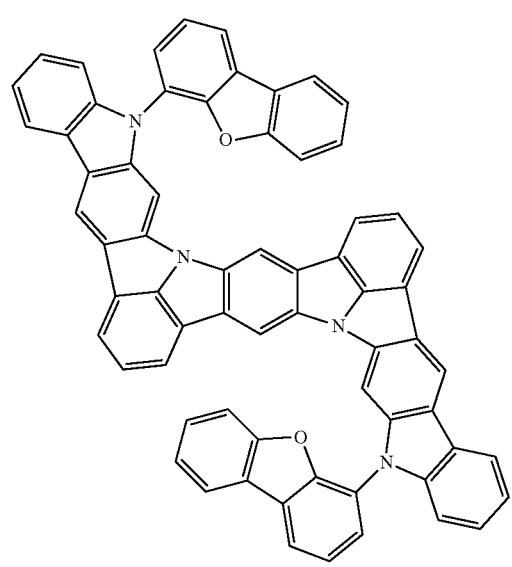

605
606
-continued
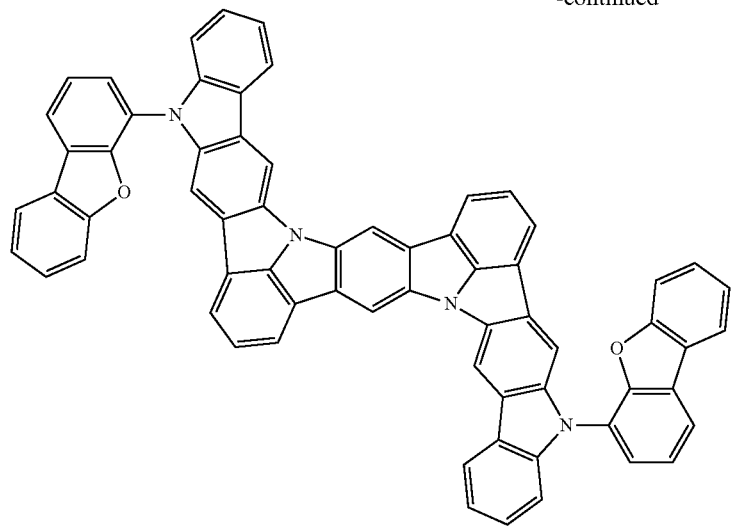
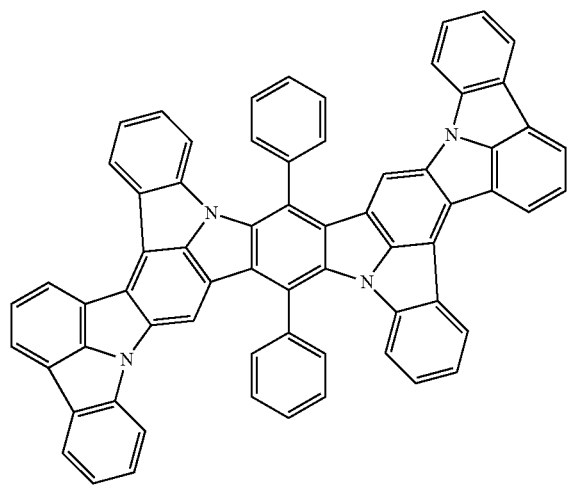
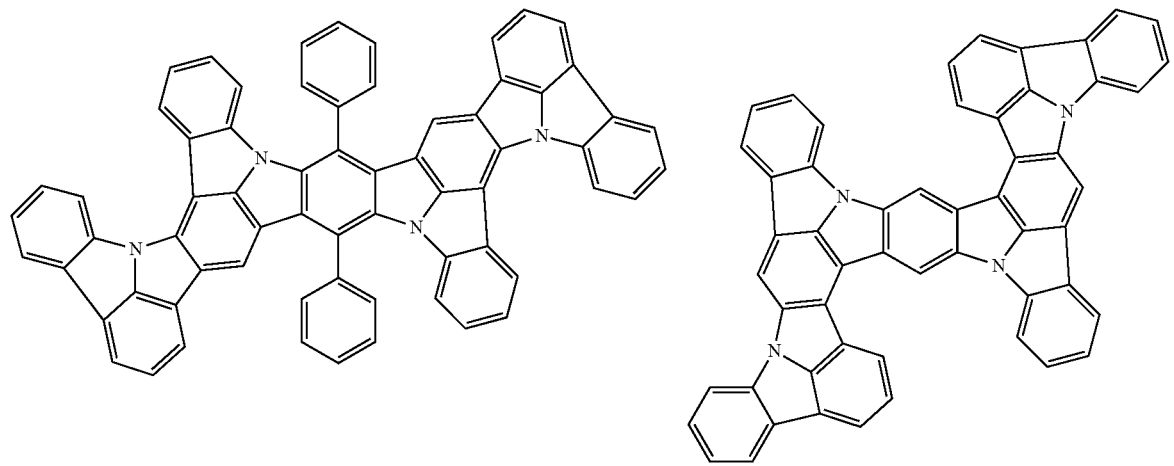

607 608
-continued
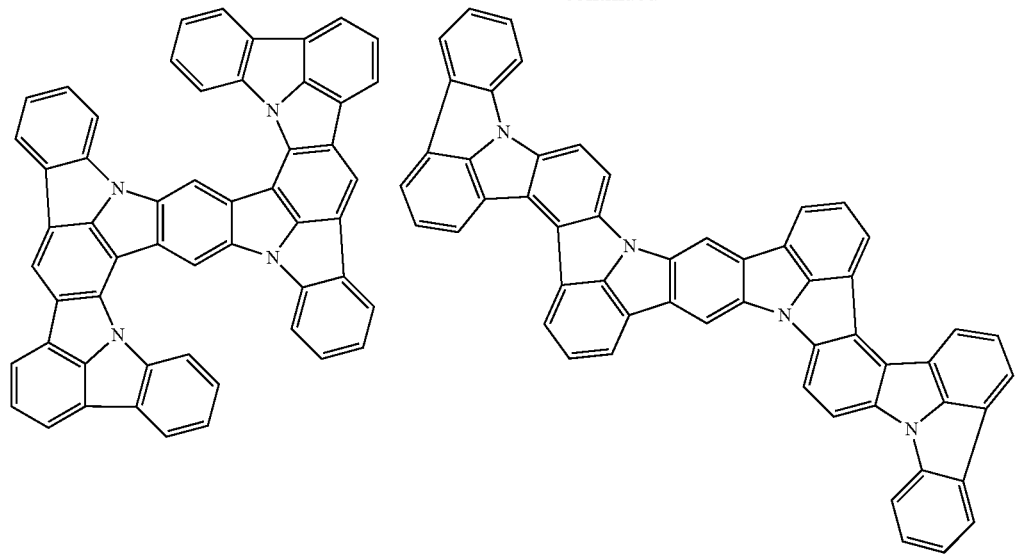
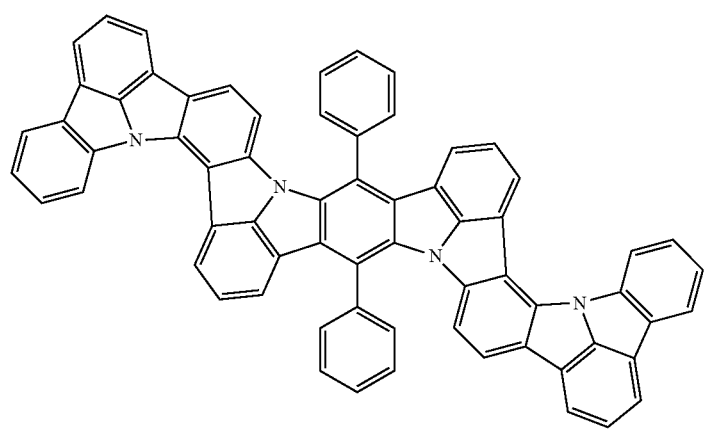
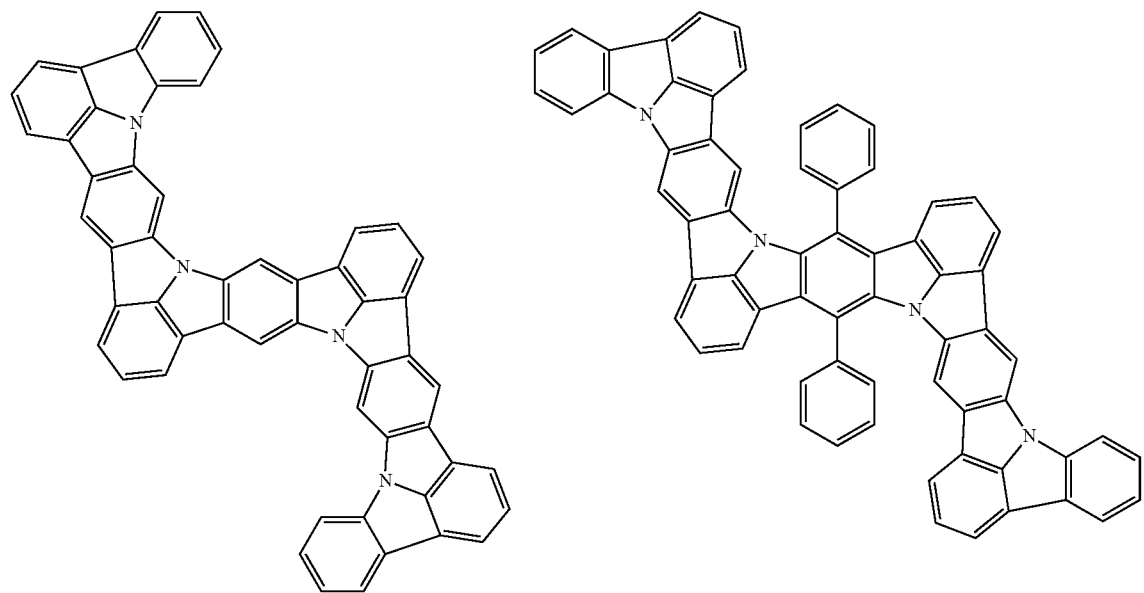

-continued
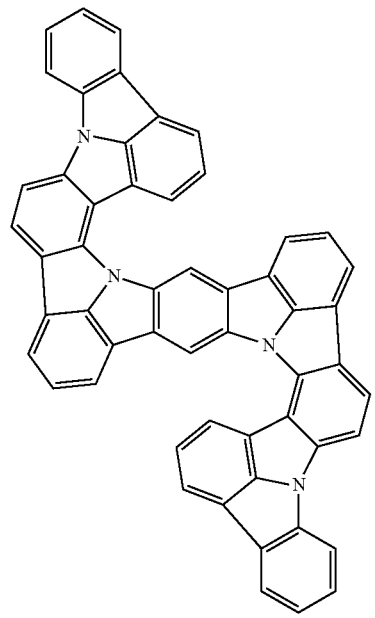
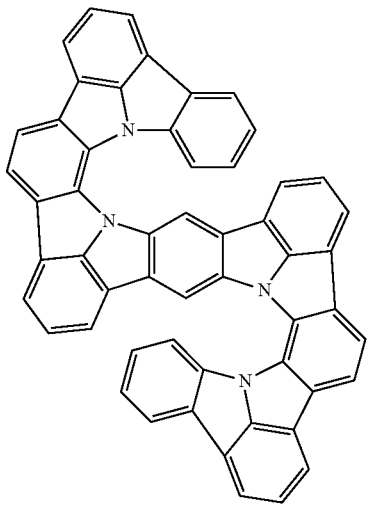
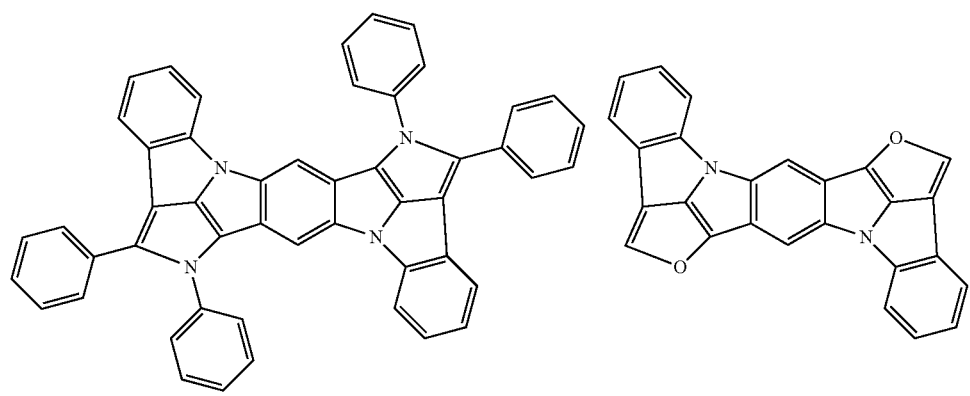
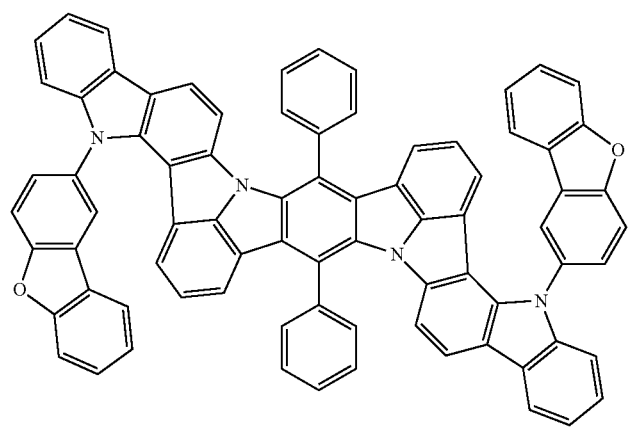

-continued
611 612
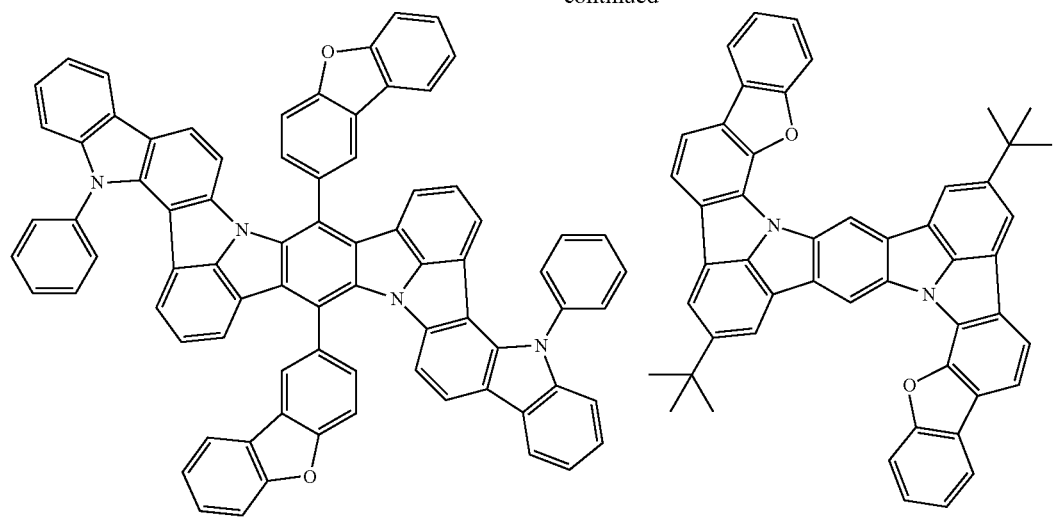
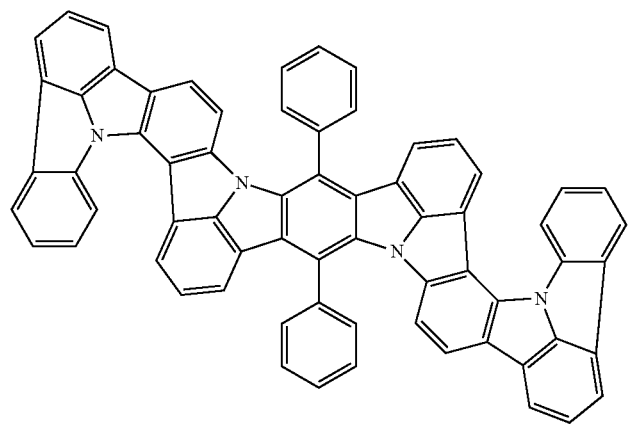
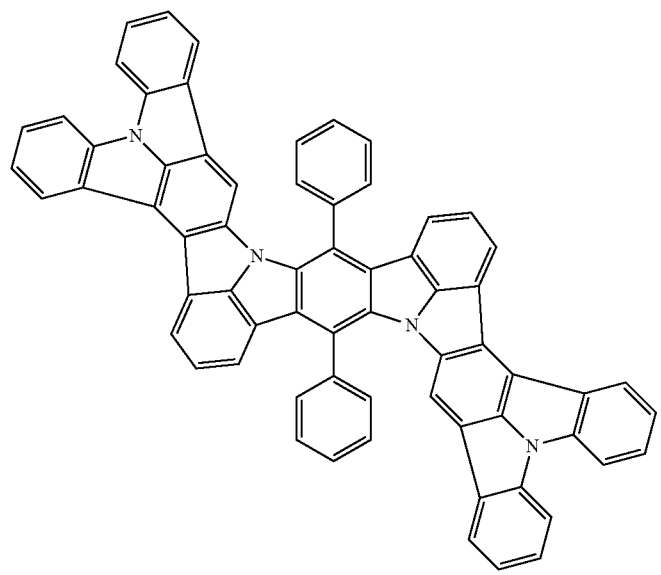

-continued
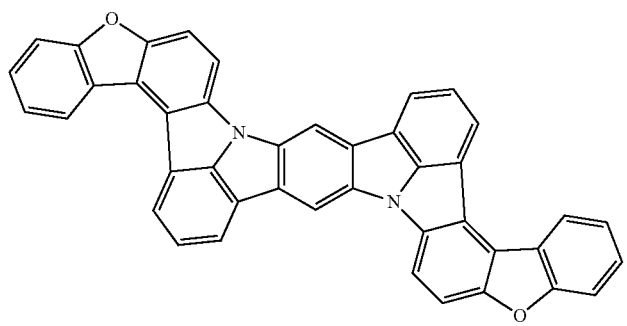
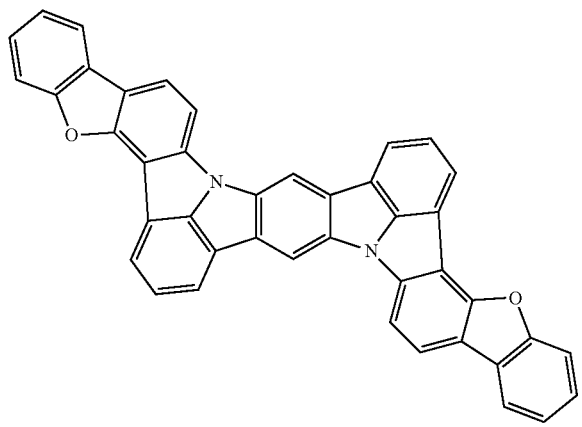
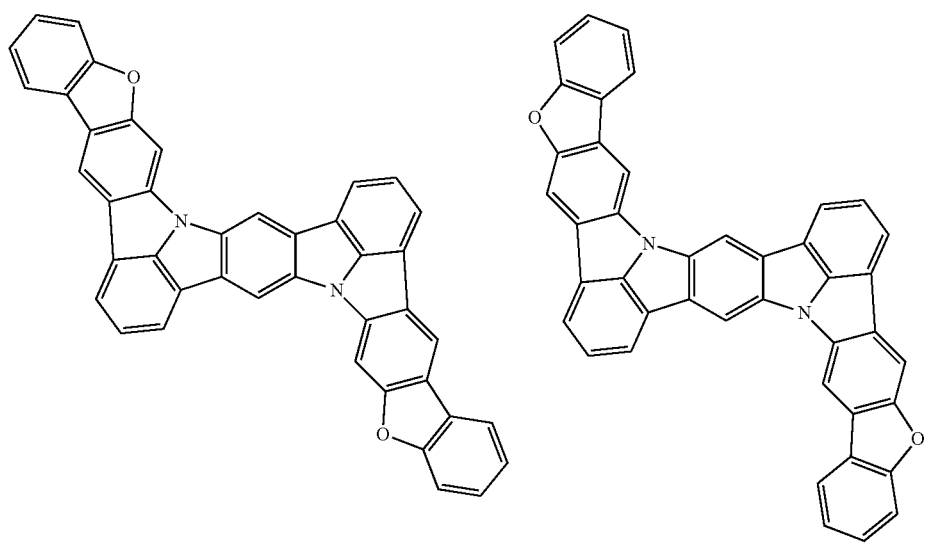

-continued
615
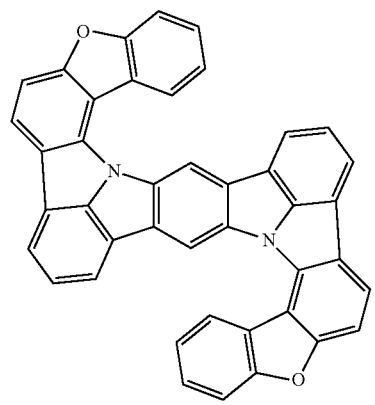 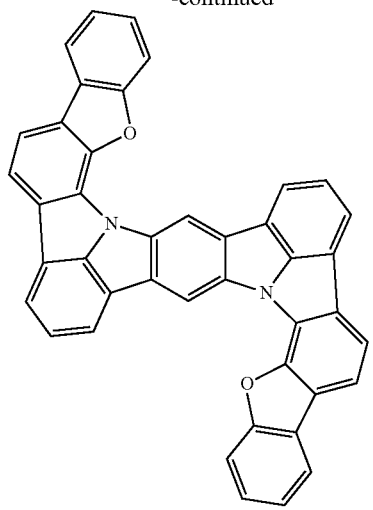
616
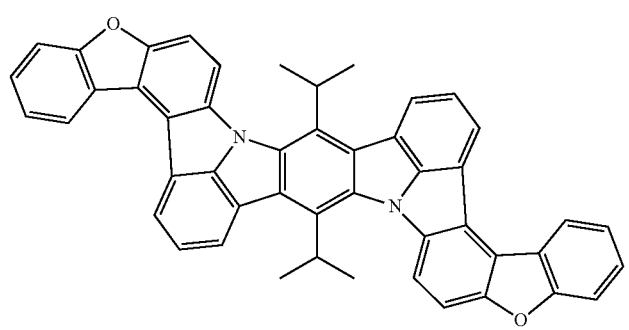
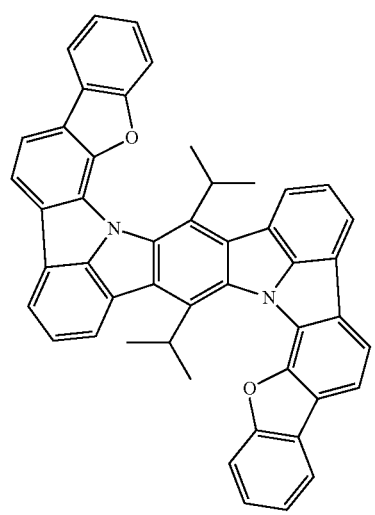
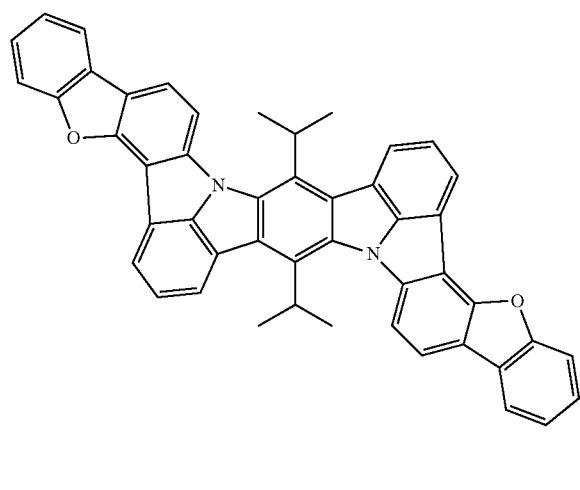 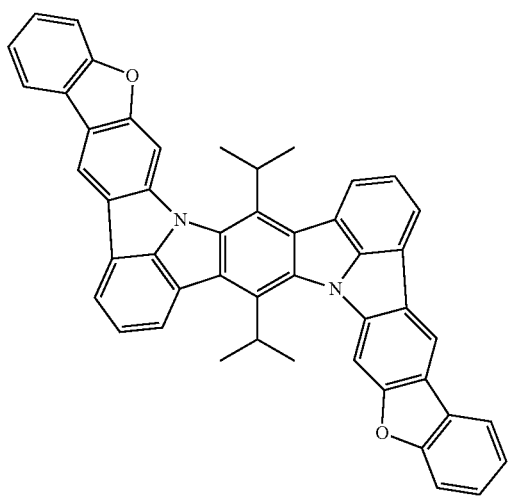

-continued
617
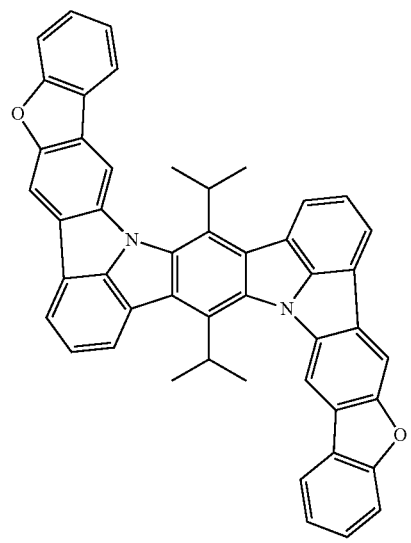
618
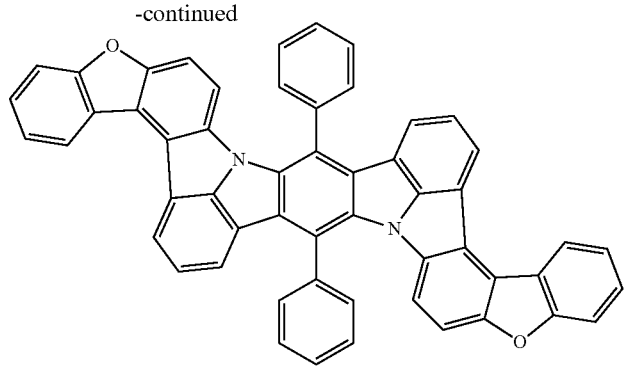
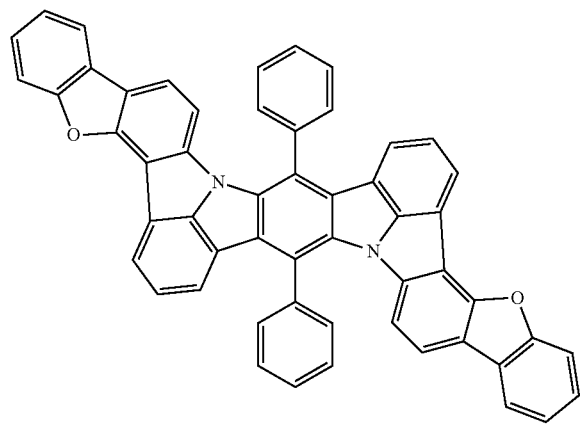
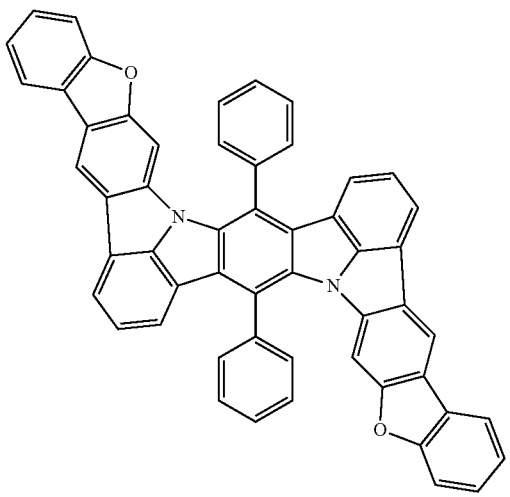
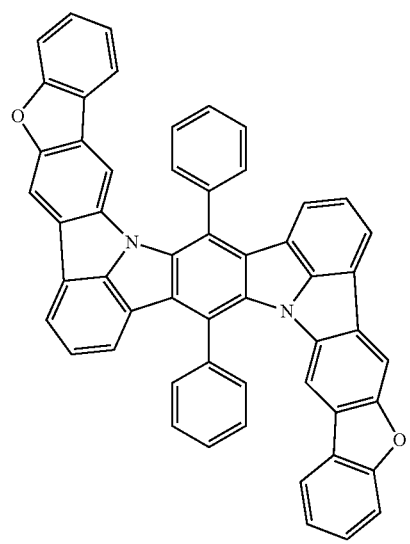
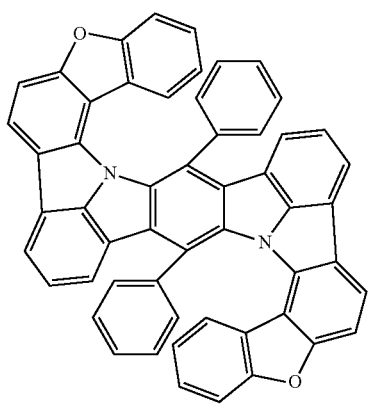
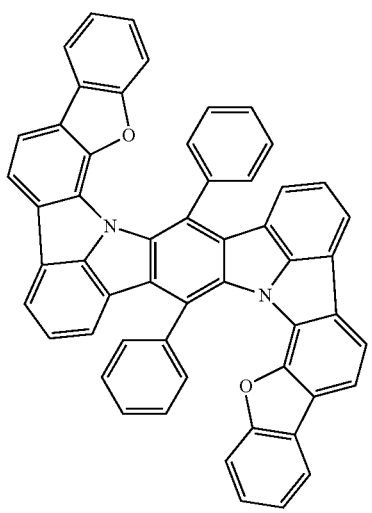

619 620
-continued
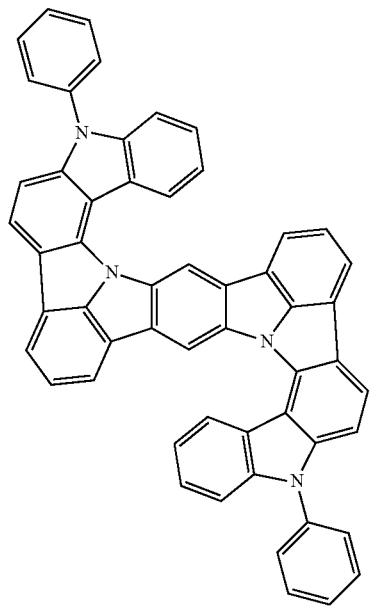 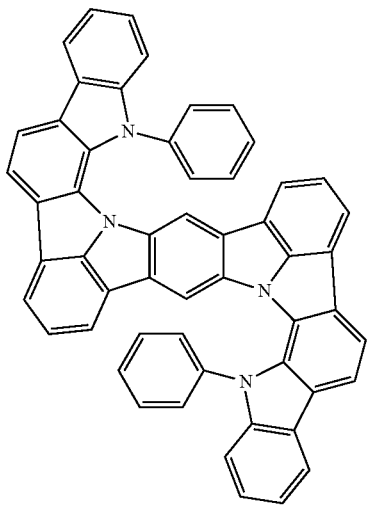
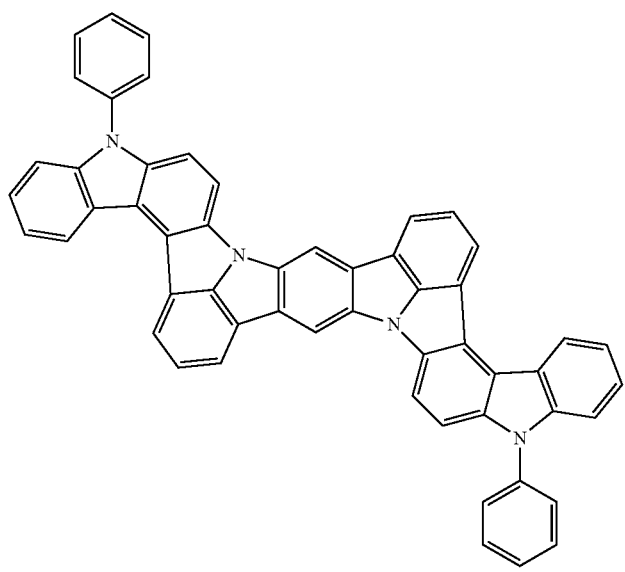

621
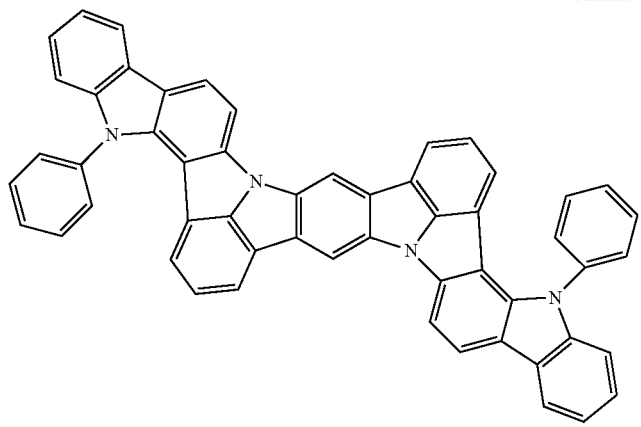
622
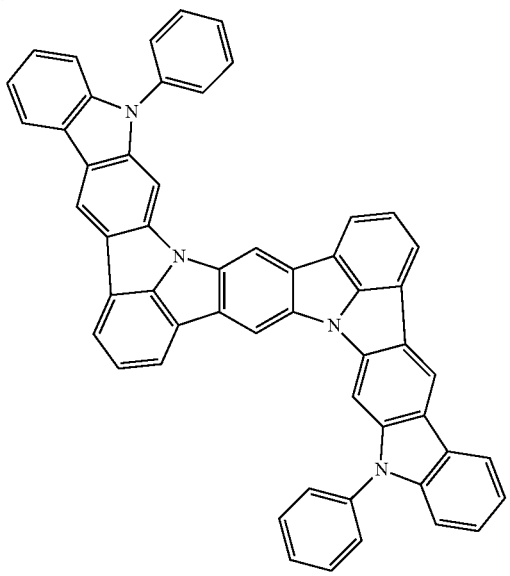
-continued
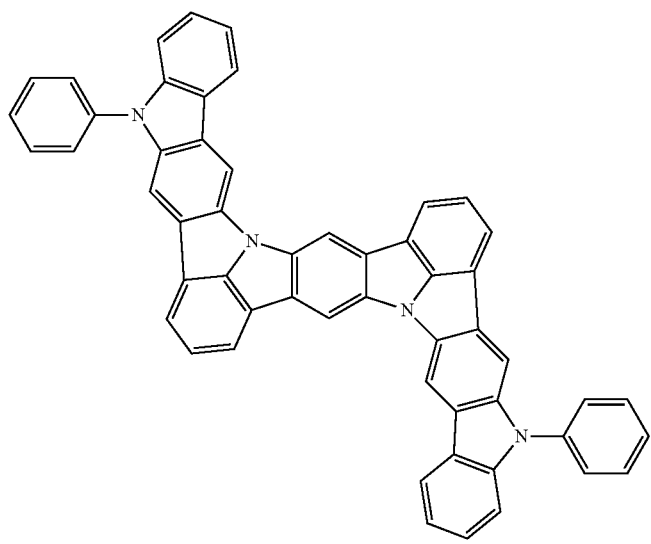
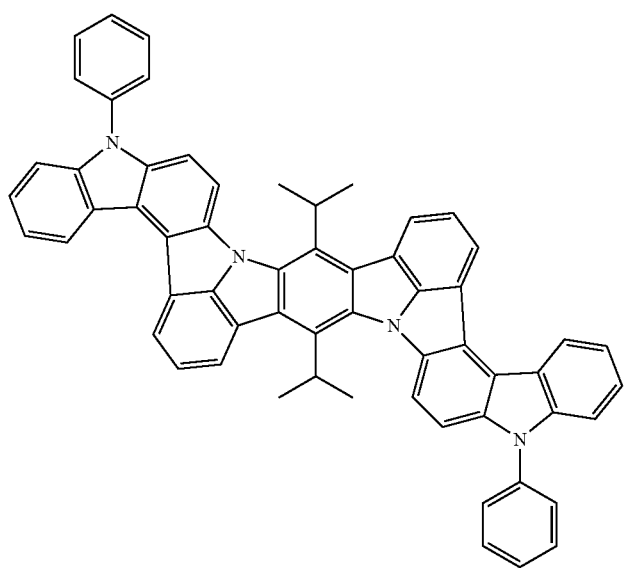

-continued
623 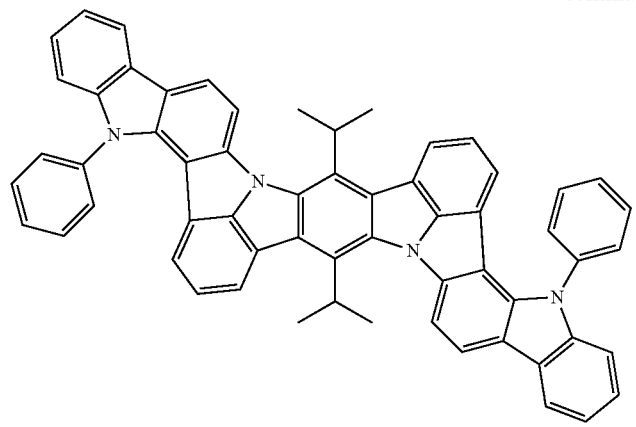
624 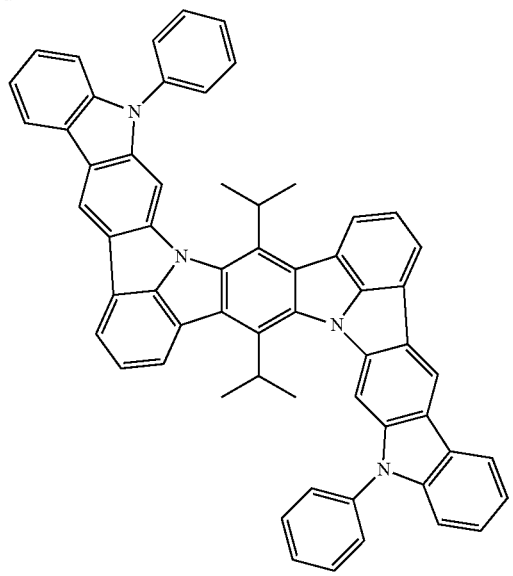
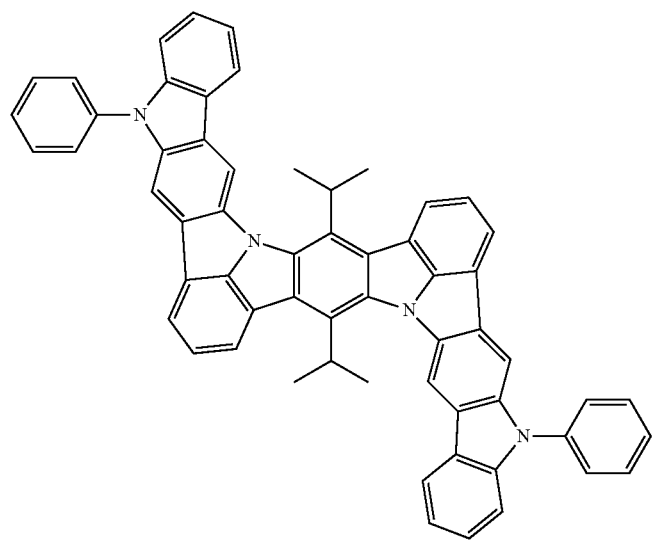
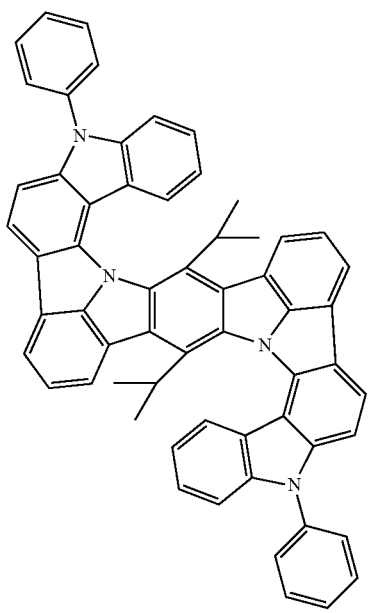

625 626
-continued
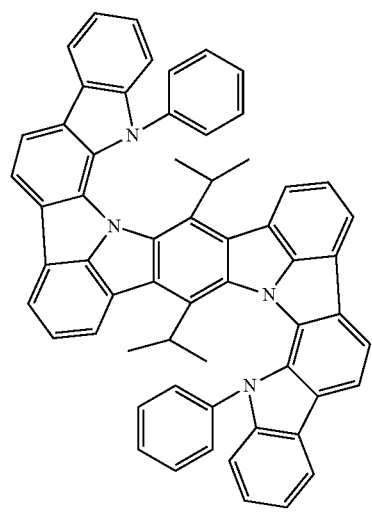 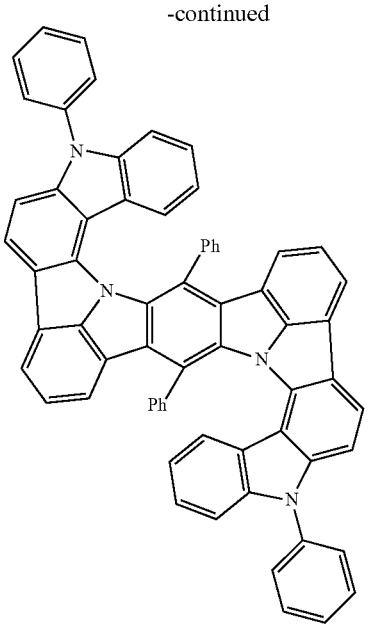 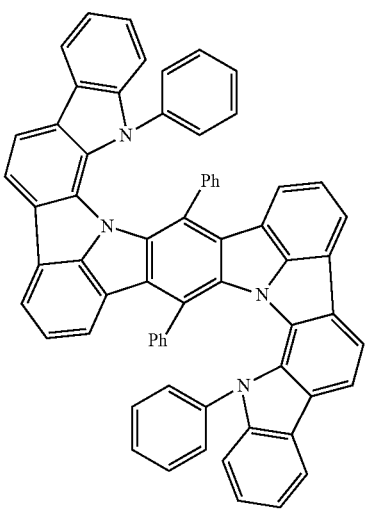
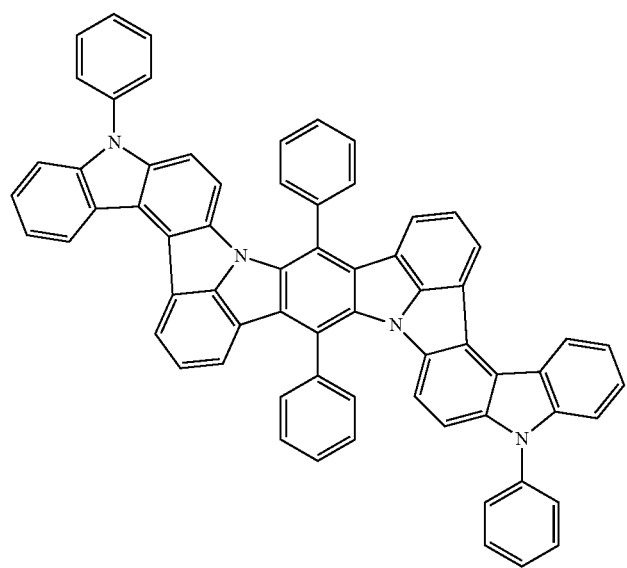

-continued
627
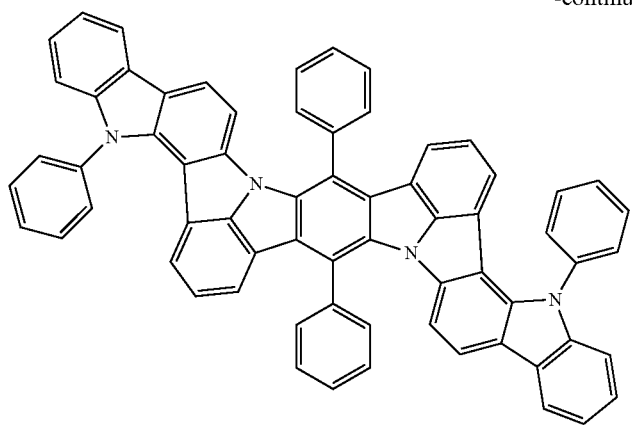
628
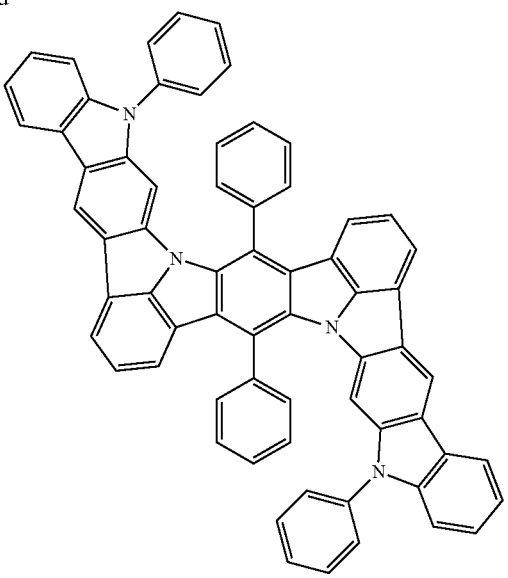
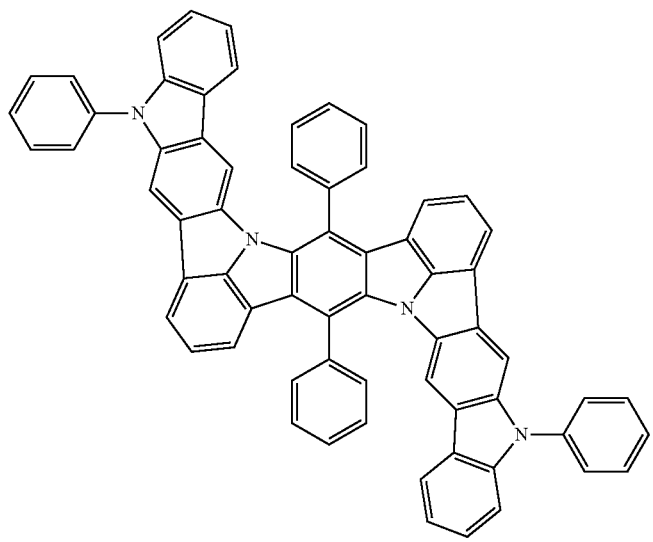
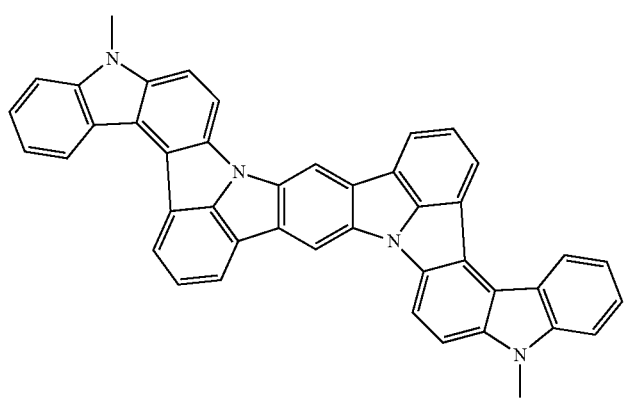

-continued
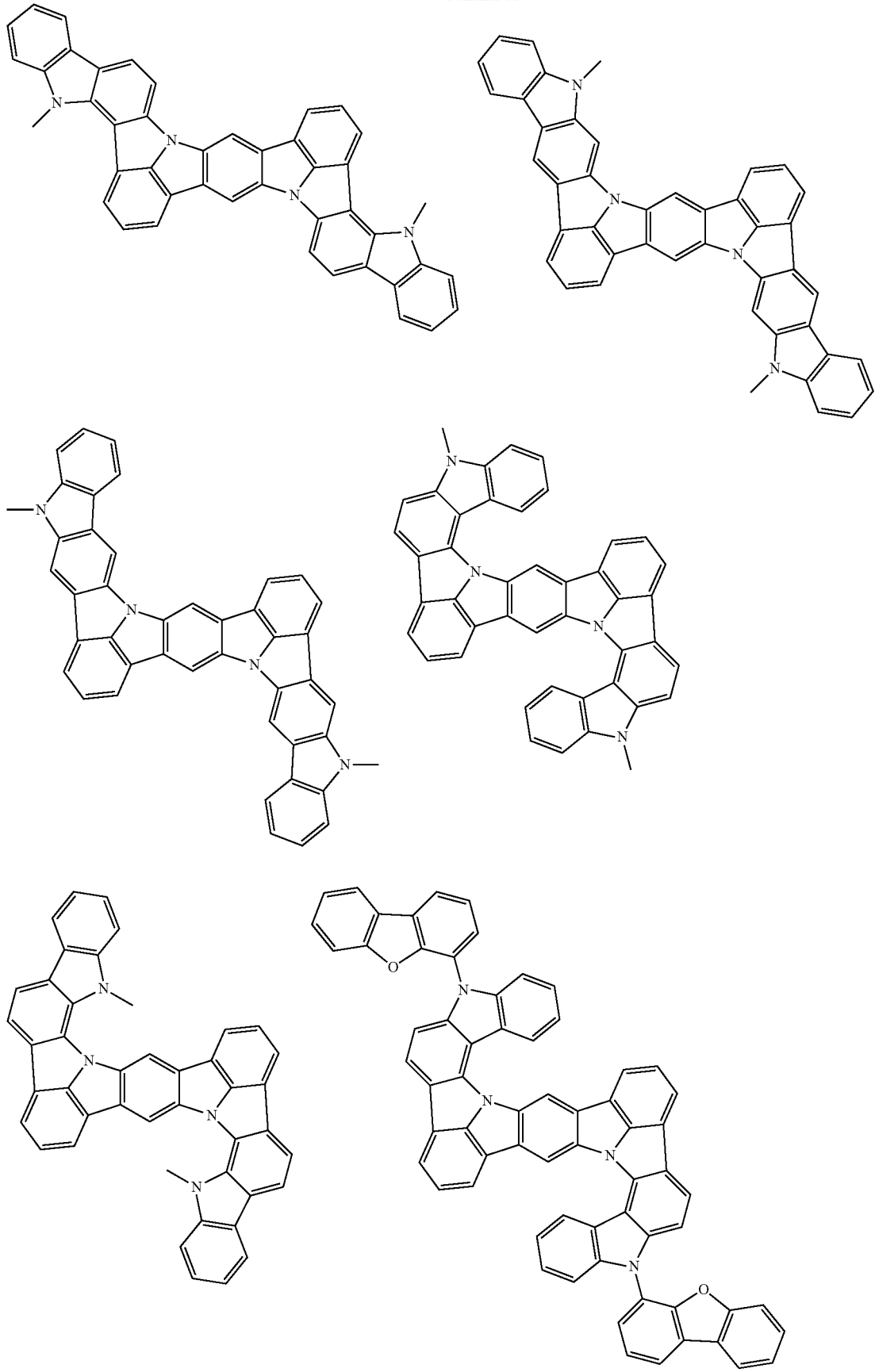

-continued
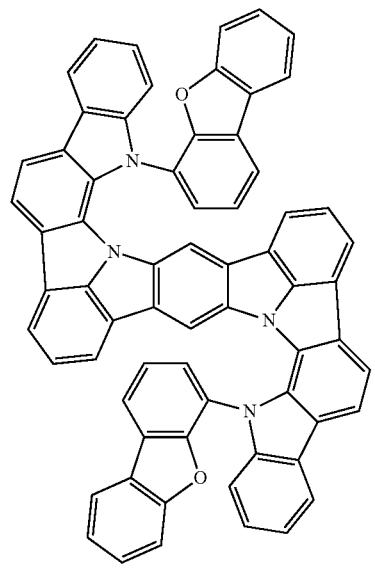
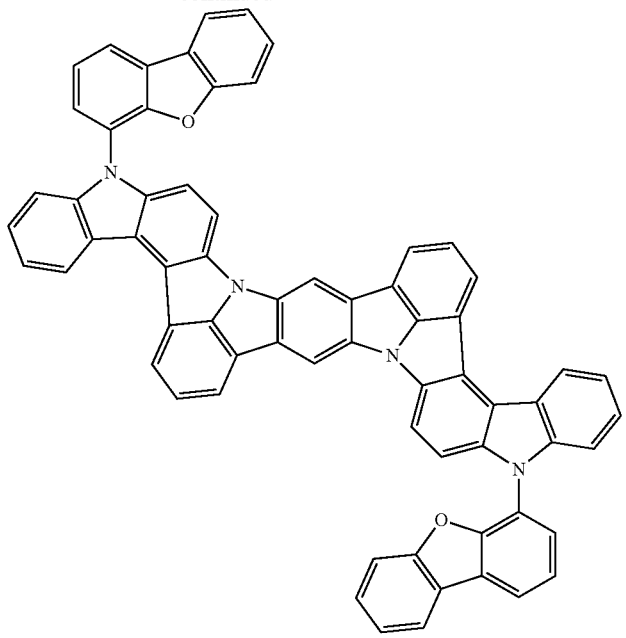
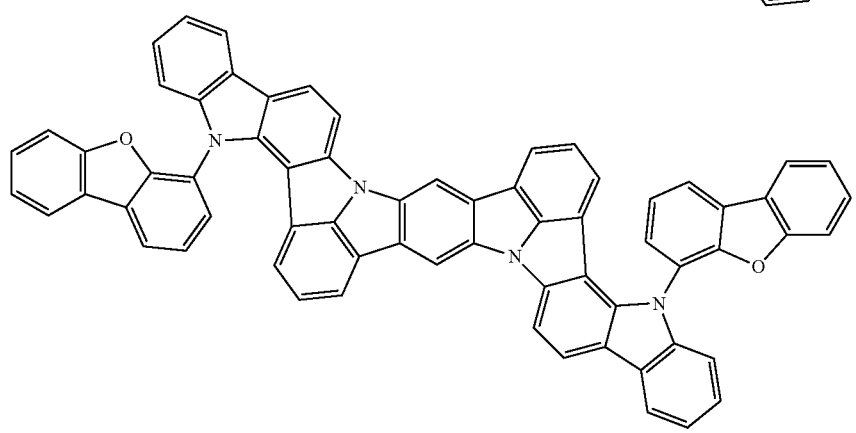
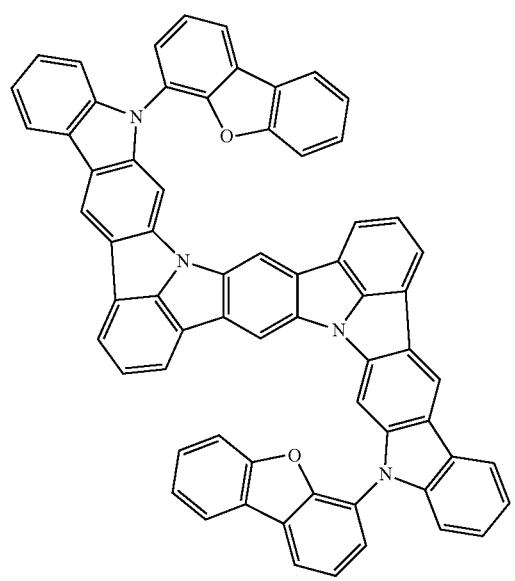

-continued
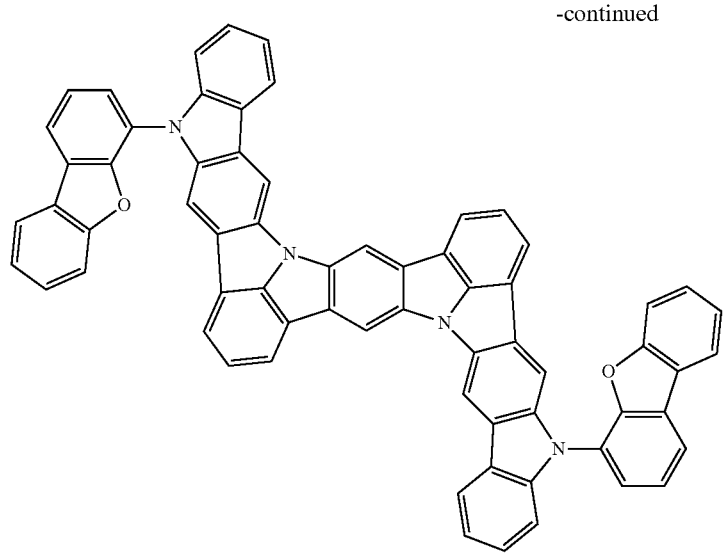
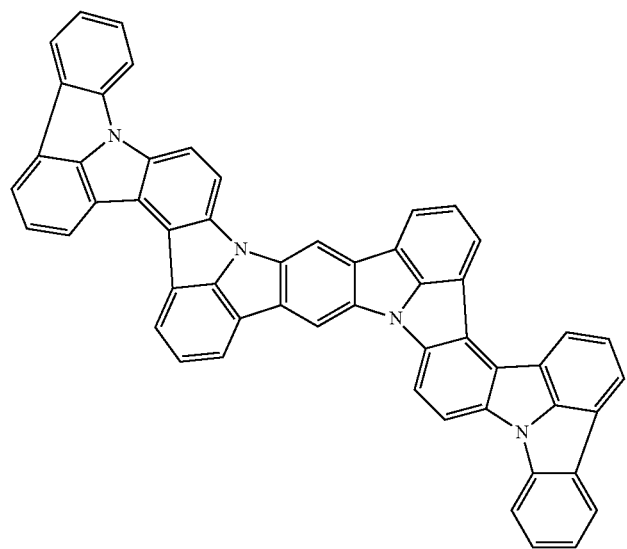
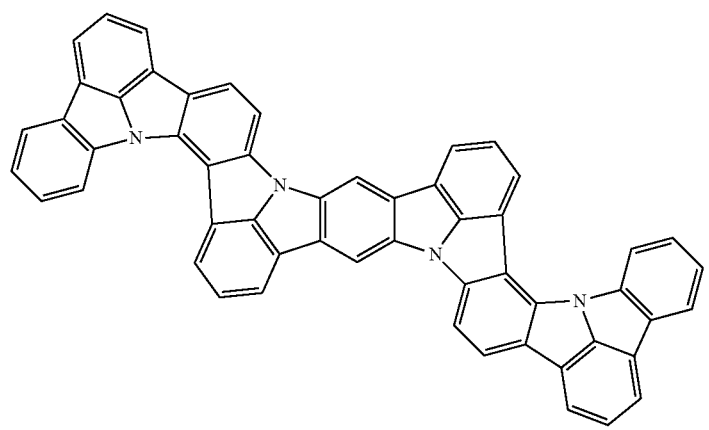

-continued
635 636
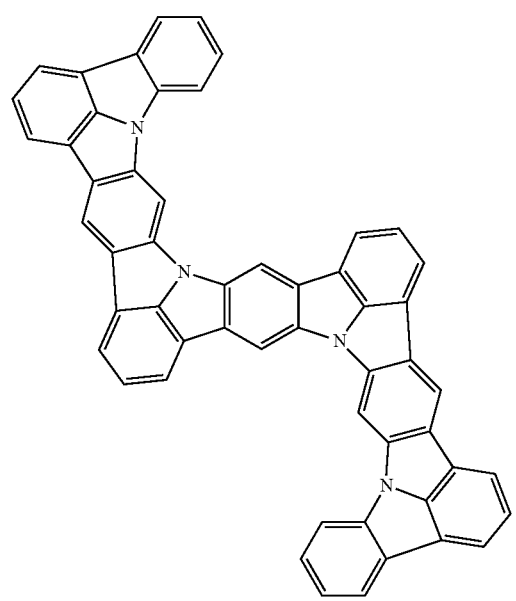 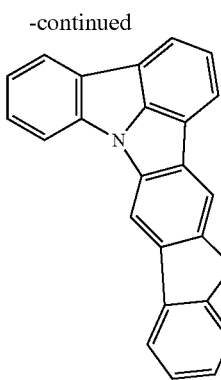
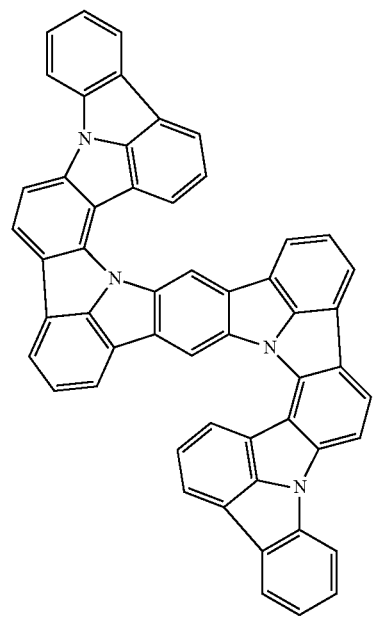 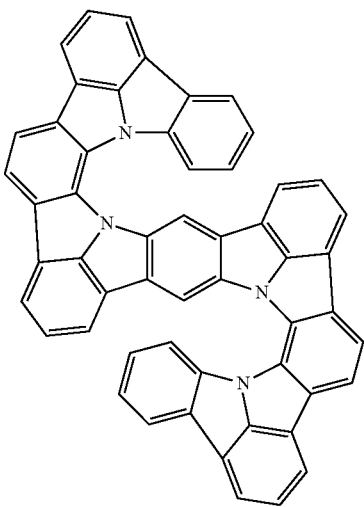
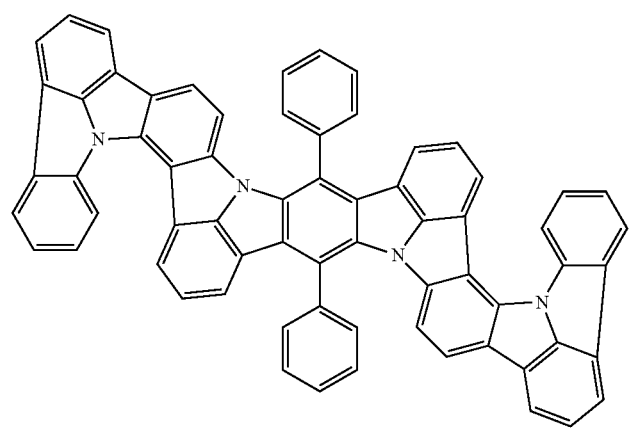

637 638
-continued
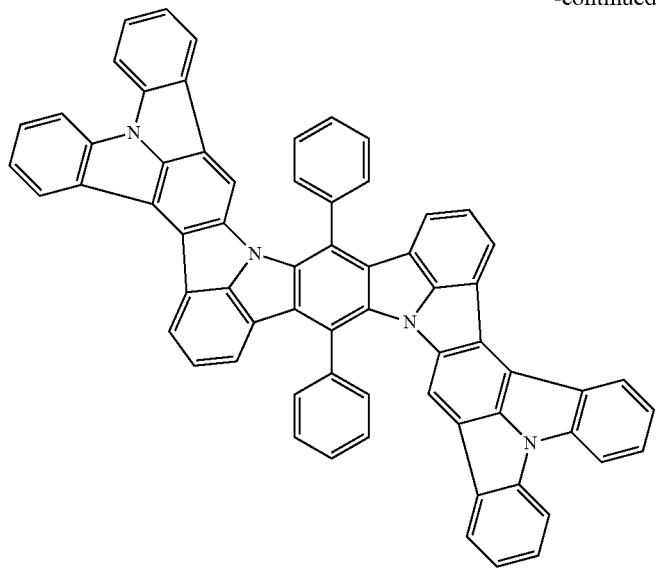
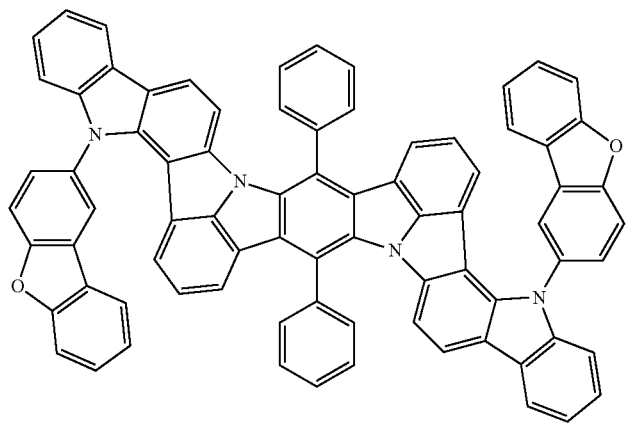
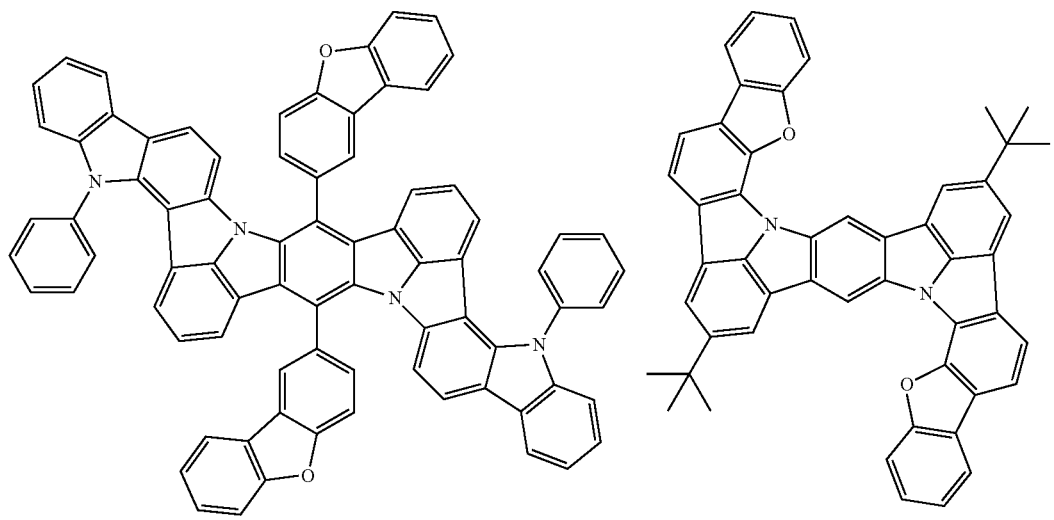

(Compound Represented by Formula (41))

The compound represented by the formula (41) is explained below.

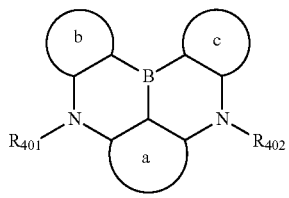
(41)

wherein, in the formula (41),
a ring, b ring and c ring are independently
a substituted or unsubstituted aromatic hydrocarbon ring having 6 to 50 ring carbon atoms, or
a substituted or unsubstituted heterocyclic ring having 5 to 50 ring atoms;
$R_{401}$ and $R_{402}$ are independently bonded to the a ring, the b ring or the c ring to form a substituted or unsubstituted heterocyclic ring or do not form a substituted or unsubstituted heterocyclic ring;
$R_{401}$ and $R_{402}$ that do not form the substituted or unsubstituted heterocyclic ring are independently
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
a substituted or unsubstituted aryl group having 6 to 50 ring carbon atoms, or
a substituted or unsubstituted monovalent heterocyclic group having 5 to 50 ring atoms;

The a ring, b ring and c ring are rings (a substituted or unsubstituted aromatic hydrocarbon ring having 6 to 50 ring carbon atoms or a substituted or unsubstituted heterocyclic ring having 5 to 50 ring atoms) fuse to the fused bicyclic structure composed of B atom and two N atoms in the center of the formula (41).

The "aromatic hydrocarbon ring" of the a ring, the b ring and the c ring has the same structure as the compound obtained by introducing a hydrogen atom into the "aryl group" described above. The "aromatic hydrocarbon ring" of the a ring contains three carbon atoms in the fused bicyclic structure in the center of the formula (41) as ring atoms. The "aromatic hydrocarbon ring" of the b ring and the c ring contain two carbon atoms in the fused bicyclic structure in the center of the formula (41) as ring atoms. As examples of "substituted or unsubstituted aromatic hydrocarbon ring having 6 to 50 ring carbon atoms", compounds in which a hydrogen atom is introduced into the "aryl group" described in the group G1 and the like can be given.

The "heterocyclic ring" of the a ring, the b ring and the c ring has the same structure as the compound obtained by introducing a hydrogen atom into the "heterocyclic group" described above. The "heterocylic ring" of the a ring contains three carbon atoms in the fused bicyclic structure in the center of the formula (41) as ring atoms. The "heterocyclic ring" of the b ring and the c ring contain two carbon atoms in the fused bicyclic structure in the center of the formula (41) as ring atoms. As examples of "substituted or unsubstituted heterocyclic ring having 5 to 50 ring atoms", compounds in which a hydrogen atom is introduced into the "heterocyclic group" described in the group G2.

$R_{401}$ and $R_{402}$ may be independently bonded to the a ring, the b ring or the c ring to form a substituted or unsubstituted heterocyclic ring. This heterocyclic ring contains the nitrogen atom in the fused bicyclic structure in the center of the formula (41). This heterocyclic ring may contain a heteroatom other than the nitrogen atom. "$R_{401}$ and $R_{402}$ are bonded to the a ring, the b ring or the c ring" means, specifically, an atom forming the a ring, the b ring or the c ring is bonded to an atom forming $R_{401}$ and $R_{402}$. For example, it is possible that $R_{401}$ is bonded to the a ring to form a nitrogen-containing heterocyclic ring having a two-ring fused structure (or three or more rings fused structure) in which a ring containing $R_{401}$ and the a ring are fused.

The same applies to the case where $R_{401}$ is bonded to the b ring, $R_{402}$ is bonded to the a ring, and $R_{402}$ is bonded to the c ring.

In one embodiment, the a ring, the b ring and the c ring in the formula (41) are independently a substituted or unsubstituted aromatic hydrocarbon ring having 6 to 50 ring carbon atoms.

In one embodiment, the a ring, the b ring and the c ring in the formula (41) are independently a substituted or unsubstituted benzene ring or a substituted or unsubstituted naphthalene ring.

In one embodiment, $R_{401}$ and $R_{402}$ in the formula (41) are independently a substituted or unsubstituted aryl group having 6 to 50 ring carbon atoms, or a substituted or unsubstituted monovalent heterocyclic group having 5 to 50 ring atoms, and preferably a substituted or unsubstituted aryl group having 6 to 50 ring carbon atoms.

In one embodiment, the compound represented by the formula (41) is a compound represented by the following formula (42).

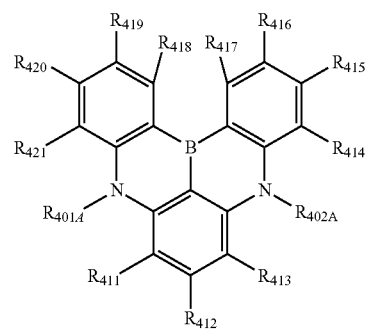
(42)

wherein in the formula (42),
$R_{401A}$ is bonded with one or more groups selected from $R_{411}$ or $R_{421}$ to form a substituted or unsubstituted heterocyclic ring, or does not form a substituted or unsubstituted heterocyclic ring; $R_{402A}$ is bonded with one or more group selected from $R_{413}$ or $R_{414}$ to form a substituted or unsubstituted heterocyclic ring, or does not form a substituted or unsubstituted heterocyclic ring;
$R_{401A}$ and $R_{402A}$ that do not form a substituted or unsubstituted heterocyclic ring are independently
a substituted or unsubstituted alkyl group having 1 to 50 carbon atoms, a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
a substituted or unsubstituted aryl group having 6 to 50 ring carbon atoms, or
a substituted or unsubstituted monovalent heterocyclic group having 5 to 50 ring atoms;

One or more pairs of two or more adjacent groups of $R_{411}$ to $R_{421}$ are bonded with each other to form a substituted or unsubstituted, saturated or unsaturated ring, or do not form a substituted or unsubstituted, saturated or unsaturated ring;

$R_{411}$ to $R_{421}$ that do not form the substituted or unsubstituted heterocyclic ring or the substituted or unsubstituted, saturated or unsaturated ring are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms; and $R_{901}$ to $R_{907}$ are as defined in the formula (1).

$R_{401A}$ and $R_{402A}$ in the formula (42) correspond to $R_{401}$ and $R_{402}$ in the formula (41).

$R_{401A}$ and $R_{411}$ may be bonded with each other to form a nitrogen-containing heterocyclic ring having two-ring fused structure (or three or more rings fused structure) which is a fused ring of a ring containing $R_{401A}$ and $R_{411}$ and the benzene ring of the a ring, for example. As examples of the nitrogen-containing heterocyclic ring, compounds correspond to nitrogen-containing heterocyclic group having two or more ring fused structure in the group G2 can be given. The same applies to the cases where $R_{401A}$ and $R_{412}$ are bonded, $R_{402A}$ and $R_{413}$ are bonded, and $R_{402A}$ and $R_{414}$ are bonded.

One or more pairs of two or more adjacent groups of $R_{411}$ to $R_{421}$ are bonded with each other to form a substituted or unsubstituted, saturated or unsaturated ring. For example, $R_{411}$ and $R_{412}$ are bonded to form a benzene ring, an indole ring, a pyrrole ring, a benzofuran ring, a benzothiophene ring or the like which fuses to the six-membered ring to which $R_{411}$ and $R_{412}$ bond, and the formed fused ring is a naphthalene ring, a carbazole ring, an indole ring, a dibenzofuran ring or a dibenzothiophene ring.

In one embodiment, $R_{411}$ to $R_{421}$ that do not contribute to form a ring are independently a hydrogen atom, a substituted or unsubstituted alkyl group having 1 to 50 carbon atoms, a substituted or unsubstituted aryl group having 6 to 50 ring carbon atoms, or a substituted or unsubstituted monovalent heterocyclic group having 5 to 50 ring atoms.

In one embodiment, $R_{411}$ to $R_{421}$ that do not contribute to form a ring are independently a hydrogen atom, a substituted or unsubstituted aryl group having 6 to 50 ring carbon atoms, or a substituted or unsubstituted monovalent heterocyclic group having 5 to 50 ring atoms.

In one embodiment, $R_{411}$ to $R_{421}$ that do not contribute to form a ring are independently a hydrogen atom or a substituted or unsubstituted alkyl group having 1 to 50 carbon atoms.

In one embodiment, $R_{411}$ to $R_{421}$ that do not contribute to form a ring are independently a hydrogen atom, a substituted or unsubstituted alkyl group having 1 to 50 carbon atoms, and at least one of $R_{411}$ to $R_{421}$ is a substituted or unsubstituted alkyl group having 1 to 50 carbon atoms.

In one embodiment, the compound represented by the formula (42) is a compound represented by the following formula (43).

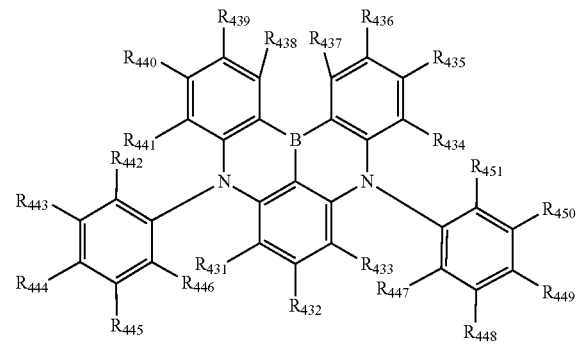

(43)

wherein in the formula (43),
$R_{431}$ is bonded with $R_{446}$ to form a substituted or unsubstituted heterocyclic ring, or does not form a substituted or unsubstituted heterocyclic ring; $R_{433}$ is bonded with $R_{447}$ to form a substituted or unsubstituted heterocyclic ring, or does not form a substituted or unsubstituted heterocyclic ring; $R_{434}$ is bonded with $R_{451}$ to form a substituted or unsubstituted heterocyclic ring, or does not form a substituted or unsubstituted heterocyclic ring; $R_{441}$ is bonded with $R_{442}$ to form a substituted or unsubstituted heterocyclic ring, or does not form a substituted or unsubstituted heterocyclic ring;

One or more pairs of two or more adjacent groups of $R_{431}$ to $R_{451}$ are bonded with each other to form a substituted or unsubstituted, saturated or unsaturated ring, or do not form a substituted or unsubstituted, saturated or unsaturated ring;

$R_{431}$ to $R_{451}$ that do not form a substituted or unsubstituted heterocyclic ring are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or a substituted or unsubstituted monovalent heterocyclic group having 5 to 50 ring atoms; and $R_{901}$ to $R_{907}$ are as defined in the formula (1).

$R_{431}$ may bond to $R_{446}$ to form a substituted or unsubstituted heterocyclic ring. For example, $R_{431}$ may bonds with $R_{446}$ to form a nitrogen-containing heterocyclic ring with three or more fused rings of the benzene ring to which $R_{46}$ bond, a nitrogen-containing ring and the benzene ring of the a ring. As examples of the nitrogen-containing heterocyclic ring, compounds correspond to nitrogen-containing heterocyclic group having three or more ring fused structure in the group G2 can be given. The same applies to the cases where $R_{433}$ and $R_{447}$ are bonded, $R_{434}$ and $R_{451}$ are bonded, and $R_{441}$ and $R_{442}$ are bonded.

In one embodiment, $R_{431}$ to R451 that do not contribute to form a ring are independently, a hydrogen atom, a substituted or unsubstituted alkyl group having 1 to 50 carbon atoms, a substituted or unsubstituted aryl group having 6 to 50 carbon atoms, or a substituted or unsubstituted monovalent heterocyclic group having 5 to 50 ring atoms.

In one embodiment, $R_{431}$ to R451 that do not contribute to form a ring are independently, a hydrogen atom, a substituted or unsubstituted aryl group having 6 to 50 carbon atoms, or a substituted or unsubstituted monovalent heterocyclic group having 5 to 50 ring atoms.

In one embodiment, $R_{431}$ to R451 that do not contribute to form a ring are independently a hydrogen atom or a substituted or unsubstituted alkyl group having 1 to 50 carbon atoms.

In one embodiment, $R_{431}$ to R451 that do not contribute to form a ring are independently a hydrogen atom, a substituted or unsubstituted alkyl group having 1 to 50 carbon atoms, and at least one of $R_{431}$ to R451 is a substituted or unsubstituted alkyl group having 1 to 50 carbon atoms.

In one embodiment, the compound represented by the formula (43) is a compound represented by the following formula (43A).

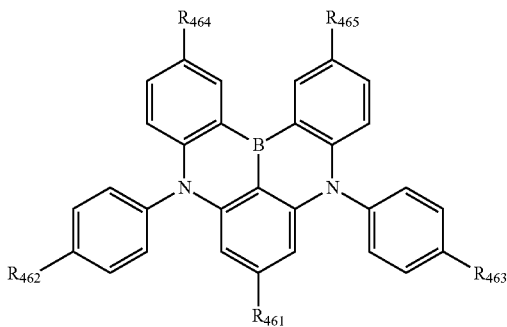

(43A)

wherein in the formula (43A), $R_{461}$ is a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, or a substituted or unsubstituted aryl group having 6 to 50 ring carbon atoms; and $R_{462}$ to R465 are independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, or a substituted or unsubstituted aryl group having 6 to 50 ring carbon atoms.

In one embodiment, $R_{461}$ to R465 are independently a substituted or unsubstituted alkyl group having 1 to 50 carbon atoms or a substituted or unsubstituted aryl group having 6 to 50 ring carbon atoms.

In one embodiment, $R_{461}$ and R465 are independently a substituted or unsubstituted alkyl group having 1 to 50 carbon atoms.

In one embodiment, the compound represented by the formula (43) is a compound represented by the following formula (43B).

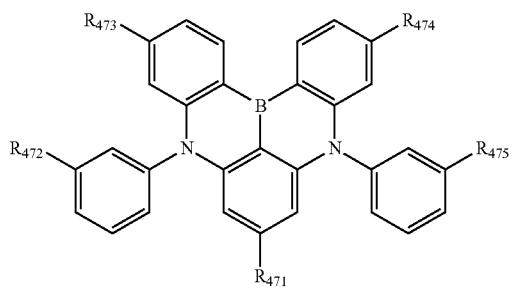

(43B)

wherein in the formula (43 B), $R_{471}$ and $R_{472}$ are independently, a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —N($R_{906}$)($R_{907}$), or a substituted or unsubstituted aryl group having 6 to 50 ring carbon atoms;

$R_{473}$ to $R_{475}$ are independently, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —N($R_{906}$)($R_{907}$), or a substituted or unsubstituted aryl group having 6 to 50 ring carbon atoms; and $R_{906}$ and $R_{907}$ are as defined in the formula (1).

In one embodiment, the compound represented by the formula (43) is the compound represented by the following formula (43B').

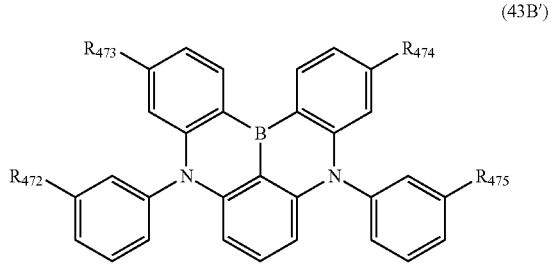

(43B')

wherein in the formula (43B'), $R_{472}$ to $R_{475}$ are as defined in the formula (43 B).

In one embodiment, at least one of $R_{471}$ to $R_{475}$ is
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—N($R_{906}$)($R_{907}$), or
a substituted or unsubstituted aryl group having 6 to 50 ring carbon atoms.

In one embodiment,
$R_{472}$ is
a hydrogen atom,
a substituted or unsubstituted alkyl group having 1 to 50 carbon atoms,
—N($R_{906}$)($R_{907}$), or
a substituted or unsubstituted aryl group having 6 to 50 ring carbon atoms; and
$R_{471}$ and $R_{473}$ to $R_{475}$ are independently
a substituted or unsubstituted alkyl group having 1 to 50 carbon atoms,
—N($R_{906}$)($R_{907}$), or
a substituted or unsubstituted aryl group having 6 to 50 ring carbon atoms.

In one embodiment, the compound represented by the formula (43) is a compound represented by the formula (43C).

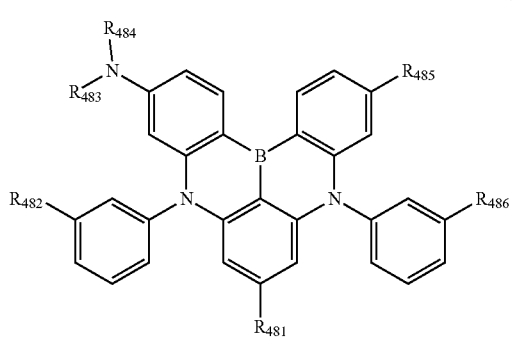

(43C)

wherein in the formula (43C), $R_{481}$ and $R_{482}$ are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms, or
a substituted or unsubstituted aryl group having 6 to 50 ring carbon atoms; and $R_{843}$ to $R_{486}$ are independently
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms, or
a substituted or unsubstituted aryl group having 6 to 50 ring carbon atoms.

In one embodiment, the compound represented by the formula (43) is the compound represented by the following formula (43C').

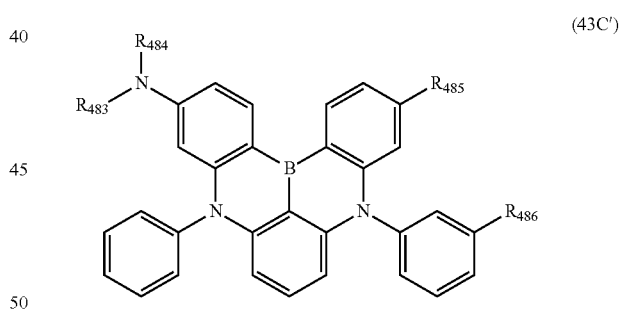

(43C')

wherein in the formula (43C'), $R_{483}$ to $R_{486}$ are as defined in the formula (43C).

In one embodiment, $R_{481}$ to $R_{486}$ are independently a substituted or unsubstituted alkyl group having 1 to 50 carbon atoms or a substituted or unsubstituted aryl group having 6 to 50 ring carbon atoms.

In one embodiment, $R_{481}$ to $R_{486}$ are independently a substituted or unsubstituted aryl group having 6 to 50 ring carbon atoms.

In one embodiment, the compound represented by the formula (43) is the compound represented by the following formula (43D).

(43D)

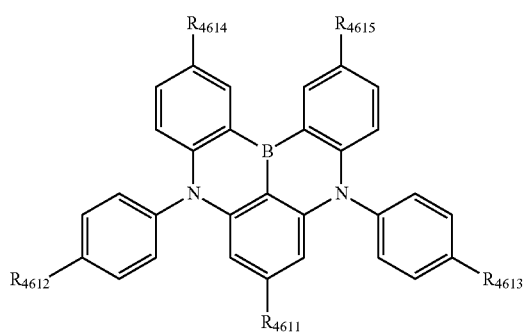

wherein in the formula (43D),

R$_{4611}$ is a hydrogen atom, an unsubstituted alkyl group including 1 to 6 carbon atoms, an unsubstituted cycloalkyl group including 3 to 10 ring carbon atoms, —Si(R$_{911}$)(R$_{912}$)(R$_{913}$), or —N(R$_{914}$)(R$_{915}$);

R$_{4612}$ to R$_{4615}$ are independently an unsubstituted alkyl group including 1 to 6 carbon atoms, an unsubstituted cycloalkyl group including 3 to 10 ring carbon atoms, or —Si(R$_{911}$)(R$_{912}$)(R$_{913}$);

R$_{911}$ to R$_{913}$ are independently an unsubstituted alkyl group including 1 to 6 carbon atoms or an unsubstituted aryl group including 6 to 18 ring carbon atoms;

R$_{914}$ to R$_{915}$ are independently an unsubstituted aryl group including 6 to 18 ring carbon atoms.

In one embodiment, in the formula (43D), R$_{4611}$ is a hydrogen atom, an unsubstituted alkyl group including 1 to 6 carbon atoms, or —N(R$_{914}$)(R$_{915}$).

In one embodiment, in the formula (43D), R$_{4612}$ to R$_{4615}$ are independently an unsubstituted alkyl group including 1 to 6 carbon atoms, or an unsubstituted cycloalkyl group including 3 to 10 ring carbon atoms.

In one embodiment, in the formula (43D), R$_{4611}$ is —N(R$_{914}$)(R$_{915}$), and R$_{4612}$ to R$_{4615}$ are independently an unsubstituted alkyl group including 1 to 6 carbon atoms.

In one embodiment, in the formula (43D), R$_{4611}$ is an unsubstituted alkyl group including 1 to 6 carbon atoms, and R$_{4612}$ to R$_{4615}$ are independently an unsubstituted alkyl group including 1 to 6 carbon atoms.

In one embodiment, in the formula (43D), R$_{4611}$ is a hydrogen atom, and R$_{4612}$ to R$_{4615}$ are independently an unsubstituted alkyl group including 1 to 6 carbon atoms, or an unsubstituted cycloalkyl group including 3 to 10 ring carbon atoms.

In one embodiment, in the formula (43D), at least one of the hydrogen atoms included in one or more selected from the group consisting of R$_{914}$ and R$_{915}$ is a deuterium atom.

The compound represented by the formula (41) can be synthesized by the following method: An intermediate is obtained by bonding the a ring, the b ring and the c ring with linking groups (a group containing N—R$_1$ and a group containing N—R$_2$) (first reaction), and a final compound is obtained by bonding the a ring, the b ring and the c ring with a linking group (a group containing B) (second reaction). In the first reaction, an amination reaction such as Buchwald-Hartwig reaction can be applied. In the second reaction, tandem hetero-Friedel-Crafts reaction or the like can be applied.

Examples of the compound represented by the formula (41) are described below. They are just exemplified compounds and the compound represented by the formula (41) is not limited to the following examples. In the following example compounds, Me represents methyl group, and tBu represents tert-butyl group.

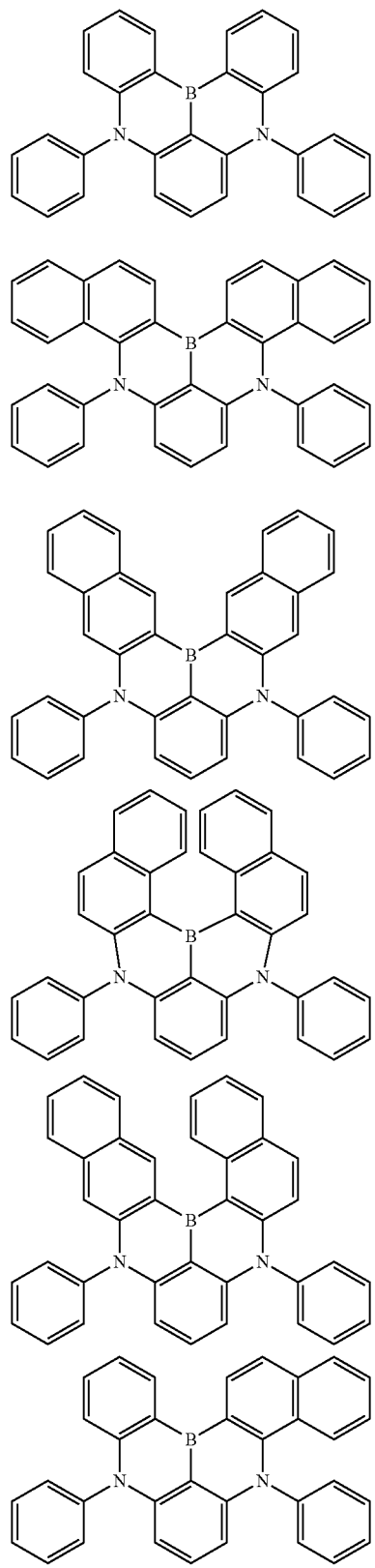

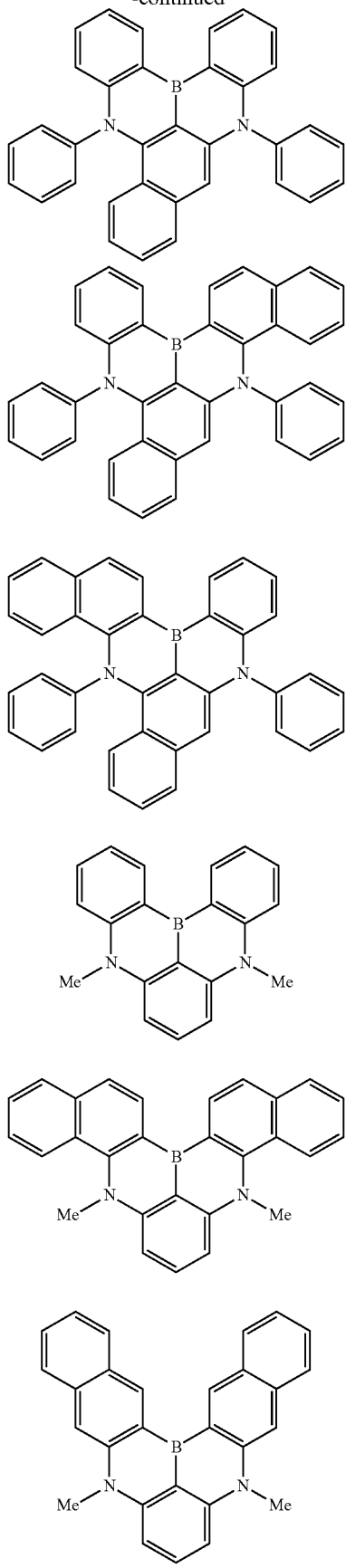
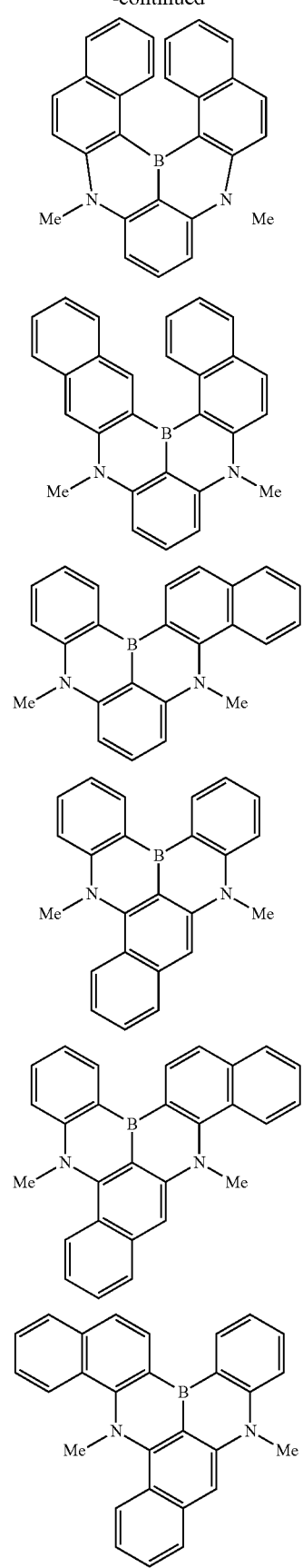

651
-continued
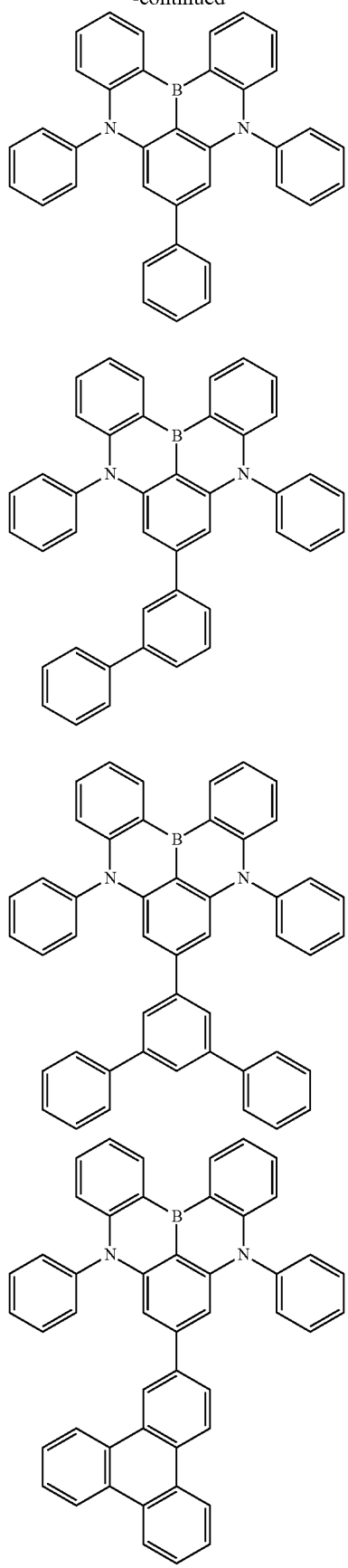
652
-continued
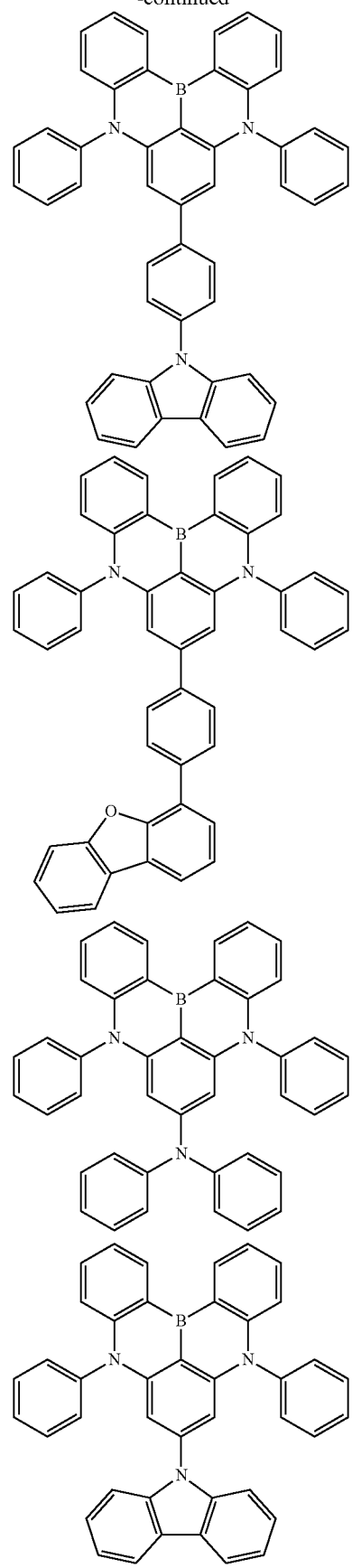

653
-continued
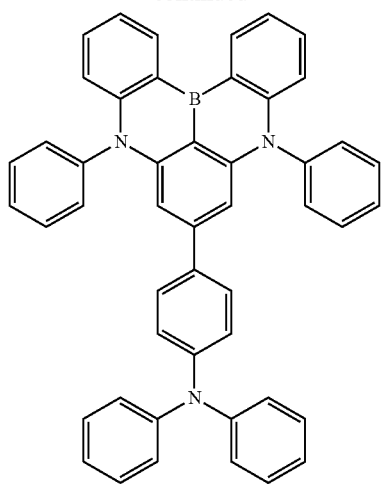
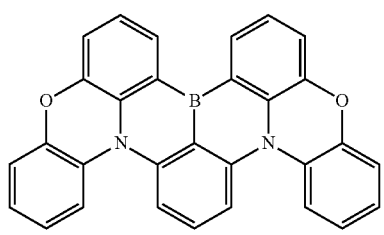
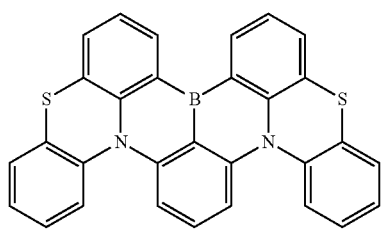
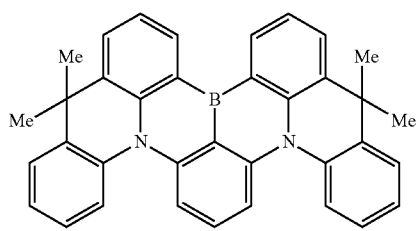
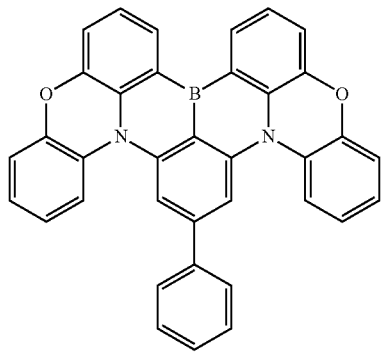
654
-continued
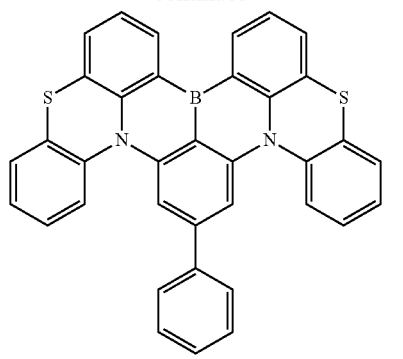
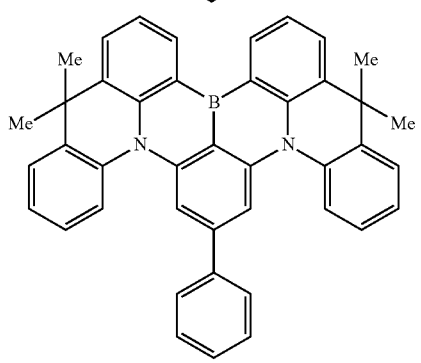
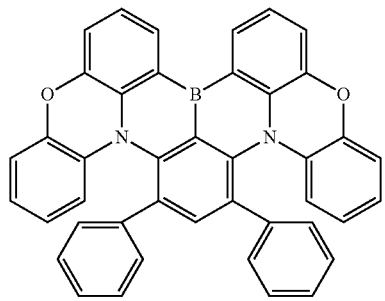
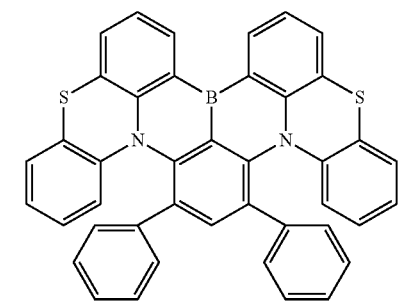
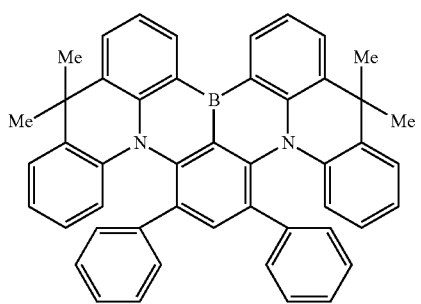

655
-continued
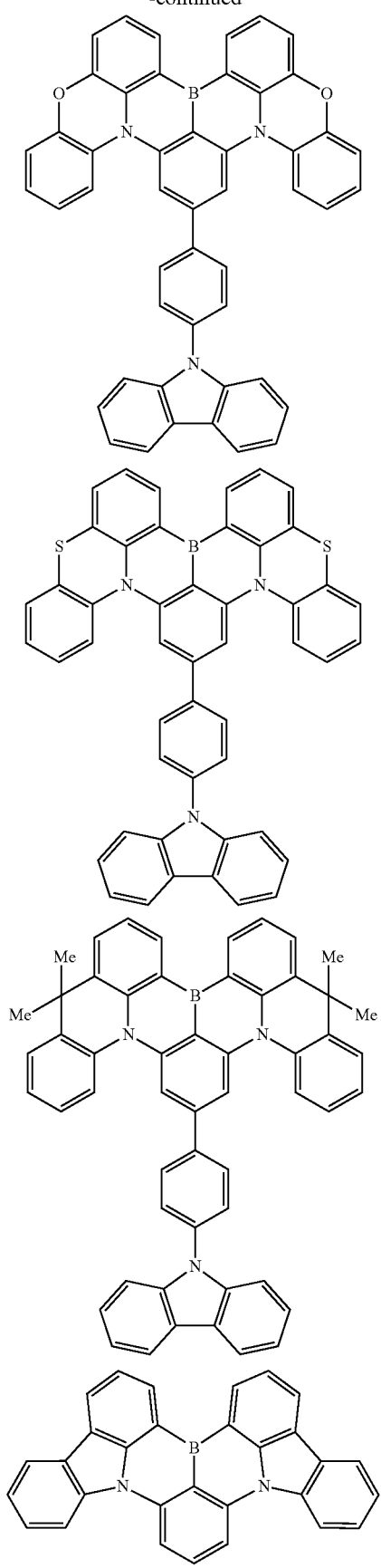
656
-continued
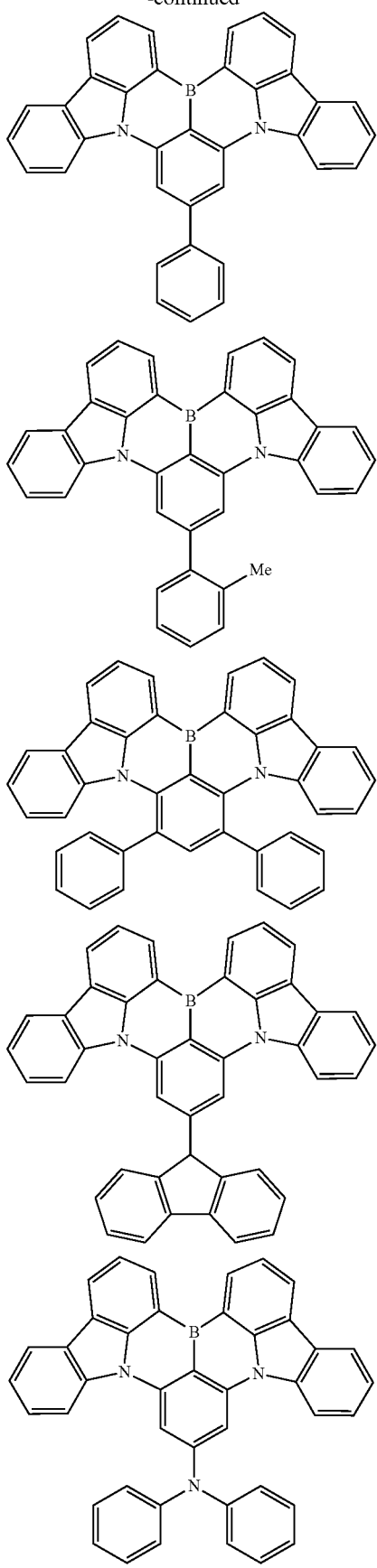

657
-continued
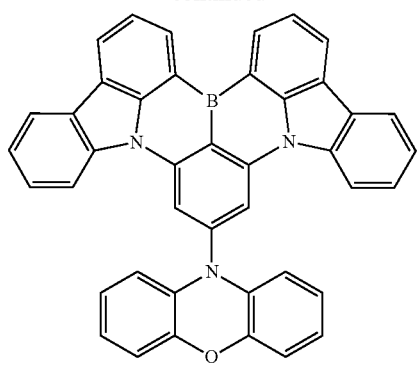
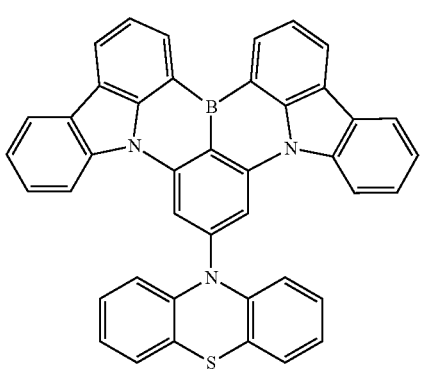
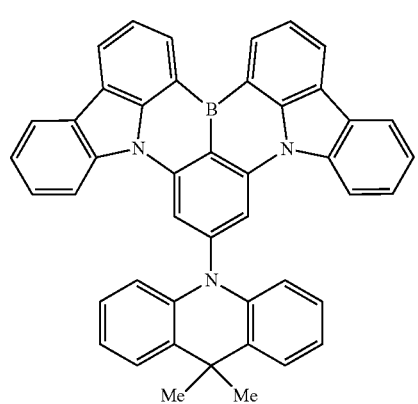
658
-continued
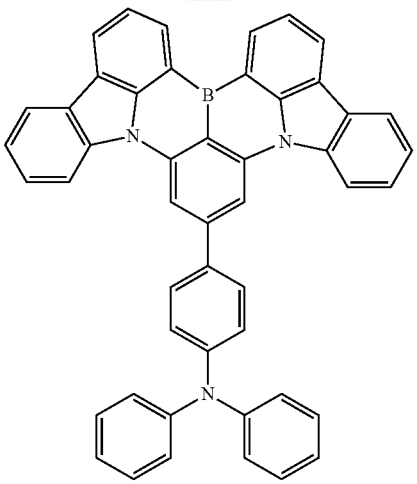
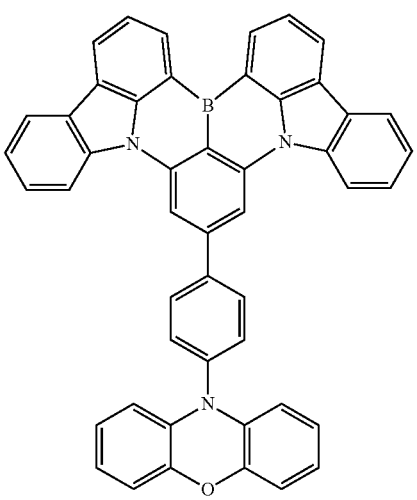
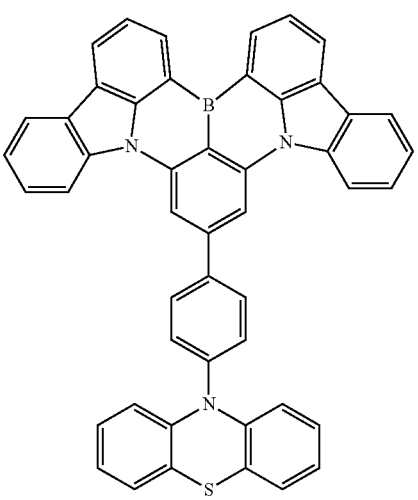

659
-continued
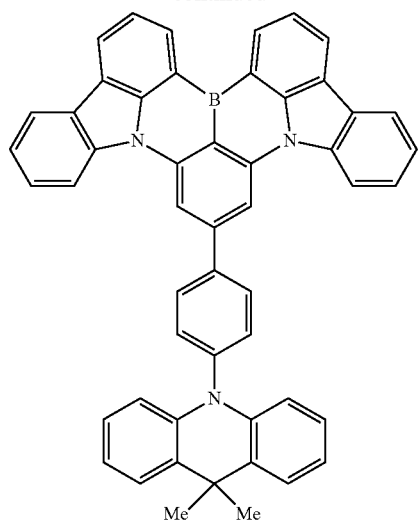
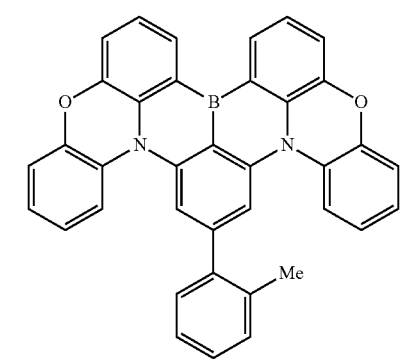
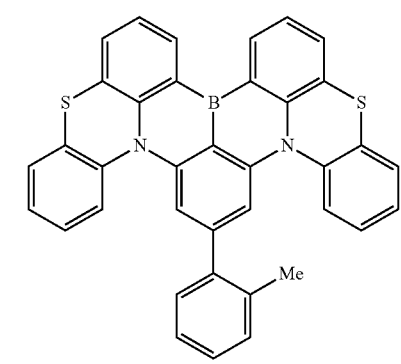
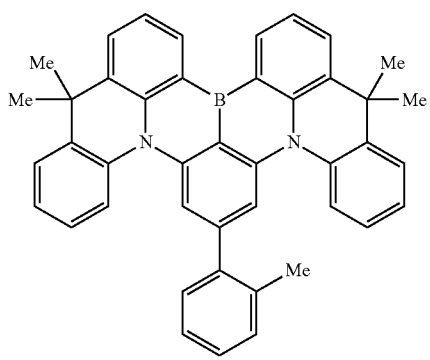
660
-continued
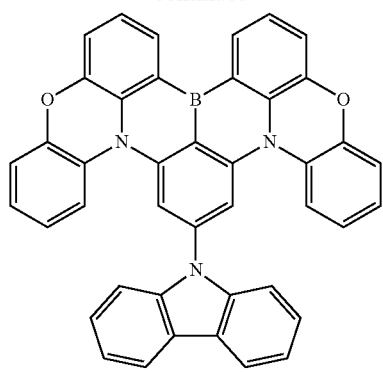
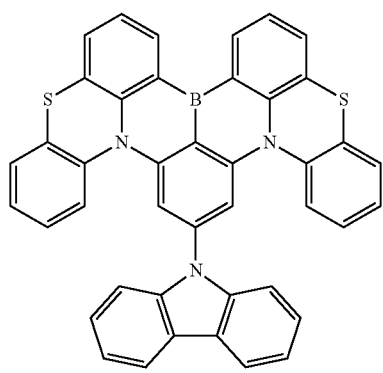
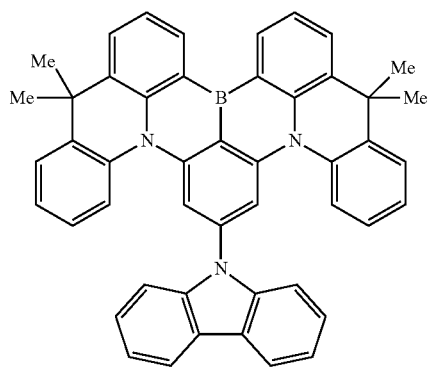
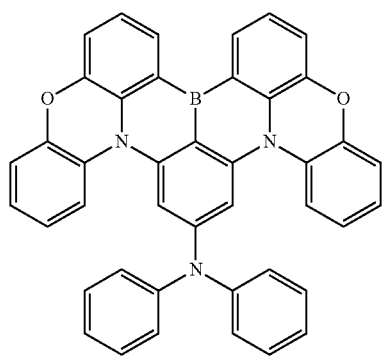

661
-continued
662
-continued
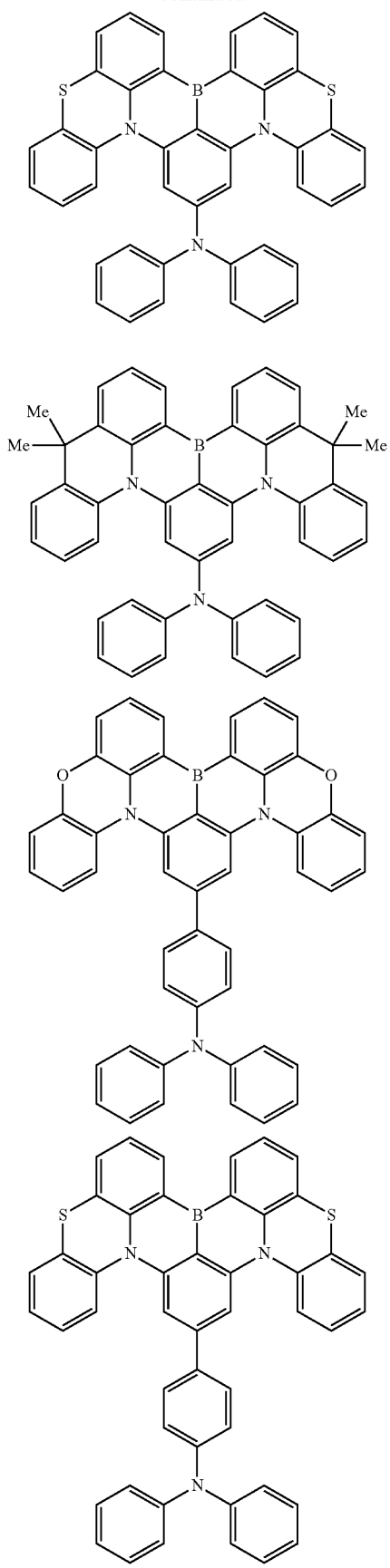
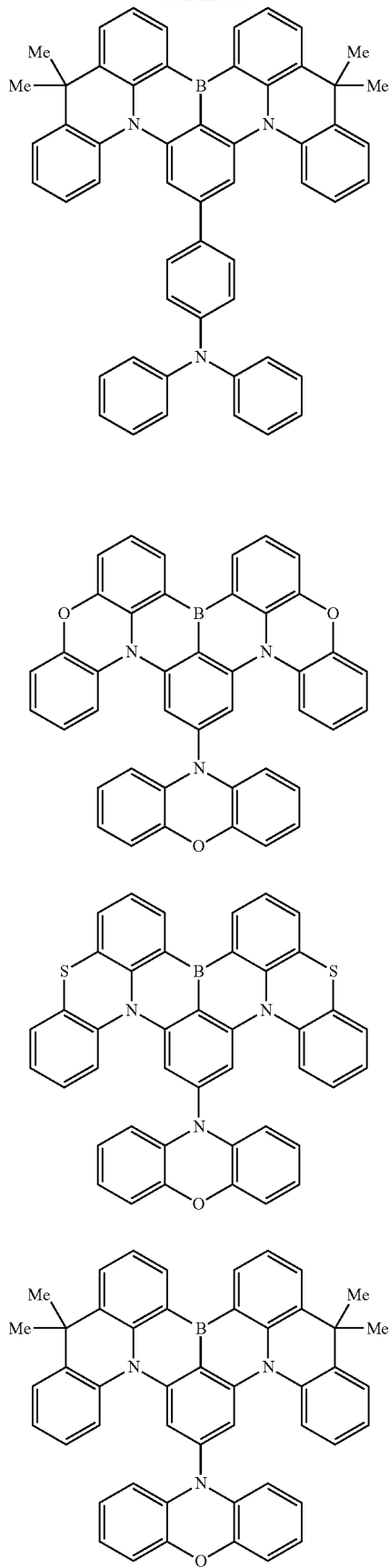

663
-continued
664
-continued
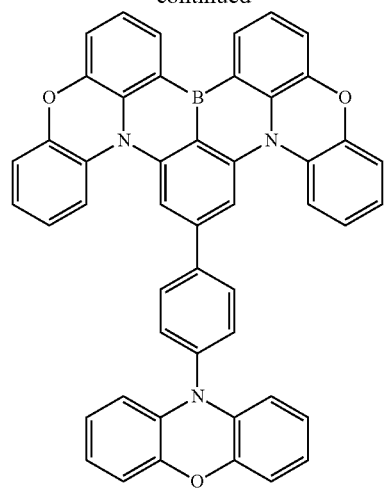
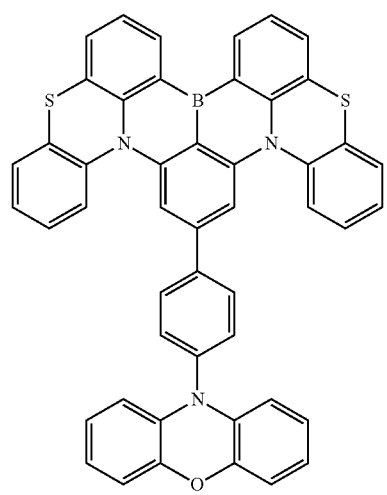
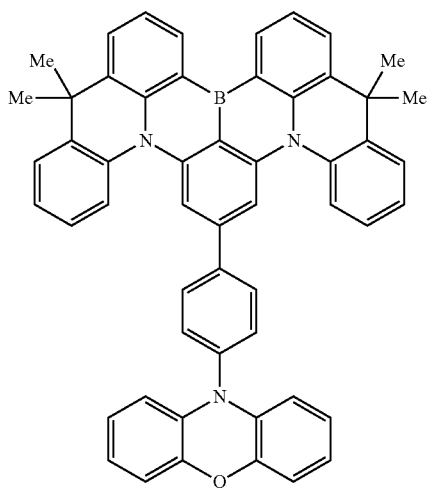
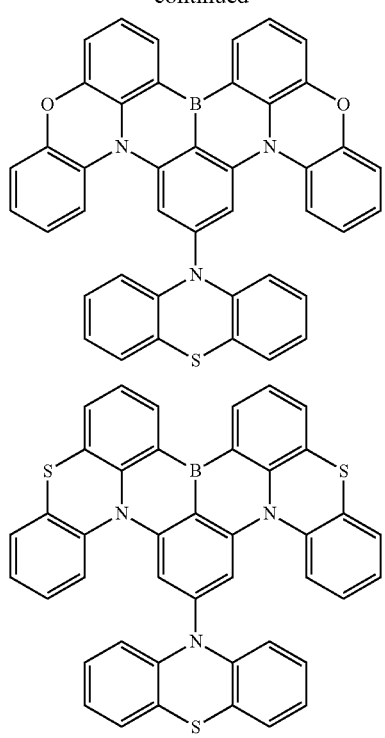
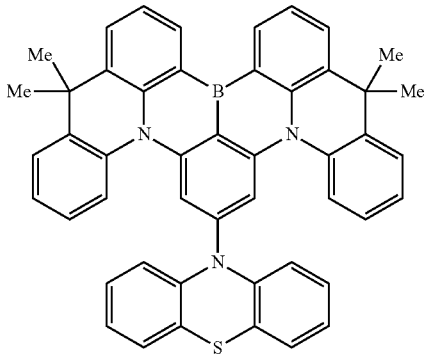
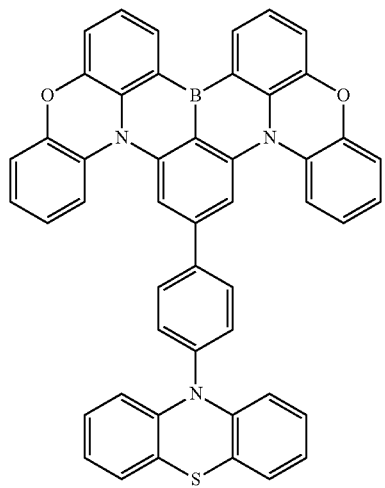

665
-continued
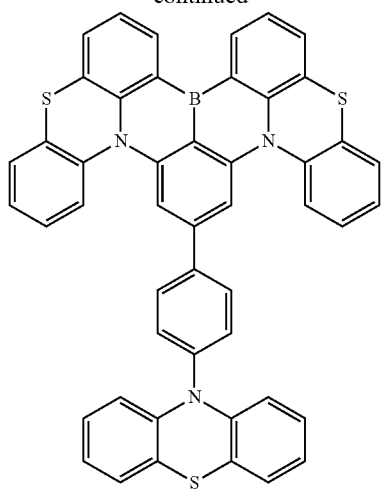
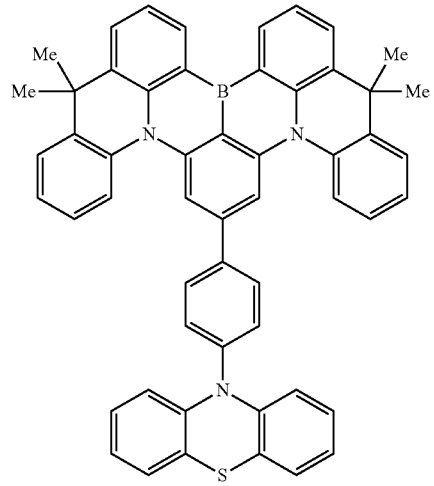
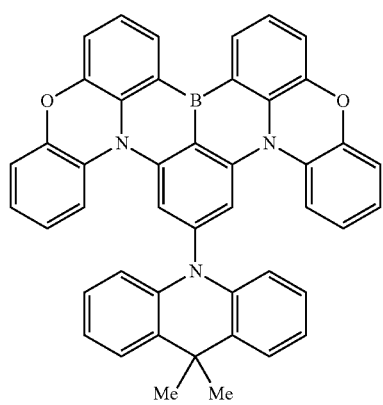
666
-continued
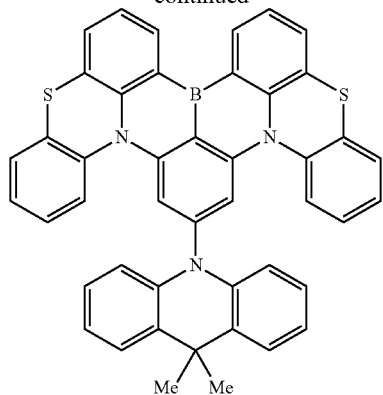
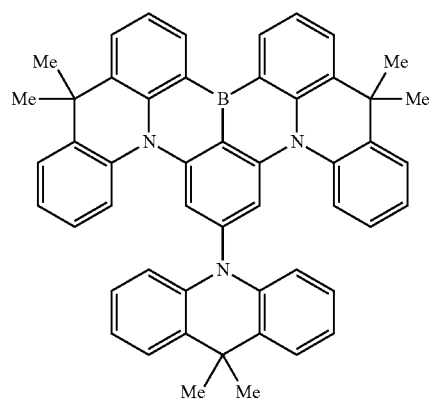
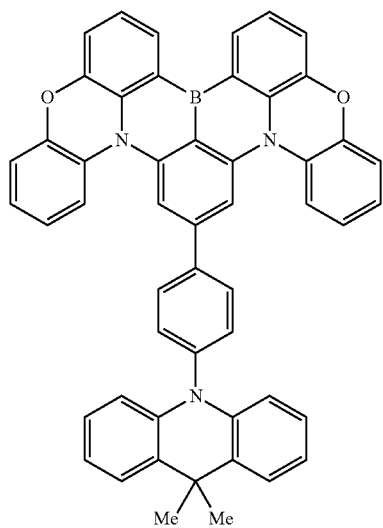

667
-continued
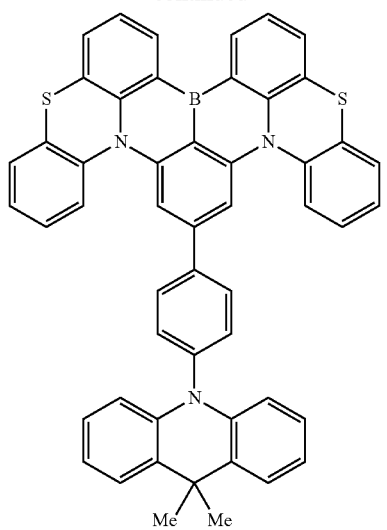
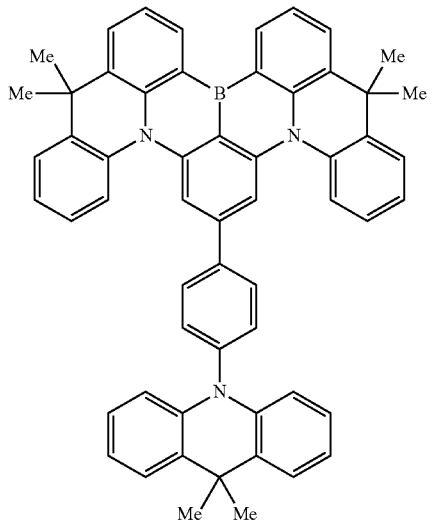
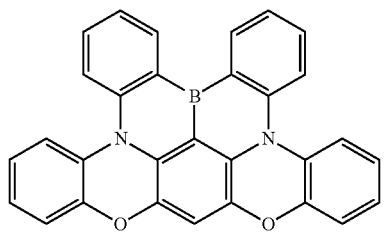
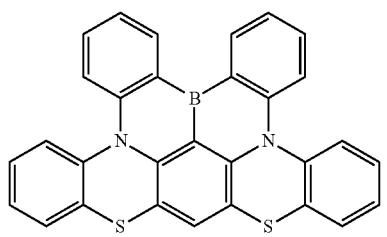
668
-continued
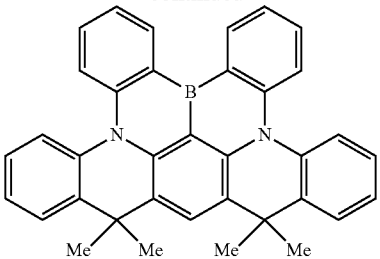
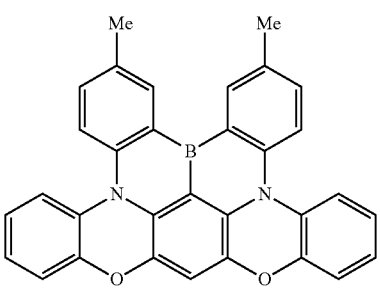
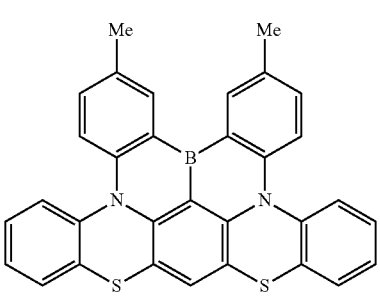
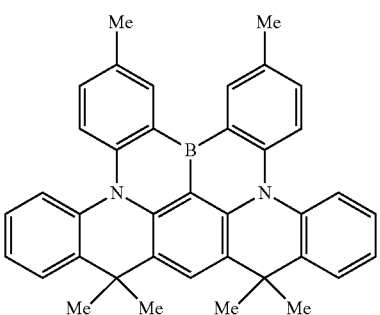
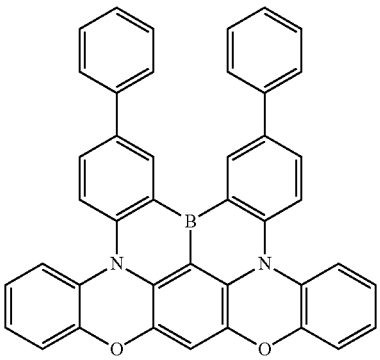

669
-continued
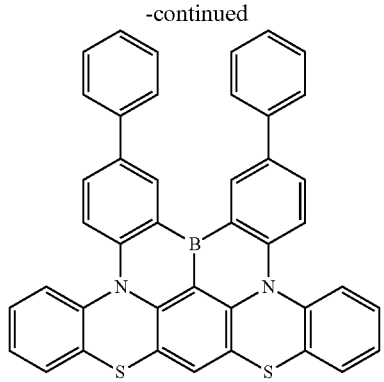
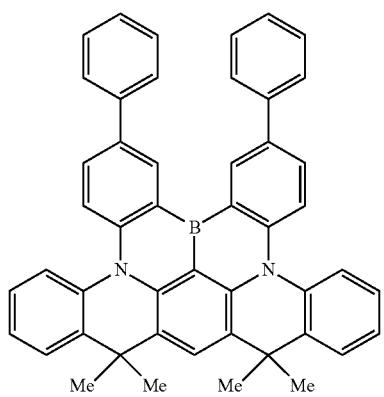
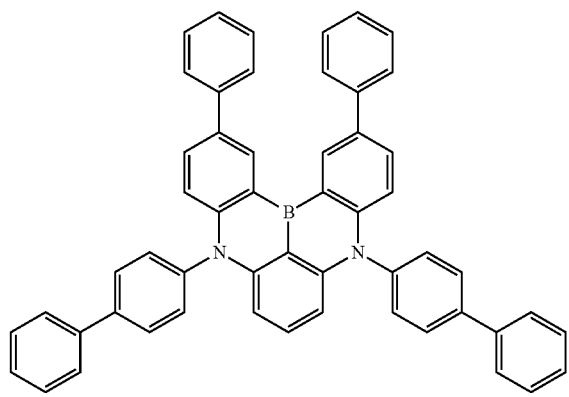
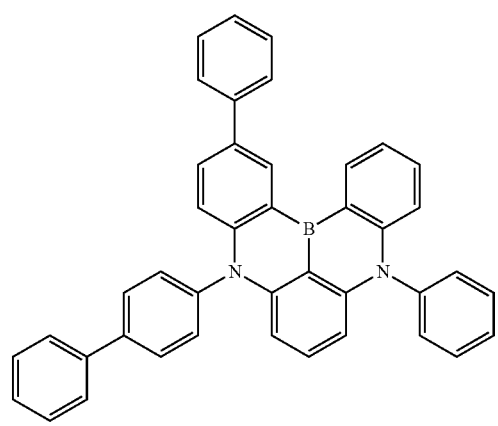
670
-continued
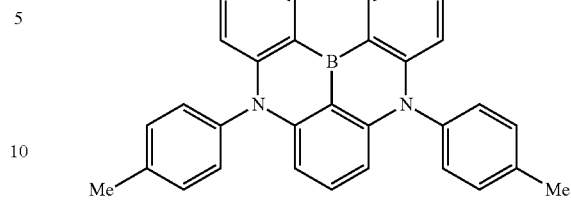
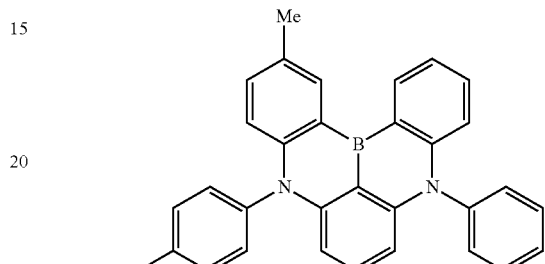
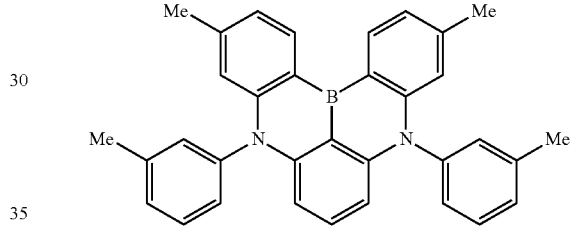
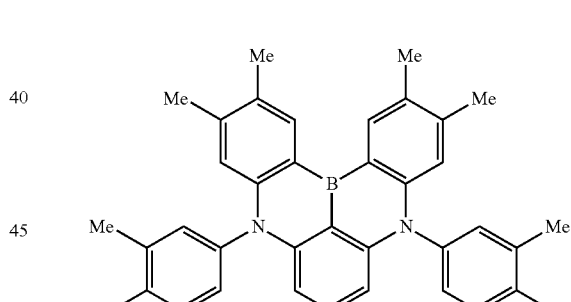
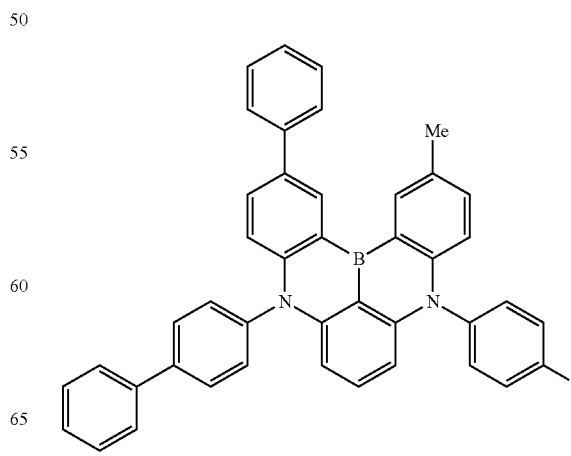

671
-continued
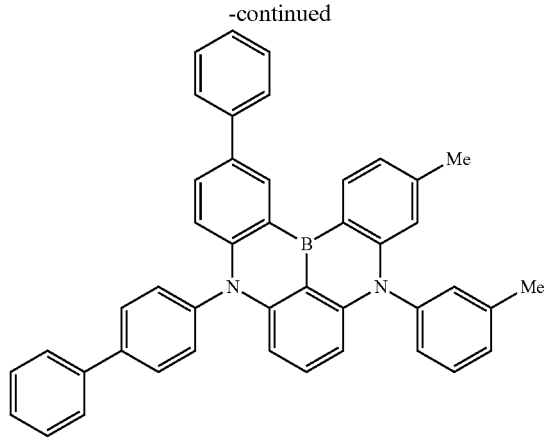
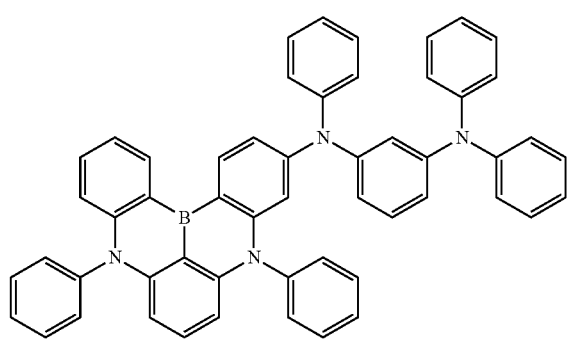
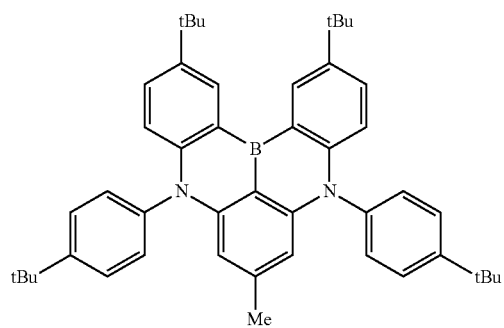
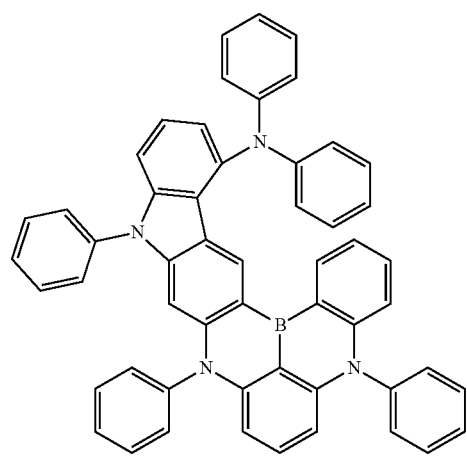
672
-continued
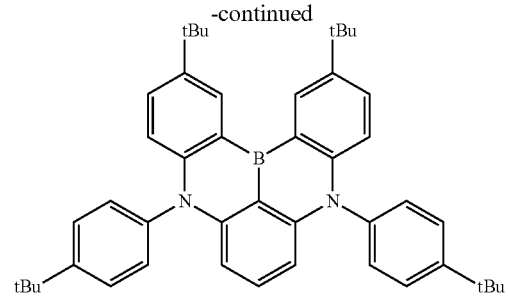
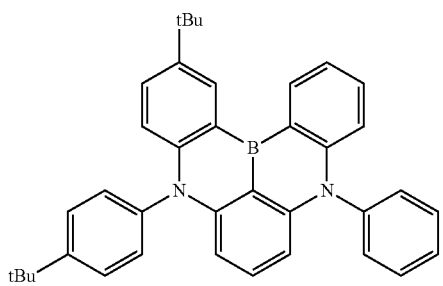
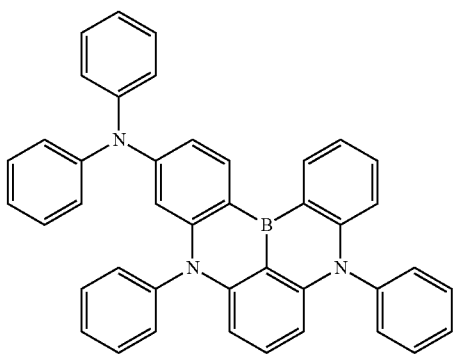
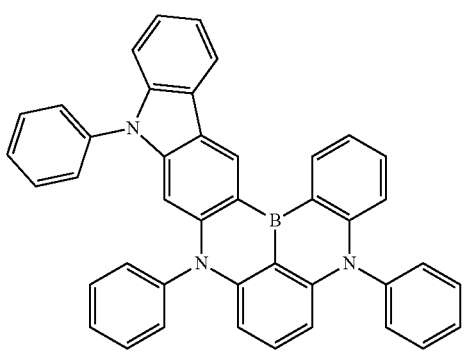
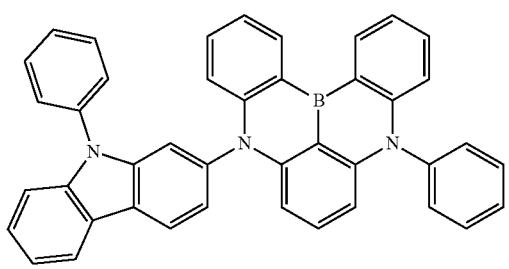

673
-continued
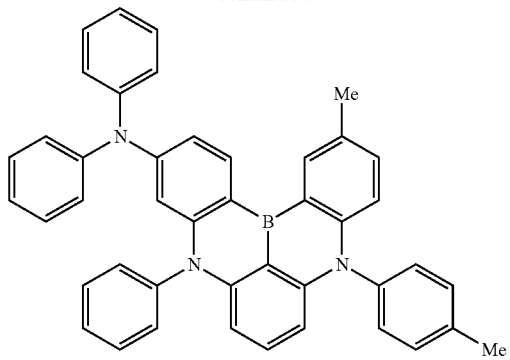
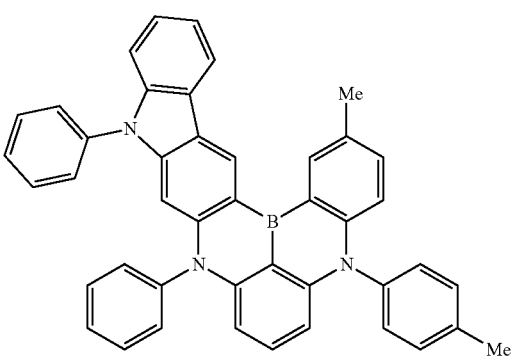
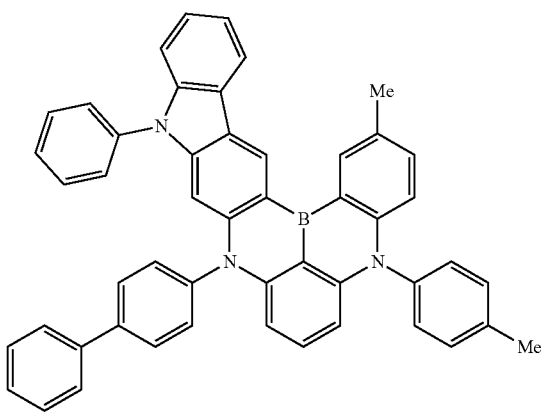
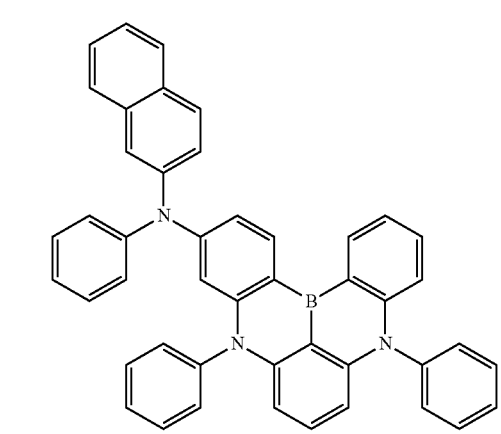
674
-continued
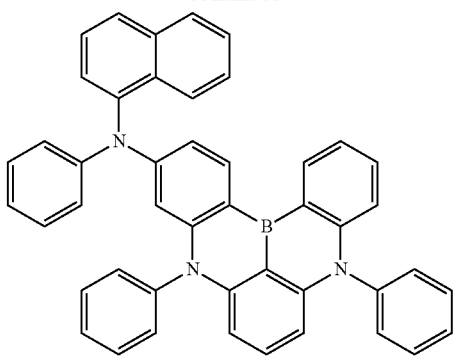
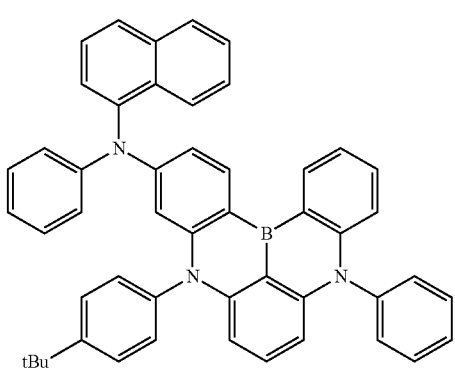
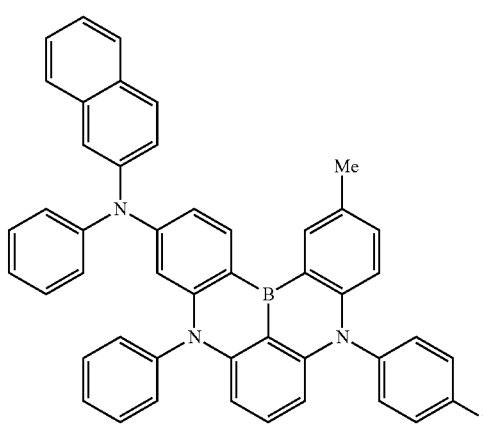
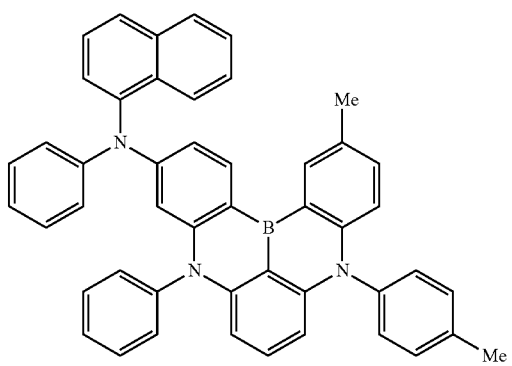

675
-continued
676
-continued
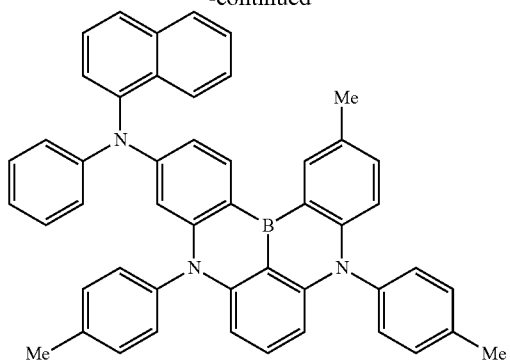
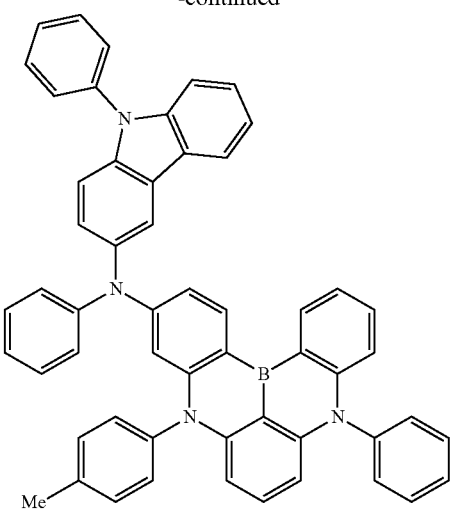
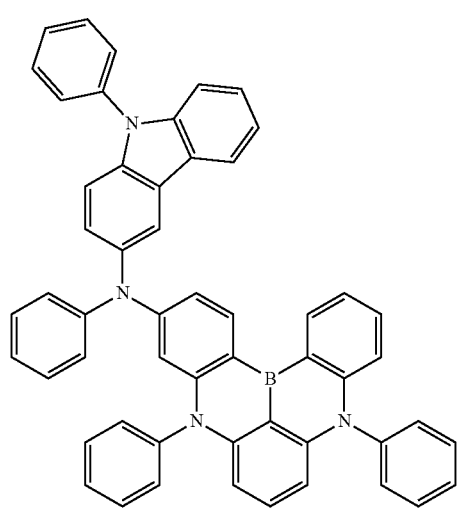
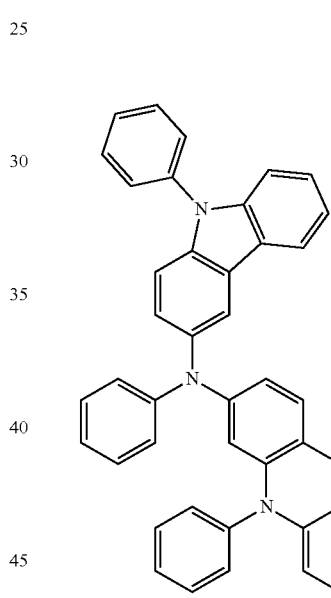
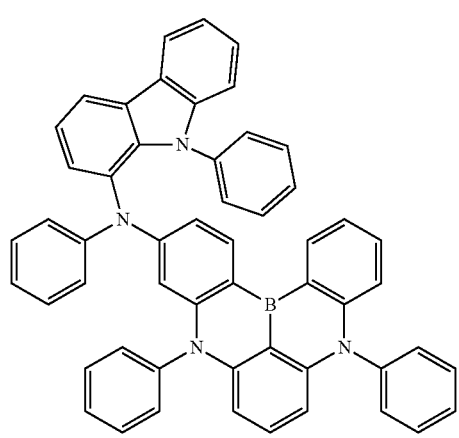
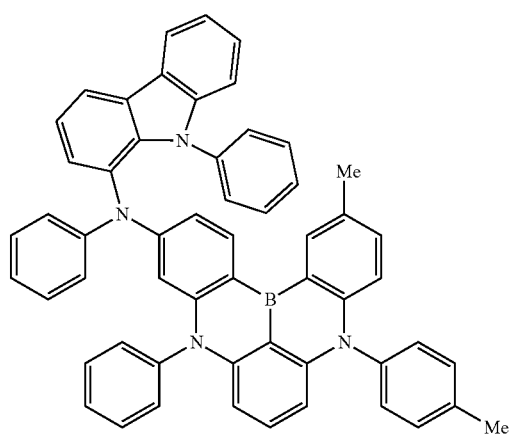

677
-continued
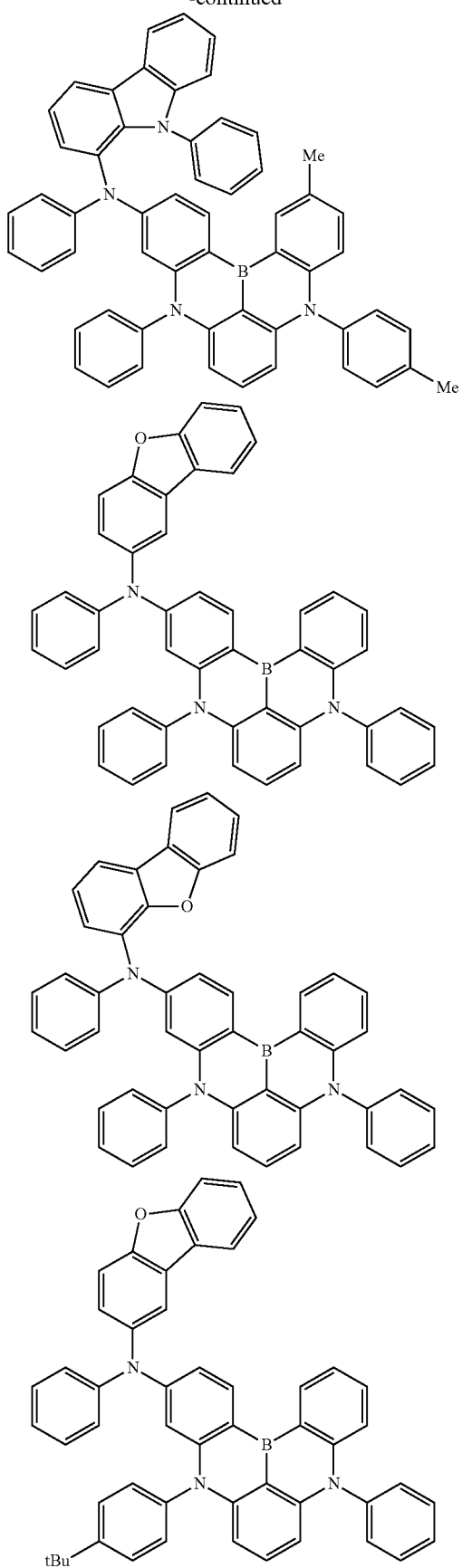
678
-continued
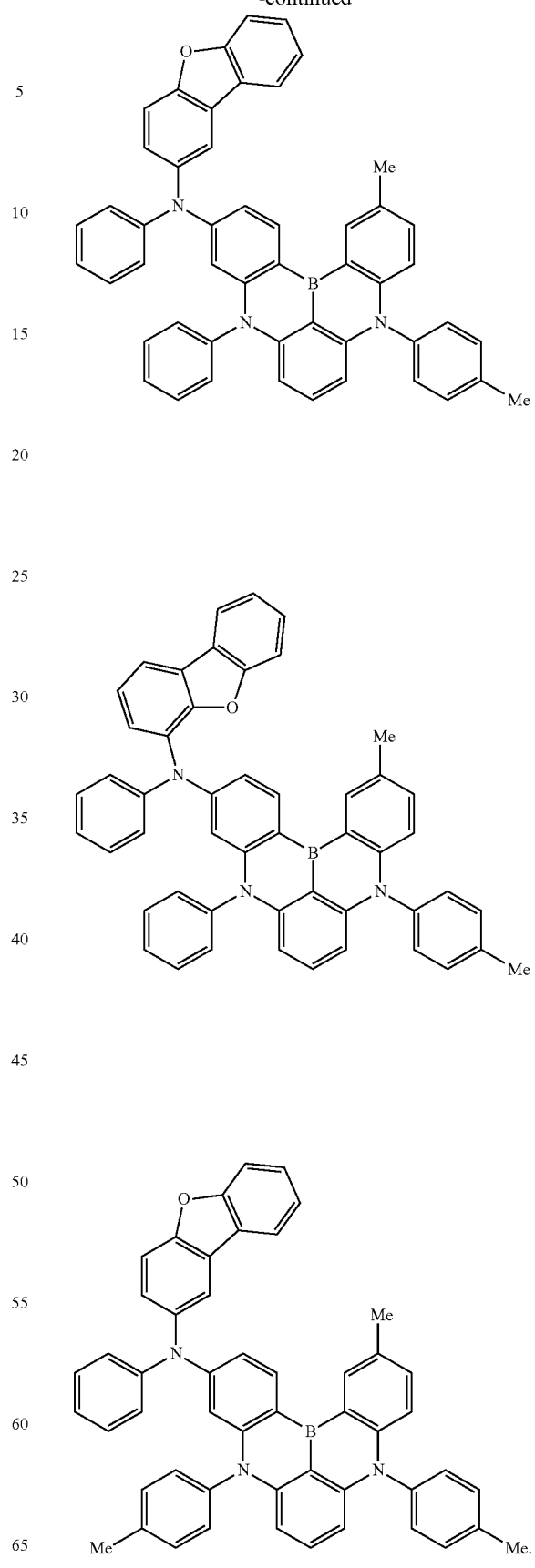

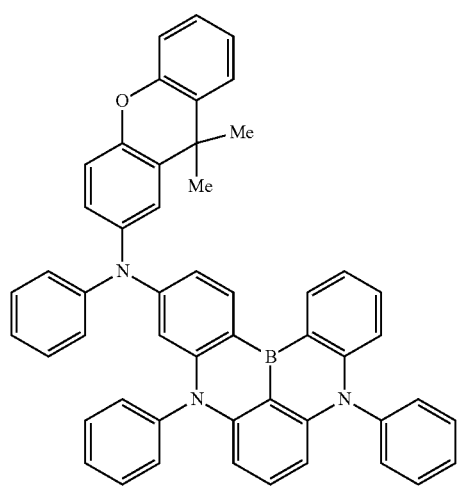
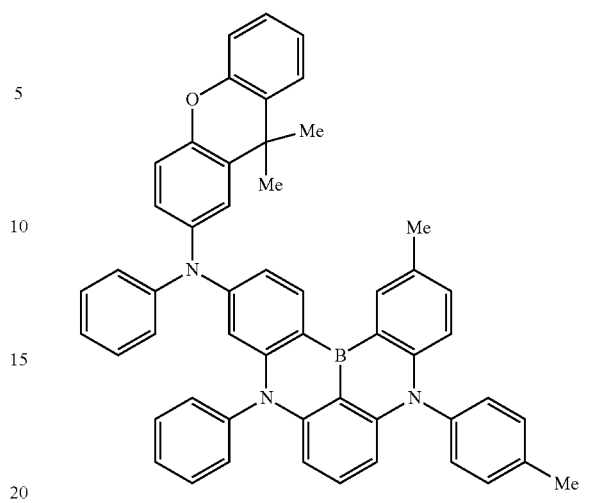
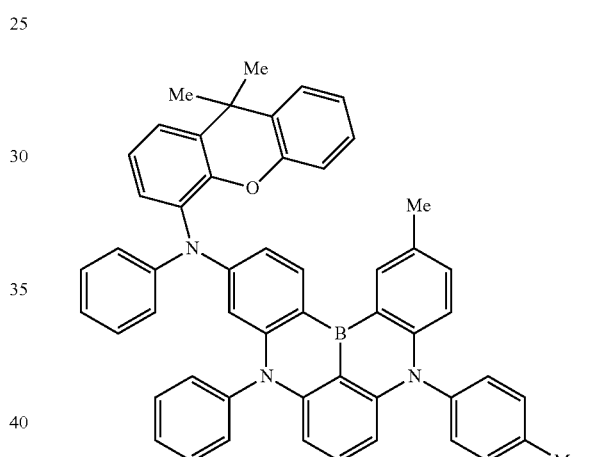
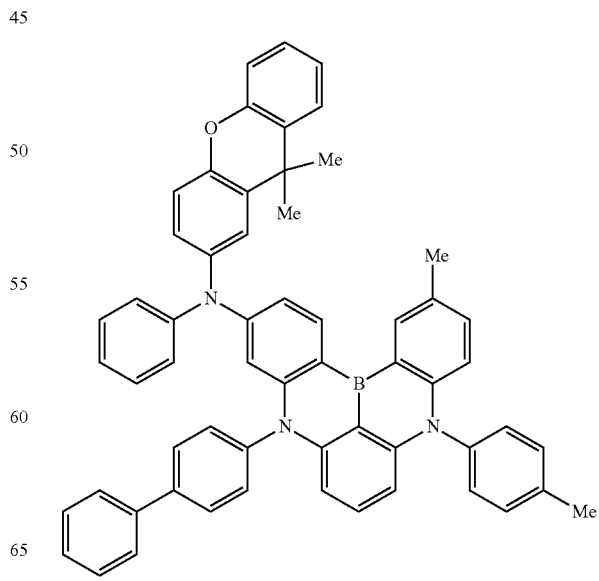

-continued
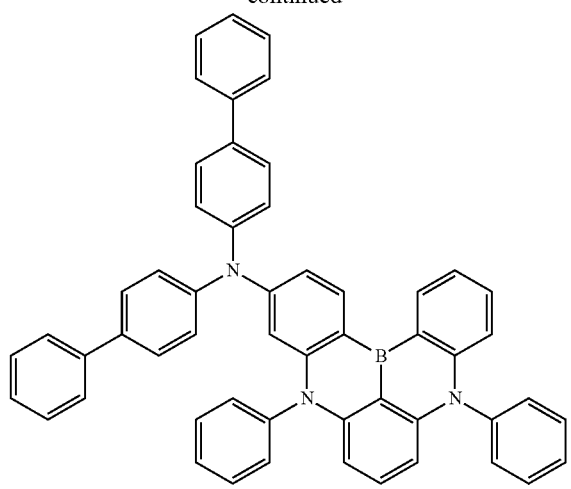
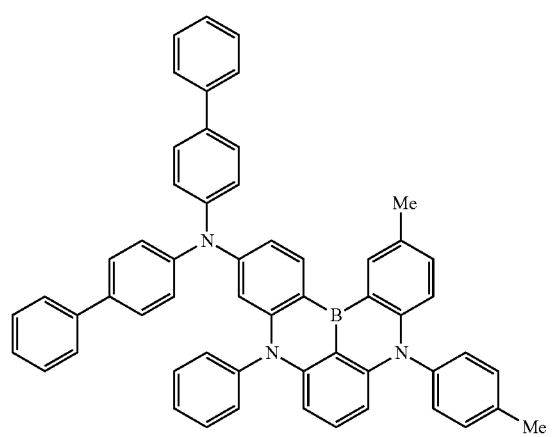
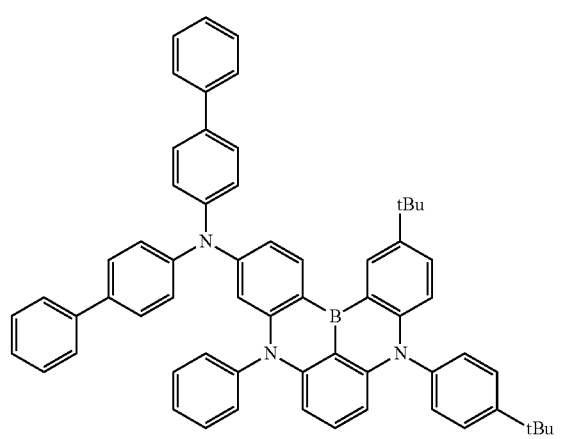
-continued
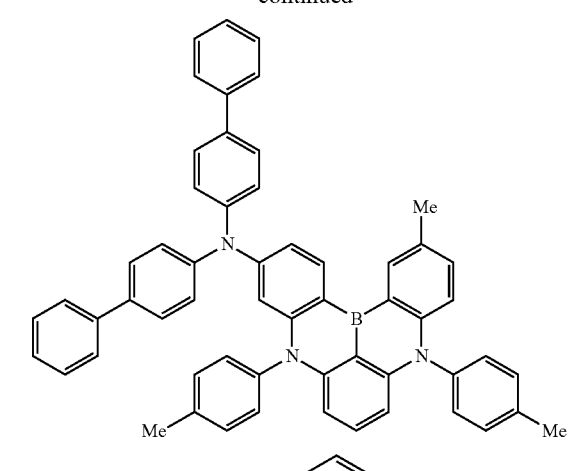
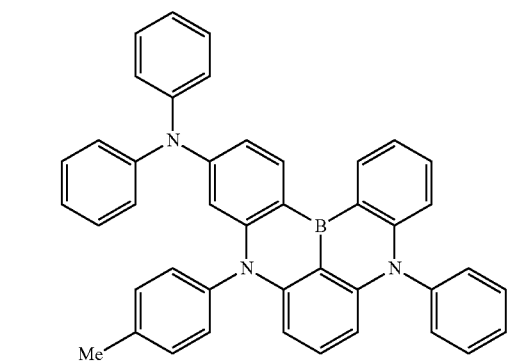
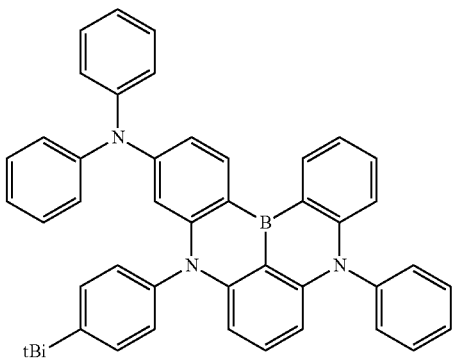

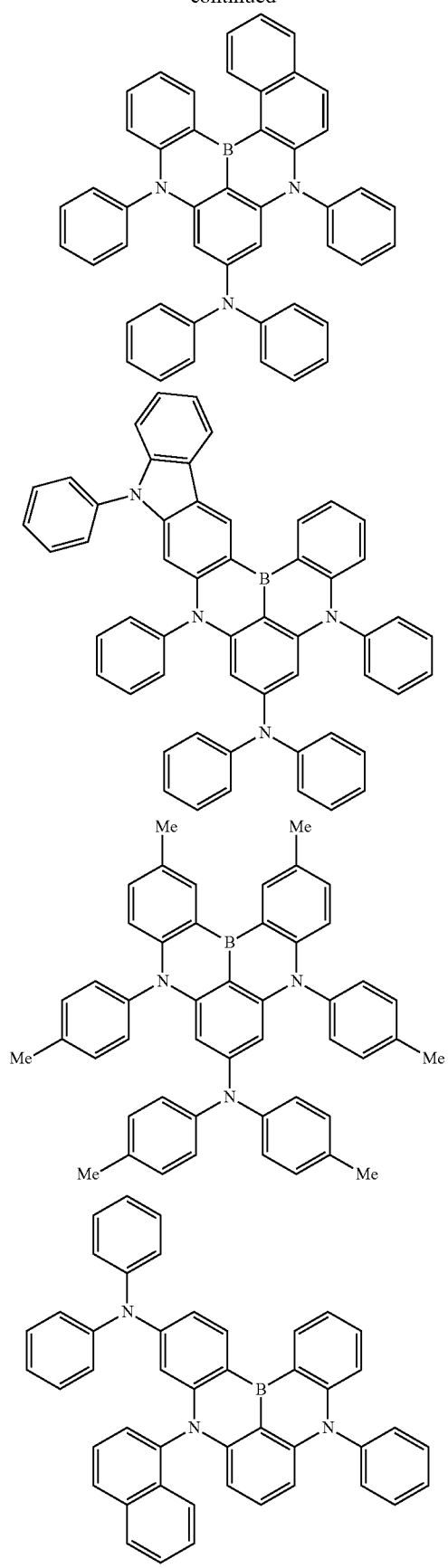
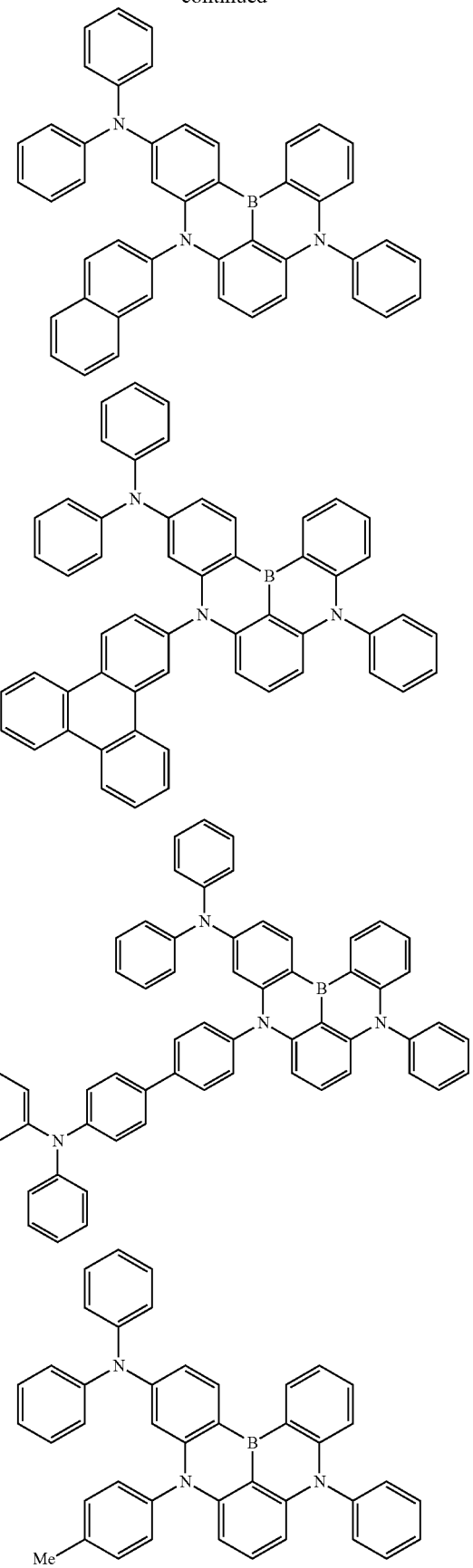

685
-continued
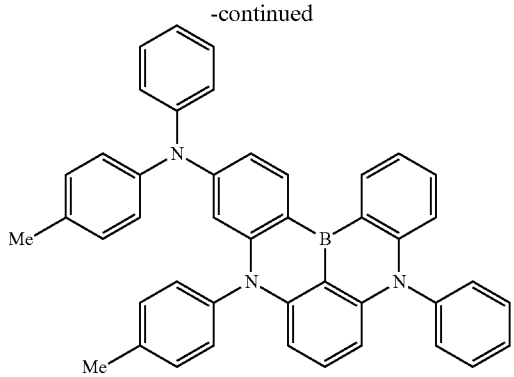
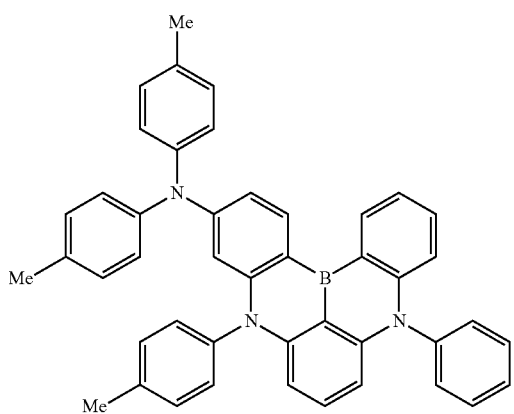
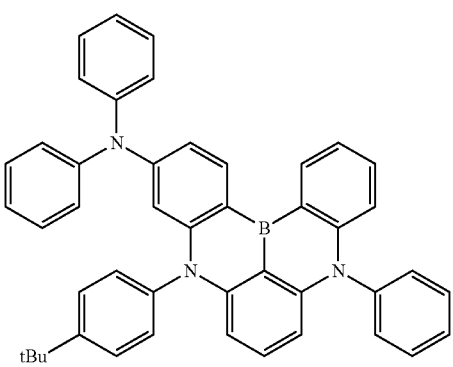
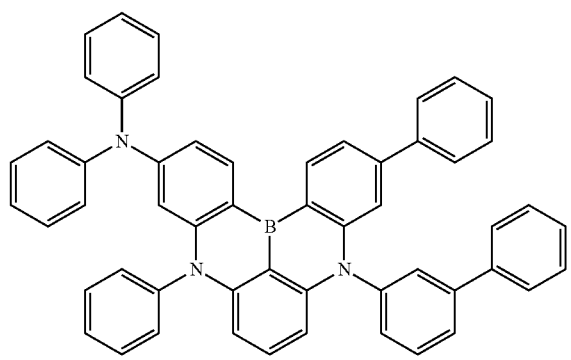
686
-continued
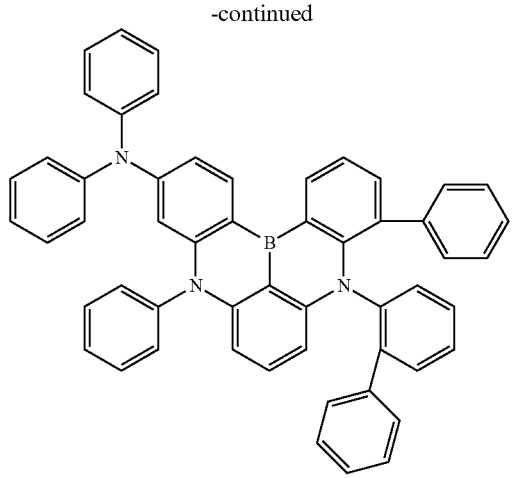
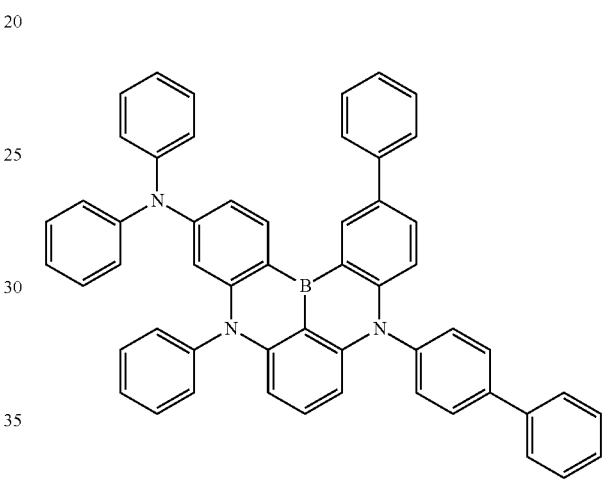
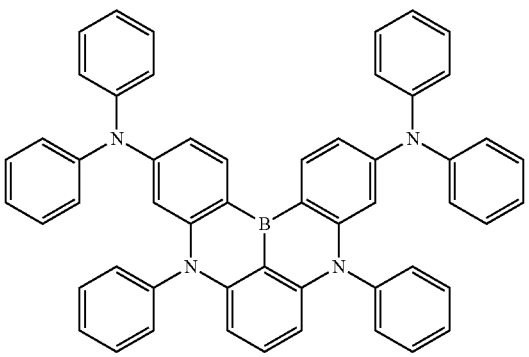
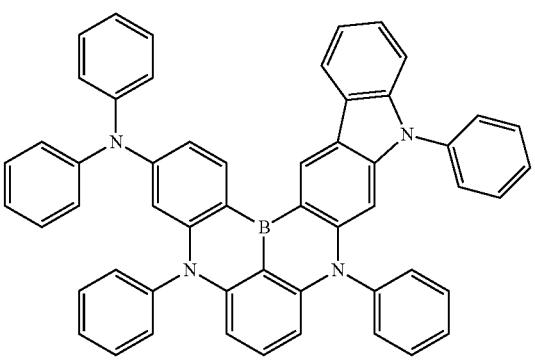

687
-continued
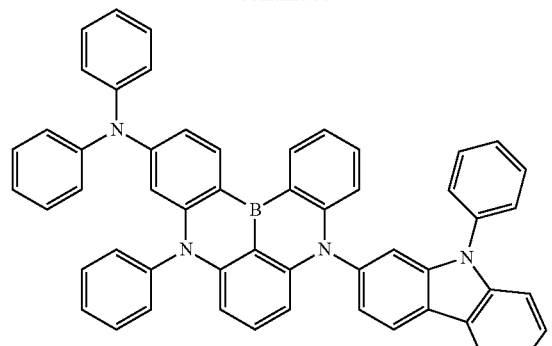
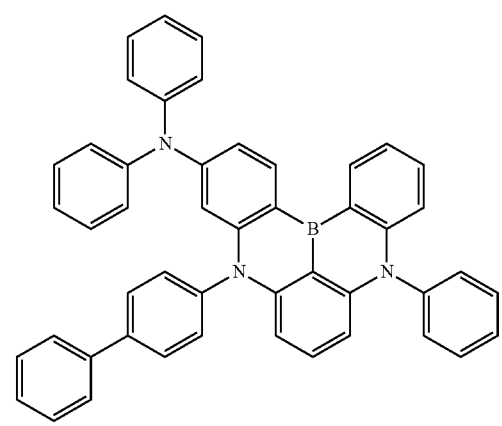
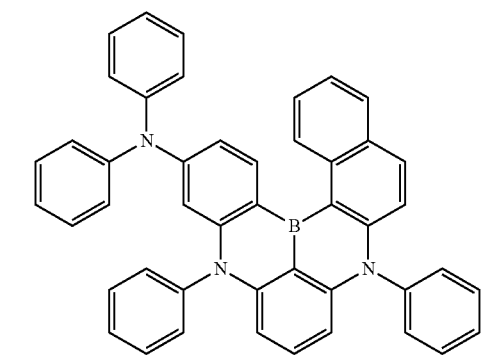
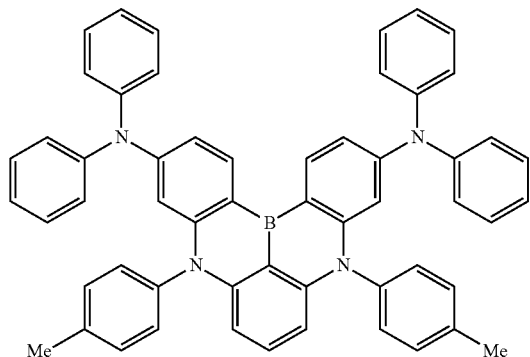
688
-continued
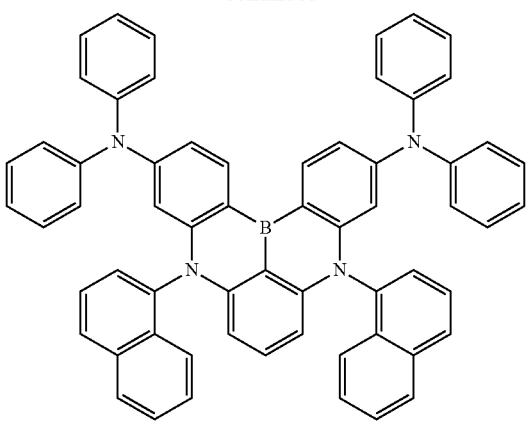
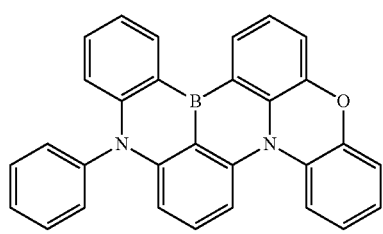
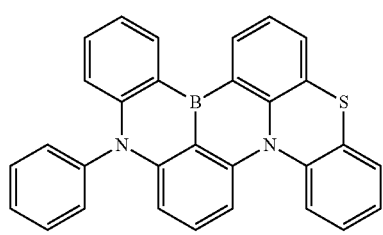
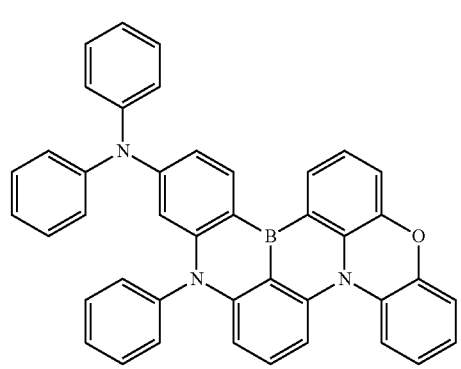
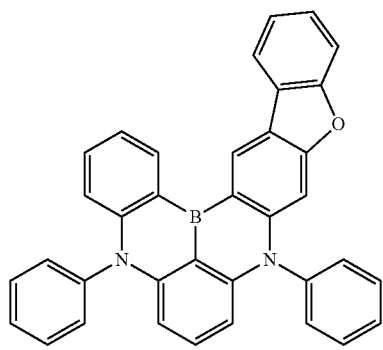

689
-continued
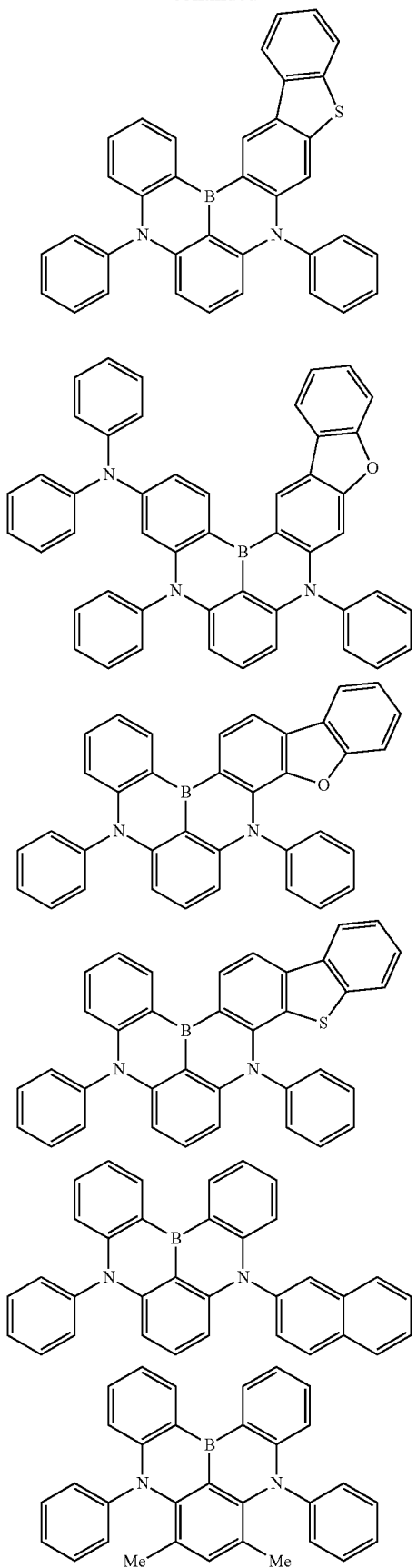
690
-continued
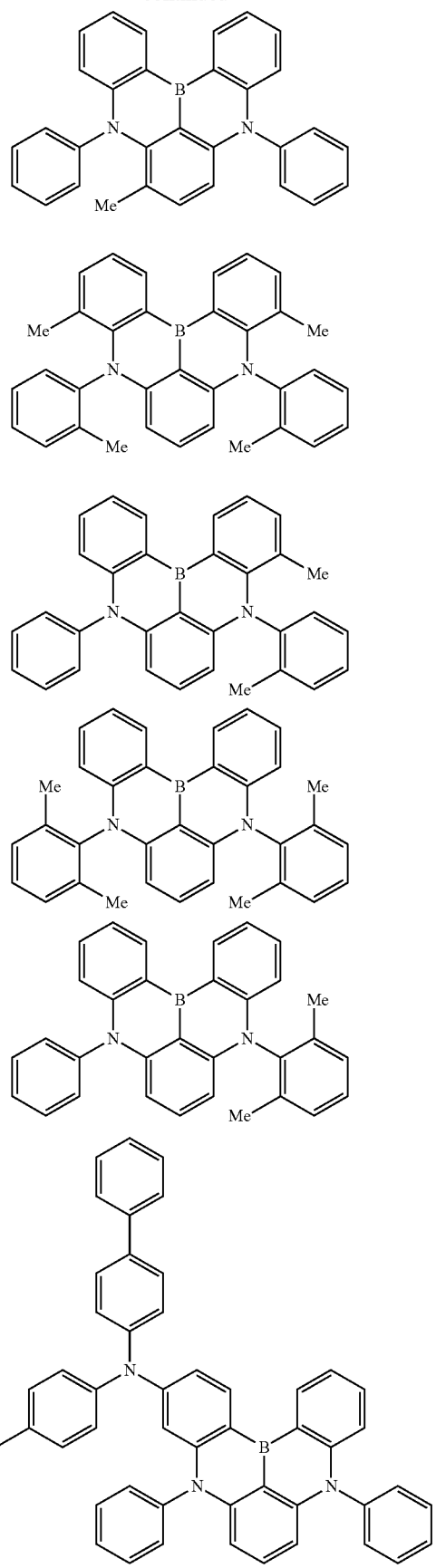

691
-continued
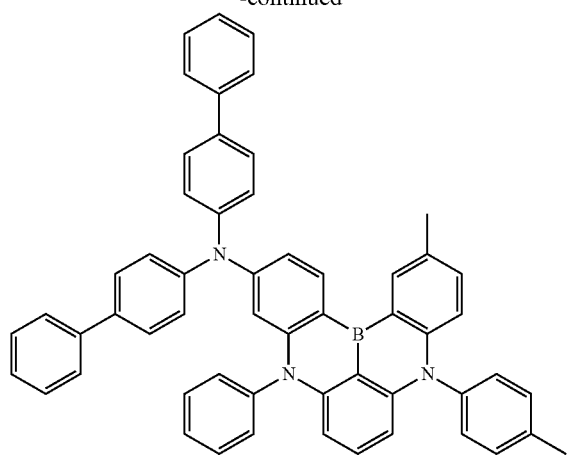
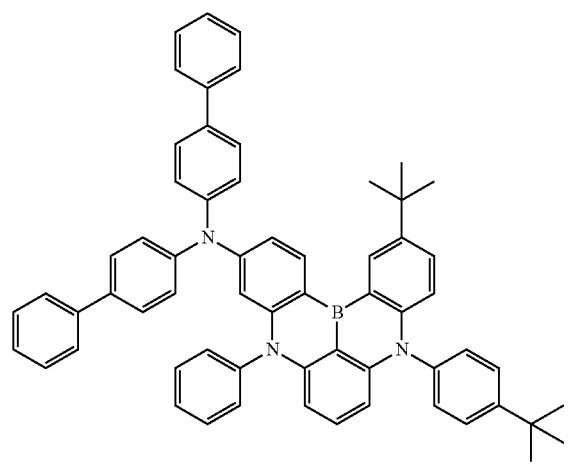
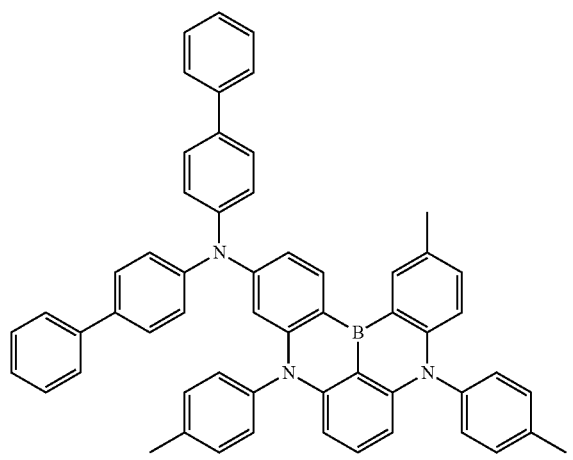
692
-continued
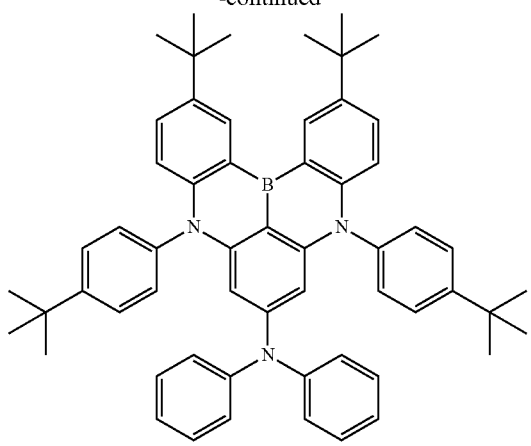
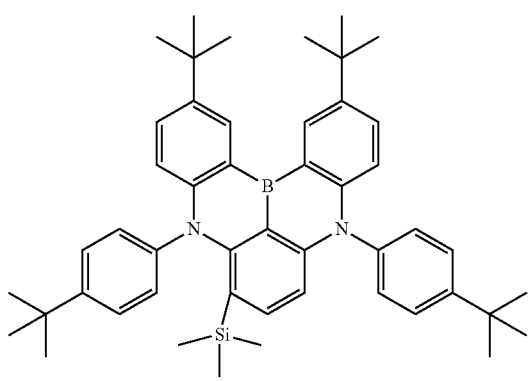
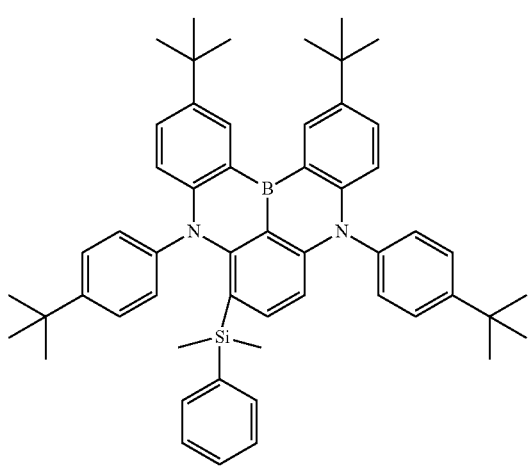
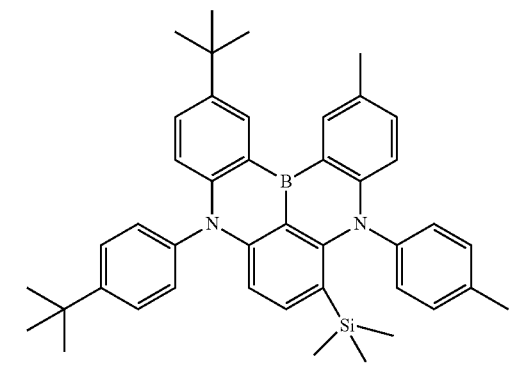

693
-continued
694
-continued
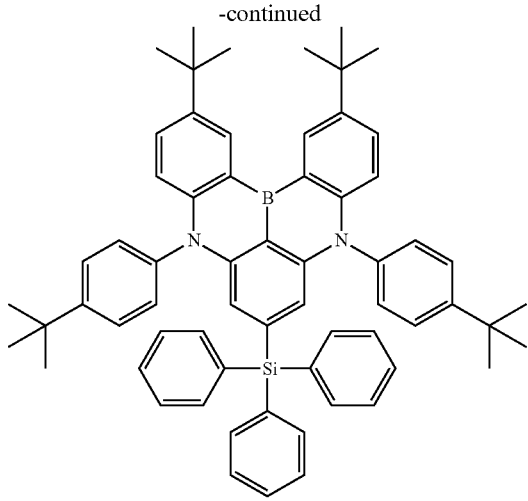
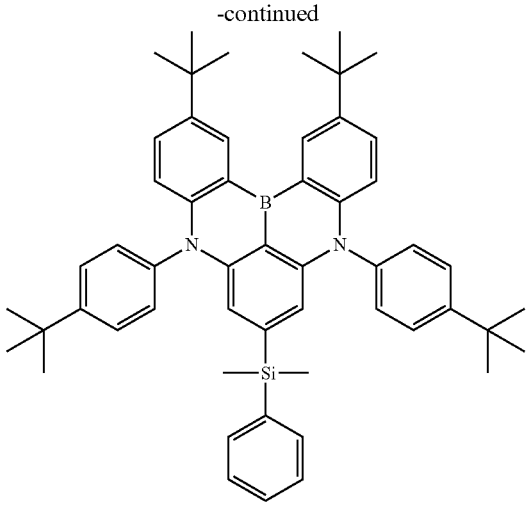
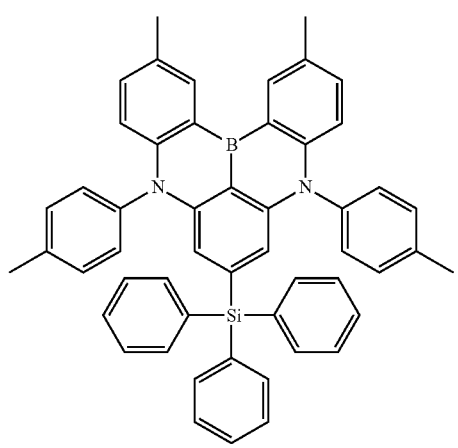
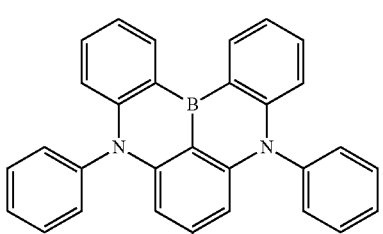
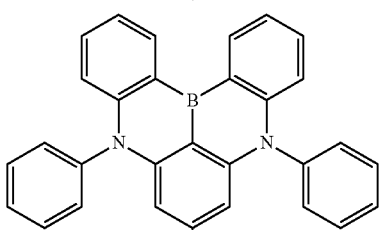
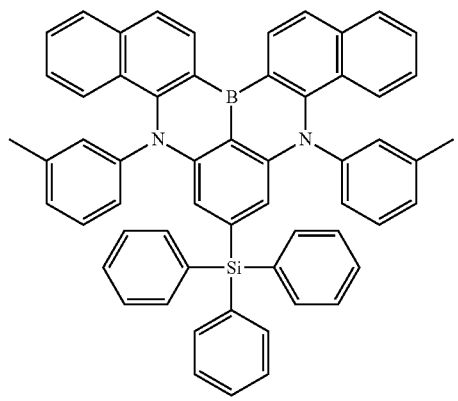
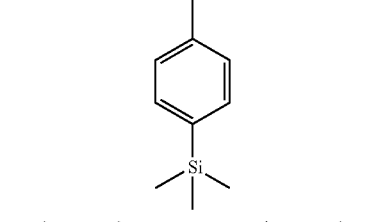
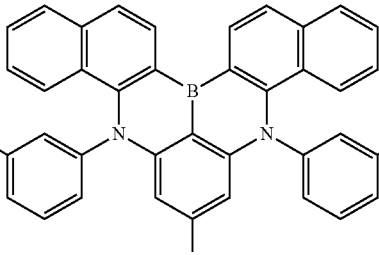

695
-continued
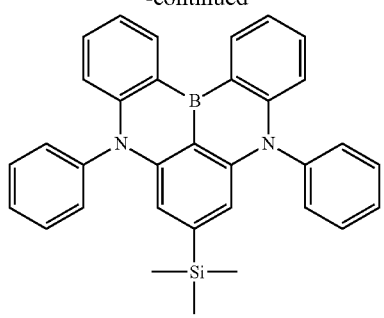
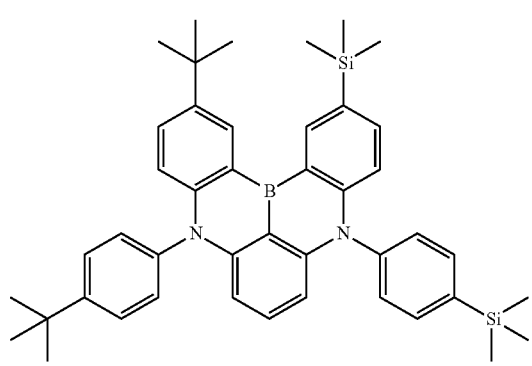
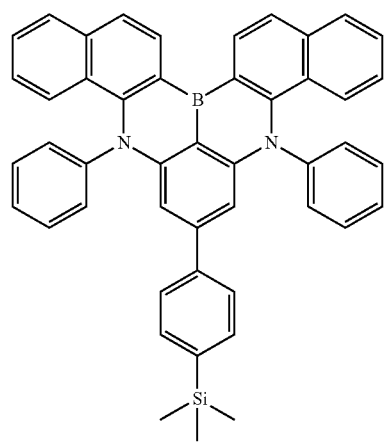
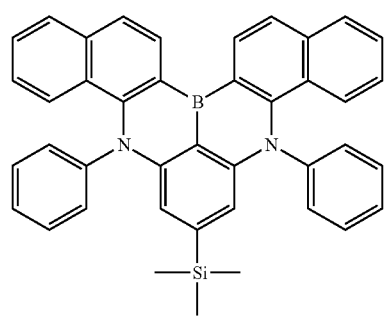
696
-continued
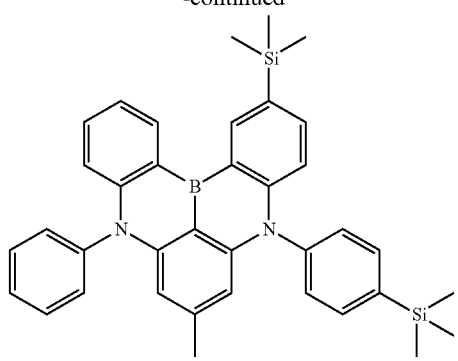
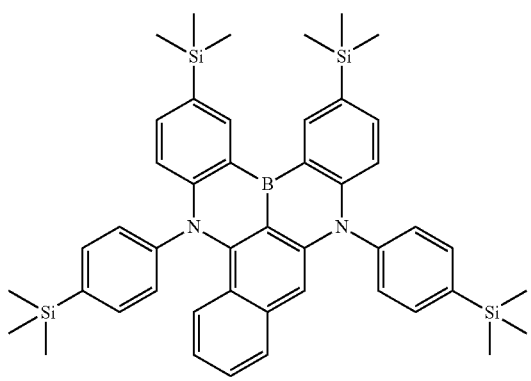
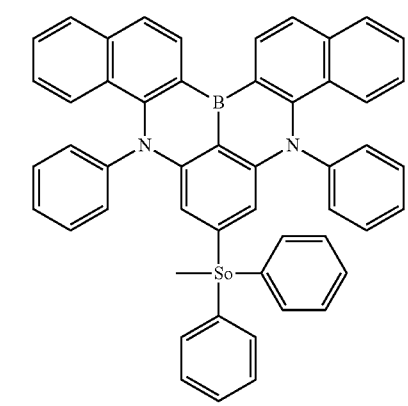
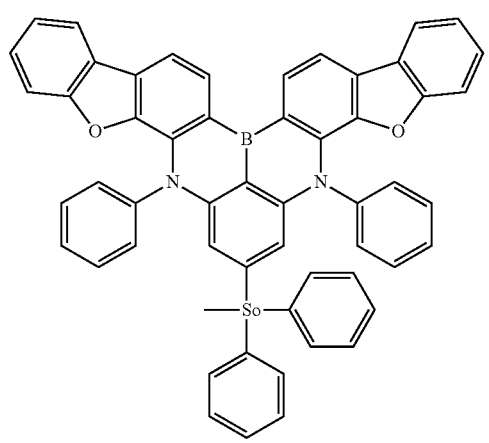

697
-continued
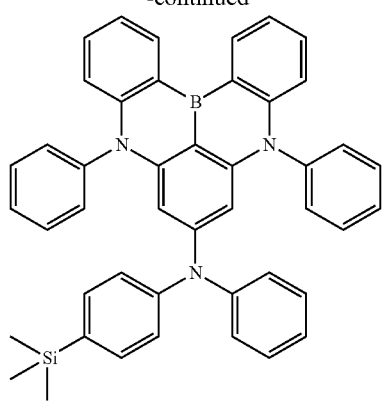
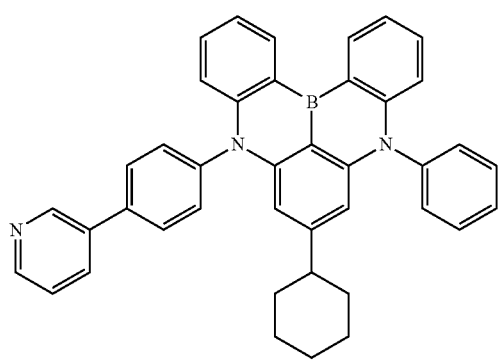
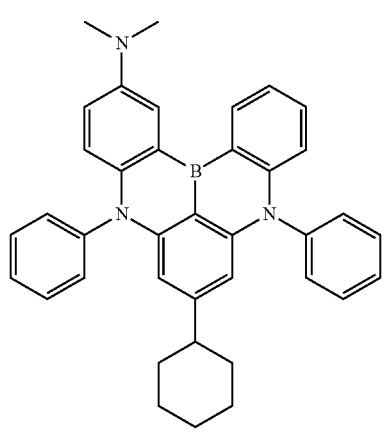
698
-continued
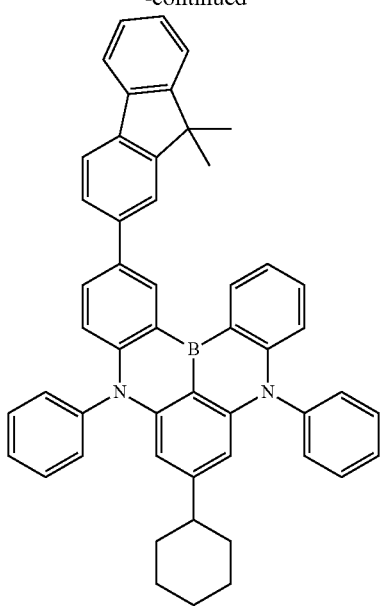
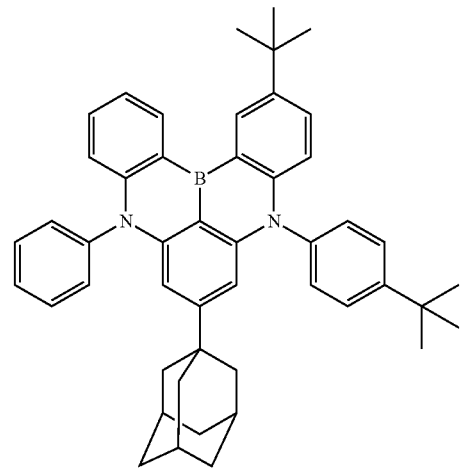
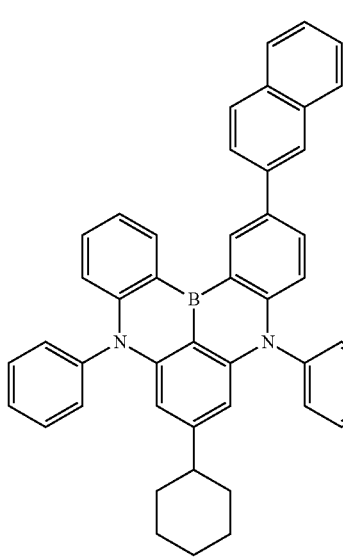

699
-continued
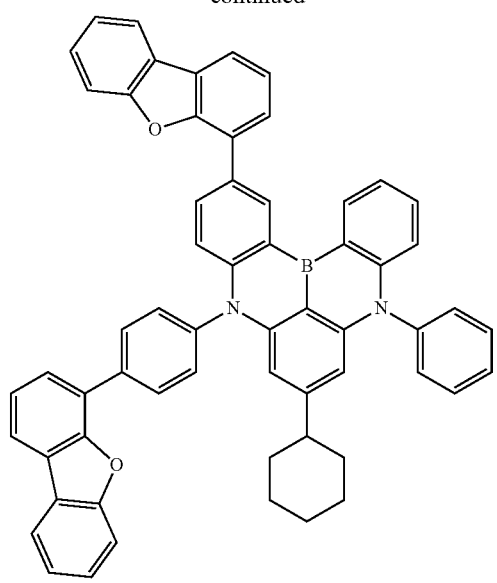
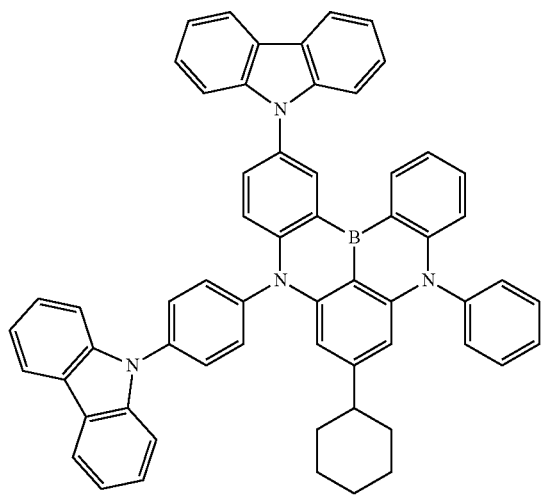
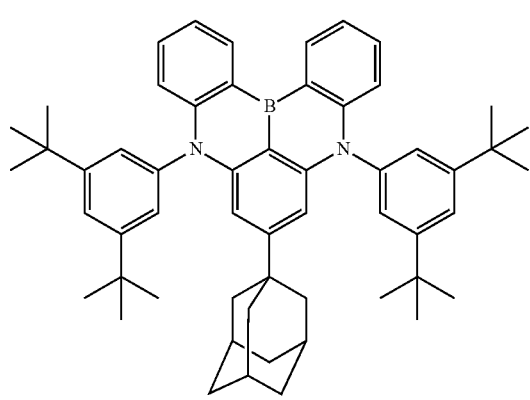
700
-continued
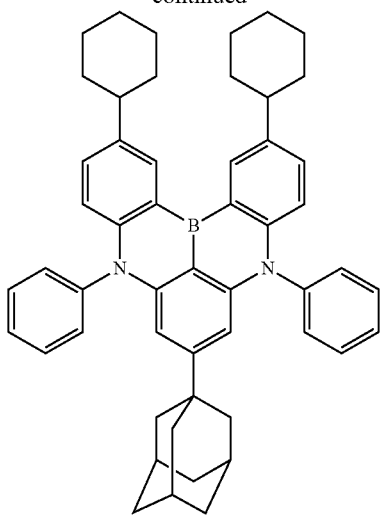
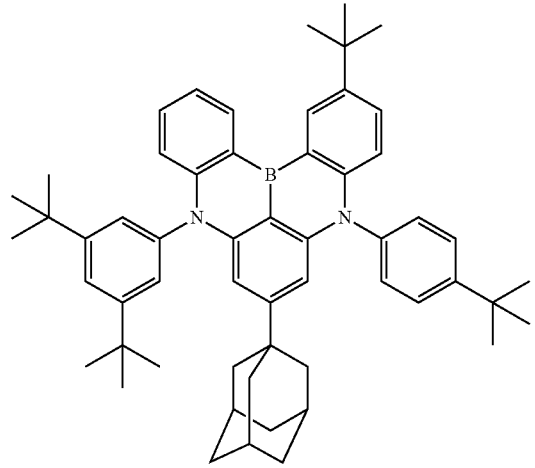
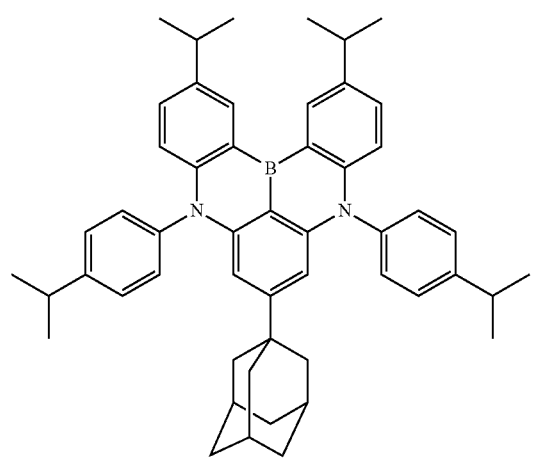

701
-continued
702
-continued
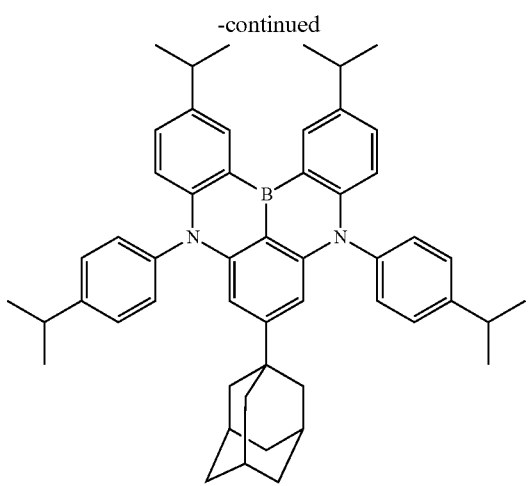
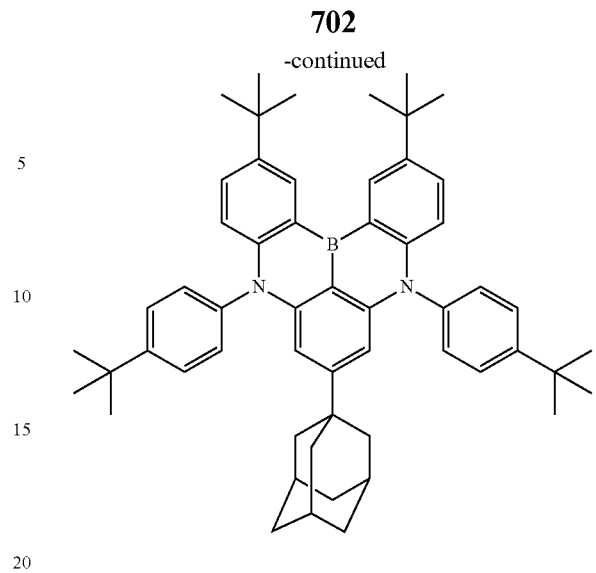
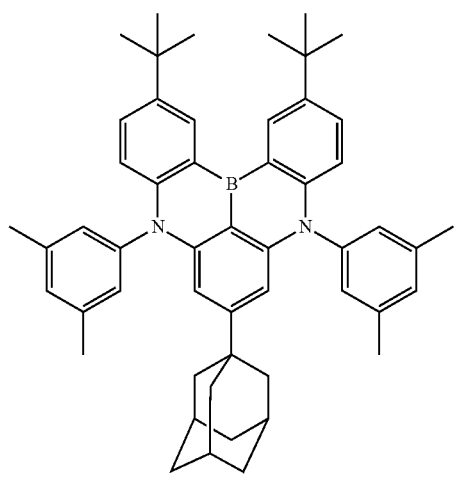
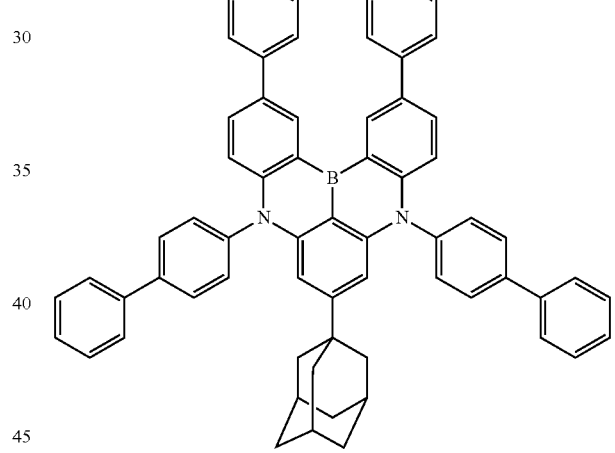
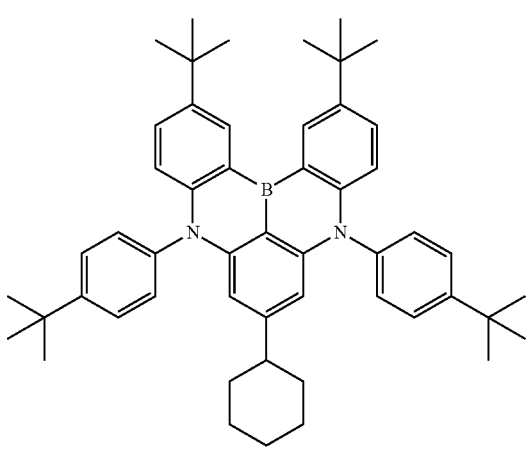
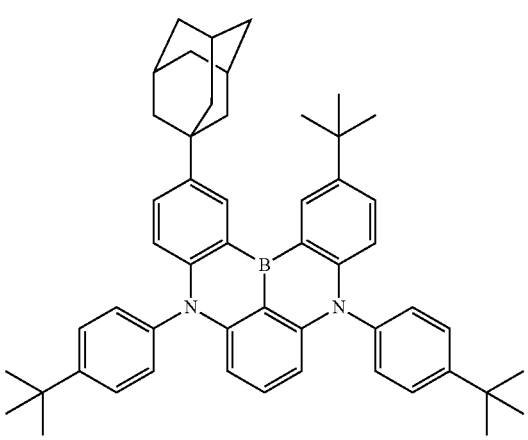

703
-continued
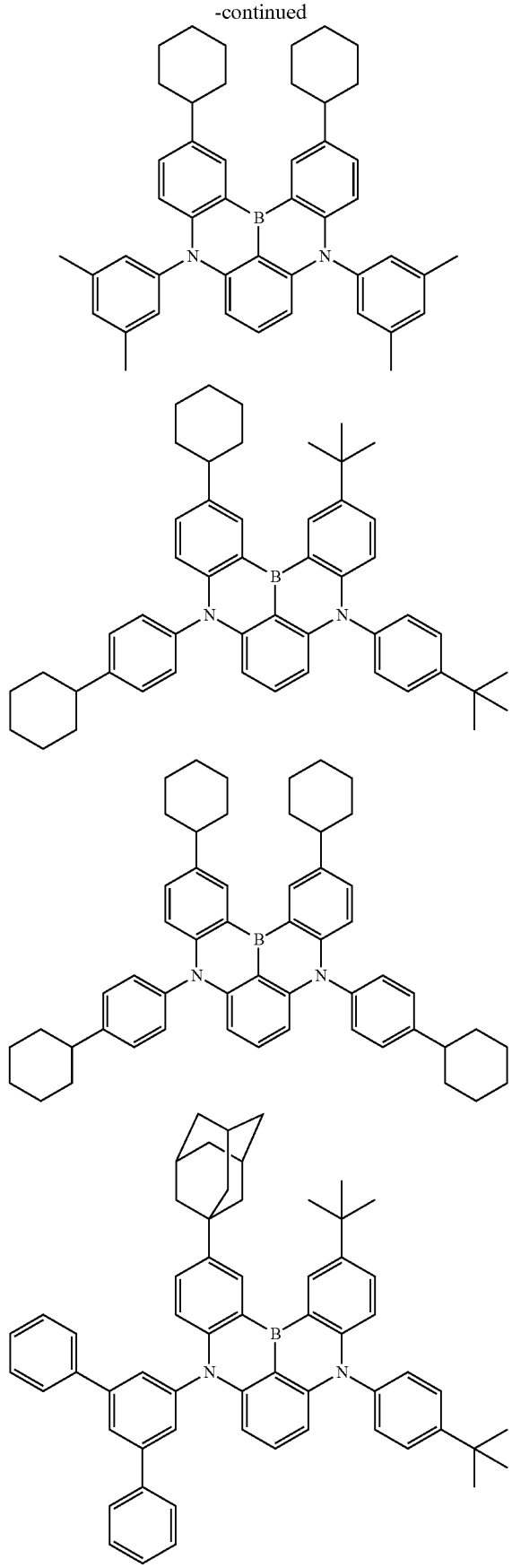
704
-continued
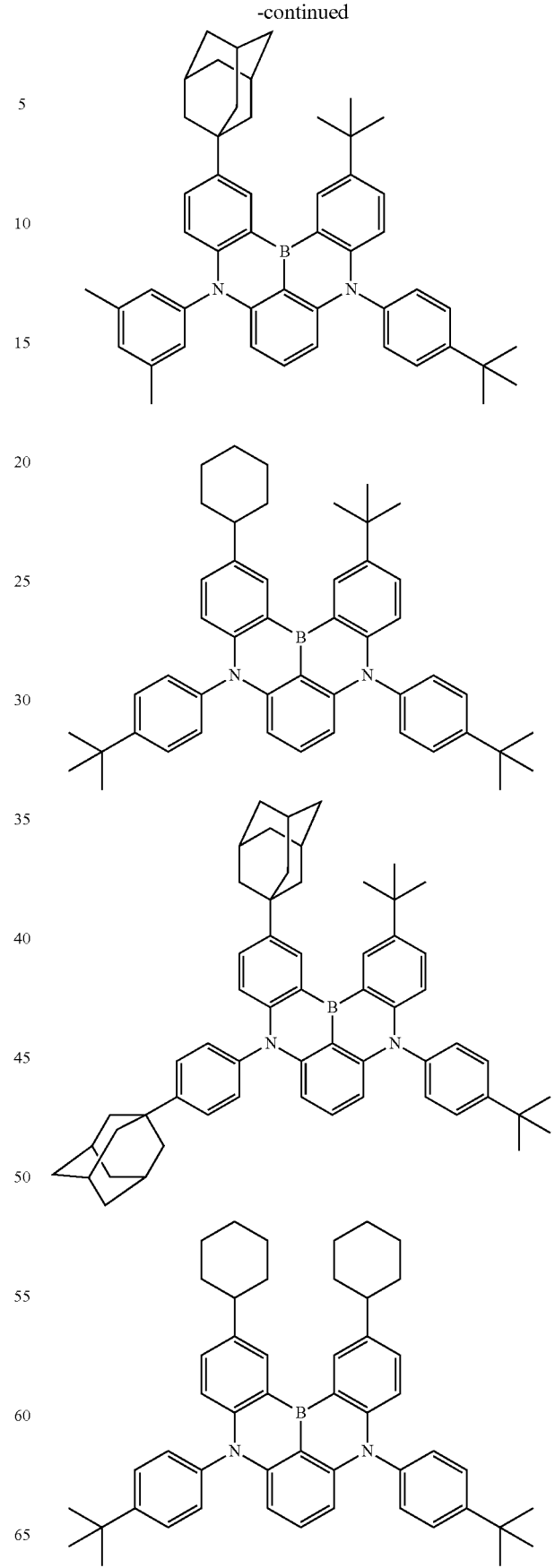

705
-continued
706
-continued
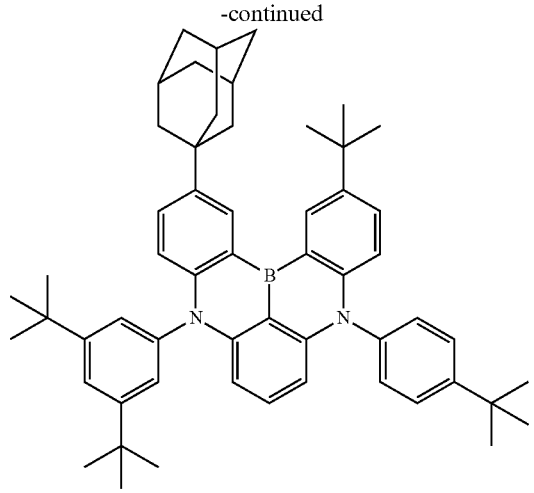
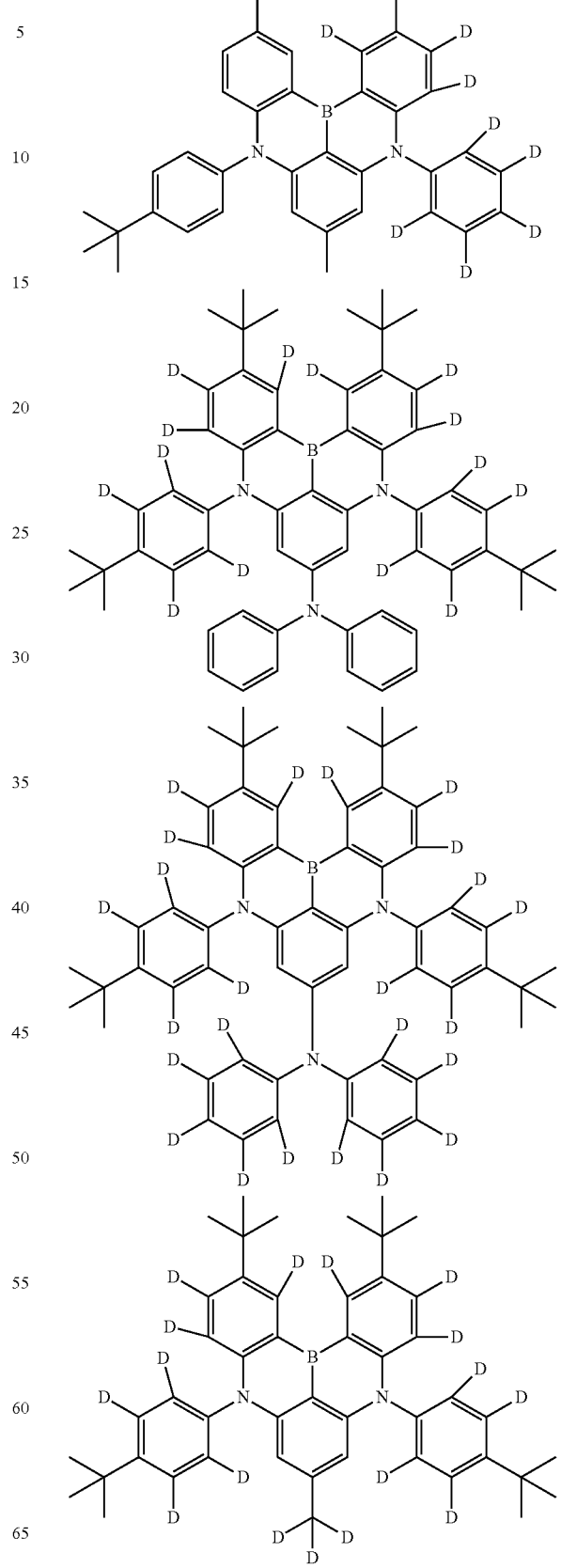

707
-continued
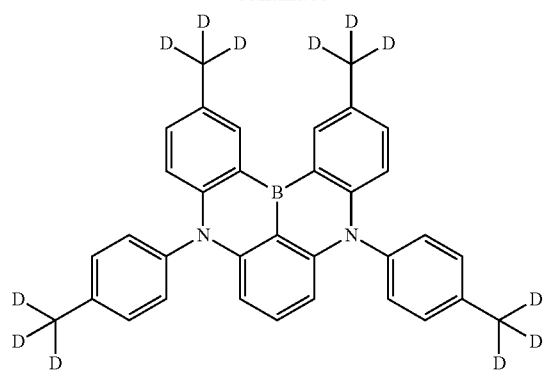
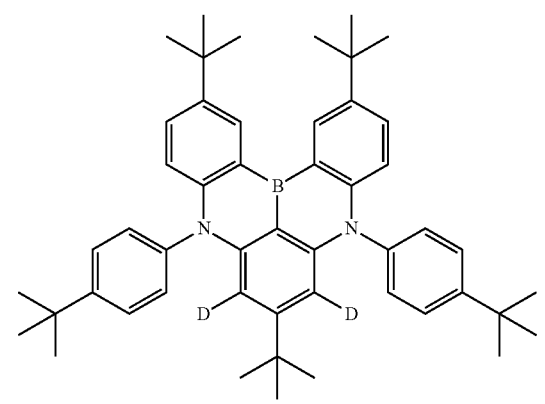
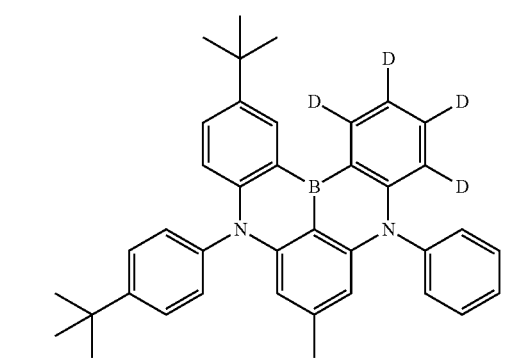
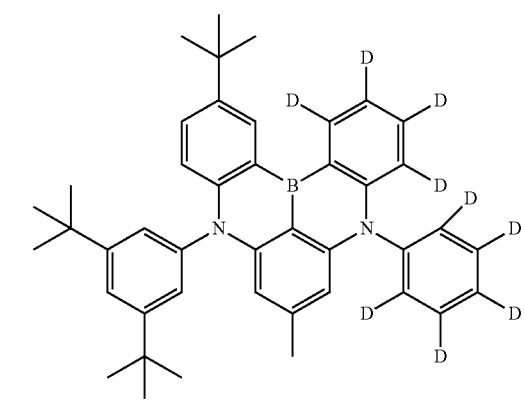
708
-continued
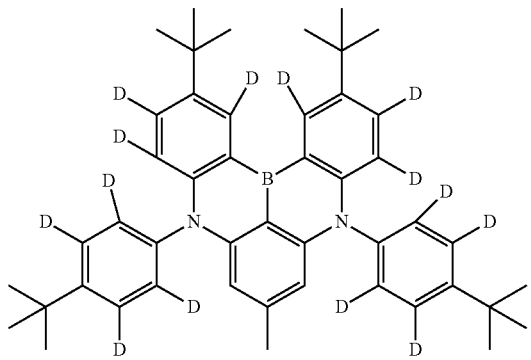
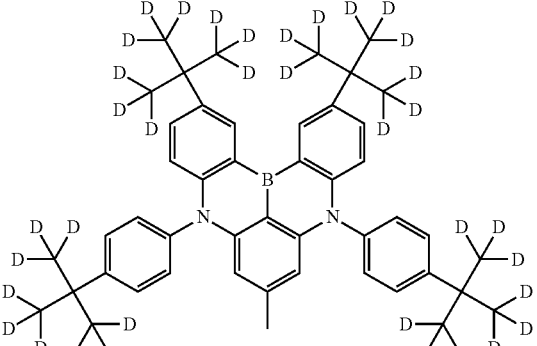
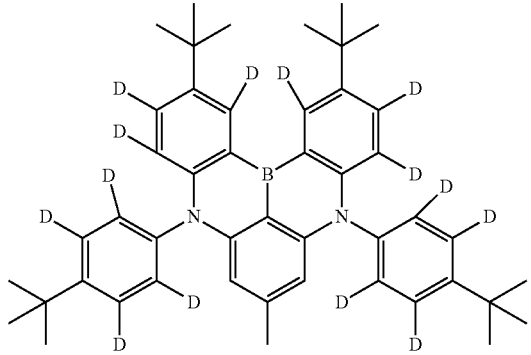
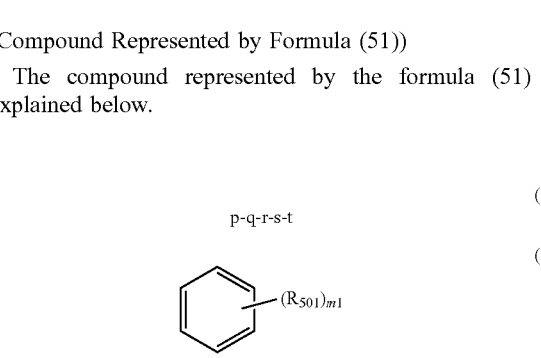
(Compound Represented by Formula (51))
The compound represented by the formula (51) is explained below.
$$p-q-r-s-t \quad (51)$$
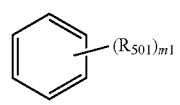
(52)
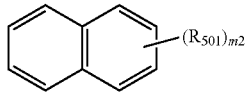
(53)
(54)

-continued

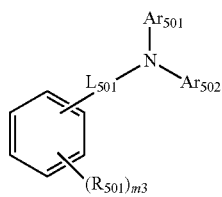
(55)

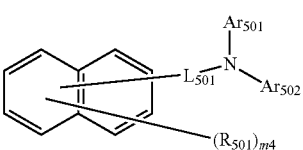
(56)

wherein, in the formula (51),
r ring is a ring represented by the formula (52) or formula (53) which is fused to an adjacent ring at an arbitrary position;
q ring and s ring are independently a ring represented by the formula (54) which is fused to an adjacent ring at an arbitrary position;
p ring and t ring are independently a ring represented by the formula (55) or the formula (56) which is fused to an adjacent ring at an arbitrary position;
when a plurality of $R_{501}$s exist, adjacent $R_{501}$s are bonded with each other to form a substituted or unsubstituted, saturated or unsaturated ring, or do not form a substituted or unsubstituted, saturated or unsaturated ring;
$X_{501}$ is an oxygen atom, a sulfur atom, or $NR_{502}$;
$R_{501}$ and $R_{502}$ that do not form the substituted or unsubstituted saturated or unsaturated ring are
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;
$R_{901}$ to $R_{907}$ are as defined in the formula (1);
$Ar_{501}$ and $Ar_{502}$ are independently
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
a substituted or unsubstituted aryl group having 6 to 50 ring carbon atoms, or
a substituted or unsubstituted monovalent heterocyclic group having 5 to 50 ring atoms;

$L_{501}$ is
a substituted or unsubstituted alkylene group having 1 to 50 carbon atoms,
a substituted or unsubstituted alkenylene group having 2 to 50 carbon atoms,
a substituted or unsubstituted alkynylene group having 2 to 50 carbon atoms,
a substituted or unsubstituted cycloalkylene group having 3 to 50 ring carbon atoms,
a substituted or unsubstituted arylene group having 6 to 50 ring carbon atoms, or
a substituted or unsubstituted divalent heterocyclic group having 5 to 50 ring atoms;
m1 is independently an integer of 0 to 2, m2 is independently an integer of 0 to 4, m3s are independently an integer of 0 to 3, and m4s are independently an integer of 0 to 5; when a plurality of $R_{501}$s exist, $R_{501}$s may be the same or different;
In the formula (51), each of the p ring to the t ring is fused to an adjacent ring by sharing two carbon atoms. The position and direction of fusing are not limited, and condensation is possible at any position and direction.
In one embodiment, in the formula (52) or (53) of the r ring, $R_{501}$ is a hydrogen atom.
In one embodiment, the compound represented by the formula (51) is represented by any one of the following formulas (51-1) to (51-6).

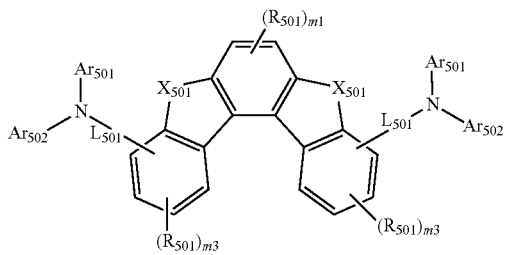
(51-1)

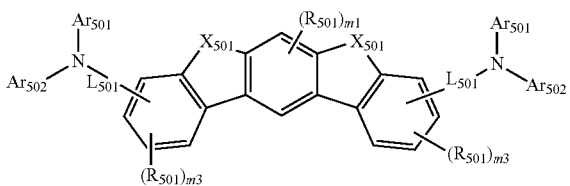
(51-2)

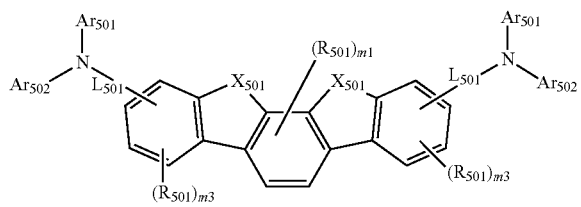
(51-3)

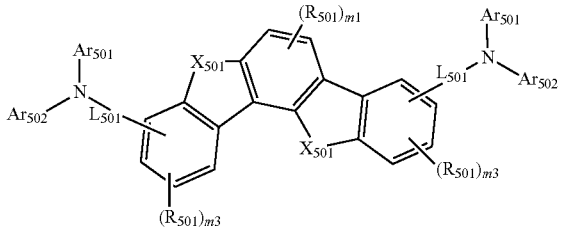
(51-4)

(51-5)
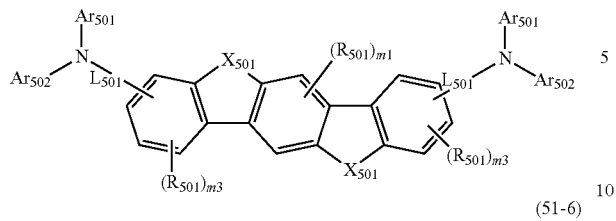
(51-6)
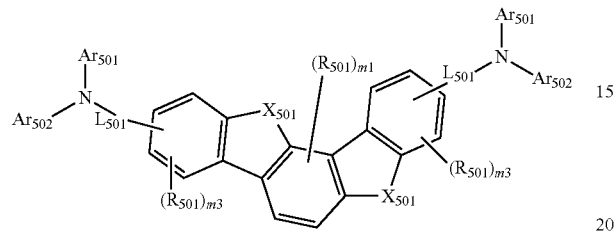
wherein in the formulas (51-1) to (51-6), $R_{501}$, $X_{501}$, $Ar_{501}$, $Ar_{502}$, $L_{501}$, m1 and m3 are as defined in the formula (51).
In one embodiment, the compound represented by the formula (51) is represented by any one of the following formulas (51-11) to (51-13).
(51-11)
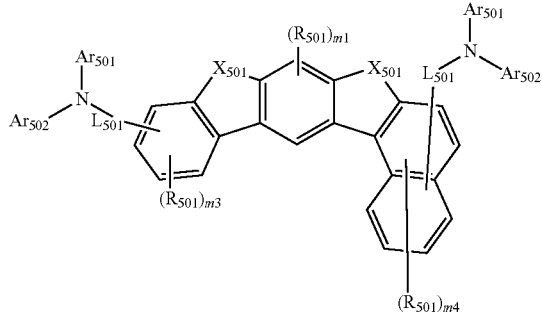
(51-12)
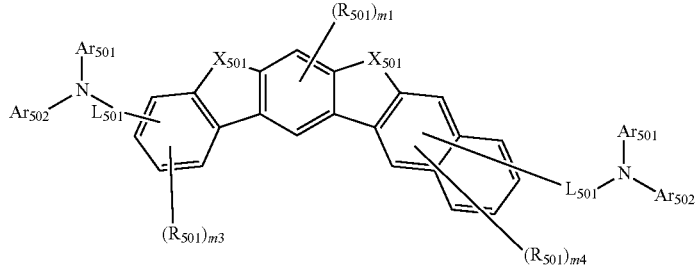
(51-13)
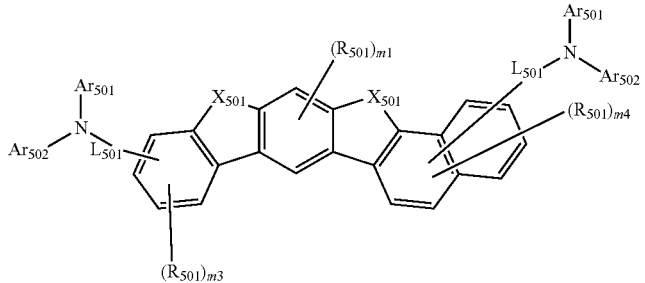
wherein in the formulas (51-11) to (51-13), $R_{501}$, $X_{501}$, $Ar_{501}$, $Ar_{502}$, $L_{501}$, m1, m3 and m4 are as defined in the formula (51).

In one embodiment, the compound represented by the formula (51) is represented by any one of the following formulas (51-21) to (51-25).
(51-21)
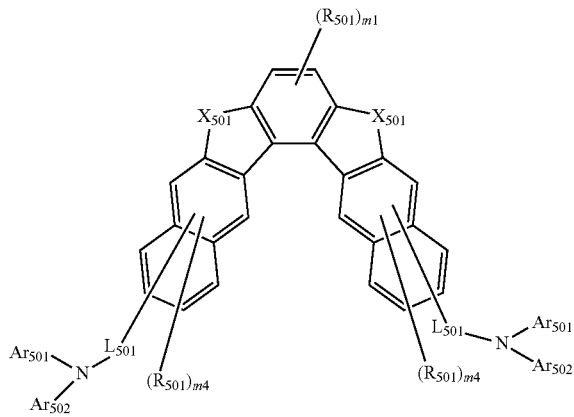
(51-22)
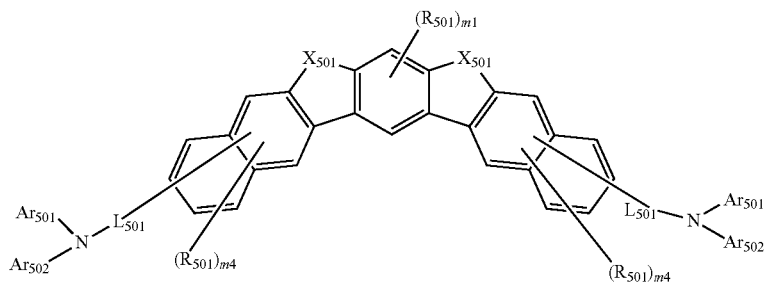
(51-23)
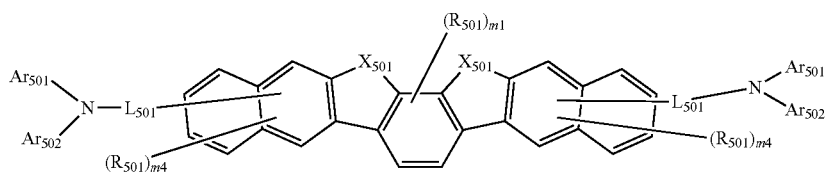
(51-24)
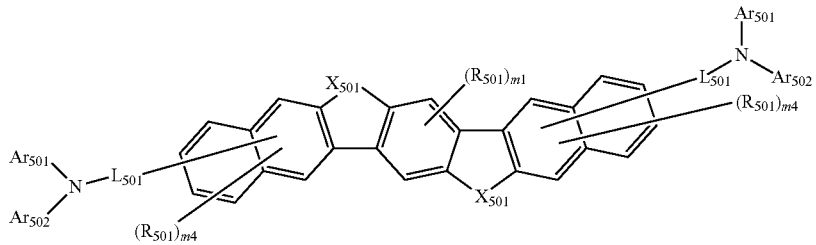
(51-25)
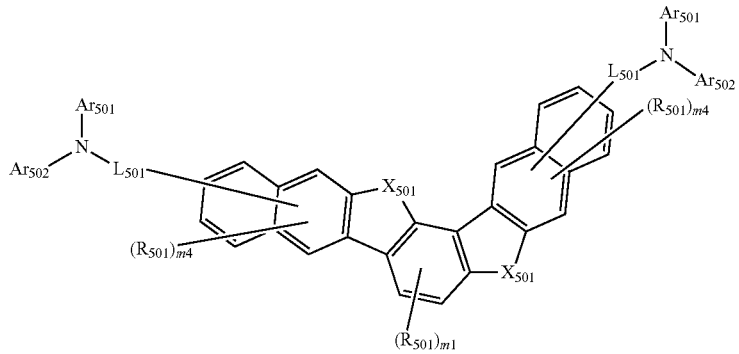
wherein in the formulas (51-21) to (51-25), $R_{501}$, $X_{501}$, $Ar_{501}$, $Ar_{502}$, $L_{501}$, m1 and m4 are as defined in the formula (51).

In one embodiment, the compound represented by the formula (51) is represented by any one of the following formulas (51-31) to (51-33).

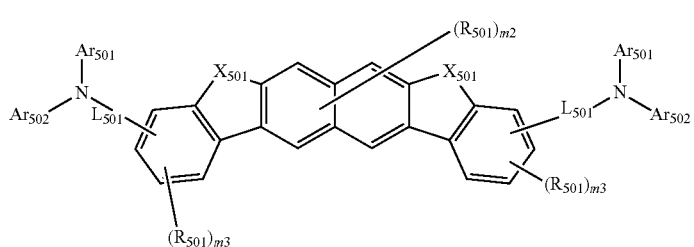

(51-31)

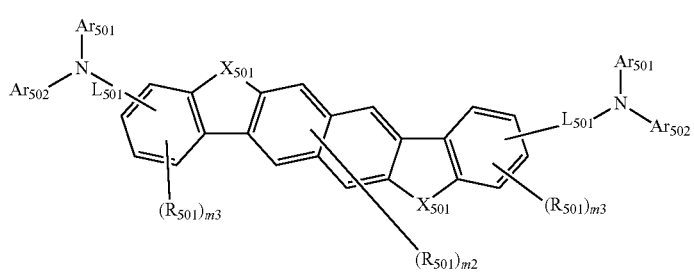

(51-32)

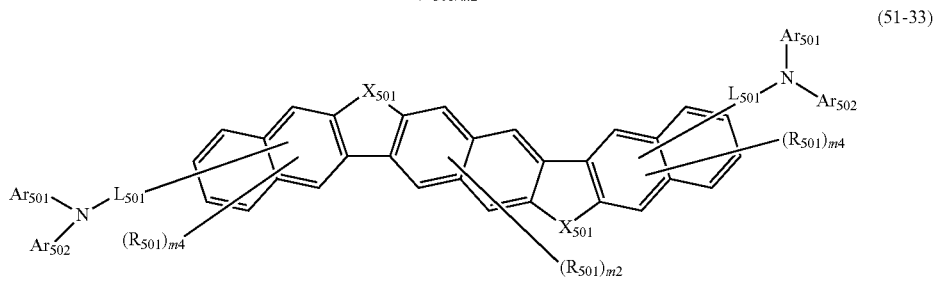

(51-33)

wherein in the formulas (51-31) to (51-33), $R_{501}$, $X_{501}$, $Ar_{501}$, $Ar_{502}$, $L_{501}$, m2 to m4 are as defined in the formula (51).

In one embodiment, $Ar_{501}$ and $Ar_{502}$ are independently a substituted or unsubstituted aryl group having 6 to 50 ring carbon atoms.

In one embodiment, one of $Ar_{501}$ and $Ar_{502}$ is a substituted or unsubstituted aryl group having 6 to 50 ring carbon atoms and the other is a substituted or unsubstituted monovalent heterocyclic ring having 5 to 50 ring atoms.

As examples of the compound represented by the formula (51), the following compounds can be given, for example. In the following example compounds, Me represents methyl group.

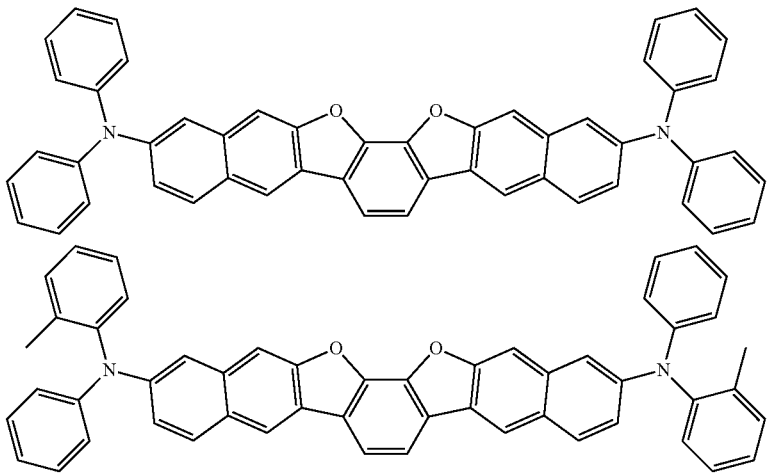

-continued
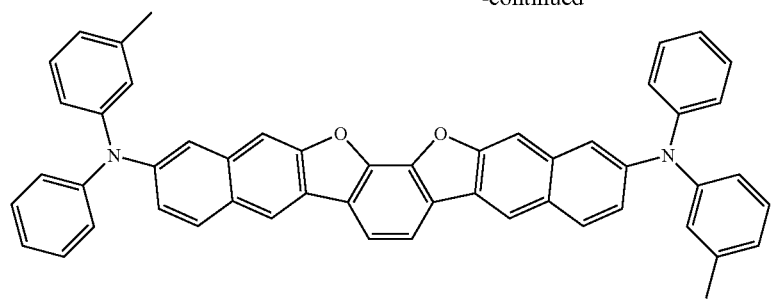
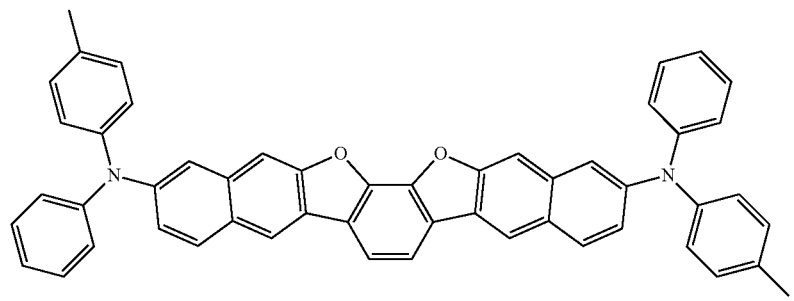
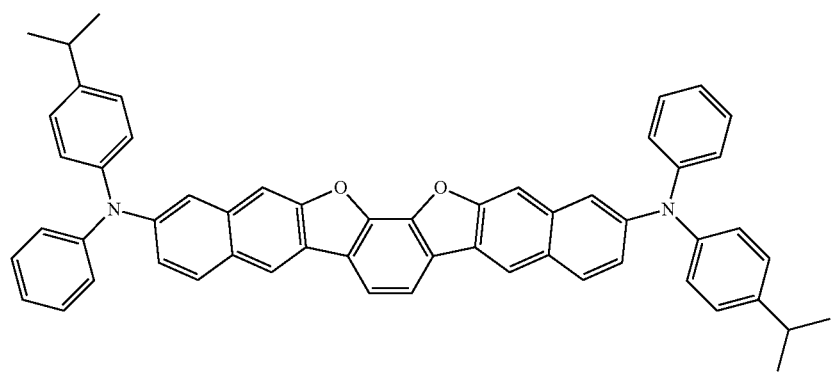
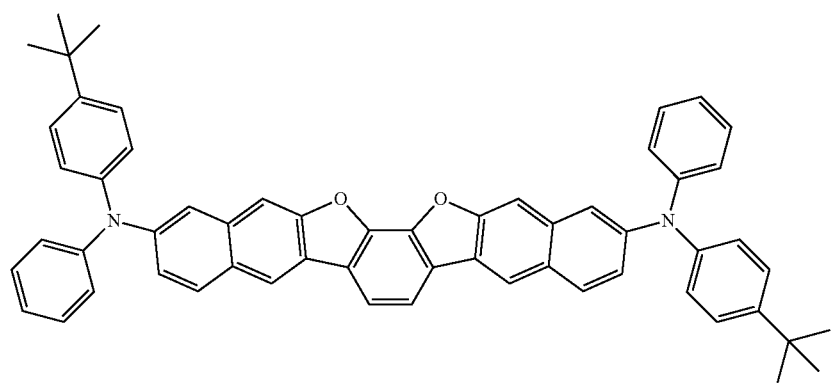
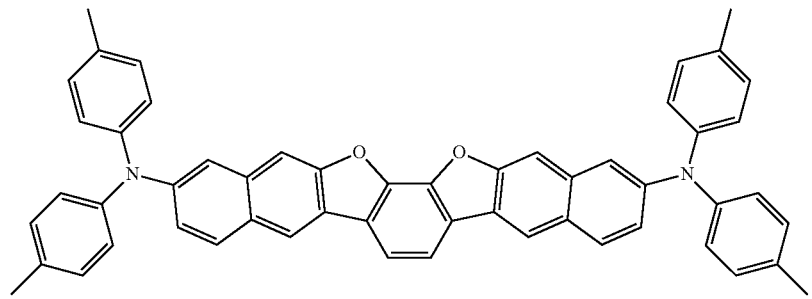

-continued
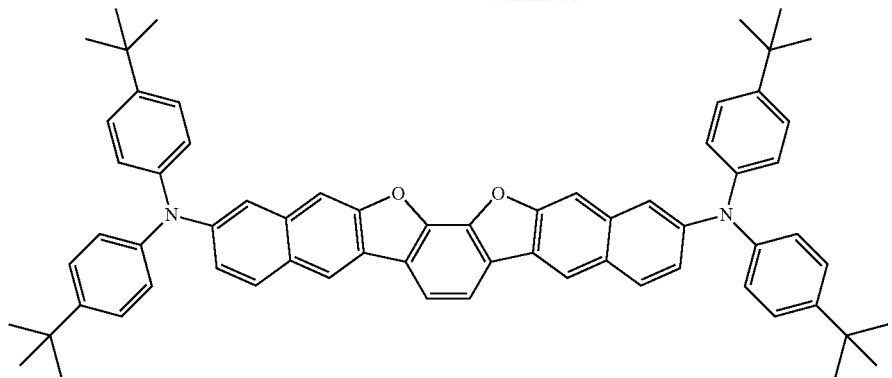
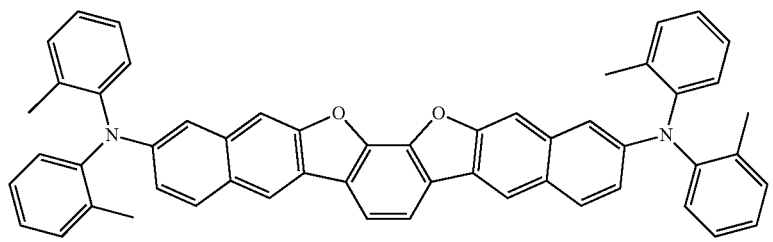
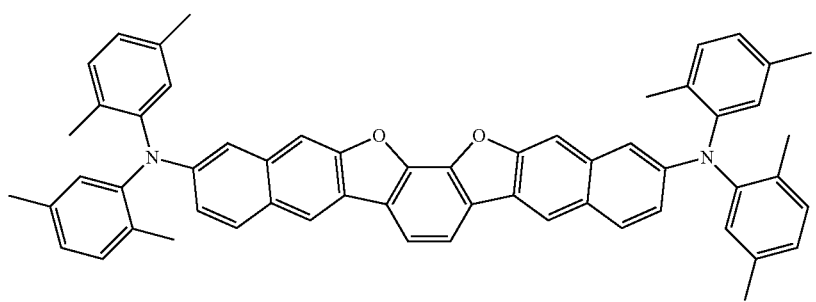
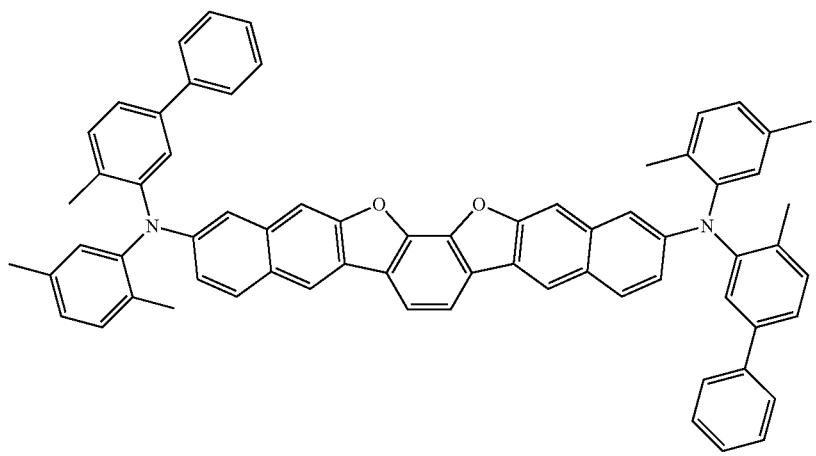

-continued
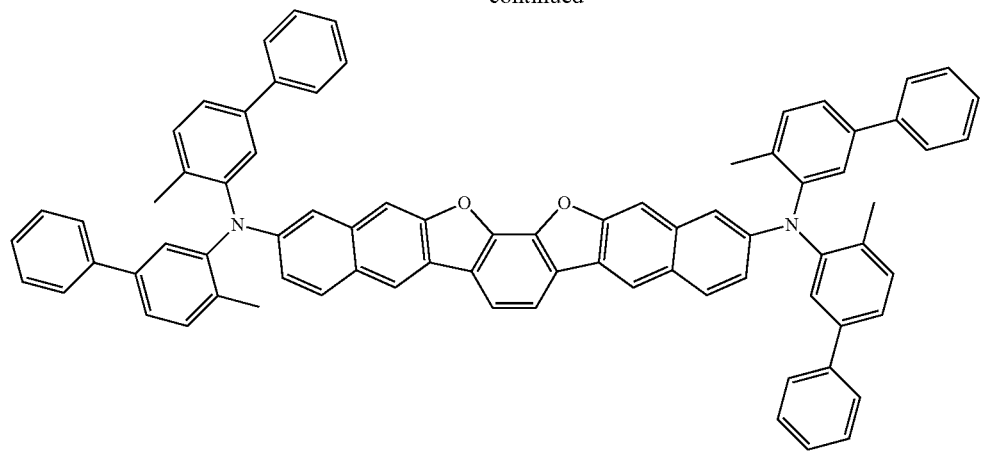
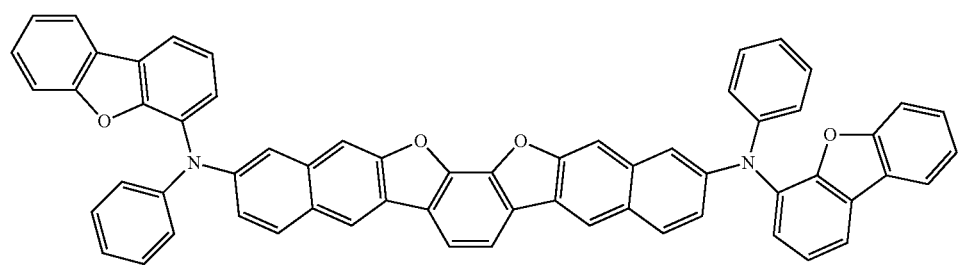
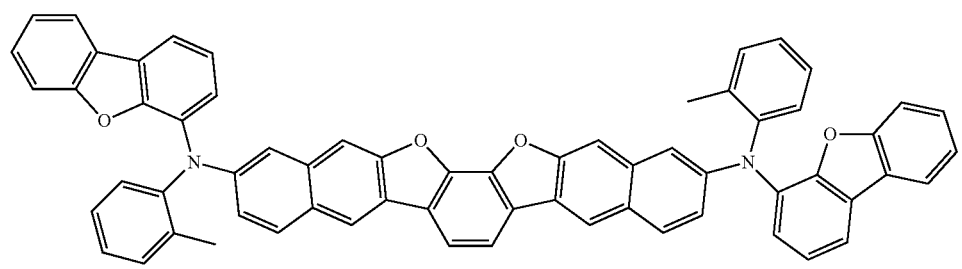
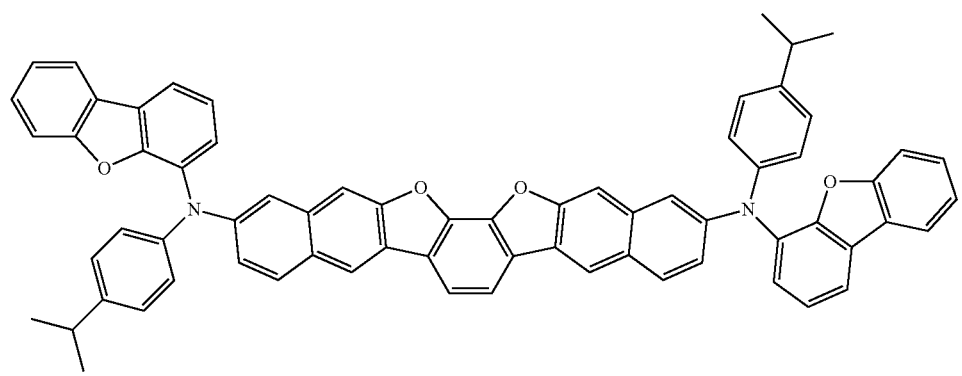
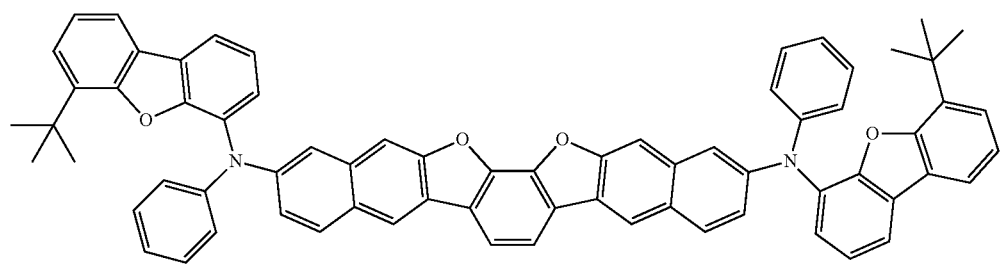

723 724
-continued
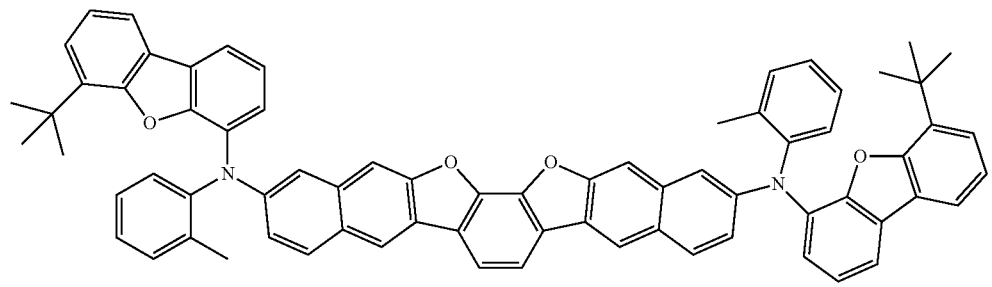
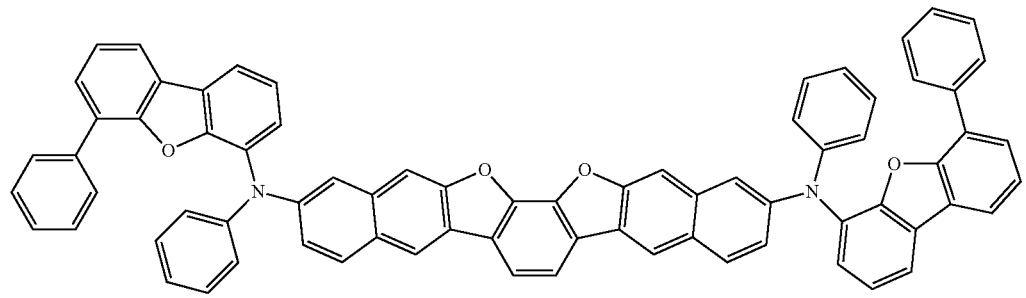
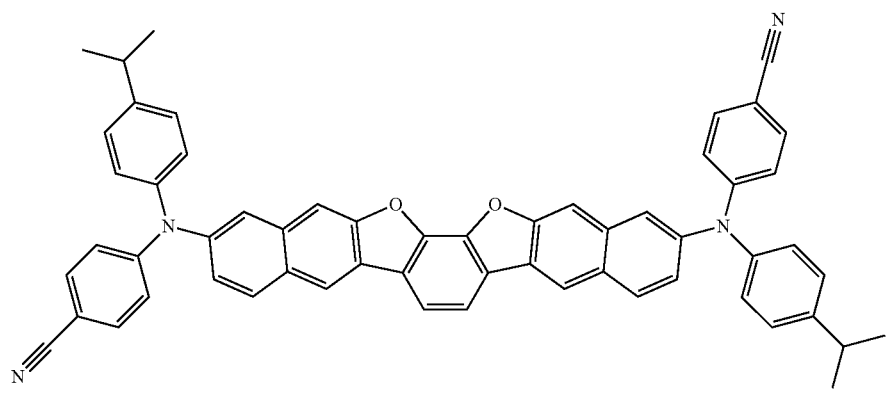
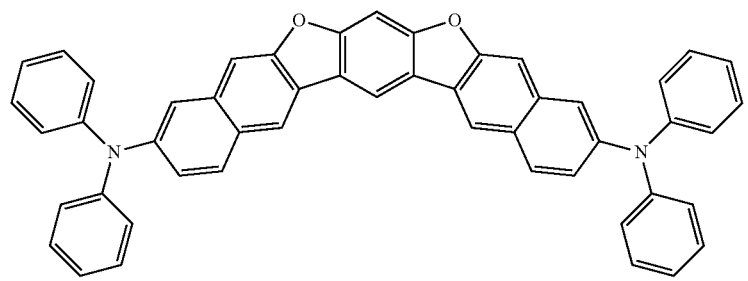
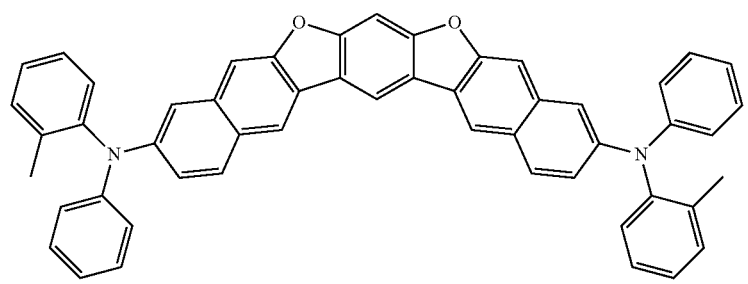

-continued
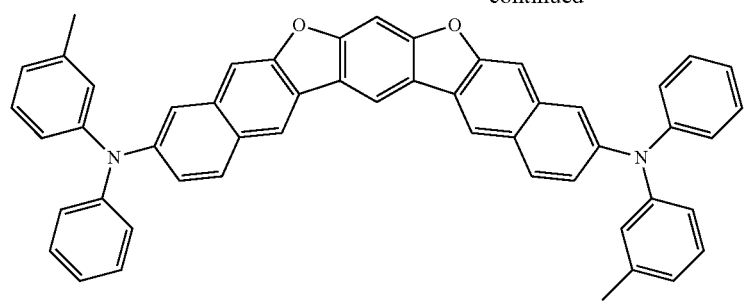
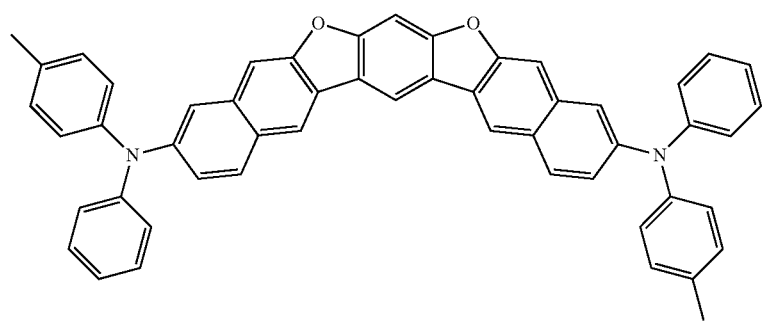
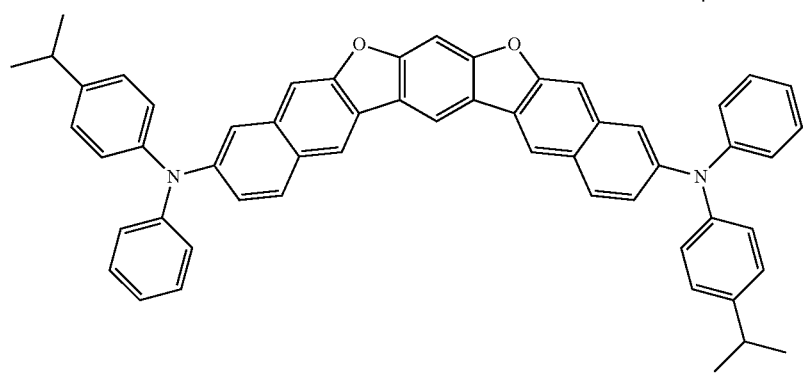
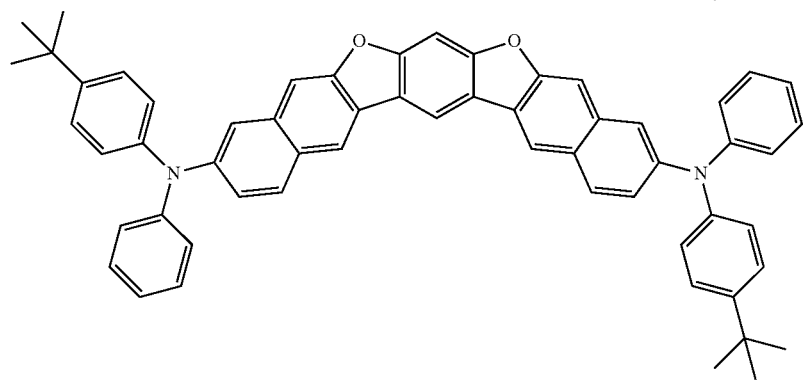
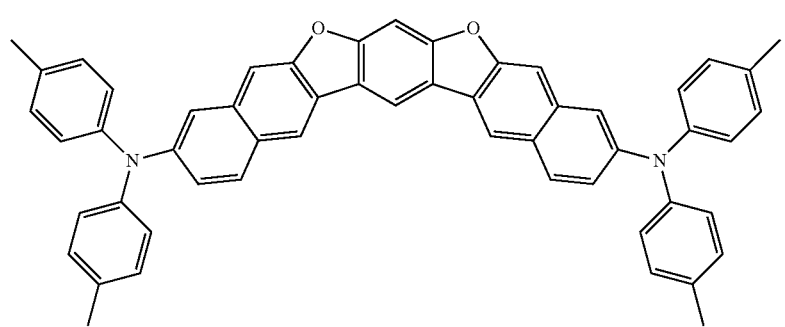

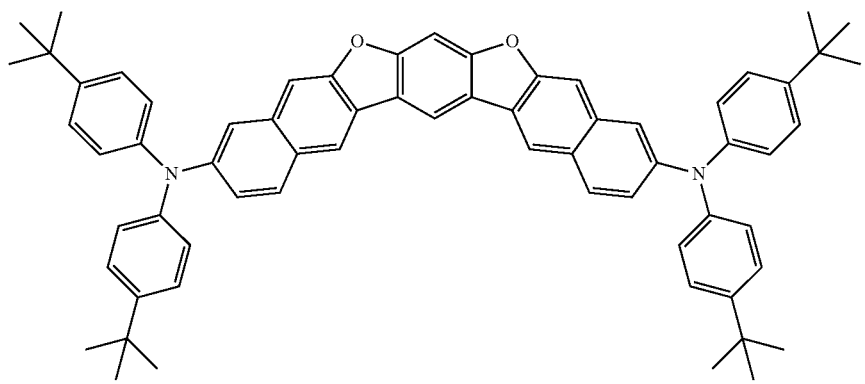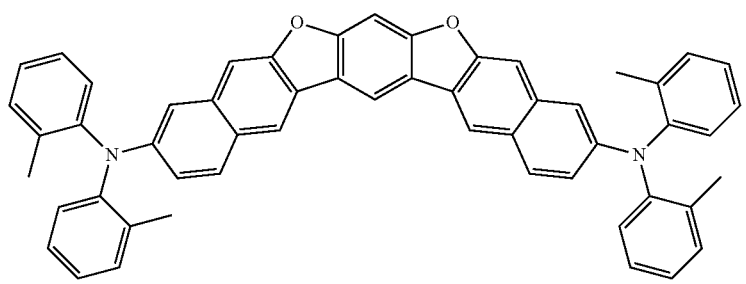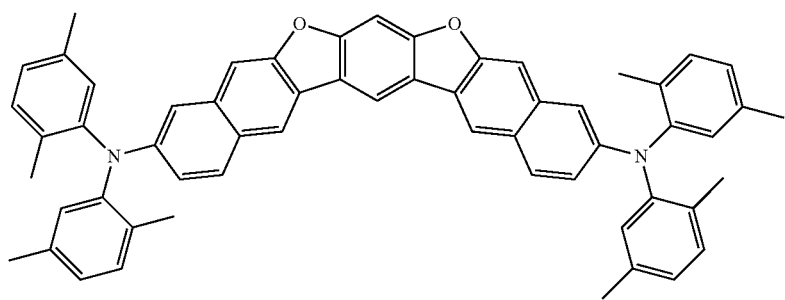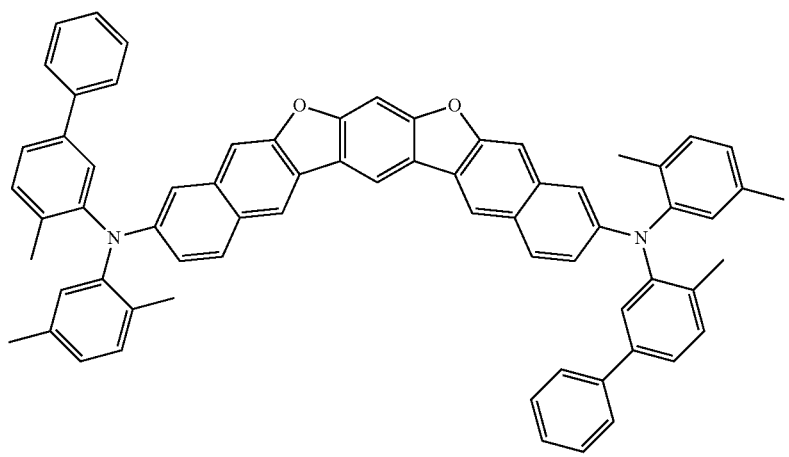

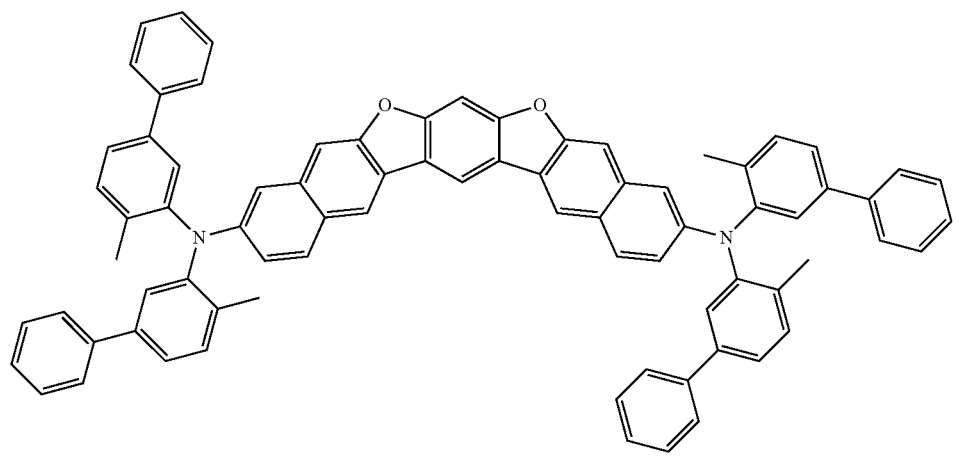
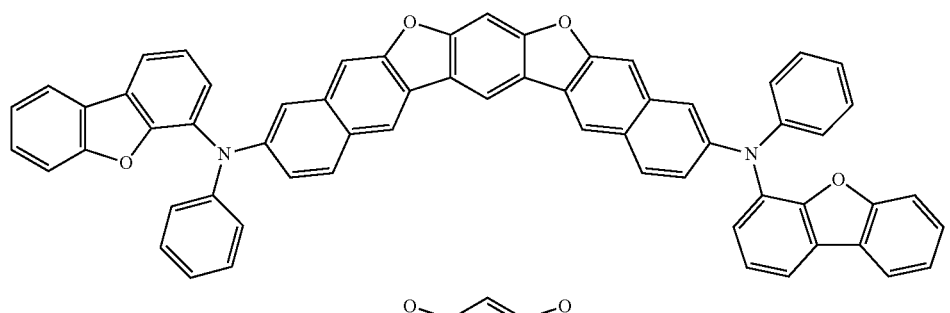
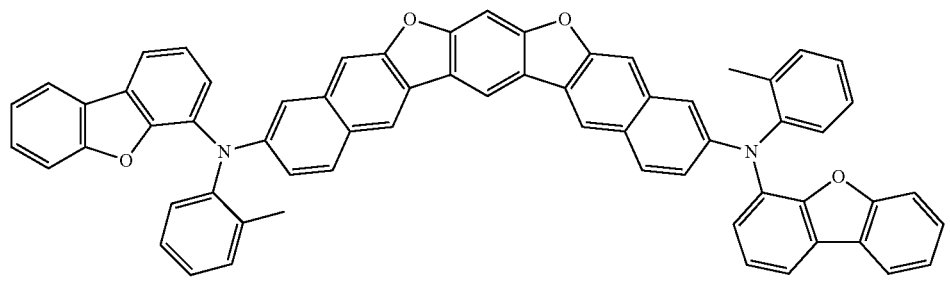
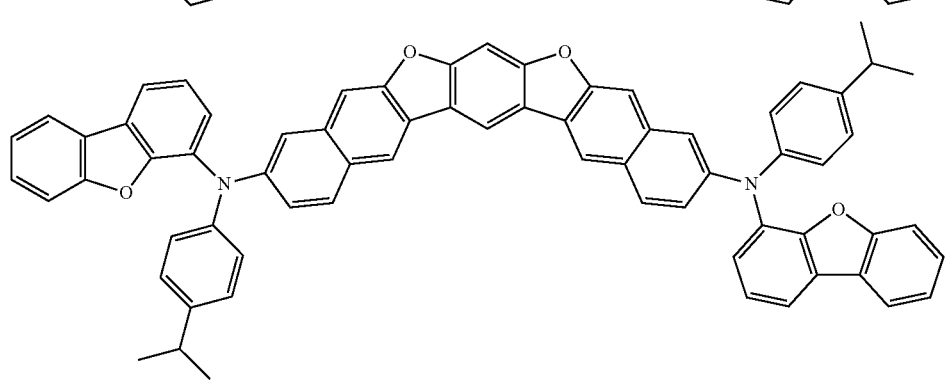
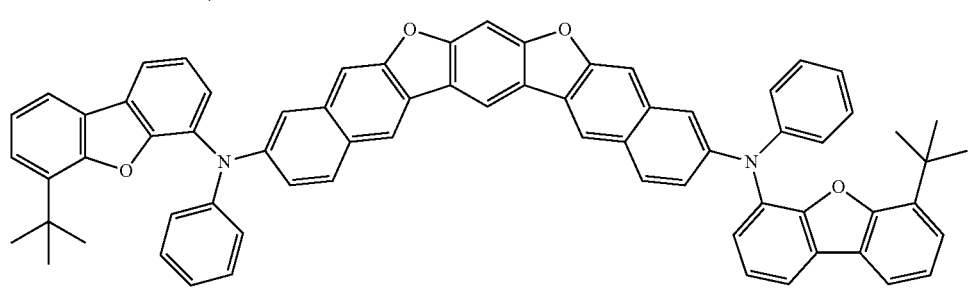

-continued
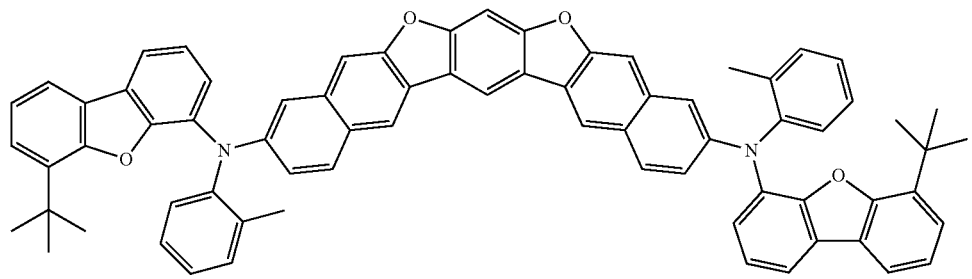
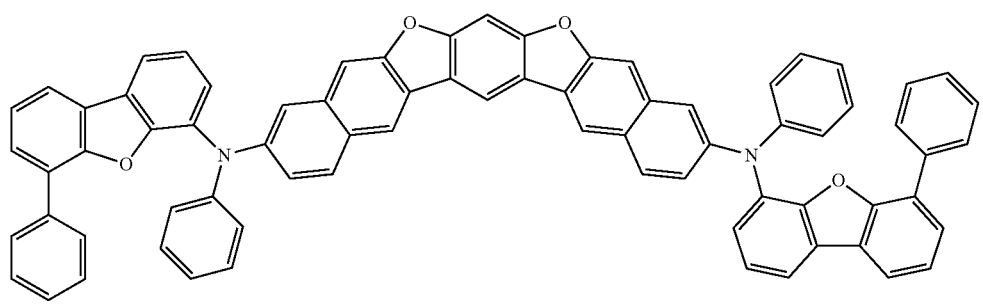
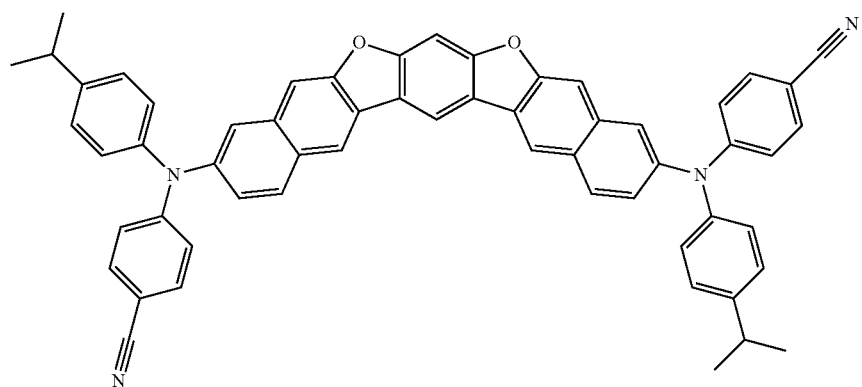
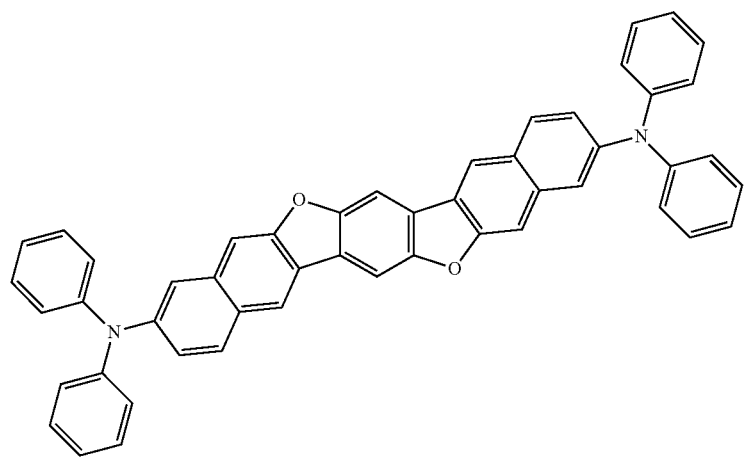

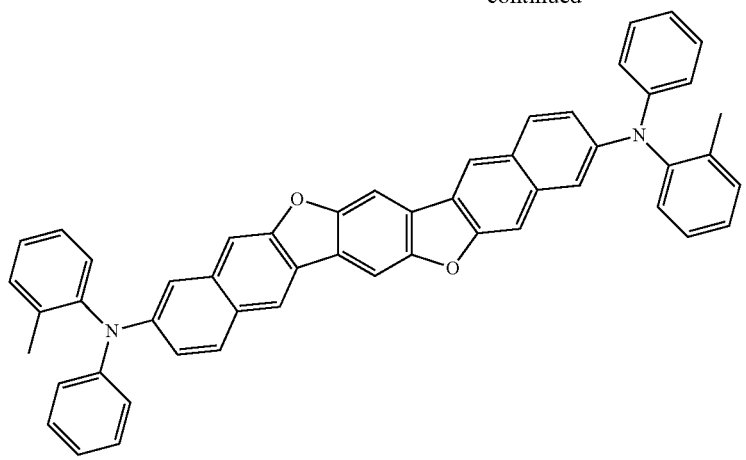
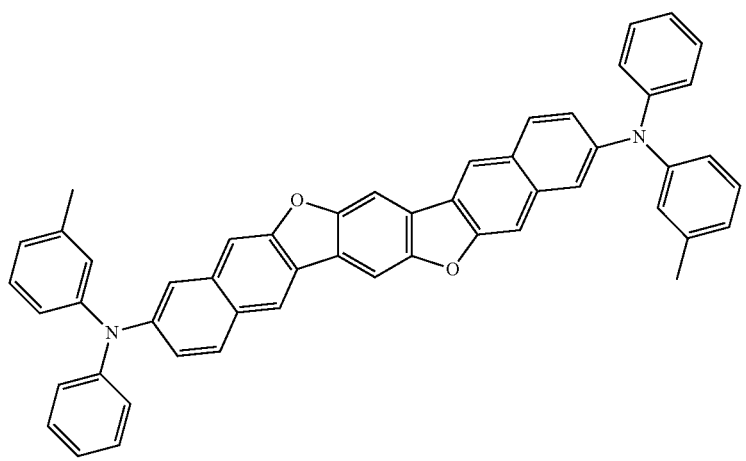
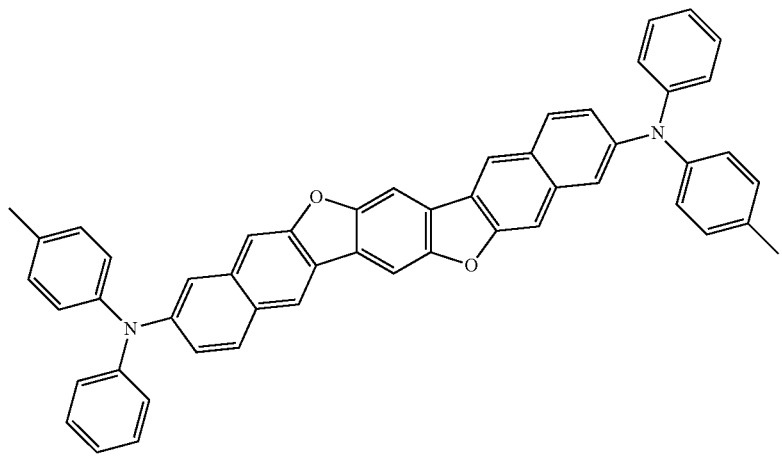

-continued
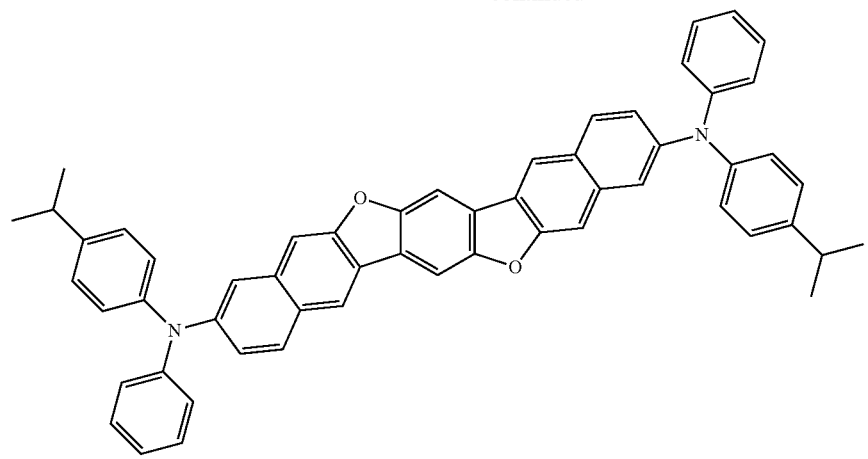
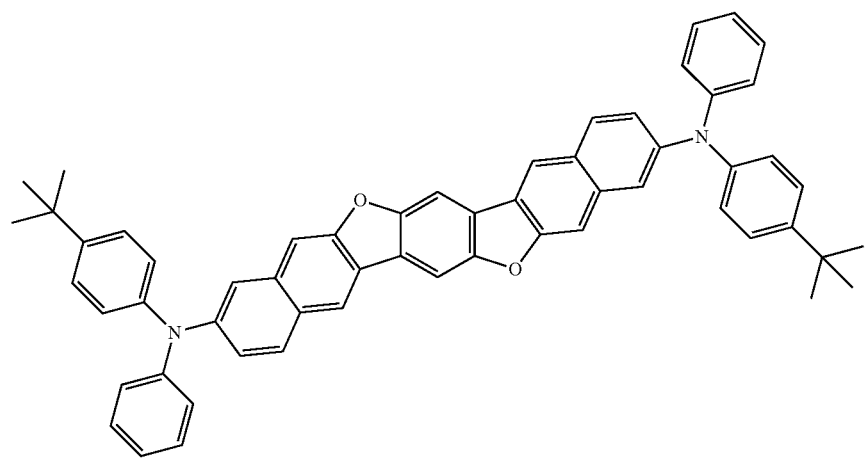
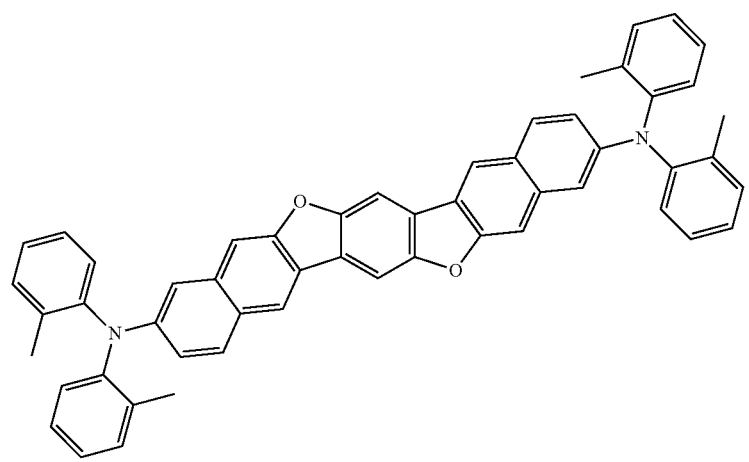

-continued
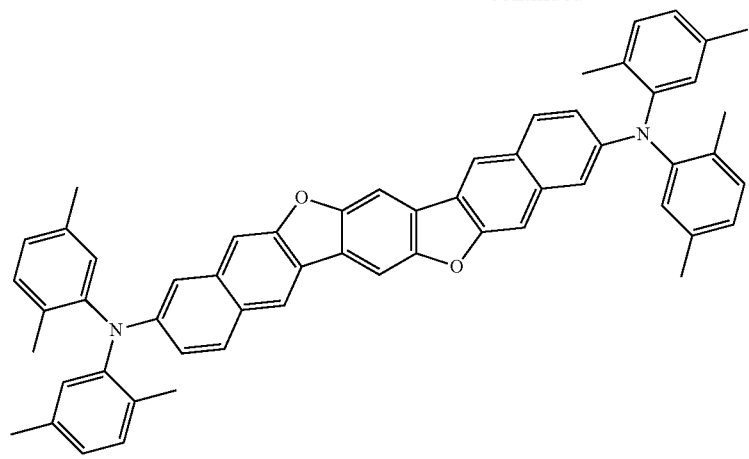
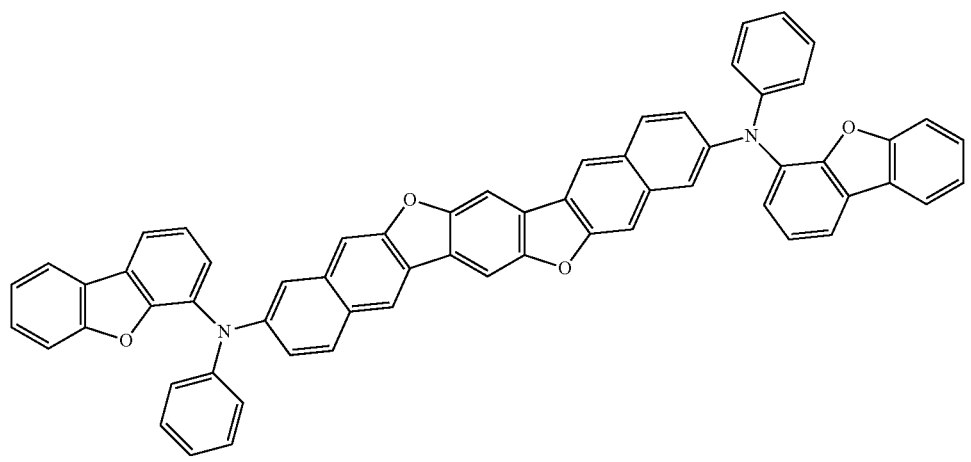
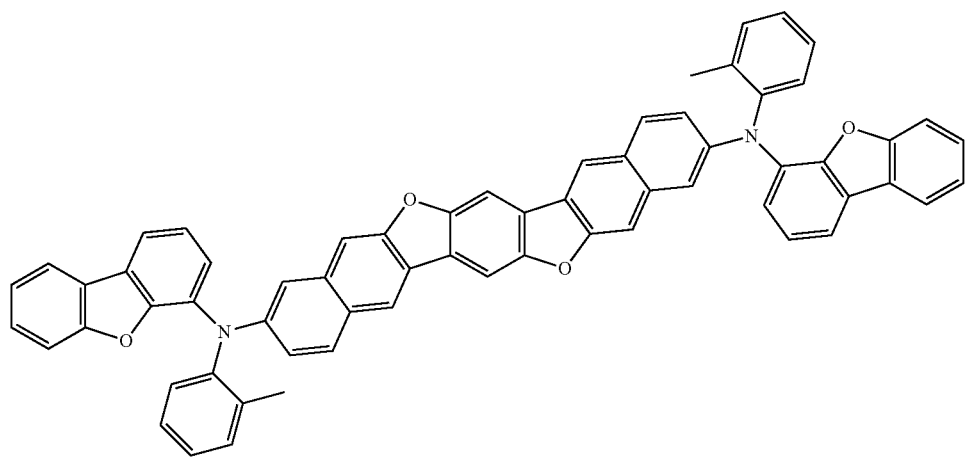 [SMILES: Cc1ccccc1N(c1ccc2cc3c(cc2c1)oc1cc2c(cc13)oc1cc3cc(N(c4ccccc4C)c4cccc5c4oc4ccccc45)ccc3cc12)c1cccc2c1oc1ccccc12]

739 740
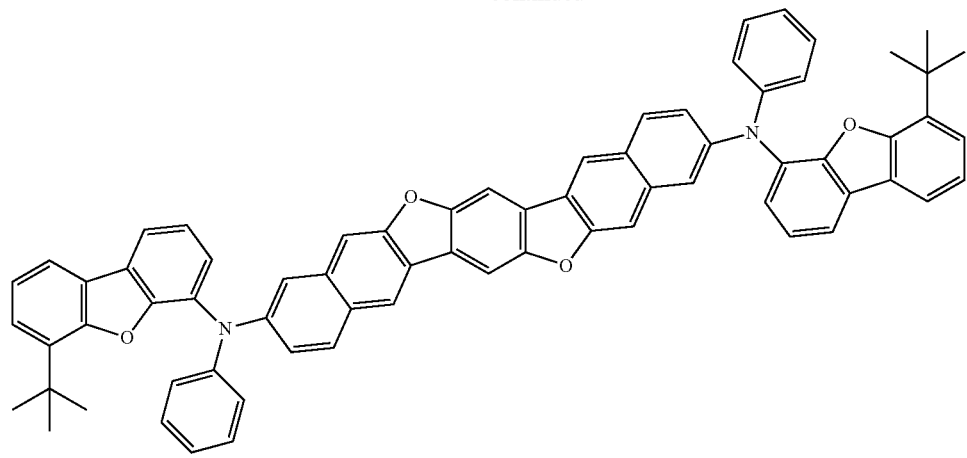
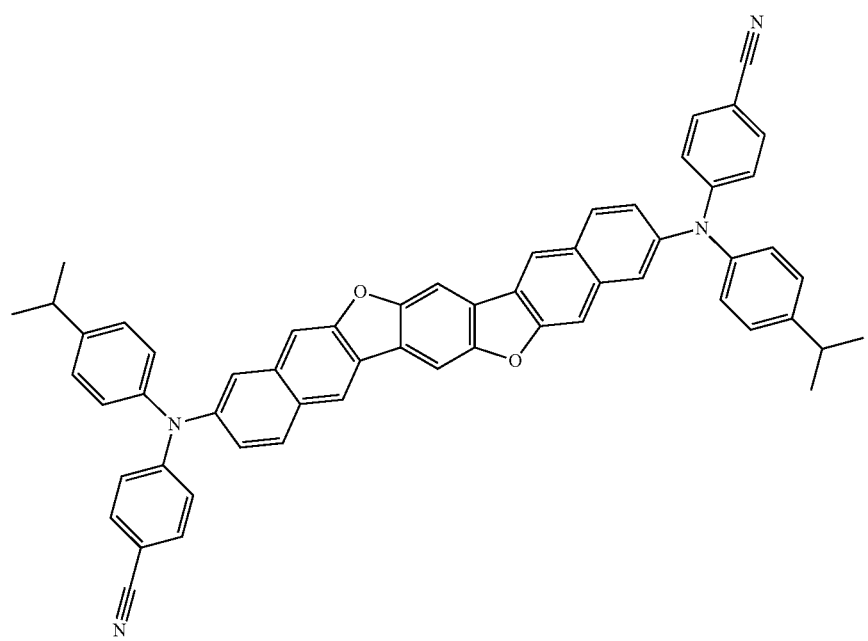
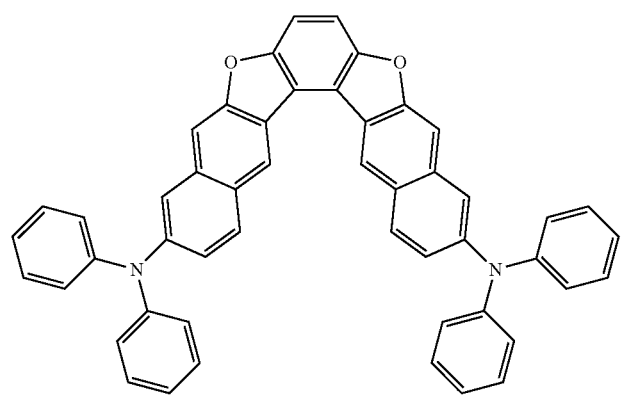

741
-continued
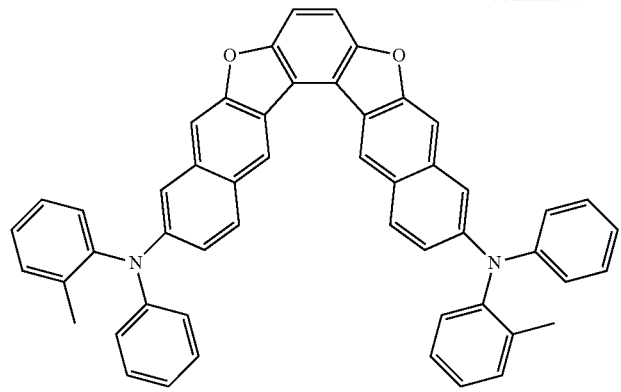
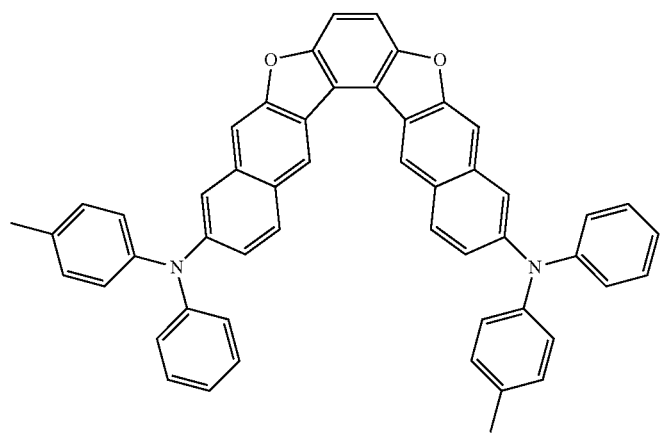
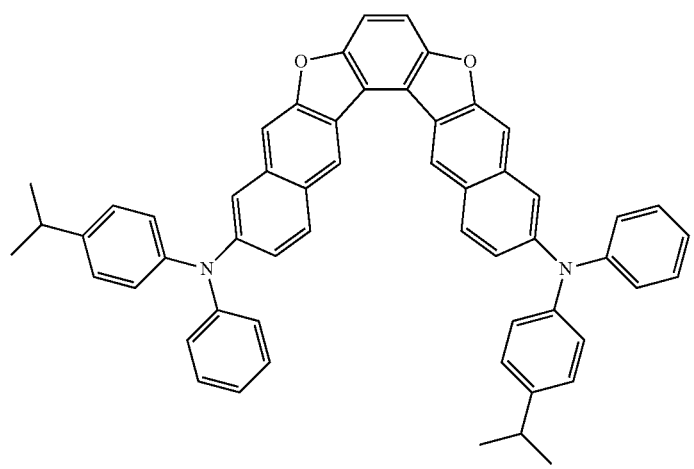
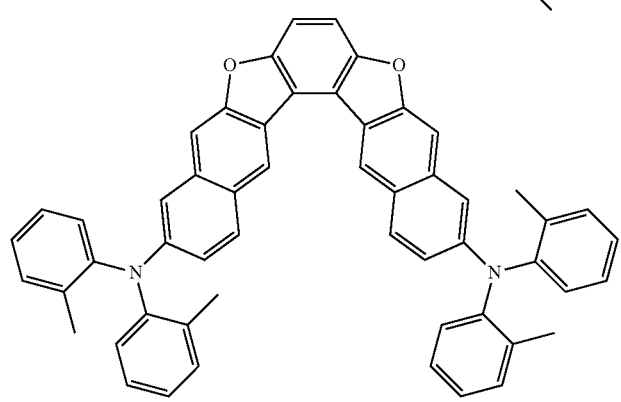
742

-continued
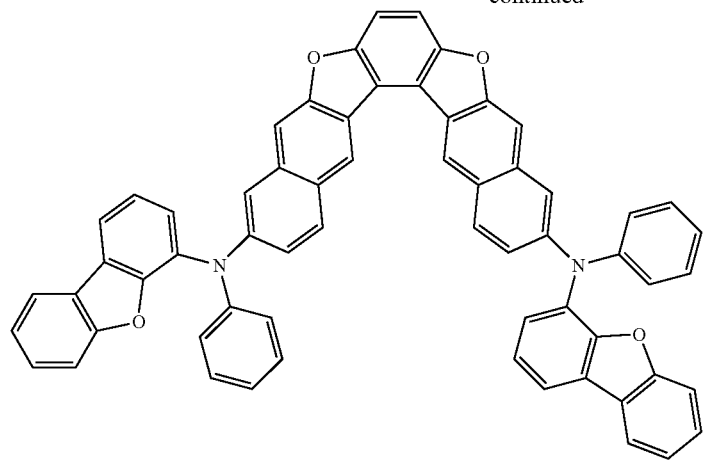
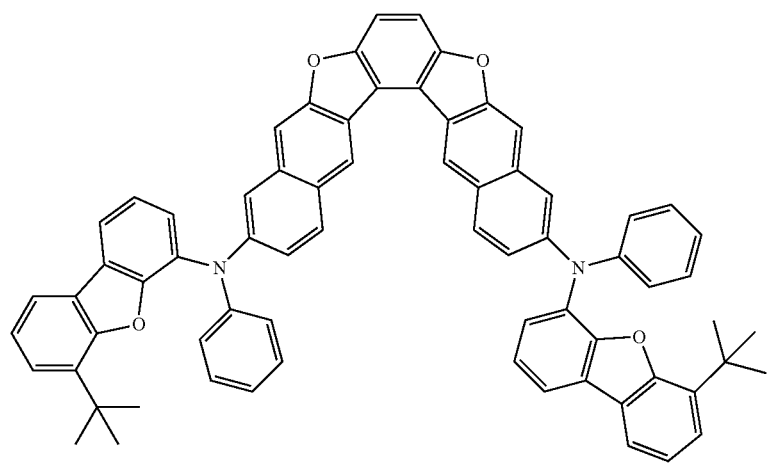
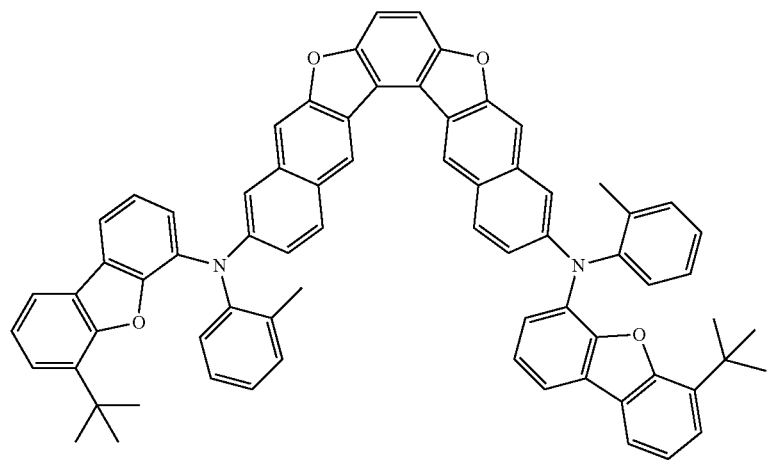

-continued
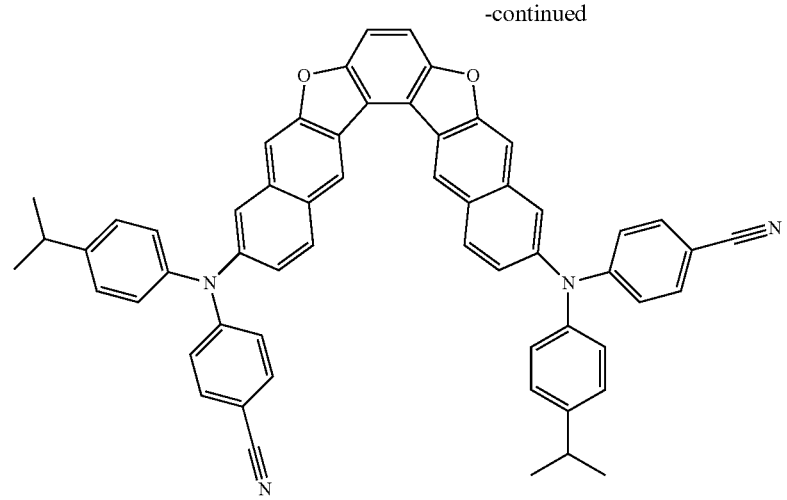
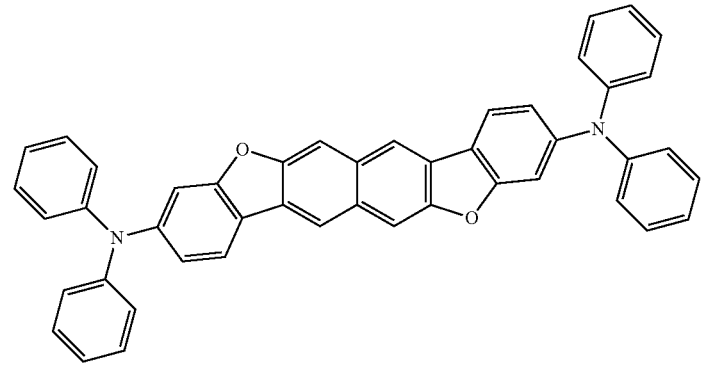
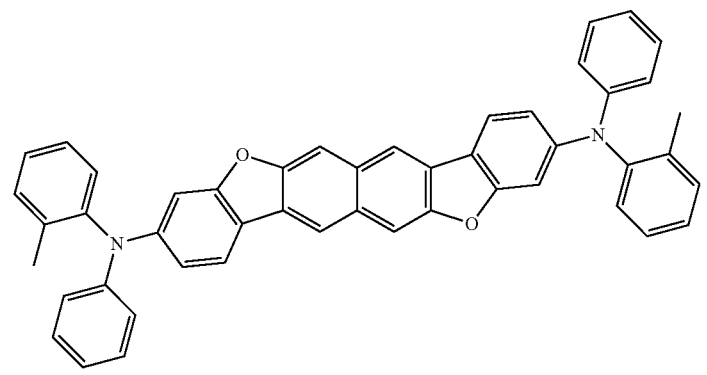
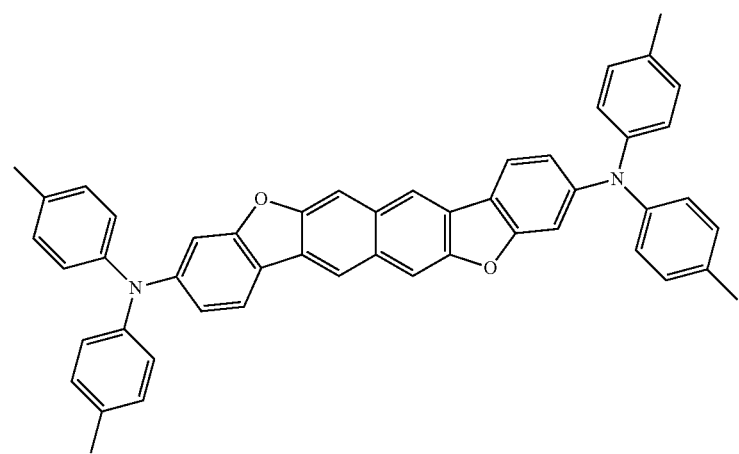

-continued
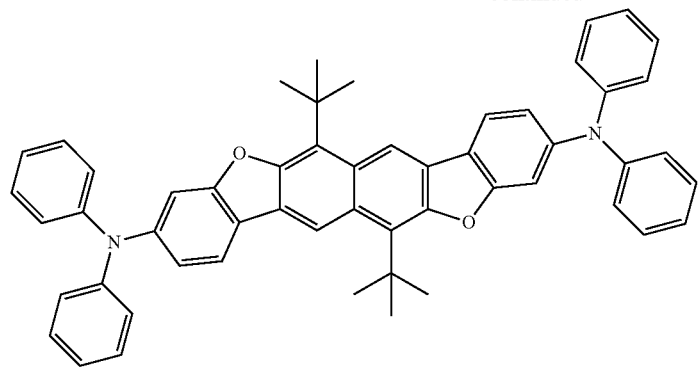
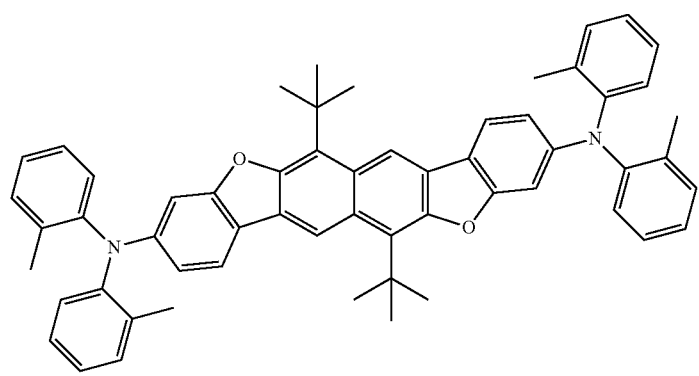
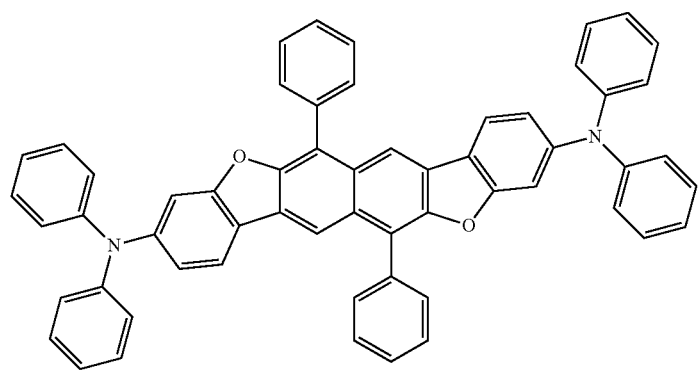
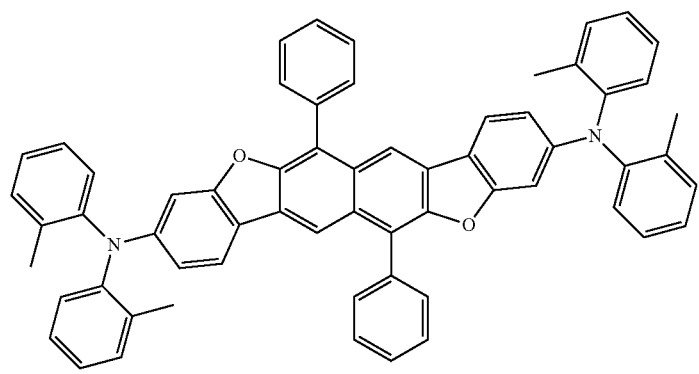

-continued
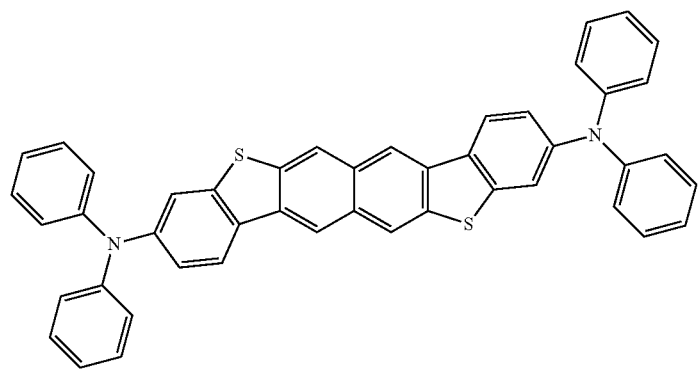
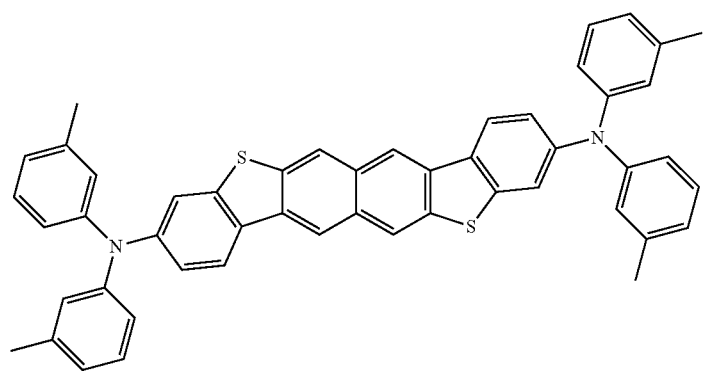
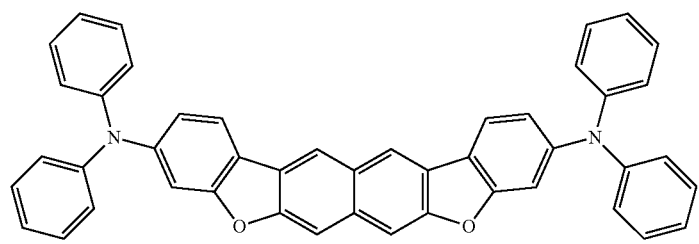
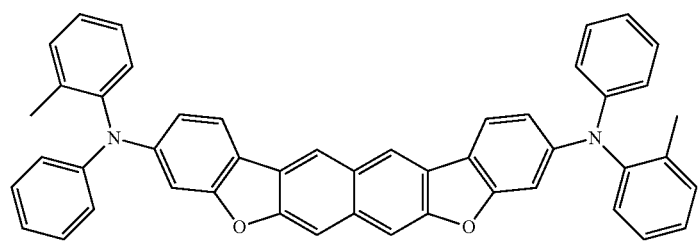
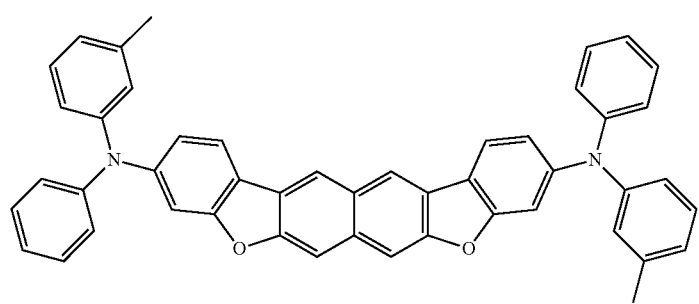

-continued
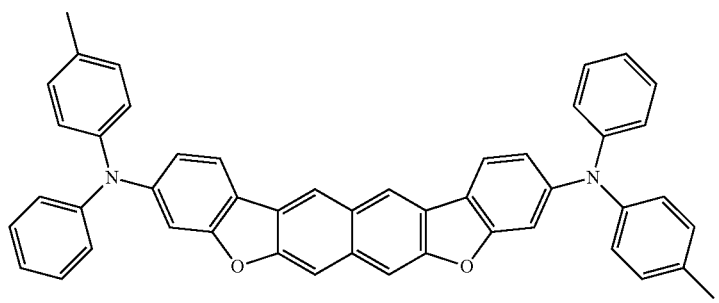
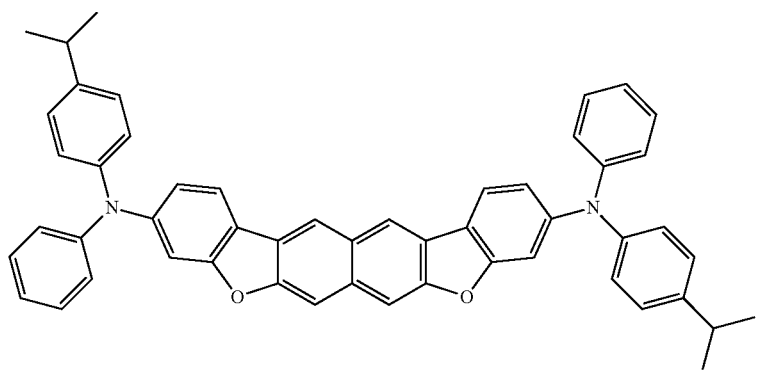
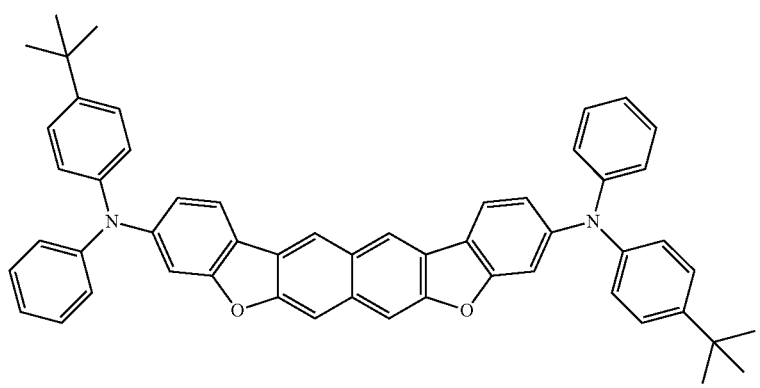
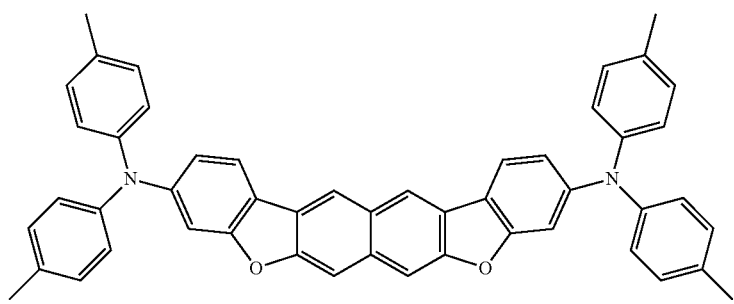
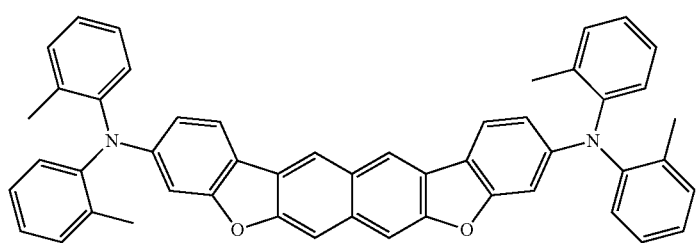

-continued
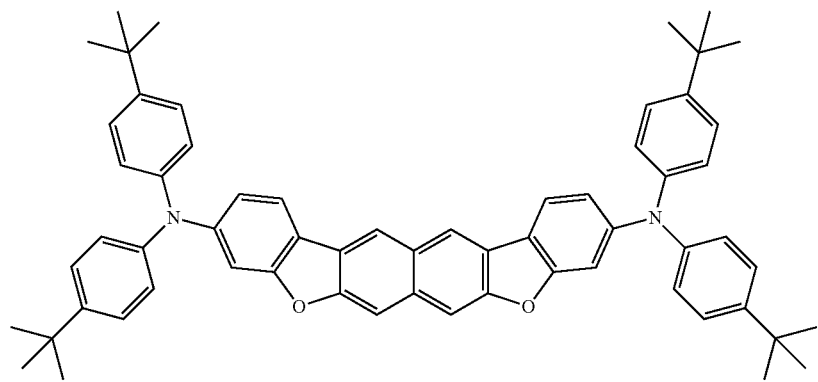
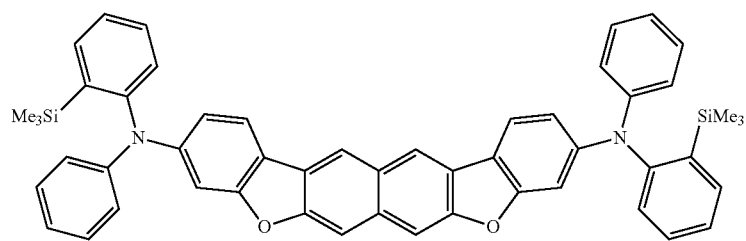
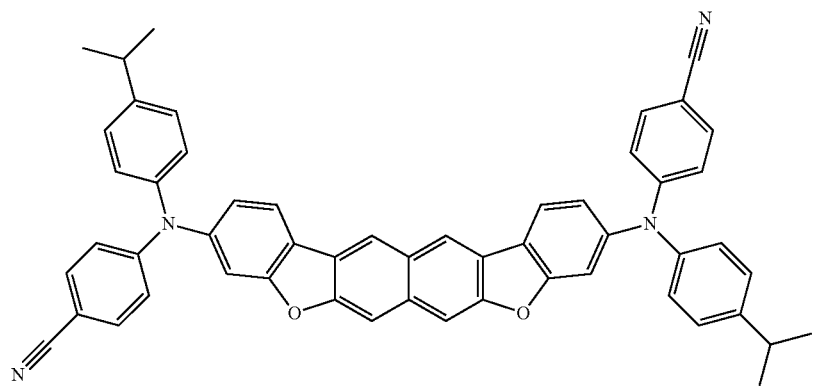
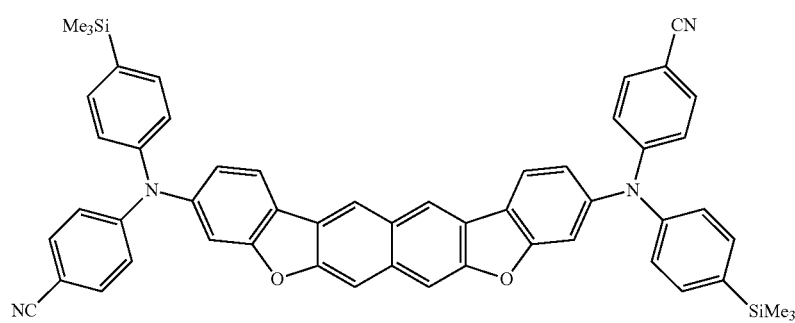
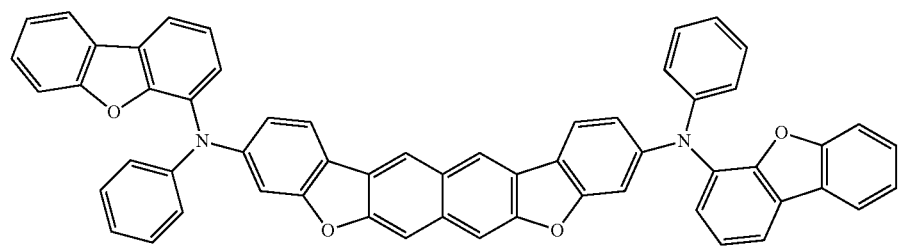

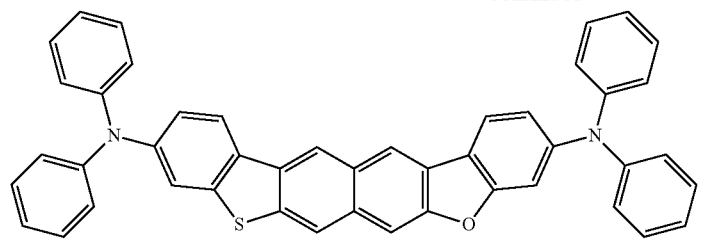
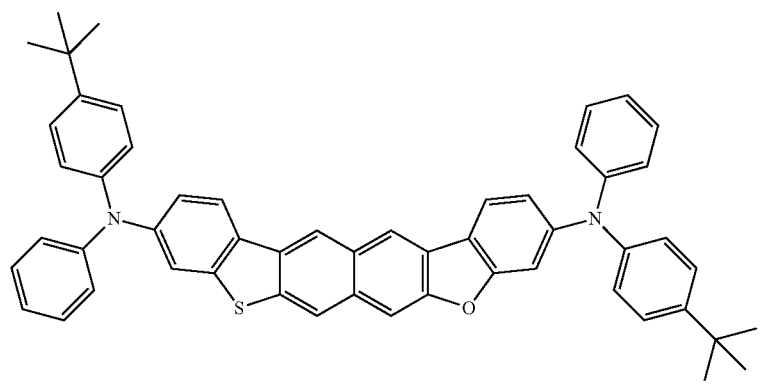
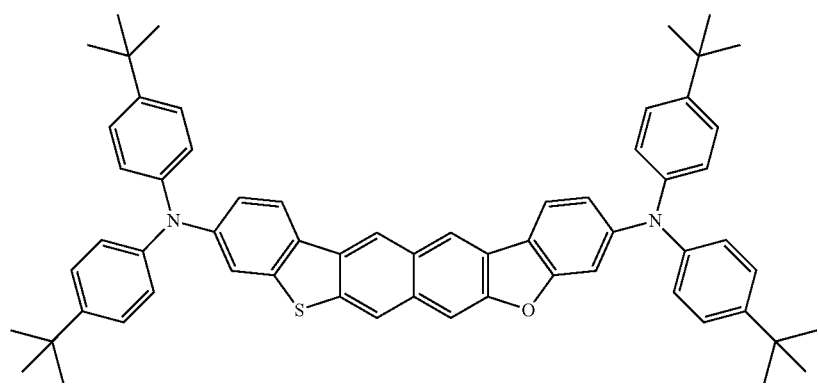
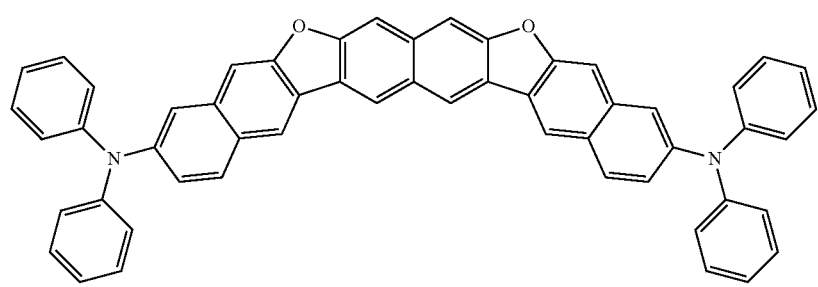
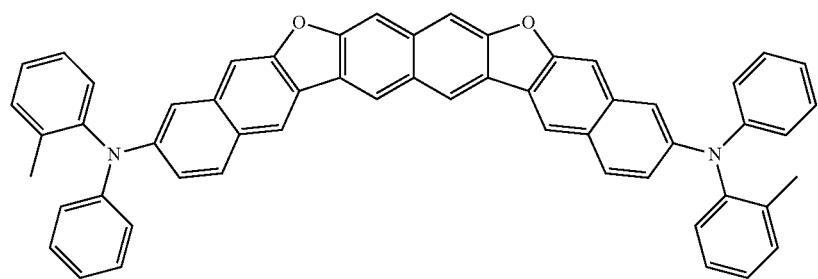

-continued
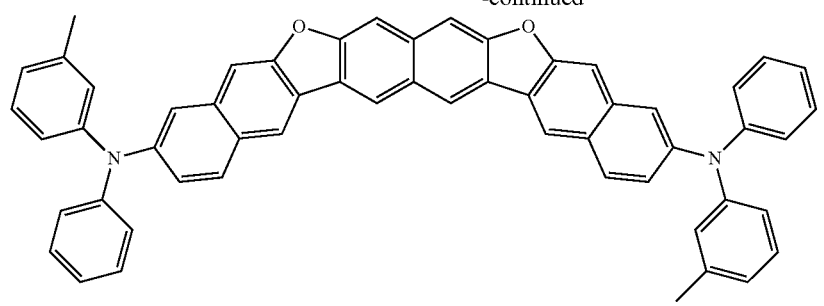
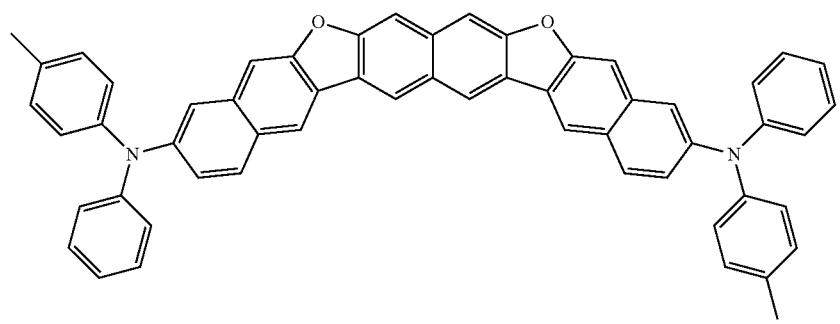
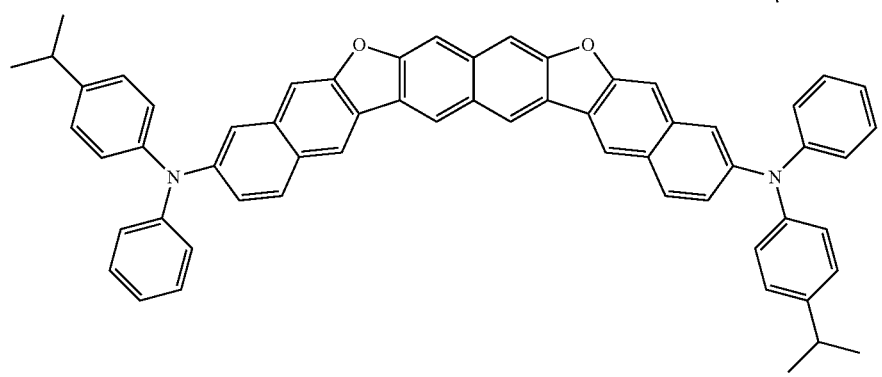
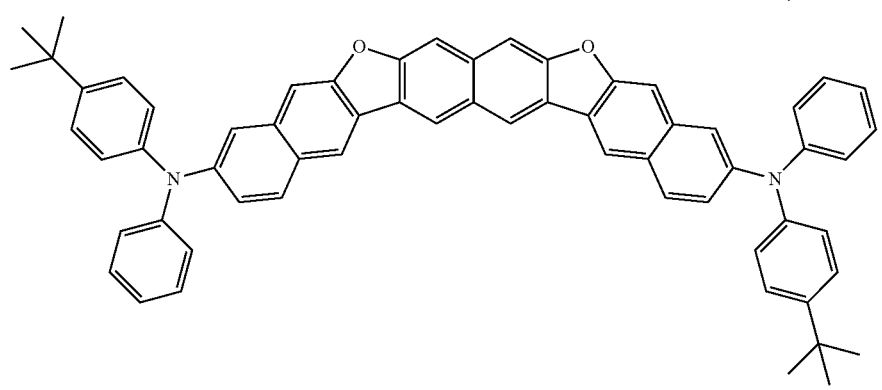
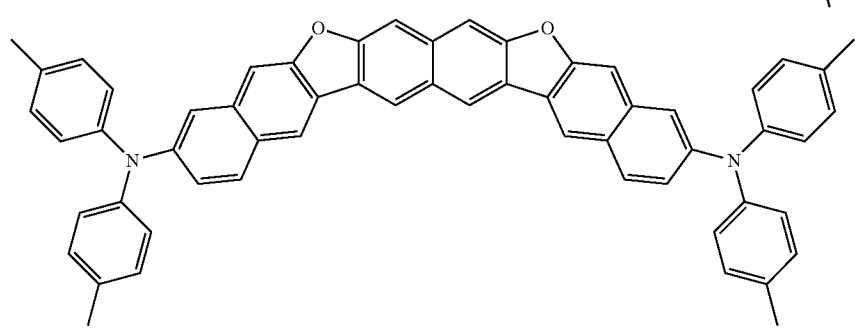

-continued
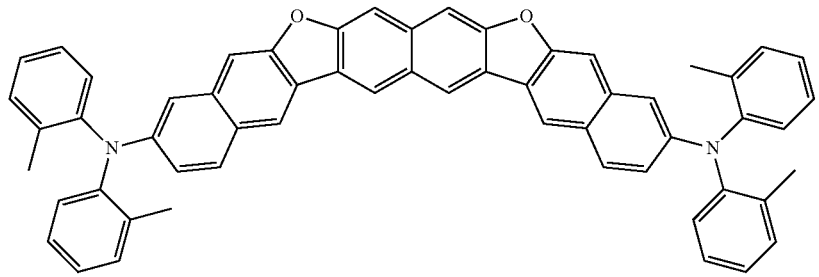
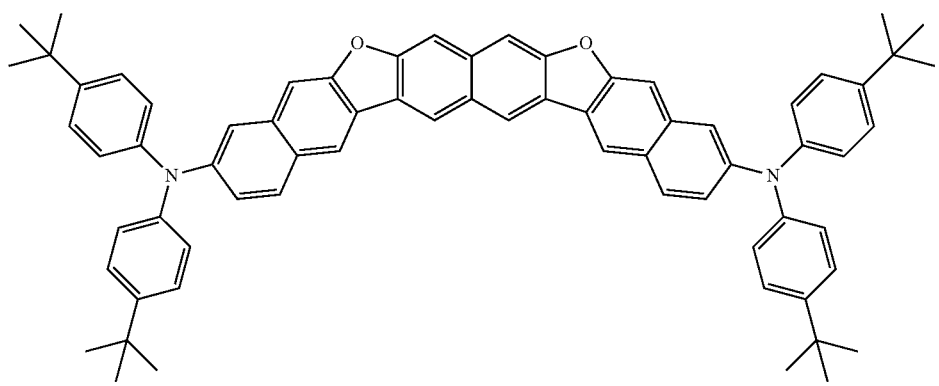
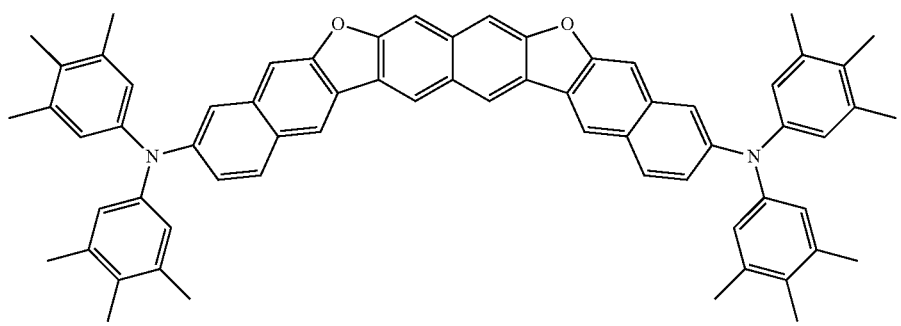
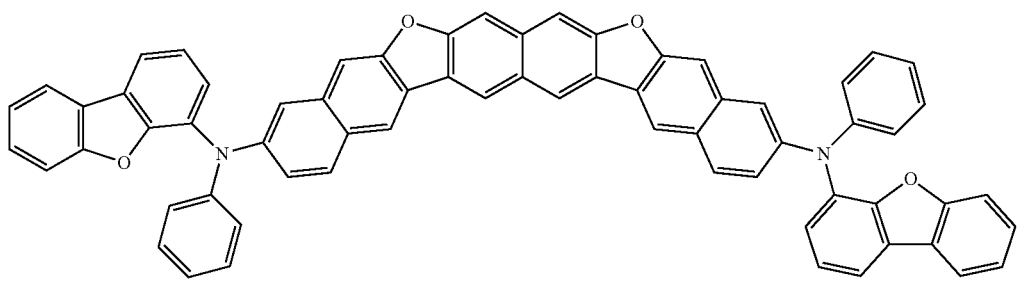
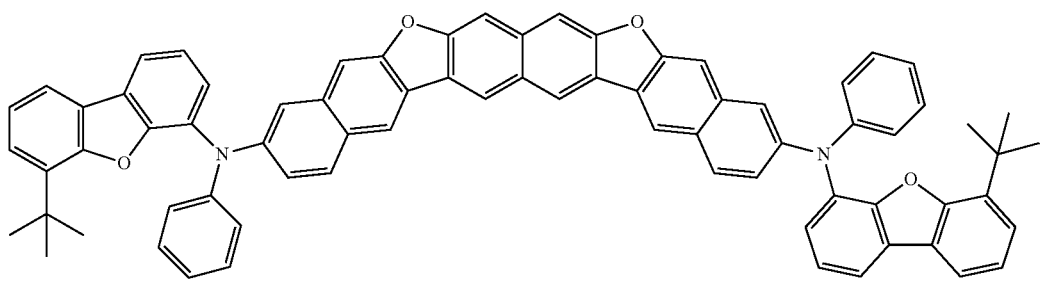

(Compound Represented by Formula (61))

The compound represented by the formula (61) is explained below.

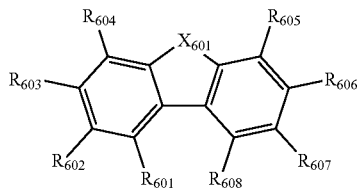
(61)

wherein, in the formula (61), at least one pair of $R_{601}$ and $R_{602}$, $R_{602}$ and $R_{603}$, and $R_{603}$ and $R_{604}$ are bonded with each other to form a divalent group represented by the formula (62);

at least one pair of $R_{605}$ and $R_{606}$, $R_{606}$ and $R_{607}$, and $R_{607}$ and $R_{608}$ are bonded with each other to form a divalent group represented by formula (63);

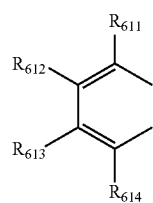
(62)

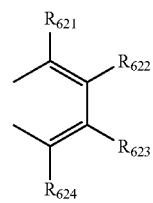
(63)

at least one of $R_{601}$ to $R_{604}$ that does not form the divalent group represented by the formula (62), and $R_{611}$ to $R_{614}$ is a monovalent group represented by the following formula (64);

at least one of $R_{605}$ to $R_{608}$ that do not form the divalent group represented by the formula (63), and $R_{621}$ to $R_{624}$ is a monovalent group represented by the following formula (64);

$X_{601}$ is an oxygen atom, a sulfur atom, or $NR_{609}$;

$R_{601}$ to $R_{608}$ that do not form the divalent group represented by the formulas (62) and (63) and that is not the monovalent group represented by the formula (64), $R_{611}$ to $R_{614}$ and $R_{621}$ to $R_{624}$ that are not the monovalent group represented by the formula (64), and $R_{609}$ are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms;

$R_{901}$ to $R_{907}$ are as defined in the formula (1);

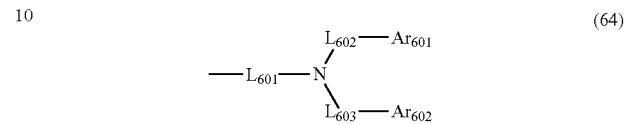
(64)

wherein, in the formula (64), $Ar_{601}$ and $Ar_{602}$ are independently a substituted or unsubstituted aryl group having 6 to 50 ring carbon atoms, or a substituted or unsubstituted monovalent heterocyclic group having 5 to 50 ring atoms;

$L_{601}$ to $L_{603}$ are independently a single bonded, a substituted or unsubstituted arylene group having 6 to 30 ring carbon atoms, a substituted or unsubstituted divalent heterocyclic group having 5 to 30 ring atoms, or a divalent linking group formed by bonding 2 to 4 above mentioned groups;

In the formula (61), positions at which the divalent group represented by the formula (62) and the divalent group represented by the formula (63) are formed are not limited, and said groups can be formed at possible positions in $R_{601}$ to $R_{608}$.

In one embodiment, the compound represented by the formula (61) is represented by any one of the following formulas (61-1) to (61-6).

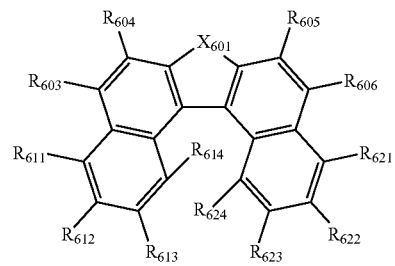
61-1

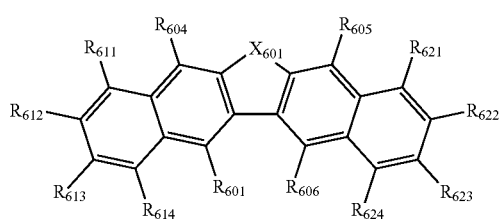
61-2

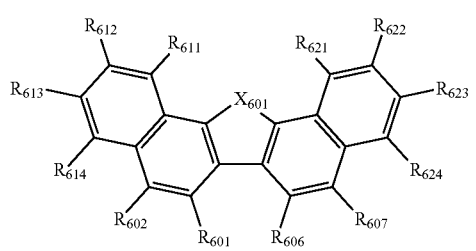
61-3 wherein in the formulas (61-1) to (61-6), $X_{601}$ is as defined in the formula (61);

at least two of $R_{601}$ to $R_{624}$ are monovalent groups represented by the formula (64);

$R_{601}$ to $R_{624}$ that are not monovalent groups represented by the formula (64) are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms; and $R_{901}$ to $R_{907}$ are as defined in the formula (1).

In one embodiment, the compound represented by the formula (61) is represented by any one of the following formulas (61-7) to (61-18).

-continued

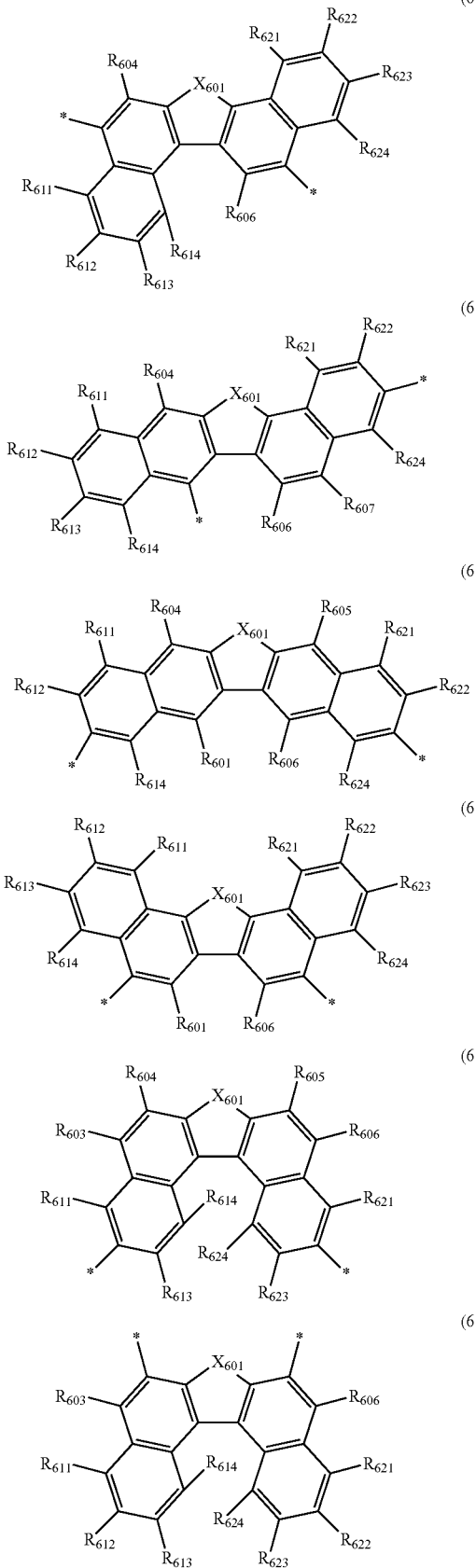

(61-13)
(61-14)
(61-15)
(61-16)
(61-17)
(61-18)

wherein in the formulas (61-7) to (61-18), $X_{601}$ is as defined in the formula (61); * is a single bond bonding to the monovalent group represented by the formula (64); and $R_{601}$ to $R_{624}$ are the same as $R_{601}$ to $R_{624}$ that are not monovalent groups represented by the formula (64).

$R_{601}$ to $R_{608}$ which do not form the divalent group represented by the formula (62) and (63) and are not monovalent groups represented by the formula (64), and $R_{611}$ to $R_{614}$ and $R_{621}$ to $R_{624}$ which are not monovalent groups represented by the formula (64) are preferably independently a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
a substituted or unsubstituted aryl group having 6 to 50 ring carbon atoms, or
a substituted or unsubstituted monovalent heterocyclic group having 5 to 50 ring atoms.

The monovalent group represented by the formula (64) is preferably represented by the following formulas (65) or (66).

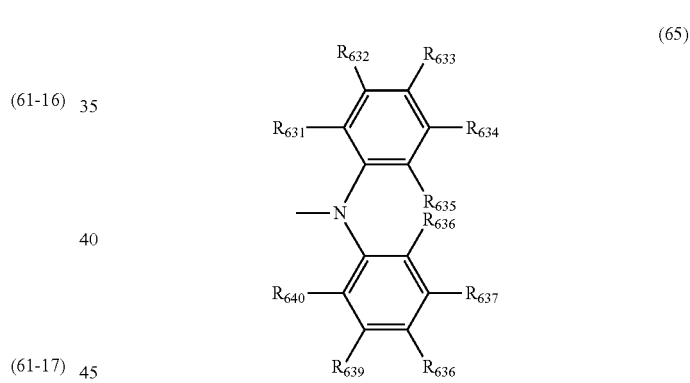

(65)

wherein in the formula (65), $R_{631}$ to $R_{640}$ are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms; and $R_{901}$ to $R_{907}$ are as defined in the formula (1).

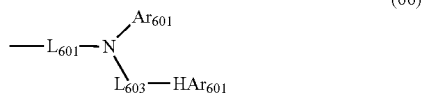
(66)

wherein in the formula (66), $Ar_{601}$, $L_{601}$ and $L_{603}$ are as defined in the formula (64); and $HAr_{601}$ is a structure represented by the following formula (67);

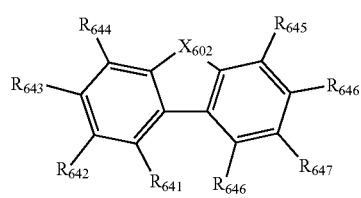
(67)

wherein in the formula (67) $X_{602}$ is an oxygen atom or a sulfur atom;
any one of $R_{641}$ to $R_{648}$ is a single bond bonding to $L_{603}$;
$R_{641}$ to $R_{648}$ which are not single bonds are independently a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms; and
$R_{901}$ to $R_{907}$ are as defined in the formula (1).)

As specific example of the compound represented by the formula (61), in addition to the compounds described in WO2014/104144, the following compounds can be given, for example. In the following example compounds, Me represents methyl group.

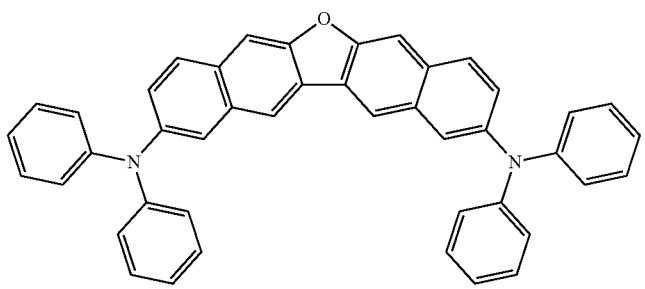

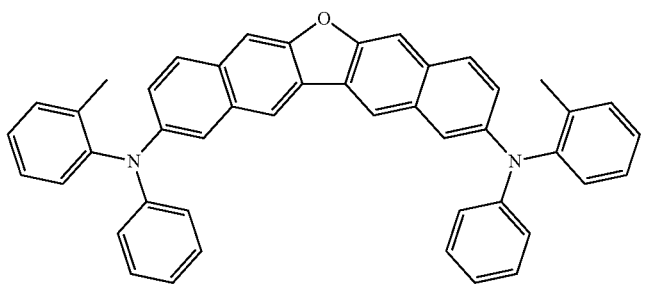

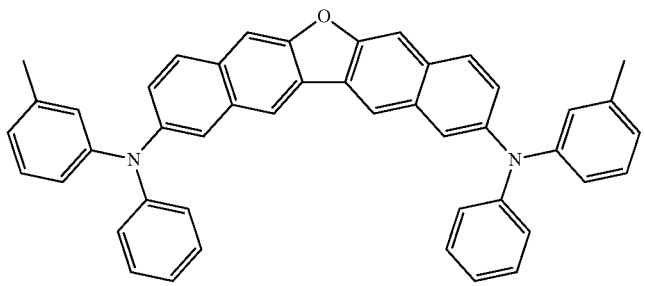

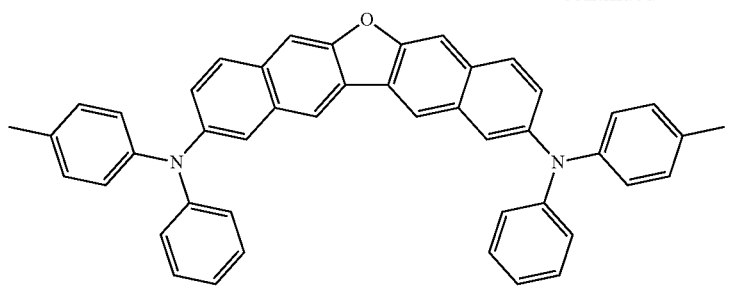
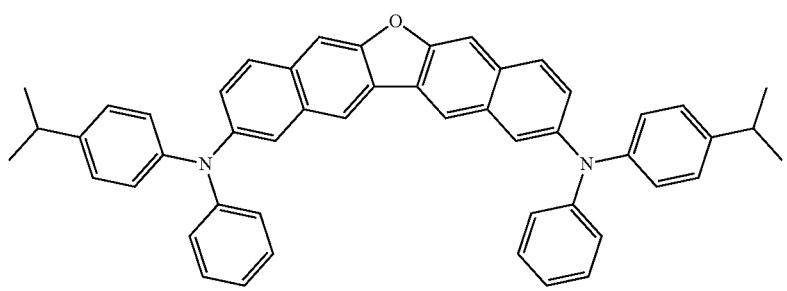
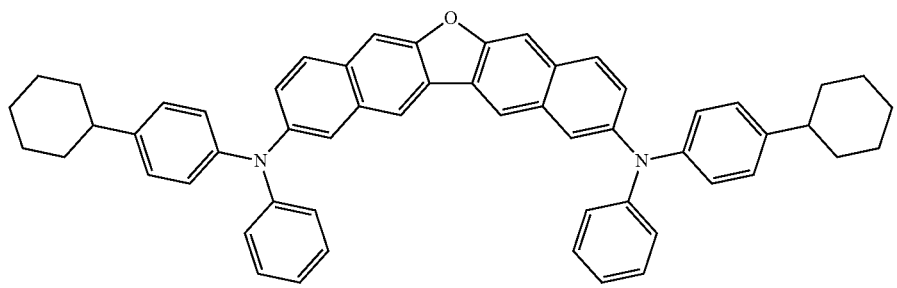
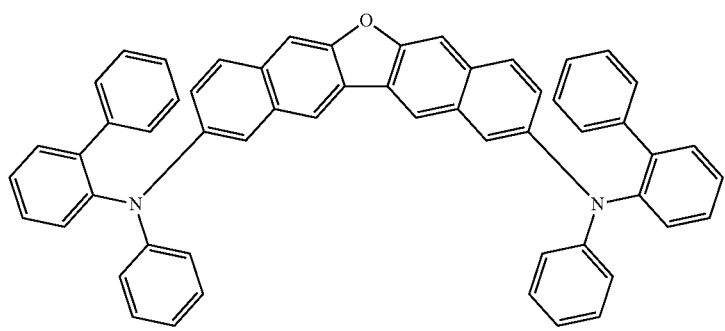
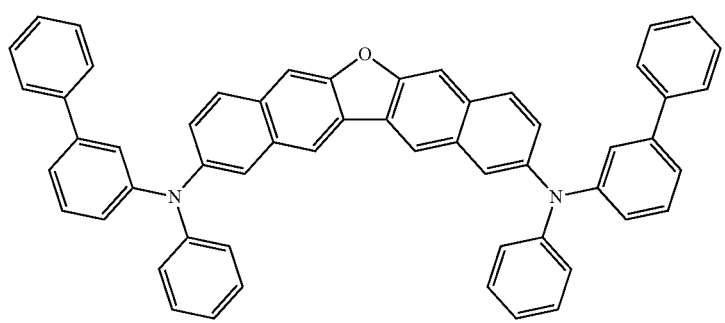

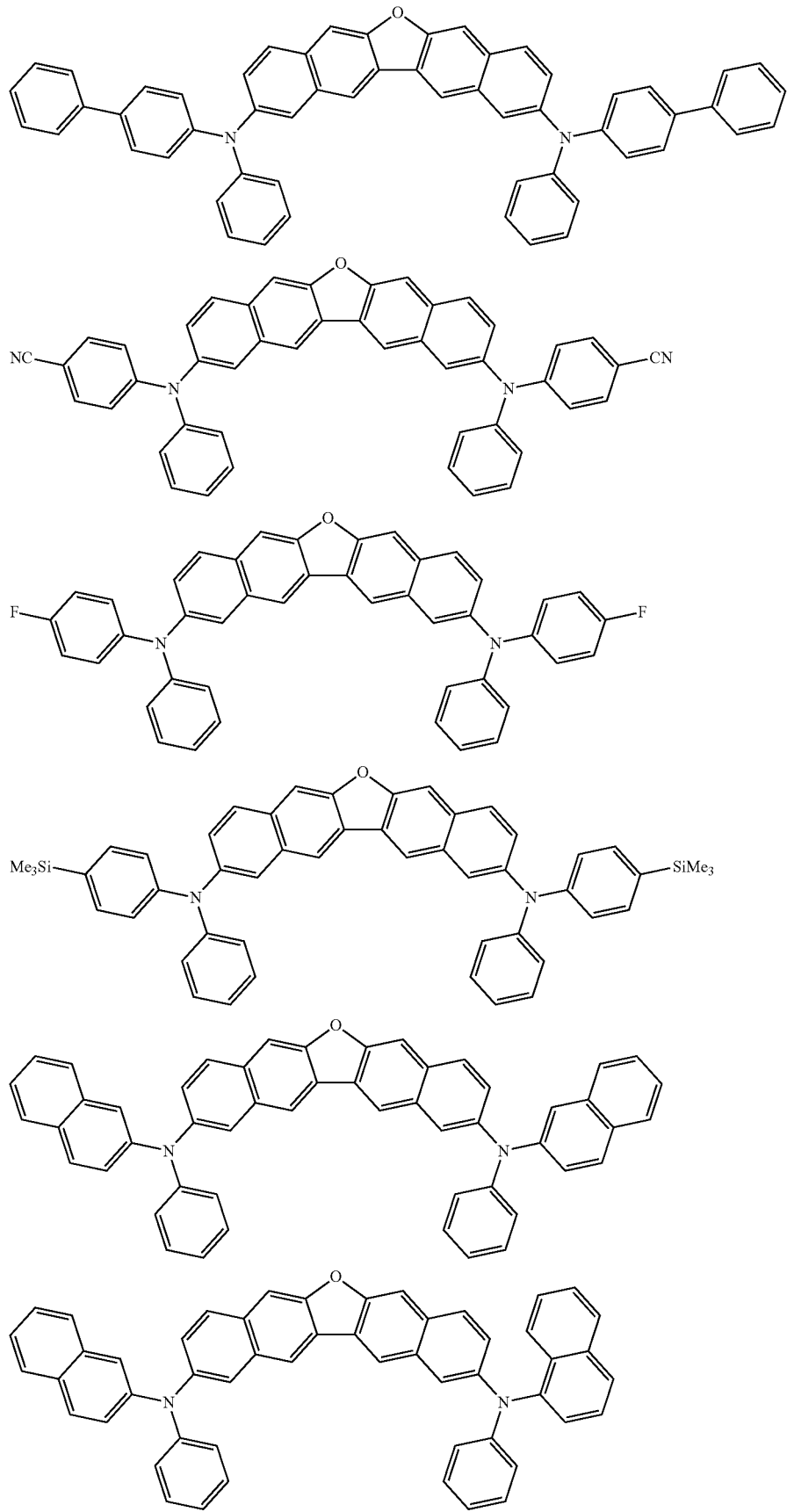

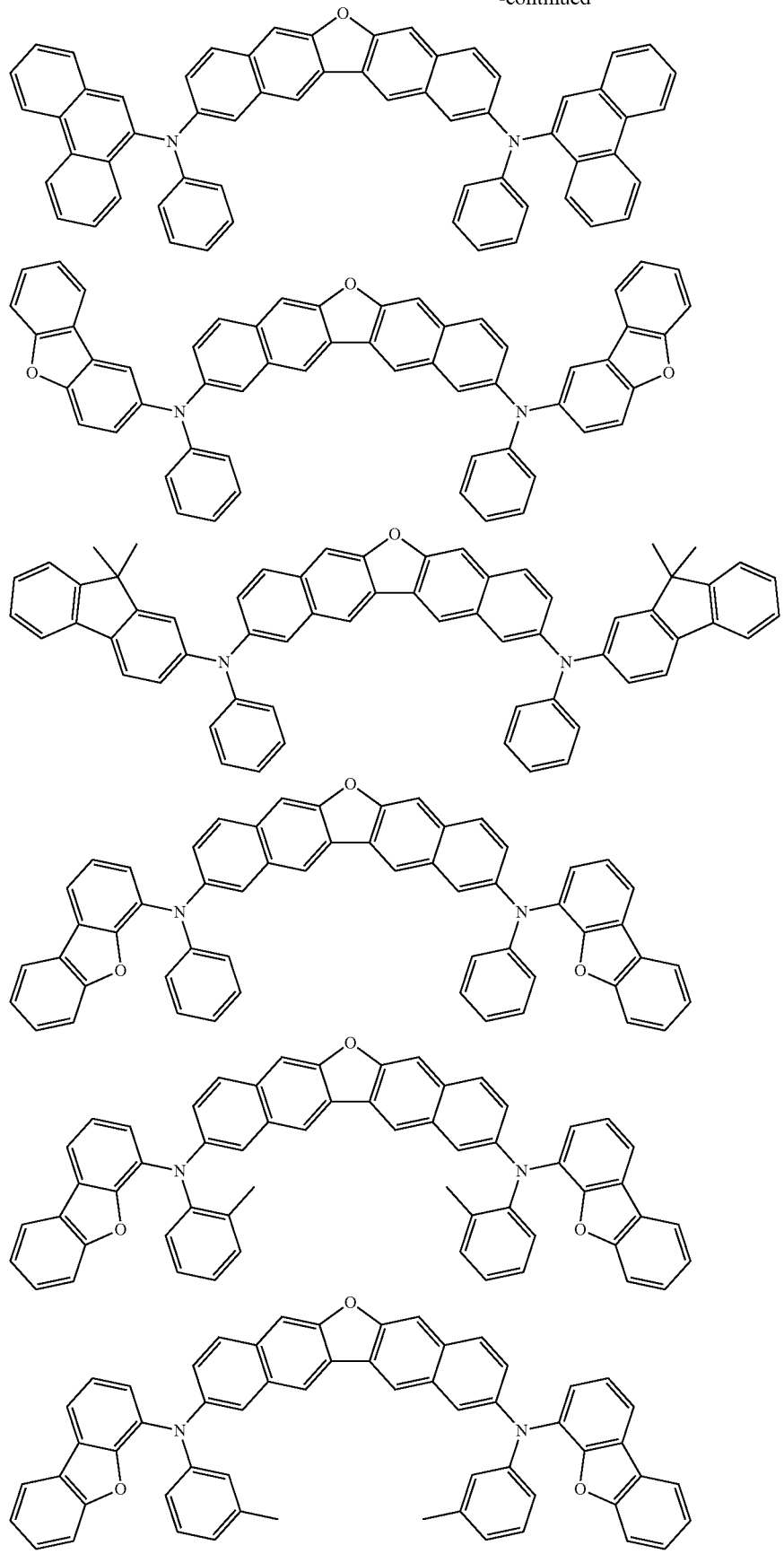

-continued
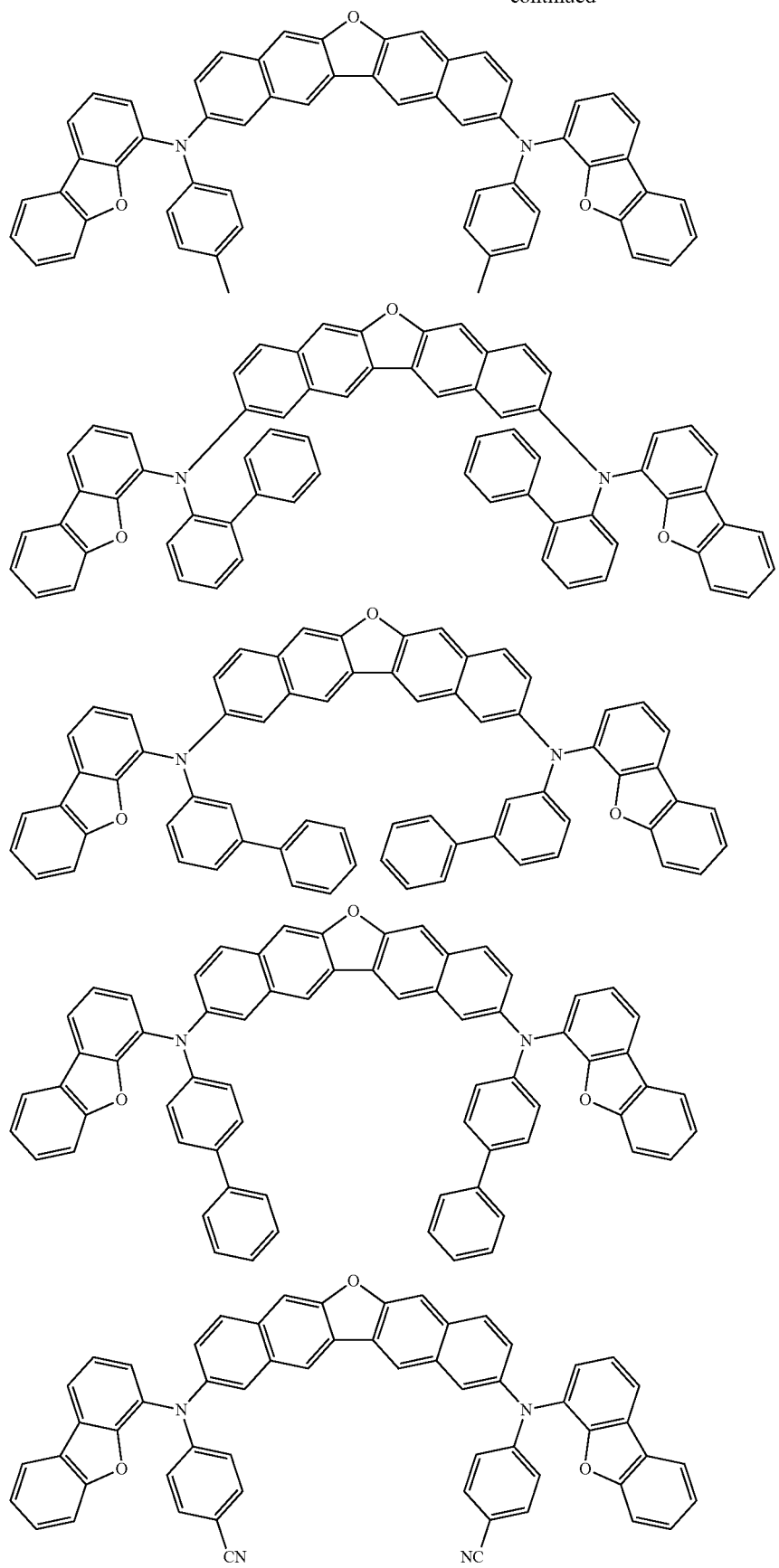

-continued
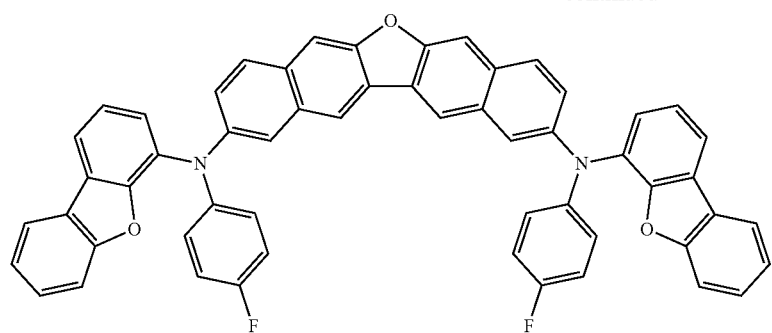
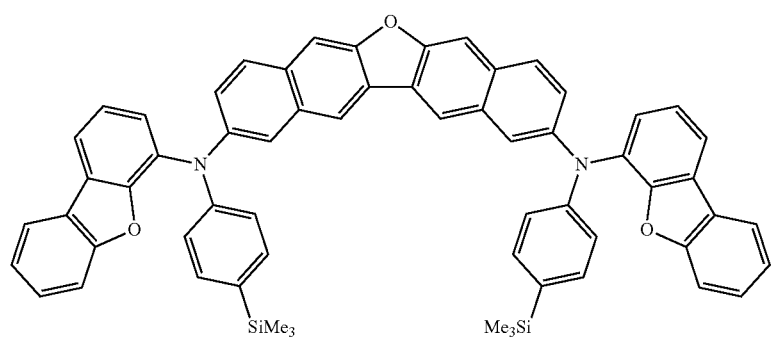
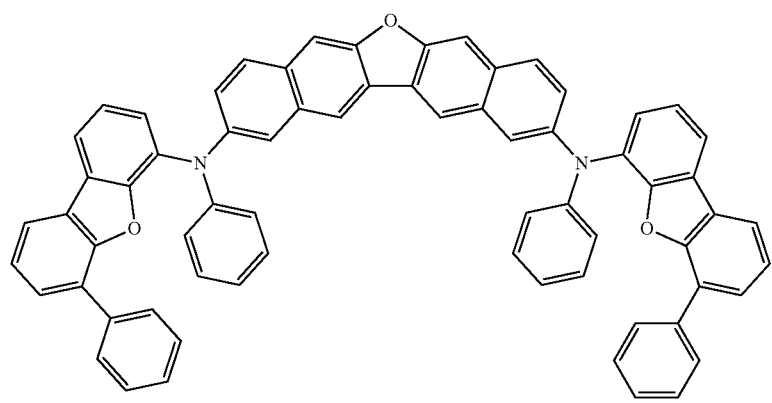
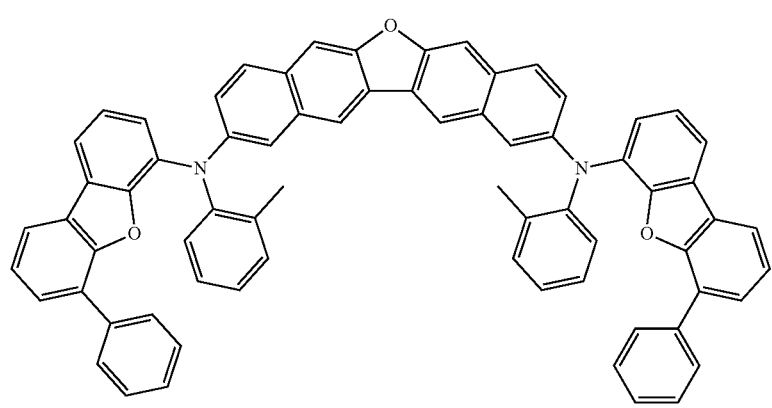

-continued

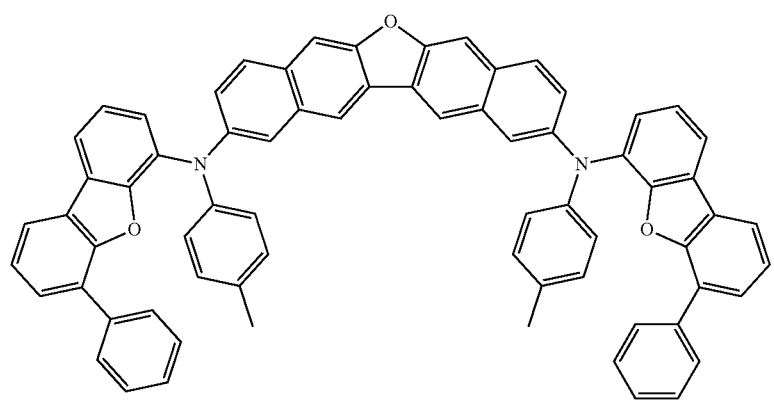
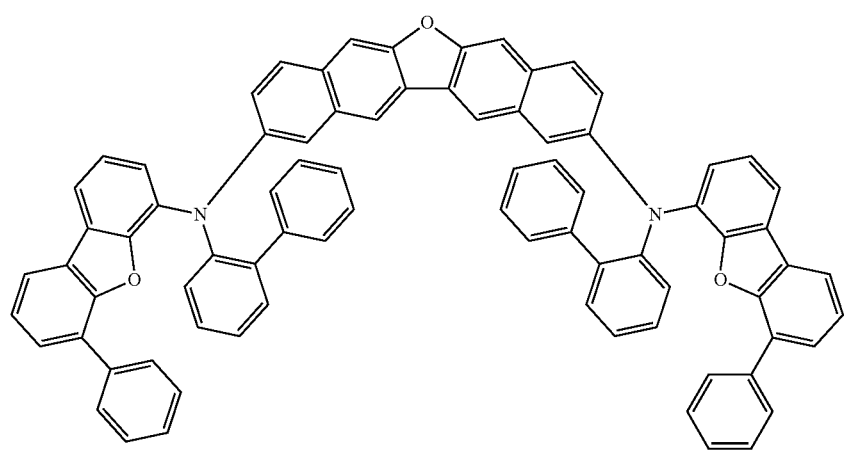
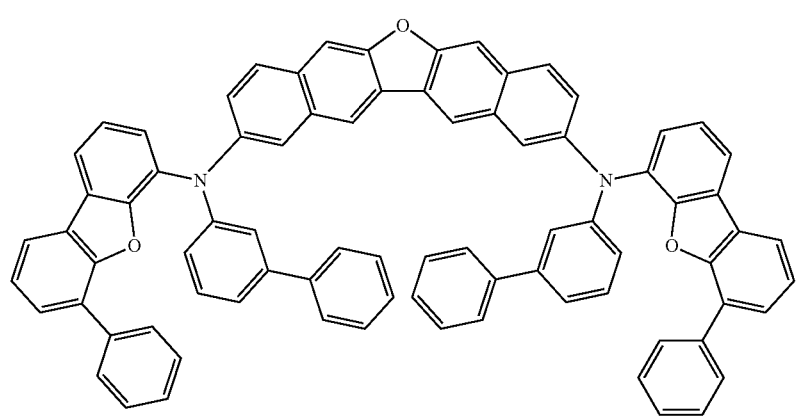

-continued
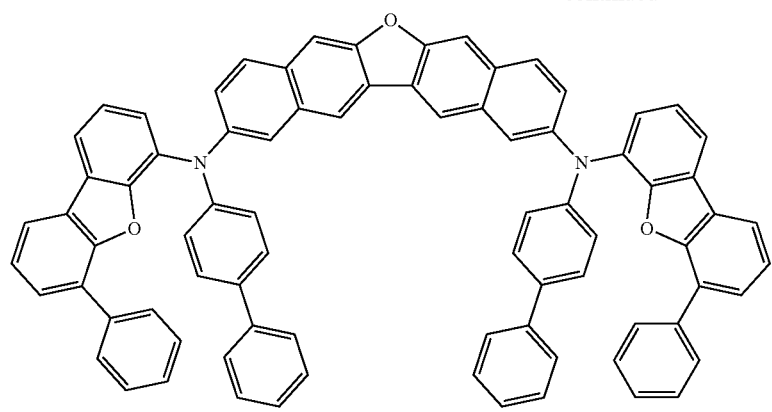
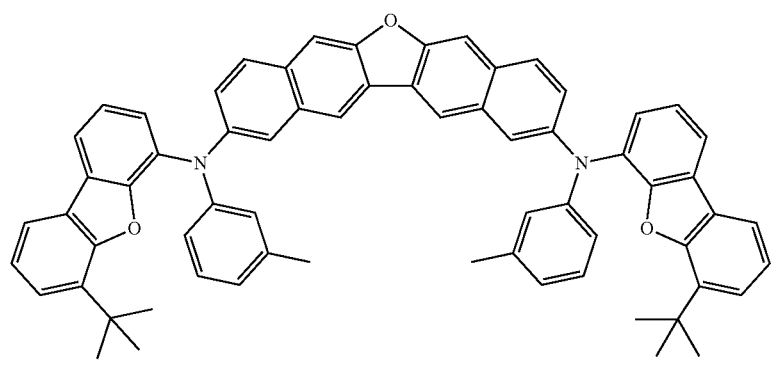

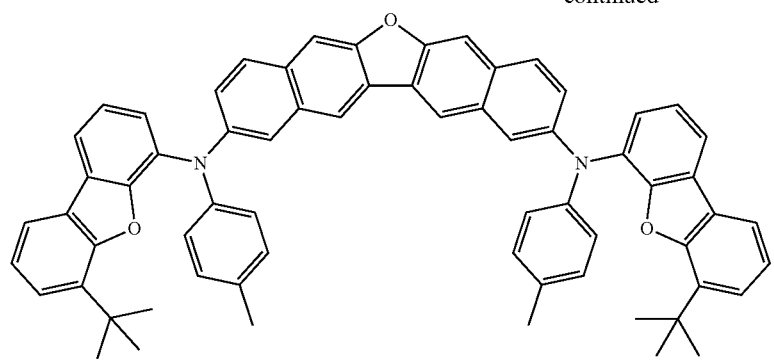
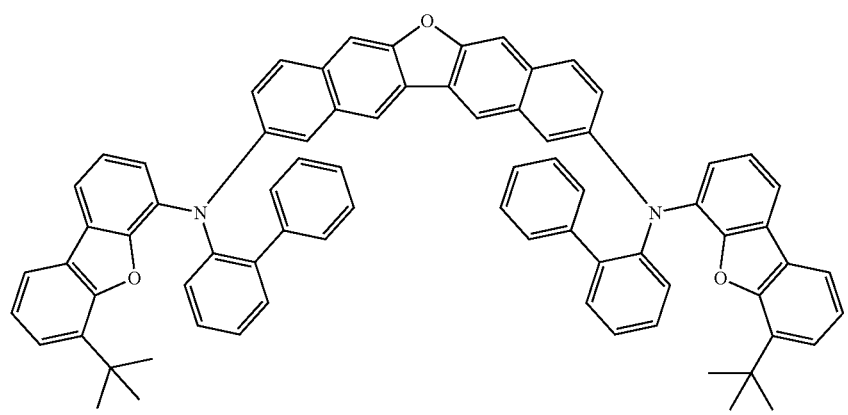
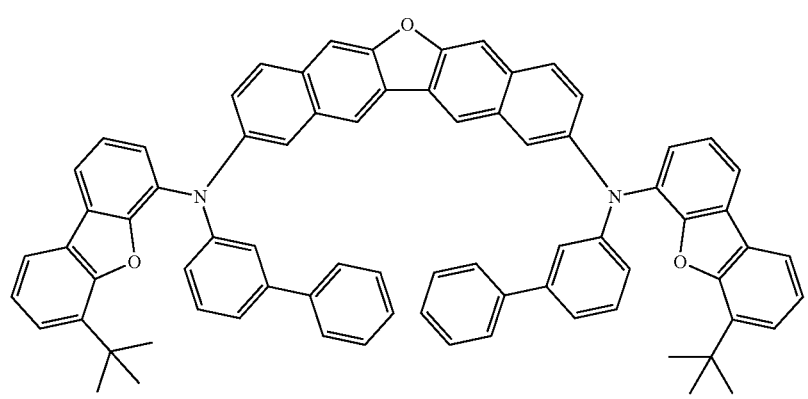
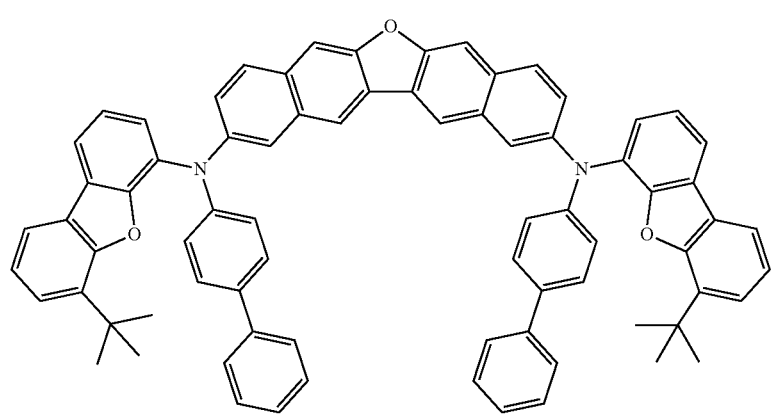

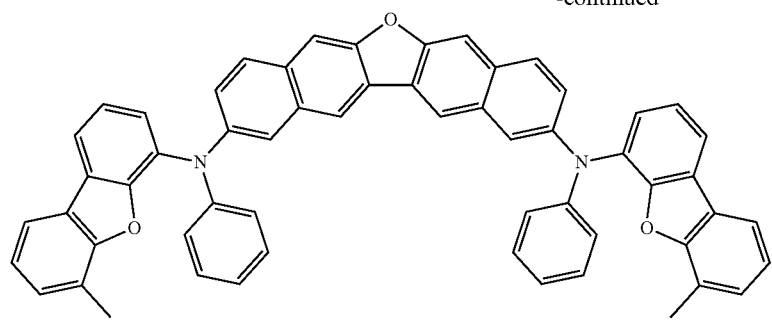

-continued
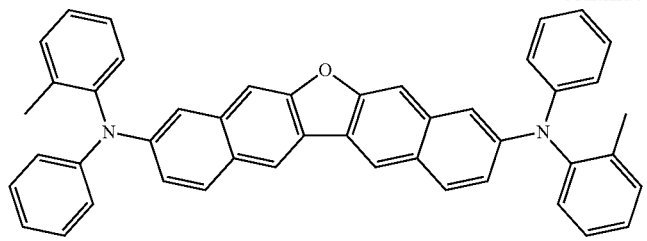
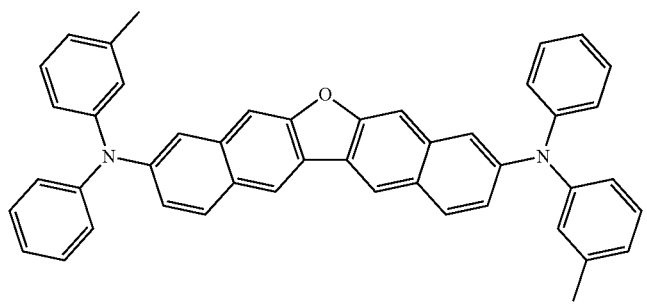
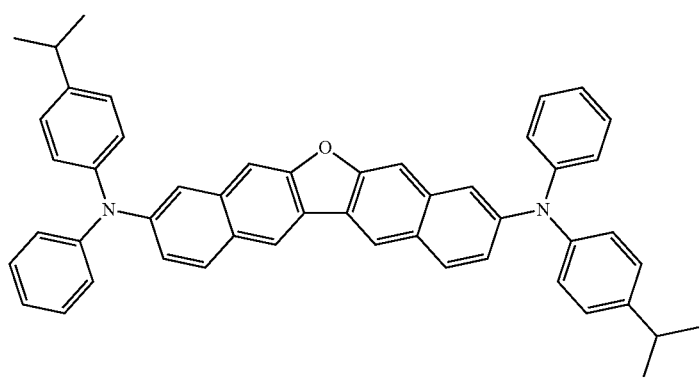
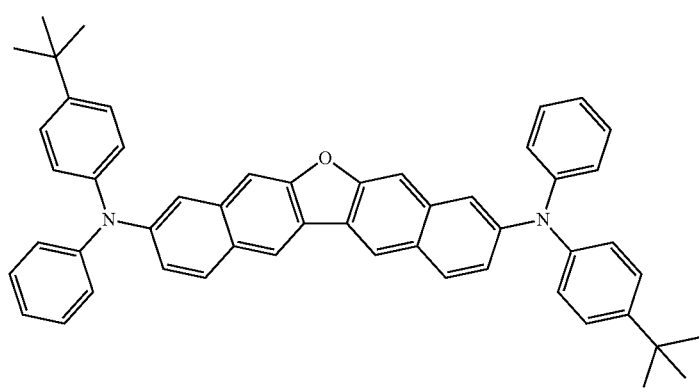
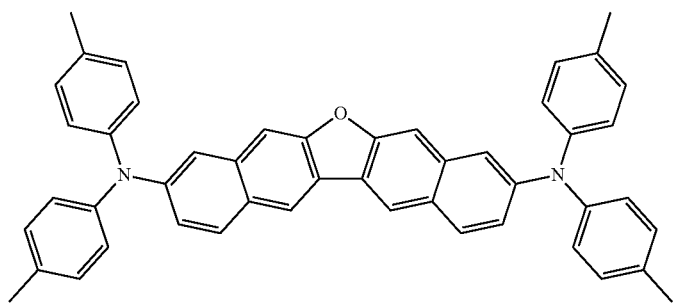

-continued
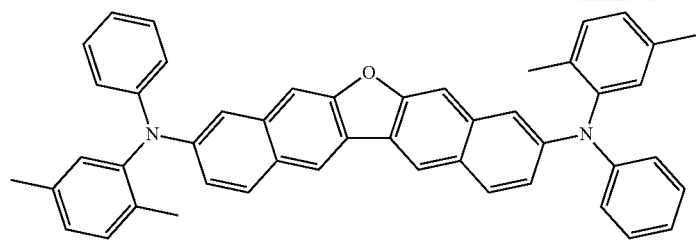
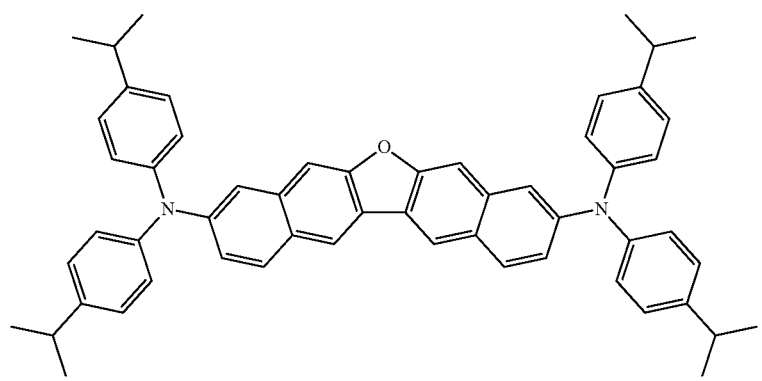
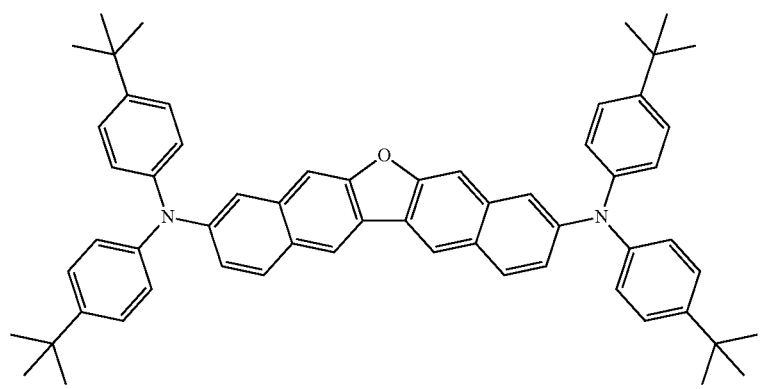
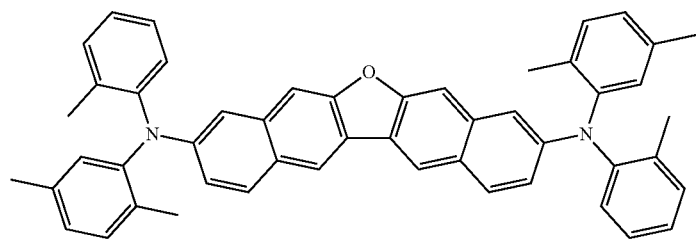
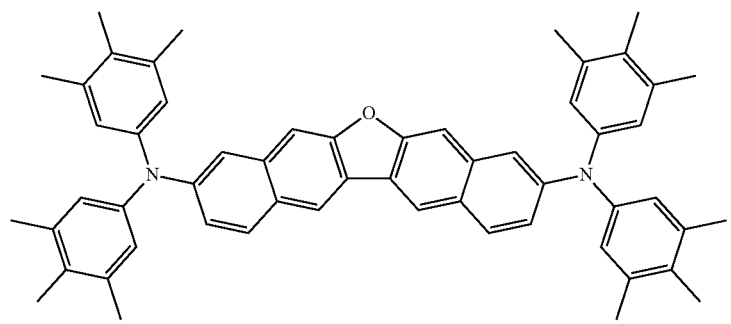

-continued
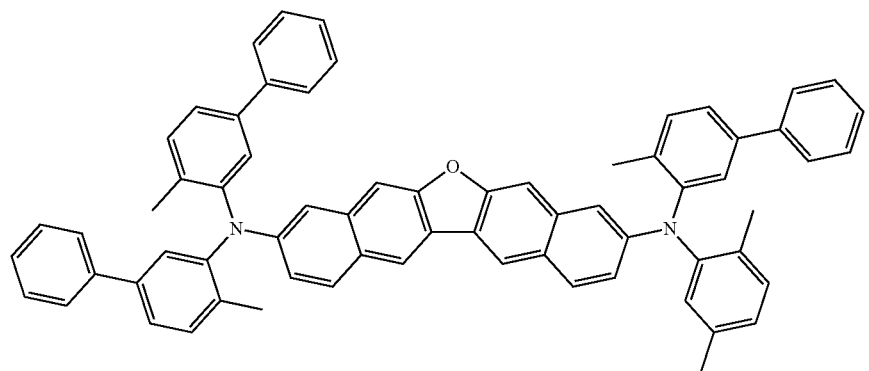
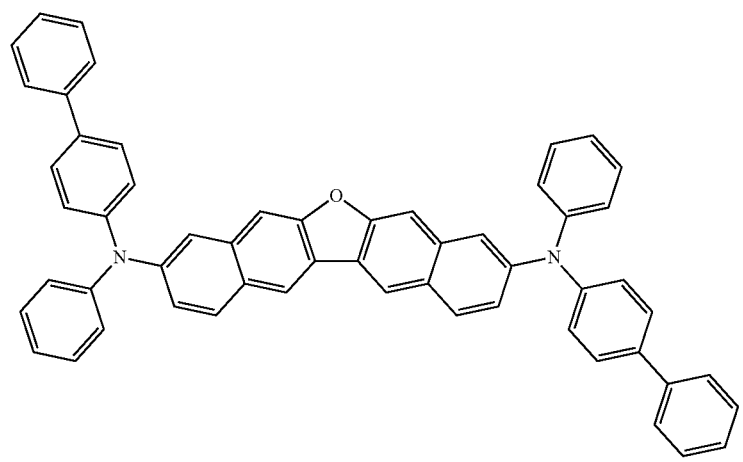
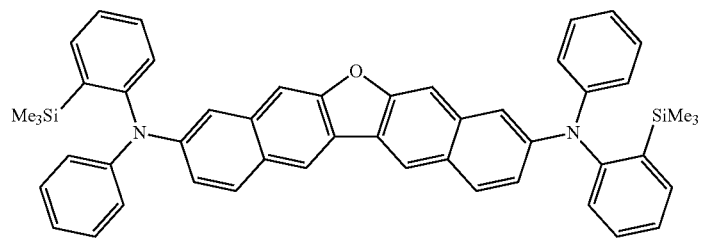
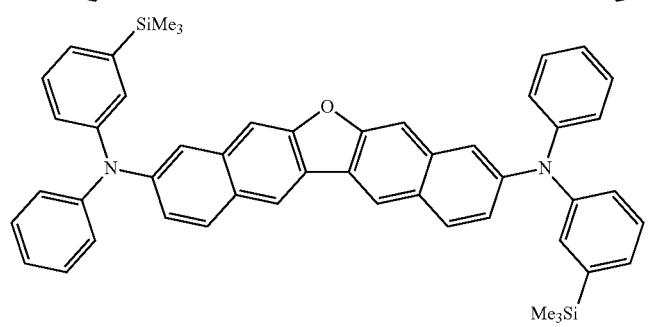
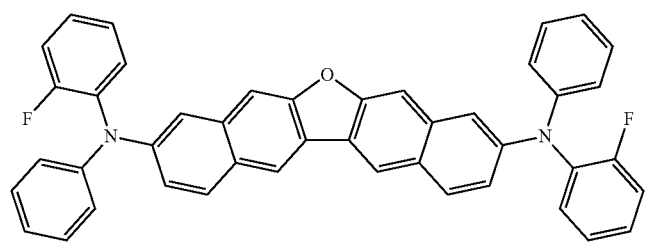

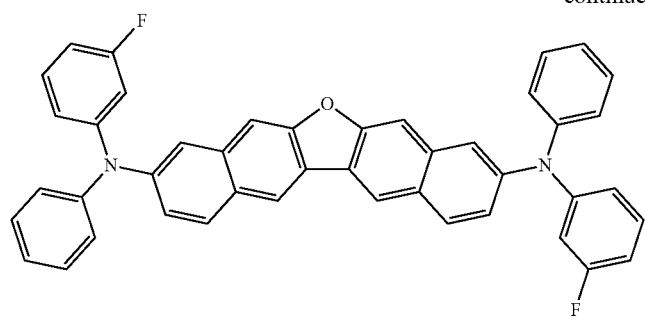
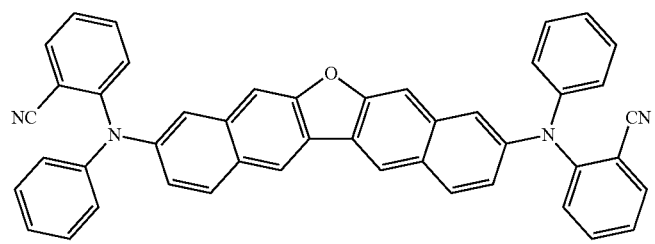
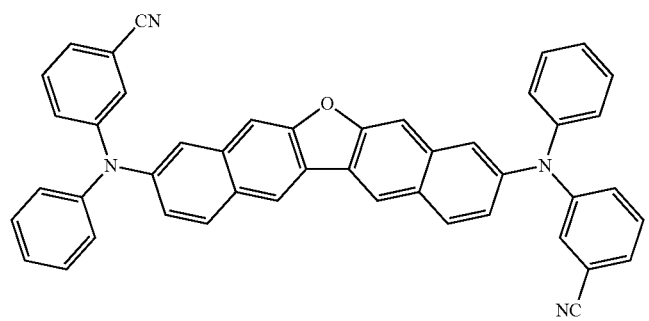
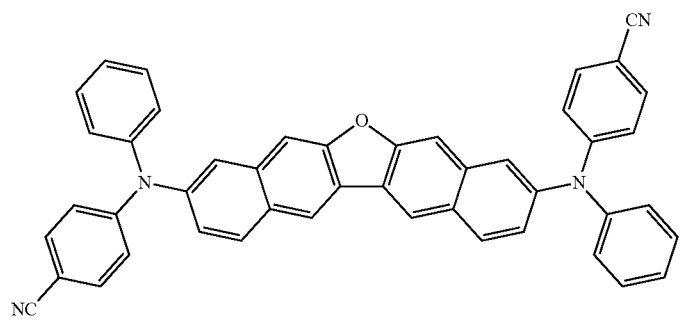
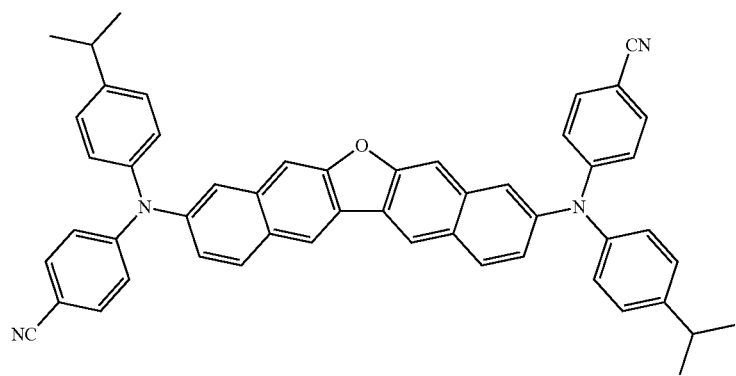

-continued
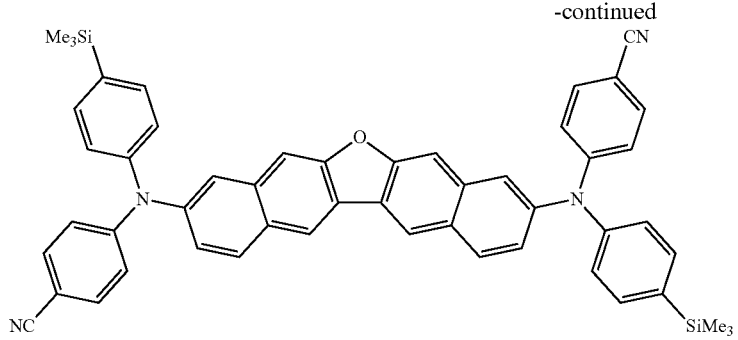
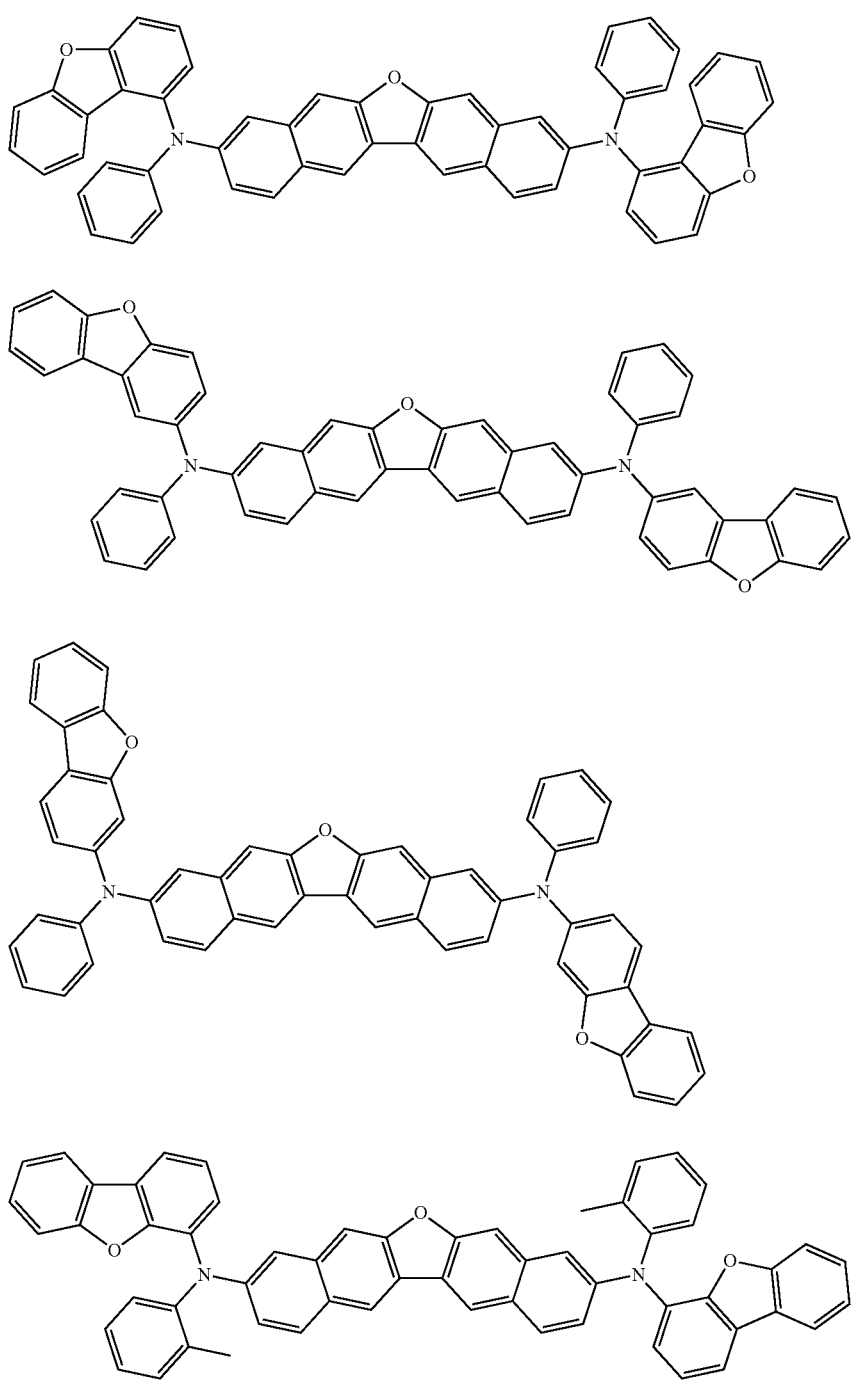

-continued
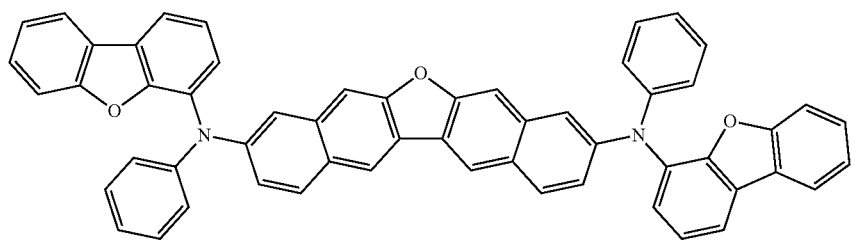
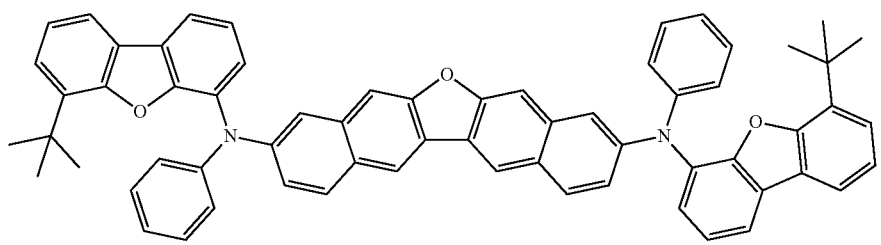
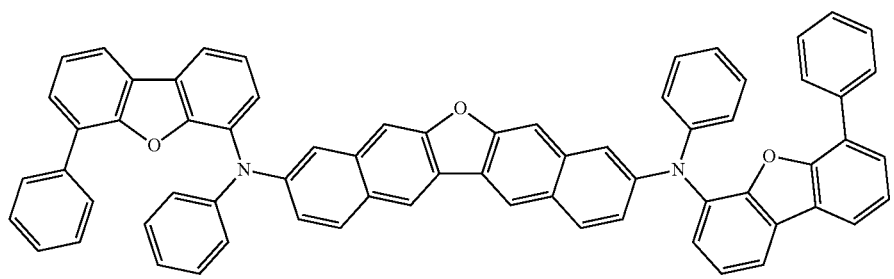
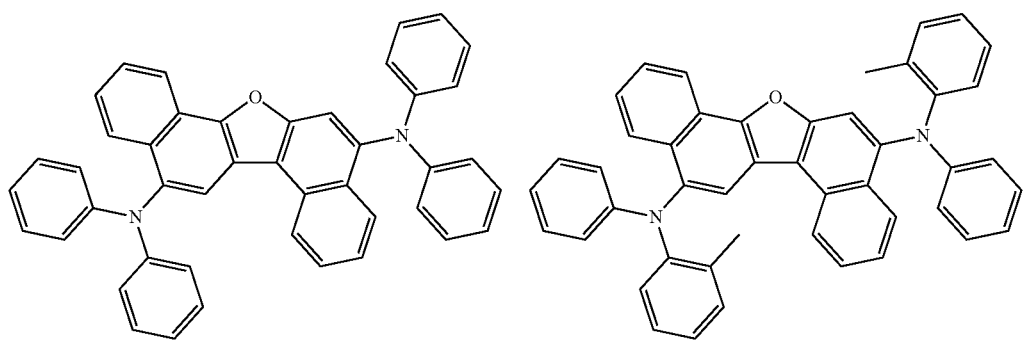
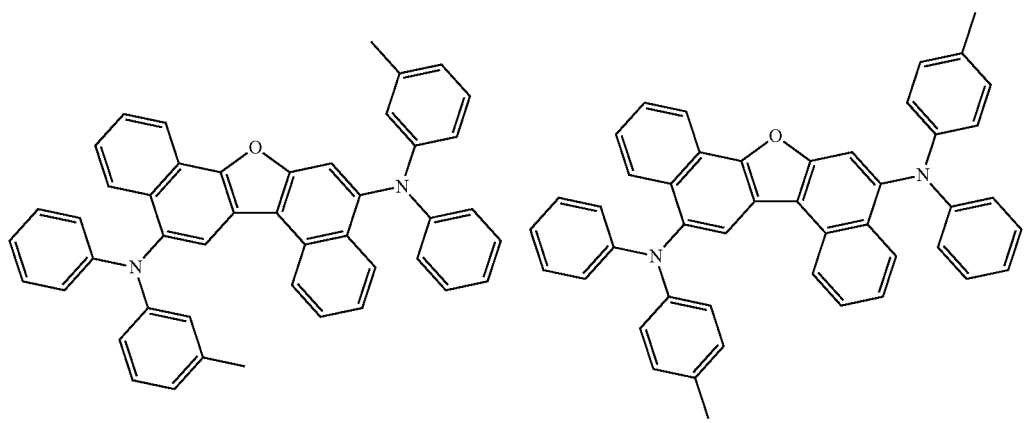

-continued
| 799 | 800 |
|---|---|
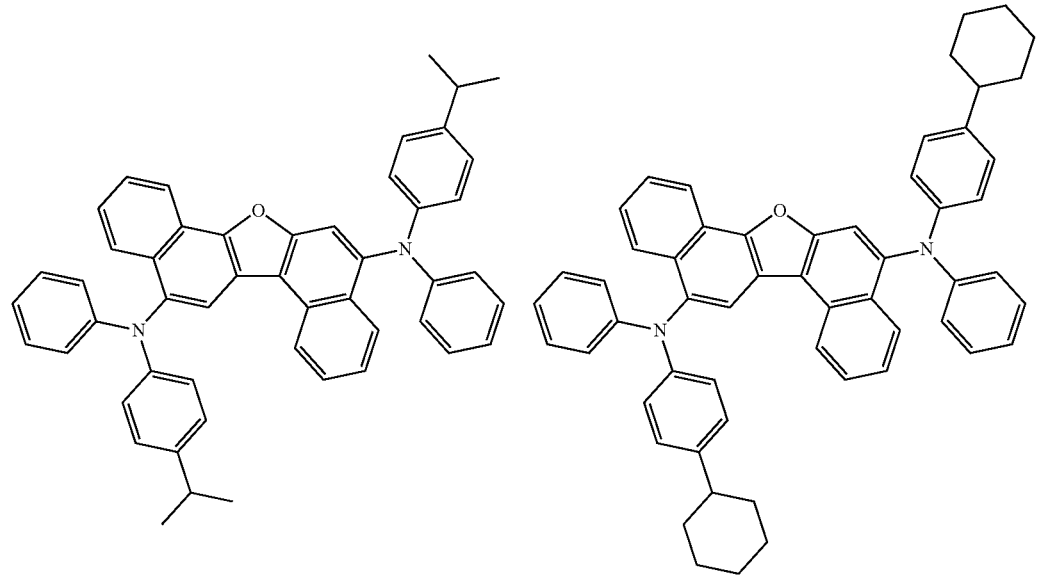
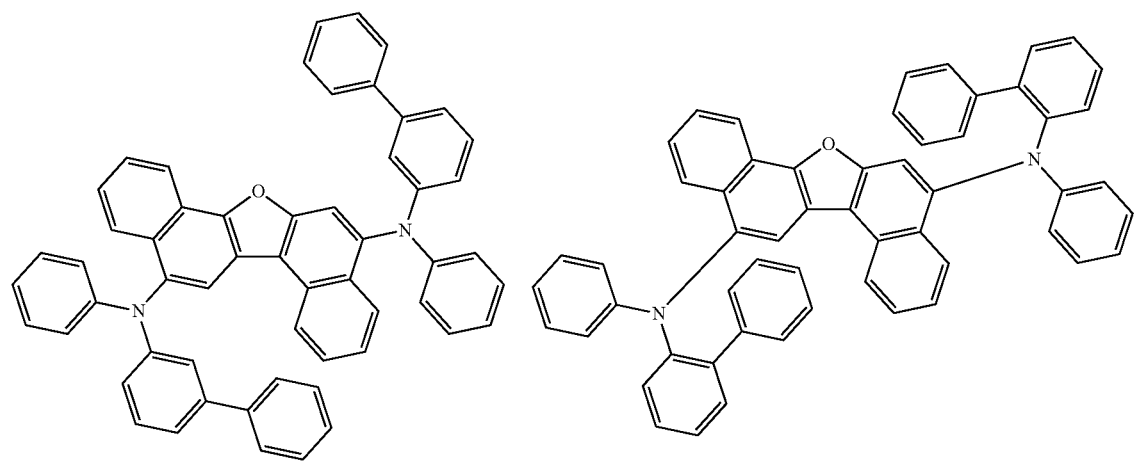
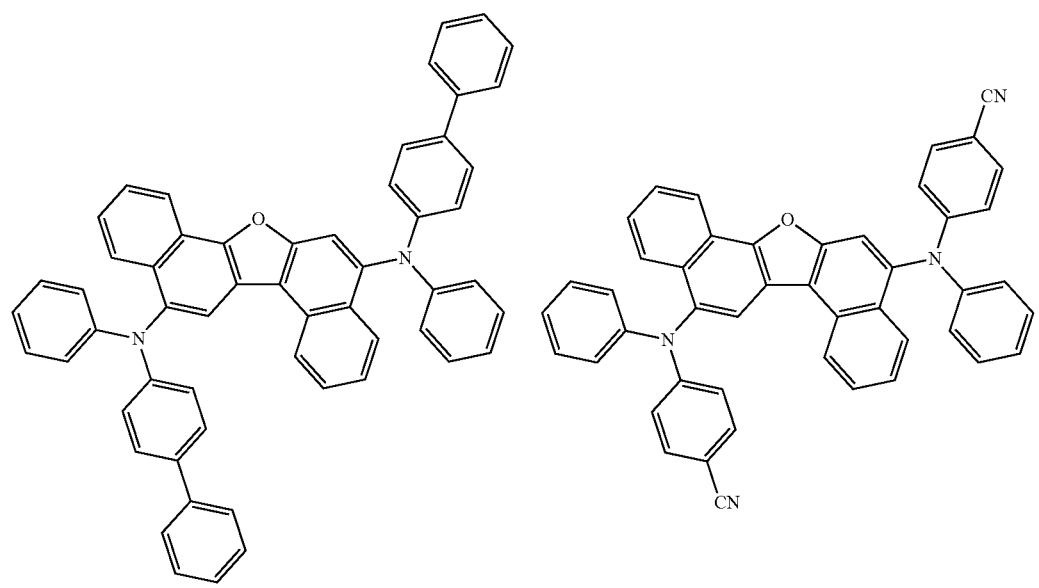

801 802
-continued
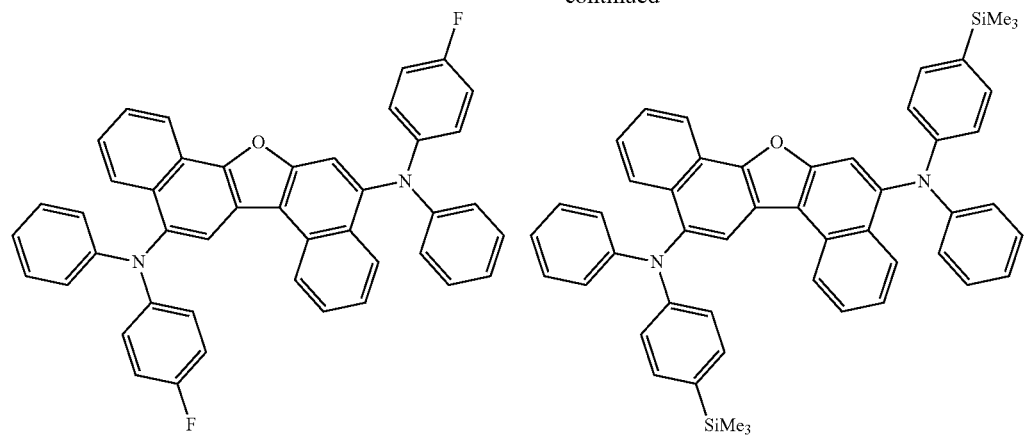
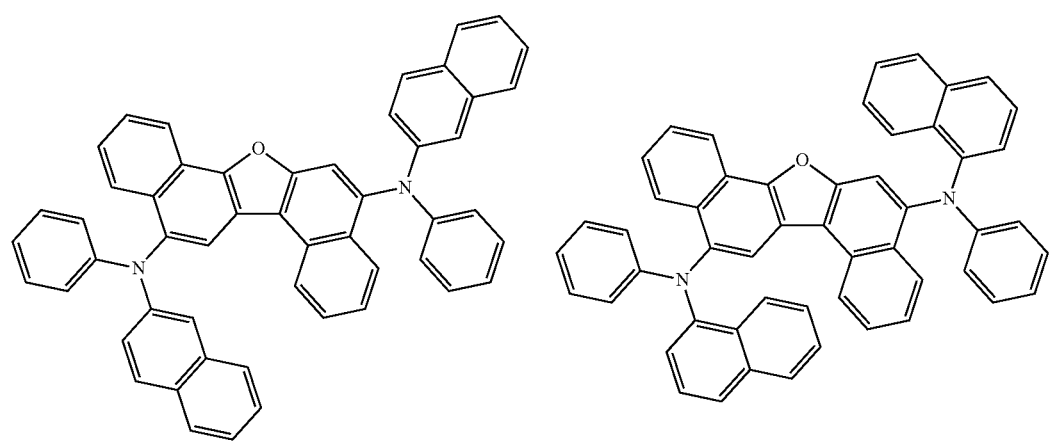
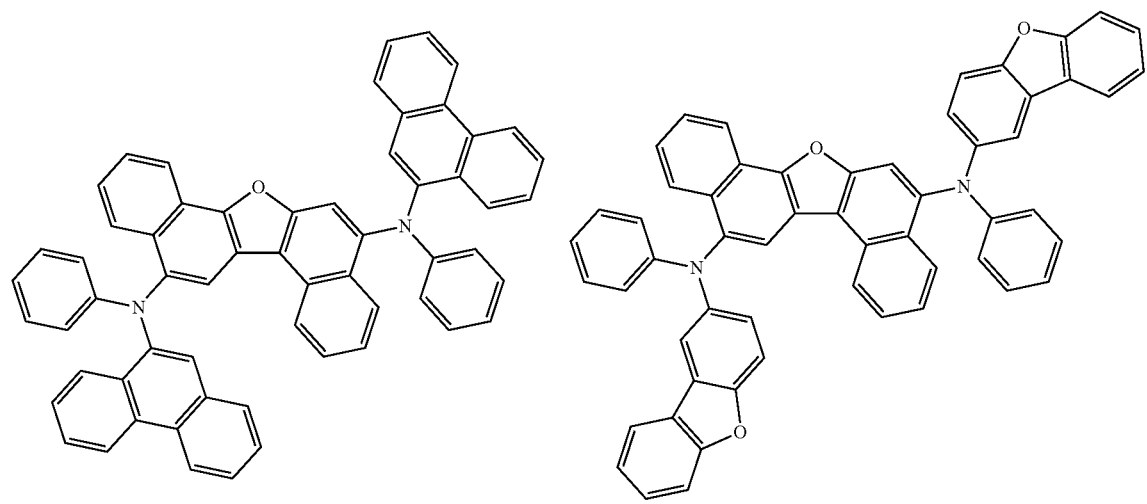

-continued
803   804
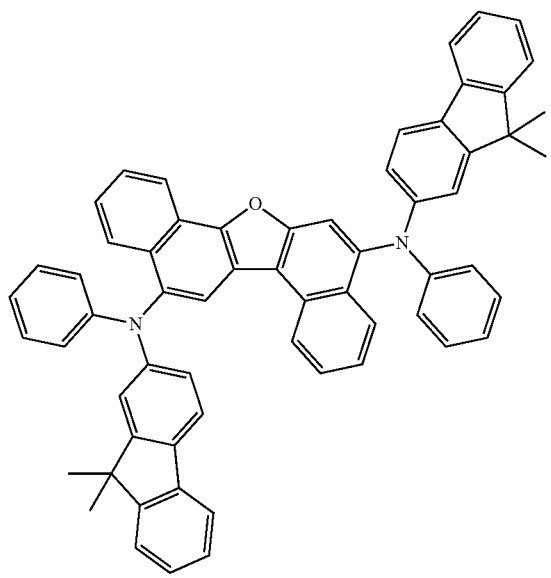 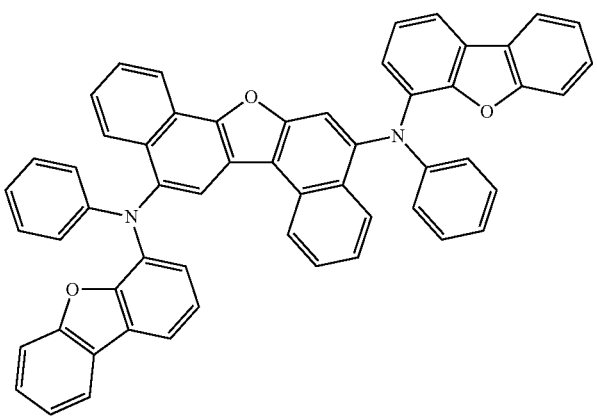
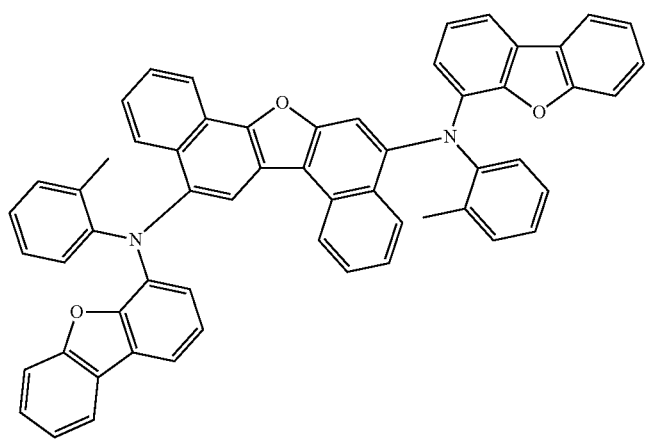
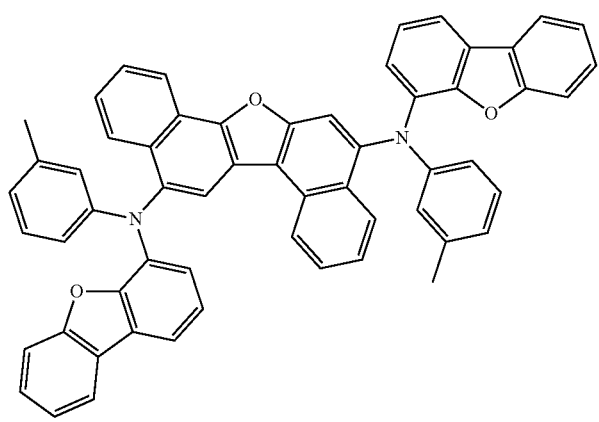

805
-continued
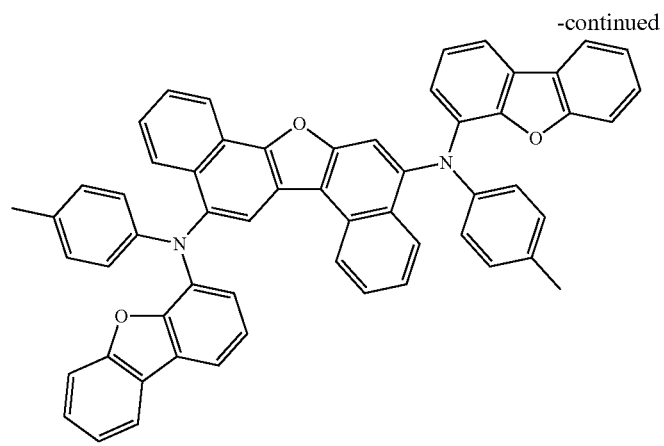
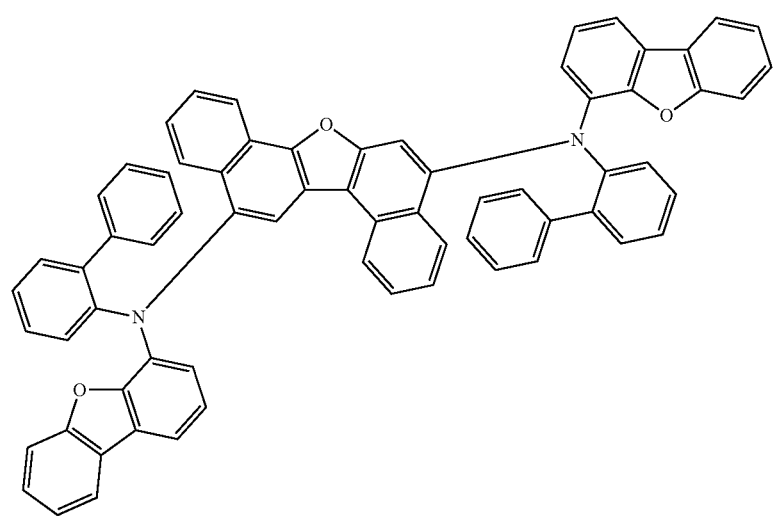
806
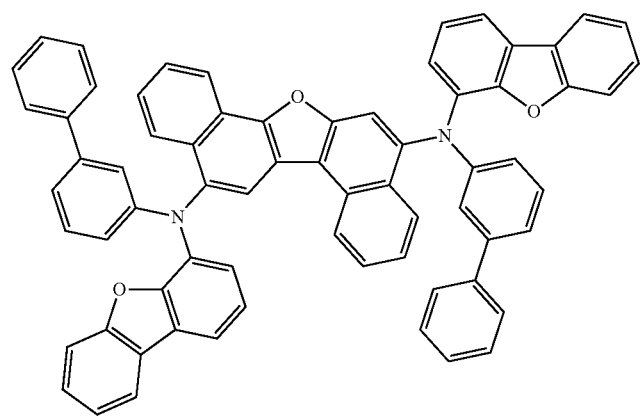

-continued
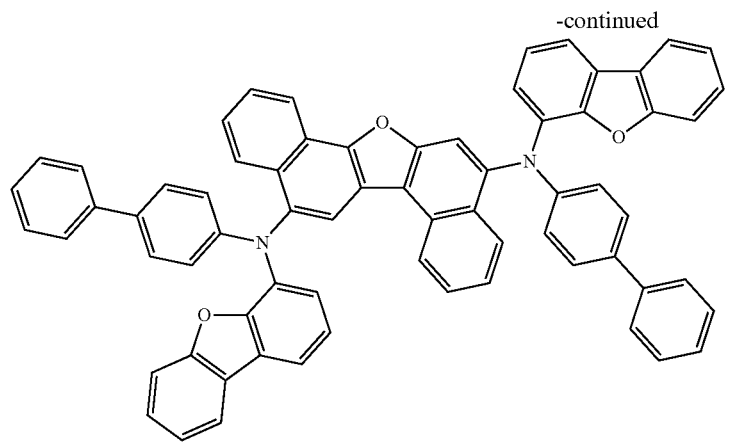
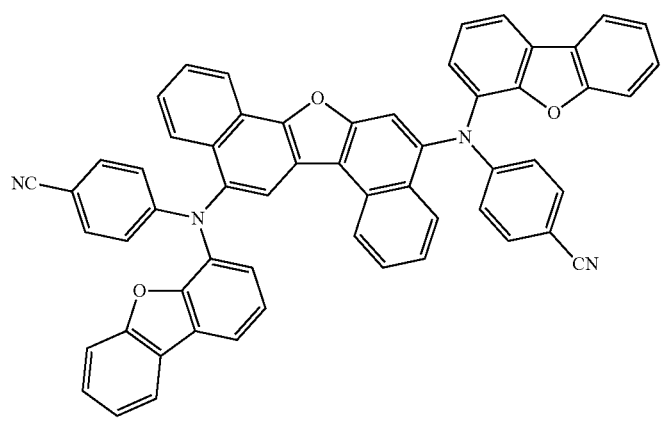
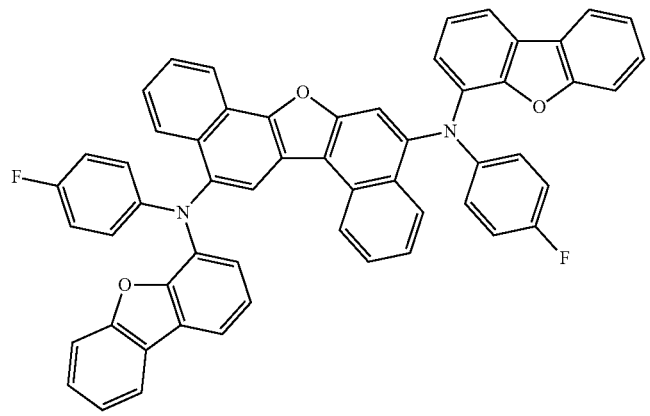
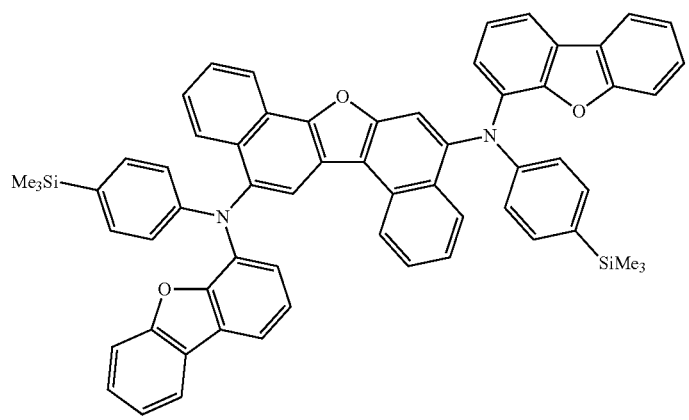

-continued
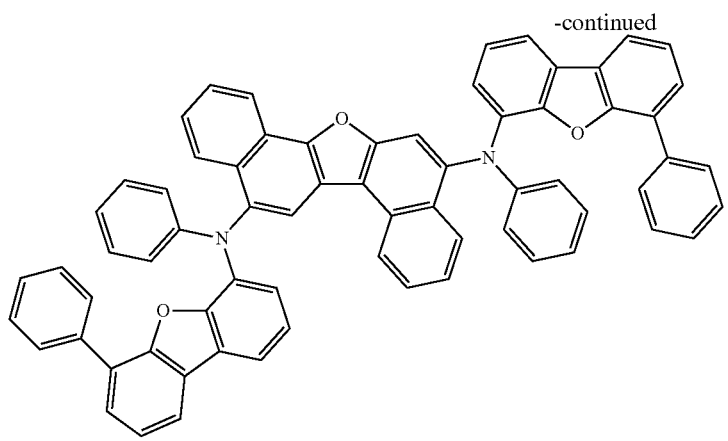
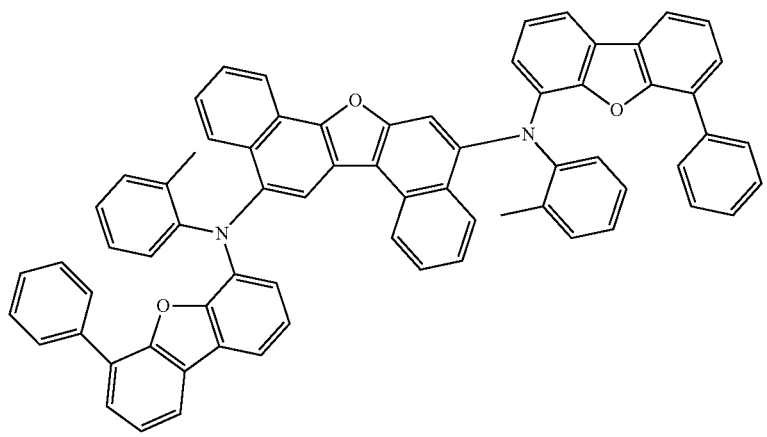
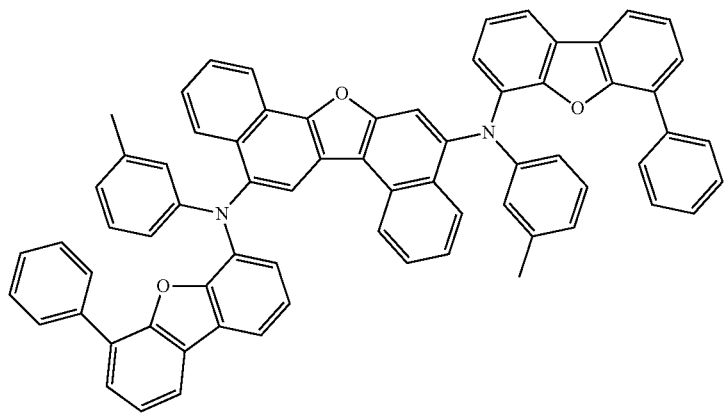
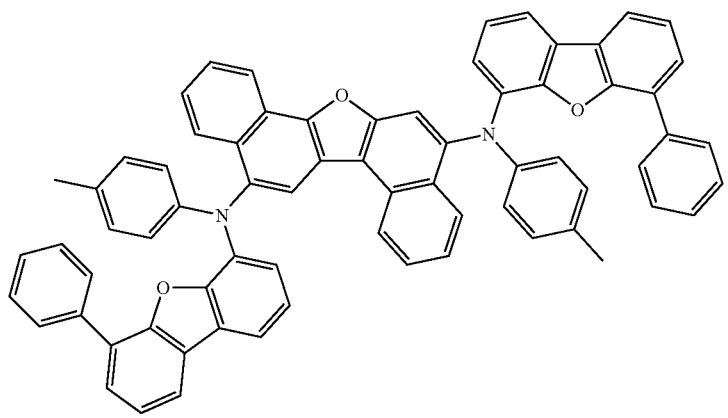

-continued
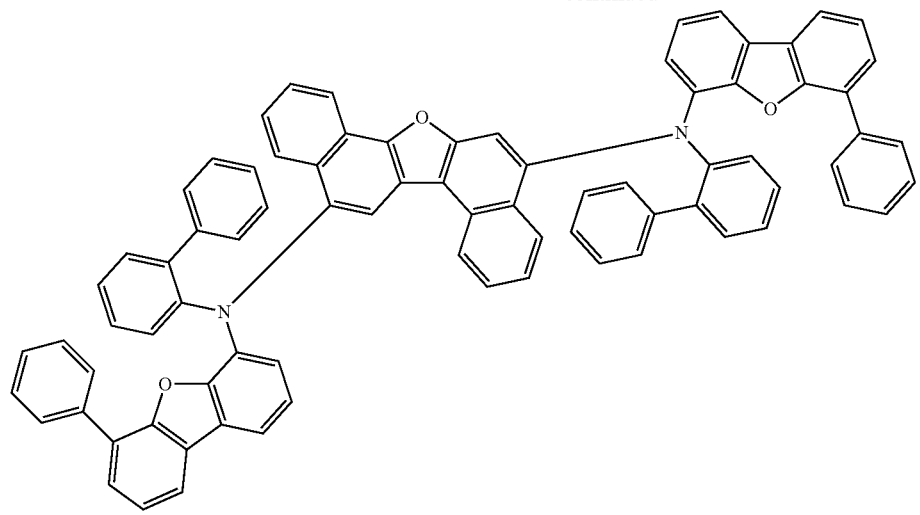
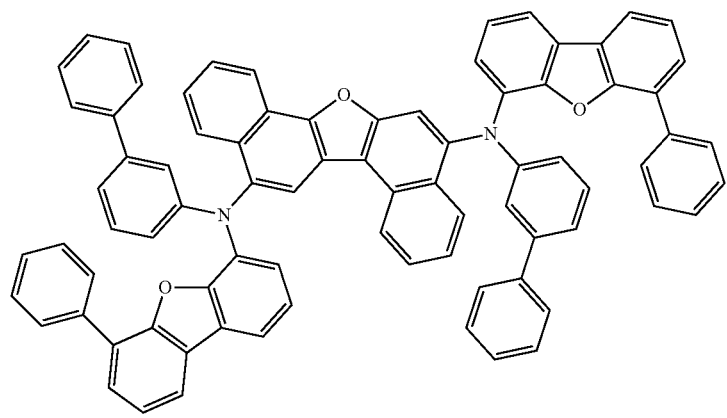
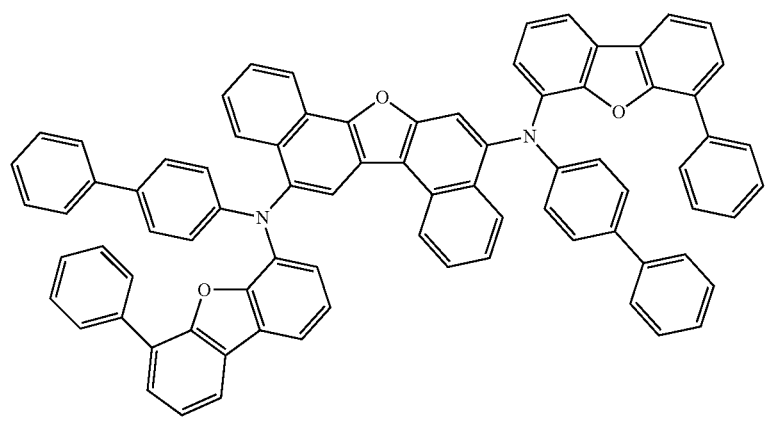

-continued
813
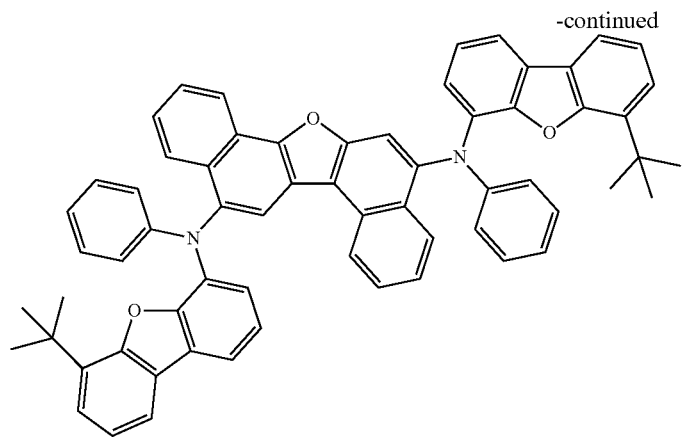
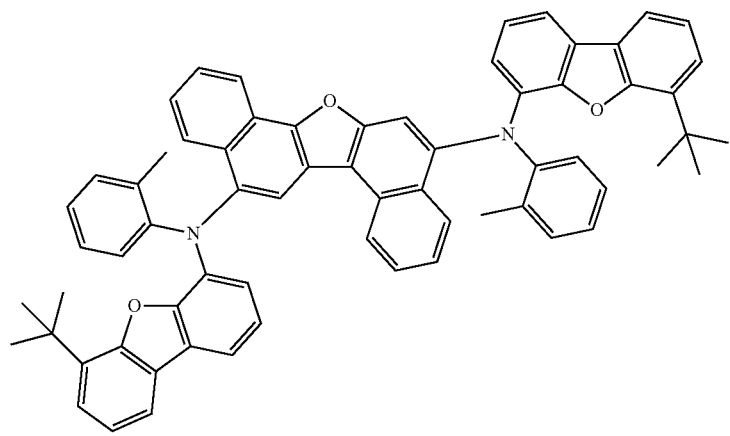
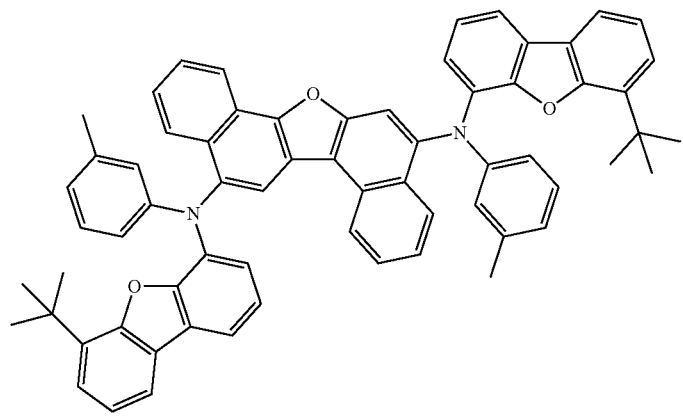
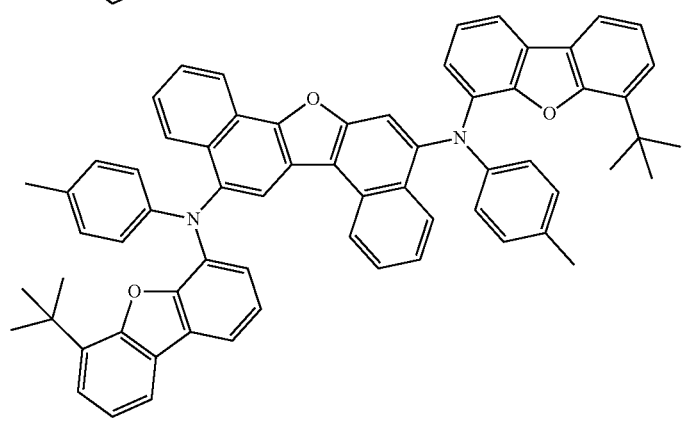
814

-continued
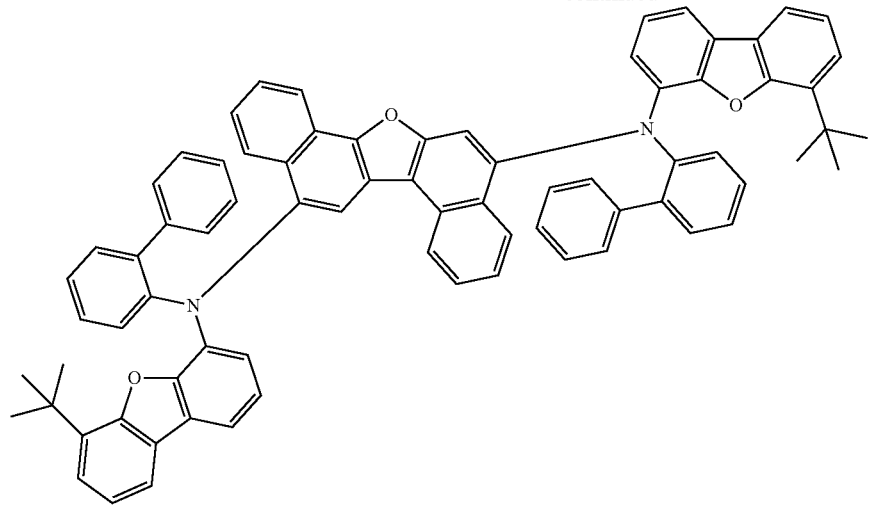
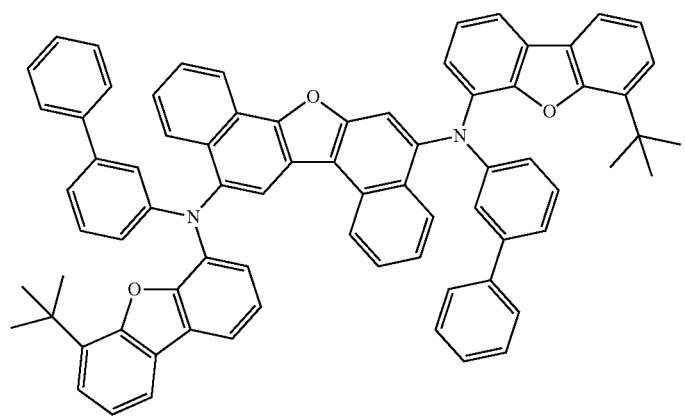
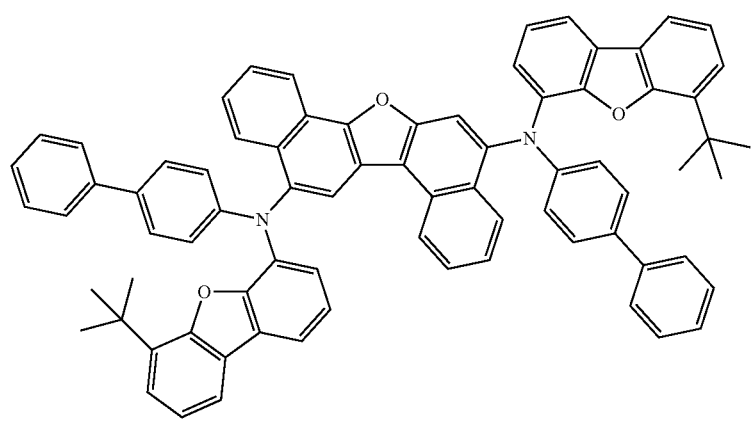

-continued
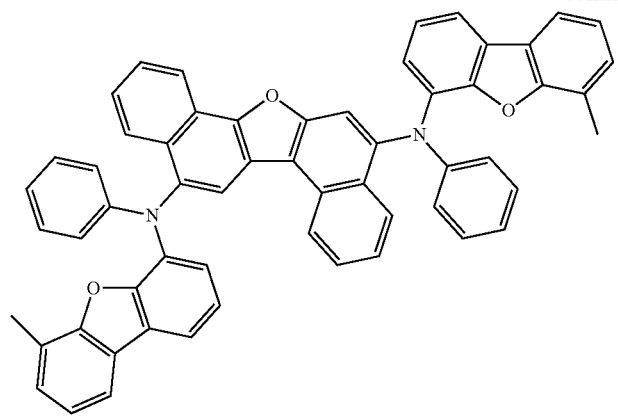
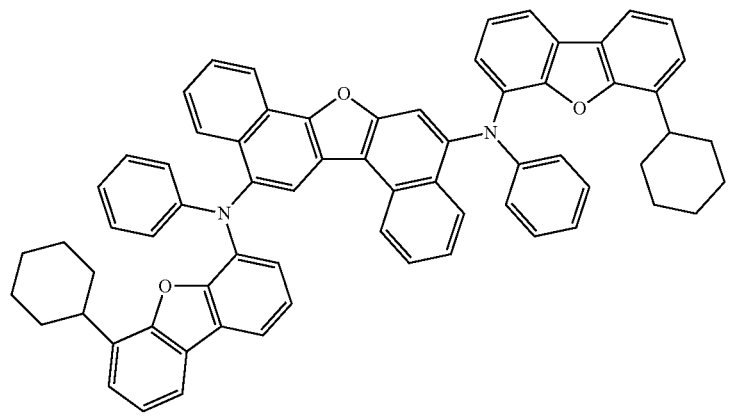
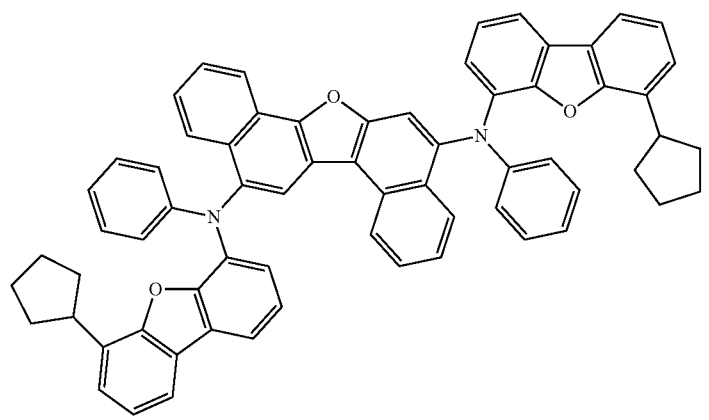
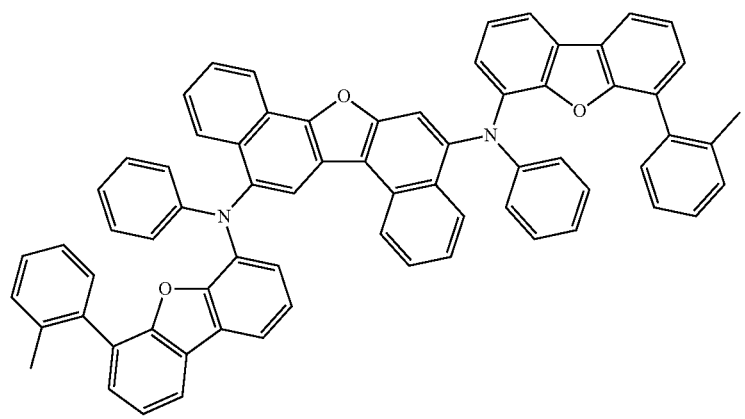

819 820
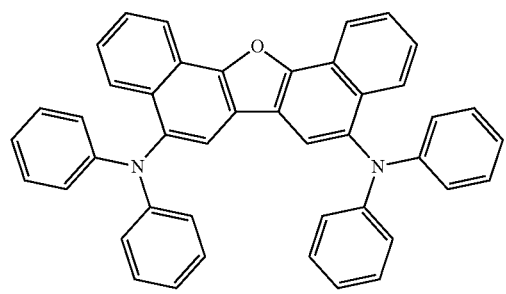 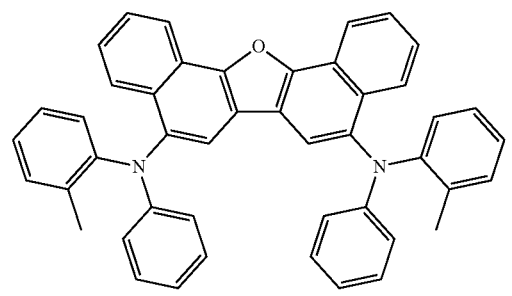
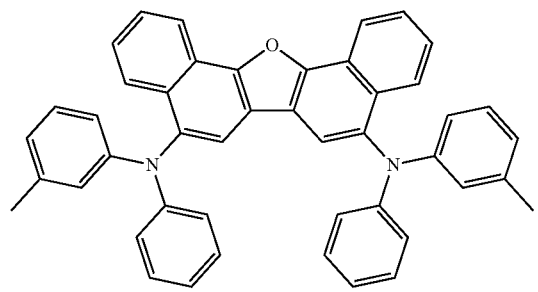 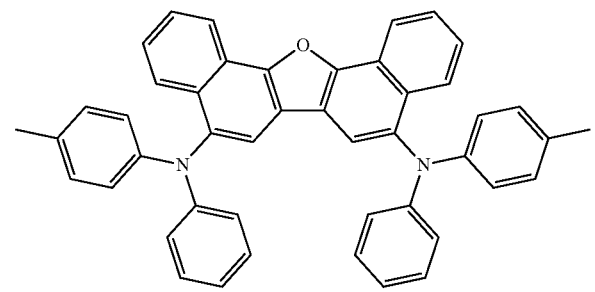
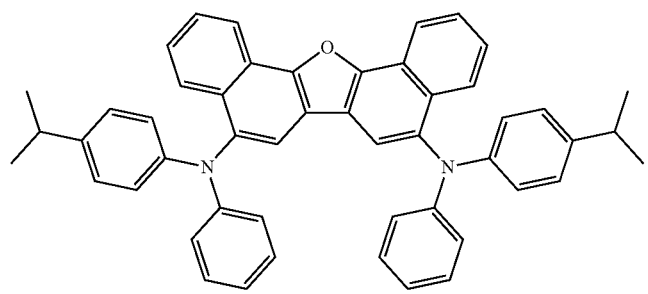 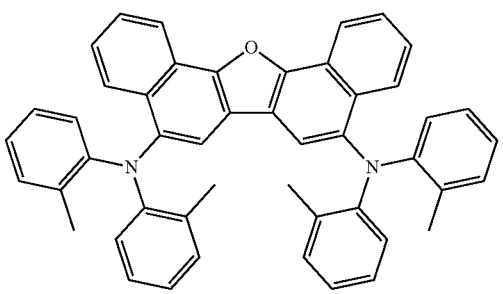
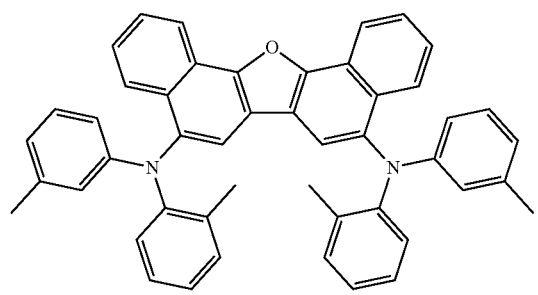 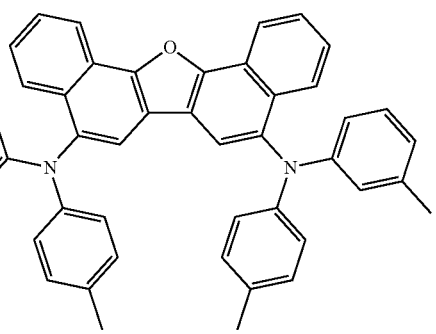
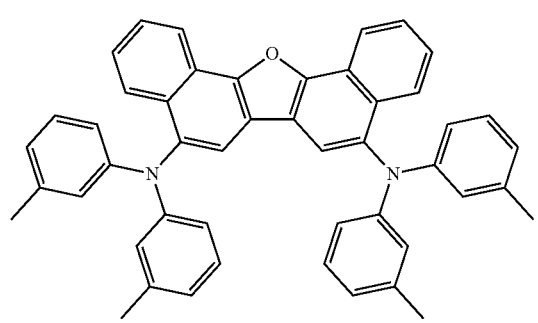 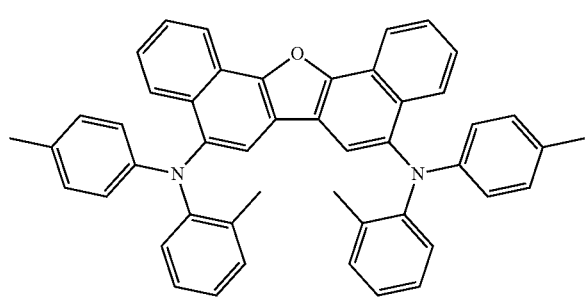

-continued
821
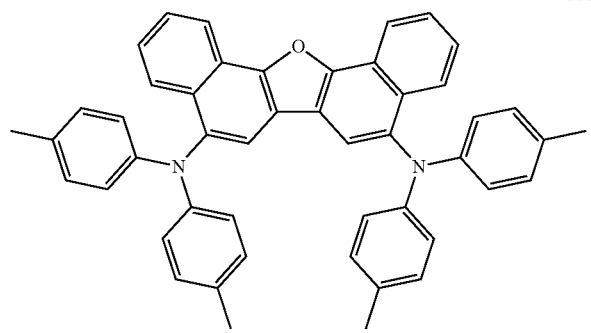
822
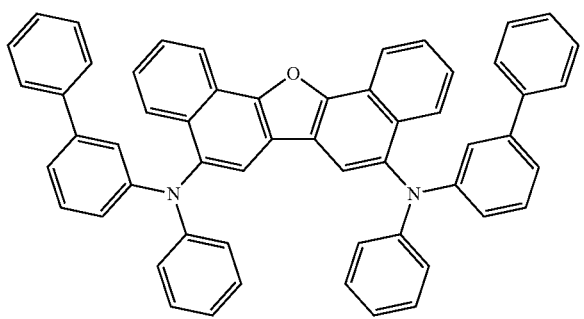
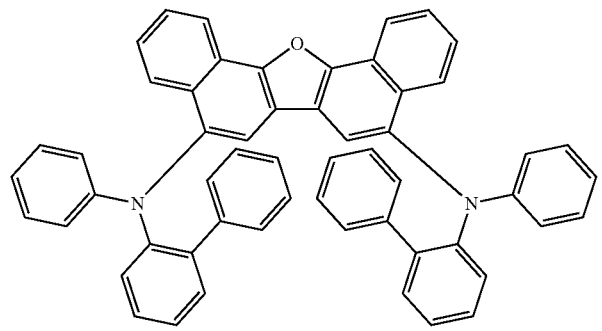
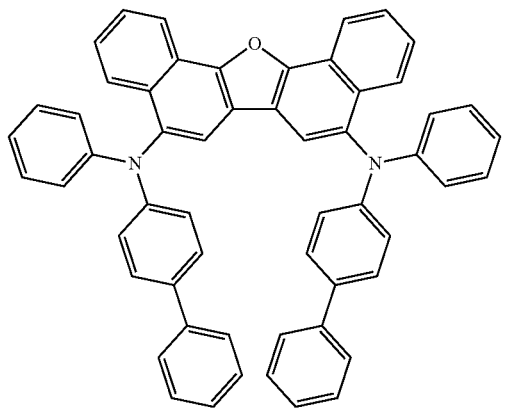
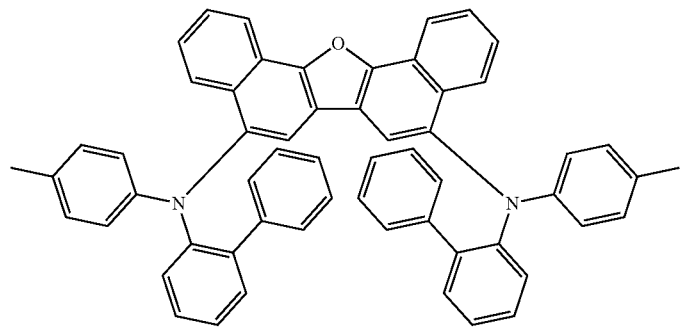
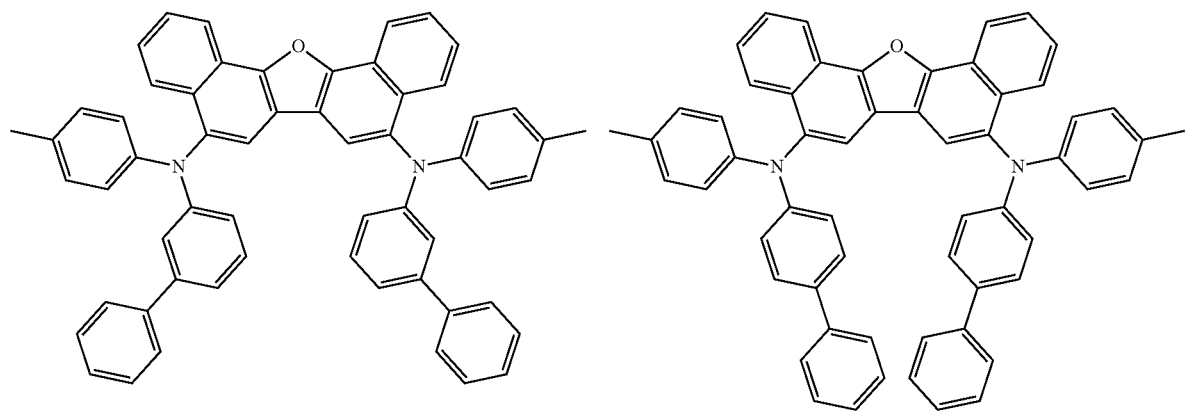

-continued
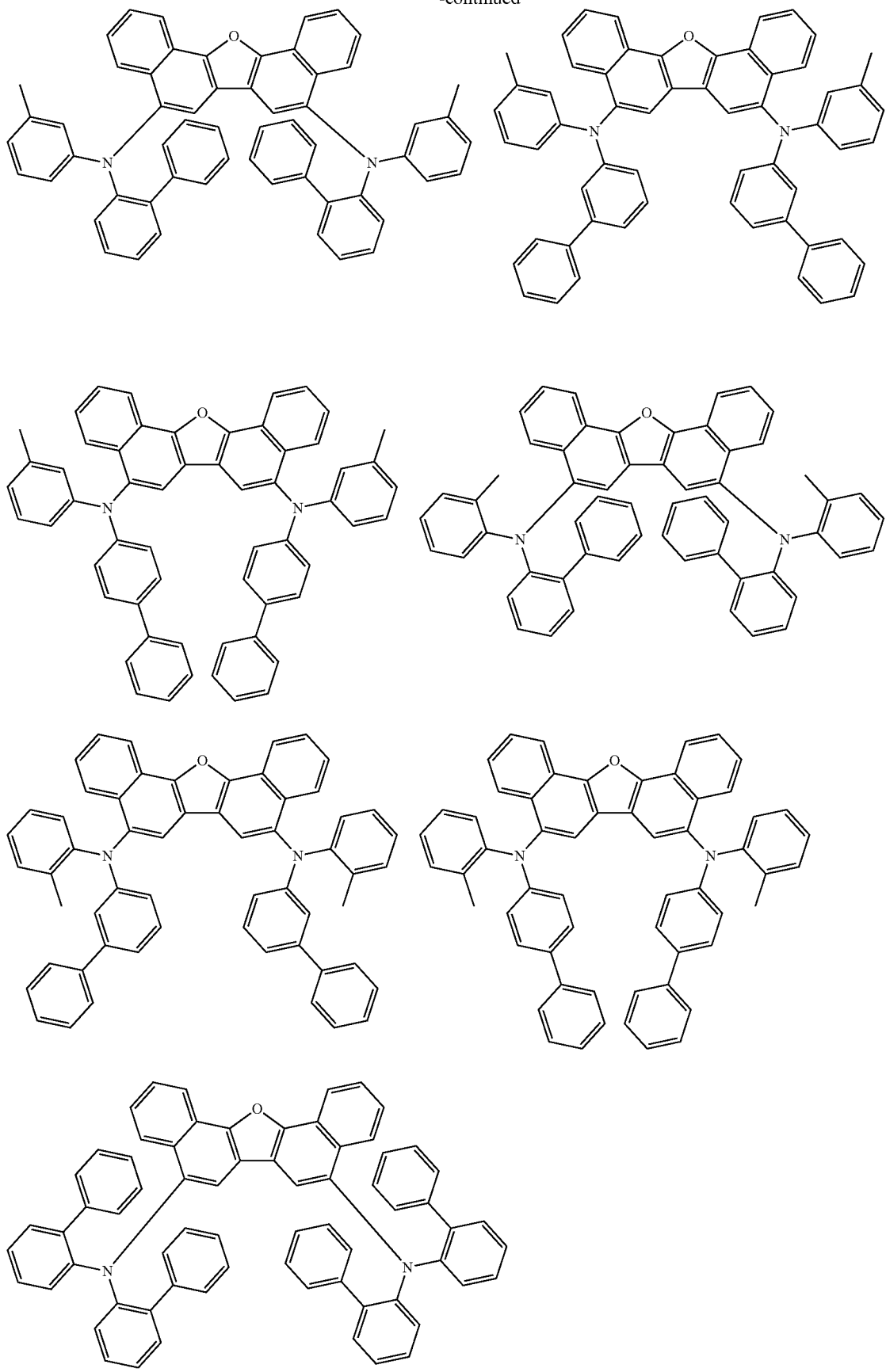

-continued
825 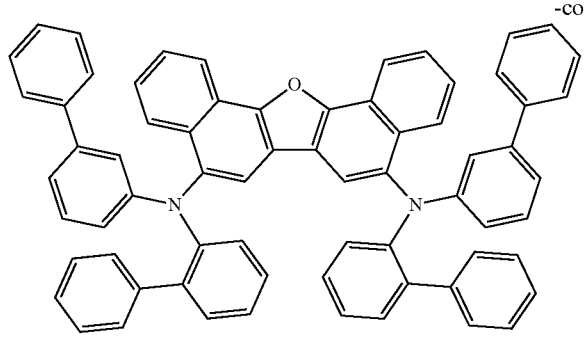 826 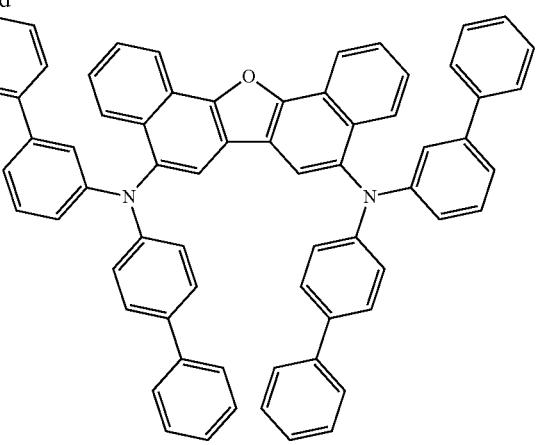
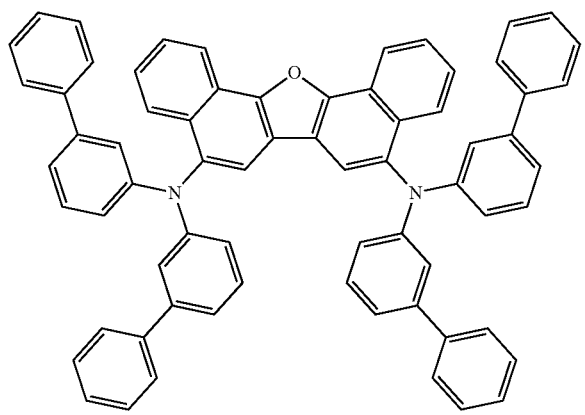
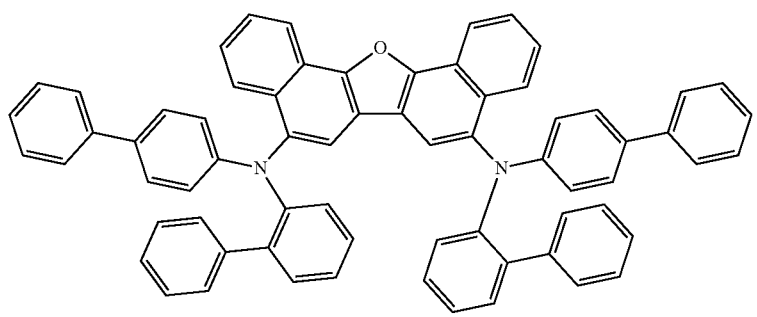
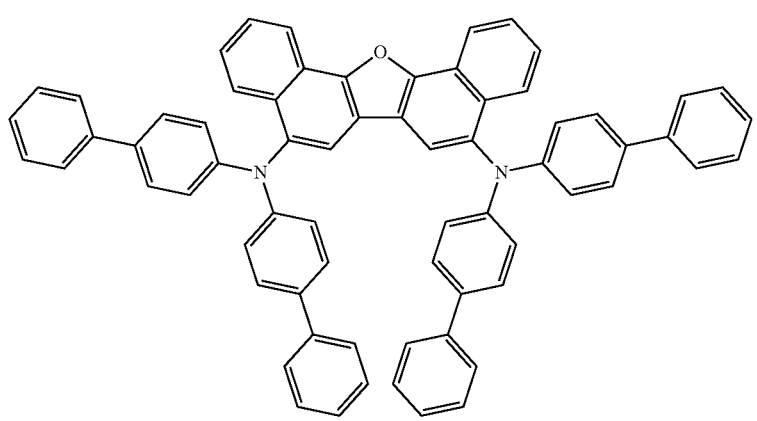

827
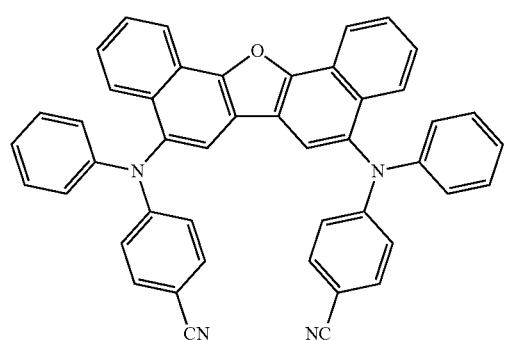
-continued
828
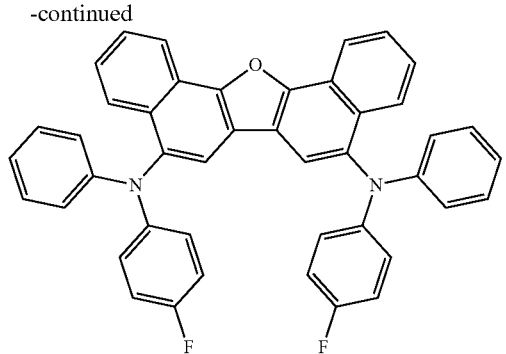
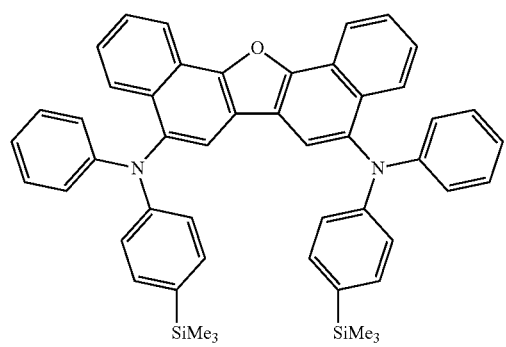
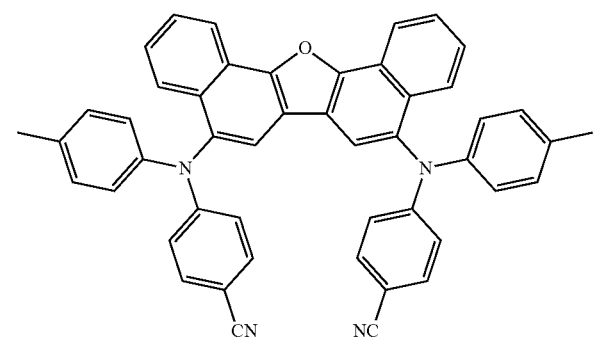
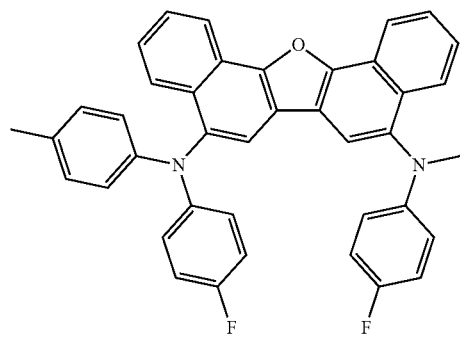
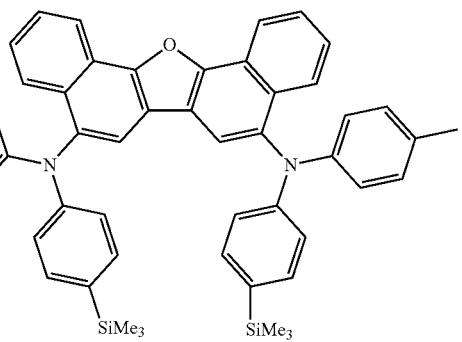
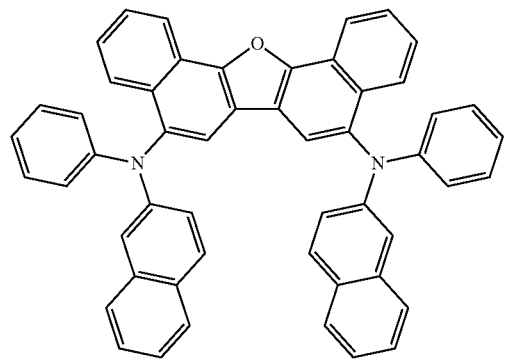
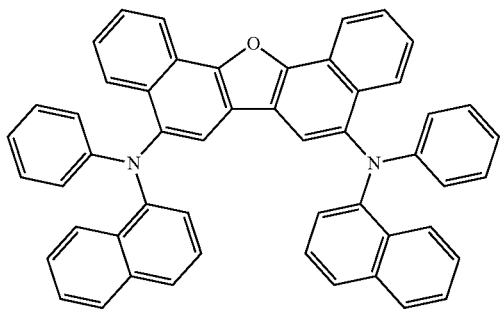

829 830
-continued
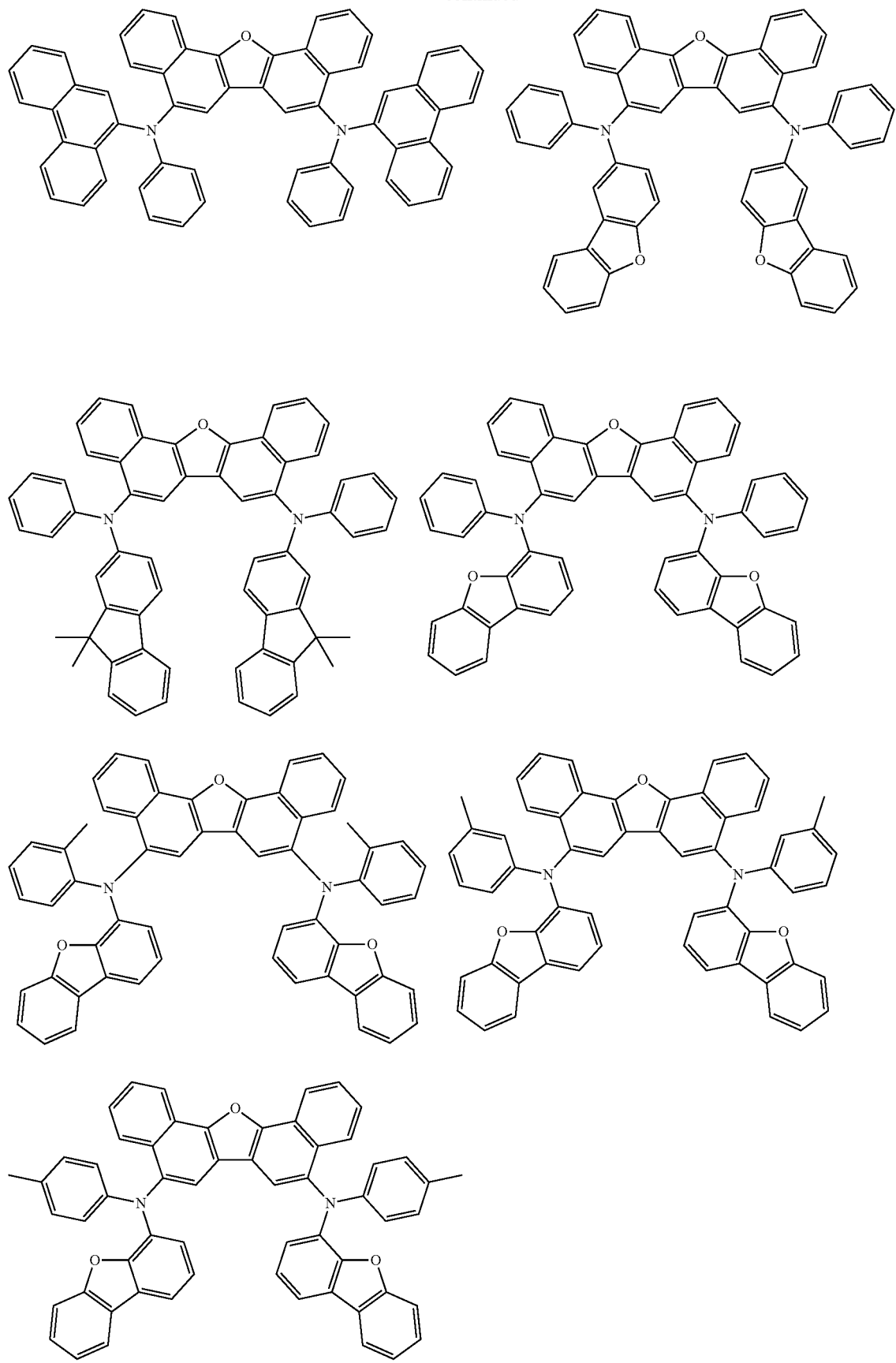

831
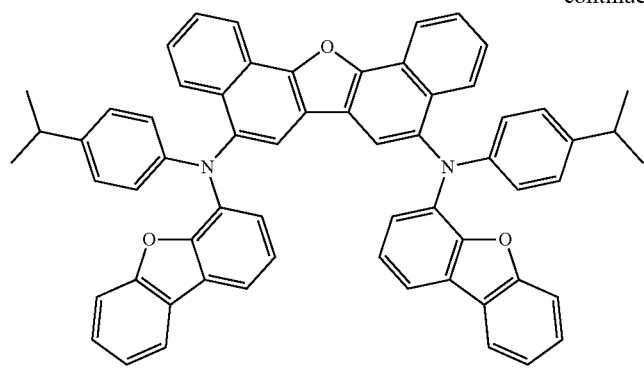
832
-continued
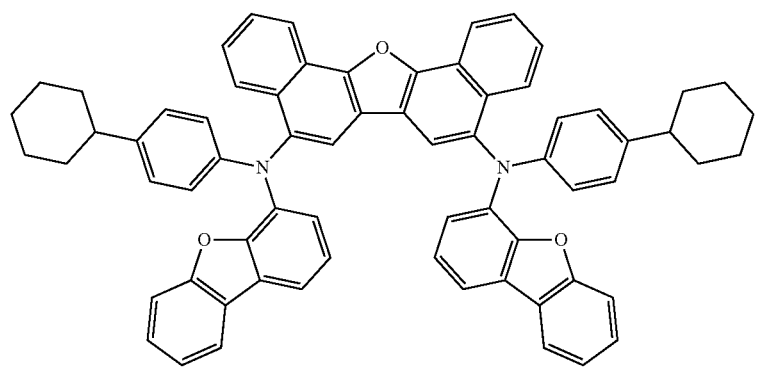
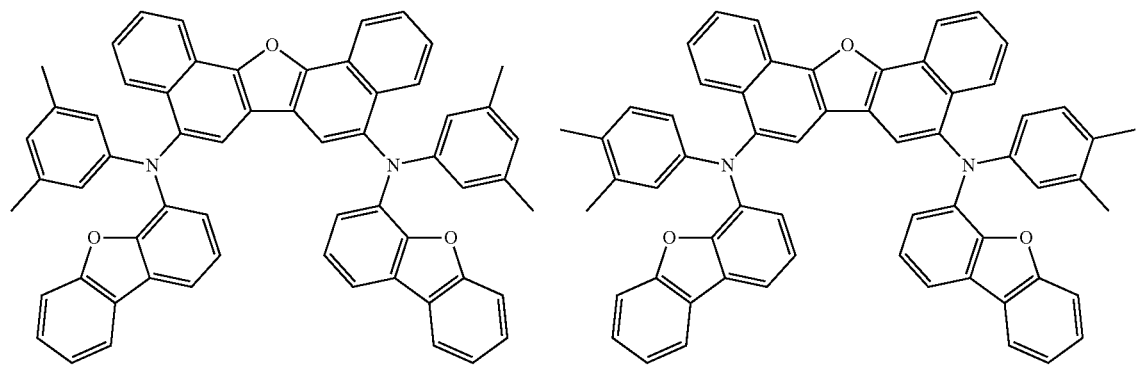
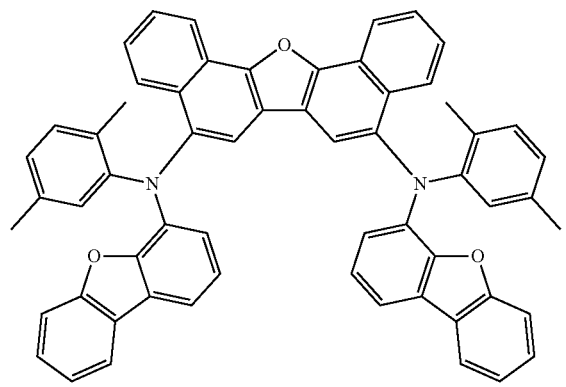

833
-continued
834
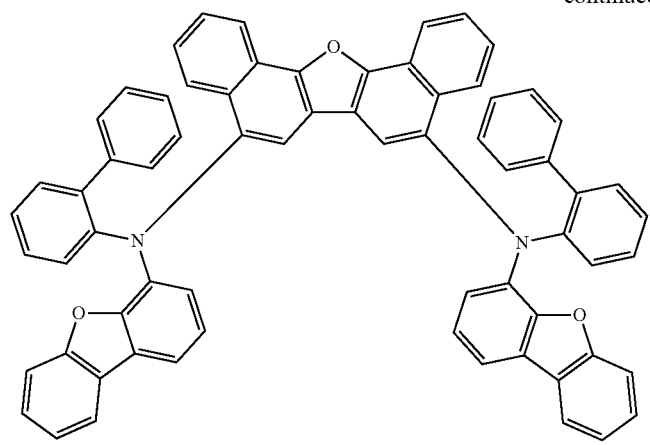
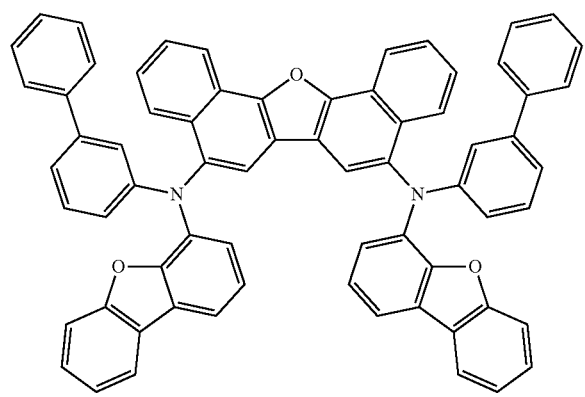
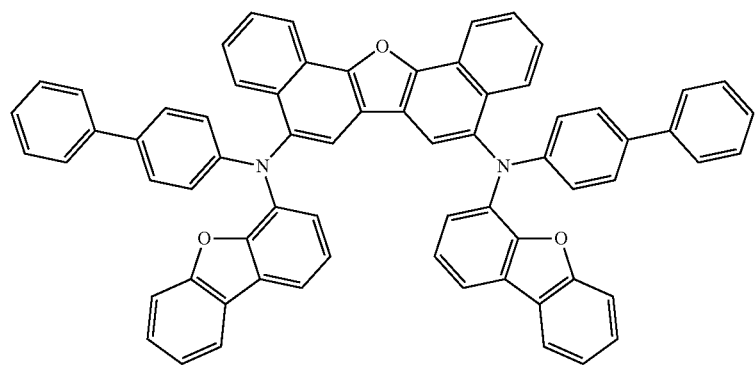
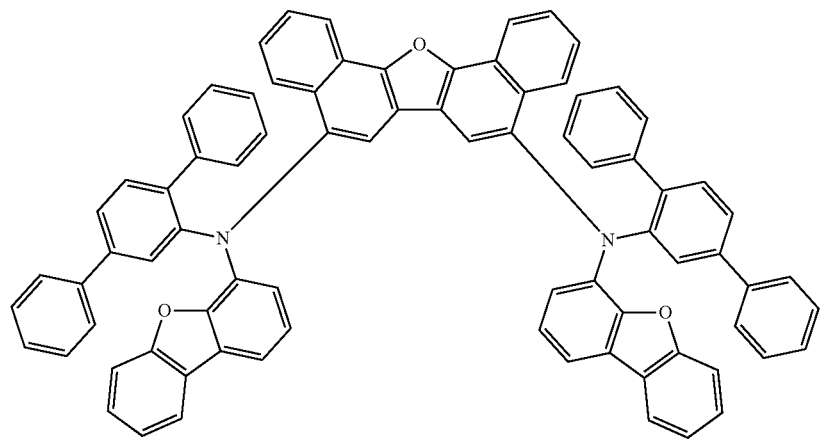

835
836
-continued
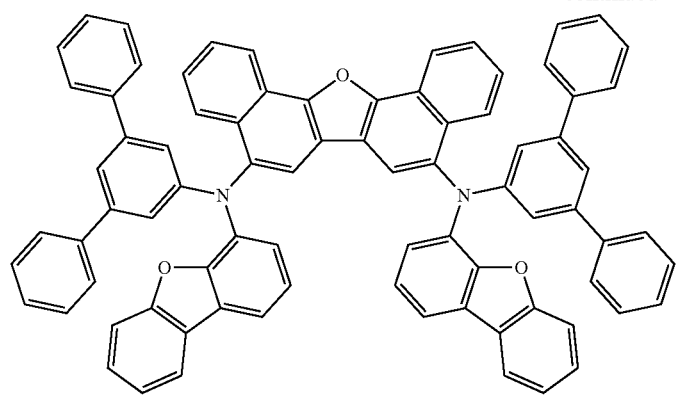
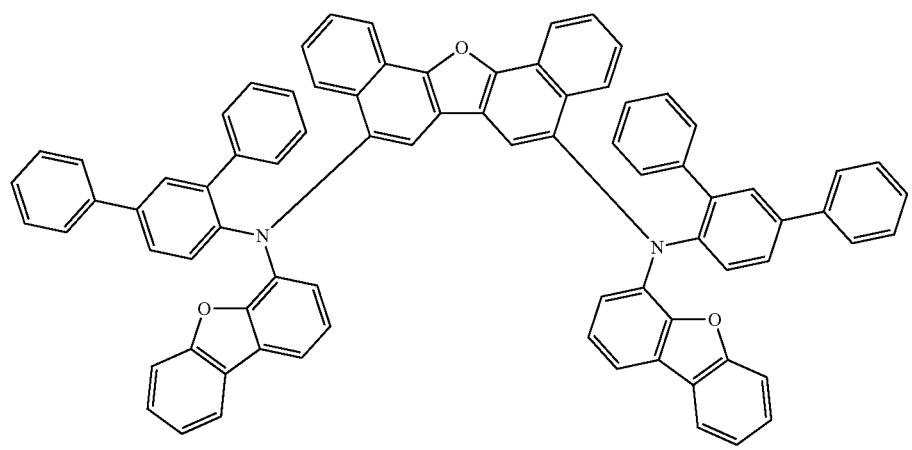
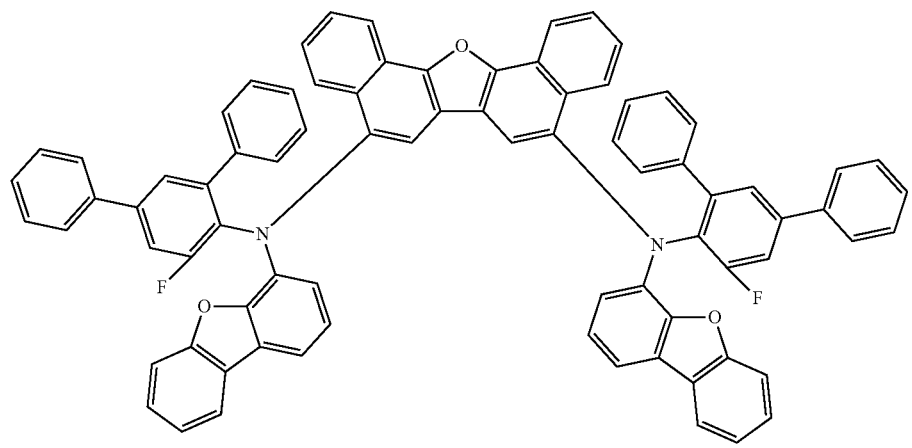
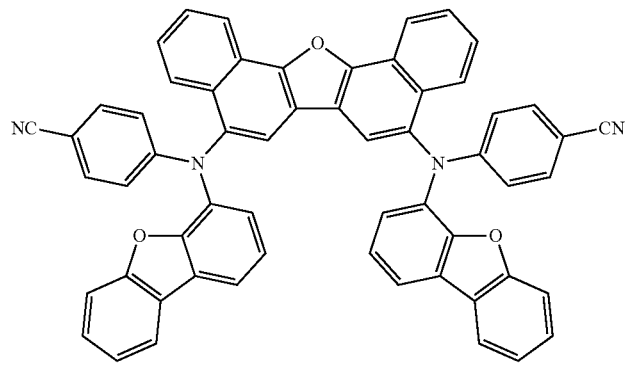

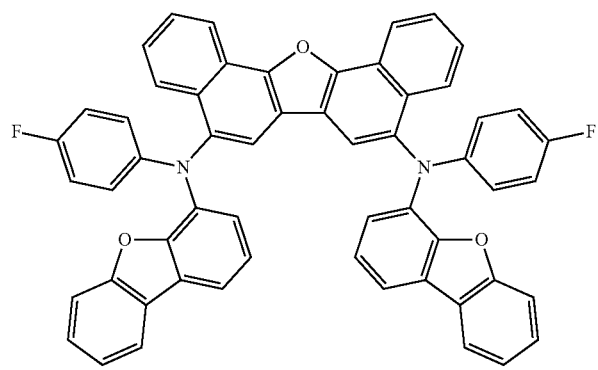
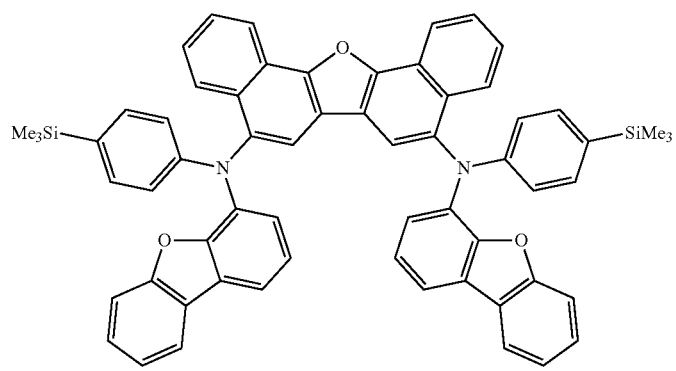
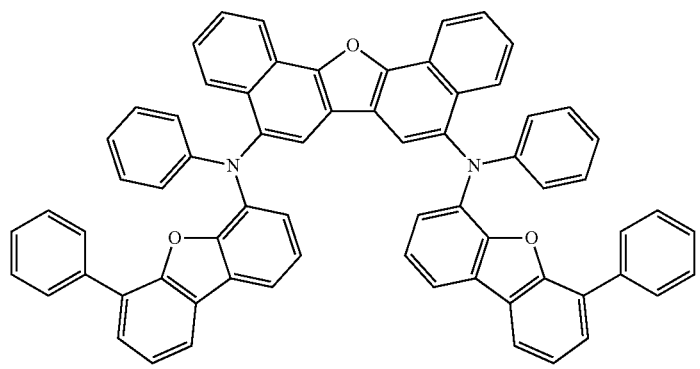
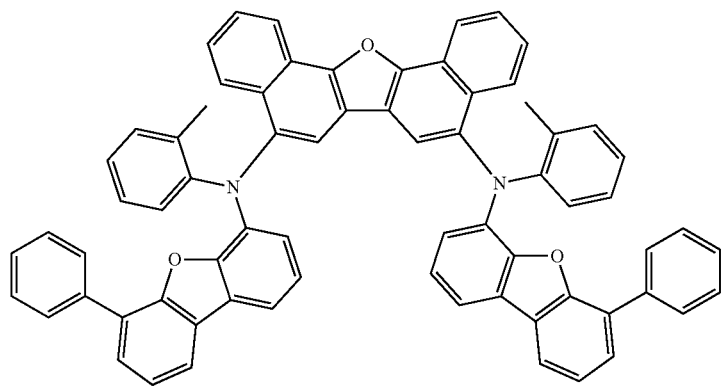

-continued
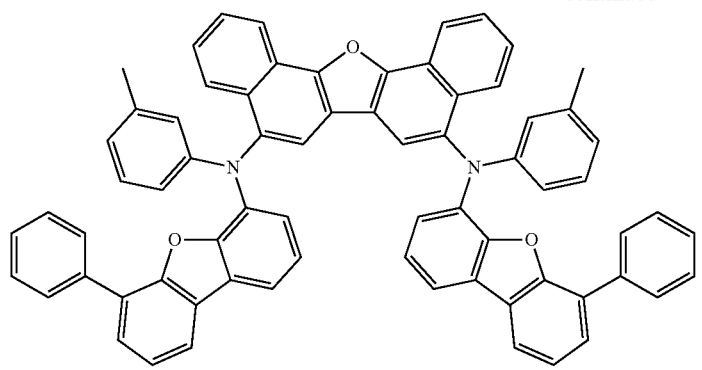
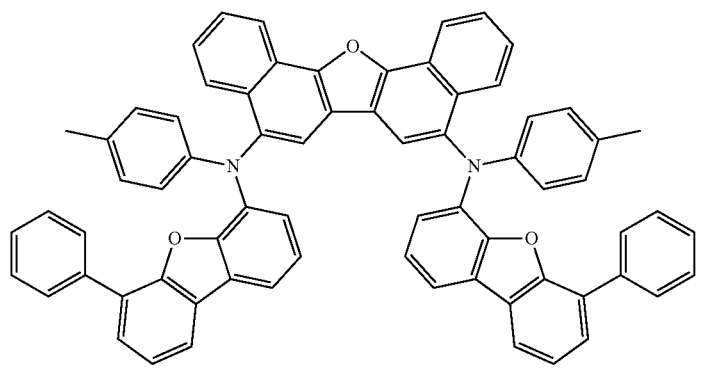
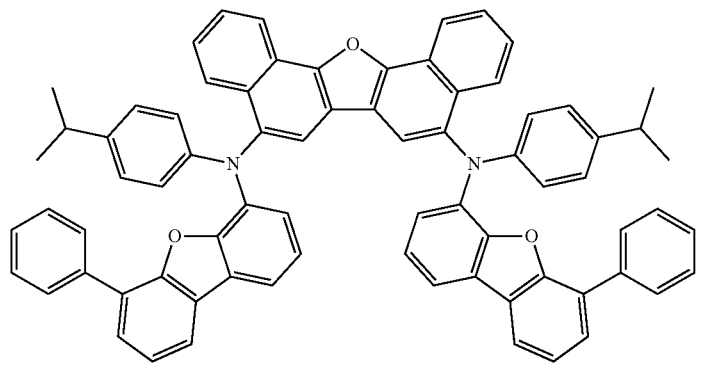
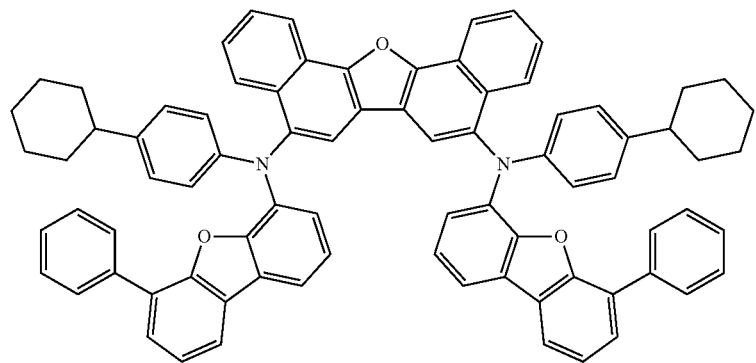

841
-continued
842
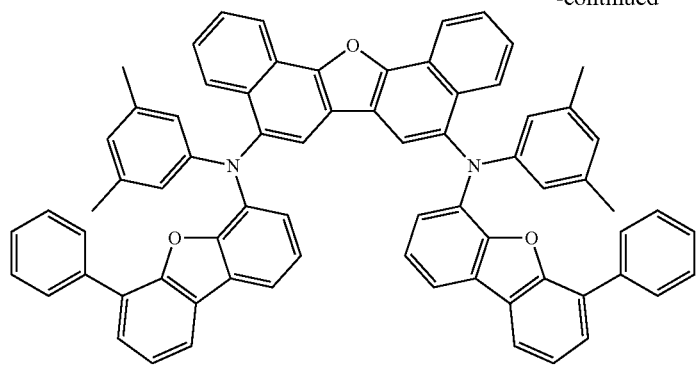
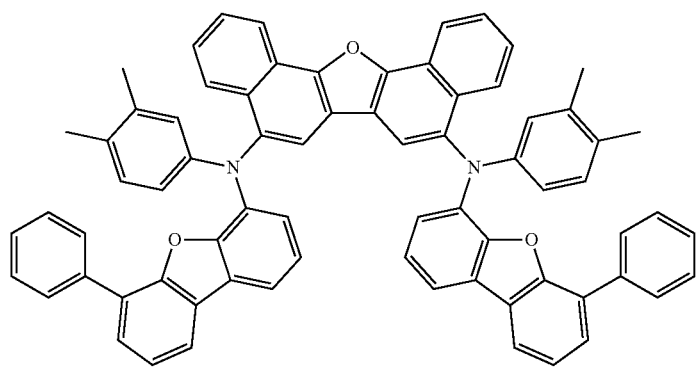
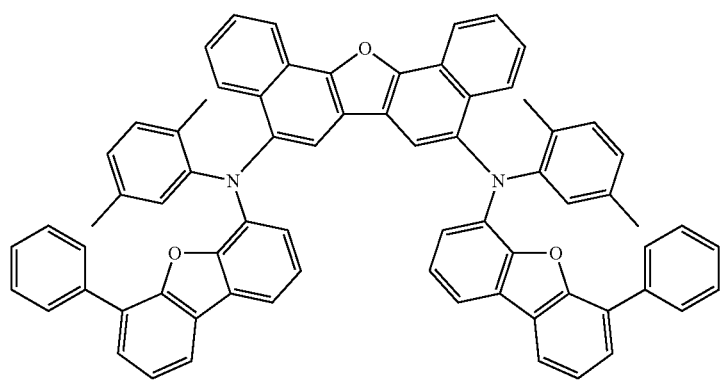
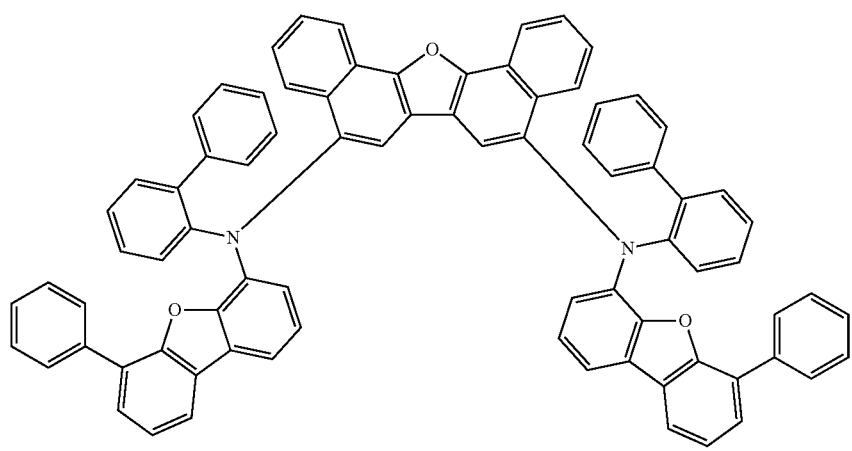

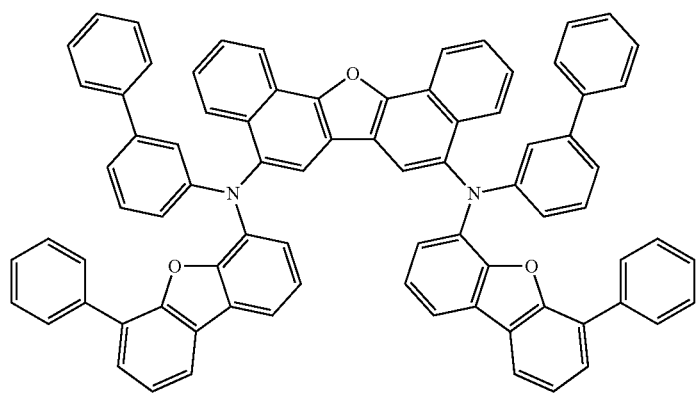
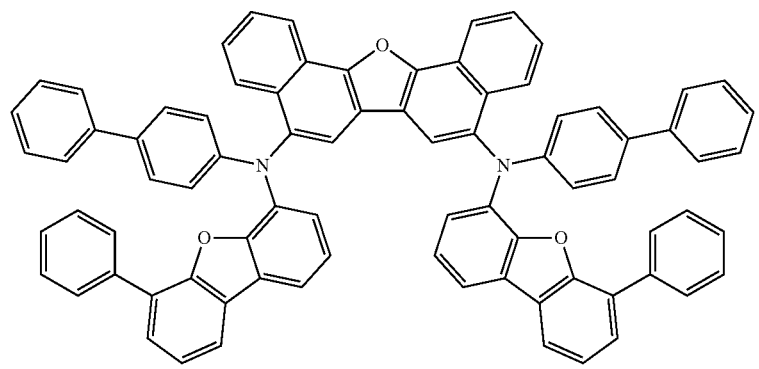
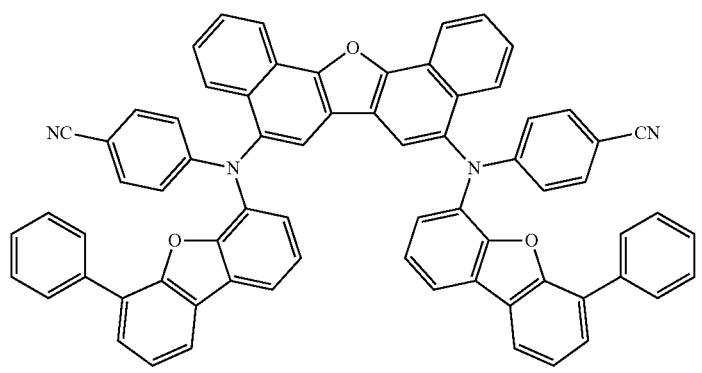
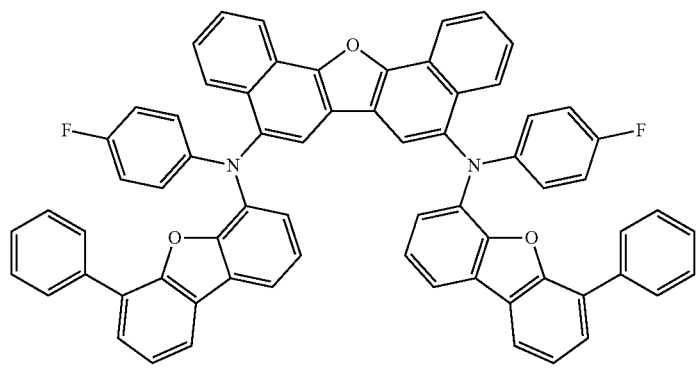

-continued
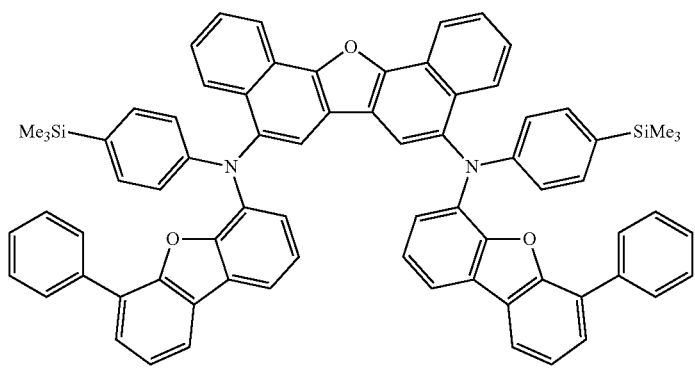
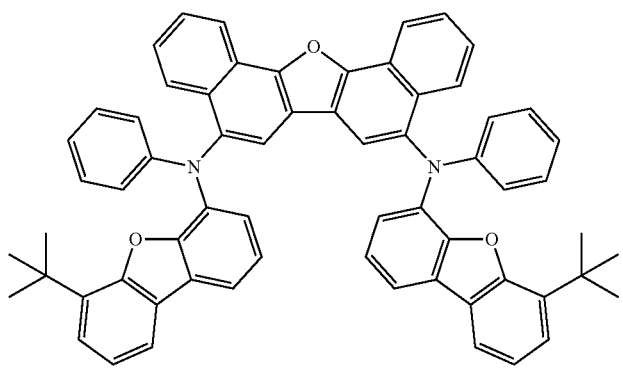
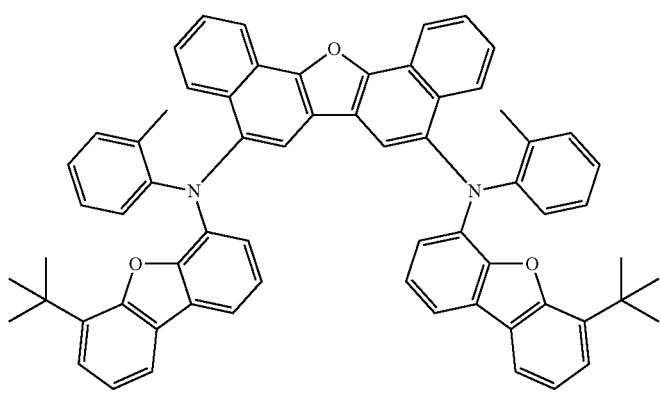
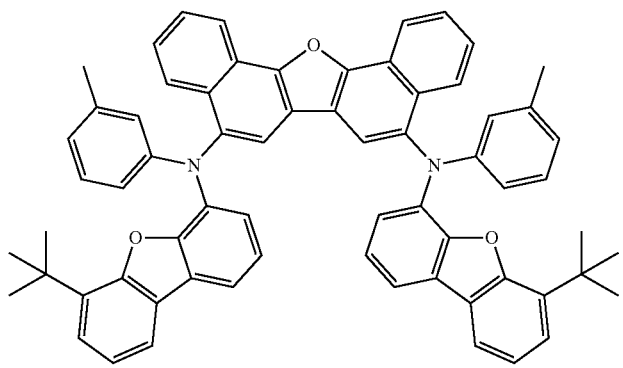

847 848
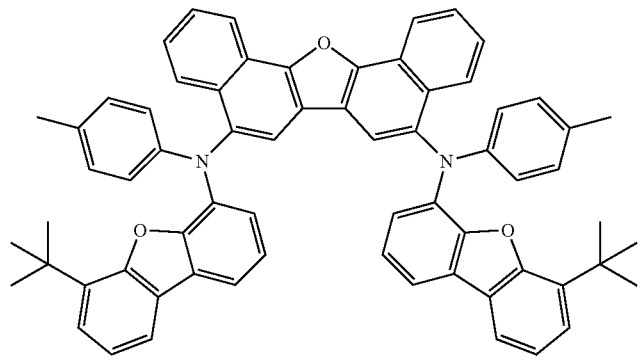
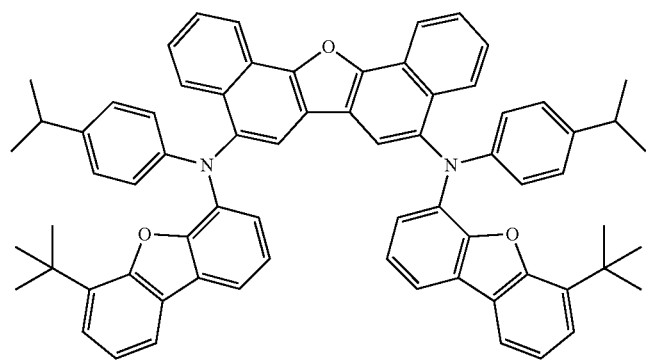
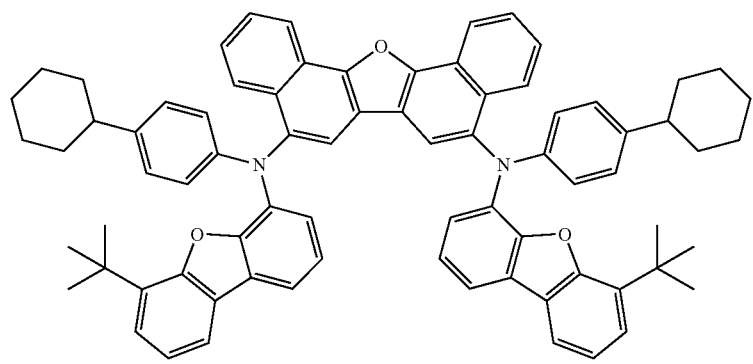
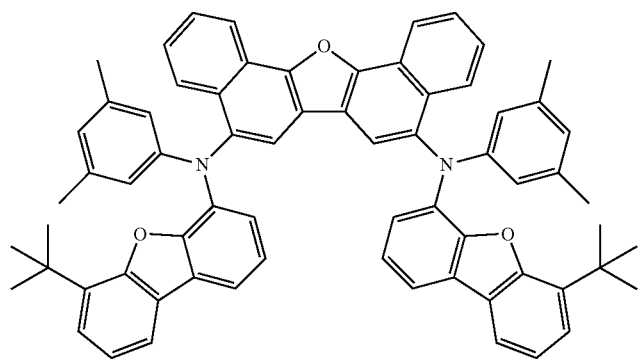

849
850
-continued
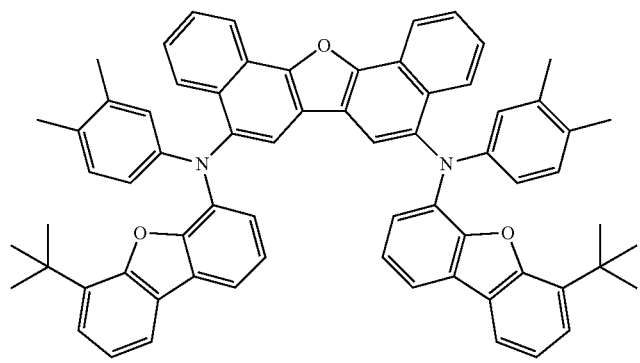
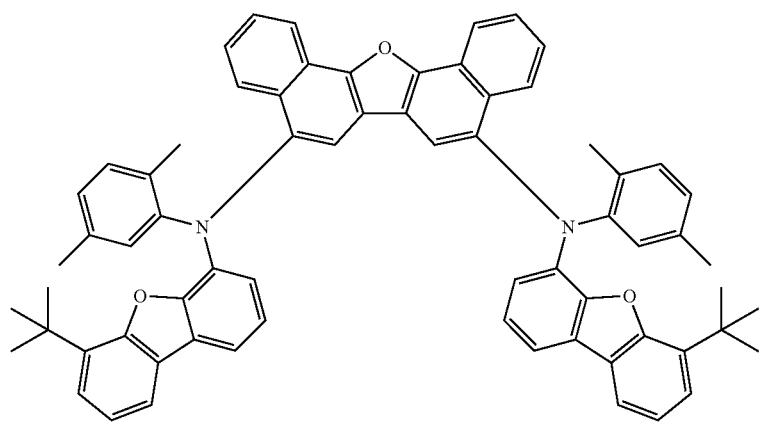
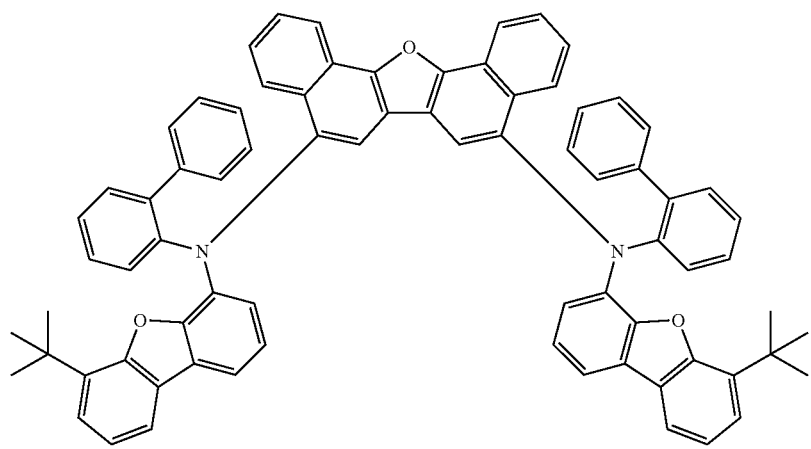
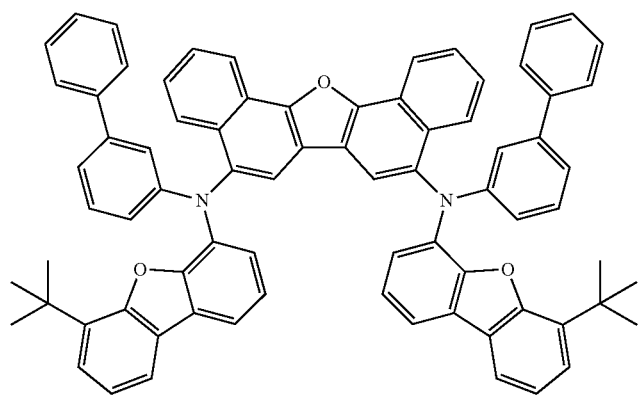

-continued
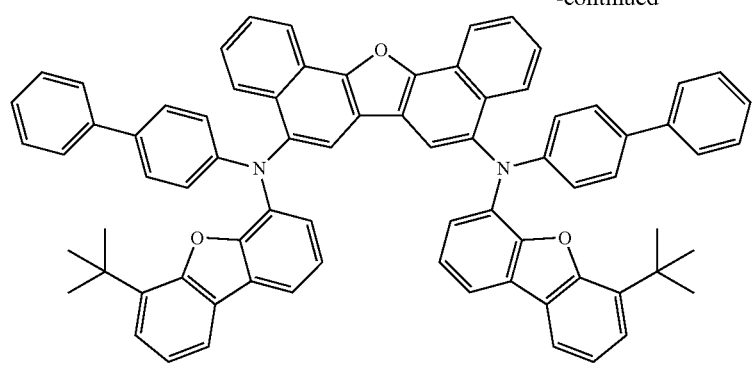
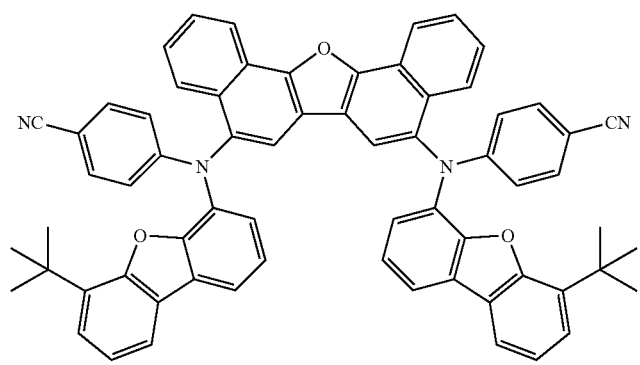
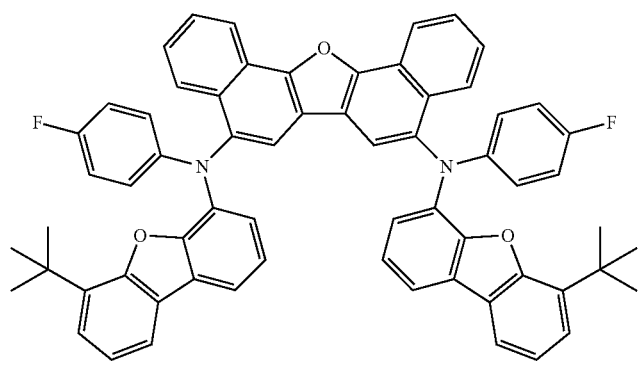
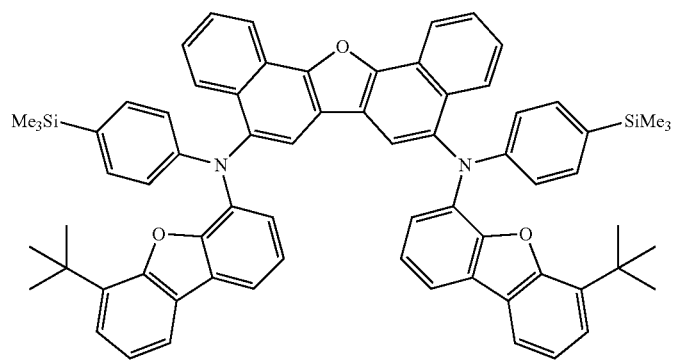

-continued
853 854
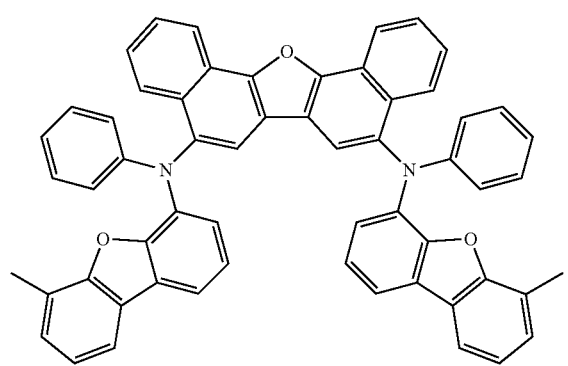 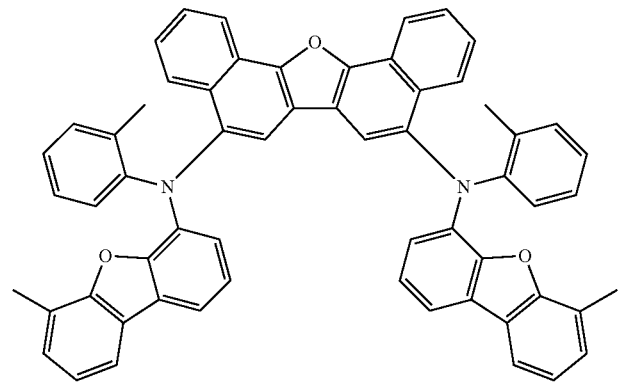
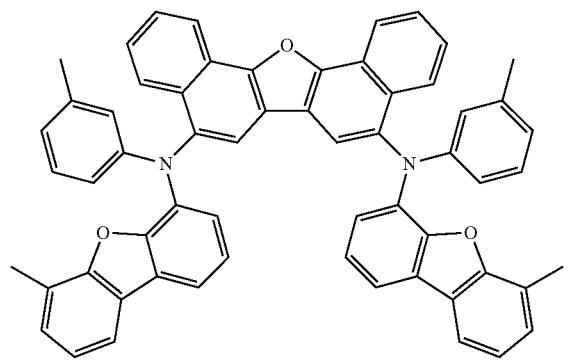 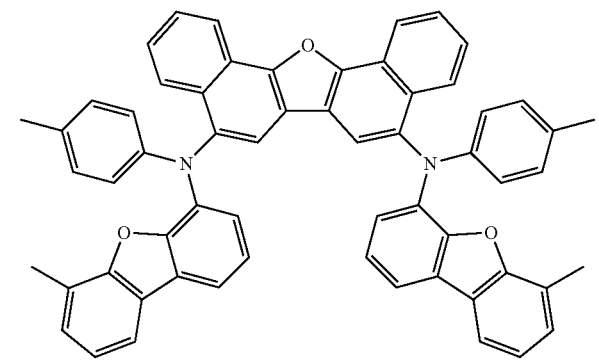
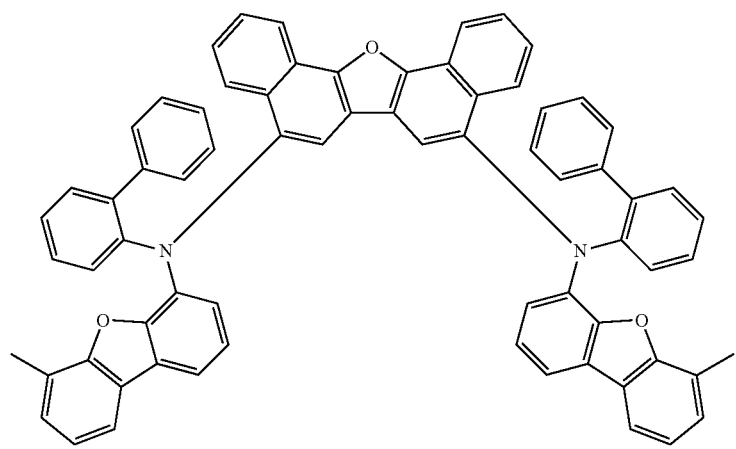
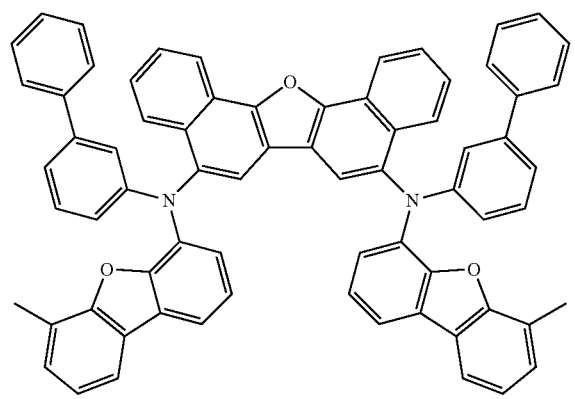

855
856
-continued
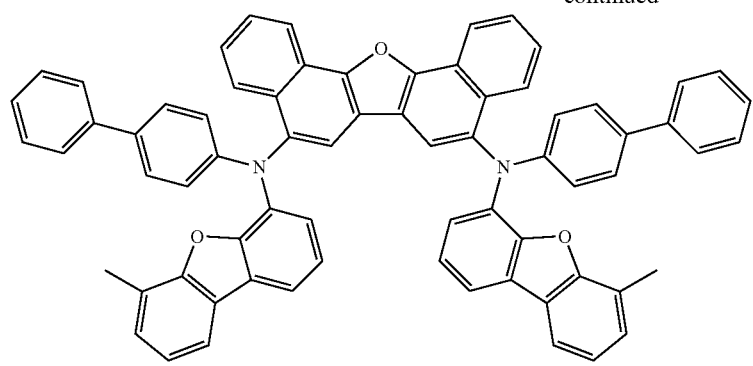
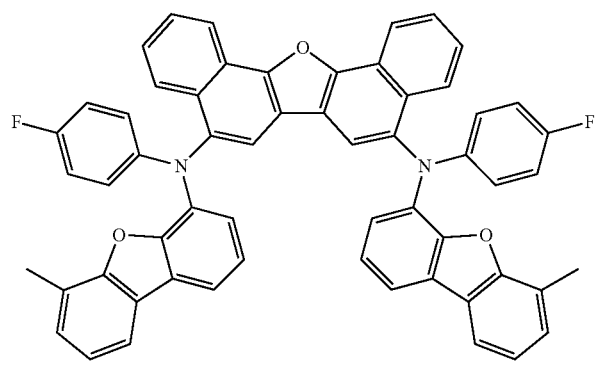
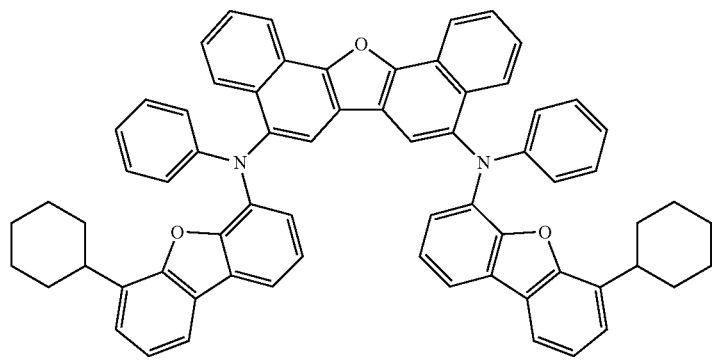
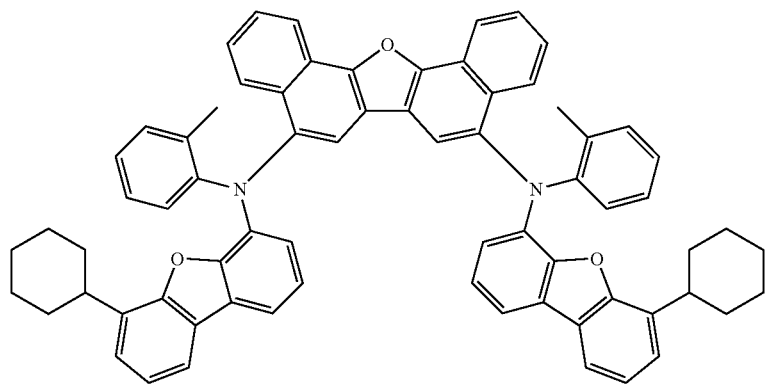

-continued
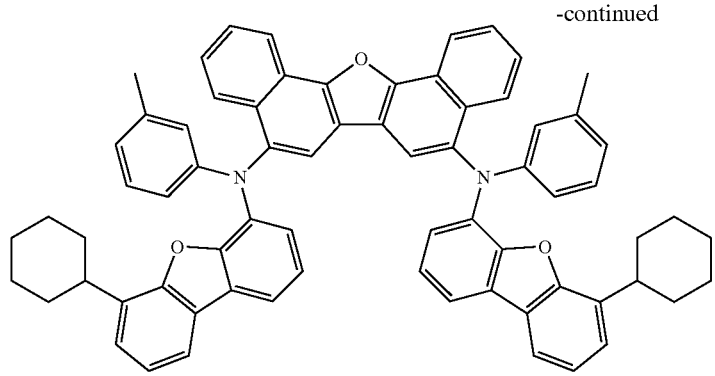
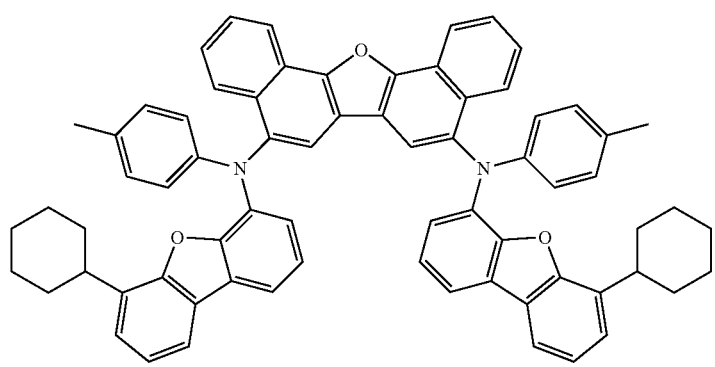
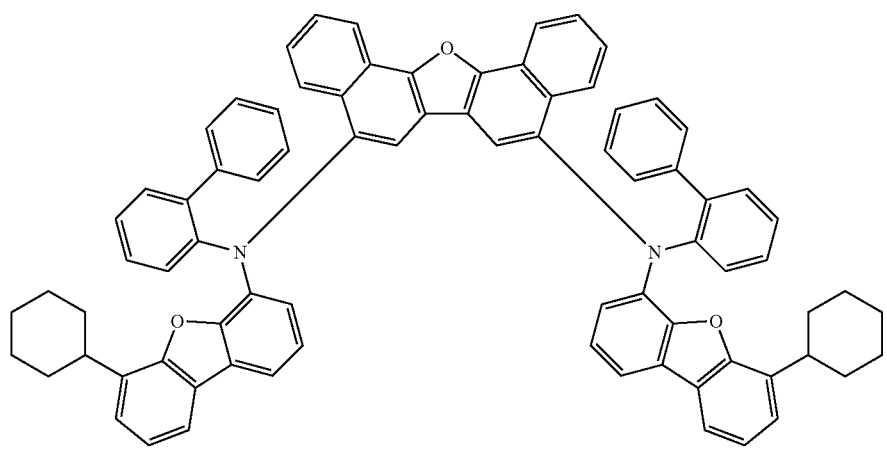
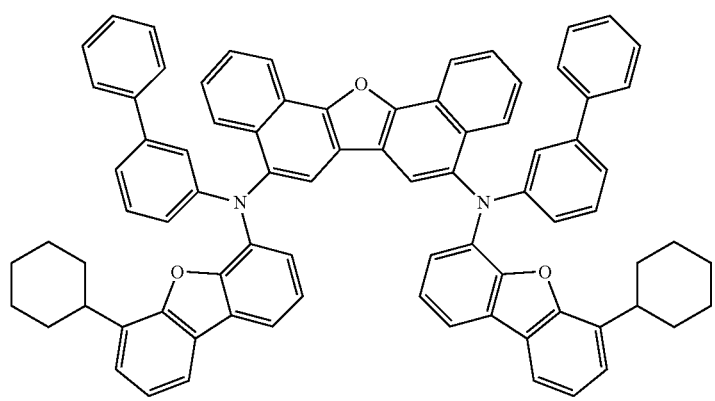

-continued
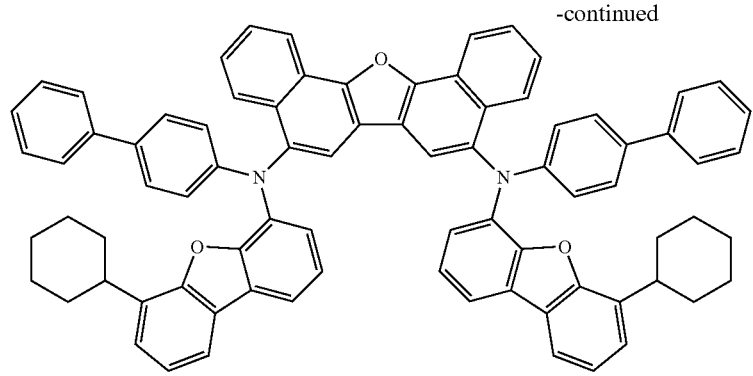
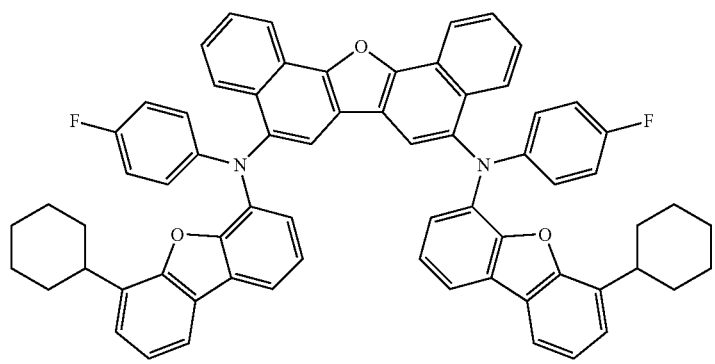
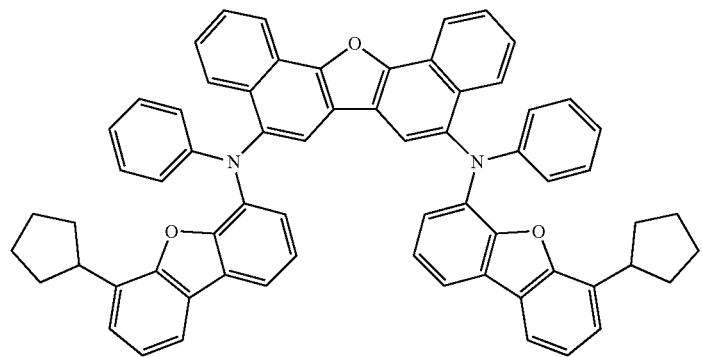
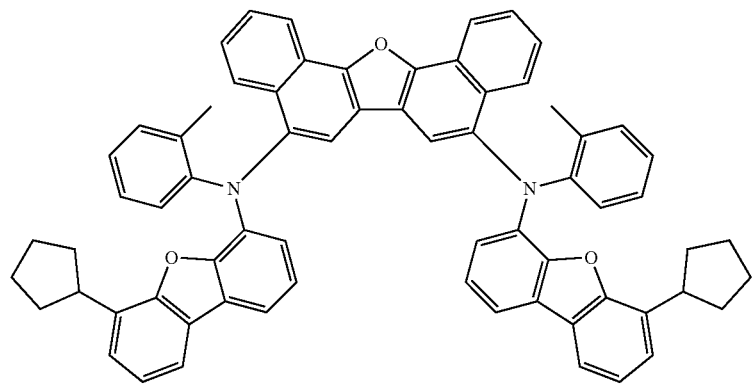

-continued
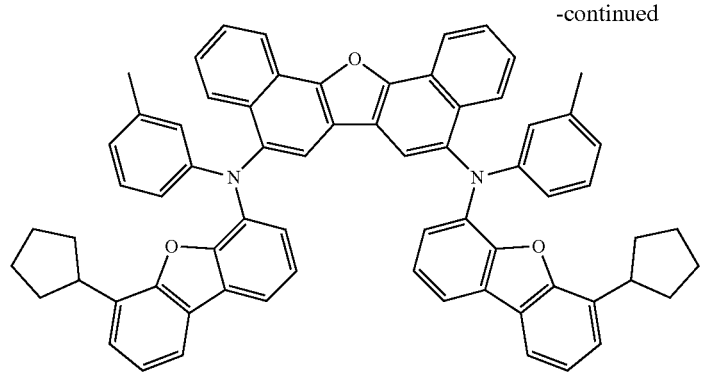
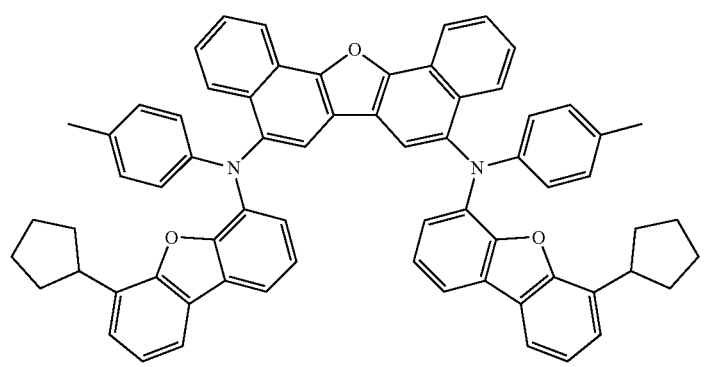
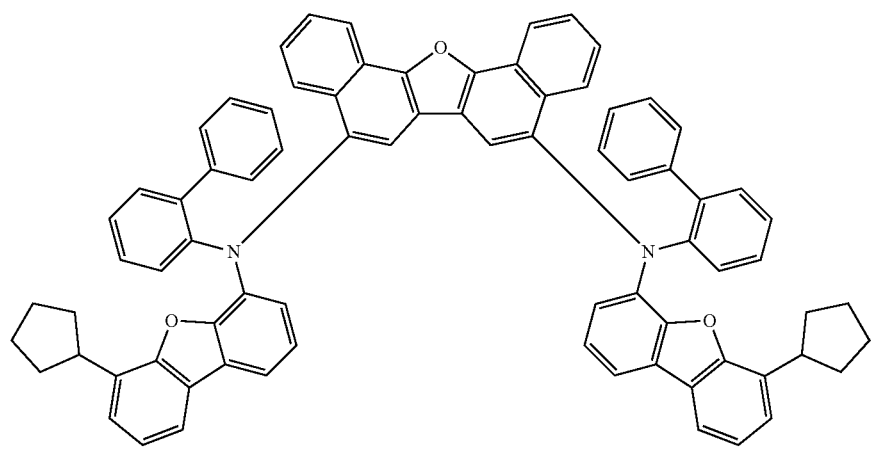
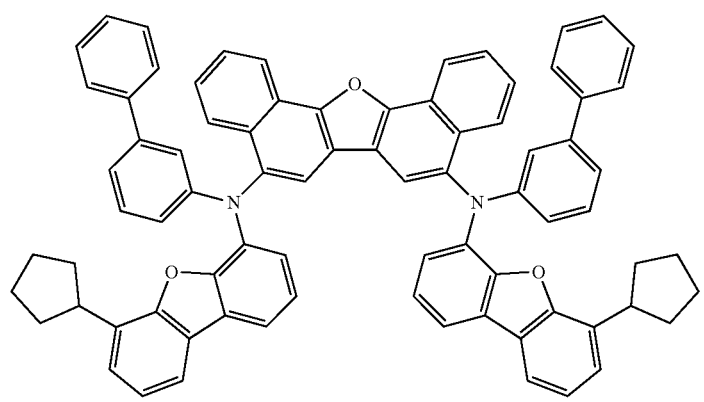

863
864
-continued
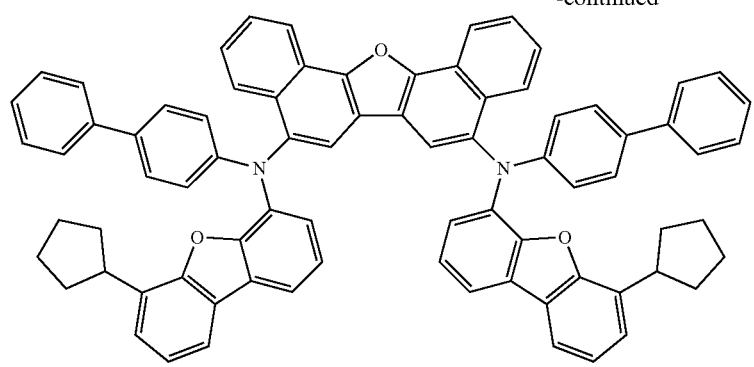
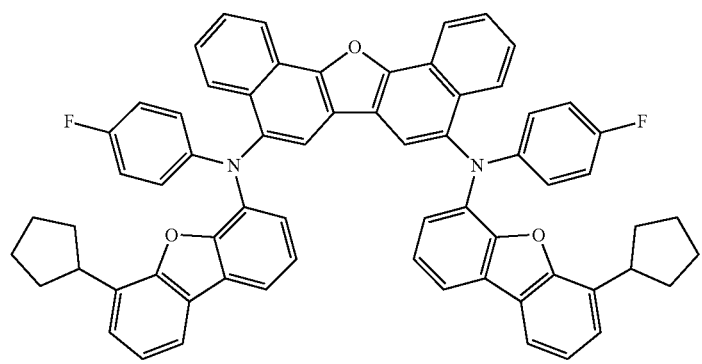
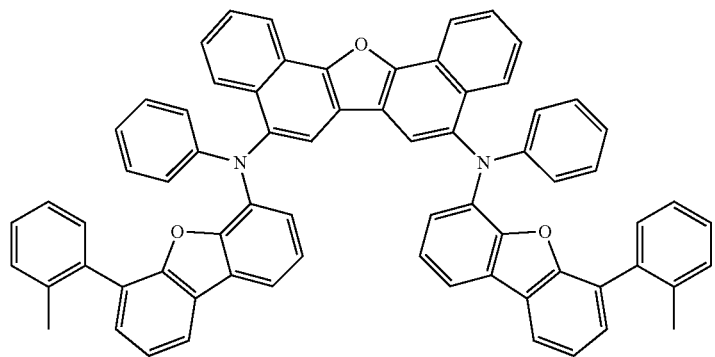
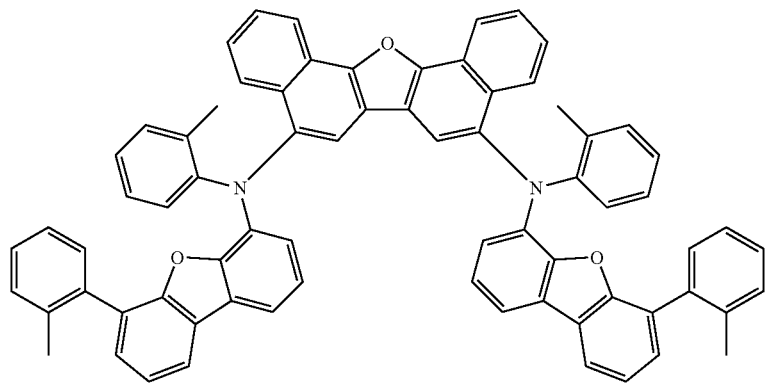

-continued
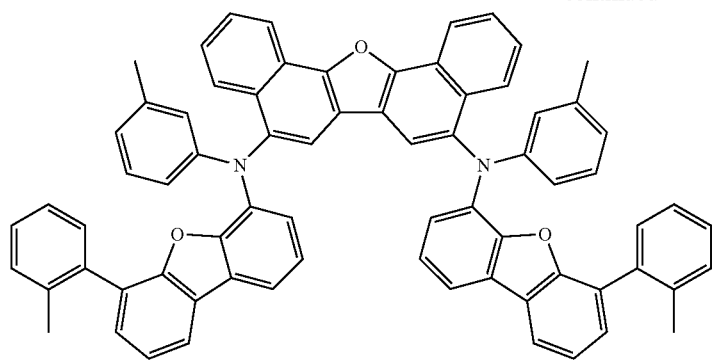
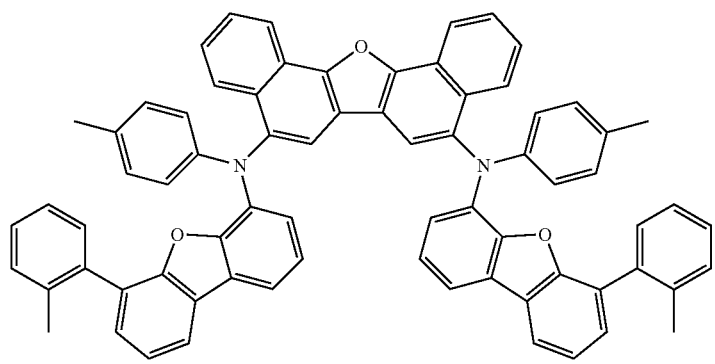
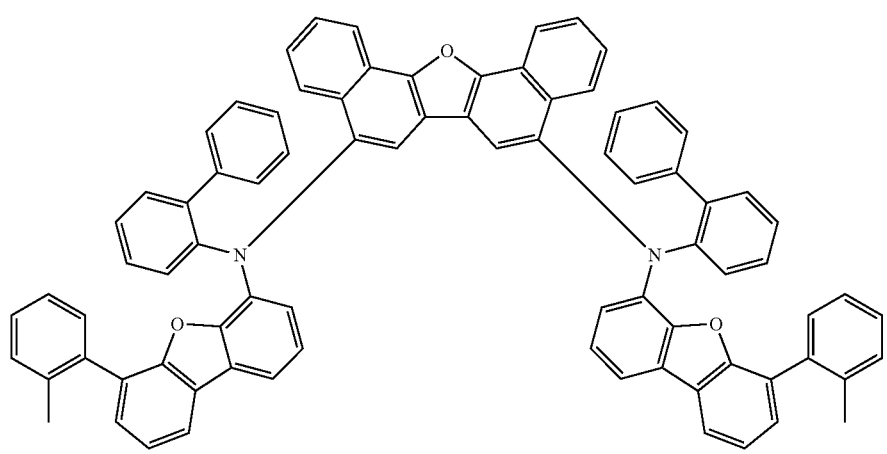
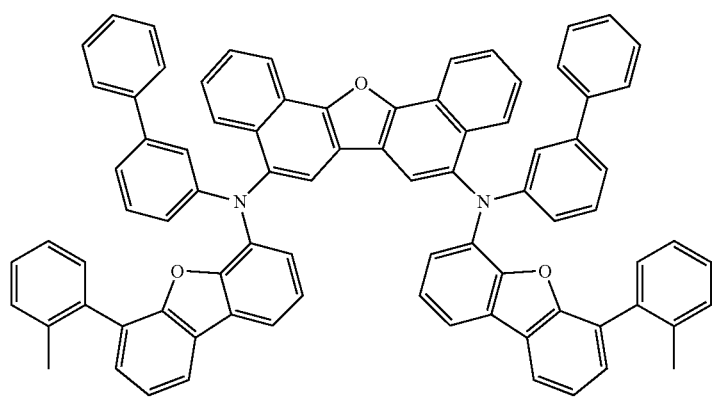

-continued
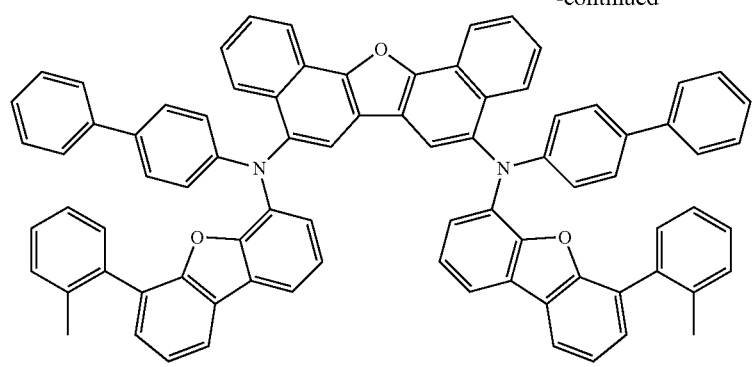
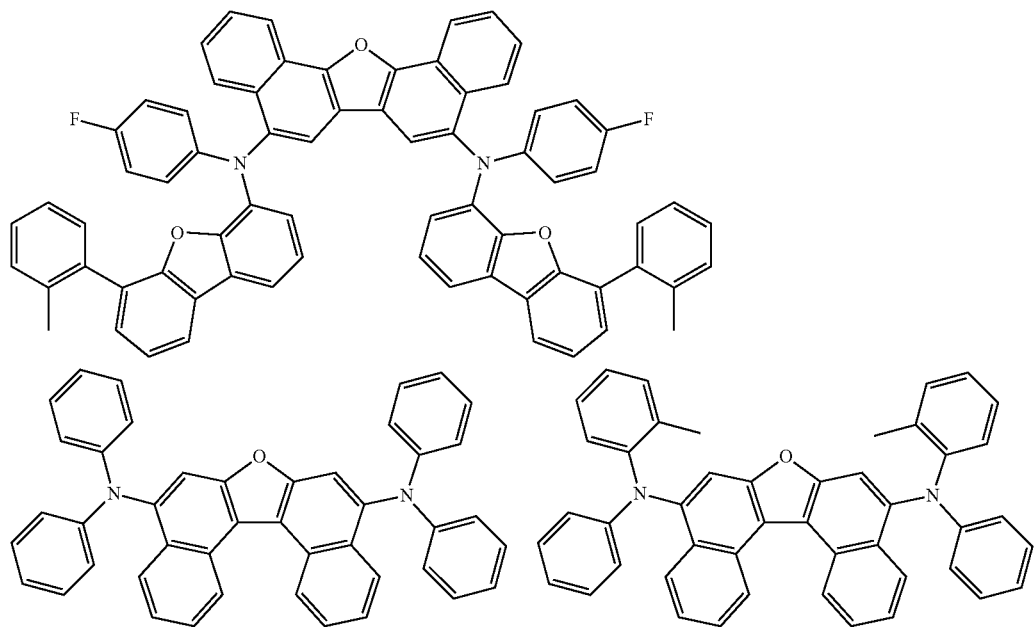
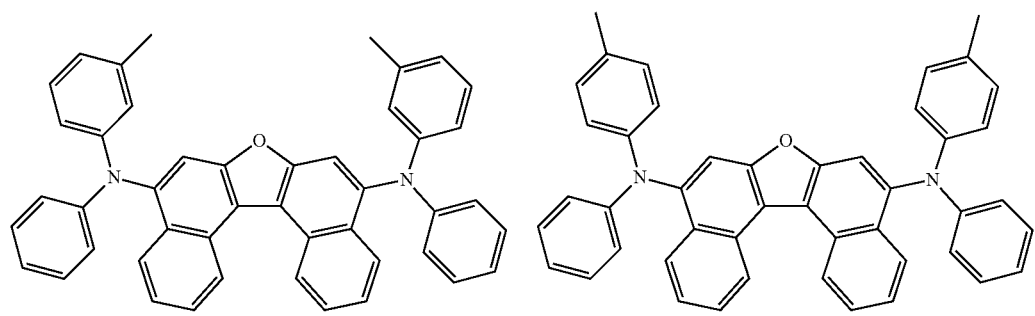
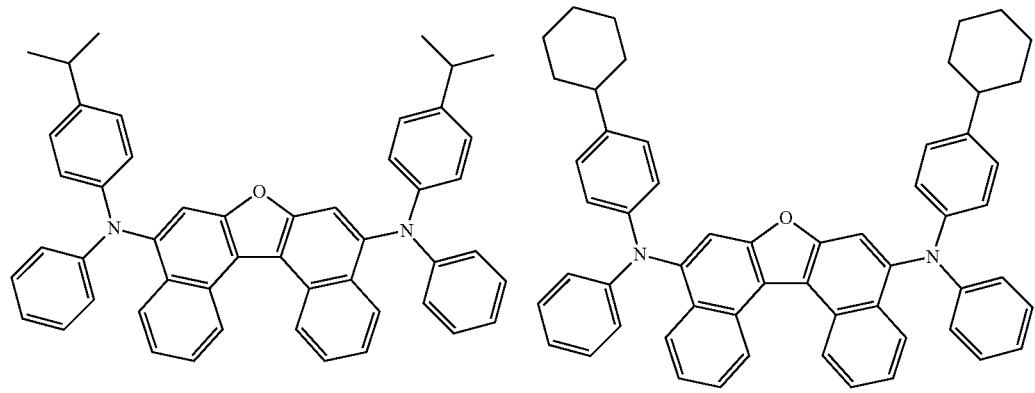

869 870
-continued
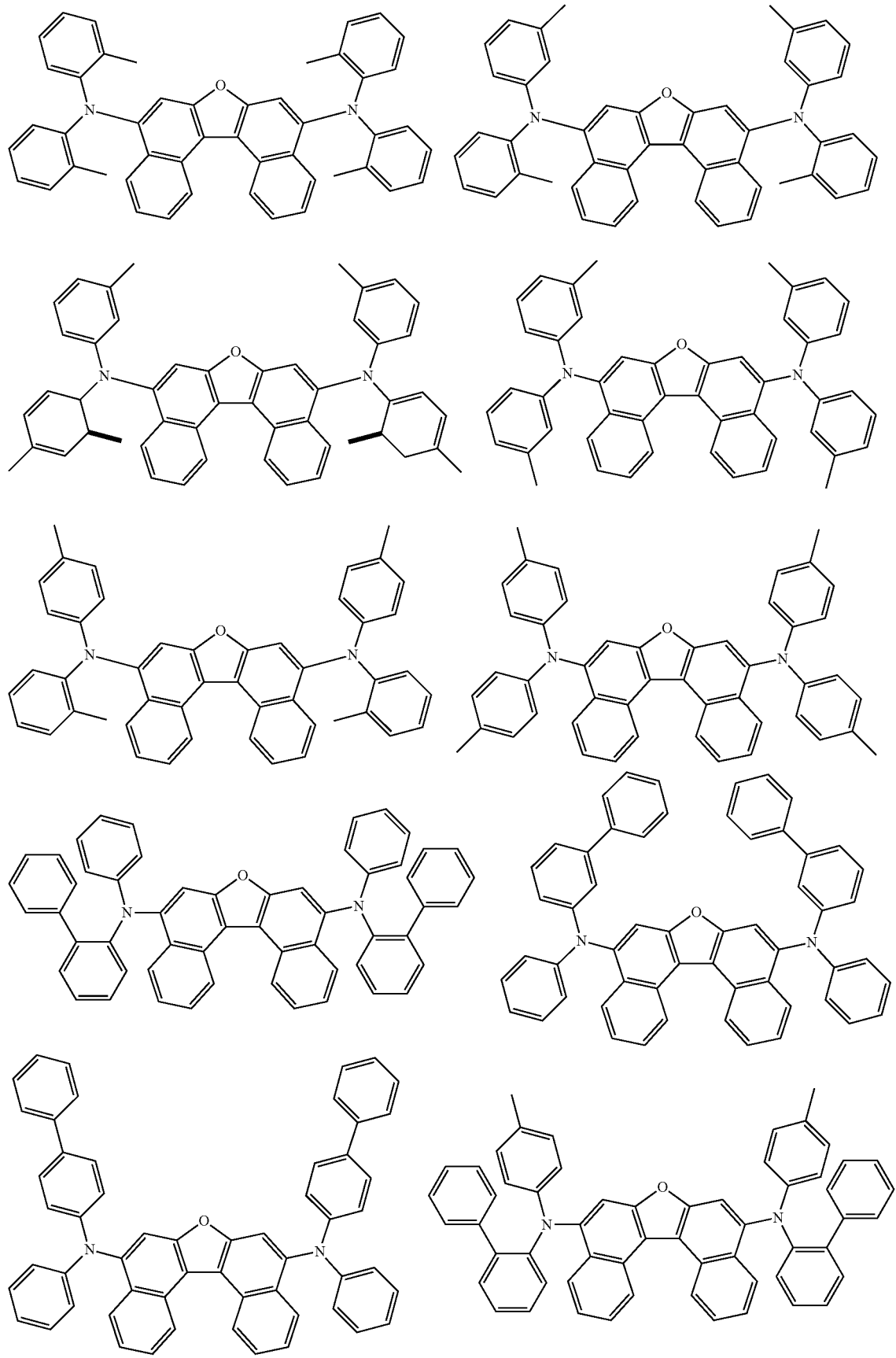

-continued
871
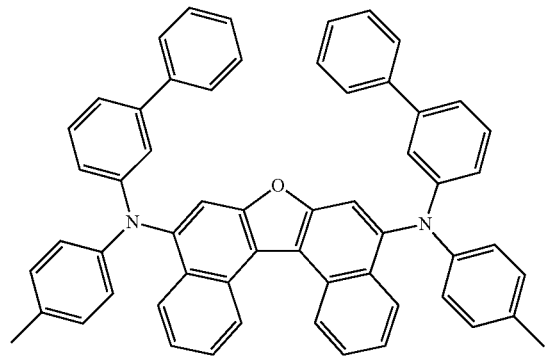
872
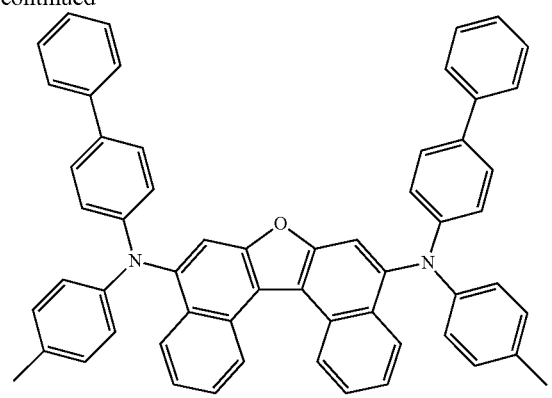
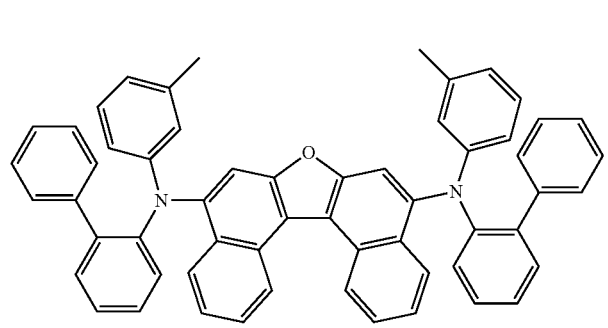
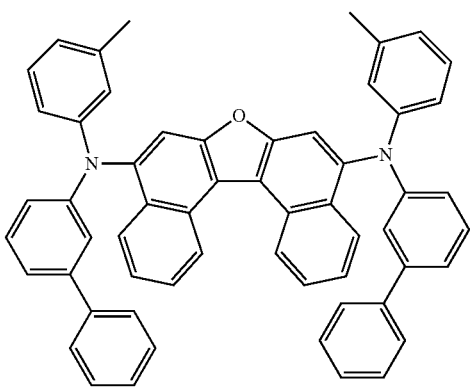
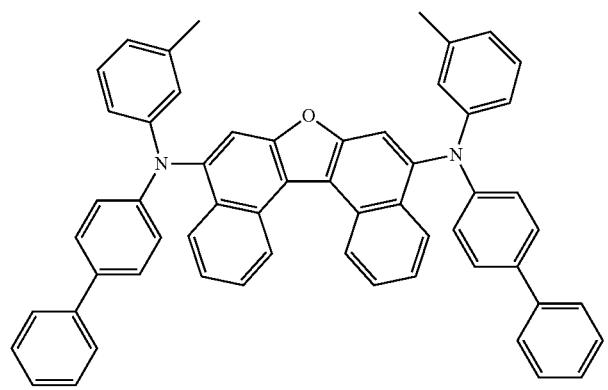
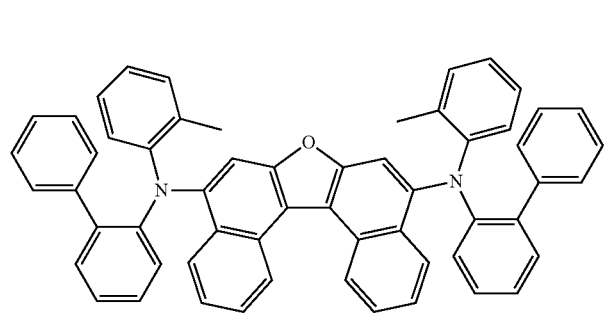
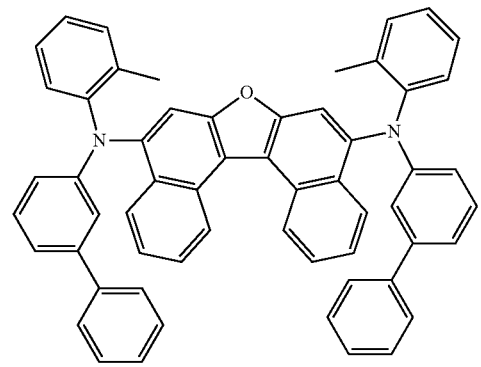

-continued
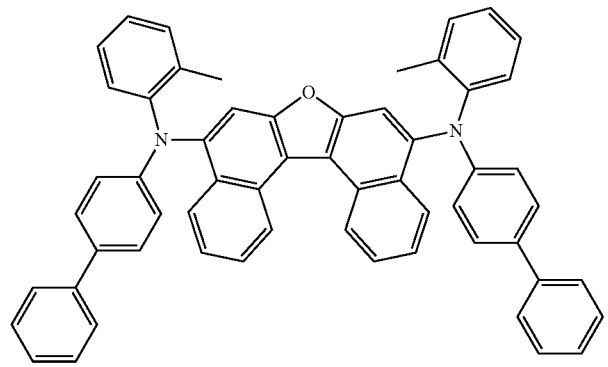
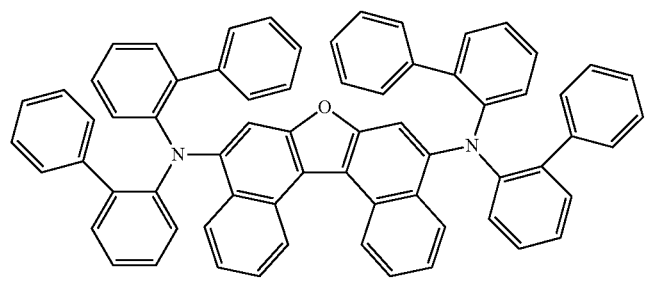
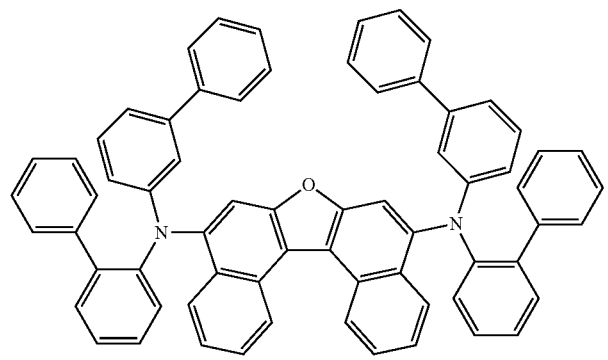
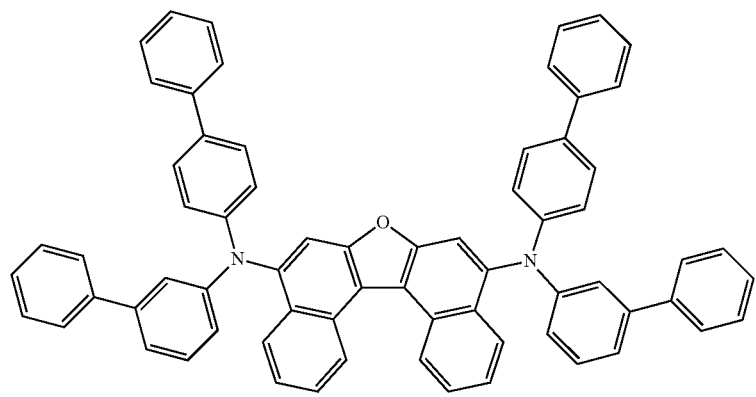

875
876
-continued
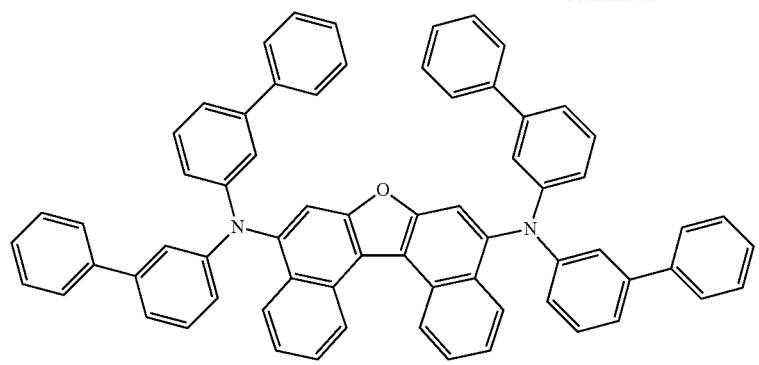
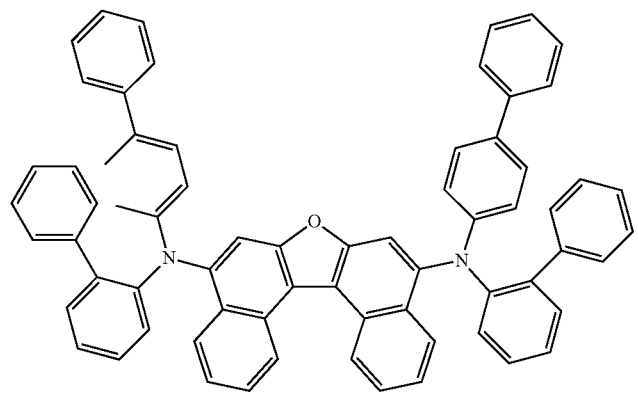
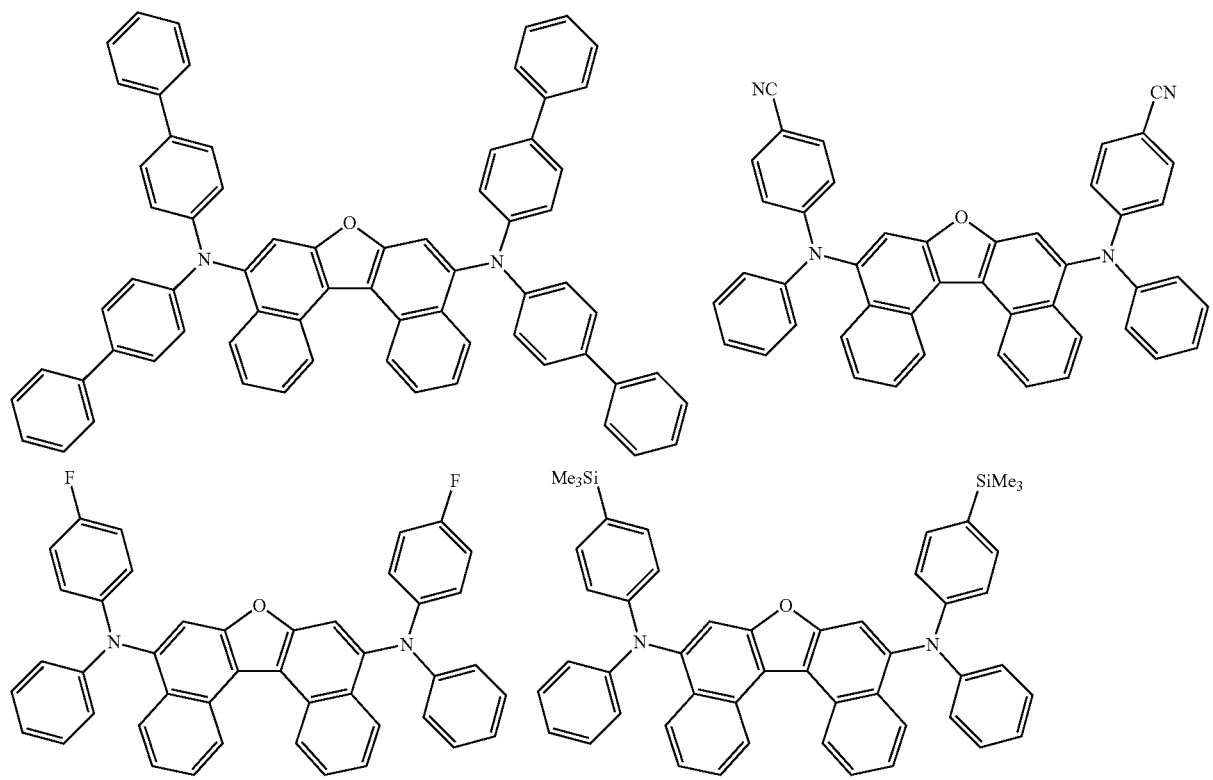

-continued
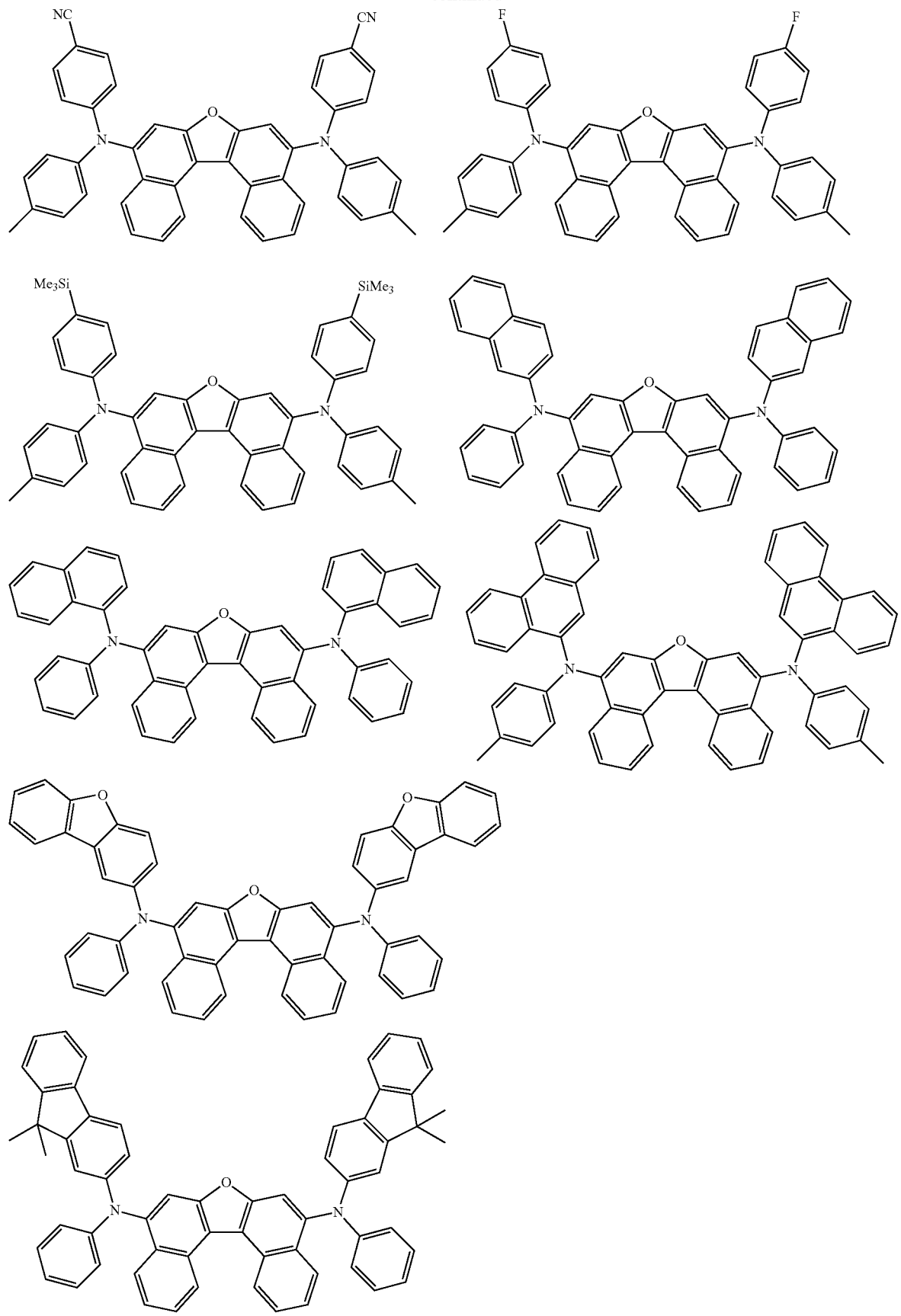

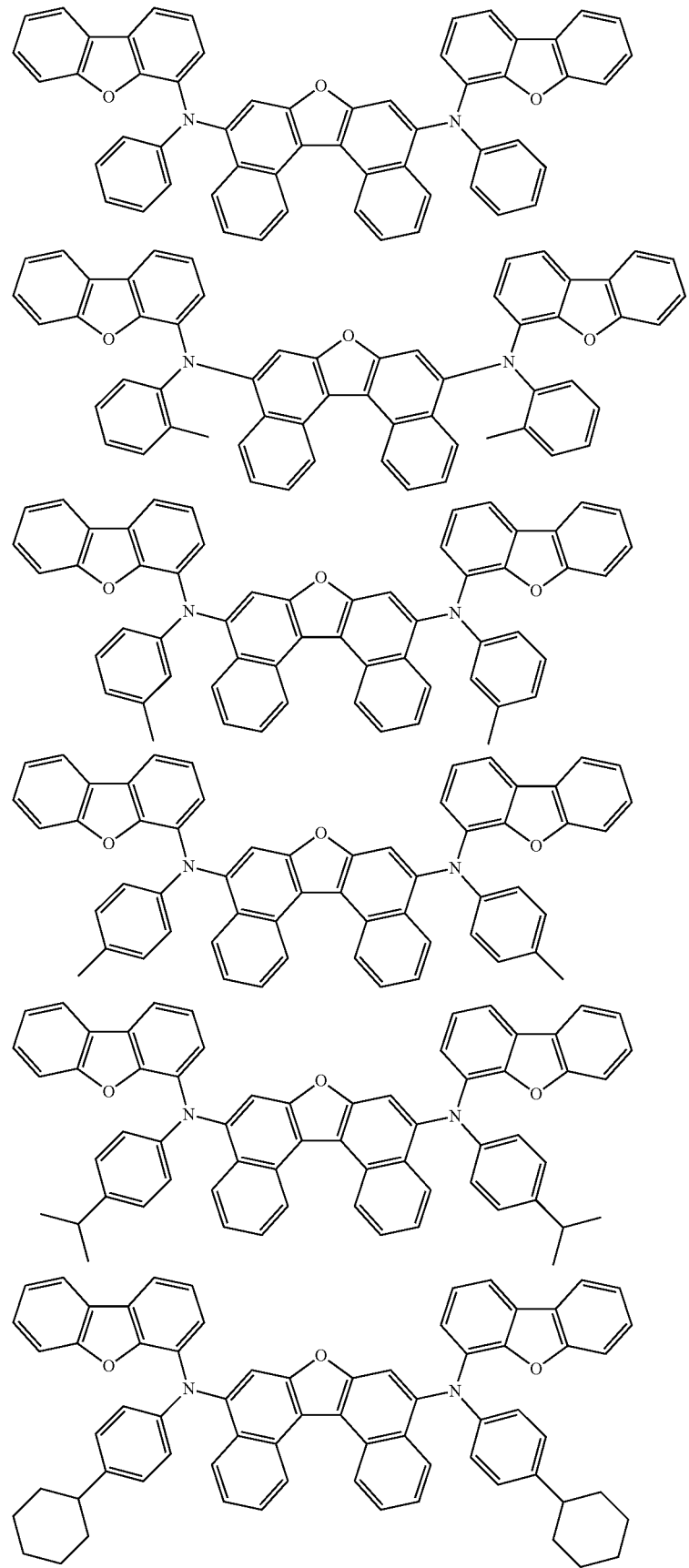

-continued
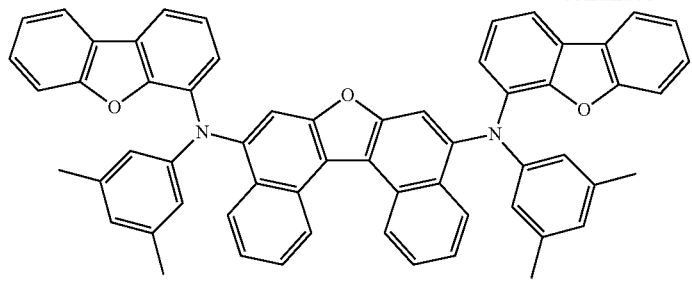
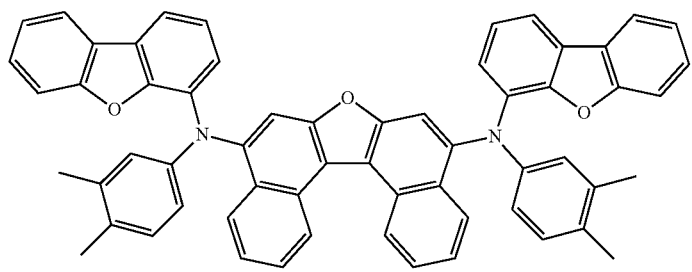
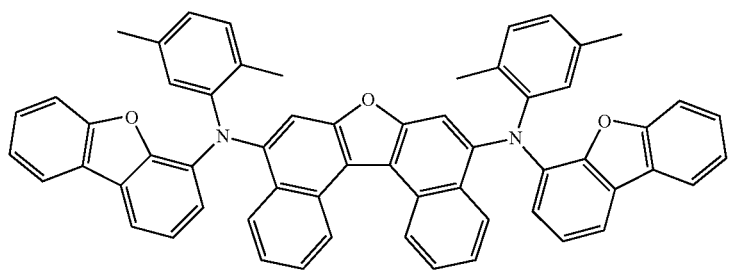
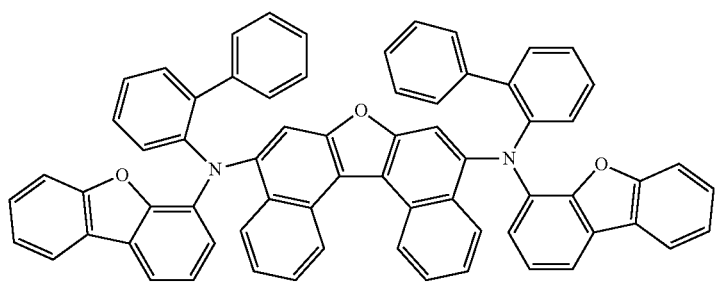
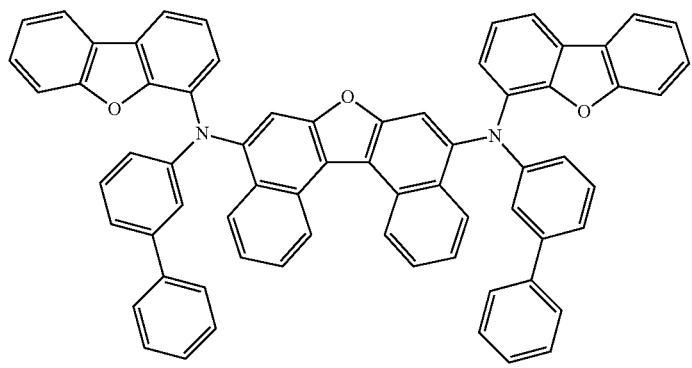

-continued
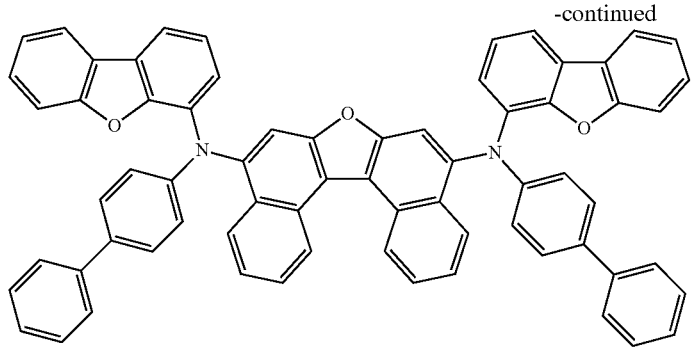
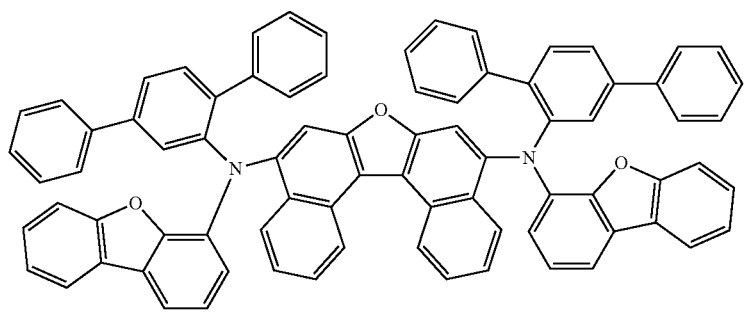
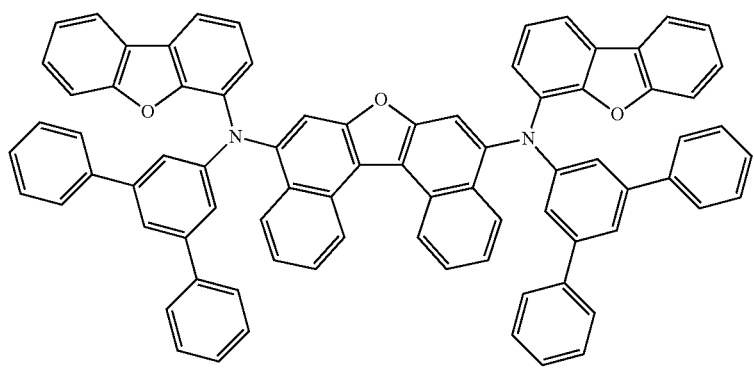
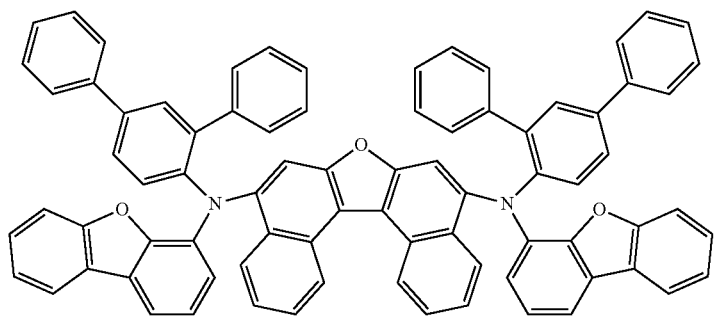
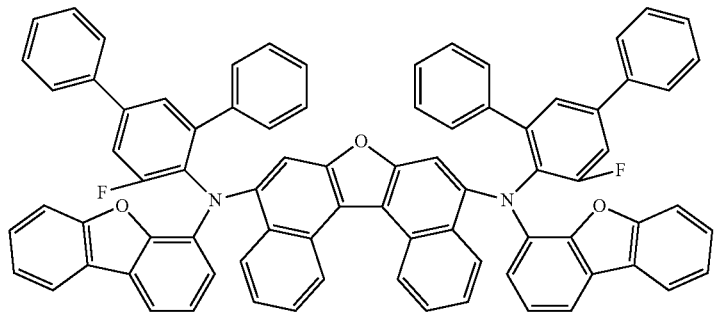

-continued
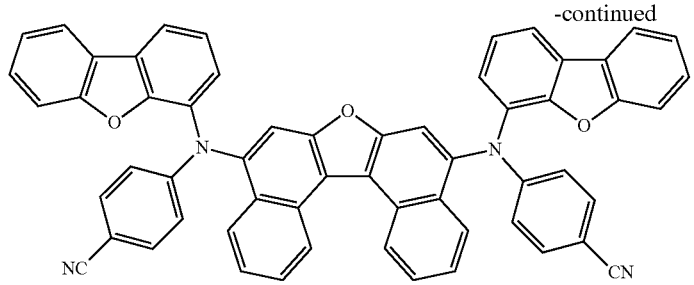
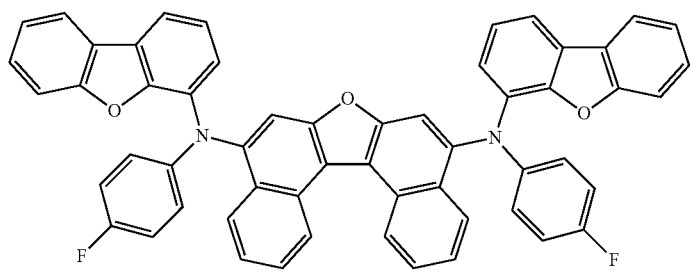
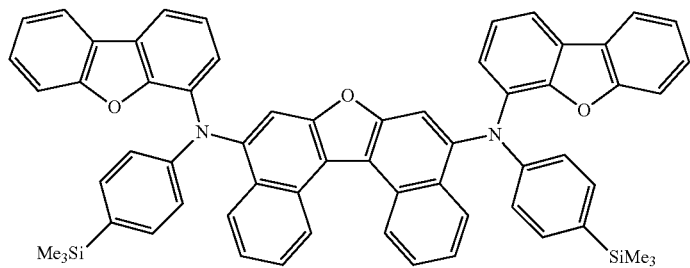
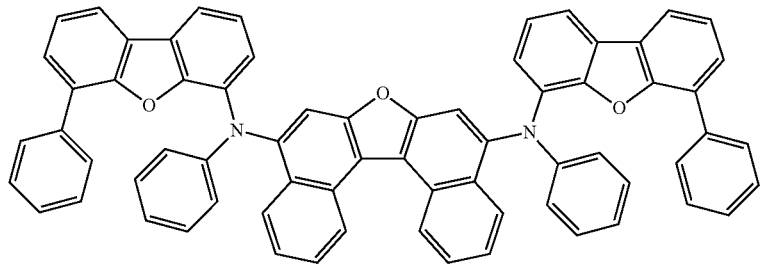
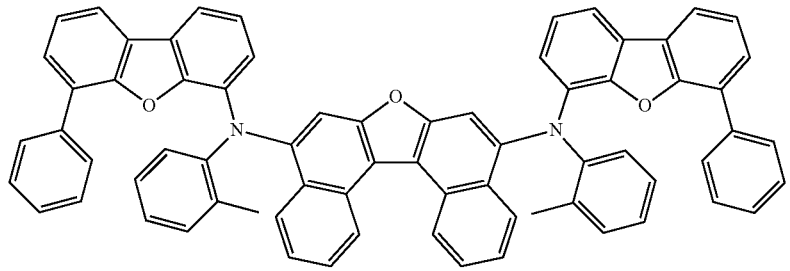
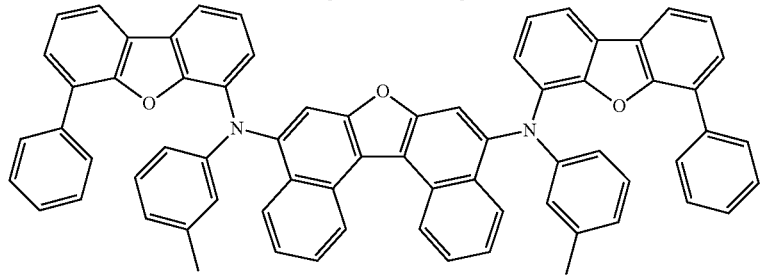

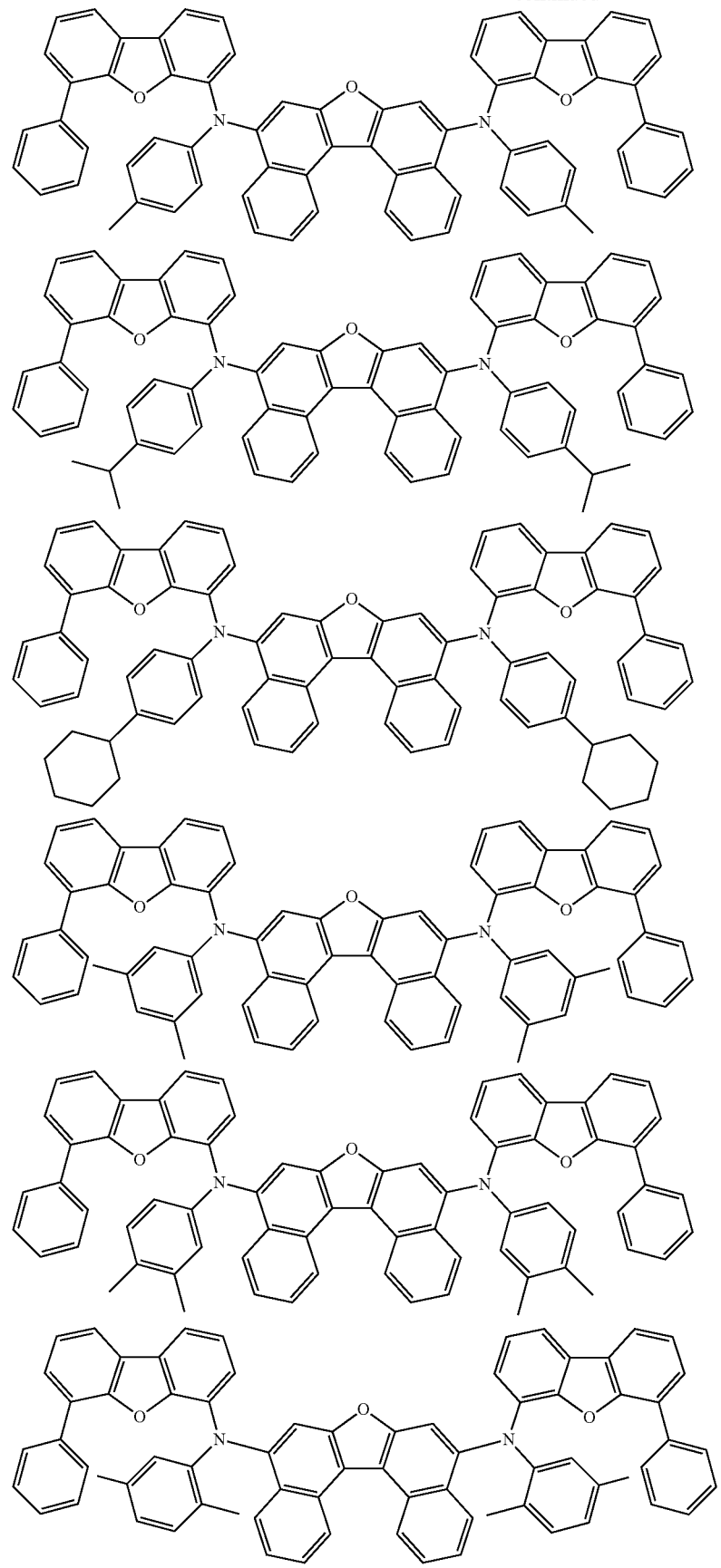

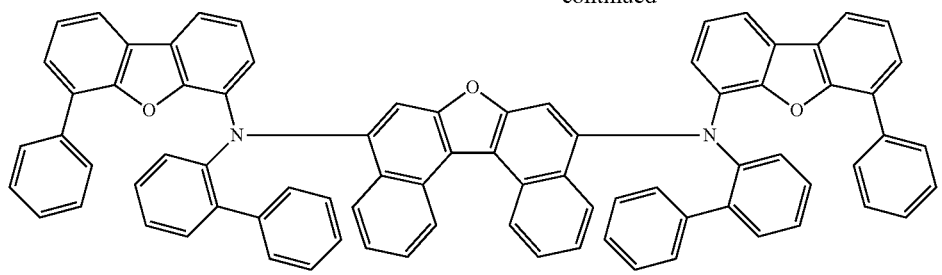
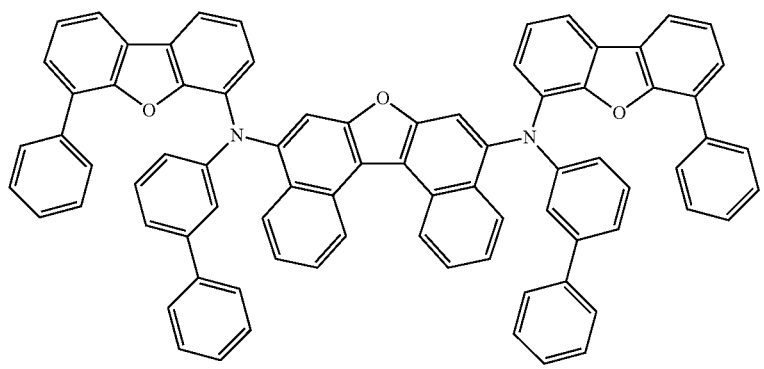
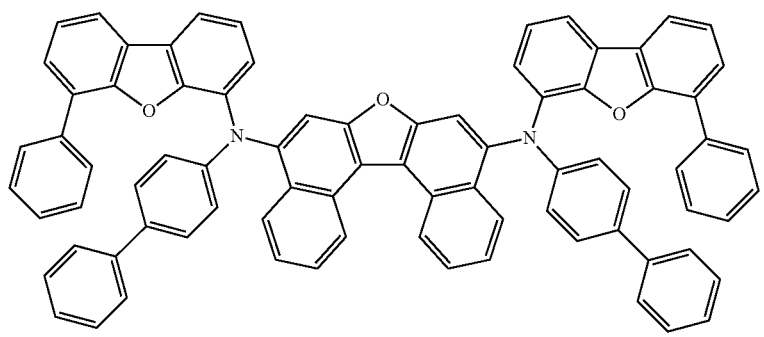
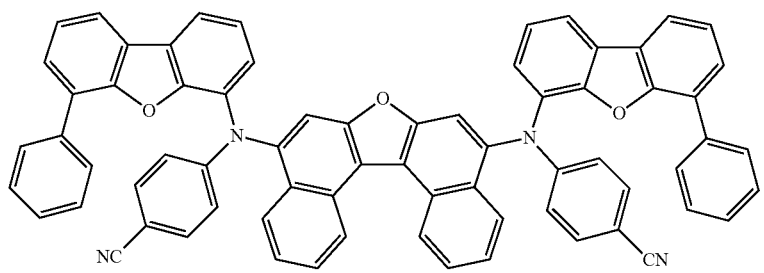
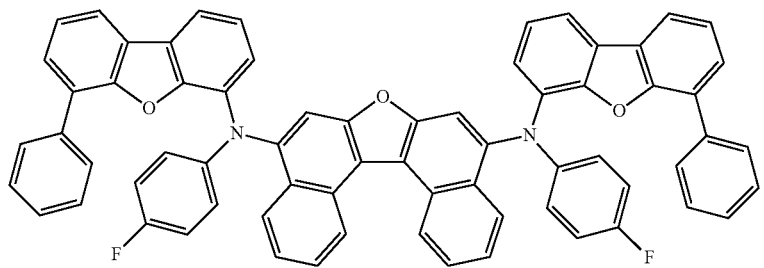

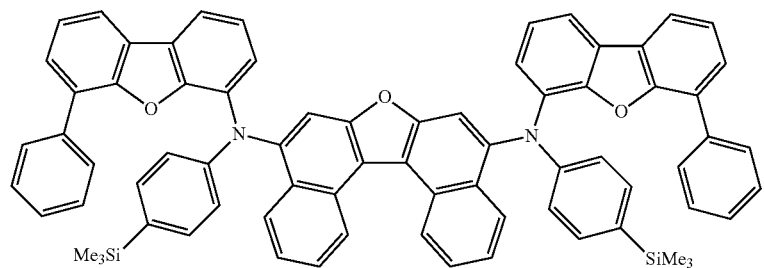
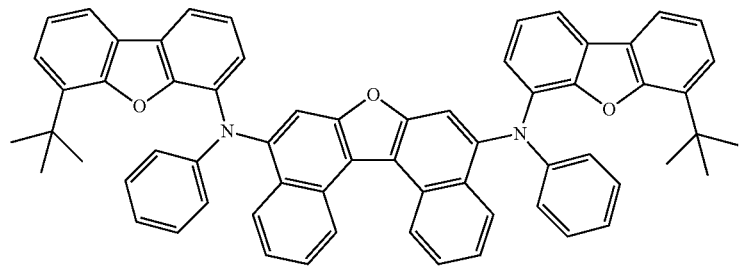
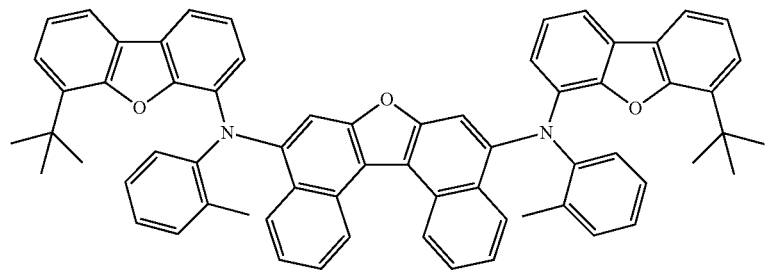
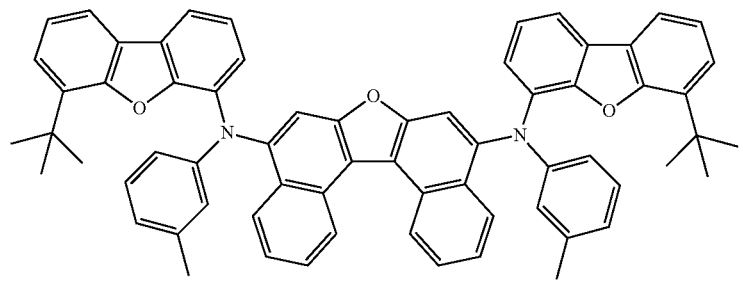
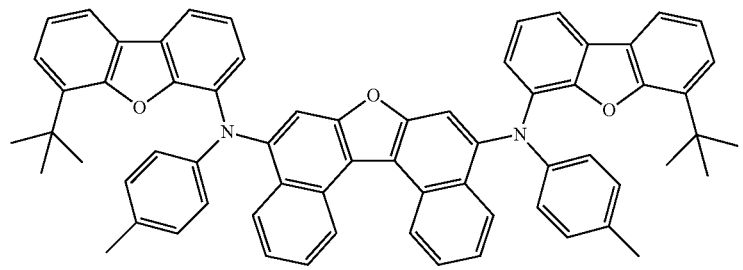
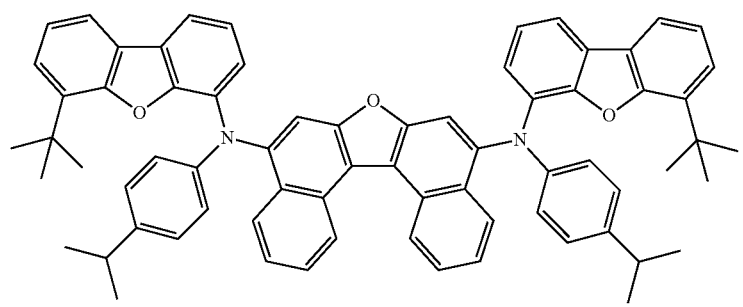

-continued
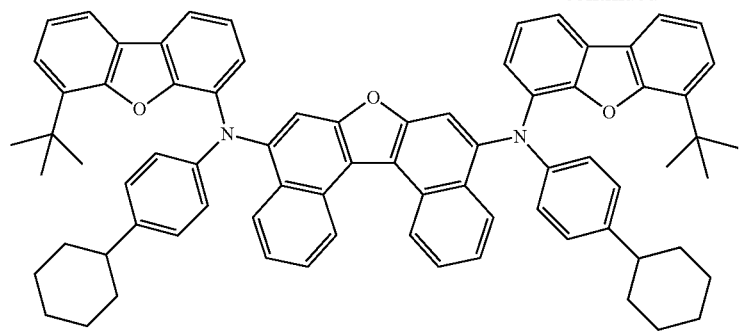
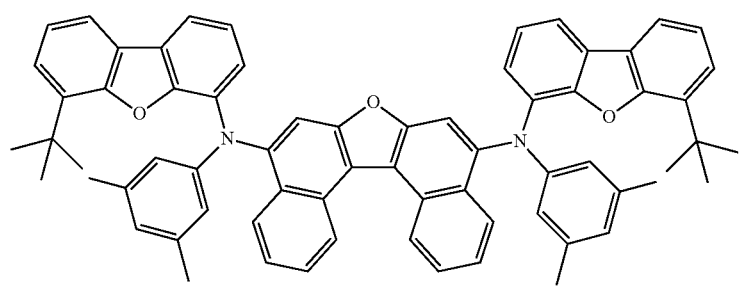
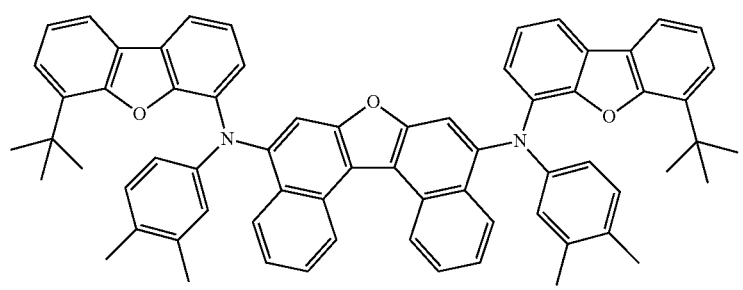
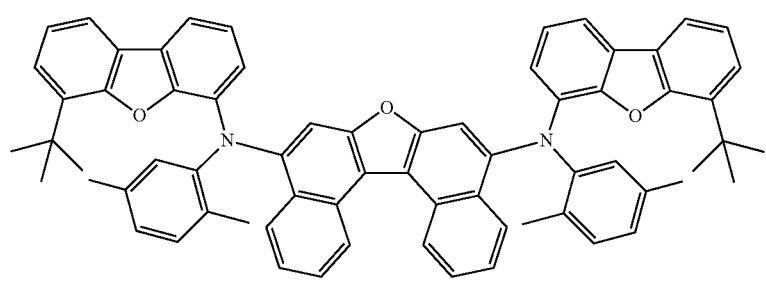
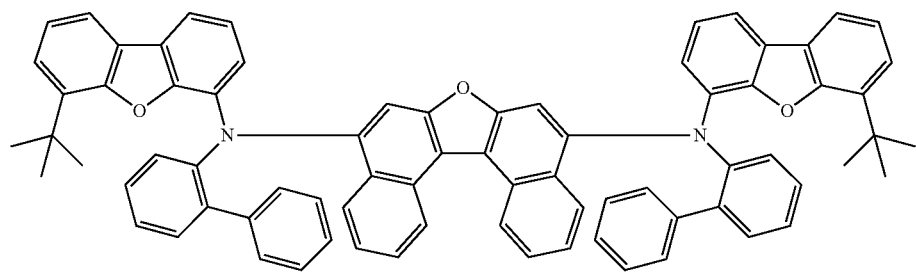

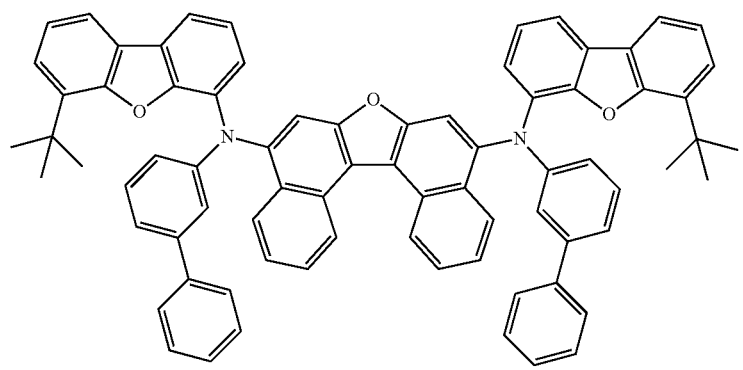
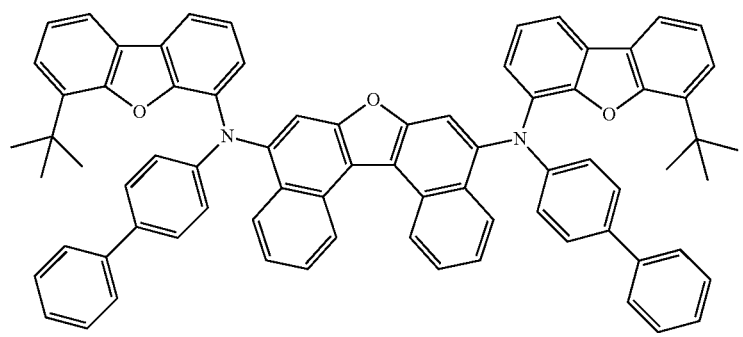
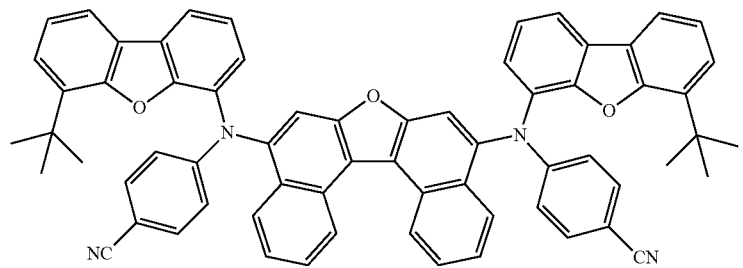
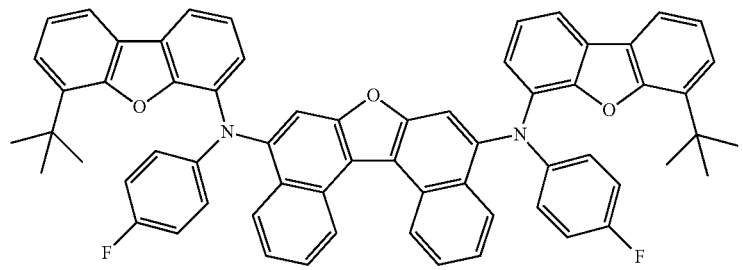
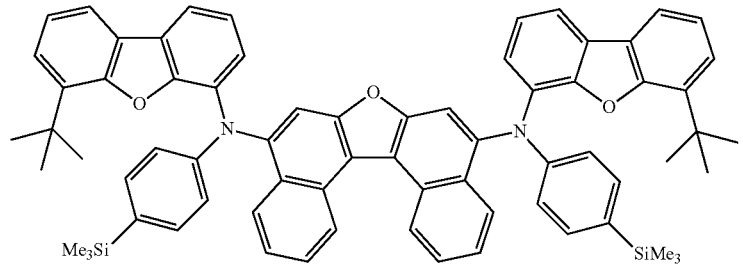

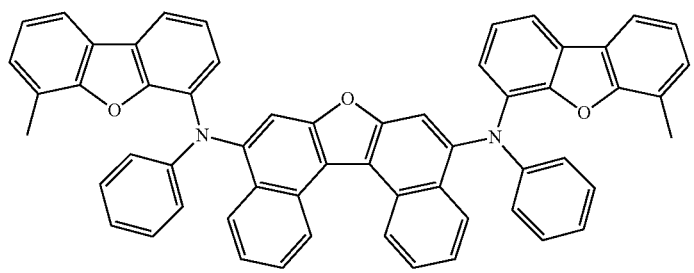
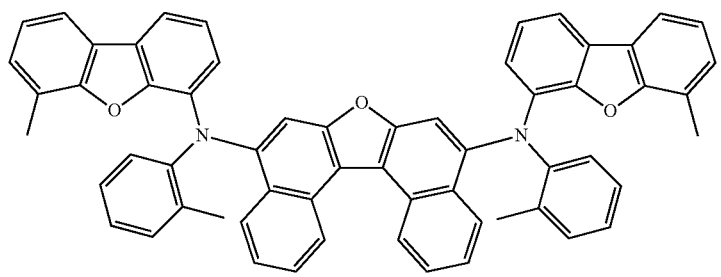
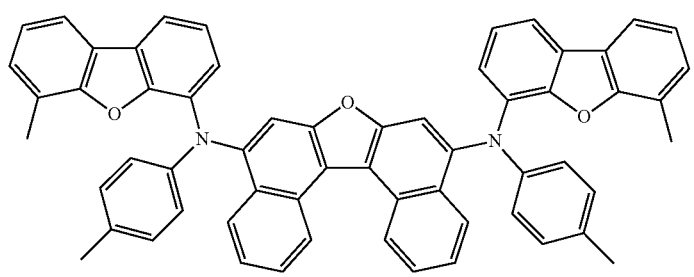
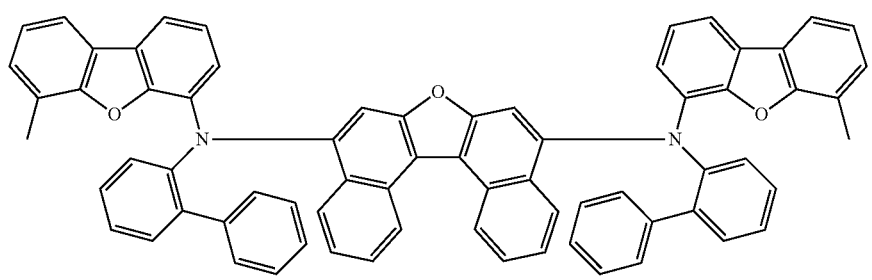
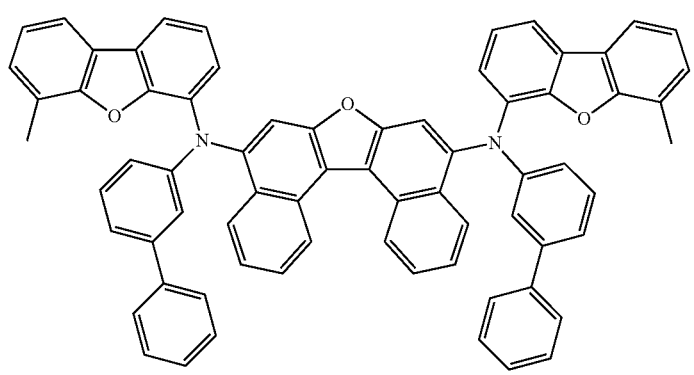

-continued
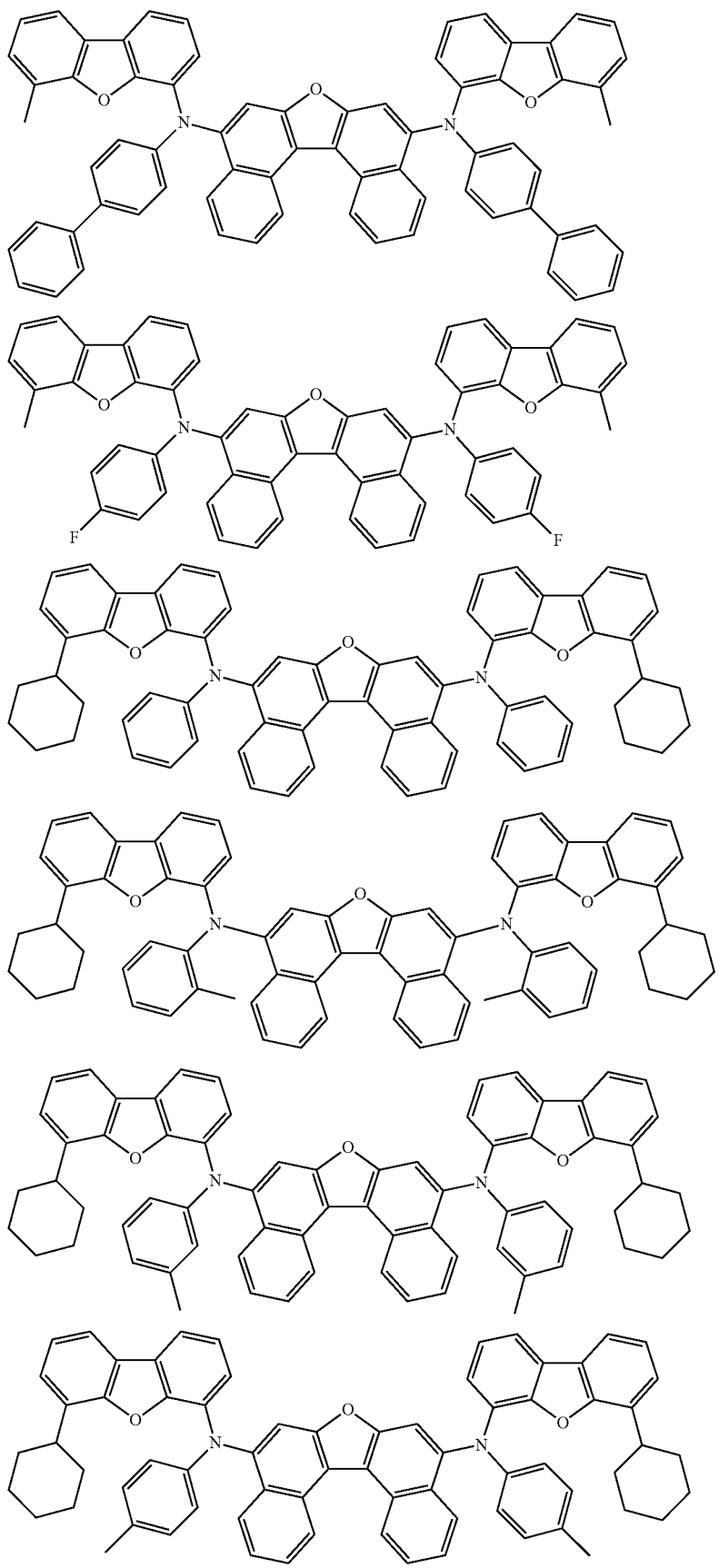

-continued
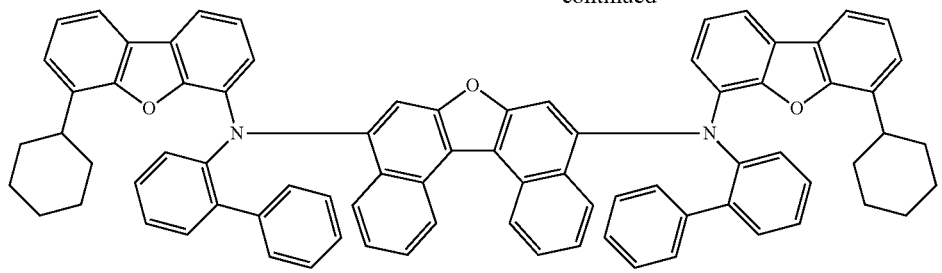
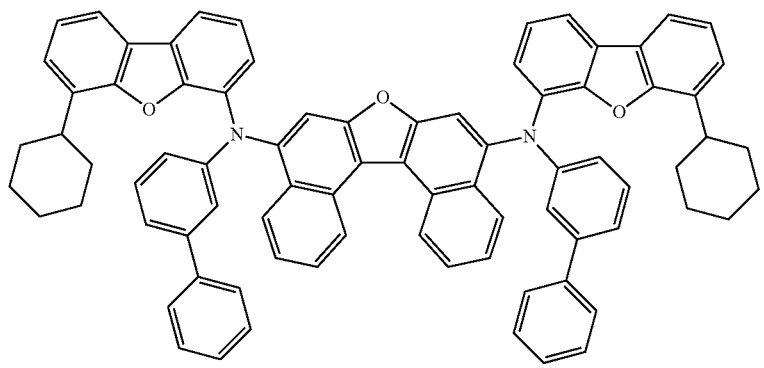
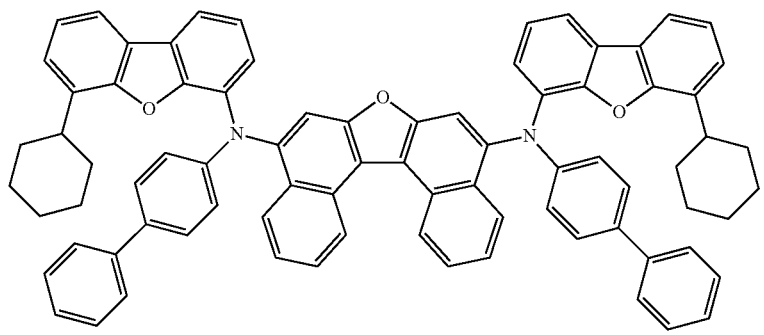
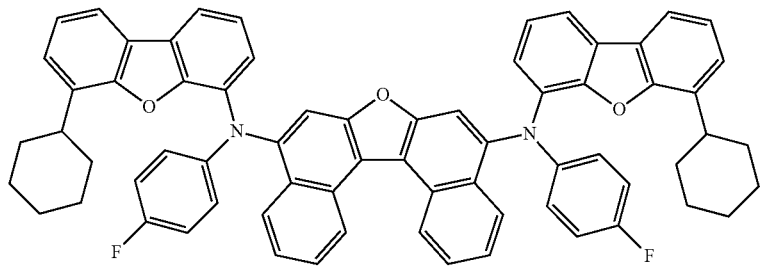
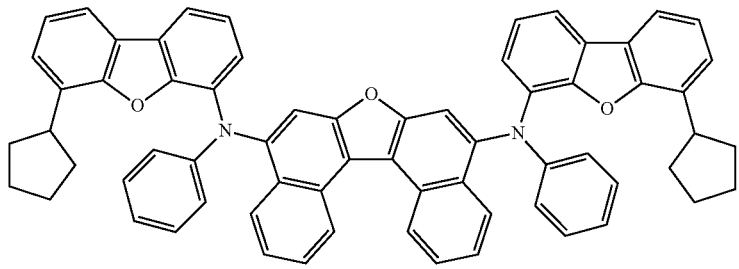

903
-continued
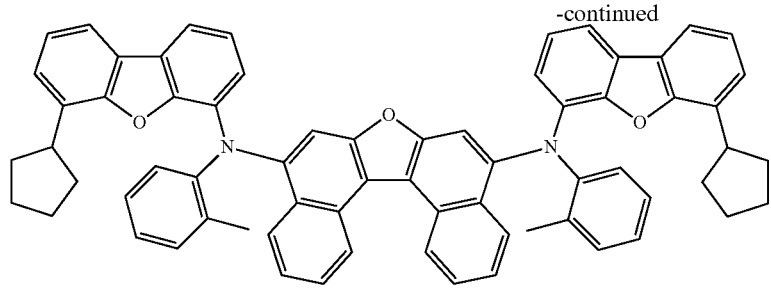
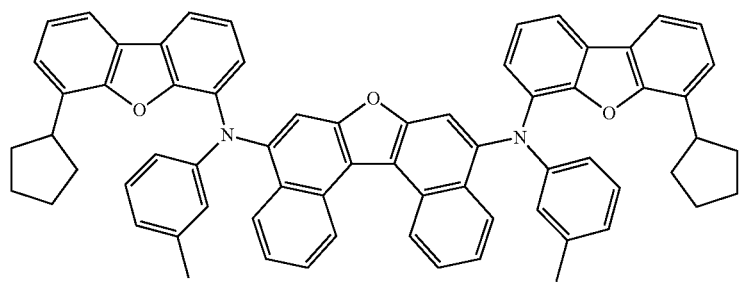
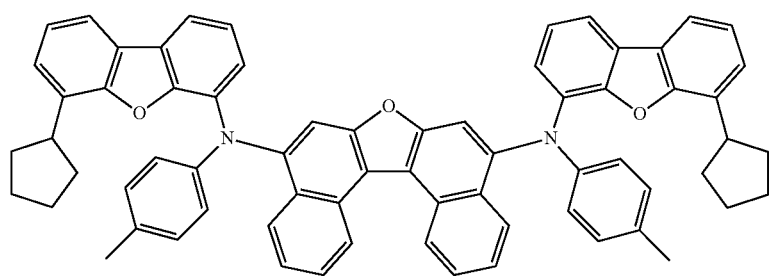
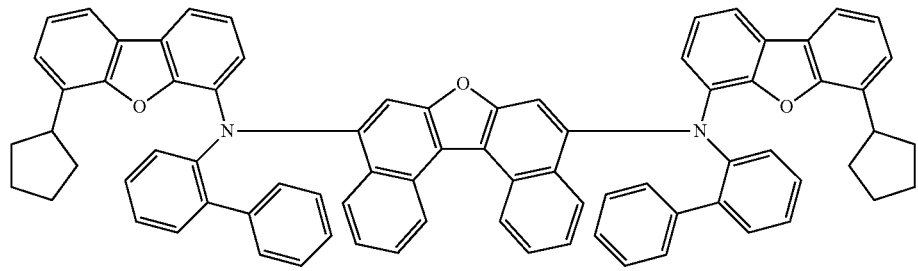
904
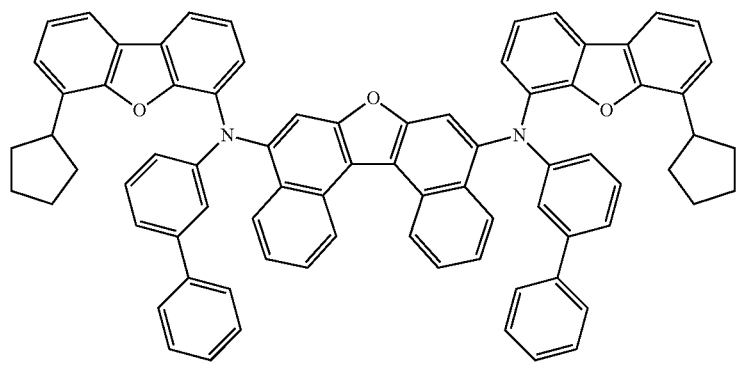

905
906
-continued
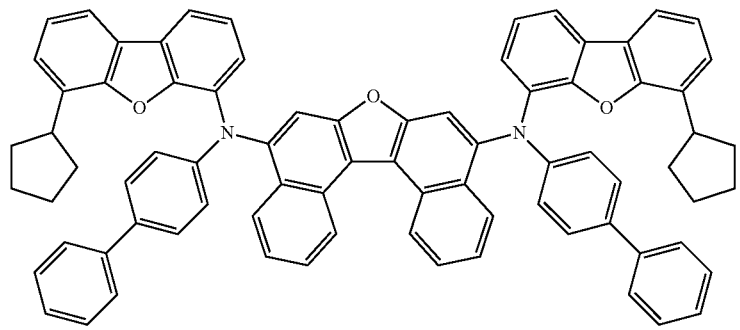
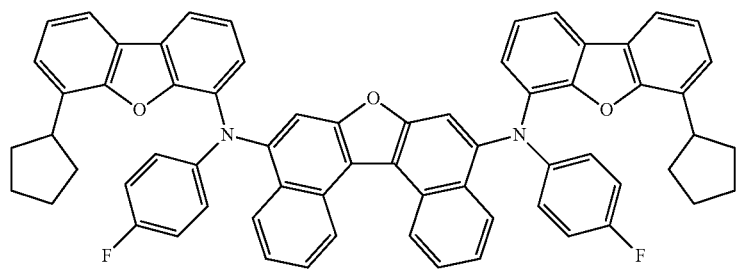
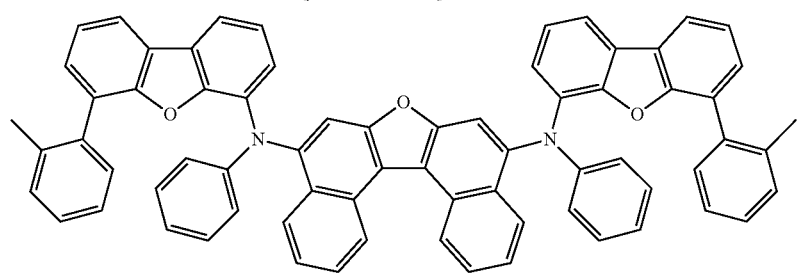
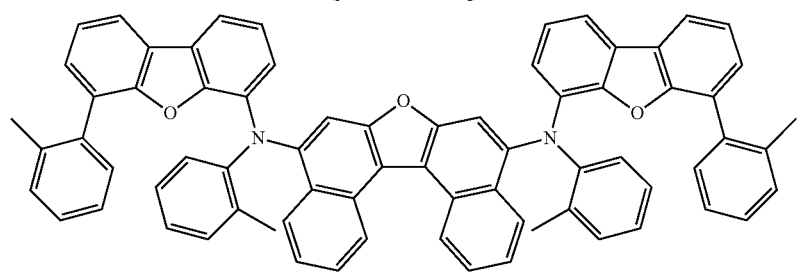
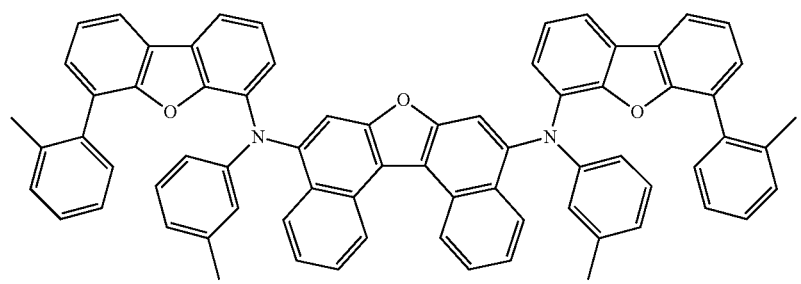
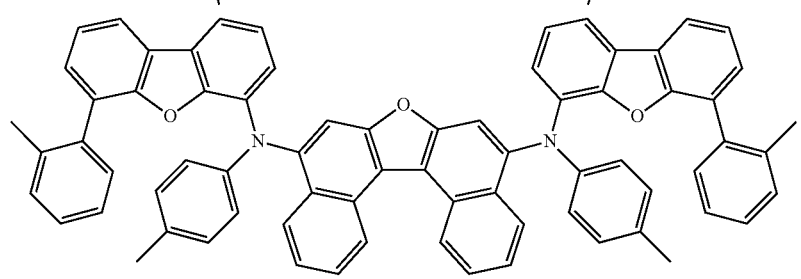

-continued
907
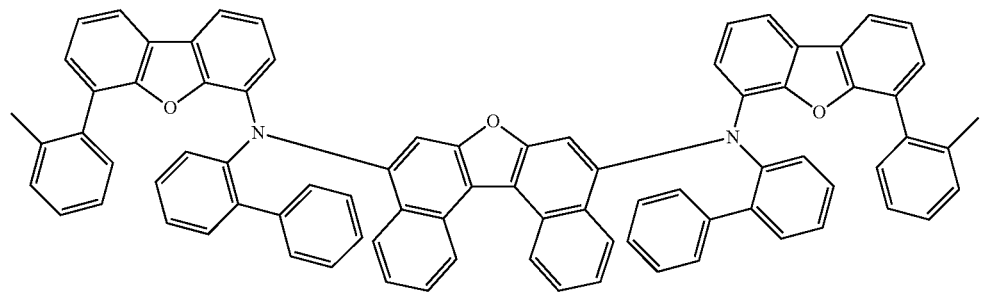
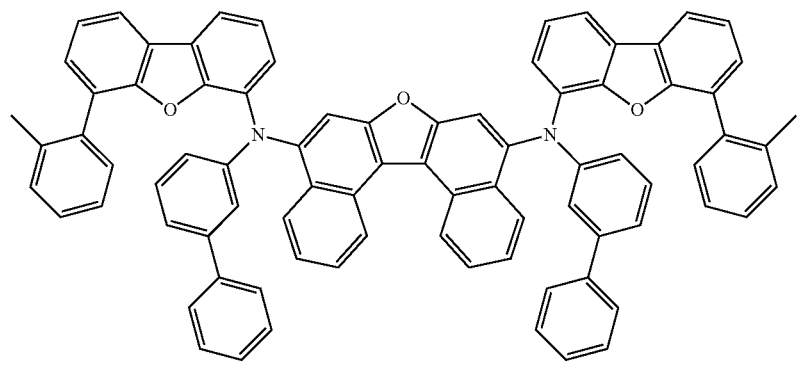
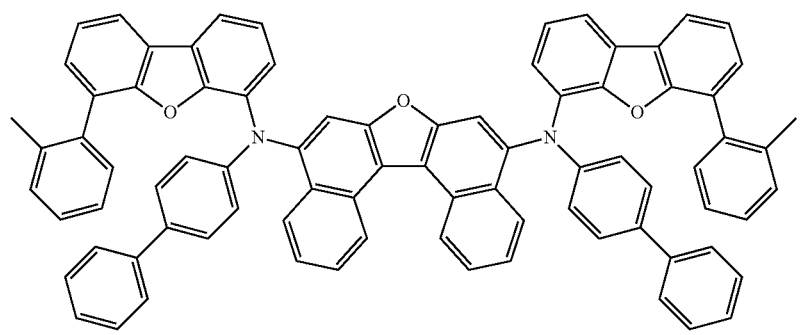
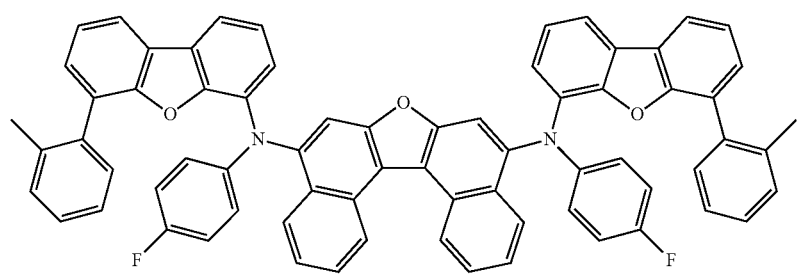
908
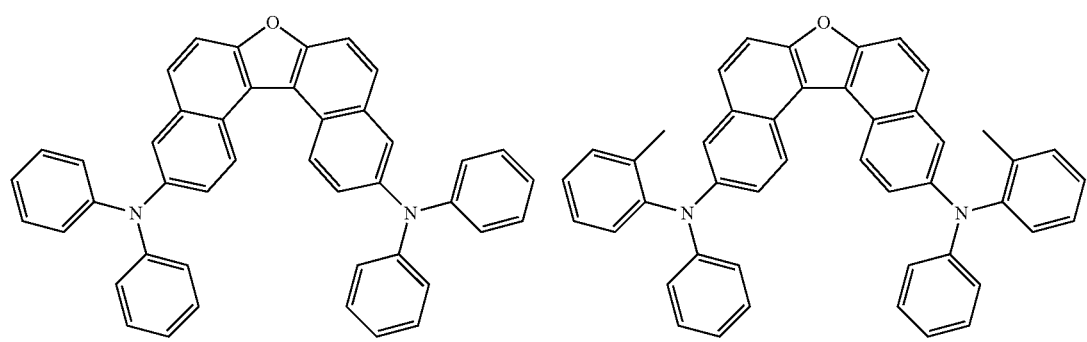

909 910
-continued
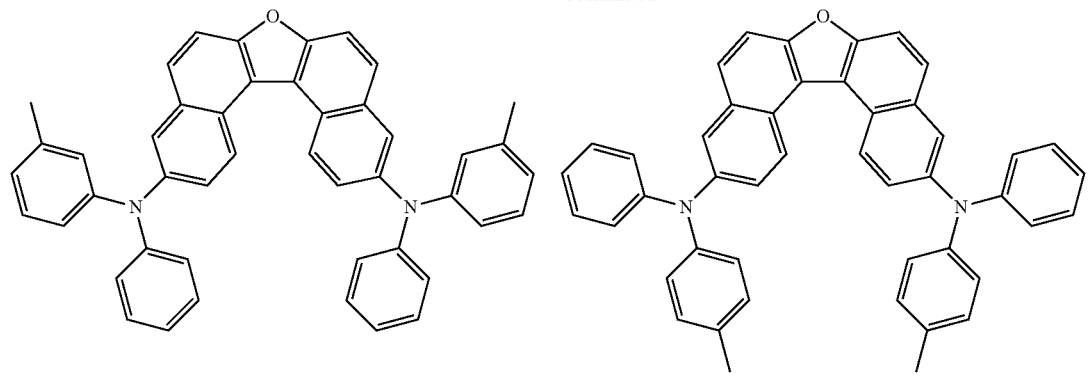
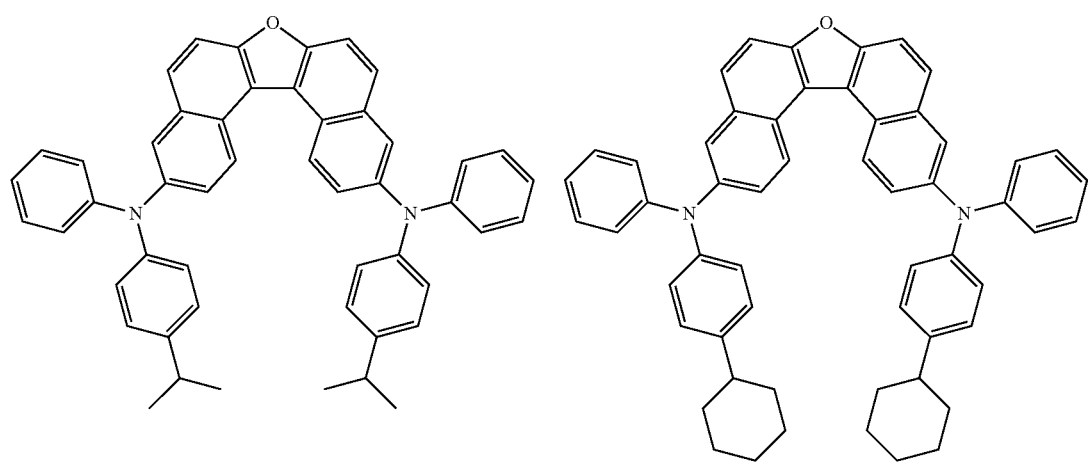
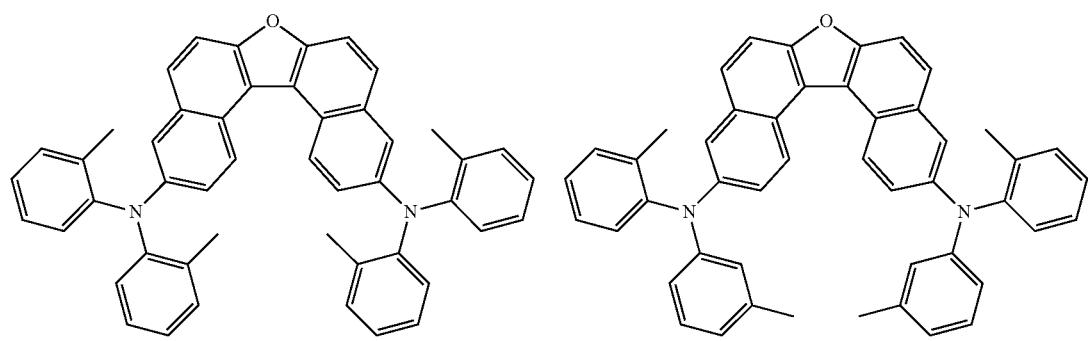
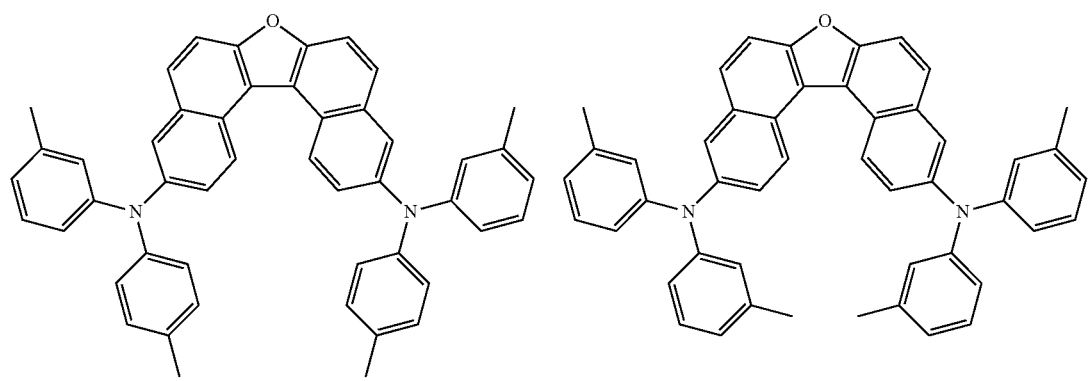

911 912
-continued
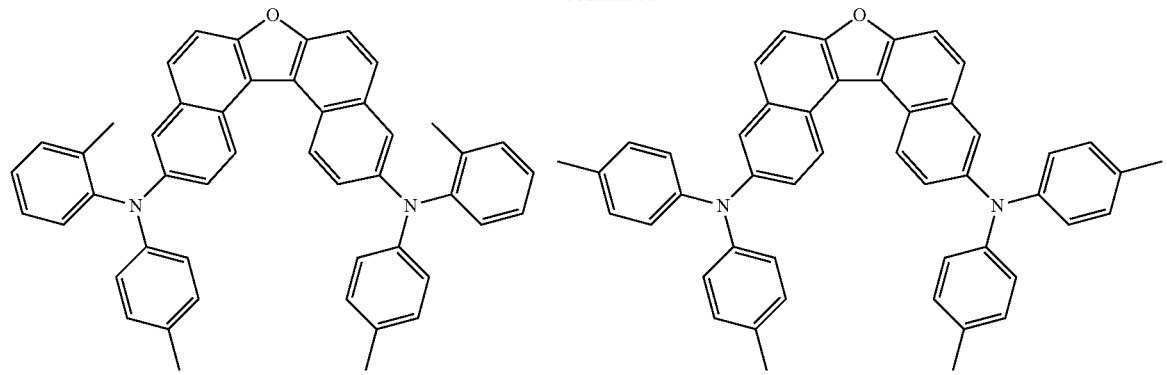
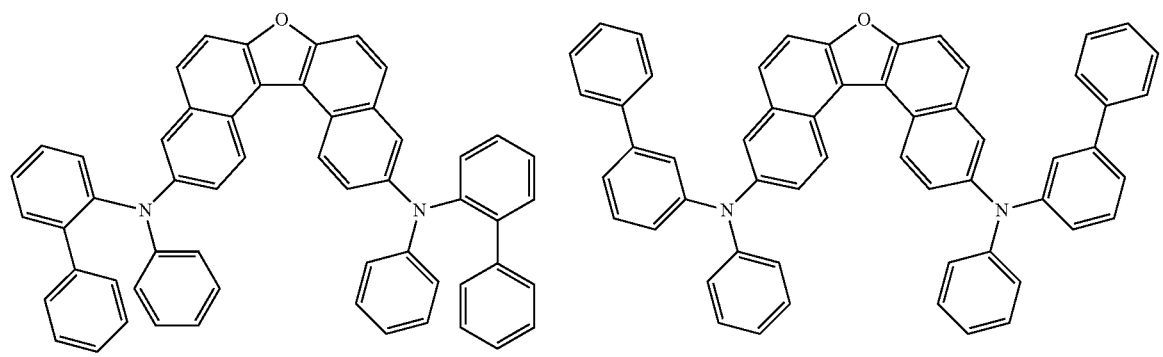
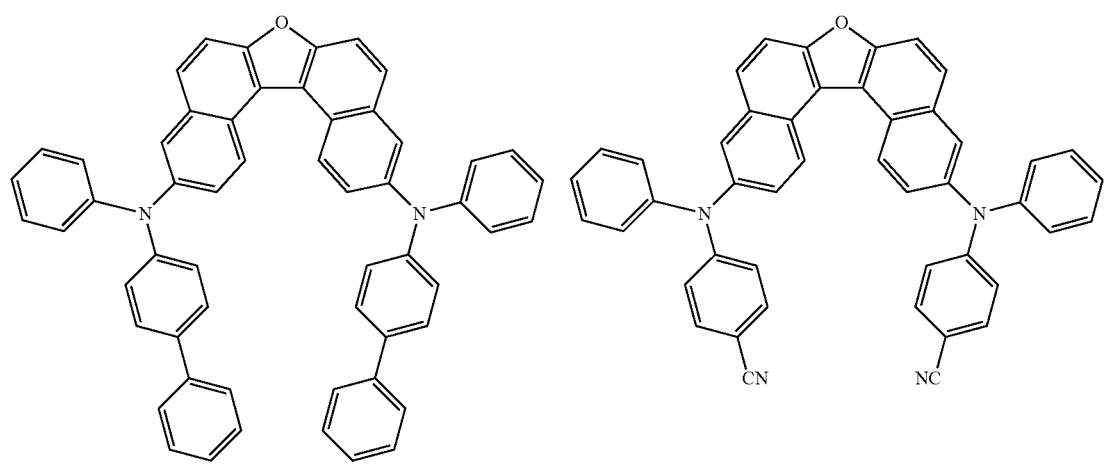
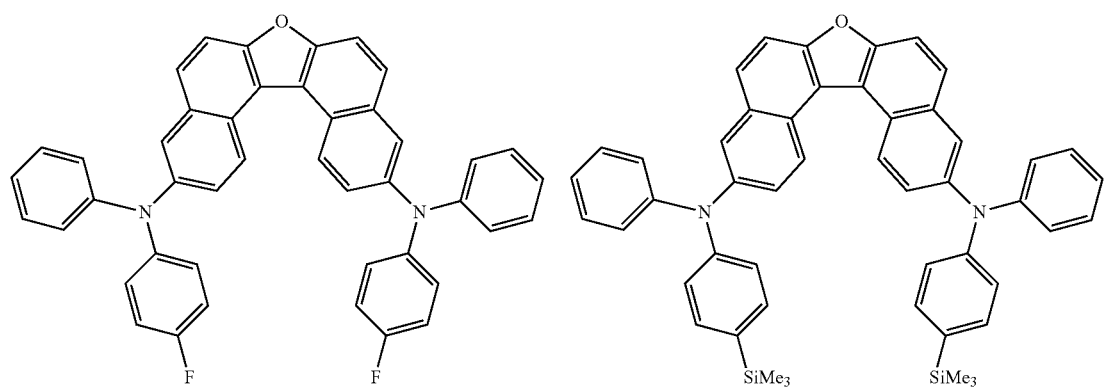

913 914
-continued
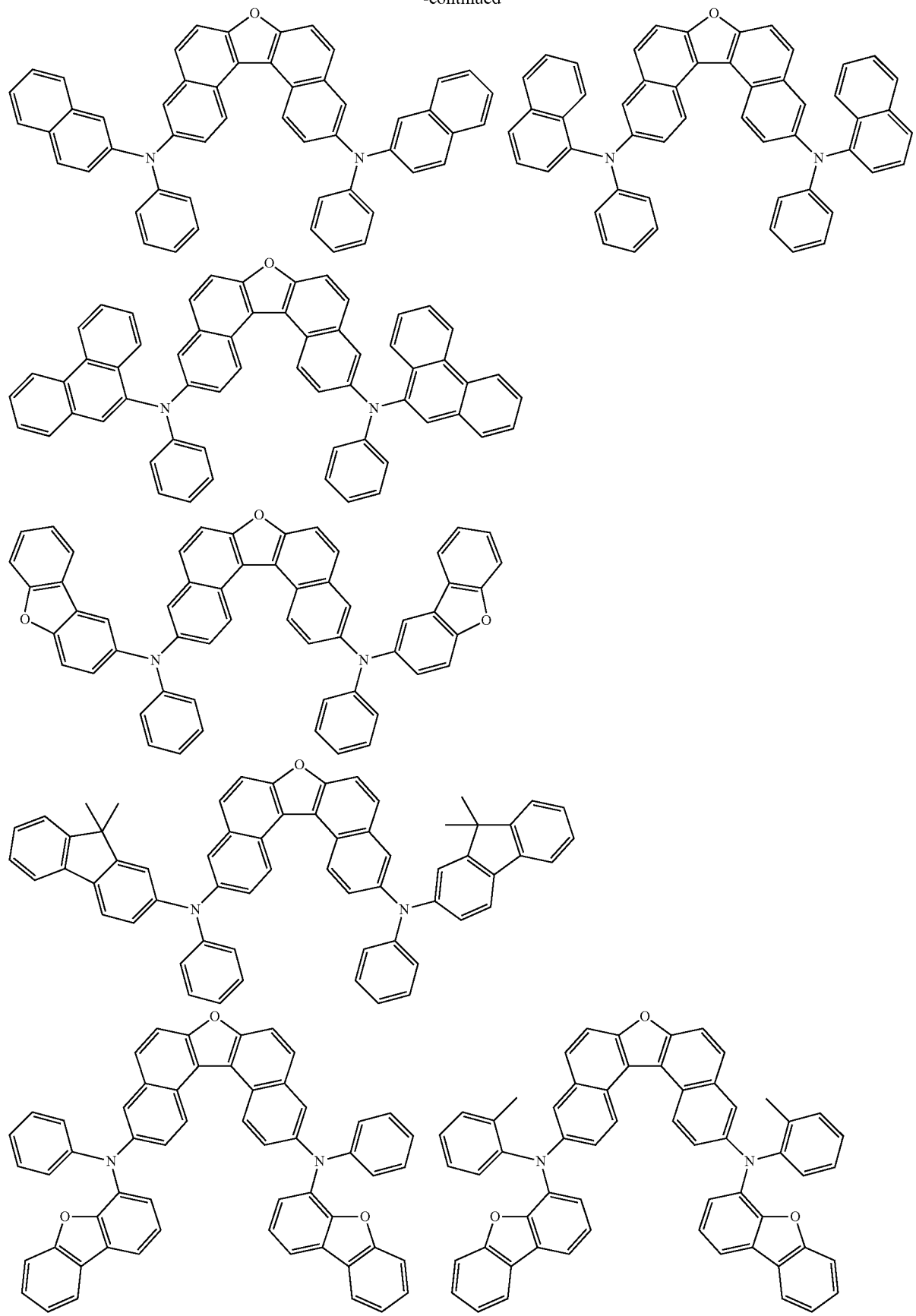

-continued
915
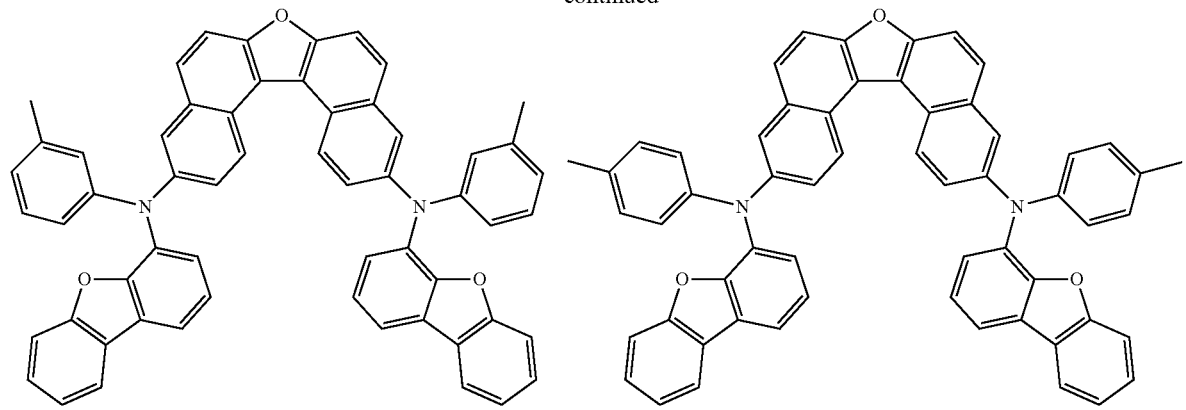
916
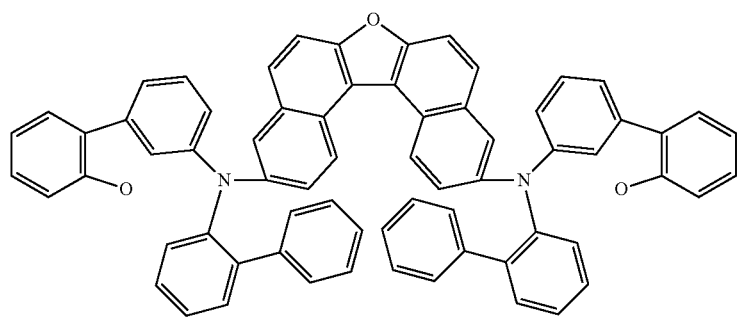
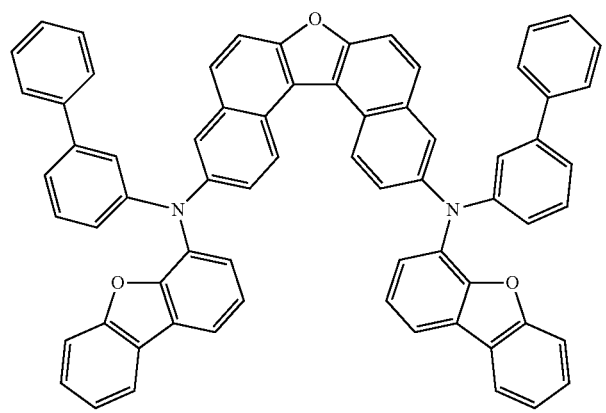
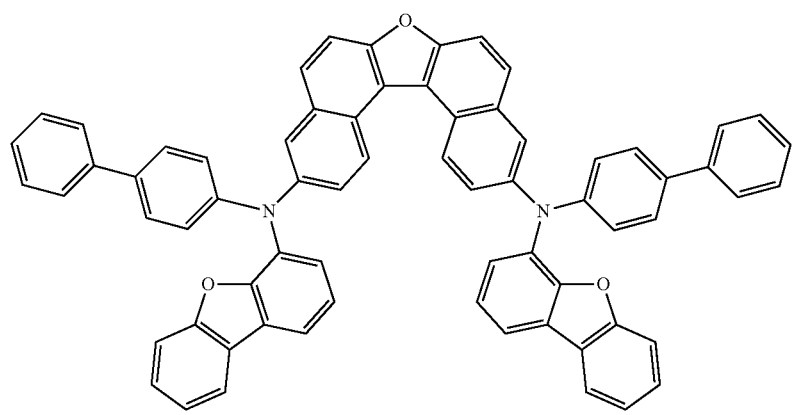

917 918
-continued
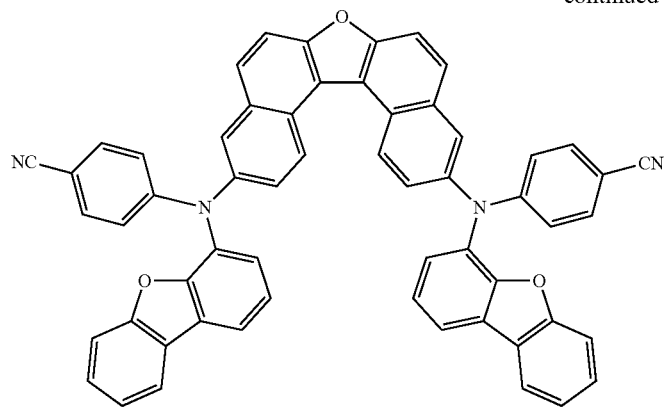
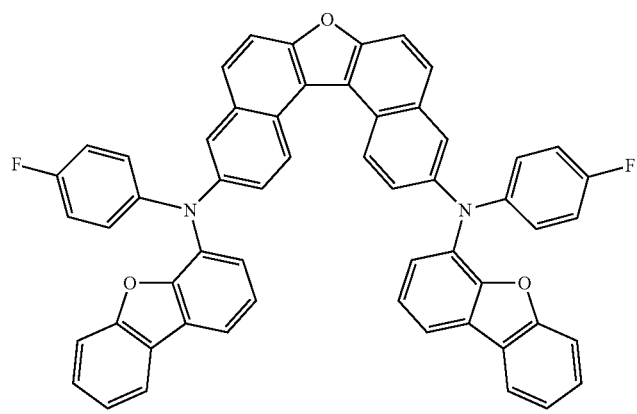
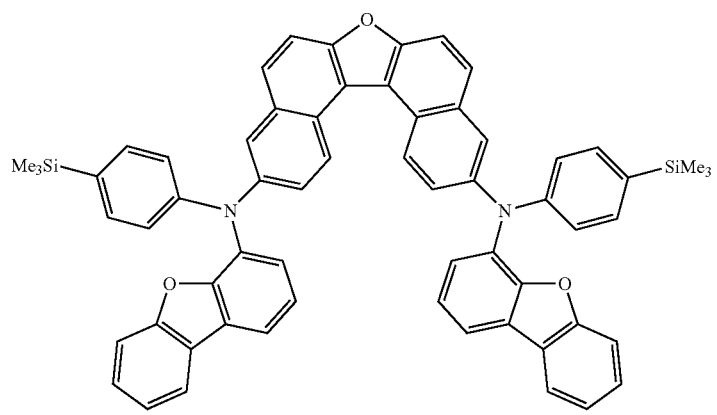
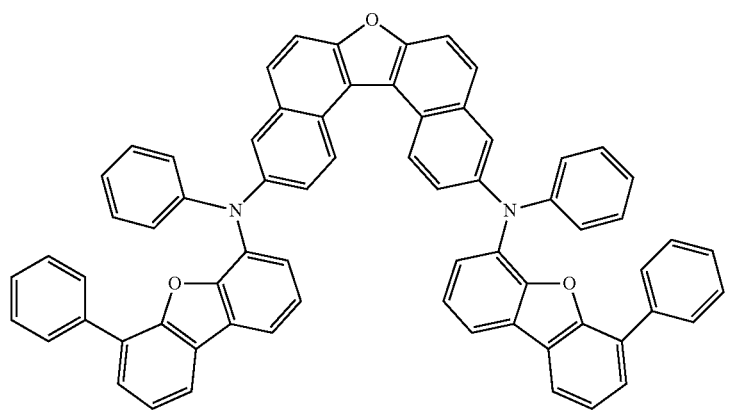

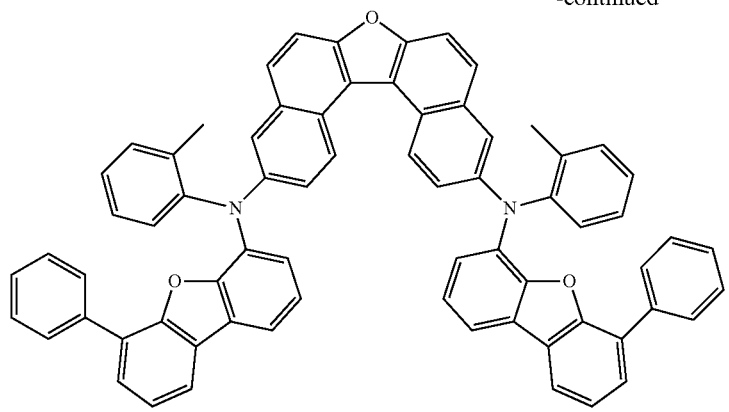
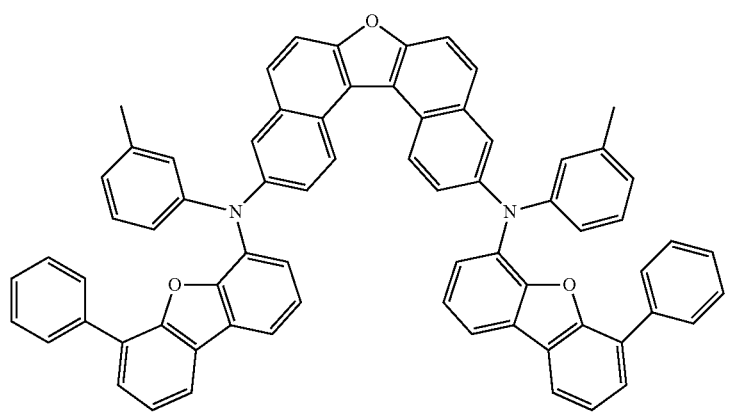 [SMILES: Cc1cccc(N(c2ccc3c(ccc4oc5ccc6cc(N(c7cccc(C)c7)c7cccc8c7oc7c(-c9ccccc9)cccc78)ccc6c5c43)c2)c2cccc3c2oc2c(-c4ccccc4)cccc23)c1]
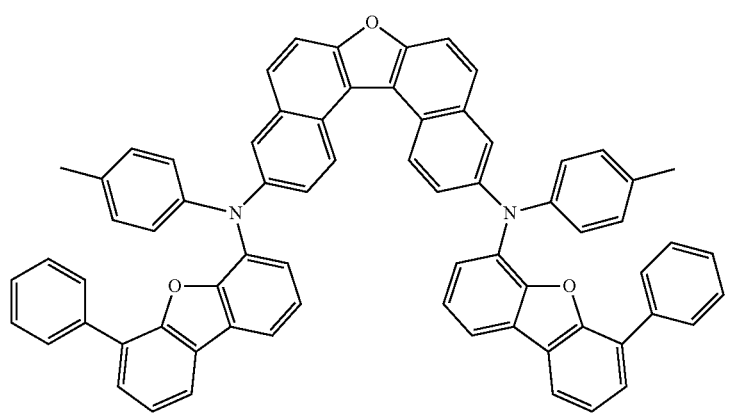
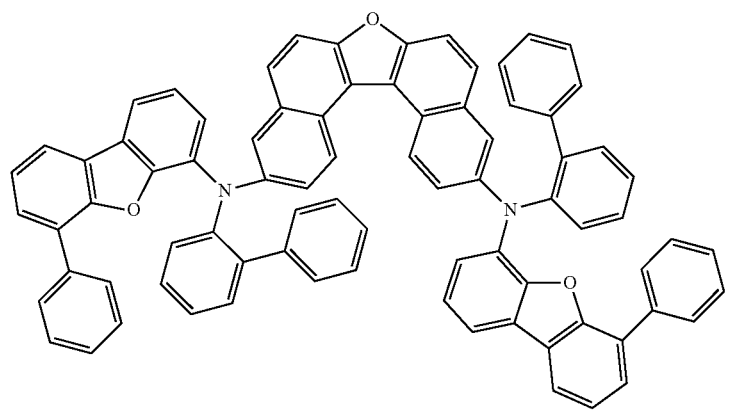

921
-continued
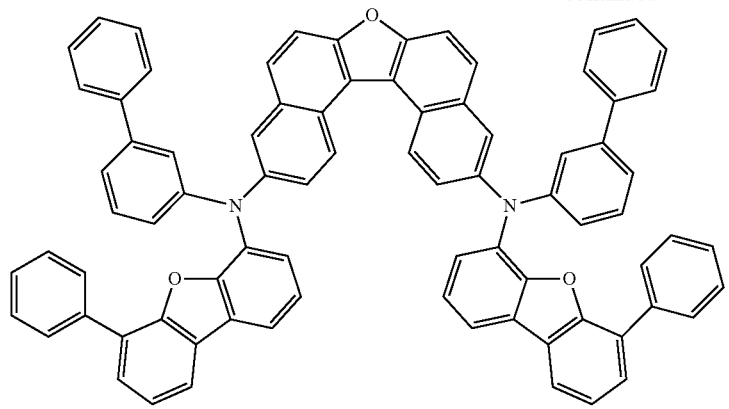
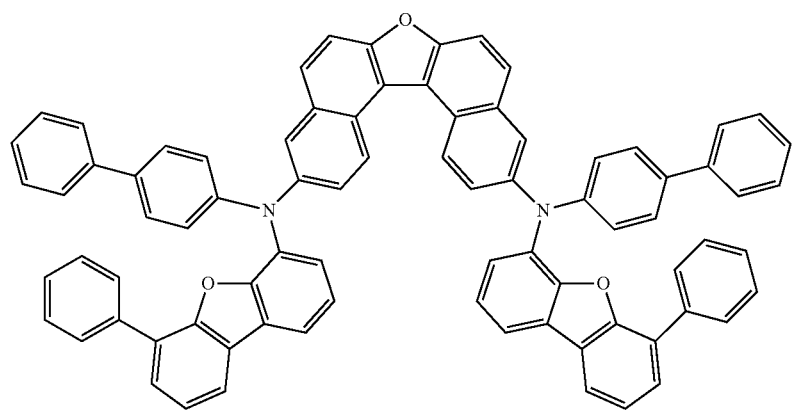
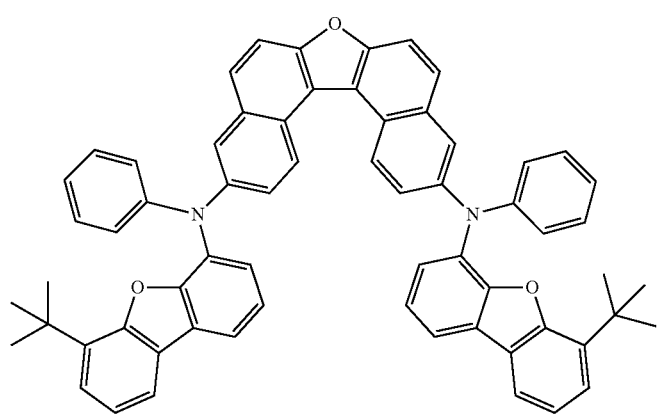
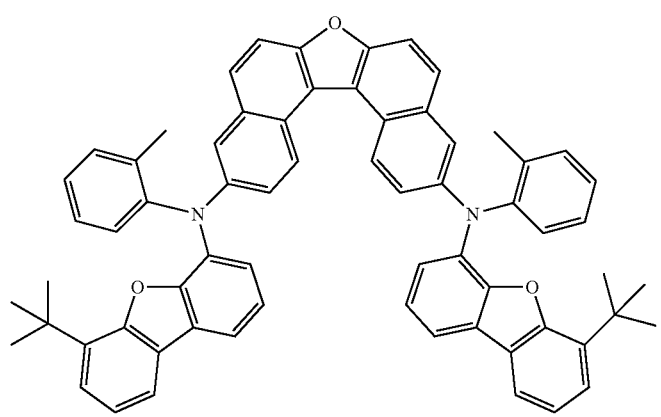
922

923
924
-continued
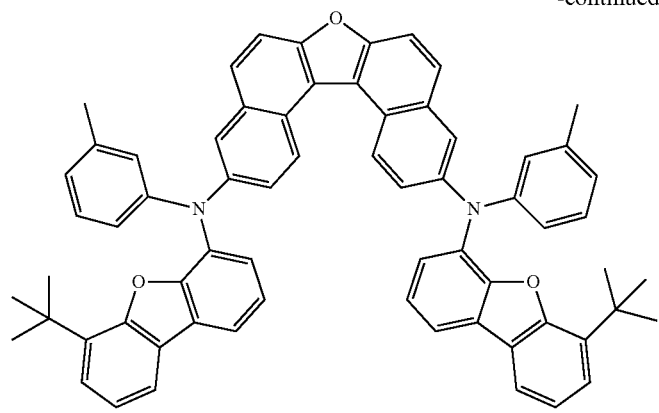
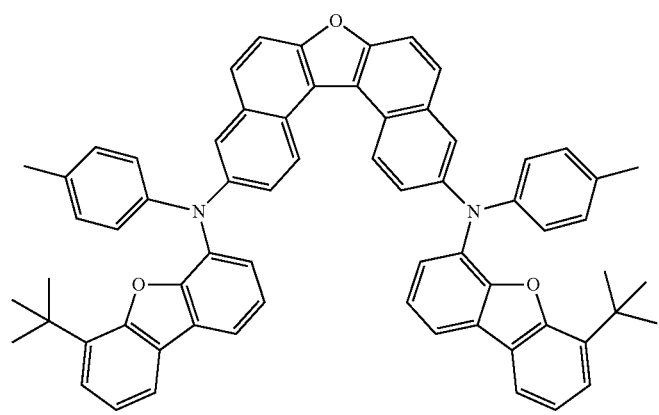
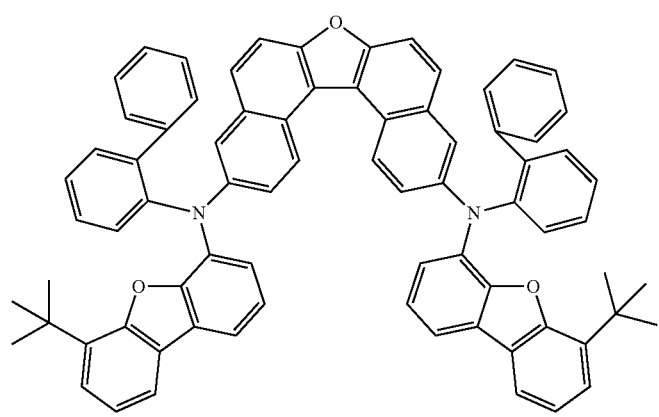
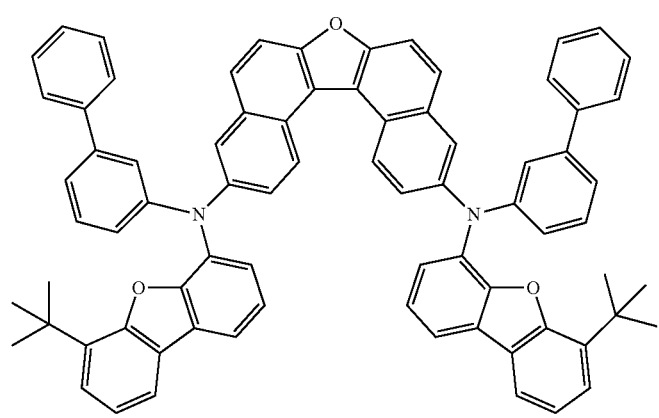

-continued
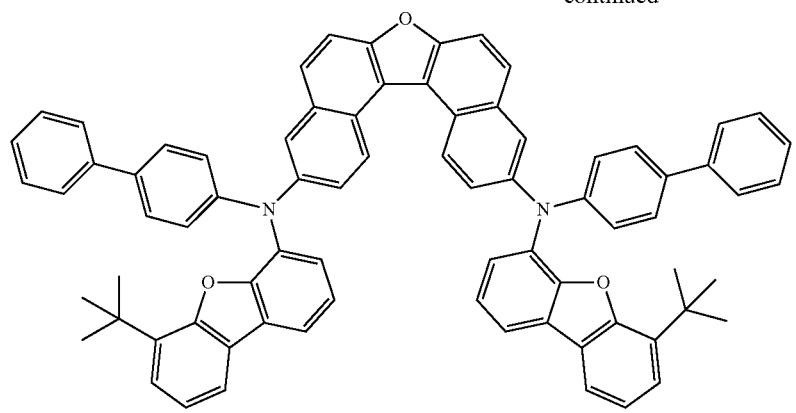
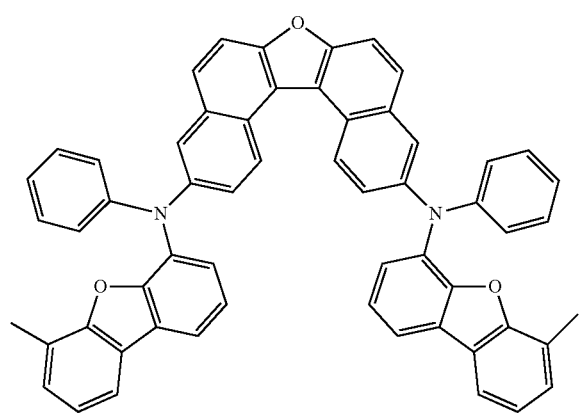
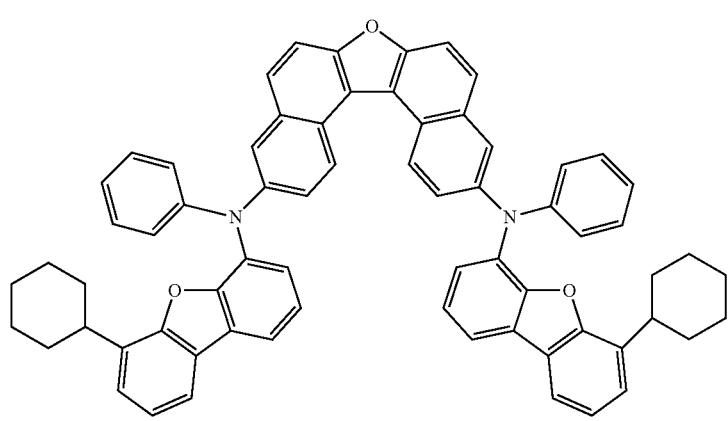 [SMILES: c1ccc(N(c2ccc3c(ccc4oc5ccc6cc(N(c7ccccc7)c7cccc8c7oc7c(C9CCCCC9)cccc78)ccc6c5c43)c2)c2cccc3c2oc2c(C4CCCCC4)cccc23)cc1]
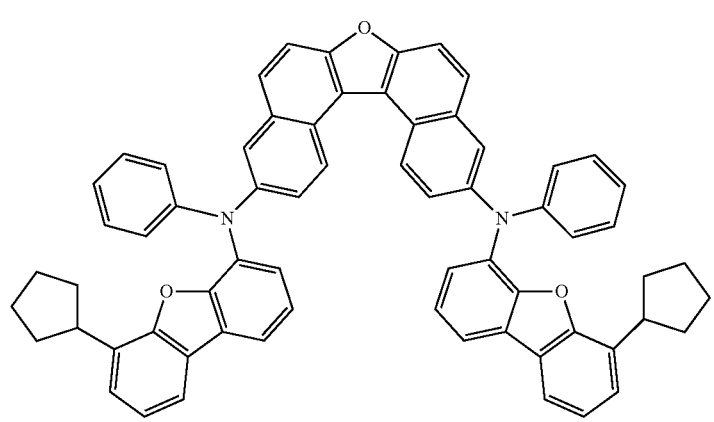

927 928
-continued
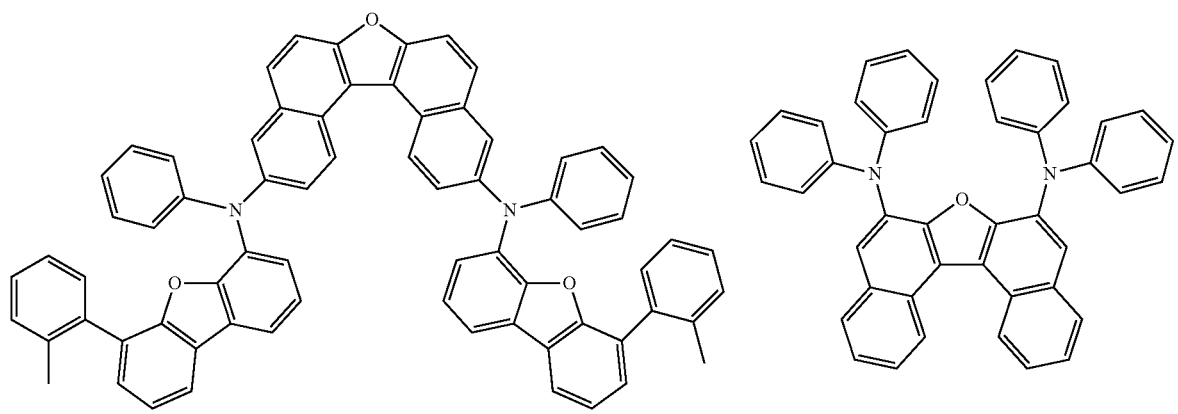
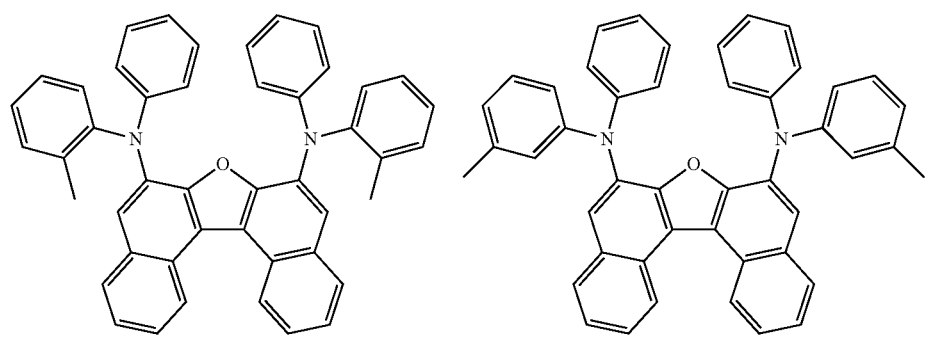
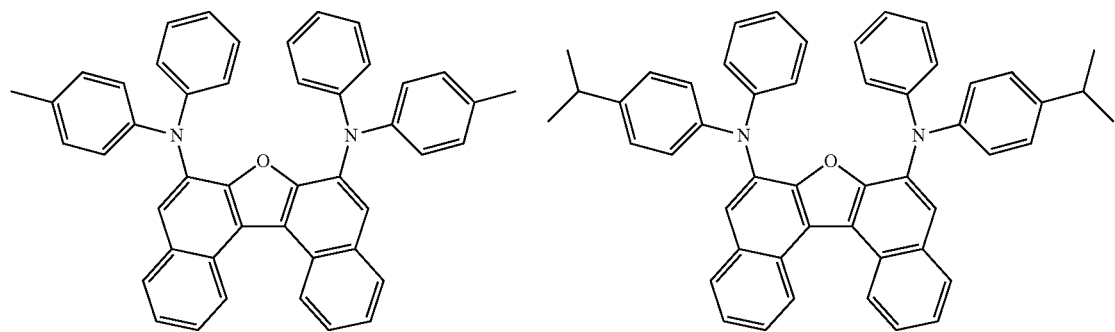
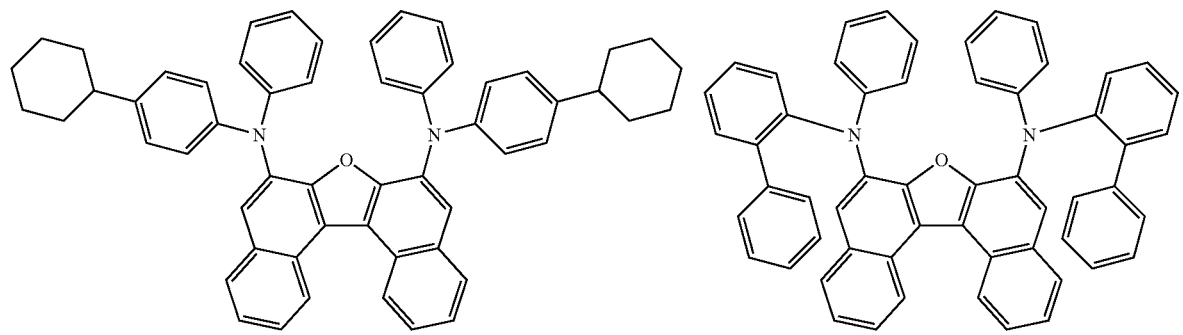

929 930
-continued
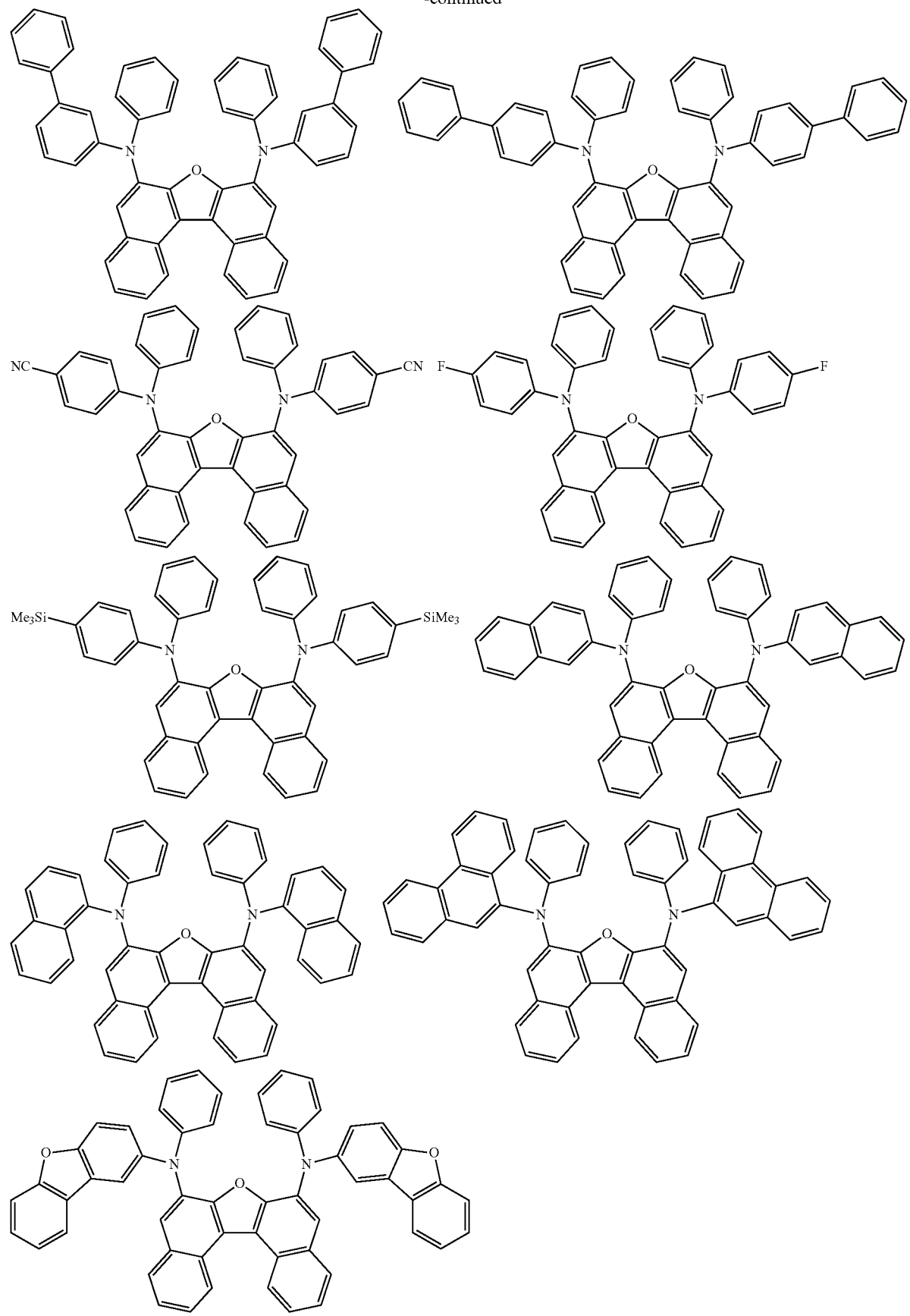

931 932
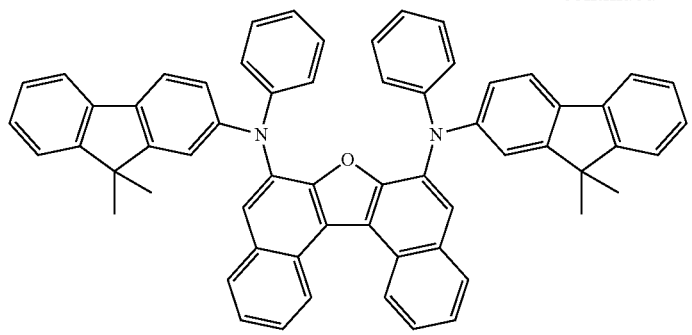
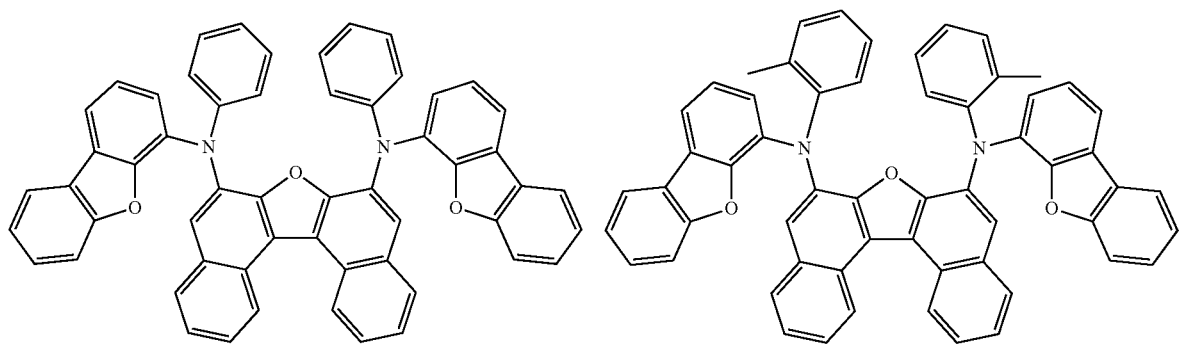
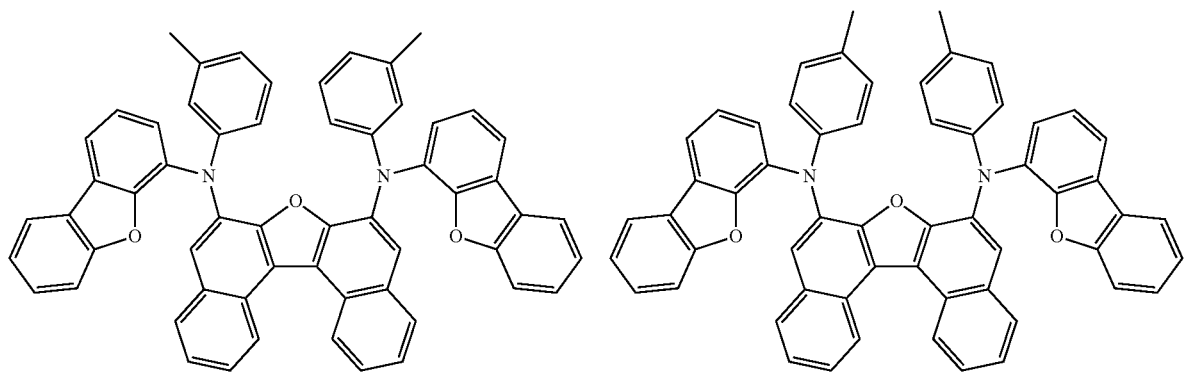
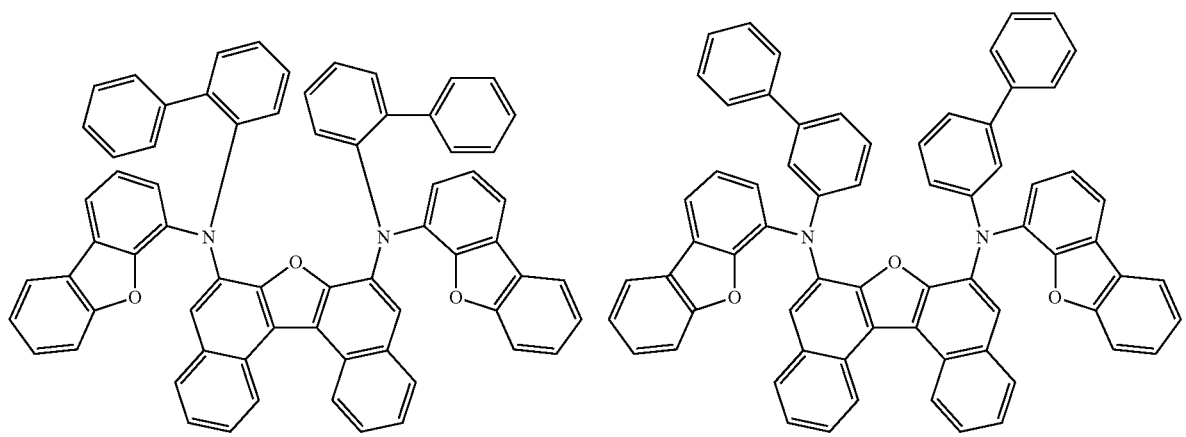

-continued
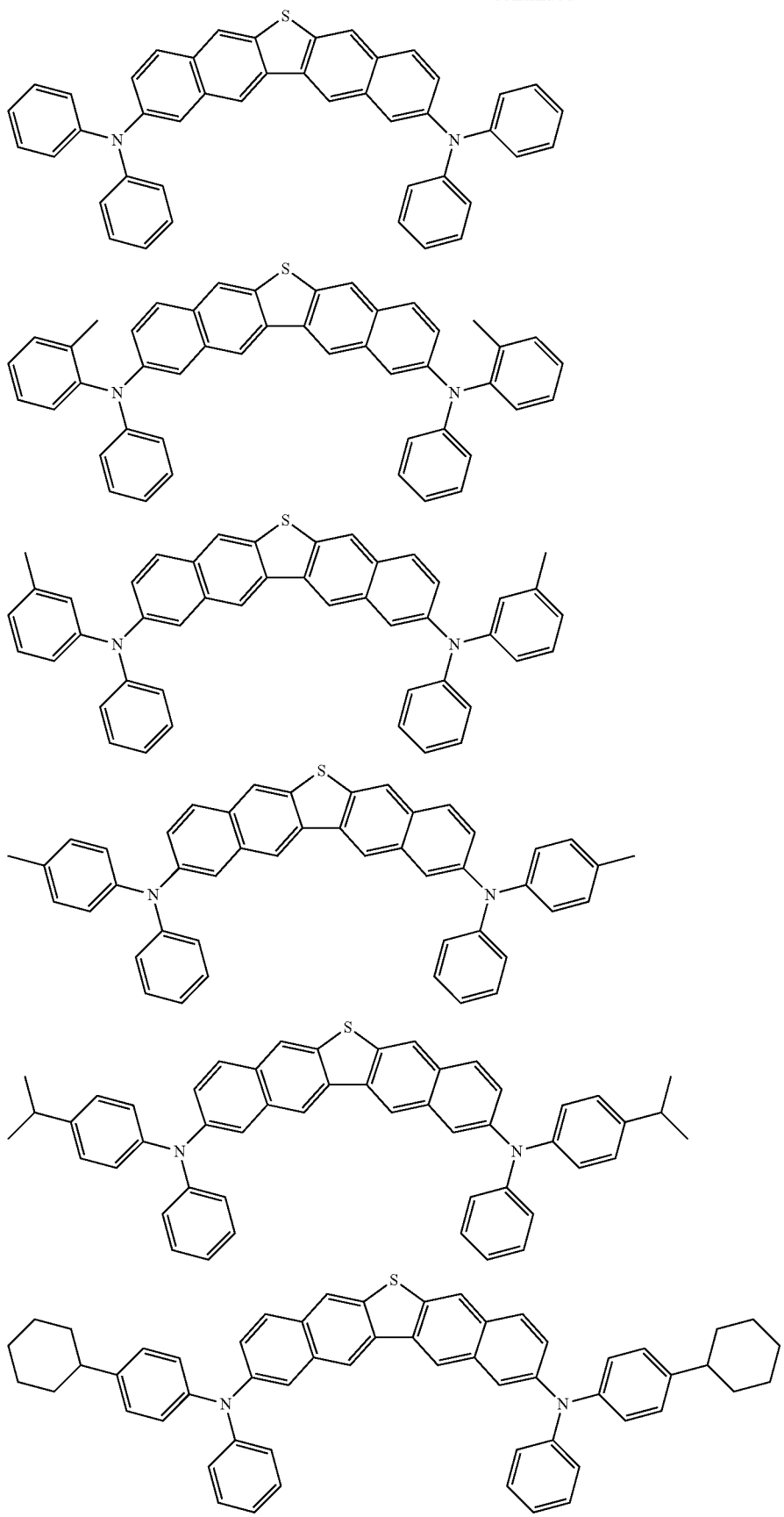

935
936
-continued
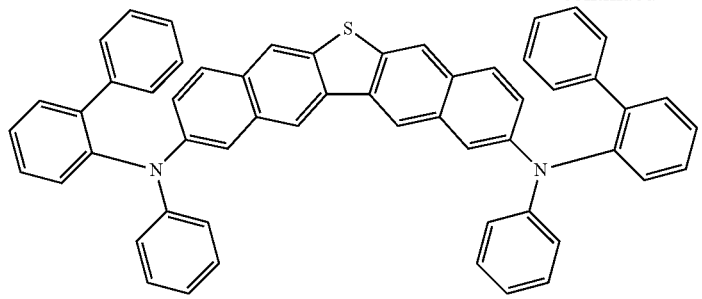
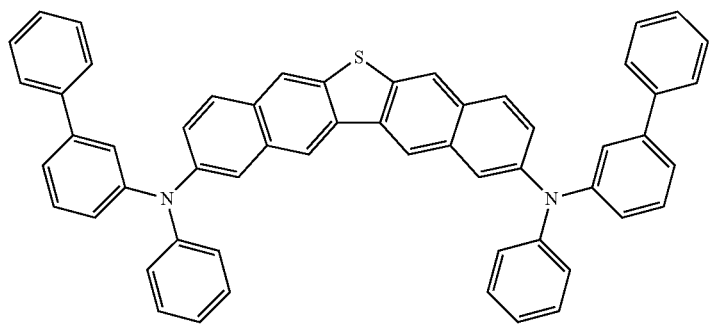
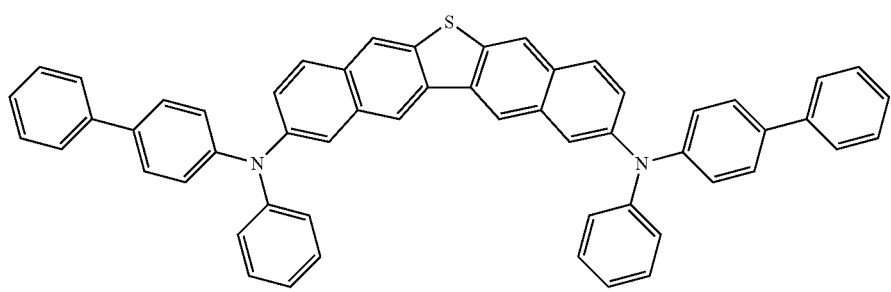
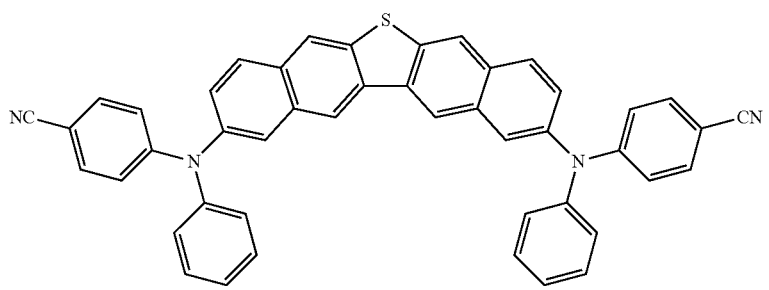
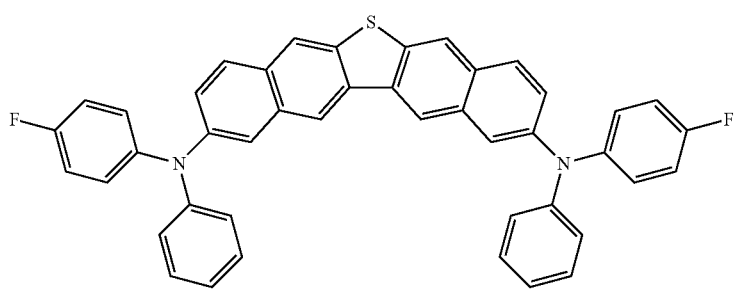

-continued
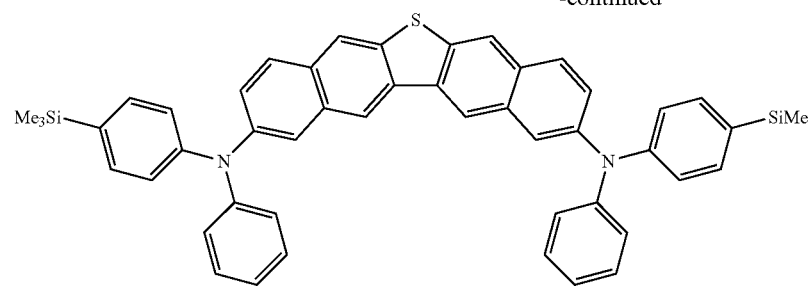
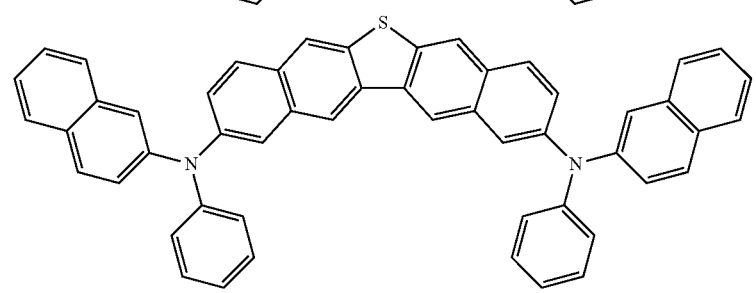
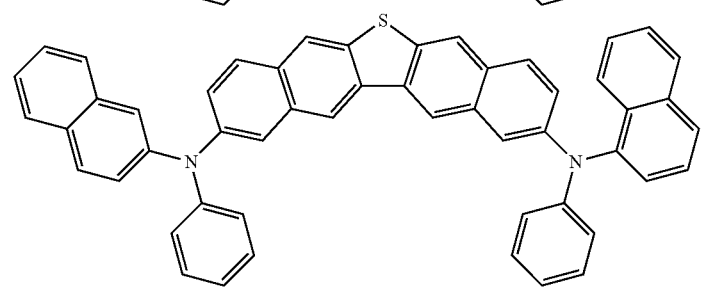
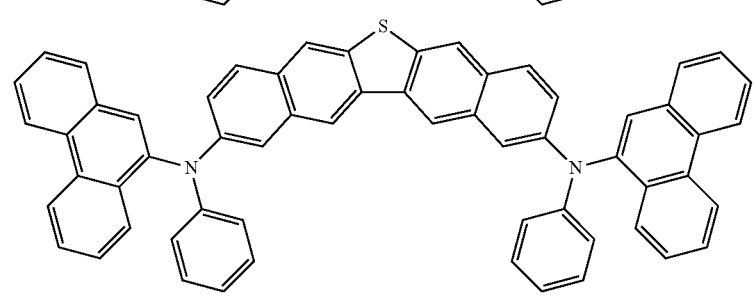
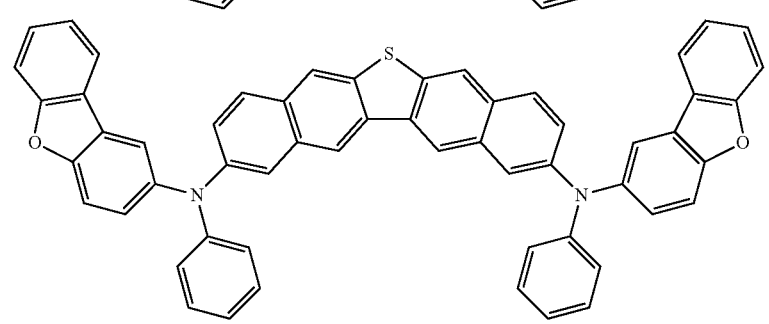
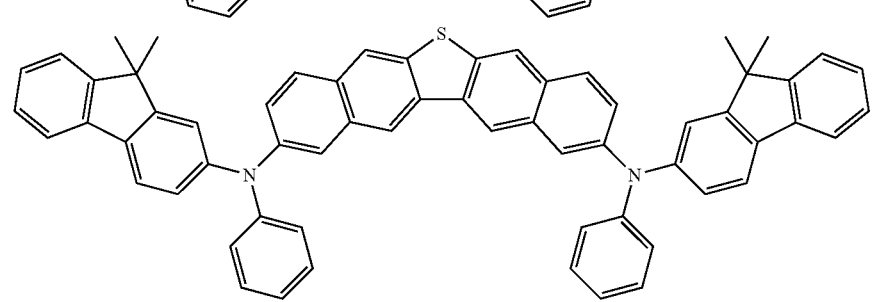

-continued
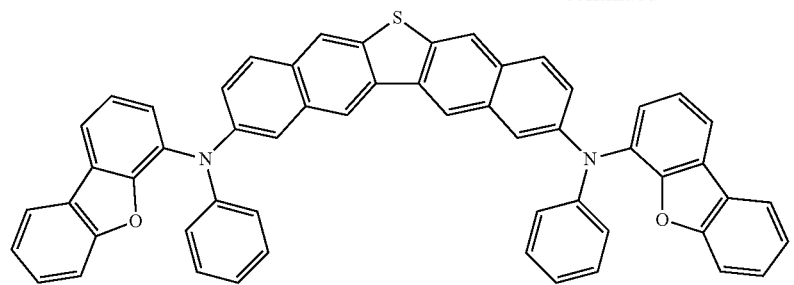
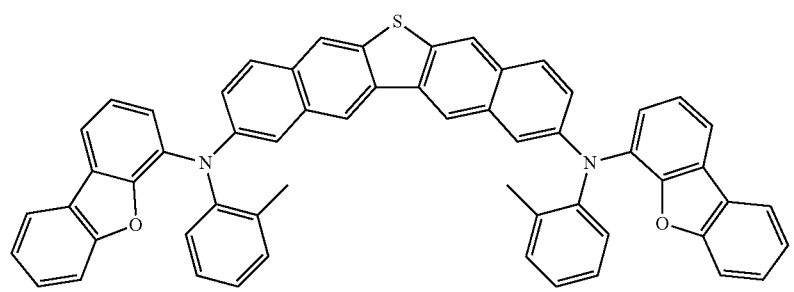
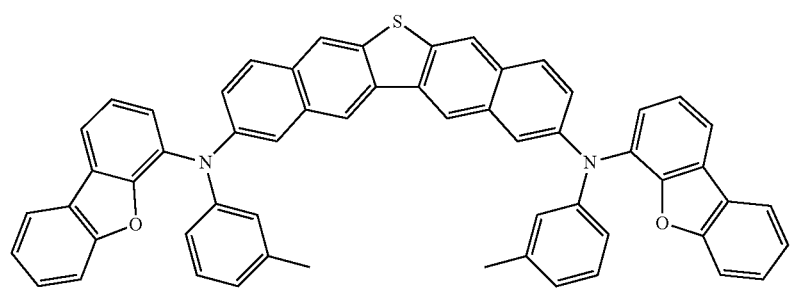
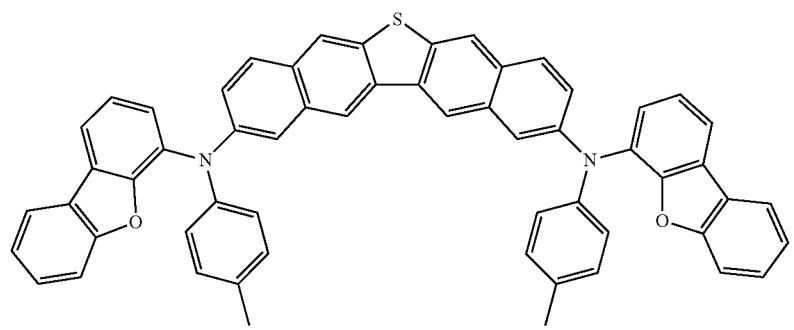
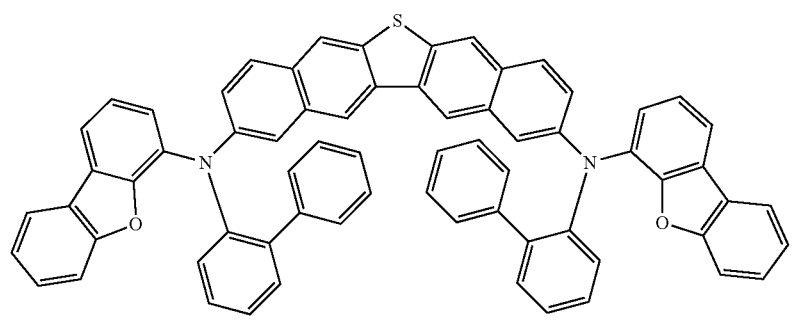

941 942
-continued
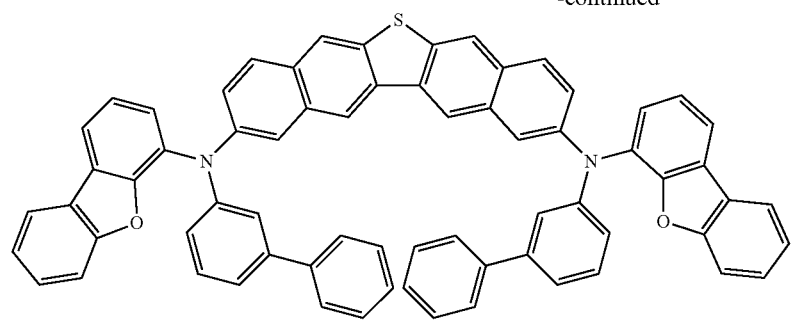
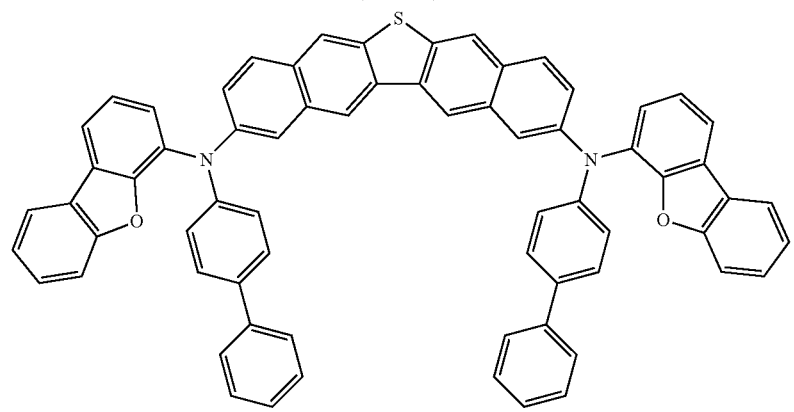
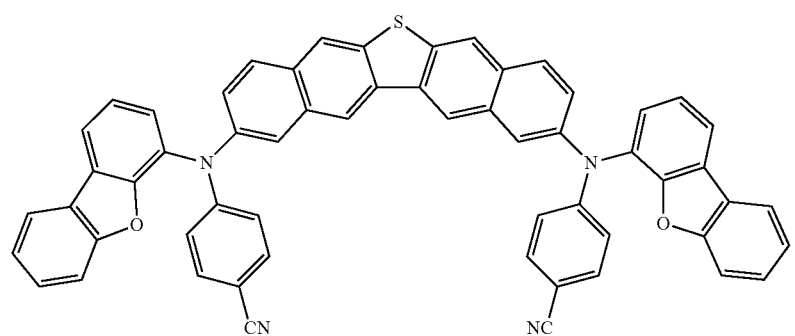
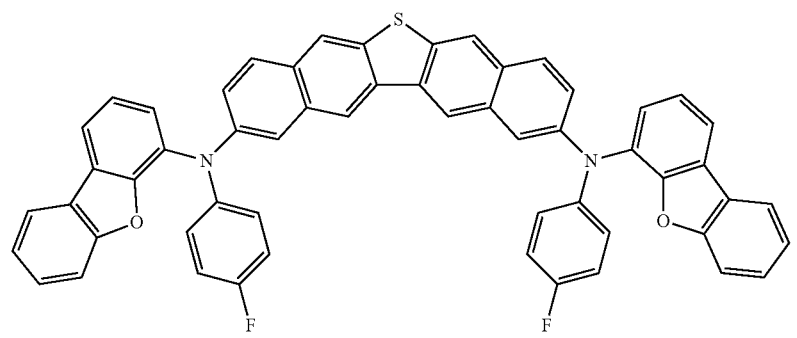
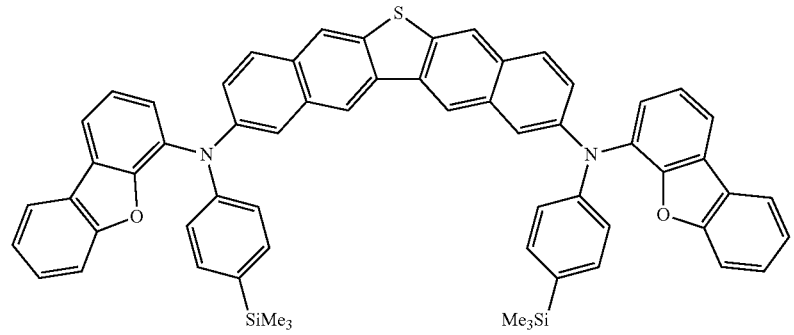

-continued
943 944
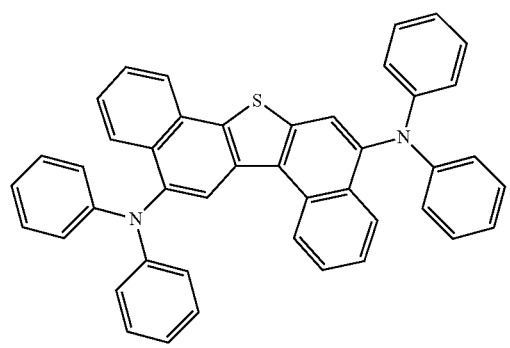
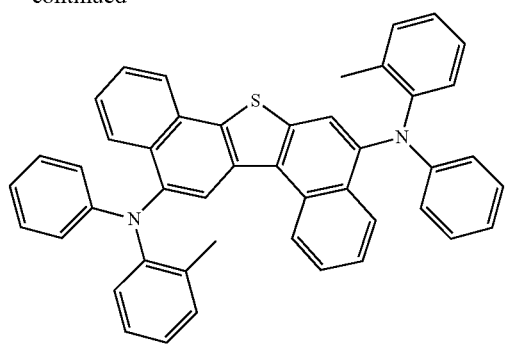
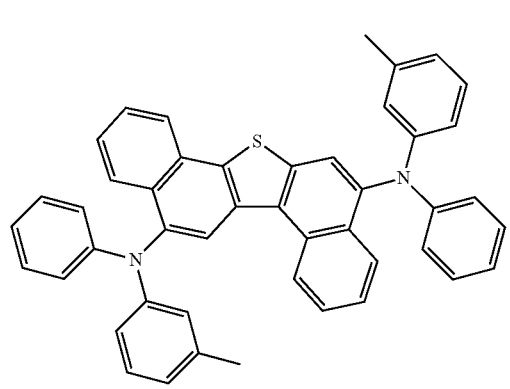
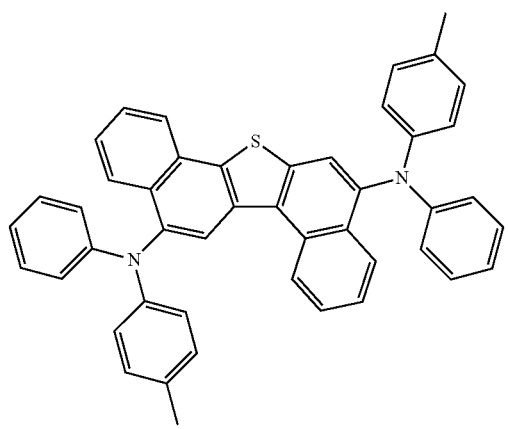
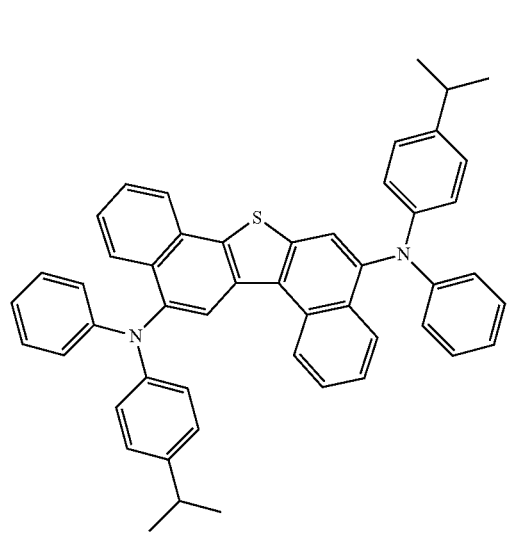
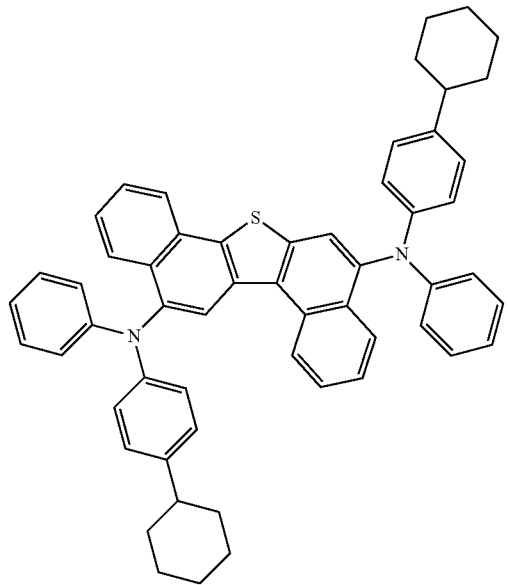

945 946
-continued
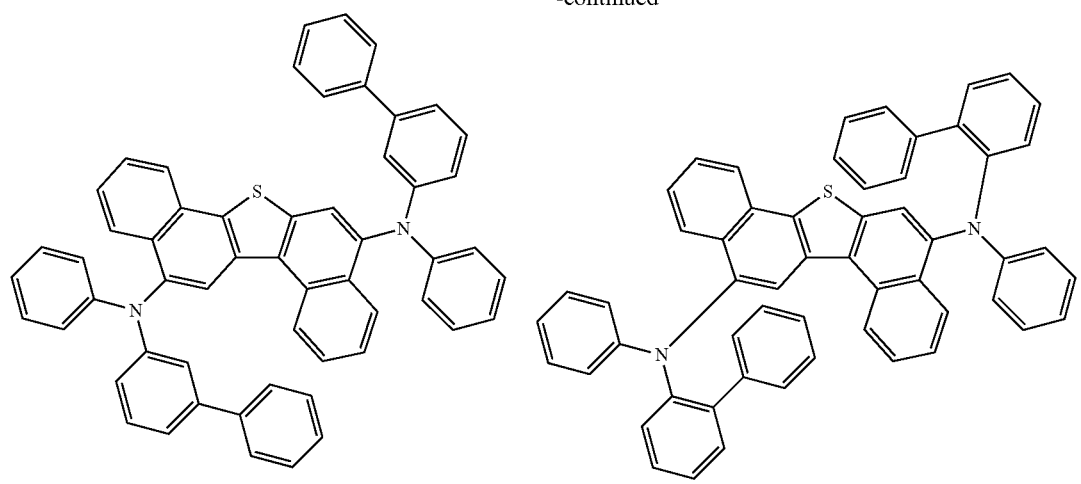
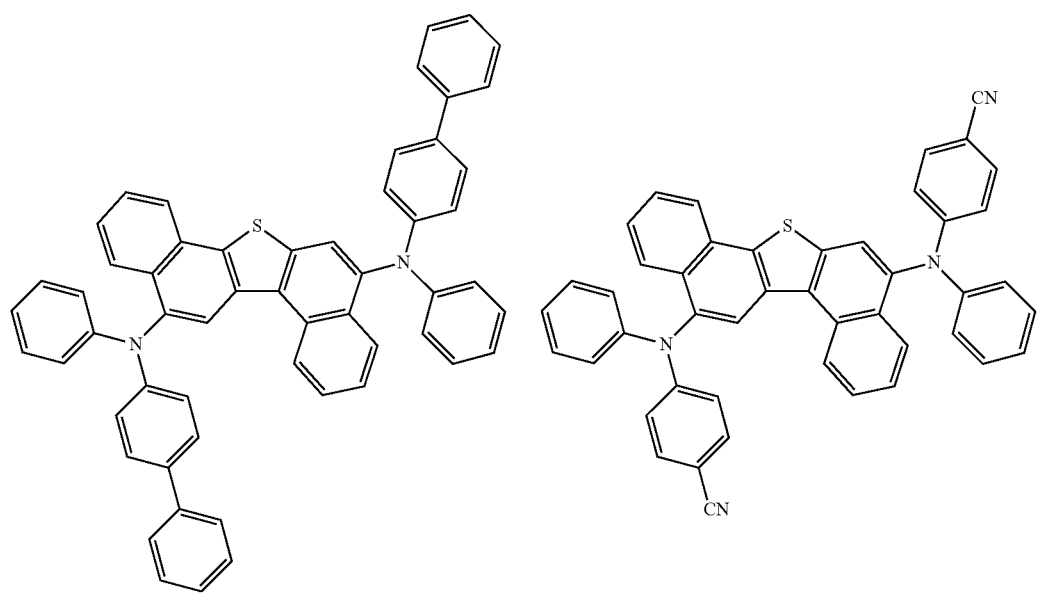
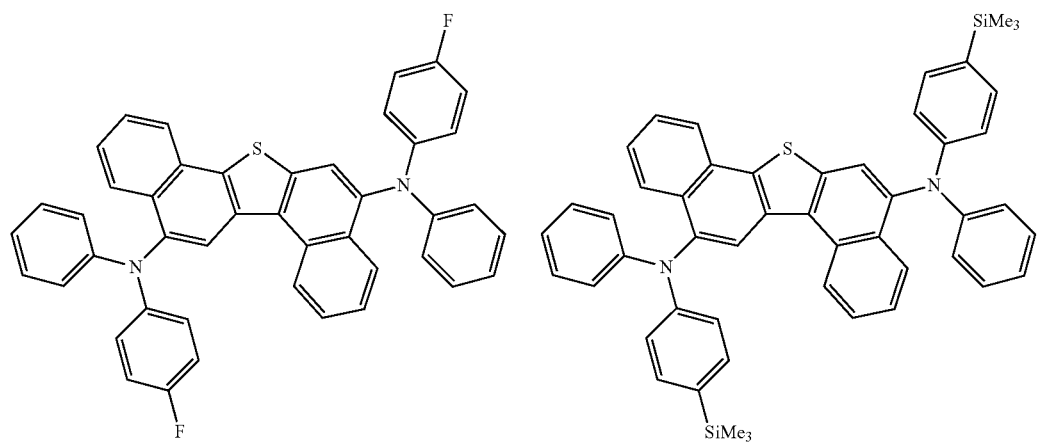

-continued
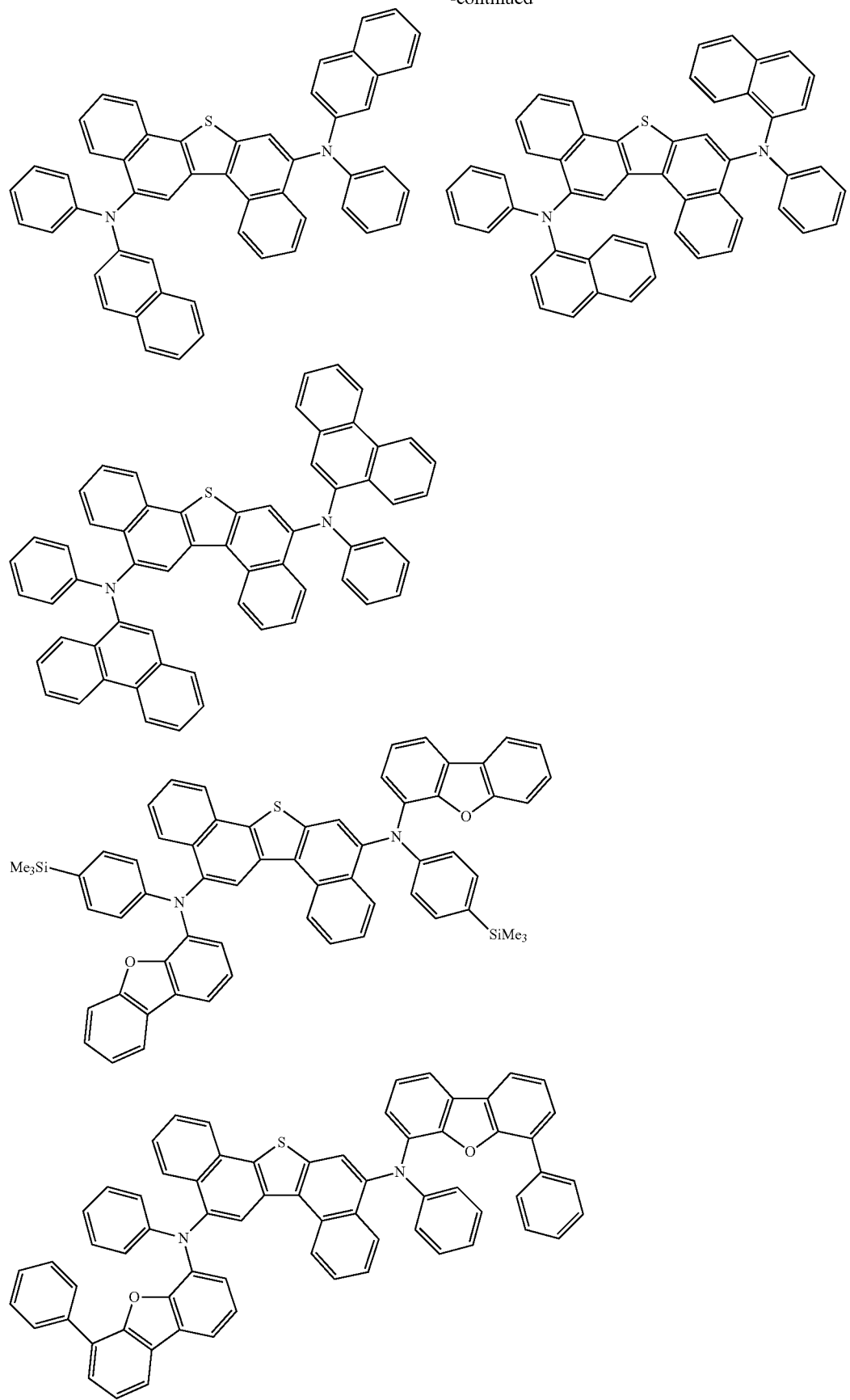

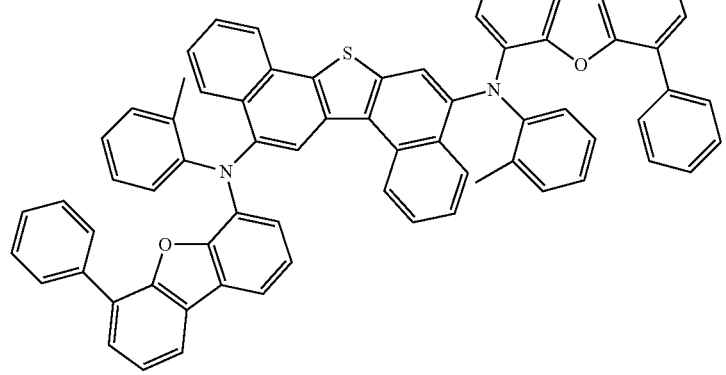
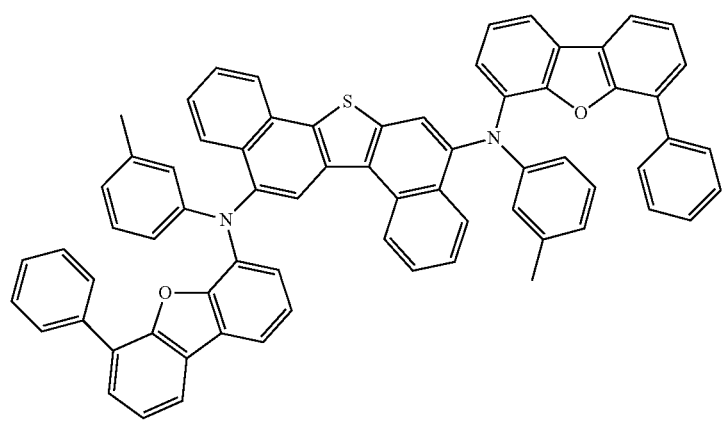
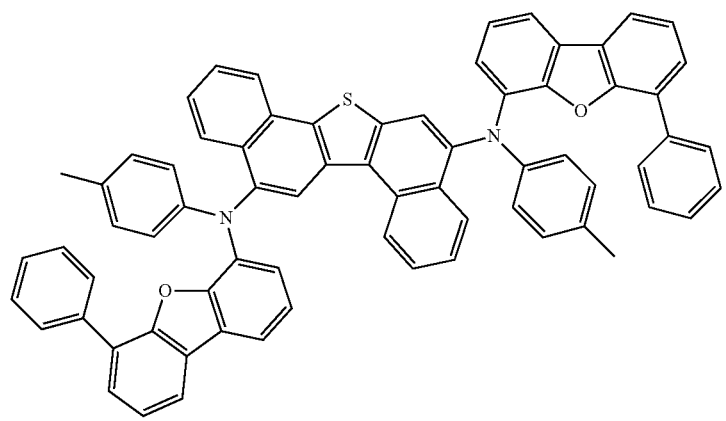

-continued
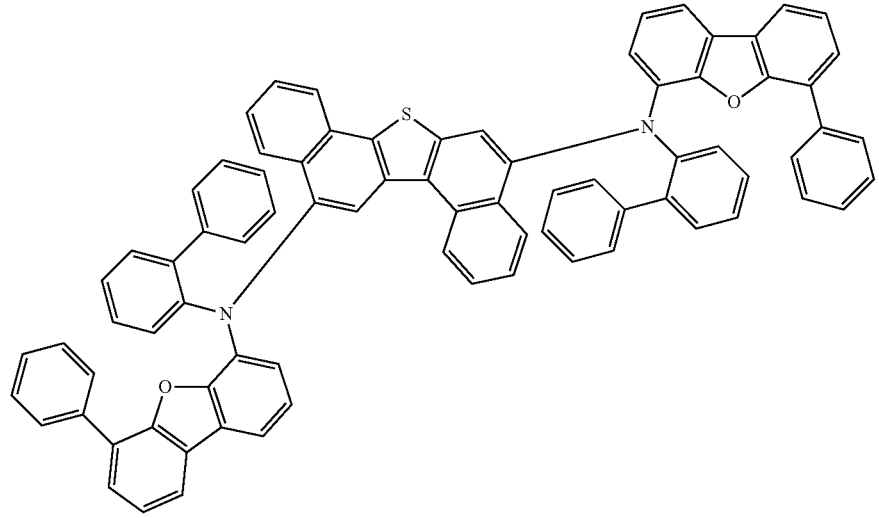
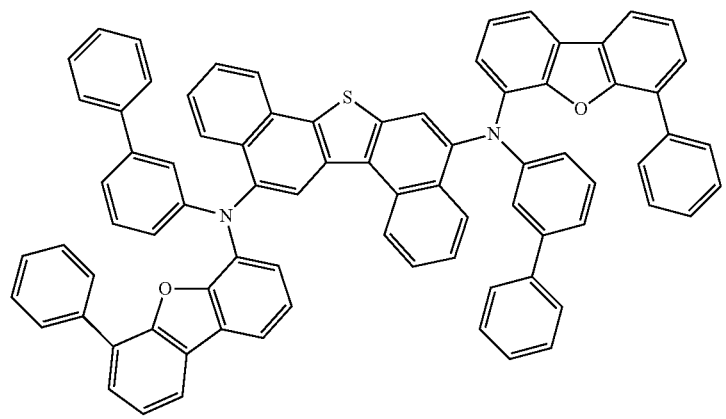
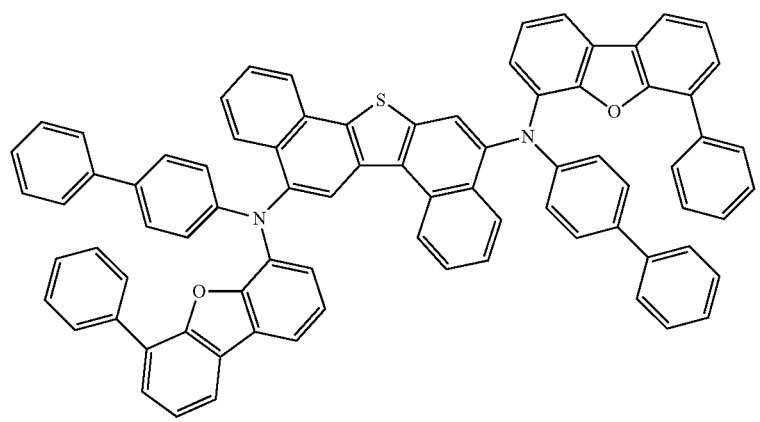

-continued
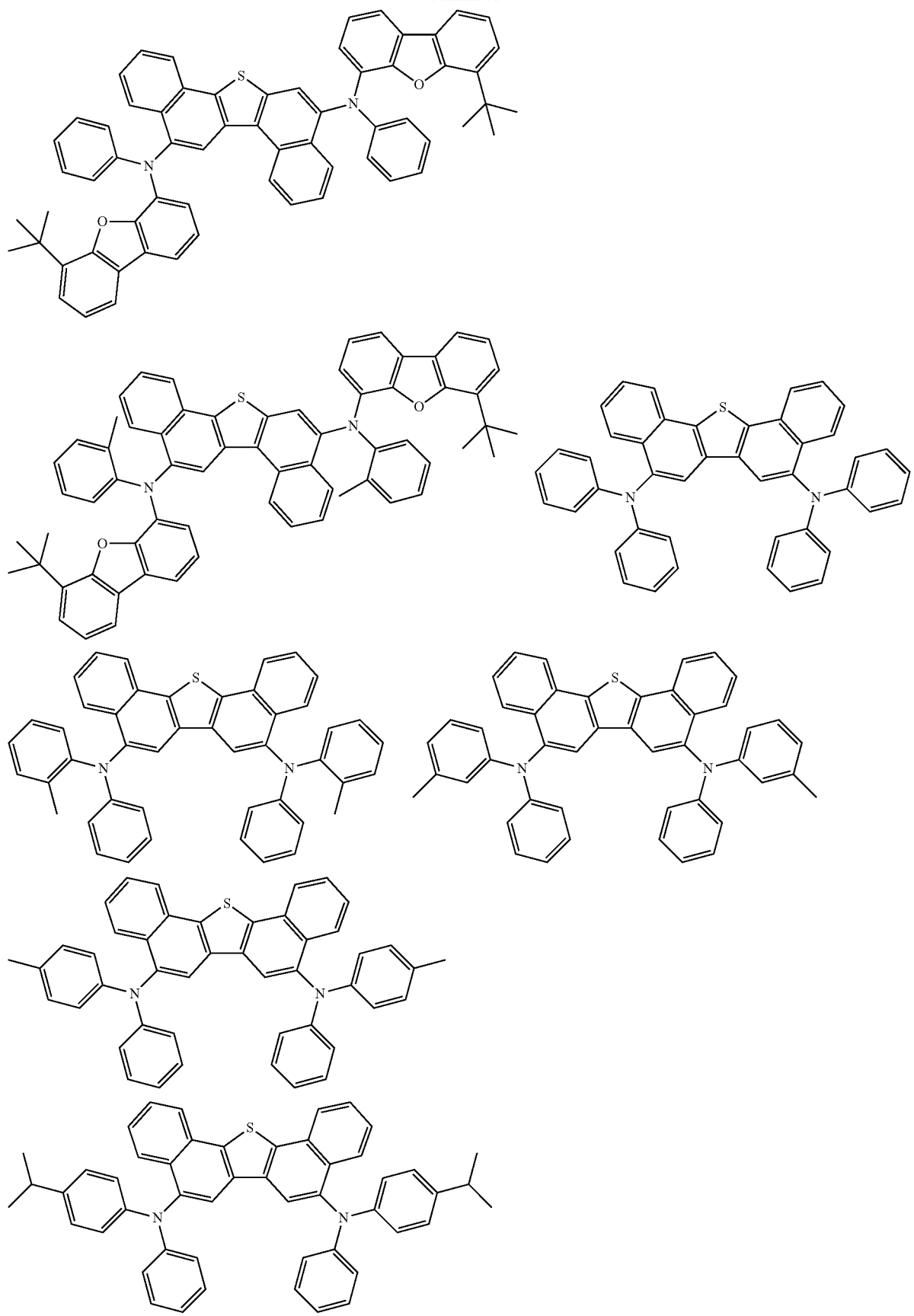

955
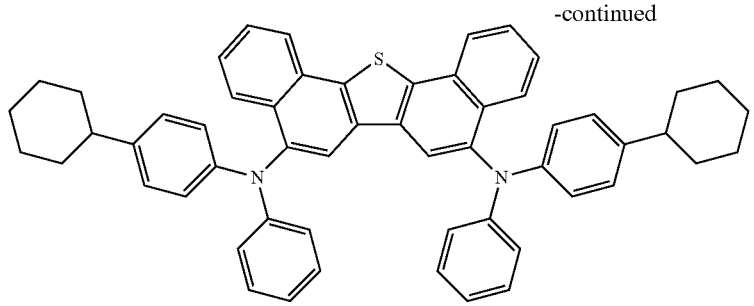
-continued
956
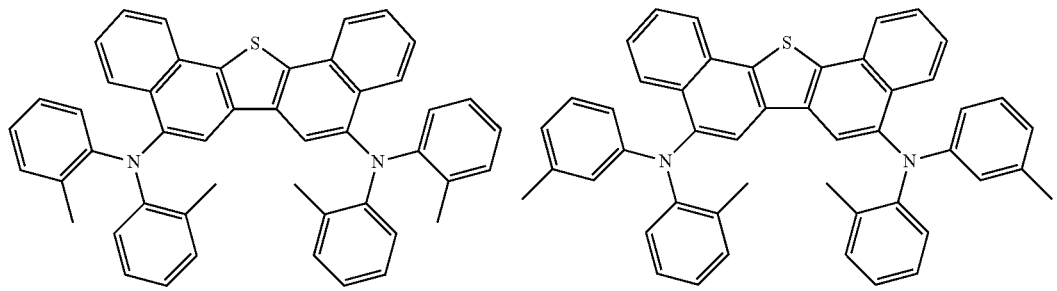
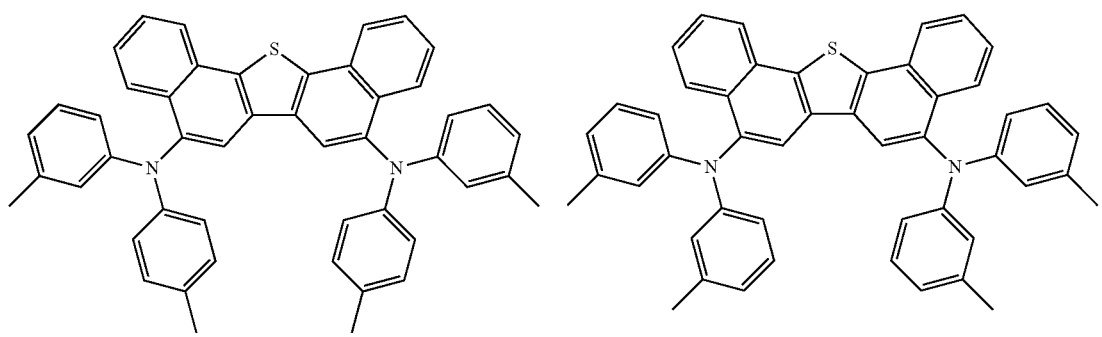
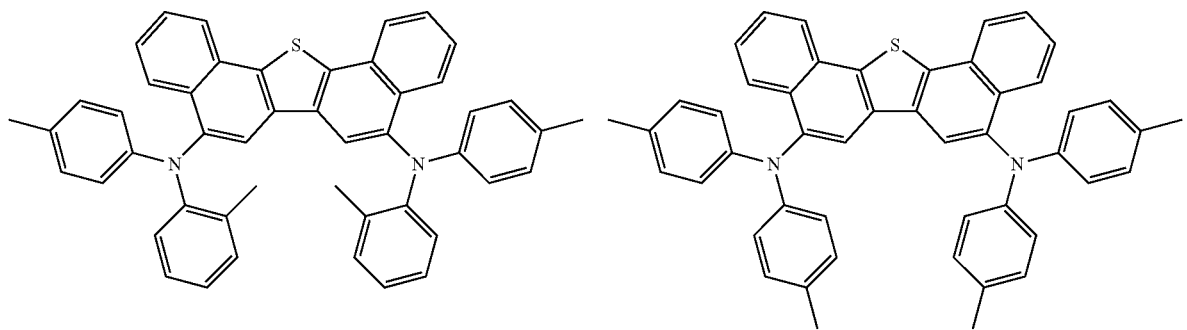
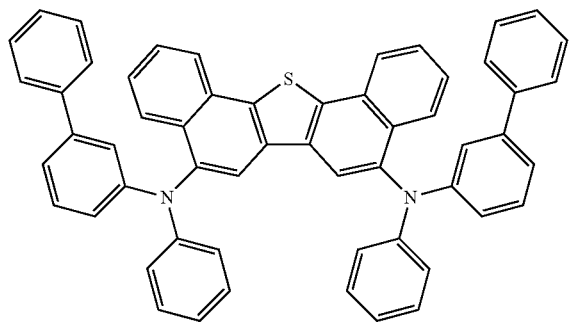
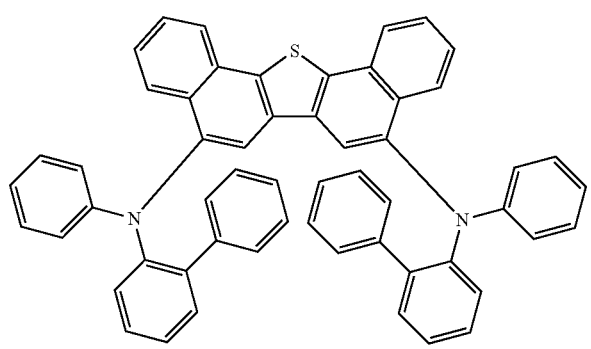

-continued
957
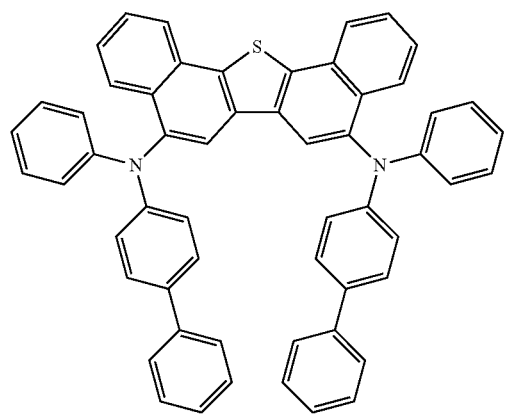
958
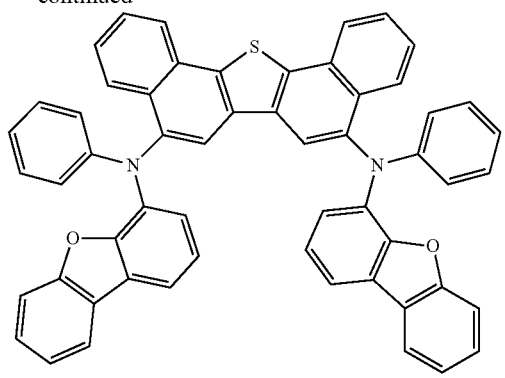
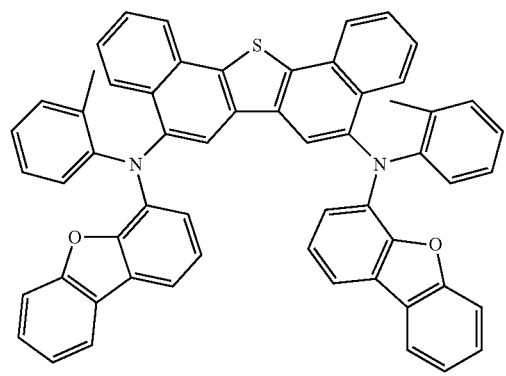
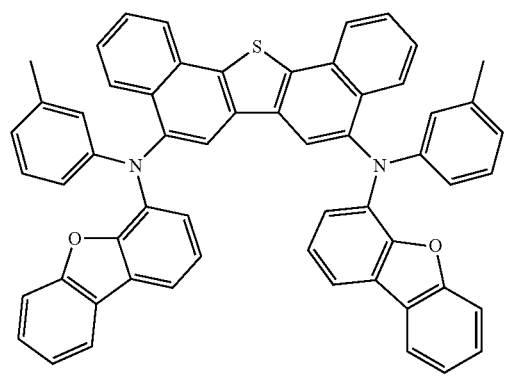
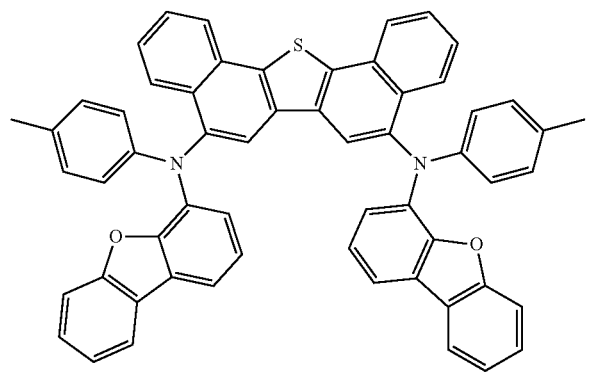
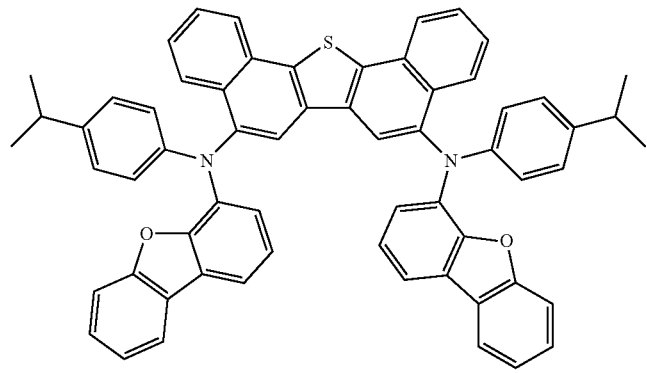

959 960
-continued
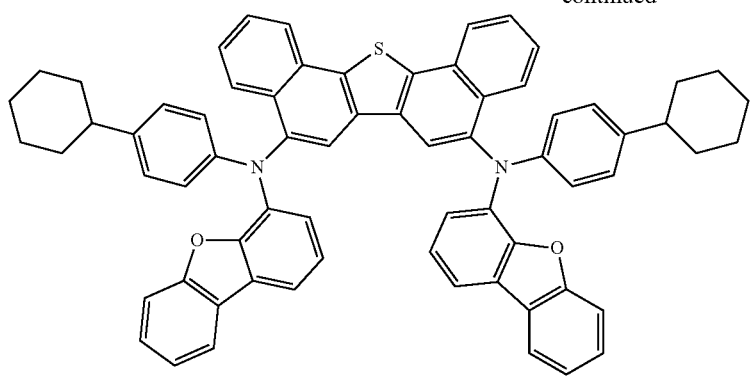
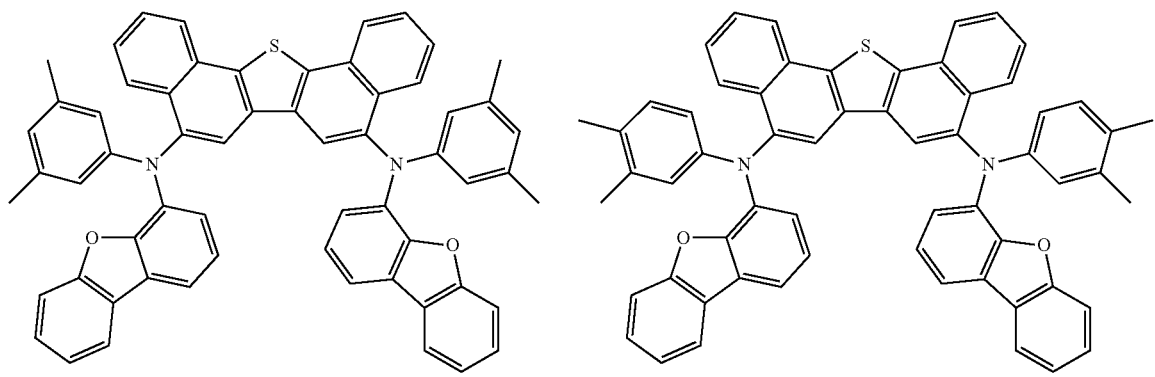
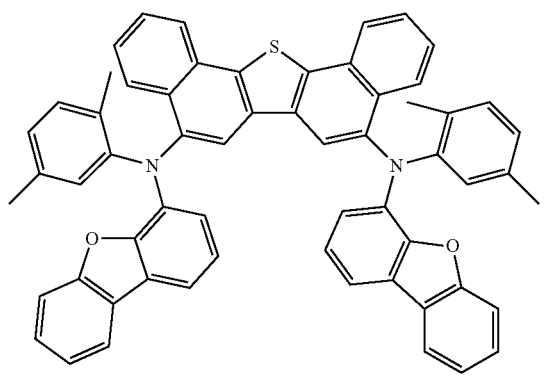
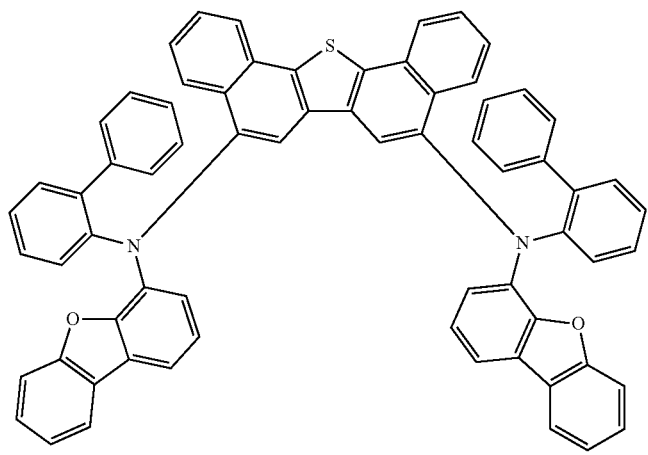

-continued
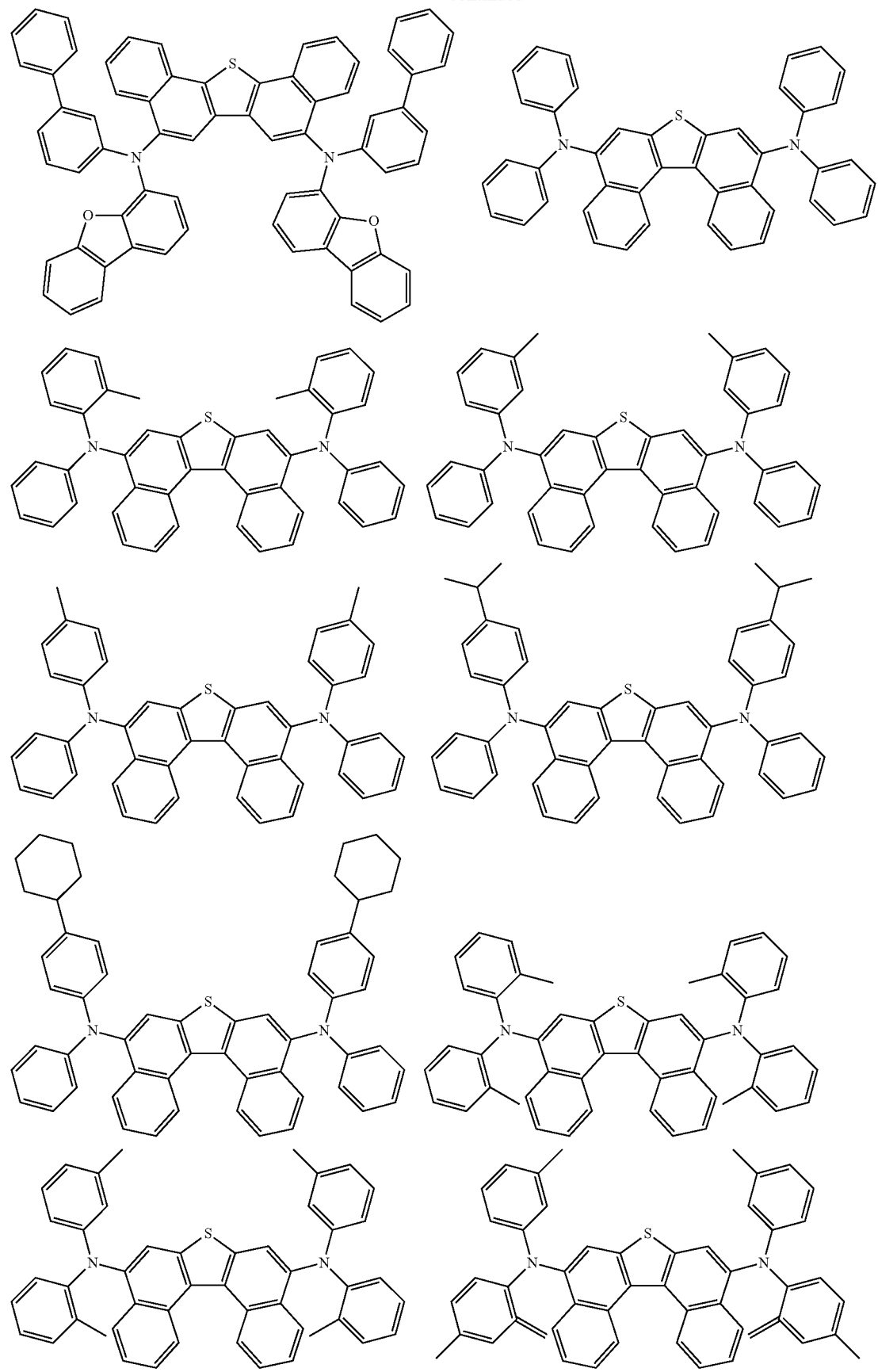
961
962

-continued
963      964
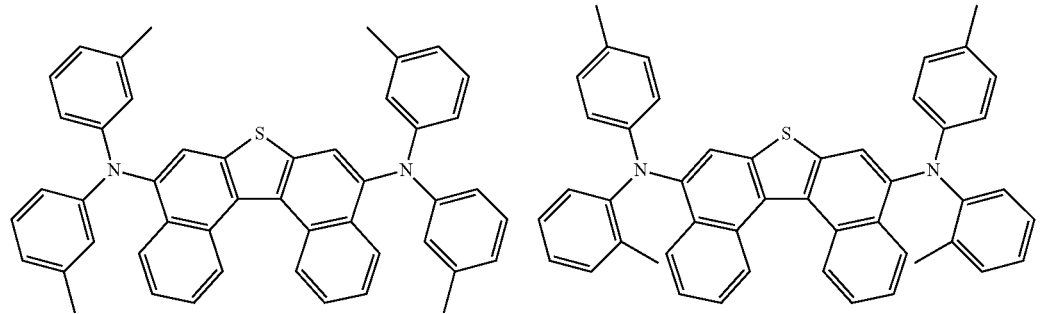
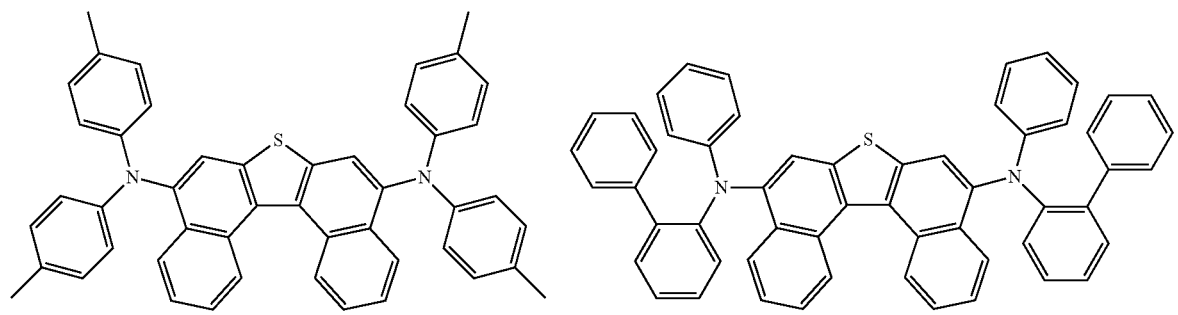
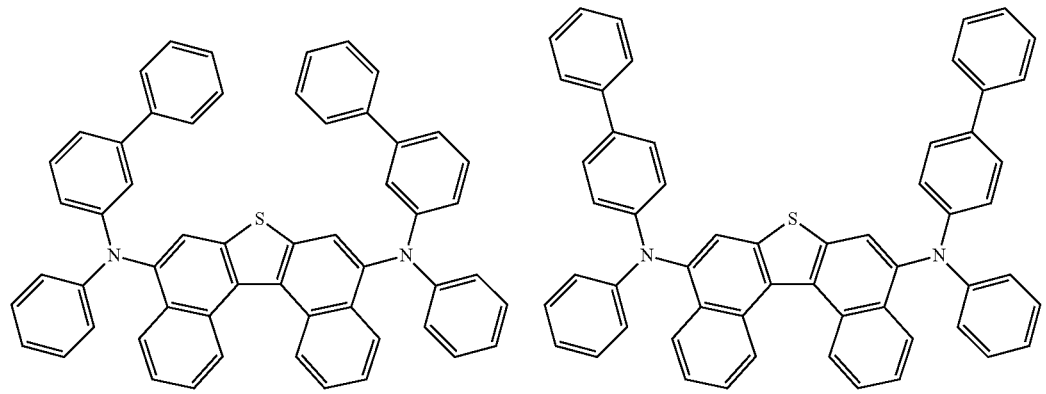
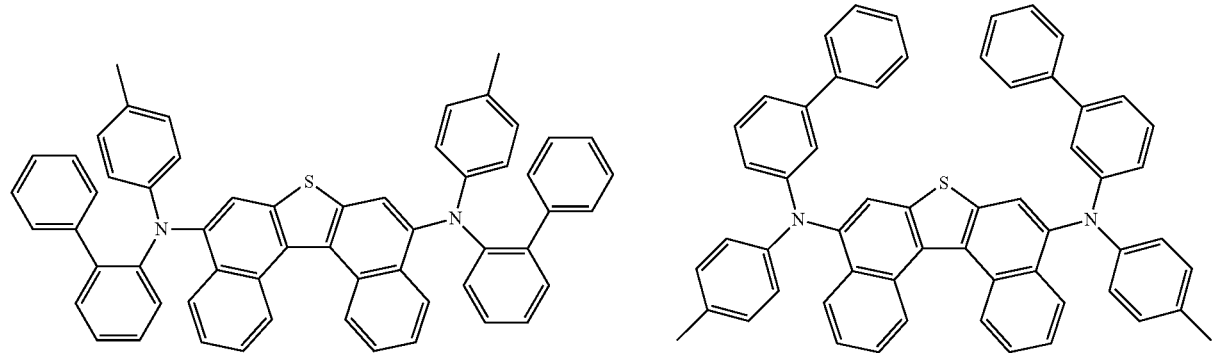

-continued
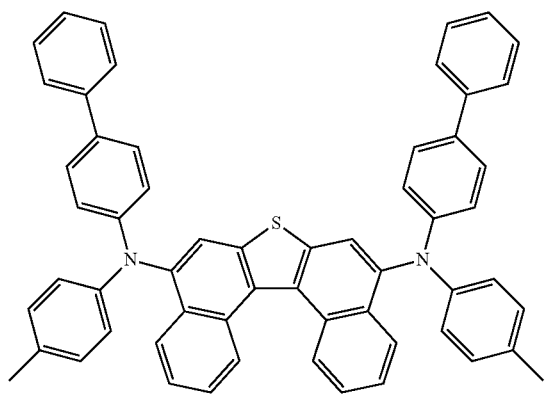
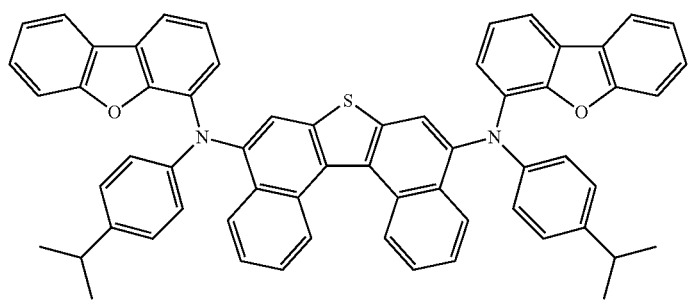
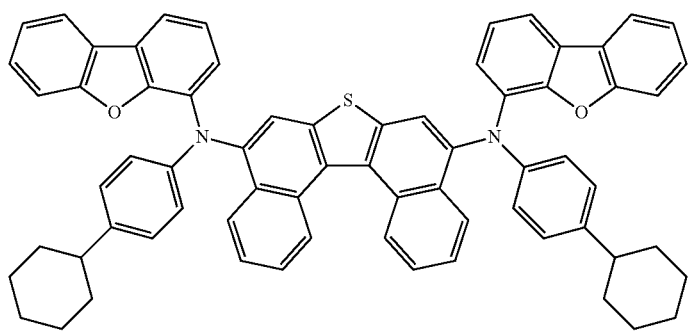
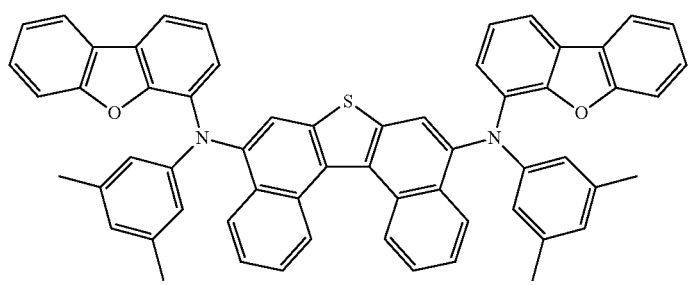
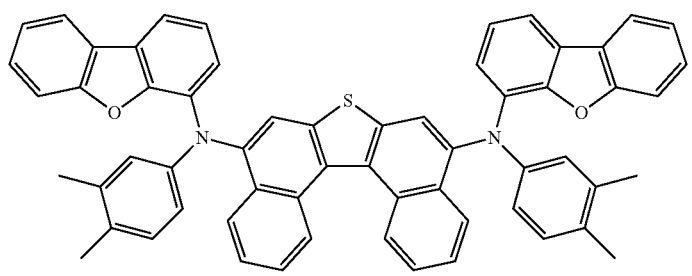

-continued
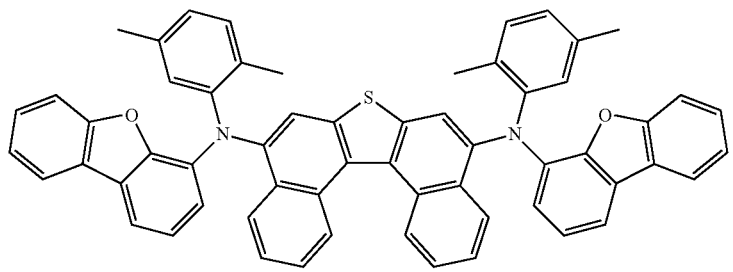
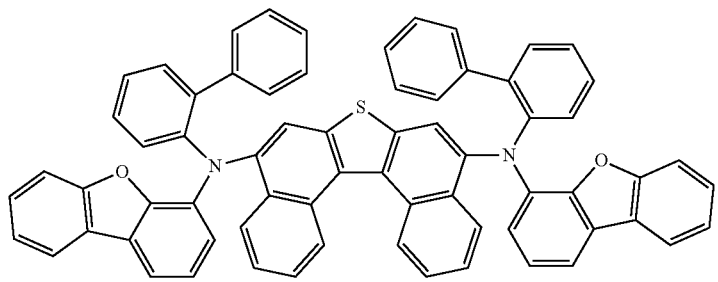
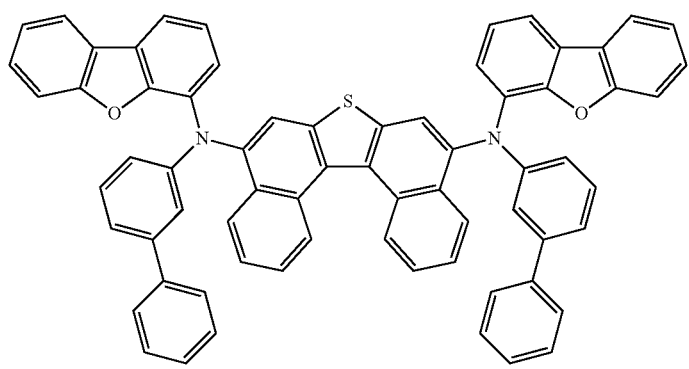
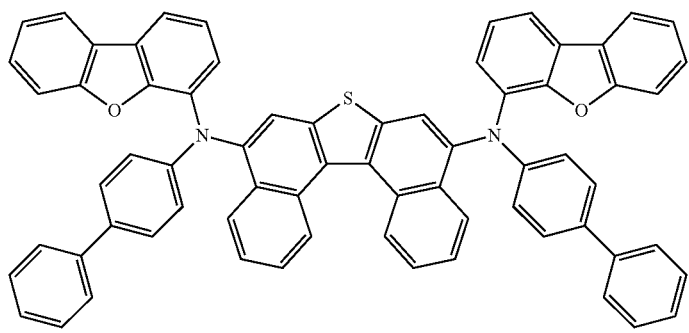
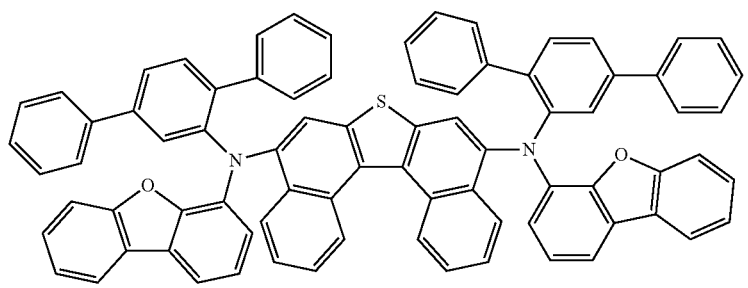

969
970
-continued
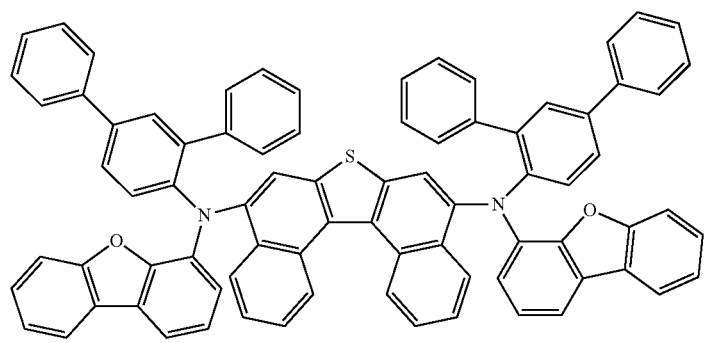
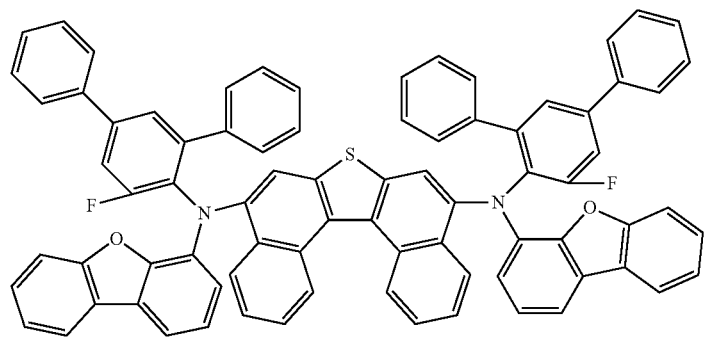
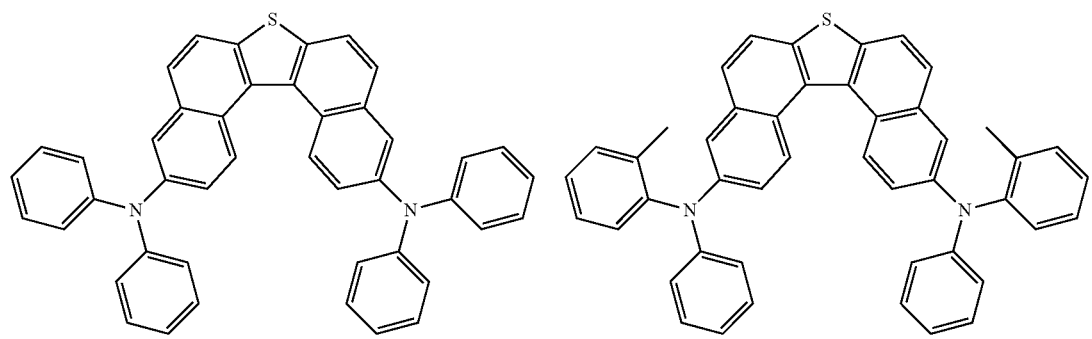
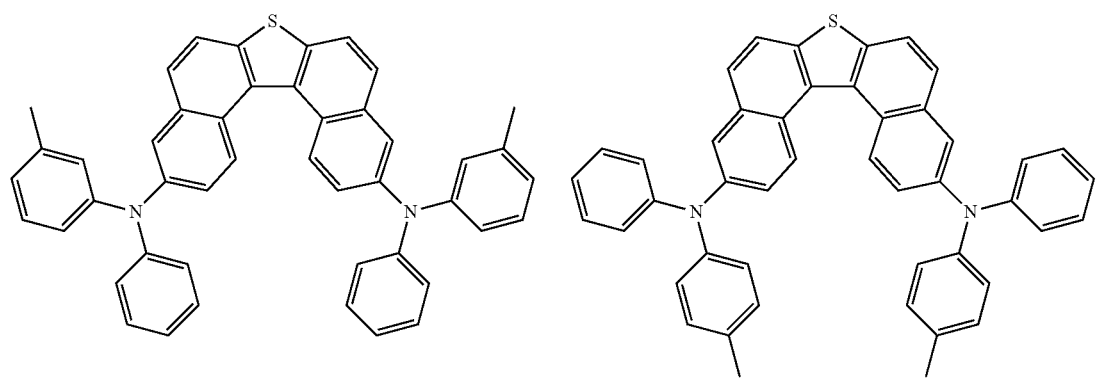

-continued
| 971 | 972 |
|---|---|
| 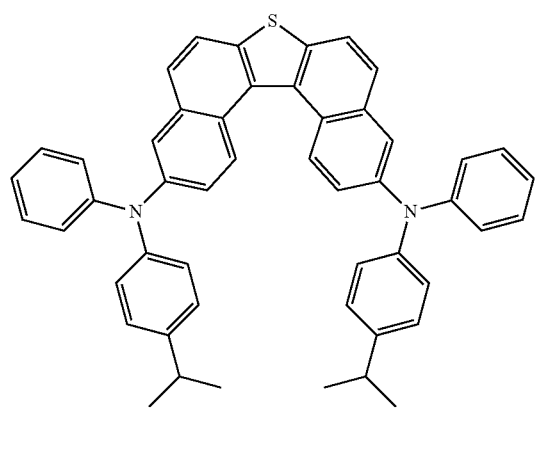 | 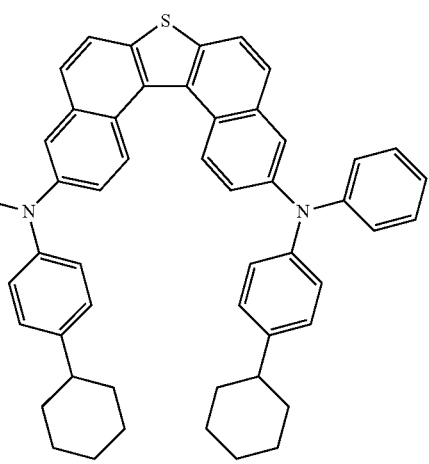 |
| 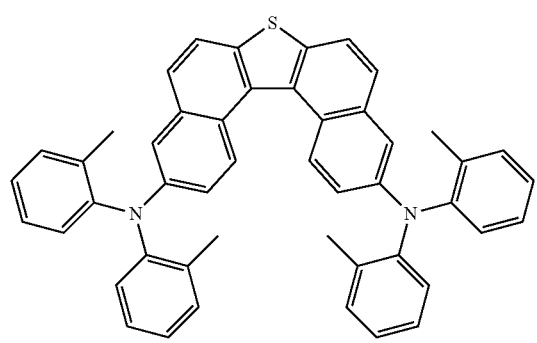 | 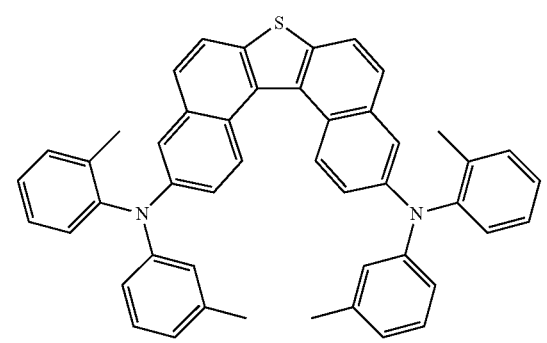 |
| 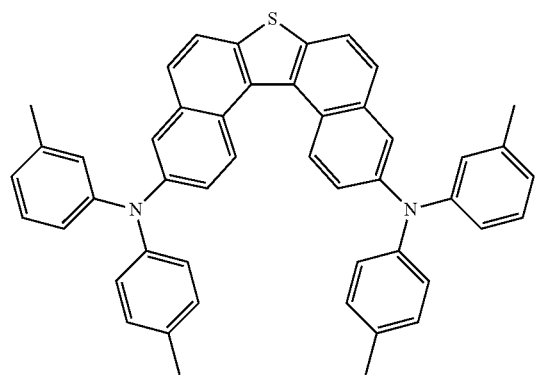 | 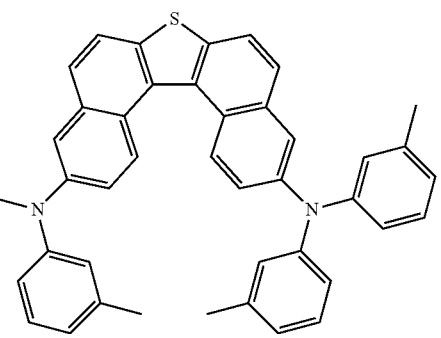 |
| 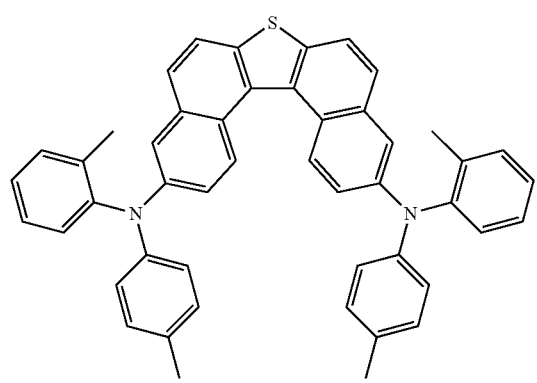 | 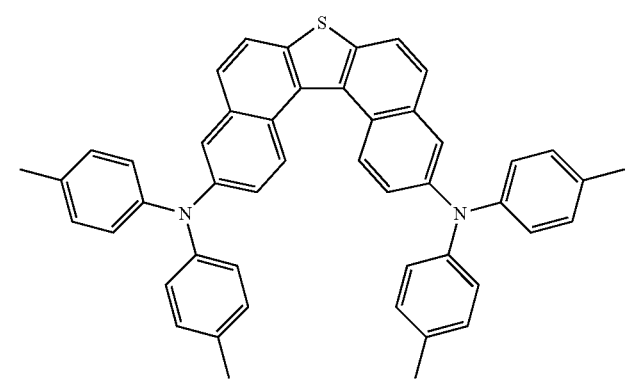 |

973 974
-continued
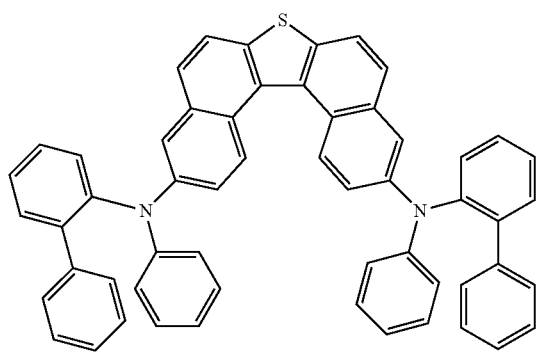 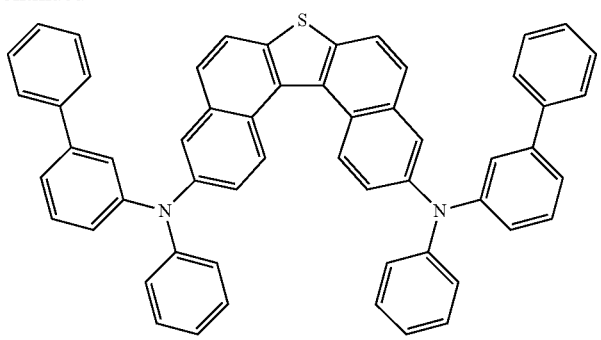
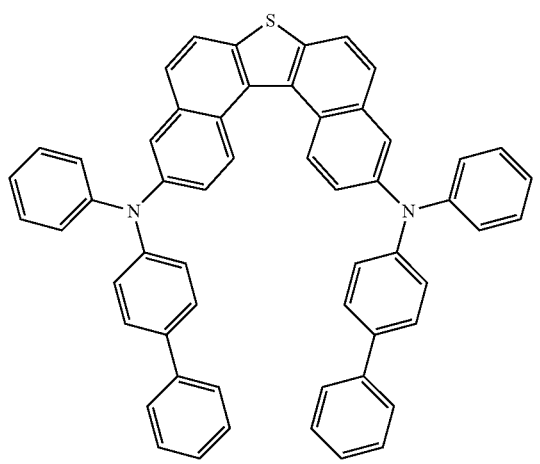 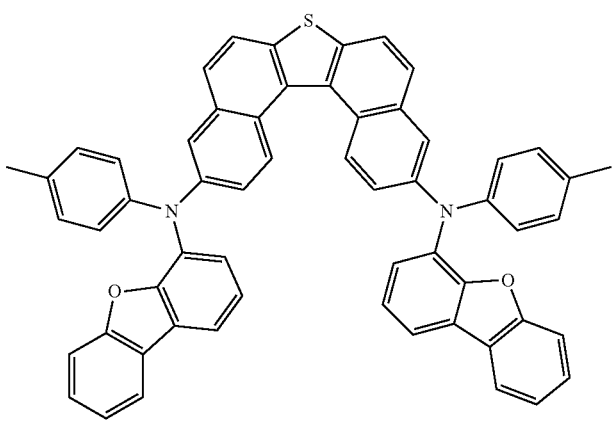
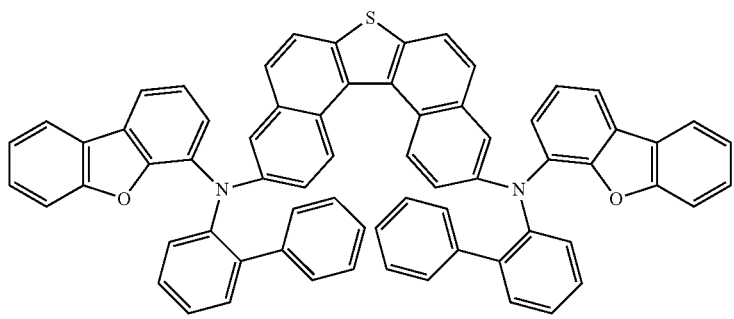
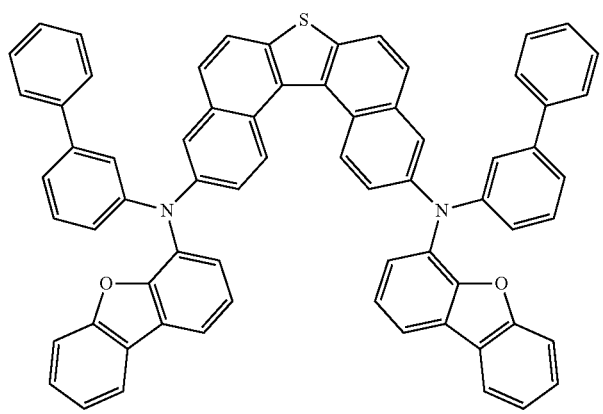

-continued
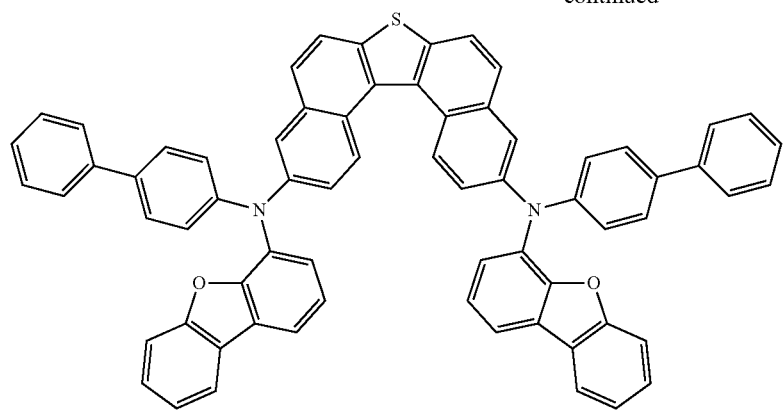
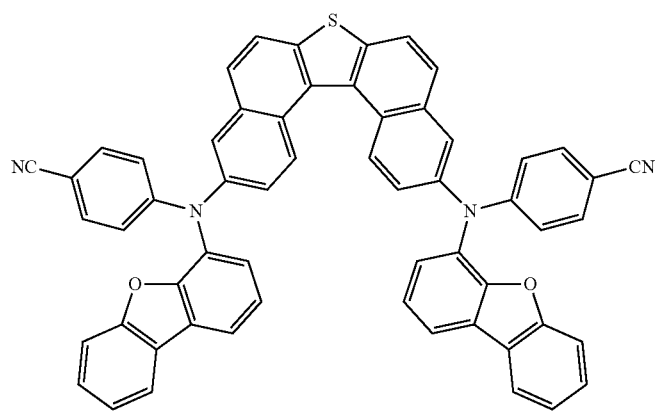
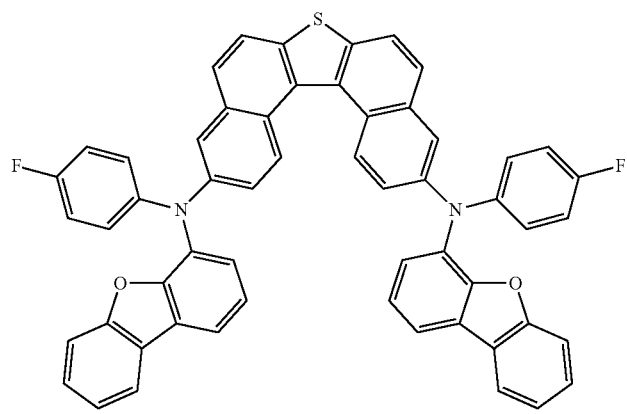
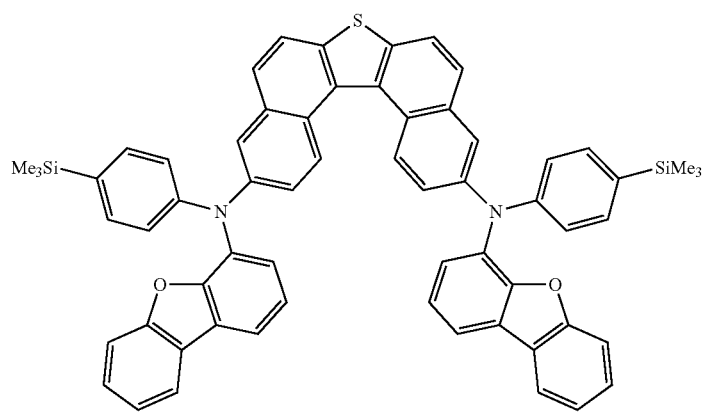

-continued
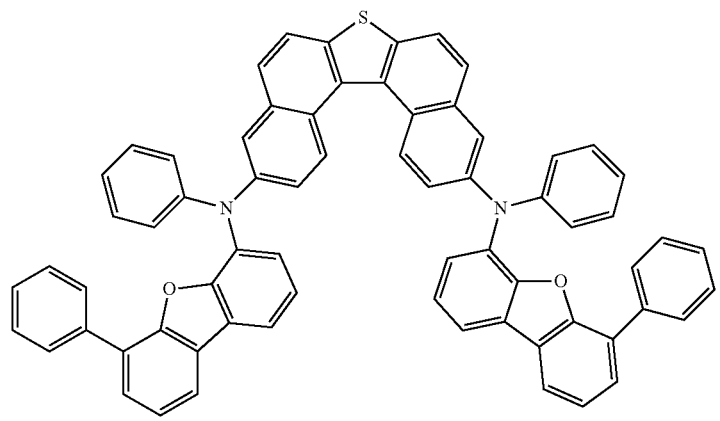
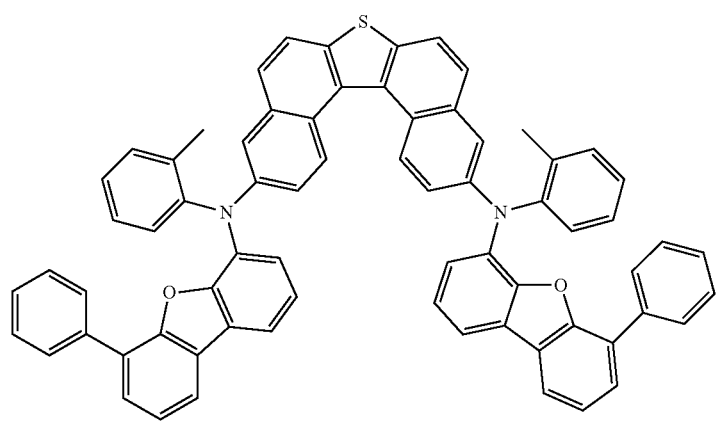
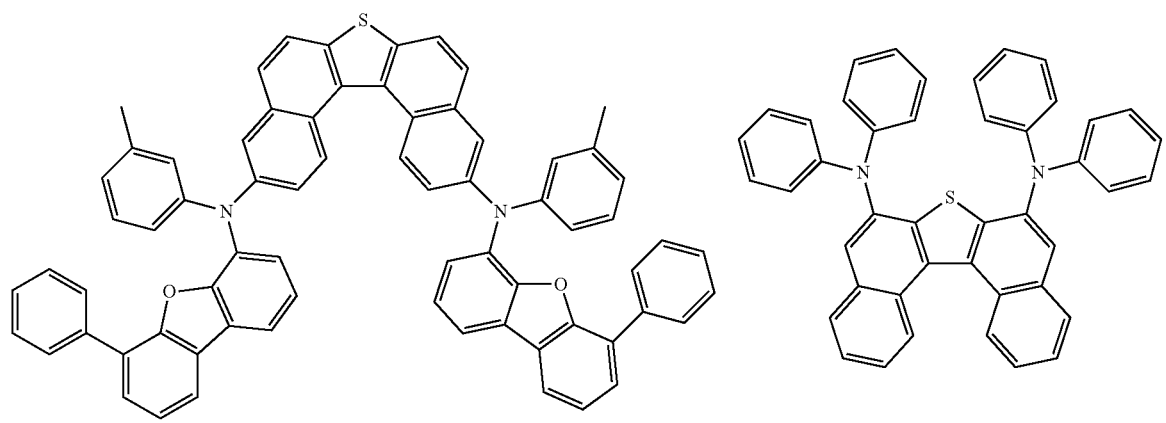
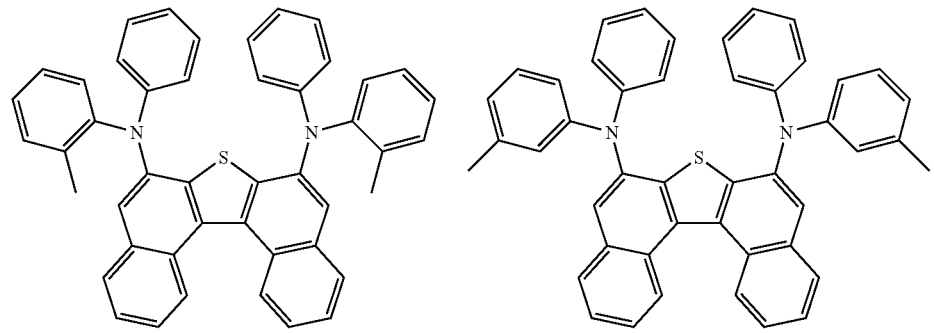

-continued
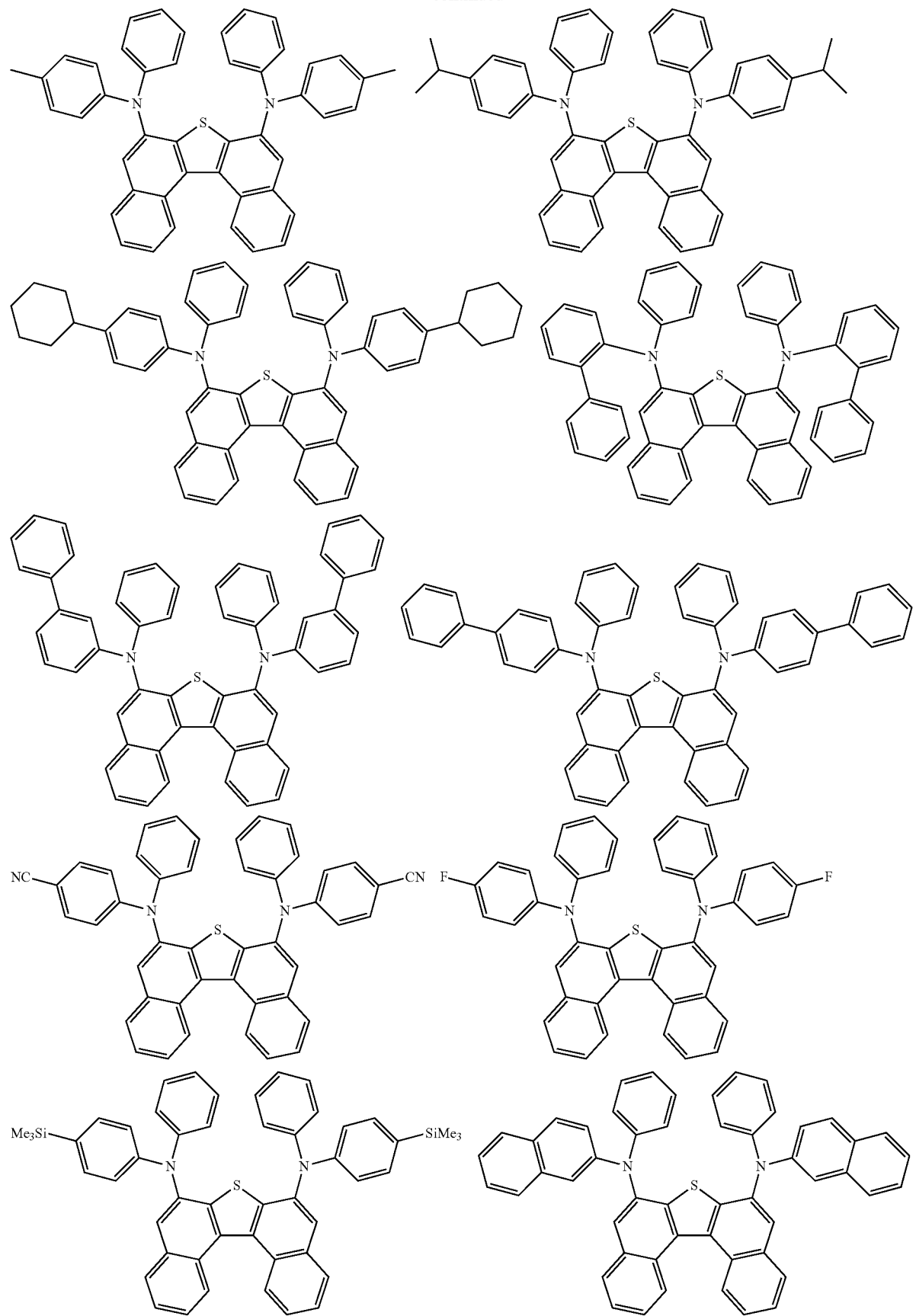

981
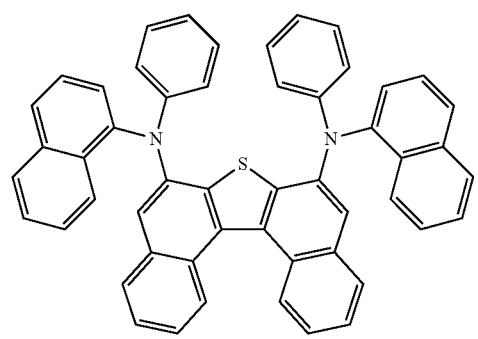
982
-continued
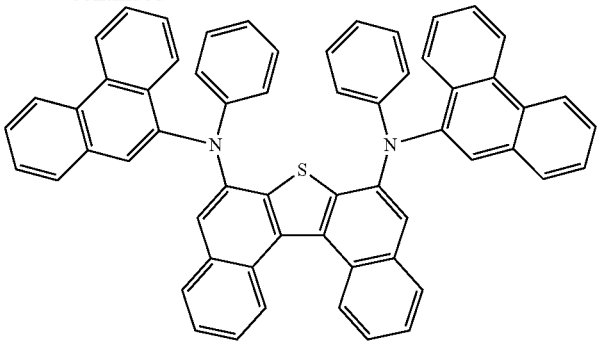
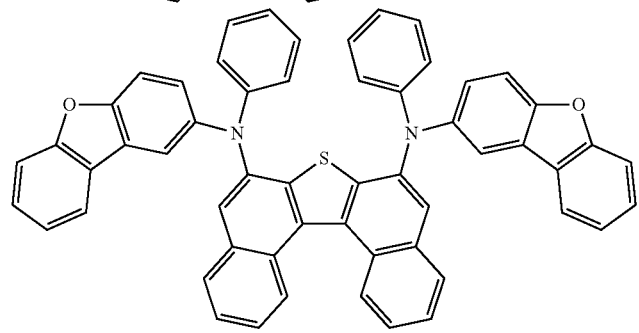
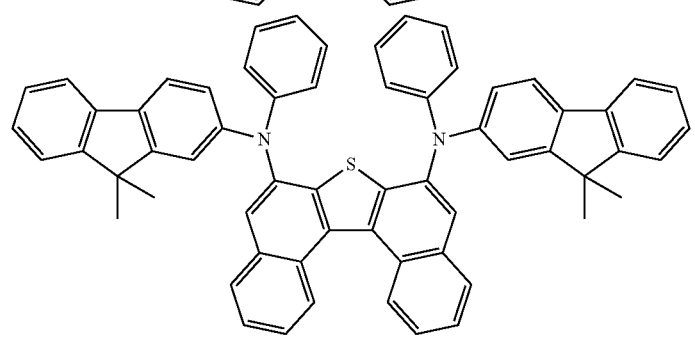
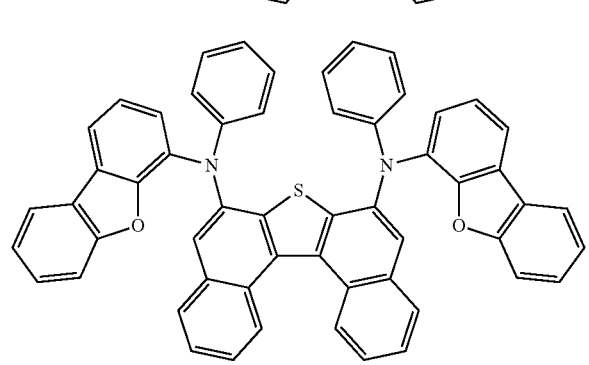
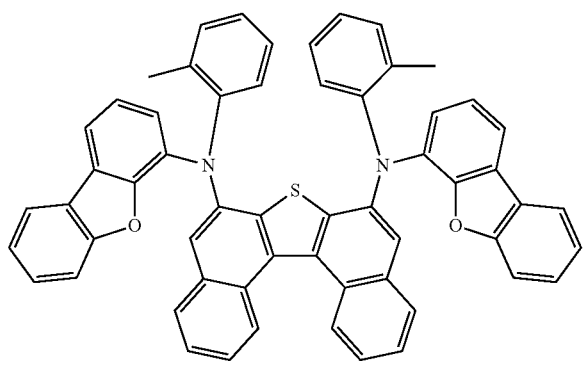
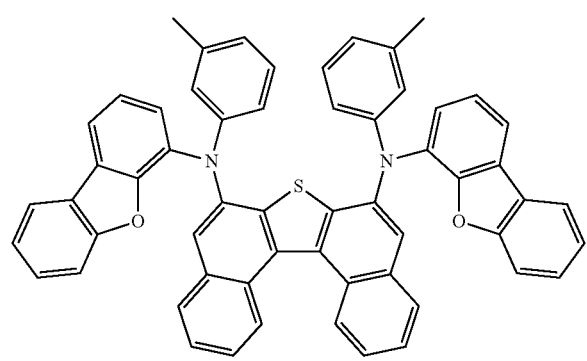
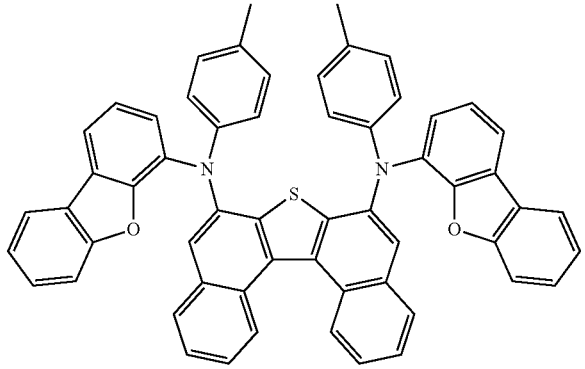

-continued

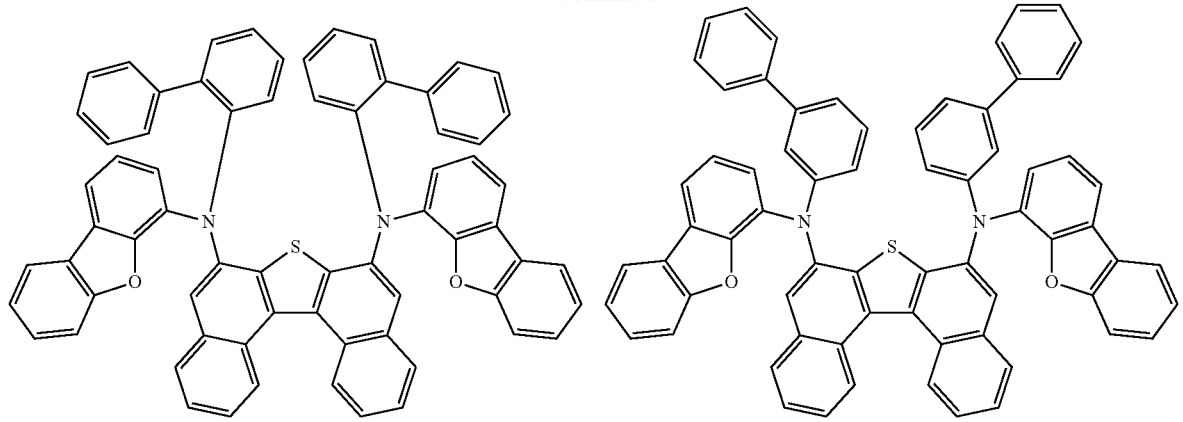

(Compound Represented by Formula (71))

The compound represented by the formula (71) is explained below.

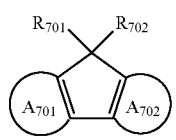

(71)

wherein, in the formula (71), $A_{701}$ ring and $A_{702}$ ring are independently
a substituted or unsubstituted aromatic hydrocarbon ring having 6 to 50 ring carbon atoms, or
a substituted or unsubstituted heterocyclic ring having 5 to 50 ring atoms;

One or more rings selected from the group consisting of A701 ring and A702 ring are bonded to the bond * of the structure represented by the following formula (72);

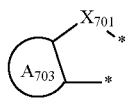

(72)

wherein, in the formula (72), $A_{703}$ rings are independently
a substituted or unsubstituted aromatic hydrocarbon ring having 6 to 50 ring carbon atoms, or
a substituted or unsubstituted heterocyclic ring having 5 to 50 ring atoms;

$X_{701}$ is $NR_{703}$, $C(R_{704})(R_{705})$, $Si(R_{706})(R_{707})$, $Ge(R_{708})(R_{709})$, O, S or Se;

$R_{701}$ and $R_{702}$ are bonded with each other to form a substituted or unsubstituted, saturated or unsaturated ring or do not form a substituted or unsubstituted saturated or unsaturated ring;

$R_{701}$ and $R_{702}$ that do not form the substituted or unsubstituted, saturated or unsaturated ring, and $R_{703}$ to $R_{709}$ are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;
$R_{901}$ to $R_{907}$ are as defined in the formula (1);

One or more selected from the group consisting of $A_{701}$ ring and A72 ring is bonded to * in the structure represented by the formula (72). That is, in one embodiment, the ring carbon atom of the aromatic hydrocarbon ring or the ring atom of the heterocyclic ring of $A_{701}$ ring is bonded to * in the structure represented by the formula (72). In one embodiment, the ring carbon atom of the aromatic hydrocarbon ring or the ring atom of the heterocyclic ring of $A_{702}$ ring is bonded to * in the structure represented by the formula (72).

In one embodiment, the group represented by the formula (73) is bonded to one or both of $A_{701}$ ring and $A_{702}$ ring.

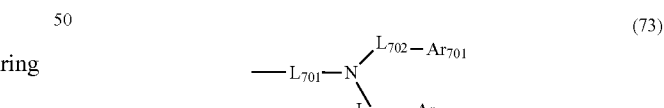

(73)

wherein in the formula (73), $Ar_{701}$ and $Ar_{702}$ are independently
a substituted or unsubstituted aryl group having 6 to 50 ring carbon atoms, or
a substituted or unsubstituted monovalent heterocyclic group having 5 to 50 ring atoms; and
$L_{701}$ to $L_{703}$ are independently
a single bonded,
a substituted or unsubstituted arylene group having 6 to 30 ring carbon atoms,
a substituted or unsubstituted divalent heterocyclic group having 5 to 30 ring atoms, or a divalent linking group formed by bonding 2 to 4 above mentioned groups.

In one embodiment, in addition to $A_{701}$ ring, the ring carbon atom of the aromatic hydrocarbon ring or the ring atom of the heterocyclic ring of $A_{702}$ ring is bonded to * in the structure represented by the formula (72). In this case, the structures represented by formula (72) may be the same or different.

In one embodiment, $R_{701}$ and $R_{702}$ are independently a substituted or unsubstituted aryl group having 6 to 50 ring carbon atoms.

In one embodiment, $R_{701}$ and $R_{702}$ are bonded with each other to form a fluorene structure.

In one embodiment, $Ar_{701}$ ring and $Ar_{702}$ ring are substituted or unsubstituted aromatic hydrocarbon rings having 6 to 50 ring carbon atoms, and they are substituted or unsubstituted benzene rings, for example.

In one embodiment, $Ar_{703}$ ring is a substituted or unsubstituted aromatic hydrocarbon ring having 6 to 50 ring carbon atoms, and it is a substituted or unsubstituted benzene ring, for example.

In one embodiment, $X_{701}$ is O or S.

As specific example of the compound represented by the formula (71), the following compounds can be given, for example. In the following example compounds, Me represents methyl group.

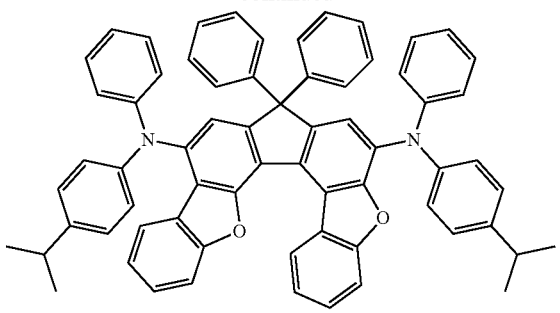

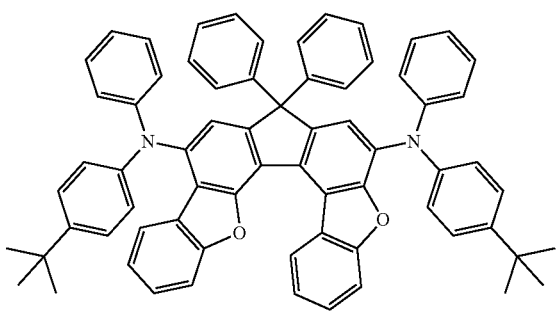

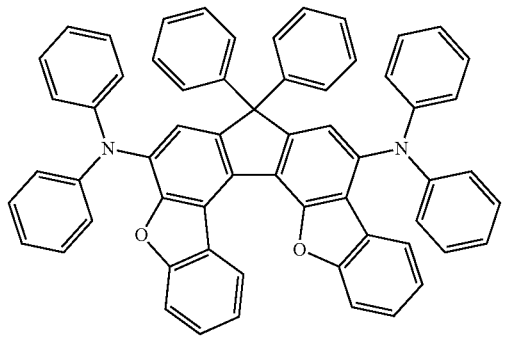

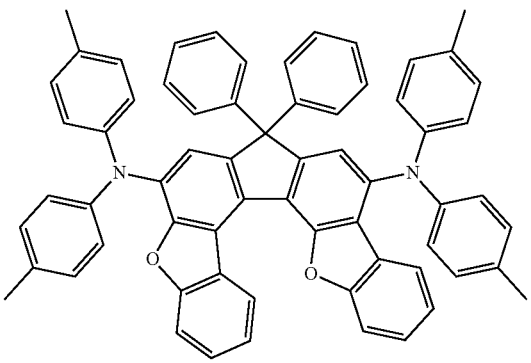

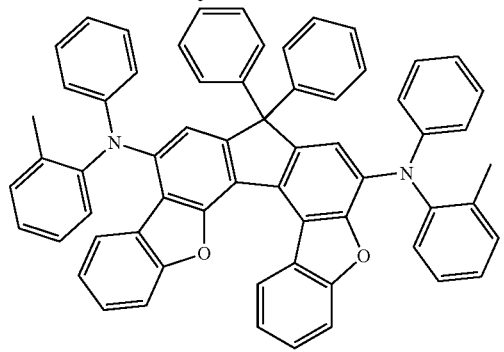

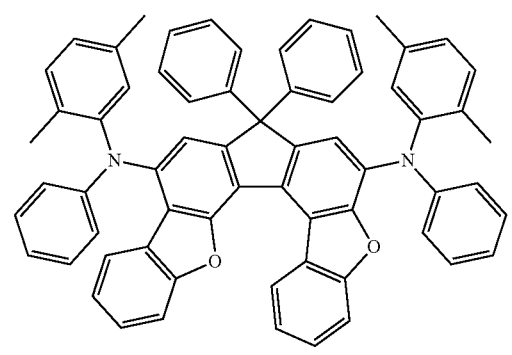

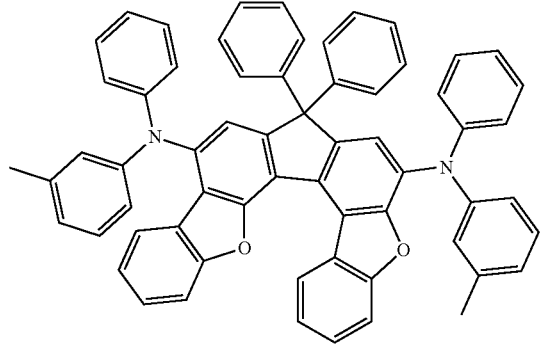

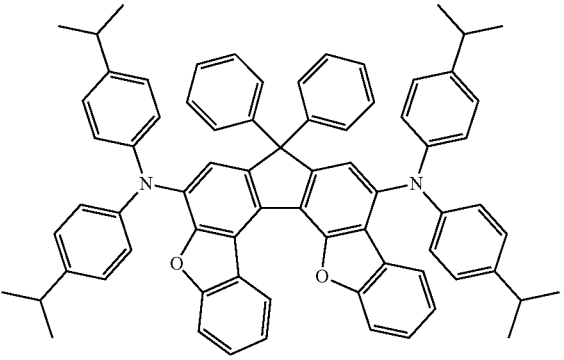

987
-continued
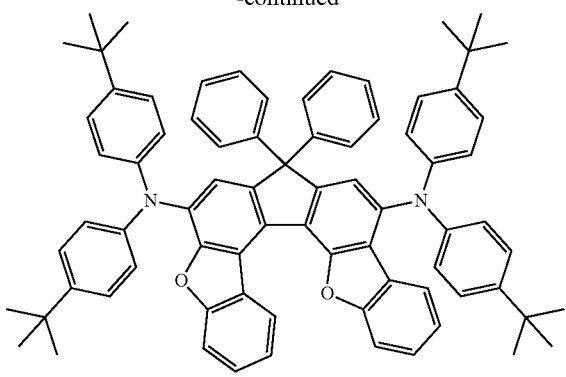
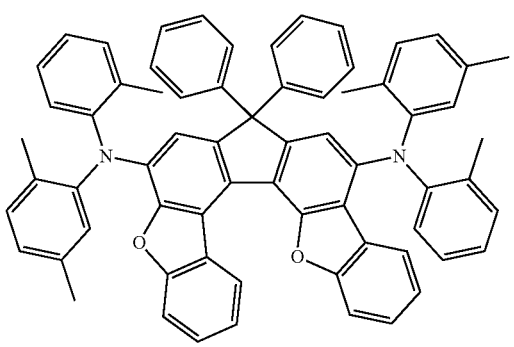
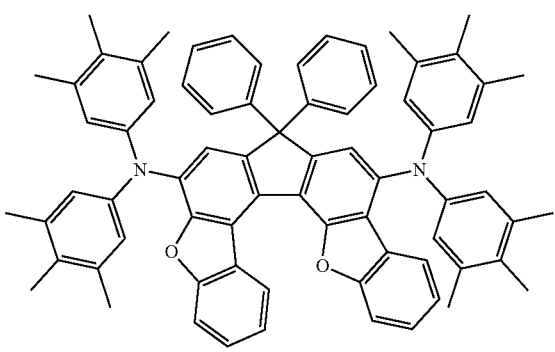
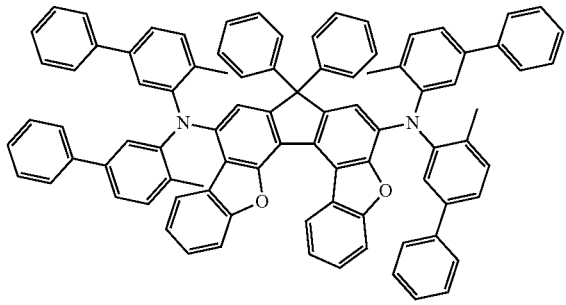
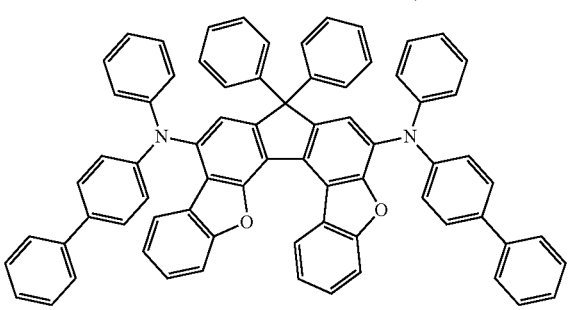
988
-continued
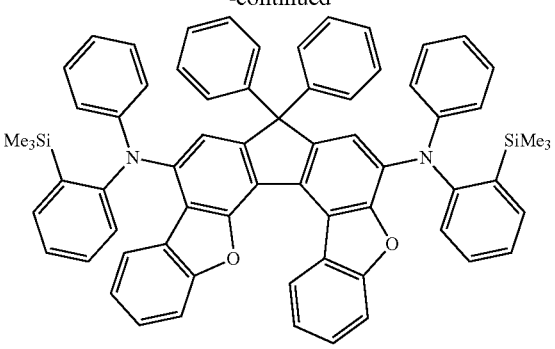
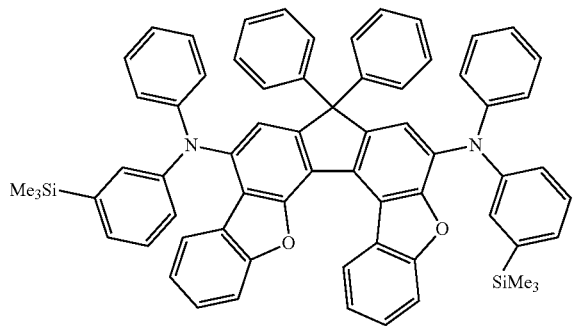
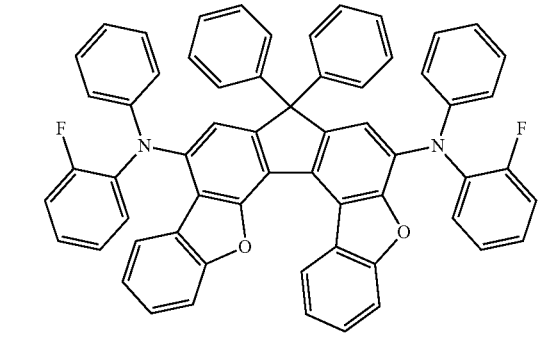
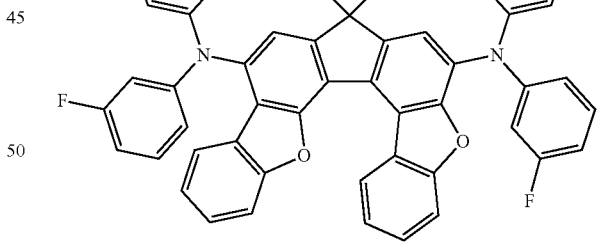
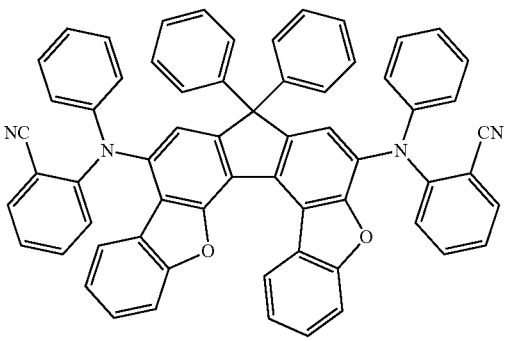

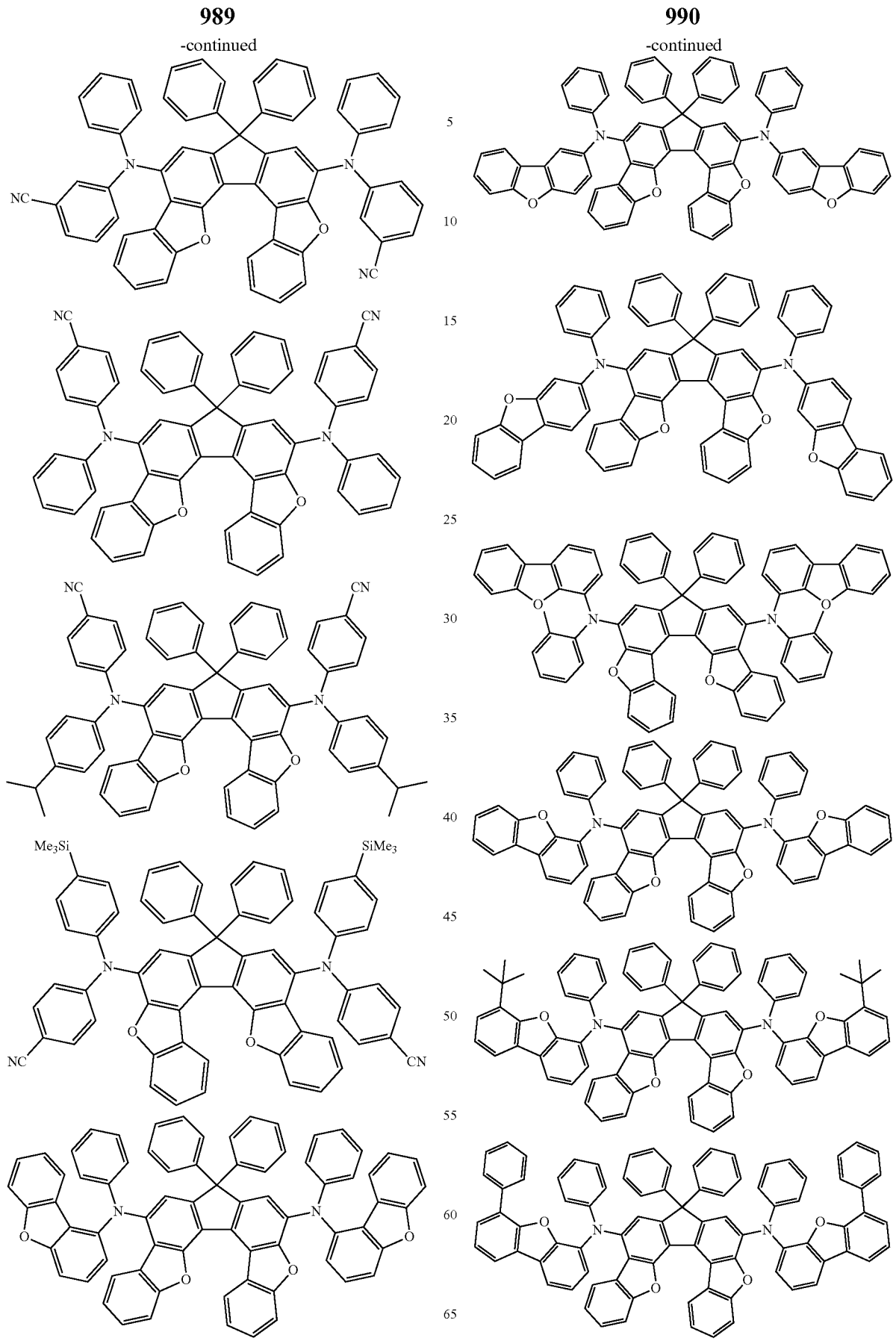

991
-continued
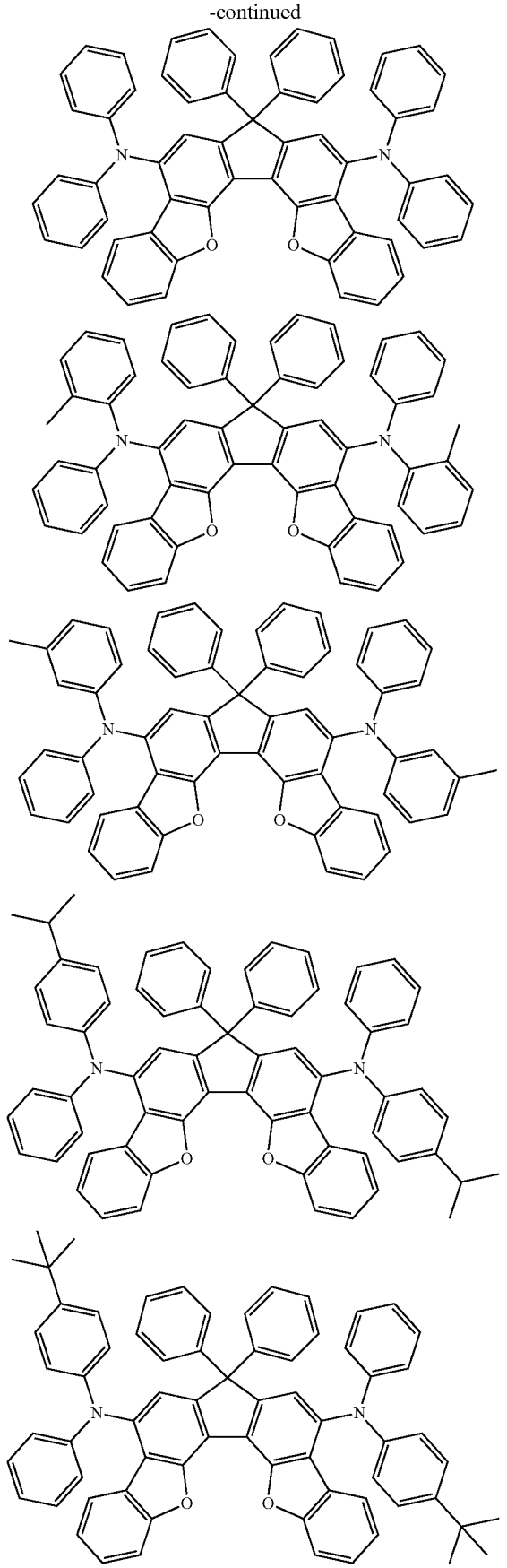
992
-continued
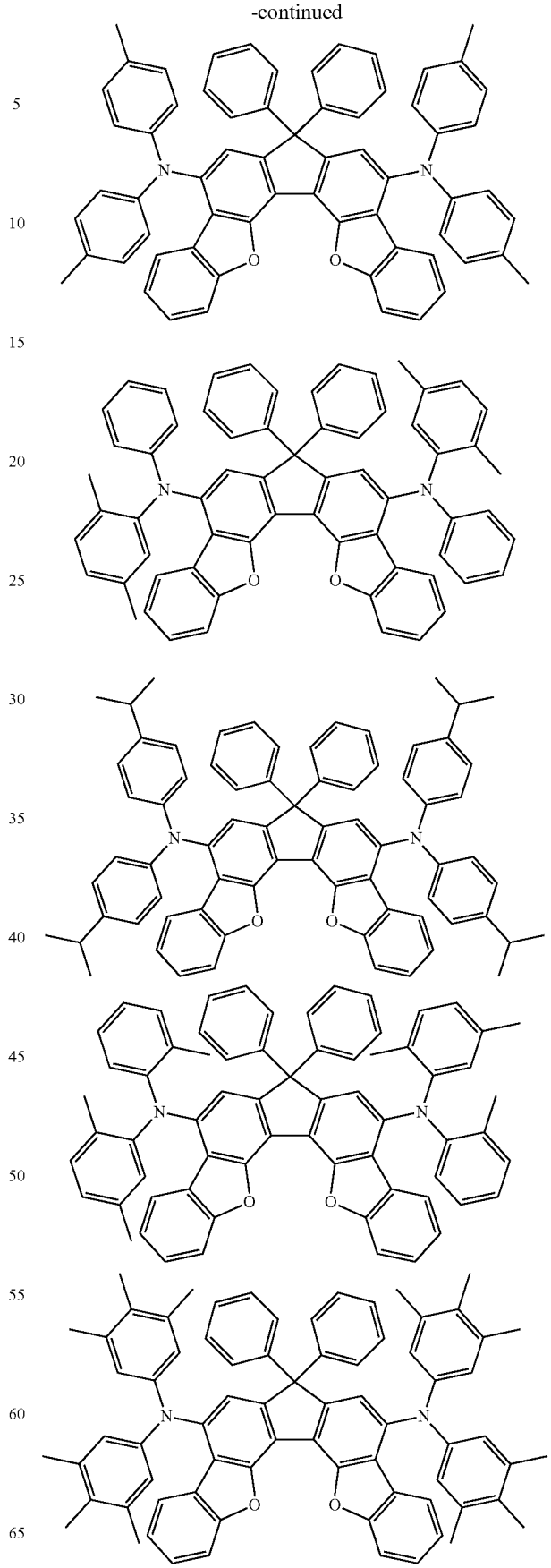

993
-continued
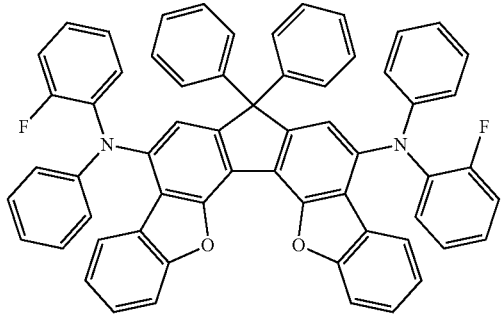
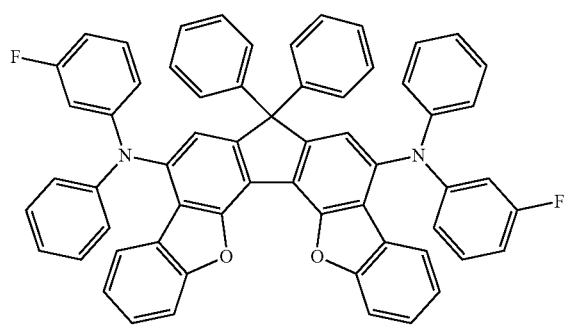
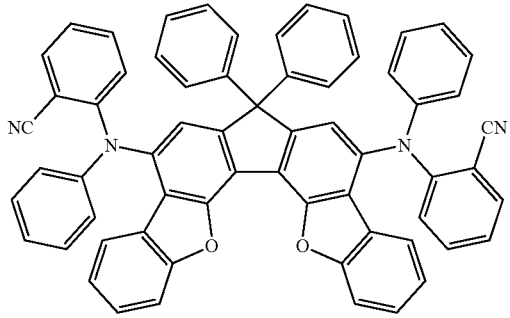
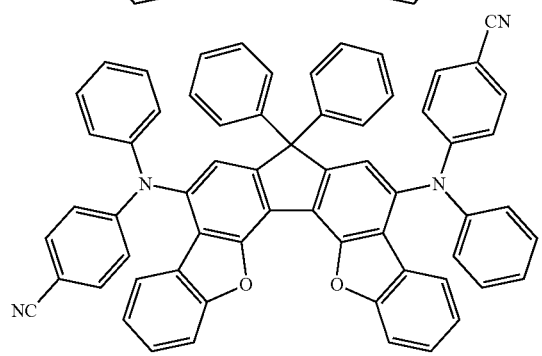
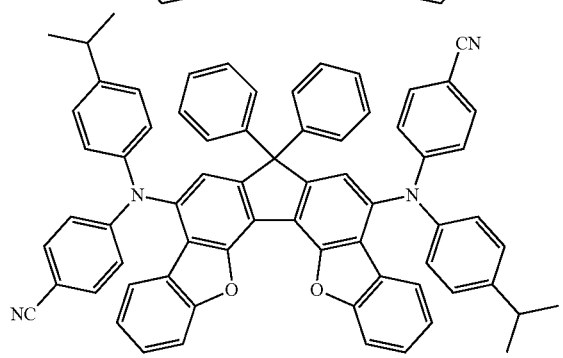
994
-continued
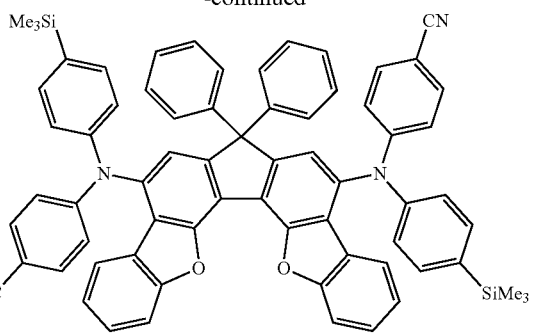
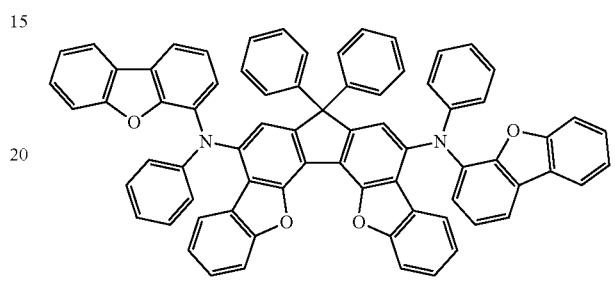
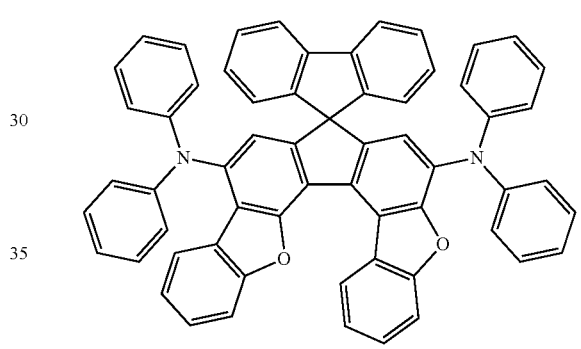
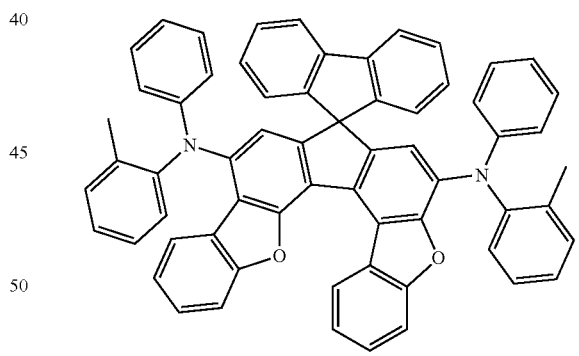
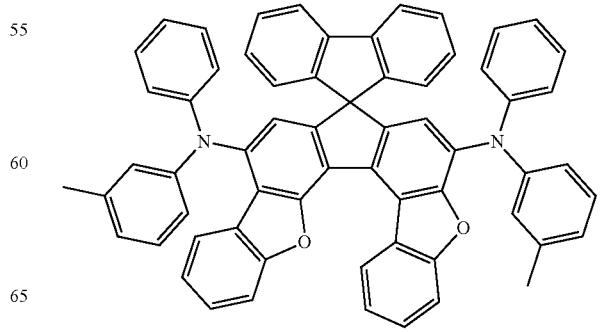

| 995 -continued | 996 -continued |
|---|---|
| 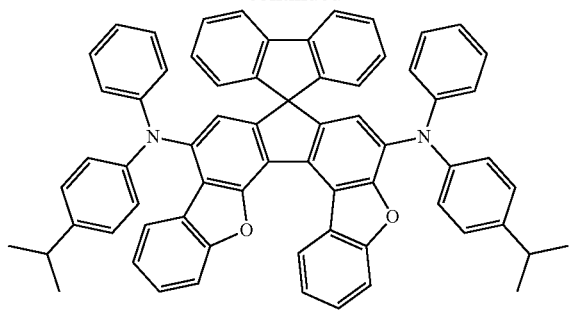 | 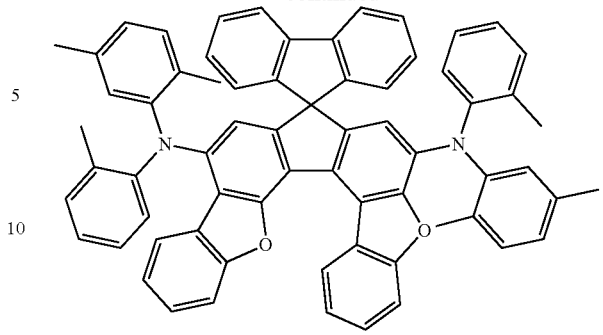 |
| 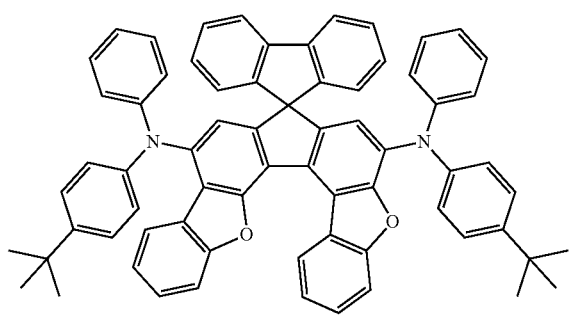 | 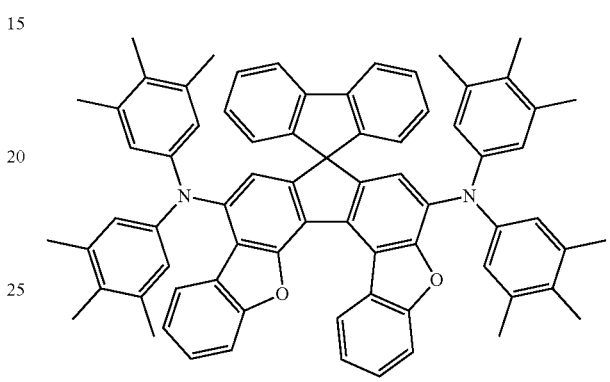 |
| 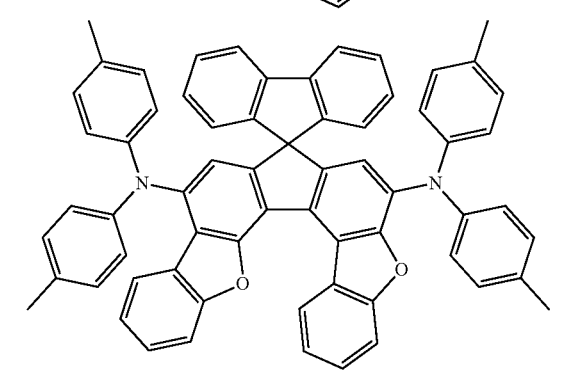 | 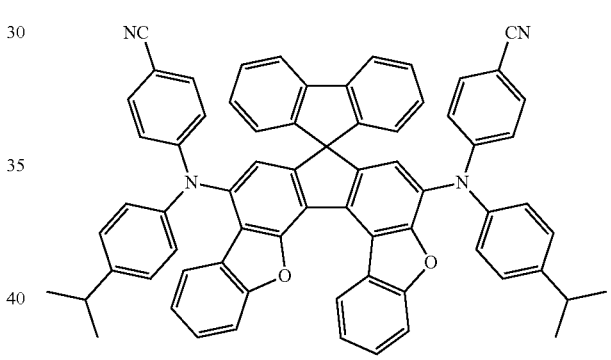 |
| 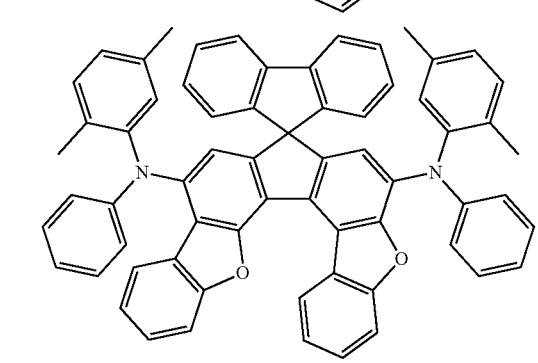 | 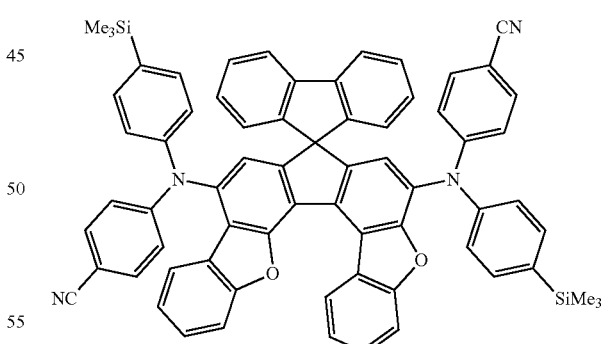 |
| 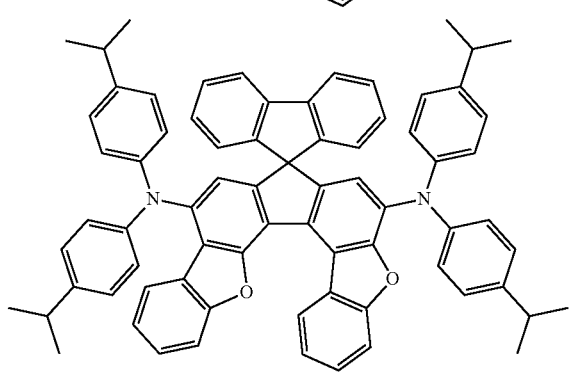 | 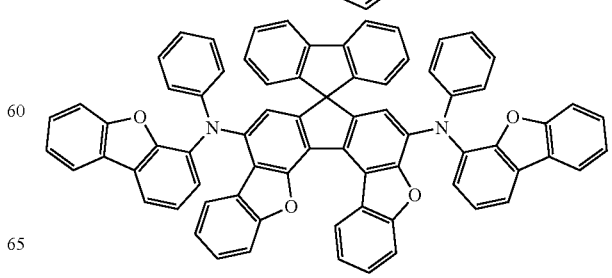 |

-continued

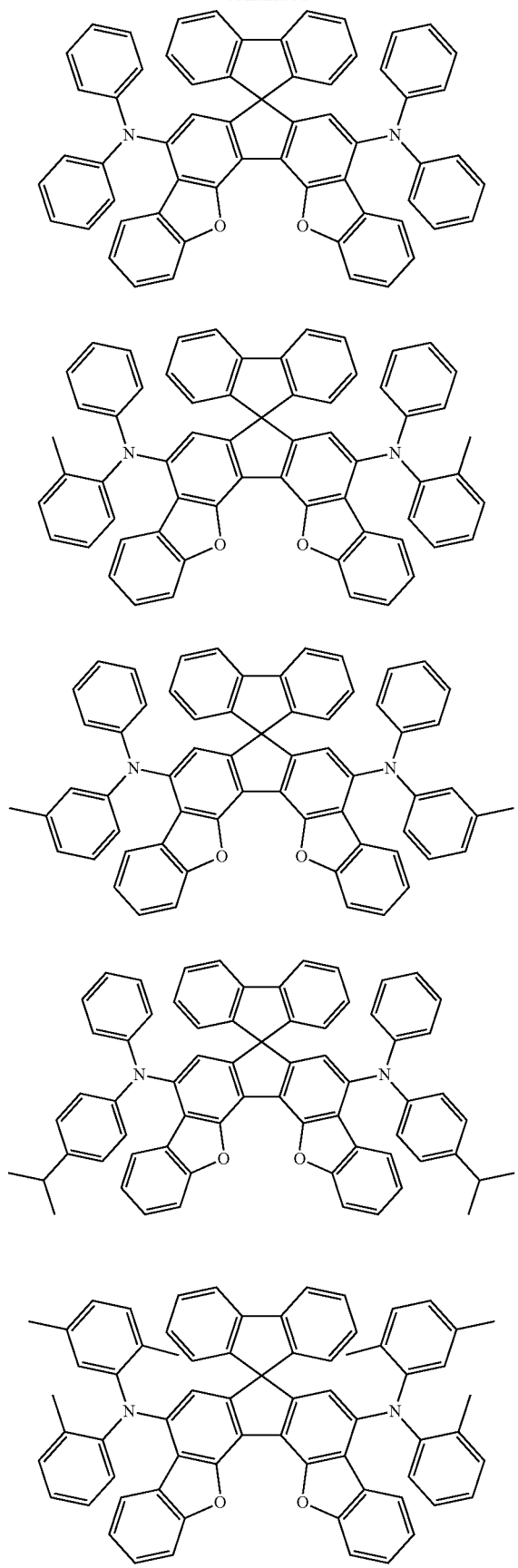

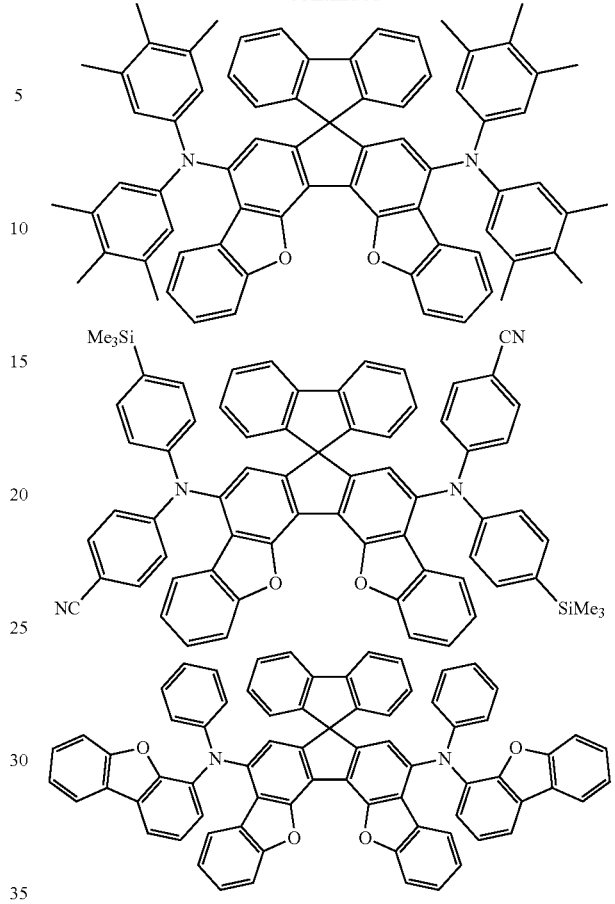

(Compound Represented by Formula (81))

The compound represented by the formula (81) is explained below.

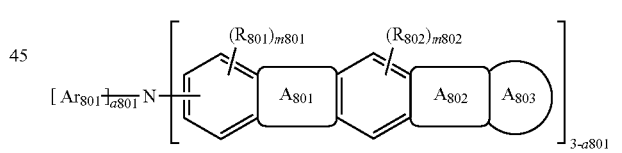

wherein, in the formula (81), $A_{801}$ ring is a ring represented by the formula (82) which is fused to an adjacent ring at an arbitrary position;

$A_{802}$ ring is a ring represented by the formula (83) which is fused to an adjacent ring at an arbitrary position;

two bonds * bond to $A_{803}$ ring at an arbitrary position;

$X_{801}$ and $X_{802}$ are independently $C(R_{803})(R_{804})$, $Si(R_{805})(R_{806})$, an oxygen atom, or a sulfur atom;

$A_{803}$ ring is a substituted or unsubstituted aromatic hydrocarbon ring having 6 to 50 ring carbon atoms, or a substituted or unsubstituted heterocyclic ring having 5 to 50 ring atoms;

$Ar_{801}$ is a substituted or unsubstituted aryl group having 6 to 50 ring carbon atoms, or a substituted or unsubstituted monovalent heterocyclic group having 5 to 50 ring atoms;

$R_{801}$ to $R_{806}$ are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—$Si(R_{901})(R_{902})(R_{903})$,
—$O$—$(R_{904})$,
—$S$—$(R_{905})$,
—$N(R_{906})(R_{907})$,
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;

$R_{901}$ to $R_{907}$ are as defined in the formula (1);

m801 and m802 are independently an integer of 0 to 2; when these are 2, $R_{801}$s or $R_{802}$s may be the same or different;

a801 is an integer of 0 to 2; when a801 is 0 or 1, the structure in the parentheses indicated by "3-a801" may be the same or different from each other; when a801 is 2, $Ar_{801}$s may be the same or different from each other.

In one embodiment, $Ar_{801}$ is a substituted or unsubstituted aryl group having 6 to 50 ring carbon atoms.

In one embodiment, $A_{803}$ ring is a substituted or unsubstituted aromatic hydrocarbon ring having 6 to 50 ring carbon atoms, and it is a substituted or unsubstituted benzene ring, a substituted or unsubstituted naphthalene ring, or a substituted or unsubstituted anthracene ring, for example.

In one embodiment, $R_{803}$ and $R_{804}$ are independently a substituted or unsubstituted alkyl group having 1 to 50 carbon atoms.

In one embodiment, a801 is 1.

As specific example of the compound represented by the formula (81), the following compounds can be given, for example.

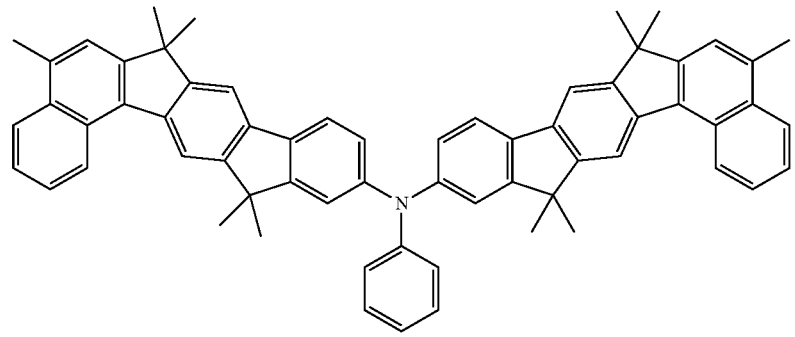

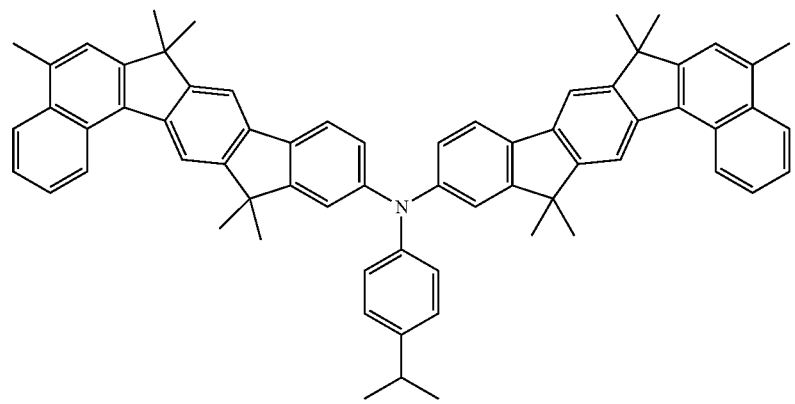

-continued
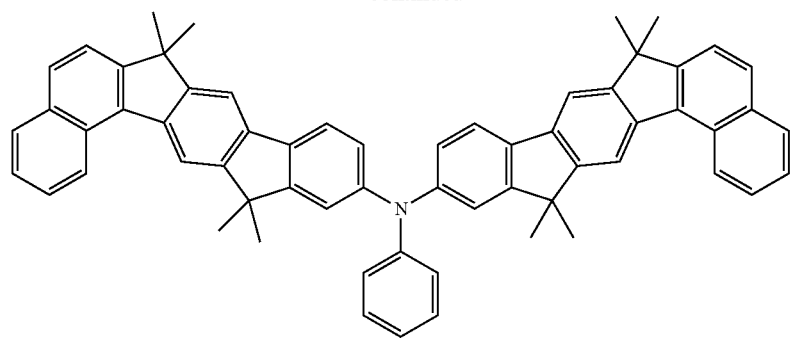
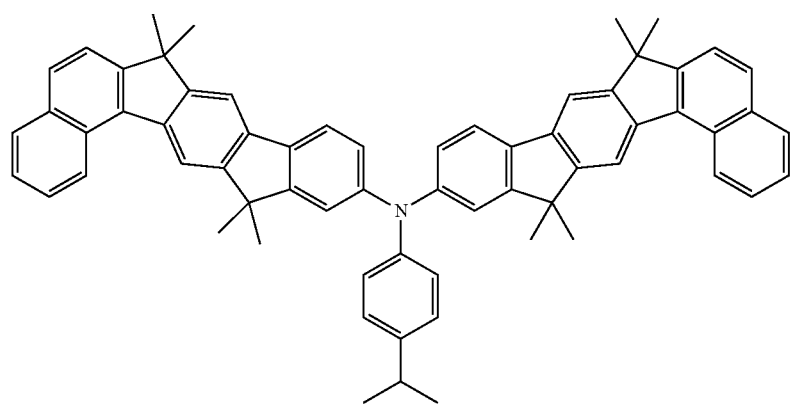
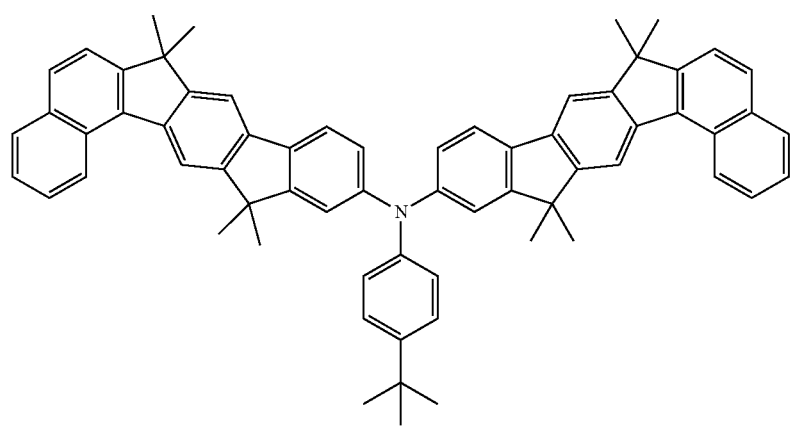
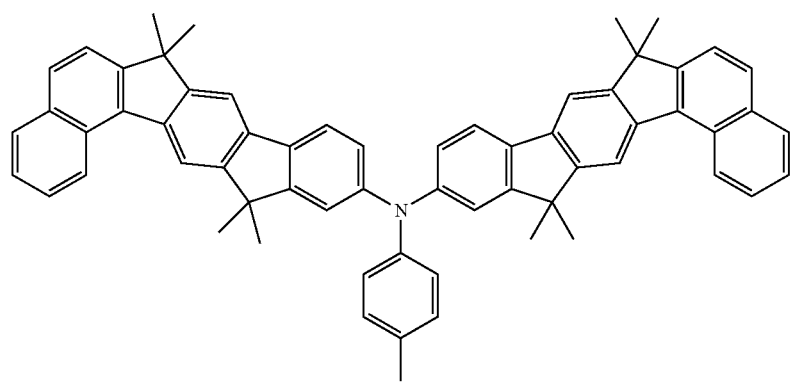

1003
-continued
1004
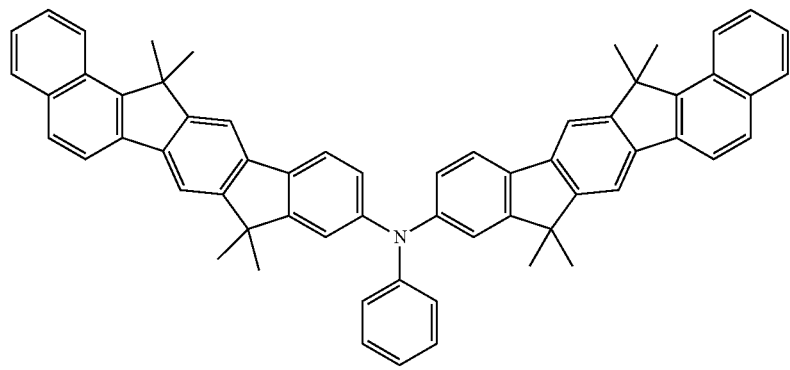
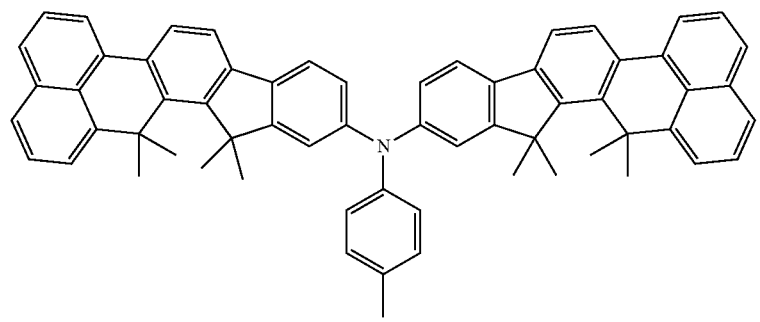
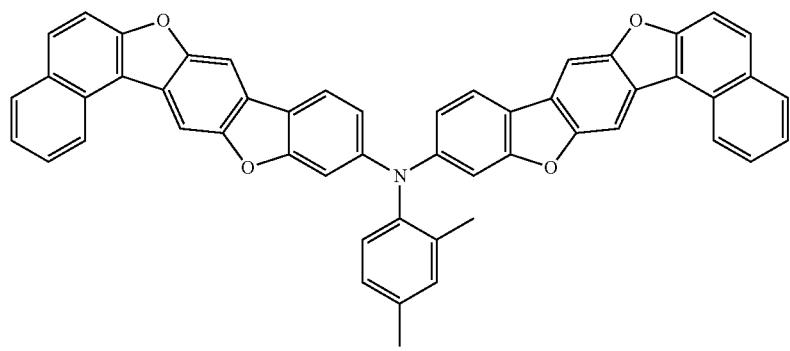
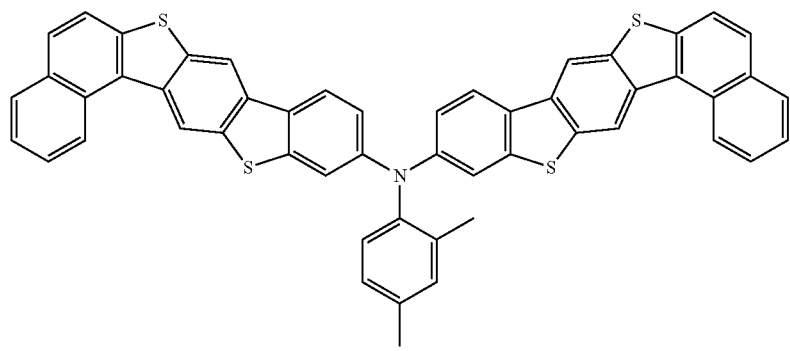

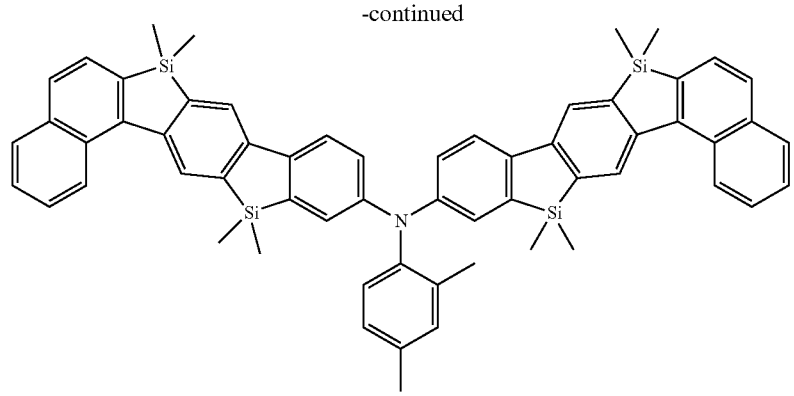

Specific examples of the above groups are as described in [Definition] of this specification.

In the organic EL device according to one aspect of the invention, known materials and device configurations may be applied as long as the device includes a cathode, an anode, and an emitting layer disposed between the cathode and the anode, and the emitting layer includes a compound represented by the following formula (1) and one or more compounds selected from the group consisting of compounds represented by each of formulas (11), (21), (31), (41), (51), (61), (71) and (81) as described above, and as long as the effect of the invention is not impaired.

In one embodiment, the emitting layer contains one or more selected from the group consisting of a compound represented by the formula (1A) and a compound represented by the formula (1B), and a compound represented by the formula (43D).

In one embodiment, the compound represented by the formula (1A) or (1B) is one or more selected from the group consisting of the compound represented by the formula BH-1, BH-2, BH-3, and BH-5 to BH-17, and the compound represented by the formula (43D) is one or more selected from the group consisting of the compound represented by the formula BD-9, BD-10, BD-11 and BD-12.

BH-2
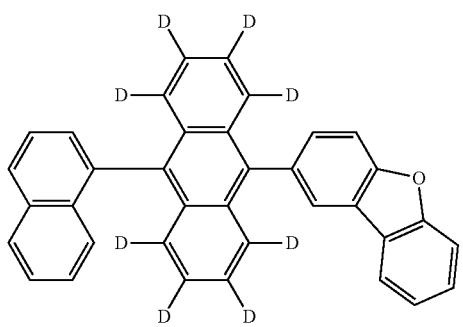

BH-3
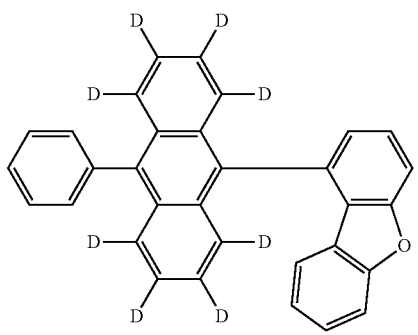

BH-1
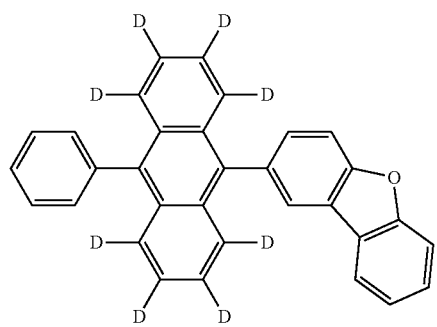

BH-5
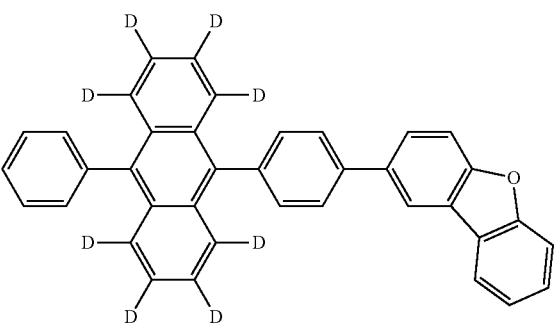

BH-6
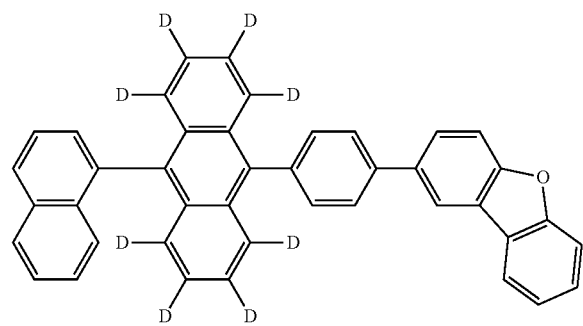
BH-10
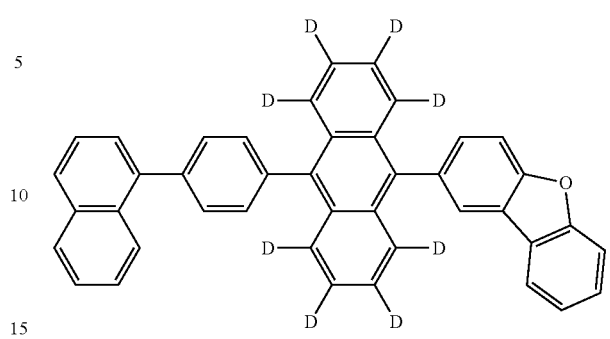
BH-7
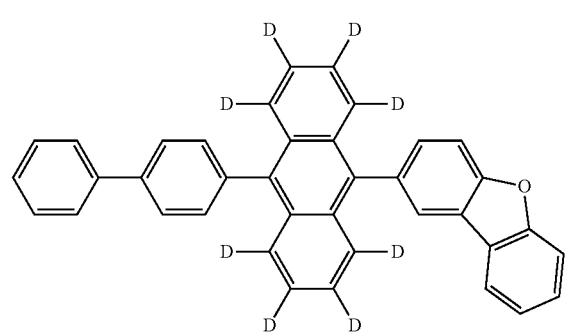
BH-11
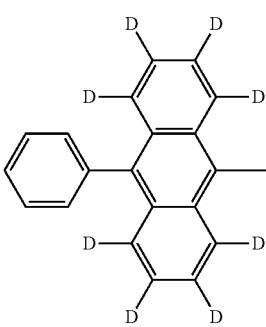
BH-8
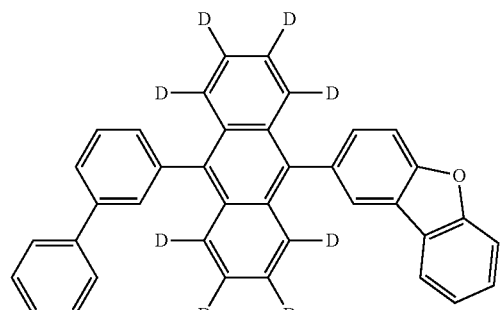
BH-12
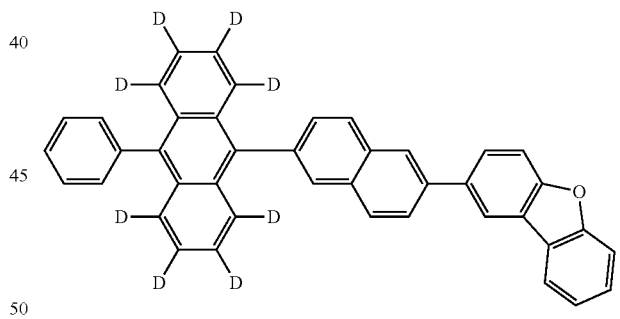
BH-9
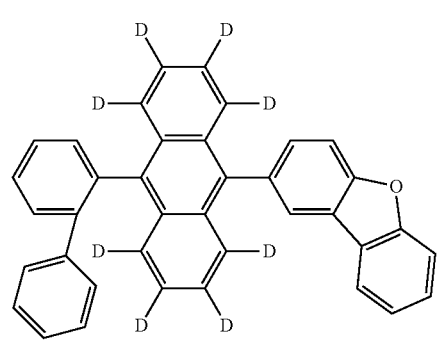
BH-13
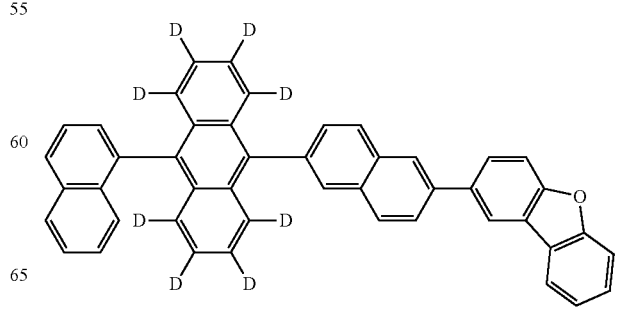

BH-14
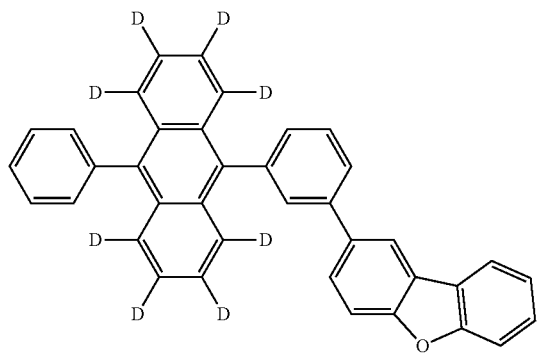
BH-15
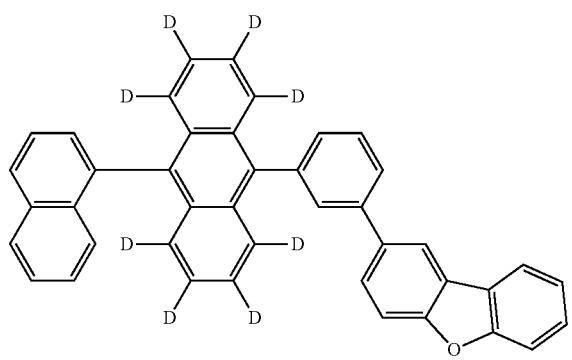
BH-16
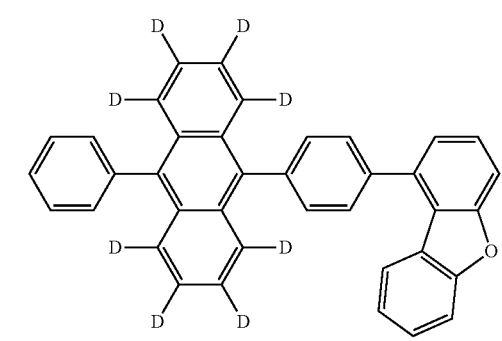
BH-17
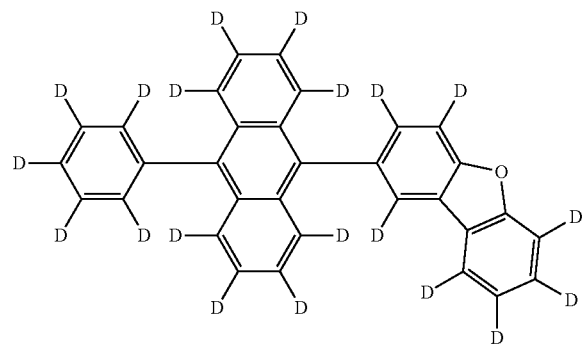
BD-9
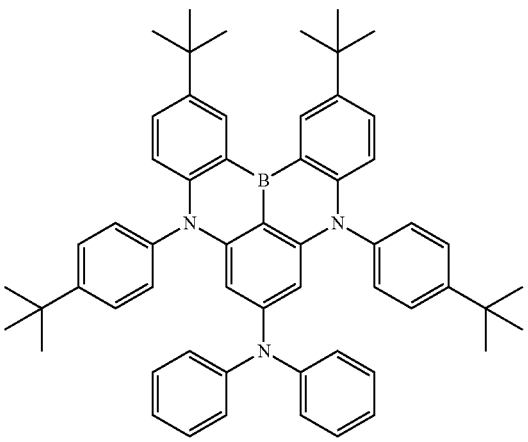
BD-10
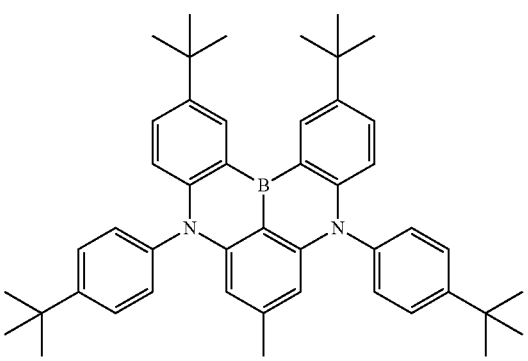
BD-11
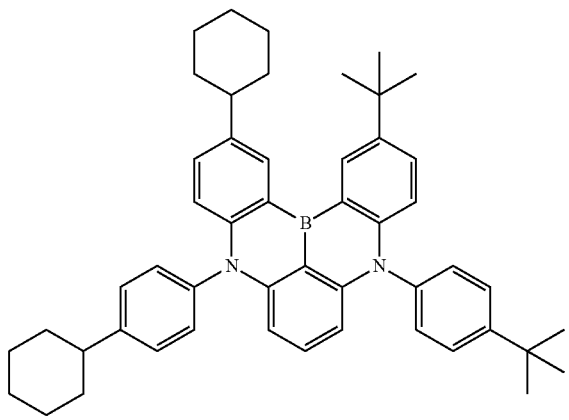

-continued

BD-12

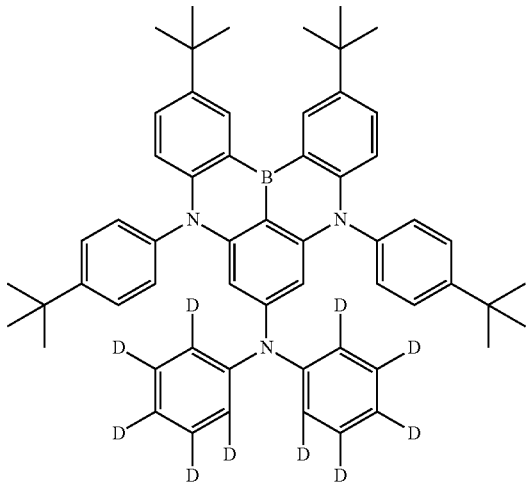

A content of the compound represented by the formula (1) in the emitting layer is preferably 80 mass % or more and 99 mass % or less based on the total mass of the emitting layer.

A content of the one or more compounds selected from the group consisting of compounds represented by each of formulas (11), (21), (31), (41), (51), (61), (71) and (81) is preferably 1 mass % or more and 20 mass % or less based on a total mass of the emitting layer.

One embodiment of the organic EL device preferably has the hole-transporting layer between the anode and the emitting layer.

One embodiment of the organic EL device preferably has the electron-transporting layer between the cathode and the emitting layer.

Specific examples of a typified device configuration of the organic EL device of the invention include structures such as
(1) an anode/an emitting layer/a cathode,
(2) an anode/a hole-injecting layer/an emitting layer/a cathode,
(3) an anode/an emitting layer/an electron-injecting-transporting layer/a cathode,
(4) an anode/a hole-injecting layer/an emitting layer/an electron-injecting-transporting layer/a cathode,
(5) an anode/an organic semiconductor layer/an emitting layer/a cathode,
(6) an anode/an organic semiconductor layer/an electron barrier layer/an emitting layer/a cathode,
(7) an anode/an organic semiconductor layer/an emitting layer/an adhesion improving layer/a cathode,
(8) an anode/a hole-injecting-transporting layer/an emitting layer/an electron-injecting-transporting layer /a cathode,
(9) an anode/an insulating layer/an emitting layer/an insulating layer/a cathode,
(10) an anode/an inorganic semiconductor layer/an insulating layer/an emitting layer/an insulating layer /a cathode,
(11) an anode/an organic semiconductor layer/an insulating layer/an emitting layer/an insulating layer /a cathode,
(12) an anode/an insulating layer/a hole-injecting-transporting layer/an emitting layer/an insulating layer /a cathode, and
(13) an anode/an insulating layer/a hole-injecting-transporting layer/an emitting layer/an electron-injecting-transporting layer/a cathode.

Among the above-described structures, a configuration of (8) is preferably used, but the configuration is not limited thereto.

In this specification, the term "hole-injecting-transporting layer" herein means "at least one of the hole-injecting layer and the hole-transporting layer", and the term "electron-injecting-transporting layer" herein means "at least one of the electron-injecting layer and the electron-transporting layer".

Hereinbelow, an explanation will be made on elements and materials other than the above-mentioned compound constituting each layer that can be used in the organic EL device according to one aspect of the invention.

(Substrate)

The substrate is used as a supporting body of the emitting device. As the substrate, glass, quarts, plastic or the like can be used. Further, a flexible substrate may be used. The flexible substrate means a substrate that can be bent. For example, a plastic substrate made of polycarbonate or vinyl polychloride or the like can be given.

(Anode)

In an anode formed on a substrate, it is preferable to use a metal having a large work function (specifically, 4.0 eV or more), an alloy, an electric conductive compound, a mixture of these or the like. Specifically, indium oxide-tin oxide (ITO: Indium Tin Oxide), indium oxide-tin oxide containing silicon or silicon oxide, indium oxide-zinc oxide, tungsten oxide, indium oxide containing zinc oxide, graphene, or the like can be given. In addition, gold (Au), platinum (Pt) or a nitride of a metal material (e.g. titanium nitride) or the like can be given.

(Hole-Injecting Layer)

The hole-injecting layer is a layer containing a substance having a high hole-injecting property. As a substance having a high hole-injecting property, a substance selected from molybdenum oxide, titanium oxide, vanadium oxide, rhenium oxide, ruthenium oxide, chromium oxide, zirconium oxide, hafnium oxide, tantalum oxide, silver oxide, tungsten oxide, manganese oxide, an aromatic amine compound, a polymer compound (oligomer, dendrimer, polymer, etc.) or the like can also be used (Hole-Transporting Layer)

The hole-transporting layer is a layer containing a substance having a high hole-transporting property. For the hole-transporting layer, aromatic amine compounds, carbazole derivatives, anthracene derivatives and the like can be used. Polymer compounds such as poly (N-vinylcarbazole) (abbreviation: PVK) and poly(4-vinyltriphenylamine) (abbreviation: PVTPA) can also be used. However, any substance other than these may be used as long as it is a substance having a higher transporting property for holes than electrons. Note that the layer containing a substance having a high hole-transporting property is not limited to a single layer, but may be a stacked body of two or more layers made of the above substances.

(Guest Material of the Emitting Layer)

The emitting layer is a layer that comprises a substance having high luminous property, and various materials can be used. For example, as the substance having high luminous property, a fluorescent compound that emits fluorescent light or a phosphorescent compound that emits phosphorescent light can be used. The fluorescent compound is a compound capable of emitting light from a singlet excited state and the phosphorescent compound is a compound capable of emitting light from a triplet excited state.

As a blue fluorescent material that can be used for the emitting layer, pyrene derivatives, styrylamine derivatives, chrysene derivatives, fluoranthene derivatives, fluorene derivatives, diamine derivatives, triarylamine derivatives and the like can be used. An aromatic amine derivative or the like can be used as a green fluorescent light-emitting material that can be used in the emitting layer. As a red fluorescent material which can be used in emitting layer, a tetracene derivative, a diamine derivative or the like can be used.

Metal complexes such as iridium complexes, osmium complexes, platinum complexes and the like are used as the blue phosphorescent material that can be used in the emitting layer. An iridium complex or the like is used as a green phosphorescent material that can be used in the emitting layer. Metal complexes such as iridium complexes, platinum complexes, terbium complexes, europium complexes and the like are used as red phosphorescent materials that can be used in the emitting layer.

(Host Material of Emitting Layer)

The emitting layer may have a structure in which the substance having high luminescent property (guest material) described above is dispersed in another substance (host material). Various materials other than the compound represented by the formula (1) (for example, the compound represented by the formula (1A) or (1B)) can be used as substances for dispersing substances with high luminescent properties, and it is preferable to use a material having a high lowest unoccupied molecular orbital level (LUMO level) and a low highest occupied molecular orbital level (HOMO level), rather than a material having a high luminous property.

As a substance (host material) for dispersing a substance having a high luminous property, 1) a metal complex such as an aluminum complex, a beryllium complex or a zinc complex, 2) a heterocyclic compound such as an oxadiazole derivative, a benzimidazole derivative, a phenanthroline derivative or the like, 3) a fused aromatic compound such as a carbazole derivative, an anthracene derivative, a phenanthrene derivative, a pyrene derivative or a chrysene derivative, and 4) an aromatic amine compound such as a triarylamine derivative or a fused polycyclic aromatic amine derivative are used.

(Electron-Transporting Layer)

The electron-transporting layer is a layer containing a substance having a high electron-transporting property. For the electron-transporting layer, 1) a metal complex such as an aluminum complex, a beryllium complex, or a zinc complex, 2) a heteroaromatic compound such as an imidazole derivative, a benzimidazole derivative, an azine derivative, a carbazole derivative or a phenanthroline derivative, and 3) a polymer compound can be used.

(Electron-Injecting Layer)

The electron-injection layer is a layer containing a substance having a high electron-injection property. For the electron-injection layer, alkali metals, alkaline earth metals or a compound thereof such as lithium (Li), ytterbium (Yb), lithium fluoride (LiF), cesium fluoride (CsF), calcium fluoride ($CaF_2$), metal complex compound such as 8-quinolinolato lithium (Liq), lithium oxide (LiOx) or the like can be used.

(Cathode)

It is preferable to use a metal, an alloy, an electrically conductive compound, a mixture thereof, or the like having a small work function (specifically, 3.8 eV or less) for the cathode. Specific examples of such cathode material include elements belonging to Group 1 or Group 2 of the periodic table of elements, that is, alkali metals such as lithium (Li) and cesium (Cs), alkaline earth metals such as magnesium (Mg), calcium (Ca), and strontium (Sr), an alloy containing these metals (for example, MgAg and AlLi), a rare earth metal such as europium (Eu) and ytterbium (Yb), and an alloy containing a rare earth metal.

In the organic EL device according to one aspect of the invention, the method for forming each layer is not particularly restricted. A conventionally known forming method such as a vacuum deposition method, a spin coating method or the like can be used. Each layer such as the emitting layer or the like can be formed by a vacuum deposition method, a molecular beam evaporation method (MBE method), or a known coating method such as a dipping method, a solution spin coating method, a casting method, a bar coating method, or the like, that uses a solution of a material forming each layer dissolved in a solvent.

In the organic EL device according to one aspect of the invention, the thickness of each layer is not particularly restricted. In general, in order to suppress occurrence of defects such as pinholes and to suppress the applied voltage and to improve luminous efficiency, the thickness is normally preferably in a range of several nm to 1 μm.

[Electronic Device]

The electronic device according to one aspect of the invention is characterized in that it is provided with the organic EL device according to one aspect of the invention.

Specific examples of the electronic device includes a display element such as an organic EL panel module; a display such as a TV, a mobile phone or a PC; and emitting devices such as lightings and lights for automobiles or the like.

EXAMPLES

The invention will specifically be explained with the examples and the comparative examples below, and shall not be limited to the contents of the examples in any way.

Synthesis Example 1 [Synthesis of Compound BH-1]

(Synthesis of Intermediate 1)

To 13.3 g (50.0 mmol) of 9-bromoanthracene-d9, 6.4 g (52.5 mmol) of phenylboronic acid and 1.2 g (1.00 mmol) of Pd[$PPh_3$]$_4$, 75 ml of toluene, 75 ml of dimethoxyethane and 75 ml (150.0 mmol) of 2M $Na_2CO_3$ aqueous solution were added under an atmosphere of argon, followed by being heated to reflux while stirring for 10 hours.

After completion of the reaction, having been cooled to room temperature, the sample was transferred to a separating funnel and extracted with dichloromethane. The resulting organic phase was dried with $MgSO_4$, followed by being filtered and concentrated. The concentrated residue was purified with silica gel column chromatography to obtain 10.9 g of white solid. By conducting FD-MS analysis, the resulting compound was identified as Intermediate 1 as follows (yield: 83%).

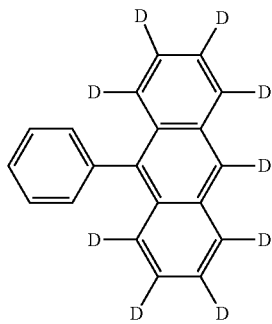

Intermediate 1

(Synthesis of Intermediate 2)

5.3 g (20.0 mmol) of Intermediate 1 was solubilized in 120 ml of dichloromethane, and the resulting solution was dropped into the solution of 3.2 g (20.0 mmol) of bromine in 12 ml of dichloromethane at room temperature, followed by being stirred for one hour.

After completion of the reaction, the sample was transferred to a separating funnel and washed with 2M $Na_2S_2O_3$ aqueous solution. The organic phase was further washed with 10% $Na_2CO_3$, and thereafter with water, and the separated organic phase was dried with $MgSO_4$, followed by being filtered and concentrated.

The concentrated residue was dispersed in methanol (100 mL), and the precipitated crystal was dried to obtain 6.5 g of white solid. By conducting FD-MS analysis, the resulting compound was identified as Intermediate 2 as follows (yield: 95%).

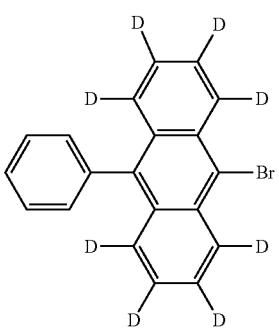

Intermediate 2

(Synthesis of Compound BH-1)

To 1.7 g (5.0 mmol) of Intermediate 2, 1.1 g (5.3 mmol) of dibenzofuran-2-boronic acid and 0.1 g (0.1 mmol) of $Pd[PPh_3]_4$, 7.5 ml of toluene, 7.5 ml of dimethoxyethane and 7.5 ml (15.0 mmol) of 2M $Na_2CO_3$ aqueous solution were added under an atmosphere of argon, followed by being heated to reflux while stirring for 10 hours.

After completion of the reaction, having been cooled to room temperature, the sample was transferred to a separating funnel and extracted with dichloromethane. The resulting organic phase was dried with $MgSO_4$, followed by being filtered and concentrated. The concentrated residue was purified with silica gel column chromatography to obtain 1.6 g of white solid. By conducting FD-MS analysis, the resulting compound was identified as Compound BH-1 as follows (yield: 75%).

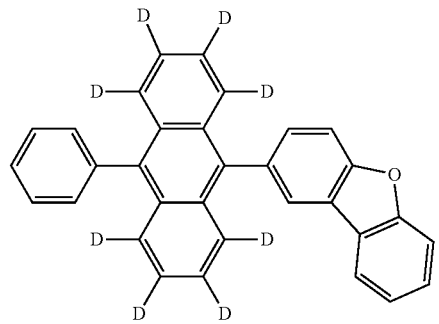

BH-1

Synthesis Example 2 [Synthesis of Compound BH-2]

(Synthesis of Intermediate 3)

To 13.3 g (50.0 mmol) of 9-bromoanthracene-d9, 9.0 g (52.5 mmol) of 1-naphthalene boronic acid and 1.2 g (1.00 mmol) of $Pd[PPh_3]_4$, 75 ml of toluene, 75 ml of dimethoxyethane and 75 ml (150.0 mmol) of 2M $Na_2CO_3$ aqueous solution were added under an atmosphere of argon, followed by being heated to reflux while stirring for 10 hours.

After completion of the reaction, having been cooled to room temperature, the sample was transferred to a separating funnel and extracted with dichloromethane. The resulting organic phase was dried with $MgSO_4$, followed by being filtered and concentrated. The concentrated residue was purified with silica gel column chromatography to obtain 13.3 g of white solid. By conducting FD-MS analysis, the resulting compound was identified as Intermediate 3 as follows (yield: 85%).

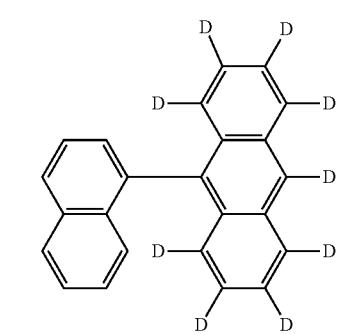

Intermediate 3

(Synthesis of Intermediate 4)

6.3 g (20.0 mmol) of Intermediate 3 was solubilized in 120 ml of dichloromethane, and the resulting solution was dropped into the solution of 3.2 g (20.0 mmol) of bromine in 12 ml of dichloromethane at room temperature, followed by being stirred for one hour.

After completion of the reaction, the sample was transferred to a separating funnel and washed with 2M $Na_2S_2O_3$ aqueous solution. The organic phase was further washed with 10% $Na_2CO_3$, and thereafter with water three times. The organic phase was dried with $MgSO_4$, followed by being filtered and concentrated.

The concentrated residue was dispersed in methanol (100 mL), and the precipitated crystal was dried to obtain 7.5 g of white solid. By conducting FD-MS analysis, the resulting compound was identified as Intermediate 4 as follows (yield: 96%).

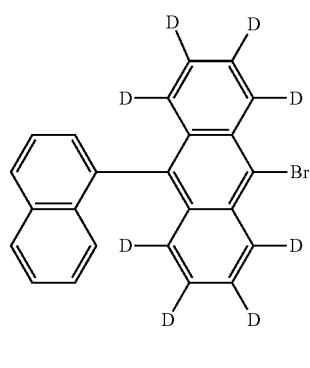

Intermediate 4

(Synthesis of Compound BH-2)

To 2.0 g (5.0 mmol) of Intermediate 4, 1.1 g (5.3 mmol) of dibenzofuran-2-boronic acid and 0.1 g (0.1 mmol) of Pd[PPh$_3$]$_4$, 7.5 ml of toluene, 7.5 ml of dimethoxyethane and 7.5 ml (15.0 mmol) of 2M Na$_2$CO$_3$ aqueous solution were added under an atmosphere of argon, followed by being heated to reflux while stirring for 10 hours.

After completion of the reaction, having been cooled to room temperature, the sample was transferred to a separating funnel and extracted with dichloromethane. The resulting organic phase was dried with MgSO$_4$, followed by being filtered and concentrated. The concentrated residue was purified with silica gel column chromatography to obtain 1.7 g of white solid. By conducting FD-MS analysis, the resulting compound was identified as Compound BH-2 as follows (yield: 70%).

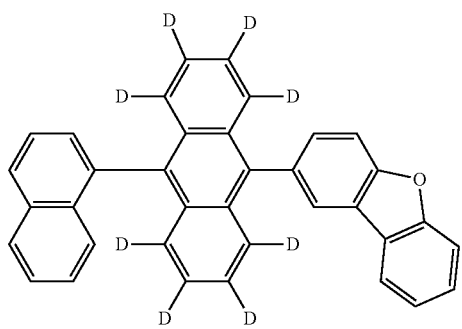

BH-2

Synthesis Example 3 [Synthesis of Compound BH-3]

Except that 1.1 g (5.3 mmol) of dibenzofuran-1-boronic acid was used instead of dibenzofuran-2-boronic acid, the reaction was carried out in the same way as in the synthesis example 1, thereby obtaining 1.3 g of white crystal. By conducting FD-MS analysis, the resulting compound was identified as Compound BH-3 as follows (yield: 62%).

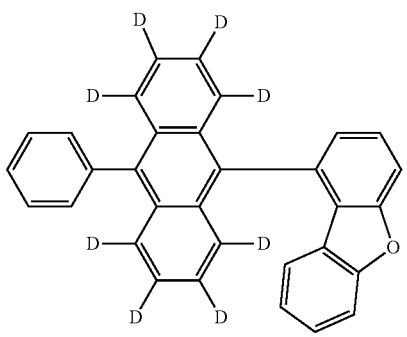

BH-3

Synthesis Example 4 [Synthesis of Compound BH-4]

Except that 1.1 g (5.3 mmol) of dibenzofuran-4-boronic acid was used instead of dibenzofuran-2-boronic acid, the reaction was carried out in the same way as in the synthesis example 1, thereby obtaining 1.2 g of white crystal. By conducting FD-MS analysis, the resulting compound was identified as Compound BH-4 as follows (yield: 55%).

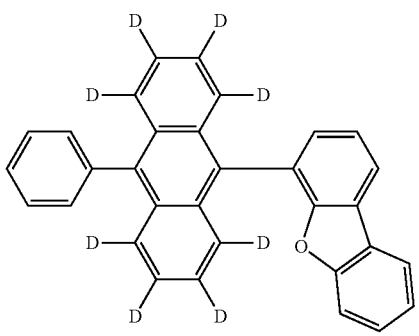

BH-4

Synthesis Example 5 [Synthesis of Compound BH-5]

Except that 1.5 g (5.3 mmol) of 4-(2-dibenzofuranyl) phenyl boronic acid was used instead of dibenzofuran-2-boronic acid, the reaction was carried out in the same way as in the synthesis example 1, thereby obtaining 1.8 g of white crystal. By conducting FD-MS analysis, the resulting compound was identified as Compound BH-5 as follows (yield: 71%).

BH-5

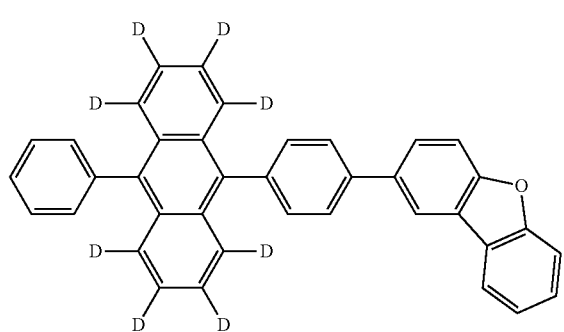

Synthesis Example 6 [Synthesis of Compound BH-6]

Except that 1.5 g (5.3 mmol) of 4-(2-dibenzofuranyl) phenyl boronic acid was used instead of dibenzofuran-2-boronic acid, the reaction was carried out in the same way as in the synthesis example 2, thereby obtaining 2.0 g of white crystal. By conducting FD-MS analysis, the resulting compound was identified as Compound BH-6 as follows (yield: 73%).

BH-6

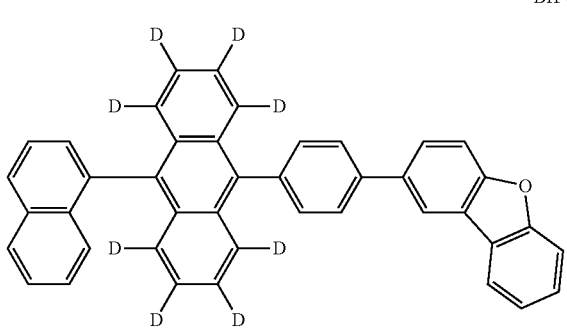

Synthesis Example 7 [Synthesis of Compound BH-7]

(Synthesis of Intermediate 5)

To 13.3 g (50.0 mmol) of 9-bromoanthracene-d9, 10.4 g (52.5 mmol) of 4-biphenylboronic acid and 1.2 g (1.00 mmol) of Pd[PPh$_3$]$_4$, 75 ml of toluene, 75 ml of dimethoxyethane and 75 ml (150.0 mmol) of 2M Na$_2$CO$_3$ aqueous solution were added under an atmosphere of argon, followed by being heated to reflux while stirring for 10 hours.

After completion of the reaction, having been cooled to room temperature, the sample was transferred to a separating funnel and extracted with dichloromethane. The resulting organic phase was dried with MgSO$_4$, followed by being filtered and concentrated. The concentrated residue was purified with silica gel column chromatography to obtain 14.1 g of white solid. By conducting FD-MS analysis, the resulting compound was identified as Intermediate 5 as follows (yield: 83%).

Intermediate 5

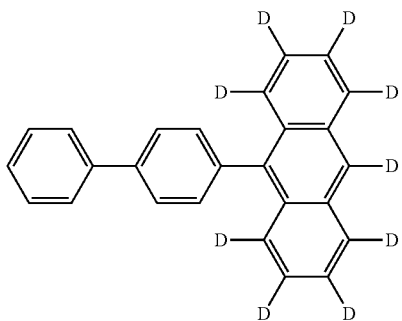

(Synthesis of Intermediate 6)

6.8 g (20.0 mmol) of Intermediate 5 was solubilized in 120 ml of dichloromethane, and the resulting solution was dropped into the solution of 3.2 g (20.0 mmol) of bromine in 12 ml of dichloromethane at room temperature, followed by being stirred for one hour.

After completion of the reaction, the sample was transferred to a separating funnel and washed with 2M Na$_2$S$_2$O$_3$ aqueous solution. The organic phase was further washed with 10% Na$_2$CO$_3$, and thereafter with water three times. The organic phase was dried with MgSO$_4$, followed by being filtered and concentrated.

The concentrated residue was dispersed in methanol (100 mL), and the precipitated crystal was dried to obtain 8.0 g of white solid. By conducting FD-MS analysis, the resulting compound was identified as Intermediate 6 as follows (yield: 96%).

Intermediate 6

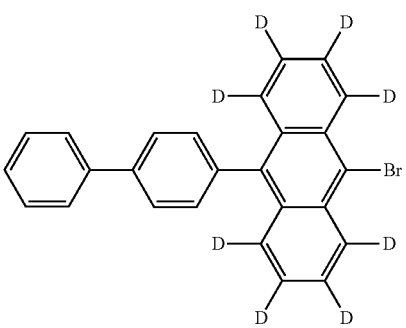

(Synthesis of Compound BH-7)

To 2.1 g (5.0 mmol) of Intermediate 6, 1.1 g (5.3 mmol) of dibenzofuran-2-boronic acid and 0.1 g (0.1 mmol) of Pd[PPh$_3$]$_4$, 7.5 ml of toluene, 7.5 ml of dimethoxyethane and 7.5 ml (15.0 mmol) of 2M Na$_2$CO$_3$ aqueous solution were added under an atmosphere of argon, followed by being heated to reflux while stirring for 10 hours.

After completion of the reaction, having been cooled to room temperature, the sample was transferred to a separating funnel and extracted with dichloromethane. The resulting organic phase was dried with MgSO$_4$, followed by being filtered and concentrated. The concentrated residue was purified with silica gel column chromatography to obtain 1.6 g of white solid. By conducting FD-MS analysis, the resulting compound was identified as Compound BH-7 as follows (yield: 64%).

BH-7

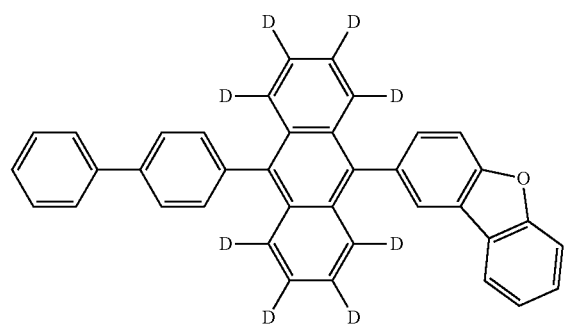

Synthesis Example 8 [Synthesis of Compound BH-8]

(Synthesis of Intermediate 7)

To 13.3 g (50.0 mmol) of 9-bromoanthracene-d9, 10.4 g (52.5 mmol) of 3-biphenylboronic acid and 1.2 g (1.00 mmol) of Pd[PPh$_3$]$_4$, 75 ml of toluene, 75 ml of dimethoxyethane and 75 ml (150.0 mmol) of 2M Na$_2$CO$_3$ aqueous solution were added under an atmosphere of argon, followed by being heated to reflux while stirring for 10 hours.

After completion of the reaction, having been cooled to room temperature, the sample was transferred to a separating funnel and extracted with dichloromethane. The resulting organic phase was dried with MgSO$_4$, followed by being filtered and concentrated. The concentrated residue was purified with silica gel column chromatography to obtain 13.6 g of white solid. By conducting FD-MS analysis, the resulting compound was identified as Intermediate 7 as follows (yield: 80%).

Intermediate 7

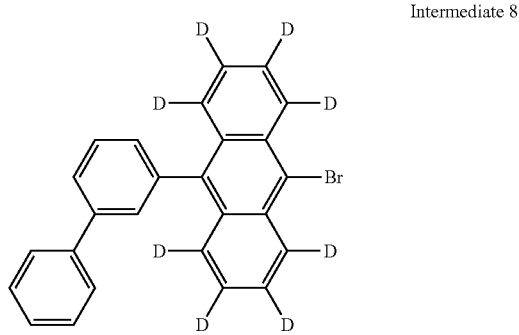 [SMILES: [2H]c1c([2H])c([2H])c2c(-c3cccc(-c4ccccc4)c3)c3c([2H])c([2H])c([2H])c([2H])c3c(Br)c2c1[2H]]

(Synthesis of Intermediate 8)

6.8 g (20.0 mmol) of Intermediate 7 was solubilized in 120 ml of dichloromethane, and the resulting solution was dropped into the solution of 3.2 g (20.0 mmol) of bromine in 12 ml of dichloromethane at room temperature, followed by being stirred for one hour.

After completion of the reaction, the sample was transferred to a separating funnel and washed with 2M Na$_2$S$_2$O$_3$ aqueous solution. The organic phase was further washed with 10% Na$_2$CO$_3$, and thereafter with water three times. The organic phase was dried with MgSO$_4$, followed by being filtered and concentrated.

The concentrated residue was dispersed in methanol (100 mL), and the precipitated crystal was dried to obtain 8.0 g of white solid. By conducting FD-MS analysis, the resulting compound was identified as Intermediate 8 as follows (yield: 96%).

Intermediate 8

(Synthesis of Compound BH-8)

To 2.1 g (5.0 mmol) of Intermediate 8, 1.1 g (5.3 mmol) of dibenzofuran-2-boronic acid and 0.1 g (0.1 mmol) of Pd[PPh$_3$]$_4$, 7.5 ml of toluene, 7.5 ml of dimethoxyethane and 7.5 ml (15.0 mmol) of 2M Na$_2$CO$_3$ aqueous solution were added under an atmosphere of argon, followed by being heated to reflux while stirring for 10 hours.

After completion of the reaction, having been cooled to room temperature, the sample was transferred to a separating funnel and extracted with dichloromethane. The resulting organic phase was dried with MgSO$_4$, followed by being filtered and concentrated. The concentrated residue was purified with silica gel column chromatography to obtain 1.5 g of white solid. By conducting FD-MS analysis, the resulting compound was identified as Compound BH-8 as follows (yield: 59%).

BH-8

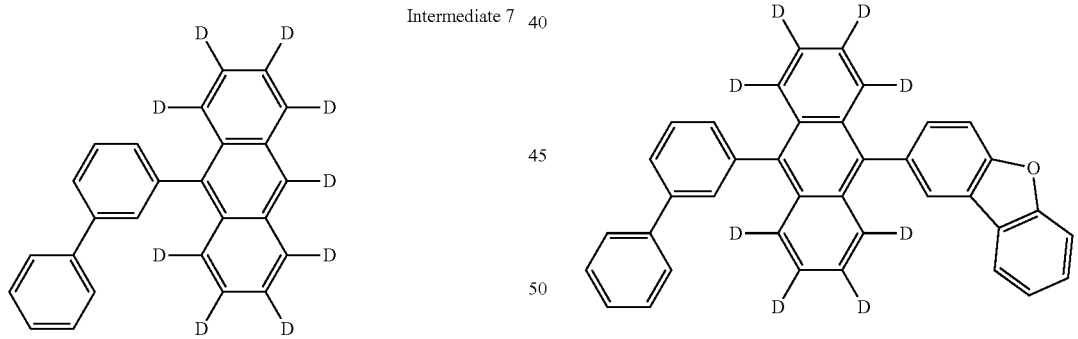

Synthesis Example 9 [Synthesis of Compound BH-9]

(Synthesis of Intermediate 9)

To 13.3 g (50.0 mmol) of 9-bromoanthracene-d9, 10.4 g (52.5 mmol) of 2-biphenylboronic acid and 1.2 g (1.00 mmol) of Pd[PPh$_3$]$_4$, 75 ml of toluene, 75 ml of dimethoxyethane and 75 ml (150.0 mmol) of 2M Na$_2$CO$_3$ aqueous solution were added under an atmosphere of argon, followed by being heated to reflux while stirring for 10 hours.

After completion of the reaction, having been cooled to room temperature, the sample was transferred to a separating funnel and extracted with dichloromethane. The resulting organic phase was dried with MgSO$_4$, followed by being filtered and concentrated. The concentrated residue was purified with silica gel column chromatography to obtain 10.9 g of white solid. By conducting FD-MS analysis, the resulting compound was identified as Intermediate 9 as follows (yield: 64%).

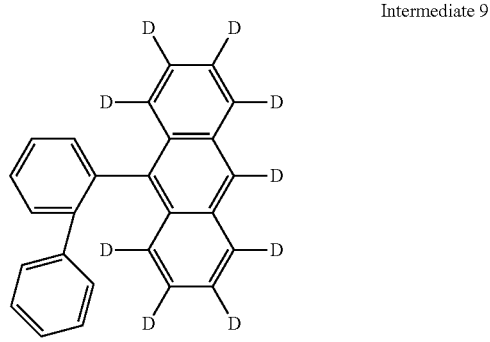 [SMILES: [2H]c1c([2H])c([2H])c2c(-c3ccccc3-c3ccccc3)c3c([2H])c([2H])c([2H])c([2H])c3c([2H])c2c1[2H]]

Intermediate 9

(Synthesis of Intermediate 10)

6.8 g (20.0 mmol) of Intermediate 9 was solubilized in 120 ml of dichloromethane, and the resulting solution was dropped into the solution of 3.2 g (20.0 mmol) of bromine in 12 ml of dichloromethane at room temperature, followed by being stirred for one hour.

After completion of the reaction, the sample was transferred to a separating funnel and washed with 2M $Na_2S_2O_3$ aqueous solution. The organic phase was further washed with 10% $Na_2CO_3$, and thereafter with water three times. The organic phase was dried with $MgSO_4$, followed by being filtered and concentrated.

The concentrated residue was dispersed in methanol (100 mL), and the precipitated crystal was dried to obtain 8.0 g of white solid. By conducting FD-MS analysis, the resulting compound was identified as Intermediate 10 as follows (yield: 96%).

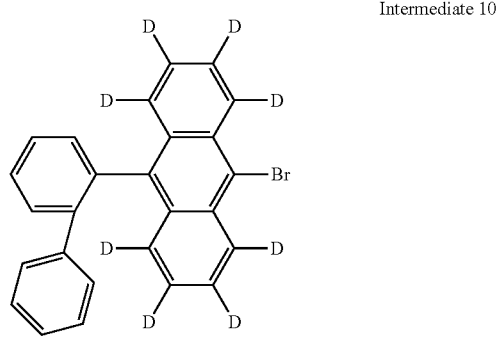 [SMILES: [2H]c1c([2H])c([2H])c2c(-c3ccccc3-c3ccccc3)c3c([2H])c([2H])c([2H])c([2H])c3c(Br)c2c1[2H]]

Intermediate 10

(Synthesis of Compound BH-9)

To 2.1 g (5.0 mmol) of Intermediate 10, 1.1 g (5.3 mmol) of dibenzofuran-2-boronic add and 0.1 g (0.1 mmol) of Pd[PPh₃]₄, 7.5 ml of toluene, 7.5 ml of dimethoxyethane and 7.5 ml (15.0 mmol) of 2M $Na_2CO_3$ aqueous solution were added under an atmosphere of argon, followed by being heated to reflux while stirring for 10 hours.

After completion of the reaction, having been cooled to room temperature, the sample was transferred to a separating funnel and extracted with dichloromethane. The resulting organic phase was dried with $MgSO_4$, followed by being filtered and concentrated. The concentrated residue was purified with silica gel column chromatography to obtain 1.6 g of white solid. By conducting FD-MS analysis, the resulting compound was identified as Compound BH-9 as follows (yield: 63%).

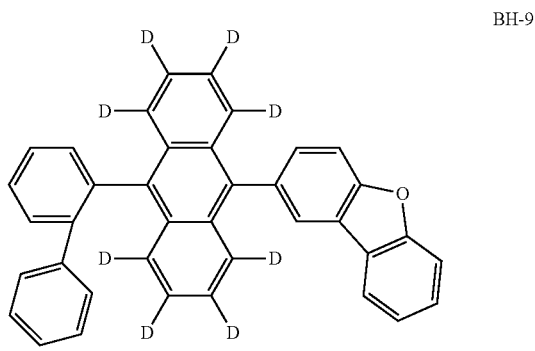 [SMILES: [2H]c1c([2H])c([2H])c2c(-c3ccccc3-c3ccccc3)c3c([2H])c([2H])c([2H])c([2H])c3c(-c3ccc4oc5ccccc5c4c3)c2c1[2H]]

BH-9

Synthesis Example 10 [Synthesis of Compound BH-10]

(Synthesis of Intermediate 11)

To 13.3 g (50.0 mmol) of 9-bromoanthracene-d9, 13.0 g (52.5 mmol) of 4-(1-naphthyl)phenylboronic acid and 1.2 g (1.00 mmol) of Pd[PPh₃]₄, 75 ml of toluene, 75 ml of dimethoxyethane and 75 ml (150.0 mmol) of 2M $Na_2CO_3$ aqueous solution were added under an atmosphere of argon, followed by being heated to reflux while stirring for 10 hours.

After completion of the reaction, having been cooled to room temperature, the sample was transferred to a separating funnel and extracted with dichloromethane. The resulting organic phase was dried with $MgSO_4$, followed by being filtered and concentrated. The concentrated residue was purified with silica gel column chromatography to obtain 15.6 g of white solid. By conducting FD-MS analysis, the resulting compound was identified as Intermediate 11 as follows (yield: 80%).

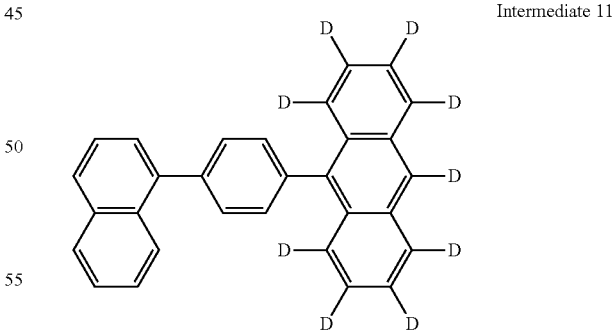

Intermediate 11

(Synthesis of Intermediate 12)

7.8 g (20.0 mmol) of Intermediate 11 was solubilized in 120 ml of dichloromethane, and the resulting solution was dropped into the solution of 3.2 g (20.0 mmol) of bromine in 12 ml of dichloromethane at room temperature, followed by being stirred for one hour.

After completion of the reaction, the sample was transferred to a separating funnel and washed with 2M $Na_2S_2O_3$ aqueous solution. The organic phase was further washed with 10% Na₂CO₃, and thereafter with water three times. The organic phase was dried with MgSO₄, followed by being filtered and concentrated.

The concentrated residue was dispersed in methanol (100 mL), and the precipitated crystal was dried to obtain 8.6 g of white solid. By conducting FD-MS analysis, the resulting compound was identified as Intermediate 12 as follows (yield: 92%).

Intermediate 12

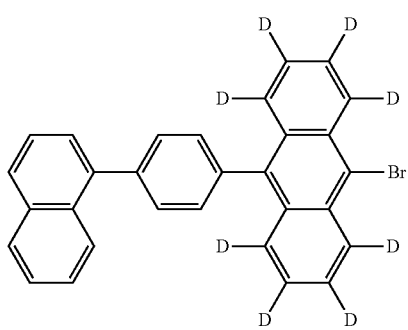

(Synthesis of Compound BH-10)

To 2.3 g (5.0 mmol) of Intermediate 12, 1.1 g (5.3 mmol) of dibenzofuran-2-boronic acid and 0.1 g (0.1 mmol) of Pd[PPh₃]₄, 7.5 ml of toluene, 7.5 ml of dimethoxyethane and 7.5 ml (15.0 mmol) of 2M Na₂CO₃ aqueous solution were added under an atmosphere of argon, followed by being heated to reflux while stirring for 10 hours.

After completion of the reaction, having been cooled to room temperature, the sample was transferred to a separating funnel and extracted with dichloromethane. The resulting organic phase was dried with MgSO₄, followed by being filtered and concentrated. The concentrated residue was purified with silica gel column chromatography to obtain 1.9 g of white solid. By conducting FD-MS analysis, the resulting compound was identified as Compound BH-10 as follows (yield: 68%).

BH-10

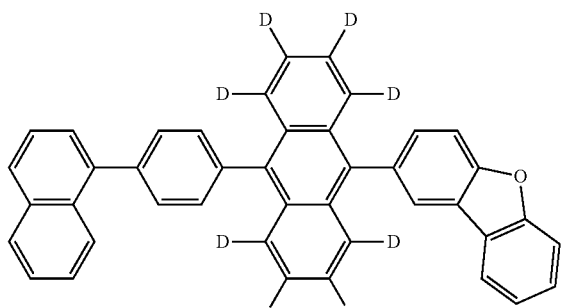

Synthesis Example 11 [Synthesis of Compound BH-11]

Except that 1.8 g (5.3 mmol) of 4-(2-dibenzofuranyl)-1-naphtalenyl boronic add was used instead of dibenzofuran-2-boronic add, the reaction was carried out in the same way as in the synthesis example 1, thereby obtaining 1.7 g of white crystal. By conducting FD-MS analysis, the resulting compound was identified as Compound BH-11 as follows (yield: 60%).

BH-11

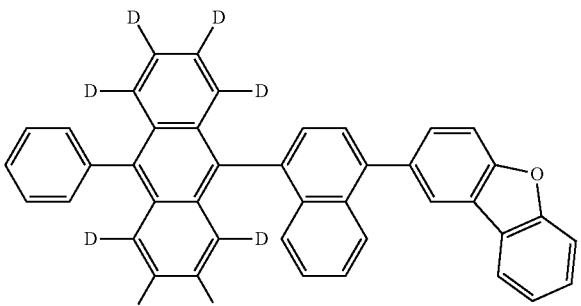

Synthesis Example 12 [Synthesis of Compound BH-12]

Except that 1.8 g (5.3 mmol) of 6-(2-dibenzofuranyl)-2-naphtalenyl boronic acid was used instead of dibenzofuran-2-boronic add, the reaction was carried out in the same way as in the synthesis example 1, thereby obtaining 1.5 g of white crystal. By conducting FD-MS analysis, the resulting compound was identified as Compound BH-12 as follows (yield: 55%).

BH-12

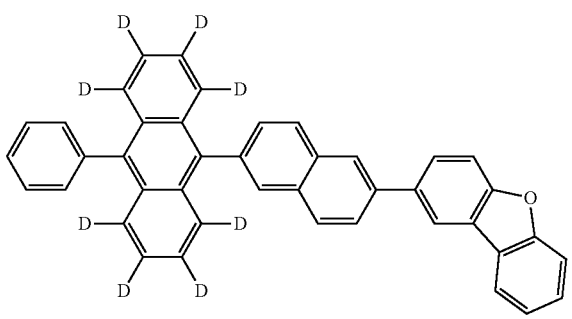

Synthesis Example 13 [Synthesis of Compound BH-13]

Except that 1.8 g (5.3 mmol) of 6-(2-dibenzofuranyl)-2-naphtalenyl boronic acid was used instead of dibenzofuran-2-boronic acid, the reaction was carried out in the same way as in the synthesis example 2, thereby obtaining 2.0 g of white crystal. By conducting FD-MS analysis, the resulting compound was identified as Compound BH-13 as follows (yield: 65%).

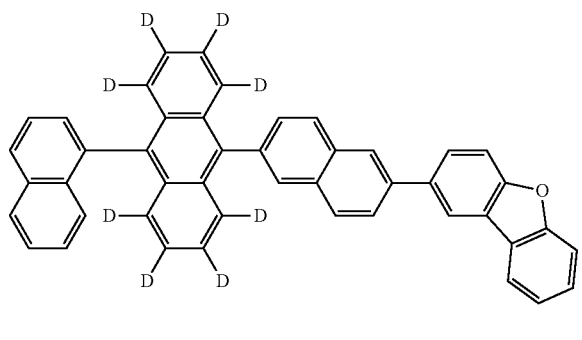

BH-13

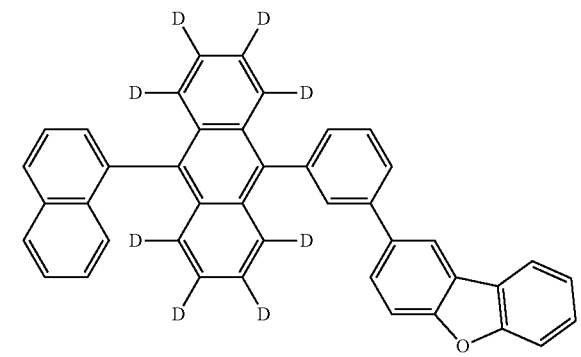

BH-15

Synthesis Example 14 [Synthesis of Compound BH-14]

Except that 1.5 g (5.3 mmol) of 3-(2-dibenzofuranyl) phenyl boronic acid was used instead of dibenzofuran-2-boronic acid, the reaction was carried out in the same way as in the synthesis example 1, thereby obtaining 1.3 g of white crystal. By conducting FD-MS analysis, the resulting compound was identified as Compound BH-14 as follows (yield: 52%).

Synthesis Example 16 [Synthesis of Compound BH-16]

Except that 1.5 g (5.3 mmol) of 4-(1-dibenzofuranyl) phenyl boronic acid was used instead of dibenzofuran-2-boronic acid, the reaction was carried out in the same way as in the synthesis example 1, thereby obtaining 1.6 g of white crystal. By conducting FD-MS analysis, the resulting compound was identified as Compound BH-16 as follows (yield: 62%).

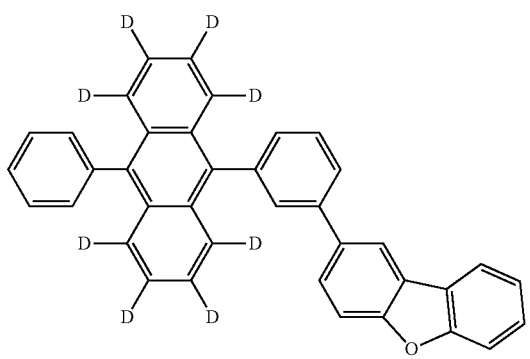

BH-14

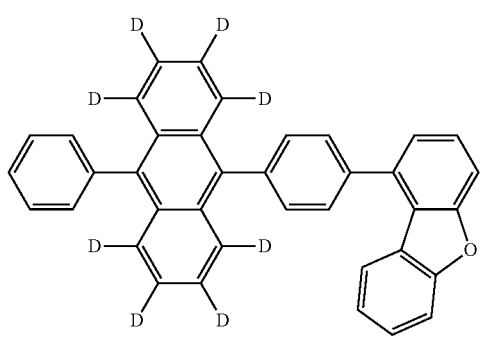

BH-16

Synthesis Example 15 [Synthesis of Compound BH-15]

Except that 1.5 g (5.3 mmol) of 3-(2-dibenzofuranyl) phenyl boronic acid was used instead of dibenzofuran-2-boronic acid, the reaction was carried out in the same way as in the synthesis example 2, thereby obtaining 1.4 g of white crystal. By conducting FD-MS analysis, the resulting compound was identified as Compound BH-15 as follows (yield: 50%).

Synthesis Example 17 [Synthesis of Compound BH-17]

(Synthesis of Intermediate 13)

To 1.33 g (5.00 mmol) of 9-bromoanthracene-d9, 0.67 g (5.25 mmol) of phenyl-d5-boronic acid and 0.12 g (0.10 mmol) of Pd[PPh$_3$]$_4$, 7.5 ml of toluene, 7.5 ml of dimethoxyethane and 7.5 ml (15.0 mmol) of 2M Na$_2$CO$_3$ aqueous solution were added under an atmosphere of argon, followed by being heated to reflux while stirring for 10 hours.

After completion of the reaction, having been cooled to room temperature, the sample was transferred to a separating funnel and extracted with dichloromethane. The resulting organic phase was dried with MgSO$_4$, followed by being filtered and concentrated. The concentrated residue was purified with silica gel column chromatography to obtain 1.07 g of white solid. By conducting FD-MS analysis, the resulting compound was identified as Intermediate 13 as follows (yield: 80%).

Intermediate 13

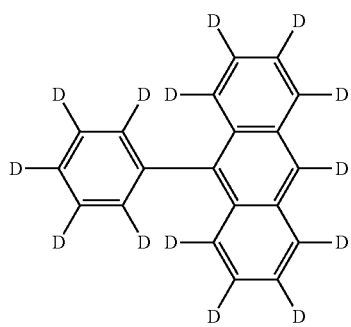

BH-17

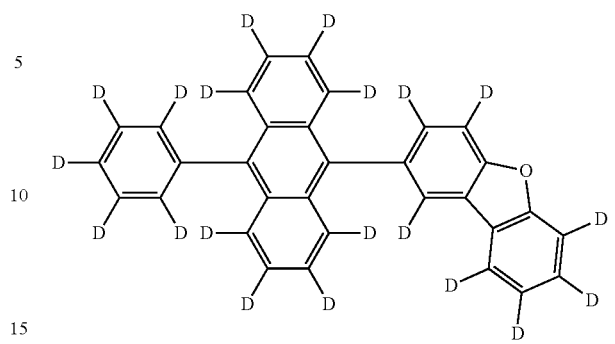

(Synthesis of Intermediate 14)

1.07 g (4.0 mmol) of Intermediate 13 was solubilized in 25 ml of dichloromethane, and the resulting solution was dropped into the solution of 0.64 g (4.0 mmol) of bromine in 3 ml of dichloromethane at room temperature, followed by being stirred for one hour.

After completion of the reaction, the sample was transferred to a separating funnel and washed with 2M $Na_2S_2O_3$ aqueous solution. The organic phase was further washed with 10% $Na_2CO_3$, and thereafter with water. The organic phase was dried with $MgSO_4$, followed by being filtered and concentrated.

The concentrated residue was dispersed in methanol (100 mL), and the precipitated crystal was dried to obtain 1.3 g of white solid. By conducting FD-MS analysis, the resulting compound was identified as Intermediate 14 as follows (yield: 95%).

Intermediate 14

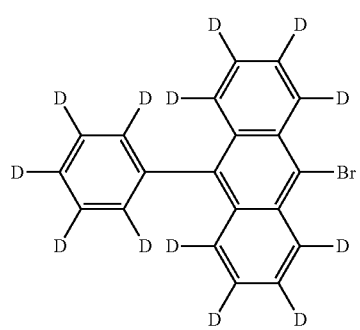

(Synthesis of Compound BH-17)

To 0.87 g (2.5 mmol) of Intermediate 14, 0.58 g (2.65 mmol) of dibenzofuran-d7-2-boronic acid and 0.06 g (0.05 mmol) of $Pd[PPh_3]_4$, 5 ml of toluene, 5 ml of dimethoxyethane and 5 ml (10.0 mmol) of 2M $Na_2CO_3$ aqueous solution were added under an atmosphere of argon, followed by being heated to reflux while stirring for 10 hours.

After completion of the reaction, having been cooled to room temperature, the sample was transferred to a separating funnel and extracted with dichloromethane. The resulting organic phase was dried with $MgSO_4$, followed by being filtered and concentrated. The concentrated residue was purified with silica gel column chromatography to obtain 0.77 g of white solid. By conducting FD-MS analysis, the resulting compound was identified as Compound BH-17 as follows (yield: 70%).

Example 1

(Fabrication of Organic EL Device)

A glass substrate of 25 mm by 75 mm by 1.1 mm thick with an ITO transparent electrode (anode) (manufactured by GEOMATEC Co., Ltd.) was subjected to ultrasonic cleaning in isopropyl alcohol for 5 minutes, and then subjected to UV-ozone cleaning for 30 minutes. The thickness of ITO was 130 nm.

The cleaned glass substrate with a transparent electrode was mounted in a substrate holder of a vacuum vapor deposition apparatus. First, compound HI was deposited on the surface where the transparent electrode was formed so as to cover the transparent electrode, thereby forming an HI film having a thickness of 5 nm. This HI film functioned as a hole-injecting layer.

Subsequent to the formation of the HI film, compound HT-1 was deposited to form an HT-1 film in a thickness of 80 nm on the HI film. This HT-1 film functioned as a hole-transporting layer (a first hole-transporting layer).

Subsequent to the formation of the HT-1 film, compound HT-2 was deposited to form an HT-2 film in a thickness of 10 nm on the HT-1 film. This HT-2 film functioned as an electron-blocking layer (a second hole-transporting layer).

Compound BH-1 (host material) and compound BD-1 (dopant material) were co-deposited on the HT-2 film so that the ratio of compound BD-1 was 4 mass % to form a BH-1:BD-1 film in a thickness of 25 nm. This BH-1:BD-1 film functioned as an emitting layer.

Compound ET-1 was deposited on the emitting layer to form an ET-1 film in a thickness of 10 nm. This ET-1 film functioned as a hole-barrier layer.

Compound ET-2 was deposited on the ET-1 layer to form an ET-2 layer in a thickness of 15 nm. This ET-2 layer functioned as an electron-transporting layer. LiF was deposited on the ET-2 layer to form a LiF film in a thickness of 1 nm. Al metal was deposited on the LiF film to form a metal cathode in a thickness of 80 nm. An organic EL device was thus fabricated.

The layer construction of the fabricated organic EL device was as follows. ITO (130)/HI (5)/HT-1 (80)/HT-2 (10)/BH-1:BD-1 (25:4 mass %)/ET-1 (10)/ET-2 (15)/LiF (1)/Al (80)

The numbers in the parenthesis denote the thickness of each layer (unit: nm).

The compounds used in Example 1 as well as the subsequent examples and comparative examples are shown below.

1031                                   1032
HI
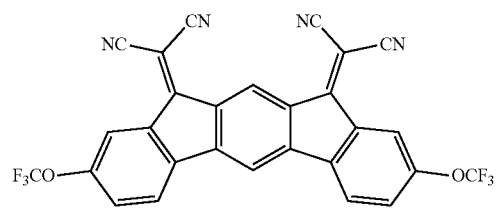
HT-1
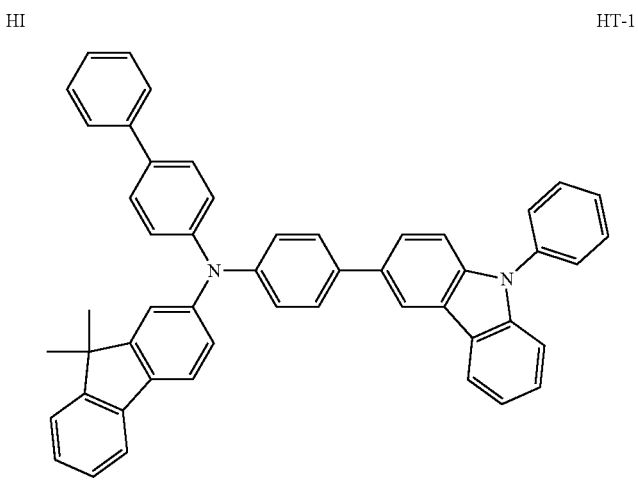
HT-2
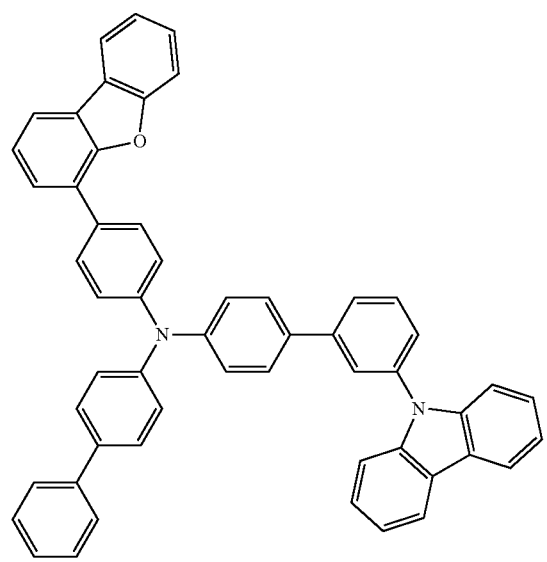
ET-1
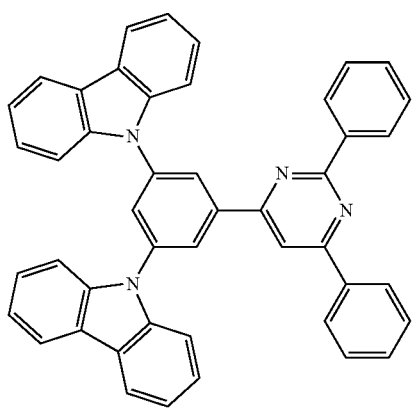
ET-2
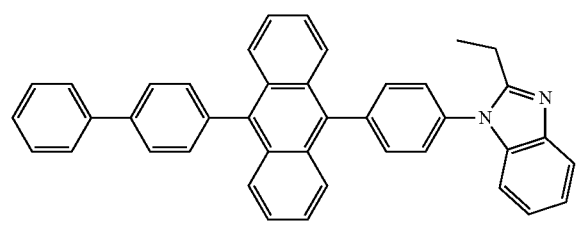
BH-1
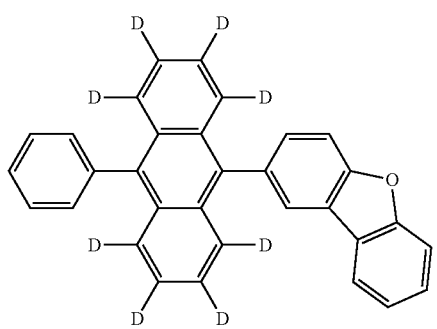

-continued
BH-1-a
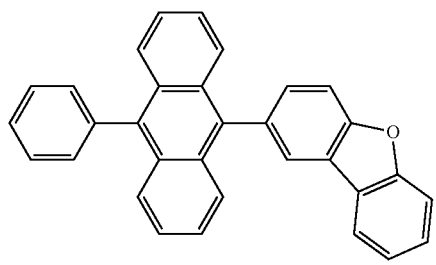
BH-2
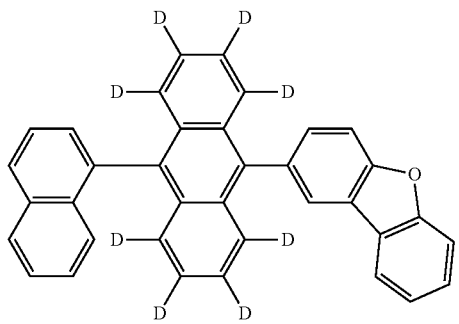
BH-2-a
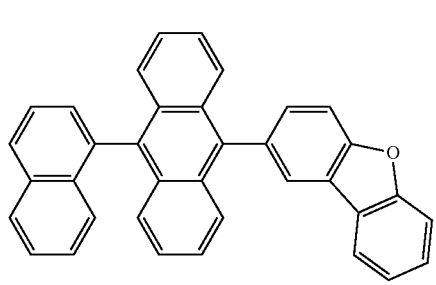
BH-3
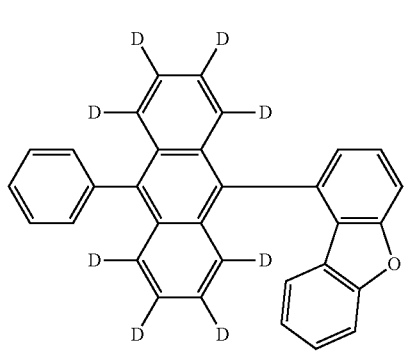
BH-3-a
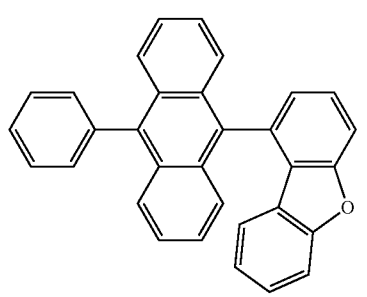
BH-4
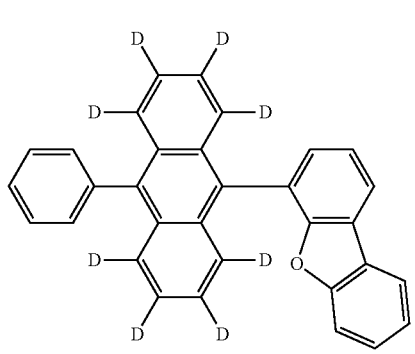
BH-4-a
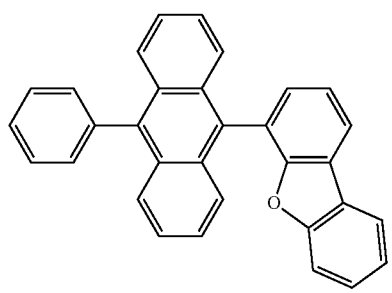
BH-5
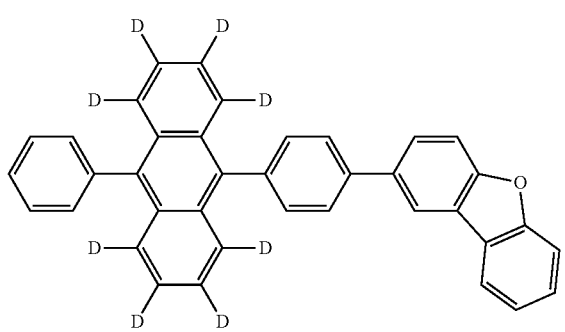

-continued
BH-5-a
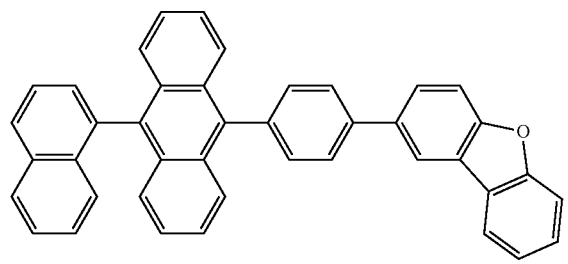
BH-6
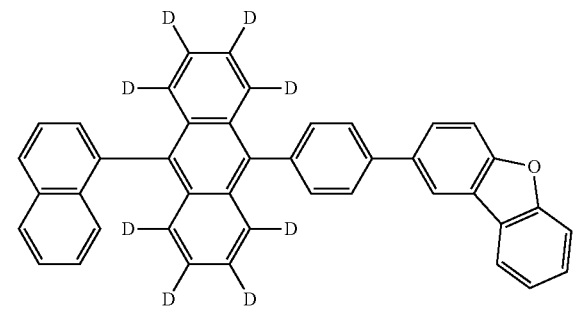
BH-6-a
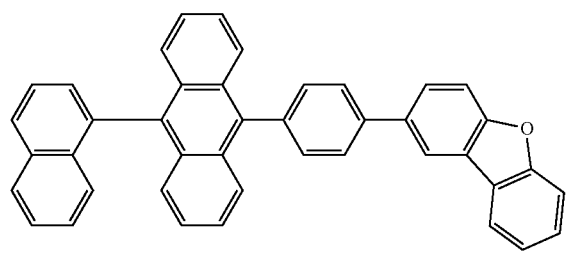
BH-7
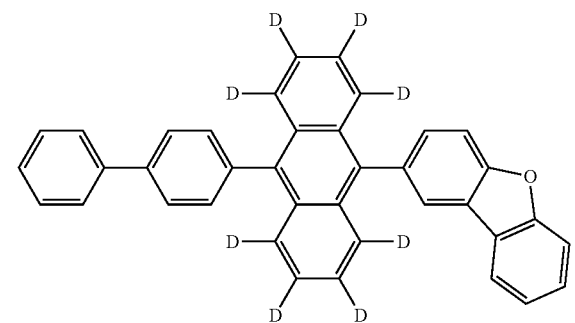
BH-7-a
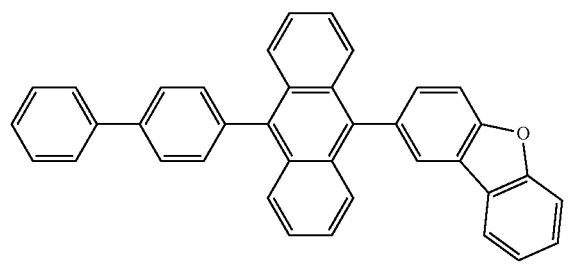
BH-8
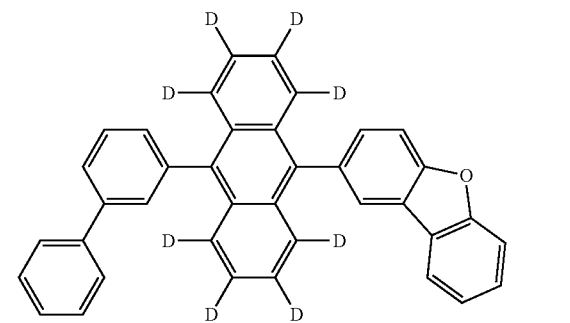
BH-8-a
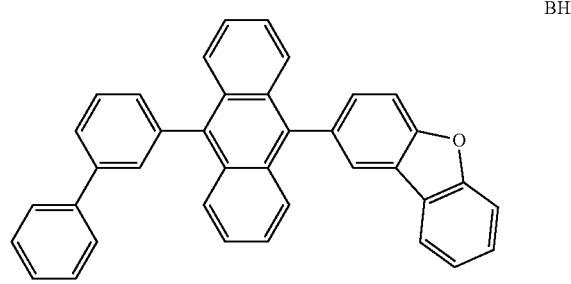
BH-9
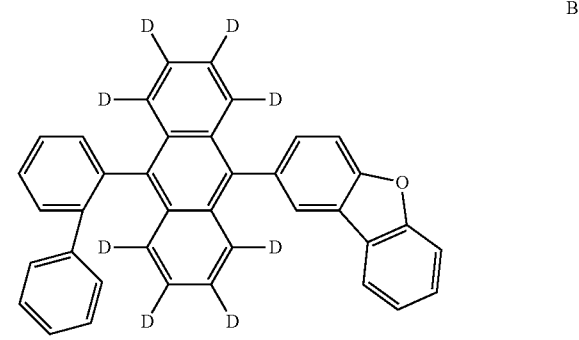

-continued
BH-9-a
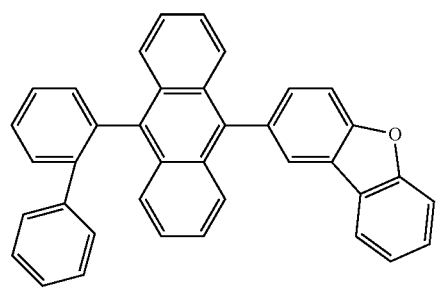
BH-10
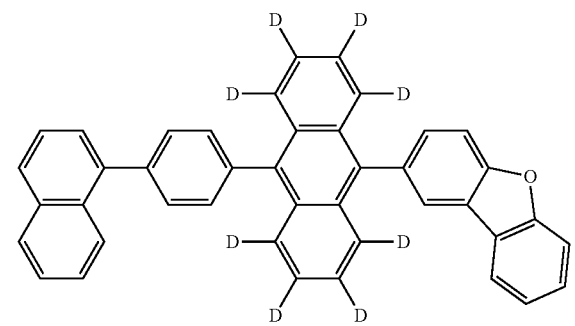
BH-10-a
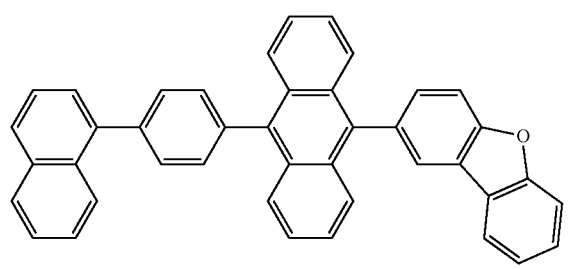
BH-11
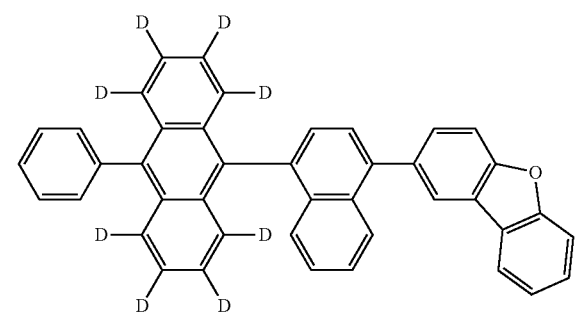
BH-11-a
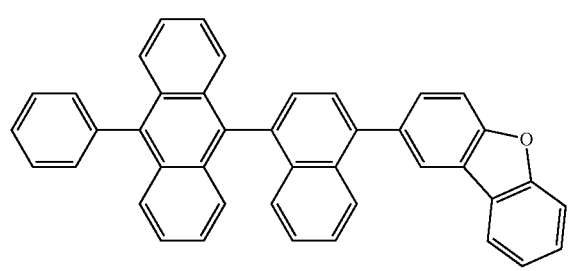
BH-12
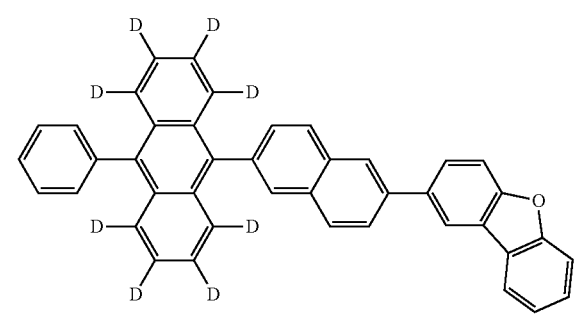
BH-12-a
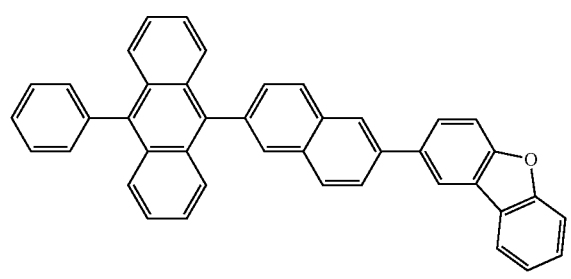
BH-13
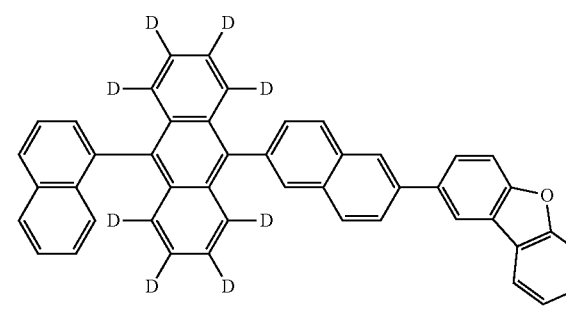

-continued
BH-13-a
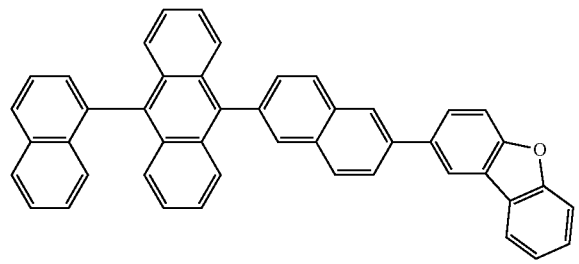
BH-14
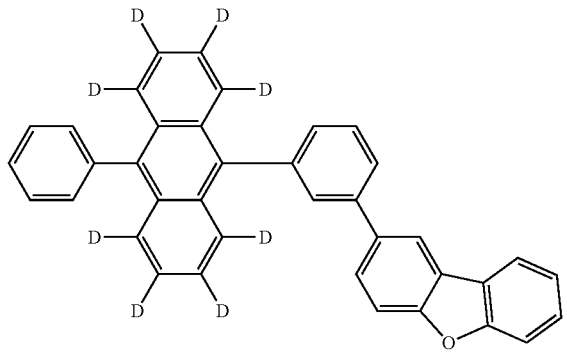
BH-14-a
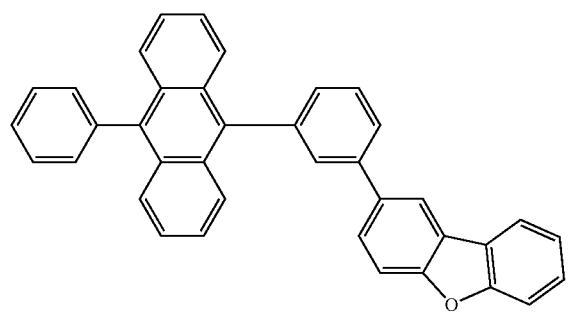
BH-15
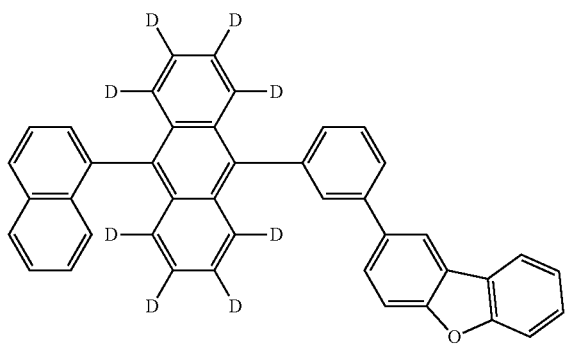
BH-15-a
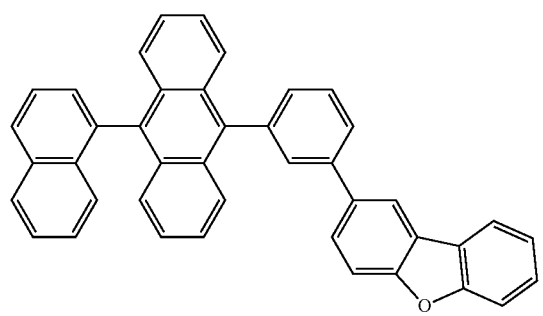
BH-16
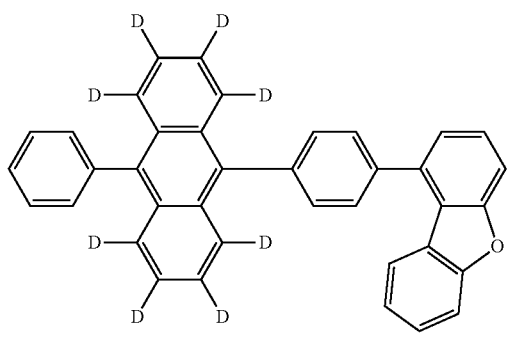
BH-16-a
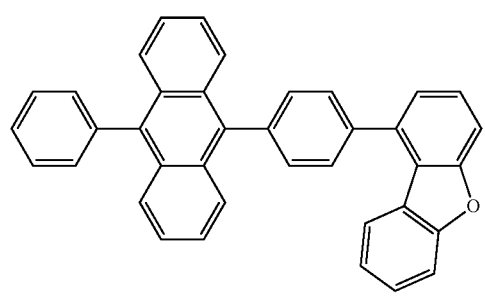
BH-17
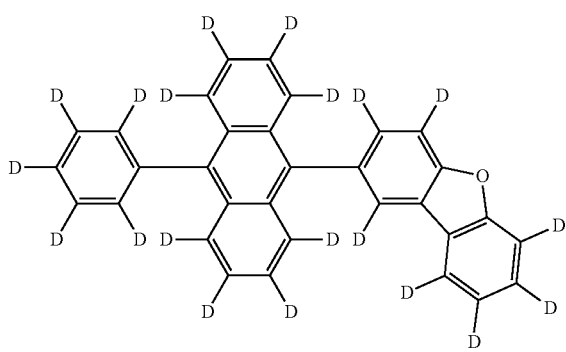

-continued
BD-1
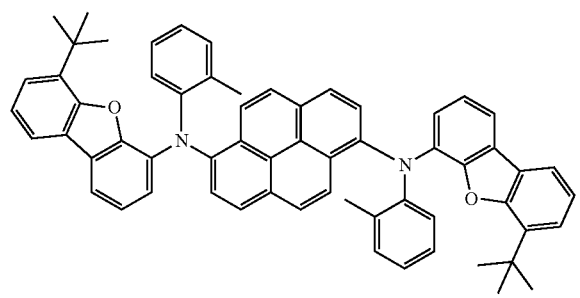
BD-2
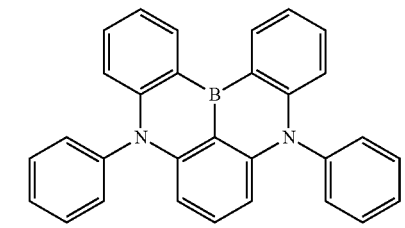
BD-3
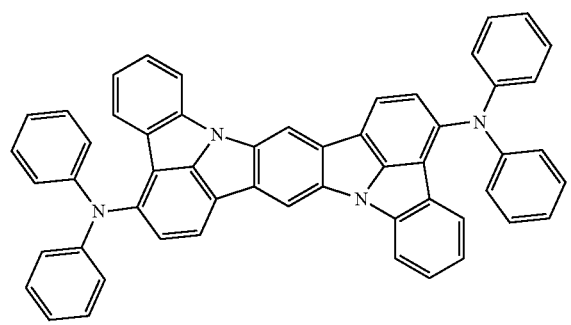
BD-4
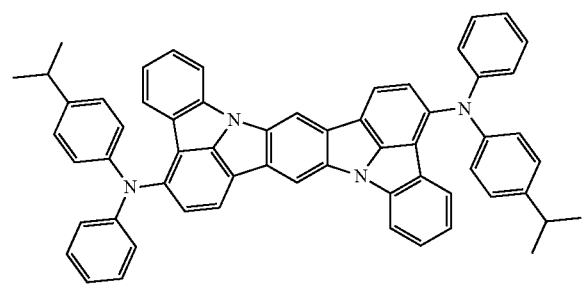
BD-5
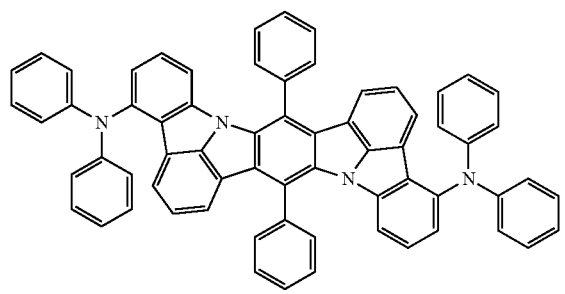
BD-6
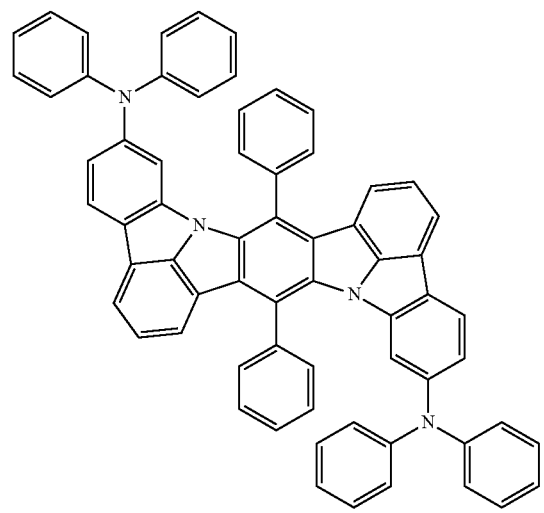

-continued
BD-7
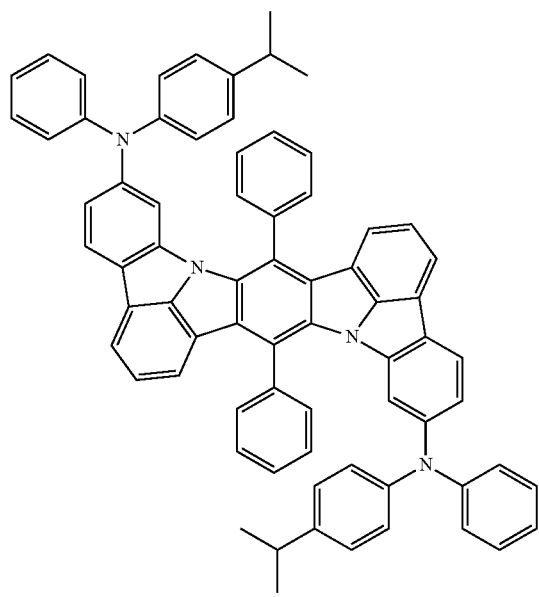
BD-8
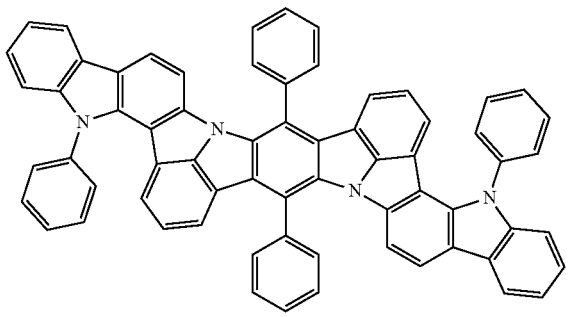
BD-9
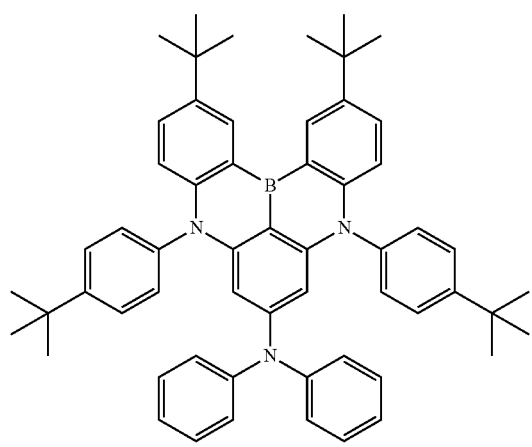
BD-10
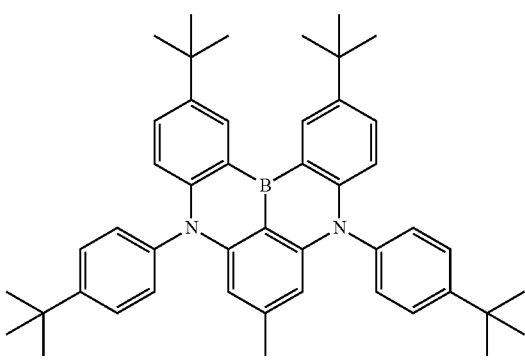
BD-11
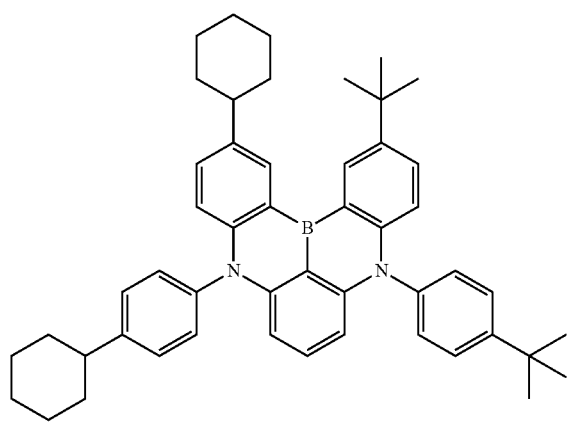
BD-12
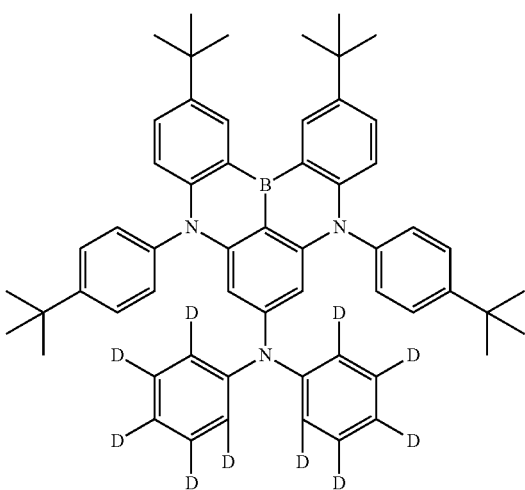

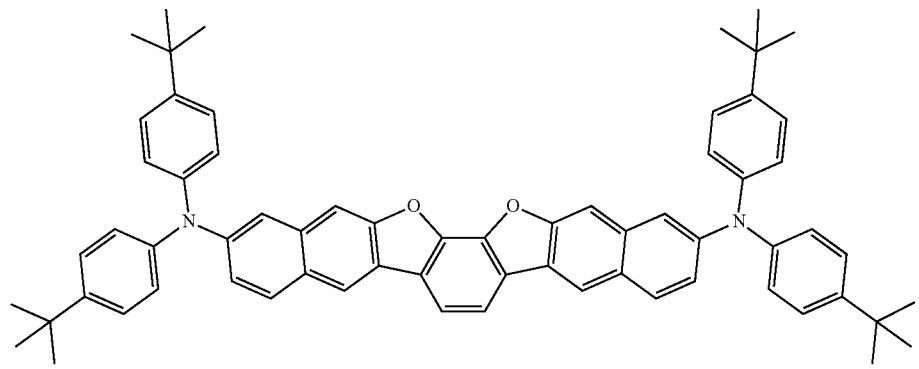

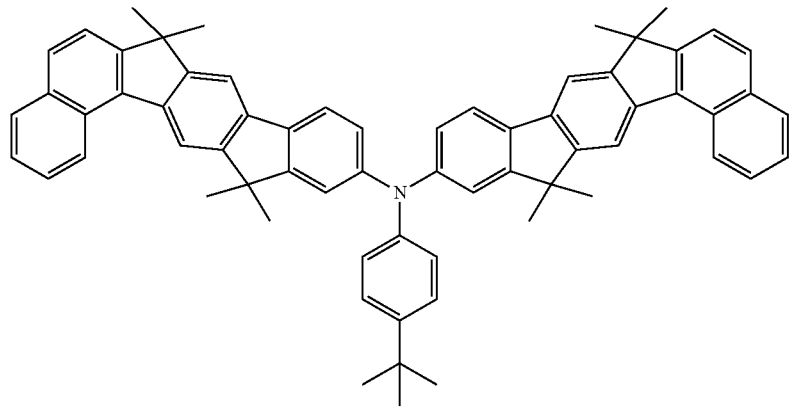

BD-18

(Evaluation of Organic EL Device)

A voltage was applied to the obtained organic EL device so that the current density was 50 mA/cm$^2$, and the time until the luminance reached 95% with respect to the initial luminance (LT95) was measured. The results are shown in Table 1.

Further, a voltage was applied to the obtained organic EL device so that the current density was 10 mA/cm$^2$, and spectral radiance spectrum was measured using a spectroradiometer "CS-1000" (manufactured by Konica Minolta, Inc.) to determine CIE1931 chromaticity coordinate (CIEx, CIEy). The results are shown in Table 1.

Comparative Example 1

Except that the compound shown in the following table was used as the host material of the emitting layer, the organic EL device was fabricated and evaluated in the same manner as in Example 1. The results are shown in Table 1.

TABLE 1

| | Emitting layer | | | | |
|---|---|---|---|---|---|
| | Host material | Dopant material | LT95(h) | Chromaticity CIEx | CIEy |
| Example 1 | BH-1 | BD-1 | 155 | 0.139 | 0.090 |
| Comparative Example 1 | BH-1-a | BD-1 | 94 | 0.139 | 0.090 |

Example 2, Comparative Example 2

Except that the compounds shown in Table 2 were used as the materials of the emitting layer, the organic EL devices were fabricated and evaluated in the same manner as in Example 1. The results are shown in Table 2.

TABLE 2

| | Emitting layer | | | | |
|---|---|---|---|---|---|
| | Host material | Dopant material | LT95(h) | Chromaticity CIEx | CIEy |
| Example 2 | BH-1 | BD-2 | 43 | 0.137 | 0.068 |
| Comparative Example 2 | BH-1-a | BD-2 | 28 | 0.137 | 0.067 |

Example 3, Comparative Example 3

Except that the compounds shown in Table 3 were used as the materials of the emitting layer, the organic EL devices were fabricated and evaluated in the same manner as in Example 1. The results are shown in Table 3.

TABLE 3

| | Emitting layer | | | | |
|---|---|---|---|---|---|
| | Host material | Dopant material | LT95(h) | Chromaticity CIEx | CIEy |
| Example 3 | BH-2 | BD-1 | 80 | 0.139 | 0.090 |
| Comparative Example 3 | BH-2-a | BD-1 | 49 | 0.139 | 0.090 |

Example 4, Comparative Example 4

Except that the compounds shown in Table 4 were used as the materials of the emitting layer, the organic EL devices were fabricated and evaluated in the same manner as in Example 1. The results are shown in Table 4.

TABLE 4

| | Emitting layer | | | | |
|---|---|---|---|---|---|
| | Host material | Dopant material | LT95(h) | Chromaticity CIEx | CIEy |
| Example 4 | BH-2 | BD-2 | 25 | 0.137 | 0.067 |
| Comparative Example 4 | BH-2-a | BD-2 | 15 | 0.137 | 0.067 |

Example 5, Comparative Example 5

Except that the compounds shown in Table 5 were used as the materials of the emitting layer, the organic EL devices were fabricated and evaluated in the same manner as in Example 1. The results are shown in Table 5.

TABLE 5

| | Emitting layer | | | | |
|---|---|---|---|---|---|
| | Host material | Dopant material | LT95(h) | Chromaticity CIEx | CIEy |
| Example 5 | BH-3 | BD-1 | 70 | 0.139 | 0.090 |
| Comparative Example 5 | BH-3-a | BD-1 | 40 | 0.139 | 0.090 |

Example 6, Comparative Example 6

Except that the compounds shown in Table 6 were used as the materials of the emitting layer, the organic EL devices were fabricated and evaluated in the same manner as in Example 1. The results are shown in Table 6.

TABLE 6

| | Emitting layer | | | | |
|---|---|---|---|---|---|
| | Host material | Dopant material | LT95(h) | Chromaticity CIEx | CIEy |
| Example 6 | BH-3 | BD-2 | 20 | 0.137 | 0.067 |
| Comparative Example 6 | BH-3-a | BD-2 | 12 | 0.137 | 0.067 |

Example 7, Comparative Example 7

Except that the compounds shown in Table 7 were used as the materials of the emitting layer, the organic EL devices were fabricated and evaluated in the same manner as in Example 1. The results are shown in Table 7.

TABLE 7

| | Emitting layer | | | | |
|---|---|---|---|---|---|
| | Host material | Dopant material | LT95(h) | Chromaticity CIEx | CIEy |
| Example 7 | BH-4 | BD-1 | 65 | 0.139 | 0.090 |
| Comparative Example 7 | BH-4-a | BD-1 | 38 | 0.139 | 0.090 |

Example 8, Comparative Example 8

Except that the compounds shown in Table 8 were used as the materials of the emitting layer, the organic EL devices were fabricated and evaluated in the same manner as in Example 1. The results are shown in Table 8.

TABLE 8

| | Emitting layer | | | | |
|---|---|---|---|---|---|
| | Host material | Dopant material | LT95(h) | Chromaticity CIEx | CIEy |
| Example 8 | BH-4 | BD-2 | 20 | 0.137 | 0.065 |
| Comparative Example 8 | BH-4-a | BD-2 | 13 | 0.137 | 0.065 |

Example 11, Comparative Example 11

Except that the compounds shown in the following table were used as the materials of the emitting layer (host material and dopant material), the organic EL devices were fabricated and evaluated in the same manner as in Example 1. The results are shown in Table 9.

TABLE 9

| | Emitting layer | | | | |
|---|---|---|---|---|---|
| | Host material | Dopant material | LT95(h) | Chromaticity CIEx | CIEy |
| Example 11 | BH-1 | BD-3 | 130 | 0.140 | 0.080 |
| Comparative Example 11 | BH-1-a | BD-3 | 83 | 0.140 | 0.080 |

Example 12, Comparative Example 12

Except that the compounds shown in the following table were used as the materials of the emitting layer (host material and dopant material), the organic EL devices were fabricated and evaluated in the same manner as in Example 1. The results are shown in Table 10.

TABLE 10

| | Emitting layer | | | | |
|---|---|---|---|---|---|
| | Host material | Dopant material | LT95(h) | Chromaticity CIEx | CIEy |
| Example 12 | BH-2 | BD-3 | 71 | 0.140 | 0.081 |
| Comparative Example 12 | BH-2-a | BD-3 | 45 | 0.140 | 0.080 |

Example 13, Comparative Example 13

Except that the compounds shown in the following table were used as the materials of the emitting layer (host material and dopant material), the organic EL devices were fabricated and evaluated in the same manner as in Example 1. The results are shown in Table 11.

TABLE 11

| | Emitting layer | | | | |
|---|---|---|---|---|---|
| | Host material | Dopant material | LT95(h) | Chromaticity CIEx | CIEy |
| Example 13 | BH-3 | BD-3 | 56 | 0.140 | 0.080 |
| Comparative Example 13 | BH-3-a | BD-3 | 36 | 0.140 | 0.080 |

Example 14, Comparative Example 14

Except that the compounds shown in the following table were used as the materials of the emitting layer (host material and dopant material), the organic EL devices were fabricated and evaluated in the same manner as in Example 1. The results are shown in Table 12.

TABLE 12

| | Emitting layer | | | Chromaticity | |
|---|---|---|---|---|---|
| | Host material | Dopant material | LT95(h) | CIEx | CIEy |
| Example 14 | BH-4 | BD-3 | 57 | 0.140 | 0.080 |
| Comparative Example 14 | BH-4-a | BD-3 | 30 | 0.140 | 0.080 |

Example 15, Comparative Example 15

Except that the compounds shown in the following table were used as the materials of the emitting layer (host material and dopant material), the organic EL devices were fabricated and evaluated in the same manner as in Example 1. The results are shown in Table 13.

TABLE 13

| | Emitting layer | | | Chromaticity | |
|---|---|---|---|---|---|
| | Host material | Dopant material | LT95(h) | CIEx | CIEy |
| Example 15 | BH-5 | BD-3 | 146 | 0.140 | 0.080 |
| Comparative Example 15 | BH-5-a | BD-3 | 82 | 0.140 | 0.080 |

Example 16, Comparative Example 16

Except that the compounds shown in the following table were used as the materials of the emitting layer (host material and dopant material), the organic EL devices were fabricated and evaluated in the same manner as in Example 1. The results are shown in Table 14.

TABLE 14

| | Emitting layer | | | Chromaticity | |
|---|---|---|---|---|---|
| | Host material | Dopant material | LT95(h) | CIEx | CIEy |
| Example 16 | BH-6 | BD-3 | 126 | 0.140 | 0.080 |
| Comparative Example 16 | BH-6-a | BD-3 | 78 | 0.140 | 0.080 |

Example 17, Comparative Example 17

Except that the compounds shown in the following table were used as the materials of the emitting layer (host material and dopant material), the organic EL devices were fabricated and evaluated in the same manner as in Example 1. The results are shown in Table 15.

TABLE 15

| | Emitting layer | | | Chromaticity | |
|---|---|---|---|---|---|
| | Host material | Dopant material | LT95(h) | CIEx | CIEy |
| Example 17 | BH-7 | BD-3 | 127 | 0.140 | 0.080 |
| Comparative Example 17 | BH-7-a | BD-3 | 80 | 0.140 | 0.080 |

Example 21, Comparative Example 21

Except that the compounds shown in the following table were used as the materials of the emitting layer (host material and dopant material), the organic EL devices were fabricated and evaluated in the same manner as in Example 1. The results are shown in Table 16.

TABLE 16

| | Emitting layer | | | Chromaticity | |
|---|---|---|---|---|---|
| | Host material | Dopant material | LT95(h) | CIEx | CIEy |
| Example 21 | BH-1 | BD-4 | 155 | 0.135 | 0.098 |
| Comparative Example 21 | BH-1-a | BD-4 | 96 | 0.135 | 0.098 |

Example 22, Comparative Example 22

Except that the compounds shown in the following table were used as the materials of the emitting layer (host material and dopant material), the organic EL devices were fabricated and evaluated in the same manner as in Example 1. The results are shown in Table 17.

TABLE 17

| | Emitting layer | | | Chromaticity | |
|---|---|---|---|---|---|
| | Host material | Dopant material | LT95(h) | CIEx | CIEy |
| Example 22 | BH-2 | BD-4 | 77 | 0.135 | 0.098 |
| Comparative Example 22 | BH-2-a | BD-4 | 50 | 0.135 | 0.099 |

Example 23, Comparative Example 23

Except that the compounds shown in the following table were used as the materials of the emitting layer (host material and dopant material), the organic EL devices were fabricated and evaluated in the same manner as in Example 1. The results are shown in Table 18.

TABLE 18

| | Emitting layer | | | | |
|---|---|---|---|---|---|
| | Host material | Dopant material | LT95(h) | Chromaticity CIEx | CIEy |
| Example 23 | BH-3 | BD-4 | 73 | 0.135 | 0.098 |
| Comparative Example 23 | BH-3-a | BD-4 | 43 | 0.135 | 0.098 |

Example 24, Comparative Example 24

Except that the compounds shown in the following table were used as the materials of the emitting layer (host material and dopant material), the organic EL devices were fabricated and evaluated in the same manner as in Example 1. The results are shown in Table 19.

TABLE 19

| | Emitting layer | | | | |
|---|---|---|---|---|---|
| | Host material | Dopant material | LT95(h) | Chromaticity CIEx | CIEy |
| Example 24 | BH-4 | BD-4 | 60 | 0.135 | 0.098 |
| Comparative Example 24 | BH-4-a | BD-4 | 41 | 0.135 | 0.098 |

Example 25, Comparative Example 25

Except that the compounds shown in the following table were used as the materials of the emitting layer (host material and dopant material), the organic EL devices were fabricated and evaluated in the same manner as in Example 1. The results are shown in Table 20.

TABLE 20

| | Emitting layer | | | | |
|---|---|---|---|---|---|
| | Host material | Dopant material | LT95(h) | Chromaticity CIEx | CIEy |
| Example 25 | BH-5 | BD-4 | 167 | 0.135 | 0.098 |
| Comparative Example 25 | BH-5-a | BD-4 | 105 | 0.135 | 0.098 |

Example 26, Comparative Example 26

Except that the compounds shown in the following table were used as the materials of the emitting layer (host material and dopant material), the organic EL devices were fabricated and evaluated in the same manner as in Example 1. The results are shown in Table 21.

TABLE 21

| | Emitting layer | | | | |
|---|---|---|---|---|---|
| | Host material | Dopant material | LT95(h) | Chromaticity CIEx | CIEy |
| Example 26 | BH-6 | BD-4 | 147 | 0.135 | 0.098 |
| Comparative Example 26 | BH-6-a | BD-4 | 92 | 0.135 | 0.098 |

Example 27, Comparative Example 27

Except that the compounds shown in the following table were used as the materials of the emitting layer (host material and dopant material), the organic EL devices were fabricated and evaluated in the same manner as in Example 1. The results are shown in Table 22.

TABLE 22

| | Emitting layer | | | | |
|---|---|---|---|---|---|
| | Host material | Dopant material | LT95(h) | Chromaticity CIEx | CIEy |
| Example 27 | BH-7 | BD-4 | 150 | 0.135 | 0.098 |
| Comparative Example 27 | BH-7-a | BD-4 | 96 | 0.135 | 0.098 |

Example 31, Comparative Example 31

Except that the compounds shown in the following table were used as the materials of the emitting layer (host material and dopant material), the organic EL devices were fabricated and evaluated in the same manner as in Example 1. The results are shown in Table 23.

TABLE 23

| | Emitting layer | | | | |
|---|---|---|---|---|---|
| | Host material | Dopant material | LT95(h) | Chromaticity CIEx | CIEy |
| Example 31 | BH-1 | BD-5 | 163 | 0.135 | 0.086 |
| Comparative Example 31 | BH-1-a | BD-5 | 98 | 0.135 | 0.086 |

Example 32, Comparative Example 32

Except that the compounds shown in the following table were used as the materials of the emitting layer (host material and dopant material), the organic EL devices were fabricated and evaluated in the same manner as in Example 1. The results are shown in Table 24.

TABLE 24

| | Emitting layer | | | | |
|---|---|---|---|---|---|
| | Host material | Dopant material | LT95(h) | Chromaticity CIEx | CIEy |
| Example 32 | BH-2 | BD-5 | 78 | 0.135 | 0.086 |
| Comparative Example 32 | BH-2-a | BD-5 | 51 | 0.135 | 0.086 |

Example 33, Comparative Example 33

Except that the compounds shown in the following table were used as the materials of the emitting layer (host material and dopant material), the organic EL devices were fabricated and evaluated in the same manner as in Example 1. The results are shown in Table 25.

TABLE 25

| | Emitting layer | | | Chromaticity | |
|---|---|---|---|---|---|
| | Host material | Dopant material | LT95(h) | CIEx | CIEy |
| Example 33 | BH-3 | BD-5 | 73 | 0.135 | 0.086 |
| Comparative Example 33 | BH-3-a | BD-5 | 39 | 0.135 | 0.086 |

Example 34, Comparative Example 34

Except that the compounds shown in the following table were used as the materials of the emitting layer (host material and dopant material), the organic EL devices were fabricated and evaluated in the same manner as in Example 1. The results are shown in Table 26.

TABLE 26

| | Emitting layer | | | Chromaticity | |
|---|---|---|---|---|---|
| | Host material | Dopant material | LT95(h) | CIEx | CIEy |
| Example 34 | BH-4 | BD-5 | 62 | 0.135 | 0.085 |
| Comparative Example 34 | BH-4-a | BD-5 | 43 | 0.135 | 0.086 |

Example 35, Comparative Example 35

Except that the compounds shown in the following table were used as the materials of the emitting layer (host material and dopant material), the organic EL devices were fabricated and evaluated in the same manner as in Example 1. The results are shown in Table 27.

TABLE 27

| | Emitting layer | | | Chromaticity | |
|---|---|---|---|---|---|
| | Host material | Dopant material | LT95(h) | CIEx | CIEy |
| Example 35 | BH-5 | BD-5 | 170 | 0.135 | 0.086 |
| Comparative Example 35 | BH-5-a | BD-5 | 105 | 0.135 | 0.086 |

Example 36, Comparative Example 36

Except that the compounds shown in the following table were used as the materials of the emitting layer (host material and dopant material), the organic EL devices were fabricated and evaluated in the same manner as in Example 1. The results are shown in Table 28.

TABLE 28

| | Emitting layer | | | Chromaticity | |
|---|---|---|---|---|---|
| | Host material | Dopant material | LT95(h) | CIEx | CIEy |
| Example 36 | BH-6 | BD-5 | 152 | 0.135 | 0.086 |
| Comparative Example 36 | BH-6-a | BD-5 | 89 | 0.135 | 0.086 |

Example 37, Comparative Example 37

Except that the compounds shown in the following table were used as the materials of the emitting layer (host material and dopant material), the organic EL devices were fabricated and evaluated in the same manner as in Example 1. The results are shown in Table 29.

TABLE 29

| | Emitting layer | | | Chromaticity | |
|---|---|---|---|---|---|
| | Host material | Dopant material | LT95(h) | CIEx | CIEy |
| Example 37 | BH-7 | BD-5 | 161 | 0.135 | 0.086 |
| Comparative Example 37 | BH-7-a | BD-5 | 102 | 0.135 | 0.086 |

Example 41, Comparative Example 41

Except that the compounds shown in the following table were used as the materials of the emitting layer (host material and dopant material), the organic EL devices were fabricated and evaluated in the same manner as in Example 1. The results are shown in Table 30.

TABLE 30

| | Emitting layer | | | Chromaticity | |
|---|---|---|---|---|---|
| | Host material | Dopant material | LT95(h) | CIEx | CIEy |
| Example 41 | BH-1 | BD-6 | 195 | 0.135 | 0.080 |
| Comparative Example 41 | BH-1-a | BD-6 | 123 | 0.135 | 0.080 |

Example 42, Comparative Example 42

Except that the compounds shown in the following table were used as the materials of the emitting layer (host material and dopant material), the organic EL devices were fabricated and evaluated in the same manner as in Example 1. The results are shown in Table 31.

TABLE 31

| | Emitting layer | | | Chromaticity | |
| --- | --- | --- | --- | --- | --- |
| | Host material | Dopant material | LT95(h) | CIEx | CIEy |
| Example 42 | BH-2 | BD-6 | 106 | 0.135 | 0.080 |
| Comparative Example 42 | BH-2-a | BD-6 | 66 | 0.135 | 0.080 |

Example 43, Comparative Example 43

Except that the compounds shown in the following table were used as the materials of the emitting layer (host material and dopant material), the organic EL devices were fabricated and evaluated in the same manner as in Example 1. The results are shown in Table 32.

TABLE 32

| | Emitting layer | | | Chromaticity | |
| --- | --- | --- | --- | --- | --- |
| | Host material | Dopant material | LT95(h) | CIEx | CIEy |
| Example 43 | BH-3 | BD-6 | 90 | 0.135 | 0.080 |
| Comparative Example 43 | BH-3-a | BD-6 | 53 | 0.135 | 0.080 |

Example 44, Comparative Example 44

Except that the compounds shown in the following table were used as the materials of the emitting layer (host material and dopant material), the organic EL devices were fabricated and evaluated in the same manner as in Example 1. The results are shown in Table 33.

TABLE 33

| | Emitting layer | | | Chromaticity | |
| --- | --- | --- | --- | --- | --- |
| | Host material | Dopant material | LT95(h) | CIEx | CIEy |
| Example 44 | BH-4 | BD-6 | 84 | 0.135 | 0.080 |
| Comparative Example 44 | BH-4-a | BD-6 | 52 | 0.135 | 0.080 |

Example 45, Comparative Example 45

Except that the compounds shown in the following table were used as the materials of the emitting layer (host material and dopant material), the organic EL devices were fabricated and evaluated in the same manner as in Example 1. The results are shown in Table 34.

TABLE 34

| | Emitting layer | | | Chromaticity | |
| --- | --- | --- | --- | --- | --- |
| | Host material | Dopant material | LT95(h) | CIEx | CIEy |
| Example 45 | BH-5 | BD-6 | 211 | 0.135 | 0.080 |
| Comparative Example 45 | BH-5-a | BD-6 | 133 | 0.135 | 0.081 |

Example 46, Comparative Example 46

Except that the compounds shown in the following table were used as the materials of the emitting layer (host material and dopant material), the organic EL devices were fabricated and evaluated in the same manner as in Example 1. The results are shown in Table 35.

TABLE 35

| | Emitting layer | | | Chromaticity | |
| --- | --- | --- | --- | --- | --- |
| | Host material | Dopant material | LT95(h) | CIEx | CIEy |
| Example 46 | BH-6 | BD-6 | 179 | 0.135 | 0.080 |
| Comparative Example 46 | BH-6-a | BD-6 | 112 | 0.135 | 0.080 |

Example 47, Comparative Example 47

Except that the compounds shown in the following table were used as the materials of the emitting layer (host material and dopant material), the organic EL devices were fabricated and evaluated in the same manner as in Example 1. The results are shown in Table 36.

TABLE 36

| | Emitting layer | | | Chromaticity | |
| --- | --- | --- | --- | --- | --- |
| | Host material | Dopant material | LT95(h) | CIEx | CIEy |
| Example 47 | BH-7 | BD-6 | 202 | 0.135 | 0.080 |
| Comparative Example 47 | BH-7-a | BD-6 | 125 | 0.135 | 0.080 |

Example 51, Comparative Example 51

Except that the compounds shown in the following table were used as the materials of the emitting layer (host material and dopant material), the organic EL devices were fabricated and evaluated in the same manner as in Example 1. The results are shown in Table 37.

TABLE 37

| | Emitting layer | | | Chromaticity | |
|---|---|---|---|---|---|
| | Host material | Dopant material | LT95(h) | CIEx | CIEy |
| Example 51 | BH-1 | BD-7 | 253 | 0.136 | 0.090 |
| Comparative Example 51 | BH-1-a | BD-7 | 146 | 0.136 | 0.090 |

Example 52, Comparative Example 52

Except that the compounds shown in the following table were used as the materials of the emitting layer (host material and dopant material), the organic EL devices were fabricated and evaluated in the same manner as in Example 1. The results are shown in Table 38.

TABLE 38

| | Emitting layer | | | Chromaticity | |
|---|---|---|---|---|---|
| | Host material | Dopant material | LT95(h) | CIEx | CIEy |
| Example 52 | BH-2 | BD-7 | 125 | 0.136 | 0.090 |
| Comparative Example 52 | BH-2-a | BD-7 | 73 | 0.136 | 0.090 |

Example 53, Comparative Example 53

Except that the compounds shown in the following table were used as the materials of the emitting layer (host material and dopant material), the organic EL devices were fabricated and evaluated in the same manner as in Example 1. The results are shown in Table 39.

TABLE 39

| | Emitting layer | | | Chromaticity | |
|---|---|---|---|---|---|
| | Host material | Dopant material | LT95(h) | CIEx | CIEy |
| Example 53 | BH-3 | BD-7 | 102 | 0.136 | 0.090 |
| Comparative Example 53 | BH-3-a | BD-7 | 64 | 0.136 | 0.090 |

Example 54, Comparative Example 54

Except that the compounds shown in the following table were used as the materials of the emitting layer (host material and dopant material), the organic EL devices were fabricated and evaluated in the same manner as in Example 1. The results are shown in Table 40.

TABLE 40

| | Emitting layer | | | Chromaticity | |
|---|---|---|---|---|---|
| | Host material | Dopant material | LT95(h) | CIEx | CIEy |
| Example 54 | BH-4 | BD-7 | 99 | 0.136 | 0.090 |
| Comparative Example 54 | BH-4-a | BD-7 | 64 | 0.136 | 0.090 |

Example 55, Comparative Example 55

Except that the compounds shown in the following table were used as the materials of the emitting layer (host material and dopant material), the organic EL devices were fabricated and evaluated in the same manner as in Example 1. The results are shown in Table 41.

TABLE 41

| | Emitting layer | | | Chromaticity | |
|---|---|---|---|---|---|
| | Host material | Dopant material | LT95(h) | CIEx | CIEy |
| Example 55 | BH-5 | BD-7 | 257 | 0.136 | 0.090 |
| Comparative Example 55 | BH-5-a | BD-7 | 161 | 0.136 | 0.091 |

Example 56, Comparative Example 56

Except that the compounds shown in the following table were used as the materials of the emitting layer (host material and dopant material), the organic EL devices were fabricated and evaluated in the same manner as in Example 1. The results are shown in Table 42.

TABLE 42

| | Emitting layer | | | Chromaticity | |
|---|---|---|---|---|---|
| | Host material | Dopant material | LT95(h) | CIEx | CIEy |
| Example 56 | BH-6 | BD-7 | 215 | 0.136 | 0.090 |
| Comparative Example 56 | BH-6-a | BD-7 | 137 | 0.136 | 0.090 |

Example 57, Comparative Example 57

Except that the compounds shown in the following table were used as the materials of the emitting layer (host material and dopant material), the organic EL devices were fabricated and evaluated in the same manner as in Example 1. The results are shown in Table 43.

TABLE 43

| | Emitting layer | | | Chromaticity | |
|---|---|---|---|---|---|
| | Host material | Dopant material | LT95(h) | CIEx | CIEy |
| Example 57 | BH-7 | BD-7 | 241 | 0.136 | 0.090 |
| Comparative Example 57 | BH-7-a | BD-7 | 141 | 0.136 | 0.090 |

Example 61, Comparative Example 61

Except that the compounds shown in the following table were used as the materials of the emitting layer (host material and dopant material), the organic EL devices were fabricated and evaluated in the same manner as in Example 1. The results are shown in Table 44.

TABLE 44

| | Emitting layer | | | Chromaticity | |
|---|---|---|---|---|---|
| | Host material | Dopant material | LT95(h) | CIEx | CIEy |
| Example 61 | BH-1 | BD-8 | 104 | 0.144 | 0.061 |
| Comparative Example 61 | BH-1-a | BD-8 | 65 | 0.144 | 0.061 |

Example 62, Comparative Example 62

Except that the compounds shown in the following table were used as the materials of the emitting layer (host material and dopant material), the organic EL devices were fabricated and evaluated in the same manner as in Example 1. The results are shown in Table 45.

TABLE 45

| | Emitting layer | | | Chromaticity | |
|---|---|---|---|---|---|
| | Host material | Dopant material | LT95(h) | CIEx | CIEy |
| Example 62 | BH-2 | BD-8 | 53 | 0.144 | 0.061 |
| Comparative Example 62 | BH-2-a | BD-8 | 37 | 0.144 | 0.061 |

Example 63, Comparative Example 63

Except that the compounds shown in the following table were used as the materials of the emitting layer (host material and dopant material), the organic EL devices were fabricated and evaluated in the same manner as in Example 1. The results are shown in Table 46.

TABLE 46

| | Emitting layer | | | Chromaticity | |
|---|---|---|---|---|---|
| | Host material | Dopant material | LT95(h) | CIEx | CIEy |
| Example 63 | BH-3 | BD-8 | 51 | 0.144 | 0.060 |
| Comparative Example 63 | BH-3-a | BD-8 | 32 | 0.144 | 0.061 |

Example 64, Comparative Example 64

Except that the compounds shown in the following table were used as the materials of the emitting layer (host material and dopant material), the organic EL devices were fabricated and evaluated in the same manner as in Example 1. The results are shown in Table 47.

TABLE 47

| | Emitting layer | | | Chromaticity | |
|---|---|---|---|---|---|
| | Host material | Dopant material | LT95(h) | CIEx | CIEy |
| Example 64 | BH-4 | BD-8 | 47 | 0.144 | 0.061 |
| Comparative Example 64 | BH-4-a | BD-8 | 29 | 0.144 | 0.061 |

Example 65, Comparative Example 65

Except that the compounds shown in the following table were used as the materials of the emitting layer (host material and dopant material), the organic EL devices were fabricated and evaluated in the same manner as in Example 1. The results are shown in Table 48.

TABLE 48

| | Emitting layer | | | Chromaticity | |
|---|---|---|---|---|---|
| | Host material | Dopant material | LT95(h) | CIEx | CIEy |
| Example 65 | BH-5 | BD-8 | 117 | 0.144 | 0.061 |
| Comparative Example 65 | BH-5-a | BD-8 | 75 | 0.144 | 0.061 |

Example 66, Comparative Example 66

Except that the compounds shown in the following table were used as the materials of the emitting layer (host material and dopant material), the organic EL devices were fabricated and evaluated in the same manner as in Example 1. The results are shown in Table 49.

TABLE 49

| | Emitting layer | | | | |
|---|---|---|---|---|---|
| | Host material | Dopant material | LT95(h) | Chromaticity CIEx | CIEy |
| Example 66 | BH-6 | BD-8 | 105 | 0.144 | 0.061 |
| Comparative Example 66 | BH-6-a | BD-8 | 65 | 0.144 | 0.061 |

Example 67, Comparative Example 67

Except that the compounds shown in the following table were used as the materials of the emitting layer (host material and dopant material), the organic EL devices were fabricated and evaluated in the same manner as in Example 1. The results are shown in Table 50.

TABLE 50

| | Emitting layer | | | | |
|---|---|---|---|---|---|
| | Host material | Dopant material | LT95(h) | Chromaticity CIEx | CIEy |
| Example 67 | BH-7 | BD-8 | 110 | 0.144 | 0.061 |
| Comparative Example 67 | BH-7-a | BD-8 | 66 | 0.144 | 0.061 |

Example 68, Comparative Example 68

Except that the compounds shown in following table were used as the materials of the emitting layer (host material and dopant material), the organic EL devices were fabricated and evaluated in the same manner as in Example 1. The results are shown in Table 51.

TABLE 51

| | Emitting layer | | | | |
|---|---|---|---|---|---|
| | Host material | Dopant material | LT95(h) | Chromaticity CIEx | CIEy |
| Example 68 | BH-1 | BD-9 | 111 | 0.141 | 0.056 |
| Comparative Example 68 | BH-1-a | BD-9 | 88 | 0.141 | 0.056 |

Example 69, Comparative Example 69

Except that the compounds shown in following table were used as the materials of the emitting layer (host material and dopant material), the organic EL devices were fabricated and evaluated in the same manner as in Example 1. The results are shown in Table 52.

TABLE 52

| | Emitting layer | | | | |
|---|---|---|---|---|---|
| | Host material | Dopant material | LT95(h) | Chromaticity CIEx | CIEy |
| Example 69 | BH-2 | BD-9 | 65 | 0.141 | 0.056 |
| Comparative Example 69 | BH-2-a | BD-9 | 46 | 0.141 | 0.056 |

Example 70, Comparative Example 70

Except that the compounds shown in following table were used as the materials of the emitting layer (host material and dopant material), the organic EL devices were fabricated and evaluated in the same manner as in Example 1. The results are shown in Table 53.

TABLE 53

| | Emitting layer | | | | |
|---|---|---|---|---|---|
| | Host material | Dopant material | LT95(h) | Chromaticity CIEx | CIEy |
| Example 70 | BH-3 | BD-9 | 60 | 0.141 | 0.056 |
| Comparative Example 70 | BH-3-a | BD-9 | 42 | 0.141 | 0.056 |

Example 71, Comparative Example 71

Except that the compounds shown in the following table were used as the materials of the emitting layer (host material and dopant material), the organic EL devices were fabricated and evaluated in the same manner as in Example 1. The results are shown in Table 54.

TABLE 54

| | Emitting layer | | | | |
|---|---|---|---|---|---|
| | Host material | Dopant material | LT95(h) | Chromaticity CIEx | CIEy |
| Example 71 | BH-5 | BD-9 | 137 | 0.141 | 0.057 |
| Comparative Example 71 | BH-5-a | BD-9 | 94 | 0.141 | 0.057 |

Example 72, Comparative Example 72

Except that the compounds shown in the following table were used as the materials of the emitting layer (host material and dopant material), the organic EL devices were fabricated and evaluated in the same manner as in Example 1. The results are shown in Table 55.

TABLE 55

| | Emitting layer | | | Chromaticity | |
|---|---|---|---|---|---|
| | Host material | Dopant material | LT95(h) | CIEx | CIEy |
| Example 72 | BH-6 | BD-9 | 118 | 0.141 | 0.056 |
| Comparative Example 72 | BH-6-a | BD-9 | 84 | 0.141 | 0.056 |

Example 73, Comparative Example 73

Except that the compounds shown in the following table were used as the materials of the emitting layer (host material and dopant material), the organic EL devices were fabricated and evaluated in the same manner as in Example 1. The results are shown in Table 56.

TABLE 56

| | Emitting layer | | | Chromaticity | |
|---|---|---|---|---|---|
| | Host material | Dopant material | LT95(h) | CIEx | CIEy |
| Example 73 | BH-7 | BD-9 | 136 | 0.141 | 0.056 |
| Comparative Example 73 | BH-7-a | BD-9 | 88 | 0.141 | 0.056 |

Example 74, Comparative Example 74

Except that the compounds shown in the following table were used as the materials of the emitting layer (host material and dopant material), the organic EL devices were fabricated and evaluated in the same manner as in Example 1. The results are shown in Table 57.

TABLE 57

| | Emitting layer | | | Chromaticity | |
|---|---|---|---|---|---|
| | Host material | Dopant material | LT95(h) | CIEx | CIEy |
| Example 74 | BH-8 | BD-9 | 89 | 0.141 | 0.056 |
| Comparative Example 74 | BH-8-a | BD-9 | 63 | 0.141 | 0.056 |

Example 75, Comparative Example 75

Except that the compounds shown in the following table were used as the materials of the emitting layer (host material and dopant material), the organic EL devices were fabricated and evaluated in the same manner as in Example 1. The results are shown in Table 58.

TABLE 58

| | Emitting layer | | | Chromaticity | |
|---|---|---|---|---|---|
| | Host material | Dopant material | LT95(h) | CIEx | CIEy |
| Example 75 | BH-9 | BD-9 | 100 | 0.141 | 0.056 |
| Comparative Example 75 | BH-9-a | BD-9 | 66 | 0.141 | 0.056 |

Example 76, Comparative Example 76

Except that the compounds shown in the following table were used as the materials of the emitting layer (host material and dopant material), the organic EL devices were fabricated and evaluated in the same manner as in Example 1. The results are shown in Table 59.

TABLE 59

| | Emitting layer | | | Chromaticity | |
|---|---|---|---|---|---|
| | Host material | Dopant material | LT95(h) | CIEx | CIEy |
| Example 76 | BH-10 | BD-9 | 90 | 0.141 | 0.056 |
| Comparative Example 76 | BH-10-a | BD-9 | 61 | 0.141 | 0.056 |

Example 77, Comparative Example 77

Except that the compounds shown in the following table were used as the materials of the emitting layer (host material and dopant material), the organic EL devices were fabricated and evaluated in the same manner as in Example 1. The results are shown in Table 60.

TABLE 60

| | Emitting layer | | | Chromaticity | |
|---|---|---|---|---|---|
| | Host material | Dopant material | LT95(h) | CIEx | CIEy |
| Example 77 | BH-11 | BD-9 | 77 | 0.141 | 0.056 |
| Comparative Example 77 | BH-11-a | BD-9 | 55 | 0.141 | 0.056 |

Example 78, Comparative Example 78

Except that the compounds shown in following table were used as the materials of the emitting layer (host material and dopant material), the organic EL devices were fabricated and evaluated in the same manner as in Example 1. The results are shown in Table 61.

TABLE 61

| | Emitting layer | | | | |
| --- | --- | --- | --- | --- | --- |
| | Host material | Dopant material | LT95(h) | Chromaticity CIEx | CIEy |
| Example 78 | BH-12 | BD-9 | 73 | 0.141 | 0.057 |
| Comparative Example 78 | BH-12-a | BD-9 | 47 | 0.141 | 0.057 |

Example 79, Comparative Example 79

Except that the compounds shown in following table were used as the materials of the emitting layer (host material and dopant material), the organic EL devices were fabricated and evaluated in the same manner as in Example 1. The results are shown in Table 62.

TABLE 62

| | Emitting layer | | | | |
| --- | --- | --- | --- | --- | --- |
| | Host material | Dopant material | LT95(h) | Chromaticity CIEx | CIEy |
| Example 79 | BH-13 | BD-9 | 66 | 0.141 | 0.056 |
| Comparative Example 79 | BH-13-a | BD-9 | 44 | 0.141 | 0.056 |

Example 80, Comparative Example 80

Except that the compounds shown in following table were used as the materials of the emitting layer (host material and dopant material), the organic EL devices were fabricated and evaluated in the same manner as in Example 1. The results are shown in Table 63.

TABLE 63

| | Emitting layer | | | | |
| --- | --- | --- | --- | --- | --- |
| | Hosting material | Dopant material | LT95(h) | Chromaticity CIEx | CIEy |
| Example 80 | BH-14 | BD-9 | 115 | 0.141 | 0.056 |
| Comparative Example 80 | BH-14-a | BD-9 | 83 | 0.141 | 0.056 |

Example 81, Comparative Example 81

Except that the compounds shown in the following table were used as the materials of the emitting layer (host material and dopant material), the organic EL devices were fabricated and evaluated in the same manner as in Example 1. The results are shown in Table 64.

TABLE 64

| | Emitting layer | | | | |
| --- | --- | --- | --- | --- | --- |
| | Hosting material | Dopant material | LT95(h) | Chromaticity CIEx | CIEy |
| Example 81 | BH-15 | BD-9 | 80 | 0.141 | 0.056 |
| Comparative Example 81 | BH-15-a | BD-9 | 55 | 0.141 | 0.056 |

Example 82, Comparative Example 82

Except that the compounds shown in the following table were used as the materials of the emitting layer (host material and dopant material), the organic EL devices were fabricated and evaluated in the same manner as in Example 1. The results are shown in Table 65.

TABLE 65

| | Emitting layer | | | | |
| --- | --- | --- | --- | --- | --- |
| | Hosting material | Dopant material | LT95(h) | Chromaticity CIEx | CIEy |
| Example 82 | BH-16 | BD-9 | 72 | 0.141 | 0.056 |
| Comparative Example 82 | BH-16-a | BD-9 | 55 | 0.141 | 0.056 |

Example 83

Except that the compounds shown in the following table were used as the materials of the emitting layer (host material and dopant material), the organic EL devices were fabricated and evaluated in the same manner as in Example 1. The results are shown in Table 66.

TABLE 66

| | Emitting layer | | | | |
| --- | --- | --- | --- | --- | --- |
| | Hosting material | Dopant material | LT95(h) | Chromaticity CIEx | CIEy |
| Example 83 | BH-17 | BD-9 | 110 | 0.141 | 0.056 |

Example 84, Comparative Example 84

Except that the compounds shown in the following table were used as the materials of the emitting layer (host material and dopant material), the organic EL devices were fabricated and evaluated in the same manner as in Example 1. The results are shown in Table 67.

TABLE 67

| | Emitting layer | | | | |
| --- | --- | --- | --- | --- | --- |
| | Hosting material | Dopant material | LT95(h) | Chromaticity CIEx | CIEy |
| Example 84 | BH-1 | BD-10 | 203 | 0.133 | 0.078 |
| Comparative Example 84 | BH-1-a | BD-10 | 143 | 0.133 | 0.078 |

Example 85, Comparative Example 85

Except that the compounds shown in the following table were used as the materials of the emitting layer (host material and dopant material), the organic EL devices were fabricated and evaluated in the same manner as in Example 1. The results are shown in Table 68.

TABLE 68

| | Emitting layer | | | | |
|---|---|---|---|---|---|
| | Hosting material | Dopant material | LT95(h) | Chromaticity CIEx | CIEy |
| Example 85 | BH-2 | BD-10 | 111 | 0.133 | 0.078 |
| Comparative Example 85 | BH-2-a | BD-10 | 77 | 0.133 | 0.078 |

Example 86, Comparative Example 86

Except that the compounds shown in the following table were used as the materials of the emitting layer (host material and dopant material), the organic EL devices were fabricated and evaluated in the same manner as in Example 1. The results are shown in Table 69.

TABLE 69

| | Emitting layer | | | | |
|---|---|---|---|---|---|
| | Hosting material | Dopant material | LT95(h) | Chromaticity CIEx | CIEy |
| Example 86 | BH-3 | BD-10 | 93 | 0.133 | 0.078 |
| Comparative Example 86 | BH-3-a | BD-10 | 64 | 0.133 | 0.078 |

Example 87, Comparative Example 87

Except that the compounds shown in the following table were used as the materials of the emitting layer (host material and dopant material), the organic EL devices were fabricated and evaluated in the same manner as in Example 1. The results are shown in Table 70.

TABLE 70

| | Emitting layer | | | | |
|---|---|---|---|---|---|
| | Hosting material | Dopant material | LT95(h) | Chromaticity CIEx | CIEy |
| Example 87 | BH-5 | BD-10 | 217 | 0.133 | 0.079 |
| Comparative Example 87 | BH-5-a | BD-10 | 154 | 0.133 | 0.079 |

Example 88, Comparative Example 88

Except that the compounds shown in following table were used as the materials of the emitting layer (host material and dopant material), the organic EL devices were fabricated and evaluated in the same manner as in Example 1. The results are shown in Table 71.

TABLE 71

| | Emitting layer | | | | |
|---|---|---|---|---|---|
| | Hosting material | Dopant material | LT95(h) | Chromaticity CIEx | CIEy |
| Example 88 | BH-6 | BD-10 | 208 | 0.133 | 0.078 |
| Comparative Example 88 | BH-6-a | BD-10 | 138 | 0.133 | 0.078 |

Example 89, Comparative Example 89

Except that the compounds shown in following table were used as the materials of the emitting layer (host material and dopant material), the organic EL devices were fabricated and evaluated in the same manner as in Example 1. The results are shown in Table 72.

TABLE 72

| | Emitting layer | | | | |
|---|---|---|---|---|---|
| | Hosting material | Dopant material | LT95(h) | Chromaticity CIEx | CIEy |
| Example 89 | BH-7 | BD-10 | 218 | 0.133 | 0.078 |
| Comparative Examole 89 | BH-7-a | BD-10 | 143 | 0.133 | 0.078 |

Example 90, Comparative Example 90

Except that the compounds shown in following table were used as the materials of the emitting layer (host material and dopant material), the organic EL devices were fabricated and evaluated in the same manner as in Example 1. The results are shown in Table 73.

TABLE 73

| | Emitting layer | | | | |
|---|---|---|---|---|---|
| | Hosting material | Dopant material | LT95(h) | Chromaticity CIEx | CIEy |
| Example 90 | BH-8 | BD-10 | 155 | 0.133 | 0.078 |
| Comparative Example 90 | BH-8-a | BD-10 | 110 | 0.133 | 0.078 |

Example 91, Comparative Example 91

Except that the compounds shown in the following table were used as the materials of the emitting layer (host material and dopant material), the organic EL devices were fabricated and evaluated in the same manner as in Example 1. The results are shown in Table 74.

TABLE 74

| | Emitting layer | | | | |
|---|---|---|---|---|---|
| | Hosting material | Dopant material | LT95(h) | Chromaticity CIEx | CIEy |
| Example 91 | BH-9 | BD-10 | 151 | 0.133 | 0.078 |
| Comparative Example 91 | BH-9-a | BD-10 | 110 | 0.133 | 0.078 |

Example 92, Comparative Example 92

Except that the compounds shown in the following table were used as the materials of the emitting layer (host material and dopant material), the organic EL devices were fabricated and evaluated in the same manner as in Example 1. The results are shown in Table 75.

TABLE 75

| | Emitting layer | | | | |
|---|---|---|---|---|---|
| | Hosting material | Dopant material | LT95(h) | Chromaticity CIEx | CIEy |
| Example 92 | BH-10 | BD-10 | 161 | 0.133 | 0.078 |
| Comparative Example 92 | BH-10-a | BD-10 | 105 | 0.133 | 0.078 |

Example 93, Comparative Example 93

Except that the compounds shown in the following table were used as the materials of the emitting layer (host material and dopant material), the organic EL devices were fabricated and evaluated in the same manner as in Example 1. The results are shown in Table 76.

TABLE 76

| | Emitting layer | | | | |
|---|---|---|---|---|---|
| | Hosting material | Dopant material | LT95(h) | Chromaticity CIEx | CIEy |
| Example 93 | BH-11 | BD-10 | 137 | 0.133 | 0.078 |
| Comparative Example 93 | BH-11-a | BD-10 | 92 | 0.133 | 0.078 |

Example 94, Comparative Example 94

Except that the compounds shown in the following table were used as the materials of the emitting layer (host material and dopant material), the organic EL devices were fabricated and evaluated in the same manner as in Example 1. The results are shown in Table 77.

TABLE 77

| | Emitting layer | | | | |
|---|---|---|---|---|---|
| | Hosting material | Dopant material | LT95(h) | Chromaticity CIEx | CIEy |
| Example 94 | BH-12 | BD-10 | 117 | 0.133 | 0.079 |
| Comparative Example 94 | BH-12-a | BD-10 | 77 | 0.133 | 0.079 |

Example 95, Comparative Example 95

Except that the compounds shown in the following table were used as the materials of the emitting layer (host material and dopant material), the organic EL devices were fabricated and evaluated in the same manner as in Example 1. The results are shown in Table 78.

TABLE 78

| | Emitting layer | | | | |
|---|---|---|---|---|---|
| | Hosting material | Dopant material | LT95(h) | Chromaticity CIEx | CIEy |
| Example 95 | BH-13 | BD-10 | 113 | 0.133 | 0.078 |
| Comparative Example 95 | BH-13-a | BD-10 | 75 | 0.133 | 0.078 |

Example 96, Comparative Example 96

Except that the compounds shown in the following table were used as the materials of the emitting layer (host material and dopant material), the organic EL devices were fabricated and evaluated in the same manner as in Example 1. The results are shown in Table 79.

TABLE 79

| | Emitting layer | | | | |
|---|---|---|---|---|---|
| | Hosting material | Dopant material | LT95(h) | Chromaticity CIEx | CIEy |
| Example 96 | BH-14 | BD-10 | 191 | 0.133 | 0.078 |
| Comparative Example 96 | BH-14-a | BD-10 | 138 | 0.133 | 0.078 |

Example 97, Comparative Example 97

Except that the compounds shown in the following table were used as the materials of the emitting layer (host material and dopant material), the organic EL devices were fabricated and evaluated in the same manner as in Example 1. The results are shown in Table 80.

TABLE 80

| | Emitting layer | | | | |
|---|---|---|---|---|---|
| | Hosting material | Dopant material | LT95(h) | Chromaticity CIEx | CIEy |
| Example 97 | BH-15 | BD-10 | 138 | 0.133 | 0.078 |
| Comparative Example 97 | BH-15-a | BD-10 | 94 | 0.133 | 0.078 |

Example 98, Comparative Example 98

Except that the compounds shown in following table were used as the materials of the emitting layer (host material and dopant material), the organic EL devices were fabricated and evaluated in the same manner as in Example 1. The results are shown in Table 81.

TABLE 81

| | Emitting layer | | | | |
|---|---|---|---|---|---|
| | Hosting material | Dopant material | LT95(h) | Chromaticity CIEx | CIEy |
| Example 98 | BH-16 | BD-10 | 141 | 0.133 | 0.078 |
| Comparative Example 98 | BH-16-a | BD-10 | 90 | 0.133 | 0.078 |

Example 99

Except that the compounds shown in following table were used as the materials of the emitting layer (host material and dopant material), the organic EL devices were fabricated and evaluated in the same manner as in Example 1. The results are shown in Table 82.

TABLE 82

| | Emitting layer | | | Chromaticity | |
|---|---|---|---|---|---|
| | Hosting material | Dopant material | LT95(h) | CIEx | CIEy |
| Example 99 | BH-17 | BD-11 | 209 | 0.133 | 0.078 |

Example 100, Comparative Example 100

Except that the compounds shown in following table were used as the materials of the emitting layer (host material and dopant material), the organic EL devices were fabricated and evaluated in the same manner as in Example 1. The results are shown in Table 83.

TABLE 83

| | Emitting layer | | | Chromaticity | |
|---|---|---|---|---|---|
| | Hosting material | Dopant material | LT95(h) | CIEx | CIEy |
| Example 100 | BH-1 | BD-11 | 191 | 0.133 | 0.076 |
| Comparative Example 100 | BH-1-a | BD-11 | 138 | 0.133 | 0.076 |

Example 101, Comparative Example 101

Except that the compounds shown in the following table were used as the materials of the emitting layer (host material and dopant material), the organic EL devices were fabricated and evaluated in the same manner as in Example 1. The results are shown in Table 84.

TABLE 84

| | Emitting layer | | | Chromaticity | |
|---|---|---|---|---|---|
| | Hosting material | Dopant material | LT95(h) | CIEx | CIEy |
| Example 101 | BH-2 | BD-11 | 97 | 0.133 | 0.076 |
| Comparative Example 101 | BH-2-a | BD-11 | 72 | 0.133 | 0.076 |

Example 102, Comparative Example 102

Except that the compounds shown in the following table were used as the materials of the emitting layer (host material and dopant material), the organic EL devices were fabricated and evaluated in the same manner as in Example 1. The results are shown in Table 85.

TABLE 85

| | Emitting layer | | | Chromaticity | |
|---|---|---|---|---|---|
| | Hosting material | Dopant material | LT95(h) | CIEx | CIEy |
| Example 102 | BH-3 | BD-11 | 91 | 0.133 | 0.076 |
| Comparative Example 102 | BH-3-a | BD-11 | 61 | 0.133 | 0.076 |

Example 103, Comparative Example 103

Except that the compounds shown in the following table were used as the materials of the emitting layer (host material and dopant material), the organic EL devices were fabricated and evaluated in the same manner as in Example 1. The results are shown in Table 86.

TABLE 86

| | Emitting layer | | | Chromaticity | |
|---|---|---|---|---|---|
| | Hosting material | Dopant material | LT95(h) | CIEx | CIEy |
| Example 103 | BH-5 | BD-11 | 207 | 0.133 | 0.077 |
| Comparative Example 103 | BH-5-a | BD-11 | 147 | 0.133 | 0.077 |

Example 104, Comparative Example 104

Except that the compounds shown in the following table were used as the materials of the emitting layer (host material and dopant material), the organic EL devices were fabricated and evaluated in the same manner as in Example 1. The results are shown in Table 87.

TABLE 87

| | Emitting layer | | | Chromaticity | |
|---|---|---|---|---|---|
| | Hosting material | Dopant material | LT95(h) | CIEx | CIEy |
| Example 104 | BH-6 | BD-11 | 181 | 0.133 | 0.076 |
| Comparative Example 104 | BH-6-a | BD-11 | 132 | 0.133 | 0.076 |

Example 105, Comparative Example 105

Except that the compounds shown in the following table were used as the materials of the emitting layer (host material and dopant material), the organic EL devices were fabricated and evaluated in the same manner as in Example 1. The results are shown in Table 88.

TABLE 88

| | Emitting layer | | | Chromaticity | |
|---|---|---|---|---|---|
| | Hosting material | Dopant material | LT95(h) | CIEx | CIEy |
| Example 105 | BH-7 | BD-11 | 199 | 0.133 | 0.076 |
| Comparative Example 105 | BH-7-a | BD-11 | 138 | 0.133 | 0.076 |

Example 106, Comparative Example 106

Except that the compounds shown in the following table were used as the materials of the emitting layer (host material and dopant material), the organic EL devices were fabricated and evaluated in the same manner as in Example 1. The results are shown in Table 89.

TABLE 89

| | Emitting layer | | | Chromaticity | |
|---|---|---|---|---|---|
| | Hosting material | Dopant material | LT95(h) | CIEx | CIEy |
| Example 106 | BH-8 | BD-11 | 153 | 0.133 | 0.076 |
| Comparative Example 106 | BH-8-a | BD-11 | 105 | 0.133 | 0.076 |

Example 107, Comparative Example 107

Except that the compounds shown in the following table were used as the materials of the emitting layer (host material and dopant material), the organic EL devices were fabricated and evaluated in the same manner as in Example 1. The results are shown in Table 90.

TABLE 90

| | Emitting layer | | | Chromaticity | |
|---|---|---|---|---|---|
| | Hosting material | Dopant material | LT95(h) | CIEx | CIEy |
| Example 107 | BH-9 | BD-11 | 145 | 0.133 | 0.076 |
| Comparative Example 107 | BH-9-a | BD-11 | 102 | 0.133 | 0.076 |

Example 108, Comparative Example 108

Except that the compounds shown in following table were used as the materials of the emitting layer (host material and dopant material), the organic EL devices were fabricated and evaluated in the same manner as in Example 1. The results are shown in Table 91.

TABLE 91

| | Emitting layer | | | Chromaticity | |
|---|---|---|---|---|---|
| | Hosting material | Dopant material | LT95(h) | CIEx | CIEy |
| Example 108 | BH-10 | BD-11 | 124 | 0.133 | 0.076 |
| Comparative Example 108 | BH-10-a | BD-11 | 97 | 0.133 | 0.076 |

Example 109, Comparative Example 109

Except that the compounds shown in following table were used as the materials of the emitting layer (host material and dopant material), the organic EL devices were fabricated and evaluated in the same manner as in Example 1. The results are shown in Table 92.

TABLE 92

| | Emitting layer | | | Chromaticity | |
|---|---|---|---|---|---|
| | Hosting material | Dopant material | LT95(h) | CIEx | CIEy |
| Example 109 | BH-11 | BD-11 | 108 | 0.133 | 0.076 |
| Comparative Example 109 | BH-11-a | BD-11 | 83 | 0.133 | 0.076 |

Example 110, Comparative Example 110

Except that the compounds shown in following table were used as the materials of the emitting layer (host material and dopant material), the organic EL devices were fabricated and evaluated in the same manner as in Example 1. The results are shown in Table 93.

TABLE 93

| | Emitting layer | | | Chromaticity | |
|---|---|---|---|---|---|
| | Hosting material | Dopant material | LT95(h) | CIEx | CIEy |
| Example 110 | BH-12 | BD-11 | 101 | 0.133 | 0.077 |
| Comparative Example 110 | BH-12-a | BD-11 | 74 | 0.133 | 0.077 |

Example 111, Comparative Example 111

Except that the compounds shown in the following table were used as the materials of the emitting layer (host material and dopant material), the organic EL devices were fabricated and evaluated in the same manner as in Example 1. The results are shown in Table 94.

TABLE 94

| | Emitting layer | | | Chromaticity | |
|---|---|---|---|---|---|
| | Hosting material | Dopant material | LT95(h) | CIEx | CIEy |
| Example 111 | BH-13 | BD-11 | 102 | 0.133 | 0.076 |
| Comparative Example 111 | BH-13-a | BD-11 | 66 | 0.133 | 0.076 |

Example 112, Comparative Example 112

Except that the compounds shown in the following table were used as the materials of the emitting layer (host material and dopant material), the organic EL devices were fabricated and evaluated in the same manner as in Example 1. The results are shown in Table 95.

TABLE 95

| | Emitting layer | | | | |
| --- | --- | --- | --- | --- | --- |
| | Hosting material | Dopant material | LT95(h) | Chromaticity CIEx | CIEy |
| Example 112 | BH-14 | BD-11 | 186 | 0.133 | 0.076 |
| Comparative Example 112 | BH-14-a | BD-11 | 130 | 0.133 | 0.076 |

Example 113, Comparative Example 113

Except that the compounds shown in the following table were used as the materials of the emitting layer (host material and dopant material), the organic EL devices were fabricated and evaluated in the same manner as in Example 1. The results are shown in Table 96.

TABLE 96

| | Emitting layer | | | | |
| --- | --- | --- | --- | --- | --- |
| | Hosting material | Dopant material | LT95(h) | Chromaticity CIEx | CIEy |
| Example 113 | BH-15 | BD-11 | 128 | 0.133 | 0.076 |
| Comparative Example 113 | BH-15-a | BD-11 | 88 | 0.133 | 0.076 |

Example 114, Comparative Example 114

Except that the compounds shown in the following table were used as the materials of the emitting layer (host material and dopant material), the organic EL devices were fabricated and evaluated in the same manner as in Example 1. The results are shown in Table 97.

TABLE 97

| | Emitting layer | | | | |
| --- | --- | --- | --- | --- | --- |
| | Hosting material | Dopant material | LT95(h) | Chromaticity CIEx | CIEy |
| Example 114 | BH-16 | BD-11 | 128 | 0.133 | 0.076 |
| Comparative Example 114 | BH-16-a | BD-11 | 87 | 0.133 | 0.076 |

Example 115

Except that the compounds shown in the following table were used as the materials of the emitting layer (host material and dopant material), the organic EL devices were fabricated and evaluated in the same manner as in Example 1. The results are shown in Table 98.

TABLE 98

| | Emitting layer | | | | |
| --- | --- | --- | --- | --- | --- |
| | Hosting material | Dopant material | LT95(h) | Chromaticity CIEx | CIEy |
| Example 115 | BH-17 | BD-11 | 190 | 0.133 | 0.076 |

Example 116, Comparative Example 116

Except that the compounds shown in the following table were used as the materials of the emitting layer (host material and dopant material), the organic EL devices were fabricated and evaluated in the same manner as in Example 1. The results are shown in Table 99.

TABLE 99

| | Emitting layer | | | | |
| --- | --- | --- | --- | --- | --- |
| | Hosting material | Dopant material | LT95(h) | Chromaticity CIEx | CIEy |
| Example 116 | BH-1 | BD-12 | 123 | 0.141 | 0.058 |
| Comparative Example 116 | BH-1-a | BD-12 | 94 | 0.141 | 0.058 |

Example 117, Comparative Example 117

Except that the compounds shown in the following table were used as the materials of the emitting layer (host material and dopant material), the organic EL devices were fabricated and evaluated in the same manner as in Example 1. The results are shown in Table 100.

TABLE 100

| | Emitting layer | | | | |
| --- | --- | --- | --- | --- | --- |
| | Hosting material | Dopant material | LT95(h) | Chromaticity CIEx | CIEy |
| Example 117 | BH-2 | BD-12 | 70 | 0.141 | 0.058 |
| Comparative Example 117 | BH-2-a | BD-12 | 52 | 0.141 | 0.058 |

Example 118, Comparative Example 118

Except that the compounds shown in following table were used as the materials of the emitting layer (host material and dopant material), the organic EL devices were fabricated and evaluated in the same manner as in Example 1. The results are shown in Table 101.

TABLE 101

| | Emitting layer | | | | |
| --- | --- | --- | --- | --- | --- |
| | Hosting material | Dopant material | LT95(h) | Chromaticity CIEx | CIEy |
| Example 118 | BH-3 | BD-12 | 66 | 0.141 | 0.058 |
| Comparative Example 118 | BH-3-a | BD-12 | 44 | 0.141 | 0.058 |

Example 119, Comparative Example 119

Except that the compounds shown in following table were used as the materials of the emitting layer (host material and dopant material), the organic EL devices were fabricated and evaluated in the same manner as in Example 1. The results are shown in Table 102.

TABLE 102

| | Emitting layer | | | | |
|---|---|---|---|---|---|
| | Hosting material | Dopant material | LT95(h) | Chromaticity CIEx | CIEy |
| Example 119 | BH-5 | BD-12 | 149 | 0.141 | 0.059 |
| Comparative Example 119 | BH-5-a | BD-12 | 101 | 0.141 | 0.059 |

Example 120, Comparative Example 120

Except that the compounds shown in following table were used as the materials of the emitting layer (host material and dopant material), the organic EL devices were fabricated and evaluated in the same manner as in Example 1. The results are shown in Table 103.

TABLE 103

| | Emitting layer | | | | |
|---|---|---|---|---|---|
| | Hosting material | Dopant material | LT95(h) | Chromaticity CIEx | CIEy |
| Example 120 | BH-6 | BD-12 | 123 | 0.141 | 0.058 |
| Comparative Example 120 | BH-6-a | BD-12 | 92 | 0.141 | 0.058 |

Example 121, Comparative Example 121

Except that the compounds shown in the following table were used as the materials of the emitting layer (host material and dopant material), the organic EL devices were fabricated and evaluated in the same manner as in Example 1. The results are shown in Table 104.

TABLE 104

| | Emitting layer | | | | |
|---|---|---|---|---|---|
| | Hosting material | Dopant material | LT95(h) | Chromaticity CIEx | CIEy |
| Example 121 | BH-7 | BD-12 | 145 | 0.141 | 0.058 |
| Comparative Example 121 | BH-7-a | BD-12 | 96 | 0.141 | 0.058 |

Example 122, Comparative Example 122

Except that the compounds shown in the following table were used as the materials of the emitting layer (host material and dopant material), the organic EL devices were fabricated and evaluated in the same manner as in Example 1. The results are shown in Table 105.

TABLE 105

| | Emitting layer | | | | |
|---|---|---|---|---|---|
| | Hosting material | Dopant material | LT95(h) | Chromaticity CIEx | CIEy |
| Example 122 | BH-8 | BD-12 | 115 | 0.141 | 0.058 |
| Comparative Example 122 | BH-8-a | BD-12 | 79 | 0.141 | 0.058 |

Example 123, Comparative Example 123

Except that the compounds shown in the following table were used as the materials of the emitting layer (host material and dopant material), the organic EL devices were fabricated and evaluated in the same manner as in Example 1. The results are shown in Table 106.

TABLE 106

| | Emitting layer | | | | |
|---|---|---|---|---|---|
| | Hosting material | Dopant material | LT95(h) | Chromaticity CIEx | CIEy |
| Example 123 | BH-9 | BD-12 | 106 | 0.141 | 0.058 |
| Comparative Example 123 | BH-9-a | BD-12 | 72 | 0.141 | 0.058 |

Example 124, Comparative Example 124

Except that the compounds shown in the following table were used as the materials of the emitting layer (host material and dopant material), the organic EL devices were fabricated and evaluated in the same manner as in Example 1. The results are shown in Table 107.

TABLE 107

| | Emitting layer | | | | |
|---|---|---|---|---|---|
| | Hosting material | Dopant material | LT95(h) | Chromaticity CIEx | CIEy |
| Example 124 | BH-10 | BD-12 | 98 | 0.141 | 0.058 |
| Comparative Example 124 | BH-10-a | BD-12 | 65 | 0.141 | 0.058 |

Example 125, Comparative Example 125

Except that the compounds shown in the following table were used as the materials of the emitting layer (host material and dopant material), the organic EL devices were fabricated and evaluated in the same manner as in Example 1. The results are shown in Table 108.

TABLE 108

| | Emitting layer | | | | |
|---|---|---|---|---|---|
| | Hosting material | Dopant material | LT95(h) | Chromaticity CIEx | CIEy |
| Example 125 | BH-11 | BD-12 | 82 | 0.141 | 0.058 |
| Comparative Example 125 | BH-11-a | BD-12 | 57 | 0.141 | 0.058 |

Example 126, Comparative Example 126

Except that the compounds shown in the following table were used as the materials of the emitting layer (host material and dopant material), the organic EL devices were fabricated and evaluated in the same manner as in Example 1. The results are shown in Table 109.

TABLE 109

| | Emitting layer | | | Chromaticity | |
|---|---|---|---|---|---|
| | Hosting material | Dopant material | LT95(h) | CIEx | CIEy |
| Example 126 | BH-12 | BD-12 | 79 | 0.141 | 0.059 |
| Comparative Example 126 | BH-12-a | BD-12 | 52 | 0.141 | 0.059 |

Example 127, Comparative Example 127

Except that the compounds shown in the following table were used as the materials of the emitting layer (host material and dopant material), the organic EL devices were fabricated and evaluated in the same manner as in Example 1. The results are shown in Table 110.

TABLE 110

| | Emitting layer | | | Chromaticity | |
|---|---|---|---|---|---|
| | Hosting material | Dopant material | LT95(h) | CIEx | CIEy |
| Example 127 | BH-13 | BD-12 | 79 | 0.141 | 0.058 |
| Comparative Example 127 | BH-13-a | BD-12 | 55 | 0.141 | 0.058 |

Example 128, Comparative Example 128

Except that the compounds shown in following table were used as the materials of the emitting layer (host material and dopant material), the organic EL devices were fabricated and evaluated in the same manner as in Example 1. The results are shown in Table 111.

TABLE 111

| | Emitting layer | | | Chromaticity | |
|---|---|---|---|---|---|
| | Hosting material | Dopant material | LT95(h) | CIEx | CIEy |
| Example 128 | BH-14 | BD-12 | 123 | 0.141 | 0.058 |
| Comparative Example 128 | BH-14-a | BD-12 | 88 | 0.141 | 0.058 |

Example 129, Comparative Example 129

Except that the compounds shown in following table were used as the materials of the emitting layer (host material and dopant material), the organic EL devices were fabricated and evaluated in the same manner as in Example 1. The results are shown in Table 112.

TABLE 112

| | Emitting layer | | | Chromaticity | |
|---|---|---|---|---|---|
| | Hosting material | Dopant material | LT95(h) | CIEx | CIEy |
| Example 129 | BH-15 | BD-12 | 93 | 0.141 | 0.058 |
| Comparative Example 129 | BH-15-a | BD-12 | 63 | 0.141 | 0.058 |

Example 130, Comparative Example 130

Except that the compounds shown in following table were used as the materials of the emitting layer (host material and dopant material), the organic EL devices were fabricated and evaluated in the same manner as in Example 1. The results are shown in Table 113.

TABLE 113

| | Emitting layer | | | Chromaticity | |
|---|---|---|---|---|---|
| | Hosting material | Dopant material | LT95(h) | CIEx | CIEy |
| Example 130 | BH-16 | BD-12 | 81 | 0.141 | 0.058 |
| Comparative Example 130 | BH-16-a | BD-12 | 61 | 0.141 | 0.058 |

Example 131

Except that the compounds shown in following table were used as the materials of the emitting layer (host material and dopant material), the organic EL devices were fabricated and evaluated in the same manner as in Example 1. The results are shown in Table 114.

TABLE 114

| | Emitting layer | | | Chromaticity | |
|---|---|---|---|---|---|
| | Hosting material | Dopant material | LT95(h) | CIEx | CIEy |
| Example 131 | BH-17 | BD-12 | 120 | 0.141 | 0.058 |

Example 132 and Comparative Example 132

Except that the compounds shown in following table were used as the materials of the emitting layer (host material and dopant material), the organic EL devices were fabricated and evaluated in the same manner as in Example 1. The results are shown in the following Table.

TABLE 115

| | Emitting layer | | | Chromaticity | |
|---|---|---|---|---|---|
| | Hosting material | Dopant material | LT95(h) | CIEx | CIEy |
| Example 132 | BH-8 | BD-3 | 98 | 0.140 | 0.080 |
| Comparative Example 132 | BH-8-a | BD-3 | 64 | 0.140 | 0.080 |

Example 133 and Comparative Example 133

Except that the compounds shown in following table were used as the materials of the emitting layer (host material and dopant material), the organic EL devices were fabricated and evaluated in the same manner as in Example 1. The results are shown in the following Table.

TABLE 116

| | Emitting layer | | | Chromaticity | |
|---|---|---|---|---|---|
| | Hosting material | Dopant material | LT95(h) | CIEx | CIEy |
| Example 133 | BH-9 | BD-3 | 100 | 0.140 | 0.080 |
| Comparative Example 133 | BH-9-a | BD-3 | 64 | 0.140 | 0.080 |

Example 134 and Comparative Example 134

Except that the compounds shown in following table were used as the materials of the emitting layer (host material and dopant material), the organic EL devices were fabricated and evaluated in the same manner as in Example 1. The results are shown in the following Table.

TABLE 117

| | Emitting layer | | | Chromaticity | |
|---|---|---|---|---|---|
| | Hosting material | Dopant material | LT95(h) | CIEx | CIEy |
| Example 134 | BH-10 | BD-3 | 94 | 0.140 | 0.080 |
| Comparative Example 134 | BH-10-a | BD-3 | 58 | 0.140 | 0.080 |

Example 135 and Comparative Example 135

Except that the compounds shown in following table were used as the materials of the emitting layer (host material and dopant material), the organic EL devices were fabricated and evaluated in the same manner as in Example 1. The results are shown in the following Table.

TABLE 118

| | Emitting layer | | | Chromaticity | |
|---|---|---|---|---|---|
| | Hosting material | Dopant material | LT95(h) | CIEx | CIEy |
| Example 135 | BH-11 | BD-3 | 83 | 0.140 | 0.081 |
| Comparative Example 135 | BH-11-a | BD-3 | 50 | 0.140 | 0.080 |

Example 136 and Comparative Example 136

Except that the compounds shown in following table were used as the materials of the emitting layer (host material and dopant material), the organic EL devices were fabricated and evaluated in the same manner as in Example 1. The results are shown in the following Table.

TABLE 119

| | Emitting layer | | | Chromaticity | |
|---|---|---|---|---|---|
| | Hosting material | Dopant material | LT95(h) | CIEx | CIEy |
| Example 136 | BH-12 | BD-3 | 73 | 0.140 | 0.080 |
| Comparative Example 136 | BH-12-a | BD-3 | 45 | 0.140 | 0.080 |

Example 137 and Comparative Example 137

Except that the compounds shown in following table were used as the materials of the emitting layer (host material and dopant material), the organic EL devices were fabricated and evaluated in the same manner as in Example 1. The results are shown in the following Table.

TABLE 120

| | Emitting layer | | | Chromaticity | |
|---|---|---|---|---|---|
| | Hosting material | Dopant material | LT95(h) | CIEx | CIEy |
| Example 137 | BH-13 | BD-3 | 65 | 0.140 | 0.080 |
| Comparative Example 137 | BH-13-a | BD-3 | 40 | 0.140 | 0.080 |

Example 138 and Comparative Example 138

Except that the compounds shown in following table were used as the materials of the emitting layer (host material and dopant material), the organic EL devices were fabricated and evaluated in the same manner as in Example 1. The results are shown in the following Table.

TABLE 121

| | Emitting layer | | | | |
|---|---|---|---|---|---|
| | Hosting material | Dopant material | LT95(h) | Chromaticity CIEx | CIEy |
| Example 138 | BH-14 | BD-3 | 127 | 0.140 | 0.080 |
| Comparative Example 138 | BH-14-a | BD-3 | 75 | 0.140 | 0.080 |

Example 139 and Comparative Example 139

Except that the compounds shown in following table were used as the materials of the emitting layer (host material and dopant material), the organic EL devices were fabricated and evaluated in the same manner as in Example 1. The results are shown in the following Table.

TABLE 122

| | Emitting layer | | | | |
|---|---|---|---|---|---|
| | Hosting material | Dopant material | LT95(h) | Chromaticity CIEx | CIEy |
| Example 139 | BH-15 | BD-3 | 88 | 0.140 | 0.080 |
| Comparative Example 139 | BH-15-a | BD-3 | 54 | 0.140 | 0.080 |

Example 140 and Comparative Example 140

Except that the compounds shown in following table were used as the materials of the emitting layer (host material and dopant material), the organic EL devices were fabricated and evaluated in the same manner as in Example 1. The results are shown in the following Table.

TABLE 123

| | Emitting layer | | | | |
|---|---|---|---|---|---|
| | Host material | Dopant material | LT95(h) | Chromaticity CIEx | CIEy |
| Example 140 | BH-16 | BD-3 | 84 | 0.140 | 0.080 |
| Comparative Example 140 | BH-16-a | BD-3 | 52 | 0.140 | 0.080 |

Example 141

Except that the compounds shown in following table were used as the materials of the emitting layer (host material and dopant material), the organic EL device was fabricated and evaluated in the same manner as in Example 1. The results are shown in the following Table.

TABLE 124

| | Emitting layer | | | | |
|---|---|---|---|---|---|
| | Host material | Dopant material | LT95(h) | Chromaticity CIEx | CIEy |
| Example 141 | BH-17 | BD-3 | 131 | 0.140 | 0.080 |

Example 142 and Comparative Example 142

Except that the compounds shown in following table were used as the materials of the emitting layer (host material and dopant material), the organic EL devices were fabricated and evaluated in the same manner as in Example 1. The results are shown in the following Table.

TABLE 125

| | Emitting layer | | | | |
|---|---|---|---|---|---|
| | Host material | Dopant material | LT95(h) | Chromaticity CIEx | CIEy |
| Example 142 | BH-8 | BD-4 | 118 | 0.135 | 0.098 |
| Comparative Example 142 | BH-8-a | BD-4 | 75 | 0.135 | 0.098 |

Example 143 and Comparative Example 143

Except that the compounds shown in following table were used as the materials of the emitting layer (host material and dopant material), the organic EL devices were fabricated and evaluated in the same manner as in Example 1. The results are shown in the following Table.

TABLE 126

| | Emitting layer | | | | |
|---|---|---|---|---|---|
| | Host material | Dopant material | LT95(h) | Chromaticity CIEx | CIEy |
| Example 143 | BH-9 | BD-4 | 112 | 0.135 | 0.098 |
| Comparative Example 143 | BH-9-a | BD-4 | 72 | 0.135 | 0.098 |

Example 144 and Comparative Example 144

Except that the compounds shown in following table were used as the materials of the emitting layer (host material and dopant material), the organic EL devices were fabricated and evaluated in the same manner as in Example 1. The results are shown in the following Table.

TABLE 127

| | Emitting layer | | | | |
|---|---|---|---|---|---|
| | Host material | Dopant material | LT95(h) | Chromaticity CIEx | CIEy |
| Example 144 | BH-10 | BD-4 | 105 | 0.135 | 0.098 |
| Comparative Example 144 | BH-10-a | BD-4 | 66 | 0.135 | 0.098 |

Example 145 and Comparative Example 145

Except that the compounds shown in following table were used as the materials of the emitting layer (host material and dopant material), the organic EL devices were fabricated and evaluated in the same manner as in Example 1. The results are shown in the following Table.

TABLE 128

| | Emitting layer | | | Chromaticity | |
|---|---|---|---|---|---|
| | Host material | Dopant material | LT95(h) | CIEx | CIEy |
| Example 145 | BH-11 | BD-4 | 90 | 0.135 | 0.098 |
| Comparative Example 145 | BH-11-a | BD-4 | 60 | 0.135 | 0.098 |

Example 146 and Comparative Example 146

Except that the compounds shown in following table were used as the materials of the emitting layer (host material and dopant material), the organic EL devices were fabricated and evaluated in the same manner as in Example 1. The results are shown in the following Table.

TABLE 129

| | Emitting layer | | | Chromaticity | |
|---|---|---|---|---|---|
| | Host material | Dopant material | LT95(h) | CIEx | CIEy |
| Example 146 | BH-12 | BD-4 | 80 | 0.135 | 0.098 |
| Comparative Example 146 | BH-12-a | BD-4 | 53 | 0.135 | 0.098 |

Example 147 and Comparative Example 147

Except that the compounds shown in following table were used as the materials of the emitting layer (host material and dopant material), the organic EL devices were fabricated and evaluated in the same manner as in Example 1. The results are shown in the following Table.

TABLE 130

| | Emitting layer | | | Chromaticity | |
|---|---|---|---|---|---|
| | Host material | Dopant material | LT95(h) | CIEx | CIEy |
| Example 147 | BH-13 | BD-4 | 70 | 0.135 | 0.098 |
| Comparative Example 147 | BH-13-a | BD-4 | 46 | 0.135 | 0.098 |

Example 148 and Comparative Example 148

Except that the compounds shown in following table were used as the materials of the emitting layer (host material and dopant material), the organic EL devices were fabricated and evaluated in the same manner as in Example 1. The results are shown in the following Table.

TABLE 131

| | Emitting layer | | | Chromaticity | |
|---|---|---|---|---|---|
| | Host material | Dopant material | LT95(h) | CIEx | CIEy |
| Example 148 | BH-14 | BD-4 | 150 | 0.135 | 0.098 |
| Comparative Example 148 | BH-14-a | BD-4 | 92 | 0.135 | 0.098 |

Example 149 and Comparative Example 149

Except that the compounds shown in following table were used as the materials of the emitting layer (host material and dopant material), the organic EL devices were fabricated and evaluated in the same manner as in Example 1. The results are shown in the following Table.

TABLE 132

| | Emitting layer | | | Chromaticity | |
|---|---|---|---|---|---|
| | Host material | Dopant material | LT95(h) | CIEx | CIEy |
| Example 149 | BH-15 | BD-4 | 102 | 0.135 | 0.098 |
| Comparative Example 149 | BH-15-a | BD-4 | 64 | 0.135 | 0.098 |

Example 150 and Comparative Example 150

Except that the compounds shown in following table were used as the materials of the emitting layer (host material and dopant material), the organic EL devices were fabricated and evaluated in the same manner as in Example 1. The results are shown in the following Table.

TABLE 133

| | Emitting layer | | | Chromaticity | |
|---|---|---|---|---|---|
| | Host material | Dopant material | LT95(h) | CIEx | CIEy |
| Example 150 | BH-16 | BD-4 | 96 | 0.135 | 0.098 |
| Comparative Example 150 | BH-16-a | BD-4 | 60 | 0.135 | 0.099 |

Example 151

Except that the compounds shown in following table were used as the materials of the emitting layer (host material and dopant material), the organic EL device was fabricated and evaluated in the same manner as in Example 1. The results are shown in the following Table.

TABLE 134

| | Emitting layer | | | Chromaticity | |
|---|---|---|---|---|---|
| | Host material | Dopant material | LT95(h) | CIEx | CIEy |
| Example 151 | BH-17 | BD-4 | 157 | 0.135 | 0.098 |

Example 152 and Comparative Example 152

Except that the compounds shown in following table were used as the materials of the emitting layer (host material and dopant material), the organic EL devices were fabricated and evaluated in the same manner as in Example 1. The results are shown in the following Table.

TABLE 135

| | Emitting layer | | | Chromaticity | |
|---|---|---|---|---|---|
| | Host material | Dopant material | LT95(h) | CIEx | CIEy |
| Example 152 | BH-8 | BD-5 | 126 | 0.135 | 0.086 |
| Comparative Example 152 | BH-8-a | BD-5 | 80 | 0.135 | 0.086 |

Example 153 and Comparative Example 153

Except that the compounds shown in following table were used as the materials of the emitting layer (host material and dopant material), the organic EL devices were fabricated and evaluated in the same manner as in Example 1. The results are shown in the following Table.

TABLE 136

| | Emitting layer | | | Chromaticity | |
|---|---|---|---|---|---|
| | Host material | Dopant material | LT95(h) | CIEx | CIEy |
| Example 153 | BH-9 | BD-5 | 126 | 0.135 | 0.086 |
| Comparative Example 153 | BH-9-a | BD-5 | 76 | 0.135 | 0.086 |

Example 154 and Comparative Example 154

Except that the compounds shown in following table were used as the materials of the emitting layer (host material and dopant material), the organic EL devices were fabricated and evaluated in the same manner as in Example 1. The results are shown in the following Table.

TABLE 137

| | Emitting layer | | | Chromaticity | |
|---|---|---|---|---|---|
| | Host material | Dopant material | LT95(h) | CIEx | CIEy |
| Example 154 | BH-10 | BD-5 | 110 | 0.135 | 0.085 |
| Comparative Example 154 | BH-10-a | BD-5 | 70 | 0.135 | 0.086 |

Example 155 and Comparative Example 155

Except that the compounds shown in following table were used as the materials of the emitting layer (host material and dopant material), the organic EL devices were fabricated and evaluated in the same manner as in Example 1. The results are shown in the following Table.

TABLE 138

| | Emitting layer | | | Chromaticity | |
|---|---|---|---|---|---|
| | Host material | Dopant material | LT95(h) | CIEx | CIEy |
| Example 155 | BH-11 | BD-5 | 103 | 0.135 | 0.086 |
| Comparative Example 155 | BH-11-a | BD-5 | 60 | 0.135 | 0.086 |

Example 156 and Comparative Example 156

Except that the compounds shown in following table were used as the materials of the emitting layer (host material and dopant material), the organic EL devices were fabricated and evaluated in the same manner as in Example 1. The results are shown in the following Table.

TABLE 139

| | Emitting layer | | | Chromaticity | |
|---|---|---|---|---|---|
| | Host material | Dopant material | LT95(h) | CIEx | CIEy |
| Example 156 | BH-12 | BD-5 | 90 | 0.135 | 0.086 |
| Comparative Example 156 | BH-12-a | BD-5 | 56 | 0.135 | 0.086 |

Example 157 and Comparative Example 157

Except that the compounds shown in following table were used as the materials of the emitting layer (host material and dopant material), the organic EL devices were fabricated and evaluated in the same manner as in Example 1. The results are shown in the following Table.

TABLE 140

| | Emitting layer | | | Chromaticity | |
|---|---|---|---|---|---|
| | Host material | Dopant material | LT95(h) | CIEx | CIEy |
| Example 157 | BH-13 | BD-5 | 80 | 0.135 | 0.086 |
| Comparative Example 157 | BH-13-a | BD-5 | 50 | 0.135 | 0.086 |

Example 158 and Comparative Example 158

Except that the compounds shown in following table were used as the materials of the emitting layer (host material and dopant material), the organic EL devices were fabricated and evaluated in the same manner as in Example 1. The results are shown in the following Table.

TABLE 141

| | Emitting layer | | | | |
|---|---|---|---|---|---|
| | Host material | Dopant material | LT95(h) | Chromaticity CIEx | CIEy |
| Example 158 | BH-14 | BD-5 | 157 | 0.135 | 0.086 |
| Comparative Example 158 | BH-14-a | BD-5 | 92 | 0.135 | 0.085 |

Example 159 and Comparative Example 159

Except that the compounds shown in following table were used as the materials of the emitting layer (host material and dopant material), the organic EL devices were fabricated and evaluated in the same manner as in Example 1. The results are shown in the following Table.

TABLE 142

| | Emitting layer | | | | |
|---|---|---|---|---|---|
| | Host material | Dopant material | LT95(h) | Chromaticity CIEx | CIEy |
| Example 159 | BH-15 | BD-5 | 110 | 0.135 | 0.086 |
| Comparative Example 159 | BH-15-a | BD-5 | 65 | 0.135 | 0.086 |

Example 160 and Comparative Example 160

Except that the compounds shown in following table were used as the materials of the emitting layer (host material and dopant material), the organic EL devices were fabricated and evaluated in the same manner as in Example 1. The results are shown in the following Table.

TABLE 143

| | Emitting layer | | | | |
|---|---|---|---|---|---|
| | Host material | Dopant material | LT95(h) | Chromaticity CIEx | CIEy |
| Example 160 | BH-16 | BD-5 | 100 | 0.135 | 0.086 |
| Comparative Example 160 | BH-16-a | BD-5 | 60 | 0.135 | 0.086 |

Example 161

Except that the compounds shown in following table were used as the materials of the emitting layer (host material and dopant material), the organic EL device was fabricated and evaluated in the same manner as in Example 1. The results are shown in the following Table.

TABLE 144

| | Emitting layer | | | | |
|---|---|---|---|---|---|
| | Host material | Dopant material | LT95(h) | Chromaticity CIEx | CIEy |
| Example 161 | BH-17 | BD-5 | 165 | 0.135 | 0.086 |

Example 162 and Comparative Example 162

Except that the compounds shown in following table were used as the materials of the emitting layer (host material and dopant material), the organic EL devices were fabricated and evaluated in the same manner as in Example 1. The results are shown in the following Table.

TABLE 145

| | Emitting layer | | | | |
|---|---|---|---|---|---|
| | Host material | Dopant material | LT95(h) | Chromaticity CIEx | CIEy |
| Example 162 | BH-8 | BD-6 | 150 | 0.135 | 0.080 |
| Comparative Example 162 | BH-8-a | BD-6 | 90 | 0.135 | 0.080 |

Example 163 and Comparative Example 163

Except that the compounds shown in following table were used as the materials of the emitting layer (host material and dopant material), the organic EL devices were fabricated and evaluated in the same manner as in Example 1. The results are shown in the following Table.

TABLE 146

| | Emitting layer | | | | |
|---|---|---|---|---|---|
| | Host material | Dopant material | LT95(h) | Chromaticity CIEx | CIEy |
| Example 163 | BH-9 | BD-6 | 155 | 0.135 | 0.080 |
| Comparative Example 163 | BH-9-a | BD-6 | 90 | 0.135 | 0.080 |

Example 164 and Comparative Example 164

Except that the compounds shown in following table were used as the materials of the emitting layer (host material and dopant material), the organic EL devices were fabricated and evaluated in the same manner as in Example 1. The results are shown in the following Table.

TABLE 147

| | Emitting layer | | | | |
|---|---|---|---|---|---|
| | Host material | Dopant material | LT95(h) | Chromaticity CIEx | CIEy |
| Example 164 | BH-10 | BD-6 | 143 | 0.135 | 0.080 |
| Comparative Example 164 | BH-10-a | BD-6 | 88 | 0.135 | 0.080 |

Example 165 and Comparative Example 165

Except that the compounds shown in following table were used as the materials of the emitting layer (host material and dopant material), the organic EL devices were fabricated and evaluated in the same manner as in Example 1. The results are shown in the following Table.

TABLE 148

| | Emitting layer | | | Chromaticity | |
|---|---|---|---|---|---|
| | Host material | Dopant material | LT95(h) | CIEx | CIEy |
| Example 165 | BH-11 | BD-6 | 124 | 0.135 | 0.080 |
| Comparative Example 165 | BH-11-a | BD-6 | 75 | 0.135 | 0.080 |

Example 166 and Comparative Example 166

Except that the compounds shown in following table were used as the materials of the emitting layer (host material and dopant material), the organic EL devices were fabricated and evaluated in the same manner as in Example 1. The results are shown in the following Table.

TABLE 149

| | Emitting layer | | | Chromaticity | |
|---|---|---|---|---|---|
| | Host material | Dopant material | LT95(h) | CIEx | CIEy |
| Example 166 | BH-12 | BD-6 | 106 | 0.135 | 0.080 |
| Comparative Example 166 | BH-12-a | BD-6 | 68 | 0.135 | 0.080 |

Example 167 and Comparative Example 167

Except that the compounds shown in following table were used as the materials of the emitting layer (host material and dopant material), the organic EL devices were fabricated and evaluated in the same manner as in Example 1. The results are shown in the following Table.

TABLE 150

| | Emitting layer | | | Chromaticity | |
|---|---|---|---|---|---|
| | Host material | Dopant material | LT95(h) | CIEx | CIEy |
| Example 167 | BH-13 | BD-6 | 90 | 0.135 | 0.081 |
| Comparative Example 167 | BH-13-a | BD-6 | 62 | 0.135 | 0.080 |

Example 168 and Comparative Example 168

Except that the compounds shown in following table were used as the materials of the emitting layer (host material and dopant material), the organic EL devices were fabricated and evaluated in the same manner as in Example 1. The results are shown in the following Table.

TABLE 151

| | Emitting layer | | | Chromaticity | |
|---|---|---|---|---|---|
| | Host material | Dopant material | LT95(h) | CIEx | CIEy |
| Example 168 | BH-14 | BD-6 | 195 | 0.135 | 0.080 |
| Comparative Example 168 | BH-14-a | BD-6 | 117 | 0.135 | 0.080 |

Example 169 and Comparative Example 169

Except that the compounds shown in following table were used as the materials of the emitting layer (host material and dopant material), the organic EL devices were fabricated and evaluated in the same manner as in Example 1. The results are shown in the following Table.

TABLE 152

| | Emitting layer | | | Chromaticity | |
|---|---|---|---|---|---|
| | Host material | Dopant material | LT95(h) | CIEx | CIEy |
| Example 169 | BH-15 | BD-6 | 138 | 0.135 | 0.080 |
| Comparative Example 169 | BH-15-a | BD-6 | 80 | 0.135 | 0.080 |

Example 170 and Comparative Example 170

Except that the compounds shown in following table were used as the materials of the emitting layer (host material and dopant material), the organic EL devices were fabricated and evaluated in the same manner as in Example 1. The results are shown in the following Table.

TABLE 153

| | Emitting layer | | | Chromaticity | |
|---|---|---|---|---|---|
| | Host material | Dopant material | LT95(h) | CIEx | CIEy |
| Example 170 | BH-16 | BD-6 | 130 | 0.135 | 0.080 |
| Comparative Example 170 | BH-16-a | BD-6 | 77 | 0.135 | 0.080 |

Example 171

Except that the compounds shown in following table were used as the materials of the emitting layer (host material and dopant material), the organic EL device was fabricated and evaluated in the same manner as in Example 1. The results are shown in the following Table.

TABLE 154

| | Emitting layer | | | Chromaticity | |
|---|---|---|---|---|---|
| | Host material | Dopant material | LT95(h) | CIEx | CIEy |
| Example 171 | BH-17 | BD-6 | 200 | 0.135 | 0.080 |

Example 172 and Comparative Example 172

Except that the compounds shown in following table were used as the materials of the emitting layer (host material and dopant material), the organic EL devices were fabricated and evaluated in the same manner as in Example 1. The results are shown in the following Table.

TABLE 155

| | Emitting layer | | | | |
| | Host material | Dopant material | LT95(h) | Chromaticity CIEx | CIEy |
|---|---|---|---|---|---|
| Example 172 | BH-8 | BD-7 | 190 | 0.136 | 0.090 |
| Comparative Example 172 | BH-8-a | BD-7 | 114 | 0.136 | 0.090 |

Example 173 and Comparative Example 173

Except that the compounds shown in following table were used as the materials of the emitting layer (host material and dopant material), the organic EL devices were fabricated and evaluated in the same manner as in Example 1. The results are shown in the following Table.

TABLE 156

| | Emitting layer | | | | |
| | Host material | Dopant material | LT95(h) | Chromaticity CIEx | CIEy |
|---|---|---|---|---|---|
| Example 173 | BH-9 | BD-7 | 179 | 0.136 | 0.090 |
| Comparative Example 173 | BH-9-a | BD-7 | 110 | 0.136 | 0.090 |

Example 174 and Comparative Example 174

Except that the compounds shown in following table were used as the materials of the emitting layer (host material and dopant material), the organic EL devices were fabricated and evaluated in the same manner as in Example 1. The results are shown in the following Table.

TABLE 157

| | Emitting layer | | | | |
| | Host material | Dopant material | LT95(h) | Chromaticity CIEx | CIEy |
|---|---|---|---|---|---|
| Example 174 | BH-10 | BD-7 | 164 | 0.136 | 0.090 |
| Comparative Example 174 | BH-10-a | BD-7 | 98 | 0.136 | 0.090 |

Example 175 and Comparative Example 175

Except that the compounds shown in following table were used as the materials of the emitting layer (host material and dopant material), the organic EL devices were fabricated and evaluated in the same manner as in Example 1. The results are shown in the following Table.

TABLE 158

| | Emitting layer | | | | |
| | Host material | Dopant material | LT95(h) | Chromaticity CIEx | CIEy |
|---|---|---|---|---|---|
| Example 175 | BH-11 | BD-7 | 147 | 0.136 | 0.090 |
| Comparative Example 175 | BH-11-a | BD-7 | 88 | 0.136 | 0.090 |

Example 176 and Comparative Example 176

Except that the compounds shown in following table were used as the materials of the emitting layer (host material and dopant material), the organic EL devices were fabricated and evaluated in the same manner as in Example 1. The results are shown in the following Table.

TABLE 159

| | Emitting layer | | | | |
| | Host material | Dopant material | LT95(h) | Chromaticity CIEx | CIEy |
|---|---|---|---|---|---|
| Example 176 | BH-12 | BD-7 | 122 | 0.136 | 0.090 |
| Comparative Example 176 | BH-12-a | BD-7 | 80 | 0.136 | 0.090 |

Example 177 and Comparative Example 177

Except that the compounds shown in following table were used as the materials of the emitting layer (host material and dopant material), the organic EL devices were fabricated and evaluated in the same manner as in Example 1. The results are shown in the following Table.

TABLE 160

| | Emitting layer | | | | |
| | Host material | Dopant material | LT95(h) | Chromaticity CIEx | CIEy |
|---|---|---|---|---|---|
| Example 177 | BH-13 | BD-7 | 118 | 0.136 | 0.090 |
| Comparative Example 177 | BH-13-a | BD-7 | 72 | 0.136 | 0.090 |

Example 178 and Comparative Example 178

Except that the compounds shown in following table were used as the materials of the emitting layer (host material and dopant material), the organic EL devices were fabricated and evaluated in the same manner as in Example 1. The results are shown in the following Table.

TABLE 161

| | Emitting layer | | | Chromaticity | |
|---|---|---|---|---|---|
| | Host material | Dopant material | LT95(h) | CIEx | CIEy |
| Example 178 | BH-14 | BD-7 | 242 | 0.136 | 0.090 |
| Comparative Example 178 | BH-14-a | BD-7 | 140 | 0.136 | 0.090 |

Example 179 and Comparative Example 179

Except that the compounds shown in following table were used as the materials of the emitting layer (host material and dopant material), the organic EL devices were fabricated and evaluated in the same manner as in Example 1. The results are shown in the following Table.

TABLE 162

| | Emitting layer | | | Chromaticity | |
|---|---|---|---|---|---|
| | Host material | Dopant material | LT95(h) | CIEx | CIEy |
| Example 179 | BH-15 | BD-7 | 155 | 0.136 | 0.090 |
| Comparative Example 179 | BH-15-a | BD-7 | 92 | 0.136 | 0.090 |

Example 180 and Comparative Example 180

Except that the compounds shown in following table were used as the materials of the emitting layer (host material and dopant material), the organic EL devices were fabricated and evaluated in the same manner as in Example 1. The results are shown in the following Table.

TABLE 163

| | Emitting layer | | | Chromaticity | |
|---|---|---|---|---|---|
| | Host material | Dopant material | LT95(h) | CIEx | CIEy |
| Example 180 | BH-16 | BD-7 | 146 | 0.136 | 0.090 |
| Comparative Example 180 | BH-16-a | BD-7 | 90 | 0.136 | 0.090 |

Example 181

Except that the compounds shown in following table were used as the materials of the emitting layer (host material and dopant material), the organic EL device was fabricated and evaluated in the same manner as in Example 1. The results are shown in the following Table.

TABLE 164

| | Emitting layer | | | Chromaticity | |
|---|---|---|---|---|---|
| | Host material | Dopant material | LT95(h) | CIEx | CIEy |
| Example 181 | BH-17 | BD-7 | 245 | 0.136 | 0.090 |

Example 182 and Comparative Example 182

Except that the compounds shown in following table were used as the materials of the emitting layer (host material and dopant material), the organic EL device was fabricated and evaluated in the same manner as in Example 1. The results are shown in the following Table.

TABLE 165

| | Emitting layer | | | Chromaticity | |
|---|---|---|---|---|---|
| | Host material | Dopant material | LT95(h) | CIEx | CIEy |
| Example 182 | BH-8 | BD-8 | 82 | 0.144 | 0.061 |
| Comparative Example 182 | BH-8-a | BD-8 | 50 | 0.144 | 0.061 |

Example 183 and Comparative Example 183

Except that the compounds shown in following table were used as the materials of the emitting layer (host material and dopant material), the organic EL devices were fabricated and evaluated in the same manner as in Example 1. The results are shown in the following Table.

TABLE 166

| | Emitting layer | | | Chromaticity | |
|---|---|---|---|---|---|
| | Host material | Dopant material | LT95(h) | CIEx | CIEy |
| Example 183 | BH-9 | BD-8 | 82 | 0.144 | 0.061 |
| Comparative Example 183 | BH-9-a | BD-8 | 50 | 0.144 | 0.061 |

Example 184 and Comparative Example 184

Except that the compounds shown in following table were used as the materials of the emitting layer (host material and dopant material), the organic EL devices were fabricated and evaluated in the same manner as in Example 1. The results are shown in the following Table.

TABLE 167

| | Emitting layer | | | Chromaticity | |
|---|---|---|---|---|---|
| | Host material | Dopant material | LT95(h) | CIEx | CIEy |
| Example 184 | BH-10 | BD-8 | 74 | 0.144 | 0.060 |
| Comparative Example 184 | BH-10-a | BD-8 | 48 | 0.144 | 0.060 |

Example 185 and Comparative Example 185

Except that the compounds shown in following table were used as the materials of the emitting layer (host material and dopant material), the organic EL devices were fabricated and evaluated in the same manner as in Example 1. The results are shown in the following Table.

TABLE 168

| | Emitting layer | | | Chromaticity | |
|---|---|---|---|---|---|
| | Host material | Dopant material | LT95(h) | CIEx | CIEy |
| Example 185 | BH-11 | BD-8 | 63 | 0.144 | 0.061 |
| Comparative Example 185 | BH-11-a | BD-8 | 42 | 0.144 | 0.061 |

Example 186 and Comparative Example 186

Except that the compounds shown in following table were used as the materials of the emitting layer (host material and dopant material), the organic EL devices were fabricated and evaluated in the same manner as in Example 1. The results are shown in the following Table.

TABLE 169

| | Emitting layer | | | Chromaticity | |
|---|---|---|---|---|---|
| | Host material | Dopant material | LT95(h) | CIEx | CIEy |
| Example 186 | BH-12 | BD-8 | 61 | 0.144 | 0.061 |
| Comparative Example 186 | BH-12-a | BD-8 | 37 | 0.144 | 0.061 |

Example 187 and Comparative Example 187

Except that the compounds shown in following table were used as the materials of the emitting layer (host material and dopant material), the organic EL devices were fabricated and evaluated in the same manner as in Example 1. The results are shown in the following Table.

TABLE 170

| | Emitting layer | | | Chromaticity | |
|---|---|---|---|---|---|
| | Host material | Dopant material | LT95(h) | CIEx | CIEy |
| Example 187 | BH-13 | BD-8 | 55 | 0.144 | 0.061 |
| Comparative Example 187 | BH-13-a | BD-8 | 33 | 0.144 | 0.061 |

Example 188 and Comparative Example 188

Except that the compounds shown in following table were used as the materials of the emitting layer (host material and dopant material), the organic EL devices were fabricated and evaluated in the same manner as in Example 1. The results are shown in the following Table.

TABLE 171

| | Emitting layer | | | Chromaticity | |
|---|---|---|---|---|---|
| | Host material | Dopant material | LT95(h) | CIEx | CIEy |
| Example 188 | BH-14 | BD-8 | 105 | 0.144 | 0.061 |
| Comparative Example 188 | BH-14-a | BD-8 | 65 | 0.144 | 0.061 |

Example 189 and Comparative Example 189

Except that the compounds shown in following table were used as the materials of the emitting layer (host material and dopant material), the organic EL devices were fabricated and evaluated in the same manner as in Example 1. The results are shown in the following Table.

TABLE 172

| | Emitting layer | | | Chromaticity | |
|---|---|---|---|---|---|
| | Host material | Dopant material | LT95(h) | CIEx | CIEy |
| Example 189 | BH-15 | BD-8 | 75 | 0.144 | 0.061 |
| Comparative Example 189 | BH-15-a | BD-8 | 50 | 0.144 | 0.061 |

Example 190 and Comparative Example 190

Except that the compounds shown in following table were used as the materials of the emitting layer (host material and dopant material), the organic EL devices were fabricated and evaluated in the same manner as in Example 1. The results are shown in the following Table.

TABLE 173

| | Emitting layer | | | Chromaticity | |
|---|---|---|---|---|---|
| | Host material | Dopant material | LT95(h) | CIEx | CIEy |
| Example 190 | BH-16 | BD-8 | 70 | 0.144 | 0.061 |
| Comparative Example 190 | BH-16-a | BD-8 | 43 | 0.144 | 0.061 |

Example 191

Except that the compounds shown in following table were used as the materials of the emitting layer (host material and dopant material), the organic EL device was fabricated and evaluated in the same manner as in Example 1. The results are shown in the following Table.

TABLE 174

| | Emitting layer | | | Chromaticity | |
|---|---|---|---|---|---|
| | Host material | Dopant material | LT95(h) | CIEx | CIEy |
| Example 191 | BH-17 | BD-8 | 107 | 0.144 | 0.061 |

Example 192 and Comparative Example 192

Except that the compounds shown in following table were used as the materials of the emitting layer (host material and dopant material), the organic EL devices were fabricated and evaluated in the same manner as in Example 1. The results are shown in the following Table.

TABLE 175

| | Emitting layer | | | Chromaticity | |
|---|---|---|---|---|---|
| | Host material | Dopant material | LT95(h) | CIEx | CIEy |
| Example 192 | BH-1 | BD-13 | 129 | 0.138 | 0.117 |
| Comparative Example 192 | BH-1-a | BD-13 | 87 | 0.138 | 0.117 |

Example 193 and Comparative Example 193

Except that the compounds shown in following table were used as the materials of the emitting layer (host material and dopant material), the organic EL devices were fabricated and evaluated in the same manner as in Example 1. The results are shown in the following Table.

TABLE 176

| | Emitting layer | | | Chromaticity | |
|---|---|---|---|---|---|
| | Host material | Dopant material | LT95(h) | CIEx | CIEy |
| Example 193 | BH-2 | BD-13 | 67 | 0.138 | 0.117 |
| Comparative Example 193 | BH-2-a | BD-13 | 44 | 0.138 | 0.117 |

Example 194 and Comparative Example 194

Except that the compounds shown in following table were used as the materials of the emitting layer (host material and dopant material), the organic EL devices were fabricated and evaluated in the same manner as in Example 1. The results are shown in the following Table.

TABLE 177

| | Emitting layer | | | Chromaticity | |
|---|---|---|---|---|---|
| | Host material | Dopant material | LT95(h) | CIEx | CIEy |
| Example 194 | BH-3 | BD-13 | 57 | 0.138 | 0.117 |
| Comparative Example 194 | BH-3-a | BD-13 | 40 | 0.138 | 0.117 |

Example 195 and Comparative Example 195

Except that the compounds shown in following table were used as the materials of the emitting layer (host material and dopant material), the organic EL devices were fabricated and evaluated in the same manner as in Example 1. The results are shown in the following Table.

TABLE 178

| | Emitting layer | | | Chromaticity | |
|---|---|---|---|---|---|
| | Host material | Dopant material | LT95(h) | CIEx | CIEy |
| Example 195 | BH-4 | BD-13 | 54 | 0.138 | 0.117 |
| Comparative Example 195 | BH-4-a | BD-13 | 40 | 0.138 | 0.117 |

Example 196 and Comparative Example 196

Except that the compounds shown in following table were used as the materials of the emitting layer (host material and dopant material), the organic EL devices were fabricated and evaluated in the same manner as in Example 1. The results are shown in the following Table.

TABLE 179

| | Emitting layer | | | Chromaticity | |
|---|---|---|---|---|---|
| | Host material | Dopant material | LT95(h) | CIEx | CIEy |
| Example 196 | BH-5 | BD-13 | 140 | 0.138 | 0.117 |
| Comparative Example 196 | BH-5-a | BD-13 | 92 | 0.138 | 0.117 |

Example 197 and Comparative Example 197

Except that the compounds shown in following table were used as the materials of the emitting layer (host material and dopant material), the organic EL devices were fabricated and evaluated in the same manner as in Example 1. The results are shown in the following Table.

TABLE 180

| | Emitting layer | | | Chromaticity | |
|---|---|---|---|---|---|
| | Host material | Dopant material | LT95(h) | CIEx | CIEy |
| Example 197 | BH-6 | BD-13 | 123 | 0.138 | 0.117 |
| Comparative Example 197 | BH-6-a | BD-13 | 80 | 0.138 | 0.117 |

Example 198 and Comparative Example 198

Except that the compounds shown in following table were used as the materials of the emitting layer (host material and dopant material), the organic EL devices were fabricated and evaluated in the same manner as in Example 1. The results are shown in the following Table.

TABLE 181

| | Emitting layer | | | Chromaticity | |
|---|---|---|---|---|---|
| | Host material | Dopant material | LT95(h) | CIEx | CIEy |
| Example 198 | BH-7 | BD-13 | 129 | 0.138 | 0.117 |
| Comparative Example 198 | BH-7-a | BD-13 | 90 | 0.138 | 0.117 |

Example 199 and Comparative Example 199

Except that the compounds shown in following table were used as the materials of the emitting layer (host material and dopant material), the organic EL devices were fabricated and evaluated in the same manner as in Example 1. The results are shown in the following Table.

TABLE 182

| | Emitting layer | | | Chromaticity | |
|---|---|---|---|---|---|
| | Host material | Dopant material | LT95(h) | CIEx | CIEy |
| Example 199 | BH-8 | BD-13 | 95 | 0.138 | 0.117 |
| Comparative Example 199 | BH-8-a | BD-13 | 67 | 0.138 | 0.117 |

Example 200 and Comparative Example 200

Except that the compounds shown in following table were used as the materials of the emitting layer (host material and dopant material), the organic EL devices were fabricated and evaluated in the same manner as in Example 1. The results are shown in the following Table.

TABLE 183

| | Emitting layer | | | Chromaticity | |
|---|---|---|---|---|---|
| | Host material | Dopant material | LT95(h) | CIEx | CIEy |
| Example 200 | BH-9 | BD-13 | 94 | 0.138 | 0.117 |
| Comparative Example 200 | BH-9-a | BD-13 | 63 | 0.138 | 0.117 |

Example 201 and Comparative Example 201

Except that the compounds shown in following table were used as the materials of the emitting layer (host material and dopant material), the organic EL devices were fabricated and evaluated in the same manner as in Example 1. The results are shown in the following Table.

TABLE 184

| | Emitting layer | | | Chromaticity | |
|---|---|---|---|---|---|
| | Host material | Dopant material | LT95(h) | CIEx | CIEy |
| Example 201 | BH-10 | BD-13 | 88 | 0.138 | 0.117 |
| Comparative Example 201 | BH-10-a | BD-13 | 63 | 0.138 | 0.117 |

Example 202 and Comparative Example 202

Except that the compounds shown in following table were used as the materials of the emitting layer (host material and dopant material), the organic EL devices were fabricated and evaluated in the same manner as in Example 1. The results are shown in the following Table.

TABLE 185

| | Emitting layer | | | Chromaticity | |
|---|---|---|---|---|---|
| | Host material | Dopant material | LT95(h) | CIEx | CIEy |
| Example 202 | BH-11 | BD-13 | 72 | 0.138 | 0.117 |
| Comparative Example 202 | BH-11-a | BD-13 | 52 | 0.138 | 0.117 |

Example 203 and Comparative Example 203

Except that the compounds shown in following table were used as the materials of the emitting layer (host material and dopant material), the organic EL devices were fabricated and evaluated in the same manner as in Example 1. The results are shown in the following Table.

TABLE 186

| | Emitting layer | | | Chromaticity | |
|---|---|---|---|---|---|
| | Host material | Dopant material | LT95(h) | CIEx | CIEy |
| Example 203 | BH-12 | BD-13 | 70 | 0.138 | 0.118 |
| Comparative Example 203 | BH-12-a | BD-13 | 48 | 0.138 | 0.118 |

Example 204 and Comparative Example 204

Except that the compounds shown in following table were used as the materials of the emitting layer (host material and dopant material), the organic EL devices were fabricated and evaluated in the same manner as in Example 1. The results are shown in the following Table.

TABLE 187

| | Emitting layer | | | Chromaticity | |
|---|---|---|---|---|---|
| | Host material | Dopant material | LT95(h) | CIEx | CIEy |
| Example 204 | BH-13 | BD-13 | 63 | 0.138 | 0.117 |
| Comparative Example 204 | BH-13-a | BD-13 | 48 | 0.138 | 0.117 |

Example 205 and Comparative Example 205

Except that the compounds shown in following table were used as the materials of the emitting layer (host material and dopant material), the organic EL devices were fabricated and evaluated in the same manner as in Example 1. The results are shown in the following Table.

TABLE 188

| | Emitting layer | | | Chromaticity | |
|---|---|---|---|---|---|
| | Host material | Dopant material | LT95(h) | CIEx | CIEy |
| Example 205 | BH-14 | BD-13 | 128 | 0.138 | 0.117 |
| Comparative Example 205 | BH-14-a | BD-13 | 84 | 0.138 | 0.117 |

Example 206 and Comparative Example 206

Except that the compounds shown in following table were used as the materials of the emitting layer (host material and dopant material), the organic EL devices were fabricated and evaluated in the same manner as in Example 1. The results are shown in the following Table.

TABLE 189

| | Emitting layer | | | Chromaticity | |
|---|---|---|---|---|---|
| | Host material | Dopant material | LT95(h) | CIEx | CIEy |
| Example 206 | BH-15 | BD-13 | 81 | 0.138 | 0.117 |
| Comparative Example 206 | BH-15-a | BD-13 | 59 | 0.138 | 0.117 |

Example 207 and Comparative Example 207

Except that the compounds shown in following table were used as the materials of the emitting layer (host material and dopant material), the organic EL devices were fabricated and evaluated in the same manner as in Example 1. The results are shown in the following Table.

TABLE 190

| | Emitting layer | | | Chromaticity | |
|---|---|---|---|---|---|
| | Host material | Dopant material | LT95(h) | CIEx | CIEy |
| Example 207 | BH-16 | BD-13 | 82 | 0.138 | 0.117 |
| Comparative Example 207 | BH-16-a | BD-13 | 56 | 0.138 | 0.117 |

Example 208

Except that the compounds shown in following table were used as the materials of the emitting layer (host material and dopant material), the organic EL device was fabricated and evaluated in the same manner as in Example 1. The results are shown in the following Table.

TABLE 191

| | Emitting layer | | | Chromaticity | |
|---|---|---|---|---|---|
| | Host material | Dopant material | LT95(h) | CIEx | CIEy |
| Example 208 | BH-17 | BD-13 | 117 | 0.138 | 0.117 |

Example 209 and Comparative Example 209

Except that the compounds shown in following table were used as the materials of the emitting layer (host material and dopant material), the organic EL devices were fabricated and evaluated in the same manner as in Example 1. The results are shown in the following Table.

TABLE 192

| | Emitting layer | | | Chromaticity | |
|---|---|---|---|---|---|
| | Host material | Dopant material | LT95(h) | CIEx | CIEy |
| Example 209 | BH-1 | BD-14 | 108 | 0.139 | 0.121 |
| Comparative Example 209 | BH-1-a | BD-14 | 72 | 0.139 | 0.121 |

Example 210 and Comparative Example 210

Except that the compounds shown in following table were used as the materials of the emitting layer (host material and dopant material), the organic EL devices were fabricated and evaluated in the same manner as in Example 1. The results are shown in the following Table.

TABLE 193

| | Emitting layer | | | Chromaticity | |
|---|---|---|---|---|---|
| | Host material | Dopant material | LT95(h) | CIEx | CIEy |
| Example 210 | BH-2 | BD-14 | 50 | 0.139 | 0.121 |
| Comparative Example 210 | BH-2-a | BD-14 | 35 | 0.139 | 0.121 |

Example 211 and Comparative Example 211

Except that the compounds shown in following table were used as the materials of the emitting layer (host material and dopant material), the organic EL devices were fabricated and evaluated in the same manner as in Example 1. The results are shown in the following Table.

TABLE 194

|  | Emitting layer | | | Chromaticity | |
|---|---|---|---|---|---|
|  | Host material | Dopant material | LT95(h) | CIEx | CIEy |
| Example 211 | BH-3 | BD-14 | 49 | 0.139 | 0.121 |
| Comparative Example 211 | BH-3-a | BD-14 | 35 | 0.139 | 0.121 |

Example 212 and Comparative Example 212

Except that the compounds shown in following table were used as the materials of the emitting layer (host material and dopant material), the organic EL devices were fabricated and evaluated in the same manner as in Example 1. The results are shown in the following Table.

TABLE 195

|  | Emitting layer | | | Chromaticity | |
|---|---|---|---|---|---|
|  | Host material | Dopant material | LT95(h) | CIEx | CIEy |
| Example 212 | BH-4 | BD-14 | 47 | 0.139 | 0.121 |
| Comparative Example 212 | BH-4-a | BD-14 | 32 | 0.139 | 0.121 |

Example 213 and Comparative Example 213

Except that the compounds shown in following table were used as the materials of the emitting layer (host material and dopant material), the organic EL devices were fabricated and evaluated in the same manner as in Example 1. The results are shown in the following Table.

TABLE 196

|  | Emitting layer | | | Chromaticity | |
|---|---|---|---|---|---|
|  | Host material | Dopant material | LT95(h) | CIEx | CIEy |
| Example 213 | BH-5 | BD-14 | 118 | 0.139 | 0.121 |
| Comparative Example 213 | BH-5-a | BD-14 | 78 | 0.139 | 0.121 |

Example 214 and Comparative Example 214

Except that the compounds shown in following table were used as the materials of the emitting layer (host material and dopant material), the organic EL devices were fabricated and evaluated in the same manner as in Example 1. The results are shown in the following Table.

TABLE 197

|  | Emitting layer | | | Chromaticity | |
|---|---|---|---|---|---|
|  | Host material | Dopant material | LT95(h) | CIEx | CIEy |
| Example 214 | BH-6 | BD-14 | 106 | 0.139 | 0.121 |
| Comparative Example 214 | BH-6-a | BD-14 | 70 | 0.139 | 0.121 |

Example 215 and Comparative Example 215

Except that the compounds shown in following table were used as the materials of the emitting layer (host material and dopant material), the organic EL devices were fabricated and evaluated in the same manner as in Example 1. The results are shown in the following Table.

TABLE 198

|  | Emitting layer | | | Chromaticity | |
|---|---|---|---|---|---|
|  | Host material | Dopant material | LT95(h) | CIEx | CIEy |
| Example 215 | BH-7 | BD-14 | 102 | 0.139 | 0.121 |
| Comparative Example 215 | BH-7-a | BD-14 | 70 | 0.139 | 0.121 |

Example 216 and Comparative Example 216

Except that the compounds shown in following table were used as the materials of the emitting layer (host material and dopant material), the organic EL devices were fabricated and evaluated in the same manner as in Example 1. The results are shown in the following Table.

TABLE 199

|  | Emitting layer | | | Chromaticity | |
|---|---|---|---|---|---|
|  | Host material | Dopant material | LT95(h) | CIEx | CIEy |
| Example 216 | BH-8 | BD-14 | 81 | 0.139 | 0.121 |
| Comparative Example 216 | BH-8-a | BD-14 | 54 | 0.139 | 0.121 |

Example 217 and Comparative Example 217

Except that the compounds shown in following table were used as the materials of the emitting layer (host material and dopant material), the organic EL devices were fabricated and evaluated in the same manner as in Example 1. The results are shown in the following Table.

TABLE 200

| | Emitting layer | | | | |
|---|---|---|---|---|---|
| | Host material | Dopant material | LT95(h) | Chromaticity CIEx | CIEy |
| Example 217 | BH-9 | BD-14 | 72 | 0.139 | 0.121 |
| Comparative Example 217 | BH-9-a | BD-14 | 54 | 0.139 | 0.121 |

Example 218 and Comparative Example 218

Except that the compounds shown in following table were used as the materials of the emitting layer (host material and dopant material), the organic EL devices were fabricated and evaluated in the same manner as in Example 1. The results are shown in the following Table.

TABLE 201

| | Emitting layer | | | | |
|---|---|---|---|---|---|
| | Host material | Dopant material | LT95(h) | Chromaticity CIEx | CIEy |
| Example 218 | BH-10 | BD-14 | 72 | 0.139 | 0.121 |
| Comparative Example 218 | BH-10-a | BD-14 | 53 | 0.139 | 0.121 |

Example 219 and Comparative Example 219

Except that the compounds shown in following table were used as the materials of the emitting layer (host material and dopant material), the organic EL devices were fabricated and evaluated in the same manner as in Example 1. The results are shown in the following Table.

TABLE 202

| | Emitting layer | | | | |
|---|---|---|---|---|---|
| | Host material | Dopant material | LT95(h) | Chromaticity CIEx | CIEy |
| Example 219 | BH-11 | BD-14 | 68 | 0.139 | 0.121 |
| Comparative Example 219 | BH-11-a | BD-14 | 50 | 0.139 | 0.121 |

Example 220 and Comparative Example 220

Except that the compounds shown in following table were used as the materials of the emitting layer (host material and dopant material), the organic EL devices were fabricated and evaluated in the same manner as in Example 1. The results are shown in the following Table.

TABLE 203

| | Emitting layer | | | | |
|---|---|---|---|---|---|
| | Host material | Dopant material | LT95(h) | Chromaticity CIEx | CIEy |
| Example 220 | BH-12 | BD-14 | 63 | 0.139 | 0.122 |
| Comparative Example 220 | BH-12-a | BD-14 | 43 | 0.139 | 0.122 |

Example 221 and Comparative Example 221

Except that the compounds shown in following table were used as the materials of the emitting layer (host material and dopant material), the organic EL devices were fabricated and evaluated in the same manner as in Example 1. The results are shown in the following Table.

TABLE 204

| | Emitting layer | | | | |
|---|---|---|---|---|---|
| | Host material | Dopant material | LT95(h) | Chromaticity CIEx | CIEy |
| Example 221 | BH-13 | BD-14 | 49 | 0.139 | 0.121 |
| Comparative Example 221 | BH-13-a | BD-14 | 40 | 0.139 | 0.121 |

Example 222 and Comparative Example 222

Except that the compounds shown in following table were used as the materials of the emitting layer (host material and dopant material), the organic EL devices were fabricated and evaluated in the same manner as in Example 1. The results are shown in the following Table.

TABLE 205

| | Emitting layer | | | | |
|---|---|---|---|---|---|
| | Host material | Dopant material | LT95(h) | Chromaticity CIEx | CIEy |
| Example 222 | BH-14 | BD-14 | 101 | 0.139 | 0.121 |
| Comparative Example 222 | BH-14-a | BD-14 | 67 | 0.139 | 0.121 |

Example 223 and Comparative Example 223

Except that the compounds shown in following table were used as the materials of the emitting layer (host material and dopant material), the organic EL devices were fabricated and evaluated in the same manner as in Example 1. The results are shown in the following Table.

TABLE 206

| | Emitting layer | | | Chromaticity | |
| | Host material | Dopant material | LT95(h) | CIEx | CIEy |
|---|---|---|---|---|---|
| Example 223 | BH-15 | BD-14 | 73 | 0.139 | 0.121 |
| Comparative Example 223 | BH-15-a | BD-14 | 48 | 0.139 | 0.121 |

Example 224 and Comparative Example 224

Except that the compounds shown in following table were used as the materials of the emitting layer (host material and dopant material), the organic EL devices were fabricated and evaluated in the same manner as in Example 1. The results are shown in the following Table.

TABLE 207

| | Emitting layer | | | Chromaticity | |
| | Host material | Dopant material | LT95(h) | CIEx | CIEy |
|---|---|---|---|---|---|
| Example 224 | BH-16 | BD-14 | 68 | 0.139 | 0.121 |
| Comparative Example 224 | BH-16-a | BD-14 | 48 | 0.139 | 0.121 |

Example 225

Except that the compounds shown in following table were used as the materials of the emitting layer (host material and dopant material), the organic EL devices were fabricated and evaluated in the same manner as in Example 1. The results are shown in the following Table.

TABLE 208

| | Emitting layer | | | Chromaticity | |
| | Host material | Dopant material | LT95(h) | CIEx | CIEy |
|---|---|---|---|---|---|
| Example 225 | BH-17 | BD-14 | 104 | 0.139 | 0.121 |

Example 226 and Comparative Example 226

Except that the compounds shown in following table were used as the materials of the emitting layer (host material and dopant material), the organic EL devices were fabricated and evaluated in the same manner as in Example 1. The results are shown in the following Table.

TABLE 209

| | Emitting layer | | | Chromaticity | |
| | Host material | Dopant material | LT95(h) | CIEx | CIEy |
|---|---|---|---|---|---|
| Example 226 | BH-1 | BD-15 | 63 | 0.140 | 0.094 |
| Comparative Example 226 | BH-1-a | BD-15 | 44 | 0.140 | 0.094 |

Example 227 and Comparative Example 227

Except that the compounds shown in following table were used as the materials of the emitting layer (host material and dopant material), the organic EL devices were fabricated and evaluated in the same manner as in Example 1. The results are shown in the following Table.

TABLE 210

| | Emitting layer | | | Chromaticity | |
| | Host material | Dopant material | LT95(h) | CIEx | CIEy |
|---|---|---|---|---|---|
| Example 227 | BH-2 | BD-15 | 33 | 0.140 | 0.094 |
| Comparative Example 227 | BH-2-a | BD-15 | 25 | 0.140 | 0.094 |

Example 228 and Comparative Example 228

Except that the compounds shown in following table were used as the materials of the emitting layer (host material and dopant material), the organic EL devices were fabricated and evaluated in the same manner as in Example 1. The results are shown in the following Table.

TABLE 211

| | Emitting layer | | | Chromaticity | |
| | Host material | Dopant material | LT95(h) | CIEx | CIEy |
|---|---|---|---|---|---|
| Example 228 | BH-3 | BD-15 | 29 | 0.140 | 0.094 |
| Comparative Example 228 | BH-3-a | BD-15 | 21 | 0.140 | 0.094 |

Example 229 and Comparative Example 229

Except that the compounds shown in following table were used as the materials of the emitting layer (host material and dopant material), the organic EL devices were fabricated and evaluated in the same manner as in Example 1. The results are shown in the following Table.

TABLE 212

| | Emitting layer | | | Chromaticity | |
| | Host material | Dopant material | LT95(h) | CIEx | CIEy |
|---|---|---|---|---|---|
| Example 229 | BH-4 | BD-15 | 32 | 0.140 | 0.094 |
| Comparative Example 229 | BH-4-a | BD-15 | 25 | 0.140 | 0.094 |

Example 230 and Comparative Example 230

Except that the compounds shown in following table were used as the materials of the emitting layer (host material and dopant material), the organic EL devices were fabricated and evaluated in the same manner as in Example 1. The results are shown in the following Table.

TABLE 213

| | Emitting layer | | | | |
|---|---|---|---|---|---|
| | Host material | Dopant material | LT95(h) | Chromaticity CIEx | CIEy |
| Example 230 | BH-5 | BD-15 | 66 | 0.140 | 0.094 |
| Comparative Example 230 | BH-5-a | BD-15 | 44 | 0.140 | 0.094 |

Example 231 and Comparative Example 231

Except that the compounds shown in following table were used as the materials of the emitting layer (host material and dopant material), the organic EL devices were fabricated and evaluated in the same manner as in Example 1. The results are shown in the following Table.

TABLE 214

| | Emitting layer | | | | |
|---|---|---|---|---|---|
| | Host material | Dopant material | LT95(h) | Chromaticity CIEx | CIEy |
| Example 231 | BH-6 | BD-15 | 63 | 0.140 | 0.094 |
| Comparative Example 231 | BH-6-a | BD-15 | 41 | 0.140 | 0.094 |

Example 232 and Comparative Example 232

Except that the compounds shown in following table were used as the materials of the emitting layer (host material and dopant material), the organic EL devices were fabricated and evaluated in the same manner as in Example 1. The results are shown in the following Table.

TABLE 215

| | Emitting layer | | | | |
|---|---|---|---|---|---|
| | Host material | Dopant material | LT95(h) | Chromaticity CIEx | CIEy |
| Example 232 | BH-7 | BD-15 | 63 | 0.140 | 0.094 |
| Comparative Example 232 | BH-7-a | BD-15 | 41 | 0.140 | 0.094 |

Example 233 and Comparative Example 233

Except that the compounds shown in following table were used as the materials of the emitting layer (host material and dopant material), the organic EL devices were fabricated and evaluated in the same manner as in Example 1. The results are shown in the following Table.

TABLE 216

| | Emitting layer | | | | |
|---|---|---|---|---|---|
| | Host material | Dopant material | LT95(h) | Chromaticity CIEx | CIEy |
| Example 233 | BH-8 | BD-15 | 45 | 0.140 | 0.094 |
| Comparative Example 233 | BH-8-a | BD-15 | 34 | 0.140 | 0.094 |

Example 234 and Comparative Example 234

Except that the compounds shown in following table were used as the materials of the emitting layer (host material and dopant material), the organic EL devices were fabricated and evaluated in the same manner as in Example 1. The results are shown in the following Table.

TABLE 217

| | Emitting layer | | | | |
|---|---|---|---|---|---|
| | Host material | Dopant material | LT95(h) | Chromaticity CIEx | CIEy |
| Example 234 | BH-9 | BD-15 | 47 | 0.140 | 0.094 |
| Comparative Example 234 | BH-9-a | BD-15 | 32 | 0.140 | 0.094 |

Example 235 and Comparative Example 235

Except that the compounds shown in following table were used as the materials of the emitting layer (host material and dopant material), the organic EL devices were fabricated and evaluated in the same manner as in Example 1. The results are shown in the following Table.

TABLE 218

| | Emitting layer | | | | |
|---|---|---|---|---|---|
| | Host material | Dopant material | LT95(h) | Chromaticity CIEx | CIEy |
| Example 235 | BH-10 | BD-15 | 42 | 0.140 | 0.094 |
| Comparative Example 235 | BH-10-a | BD-15 | 30 | 0.140 | 0.094 |

Example 236 and Comparative Example 236

Except that the compounds shown in following table were used as the materials of the emitting layer (host material and dopant material), the organic EL devices were fabricated and evaluated in the same manner as in Example 1. The results are shown in the following Table.

TABLE 219

| | Emitting layer | | | | |
|---|---|---|---|---|---|
| | Host material | Dopant material | LT95(h) | Chromaticity CIEx | CIEy |
| Example 236 | BH-11 | BD-15 | 37 | 0.140 | 0.094 |
| Comparative Example 236 | BH-11-a | BD-15 | 28 | 0.140 | 0.094 |

Example 237 and Comparative Example 237

Except that the compounds shown in following table were used as the materials of the emitting layer (host material and dopant material), the organic EL devices were fabricated and evaluated in the same manner as in Example 1. The results are shown in the following Table.

TABLE 220

| | Emitting layer | | | Chromaticity | |
| --- | --- | --- | --- | --- | --- |
| | Host material | Dopant material | LT95(h) | CIEx | CIEy |
| Example 237 | BH-12 | BD-15 | 35 | 0.140 | 0.095 |
| Comparative Example 237 | BH-12-a | BD-15 | 27 | 0.140 | 0.095 |

Example 238 and Comparative Example 238

Except that the compounds shown in following table were used as the materials of the emitting layer (host material and dopant material), the organic EL devices were fabricated and evaluated in the same manner as in Example 1. The results are shown in the following Table.

TABLE 221

| | Emitting layer | | | Chromaticity | |
| --- | --- | --- | --- | --- | --- |
| | Host material | Dopant material | LT95(h) | CIEx | CIEy |
| Example 238 | BH-13 | BD-15 | 33 | 0.140 | 0.094 |
| Comparative Example 238 | BH-13-a | BD-15 | 27 | 0.140 | 0.094 |

Example 239 and Comparative Example 239

Except that the compounds shown in following table were used as the materials of the emitting layer (host material and dopant material), the organic EL devices were fabricated and evaluated in the same manner as in Example 1. The results are shown in the following Table.

TABLE 222

| | Emitting layer | | | Chromaticity | |
| --- | --- | --- | --- | --- | --- |
| | Host material | Dopant material | LT95(h) | CIEx | CIEy |
| Example 239 | BH-14 | BD-15 | 63 | 0.140 | 0.094 |
| Comparative Example 239 | BH-14-a | BD-15 | 43 | 0.140 | 0.094 |

Example 240 and Comparative Example 240

Except that the compounds shown in following table were used as the materials of the emitting layer (host material and dopant material), the organic EL devices were fabricated and evaluated in the same manner as in Example 1. The results are shown in the following Table.

TABLE 223

| | Emitting layer | | | Chromaticity | |
| --- | --- | --- | --- | --- | --- |
| | Host material | Dopant material | LT95(h) | CIEx | CIEy |
| Example 240 | BH-15 | BD-15 | 41 | 0.140 | 0.094 |
| Comparative Example 240 | BH-15-a | BD-15 | 30 | 0.140 | 0.094 |

Example 241 and Comparative Example 241

Except that the compounds shown in following table were used as the materials of the emitting layer (host material and dopant material), the organic EL devices were fabricated and evaluated in the same manner as in Example 1. The results are shown in the following Table.

TABLE 224

| | Emitting layer | | | Chromaticity | |
| --- | --- | --- | --- | --- | --- |
| | Host material | Dopant material | LT95(h) | CIEx | CIEy |
| Example 241 | BH-16 | BD-15 | 38 | 0.140 | 0.094 |
| Comparative Example 241 | BH-16-a | BD-15 | 26 | 0.140 | 0.094 |

Example 242

Except that the compounds shown in following table were used as the materials of the emitting layer (host material and dopant material), the organic EL device was fabricated and evaluated in the same manner as in Example 1. The results are shown in the following Table.

TABLE 225

| | Emitting layer | | | Chromaticity | |
| --- | --- | --- | --- | --- | --- |
| | Host material | Dopant material | LT95(h) | CIEx | CIEy |
| Example 242 | BH-17 | BD-11 | 67 | 0.140 | 0.094 |

Example 243 and Comparative Example 243

Except that the compounds shown in following table were used as the materials of the emitting layer (host material and dopant material), the organic EL devices were fabricated and evaluated in the same manner as in Example 1. The results are shown in the following Table.

TABLE 226

| | Emitting layer | | | Chromaticity | |
| --- | --- | --- | --- | --- | --- |
| | Host material | Dopant material | LT95(h) | CIEx | CIEy |
| Example 243 | BH-1 | BD-16 | 95 | 0.141 | 0.098 |
| Comparative Example 243 | BH-1-a | BD-16 | 62 | 0.141 | 0.098 |

Example 244 and Comparative Example 244

Except that the compounds shown in following table were used as the materials of the emitting layer (host material and dopant material), the organic EL devices were fabricated and evaluated in the same manner as in Example 1. The results are shown in the following Table.

TABLE 227

| | Emitting layer | | | | |
|---|---|---|---|---|---|
| | Host material | Dopant material | LT95(h) | Chromaticity CIEx | CIEy |
| Example 244 | BH-2 | BD-16 | 54 | 0.141 | 0.098 |
| Comparative Example 244 | BH-2-a | BD-16 | 35 | 0.141 | 0.098 |

Example 245 and Comparative Example 245

Except that the compounds shown in following table were used as the materials of the emitting layer (host material and dopant material), the organic EL devices were fabricated and evaluated in the same manner as in Example 1. The results are shown in the following Table.

TABLE 228

| | Emitting layer | | | | |
|---|---|---|---|---|---|
| | Host material | Dopant material | LT95(h) | Chromaticity CIEx | CIEy |
| Example 245 | BH-3 | BD-16 | 45 | 0.141 | 0.098 |
| Comparative Example 245 | BH-3-a | BD-16 | 35 | 0.141 | 0.098 |

Example 246 and Comparative Example 246

Except that the compounds shown in following table were used as the materials of the emitting layer (host material and dopant material), the organic EL devices were fabricated and evaluated in the same manner as in Example 1. The results are shown in the following Table.

TABLE 229

| | Emitting layer | | | | |
|---|---|---|---|---|---|
| | Host material | Dopant material | LT95(h) | Chromaticity CIEx | CIEy |
| Example 246 | BH-4 | BD-16 | 45 | 0.141 | 0.098 |
| Comparative Example 246 | BH-4-a | BD-16 | 30 | 0.141 | 0.098 |

Example 247 and Comparative Example 247

Except that the compounds shown in following table were used as the materials of the emitting layer (host material and dopant material), the organic EL devices were fabricated and evaluated in the same manner as in Example 1. The results are shown in the following Table.

TABLE 230

| | Emitting layer | | | | |
|---|---|---|---|---|---|
| | Host material | Dopant material | LT95(h) | Chromaticity CIEx | CIEy |
| Example 247 | BH-5 | BD-16 | 104 | 0.141 | 0.098 |
| Comparative Example 247 | BH-5-a | BD-16 | 70 | 0.141 | 0.098 |

Example 248 and Comparative Example 248

Except that the compounds shown in following table were used as the materials of the emitting layer (host material and dopant material), the organic EL devices were fabricated and evaluated in the same manner as in Example 1. The results are shown in the following Table.

TABLE 231

| | Emitting layer | | | | |
|---|---|---|---|---|---|
| | Host material | Dopant material | LT95(h) | Chromaticity CIEx | CIEy |
| Example 248 | BH-6 | BD-16 | 92 | 0.141 | 0.098 |
| Comparative Example 248 | BH-6-a | BD-16 | 60 | 0.141 | 0.098 |

Example 249 and Comparative Example 249

Except that the compounds shown in following table were used as the materials of the emitting layer (host material and dopant material), the organic EL devices were fabricated and evaluated in the same manner as in Example 1. The results are shown in the following Table.

TABLE 232

| | Emitting layer | | | | |
|---|---|---|---|---|---|
| | Host material | Dopant material | LT95(h) | Chromaticity CIEx | CIEy |
| Example 249 | BH-7 | BD-16 | 95 | 0.141 | 0.098 |
| Comparative Example 249 | BH-7-a | BD-16 | 70 | 0.141 | 0.098 |

Example 250 and Comparative Example 250

Except that the compounds shown in following table were used as the materials of the emitting layer (host material and dopant material), the organic EL devices were fabricated and evaluated in the same manner as in Example 1. The results are shown in the following Table.

TABLE 233

| | Emitting layer | | | | |
|---|---|---|---|---|---|
| | Host material | Dopant material | LT95(h) | Chromaticity CIEx | CIEy |
| Example 250 | BH-8 | BD-16 | 72 | 0.141 | 0.098 |
| Comparative Example 250 | BH-8-a | BD-16 | 50 | 0.141 | 0.098 |

Example 251 and Comparative Example 251

Except that the compounds shown in following table were used as the materials of the emitting layer (host material and dopant material), the organic EL devices were fabricated and evaluated in the same manner as in Example 1. The results are shown in the following Table.

TABLE 234

| | Emitting layer | | | | |
|---|---|---|---|---|---|
| | Host material | Dopant material | LT95(h) | Chromaticity CIEx | CIEy |
| Example 251 | BH-9 | BD-16 | 68 | 0.141 | 0.098 |
| Comparative Example 251 | BH-9-a | BD-16 | 51 | 0.141 | 0.098 |

Example 252 and Comparative Example 252

Except that the compounds shown in following table were used as the materials of the emitting layer (host material and dopant material), the organic EL devices were fabricated and evaluated in the same manner as in Example 1. The results are shown in the following Table.

TABLE 235

| | Emitting layer | | | | |
|---|---|---|---|---|---|
| | Host material | Dopant material | LT95(h) | Chromaticity CIEx | CIEy |
| Example 252 | BH-10 | BD-16 | 63 | 0.141 | 0.098 |
| Comparative Example 252 | BH-10-a | BD-16 | 48 | 0.141 | 0.098 |

Example 253 and Comparative Example 253

Except that the compounds shown in following table were used as the materials of the emitting layer (host material and dopant material), the organic EL devices were fabricated and evaluated in the same manner as in Example 1. The results are shown in the following Table.

TABLE 236

| | Emitting layer | | | | |
|---|---|---|---|---|---|
| | Host material | Dopant material | LT95(h) | Chromaticity CIEx | CIEy |
| Example 253 | BH-11 | BD-16 | 54 | 0.141 | 0.098 |
| Comparative Example 253 | BH-11-a | BD-16 | 42 | 0.141 | 0.098 |

Example 254 and Comparative Example 254

Except that the compounds shown in following table were used as the materials of the emitting layer (host material and dopant material), the organic EL devices were fabricated and evaluated in the same manner as in Example 1. The results are shown in the following Table.

TABLE 237

| | Emitting layer | | | | |
|---|---|---|---|---|---|
| | Host material | Dopant material | LT95(h) | Chromaticity CIEx | CIEy |
| Example 254 | BH-12 | BD-16 | 55 | 0.141 | 0.098 |
| Comparative Example 254 | BH-12-a | BD-16 | 37 | 0.141 | 0.098 |

Example 255 and Comparative Example 255

Except that the compounds shown in following table were used as the materials of the emitting layer (host material and dopant material), the organic EL devices were fabricated and evaluated in the same manner as in Example 1. The results are shown in the following Table.

TABLE 238

| | Emitting layer | | | | |
|---|---|---|---|---|---|
| | Host material | Dopant material | LT95(h) | Chromaticity CIEx | CIEy |
| Example 255 | BH-13 | BD-16 | 50 | 0.141 | 0.098 |
| Comparative Example 255 | BH-13-a | BD-16 | 33 | 0.141 | 0.098 |

Example 256 and Comparative Example 256

Except that the compounds shown in following table were used as the materials of the emitting layer (host material and dopant material), the organic EL devices were fabricated and evaluated in the same manner as in Example 1. The results are shown in the following Table.

TABLE 239

| | Emitting layer | | | Chromaticity | |
|---|---|---|---|---|---|
| | Host material | Dopant material | LT95(h) | CIEx | CIEy |
| Example 256 | BH-14 | BD-16 | 90 | 0.141 | 0.098 |
| Comparative Example 256 | BH-14-a | BD-16 | 61 | 0.141 | 0.098 |

Example 257 and Comparative Example 257

Except that the compounds shown in following table were used as the materials of the emitting layer (host material and dopant material), the organic EL devices were fabricated and evaluated in the same manner as in Example 1. The results are shown in the following Table.

TABLE 240

| | Emitting layer | | | Chromaticity | |
|---|---|---|---|---|---|
| | Host material | Dopant material | LT95(h) | CIEx | CIEy |
| Example 257 | BH-15 | BD-16 | 70 | 0.141 | 0.098 |
| Comparative Example 257 | BH-15-a | BD-16 | 47 | 0.141 | 0.098 |

Example 258 and Comparative Example 258

Except that the compounds shown in following table were used as the materials of the emitting layer (host material and dopant material), the organic EL devices were fabricated and evaluated in the same manner as in Example 1. The results are shown in the following Table.

TABLE 241

| | Emitting layer | | | Chromaticity | |
|---|---|---|---|---|---|
| | Host material | Dopant material | LT95(h) | CIEx | CIEy |
| Example 258 | BH-16 | BD-16 | 63 | 0.141 | 0.098 |
| Comparative Example 258 | BH-16-a | BD-16 | 42 | 0.141 | 0.098 |

Example 259

Except that the compounds shown in following table were used as the materials of the emitting layer (host material and dopant material), the organic EL device was fabricated and evaluated in the same manner as in Example 1. The results are shown in the following Table.

TABLE 242

| | Emitting layer | | | Chromaticity | |
|---|---|---|---|---|---|
| | Host material | Dopant material | LT95(h) | CIEx | CIEy |
| Example 259 | BH-17 | BD-16 | 99 | 0.141 | 0.098 |

Example 260 and Comparative Example 260

Except that the compounds shown in following table were used as the materials of the emitting layer (host material and dopant material), the organic EL devices were fabricated and evaluated in the same manner as in Example 1. The results are shown in the following Table.

TABLE 243

| | Emitting layer | | | Chromaticity | |
|---|---|---|---|---|---|
| | Host material | Dopant material | LT95(h) | CIEx | CIEy |
| Example 260 | BH-1 | BD-17 | 95 | 0.140 | 0.096 |
| Comparative Example 260 | BH-1-a | BD-17 | 63 | 0.140 | 0.096 |

Example 261 and Comparative Example 261

Except that the compounds shown in following table were used as the materials of the emitting layer (host material and dopant material), the organic EL devices were fabricated and evaluated in the same manner as in Example 1. The results are shown in the following Table.

TABLE 244

| | Emitting layer | | | Chromaticity | |
|---|---|---|---|---|---|
| | Host material | Dopant material | LT95(h) | CIEx | CIEy |
| Example 261 | BH-2 | BD-17 | 44 | 0.140 | 0.096 |
| Comparative Example 261 | BH-2-a | BD-17 | 30 | 0.140 | 0.096 |

Example 262 and Comparative Example 262

Except that the compounds shown in following table were used as the materials of the emitting layer (host material and dopant material), the organic EL devices were fabricated and evaluated in the same manner as in Example 1. The results are shown in the following Table.

TABLE 245

| | Emitting layer | | | Chromaticity | |
|---|---|---|---|---|---|
| | Host material | Dopant material | LT95(h) | CIEx | CIEy |
| Example 262 | BH-3 | BD-17 | 45 | 0.140 | 0.096 |
| Comparative Example 262 | BH-3-a | BD-17 | 30 | 0.140 | 0.096 |

Example 263 and Comparative Example 263

Except that the compounds shown in following table were used as the materials of the emitting layer (host material and dopant material), the organic EL devices were fabricated and evaluated in the same manner as in Example 1. The results are shown in the following Table.

TABLE 246

|  | Emitting layer | | | Chromaticity | |
|---|---|---|---|---|---|
|  | Host material | Dopant material | LT95(h) | CIEx | CIEy |
| Example 263 | BH-4 | BD-17 | 45 | 0.140 | 0.096 |
| Comparative Example 263 | BH-4-a | BD-17 | 30 | 0.140 | 0.096 |

Example 264 and Comparative Example 264

Except that the compounds shown in following table were used as the materials of the emitting layer (host material and dopant material), the organic EL devices were fabricated and evaluated in the same manner as in Example 1. The results are shown in the following Table.

TABLE 247

|  | Emitting layer | | | Chromaticity | |
|---|---|---|---|---|---|
|  | Host material | Dopant material | LT95(h) | CIEx | CIEy |
| Example 264 | BH-5 | BD-17 | 105 | 0.140 | 0.096 |
| Comparative Example 264 | BH-5-a | BD-17 | 71 | 0.140 | 0.096 |

Example 265 and Comparative Example 265

Except that the compounds shown in following table were used as the materials of the emitting layer (host material and dopant material), the organic EL devices were fabricated and evaluated in the same manner as in Example 1. The results are shown in the following Table.

TABLE 248

|  | Emitting layer | | | Chromaticity | |
|---|---|---|---|---|---|
|  | Host material | Dopant material | LT95(h) | CIEx | CIEy |
| Example 265 | BH-6 | BD-17 | 90 | 0.140 | 0.096 |
| Comparative Example 265 | BH-6-a | BD-17 | 60 | 0.140 | 0.096 |

Example 266 and Comparative Example 266

Except that the compounds shown in following table were used as the materials of the emitting layer (host material and dopant material), the organic EL devices were fabricated and evaluated in the same manner as in Example 1. The results are shown in the following Table.

TABLE 249

|  | Emitting layer | | | Chromaticity | |
|---|---|---|---|---|---|
|  | Host material | Dopant material | LT95(h) | CIEx | CIEy |
| Example 266 | BH-7 | BD-17 | 90 | 0.140 | 0.096 |
| Comparative Example 266 | BH-7-a | BD-17 | 63 | 0.140 | 0.096 |

Example 267 and Comparative Example 267

Except that the compounds shown in following table were used as the materials of the emitting layer (host material and dopant material), the organic EL devices were fabricated and evaluated in the same manner as in Example 1. The results are shown in the following Table.

TABLE 250

|  | Emitting layer | | | Chromaticity | |
|---|---|---|---|---|---|
|  | Host material | Dopant material | LT95(h) | CIEx | CIEy |
| Example 267 | BH-8 | BD-17 | 72 | 0.140 | 0.096 |
| Comparative Example 267 | BH-8-a | BD-17 | 50 | 0.140 | 0.096 |

Example 268 and Comparative Example 268

Except that the compounds shown in following table were used as the materials of the emitting layer (host material and dopant material), the organic EL devices were fabricated and evaluated in the same manner as in Example 1. The results are shown in the following Table.

TABLE 251

|  | Emitting layer | | | Chromaticity | |
|---|---|---|---|---|---|
|  | Host material | Dopant material | LT95(h) | CIEx | CIEy |
| Example 268 | BH-9 | BD-17 | 72 | 0.140 | 0.096 |
| Comparative Example 268 | BH-9-a | BD-17 | 50 | 0.140 | 0.096 |

Example 269 and Comparative Example 269

Except that the compounds shown in following table were used as the materials of the emitting layer (host material and dopant material), the organic EL devices were fabricated and evaluated in the same manner as in Example 1. The results are shown in the following Table.

TABLE 252

| | Emitting layer | | | Chromaticity | |
|---|---|---|---|---|---|
| | Host material | Dopant material | LT95(h) | CIEx | CIEy |
| Example 269 | BH-10 | BD-17 | 59 | 0.140 | 0.096 |
| Comparative Example 269 | BH-10-a | BD-17 | 48 | 0.140 | 0.096 |

Example 270 and Comparative Example 270

Except that the compounds shown in following table were used as the materials of the emitting layer (host material and dopant material), the organic EL devices were fabricated and evaluated in the same manner as in Example 1. The results are shown in the following Table.

TABLE 253

| | Emitting layer | | | Chromaticity | |
|---|---|---|---|---|---|
| | Host material | Dopant material | LT95(h) | CIEx | CIEy |
| Example 270 | BH-11 | BD-17 | 59 | 0.140 | 0.096 |
| Comparative Example 270 | BH-11-a | BD-17 | 40 | 0.140 | 0.096 |

Example 271 and Comparative Example 271

Except that the compounds shown in following table were used as the materials of the emitting layer (host material and dopant material), the organic EL devices were fabricated and evaluated in the same manner as in Example 1. The results are shown in the following Table.

TABLE 254

| | Emitting layer | | | Chromaticity | |
|---|---|---|---|---|---|
| | Host material | Dopant material | LT95(h) | CIEx | CIEy |
| Example 271 | BH-12 | BD-17 | 56 | 0.140 | 0.096 |
| Comparative Example 271 | BH-12-a | BD-17 | 38 | 0.140 | 0.096 |

Example 272 and Comparative Example 272

Except that the compounds shown in following table were used as the materials of the emitting layer (host material and dopant material), the organic EL devices were fabricated and evaluated in the same manner as in Example 1. The results are shown in the following Table.

TABLE 255

| | Emitting layer | | | Chromaticity | |
|---|---|---|---|---|---|
| | Host material | Dopant material | LT95(h) | CIEx | CIEy |
| Example 272 | BH-13 | BD-17 | 50 | 0.140 | 0.096 |
| Comparative Example 272 | BH-13-a | BD-17 | 34 | 0.140 | 0.096 |

Example 273 and Comparative Example 273

Except that the compounds shown in following table were used as the materials of the emitting layer (host material and dopant material), the organic EL devices were fabricated and evaluated in the same manner as in Example 1. The results are shown in the following Table.

TABLE 256

| | Emitting layer | | | Chromaticity | |
|---|---|---|---|---|---|
| | Host material | Dopant material | LT95(h) | CIEx | CIEy |
| Example 273 | BH-14 | BD-17 | 97 | 0.140 | 0.096 |
| Comparative Example 273 | BH-14-a | BD-17 | 63 | 0.140 | 0.096 |

Example 274 and Comparative Example 274

Except that the compounds shown in following table were used as the materials of the emitting layer (host material and dopant material), the organic EL devices were fabricated and evaluated in the same manner as in Example 1. The results are shown in the following Table.

TABLE 257

| | Emitting layer | | | Chromaticity | |
|---|---|---|---|---|---|
| | Host material | Dopant material | LT95(h) | CIEx | CIEy |
| Example 274 | BH-15 | BD-17 | 61 | 0.140 | 0.096 |
| Comparative Example 274 | BH-15-a | BD-17 | 42 | 0.140 | 0.096 |

Example 275 and Comparative Example 275

Except that the compounds shown in following table were used as the materials of the emitting layer (host material and dopant material), the organic EL devices were fabricated and evaluated in the same manner as in Example 1. The results are shown in the following Table.

TABLE 258

| | Emitting layer | | | Chromaticity | |
|---|---|---|---|---|---|
| | Host material | Dopant material | LT95(h) | CIEx | CIEy |
| Example 275 | BH-16 | BD-17 | 67 | 0.140 | 0.096 |
| Comparative Example 275 | BH-16-a | BD-17 | 45 | 0.140 | 0.096 |

Example 276

Except that the compounds shown in following table were used as the materials of the emitting layer (host material and dopant material), the organic EL devices were fabricated and evaluated in the same manner as in Example 1. The results are shown in the following Table.

TABLE 259

| | Emitting layer | | | Chromaticity | |
|---|---|---|---|---|---|
| | Host material | Dopant material | LT95(h) | CIEx | CIEy |
| Example 276 | BH-17 | BD-17 | 95 | 0.140 | 0.096 |

Example 277 and Comparative Example 277

Except that the compounds shown in following table were used as the materials of the emitting layer (host material and dopant material), the organic EL devices were fabricated and evaluated in the same manner as in Example 1. The results are shown in the following Table.

TABLE 260

| | Emitting layer | | | Chromaticity | |
|---|---|---|---|---|---|
| | Host material | Dopant material | LT95(h) | CIEx | CIEy |
| Example 277 | BH-1 | BD-18 | 77 | 0.143 | 0.109 |
| Comparative Example 277 | BH-1-a | BD-18 | 52 | 0.143 | 0.109 |

Example 278 and Comparative Example 278

Except that the compounds shown in following table were used as the materials of the emitting layer (host material and dopant material), the organic EL devices were fabricated and evaluated in the same manner as in Example 1. The results are shown in the following Table.

TABLE 261

| | Emitting layer | | | Chromaticity | |
|---|---|---|---|---|---|
| | Host material | Dopant material | LT95(h) | CIEx | CIEy |
| Example 278 | BH-2 | BD-18 | 36 | 0.143 | 0.109 |
| Comparative Example 278 | BH-2-a | BD-18 | 29 | 0.143 | 0.109 |

Example 279 and Comparative Example 279

Except that the compounds shown in following table were used as the materials of the emitting layer (host material and dopant material), the organic EL devices were fabricated and evaluated in the same manner as in Example 1. The results are shown in the following Table.

TABLE 262

| | Emitting layer | | | Chromaticity | |
|---|---|---|---|---|---|
| | Host material | Dopant material | LT95(h) | CIEx | CIEy |
| Example 279 | BH-3 | BD-18 | 36 | 0.143 | 0.109 |
| Comparative Example 279 | BH-3-a | BD-18 | 25 | 0.143 | 0.109 |

Example 280 and Comparative Example 280

Except that the compounds shown in following table were used as the materials of the emitting layer (host material and dopant material), the organic EL devices were fabricated and evaluated in the same manner as in Example 1. The results are shown in the following Table.

TABLE 263

| | Emitting layer | | | Chromaticity | |
|---|---|---|---|---|---|
| | Host material | Dopant material | LT95(h) | CIEx | CIEy |
| Example 280 | BH-4 | BD-18 | 33 | 0.143 | 0.109 |
| Comparative Example 280 | BH-4-a | BD-18 | 24 | 0.143 | 0.109 |

Example 281 and Comparative Example 281

Except that the compounds shown in following table were used as the materials of the emitting layer (host material and dopant material), the organic EL devices were fabricated and evaluated in the same manner as in Example 1. The results are shown in the following Table.

TABLE 264

| | Emitting layer | | | Chromaticity | |
|---|---|---|---|---|---|
| | Host material | Dopant material | LT95(h) | CIEx | CIEy |
| Example 281 | BH-5 | BD-18 | 81 | 0.143 | 0.109 |
| Comparative Example 281 | BH-5-a | BD-18 | 53 | 0.143 | 0.109 |

Example 282 and Comparative Example 282

Except that the compounds shown in following table were used as the materials of the emitting layer (host material and dopant material), the organic EL devices were fabricated and evaluated in the same manner as in Example 1. The results are shown in the following Table.

TABLE 265

|  | Emitting layer | | | Chromaticity | |
|---|---|---|---|---|---|
|  | Host material | Dopant material | LT95(h) | CIEx | CIEy |
| Example 282 | BH-6 | BD-18 | 72 | 0.143 | 0.109 |
| Comparative Example 282 | BH-6-a | BD-18 | 50 | 0.143 | 0.109 |

Example 283 and Comparative Example 283

Except that the compounds shown in following table were used as the materials of the emitting layer (host material and dopant material), the organic EL devices were fabricated and evaluated in the same manner as in Example 1. The results are shown in the following Table.

TABLE 266

|  | Emitting layer | | | Chromaticity | |
|---|---|---|---|---|---|
|  | Host material | Dopant material | LT95(h) | CIEx | CIEy |
| Example 283 | BH-7 | BD-18 | 72 | 0.143 | 0.109 |
| Comparative Example 283 | BH-7-a | BD-18 | 52 | 0.143 | 0.109 |

Example 284 and Comparative Example 284

Except that the compounds shown in following table were used as the materials of the emitting layer (host material and dopant material), the organic EL devices were fabricated and evaluated in the same manner as in Example 1. The results are shown in the following Table.

TABLE 267

|  | Emitting layer | | | Chromaticity | |
|---|---|---|---|---|---|
|  | Host material | Dopant material | LT95(h) | CIEx | CIEy |
| Example 284 | BH-8 | BD-18 | 54 | 0.143 | 0.109 |
| Comparative Example 284 | BH-8-a | BD-18 | 40 | 0.143 | 0.109 |

Example 285 and Comparative Example 285

Except that the compounds shown in following table were used as the materials of the emitting layer (host material and dopant material), the organic EL devices were fabricated and evaluated in the same manner as in Example 1. The results are shown in the following Table.

TABLE 268

|  | Emitting layer | | | Chromaticity | |
|---|---|---|---|---|---|
|  | Host material | Dopant material | LT95(h) | CIEx | CIEy |
| Example 285 | BH-9 | BD-18 | 54 | 0.143 | 0.109 |
| Comparative Example 285 | BH-9-a | BD-18 | 37 | 0.143 | 0.109 |

Example 286 and Comparative Example 286

Except that the compounds shown in following table were used as the materials of the emitting layer (host material and dopant material), the organic EL devices were fabricated and evaluated in the same manner as in Example 1. The results are shown in the following Table.

TABLE 269

|  | Emitting layer | | | Chromaticity | |
|---|---|---|---|---|---|
|  | Host material | Dopant material | LT95(h) | CIEx | CIEy |
| Example 286 | BH-10 | BD-18 | 51 | 0.143 | 0.109 |
| Comparative Example 286 | BH-10-a | BD-18 | 35 | 0.143 | 0.109 |

Example 287 and Comparative Example 287

Except that the compounds shown in following table were used as the materials of the emitting layer (host material and dopant material), the organic EL devices were fabricated and evaluated in the same manner as in Example 1. The results are shown in the following Table.

TABLE 270

|  | Emitting layer | | | Chromaticity | |
|---|---|---|---|---|---|
|  | Host material | Dopant material | LT95(h) | CIEx | CIEy |
| Example 287 | BH-11 | BD-18 | 48 | 0.143 | 0.109 |
| Comparative Example 287 | BH-11-a | BD-18 | 31 | 0.143 | 0.109 |

Example 288 and Comparative Example 288

Except that the compounds shown in following table were used as the materials of the emitting layer (host material and dopant material), the organic EL devices were fabricated and evaluated in the same manner as in Example 1. The results are shown in the following Table.

TABLE 271

| | Emitting layer | | | | |
|---|---|---|---|---|---|
| | Host material | Dopant material | LT95(h) | Chromaticity CIEx | CIEy |
| Example 288 | BH-12 | BD-18 | 43 | 0.143 | 0.110 |
| Comparative Example 288 | BH-12-a | BD-18 | 31 | 0.143 | 0.110 |

Example 289 and Comparative Example 289

Except that the compounds shown in following table were used as the materials of the emitting layer (host material and dopant material), the organic EL devices were fabricated and evaluated in the same manner as in Example 1. The results are shown in the following Table.

TABLE 272

| | Emitting layer | | | | |
|---|---|---|---|---|---|
| | Host material | Dopant material | LT95(h) | Chromaticity CIEx | CIEy |
| Example 289 | BH-13 | BD-18 | 36 | 0.143 | 0.109 |
| Comparative Example 289 | BH-13-a | BD-18 | 25 | 0.143 | 0.109 |

Example 290 and Comparative Example 290

Except that the compounds shown in following table were used as the materials of the emitting layer (host material and dopant material), the organic EL devices were fabricated and evaluated in the same manner as in Example 1. The results are shown in the following Table.

TABLE 273

| | Emitting layer | | | | |
|---|---|---|---|---|---|
| | Host material | Dopant material | LT95(h) | Chromaticity CIEx | CIEy |
| Example 290 | BH-14 | BD-18 | 71 | 0.143 | 0.109 |
| Comparative Example 290 | BH-14-a | BD-18 | 48 | 0.143 | 0.109 |

Example 291 and Comparative Example 291

Except that the compounds shown in following table were used as the materials of the emitting layer (host material and dopant material), the organic EL devices were fabricated and evaluated in the same manner as in Example 1. The results are shown in the following Table.

TABLE 274

| | Emitting layer | | | | |
|---|---|---|---|---|---|
| | Host material | Dopant material | LT95(h) | Chromaticity CIEx | CIEy |
| Example 291 | BH-15 | BD-18 | 56 | 0.143 | 0.109 |
| Comparative Example 291 | BH-15-a | BD-18 | 38 | 0.143 | 0.109 |

Example 292 and Comparative Example 292

Except that the compounds shown in following table were used as the materials of the emitting layer (host material and dopant material), the organic EL devices were fabricated and evaluated in the same manner as in Example 1. The results are shown in the following Table.

TABLE 275

| | Emitting layer | | | | |
|---|---|---|---|---|---|
| | Host material | Dopant material | LT95(h) | Chromaticity CIEx | CIEy |
| Example 292 | BH-16 | BD-18 | 46 | 0.143 | 0.109 |
| Comparative Example 292 | BH-16-a | BD-18 | 32 | 0.143 | 0.109 |

Example 293 and Comparative Example 293

Except that the compounds shown in following table were used as the materials of the emitting layer (host material and dopant material), the organic EL device was fabricated and evaluated in the same manner as in Example 1. The results are shown in the following Table.

TABLE 276

| | Emitting layer | | | | |
|---|---|---|---|---|---|
| | Host material | Dopant material | LT95(h) | Chromaticity CIEx | CIEy |
| Example 293 | BH-17 | BD-18 | 75 | 0.143 | 0.109 |

From the results of Tables 1 to 276, it can be recognized that, if the compound represented by the formula (1) (host material) having a deuterium atom at the particular position is used in combination with the particular dopant material in the emitting layer of the organic EL device, the lifetime of the organic EL device is prolonged compared with the case where the compound (host material) having no deuterium atom at the particular position is used in combination with the corresponding dopant material.

Several embodiments and/or examples of the present invention have been described in detail above. However, without substantially departing from novel teachings and effects of the present invention, the person skilled in the art can readily make a number of modifications to the embodiments and/or examples which are exemplifications of these teachings and effects. Thus, these modifications are included in the scope of the present invention.

The documents described in this specification and the contents of the application that serves as the basis of priority claim under Paris convention are incorporated herein by reference in its entirety.

The invention claimed is:
1. An organic electroluminescence device comprising:
a cathode,
an anode, and
an emitting layer disposed between the cathode and the anode, wherein
the emitting layer comprises a compound represented by the following formula (1) and one or more compounds selected from the group consisting of compounds represented by each of formulas (11), (21), (31), (41), (51), (61), (71) and (81):

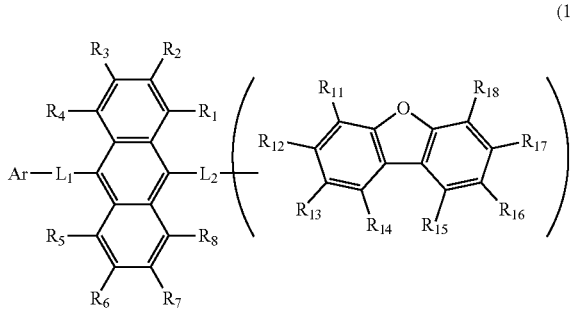
(1)

wherein in the formula (1),
$R_1$ to $R_8$ are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;
$R_{901}$ to $R_{907}$ are independently
a hydrogen atom,
a substituted or unsubstituted alkyl group having 1 to 50 carbon atoms,
a substituted or unsubstituted cycloalkyl group having 3 to 50 ring carbon atoms,
a substituted or unsubstituted aryl group having 6 to 50 ring carbon atoms, or
a substituted or unsubstituted monovalent heterocyclic group having 5 to 50 ring atoms;
when two or more of $R_{901}$ to $R_{907}$ exist, two or more of $R_{901}$ to $R_{907}$ may be the same with or different from each other;
at least one of $R_1$ to $R_8$ is a deuterium atom;
two or more adjacent groups of $R_1$ to $R_4$ and two or more adjacent groups of $R_5$ to $R_8$ do not form a ring;
$L_1$ and $L_2$ are independently
a single bond,
a substituted or unsubstituted arylene group having 6 to 30 ring carbon atoms, or
a substituted or unsubstituted divalent heterocyclic group having 5 to 30 ring atoms;
Ar is
a substituted or unsubstituted aryl group having 6 to 50 ring carbon atoms, or
a substituted or unsubstituted monovalent heterocyclic group having 5 to 50 ring atoms;
one of $R_{11}$ to $R_{18}$ is a single bond bonding to $L_2$;
$R_{11}$ to $R_{18}$ which are not single bonds bonding to $L_2$ are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;
$R_{901}$ to $R_{907}$ are as defined in $R_1$ to $R_8$; and
two or more adjacent groups of $R_{11}$ to $R_{18}$ do not form a ring;

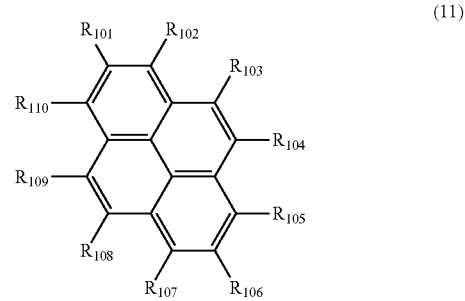
(11)

wherein, in the formula (11),
one or more pairs of two or more adjacent groups of $R_{101}$ to $R_{110}$ are bonded with each other to form a substituted or unsubstituted, saturated or unsaturated ring, or do not form a substituted or unsubstituted, saturated or unsaturated ring;
at least one of $R_{101}$ to $R_{110}$ is a monovalent group represented by the formula (12);
$R_{101}$ to $R_{110}$ that do not form the substituted or unsubstituted, saturated or unsaturated ring and that are not a monovalent group represented by the following formula (12) are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms, —Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;
$R_{901}$ to $R_{907}$ are as defined in the formula (1);

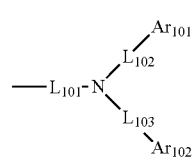
(12)

wherein, in the formula (12), $Ar_{101}$ and $Ar_{102}$ are independently
a substituted or unsubstituted aryl group having 6 to 50 ring carbon atoms, or
a substituted or unsubstituted monovalent heterocyclic group having 5 to 50 ring atoms;
$L_{101}$ to $L_{103}$ are independently
a single bonded,
a substituted or unsubstituted arylene group having 6 to 30 ring carbon atoms, or
a substituted or unsubstituted divalent heterocyclic group having 5 to 30 ring atoms;

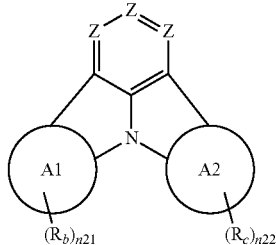
(21)

wherein, in the formula (21),
Z's are independently $CR_a$ or N;
A1 ring and A2 ring are independently a substituted or unsubstituted aromatic hydrocarbon ring having 6 to 50 ring carbon atoms, or a substituted or unsubstituted heterocyclic ring having 5 to 50 ring atoms;
when a plurality of $R_a$s exist, one or more pairs of two or more adjacent groups of $R_a$ are bonded with each other to form a substituted or unsubstituted, saturated or unsaturated ring, or do not form a substituted or unsubstituted, saturated or unsaturated ring;
when a plurality of $R_b$s exist, one or more pairs of two or more adjacent groups of $R_b$ are bonded with each other to form a substituted or unsubstituted, saturated or unsaturated ring, or do not form a substituted or unsubstituted, saturated or unsaturated ring;
when a plurality of $R_c$s exist, one or more pairs of two or more adjacent groups of $R_c$ are bonded with each other to form a substituted or unsubstituted, saturated or unsaturated ring, or do not form a substituted or unsubstituted, saturated or unsaturated ring;

n21 and n22 are independently an integer of 0 to 4;
$R_a$ to $R_c$ that do not form the substituted or unsubstituted, saturated or unsaturated ring are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;
$R_{901}$ to $R_{907}$ are as defined in the formula (1);

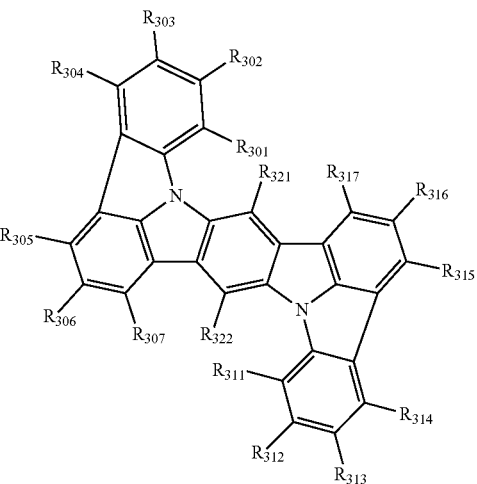
(31)

wherein, in the formula (31),
one or more pairs of two or more adjacent groups of $R_{301}$ to $R_{307}$ and $R_{311}$ to $R_{317}$ form a substituted or unsubstituted, saturated or unsaturated ring, or do not form a substituted or unsubstituted saturated or unsaturated ring;
$R_{301}$ to $R_{307}$ and $R_{311}$ to $R_{317}$ that do not form the substituted or unsubstituted, saturated or unsaturated ring are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms, —Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;

$R_{321}$ and $R_{322}$ are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;

$R_{901}$ to $R_{907}$ are as defined in the formula (1);

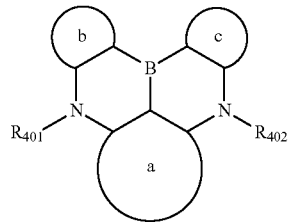

(41)

wherein, in the formula (41),
a ring, b ring and c ring are independently
a substituted or unsubstituted aromatic hydrocarbon ring having 6 to 50 ring carbon atoms, or
a substituted or unsubstituted heterocyclic ring having 5 to 50 ring atoms;
  at least one of the ring b or ring c is a substituted or unsubstituted heterocyclic ring including 5 to 50 ring atoms;
  $R_{401}$ and $R_{402}$ are independently bonded to the a ring, the b ring or the c ring to form a substituted or unsubstituted heterocyclic ring or do not form a substituted or unsubstituted heterocyclic ring;
  $R_{401}$ and $R_{402}$ that do not form the substituted or unsubstituted heterocyclic ring are independently
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
a substituted or unsubstituted aryl group having 6 to 50 ring carbon atoms, or a substituted or unsubstituted monovalent heterocyclic group having 5 to 50 ring atoms; and
at least one of the hydrogen atoms in formula (41) is a deuterium atom:

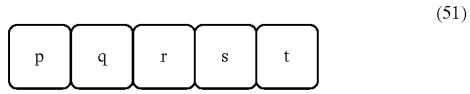

(51)

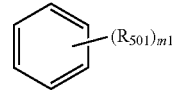

(52)

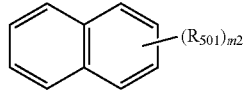

(53)

(54)

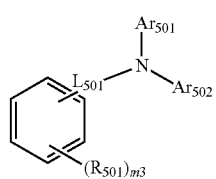

(55)

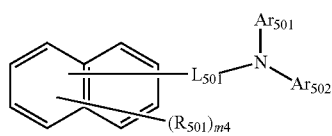

(56)

wherein, in the formula (51),
r ring is a ring represented by the formula (52) or formula (53) which is fused to an adjacent ring at an arbitrary position;

q ring and s ring are independently a ring represented by the formula (54) which is fused to an adjacent ring at an arbitrary position;

p ring and t ring are independently a ring represented by the formula (55) or the formula (56) which is fused to an adjacent ring at an arbitrary position;

when a plurality of $R_{501}$s exist, adjacent $R_{501}$s are bonded with each other to form a substituted or unsubstituted, saturated or unsaturated ring, or do not form a substituted or unsubstituted, saturated or unsaturated ring;

$X_{501}$ is an oxygen atom, a sulfur atom, or $NR_{502}$;

$R_{501}$ and $R_{502}$ that do not form the substituted or unsubstituted saturated or unsaturated ring are
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms, —Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;

$R_{901}$ to $R_{907}$ are as defined in the formula (1);

$Ar_{501}$ and $Ar_{502}$ are independently
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
a substituted or unsubstituted aryl group having 6 to 50 ring carbon atoms, or
a substituted or unsubstituted monovalent heterocyclic group having 5 to 50 ring atoms;

$L_{501}$ is
a substituted or unsubstituted alkylene group having 1 to 50 carbon atoms,
a substituted or unsubstituted alkenylene group having 2 to 50 carbon atoms,
a substituted or unsubstituted alkynylene group having 2 to 50 carbon atoms,
a substituted or unsubstituted cycloalkylene group having 3 to 50 ring carbon atoms,
a substituted or unsubstituted arylene group having 6 to 50 ring carbon atoms, or
a substituted or unsubstituted divalent heterocyclic group having 5 to 50 ring atoms;

m1 is an integer of 0 to 2, m2 is an integer of 0 to 4, m3s are independently an integer of 0 to 3, and m4s are independently an integer of 0 to 5; when a plurality of $R_{501}$s exist, $R_{501}$s may be the same or different;

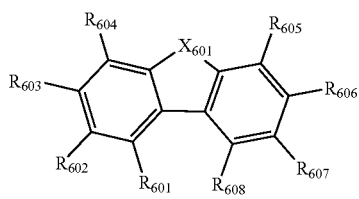
(61)

wherein, in the formula (61),
at least one pair of $R_{601}$ and $R_{602}$, $R_{602}$ and $R_{603}$, and $R_{603}$ and $R_{604}$ are bonded with each other to form a divalent group represented by the formula (62);
at least one pair of $R_{605}$ and $R_{606}$, $R_{606}$ and $R_{607}$, and $R_{607}$ and $R_{608}$ are bonded with each other to form a divalent group represented by formula (63);

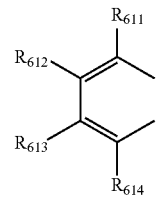
(62)

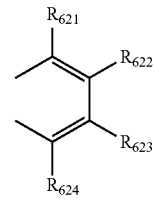
(63)

at least one of $R_{601}$ to $R_{604}$ that does not form the divalent group represented by the formula (62), and $R_{611}$ to $R_{614}$ is a monovalent group represented by the following formula (64);
at least one of $R_{605}$ to $R_{608}$ that do not form the divalent group represented by the formula (63), and $R_{621}$ to $R_{624}$ is a monovalent group represented by the following formula (64);
$X_{601}$ is an oxygen atom, a sulfur atom, or $NR_{609}$;
$R_{601}$ to $R_{608}$ that do not form the divalent group represented by the formulas (62) and (63) and that is not the monovalent group represented by the formula (64), $R_{611}$ to $R_{614}$ and $R_{621}$ to $R_{624}$ that are not the monovalent group represented by the formula (64), and $R_{609}$ are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;

$R_{901}$ to $R_{907}$ are as defined in the formula (1);

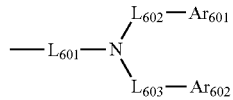
(64)

wherein, in the formula (64), $Ar_{601}$ and $Ar_{602}$ are independently
a substituted or unsubstituted aryl group having 6 to 50 ring carbon atoms, or a substituted or unsubstituted monovalent heterocyclic group having 5 to 50 ring atoms;
$L_{601}$ to $L_{603}$ are independently
a single bonded,
a substituted or unsubstituted arylene group having 6 to 30 ring carbon atoms,
a substituted or unsubstituted divalent heterocyclic group having 5 to 30 ring atoms, or
a divalent linking group formed by bonding 2 to 4 above mentioned groups;

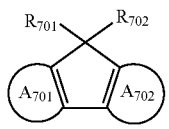

(71)

wherein, in the formula (71),
$A_{701}$ ring and $A_{702}$ ring are independently
a substituted or unsubstituted aromatic hydrocarbon ring having 6 to 50 ring carbon atoms, or
a substituted or unsubstituted heterocyclic ring having 5 to 50 ring atoms;
One or more rings selected from the group consisting of $A_{701}$ ring and $A_{702}$ ring are bonded to the bond * of the structure represented by the following formula (72);

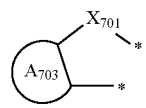

(72)

wherein, in the formula (72),
$A_{703}$ rings are independently
a substituted or unsubstituted aromatic hydrocarbon ring having 6 to 50 ring carbon atoms, or
a substituted or unsubstituted heterocyclic ring having 5 to 50 ring atoms;
$X_{701}$ is $NR_{703}$, $C(R_{704})(R_{705})$, $Si(R_{706})(R_{707})$, $Ge(R_{708})(R_{709})$, O, S or Se;
$R_{701}$ and $R_{702}$ are bonded with each other to form a substituted or unsubstituted, saturated or unsaturated ring or do not form a substituted or unsubstituted saturated or unsaturated ring;
$R_{701}$ and $R_{702}$ that do not form the substituted or unsubstituted, saturated or unsaturated ring, and $R_{703}$ to $R_{709}$ are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—$Si(R_{901})(R_{902})(R_{903})$,
—O—$(R_{904})$,
—S—$(R_{905})$,
—$N(R_{906})(R_{907})$,
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;
$R_{901}$ to $R_{907}$ are as defined in the formula (1);

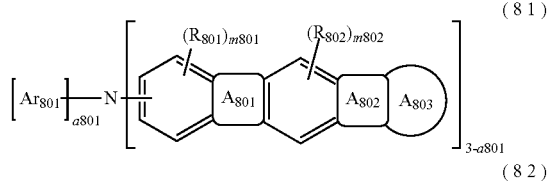

(81)

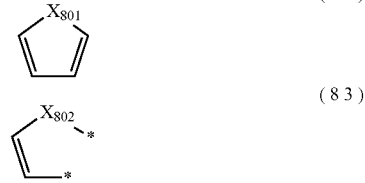

(82)

(83)

wherein, in the formula (81),
$A_{801}$ ring is a ring represented by the formula (82) which is fused to an adjacent ring at an arbitrary position;
$A_{802}$ ring is a ring represented by the formula (83) which is fused to an adjacent ring at an arbitrary position;
two bonds * bond to $A_{803}$ ring at an arbitrary position;
$X_{801}$ and $X_{802}$ are independently $C(R_{803})(R_{804})$, $Si(R_{805})(R_{806})$, an oxygen atom, or a sulfur atom;
$A_{803}$ ring is a substituted or unsubstituted aromatic hydrocarbon ring having 6 to 50 ring carbon atoms, or a substituted or unsubstituted heterocyclic ring having 5 to 50 ring atoms;
$Ar_{801}$ is a substituted or unsubstituted aryl group having 6 to 50 ring carbon atoms, or a substituted or unsubstituted monovalent heterocyclic group having 5 to 50 ring atoms;
$R_{801}$ to $R_{806}$ are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—$Si(R_{901})(R_{902})(R_{903})$,
—O—$(R_{904})$,
—S—$(R_{905})$,
—$N(R_{906})(R_{907})$,
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;
$R_{901}$ to $R_{907}$ are as defined in the formula (1);
m801 and m802 are independently an integer of 0 to 2; when these are 2, a plurality of $R_{801}$s or $R_{802}$s may be the same or different;
a801 is an integer of 0 to 2; when a801 is 0 or 1, the structure in the parentheses indicated by "3-a801" may be the same as or different from each other; when a801 is 2, $Ar_{801}$s may be the same or different from each other.

2. The organic electroluminescence device according to claim 1, wherein in the formula (1), at least two of $R_1$ to $R_8$ are deuterium atoms.

3. The organic electroluminescence device according to claim 1, wherein in the formula (1), $R_1$ to $R_8$ are all deuterium atoms.

4. The organic electroluminescence device according to claim 1, wherein in the formula (1), one or more of $L_1$ and $L_2$ are a substituted or unsubstituted arylene group having 6 to 30 ring carbon atoms in which at least one of hydrogen atoms is a deuterium atom, or a substituted or unsubstituted divalent heterocyclic group having 5 to 30 ring atoms in which at least one of hydrogen atoms is a deuterium atom.

5. The organic electroluminescence device according to claim 1, wherein in the formula (1), wherein L1 and L2 are independently a single bond, or a substituted or unsubstituted arylene group having 6 to 14 ring carbon atoms.

6. The organic electroluminescence device according to claim 1, wherein Ar is a substituted or unsubstituted aryl group having 6 to 50 ring carbon atoms in which at least one of hydrogen atoms is a deuterium atom, or a substituted or unsubstituted monovalent heterocyclic group having 5 to 50 ring atoms in which at least one of hydrogen atoms is a deuterium atom.

7. The organic electroluminescence device according to claim 1, wherein in the formula (1), Ar is a substituted or unsubstituted aryl group having 6 to 50 ring carbon atoms.

8. The organic electroluminescence device according to claim 7, wherein in the formula (1), Ar is selected from groups represented by any of the following formulas (a1) to (a4):

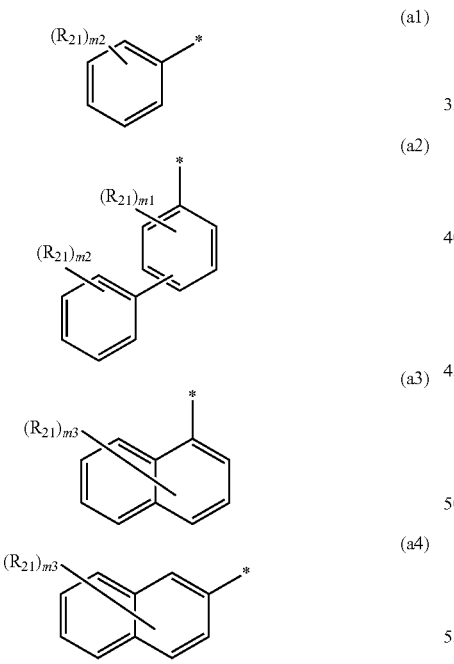

wherein in the formulas (a1) to (a4), "*" is a single bond which bonds to $L_1$;

$R_{21}$ is
a halogen atom, a cyano group, a nitro group,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;

$R_{901}$ to $R_{907}$ are as defined in the formula (1);
m1 is an integer of 0 to 4;
m2 is an integer of 0 to 5;
m3 is an integer of 0 to 7;
when each of m1 to m3 is two or more, a plurality of $R_{21}$'s are the same as or different from each other; and
when each of m1 to m3 is 2 or more, adjacent $R_{21}$'s form a substituted or unsubstituted, saturated or unsaturated ring by bonding with each other, or do not form a substituted or unsubstituted, saturated or unsaturated ring.

9. The organic electroluminescence device according to claim 1, wherein in the formula (1), $R_{11}$ to $R_{18}$ which are not a single bond bonded with $L_2$ are hydrogen atoms.

10. The organic electroluminescence device according to claim 1, wherein in the formula (1), $R_{11}$ to $R_{18}$ which are not a single bond bonded with $L_2$ are deuterium atoms.

11. The organic electroluminescence device according to claim 1, wherein the compound represented by the formula (1) is a compound represented by the following formula (2):

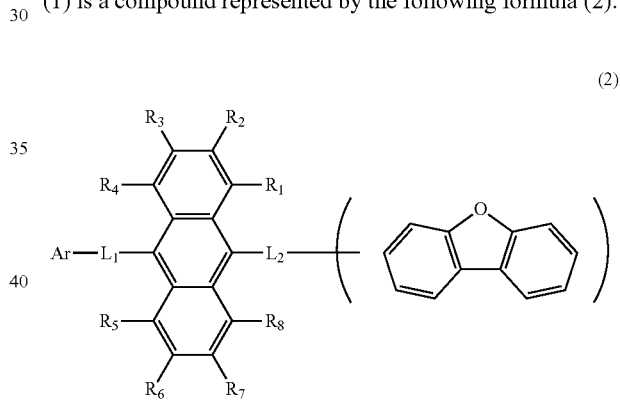

wherein in the formula (2), $R_1$ to $R_8$, Ar, $L_1$ and $L_2$ are as defined in the formula (1).

12. The organic electroluminescence device according to claim 1, wherein the compound represented by the formula (1) is a compound represented by the following formula (3):

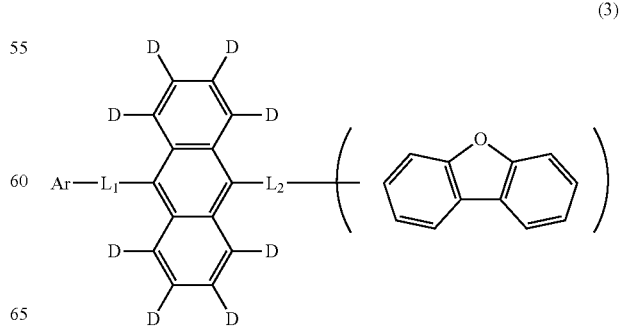

wherein in the formula (3), Ar, $L_1$ and $L_2$ are as defined in the formula (1).

13. The organic electroluminescence device according to claim 1, wherein relative to the total amount of the compound represented by formula (1) and a compound having a structure same as the compound represented by the formula (1) and containing only protium atoms as hydrogen atoms, in the emitting layer, the content ratio of the latter is 99 mol % or less.

14. The organic electroluminescence device according to claim 1, wherein in the formula (11), two of $R_{101}$ to $R_{110}$ are a group represented by the formula (12).

15. The organic electroluminescence device according to claim 1, wherein the compound represented by the formula (11) is a compound represented by the following formula (13):

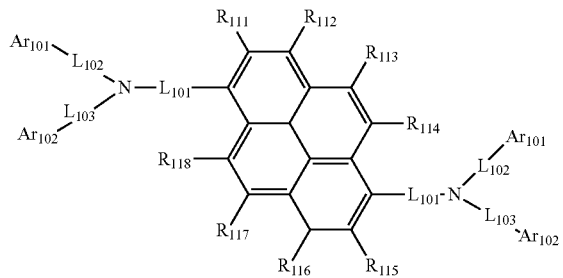

(13)

wherein in the formula (13), $R_{111}$ to $R_{118}$ in the formula (11) are the same as $R_{101}$ to $R_{110}$ that are not a monovalent group represented by the formula (12); and $Ar_{101}$, $Ar_{102}$, $L_{101}$, $L_{102}$ and $L_{103}$ are as defined in the formula (12).

16. The organic electroluminescence device according to claim 15, wherein the compound represented by the formula (13) is a compound represented by the following formula (14):

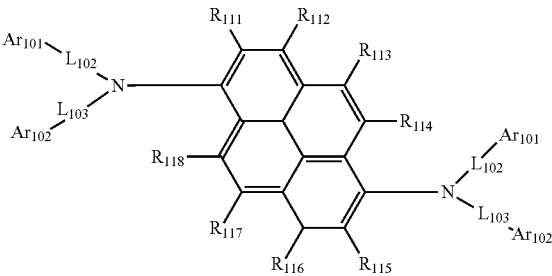

(14)

wherein in the formula (14), $R_{111}$ to $R_{118}$ are as defined in the formula (13); and $Ar_{101}$, $Ar_{102}$, $L_{102}$ and $L_{103}$ are as defined in the formula (12).

17. The organic electroluminescence device according to claim 15, wherein the compound represented by the formula (13) is a compound represented by the formula (15):

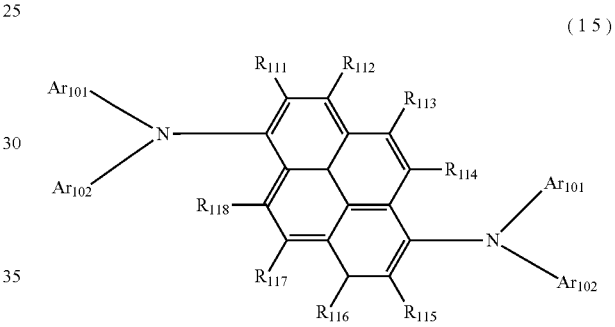

(15)

wherein in the formula (15), $R_{111}$ to $R_{118}$ are as defined in the formula (13); and $Ar_{101}$ and $Ar_{102}$ are as defined in the formula (12).

18. The organic electroluminescence device according to claim 15, wherein the compound represented by the formula (13) is a compound represented by the formula (17):

(17)

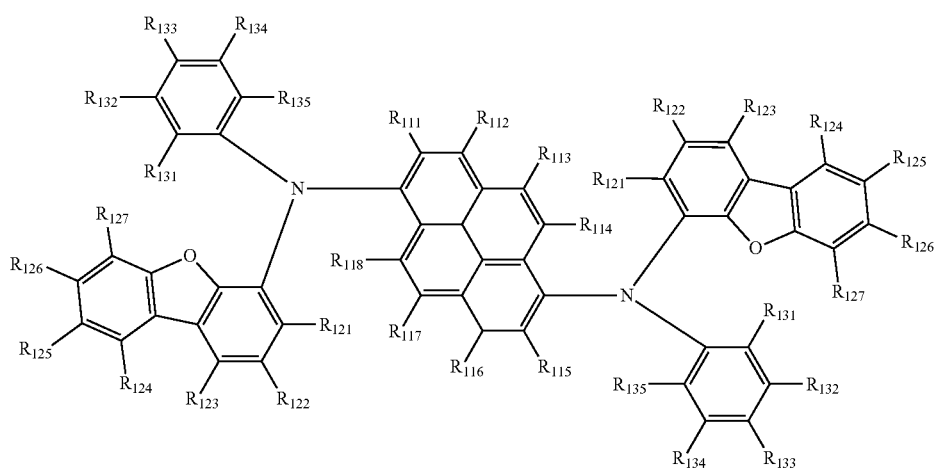

wherein in the formula (17), $R_{111}$ to $R_{118}$ are as defined in the formula (13);
one ore more pairs of adjacent two or more of $R_{121}$ to $R_{127}$ form a substituted or unsubstituted, saturated or unsaturated ring by bonding with each other, or do not form a substituted or unsubstituted, saturated or unsaturated ring;
$R_{121}$ to $R_{127}$ that do not form the substituted or unsubstituted, saturated or unsaturated ring are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;
$R_{901}$ to $R_{907}$ are as defined in the formula (1); and
$R_{131}$ to $R_{135}$ are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;
$R_{901}$ to $R_{907}$ are as defined in the formula (1).

19. The organic electroluminescence device according to claim 1, wherein in the formula (41), $R_{401}$ and $R_{402}$ are independently a substituted or unsubstituted aryl group having 6 to 50 ring carbon atoms, or a substituted or unsubstituted monovalent heterocyclic group having 5 to 50 ring atoms.

20. The organic electroluminescence device according to claim 1, wherein in the formula (41), $R_{401}$ and $R_{402}$ are independently a substituted or unsubstituted aryl group having 6 to 50 ring carbon atoms.

21. The organic electroluminescence device according to claim 1, wherein the compound represented by the formula (41) is a compound represented by the following formula (42):

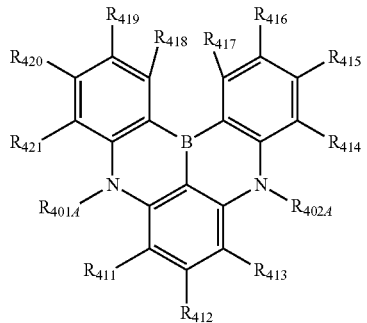

(42)

wherein in the formula (42),
$R_{401A}$ forms a substituted or unsubstituted heterocyclic ring by bonding with one or more selected from the group consisting of $R_{411}$ and $R_{421}$, or does not form a substituted or unsubstituted heterocyclic ring;
$R_{402A}$ forms a substituted or unsubstituted heterocyclic ring by bonding with one or more selected from the group consisting of $R_{413}$ and $R_{414}$, or does not form a substituted or unsubstituted heterocyclic ring;
$R_{401A}$ and $R_{402A}$ that do not form the substituted or unsubstituted heterocyclic ring are independently
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;
one or more pairs of adjacent two or more of $R_{411}$ to $R_{421}$ form a substituted or unsubstituted, saturated or unsaturated ring, or do not form a substituted or unsubstituted, saturated or unsaturated ring;
$R_{411}$ to $R_{421}$ that do not form the substituted or unsubstituted heterocyclic ring and the substituted or unsubstituted, saturated or unsaturated ring are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms; and
$R_{901}$ to $R_{907}$ are as defined in the formula (1).

22. The organic electroluminescence device according to claim 1, wherein the compound represented by the formula (41) is a compound represented by the following formula (43):

(43)

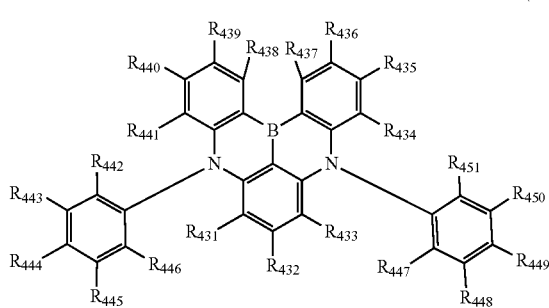

wherein in the formula (43)
$R_{431}$ forms a substituted or unsubstituted heterocyclic ring by bonding with $R_{446}$, or does not form a substituted or unsubstituted heterocyclic ring;
$R_{433}$ forms a substituted or unsubstituted heterocyclic ring by bonding with $R_{447}$, or does not form a substituted or unsubstituted heterocyclic ring;
$R_{434}$ forms a substituted or unsubstituted heterocyclic ring by bonding with $R_{451}$, or does not form a substituted or unsubstituted heterocyclic ring;
$R_{441}$ forms a substituted or unsubstituted heterocyclic ring by bonding with $R_{442}$, or does not form a substituted or unsubstituted heterocyclic ring;
one or more pairs of adjacent two or more of $R_{431}$ to $R_{451}$ form a substituted or unsubstituted, saturated or unsaturated ring by bonding with each other, or do not form a substituted or unsubstituted, saturated or unsaturated ring;
$R_{431}$ to $R_{451}$ that do not form the substituted or unsubstituted heterocyclic ring or the substituted or unsubstituted, saturated or unsaturated ring are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms; and
$R_{901}$ to $R_{907}$ are as defined in the formula (1).

23. The organic electroluminescence device according to claim 1, which further comprises a hole-transporting layer between the anode and the emitting layer.

24. The organic electroluminescence device according to claim 1, which further comprises an electron-transporting layer between the cathode and the emitting layer.

25. An electronic apparatus wherein the organic electroluminescence device according to claim 1 is provided.

26. The organic electroluminescence device according to claim 1, wherein at least one of the ring b or ring c is a substituted or unsubstituted heterocyclic ring including 5 to 50 ring atoms, said heterocyclic ring contains O or S.

27. The organic electroluminescence device according to claim 1, wherein at least one of the ring b or ring c is a substituted or unsubstituted heterocyclic ring including 5 to 50 ring atoms, wherein a substituent in said substituted or unsubstituted heterocyclic ring are selected from the group consisting of:
an alkyl group including 1 to 50 carbon atoms,
an aryl group including 6 to 50 ring carbon atoms,
a monovalent heterocyclic group including 5 to 50 ring atoms, and
Si($R_{901}$)($R_{902}$)($R_{903}$).

28. The organic electroluminescence device according to claim 26, wherein a substituent in said substituted or unsubstituted heterocyclic ring are selected from the group consisting of:
an alkyl group including 1 to 50 carbon atoms,
an aryl group including 6 to 50 ring carbon atoms,
a monovalent heterocyclic group including 5 to 50 ring atoms, and
Si($R_{901}$)($R_{902}$)($R_{903}$).

* * * * *